US009273358B2

(12) United States Patent
Philibert et al.

(10) Patent No.: US 9,273,358 B2
(45) Date of Patent: *Mar. 1, 2016

(54) COMPOSITIONS AND METHODS FOR DETECTING PREDISPOSITION TO A SUBSTANCE USE DISORDER

(71) Applicants: Robert Philibert, Iowa City, IA (US); Anup Madan, Bellevue, WA (US)

(72) Inventors: Robert Philibert, Iowa City, IA (US); Anup Madan, Bellevue, WA (US)

(73) Assignees: Robert Philibert, Iowa City, IA (US); Anup Madan, Bellevue, WA (US)

( * ) Notice: Subject to any disclaimer, the term of this patent is extended or adjusted under 35 U.S.C. 154(b) by 32 days.

This patent is subject to a terminal disclaimer.

(21) Appl. No.: 14/039,023

(22) Filed: Sep. 27, 2013

(65) Prior Publication Data

US 2014/0094389 A1 Apr. 3, 2014

Related U.S. Application Data

(63) Continuation of application No. 13/284,425, filed on Oct. 28, 2011, now Pat. No. 8,637,652, which is a continuation of application No. PCT/US2010/032815, filed on Apr. 28, 2010.

(60) Provisional application No. 61/173,274, filed on Apr. 28, 2009.

(51) Int. Cl.
*C12Q 1/37* (2006.01)
*C12Q 1/68* (2006.01)
*C07H 21/02* (2006.01)

(52) U.S. Cl.
CPC ............ *C12Q 1/6883* (2013.01); *C12Q 1/6869* (2013.01); *C12Q 2600/112* (2013.01); *Y10T 436/143333* (2015.01)

(58) Field of Classification Search
None
See application file for complete search history.

(56) References Cited

U.S. PATENT DOCUMENTS

| 2005/0153347 A1 | 7/2005 | Shapero et al. |
| 2007/0292880 A1 | 12/2007 | Philibert et al. |
| 2009/0075827 A1 | 3/2009 | Young et al. |

OTHER PUBLICATIONS

Agatsuma et al., "Monoamine oxidase A knockout mice exhibit impaired nicotine preference but normal responses to novel stimuli," *Hum. Mol. Genet.*, 2006, 15(18):2721-2731.
Alia-Klein et al., "Brain Monoamine Oxidase A Activity Predicts Trait Aggression," *J Neurosci.*, 2008, 28(19):5099-5104.
Benjamini and Hochberg, "Controlling the false discovery rate: a practical and powerful approach to multiple testing," *J. Royal Statist. Soc., Series B, Methodological*, 1995, 57:289-300.
Berlin and Anthenelli, "Monoamine oxidases and tobacco smoking," *Int J Neuropsychopharmacol.*, 2001, 4(1):33-42.
Bierut et al., "Novel genes identified in a high-density genome wide association study for nicotine dependence," *Hum Mol Genet.*, 2007, 16(1):24-35.
Bleich et al., "Epigenetic DNA hypermethylation of the HERP gene promoter induces down-regulation of its mRNA expression in patients with alcohol dependence," *Alcohol Clin Exp Res.* 30(4):587-591, 2006.

(Continued)

*Primary Examiner* — Reza Ghafoorian
(74) *Attorney, Agent, or Firm* — Fish & Richardson P.C.

(57) ABSTRACT

The present invention provides screening kits, compositions, and diagnostic methods for determining whether a subject has a predisposition to, or likelihood of having, a substance use disorder by determining a nucleic acid methylation profile from a biological sample from the subject, wherein a given profile indicates that the subject has a predisposition to a substance use disorder.

58 Claims, 9 Drawing Sheets

(56) References Cited

OTHER PUBLICATIONS

Bonsch et al., "DNA hypermethylation of the alpha synuclein promoter in patients with alcoholism," *Neuroreport*, 2005, 16(2):167-170.
Bradley et al., "Relationship of serotonin transporter gene polymorphisms and haplotypes to mRNA transcription," *Am J Med Genet B Neuropsychiatr Genet.*, 2005, 136(1):58-61.
Breitling et al., "Tobacco-Smoking-Related Differential DNA Methylation: 27K Discovery and Replication," *Am. J. Human Genet.*, 2011, 88:450-457.
Breton et al., "Prenatal Tobacco Smoke Exposure Affects Global and Gene-Specific DNA Methylation," *Am J Respir Crit Care Med.*, Sep. 1, 2009, 180(5):462-467, Epub Jun. 4, 2009.
Brunner et al., "Abnormal behavior associated with a point mutation in the structural gene for monoamine oxidase A," *Science*, 1993, 262(5133):578-80.
Bucholz et al., "A new, semi-structured psychiatric interview for use in genetic linkage studies; a report on the reliability of the SSAGA," *J. Stud. Alcohol*, 1994, 55:149-158.
Buckanovich et al., "The onconeural antigen Nova-1 is a neuron-specific RNA-binding protein, the activity of which is inhibited by paraneoplastic antibodies," *J Neurosci.*, 1996, 16(3):1114-1122.
Bussiere et al., "Stress protein expression cDNA array study supports activation of neutrophils during acute magnesium deficiency in rats," *Magnes Res.*, 2002, 15(1-2):37-42.
Carr et al., "Sequence analysis and editing for bisulphite genomic sequencing projects," *Nucl Acids Res.*, 2007, 35(10):e79-.
Caspi et al., "Influence of Life Stress on Depression: Moderation by a Polymorphism in the 5-HTT Gene," *Science*, 2003, 301(5631):386-389.
Caspi et al., "Role of genotype in the cycle of violence in maltreated children," *Science*, 2002, 297(5582):851-4.
Center for Disease Control, "Annual Smoking-Attributable Mortality, Years of Potential Life Lost, and Productivity Losses—United States, 1997-2001," *Morbidity and Mortality Weekly*, 2005, 54(25):625-628.
Center for Disease Control, "State-Specific Prevalence and Trends in Adult Cigarette Smoking—United States, 1998-2007," *JAMA*, 2009, 302(3):250-252.
Chang et al., "Smoking and drinking can induce p15 methylation in the upper aerodigestive tract of healthy individuals and patients with head and neck squamous cell carcinoma," *Cancer*, 101(1):125-132, 2004.
Chen et al., "Structure of the human gene for monoamine oxidase type A," *Nucleic Acids Res.*, 1991, 19(16):4537-4541.
Cirulli and Goldstein. "In vitro assays fail to predict in vivo effects of regulatory polymorphisms," *Hum Mol Genet.*, 2007, 16(16):1931-1939.
David et al., "Pharmacogenetic clinical trial of sustained-release bupropion for smoking cessation," *Nicotine & Tobacco Research*, 2007, 9(8):821-833.
Dempster, "The quantification of COMT mRNA in post mortem cerebellum tissue: diagnosis, genotype, methylation and expression," *BMC Med Genet.* 7:10, 2006.
Dindot et al., "Epigenetic profiling at mouse imprinted gene clusters reveals novel epigenetic and genetic features at differentially methylated regions," *Genome Res.*, 2009, 19:1374-1383.
Doi et al., "Differential methylation of tissue- and cancer-specific CpG island shores distinguishes human induced pluripotent stem cells, embryonic stem cells and fibroblasts," *Nat. Genet.*, 2009, 41:1350-1353.
Ehrich et al., "A new method for accurate assessment of DNA quality after bisulfite treatment," *Nucleic Acids Res.*, 2007, 35(5):e29.
Ehrich et al., "Quantitative high-throughput analysis of DNA methylation patterns by base-specific cleavage and mass spectrometry," *Proc Natl Acad Sci USA*, 2005, 102(44):15785-15790.
Farthing et al., "Global Mapping of DNA Methylation in Mouse Promoters Reveals Epigenetic Reprogramming of Pluripotency Genes," *PLoS Genet.*, 2008, 4:e1000116.
Fowler et al., "Brain monoamine oxidase A inhibition in cigarette smokers," *Proc Natl Acad Sci USA*, 1996, 93(24):14065-14069.
Fowler et al., "Inhibition of monoamine oxidase B in the brains of smokers," *Nature*, 1996, 379(6567):733-736.
Fowler et al., "Monoamine Oxidase and Cigarette Smoking," *NeuroToxicology*, 2003, 24(1):75-82.
Frazzetto et al., "Early Trauma and Increased Risk for Physical Aggression during Adulthood: The Moderating Role of MAOA Genotype," *PLoS One*, 2007, 2(5):e486.
Frommer et al., "A genomic sequencing protocol that yields a positive display of 5-methylcytosine residues in individual DNA strands," *Proc. Nat. Acad. Sci.*, 1992, 89(5):1827-1831.
Gene Ontology Consortium, "The Gene Ontology (GO) database and informatics resource," *Nucl Acids Res.*, 2004, 32(suppl_1):D258-261.
George and Weinberger, "Monoamine oxidase inhibition for tobacco pharmacotherapy," *Clin Pharmacol Ther.*, 2007, 83(4):619-621.
Greenman et al., "Patterns of somatic mutation in human cancer genomes," *Nature*, 2007. 446(7132):153-158.
Guillem et al., "Monoamine oxidase A rather than monoamine oxidase B inhibition increases nicotine reinforcement in rats," *Eur J Neurosci.*, 2006, 24(12):3532-3540.
Guo et al., "The VNTR 2 repeat in MAOA and delinquent behavior in adolescence and young adulthood: associations and MAOA promoter activity," *Eur J Hum Genet.*, 2008, 16(5):626-634.
Hao and Rajewsky, "Homeostasis of peripheral B cells in the absence of B cell influx from the bone marrow," *J Exp Med.*, 2001, 194(8):1151-1164.
Heatherton et al., "The Fagerstrom Test for Nicotine Dependence: a revision of the Fagerstrom Tolerance Questionnaire," *Br J Addict.*, 1991, 86(9):1119-1127.
Hillemacher et al., "Promoter specific methylation of the dopamine transporter gene is altered in alcohol dependence and associated with craving," *J. Psychiatr Res.*, 2009, 43(4):388-392, Epub May 27, 2008.
Hotamisligil and Breakefield, "Human monoamine oxidase A gene determines levels of enzyme activity," *Am J Hum Genet.*, 1991, 49(2):383-392.
Isensee et al., "Smoking increases the risk of panic: findings from a prospective community study," *Arch Gen Psychiatry*, 2003, 60(7):692-700.
Kaartinen et al., "Vestibular dysgenesis in mice lacking Abr and Bcr Cdc42/RacGAPs," *Develop. Dynamics*, 2002, 223:517-525.
Kawaji et al., "Dynamic usage of transcription start sites within core promoters," *Genome Biology*, 2006, 7(12):R118.
Kim-Cohen et al., "MAOA, maltreatment, and gene-environment interaction predicting children's mental health: new evidence and a meta-analysis," *Mol Psychiatry*, 2006, 11(10):903-913.
Koike et al., "Gene expression profile of residual breast cancer after doxorubicin and cyclophosphamide neoadjuvant chemotherapy," *Oncol Rep*, 2009, 22(4):805-813.
Kumra and Markoff, "Who's Smoking Now?: The Epidemiology of Tobacco Use in the United States and Abroad," *Clinics in Chest Medicine*, 2000, 21(1):1-9.
Lahiri and Schnabel, "DNA isolation by a rapid method from human blood samples: effects of MgC12, EDTA, storage time, and temperature on DNA yield and quality," *Biochem Genet.*, 1993, 31(7-8):321-328.
Lahiri et al., "A rapid non-enzymatic method for the preparation of HMW DNA from blood for RFLP studies," *Nucleic Acids Research.*, 1991, 19(19):5444.
Lambe and George, "Perspective: Translational Studies on Glutamate and Dopamine Neurocircuitry in Addictions: Implications for Addiction Treatment," *Neuropsychopharmacology*, 2008, 34(2):255-256.
Launay et al., "Smoking Induces Long-Lasting Effects through a Monoamine-Oxidase Epigenetic Regulation," *PLoS One*, 2009, 4(11):e7959.
Levine et al., "Transcription regulation and animal diversity," *Nature*, 2003, 424(6945):147-151.
Liang et al., "Distinct localization of histone H3 acetylation and H3-K4 methylation to the transcription start sites in the human genome," *Proc Natl Acad Sci USA*, 2004, 101(19), 7357-7362.

(56) References Cited

OTHER PUBLICATIONS

Ma et al., "Identification of Cancer Associated Gene Clusters and Genes Via Clustering Penalization," *Statistics and Its Interface*, 2009, 2:1-11.

Macdonald et al., "Oxidative stress and gene expression in sepsis," *Br J Anaesth.*, 2003, 90(2):221-232.

Merril et al., "A silver stain for the rapid quantitative detection of proteins or nucleic acids on membranes or thin layer plates," *Analytical Biochemistry*, 1986, 156(1):96-110.

Miller et al., "Reboxetine: Functional inhibition of monamine transporters and nicotinic acetylcholine receptors," *J Pharmacol Exp Ther.*, 2002, 302(2):687-695.

Minakuchi et al., "Identification and characterization of SEB, a novel protein that binds to the acute undifferentiated leukemia-associated protein SET," *European Journal of Biochemistry*, 2001, 268(5):1340-1351.

Monks et al., "Genetic inheritance of gene expression in human cell lines," *Am J Hum Genet.*, 2004, 75(6):1094-1105.

Morello et al., "Differential Gene Expression of Blood-Derived Cell Lines in Familial Combined Hyperlipidemia," *Arterioscler Thromb Vasc Biol.*, 2004, 24(11):2149-2154.

Mouritzen et al., The ProbeLibraryTM—Expression profiling 99% of all human genes using only 90 dual-labeled real-time PCR probes, *BioTechniques*, vol. 37, No. 3 (2004).

Nielsen et al., "Increased OPRM1 DNA Methylation in Lymphocytes of Methadone-Maintained Former Heroin Addicts," *Neuropsychopharmacology*, Mar. 2009, 34(4):867-873, Epub Jul. 23, 2008.

Philibert et al., "Association of an X-chromosome dodecamer insertional variant allele with mental retardation," *Molecular Psychiatry*, 1998, 3(4):303-309 [erratum appears in Mol Psychiatry Mar. 1999;4(2):197].

Philibert et al., "MAOA methylation is associated with nicotine and alcohol dependence in women," *Am. J. Med. Genet. B. Neuropsychiatr. Genet.*, 2008, 147(B):565-570.

Philibert et al., "Serotonin transporter mRNA levels are associated with the methylation of an upstream CpG island," *Am J Med Genet B Neuropsychiatr Genet.*, 2007, 144(B):101-105.

Philibert et al., "The Effect of Smoking on MAOA Promoter Methylation in DNA Prepared from Lymphoblasts and Whole Blood," *Am J Med Genet B Neuropsychiatr Genet.*, 2010, 153B:619-28; [Epub ahead of print, 2009].

Philibert et al., "Transcriptional profiling of subjects from the Iowa adoption studies," *Am J Med Genet B Neuropsychiatr Genet.*, 2007, 144(5):683-690.

Rodd et al., "Differential gene expression in the nucleus accumbems with ethanol self-administration in inbred alcohol-preferring rats," *Pharmacol. Biochem. Behavior*, 2008, 89:481-498.

Sabol et al., "A functional polymorphism in the monoamine oxidase A gene promoter," *Hum Genet.*, 1998, 103(3):273-279.

Shiozawa et al., "Annexin II/Annexin II receptor axis regulates adhesion, migration, homing, and growth of prostate cancer," *J Cell Biochem.*, Oct. 1, 2008, 105(2):370-380.

Tessema et al., "Concomitant promoter methylation of multiple genes in lung adenocarcinomas from current, former and never smokers," *Carcinogenesis*, 2009, 30(7):1132-1138.

Tough and Sprent, "Lifespan of lymphocytes," *Immunol Res.*, 1995, 14(1):1-12.

Villegier et al, "Serotonergic mechanism underlying tranylcypromine enhancement of nicotine self-administration," *Neuropharmacology*, 2007, 52(6):1415-1425.

Vink et al., "Genome-wide association study of smoking initiation and current smoking," *Am J Hum Genet.*, 2009, 84(3):367-379.

Wang et al., "Strain- and region-specific gene expression profiles in mouse brain in response to chronic nicotine treatment," *Genes Brain Behav.*, Feb. 2008, 7(1):78-87, Epub May 14, 2007.

Wooters et al., "The monoamine oxidase inhibitor phenelzine enhances the discriminative stimulus effect of nicotine in rats," *Behav Pharmacol.*, 2007, 18(7):601-608.

Wright et al., "Estrogen Regulates Vesicle Trafficking Gene Expression in EFF-3, EFM-19 and MCF-7 Breast Cancer Cells," *Int J Clin Exp Pathol.*, 2009, 2(5):463-475.

Yates et al., "An adoption study of DSM-IIIR alcohol and drug dependence severity," *Drug and Alcohol Dependence*, 1996, 41(1):9-15.

Yates et al., "The Iowa Adoption Studies Methods and Results," *On the Way to Individuality: Methodological Issues in Behavioral Genetics*, 1998, Hauppauge NY, Nova Science Publishers, pp. 95-125, LaBuda et al, Eds.

Yu and Boulton, "Irreversible inhibition of monoamine oxidase by some components of cigarette smoke," *Life Sci.*, 1987, 41(6):675-682.

Zeeberg et al., "GoMiner: a resource for biological interpretation of genomic and proteomic data," *Genome Biology*, 2003, 4(4):R28, Epub Mar. 25, 2003.

International Preliminary Report on Patentability for PCT/US2010/32815 issued Oct. 16, 2012, 8 pages.

International Search Report and Written Opinion for PCT/US2010/32815 mailed Sep. 27, 2012, 13 pages.

Figure 1

```
43398775            TAGTGAGGGC TGGAGGCTGC GCAGACCTCG ACGGGCCCTA CATGACGTCA
43398825            CAAAGGGGCC AGACCAAGTG GGGCAGCACC CTGCGACCCT GCGATCCTGC
43398875            CTGGCTCAGC CGCCTTCATA TATCTGCTTC CTTAAGTCCA CTCTTGCCCA
43398925            GATAGCTTTC AGTTAAAACT AAAGAATGAA AGCACTAGGT TGAGAGCCCA
43398975  CpG1-6    CGCGGCTACA CCCACGTCTA CTCCCCCACT CTCGCCAGGC AACCGCGCCC
43399025  CpG7-11   CCCGCCTGCA GTGGCATCGT CCGGCCACGC CCAGTGGCAG GGTTTCCAGC
43399075  CpG12-15  GCGAGCCTGC AGGCAGGCCG GGAAGGCGGA GCCAGGCCGG CCTAGAGTCA
43399125  CpG16-18  CTTCTCCCCG CCCCTGACTG GGCCGGGAGC CCGGGGCTGG TCTCTAAGAG
43399175            TGGGTACCGA G[AACAGCCTG ACCGTGGAGA AG]GGCTGCGG GAAGCAGAAC
43399225            ACCGCCCCCA GCGCCCAGCG TGCTCCAGAA ACATGAGCAC AAACGCCTCA
43399275            GCCTCCTTCC CCGGCGGCAC CGGCACCGGC ACCAGTACCC GCACCAGTAC
43399325            CGGCACCGGC ACCAGTACCC GCACCAGTAC CGGCACCGGC ACCAGTACCC
43399375            GCACCAGTAC CGGCACCGGC ACCGAGCGCA AGGCGGAGGG CCCGCCCGAA
43399425  CpG19-21  GCCGGGGGCA CAACTGCCCA GGTCCCGAAC CCGGACTCCA GCTTGGACGA
43399475  CpG22-26  CACCTCCTAC AGCCTG[TCCG AATGGAGCGT CCGTT]CTGAG TGGCGGTCCG
43399525  CpG27-30  TCTCGGATCC GCTAGCCAGT TCCCAGTGGA GCACGTCCTC AACTGCCGAG
43399575  CpG31-32  GCCGCCTCCT GGAGCTCCAG CATACACTCC CCAATCAGCA CTACCGGTCT
43399625  CpG33-36  TAGCGAGAGT ACTGACTCCG ACTCCAAGAG TGGCCTCCGG GGTTTCAGCG
43399675  CpG37-39  CTTACAACCC GAGCAGTCGG ATCCCCAAGT CTACCACCAG CTCGAACTCC
43399725  CpG40-42  TCCGATGGGG CCGTCACAGC CTCCAATCAG GACACCGGCA TTCCCTGGGT
43399775  CpG43-45  ATTAGTAACA GGACCTACCC CGCCCGTAAA CTCCCCCGTA GAGTCATTGC
43399825  CpG46     AAGGGTCTGC CTTCTCCTCA GGGTTCAGCA CCCCACGGGG TTTGGTAAAA
43399875  CpG47-49  GGACCGACCC TGCCCCCGGA TTCCAACCTG ACCTCAGTGT CCGACTACAC
43399925  CpG50-51  TTGGATATTT GTACGGGGAC CTCCTATACC CAATGACCTT TCGCAAGTGT
43399975  CpG52     CAATACAAGC ACCTCCTACA CCCAGTAACA CCCCCGAGTG TCAGTACAAG
43400025  CpG53     GGTCTGCCGC ATCCTCAGTG TCCAGCTTCC CCTGGGGTTT GGTACCAGGA
43400075  CpG54     CCACCTCTAC CCAATAACAT TTCCCCAGTG TCGCCACAAG CACCTCCTGC
43400125  CpG55     ACCCCATAAC ATCCCCCCAG TGTCAAGGCA GGCGTCTACC CCCACCTCAG
43400175  CpG56-57  TGCCTGACAC TCCGCGGGGT TCAATACAAG AACCTCCTGC ACCCAGTAAT
43400225  CpG58-60  CCTTTCCAGC TGCCGACACA AGGACATTCT AAACCTAATA ACTCTCGCCG
43400275  CpG61-63  AGTGTCAGTA CAAGGGTCCG CCCCGCTCTC AGTGCCCAGC TCCCCCCGGG
43400325  CpG64-66  TATCAGCTGA AACATCAGCT CCGCCCCTgg gCGctccCGg agtatcagca
43400375  CpG67-70  aaagggttCG cccCGcccac agtgccCGgc tccccCGgg tatcaaaaga
43400425  CpG71-74  aggatCGgct cCGccccCGg gctcccCGgg ggagttgata gaagggtcct
43400475  CpG75-77  tcccaccctt tgcCGtcccc actcctgtgc ctaCGaccca ggagCGtgtc
43400525  CpG78-80  agccaaagca tggagaatca agagaaggCG agtatCGCGg gccacatgtt
43400575  CpG81-86  CGaCGtagtC GtgatCGgag gtggcatttc agGTCAGTGT GGACCGTAGC
43400625            GGTGGCCTGG GGGACCCTGG CCAGTGAGGG GTAGGGGAAC CTACAGTAGC
43400675  CpG87     TCTTGTGGTG TTTGGGGGTC TCTCATGCAT GCGAGAGTGT AGTGTAGCCA
43400725  CpG88     TGGCTTGGCC CCATATCCTG CGAGGTAGGA GTGGGGGTTG TGCCAGTTTT
43400775            GCTGGTGGTG TGACTGGGGG AGGCAGACAC AATAATTTTA CTACTACTAC
                    (SEQ ID NO: 9)
```

**Figure 8. Sequence and Probe Placement for the *AX2R* Promoter** ggttgaggctgcagtgagctatgctttgtgccactgcactccagcctgggggacacagccagacctgtctcaaaaaaaag
ccaaaaatactgtggagtggccctttcttcaagcatctgcttgcttgtttctaacaccactcattctattgccctactgagcttgaaatgataatgctttcttc
aggtgccaggtctggagtgctgtgtcacctatctcaaaaCGgctgtctcaaaactcaacaggagcacctaaCGgtactgggtgcaacattgcta  CpG 1-2
gcaCGgatcaaacacagcagtccagtaacctggaacaacaggctctgCGaaaccaaggaictctgacaaagaaaaattgccaattccaaacatagc  CpG 3-4
ctgttttagtagagaaatgaatggCGttgtcatCGaaaaaacacagactCGattgtgacagtaaatacCGccacaaaCGcaggtacagggacagc  CpG 5-9
CGacacCGagaaccaaggagaagCGgctgagagctgCGcctccaCGgaataactgccagcCGgcacagtgCGagtgagaaacCG  CpG 10-17
gccactccatgaaaCGaccagtactgccaCGgaaaagaatcCGaCGtCGccaacaagCGgtcctaccaggagaaaCGcctgctttg  CpG 18-24
aagaaaacagccaggaaCGCGactgaaagacacttgctcccaggagaagaattggcatttgttccaaaacacagctgtgataaacCGagaaccttC  CpG 25-28
GgagtgtttgcacCGaaaCGgggtcaccoagcctcagCGtcctgggtcttagcaagcctcacagaagcgaaCGgcagtgctaacacC  CpG 29-33
GaggagcacctagagCGgcaaaactaigcagtaatgccatCGaCGaaaggccagttaggccaaaagaatagaatatttagttcCGggaattac  CpG 33-35
aggcagCGcaaaccagacagcagcataaagctgagggtcagcaaaacaaaattaggaacaattttttttaaagggcagttagctgaaaacacaC  CpG 36-37
Gcacacacaataaaacaatacatttgggaagattcatcaaatgaaaattcaaaactaagcaaaacatggaaaacatggactctacaaagaagaaaatgc
(SEQ ID NO:21)

SEQUENCE LISTING

<160> NUMBER OF SEQ ID NOS: 21

<210> SEQ ID NO 1
<211> LENGTH: 30
<212> TYPE: DNA
<213> ORGANISM: Artificial Sequence
<220> FEATURE:
<223> OTHER INFORMATION: synthetic primer

<400> SEQUENCE: 1
ttaaagaatg aaagtattag gttgagagtt                                           30

<210> SEQ ID NO 2
<211> LENGTH: 25
<212> TYPE: DNA
<213> ORGANISM: Artificial Sequence
<220> FEATURE:
<223> OTHER INFORMATION: synthetic primer

<400> SEQUENCE: 2
atacccactc ttaaaaacca acccc                                                25

<210> SEQ ID NO 3
<211> LENGTH: 23
<212> TYPE: DNA
<213> ORGANISM: Artificial Sequence
<220> FEATURE:
<223> OTHER INFORMATION: synthetic primer

<400> SEQUENCE: 3
gggtgttgaa ttttgaggag aag                                                  23

<210> SEQ ID NO 4
<211> LENGTH: 22
<212> TYPE: DNA
<213> ORGANISM: Artificial Sequence
<220> FEATURE:
<223> OTHER INFORMATION: synthetic primer

<400> SEQUENCE: 4
aaaacacaac tacccaaatc cc                                                   22

<210> SEQ ID NO 5
<211> LENGTH: 28
<212> TYPE: DNA
<213> ORGANISM: Artificial Sequence
<220> FEATURE:
<223> OTHER INFORMATION: synthetic primer

<400> SEQUENCE: 5
ggggagttga tagaagggtt ttttttat                                             28

<210> SEQ ID NO 6
<211> LENGTH: 25
<212> TYPE: DNA
<213> ORGANISM: Artificial Sequence
<220> FEATURE:
<223> OTHER INFORMATION: synthetic primer

<400> SEQUENCE: 6
tatatctacc tcccccaatc acacc                                                25

<210> SEQ ID NO 7
<211> LENGTH: 29
<212> TYPE: DNA
<213> ORGANISM: Artificial Sequence

```
<220> FEATURE:
<223> OTHER INFORMATION: synthetic primer

<400> SEQUENCE: 7
aaagggtggg aaggattttt ttattaatt                                    29

<210> SEQ ID NO 8
<211> LENGTH: 25
<212> TYPE: DNA
<213> ORGANISM: Artificial Sequence
<220> FEATURE:
<223> OTHER INFORMATION: synthetic primer

<400> SEQUENCE: 8
catcctcaat atccaacttc cccta                                        25

<210> SEQ ID NO 9
<211> LENGTH: 2050
<212> TYPE: DNA
<213> ORGANISM: Artificial Sequence
<220> FEATURE:
<223> OTHER INFORMATION: synthetic polynucleotide

<400> SEQUENCE: 9
tagtgagggc tggaggctgc gcagacctcg acgggccta catgacgtca caaaggggcc      60
agaccaagtg gggcagcacc ctgcgaccct gcgatcctgc ctggctcagc cgccttcata    120
tatctgcttc cttaagtcca ctcttgccca gatagctttc agttaaaact aaagaatgaa    180
agcactaggt tgagagccca cgcggctaca cccacgtcta ctcccccact ctcgccaggc    240
aaccgcgccc cccgcctgca gtggcatcgt ccggccacgc ccagtggcag ggtttccagc    300
gcgagcctgc aggcaggccg ggaaggcgga gccaggccgg cctagagtca cttctccccg    360
cccctgactg ggccgggagc ccggggctgg tctctaagag tgggtaccga aacagcctg     420 accgtggaga agggctgcgg gaagcagaac accgccccca gcgcccagcg tgctccagaa    480
acatgagcac aaacgcctca gcctccttcc ccggcggcac cggcaccggc accagtaccc    540
gcaccagtac cggcaccggc accagtaccc gcaccagtac cggcaccggc accagtaccc    600
gcaccagtac cggcaccggc accgagcgca aggcggaggg cccgcccgaa gccggggggca   660 caactgccca ggtcccgaac ccggactcca gcttggacga cacctcctac agcctgtccg    720
aatggagcgt ccgttctgag tggcggtccg tctcggatcc gctagccagt tcccagtgga    780
gcacgtcctc aactgccgag gccgcctcct ggagctccag catacactcc ccaatcagca    840
ctaccggtct agcgagagt actgactccg actccaagag tggcctccgg ggtttcagcg     900
cttacaaccc gagcagtcgg atccccaagt ctaccaccag ctcgaactcc tccgatgggg    960
ccgtcacagc ctccaatcag dacaccggca ttccctgggt attagtaaca ggacctaccc   1020 cgccccgtaaa ctcccccgta gagtcattgc aagggtctgc cttctcctca gggttcagca   1080
ccccacgggg tttggtaaaa ggaccgaccc tgccccgga ttccaacctg acctcagtgt    1140
ccgactacac ttggatattt gtacggggac tcctatacc caatgacctt tcgcaagtgt    1200
caatacaagc acctcctaca cccagtaaca ccccgagtg tcagtacaag ggtctgccgc    1260
atcctcagtg tccagcttcc cctggggttt ggtaccagga ccacctctac ccaataacat    1320
ttccccagtg tcgccacaag cacctcctgc accccataac atcccccag tgtcaaggca     1380 ggcgtctacc cccacctcag tgcctgacac tccgcgggt tcaatacaag aacctcctgc    1440
acccagtaat cctttccagc tgccgacaca aggacattct aaacctaata actctcgccg    1500
```

-continued

```
agtgtcagta caagggtccg ccccgctctc agtgcccagc tcccccgggg tatcagctga    1560
aacatcagct ccgccctgg gcgctccgg agtatcagca aaagggttcg ccccgcccac      1620
agtgcccggc tccccggg tatcaaaaga aggatcggct ccgccccgg gctcccggg        1680 ggagttgata gaagggtcct tcccaccctt tgccgtcccc actcctgtgc ctacgacccca   1740 ggagcgtgtc agccaaagca tggagaatca agagaaggcg agtatcgcgg ccacatgtt    1800 cgacgtagtc gtgatcggag gtggcatttc aggtcagtgt ggaccgtagc ggtggcctgg   1860
gggaccctgg ccagtgaggg gtaggggaac ctacagtagc tcttgtggtg tttgggggtc   1920
tctcatgcat gcgagagtgt agtgtagcca tggcttggcc ccatatcctg cgaggtagga   1980 gtggggggttg tgccagtttt gctggtggtg tgactggggg aggcagacac aataatttta   2040
ctactactac                                                           2050
```

<210> SEQ ID NO 10
<211> LENGTH: 24
<212> TYPE: DNA
<213> ORGANISM: Artificial Sequence
<220> FEATURE:
<223> OTHER INFORMATION: synthetic primer

<400> SEQUENCE: 10
agtgttggtg tatttatttt aaaa                                            24

<210> SEQ ID NO 11
<211> LENGTH: 25
<212> TYPE: DNA
<213> ORGANISM: Artificial Sequence
<220> FEATURE:
<223> OTHER INFORMATION: synthetic primer

<400> SEQUENCE: 11
tcctaaaaac aaatatcttt caatc                                           25

<210> SEQ ID NO 12
<211> LENGTH: 27
<212> TYPE: DNA
<213> ORGANISM: Artificial Sequence
<220> FEATURE:
<223> OTHER INFORMATION: synthetic primer

<400> SEQUENCE: 12
taacaatact aatcatttca taaaata                                         27

<210> SEQ ID NO 13
<211> LENGTH: 27
<212> TYPE: DNA
<213> ORGANISM: Artificial Sequence
<220> FEATURE:
<223> OTHER INFORMATION: synthetic primer

<400> SEQUENCE: 13
agtttagtaa tttggaataa taggttt                                         27

<210> SEQ ID NO 14
<211> LENGTH: 50
<212> TYPE: DNA
<213> ORGANISM: Artificial Sequence
<220> FEATURE:
<223> OTHER INFORMATION: synthetic probe

<400> SEQUENCE: 14
ttcaggtgcc aggtctggag tgctggtgca cctatctcaa aacgctgtct                50

<210> SEQ ID NO 15
<211> LENGTH: 50
<212> TYPE: DNA
<213> ORGANISM: Artificial Sequence
<220> FEATURE:
<223> OTHER INFORMATION: synthetic probe

<400> SEQUENCE: 15
gcaaacagca gtccagtaac ctggaacaac aggctctgcg aaaccaagga            50

<210> SEQ ID NO 16
<211> LENGTH: 57
<212> TYPE: DNA
<213> ORGANISM: Artificial Sequence
<220> FEATURE:
<223> OTHER INFORMATION: synthetic probe

<400> SEQUENCE: 16
agaaatgaat ggcgttgtca tcgaaaaaac acagactcga ttgtgacaga aataccg    57

<210> SEQ ID NO 17
<211> LENGTH: 50
<212> TYPE: DNA
<213> ORGANISM: Artificial Sequence
<220> FEATURE:
<223> OTHER INFORMATION: synthetic probe

<400> SEQUENCE: 17
tgcgcctcca cggataact gccagccggc acagtgcgag tgagaaaccg             50

<210> SEQ ID NO 18
<211> LENGTH: 50
<212> TYPE: DNA
<213> ORGANISM: Artificial Sequence
<220> FEATURE:
<223> OTHER INFORMATION: synthetic probe

<400> SEQUENCE: 18
ggaaaagaat ccgacgtcgc caacaagcgg tgctaccagg agaaacgcct            50

<210> SEQ ID NO 19
<211> LENGTH: 50
<212> TYPE: DNA
<213> ORGANISM: Artificial Sequence
<220> FEATURE:
<223> OTHER INFORMATION: synthetic probe

<400> SEQUENCE: 19
aaaacacagc tggataaacc gagaaccttc ggagtggttg caccgaaacg            50

<210> SEQ ID NO 20
<211> LENGTH: 50
<212> TYPE: DNA
<213> ORGANISM: Artificial Sequence
<220> FEATURE:
<223> OTHER INFORMATION: synthetic probe

<400> SEQUENCE: 20
gaagcaaccg gcagtgctaa caccgaggag cacctagagc ggcaaaacta            50

<210> SEQ ID NO 21
<211> LENGTH: 1119
<212> TYPE: DNA
<213> ORGANISM: Artificial Sequence
<220> FEATURE:

-continued

<223> OTHER INFORMATION: synthetic polynucleotide

<400> SEQUENCE: 21

```
ggttgaggct gcagtgagct atgcttgtgc cactgcactc cagcctgggg gacacagcca      60
gaccctgtct caaaaaaagt gaaaaaaaaa aaaaagccaa aaaatactgt ggagtggccc     120
tttcttcaag catctgcttg ctttctctaa caccactcat tctattgccc ctactgagct     180
tgaaatgata atgctttctt caggtgccag gtctggagtg ctggtgcacc tatctcaaaa     240
cgctgtctca aaactccaac agggagcacc taacggtact gggtgcaaca ttgctagcac     300
ggagcaaaca gcagtccagt aacctggaac aacaggctct gcgaaaccaa ggactctgac     360
aaagaaaaat tgccaattcc aaacatagcc tgttttagag aaatgaatgg cgttgtcatc     420
gaaaaaacac agactcgatt gtgacagaaa taccgccaca aacgcaggta cagggacagc     480
cgacaccgag aaccaaggga agcggctgag agctgcgcct ccacggaata actgccagcc     540
ggcacagtgc gagtgagaaa ccggccactc catgaaacga ccagtactgc cacggaaaag     600
aatccgacgt cgccaacaag cggtgctacc aggagaaacg cctgcttttg aagaaaacag     660
ccaggaacgc gactgaaaga cacttgctcc caggaagaat tggcatttgt tccaaaacac     720
agctggataa accgagaacc ttcggagtgg ttgcaccgaa acggggtcac ccagcacctc     780
agcgtcctgg gctctagcaa gcctcacaga agcaaccggc agtgctaaca ccgaggagca     840
cctagagcgg caaaactagc agtaatgcca tcgacgaaag gccagttagg ccaaaagaat     900
agaatattta gttccgggaa ttacaggcca gcgcaaacca gacagcataa agctgagggt     960
cagcaaaaca aaaattagga acaatttttt tttaaagggc aagttagctg aaaaacacac    1020
gcacacacaa taaaaacaat acatttggga agattcatca aatgaaaatt caaaactaag    1080
caaaacatgg aaaaatggac tctacaaaga agaaaatgc                           1119
```

COMPOSITIONS AND METHODS FOR DETECTING PREDISPOSITION TO A SUBSTANCE USE DISORDER

RELATED APPLICATION

This application is a Continuation of, and claims the benefit of priority under 35 U.S.C. 120 to, U.S. application Ser. No. 13/284,425, filed Oct. 28, 2011, which claims the benefit of priority under 35 U.S.C. §119 to PCT/US2010/032815, filed Apr. 28, 2010, which claims the benefit of priority under 35 U.S.C. §119(e) to U.S. Application No. 61/173,274, filed Apr. 28, 2009. The entirety of each of these disclosures is incorporated herein by reference.

STATEMENT OF GOVERNMENT SUPPORT

Work related to this invention was funded by the U.S. government (NIH Grants DA015789, DA010923, DA02173603, MH080898, and P30DA027827). The government has certain rights in this patent.

BACKGROUND

Substance use disorders cause serious problems, both for the affected individuals and for society in general. Despite intensive research, however, a reliable laboratory test for diagnosing a patient as having, or for being at risk for developing, such conditions has not been developed. Such diagnoses are still generally made clinically, on the basis of observed behavior. Given the difficulties of defining normal experience and behavior and the lack of reliable objective indicators, it is not surprising that to date systems of diagnosis in psychiatry have been less than satisfactory. A reliable laboratory test would be of practical value in everyday clinical practice, for example, in assisting doctors in prescribing the appropriate treatment for their patients. Thus, methods of identifying subjects that have, or are at risk for developing, substance use disorders are needed.

SUMMARY OF CERTAIN EMBODIMENTS OF THE INVENTION

The present invention provides a screening kit for determining whether a human subject has the likelihood of using, abusing or being dependent upon a substance comprising: (a) a solid substrate, at least one probe specific for methylation status of a CpG dinucleotide repeat motif expressed by a peripheral blood cell or its derivative, wherein the methylation status of the CpG dinucleotide is associated with nicotine use, abuse or dependence; and/or (b) a solid substrate, at least one probe specific for methylation status a CpG dinucleotide repeat motif expressed by a peripheral blood cell or its derivative, wherein the methylation status of the CpG dinucleotide is associated with alcohol use, abuse or dependence; and/or (c) a solid substrate, at least one probe specific for methylation status a CpG dinucleotide repeat motif expressed by a peripheral blood cell or its derivative, wherein the methylation status of the CpG dinucleotide is associated with cannabis use, abuse or dependence. As used herein, the term "methylation status" means the determination whether a certain target DNA, such as a CpG dinucleotide, is methylated. As used herein the term "CpG dinucleotide repeat motif" means a series of two or more CpG dinucleotides positioned in a DNA sequence.

In certain embodiments of the present invention, the substance is nicotine and the CpG dinucleotide repeat motif is located in a gene from Table 5 or Table 9 or Appendix C. In certain embodiments of the present invention, the substance is alcohol and the CpG dinucleotide repeat motif is located in a gene from Table 6 or Table 13 or Appendix E. In certain embodiments of the present invention, the substance is cannabis and the CpG dinucleotide repeat motif is located in a gene from Table 7 or Table 14.

The present invention also provides a screening kit for determining whether a subject has a predisposition to, or likelihood of having, a substance use disorder including at least one probe specific for a methylated monoamine oxidase A (MAOA) or monoamine oxidase B (MAOB) locus or a aryl hydrocarbon receptor repressor (AHRR) locus in a peripheral blood cell, wherein the methylation of MAOA or AHRR is associated with a substance use disorder. In certain embodiments, the kit further includes a solid substrate, wherein each probe is bound onto the substrate in a distinct spot. In certain embodiments, the substance use disorder is nicotine dependence. In certain embodiments, the probe detects methylation at CpG residue 18, 42, 48, 52, 64, 65, 66, 67, 68, 69, and/or 77 (for MAOA) and at CpG residues in the AHRR gene. In certain embodiments, the substance use disorder is alcohol dependence. In certain embodiments, the probe detects methylation at CpG residue 27, 38, 41 and/or 48 (for MAOA). In certain embodiments, the substance use disorder is cannabis dependence. In certain embodiments, the subject is female and the probe detects methylation at CpG residue 69 and/or 88 (for MAOA). In certain embodiments, the subject is male and the probe detects methylation at CpG residue 11-12, 13, 64, 69, 72 and/or 73 of MAOA. In certain embodiments, the substrate is a polymer, glass, semiconductor, paper, metal, gel or hydrogel. In certain embodiments, the kit further includes at least one control probe, wherein the at least one control probe is bound onto the substrate in a distinct spot. In certain embodiments, the solid substrate is a microarray or microfluidics card. In certain embodiments, the probe is an oligonucleotide probe or a nucleic acid derivative probe.

The present invention provides a screening kit that uses bisulfite treated DNA for determining whether a subject has the likelihood of using, abusing or being dependent upon a substance comprising: (a) a single base pair extension probe, with at least one probe specific for methylation status of a CpG dinucleotide repeat motif expressed by a peripheral blood cell or its derivative, wherein the methylation status of the CpG dinucleotide is associated with nicotine use, abuse or dependence; and/or (b) a single base pair extension probe, at least one probe specific for methylation status of a CpG dinucleotide repeat motif expressed by a peripheral blood cell or its derivative, wherein the methylation status of the CpG dinucleotide is associated with alcohol use, abuse or dependence; and/or (c) a single base pair extension probe, at least one probe specific for methylation status of a CpG dinucleotide repeat motif expressed by a peripheral blood cell or its derivative, wherein the methylation status of the CpG dinucleotide is associated with cannabis use, abuse or dependence. As used herein, a "single base pair extension probe" is a nucleic acid that selectively recognizes a single nucleotide polymorphism (i.e., either the A or the G of an A/G polymorphism). Generally, these probes take the form of a DNA primer (e.g., as in PCR primers) that are modified so that incorporation of the primer releases a fluorophore. One example of this is a Taqman® probe that uses the 5' exonuclease activity of the enzyme Taq Polymerase for measuring the amount of target sequences in the samples. TaqMan® probes consist of a 18-22 bp oligonucleotide probe, which is labeled with a reporter fluorophore at the 5' end, and a quencher fluorophore at the 3' end. Incorporation of the probe molecule into a PCR chain (which occurs because the probe set is contained in a mixture of PCR primers) liberates the reporter fluorophore from the effects of the quencher. The primer must be able to recognize the target binding site. Some primer extension probes can be "activated" directly by DNA polymerase without a full PCR extension cycle.

The present invention provides a screening kit that uses bisulfite treated DNA for determining whether a subject has the likelihood of having a substance use disorder or substance use syndrome comprising: (a) a nucleic acid primer, with at least one primer specific for methylation status of a CpG dinucleotide repeat motif region contained by a peripheral blood cell or its derivative, wherein the methylation status of the CpG dinucleotide is associated with nicotine use, abuse or dependence; and/or (b) a nucleic acid primer, at least one primer specific for methylation status of a CpG dinucleotide repeat motif region contained by a peripheral blood cell or its derivative, wherein the methylation status of the CpG dinucleotide is associated with alcohol use, abuse or dependence; and/or (c) a nucleic acid primer, at least one primer specific for methylation status of a CpG dinucleotide repeat motif region contained by a peripheral blood cell or its derivative, wherein the methylation status of the CpG dinucleotide is associated with cannabis use, abuse or dependence. In certain embodiments, the kit may contain a number of primers that is any integer between 1 and 10,000, such as 1, 2, 3, 4, 5, 6, 7, 8, 9, 10, . . . 9997, 9998, 9999, 10,000. As used herein, the term "nucleic acid primer" encompasses both DNA and RNA primers.

The present invention provides a diagnostic method using bisulfite treated DNA for determining whether a subject has the likelihood of having a substance use disorder or substance use syndrome comprising: (a) determining methylation status of a CpG dinucleotide repeat motif region in a peripheral blood cell or its derivative, wherein the methylation status of the CpG dinucleotide is associated with nicotine use, abuse or dependence; and/or (b) determining methylation status of a CpG dinucleotide repeat motif region in a peripheral blood cell or its derivative, wherein the methylation status of the CpG dinucleotide is associated with alcohol use, abuse or dependence; and/or (c) determining methylation status of a CpG dinucleotide repeat motif region in a peripheral blood cell or its derivative, wherein the methylation status of the CpG dinucleotide is associated with cannabis use, abuse or dependence. In certain embodiments, the method determines the methylation status of a plurality of CpG dinucleotide repeat motif regions. Such a plurality may be any integer between 1 and 10,000, such as at least 100.

The present invention provides a diagnostic method for determining whether a subject has a predisposition to, or likelihood of having, a substance use disorder, by determining a nucleic acid methylation profile from a single type of peripheral blood cell or blood cell derivative from the subject, the method comprising: (a) obtaining a profile associated with the sample, wherein the profile comprises quantitative data for methylation of a monoamine oxidase A (MAOA) locus or for methylation of a AHRR locus in the blood cell; (b) inputting the data into an analytical process that uses the data to classify the sample, wherein the classification is a "substance use disorder" classification or a "healthy" classification; and (c) classifying the sample according to the output of the process.

In certain embodiments of the present invention, the blood cell is a lymphocyte, such as a monocyte, a basophil, an eosinophil, and/or a neutrophil. In certain embodiments, the blood cell type is a mixture of peripheral white blood cells. In certain embodiments, the peripheral blood cell has been transformed into a cell line.

In certain embodiments, the analytical process comprises comparing the obtained profile with a reference profile. In certain embodiments, the reference profile comprises data obtained from one or more healthy control subjects, or comprises data obtained from one or more subjects diagnosed with a substance use disorder. In certain embodiments, the method further comprises obtaining a statistical measure of a similarity of the obtained profile to the reference profile. In certain embodiments, the blood cell or blood cell derivative is a peripheral blood cell. In certain embodiments, the profile is obtained by sequencing of methylated DNA, such as by digital sequencing.

The present invention provides a diagnostic method for determining whether a subject has a predisposition to, or likelihood of having, a substance use disorder, by determining a nucleic acid methylation profile from a single type of blood cell or blood cell derivative from the subject, the method involves: (a) obtaining a profile associated with the sample, wherein the profile determines quantitative data for methylation of a monoamine oxidase A (MAOA) locus or for methylation of a AHRR locus in the blood cell; (b) inputting the data into an analytical process that uses the data to classify the sample, wherein the classification is a "substance use disorder" classification or a "healthy" classification; and (c) classifying the sample according to the output of the process. In certain embodiments, the analytical process involves comparing the obtained profile with a reference profile. In certain embodiments, the reference profile provides data obtained from one or more healthy control subjects, or provides data obtained from one or more subjects diagnosed with a substance use disorder. In certain embodiments, the method further involves obtaining a statistical measure of a similarity of the obtained profile to the reference profile. In certain embodiments, the blood cell or blood cell derivative is a peripheral blood cell. In certain embodiments, the blood cell is a lymphocyte. In certain embodiments, the lymphocyte type is a B-lymphocyte. In certain embodiments, the B-lymphocytes have been immortalized. In certain embodiments, the blood cell type is a monocyte. In certain embodiments, the blood cells type is a basophil. In certain embodiment, the substance use disorder is nicotine dependence, alcohol dependence, or cannabis dependence.

In certain embodiments, a solid substrate may contain a number of probes that is any integer between 1 and 10,000 probes, such as 1, 2, 3, 4, 5, 6, 7, 8, 9, 10, . . . 9997, 9998, 9999, 10,000. In one kit, all of the probes may be physically located on a single solid substrate or on multiple substrates.

In certain embodiments, the current invention can also take the form of a PCR (polymerize chain reaction) assay. In some cases, this will take the form of real time PCR assays (RT-PCR) assays. In certain embodiments of these PCR assays, a kit may contain two primers that specifically amplify a region of a MAOA locus or a AHRR locus and gene specific probe that selectively recognizes the amplified region. Together, the primers and the gene specific probes are referred to as a primer-probe set. By measuring the amount of gene specific probe that has hybridized to an amplified segment at a given point of the PCR reaction or throughout the PCR reaction, one who is skilled in the art can infer the amount of nucleic acid originally present at the start of the reaction. In some cases, the amount of probe hybridized is measured through fluorescence spectrophotometry. The number of primer-probe sets can be any integer between 1 and 10,000 probes, such as 1, 2, 3, 4, 5, 6, 7, 8, 9, 10, . . . 9997, 9998, 9999, 10,000. In one kit, all of the probes may be physically located in a single reaction well or in multiple reaction wells. The probes may be in dry or in liquid form. They may be used in a single reaction or in a series of reactions. In certain embodiments, the probe is an oligonucleotide probe. In certain embodiments, the probe is a nucleic acid derivative probe.

The term "substrate" refers to any solid support to which the probes may be attached. The substrate material may be modified, covalently or otherwise, with coatings or functional groups to facilitate binding of probes. Suitable substrate materials include polymers, glasses, semiconductors, papers, metals, gels and hydrogels among others. Substrates may have any physical shape or size, e.g., plates, strips, or microparticles.

The term "spot" refers to a distinct location on a substrate to which probes of known sequence or sequences are attached. A spot may be an area on a planar substrate, or it may be, for example, a microparticle distinguishable from other microparticles.

The term "bound" means affixed to the solid substrate. A spot is "bound" to the solid substrate when it is affixed in a particular location on the substrate for purposes of the screening assay.

In certain embodiments of the kit of the present invention, the substrate is a polymer, glass, semiconductor, paper, metal, gel or hydrogel. In certain embodiments of the present invention, the kit further includes a solid substrate and at least one control probe, wherein the at least one control probe is bound onto the substrate in a distinct spot.

In certain embodiments of the present invention, the solid substrate is a microarray. An "array" or "microarray" is used synonymously herein to refer to a plurality of probes attached to one or more distinguishable spots on a substrate. A microarray may include a single substrate or a plurality of substrates, for example a plurality of beads or microspheres. A "copy" of a microarray contains the same types and arrangements of probes.

The present invention also provides a composition for determining whether a subject has a predisposition to, or likelihood of having, a substance use disorder by determining a nucleic acid methylation profile from a single type of blood cell or blood cell derivative from the subject, the method including obtaining a profile associated with the sample, wherein the profile includes quantitative data for MAOA; (b) inputting the data into an analytical process that uses the data to classify the sample, wherein the classification is a "substance use disorder" classification or a "healthy" classification; and (c) classifying the sample according to the output of the process. In certain embodiments, a solid substrate may contain a number of probes that is any integer between 1 and 10,000 probes, such as 1, 2, 3, 4, 5, 6, 7, 8, 9, 10, . . . 9997, 9998, 9999, 10,000.

As used herein, the term "healthy" means that a subject does not manifest a particular condition, and is no more likely that at random to be susceptible to a particular condition.

The present invention also provides a composition for determining whether a subject has a predisposition to, or likelihood of having nicotine dependence, alcohol dependence or cannabis dependence including (a) a solid substrate; (b) at least one probe specific for a methylated MAOA gene or AHRR gene associated with nicotine dependence, alcohol dependence or cannabis dependence wherein each probe is bound onto the substrate in a distinct spot. In certain embodiments, a solid substrate may contain a number of probes that is any integer between 1 and 10,000 probes, such as 1, 2, 3, 4, 5, 6, 7, 8, 9, 10, . . . 9997, 9998, 9999, 10,000.

In addition to the specific biomarker sequences identified in this application by name, accession number, or sequence, the invention also contemplates use of biomarker variants that are at least 90% or at least 95% or at least 97% identical to the exemplified sequences and that are now known or later discover and that have utility for the methods of the invention. These variants may represent polymorphisms, splice variants, mutations, and the like. Various techniques and reagents find use in the diagnostic methods of the present invention. In one embodiment of the invention, blood samples, or samples derived from blood, e.g. plasma, circulating, etc. are assayed for the presence of polypeptides. Typically a blood sample is drawn, and a derivative product, such as plasma or serum, is tested. Such polypeptides may be detected through specific binding members. The use of antibodies for this purpose is of particular interest. Various formats find use for such assays, including antibody arrays; ELISA and RIA formats; binding of labeled antibodies in suspension/solution and detection by flow cytometry, mass spectroscopy, and the like. Detection may utilize one or a panel of antibodies, preferably a panel of antibodies in an array format. Expression signatures typically utilize a detection method coupled with analysis of the results to determine if there is a statistically significant match with a disease signature.

The present invention also provides a composition for determining whether a subject has a predisposition to, or likelihood of having nicotine dependence, alcohol dependence or cannabis dependence including a PCR or RT-PCR assay kit containing at least one primer-probe set specific for a methylated MAOA nucleic acid or a methylated AHRR nucleic acid.

The present invention also provides a diagnostic method for determining whether a subject has a predisposition to, or likelihood of having, a substance use disorder by determining a nucleic acid methylation profile from a single type of blood cell or a blood cell derivative from the subject, the method involves (a) obtaining a profile associated with the sample, wherein the profile comprises quantitative data for at least one methylated MAOA nucleic acid or for at least one methylated AHRR nucleic acid; (b) inputting the data into an analytical process that uses the data to classify the sample, wherein the classification is a "substance use disorder" classification or a "healthy" classification; and (c) classifying the sample according to the output of the process. In certain embodiments, the analytical process comprises comparing the obtained profile with a pre-determined reference profile. In certain embodiments the reference profile comprises data obtained from one or more healthy control subjects, or comprises data obtained from one or more subjects diagnosed with a substance use disorder. In certain embodiments, the method further involves obtaining a statistical measure of a similarity of the obtained profile to the reference profile.

In certain embodiments the blood cell is a lymphocyte. In certain embodiments the lymphocyte type is a B-lymphocyte. In certain embodiments, the B-lymphocytes have been immortalized. In certain embodiments, the blood cell type is a monocyte. In certain embodiments, the blood cell type is a basophil.

The present invention provides a diagnostic method for determining whether a subject has a predisposition to, or likelihood of having, a substance use disorder. As used herein the term "predisposition" is defined as a tendency or susceptibility to manifest a condition. A subject is more likely than a control subject to manifest the condition. The term "substance use disorder" includes both abuse and dependence on a substance. The method involves determining a nucleic acid methylation profile from cells in a biological sample from the subject, wherein a given profile indicates that the subject has a predisposition to, or likelihood of having, a substance use disorder. The substance use disorder to be diagnosed may include nicotine dependence and/or alcohol dependence.

The present invention also provides a method for diagnosing a predisposition to, or likelihood of having, a substance use disorder, where the method involves (a) determining a nucleic acid methylation profile of MAOA or AHRR from a single type of cell from a biological sample from the subject; and (b) comparing the nucleic acid methylation profile with a nucleic acid methylation profile characteristic of the condition to determine if the patient has the a predisposition to, or likelihood of having, a substance use disorder.

The present invention further provides a method for evaluating and treating a patient experiencing a substance use disorder, where the method involves (a) obtaining a baseline laboratory profile comprising collecting blood from the patient to determine the patient's baseline nucleic acid methylation of MAOA or AHRR profile level from a single type of cell; (b) treating the patient for the substance use disorder; (c) obtaining a post-treatment laboratory profile comprising collecting blood from the patient to determine the patient's post-treatment nucleic acid methylation profile level from the same type of cell tested previously; and (d) comparing the baseline and post-treatment laboratory profile to evaluate the effectiveness of the treatment.

BRIEF DESCRIPTION OF THE FIGURES

FIG. 1. The sequence and structure of the MAOA promoter region (SEQ ID NO:9). The first CpG island begins at by 43398975 and contains 18 CpG residues. A second CpG island begins at by 43399493 and contains 70 CpG residues. The position of each of the CpG residues is noted in the figure. The first exon of MAOA is denoted by small letters and is wholly contained within the second island. The positions of the primers used to amplify the MAOA VNTR are denoted by boxed letters. The transcription start site (TSS) is at bp43400353 between CpG residues 64 and 65.

FIG. 8. The sequence of the AX2R promoter associated CpG island according to the UCSC Genome Browser, Build 18. The area corresponding to the probes listed in Table 11 are highlighted and boxed. The CpG residues in the island are numbered 1 through 37 and correspond to the numbers given in Table 12.

DETAILED DESCRIPTION

DNA Methylation

Figure 2:
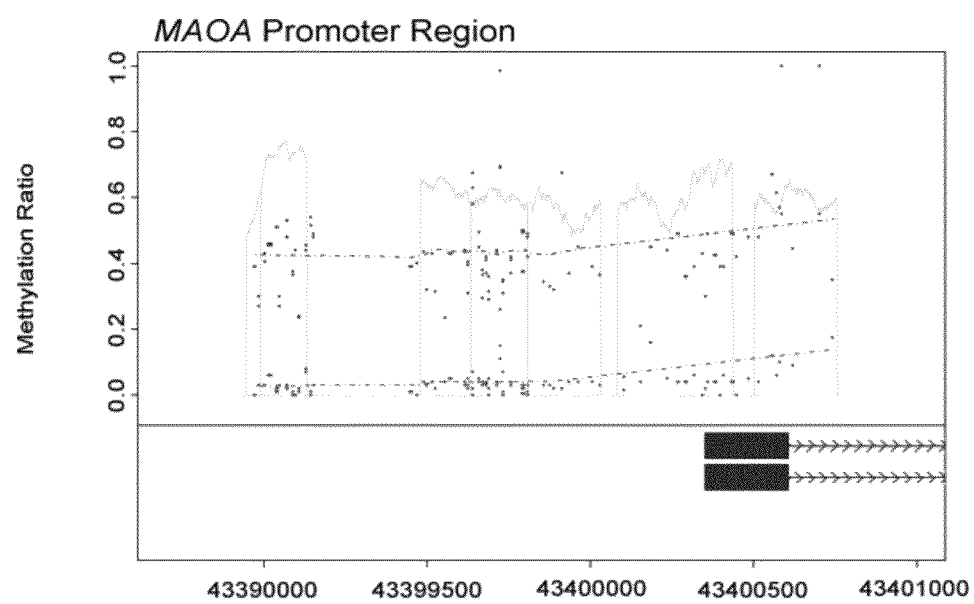
FIG. 2. The average methylation ratios (methyl CpG/total CpG) at each CpG residue for each sex. The by position on the X chromosome is given on the X axis and corresponds to the position of each of the residues in FIG. 1. The average values for female subjects are depicted by blue squares, while the average values for males are depicted by red circles. The position of MAOA exon 1 is denoted by the box with the direction of transcription being indicated by the line with arrows.

DNA does not exist as naked molecules in the cell. For example, DNA is associated with proteins called histones to form a complex substance known as chromatin. Chemical modifications of the DNA or the histones alter the structure of the chromatin without changing the nucleotide sequence of the DNA. Such modifications are described as "epigenetic" modifications of the DNA. Changes to the structure of the chromatin can have a profound influence on gene expression. If the chromatin is condensed, factors involved in gene expression may not have access to the DNA, and the genes will be switched off. Conversely, if the chromatin is "open," the genes can be switched on. Some important forms of epigenetic modification are DNA methylation and histone deacetylation. DNA methylation is a chemical modification of the DNA molecule itself and is carried out by an enzyme called DNA methyltransferase. Methylation can directly switch off gene expression by preventing transcription factors binding to promoters. A more general effect is the attraction of methyl-binding domain (MBD) proteins. These are associated with further enzymes called histone deacetylases (HDACs), which function to chemically modify histones and change chromatin structure. Chromatin-containing acetylated histones are open and accessible to transcription factors, and the genes are potentially active. Histone deacetylation causes the condensation of chromatin, making it inaccessible to transcription factors and causing the silencing of genes.

CpG islands are short stretches of DNA in which the frequency of the CpG sequence is higher than other regions. The "p" in the term CpG indicates that cysteine ("C") and guanine ("G") are connected by a phosphodiester bond. CpG islands are often located around promoters of housekeeping genes and many regulated genes. At these locations, the CG sequence is not methylated. By contrast, the CG sequences in inactive genes are usually methylated to suppress their expression.

About 56% of human genes and 47% of mouse genes are associated with CpG islands. Often, CpG islands overlap the promoter and extend about 1000 base pairs downstream into the transcription unit. Identification of potential CpG islands during sequence analysis helps to define the extreme 5' ends of genes, something that is notoriously difficult with cDNA-based approaches.

The methylation of a CpG island can be determined by the art worker using any method suitable to determine such methylation. For example, the art worker can use a bisulfite reaction-based method for determining such methylation.

The present invention provides methods to determine the nucleic acid methylation of MAOA or AHRR of a patient in order to predict the clinical course and eventual outcome of patients suspected of being predisposed or of having a substance use disorder. Previously, the only way to determine possible diagnoses was through subjective psychiatric evaluations. The present methods provide an objective component to diagnosis process.

Nicotine dependence is the physical vulnerability of a person's body to the chemical nicotine, which is potently addicting when delivered by various tobacco products. Smoke from cigarettes, cigars and pipes contains thousands of chemicals, including nicotine. Nicotine is also found in chewing tobacco. Alcohol dependence is the physical vulnerability of a person's body to the chemical ethyl alcohol.

In particular, in certain embodiments of the invention, the methods may be practiced as follows. A sample, such as a blood sample, is taken from a patient. In certain embodiments, a single cell type, e.g., lymphocytes, basophils, or monocytes isolated from the blood, may be isolated for further testing. The DNA is harvested from the sample and examined to determine if the MAOA region and/or the AHRR region is methylated. For example, the DNA of interest can be treated with bisulfite to deaminate unmethylated cytosine residues to uracil. Since uracil bas pairs with adenosine, thymidines are incorporated into subsequent DNA strands in the place of unmethylated cytosine residues during subsequence PCR amplifications. Next, the target sequence is amplified by PCR, and probed with a MAOA- or AHRR-specific probe. Only DNA from the patient that was methylated will bind to the probe. A specific profile associates with a specific condition. For example, certain methylated CpG islands in MAOA are found with women having nicotine dependence (or are predisposed to having nicotine dependence), and certain methylated CpG islands in MAOA are found with women having alcohol dependence (or are predisposed to having alcohol dependence). Namely, methylated CpG islands 18, 42, 48, 52, 64-69 and 77 (in MAOA) are associated with nicotine dependence, and methylated CpG islands 27, 38, 41 and 48 (in MAOA) are associated with alcohol dependence.

Methods of determining the patient nucleic acid profile are well known to the art worker and include any of the well-known detection methods. Various PCR methods are described, for example, in *PCR Primer: A Laboratory Manual*, Dieffenbach 7 Dveksler, Eds., Cold Spring Harbor Laboratory Press, 1995. Other analysis methods include, but are not limited to, nucleic acid quantification, restriction enzyme digestion, DNA sequencing, hybridization technologies, such as Southern Blotting, etc., amplification methods such as Ligase Chain Reaction (LCR), Nucleic Acid Sequence Based Amplification (NASBA), Self-sustained Sequence Replication (SSR or 3SR), Strand Displacement Amplification (SDA), and Transcription Mediated Amplification (TMA), Quantitative PCR (qPCR), or other DNA analyses, as well as RT-PCR, in vitro translation, Northern blotting, and other RNA analyses. In another embodiment, hybridization on a microarray is used.

As used herein, the term "nucleic acid probe" or a "probe specific for" a nucleic acid means a nucleic acid sequence that has at least about 80%, e.g., at least about 90%, e.g., at least about 95% contiguous sequence identity or homology to the nucleic acid sequence encoding the targeted sequence of interest. A probe (or oligonucleotide or primer) of the invention has at least about 7-50, e.g., at least about 10-40, e.g., at least about 15-35, nucleotides. The oligonucleotide probes or primers of the invention may comprise at least about seven nucleotides at the 3' of the oligonucleotide that have at least about 80%, e.g., at least about 85%, e.g., at least about 90% contiguous identity to the targeted sequence of interest.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as $^{32}P$, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art.

"Stringent conditions" are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS. Other examples of stringent conditions are well known in the art.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. The terms "nucleic acid," "nucleic acid molecule," or "polynucleotide" are used interchangeably and may also be used interchangeably with gene, cDNA, DNA and/or RNA encoded by a gene.

The term "nucleotide sequence" refers to a polymer of DNA or RNA which can be single-stranded or double-stranded, optionally containing synthetic, non-natural or altered nucleotide bases capable of incorporation into DNA or RNA polymers. A DNA molecule or polynucleotide is a polymer of deoxyribonucleotides (A, G, C, and T), and an RNA molecule or polynucleotide is a polymer of ribonucleotides (A, G, C and U).

A "gene," for the purposes of the present disclosure, includes a DNA region encoding a gene product, as well as all DNA regions which regulate the production of the gene product, whether or not such regulatory sequences are adjacent to coding and/or transcribed sequences. The term "gene" is used broadly to refer to any segment of nucleic acid associated with a biological function. Genes include coding sequences and/or the regulatory sequences required for their expression. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. For example, "gene" refers to a nucleic acid fragment that expresses mRNA, functional RNA, or specific protein, including regulatory sequences. "Functional RNA" refers to sense RNA, antisense RNA, ribozyme RNA, siRNA, or other RNA that may not be translated but yet has an effect on at least one cellular process. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters.

"Gene expression" refers to the conversion of the information, contained in a gene, into a gene product. It refers to the transcription and/or translation of an endogenous gene, heterologous gene or nucleic acid segment, or a transgene in cells. In addition, expression refers to the transcription and stable accumulation of sense (mRNA) or functional RNA. Expression may also refer to the production of protein. The term "altered level of expression" refers to the level of expression in transgenic cells or organisms that differs from that of normal or untransformed cells or organisms.

A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

A "coding sequence," or a sequence that "encodes" a selected polypeptide, is a nucleic acid molecule that is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral (e.g., DNA viruses and retroviruses) or prokaryotic DNA, and especially synthetic DNA sequences. A transcription termination sequence may be located 3' to the coding sequence.

Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

By "fragment" is intended a polypeptide consisting of only a part of the intact full-length polypeptide sequence and structure. The fragment can include a C-terminal deletion an N-terminal deletion, and/or an internal deletion of the native polypeptide. A fragment of a protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, or any integer between 5 amino acids and the full-length sequence.

Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

"Naturally occurring" is used to describe a composition that can be found in nature as distinct from being artificially produced. For example, a nucleotide sequence present in an organism, which can be isolated from a source in nature and which has not been intentionally modified by a person in the laboratory, is naturally occurring.

"Functional RNA" refers to sense RNA, antisense RNA, ribozyme RNA, siRNA, or other RNA that may not be translated but yet has an effect on at least one cellular process.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences.

A "5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

A "3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

A "promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

"Constitutive expression" refers to expression using a constitutive promoter. "Conditional" and "regulated expression" refer to expression controlled by a regulated promoter.

"Operably-linked" refers to the association of nucleic acid sequences on a single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. In addition, expression refers to the transcription and stable accumulation of sense (mRNA) or functional RNA. Expression may also refer to the production of protein.

The term "altered level of expression" refers to the level of expression in cells or organisms that differs from that of normal cells or organisms.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, J M B, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., J M B, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, J M B, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, the invention also provides nucleic acid molecules and peptides that are substantially identical to the nucleic acid molecules and peptides presented herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

In a further embodiment of the invention, there are provided articles of manufacture and kits containing probes, oligonucleotides or antibodies which can be used, for instance, for the diagnostic applications described above. The article of manufacture comprises a container with a label. Suitable containers include, for example, bottles, vials, and test tubes. The containers may be formed from a variety of materials such as glass or plastic. The container holds a composition which includes an agent that is effective for diagnostic applications, such as described above. The label on the container indicates that the composition is used for a specific diagnostic application. The kit of the invention will typically comprise the container described above and one or more other containers comprising materials desirable from a commercial and user standpoint, including buffers, diluents, filters and package inserts with instructions for use.

The probes of the present invention can be labeled using techniques known to those of skill in the art. For example, the labels used in the assays of invention can be primary labels (where the label comprises an element that is detected directly) or secondary labels (where the detected label binds to a primary label, e.g., as is common in immunological labeling). An introduction to labels (also called "tags"), tagging or labeling procedures, and detection of labels is found in Polak and Van Noorden (1997) Introduction to Immunocytochemistry, second edition, Springer Verlag, N.Y. and in Haugland (1996) Handbook of Fluorescent Probes and Research Chemicals, a combined handbook and catalogue Published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetramethylrhodamine isothiocyanate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P), enzymes (e.g., horse-radish peroxidase, alkaline phosphatase) spectral colorimetric labels such as colloidal gold or colored glass or plastic (e.g., polystyrene, polypropylene, latex) beads. The label may be coupled directly or indirectly to a component of the detection assay (e.g., the labeled nucleic acid) according to methods well known in the art. As indicated above, a wide variety of labels may be used, with the choice of label depending on sensitivity required, ease of conjugation with the compound, stability requirements, available instrumentation, and disposal provisions. In general, a detector that monitors a probe-substrate nucleic acid hybridization is adapted to the particular label that is used. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeled nucleic acids is digitized for subsequent computer analysis.

Preferred labels include those that use (1) chemiluminescence (using Horseradish Peroxidase and/or Alkaline Phosphatase with substrates that produce photons as breakdown products) with kits being available, e.g., from Molecular Probes, Amersham, Boehringer-Mannheim, and Life Technologies/Gibco BRL; (2) color production (using both Horseradish Peroxidase and/or Alkaline Phosphatase with substrates that produce a colored precipitate) (kits available from Life Technologies/Gibco BRL, and Boehringer-Mannheim); (3) hemifluorescence using, e.g., Alkaline Phosphatase and the substrate AttoPhos (Amersham) or other substrates that produce fluorescent products, (4) Fluorescence (e.g., using Cy-5 (Amersham), fluorescein, and other fluorescent labels); (5) radioactivity using kinase enzymes or other end-labeling approaches, nick translation, random priming, or PCR to incorporate radioactive molecules into the labeled nucleic acid. Other methods for labeling and detection will be readily apparent to one skilled in the art.

Fluorescent labels are highly preferred labels, having the advantage of requiring fewer precautions in handling, and being amendable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Fluorescent moieties, which are incorporated into the labels of the invention, are generally are known, including Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent labels are commercially available from the SIGMA Chemical Company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka ChemicaBiochemika Analytika (Fluka Chemie A G, Buchs, Switzerland), and Applied Biosystems™ (Foster City, Calif.), as well as many other commercial sources known to one of skill.

Means of detecting and quantifying labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems that are widely available.

The present invention is further detailed in the following Examples, which are offered by way of illustration and are not intended to limit the invention in any manner. Standard techniques well known in the art or the techniques specifically described below are utilized. All patent and literature references cited in the present specification are hereby incorporated by reference in their entirety.

EXAMPLE 1

MAOA Methylation is Associated with Nicotine and Alcohol Dependence

Over the past several years, it has become increasingly evident that gene-environment interactions (G×E) and residual gene-environment correlations (rGE) have a prominent role in the etiology of most common behavioral illnesses. However, the exact processes underlying these interactions and the extent of their relative contributions are unclear. At the molecular level, epigenetic phenomena such as DNA methylation and histone modification are thought to contribute to these processes. Unfortunately, empirical data to support this hypothesis at behaviorally relevant loci have been scarce.

Two candidate loci at which epigenetic phenomena may participate in GxE, rGE or E effects are the *Serotonin Transporter* (SLC6A4) and *Monoamine Oxidase* A (MAOA). The protein products of both of these two loci play prominent roles in regulating serotonergic and monoaminergic transmission, respectively. These moderating roles have come under increasing scrutiny due to recent studies which have demonstrated prominent GxE effects for depression at SLC6A4 (Caspi et al., *Science.* 301(5631), 386-9 (2003)) and for aggression at MAOA (Kim-Cohen et al., *Mol. Psychiatry.* 11(10), 903-913 (2006); Caspi et al., *Science.* 297(5582), 851-4 (2002)). Hence, there is a great deal of curiosity as to the mechanisms through which E or GxE effects could influence biological processes at these loci.

One mechanism through which GxE or E effects could become manifest at the molecular level is through altering relevant gene expression through methylation of gene promoters in response to environmental stressors. In the initial study of the relationship between promoter methylation and behavioral phenomena, the inventors conducted quantitative methylation analyses of the SLC6A4 associated promoter CpG island and demonstrated that methylation of this promoter is both sex dependent and associated with increased vulnerability to major depression. However, whether there is a similar promoter associated CpG island at MAOA, and if it exists, whether its methylation has behavioral consequences was unclear.

Two types of disorders that could potentially be influenced by methylation induced changes in MAOA activity are Antisocial Personality Disorder (ASPD) and substance use disorders (SUD). Already, genetic variation in a variable nucleotide repeat (VNTR) located immediately upstream of the MAOA minimal central promoter has been associated with different vulnerability to ASPD and two forms of SUD: alcohol dependence (AD) and nicotine dependence (ND).

In this report, using a set of similar techniques to prior methylation and gene expression analyses of SCL6A4 (Philibert et al., *American Journal of Medical Genetics Part B: Neuropsychiatric Genetics*, (2007)) and the resources of the Iowa Adoption Studies (IAS), a large longitudinal adoption study focusing on the role of GxE effects in SUD, the inventors examined the relationship of MAOA genotype and methylation to SUD and ASPD.

Methods

The procedures used in the IAS have been described in detail elsewhere (Yates et al., *Drug and Alcohol Dependence.* 41(1), 9 (1996)). Briefly, the IAS is a case and control adoption study of G, E and GxE effects in SUD and ASPD. This study, founded by Remi Cadoret, contrasts the outcomes of 475 adoptees from the State of Iowa who are at high biological risk for SUD or ASPD (i.e., one of their biological parents was severely affected) with those of 475 adoptees who were not at biological risk for either SUD or ASPD. After birth, each of these adoptees was randomly placed in an adoptive home. Since their inception in the study, the adoptees and their adoptive environments have been serially assessed. The subjects included in this pilot study were the first 95 males and 96 females to participate in this wave of the study. The overall study design and all procedures described in this communication were approved by the University of Iowa Institutional Review Board.

Briefly, the behavioral and biological material used in these studies was obtained from subjects who participated in the last two waves of the Iowa Adoptions Studies (IAS). In both of these waves, each subject was interviewed with a version of the Semi Structured Assessment for the Genetics of Alcoholism, Version 2 (SSAGA-II) (Bucholz et al., *J Stud Alcohol.* 55(2), 149-58 (1994)). In addition, in the latest round of the study, phlebotomy was performed on each of the participants. Symptom counts and categorical diagnoses for each of the disorders (ASPD, AD, ND) were derived from SSAGA-II data using the individual dependence or personality disorder criteria from DSM-IV (Association, AP, *Diagnostic and Statistical Manual of Mental Disorder, Fourth Edition.* 1994, Washington D.C.: American Psychiatric Association), with the highest total symptom count from these two interviews being defined as the lifetime symptom count.

RNA and DNA used in the studies were derived from lymphoblast cell lines using biomaterial contributed by the participants. These lymphoblast cell lines were prepared using standard EBV transfection techniques from the specimens contributed by the study participants (Klaus, G G B, *Lymphocytes: A practical Approach.* 1987, Oxford: IRL Press. 149-162). Total RNA was prepared from lymphoblast using a Midi RNA purification kit from Invitrogen™ (Carlsbad, Calif.) according to the manufacturer's instructions. DNA was prepared from lymphoblast cell pellets using cold protein precipitation (Lahiri et al., *Nucleic Acids Research.* 19(19), 5444 (1991)).

PCR amplification of the MAOA variable nucleotide repeat (VNTR) polymorphism was conducted using the method of Sabol and colleagues (Sabol et al., *Hum Genet.* 103(3), 273-9 (1998)). The resulting PCR products were electrophoresed on a 6% non-denaturing polyacrylamide gel and imaged using silver staining (Merril et al., *Analytical Biochemistry.* 156(1), 96-110 (1986)). The resulting alleles were compared to internal standards and the genotypes were called by two individuals blind to affected status.

RTPCR was conducted as previously described (Philibert et al., *American Journal of Medical Genetics Part B: Neuropsychiatric Genetics*, (2007); Bradley et al., *Am J Med Genet B Neuropsychiatr Genet.* 136(1), 58-61 (2005)). Briefly, RNA was reverse transcribed using an Applied Biosystems™ cDNA archiving kit (Foster City, Calif.). Then, 12.5 ng aliquots of cDNA were robotically dispensed and RTPCR performed using reagents from Applied Biosystems™ including primer-probe sets for MAOA (Hs 00165140) and the endogenous control loci GAPDH (from the GAPDH Control kit) and LDHA (Hs 00855332).

The existence, location, size and sequence of the MAOA CpG islands were determined using the default browser settings of the University of California Genome Browser (UCSC) website (world-wide-web at genome.ucsc.edu). The sequences for these islands are freely available from the website or from the authors on request.

Quantitative methylation analyses for each of the samples at these CpG residues were conducted by Sequenom® Inc. (San Diego, Calif.) as previously described (Philibert et al., [erratum appears in Mol Psychiatry 1999 March; 4(2):197.]. *Molecular Psychiatry.* 3(4), 303-9 (1998)). First, aliquots of purified DNA were treated using bisulfite modification (Frommer et al., *Proceedings of the National Academy of Sciences.* 89(5), 1827-1831 (1992)). Treatment of DNA with bisulfite deaminates unmethylated cytosine residues to uracil. Since uracil base pairs with adenosine, thymidines are incorporated into subsequent DNA strands in the place of unmethylated cytosine residues during subsequent PCR amplifications. Next, contigs covering the CpG islands (see FIG. 1) were PCR amplified. Because of the size of the region, the CpG enriched regions were PCR amplified in four separate reactions. The primers for each of those PCR amplifications are as follows: Amplicon A (from BP 43398925 to 43399181):F-TTA AAG AAT GAA AGT ATT AGG TTG AGA GTT (SEQ ID NO:1) and R-ATA CCC ACT CTT AAA AAC CAA CCC C (SEQ ID NO:2); Amplicon B (from BP 43399430 to 43399858): F-GGG TGT TGA ATT TTG AGG AGA AG (SEQ ID NO:3) and R-AAA ACA CAA CTA CCC AAA TCC C (SEQ ID NO:4); Amplicon C (from BP 43400453 to 43400805): F-GGG GAG TTG ATA GAA GGG TTT TTT TTA T (SEQ ID NO:5) and R-TAT ATC TAC CTC CCC CAA TCA CAC C (SEQ ID NO:6) and Amplicon D (from BP 43400486 to 43400035): F-AAA GGG TGG GAA GGA TTT TTT TAT TAA TT (SEQ ID NO:7) and R-CAT CCT CAA TAT CCA ACT TCC CCT A (SEQ ID NO:8) using standard touchdown PCR conditions (Philibert et al., *Am J Med Genet B Neuropsychiatr Genet.* 144(1), 101-5 (2007)). Methylation ratios for each of the CpG residues (methyl CpG/total CpG) were then determined using a MassARRAY™ mass spectrometer using proprietary peak picking and spectra interpretation tools (Ehrich et al., *Proc Natl Acad Sci USA.* 102(44), 15785-90 (2005); Ehrich et al., *Nucleic Acids Res.* 35(5), e29 (2007)).

The data were analyzed using the JMP (version 7; SAS Institute, Cary, S.C.) using Pearson's correlation coefficients, regression [analysis of variance (ANOVA) and ordinal logistic regression (OLR)] or Chi-square testing as indicated in the text (Fleiss, J L, *Statistical Methods for Rates and Proportions.* 2nd ed. 1981, New York, N.Y.: John Wiley & Sons Inc.). All tests were two-tailed and all analyses were conducted by gender.

Results

The characteristics of the IAS subjects who contributed the biomaterials to this study are given in Table 1. In total, 96 female and 95 male subjects provided biomaterials for the study. The male subjects were significantly older than the female subjects (t-test, p<0.002) and had a significantly higher symptom count for ASPD (Chi-Square, p<0.001).

TABLE 1

Demographic and Clinical Characteristics of the IAS Subjects

|  | Male | Female |
| --- | --- | --- |
| N | 95 | 96 |
| Age (years ± SD) | 42.4 ± 8.5 | 38.8 ± 6.8 |
| Ethnicity | | |
| White | 87 | 91 |
| African American | 5 | 2 |
| White of Hispanic Origin | 2 | 1 |
| Other | 1 | 2 |

| DSM IV Symptom Counts | | | | | | |
| --- | --- | --- | --- | --- | --- | --- |
| | ASPD | | AD | | ND | |
| # Symptoms | M | F | M | F | M | F |
| 0 | 18 | 41 | 35 | 49 | 47 | 50 |
| 1 | 26 | 30 | 25 | 25 | 4 | 6 |

TABLE 1-continued

Demographic and Clinical Characteristics of the IAS Subjects

| 2 | 21 | 9 | 16 | 13 | 10 | 7 |
| --- | --- | --- | --- | --- | --- | --- |
| 3 | 7 | 7 | 11 | 3 | 15 | 8 |
| 4 | 10 | 5 | 2 | 2 | 6 | 14 |
| 5 | 9 | 3 | 3 | 3 | 8 | 8 |
| 6 | 4 | 3 | 2 | 0 | 3 | 3 |
| 7 | 0 | 0 | 1 | 0 | 2 | 0 |

The MAOA VNTR genotypes for the subjects are given in Table 2. The testing for Hardy Weinberg equilibrium in the female subjects was unremarkable.

TABLE 2

MAOA VNTR Genotype.

| Genotype | Female Subjects | Male Subjects* |
| --- | --- | --- |
| 2, 2 | 0 | 1 |
| 2, 4 | 1 | — |
| 3, 3 | 18 | 34 |
| 3, 4 | 41 | — |
| 3, 5 | 1 | — |
| 3.5, 3.5 | 0 | 1 |
| 3.5, 4 | 1 | — |
| 4, 4 | 31 | 59 |
| 4, 5 | 3 | — |

*Male subjects are hemizygous with respect to this X-chromosome locus.

Sequence analysis of MAOA demonstrated the presence of two CpG islands in the gene (FIG. 1). The first island, stretching from by 43398975 to by 43399158, contains 18 CpG residues and is approximately 1200 bp upstream of the transcription start site for MAOA. The second CpG island begins at by 43399493 and contains 70 CpG residues. Exon 1 of MAOA is wholly contained within the CpG island with the transcription start site (TSS) for the gene occurring between CpG residues 64 and 65. The MAOA VNTR is found between the two CpG islands.

The average methylation ratio at each of these residues is shown in FIG. 2. As the figure demonstrates, females have consistently higher methylation ratios at each CpG residue than males (who are hemizygous for this gene). Please note that secondary to methodological limitations with respect to the ability of the mass spectrograph to resolve individual residues, the values for CpG residues, 1-2, 5-7, 11-12, 19-20, 30-31, 43-44, 55-57, 67-68, 72-73, and 79-80 are shown as aggregates.

The interrelationships of MAOA methylation between individual residues for each gender were studied. The correlation between methylation was higher between residues in the smaller 5' CpG island than it was in between residues in the larger CpG island that encompasses Exon 1. Of particular potential interest, methylation of the two residues immediately flanking the TSS, CpG 64 and 65, is poorly correlated with methylation throughout the rest of the island. However, methylation at the residues CpG 58-63 and CpG 66-70 is highly inter-correlated.

Figure 3:
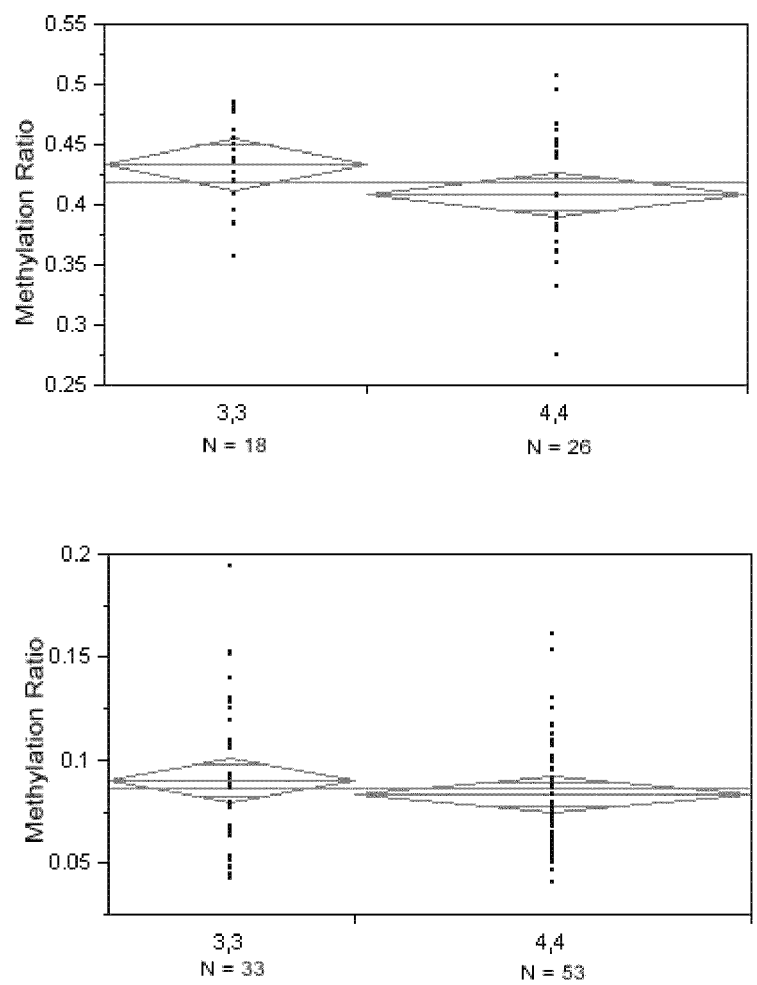
FIG. 3. The relationship of MAOA VNTR genotype to methylation in females (above) and males (below). There was a trend for association for female 3,3 homozygotes to have higher average methylation (methyl CpG/total CpG) than female 4,4 homozygotes (43.3%±3.8 vs 40.9%±5.2; p<0.10). There was no significant difference between males hemizygous for the 3 repeat allele as compared to those with the 4 allele although the arithmetic difference was in the same direction (9.0±3.7 vs 8.3±2.6; p<0.32).

In order to test the hypothesis that MAOA genotype influences the amount of methylation, the relationship of average methylation to genotype at the VNTR (FIG. 3) for each gender was analyzed. There was a trend for female 3,3 homozygotes to have a higher average methylation than female 4,4 homozygotes (43.3%±3.8 vs 40.9%±5.2; p<0.10). There was no significant difference between males hemizygous for the 3 repeat allele as compared to those with the 4 allele although the arithmetic difference was in the same direction (9.0±3.7 vs 8.3±2.6; p<0.32).

The relationship between symptom counts for ASPD, AD and ND with average methylation for each gender was then analyzed using ordinal regression analysis. There was no relationship between ASPD and overall methylation for neither men (OLR, p<0.37) or women (OLR, p>0.70). There also were not any significant relationships between average methylation and AD (OLR, p<0.23) and ND (OLR, p<0.68) in male subjects. However, there were strong relationships between average overall methylation and symptom counts for AD (OLR, p<0.008) and ND (OLR, p<0.002) in female subjects.

In order to identify the residues driving the strong correlations between overall methylation and symptom counts for AD and ND in women, the relationship between methylation at individual CpG residues and symptom counts was analyzed. With respect to former, methylation at CpG residues 27, 38, 41, and 48 were nominally significantly associated (p<0.05 before correction for multiple comparisons) with AD symptom count in female subjects. With respect to the latter, methylation at CpG residues 18, 42, 48, 52, 64, 65, 67-68, 69, and 77 were nominally associated (p<0.05 before correction for multiple comparisons) with ND symptom counts.

Finally, in an attempt to discern whether gene expression was correlated with MAOA genotype or methylation, the inventors attempted to measure MAOA gene expression using our previously described techniques (Philibert et al., *American Journal of Medical Genetics Part B: Neuropsychiatric Genetics*, (2007); Philibert, et al., *Am J Med Genet B Neuropsychiatr Genet.* 144(1), 101-5 (2007); Philibert et al., *Am J Med Genet B Neuropsychiatr Genet.* 144(5), 683-90 (2007)). Unfortunately, despite several attempts, we could not reliably detect MAOA gene expression.

Discussion

In summary, it was discovered that MAOA methylation is associated with ND and AD in women, but not men. In addition, a significant relationship between ASPD and CpG methylation was not found in men or women. Finally, there was a trend for MAOA genotype to be associated with methylation in women.

The results with respect to ND are perhaps the most compelling. Review of the animal model literature shows that MAOA knockout mice exhibit impaired nicotine preference but have normal responses to other novel stimuli (Agatsuma et al., *Hum. Mol. Genet.* 15(18), 2721-2731 (2006)). Furthermore, treatment of rats with the monoamine oxidase inhibitor phenelzine enhances the discriminant stimulus effect of nicotine (Wooters et al., *Behav Pharmacol.* 18(7), 601-8 (2007)) and increases nicotine self administration (Villegier et al, *Neuropharmacology.* 52(6), 1415-25 (2007); Guillem et al., *Eur J Neurosci.* 24(12), 3532-40 (2006)). Review of the literature with respect to humans reveals that the targeting of neurotransmitter systems regulated by MAOA, using agents such as reboxetine, a selective norepinephrine reuptake inhibitor, or bupropion, which targets the dopaminergic system, have been shown to be clinically effective in the treatment of ND (Miller et al., *J Pharmacol Exp Ther.* 302(2), 687-695 (2002); George, T and Weinberger, A: Monoamine Oxidase Inhibition for Tobacco Pharmacotherapy. *Mol Ther*, (2007); David et al., Tobacco Research. 9(8), 821-833 (2007)). Finally, platelet MAOA activity is reduced in smokers (Berlin et al., *Int J. Neuropsychopharmacol.* 4(1), 33-42 (2001)).

This evidence is made even more compelling by closer inspection and consideration of the MAOA methylation data with respect to ND in the female subjects. The control of transcription initiation is one of the major mechanisms through which cells regulate gene expression (Levine et al., *Nature.* 424(6945), 147-151 (2003)). Hence, the TSS is a frequent target of epigenetic modifications including methylation and histone modification (Kawaji et al., *Genome Biology.* 7(12), R118 (2006); Liang et al., *Proc Natl Acad Sci USA.* 101(19), 7357-62 (2004)). Therefore, it is expected that any significant changes in ND association MAOA methylation preferentially affects the MAOA TSS. This is indeed what is observed with a strong clustering of CpG residues that are either nominally significantly associated or with a trend for association (p<0.10) surrounding the TSS.

It is important to note that the primary outcome measure with respect to methylation in this study was overall methylation, not individual CpG residue methylation. This is because it was not known prior to the study which CpG residues might be most important.

Surprisingly, the inventors did not find any relationship between MAOA methylation and ASPD. Nor did the inventors find a significant relationship between genotype and methylation. Once again, this may simply be a function of low power. At the same time, these findings do not preclude specific GxE effects on ASPD at this locus because they did not examine the relationship of environmental factors hypothesized to elicit such effects, such as maltreatment, in this study.

In summary, it was discovered that methylation of the MAOA promoter is associated with ND and AD in females.

EXAMPLE 2

The Effect of Smoking on MAOA Promoter Methylation in DNA Prepared from Lymphoblasts and Whole Blood Monoamine Oxidase A (MAOA) plays a key role in modulating monoaminergic neurotransmission through its catabolism of dopamine, norepinephrine, epinephrine, serotonin and related neurotransmitter catabolism byproducts. The MAOA gene is located on Xp11 and consists of 15 exons that are transcribed to 4.1 kb mRNA and translated into a 527 amino acid protein (Chen Z Y et al. 1991. Structure of the human gene for monoamine oxidase type A. *Nucleic Acids Res* 19(16):4537-41). Two regulatory motifs for the gene have been previously described. The first is a 44 bp variable nucleotide repeat (VNTR) that is found approximately 1200 bp upstream of the transcription start site (TSS) (Hotamisligil G S, Breakefield X O. 1991. Human monoamine oxidase A gene determines levels of enzyme activity. *Am J Hum Genet.* 49(2):383-92). The second is a set of two promoter associated CpG islands that flank either side of the VNTR (See Example 1 above).

As discussed above, it was demonstrated that increased lifetime symptom counts for Alcohol (AD) and Nicotine Dependence (ND) were associated with decreased MAOA methylation, with the effects being most prominent in women in the region of the gene surrounding the TSS. Furthermore, evidence was provided that the three-repeat (3R) allele of the VNTR was associated with increased methylation at this locus. In the present study several further questions were raise. First, were these findings simply a type I error due to multiple tests across CpG island loci? Second, given the direct pharmacological effects of nicotine consumption, is decreased methylation associated with current smoking only, or is there an effect of history of smoking as well? Third, are some regions of the promoter more important in characterizing this process? Finally, do lymphoblasts provide better or worse resolution than alternative media, such as whole blood, for the examination of epigenetic effects in substance use research?

These are important concerns because MAOA is hypothesized to play a key role in ND and other complex behavioral illnesses. MAOA inhibitors are used in the treatment of ND as well as other frequently co-morbid syndromes, such as major depression (MD) (George T P, Weinberger A H. 2008. Monoamine oxidase inhibition for tobacco pharmacotherapy. *Clin Pharmacol Ther* 83(4):619-21). Furthermore, MAOA VNTR gene-environment (GxE) interaction specific to the 3-epeat allele (3R) may be important in the etiology of antisocial conduct (Caspi A et al. 2002. Role of genotype in the cycle of violence in maltreated children. *Science* 297(5582): 851-4; Frazzetto G et al., 2007. Early Trauma and Increased Risk for Physical Aggression during Adulthood: The Moderating Role of MAOA Genotype. *PLoS ONE* 2(5):e486). Finally, the present researchers have recently confirmed earlier findings that a similar GxE effect specific to the 4R allele may moderate vulnerability to MD (Beach S R et al., in submission. Child Maltreatment and MAOA Genotype in Depression and Antisocial Personality Disorder: Genetic Moderation of Family Environment). Therefore, the development of a detailed understanding of the molecular underpinnings of genetic and epigenetic effects at this locus is beneficial to the understanding and treatment of complex behavioral illness.

To help accomplish this goal and more finely hone our understanding of genetic and epigenetic effects at this locus, the inventors recently re-examined the original findings using the insights derived from our prior study and the resources provided by 289 additional participants in the IAS.

Methods

The study design and clinical measures in the IAS have been described in detail elsewhere (Yates W R et al. 1996. An adoption study of DSM-IIIR alcohol and drug dependence severity. Drug and Alcohol Dependence 41(1):9). The behavioral and demographic data were obtained from subjects participating in the last two waves of the IAS (1997-2003; 2004-2009). In each wave, subjects were interviewed with a version of the Semi-Structured Assessment for the Genetics of Alcoholism, version 2 (SSAGA-II) (Bucholz K K et al. 1994. A new, semi-structured psychiatric interview for use in genetic linkage studies: a report on the reliability of the SSAGA. *J Stud Alcohol* 55(2):149-58). In addition, in the last wave subjects were phlebotomized to provide biomaterial for the preparation of DNA and lymphoblast cell lines. All these procedures were approved by the University of Iowa Institutional Review Board.

The clinical and laboratory methods used in this study are very similar to those used previously. With respect to the behavioral data, symptom counts and categorical diagnoses for nicotine dependence were derived from SSAGA-II data using criteria from DSM-IV (American Psychiatric Association 1994). The highest total symptom count from these two interviews was defined as the lifetime symptom count. Smoking status was also determined using SSAGA data. Those who denied a history of daily smoking at both interviews were classified as "non-smokers." Those subjects who were daily smokers at the time of the first interview, but had totally quit at time 2 were classified as "quitters." Those who smoked daily at the time of both interviews were classified as "continuous smokers."

DNA from two different cellular sources was used in this study. The lymphoblast (LB) DNA for all 289 subjects was prepared from cell lines using blood contributed by the participants. These cell lines were derived using standard EBV transfection techniques (Klaus G G B. 1987. Lymphocytes: A practical Approach. Oxford: IRL Press. p. 149-162) and the DNA was harvested using the method of Lahiri and Schnabel (Lahiri D K, Schnabel B. 1993. DNA isolation by a rapid method from human blood samples: effects of MgCl2, EDTA, storage time, and temperature on DNA yield and quality. *Biochem Genet*. 31(7-8):321-8). For a subset of the female subjects (n=78), we also analyzed DNA that was prepared from the whole blood sample (WB DNA) drawn at the same time as the specimen used to prepare the cell lines. This DNA was also extracted using the method of Lahiri and Schnabel (Lahiri D K, Schnabel B. 1993. DNA isolation by a rapid method from human blood samples: effects of $MgCl_2$, EDTA, storage time, and temperature on DNA yield and quality. *Biochem Genet*. 31(7-8):321-8), and the methylation signatures of both types of DNA were determined at the same time.

Genotyping of the MAOA variable nucleotide repeat (VNTR) polymorphism was conducted as previously described (see Example 1 above). Quantitatative methylation determination was performed under contract by Sequenom® Inc. (San Diego, Calif.) using the same methods previously described (Philibert R A et al. 1998. Association of an X-chromosome dodecamer insertional variant allele with mental retardation. [erratum appears in *Mol Psychiatry* 1999 March; 4(2):197.]. *Molecular Psychiatry* 3(4):303-9). First, aliquots of purified DNA underwent bisulfite modification. The modified DNA samples were then used as a template for the PCR amplification of three contigs covering the MAOA promoter islands using standard touchdown conditions (Philibert R et al. 2007. Serotonin transporter mRNA levels are associated with the methylation of an upstream CpG island. *Am J Med Genet B Neuropsychiatr Genet*. 144(1):101-5). Amplicon A stretches from BP 43398925 to 43399181, covers CpG residues 1 to 18, and uses the following primers: F-TAA AGA ATG AAA GTA TTA GGT TGA GAG TT (SEQ ID NO:1) and R-ATA CCC ACT CTT AAA AAC CAA CCC C (SEQ ID NO:2). Amplicon B stretches from BP 43399430 to 43399858, covers CpG residues 19 to 45, and uses the following primers: F-GGG TGT TGA ATT TTG AGG AGA AG (SEQ ID NO:3) and R-AAA CAC AAC TAC CCA AAT CCC (SEQ ID NO:4); Amplicon C stretches from BP 43400453 to 43400805, covers CpG residues 46 to 74, and uses the following primers: F-GGG GAG TTG ATA GAA GGG TTT TTT TTA T (SEQ ID NO:5) and R-TAT ATC TAC CTC CCC CAA TCA CAC C (SEQ ID NO:6). A fourth contig that covered CpG 75-88 was not used in this study because the residues in this amplicon were neither correlated with methylation in other amplicons nor with substance use in Example 1.

After amplification, the methylation ratios for each of the CpG residues (methyl CpG/total CpG) in these contigs were then determined using a MassARRAY™ system mass spectrometer (Sequenom®). These data were then analyzed with proprietary peak picking and spectra interpretation tools to generate the methyl CpG/total CpG ratios (Ehrich M et al. 2005. Quantitative high-throughput analysis of DNA methylation patterns by base-specific cleavage and mass spectrometry. *Proc Natl Acad Sci USA* 102(44):15785-90; Ehrich M, et al. 2007. A new method for accurate assessment of DNA quality after bisulfite treatment. *Nucleic Acids Res* 35(5): e29). The peak for some residues could not be de-convoluted by the spectral interpretation tools. In those cases (CpG 5-7, 8-9, 11-12, 19-20, 30-31, 61-62, 67-68, 72-73), the value for each residue is presented as an average of the aggregated values. In addition, no signal could be reliably observed for CpG residues 24, 26, and 28.

Because the methylation data had differing means and standard deviations at each loci, all methylation data were Z-transformed before comparison to genotype or clinical data. All data were analyzed using the JMP (version 7; SAS Institute, Cary, S.C.) using Pearson's correlation coefficients, regression, analysis of variance (ANOVA), T-tests, and ordinal logistic regression (OLR)] as indicated in the text (Fleiss 1981). Factor analyses were conducted using SAS Version 9.1 (SAS Institute, Cary, N.C.). For analyses of VNTR genotype data, genotypes that contained uncommon alleles (i.e. 2, 3.5, and 5 repeats) were excluded and the remaining genotype data were analyzed using an additive model. All tests were two-tailed.

Results

The basic behavioral and demographic characteristics of this cohort of 289 IAS subjects are given in Table 3. As with the prior cohort, most of the subjects are White and well into adulthood. The male subjects do not differ from the female subjects with respect to age nor ethnicity. Consistent with the study design of the IAS, the sample is enriched for behavioral illness with 100 subjects reporting 3 or more lifetime criteria for ND.

TABLE 3

Demographic and Clinical Characteristics of the IAS Subjects

|  | Male | Female |
|---|---|---|
| N | 125 | 164 |
| Age (years ± SD) | 41.1 ± 7.7 | 40.9 ± 7.7 |
| Ethnicity |  |  |
| White | 117 | 155 |
| African American | 3 | 2 |
| White of Hispanic Origin | 4 | 4 |
| Other | 1 | 3 |
| DSM IV Symptom Counts for ND | | |
| # Symptoms | Males | Females |
| 0 | 55 | 84 |
| 1 | 9 | 12 |
| 2 | 8 | 11 |
| 3 | 12 | 9 |
| 4 | 20 | 18 |
| 5 | 9 | 19 |
| 6 | 11 | 9 |
| 7 | 1 | 2 |

The genotype distribution of the subjects is given in Table 4. No relationship emerged between the MAOA VNTR genotype and lifetime symptom count for ND for males (p<0.98, OLR) or females (p<0.19, OLR).

TABLE 4

MAOA VNTR Genotype.

| Genotype | Female Subjects (n = 164) | Male Subjects (n = 125) |
|---|---|---|
| 2, 2 | 0 | 1 |
| 2, 4 | 0 | — |
| 3, 3 | 21 | 43 |
| 3, 3.5 | 1 | — |
| 3, 4 | 64 | — |
| 3, 5 | 1 | — |
| 3.5, 3.5 | 0 | 4 |
| 3.5, 4 | 2 | — |
| 4, 4 | 71 | 76 |
| 4, 5 | 2 | — |
| 5, 5 | 0 | 1 |
| Unknown | 2 | — |

*male subjects are hemizygous with respect to this X-chromosome locus.

Figure 4:
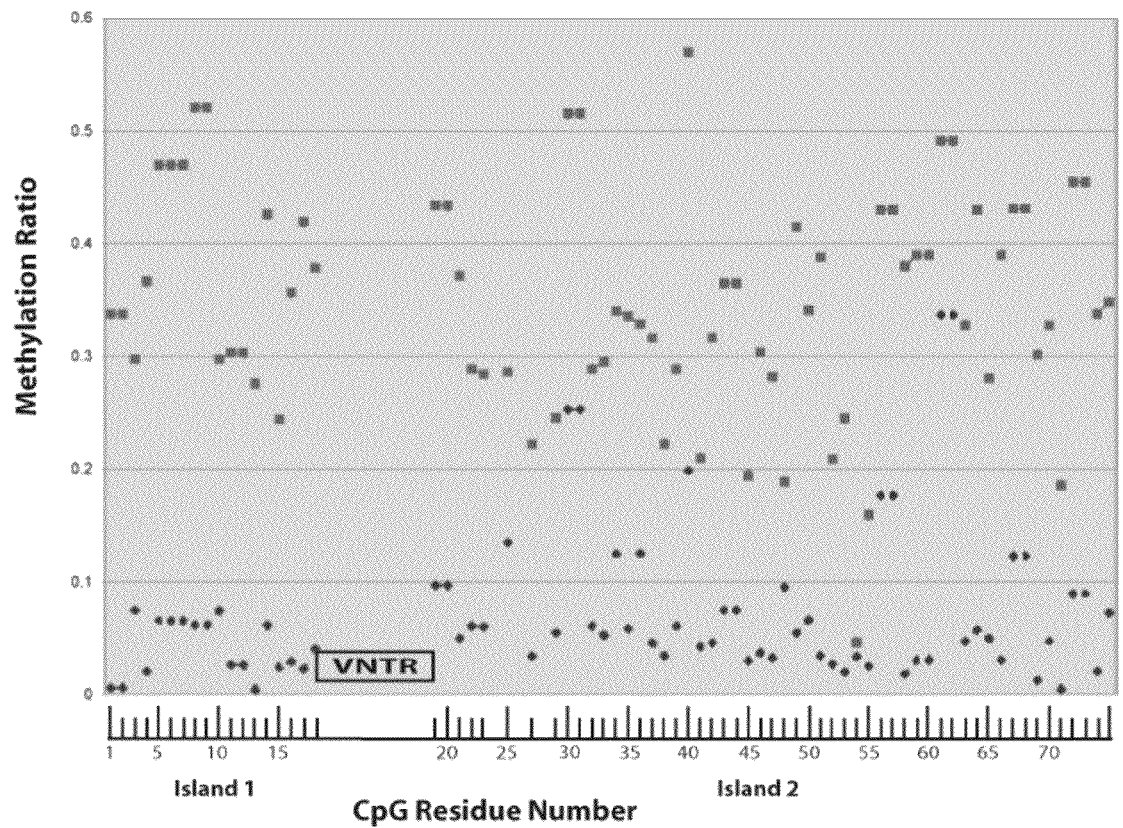
FIG. 4. The average methylation (methyl CpG/total CpG) at each CpG residue for each sex. The first island consists of 18 CpG residues while the second larger island consists of 70 residues, of which only the first 56 were analyzed in this study. Tic marks at the positions corresponding to CpG 24, 26 and 28 are missing because average methylation could not be reliably determined at those residues. The average methylation value for females at each residue is depicted by a pink square while the corresponding value for males is depicted by a blue diamond. The overall average methylation value is depicted by the value corresponding at position 75 (34.8% and 7.2% for females and males, respectively). The exact position of the transcription start site is between CpG 65 and CpG 66.

The untransformed sex averaged methyl CpG/total CpG ratio for each residue is given in FIG. 4. The first CpG island contains 18 CpG residues and begins approximately ~1200 bp before the transcription start site of MAOA. The VNTR lies between the two CpG islands. The second island consists of 70 CpG residues, the first 56 residues of which were measured in this study. The TSS is located between CpG residues 64 and 65. Overall, males have a average methylation ratio (methyl CpG/total CpG) of 7.2% and females have an average methylation ratio of 34.8%.

Not surprisingly, because MAOA is an X chromosome gene, females consistently had a higher average methylation ratio at every CpG residue. Ethnicity was not associated with average methylation. However, a trend emerged for increasing age to be associated with increasing methylation in females (p<0.07; ANOVA) but not males (p<0.30; ANOVA).

Average and Locus Specific Methylation.

Figure 5:
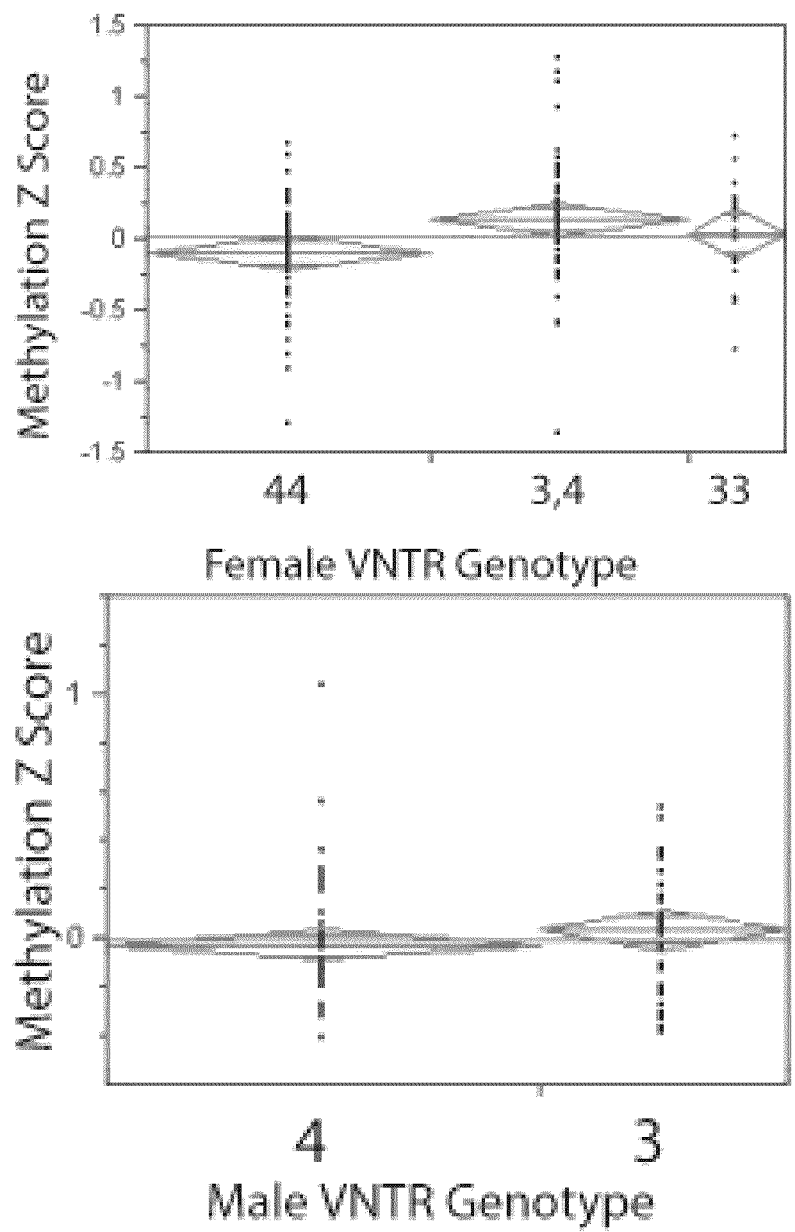
FIG. 5. The relationship of MAOA VNTR genotype to methylation in females (above) and males (below). There was no significant difference between males with the 3R (n=35; mean Z score −0.03, non-transformed average methylation (NTWAM) is 7.1%), and those with a 4R allele (n=61; mean Z score −0.03, NTWAM is 7.2%). Female 4R homozygotes (Z=−0.101, NTWAM 33.6%) had significantly lower methylation than 3,4 heterozygotes (Z=0.137, NTWA 36.2%; p<0.01). The difference between 4R and 3R homozygotes (Z=0.007, NTWAM, 34.7%) was not statistically different (p<0.39).

The relationship between the Z-transformed average methylation ratios across the 74 residues examined and VNTR genotype is shown in FIG. 5. The average Z-transformed methylation ratio was greater in DNA from heterozygous females (3R,4R) than in DNA from 4R homozygotes (p<0.04; T-test). Although the directionality of differential methylation was consistent with prior findings, hemizygous males and homozygous females for the 3R allele did not have significantly higher average amounts of methylation than did their 4R counterparts (p<0.24 and p<0.20, respectively).

Next, the inventors examined the relationship between global or TSS region specific methylation, which was defined as being the average of Z-transformed values for residues CpG 61-70, and lifetime ND symptom count for all 289 subjects. Although the pattern of relationships was similar to prior findings, the relationship between global methylation and lifetime ND symptom count was not statistically significant for males (p<0.19) or females (p<0.12). However, before correction for multiple comparisons, eight individual CpG residues (CpG 22, 25, 32, 36, 39, 64, 65 and 69), including three in the TSS region, were nominally associated (p<0.05) with ND symptom for the male subjects but no such relationships emerged in the female subjects.

Because the inventors noted that a substantial number of subjects had quit smoking, yet were still counted as affected using the lifetime symptom count criterion, the inventors next examined current smoking status for 274 subjects whose smoking status could be easily classified. First, for these analyses of current smoking status, those who denied a history of smoking one or more days per week were designated non-smokers (male n=59 and female n=83). "Daily smokers" were defined as those who smoked 7 days per week at the times of both the first and second interviews (male n=42 and female n=45). Finally, "quitters" were defined as those subjects who smoked daily at the time of the first interview, but denied smoking regular smoking (1 or more days per week) at the time of the second interview (male n=20 and female n=27). The 15 subjects excluded from these three groups were removed because either they were never truly daily smokers at both interviews (i.e., did not smoke every day; n=10), did not fully quit smoking (n=4), or started smoking after the first interview (n=1).

Figure 6:
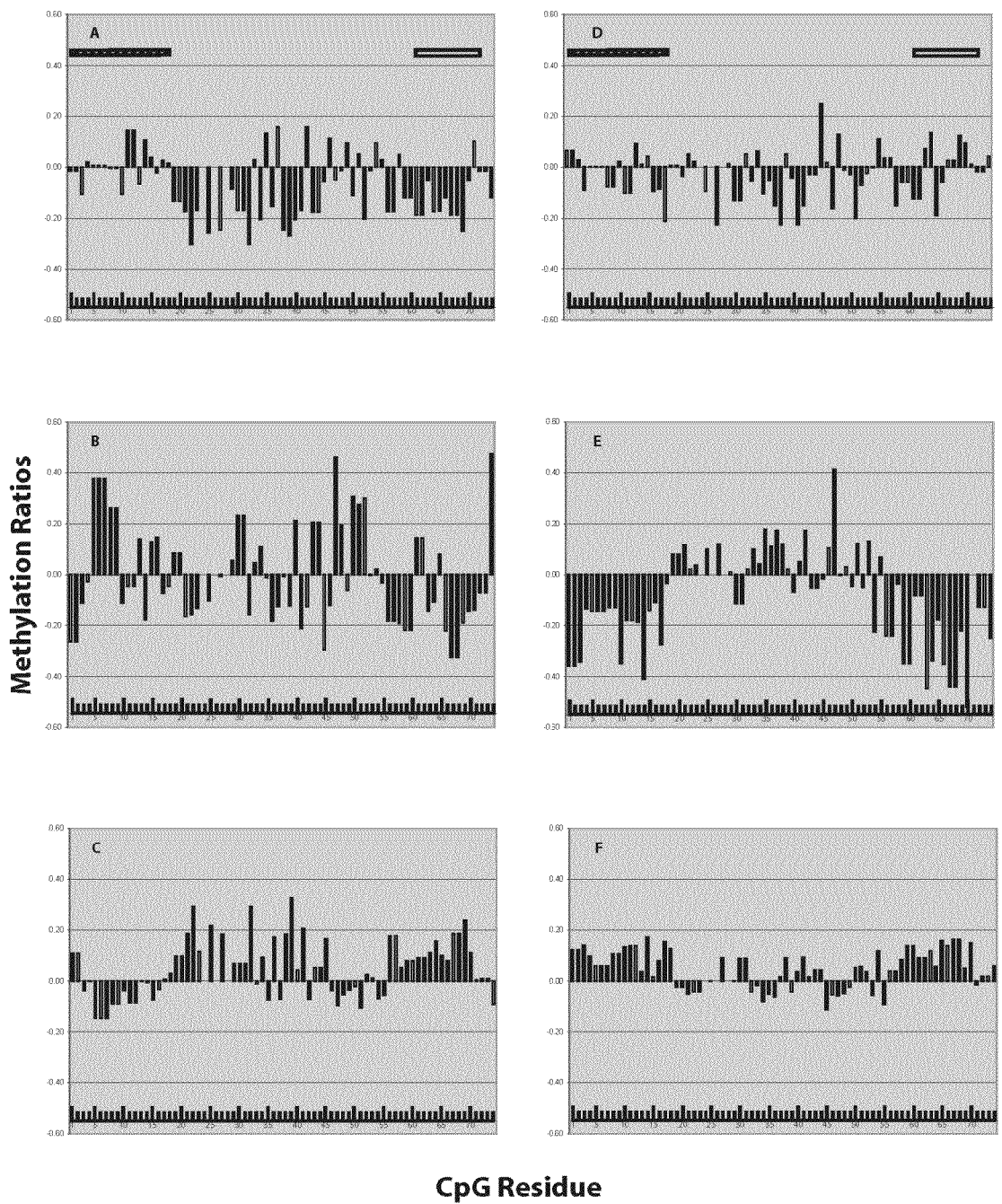
FIGS. 6A-6F. Plot of average methylation Z score at each residue in LB DNA for each grouping of smoking status. CpG residues are in order from left to right. The hatched bar indicates the residues in the first promoter island. The open bar indicates the TSS region. Group A. Current daily male smokers (n=42). Group B. Males who have quit smoking (n=20). Group C. Males who have never smoked daily (n=59). Group D. Current daily female smokers (n=45). Group E. Females who have quit (n=27). Group F. Females who have never smoked daily (n=83).

Using these definitions of smoking status, the examined the relationship between global and site-specific methylation and current daily smoking status. The distribution of the differential methylation at each residue for male and female "lifetime daily smokers," "quitters" and non-smokers" is illustrated in FIG. 6. The results are most marked for the male subjects. As compared to non-smokers, smokers had lower amounts of methylation globally (p<0.02; T-test) and at the transcription start site (p<0.009; T-test) with 7 residues meeting nominal significance level before correction for multiple comparisons. As FIG. 6 demonstrates, smoking is associated with a pervasive decrease in methylation across the second larger CpG island with particular consistency in two areas. The first is from CpG 19 to CpG 32. The second is from CpG 55 to CpG 69, a region that includes the TSS. In contrast, the methylation pattern in those male subjects who quit in the five years prior to the blood draw is decidedly mixed across both islands, with both elevated and decreased methylation at particular residues. Finally, in those male subjects without a history of daily smoking, the net methylation is pervasively increased across the larger CpG island, but somewhat mixed and perhaps decreased overall in the first CpG island.

The methylation pattern in LB DNA from female smokers is similar to that of the male smokers but less intense and consistent. A clear contrast is seen between the amount and pattern methylation observed in those females who quit smoking as compared to those who never smoked, with a trend for reduced overall methylation (p<0.08; T-test) and a significant reduction of methylation at the TSS (p<0.04; T-test) in those who quit.

Factor Analytic Results.

To determine whether methylation data could aggregated in a meaningful way, the inventors used the FACTOR procedure in the SAS computer program (SAS Institute, Cary N.C.) to factor analyze the set of CpG residues for which >95% of both male and female participants had scores. This approach provided a stable three dimensional factor structure accounting for 39% of the reliable variance. The inventors used a varimax rotation to identify regions of covariation in degree of methylation. Use of the three factor scores has the advantage of summarizing the reliable signal in the data, while minimizing the number of separate contrasts required to describe effects, which enhances the signal to noise ratio in the data.

The three regions identified by the factor analysis were: Factor 1 (CpG 19-CpG 45), Factor 2 (CpG 58-CpG 74), and Factor 3 (CpG 1-CpG 18). Use of average scores across the identified region provided a similar pattern of results as use of factor scores. Therefore, factor scores were used in all analyses reported below.

Replicating and extending the analyses reported above for genotype, the inventors found that methylation was greater for heterozygous (3R,4R) or homozygous (4R) females, but the effect was confined to Factor 3 (i.e., CpG 1-CpG 18), $F(1,137)=4.50$, $p<0.05$. The average factor scores for the three groups across CpG 1-18 were (−0.17 vs. 0.23 vs. −0.10) for homozygous 4R, heterozygous 3R,4R and homozygous 3R females respectively. The inventors also found a significant effect of genotype for males, but in this case the effect was confined to factor 1(CpG 19-CpG 45), $F(1,122)=5.25$, $p<0.03$. The average factor scores for the two groups across CpG 19-45 were (−0.11 vs. 0.20) for the hemizygous 4R vs. 3R males respectively. For both males and females, the 4R allele was associated with significantly less methylation.

Replicating and extending the analysis of global methylation effects, a significant association between methylation in the region of CpG 19-45 and days smoking at time 1 (p<0.002) and time 2 (p<0.02) for males was found. A significant association also emerged between days smoking and methylation in the region around the TSS (i.e., Factor 2; CpG 56-74) for males, but only at time 1 (p<0.02). For females, the only significant association emerged between factor 3 (CpG 1-18) and smoking at time 1 (p<0.04). For ND symptom count, we found trends for males p<0.07, for factor 1(CpG 19-45) and p<0.1 for factor 2 (CpG 56-74), but no significant associations for females.

The inventors next replicated and extended the analyses contrasting continuous smokers, quitters, and non-smokers. The inventors found significant group differences for males in methylation of factor 1 (CpG 19-45), $F(2, 117)=5.46$, $p<0.01$, and factor 2 (CpG 56-74), $F(2, 117)=3.91$, $p<0.05$. The average factor scores for the three groups across CpG 19-45 were (−0.19 vs. −0.25 vs. −0.15) for non-smokers, continuous smokers, and quitters respectively. Males who never smoked had the highest level of methylation whereas continuous smokers had the least, and quitters were intermediate. For Factor 2 (CpG 56-74), those who never smoked also had the highest methylation, but the quitters had the least. The average factors scores for the three groups were (0.15 vs. −0.15 vs. −0.29) for non-smokers, continuous smokers, and quitters, respectively. For females, only Factor 3 (CpG 1-18) reliably differentiated the groups $F(2,150)=3.04$, $p=0.05$. Females who never smoked had the highest methylation and those who had quit had the lowest. The average factors scores for the three groups were (0.15 vs. −0.15 vs. −0.41) for non-smokers, continuous smokers, and quitters, respectively.

Comparison of Lymphoblasts to Whole Blood.

Finally, because there is considerable controversy in the field as to which source(s) of DNA can or should be used in methylation studies, the inventors next compared the relationship of smoking status to ND in 78 of the female subjects included in the above analyses using DNA prepared from whole blood (WB) or from the lymphoblast line (LB) derived from the same sample of blood. Each set of samples had a similar amount of overall methylation (LB 33.3% vs WB 34.0%, p<0.45; T-test). The distribution with respect to VNTR allele status was virtually identical (data not shown). With respect to smoking status, there was a trend for decreased overall methylation in DNA of smokers (n=24) as compared to that from non-smoking females (n=38) when the DNA was derived from the lymphoblasts (p<0.09; T-test). However, there was no difference when the same comparison was performed using DNA prepared from whole blood (p<0.89; T-test). To gain a better understanding of this, the inventors plotted the methylation signatures at each residue for those who were daily smokers, recently quit, or who had never smoked. Although the same patterns are present in the DNA from both sources, visual inspection of the methylation plots demonstrates greater consistency and intensity of the differential methylation patterns in the DNA derived from lymphoblasts as compared to that from whole blood.

To compare the results of the methylation results from the two sources of DNA in a more quantitative manner, the inventors next examined average methylation in the three regions identified in the factor analysis using a 3 (smoking status) by 2 (LB vs. WB DNA) ANOVA for each region. As before, only the region identified by Factor 3 (CpG 1-18) reliably differentiated the three smoking status groups $F(2,74)=4.61$, $p<0.02$. There was no interaction with type of assessment (WB or LB DNA) for this region, suggesting that, given enough observations, a method using either source of DNA would have identified the pattern—even though the spread of the distribution of means was slightly more pronounced for LB than for WB samples (0.21, −0.09, −0.38 vs. 0.15, −0.03, −0.34 for non-smokers, continuous smokers, and quitters, respectively for LB vs. WB samples). There was, however, a trend toward significance for the interaction of smoking status with assessment method for Factor 1 (CpG 19-45) $F(2,74)=2.45$, $p<0.1$, suggesting that the two approaches might lead to somewhat different conclusions for that region of the CpG island. In particular, the pattern of means for the three smoking status groups was (0.10, −0.11, −0.03 vs. −0.14, 0.16, 0.11) for non-smokers, continuous smokers, and quitters respectively for LB vs. WB samples, indicating a reversal of the relative positions of never smokers and quitters in average level of methylation in this region depending on which assessment method was used.

Discussion

In summary, using another sample of subjects from the IAS, the inventors replicated and extended their previous findings to show that a significant portion of the methylation signature status at MAOA is associated with current smoking status, that quitting has an effect on methylation status, and that gender and region of the CpG island examined are also important for accurate specification of associations between smoking and level of methylation. The inventors also examined an important methodological issue by using methylation data on the same subjects using two different sources of DNA, and by examining relationships using a factor analytic approach to reduce the number of dimensions required to describe the methylation results.

The current data provide compelling evidence that the methylation status of the two CpG islands associated with the MAOA promoter is dependent upon smoking status. The real question is why? The answer may be to increase the amount of MAOA protein that is produced. Previous work by others has shown that acute exposure to smoke decreased human brain MAOA activity (Fowler J S, et al. 1996. Brain monoamine oxidase A inhibition in cigarette smokers. *Proc Natl Acad Sci USA* 93(24):14065-9), and that this decrease in protein activity may be a direct pharmacological/toxicological effect of substances in tobacco smoke (Berlin I, Anthenelli R M. 2001. Monoamine oxidases and tobacco smoking *Int J Neuropsychopharmacol* 4(1):33-42; Fowler J S et al. 2003. Monoamine Oxidase and Cigarette Smoking *NeuroToxicology* 24(1):75-82.). Since promoter methylation, particularly at the TSS generally decreases mRNA transcription, it seems plausible that the association of decreased methylation with increasing ND symptom count could result from the attempt of the cell to upregulate MAOA RNA production in the face of increased MAOA protein turnover or inhibition caused by smoking.

Whereas this appears to readily explain the contrast in methylation between current smokers and non-smokers, this rationale does not fully explain the effect of "quitting" on MAOA methylation that does not appear to lead to uniform changes and a return to methylation levels similar to those who never smoked. Indeed, on most indices the quitters were as different from non-smokers as the continuous smokers, albeit more variable in their methylation profiles. However, at this time one should be cautious in the interpretation of this portion of these findings. The window of time for "quitting" for these subjects used in this study was rather large and it is highly likely that the subjects differed significantly between one another with respect to total time of smoking abstinence. Therefore, aggregating all "quitters" together in analyses may be insensitive important heterogeneity in this group. Still, taken at face value, these data suggest that the process of returning to non-smoking methylation status may be a lengthy one and that the process may be dynamic at the molecular level as well as at the clinical level.

The finding that female 4R homozygotes have significantly lower methylation than 3R,4R heterozygotes and arithmetically lower methylation than 3R homozygotes is consistent with the inventors' prior work in which they showed a trend for the 4R homozygotes to have lower average methylation than 3R homozygotes (40.9% vs 43.3%; $p<0.10$). In unpublished data from that analysis, the average methylation of the 3,4 heterozygotes was only slightly less than that of the 3R homozygotes (42.9%). Hence, when the data is pooled, it is clear that the average methylation of the 4R homozygotes is significantly lower than that of both 3,4 heterozygotes as well as the 3R homozygotes. In addition, this pattern was found for males when factor scores were examined, albeit only for CpG residues in the region from 19-45. Unfortunately, at this time, there is not a good explanation for the observation that the "low activity" 3R allele is associated with greater average methylation overall, and in particular, the region of the first CpG island. The inventors' expectation going into these studies was that the 4R allele would have greater methylation than the 3R allele in order to compensate for the greater amount of gene transcription that has been shown in most, but not all, transfection studies (Beach S R et al., in submission, Child Maltreatment and MAOA Genotype in Depression and Antisocial Personality Disorder: Genetic Moderation of Family Environment; Cirulli E T, Goldstein D B. 2007. In vitro assays fail to predict in vivo effects of regulatory polymorphisms. *Hum Mol Genet.* 16(16):1931-1939; Guo G et al. 2008. The VNTR 2 repeat in MAOA and delinquent behavior in adolescence and young adulthood: associations and MAOA promoter activity. *Eur J Hum Genet.* 16(5):626-34; Sabol S Z et al. 1998. A functional polymorphism in the monoamine oxidase A gene promoter. *Hum Genet.* 103(3): 273-9). But this is not the case, suggesting that more complex regulatory processes may be at work or that transfections of these MAOA alleles does not fully capture the transcriptional complexity present at this locus.

Figure 7:
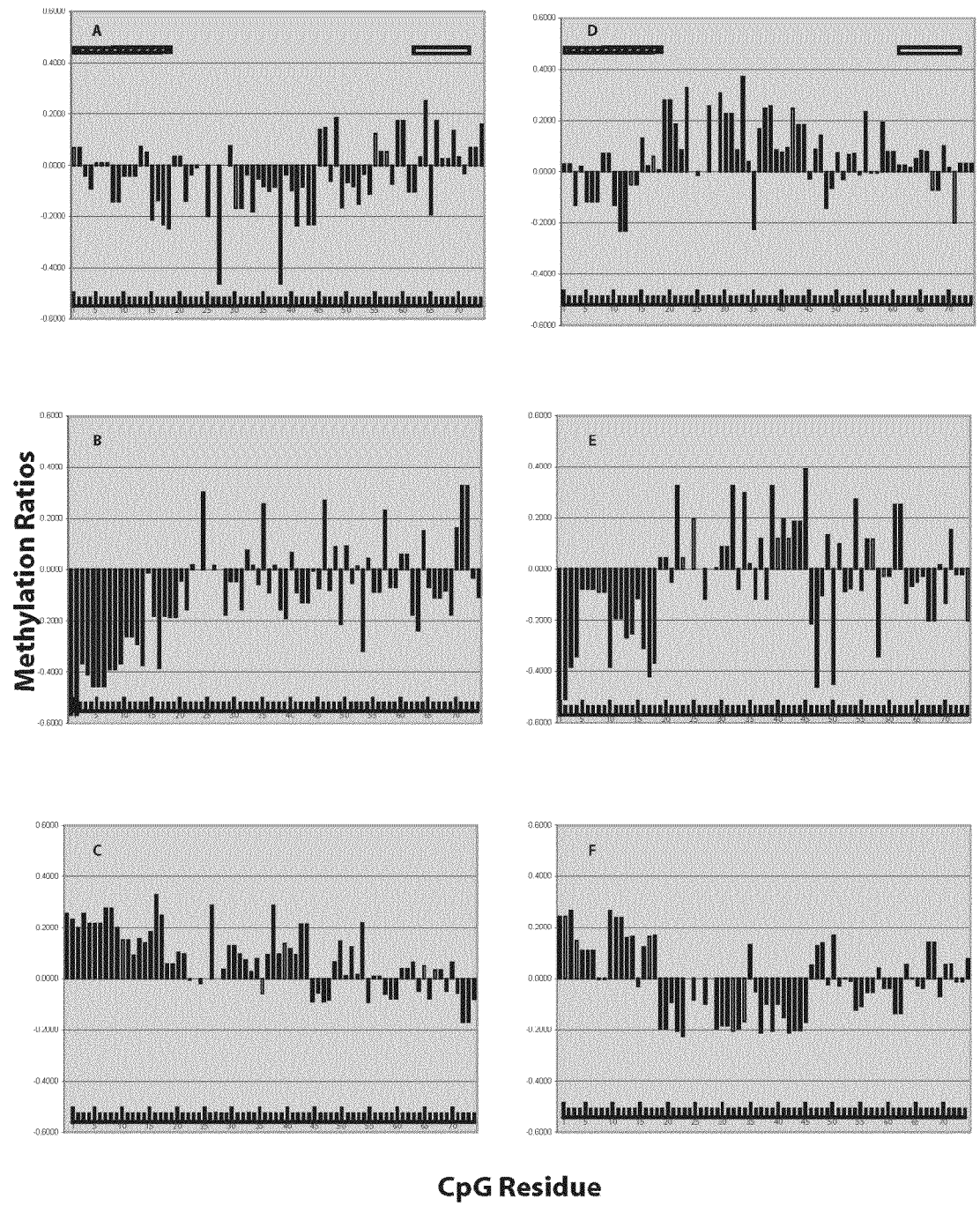
FIGS. 7A-7F. Plot of average methylation Z score at each residue in LB (A, B and C) or WB (D, E and F) DNA from 77 female subjects of function of smoking status. The CpG residues are in order from left to right. The hatched bar indicates the residues from the first promoter island. The open bar indicates the TSS region. Group A and D. Female daily smokers (n=24). Group B and E. Females who have quit smoking (n=15). Group C and F. Females who have never smoked daily (n=38).

Lymphoblast cultures are homogenous cell lines that are derived from long lived peripheral β-lymphocyte populations and are relatively unaffected by acute changes in the health status of the host (Hao Z, Rajewsky K. 2001. Homeostasis of peripheral B cells in the absence of B cell influx from the bone marrow. *J Exp Med* 194(8):1151-64; Tough D F, Sprent J. 1995. Lifespan of lymphocytes. *Immunol Res* 14(1):1-12). Others have demonstrated that the epigenetic signature is preserved in lymphoblasts (Monks S A et al. 2004. Genetic inheritance of gene expression in human cell lines. *Am J Hum Genet.* 75(6):1094-105; Morello F et al. 2004. Differential Gene Expression of Blood-Derived Cell Lines in Familial Combined Hyperlipidemia. *Arterioscler Thromb Vasc Biol* 24(11):2149-2154). The present observation of nearly identical amounts of total methylation and allele specific methylation in the WB and LB samples further supports this supposition. In contrast, there are several reasons to believe that the methylation signatures in WB DNA may be more variable. Peripheral white blood cells are a varying mixture of neutrophils, lymphocytes, eosinophils, basophils and monocytes, each of which probably has a slightly different methylation signature. The composition of this cell mix can change suddenly. In particular, the neutrophil portion of this mixture is subject to marked swings in population secondary to margination of these cells to the blood stream in response to processes such as stress, infection or drug ingestion (e.g., lithium). Because these processes are associated with changes in neutrophil protein and gene expression signatures (Bussiere F I et al. 2002. Stress protein expression cDNA array study supports activation of neutrophils during acute magnesium deficiency in rats. *Magnes Res* 15(1-2):37-42; Macdonald J, Galley H F, Webster N R. 2003. Oxidative stress and gene expression in sepsis. *Br J Anaesth* 90(2):221-232), it is likely that as part of these processes, changes in methylation signatures also occur, leading to greater variability in WB than LB DNA. In light of this source of variability in the constituent elements of WB DNA and the likelihood that the various cell types in blood differ slightly in their methylation signatures, it is reasonable to assume that WB DNA may have greater variability in its methylation signature. However, this does not mean it should not be used in these types of studies. Careful review of FIG. 7 demonstrates that the same patterns are evident in both sources of DNA and the current data are from just one locus.

The apparent differences in the methylation profiles with respect to smoking status are intriguing. Although the inventors initially analyzed only overall and TSS specific methylation, one advantage of using factor analytic scores is that they provide a potentially useful way of defining and then summarizing methylation for all regions of the CpG island, allowing better specification of possible differences between groups and between genders. For example, average factor analytic scores for males show an orderly transition from decreased to increased methylation as a function of smoking status that is most apparent for Factor 1 comprising the region from CpG 19 to CpG 45. For females, non-smokers also demonstrate the highest methylation, but this is most evident on Factor 3 comprising the region from CpG 1 to CpG 18. Both male and female quitters demonstrated lower levels of methylation than did non-smokers on Factor 2 (i.e., the region containing the TSS) with continuous smokers being intermediate (−0.29 vs −0.14 vs 0.14 for males; −0.26, −0.02, 0.13 for females), suggesting that effects of smoking status at the TSS may be more similar than different for males and females, and that quitting smoking may be associated with lowered methylation for both.

EXAMPLE 3

Genome-Wide Methylation Analysis

Genome wide methylation analyses were conducted using lymphoblast DNA from 10 well controls, 8 subjects with active alcohol dependence, 7 subjects with active Nicotine Dependence and 4 subjects with active Cannabis Dependence from the Iowa Adoption Studies. Briefly, 10 μg of highly purified lymphoblast DNA from each subject was digested with to completion with MseI, purified and a 300 ng aliquot (input) stored for further analysis. Then, 5 μg aliquots of each sample were denatured at 95° C. for 10 min, and subsequently rapidly chilled. The denatured DNA was then resuspended in immunoprecipitation buffer, then sequentially immunoprecipitated with mouse anti 5-methylcytosine (Abcam, USA), and sheep anti-mouse IgG antibodies. The resulting immunoprecipitated DNA was then cleaved from the precipitated complex by overnight proteinase K digestion and purified. Then, aliquots of both the input and enriched (immunoprecipitated) DNA were amplified with a Whole Gene Amplification-2 (WGA-2) kit (Sigma, USA) according to manufacturer's instructions. The resulting DNA was purified and quantified. Then, 5 μg aliquots of resulting amplified DNA samples were shipped to Roche-Nimblegen (Indianapolis) for labeling and hybridization under contract. In short, the input and enriched DNA samples were labeled with Cy-3 and Cy-5, respectively and then matching specimens were be hybridized to the 385 K NimbleGen promoter array and scanned.

Analysis of Genome Wide Data:

Cy3-Cy5 ratios for probe were computed, $\log_2$ transformed, then scaled by subtracting the bi-weight mean from each value for each feature. The resulting values were then analyzed in relation to all features and directly neighboring features by fixed window Kolmogorov-Smirnov test to identify significantly differentially regulated promoter regions in subjects. The resulting peak scores for each differentially region for each subject were exported and the results from cases and controls contrasted using standard t-tests to determine differentially regulated individual gene promoter regions in type of substance use syndrome.

Three tables are given (Table 5, 6 and 7) with respect to the identity of gene promoter region differentially regulated in Nicotine, Alcohol and Cannabis Dependence. These promoter-associated islands are listed according to their HUGO identification of the gene to which they are associated.

TABLE 5

Genes whose methylation is differentially regulated in DNA from subjects with active Nicotine Dependence as compared to DNA from well Controls.

ACCN3
ATP6V0A4
C10orf39
C10orf53
C21orf123
CACNA1G
CCDC49
CCNC
CD8A
CDH16
CIDEB
CLEC10A
CYP2B6
DOK2
DYDC1
EFNA3
FABP6
FAM107B
FKBPL
FLJ32569
FLJ40365
FLJ43870
GALP
GJB1
GMPPA
HOXA5
HRASLS2
KCNQ1DN
KHSRP
KIAA1843
KIRREL2
KLK9
LCA10
LIMS3
LOC155006
LOC285095
LOC643274
LOC645811
LOC646836
LOC653176
LOC653700
LPHN1
LTB4R
LW-1
MAFG
MAGEA4

TABLE 5-continued

Genes whose methylation is differentially regulated in DNA from subjects with active Nicotine Dependence as compared to DNA from well Controls.

MATK
MCART1
MGC4728
MYADML
N/A
NCAM1
NCR3
NOXO1
NUDT1
NUMB
OPN1LW
OR2B11
OR6V1
PAQR5
PAX3
PDCD4
PNCK
PPAN
PRAME
PSG7
PTPRT
RIBC1
RP11-159H20.4
S100A1
S100A13
SCN5A
SELS
SH3PX3
SLC35E1
SPIN-2
TAC3
TBX4
TCOF1
TNFSF9
TOMM40
VMD2L1
WFIKKN1
ZCCHC13
ZFP64
ZNF274
ZNF320
ZNF516

TABLE 6

Genes whose methylation is differentially regulated in DNA from subjects with active Alcohol Dependence as compared to DNA from well Controls.

| ZGP1 | FBXW5 | MLX | SHARPIN |
|---|---|---|---|
| BHLHB8 | FLJ40448 | MPG | SLITRK4 |
| C6orf26 | FRG1 | N/A | SNAPC2 |
| C20orf70 | GIYD2 | OPRS1 | SULT1A3 |
| CACNA1S | KIAA1875 | PANX2 | TBX2 |
| CMTM2 | KLK8 | PIP5KL1 | THTPA |
| COL6A2 | LOC339047 | PPP1CA | TMEM101 |
| COLEC11 | LOC440354 | PRSS27 | TMEM121 |
| CSAG2 | LOC442628 | PSG3 | TRIM17 |
| ELF3 | LOC644122 | REEP6 | TYRO3 |
| FAM3A | LOC645598 | RFNG | |

TABLE 7

Genes whose methylation is differentially regulated in DNA from subjects with active Cannabis Dependence as compared to DNA from well Controls.

| IL32 | ZNF42 | SPANXA1 | TOMM40 |
|---|---|---|---|
| PEO1 | FNDC8 | TMEM88 | SERTAD3 |
| LOC653210 | FAM84A | C14orf120 | IER2 |

TABLE 7-continued

Genes whose methylation is differentially regulated in DNA from subjects with active Cannabis Dependence as compared to DNA from well Controls.

| C7orf21 | PTPN20A | IGFBP6 | ARHGEF1 |
|---|---|---|---|
| PTPN20A | RBP5 | ACSS2 | PEO1 |
| KRT17 | LOC642358 | FXYD1 | BMF |
| PTPN20B | PAQR8 | CMTM1 | KIAA0310 |
| LOC653107 | DNAI1 | H2AFB3 | DNAJC19 |
| GIYD2 | LOC653680 | KIAA0892 | SEPT6 |
| FTL | HSPA1A | ZNF409 | MAGED4 |
| FLJ21767 | SIRT2 | IRF7 | HSD11B1L |
| LOC653107 | UBOX5 | LOC653257 | GIYD2 |
| CSH2 | TUBA2 | RTN2 | EGLN2 |
| CSAG3A | KCNK7 | KCNK7 | PRCP |
| MGC12760 | ZNF580 | SULT1A3 | CYBA |
| MUC4 | RNASEH2A | N/A | TUSC4 |
| RRP22 | SCT | LOC339123 | BCKDK |
| S100A13 | LOC653210 | LOC644083 | GH2 |
| TRIM74 | LOC644733 | ATP6V0C | BOLA2 |
| BAD | RBM10 | PAIP2 | PITRM1 |
| CSAG3A | DARC | LOC653483 | LOC401019 |
| ANKRD25 | LIME1 | MEIS3 | FAM39A |
| SNRPN | MAGEA2B | MAGED4 | CKAP1 |
| FKRP | FLJ21767 | CA5BL | GMFG |
| RNF126 | SNRPN | ARRB2 | CYP2D6 |
| ITGB4BP | COX6B2 | RIPK3 | BAG1 |
| PEO1 | C1orf142 | CKS1B | Rgr |
| LRDD | C7orf21 | TSEN34 | LOC653107 |
| CHMP5 | CACNA1C | SFTPC | DEDD2 |
| CRAT | CSAG3A | OBP2B | PITX3 |
| FAM39A | MGC12760 | BAGE | |
| FAM39A | FLJ36046 | CRYAB | |
| ECM1 | PEO1 | LOC389833 | |

EXAMPLE 4

Methylation Profiling of Nicotine Dependence

Nicotine dependence (ND) is one of the largest public health challenges in the developed world. Despite extensive treatment and prevention efforts, approximately 20% of U.S. adults still smoke on a daily basis which results in 440,000 premature deaths and $92 billion dollars of economic costs annually (Center for Disease Control. 2005 Annual Smoking-Attributable Mortality, Years of Potential Life Lost, and Productivity Losses—United States, 1997-2001. Morbidity and Mortality Weekly 54(25):625-628; Center for Disease Control. 2009. State-Specific Prevalence and Trends in Adult Cigarette Smoking—United States, 1998-2007. JAMA 302 (3):250-252.) Not surprisingly, a large number of studies have been conducted to identify the genetic and environmental factors associated with smoking. While the analyses of both types of factors have been informative and useful in the provision of better treatment and prevention measures, the rate of smoking in the general population may have reached a nadir and in fact may be increasing in young adults (Kumra V, Markoff B A. 2000. WHO'S SMOKING NOW?: The Epidemiology of Tobacco Use in the United States and Abroad. Clinics in Chest Medicine 21(1):1-9.). Hence, there is increased urgency to understand the biology underlying ND. Unfortunately, even though recent genome wide analyses have clearly identified significant genetic variation for ND (Bierut L J, Madden P A, Breslau N, Johnson E O, Hatsukami D, Pomerleau O F, Swan G E, Rutter J, Bertelsen S, Fox L and others. 2007. Novel genes identified in a high-density genome wide association study for nicotine dependence. Hum Mol Genet. 16(1):24-35; Vink J M, Smit A B, de Geus E J, Sullivan P, Willemsen G, Hottenga J J, Smit J H, Hoogendijk W J, Zitman F G, Peltonen L and others. 2009. Genome-wide association study of smoking initiation and current smoking Am J Hum Genet. 84(3):367-79.), the majority of the biological vulnerability for initiation and maintenance of smoking behaviors remains unexplained.

Recently there has been an increasing appreciation that a portion of the biology responsible for the initiation and maintenance of smoking behaviors may be epigenetic. Over the past two years, a number of studies have demonstrated that smoking itself induces biological changes at loci such as monoamine oxidase A (MAOA) and monoamine oxidase B (MAOB) which are known to be important in human behavior (Fowler J S, Logan J, Wang G-J, Volkow N D. 2003. Monoamine Oxidase and Cigarette Smoking NeuroToxicology 24(1):75-82; Fowler J S, Volkow N D, Wang G J, Pappas N, Logan J, Shea C, Alexoff D, MacGregor R R, Schlyer D J, Zezulkova I and others. 1996b. Brain monoamine oxidase A inhibition in cigarette smokers. Proc Natl Acad Sci USA 93(24):14065-9). Whereas some of the biological effects are known to be due to the direct effects of cigarette smoke (Yu P H, Boulton A A. 1987. Irreversible inhibition of monoamine oxidase by some components of cigarette smoke. Life Sci 41(6):675-82), it is also becoming evident that smoking may directly affect the methylation status of genes (Breton C V, Byun H-M, Wenten M, Pan F, Yang A, Gilliland F D. 2009. Prenatal Tobacco Smoke Exposure Affects Global and Gene-Specific DNA Methylation. Am J Respir Crit. Care Med: 200901-01350C; Philibert R, Beach S R, Gunter T, Brody G H, Madan A. 2009. The Effect of Smoking on MAOA Promoter Methylation in DNA Prepared from Lymphoblasts and Whole Blood. Am J Med Genet B Neuropsychiatr Genet September 23; [Epub ahead of print]). These findings are intriguing because altered DNA methylation is an integral part of the biological processes in the carcinogenic pathway (Tessema M, Yu Y Y, Stidley C A, Machida E O, Schuebel K E, Baylin S B, Belinsky S A. 2009. Concomitant promoter methylation of multiple genes in lung adenocarcinomas from current, former and never smokers. Carcinogenesis 30(7): 1132-1138) and they suggest the possibility that methylation may also affect behaviorally relevant genes.

There is strong support for the hypothesis that smoking alters DNA methylation of behaviorally relevant genes at the Xp13 locus containing MAOA and MAOB. Monoamine oxidase activity is essential for the normal catabolism of monoaminergic neurotransmitters. Classically, disruption of this oxidase activity is associated with aberrant behavior, especially aggression (Brunner H G, Nelen M, Breakefield X O, Ropers H H, van Oost B A. 1993. Abnormal behavior associated with a point mutation in the structural gene for monoamine oxidase A. Science 262(5133):578-80). Since that seminal discovery, there has been an increasing body of evidence, including a set of elegant neuroimaging analyses by Volkow and associates, that implicates altered MAOA and MAOB protein activity in the CNS and non-CNS pathophysiology associated with smoking (Alia-Klein N, Goldstein R Z, Kriplani A, Logan J, Tomasi D, Williams B, Telang F, Shumay E, Biegon A, Craig I W and others. 2008. Brain Monoamine Oxidase A Activity Predicts Trait Aggression. J Neurosci 28(19):5099-5104; Fowler J S, Logan J, Wang G-J, Volkow N D. 2003. Monoamine Oxidase and Cigarette Smoking NeuroToxicology 24(1):75-82; Fowler J S, Volkow N D, Wang G J, Pappas N, Logan J, MacGregor R, Alexoff D, Shea C, Schlyer D, Wolf A P and others. 1996a. Inhibition of monoamine oxidase B in the brains of smokers. Nature 379 (6567):733-6; Fowler J S, Volkow N D, Wang G J, Pappas N, Logan J, Shea C, Alexoff D, MacGregor R R, Schlyer D J, Zezulkova I and others. 1996b. Brain monoamine oxidase A inhibition in cigarette smokers. Proc Natl Acad Sci USA 93(24):14065-9). Some of these changes in smoking associated monoamine oxidase activity are secondary to direct effects of smoke (Yu P H, Boulton A A. 1987. Irreversible inhibition of monoamine oxidase by some components of cigarette smoke. Life Sci 41(6):675-82). However, an emerging literature has indicated that altered epigenetic regulation of both of these genes may also be playing a role in altering monoamine oxidase activity (Launay J-M, Del Pino M, Chironi G, Callebert J, Peoc'h K, Megnien J-L, Mallet J, Simon A, Rendu F. 2009. Smoking Induces Long-Lasting Effects through a Monoamine-Oxidase Epigenetic Regulation. PLoS ONE 4(11):e7959; Philibert R, Beach S R, Gunter T, Brody G H, Madan A. 2009. The Effect of Smoking on MAOA Promoter Methylation in DNA Prepared from Lymphoblasts and Whole Blood. Am J Med Genet B Neuropsychiatr Genet September 23; [Epub ahead of print]; Philibert R A, Gunter T D, Beach S R, Brody G H, Madan A. 2008. MAOA methylation is associated with nicotine and alcohol dependence in women. Am J Med Genet B Neuropsychiatr Genet. 147B(5): 565-70). Taken together with a recent genome wide study of methylation of the effects of maternal prenatal smoking (Breton C V, Byun H-M, Wenten M, Pan F, Yang A, Gilliland F D. 2009. Prenatal Tobacco Smoke Exposure Affects Global and Gene-Specific DNA Methylation. Am J Respir Crit. Care Med:200901-01350C) and studies by others indicating that altered methylation loci such as OPRMJ, DAT and SNCA (Bonsch D, Lenz B, Kornhuber J, Bleich S. 2005. DNA hypermethylation of the alpha synuclein promoter in patients with alcoholism. Neuroreport 16(2):167-70; Hillemacher T, Frieling H, Hartl T, Wilhelm J, Kornhuber J, Bleich S. 2009. Promoter specific methylation of the dopamine transporter gene is altered in alcohol dependence and associated with craving. Journal of Psychiatric Research 43(4):388-392; Nielsen D A, Yuferov V, Hamon S, Jackson C, Ho A, Ott J, Kreek M J. 2008. Increased OPRM1 DNA Methylation in Lymphocytes of Methadone-Maintained Former Heroin Addicts. Neuropsychopharmacology) in other addictive behaviors, a nascent literature is emerging that supports the assertion that various addictive substances may alter DNA methylation at a broad number of loci relevant to behavior, and that better understanding changes in methylation may enhance our understanding of the biology of addiction.

Since DNA methylation is a major mechanism through which gene expression and ultimately behavior is regulated, these findings also suggest that smoking induced altered DNA methylation may be in part responsible for some of the processes which maintain smoking as well as some of the other behavioral phenomena associated with smoking, such as increased risk for panic disorder (Isensee B, Wittchen H U, Stein M B, Hofler M, Lieb R. 2003. Smoking increases the risk of panic: findings from a prospective community study. Arch Gen Psychiatry 60(7):692-700). Capturing a broader understanding of that biology may generate critical insights that may be important to the development of better treatment and prevention measures for smoking and associated phenomena. Therefore, in order to begin the facilitation of this better understanding of this altered DNA methylation on a more systematic basis, an analysis was conducted of DNA methylation at 18,028 promoter associated CpG islands using lymphoblast DNA from 23 actively smoking ND subjects and 18 age and ethnicity matched controls from the Iowa Adoption Studies.

Methods

The design and diagnostic measures used in the IAS have been extensively described previously and all have been approved by the University of Iowa Institutional Review Board (Yates W R, Cadoret R J, Troughton E, Stewart M A. 1996. An adoption study of DSM-IIIR alcohol and drug dependence severity. Drug and Alcohol Dependence 41(1): 9). The clinical data used in the study was derived from the latest two rounds of structured interviews conducted in our studies (1999-2003 and 2004-2009). The core instrument for these studies was an adaptation of the Structured Assessment for the Genetic Studies of Alcoholism, version 2 (SSAGA-II) (Bucholz KK, Cadoret R, Cloninger C R, Dinwiddie S H, Hesselbrock V M, Nurnberger J I, Jr., Reich T, Schmidt I, Schuckit M A. 1994. A new, semi-structured psychiatric interview for use in genetic linkage studies: a report on the reliability of the SSAGA. J Stud Alcohol 55(2):149-58). The lifetime symptom counts for ND and Fagerstrom Tests for Nicotine Dependence (FTND) scores were compiled from this data using DSM-IV criteria and published scales as previously described (Heatherton T F, Kozlowski L T, Frecker R C, Fagerstrom K O. 1991. The Fagerstrom Test for Nicotine Dependence: a revision of the Fagerstrom Tolerance Questionnaire. Br J Addict 86(9):1119-27; Philibert R A, Ryu G Y, Yoon J G, Sandhu H, Hollenbeck N, Gunter T, Barkhurst A, Adams W, Madan A. 2007. Transcriptional profiling of subjects from the Iowa adoption studies. Am J Med Genet B Neuropsychiatr Genet. 144(5):683-90). These scores and the rest of the available clinical data were then reviewed by two board-certified psychiatrists to provide two pools of individuals; a set of cases with severe, active ND and a set of age and ethnicity matched controls without a history of behavioral illness or significant alcohol, nicotine or illicit substance use.

The lymphoblast DNA used in the study was prepared from standard EBV transfected cell lines that were grown in standard bovine serum-based growth media supplemented with l-glutamine and penicillin-streptomycin as previously described (Philibert R A, Ryu G Y, Yoon J G, Sandhu H, Hollenbeck N, Gunter T, Barkhurst A, Adams W, Madan A. 2007. Transcriptional profiling of subjects from the Iowa adoption studies. Am J Med Genet B Neuropsychiatr Genet. 144(5):683-90). The media was changed for each of these cell lines 24 hours prior to the extraction of DNA.

Input and methylation enriched fractions of DNA were prepared per the standard Nimblegen protocol (Roche Nimblegen I. 2007. Sample Preparation Protocol For DNA methylation Microarrays v3.0. Indianapolis). Briefly, 20 µg of DNA was reduced in complexity by digestion with Mse I, column, and a small aliquot taken for future analysis (i.e. input DNA). Five µg of the remainder of the digested DNA from each subject was resuspended in immunoprecipitation buffer (50 mM $NaPO_4$, 700 mM NaCl, 0.25% Triton X-100) and hybridized with 1 µg of monoclonal mouse anti-5-methyl cytidine antibody (Calbiochem USA) at 4° C. overnight. The resulting solution was then hybridized to a magnetic bead coupled secondary antibody (Dynabeads M-280, Invitrogen USA) and the DNA-antibody moiety purified by magnetic separation. The DNA was removed from the antibody complex by overnight digestion with protease K and column purified. Then 100 ng aliquots of both the methyl enriched DNA fraction and the input DNA were amplified using a WGA2 genome amplification kit used according to manufacturer's instructions (Sigma, St. Louis). After purification, this DNA was then frozen at −20° C. until use in the microarray analyses.

Hybridization to the 385K RefSeq whole genome promoter array (HG18 RefSeq) was conducted by Roche-Nimblegen (Indianapolis) under contract. These arrays contain 50-75 mer probes to 18,028 annotated RefSeq gene promoters with an average probe spacing of 100 bp. The resulting data, including the scaled $log_2$ weighted ratios of the Cy3 (input) and Cy5 (methyl enriched) hybridization signals used in this report, were returned via courier.

The resulting data were then analyzed using a two-step process. In the first step, t-tests were conducted to identify probes whose hybridization values differed between the cases and controls at a significance level of p<0.01 (uncorrected). A clustering algorithm was then applied to this reduced probe set to identify probes which co-localized.

Bisulfite confirmation of differential methylation was conducted using standard procedures. Briefly, the DNA for each subject was first bisulfite modified then amplified using an Epitech® 96 Bisulfite and an Epitech® Whole Bisulfitome kit (both Qiagen, USA) according to manufacturer's instructions. The DNA samples were then amplified using a nested PCR protocol ($1^{st}$ round primers, AGT GTT GGT GTA TTT ATT TTA AAA (SEQ ID NO:10) and TCC TAA AAA CAA ATA TCT TTC AAT C (SEQ ID NO:11); $2^{nd}$ round primers TAA CAA TAC TAA TCA TTT CAT AAA ATA (SEQ ID NO:12) and AGT TTA GTA ATT TGG AAT AAT AGG TTT (SEQ ID NO:13)). The resulting PCR products were gel purified, cloned using a StrataClone TA cloning kit (Stratagene USA), then sequenced at the University of Iowa DNA facility. The methylation status of each residue was then determined using CpG Viewer (Carr I M, Valleley E M A, Cordery S F, Markham A F, Bonthron D T. 2007. Sequence analysis and editing for bisulphite genomic sequencing projects. Nucl Acids Res 35(10):e79-) and the resulting data was analyzed via chi-square testing.

Gene pathway analysis was conducted using the web version of GOMiner™ using the default settings (Zeeberg B, Feng W, Wang G, Wang M, Fojo A, Sunshine M, Narasimhan S, Kane D, Reinhold W, Lababidi S and others. 2003. GoMiner: a resource for biological interpretation of genomic and proteomic data. Genome Biology 4(4):R28) while frequency analyses were conducted using the binomial test (Fleiss J L. 1981. Statistical Methods for Rates and Proportions. New York, N.Y.: John Wiley & Sons Inc.). Comparison of Cy3/Cy5 weighted values was conducted using logistic regression (Fleiss J L. 1981. Statistical Methods for Rates and Proportions. New York, N.Y.: John Wiley & Sons Inc.).

Results

The clinical and demographic information for the 41 subjects used in the case and control analyses are given in Table 8. All subjects were White with the average age of the cases being 43±7 years old and the controls 46±7 years old (p<0.17). The cases averaged over a pack of cigarettes per day at the time of phlebotomy with almost all of them having smoked heavily for over 20 years.

TABLE 8

Clinical and Demographic Data

| | Cases | | Controls | |
|---|---|---|---|---|
| | Male | Female | Male | Female |
| N | 10 | 13 | 10 | 8 |
| Age (years ± SD) | 47 ± 8 | 41 ± 5 | 47 ± 9 | 46 ± 5 |
| DSM IV ND Symptom Count | 4.8 ± 2.0 | 5.2 ± 1.0 | — | — |
| FTND | 4.7 ± 2.7 | 4.4 ± 2.4 | — | — |
| Daily Cigarette Consumption | 25 ± 9 | 22 ± 9 | — | — |
| Years Smoking | 24 ± 10 | 21 ± 7 | — | — |

*Fagerstrom Test for Nicotine Dependence Scale (FTND), DSM IV Diagnostics and Statistics Manual Version 4

The methylation signals were analyzed as a group and by gender. The first analysis contrasted the signal from all cases versus all controls. The second analysis, consistent with prior strategies for analyzing behavioral data featured gender specific analyses.

As the initial step of all cases (n=23) vs controls (n=18) contrast, t-tests were conducted comparing the scaled and weighted Cy5/Cy3 ratios of the cases to that of the controls. Overall, the hybridization signal for 2534 probes differed at an uncorrected p-value of p<0.01. Because the clinical phenomenology associated with ND differs between males and females in our population, we then conducted gender specific analyses using the same methods. In this contrast, the male ND cases had 1790 probes that were differentially methylated at a p value of <0.01 while the female ND cases had 2070 probes that were differentially methylated at an uncorrected p value of p<0.01. Fifteen of the significant probes in the female only contrast were also found to be significant in the male only contrast (p<0.03) with two of those probes localizing to the same gene promoter (SLCO2B1).

Since our prior work in this area has demonstrated that methylation analyses are inherently noisy, we performed a cluster analysis of all significant probes from the combined set (<0.01) in order to increase the likelihood that the gene promoters selected for further analysis would represent real signal. The distribution of these differentially hybridizing probes was significantly nonrandom with 237 of the probes, localizing to just 113 gene promoters (p<0.0001). Seven gene promoters had three significant probes. Table 9 gives the HUGO approved names for the 106 genes that have names and which have two or more significant probes localizing to the gene promoter.

TABLE 9

List of Genes with Two or More Significant Probes

3 Significant Probes

| ANKRD13A | ATG2A | AX2R | CSNK1G2 | NOVA1 | SETBP1 | SLMO2 |

2 Significant Probes

| AFAP1L1 | ATP11A | C15orf57 | C16orf61 | C6orf195 | C7orf45 | C9orf72 |
| CAMTA1 | CARHSP1 | CCDC144NL | CCNH | CCT6B | CFTR | CMIP |
| CNTD1 | COL4A3 | CSMD1 | CTBP2 | D2HGDH | DDX41 | DLGAP2 |
| DMRTA2 | DOPEY2 | EBF2 | EIF4H | ELL | EMP3 | ENTPD2 |
| ENTPD2 | EPOR | FER | FGR | FHDC1 | FHOD1 | FOXC1 |
| FXN | GDF10 | GFPT2 | GPM6A | GRIK2 | HIRIP3 | HIST1H2BK |
| HIST2H2AA3 | HSD17B4 | IFNA17 | ISL2 | JPH2 | KBTBD2 | LAX1 |
| LBX1 | LOC254559 | LRRC66 | LRRN2 | MAT2B | NECAB3 | NID2 |
| NUBP1 | OTOP1 | PARP4 | PDE5A | PNLDC1 | PNMA5 | PPIA |
| PRKAR1A | PRR7 | PTDSS2 | PTPRN2 | RAC1 | RBM20 | RNPS1 |
| RPIA | RPL39L | RPS17 | SAV1 | SCG5 | SFRS17A | SGOL2 |
| SH2D4B | SKP1 | SLC25A21 | SLC5A5 | SLCO2B1 | SOX17 | SSTR1 |
| STK40 | TACR3 | TBC1D8B | TESC | THOP1 | TMC2 | TOPORS |
| TP53INP1 | ZIC5 | ZNF148 | ZNF830 | ZPLD1 | | |

The list of RefSeq genes with CpG islands containing two or more significantly probes that were symmetrically associated with active nicotine dependence (p < 0.01 nominal) in the genome wide analysis. Briefly, to generate this list, the normalized Log 2 hybridization ratios scores were analyzed a two-step process. In the first step, genome wide t-tests were conducted to identify probes whose hybridization values differed between the cases and controls at a significance level of p < 0.01 (uncorrected). A clustering algorithm was then applied to this reduced probe set to identify probes which co-localized to a 1000 bp sliding winding in the same island. Then, the genomic location of the CpG was checked against the HG 18 build of the human genome to identify RefSeq annotated genes associated with the island.

These 106 named genes from Table 9 were then subjected to pathway analysis using GOMiner™ (Zeeberg and others 2003) to identify gene pathways whose methylation patterns are differentially affected by smoking. In brief, the results of the analysis show that epigenetic change in proteins associated with cell proliferation and transmembrane transport are recurrent themes in these analyses (Table 10).

TABLE 10

Gene Pathway Analysis of the 113 Promoters with 2 or More Significant Probes.

| Go Miner | Category | Changed Genes/Total Genes | P Value |
| --- | --- | --- | --- |
| GO: 0007215 | Glutamate Signaling Pathway | 2/5 | <0.001 |
| GO: 0008285 | Negative Regulation of Cell Proliferation | 6/128 | <0.002 |
| GO: 0016607 | Nuclear Speck | 4/59 | <0.002 |
| GO: 0016614 | Oxidoreductase Activity Acting on CH—OH | 4/60 | <0.003 |
| GO: 0003007 | Heart Morphogenesis | 2/9 | <0.003 |
| GO: 0000786 | Nucleosome | 2/11 | <0.005 |
| GO: 0042626 | ATPase Activity Coupled to Transmembrane Movement of Substances | 2/11 | <0.005 |
| GO: 0022804 | Active Transmembrane Transporter Activity | 3/37 | <0.005 |
| GO: 0016820 | Hydrolase Activity Acting on Acid Anhydrides | 2/12 | <0.006 |
| GO: 0043492 | ATPase Activity Coupled to Movement of Substances | 2/12 | <0.006 |
| GO: 0022414 | Reproductive Process | 6/178 | <0.006 |
| GO: 0016604 | Nuclear Body | 4/79 | <0.006 |
| GO: 0007548 | Sex Differentiation | 3/45 | <0.008 |
| GO: 0051082 | Unfolded Protein Binding | 3/45 | <0.008 |

TABLE 10-continued

Gene Pathway Analysis of the 113 Promoters with 2 or More Significant Probes.

| Go Miner | Category | Changed Genes/Total Genes | P Value |
|---|---|---|---|
| GO: 0015276 | Ligand-Gated Ion Channel Activity | 2/15 | <0.008 |
| GO: 0022834 | Ligand-Gated Channel Activity | 2/15 | <0.008 |
| GO: 0000003 | Reproduction | 8/324 | <0.009 |
| GO: 0030551 | Cyclic Nucleotide Binding | 2/16 | <0.009 |
| GO: 0003006 | Reproductive Developmental Process | 3/49 | <0.01 |
| GO: 0022892 | Substrate-Specific Transporter Activity | 7/265 | <0.01 |

In order to validate the microarray analyses, we conducted sequencing of plasmid clones of bisulfite PCR products from 15 randomly selected cases (92 clones in total) and 15 randomly selected controls (77 clones in total) with respect to the AX2R promoter across the three significant probe regions identified in our initial analyses which localized to this gene. FIG. 8 shows the structure of the tiled region of the AX2R gene promoter. Table 11 gives the Cy3/Cy5 methylation ratios for the cases and controls, as well as their uncorrected p-values. When evaluating the strength of these p-values, it is important to note that these probes all recognize the same DNA contig produced by the Mse I digest.

by the consistently elevated Cy3/Cy5 ratios across the promoter region, there was a relative decrease in the amount of methylation in the ND subjects as compared to the controls. This was particularly evident in the second, third and fourth probes covering the region. Bisulfite sequencing of this region of plasmid clones containing inserts from the PCR products of the bisulfite converted DNA samples from cases and controls confirmed those observations and demonstrated a nearly twofold greater amount of unmethylated residues in

TABLE 11

Sequence and Significance of AX2R Probes

| Probe Sequence | Cy3/Cy5 ratio (input to methyl enriched fraction) | | | |
|---|---|---|---|---|
| | Avg Cases | Avg Controls | Difference | Pvalue* |
| ttcaggtgccaggtctggagtgctggtgcacctatctcaaaacgctgtct (SEQ ID NO: 14) | 1.58 | 1.32 | 0.27 | <0.03 |
| gcaaacagcagtccagtaacctggaacaacaggctctgcgaaaccaagga (SEQ ID NO: 15) | 1.84 | 1.48 | 0.36 | <0.005 |
| agaaatgaatggcgttgtcatcgaaaaaacacagactcgattgtgacagaaataccg (SEQ ID NO: 16) | 1.66 | 1.34 | 0.32 | <0.005 |
| tgcgcctccacggaataactgccagccggcacagtgcgagtgagaaaccg (SEQ ID NO: 17) | 1.74 | 1.40 | 0.34 | <0.009 |
| ggaaaagaatccgacgtcgccaacaagcggtgctaccaggagaaacgcct (SEQ ID NO: 18) | 1.52 | 1.29 | 0.23 | <0.09 |
| aaaacacagctggataaaccgagaaccttcggagtggttgcaccgaaacg (SEQ ID NO: 19) | 1.52 | 1.29 | 0.23 | <0.09 |
| gaagcaaccggcagtgctaacaccgaggagcacctagagcggcaaaacta (SEQ ID NO: 20) | 1.18 | 0.86 | 0.32 | <0.04 |

Table 12 gives the average methylation ratios for the sequenced CpG residues in the targeted region. As evidenced the smoking subjects as compared to the controls (average methylation in cases vs controls; 77.6% vs 88.8%, p<0.0001).

TABLE 12

Average Methylation at Bisulfite Sequenced Residues at AX2R

| CG 4 | CG 5 | CG 6 | CG 7 | CG 8 | CG 9 | CG 10 | CG 11 | CG 12 | CG 13 | CG 14 | CG 15 | CG 16 | CG 17 |
|---|---|---|---|---|---|---|---|---|---|---|---|---|---|
| Cases* | | | | | | | | | | | | | |
| 85% | 77% | 78% | 71% | 79% | 78% | 78% | 76% | 79% | 80% | 78% | 71% | 78% | 77% |
| Controls | | | | | | | | | | | | | |
| 88% | 91% | 87% | 92% | 88% | 91% | 87% | 90% | 92% | 92% | 88% | 74% | 94% | 88% |

Average number of residues successfully counted per CpG residue in the cases and controls was 74 and 89, respectively.

Finally, in order to compare our results with respect to previous published results using peripheral lymphocyte DNA (Launay J-M, Del Pino M, Chironi G, Callebert J, Peoc'h K, Megnien J-L, Mallet J, Simon A, Rendu F. 2009. Smoking Induces Long-Lasting Effects through a Monoamine-Oxidase Epigenetic Regulation. PLoS ONE 4(11):e7959), we compared the probe values between cases and controls at this X-chromosome locus. Consistent with prior findings, the amount of methylation at the MAOB promoter was significantly decreased in both males (LR; p<0.006) and females (LR; p<0.007).

Discussion

In summary, it is reported that smoking is associated with both altered overall and locus specific alterations in DNA methylation with particular enrichment of altered methylation in pathways associated with glutamate signaling, cell proliferation and detoxification. Strengths of this study are the well characterized subjects, the similarity of the whole genome promoter array results for males and females, and the sequencing confirmation.

The vast majority of the loci with differential methylation in this study are not directly involved with neurotransmission. Consistent with the role of smoking in cancer and altered DNA methylation part of the oncogenic process, it is logical to find that each of the 7 genes with 3 significant probes have suggested roles in carcinogenesis (Buckanovich R J, Yang Y Y, Darnell R B. 1996. The onconeural antigen Nova-1 is a neuron-specific RNA-binding protein, the activity of which is inhibited by paraneoplastic antibodies. J Neurosci 16(3): 1114-1122; Greenman C, Stephens P, Smith R, Dalgliesh G L, Hunter C, Bignell G, Davies H, Teague J, Butler A, Stevens C and others. 2007. Patterns of somatic mutation in human cancer genomes. Nature 446(7132):153-8; Koike Folgueira M A, Brentani H, Carraro D M, De Camargo Banos Filho M, Hirata Katayama M L, Santana de Abreu A P, Mantovani Barbosa E, De Oliveira C T, Patrao D F, Mota L D and others. 2009. Gene expression profile of residual breast cancer after doxorubicin and cyclophosphamide neoadjuvant chemotherapy. Oncol Rep 22(4):805-13; Ma S, Huang J K, Shen S. 2009. Identification of Cancer Associated Gene Clusters and Genes Via Clustering Penalization. Statistics and Its Interface 2:1-11; Masayoshi M, Naoki K, Manuel J G-R, Tatsuo A, Terry D C, Kunihiro U, Yoshifumi A. 2001. Identification and characterization of SEB, a novel protein that binds to the acute undifferentiated leukemia-associated protein SET. European Journal of Biochemistry 268(5):1340-1351; Wright P K, May F E, Darby S, Saif R, Lennard T W, Westley B R. 2009. Estrogen Regulates Vesicle Trafficking Gene Expression in EFF-3, EFM-19 and MCF-7 Breast Cancer Cells. Int J Clin Exp Pathol 2(5):463-75; Yusuke S, Aaron M H, Younghun J, Anne M Z, Elisabeth A P, Jingcheng W, Jianhua W, Ganwei L, Roodman G D, Robert D L and others. 2008 Annexin II/Annexin II receptor axis regulates adhesion, migration, homing, and growth of prostate cancer. p 370-380). This suggests that the processes affected by smoking in other cells may be reflected in the differential methylation of the lymphoblasts, and that the lymphoblast model may provide a reasonable representation of systemic methylation changes.

In light of this apparent enrichment of genes involved carcinogenesis, it is notable that most significant Gene Ontology (Gene Ontology C. 2004. The Gene Ontology (GO) database and informatics resource. Nucl Acids Res 32(suppl_1):D258-261) pathway identified in the GOMiner™ analysis in this study is the glutamate signaling pathway (on the basis of GRIK2 and SSTR1). GRIK2 gene expression is decreased in the brains of smoking mice (Wang J, Gutala R, Hwang Y, Kim J, Konu O, Ma J, Li M. 2008. Strain- and region-specific gene expression profiles in mouse brain in response to chronic nicotine treatment. p 78-87) and genetic variation in GRIK2 (Vink J M, Smit A B, de Geus E J, Sullivan P, Willemsen G, Hottenga J J, Smit J H, Hoogendijk W J, Zitman F G, Peltonen L and others. 2009. Genome-wide association study of smoking initiation and current smoking Am J Hum Genet. 84(3):367-79) was linked to smoking in recently published GWAS of smoking. These recent and other prior findings support a role for glutamate signaling in the mood altering and drug reinforcing effects of nicotine (Lambe E K, George T P. 2008. Perspective: Translational Studies on Glutamate and Dopamine Neurocircuitry in Addictions: Implications for Addiction Treatment. Neuropsychopharmacology 34(2):255-256). These current results add to that body of evidence and further suggest that the role of glutamate signaling system should receive greater attention in analyses of mechanisms of addiction associated with smoking.

It will be important to identify which of these methylations are static and which are dynamic. In our previous work at MAOA, we found that reduction in methylation was particularly pronounced as a result of smoking cessation and given MAOA's prominence in catabolizing dopamine, we speculated that this epigenetic change could be part of the withdrawal syndrome. Given the current systematic findings, the findings of others with respect to methylation of the MAOB gene promoter (Launay J-M, Del Pino M, Chironi G, Callebert J, Peoc'h K, Megnien J-L, Mallet J, Simon A, Rendu F. 2009. Smoking Induces Long-Lasting Effects through a Monoamine-Oxidase Epigenetic Regulation. PLoS ONE 4(11):e7959) and our results at MAOB, it is unlikely that the MAOA promoter is the only regulatory motif changed after smoking cessation. If so, by studying withdrawal on a genome wide basis, it may be possible to more readily identify the pathways involved in nicotine craving and devise more effective interventions to short circuit this disruptive syndrome that obfuscates effective treatment.

EXAMPLE 5

Methylation Profiling of Alcohol Dependence

The list of RefSeq genes with CpG islands containing two or more significantly probes that were symmetrically associated with active alcohol dependence (p<0.001 nominal) in the genome wide analysis is provided in Table 13. Briefly, to generate this list, the normalized Log 2 hybridization ratios scores were analyzed a two-step process. In the first step, genome wide t-tests were conducted to identify probes whose hybridization values differed between the alcohol cases and controls at a significance level of p<0.001 (uncorrected). A clustering algorithm was then applied to this reduced probe set to identify probes which co-localized to a 1000 bp sliding winding in the same island. Then, the genomic location of the CpG was checked against the HG 18 build of the human genome to identify RefSeq annotated genes associated with the island.

TABLE 13

ABCA12
ABL2
AGBL1
AK097539

TABLE 13-continued

AK125749
AK128353
AK129763
AK309744
AK311380
AKAP12
AMPH
ANKRD53
APBA1
APBB2
ARHGAP10
ARHGEF16
ARL17
ATP6V1E1
BC032407
BC051727
C11orf64
C12orf53
C1orf101
C20orf117
C7orf50
C9orf72
C9orf82
CCBL1
CDC123
CDH5
CHR11:002610294
COL2A1
COPS7A
CPNE4
CR936796
CSMD1
CSRNP3
DGKH
DNHD1
DOCK11
DOCK4
DPY19L4
DYNC1LI1
EDEM2
EMILIN3
EXOC6B
FAM125B
FBXL4
FCGBP
FLJ16779
FOXN3
FXR1
GAD2
GNB3
GRAP2
GTF2I
HCCA2
HEXIM1
HEXIM2
HIP1R
HISPPD1
HOXA2
HSF1
IMAA
IMMT
INTS10
ITGA5
KCNH5
KCNQ1
KLHDC1
KLHL9
LHFPL3
LNPEP
LOC100133545
LOC284805
LRSAM1
MECP2
MIB2
MLL
MPZL1
MYO9B
NAT9
NBPF14
NEAT1

TABLE 13-continued

NF2
NME2P1
NOC2L
NPAS1
ODZ2
ODZ4
PARK2
PDAP1
PDGFA
PDGFRA
PDLIM1
PDXDC2
PDZD2
PEX7
PIH1D1
PLSCR3
PNRC1
PON2
PPM1A
PSG6
QSER1
RAB26
RMND5A
ROS1
RPIA
RSPO1
RUNDC2C
SCT
SDF4
SLCO2B1
SMCR7L
SNTB2
SPATA5
SPDYE3
SPNS2
SRL
STAM2
STK36
SYT13
TANC1
TJP2
TMEM205
TNRC6B
TRAF3IP2
TXNDC11
USP45
UVRAG
VCPIP1
WAC
WASF2
WDR78
WSCD2
XPR1
XRCC5
ZBTB7B
ZDHHC2
ZFHX4
ZFP92
ZNF221
ZNF263
ZNF33A
ZNF423
ZNF623
ZSCAN5A

EXAMPLE 6

Methylation Profiling of Cannabis Dependence

Table 14 provides a list of CpG residues whose methylation was significantly associated with Cannabis Dependences at a nominal p-value of $p<0.05$. For female subjects: CpG 69 and CpG 88. For male subjects: CpG 11-12, 13, 64, 69, 72-73. Unpublished data from Philibert et al., 2008 "MAOA methylation is associated with nicotine and alcohol dependence in women."

The list of RefSeq genes with CpG islands containing two or more significantly probes that were symmetrically associated with active cannabis dependence (p<0.01 nominal) in the genome wide analysis is provided in Table 14. Briefly, to generate this list, the normalized Log 2 hybridization ratios scores were analyzed a two-step process. In the first step, genome wide t-tests were conducted to identify probes whose hybridization values differed between the cannabis cases and controls at a significance level of p<0.01 (uncorrected). A clustering algorithm was then applied to this reduced probe set to identify probes which co-localized to a 1000 bp sliding winding in the same island. Then, the genomic location of the CpG was checked against the HG 18 build of the human genome to identify RefSeq annotated genes associated with the island.

TABLE 14

| | | | | |
|---|---|---|---|---|
| AK056486 | ANKHD1 | LOC283050 | FNTB | SRRD |
| HES4 | RNF14 | GSTO2 | WDR25 | PATZ1 |
| BC033949 | EBF1 | BC132944 | AKT1 | DNAL4 |
| SDF4 | RREB1 | PWWP2B | TMCO5A | CYP2D7P1 |
| AURKAIP1 | TXNDC5 | DRD4 | MGA | MIOX |
| AX747988 | ABT1 | PNPLA2 | CDAN1 | SHOX |
| MSTP2 | GLP1R | HCCA2 | TSPAN3 | CD99 |
| ECE1 | C6orf130 | HCCA2 | C16orf13 | RPL39 |
| C1orf212 | TRERF1 | AK126380 | TMEM159 | MCF2 |
| TEKT2 | TAAR1 | IGF2 | ATP2A1 | |
| STK40 | UST | INS-IGF2 | IMAA | |
| CYP4Z1 | AKAP12 | TRPM5 | IRX3 | |
| PARS2 | FNDC1 | KCNQ1 | RTN4RL1 | |
| NBPF16 | IGF2R | KCNQ1 | TEKT1 | |
| MSTO1 | IGF2R | KCNQ1 | SLC25A35 | |
| KIAA0907 | BC087858 | SLC22A18AS | GAS7 | |
| TOMM40L | AK299216 | NAP1L4 | HS3ST3B1 | |
| PTGS2 | HOXA | OSBPL5 | C17orf76 | |
| AK095633 | AK093987 | MRGPRE | USP22 | |
| OR2T1 | CDK13 | DENND5A | STAT5B | |
| MYT1L | C7orf40 | CALCB | KPNB1 | |
| TSSC1 | GTF2IRD1 | SYT13 | TMEM100 | |
| AK055918 | LMTK2 | APLNR | AXIN2 | |
| EPAS1 | SLC26A5 | MACROD1 | ASPSCR1 | |
| TMEM177 | C7orf60 | KCNK4 | TBCD | |
| GAL3ST2 | FLJ43663 | EHD1 | SETBP1 | |
| EFHB | EXOC4 | PPP2R5B | ST8SIA5 | |
| GLT8D1 | MFHAS1 | CAPN1 | LIPG | |
| GLT8D1 | NUDT18 | PITPNM1 | CTDP1 | |
| ITIH4 | UNC5D | PITPNM1 | BSG | |
| KIAA1013 | DPY19L4 | GPR83 | GPX4 | |
| PDZRN3 | LY6K | NCAM1 | SBNO2 | |
| CGGBP1 | DNAJB5 | OPCML | STK11 | |
| RG9MTD1 | UNC13B | IFFO1 | KIAA1532 | |
| IGSF11 | FXN | SLC2A3 | ALKBH7 | |
| AMOTL2 | C9orf85 | NDUFA4L2 | ICAM1 | |
| GNB4 | PCSK5 | PEBP1 | KCNA7 | |
| RPL39L | AK309476 | SIRT4 | ETFB | |
| MFSD7 | MEGF9 | OASL | ZNF530 | |
| AX748388 | CIZ1 | RSRC2 | TCF15 | |
| CRMP1 | USP20 | RIMBP2 | PSMF1 | |
| PDGFRA | NTNG2 | IFT88 | BTBD3 | |
| H2AFZ | GTF3C5 | PARP4 | SLC12A5 | |
| LARP7 | CAMSAP1 | ESD | EYA2 | |
| CLCN3 | LCNL1 | TPPP2 | ZNF217 | |
| ANKRD37 | C10orf18 | EFS | TPD52L2 | |
| AHRR | STOX1 | C14orf147 | DNAJC5 | |
| IRX1 | CHST3 | SOCS4 | SIK1 | |

EXAMPLE 7

Dose Dependent Impact of Recent Alcohol Use on Genome-Wide DNA Methylation Signatures Together, alcohol use and dependence affect 8% of the adult United States each year and cause over 200 billion dollars of economic damage annually. The mechanism(s) through which alcohol exerts this toll varies. During acute intoxication, much of the economic damage and personal injury results from the increased rate of accidental injury. But after returning to sobriety, the risk for further damage from accidental injury markedly diminishes. However, in the case of the sustained heavy use of alcohol, the risk for increased morbidity does not remit after return to sobriety and the individual remains at increased risk for a large number of medical conditions including hypertension, heart disease, and impaired executive function in the absence of acute intoxication. At the microscopic level, this increased risk can be directly linked to adverse impact on tissue and organ damage. However, at the molecular level, the direct effects of long term alcohol use seem more complex with chronic changes in a number of biochemical pathways being noted.

Some of these cellular changes may be legacies of altered protein folding and trafficking bequeathed to the cell from periods of intoxication. However, most cellular proteins have limited lifetimes before they are intracellularly recycled. Hence, they are unlikely to be directly responsible for some of the chronic dysfunction seen in cells prepared from abstinent alcoholics. Instead, some of these alterations may result from alcohol induced changes in genomic tone, which is defined as the stable transcriptional repertoire of a cell.

The factors that control the "genomic tone" or transcriptional repertoire of the given cell are diverse but can be generally categorized as genetic variation, tissue specific transcriptional activators/repressors and epigenetic factors. Conceivably, chronic alcohol use could affect the type and distribution of both transcriptional and epigenetic factors thus changing the genomic tone of the given cell. Unfortunately, systematic methods for assessing tissue specific transcription factors are not commonly available. In contrast, recent advances in DNA methylation assessment technologies have made genome wide assessment of DNA methylation more accessible.

This advancement is particularly welcome because in prior work using more restricted approaches, we and others have presented evidence that alterations in DNA methylation may be in part responsible for altered genomic tone observed in peripheral blood cells from subjects who chronically use alcohol. However, these studies were limited by the low number of genes surveyed and the limited number of subjects surveyed. In this communication, using the Illumina Human-Methylation450 BeadChip, which interrogates over 485,000 CpG residues, we examine the relationship between alcohol consumption and degree of DNA methylation in lymphoblast DNA prepared from 165 female subjects from the Iowa Adoption Studies, the largest case and control adoption studies of substance use in the world.

Methods

The protocols and procedures used in the Iowa Adoptions Studies (IAS) have been described in detail elsewhere (Yates et al., 1998, The Iowa Adoption Studies Methods and Results; In: LaBuda et al, Ed's., *On the Way to Individuality: Methodological Issues in Behavioral Genetics*, Hauppauge N.Y.; Nova Science Publishers, pp 95-125). In brief, the IAS is a case and control adoption study of the effects of genetic, environmental and gene-environment interactions in the etiology of substance use and antisocial personality. The data used in the current study is derived from interviews with the Semi-Structured Interview for the Assessment of the Genetics of Alcoholism, Version II (Bucholz et al., 1994, A new, semi-structured psychiatric interview for use in genetic linkage studies; a report on the reliability of the SSAGA, *J. Stud.*

*Alcohol*, 55:149-58), during each of the last two waves of the IAS study (1999-2004 and 2005-2009). Using this data, subjects were classified on the basis of their alcohol use in the past six months prior to assessment into four categories: 1) abstinent (no use in the past six months); 2) mild users (use of alcohol in between 1-8 weeks in the past 6 months); 3) moderate users (use of alcohol in between 9 and 25 weeks in the past six months); and 4) heavy users (alcohol use in every week in the past six months). The lymphoblast DNA was derived by Ebstein Barr virus mediated transformation (Caputo et al., 1991, An Effective Method for Establishing Human B Lymphoblastic Cell Lines Using Epstein Barr Virus, *J. Tiss. Cult. Meth.*, 13:39-44) of lymphocytes obtained from blood donated by 165 female subjects during the last wave of the study.

The lymphoblast DNA used in this study was prepared from growth-entrained lymphoblast cell lines using our standard procedures (Philibert et al., 2008, MAOA methylation is associated with nicotine and alcohol dependence in women, *Am. J. Med. Genet. B. Neuropsychiatr. Genet.*, 147:565-70). In brief, on the day before DNA preparation, one-half of the cell media for each culture flask was exchanged. DNA was then prepared from the cell lines twenty four hours later using cold protein precipitation (Lahiri et al., 1993, DNA isolation by a rapid method from human blood samples: effects of $MgCl_2$, EDTA, storage time, and temperature on DNA yield and quality, *Biochem. Genet.*, 31:321-8). After quantification and purity assessment using a Nanodrop (Thermo Scientific, USA) spectrophotometer, DNA was stored at −20° C. and RNA was −80 C until use.

Genome wide DNA methylation of the DNA was assessed using the Illumina HumanMethylation450 BeadChip under contract by the University of Minnesota Genome Center using the protocol specified by the manufacturer and the contractor. The resulting microarray data were inspected for complete bisulfite conversion of the DNA, and average beta values (i.e. average methylation) for each CpG residue were determined using the GenomeStudio V2009.2; Methylation module Version 1.5.5., version 3.2 (Illumina, San Diego). The resulting beta values were exported into Microsoft Excel and JMP (SAS Institute, USA) for data analysis. The HumanMethylation450 BeadChip contains 485,577 probes that recognize at least 20216 unique features. With respect to this sample, >99.7% of the 485,577 probes yielded statistically reliable data.

The methylation status of the serotonin transporter (SLC6A4) promoter region was previously assessed for 163 of the 165 samples using MALDI-TOF mass spectroscopy by Sequenom (San Diego, Calif.) as described previously (Philibert et al., 2008, MAOA methylation is associated with nicotine and alcohol dependence in women, *Am. J. Med. Genet. B. Neuropsychiatr. Genet.*, 147:565-70). Using the sequence annotation files from both the current and the prior studies, we identified CpG residues that were assessed using both technologies. The methylation values for each residue were compared using Least Squares regression.

After logarithmic conversion, data were inspected for outliers and the initial data analyses were conducted using genome wide t-tests. Subsequently, beta values for each of the probes were aligned according to their physical location and the data re-analyzed using paired t-tests over a 11-probe sliding window in order to more adroitly capture methylation signatures over larger regions (Dindot et al., 2009, Epigenetic profiling at mouse imprinted gene clusters reveals novel epigenetic and genetic features at differentially methylated regions, *Genome Res.*, 19:1374-83; Farthing et al., 2008, Global Mapping of DNA Methylation in Mouse Promoters Reveals Epigenetic Reprogramming of Pluripotency Genes, *PLoS Genet.*, 4:e100-16). All genome wide comparisons were corrected for multiple comparisons using the method of Benjamini and Hochberg (1995, Controlling the false discovery rate: a practical and powerful approach to multiple testing, *J. Royal Statist. Soc., Series B, Methodological*, 57:289-300). For select loci, data were analyzed with respect to alcohol use status using ANOVA.

Pathway analysis of differentially methylated genes was conducted using GoMiner™ using default settings (Zeeberg et al., 2003, GoMiner: a resource for biological interpretation of genomic and proteomic data, *Genome Biol.*, 4:1-8). All values reported include nominal and FDR corrected values.

Results

The demographic and clinical characteristics of the 165 female subjects are shown in Table 15. Overall, the subjects were largely white and tended to be their mid-to-late 40s. Consistent with enrichment of the sample for the diathesis of substance use, the majority of the subjects in the study reported the use of alcohol in the past six months with the 28 subjects in the "heavy" use group reporting alcohol use every week for the past 26 weeks while the 50 "moderate" drinkers and the 47 "mild" drinkers reported drinking in 9-25 weeks, and 1 to 8 weeks in the past 26 weeks, respectively. Their current drinking pattern was reflective of their lifetime history of drinking alcohol. Only 5 of the 40 individuals who reported recent abstinence also reported 1 or more symptoms of lifetime alcohol dependence. In contrast, 19 of 28 of the heavy drinking reported one or more symptoms (p<0.01) with 7 of them meeting criteria for a lifetime diagnosis of alcohol dependence (3 or more symptoms). Approximately 50% of the subjects also reported a past or former history of smoking with 27% continuing to smoke at the time of phlebotomy. However, despite the strong epidemiological associations of smoking and drinking behaviors, in this cohort of 165 subjects, there were no significant differences in the rates of smoking between the three groups.

In our initial analyses, we contrasted the methylation values for the 40 abstinent individuals with the values for the 47 mild, 50 moderate and 28 heavy drinkers using genome wide t-tests. The results of those analyses are shown in Table 16. As the table indicates, although some of the values show strong consistency across several partially independent comparisons, by themselves none of the comparisons between individual groups (e.g. heavy drinker vs. mild) are statistically significant after genome wide comparison (best p-value after correction is p<0.25). However, when the moderate and heavy drinkers are pooled together, the comparison at cg05600126, a probe in ABR, a gene known to be involved in vestibular function (Kaartinen et al., 2002, Vestibular dysgenesis in mice lacking Abr and Bcr Cdc42/RacGAPs, *Develop. Dynamics*, 223:517-25), reaches genome wide significance after genome wide correction (p<0.05; Table 17) with several other probes nearly reaching significance.

There appears to be a dose dependent effect of weeks of drinking on both the strength of the overall comparisons (Table 18). Overall, 1711 of the 485,577 probes on the array were nominally significant at the p<0.001 level in the heavy vs. abstinent group comparison (expected value; 486 probes at p<0.001). This number diminishes to 390 probes when comparing the moderate to the abstinent and 128 probes at the p<0.001 level when comparing the mild drinkers to the abstinent drinkers despite the fact that the heavy drinker group was the smallest of the three groups.

This effect is also reflected in the distribution of the differentially methylated probes with respect to their island status. In previous work, it was shown that changes in cell fate preferentially affected CpG methylation based on the location of the residue with respect to their location in the CpG island. To examine whether this was happening with respect to alcohol use, we examined the location of the significantly differentially methylated probes (at the p<0.001 level) using the information contained in the Illumina file annotations. As Table 18 demonstrates, alcohol seems to preferentially affect the probes found in the center of the CpG islands with the proportion of all differentially methylated probes which localized to the center of the islands rising reaching 52% (p<0.0001) in the heavy drinking group.

Next, using a sliding 11 probe window, we examined whether using information from adjacent probes would strengthen the findings with respect with to alcohol use. The effect on significance was profound with values for 19 regional comparisons reaching genome wide significance at the p<0.001 level (Table 19). Not surprisingly, many of the regions are overlapping with the top 4 region comparisons all being found in BLCAP, a chromosome 6 gene with 121 probes localizing to it.

Using the 1711 probes nominally differentiated at the p<0.001 level, we conducted pathway analyses using GoMiner. As Table 20 indicates, pathways that involve large networks of genes, in particular those affecting basic nucleic acid and cellular metabolic processes, were strongly affected which suggests that the effect of alcohol consumption over the most recent 6 months on gene methylation are widespread and not limited to small, circumscribed pathways.

Finally, to determine whether our current array based measurements were valid, we compared the degree of methylation determined by the Illumina platform with the values determine previously for these 165 subjects at the serotonin transporter promoter associated CpG island (SLC6A4) using MALDI-TOF mass spectrophotometer. Overall, 4 CpG residues at this locus were surveyed by both approaches. At each CpG residue, the degree of methylation determined by each method was correlated with the average adjusted r2 equaling ~0.34, which strongly suggests that the current measurements are reliable.

Discussion

In summary, we demonstrate that the pattern of alcohol use over the most recent 6 months is associated with widespread changes in the methylation of lymphoblast DNA derived from middle aged women. These changes are modest, but widespread, affecting a broad portfolio of cellular metabolic processes. Limitations of the current findings include the fact that lymphoblasts are not primary human cells, the modest degree of differential methylation observed at any individual probe and the likely confounding effect of prior alcohol use history on six month use history. Strengths of the manuscript include the high significant multipoint analyses, the internal consistency of the multiple comparisons and the independent verification of methylation signatures at the SLC6A4 locus.

The "dose" dependency of differential DNA methylation observed in the current study was to be expected. Depending on context, alcohol can be viewed as either as a drug or a solvent which makes conceptualizing the observed epigenetic changes described herein as gradated responses to a cellular toxin natural. However, it is important to realize the primary alcohol use variable employed in the current study was number of weeks in the past six months in which the subject drank. To a certain extent, our choice to employ this measure is because our diagnostic instrument, the SSAGA, readily provides this as a recent use metric. It may well be that the choice of a different metric, such as the number of alcoholic beverages consumed in the past two weeks, may have produced more robust findings. However, because of the manner in which the alcohol use questions are asked in our version of this instrument, information for all subjects is not always available or directly comparable. Hence, it may well be that other approaches to quantifying recent alcohol consumption may produce more robust findings. But we feel that the current classification system which captures the pattern of use over an extended period of time may be equally effective and that further analyses using replicate data sets using more complex (e.g. factor analyses) may be the best way to more adroitly define which recent alcohol use measures are most correlated with DNA methylation changes.

The stepwise effect of alcohol use severity on the distribution of the differentially methylated probes with respect to CpG island status is intriguing. In previous work, it was demonstrated that DNA methylation changes associated with assumption of cell fate preferentially affected the less dense outer area of the CpG islands referred to, poetically, as the "shore" (Doi et al., 2009, Differential methylation of tissue- and cancer-specific CpG island shores distinguishes human induced pluripotent stem cells, embryonic stem cells and fibroblasts, Nat. Genet., 41:1350-3). In this survey of the effects of alcohol intake, we observed that overall that greater consumption of alcohol is associated with increased levels of genome wide methylation and that the changes in the most chronically exposed subjects preferentially affects the centers of these islands. Because two thirds of all CpG islands in the genome are promoter associated and hypermethylation of promoter-associated CpG islands is thought to silence gene transcription, it is tempting to speculate that this increased methylation observed at these islands is associated with decreased gene expression at these loci. Unfortunately, because the magnitude of many of these changes in methylation are relatively small and others have observed that the relationship between DNA methylation and gene expression may be complex and weak, directly demonstrating that these changes have biological relevance at any given locus may be difficult. However, the finding that the expression of BLCAP, a gene region that is significantly hypermethylated in our study, was significantly decreased in the nucleus accumbens of ethanol treated rats is encouraging (Rodd et al., 2008, Differential gene expression in the nucleus accumbens with ethanol self-administration in inbred alcohol-preferring rats, Pharmacol. Biochem. Behavior, 89:481-98).

The directionality of the overall changes observed herein is consistent with prior findings. In our single point and sliding window analyses, almost of all of the top thirty most significantly differentially methylated probes or regions were more methylated in heavy alcohol use group. This is very consistent with prior finding by ourselves and others. However, there are a number of exceptions to this rule in this study and we expect that a fuller understanding of differentially regulated pathways in alcoholism to include a rich tapestry of both up-regulated and down-regulated genes.

The results of the gene pathway analyses may seem surprising at first glance. Because many prior investigations of effects of alcohol have focused on the CNS, there is a strong bias in the extant literature with respect to CNS relevant pathways. However, in our pathway analyses, none of the most significant pathways implicated in the current study directly concern neurotransmission. Instead, the most differentially methylated pathways identified in the current study concern general cell metabolic functions such as membrane trafficking and nucleotide synthesis. This may be because that once ingested, alcohol evenly disperses itself through all tissue and although it may affect neurotransmission systems, such as the GABAergic system more prominently than others, none of these are directly receptor mediated effects. Instead, many of the most profound effects of acute alcohol ingestion on somatic function derive from the effect of alcohol on membrane polarity and the isoelectric properties of the cytosolic environment. Because these properties of the membrane and cytosolic compartments are so critical to cellular homeostasis, the processes found in these regions are those which are most affected in the pathway analyses.

In this regard, it is also important to note that despite the fact that alcohol and nicotine use are frequently co-morbid, there were no differences in the frequency of smoking between the four alcohol use groups and controlling for smoking had no effect on the outcomes of the current study. Taken in conjunction with previous findings, these findings suggest that cigarette smoke and alcohol ingestion present unique toxicological challenges to cells that have distinct effects on methylation.

A critical question that is not addressed by the current study is the longevity of the methylation signatures associated with chronic alcohol use. In prior studies of the MAOA locus, we have demonstrated that cessation of smoking has dramatic effects on CpG methylation. Unfortunately, the number of abstinent or nearly abstinent subjects contained within the current study is too small to conduct meaningful tests at the most significant loci for these purposes. Furthermore, not all abstinent individuals in this study were abstinent for the same reasons. Some are abstinent secondary to personal choice while others in our study are abstinent secondary to medical or legal necessity. Controlling for those and other potential confounders such as diet and lifestyle issues in small samples such as this may be difficult.

Assuming that the current findings are replicated, particularly in primary lymphocytes, some of the most critical questions to be addressed concern the relationship of differential DNA methylation to the overall genomic tone of the cell. DNA methylation is assumed to be intimately involved in regulation of genomic tone. Hence, will reversal of the DNA methylation changes restore normal genomic tone? This is an important question because cells isolated from alcoholics also have more structural changes such as shorter telomeres and manifest other signs of cellular senescence such as abnormal post-translational modifications of proteins. Will these indicators of cellular dysfunction similarly revert if the methylation patterns can be reversed through dietary or pharmacological means? If so, defining the methods through which to accomplish this process could have substantial impact in the rehabilitation of those suffering from the mental and physical ravages of alcoholism.

In summary, we report that recent chronic alcohol intake is associated with significant changes in CpG methylation, and in particular, increased hypermethylation of CpG islands. We suggest further studies to confirm and extend these findings using primary cells and convergent epigenetic approaches are indicated.

TABLE 15

Clinical Characteristics of the 165 Female Iowa Adoptions Studies Probands

| | DRINKING STATUS | | | |
|---|---|---|---|---|
| | Abstinent | Mild | Moderate | Heavy |
| N | 40 | 47 | 50 | 28 |
| Age | 47 ± 8 | 46 ± 8 | 44 ± 8 | 46 ± 8 |
| Ethnicity | | | | |
| White | 38 | 45 | 49 | 26 |
| Other | 2 | 2 | 1 | 2 |
| Smoking Status | | | | |
| Current Smoker | 7 | 9 | 13 | 9 |
| Former Smoker | 11 | 11 | 15 | 9 |
| Never | 22 | 27 | 22 | 10 |
| Lifetime DSM IV Alcohol Dependence Symptom Counts Sxs | | | | |
| 0 | 35 | 28 | 31 | 9 |
| 1 | 4 | 9 | 8 | 7 |
| 2 | 4 | 5 | 5 | 5 |
| 3 | 3 | 2 | 2 | 3 |
| 4 | 1 | 1 | 2 | 4 |
| 5 | 0 | 0 | 1 | 0 |
| 6 | 1 | 0 | 1 | 0 |
| 7 | 1 | 1 | 0 | 0 |

TABLE 16

The Top 30 Most Significantly Associated Probes for Individual Alcohol Group Comparison.

| Probe ID | GENE | Placement | Island Status | Average Methylation for each use group | | | | Nominal p-values for group comparisons | | |
|---|---|---|---|---|---|---|---|---|---|---|
| | | | | Abs | Mild | Mod | Heavy | Heavy vs Abs | Mod vs Abs | Heavy vs Mild |
| cg24023553 | | | N Shore | 0.10 | 0.11 | 0.11 | 0.12 | 2.64 E−06 | 0.0021 | 0.0280 |
| cg20310749 | SHC4 | TSS1500 | S Shore | 0.05 | 0.06 | 0.06 | 0.07 | 2.68 E−06 | 0.0068 | 0.0008 |
| cg23865067 | ARPP19 | Body | N Shore | 0.08 | 0.08 | 0.08 | 0.09 | 3.58 E−06 | 0.0080 | 0.1053 |
| cg05559557 | | | Island | 0.89 | 0.90 | 0.90 | 0.90 | 3.75 E−06 | 0.0565 | 0.0042 |
| cg24268236 | CEP63 | TSS200 | Island | 0.09 | 0.09 | 0.09 | 0.10 | 3.98 E−06 | 0.0014 | 0.5055 |
| cg09966309 | RPS6KA2 | Body | | 0.27 | 0.22 | 0.21 | 0.15 | 5.85 E−06 | 0.0026 | 0.0510 |
| cg23818046 | CENPK | TSS1500 | Island | 0.06 | 0.07 | 0.07 | 0.07 | 6.06 E−06 | 0.0005 | 0.0774 |
| cg22640209 | DOCK10 | Body | N Shore | 0.05 | 0.06 | 0.06 | 0.06 | 6.92 E−06 | 0.0023 | 0.0045 |
| cg05128246 | KHDRBS3 | Body | Island | 0.04 | 0.04 | 0.04 | 0.05 | 7.61 E−06 | 0.0029 | 0.0682 |
| cg07211915 | MAP3K15 | TSS200 | Island | 0.44 | 0.46 | 0.45 | 0.48 | 7.61 E−06 | 0.0017 | 0.1484 |
| cg02606081 | HRAS | TSS1500 | Island | 0.13 | 0.13 | 0.14 | 0.15 | 8.47 E−06 | 0.0026 | 0.0085 |
| cg12502823 | MGC70857 | Body | Island | 0.06 | 0.07 | 0.07 | 0.08 | 8.86 E−06 | 0.0007 | 0.1258 |
| cg05497240 | C5orf4 | 3'UTR | | 0.83 | 0.84 | 0.85 | 0.85 | 8.89 E−06 | 0.0038 | 0.0005 |
| cg26248486 | BBS10 | TSS200S | Shore | 0.07 | 0.07 | 0.07 | 0.07 | 1.00 E−05 | 0.0249 | 0.0003 |
| cg26213873 | CTTNBP2NL | 5'UTR | Island | 0.10 | 0.11 | 0.12 | 0.12 | 1.03 E−05 | 0.0427 | 0.0000 |

TABLE 16-continued

The Top 30 Most Significantly Associated Probes for Individual Alcohol Group Comparison.

| Probe ID | GENE | Placement | Island Status | Average Methylation for each use group | | | | Nominal p-values for group comparisons | | |
|---|---|---|---|---|---|---|---|---|---|---|
| | | | | Abs | Mild | Mod | Heavy | Heavy vs Abs | Mod vs Abs | Heavy vs Mild |
| cg16480634 | ACTR2 | 3'UTR | | 0.61 | 0.65 | 0.62 | 0.68 | 1.04 E−05 | 0.1278 | 0.5470 |
| cg17879912 | TNFAIP8 | Body | | 0.77 | 0.78 | 0.79 | 0.80 | 1.11 E−05 | 0.0034 | 0.0049 |
| cg23554129 | | | Island | 0.11 | 0.11 | 0.12 | 0.12 | 1.13 E−05 | 0.0024 | 0.0019 |
| cg00717297 | TMEM120B | Body | | 0.85 | 0.86 | 0.86 | 0.87 | 1.14 E−05 | 0.0001 | 0.0055 |
| cg12999103 | ATP13A2 | Body | Island | 0.12 | 0.12 | 0.12 | 0.13 | 1.28 E−05 | 0.0004 | 0.0409 |
| cg16551665 | CDK5R1 | TSS200 | Island | 0.12 | 0.12 | 0.12 | 0.13 | 1.32 E−05 | 0.0006 | 0.0130 |
| cg03461296 | TAF4 | Body | N Shore | 0.83 | 0.84 | 0.84 | 0.85 | 1.36 E−05 | 0.0246 | 0.0041 |
| cg12361155 | ADO | TSS200 | Island | 0.07 | 0.07 | 0.07 | 0.08 | 1.43 E−05 | 0.0366 | 0.0367 |
| cg25253419 | NUCB1 | TSS200S | Shore | 0.09 | 0.10 | 0.10 | 0.11 | 1.46 E−05 | 0.0172 | 0.0064 |
| cg18634443 | TBPL1 | 3'UTR | | 0.63 | 0.66 | 0.66 | 0.67 | 1.54 E−05 | 0.3750 | 0.0003 |
| cg05353415 | GLI3 | 5'UTR | Island | 0.07 | 0.08 | 0.08 | 0.08 | 1.58 E−05 | 0.6627 | 0.0053 |
| cg02988255 | GPR44 | Body | Island | 0.78 | 0.79 | 0.80 | 0.81 | 1.61 E−05 | 0.0014 | 0.0013 |
| cg05944623 | PRPF31 | 5'UTR | Island | 0.08 | 0.08 | 0.08 | 0.09 | 1.62 E−05 | 0.0001 | 0.0079 |
| cg01766534 | MRPL44 | 1stExon | Island | 0.08 | 0.08 | 0.08 | 0.09 | 1.64 E−05 | 0.0025 | 0.0320 |
| cg15090909 | TBC1D9B | Body | Island | 0.86 | 0.87 | 0.87 | 0.88 | 1.69 E−05 | 0.0022 | 0.0006 |

Abbreviations: Abs = abstinent, Mod = moderate, S = south, and N = north.
All methylation values are average beta values.

TABLE 17

The Top 30 Most Significantly Associated Probes in the Abstinent vs Pooled Moderate and Heavy Drinkers Analysis

| Probe ID | GENE | Placement | Island Status | Average Methylation | | | H vs Abs | Mod vs Abs | H&Mod vs Abs | BH Corrected Value |
|---|---|---|---|---|---|---|---|---|---|---|
| | | | | Abst | Mod | Heavy | | | | |
| cg05600126 | ABR | Body | N Shore | 0.80 | 0.83 | 0.83 | 3.15E−05 | 7.58E−06 | 1.02E−07 | 0.05 |
| cg00004209 | | | N Shelf | 0.74 | 0.78 | 0.78 | 0.000201 | 5.49E−05 | 6.12E−07 | 0.07 |
| cg26213873 | CTTNBP2NL | 5'UTR | Island | 0.10 | 0.12 | 0.12 | 1.03E−05 | 2.32E−05 | 8.21E−07 | 0.07 |
| cg02678356 | ZXDA | 1stExon | S Shore | 0.22 | 0.28 | 0.29 | 0.000266 | 1.27E−05 | 8.49E−07 | 0.07 |
| cg09978321 | CEBPG | TSS200 | Island | 0.02 | 0.03 | 0.03 | 0.000122 | 5.81E−06 | 9.01E−07 | 0.07 |
| cg03033398 | ZNF746 | Body | S Shelf | 0.83 | 0.85 | 0.85 | 5.20E−05 | 3.61E−05 | 9.10E−07 | 0.07 |
| cg27044202 | TRIM66 | TSS1500 | | 0.86 | 0.88 | 0.88 | 6.30E−05 | 4.81E−05 | 1.73E−06 | 0.11 |
| cg21050392 | HYLS1 | 5'UTR | S Shore | 0.06 | 0.07 | 0.07 | 0.000135 | 1.17E−05 | 1.76E−06 | 0.11 |
| cg07832337 | ATP2C2 | 5'UTR | Island | 0.11 | 0.06 | 0.06 | 4.03E−05 | 0.000115 | 2.07E−06 | 0.11 |
| cg16131534 | TBC1D22A | TSS1500 | Island | 0.05 | 0.06 | 0.06 | 0.000473 | 3.18E−06 | 2.64E−06 | 0.13 |
| cg03589311 | VPS52 | Body | S Shelf | 0.88 | 0.89 | 0.89 | 0.000831 | 1.30E−05 | 3.52E−06 | 0.13 |
| cg23246509 | TMEM109 | 3'UTR | N Shelf | 0.83 | 0.85 | 0.85 | 7.20E−05 | 0.000151 | 3.72E−06 | 0.13 |
| cg02800384 | BANP | Body | Island | 0.88 | 0.90 | 0.89 | 0.002061 | 5.30E−05 | 5.15E−06 | 0.13 |
| cg17714794 | BNIP1 | 1stExon | | 0.06 | 0.07 | 0.07 | 0.000365 | 5.21E−05 | 5.19E−06 | 0.13 |
| cg05497240 | C5orf4 | 3'UTR | | 0.83 | 0.85 | 0.85 | 8.89E−06 | 0.000503 | 5.32E−06 | 0.13 |
| cg23363818 | ZNF433 | Body | N Shelf | 0.73 | 0.76 | 0.76 | 0.000453 | 5.95E−05 | 5.90E−06 | 0.13 |
| cg07086112 | RHOBTB2 | Body | N Shelf | 0.77 | 0.79 | 0.79 | 0.000840 | 6.17E−05 | 6.07E−06 | 0.13 |
| cg20258580 | IGF1R | Body | Island | 0.85 | 0.86 | 0.87 | 0.000107 | 0.000146 | 6.19E−06 | 0.13 |
| cg00164894 | USP24 | Body | | 0.79 | 0.81 | 0.81 | 0.000189 | 0.000253 | 6.30E−06 | 0.13 |
| cg24885794 | SGCE | TSS1500 | Island | 0.39 | 0.42 | 0.42 | 0.000854 | 4.57E−05 | 6.32E−06 | 0.13 |
| cg03279631 | | | | 0.82 | 0.85 | 0.86 | 0.000875 | 0.000682 | 6.38E−06 | 0.13 |
| cg26248486 | BBS10 | TSS200S | Shore | 0.07 | 0.07 | 0.07 | 1.00E−05 | 0.000338 | 6.79E−06 | 0.13 |
| cg12740512 | C20orf94 | 5'UTR | S Shore | 0.05 | 0.05 | 0.05 | 0.000414 | 1.66E−05 | 6.89E−06 | 0.13 |
| cg13563193 | PDCD5 | Body | Island | 0.04 | 0.05 | 0.05 | 0.000878 | 2.97E−05 | 7.01E−06 | 0.13 |
| cg01534273 | FAM108A1 | Body | Island | 0.55 | 0.60 | 0.61 | 0.000266 | 0.000110 | 7.08E−06 | 0.13 |
| cg18634443 | TBPL1 | 3'UTR | | 0.63 | 0.66 | 0.67 | 1.54E−05 | 0.000345 | 7.27E−06 | 0.13 |
| cg03721017 | ELL | Body | S Shore | 0.85 | 0.87 | 0.87 | 0.000182 | 0.000649 | 7.49E−06 | 0.13 |
| cg03936229 | MSI2 | Body | | 0.81 | 0.82 | 0.83 | 0.000153 | 0.000244 | 7.59E−06 | 0.13 |
| cg07574621 | XPC | TSS200 | Island | 0.02 | 0.03 | 0.03 | 9.96E−05 | 0.000307 | 7.78E−06 | 0.13 |
| cg09008753 | SMAP1 | Body | S Shore | 0.06 | 0.06 | 0.06 | 0.000709 | 2.72E−05 | 9.12E−06 | 0.13 |

* Nominal P-value before Benjamini-Hochberg Step Up correction, Abbreviations: Abs = abstinent, Mod = moderate, H = heavy, S = south, and N = north.
All methylation values are average beta values.

TABLE 18

Relative enrichment of CpG values with respect to Island Status and Extent of Alcohol Use

| Location | All Probes | | Mild User | | Moderate User | | Heavy User | |
|---|---|---|---|---|---|---|---|---|
| Island | 150254 | 30.94% | 47 | 36.7% | 203 | 37.9% | 894 | 52.3% |
| S_Shore | 49197 | 10.13% | 6 | 4.7% | 26 | 4.9% | 48 | 2.8% |
| N_Shore | 62870 | 12.95% | 17 | 13.3% | 67 | 12.5% | 200 | 11.7% |
| N_Shelf | 24844 | 5.12% | 7 | 5.5% | 21 | 3.9% | 36 | 2.1% |
| S_Shelf | 22300 | 4.59% | 21 | 16.4% | 73 | 13.6% | 186 | 10.9% |
| No Annotation | 176112 | 36.27% | 30 | 23.4% | 146 | 27.2% | 347 | 20.3% |
| | 485577 | | 128 | | 536 | | 1711 | |

TABLE 19

The Top 30 Most Significantly Associated 11 Probe Regions.

| Probe ID | GENE | Placement | Island Status | Average Methylation Abs | Average Methylation Heavy | P value* | Step Up P-value |
|---|---|---|---|---|---|---|---|
| cg24338351 | BLCAP | 5'UTR | Island | 0.69 | 0.76 | 1.86E−10 | 4.75E−05 |
| cg24675557 | BLCAP | 5'UTR | Island | 0.68 | 0.75 | 2.36E−10 | 4.75E−05 |
| cg01466133 | BLCAP | 5'UTR | Island | 0.71 | 0.77 | 3.86E−10 | 4.75E−05 |
| cg20479660 | BLCAP | 5'UTR | Island | 0.68 | 0.74 | 3.91E−10 | 4.75E−05 |
| cg07557337 | RAB1B | TSS200 | Island | 0.07 | 0.07 | 1.29E−08 | 0.0011 |
| cg26522319 | C1orf103 | 1stExon | Island | 0.05 | 0.06 | 1.53E−08 | 0.0011 |
| cg02898883 | RAB1B | TSS1500 | Island | 0.07 | 0.07 | 1.69E−08 | 0.0011 |
| cg03436478 | SGCE, PEG10 | | S_Shore | 0.51 | 0.52 | 2.28E−08 | 0.0013 |
| cg09337653 | SIN3A, SIN3A | | Island | 0.08 | 0.08 | 3.29E−08 | 0.0016 |
| cg27535677 | | | N_Shore | 0.70 | 0.75 | 3.30E−08 | 0.0016 |
| cg20041873 | SGCE, PEG10 | | S_Shore | 0.51 | 0.53 | 3.86E−08 | 0.0017 |
| cg07156273 | BLCAP | 5'UTR | Island | 0.71 | 0.77 | 4.87E−08 | 0.0019 |
| cg24141738 | ERMAP, CCDC23 | | Island | 0.04 | 0.05 | 5.25E−08 | 0.0019 |
| cg15473473 | BLCAP | 5'UTR | Island | 0.71 | 0.77 | 6.14E−08 | 0.0020 |
| cg04303139 | SGCE, PEG10 | | S_Shore | 0.51 | 0.52 | 6.34E−08 | 0.0020 |
| cg01758634 | SIN3A | TSS1500 | Island | 0.07 | 0.08 | 6.87E−08 | 0.0020 |
| cg05509218 | SGCE, PEG10 | | S_Shore | 0.49 | 0.51 | 8.89E−08 | 0.0025 |
| cg22421148 | BLCAP | 5'UTR | Island | 0.66 | 0.73 | 9.73E−08 | 0.0026 |
| cg03759229 | | | N_Shore | 0.68 | 0.73 | 1.14E−07 | 0.0029 |
| cg22893248 | ACTR3C | 1stExon | Island | 0.07 | 0.10 | 1.25E−07 | 0.0030 |
| cg20631204 | ZNF562 | TSS200 | Island | 0.11 | 0.13 | 1.34E−07 | 0.0031 |
| cg02639123 | ACTR3C, LRRC61 | | S_Shore | 0.21 | 0.23 | 1.47E−07 | 0.0031 |
| cg01959416 | ACTR3C, LRRC61 | | S_Shore | 0.07 | 0.10 | 1.47E−07 | 0.0031 |
| cg12862537 | BLCAP | 5'UTR | Island | 0.76 | 0.82 | 1.63E−07 | 0.0031 |
| cg22497095 | | | N_Shore | 0.70 | 0.75 | 1.64E−07 | 0.0031 |
| cg21516287 | ACTR3C, LRRC61 | | S_Shore | 0.14 | 0.16 | 1.68E−07 | 0.0031 |
| cg26544607 | ARRDC3 | | S_Shelf | 0.07 | 0.07 | 1.88E−07 | 0.0032 |
| cg04558861 | LIN37 | TSS200 | N_Shore | 0.12 | 0.13 | 1.89E−07 | 0.0032 |
| cg22510412 | BLCAP | 5'UTR | Island | 0.64 | 0.70 | 2.00E−07 | 0.0032 |
| cg19998456 | GGA1 | TSS200 | Island | 0.05 | 0.06 | 2.03E−07 | 0.0032 |

*Nominal P-value before Benjamini-Hochberg Step Up correction.
Abbreviations: Abs = abstinent, S = south, and N = north.
All methylation values are average beta values.

TABLE 20

The Top 30 Most Differentially Regulated Gene Ontology Pathways

| GO Category | Category Name | Genes Total | Genes Changed | $Log^{10}$ P-Value | FDR |
|---|---|---|---|---|---|
| GO: 0005622 | intracellular | 1123 | 1951 | 21.91 | 0 |
| GO: 0044424 | intracellular part | 10940 | 925 | −19.83 | 0 |
| GO: 0044237 | cellular met. process | 7595 | 690 | −18.24 | 0 |
| GO: 0006139 | nucleobase nucleoside nucleotide and nucleic acid met. process | 4399 | 440 | −16.19 | 0 |
| GO: 0044260 | cellular macromolecule met. process | 5765 | 543 | −15.58 | 0 |

TABLE 20-continued

The Top 30 Most Differentially Regulated Gene Ontology Pathways

| GO Category | Category Name | Genes Total | Genes Changed | $Log^{10}$ P-Value | FDR |
|---|---|---|---|---|---|
| GO: 0034641 | cellular nitrogen compound met. process | 4797 | 467 | −15.22 | 0 |
| GO: 0005634 | nucleus | 5248 | 500 | −14.80 | 0 |
| GO: 0043231 | intracellular membrane bounded organelle | 8408 | 732 | −14.74 | 0 |
| GO: 0043227 | membrane bounded organelle | 8414 | 732 | −14.66 | 0 |
| GO: 0043229 | intracellular organelle | 9334 | 795 | −14.43 | 0 |
| GO: 0090304 | nucleic acid met. process | 3811 | 385 | −14.34 | 0 |
| GO: 0043226 | organelle | 9349 | 795 | −14.21 | 0 |
| GO: 0044238 | primary met. process | 7696 | 678 | −14.06 | 0 |
| GO: 0006807 | nitrogen compound met. process | 4893 | 468 | −13.82 | 0 |
| GO: 0008152 | met. process | 8521 | 734 | −13.53 | 0 |
| GO: 0044428 | nuclear part | 2407 | 262 | −12.72 | 0 |
| GO: 0043170 | macromolecule met. process | 6318 | 569 | −12.42 | 0 |
| GO: 0005488 | binding | 11509 | 925 | −11.14 | 0 |
| GO: 0044446 | intracellular organelle | 5465 | 498 | −11.10 | 0 |
| GO: 0044422 | organelle part | 5532 | 501 | −10.73 | 0 |
| GO: 0031323 | regulation of cellular met. process | 3834 | 368 | −10.37 | 0 |
| GO: 0050794 | regulation of cellular process | 6319 | 557 | −10.23 | 0 |
| GO: 0080090 | regulation of primary met. process | 3632 | 350 | −9.99 | 0 |
| GO: 0051325 | interphase | 329 | 58 | −9.96 | 0 |
| GO: 0005654 | nucleoplasm | 1204 | 145 | −9.84 | 0 |
| GO: 0034645 | cellular macromolecule biosynthetic process | 3598 | 346 | −9.74 | 0 |
| GO: 0009059 | macromolecule biosynthetic process | 3664 | 350 | −9.51 | 0 |
| GO: 0051171 | regulation of nitrogen compound me process | 3153 | 309 | −9.47 | 0 |
| GO: 0007049 | cell cycle | 1142 | 138 | −9.47 | 0 |
| GO: 0005515 | protein binding | 6815 | 589 | −9.47 | 0 | metabolic = met.,
FDR = false discovery rate.

EXAMPLE 8

Coordinated Changes in AHRR Methylation in Lymphoblasts and Pulmonary Macrophages from Smokers Despite extensive preventative and treatment interventions, approximately 19% of American adults smoke on a daily basis (Center for Disease Control (CDC) 2011). This is a substantial problem because smoking is the leading preventable cause of premature morbidity and mortality. Smoking causes approximately 450,000 premature deaths annually through its effects on the incidence of cancer, heart disease and chronic obstructive pulmonary disease (CDC 2005). National data indicate that while both prevalence of smoking and mortality from lung cancer have significantly decreased for men between 1975 and 2007, these rates did not decrease for any racial or ethnic group or for women. In addition, projections suggest that because women who were born around 1960 have higher prevalence of smoking and morbidity than other cohorts, this gender disparity may increase.

Many of the effects of smoking on the lung are thought to result from the direct effects of cigarette smoke on pulmonary epithelium and alveolar macrophages. However, the exact mechanism(s) through which smoking increases the risk for disease in non-pulmonary tissues such as blood and brain are unclear. Recently, sets of convergent findings have suggested that a portion of that vulnerability may be driven by differential DNA methylation acquired by smoking.

Altered DNA methylation that results from genetic lesions present at conception has long been established as a cause of disorders affecting early development of disease in the soma and the CNS. With respect to non-CNS disease, altered imprinting that usually results from maternal monosomy at 15QQ causes Prader-Willi syndrome. With respect to the CNS disease, almost all cases of Rett Syndrome result from mutations in MECBP2 which exert their effects by altering DNA methylation. Guided by clues such as the observations that addition of folate, a methyl donor, to the diets of pregnant women, markedly decreases the frequency of neural tube defects, the field has embraced the concept that alterations in DNA methylation may be associated with acquired early onset developmental disorders as well. However, whether environmentally acquired alterations could increase likelihood of disease in adults has been an open question. A number of single gene and genome wide studies provide evidence that altered DNA methylation is associated with smoking and may be a cause of smoking associated illness. In particular, using both genome wide and single gene approaches, we have demonstrated that altered DNA methylation is associated with smoking (see above Examples). However, these studies have been hindered by low coverage of the total number of genes and CpG residues in the human genome and discrepancies as to the appropriateness of certain forms of biomaterials for studies of epigenetic phenomena.

In this communication, we report our results with respect to smoking status on genome wide methylation and focal gene expression using two independent sets of biomaterials: 1) lymphoblast DNA and RNA derived from 119 female subjects from the Iowa Adoption Studies (IAS) and 2) alveolar macrophage DNA from cells isolated from the lungs of 10 smokers and 9 non-smokers.

Methods

Human Subjects. The first set of biomaterials was obtained from subjects participating in the Iowa Adoptions Studies (IAS) (Yates et al., 1998, The Iowa Adoption Studies Methods and Results. In: LaBuda et al., Ed's, *On the Way to Individuality: Methodological Issues in Behavioral Genetics*, Hauppauge N.Y., Nova Science Publishers, pp 95-125). In brief, the IAS is a case and control adoption study of the role of genetic, environmental and gene-environment interactions in the etiology of common behavioral illness. The clinical material used in the current study is derived from interviews with the Semi-Structured Interview for the Assessment of the Genetics of Alcoholism, Version II (Bucholz et al., 1994, A new, semi-structured psychiatric interview for use in genetic linkage studies: a report on the reliability of the SSAGA, *J. Stud. Alcohol*, 55:149-58), during each of the last two waves of the IAS study (1999-2004 and 2005-2009). The biological material used in this study, lymphoblast cell lines, was derived by Epstein Barr virus mediated transformation (Caputo et al., 1991, An Effective Method for Establishing Human B Lymphoblastic Cell Lines Using Epstein Barr Virus, *J. Tiss. Cult. Meth.*, 13:39-44) of lymphocytes obtained from blood donated by 165 female subjects during the last wave of the study.

The second set of biomaterials for the current study was alveolar macrophages obtained by bronchoalveolar lavage. Subjects were recruited from the community via advertisements and word-of-mouth. In order to be included, case (smoking) subjects had to be actively smoking with at least 10 pack year history of smoking. To be included as a control, the subject had to deny ever smoking cigarettes. Subjects were excluded if they had any significant co-morbid conditions such as pregnancy, or if a baseline spirometry revealed the Forced Expiratory Volume in the first second (FEV1) was less than 60% of predicted. All of these procedures and protocols were approved by the University of Iowa Institutional Review Board.

Bronchoalveolar Lavage. To obtain human alveolar macrophages, a bronchoalveolar lavage was performed. After informed consent was obtained, subjects underwent standard flexible bronchoscopy. After the application of local anesthesia, bronchoalveolar lavage was performed by instilling 20 ml of normal saline into a tertiary bronchus up to five times in three different lung segments. The first collection out of five was discarded for possible contamination from upper airway secretions or by lidocaine, which is used to locally anesthetize the subject during the procedure. The remaining lavage was transported to the laboratory where fluid was filtered through sterile gauze and centrifuged at 200×g for 5 min to pellet cellular material. The resulting pellet was suspended in phosphate buffered saline and centrifuged at 16,000×g for one minute. The macrophages were suspended in medium, labeled with Wright stain and microscopically examined to ensure that greater than 95% of the cells were macrophages.

DNA and RNA Isolation. The lymphoblast DNA and RNA used in this study was prepared from growth-entrained cell lines according to our standard procedures (Philibert et al., 2008, MAOA methylation is associated with nicotine and alcohol dependence in women, *Am. J. Med. Genet. B. Neuropsychiatr. Genet.*, 147B:565-70). In brief, on the day before DNA preparation, one-half of the cell media for each culture flask was exchanged. Twenty four hours later, DNA was prepared from the cell lines using cold protein precipitation. Simultaneously, RNA was purified from independent aliquots of the same culture using RNA Midi kits (Invitrogen, USA) according the instructions of the manufacturer. After quantification and purity assessment using a Nanodrop (Thermo Scientific, USA) spectrophotometer, DNA was stored at −20° C. and RNA was stored at −80° C. until use.

DNA and RNA were isolated from alveolar macrophages using the Qiagen DNAeasy™ kit (Qiagen, Valencia, Calif.) and MirVana (Applied Biosystems, Austin, Tex.) reagents according to manufacturer's instructions. Quality assessment was by Nanodrop and Experion (Bio-Rad Experion Automated Electrophoresis Station). After preparation, DNA was stored at −20° C. and RNA was stored at −80° C. until use.

DNA Methylation. Genome wide DNA methylation of the DNA was assessed using the Illumina HumanMethylation450 BeadChip under contract by the University of Minnesota Genome Center using the protocol specified by the manufacturer and the contractor. The resulting microarray data were inspected for complete bisulfite conversion of the DNA, and average beta values (i.e. average methylation) for each CpG residue were determined using the GenomeStudio V2009.2; Methylation module Version 1.5.5., version 3.2 (Illumina, San Diego). The resulting beta values were exported into Microsoft Excel and JMP (SAS Institute, USA) for data analysis. The HumanMethylation450 BeadChip contains 485,577 probes that recognize at least 20216 unique features (i.e. potential transcripts). With respect to this sample, >99.76% of the 485,577 probes yielded statistically reliable data.

Data Analysis. After logarithmic conversion, data were inspected for outliers or confounding by plate or chip variables, then the initial data analyses were conducted using genome wide t-tests. Subsequently, beta values for each of the probes were aligned according to their physical location and the data re-analyzed using paired t-tests over a 11-probe sliding window in order to more adroitly capture methylation signatures over larger regions (Dindot et al., 2009, Epigenetic profiling at mouse imprinted gene clusters reveals novel epigenetic and genetic features at differentially methylated regions, *Genome Res.*, 19:1374-83; Farthing et al., 2008, Global Mapping of DNA Methylation in Mouse Promoters Reveals Epigenetic Reprogramming of Pluripotency Genes, *PLoS Genet.*, 4:e100-16). All genome wide comparisons were corrected for multiple comparisons using the method of Benjamini and Hochberg (1995, Controlling the false discovery rate: A practical and powerful approach to multiple testing, *J. Royal Statistical Soc., Series B, Methodological*, 57:289-300). For select loci, data were analyzed with respect to alcohol use status using ANOVA.

Pathway analysis of differentially methylated genes was conducted using GoMiner™ using default settings (0.05 settings for reports and all gene ontology as the root category setting) using the gene set specified in the text as the "changed" gene set (Zeeberg et al., 2003, GoMiner: a resource for biological interpretation of genomic and proteomic data, *Genome Biol.*, 4:1-8). All values reported include nominal and FDR corrected values.

Specific qRT-PCR Analysis of AHRR. The relative expression of AHRR was determined using primer probe sets from ABI, a Fluidigm BioMark™ System and proprietary BioMark Real-Time Analysis software according to manufacturer's guidelines. Briefly, first, RNA was converted to cDNA using an ABI cDNA archiving kit according to manufacturer's suggestions. Then after a brief pre-amplification step, each cDNA sample was amplified in quadruplicate with using primer probes for AHRR (Hs01005075) and five housekeeping genes (CALR, RPL7A, PRS19, RPS20 and UBC) obtained from Applied Biosystems (Foster City, USA). The Ct counts exported to the database, normalized using the geometric mean of five housekeeping genes, then converted to Z scores for statistical analysis.

Results

Iowa Adoption Study Cohort. The demographic and clinical characteristics of the 165 female subjects whose genome wide methylation status was assessed are shown in Table 21. Overall, the subjects were largely white and tended to be in their mid-to-late 40s. Consistent with enrichment of the sample for the diathesis of substance use, the majority of the subjects in the study reported daily smoking at some period of their lives (85 of 165). However, many of these individuals (n=46) have quit smoking or were not smoking every day at the time of phlebotomy leaving only 39 subjects reporting daily smoking (i.e. seven days per week every week) at the time of phlebotomy. Because our prior studies have indicated that they methylation signature of those subjects who had recently quit smoking is highly variable, those 46 individuals were excluded from further study (Philibert et al., 2010, The effect of smoking on MAOA promoter methylation in DNA prepared from lymphoblasts and whole blood, *Am. J. Med. Genet. B. Neuropsychiatr. Genet.*, 153B:619-28). The number of cigarettes smoked daily by the 39 subjects who smoked daily varied from 4 to 40 with the average number of cigarettes consumed daily being 19 cigarettes or about a pack per day for greater than 20 years. Cigarette smoking tended to be the only form of nicotine use currently being manifested by these 39 subjects with none of the subjects reporting the concomitant use of cigars, chew or other forms of nicotine usage in 2 weeks prior to assessment. There were no significant differences between the three groups (current smokers, never smokers, non-daily smokers/quitters) with respect to alcohol use in the past six months or age.

We contrasted the methylation values for the 39 smokers (average beta value 0.443) with the values for the 80 non-smokers (average beta value 0.446) using single point genome wide t-tests. The results of those analyses are shown in Table 22. As the table indicates, only one probe, cg14817490, which maps to intron 3 of the of the aryl hydrocarbon receptor repressor (AHRR), survived genome wide Benjamini-Hochberg correction for multiple comparisons. However, it is interesting to note that 3 other probes from AHRR, cg05575921, cg14454127, and cg03991871, were ranked among the top 13 probes and that none of them were from the rather small promoter associated CpG island. Instead, all 4 of the top AHRR probes target the gene body which contains three (>100 CpG residues) large CpG island according the UCSC genome browser. Finally, we note that cg03636183, a probe that was reported to be significantly associated with smoking status in lymphocyte DNA, was also nominally associated (p<0.003; rank 802nd of 485577 probes; smoker average 0.67; non-smoker average 0.74) with smoking status in the current study (Breitling et al., 2011, Tobacco-Smoking-Related Differential DNA Methylation: 27K Discovery and Replication, *Am. J. Human Genet.*, 88:450-7).

One possible concern is that some of the differential methylation signature could be secondary to alcohol use. Therefore, even though there were no significant differences between the rate of drinking for smoker and non-smoker groups, we analyzed the data for alcohol-related changes. The relationship of methylation to alcohol intake over the past 6 months to the methylation at loci controlling for alcohol use status was examined. Only two of the top 30 probes, cg07812589 and cg17231418, were even nominally related to amount of alcohol intake in the past 6 months, both at a p-value of 0.04<x<0.05. Hence, there does not appear to be any effect of alcohol intake on the methylation status at the most differentially methylated loci.

Next, as part of our analyses, we conducted a sliding window analysis using an 11-probe window and the same groups of case and control subjects. Table 23 describes the result of those analyses. The addition of the methylation data immediately flanking each probe increased the overall significance of the findings with 36 comparisons surviving genome wide correction. Not surprisingly, many of the top thirty probes from the analysis tended to lie immediately adjacent to one another. Interestingly, despite the strength of four AHRR probes in the single probe analyses, the gene region containing these probes, which is interrogated by 149 separate markers, was not included in this list of top regions. Inspection of this locus shows that differential methylation was largely confined to the 2 or 3 probe windows surrounding each of these residues with each of these areas being several thousand base pairs apart (Appendix A).

Using GoMiner™, we conducted gene pathway analyses using the information from the 273 probes that were nominally differentially methylated at the p<0.001 level. Table 24 shows the top 30 most differentially methylated pathways. Overall, only one pathway, protein kinase C (PKC) activity, survived false discovery rate (FDR) correction at the p<0.05 level. However, a recurrent theme of differential methylation in gene pathways affecting ion transport was found in many of the other less significant top thirty pathways.

Human Alveolar Macrophage Data. Because some may have concerns about the reliability of lymphoblast ability to model the changes found in their cognate lymphocytes and other primary cell types, we repeated these same case and control analyses using DNA from pulmonary alveolar macrophages again using a case and control paradigm. The case macrophages were isolated from the lungs of 10 smokers with at least a 10 year history of ≥1 ppd smoking (6 male and 3 female) while the control macrophage biomaterial set was isolated from 9 non-smokers (6 male and 4 female). Although these two groups were roughly matched for ethnicity (smokers: 8 White, 2 African Americans; non-smokers: 9 White), the control group was significantly younger than the smoking group (smokers 31±3 yrs, non-smokers 40±4 yrs, p<0.01).

The results of the genome wide single probe contrasts are illustrated in Table 25. Overall, the effects of smoking were much more profound with 1381 probes surviving correction for genome wide comparison at a p<0.05 level. Of considerable interest given recent data suggesting a prominent role for AHRR in carcinogenesis, 8 probes from AHRR, including the $3^{rd}$ ranked probe, cg25648203, were significantly associated after correction for genome wide comparisons. But of the top 4 AHRR probes from the lymphoblast analyses, only cg05575921 was significantly associated after Bonferroni correction.

We next repeated the sliding window analyses for the macrophage data using the same method delineated above. Once again, the results (see Table 26) were more robust than those for the lymphoblast data with 40 eleven probe regions being significantly associated after correction for multiple comparisons. Although many highly interesting genes were once again implicated in this analysis, AHRR was once again notable with the 28th ranked 11 probe region being found in the body of the AHRR.

As a last part of our set of analyses with respect to the macrophage methylation data, we repeated the GoMiner pathway analyses using the list of 1381 probes which were significantly associated in the above analyses as our changed gene set. Table 27 shows those results of those analyses. In brief, pathways involved with wound healing, inflammation and G-protein/ras signaling were particularly prominent.

Figure 9:
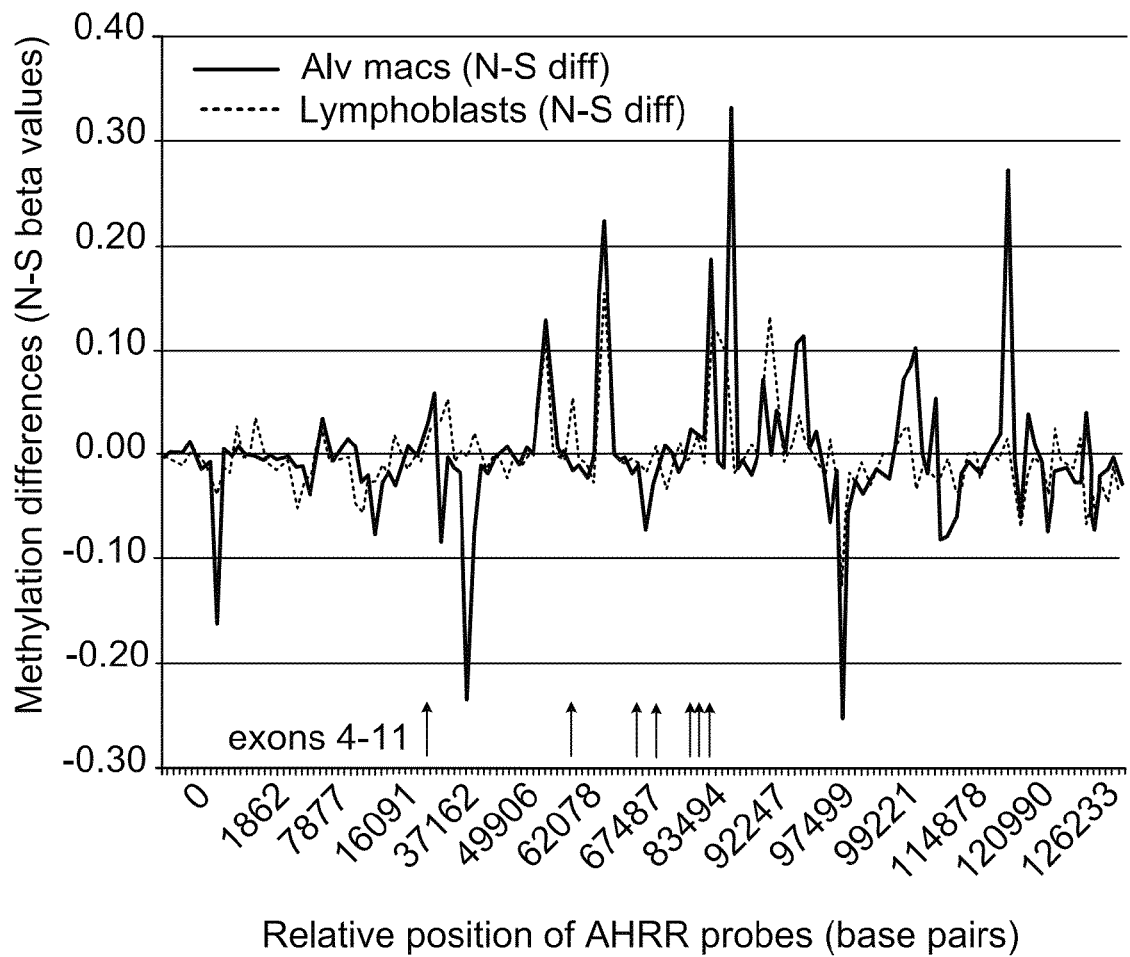
FIG. 9. Comparison of the smoking associated differential methylation signatures (average non-smoker beta-value minus average smoker beta value) for lymphoblast (red) and pulmonary macrophage (blue) DNA. The relative position of the 146 probes listed in Appendix A on the X-axis with the position of AHRR exons 4 (left) through 11 (right) being noted. Please also note that exon 7 and 8 are sufficiently close to represented by a single arrow.

Comparison of Lymphoblast and Macrophage Data. In both the macrophage and lymphoblast analyses, probes from AHRR were repeatedly associated with smoking status. Therefore, we compared the methylation signatures from these two biomaterials with respect to smoking status. Appendix A details the average methylation and single point analyses for each of the 146 probes for the gene for each biomaterial. In brief, 14 probes in the lymphoblast analyses and 40 of the probes in the macrophage analyses were associated with smoking status at a $p<0.05$ with 8 of the 14 probes in the lymphoblast analyses also being nominally significantly associated with smoking status in the macrophages with the direction of methylation being consistent at each probe (greater methylation in smokers). The overall methylation signature between the control lymphoblasts and macrophages at AHRR was highly correlated ($r=0.95$). FIG. 9 illustrates the relationship between the differential methylation at each of the 146 residues listed in Appendix A for the lymphoblast and macrophage DNA samples. As FIG. 9 shows, the differential methylation signature was also highly correlated across the gene with over 20% of the differential methylation signature that was associated with smoking status being shared between the two DNA sources ($r=0.45$; $p<0.001$).

An advantage of lymphoblasts is the ability to easily create high-quality RNA for gene expression studies. Therefore, to determine whether this differential methylation had functional consequences on lymphoblast gene expression, we then analyzed the relationship between AHRR gene expression and methylation status at cg05575921, the AHRR probe with the most consistent associations in the two analyses, using RNA prepared from the case and control samples. Interestingly, increasing methylation at this probe was associated with decreasing lymphoblast AHRR gene expression ($p<0.03$, $n=108$), which suggests that the CpG residues in this region may have a functional in vivo role in regulating gene expression at this locus.

Discussion

In summary, we report that cigarette smoking is associated with significant changes in genome wide methylation, and in particular, AHRR methylation, in DNA derived from pulmonary alveolar macrophages and lymphoblasts. Strengths of this manuscript include confirmation of the findings from lymphoblast DNA, which are immortalized lymphocytes, with data from primary tissue from the lungs of smokers and the presentation of evidence that these changes at AHRR may be functional. Possible limitations include the relative poor matching of the subjects who contributed lymphoblast and pulmonary macrophage DNA.

The most significant and consistent finding in the current study is with respect to AHRR locus. AHHR is a feedback inhibition modulator of AHR that exerts its effects by competing with AHR for binding with its cognate nuclear receptor dimer partner (AHR nuclear translocator) or at xenobiotic response elements in AHR regulated genes. This feedback modulation plays a pivotal role in AHR regulation and may be critical in moderating AHR role in oncogenesis and altered immune function. Our finding of smoking associated methylation at AHRR is highly plausible for several reasons. First and foremost, smoking is the leading preventable cause of cancer. Hence, this association may explain part of the connection. Second, the direction of the differential methylation was consistent among the 8 AHRR probes with nominal significance in both lymphoblast and macrophage comparisons with a high degree of shared smoking associated differential methylation. Third, AHRR was the only gene locus that had significant localizations in both studies after correction for multiple comparisons. Fourth, previous studies have shown that smoking induces production of the aryl hydrocarbon receptor (AHR), a process which is thought to be critical for certain forms of smoking related forms of carcinogenesis. Assuming that the decreased methylation at AHRR seen in smokers in the current study may result from a feedback mechanism associated with smoking induction of AHR transcription, the current findings are very consistent with previous findings and suggest potential avenues for addressing AHR mediated neoplastic transformation. Unfortunately, even given the promising gene expression findings, rigorous testing of this hypothesis may be difficult because review of the Ensembl and UCSC genome browser databases demonstrates the presence of three large CpG islands that are interspersed throughout the gene and at least 11 AHRR transcripts, each of which codes for a differently sized protein that may have unique competitive properties with respect to AHR. Hence, while the current findings are encouraging, a more definitive understanding of relationship between AHHR methylation and both AHRR gene expression and AHR function may require more complex and detailed examination of this region.

The pathway analyses of the macrophage data were illuminating and consistent with our understanding of the effects of smoking. The macrophage data was characterized by changes in inflammation, wound healing and Ras/G-protein signaling pathways. The repeated finding of altered methylation in Ras/G-protein signaling pathways seems logical since activation of these proteins are thought to be part of the oncogenic process for many types of cancers. Similarly, the recurrent identification of wound healing and inflammatory pathways seems logical since smoking is the leading cause of Chronic Obstructive Pulmonary Disease (COPD), a syndrome in which the vast morbidity of the pathology is secondary to inflammatory moderated remodeling of the lung epithelium. In contrast, the results of the lymphoblast analyses were less robust with only two pathways, related to peptidyl-threonine modification (PKC), surviving FDR correction. However, it is important to note that, while both pathways are closely related, with the basis of their significance in our analyses relying on the same five probes, the omission of one probe from either of these comparisons would result in nonsignificant findings.

The comparative weakness of the methylation findings in lymphoblasts as compared to macrophages highlight the importance of incorporating studies of primary tissues directly exposed to the substance in question. Overall, the smoking associated differential methylation was markedly more pronounced in the alveolar macrophage DNA than in the lymphoblast DNA. This is probably because circulating lymphocytes are less exposed to the direct effects of smoke than the macrophages resident in the lung. However, it is possible that our conversion of these same lymphocytes into the transformed lymphoblast cell lines may further weaken the smoking induced signal. The latter possibility needs to be considered because although lymphoblast cell lines are excellent models of the lymphocytes from which they are derived, lymphoblast lines are vulnerable to clonal selection artifacts and there are well documented differences between lymphocyte and lymphoblast gene expression. The fact that the lymphoblasts by definition proliferate in non-smoking conditions, may impact the data. If the smoking methylation changes are dependent on continued in vivo smoke exposure, then replication in culture may mute the findings. This supports the importance of examining primary cells along with lymphoblasts.

It should be recognized that most investigators use Ficoll separated mononuclear cell pellets rather than purified lymphocytes. Since these "lymphocyte pellets" contain a variety of cell types including B-lymphocytes, T-lymphocytes, monocytes and Natural Killer T-cell, it may well be that use of this heterogeneous cell mix may have obscured other potential findings which may explain why only one differentially methylated probe was previously identified despite using a similar number of subjects.

Beyond the relative merits of lymphocyte and lymphoblast preparations, the current findings suggest that the lymphoblast lines paired with primary pulmonary macrophages will be useful in other investigations of the epigenetics of smoking because: 1) smoking has a broad effect on tissues throughout the body including the blood, and 2) integration of histone modification and gene expression status with DNA methylation status will require large numbers of cells. Some types of histone modification examinations necessitate relatively larger amounts of fresh cellular material. This suggests the utility of lymphoblasts in histone modification studies. A clear picture of lymphoblast gene expression and DNA methylation data relative to a primary smoking-relevant cell (alveolar macrophages) data will be needed for these potential future studies. In this respect, our convergent finding in lymphocytes and macrophages with respect to AHRR are reassuring.

One potential direction for future work is the determination of the specific AHRR transcripts that are differentially affected by differential methylation. The Taqman™ gene expression probe for AHRR used in this study (Hs01005075) recognizes the exon 3-exon 4 boundary that is included in most splice variants. However, given the numerous splice variants produced by this gene, the epigenetic complexity of the gene (e.g. three large CpG islands not associated with the promoter), and its putative role in oncogenesis, future studies that examine specific splice variants altered by smoking is warranted.

The relationship of gene methylation to histone code modification should also be explored. In particular, the relationship of H3K4 and H3K27 methylation and H3K27 acetylation to AHRR gene expression should be examined because of the strong relationship of these modifications to gene expression. Though DNA methylation is thought to have a weaker relationship to gene expression, if we can establish a stronger understanding of the histone-DNA modification relationship on a genome wide level, it well may be that we can use DNA methylation at loci such as AHRR as a proxy for histone status, and thereby gene expression status. Studies of DNA methylation are much cheaper and easier to conduct than histone modification studies. A better understanding of the relationship of peripheral blood methylation to methylation in other tissues, such as brain, may allow more informative studies of the role of DNA methylation and other forms of epigenetic changes in normal and disease related human development.

In summary, we report that cigarette smoking is associated with genome wide changes in lymphoblast and pulmonary macrophage DNA methylation, in particular at AHRR. We suggest replication and extension of the current findings and further investigations of the role of epigenetic changes in smoking altered gene expression.

TABLE 21

Clinical Characteristics of the 165 Female Iowa Adoptions Studies Probands

|  | Non-Smoker | Quit or Quitting | Daily Smoker |
|---|---|---|---|
| N | 80 | 46 | 39 |
| Age | 46 ± 8 | 47 ± 8 | 43 ± 6 |
| Ethnicity |  |  |  |
| White | 80 | 44 | 39 |
| Other | 0 | 4 | 0 |
| Alcohol in Past 6 months |  |  |  |
| Yes | 58 | 35 | 29 |
| No | 22 | 11 | 7 |
| Daily Cigarette Usage |  |  | 19 ± 9 |

TABLE 22

The Top 30 Most Significantly Differentially Methylated Probes in Lymphoblast DNA

| Probe ID | GENE | Placement | Island Status | N-Smoker Avg | Smoker AVG | T-test | Corrected P-value |
|---|---|---|---|---|---|---|---|
| cg14817490 | AHRR | Body |  | 0.24 | 0.12 | 2.71E−08 | 0.02 |
| cg05575921 | AHRR | Body | N Shore | 0.85 | 0.70 | 1.34E−06 | 0.29 |
| cg07313705 |  | S Shelf |  | 0.07 | 0.10 | 1.78E−06 | 0.29 |
| cg14454127 | AHRR | Body |  | 0.44 | 0.31 | 2.72E−06 | 0.34 |
| cg02486161 | NOD2 | 3'UTR |  | 0.70 | 0.59 | 2.53E−05 | 0.99 |
| cg14983684 | RAD51L1 | Body |  | 0.75 | 0.71 | 2.58E−05 | 0.99 |
| cg23939642 | SLC38A10 | Body |  | 0.50 | 0.33 | 2.66E−05 | 0.99 |
| cg25325005 | PLEC1 | Body | N Shelf | 0.63 | 0.41 | 2.96E−05 | 0.99 |
| cg23335946 | C1orf25 | 1$^{st}$Exon | Island | 0.08 | 0.09 | 3.14E−05 | 0.99 |
| cg20776920 | UNC5D | TSS1500 | N Shore | 0.87 | 0.83 | 3.21E−05 | 0.99 |
| cg26812418 | CPE | TSS200 | Island | 0.05 | 0.07 | 4.09E−05 | 0.99 |
| cg07812589 |  |  |  | 0.26 | 0.20 | 4.59E−05 | 0.99 |
| cg03991871 | AHRR | Body | N Shore | 0.78 | 0.67 | 4.97E−05 | 0.99 |

TABLE 22-continued

The Top 30 Most Significantly Differentially Methylated Probes in Lymphoblast DNA

| Probe ID | GENE | Placement | Island Status | N-Smoker Avg | Smoker AVG | T-test | Corrected P-value |
|---|---|---|---|---|---|---|---|
| cg27545205 | | | Island | 0.02 | 0.02 | 5.26E−05 | 0.99 |
| cg10951975 | TRPM4 | Body | Island | 0.35 | 0.22 | 5.49E−05 | 0.99 |
| cg20370184 | SLC44A4 | Body | | 0.27 | 0.12 | 5.64E−05 | 0.99 |
| cg07999887 | CPNE3 | 5'UTR | Island | 0.02 | 0.02 | 5.92E−05 | 0.99 |
| cg08644463 | GNAI3 | Body | | 0.87 | 0.83 | 6.83E−05 | 0.99 |
| cg04366249 | SGCE | 1stExon | Island | 0.05 | 0.07 | 7.34E−05 | 0.99 |
| cg12741529 | C3orf17 | Body | | 0.87 | 0.85 | 7.75E−05 | 0.99 |
| cg08940570 | LOXL3 | 5'UTR | N Shore | 0.80 | 0.66 | 9.09E−05 | 0.99 |
| cg23754924 | RGMA | Body | Island | 0.10 | 0.13 | 9.56E−05 | 0.99 |
| cg24547565 | RUSC1 | TSS1500 | N Shore | 0.51 | 0.62 | 9.85E−05 | 0.99 |
| cg17093877 | MGC16275 | Body | N Shelf | 0.57 | 0.43 | 0.00010 | 0.99 |
| cg21545248 | HMGXB3 | Body | | 0.77 | 0.71 | 0.00011 | 0.99 |
| cg22012583 | LASS2 | TSS1500 | Island | 0.37 | 0.25 | 0.00011 | 0.99 |
| cg17231418 | ESX1 | Body | Island | 0.26 | 0.39 | 0.00011 | 0.99 |
| cg12668122 | TMEM108 | Body | | 0.40 | 0.31 | 0.00012 | 0.99 |
| cg19776793 | SLC38A10 | Body | | 0.43 | 0.25 | 0.00013 | 0.99 |
| cg02724404 | LYSMD4 | TSS1500 | S Shore | 0.88 | 0.84 | 0.00013 | 0.99 |

All average methylation values are non-log transformed beta-values. Island status refers to the position of the probe relative to the island. Classes include: 1) Island, 2) N (north) shore, 3) S (south) shore, 4) N (north shelf), 5) S (south) shelf and 6) blank denoting that the probe does not map to an island.

TABLE 23

The Top 30 Most Significantly Differentially Methylated Regions in Lymphoblast DNA

| Probe ID | GENE | Placement | Island Status | Average Methylation | | P value* | Corrected P-value |
|---|---|---|---|---|---|---|---|
| | | | | N-Smoker | Smoker | | |
| cg13581859 | HLA-DPB1 | Body | Island | 0.66 | 0.79 | 2.31E−09 | 0.002 |
| cg25511667 | HLA-DPB1 | Body | Island | 0.69 | 0.85 | 7.34E−09 | 0.002 |
| cg14801692 | HLA-DPB1 | Body | Island | 0.62 | 0.70 | 1.40E−08 | 0.003 |
| cg03636880 | HLA-DPB1 | Body | Island | 0.64 | 0.77 | 1.81E−08 | 0.003 |
| cg01132696 | HLA-DPB1 | Body | Island | 0.64 | 0.81 | 2.30E−08 | 0.003 |
| cg10850215 | HLA-DPB1 | Body | Island | 0.64 | 0.76 | 3.07E−08 | 0.003 |
| cg02692313 | HLA-DPB1 | Body | Island | 0.66 | 0.83 | 4.14E−08 | 0.003 |
| cg03229061 | HLA-DPB1 | Body | Island | 0.62 | 0.71 | 4.53E−08 | 0.003 |
| cg17588455 | HLA-DPB1 | Body | Island | 0.62 | 0.73 | 5.55E−08 | 0.003 |
| cg19990651 | HLA-DPB1 | Body | Island | 0.65 | 0.83 | 6.80E−08 | 0.004 |
| cg14870156 | HLA-DPB1 | Body | Island | 0.66 | 0.79 | 7.47E−08 | 0.004 |
| cg06437840 | HLA-DPB1 | Body | Island | 0.52 | 0.69 | 8.16E−08 | 0.004 |
| cg26645432 | HLA-DPB1 | Body | Island | 0.71 | 0.86 | 1.00E−07 | 0.004 |
| cg20223237 | HLA-DPB1 | Body | Island | 0.73 | 0.88 | 1.24E−07 | 0.005 |
| cg25796439 | ISM1 | TSS1500 | Island | 0.08 | 0.08 | 1.26E−07 | 0.006 |
| cg12893780 | HLA-DPB1 | Body | Island | 0.67 | 0.82 | 1.84E−07 | 0.006 |
| cg19759481 | HOXA5 | TSS200 | Island | 0.63 | 0.54 | 1.99E−07 | 0.007 |
| cg04863892 | HOXA5 | TSS200 | Island | 0.68 | 0.60 | 2.53E−07 | 0.008 |
| cg01992382 | TNXB | Body | Island | 0.42 | 0.47 | 2.74E−07 | 0.008 |
| cg01370449 | HOXA5 | TSS200 | Island | 0.69 | 0.63 | 3.11E−07 | 0.010 |
| cg12746059 | PCDH10 | TSS200 | Island | 0.08 | 0.09 | 3.95E−07 | 0.02 |
| cg13349035 | HLA-DPB1 | Body | N Shore | 0.68 | 0.80 | 4.72E−07 | 0.02 |
| cg09549073 | HOXA5 | 5'UTR | Island | 0.68 | 0.60 | 6.91E−07 | 0.02 |
| cg02916332 | HOXA5 | TSS1500 | Island | 0.64 | 0.58 | 7.89E−07 | 0.02 |
| cg12128839 | HOXA5 | TSS200 | Island | 0.56 | 0.47 | 8.21E−07 | 0.02 |
| cg17569124 | HOXA5 | TSS1500 | Island | 0.57 | 0.48 | 8.90E−07 | 0.02 |
| cg06831576 | CDH8 | TSS200 | Island | 0.11 | 0.15 | 1.00E−06 | 0.02 |
| cg04525757 | FOXG1 | TSS1500 | N Shore | 0.14 | 0.15 | 1.25E−06 | 0.03 |
| cg26242583 | LUZP2 | TSS200 | Island | 0.11 | 0.13 | 1.35E−06 | 0.03 |
| cg19714132 | FOXG1 | TSS1500 | N Shore | 0.19 | 0.21 | 1.58E−06 | 0.03 |

*Nominal P-value before Benjamini-Hochberg correction. Corrected value is per Benjamini-Hochberg method.

TABLE 24

The Top 30 Most Differentially Regulated Pathways in Lymphoblast DNA

| GO Category | Category Name | Genes Total | Genes Changed | Log$^{10}$ P-Value | FDR |
|---|---|---|---|---|---|
| GO: 0018107 | peptidyl-threonine phosphorylation | 27 | 5 | −5.03 | 0.01 |
| GO: 0018210 | peptidyl-threonine modification | 30 | 5 | −4.80 | 0.01 |
| GO: 0060914 | heart formation | 9 | 3 | −4.00 | 0.09 |
| GO: 0009653 | anatomical structure morphogenesis | 1490 | 31 | −3.53 | 0.15 |
| GO: 0045121 | membrane raft | 160 | 8 | −3.45 | 0.14 |
| GO: 0007548 | sex differentiation | 181 | 8 | −3.10 | 0.24 |
| GO: 0005024 | TGF beta receptor activity | 18 | 3 | −3.05 | 0.20 |
| GO: 0007530 | sex determination | 18 | 3 | −3.05 | 0.20 |
| GO: 0003007 | heart morphogenesis | 104 | 6 | −3.03 | 0.18 |
| GO: 0004675 | transmembrane receptor protein serine threonine kinase activity | 19 | 3 | −2.97 | 0.19 |
| GO: 0003197 | endocardial cushion development | 5 | 2 | −2.94 | 0.22 |
| GO: 0005026 | TGF beta receptor activity type II | 5 | 2 | −2.94 | 0.22 |
| GO: 0060021 | palate development | 46 | 4 | −2.82 | 0.26 |
| GO: 0051015 | actin filament binding | 48 | 4 | −2.75 | 0.33 |
| GO: 0030501 | pos. reg. of bone mineralization | 23 | 3 | −2.73 | 0.33 |
| GO: 0070169 | pos. reg. of biomineral tissue dev. | 24 | 3 | −2.67 | 0.33 |
| GO: 0003128 | heart field specification | 7 | 2 | −2.63 | 0.31 |
| GO: 0003129 | heart induction | 7 | 2 | −2.63 | 0.31 |
| GO: 0051864 | histone demethylase activity | 7 | 2 | −2.63 | 0.31 |
| GO: 0061311 | cell surface receptor linked signaling pathway involved in heart dev. | 7 | 2 | −2.63 | 0.31 |
| GO: 0060389 | SMAD protein phosphorylation | 25 | 3 | −2.62 | 0.30 |
| GO: 0001649 | osteoblast differentiation | 86 | 5 | −2.62 | 0.29 |
| GO: 0005901 | caveola | 53 | 4 | −2.59 | 0.29 |
| GO: 0031095 | platelet tubular network membrane | 8 | 2 | −2.51 | 0.32 |
| GO: 0035173 | histone kinase activity | 8 | 2 | −2.51 | 0.32 |
| GO: 0046541 | saliva secretion | 8 | 2 | −2.51 | 0.32 |
| GO: 0045669 | pos. reg. of osteoblast differentiation | 28 | 3 | −2.48 | 0.33 |
| GO: 0070838 | divalent metal ion transport | 229 | 8 | −2.45 | 0.32 |
| GO: 0045778 | pos. reg. of ossification | 29 | 3 | −2.43 | 0.33 |
| GO: 0030154 | cell differentiation | 2041 | 35 | −2.43 | 0.32 | dev. = development,
pos. reg. = positive regulation,
FDR = false discovery rate.

TABLE 25

The Top 30 Most Significantly Differentially Methylated Probes in Alveolar Macrophage DNA

| Probe ID | GENE | Placement | Island Status | N-Smoker Avg | Smoker AVG | T-test | Corrected P-value |
|---|---|---|---|---|---|---|---|
| cg06961313 | MR1 | TSS1500 | | 0.80 | 0.57 | 1.06E−10 | 5.16201E−05 |
| cg00738897 | | | S_Shore | 0.71 | 0.55 | 1.90E−09 | 0.0003 |
| cg25648203 | AHRR | Body | | 0.38 | 0.72 | 1.97E−09 | 0.0003 |
| cg00506299 | RFTN1 | Body | | 0.23 | 0.46 | 2.67E−09 | 0.0003 |
| cg27229484 | ZC3H12A | Body | | 0.26 | 0.53 | 3.34E−09 | 0.0003 |
| cg05951221 | | | Island | 0.28 | 0.42 | 5.85E−09 | 0.0005 |
| cg01432692 | | | | 0.20 | 0.37 | 7.69E−09 | 0.0005 |
| cg09374353 | EHD1 | 3'UTR | N_Shore | 0.12 | 0.39 | 1.05E−08 | 0.0006 |
| cg14310198 | RAPGEF1 | Body | | 0.48 | 0.70 | 1.90E−08 | 0.0010 |
| cg21566642 | | | Island | 0.33 | 0.56 | 2.12E−08 | 0.0010 |
| cg17576603 | DAB2 | 5'UTR | | 0.39 | 0.62 | 3.36E−08 | 0.0013 |
| cg17574812 | ABHD6 | Body | | 0.26 | 0.49 | 3.55E−08 | 0.0013 |
| cg06634140 | | | | 0.30 | 0.54 | 3.73E−08 | 0.0013 |
| cg11254522 | FGR | Body | | 0.35 | 0.50 | 3.99E−08 | 0.0013 |
| cg07457727 | | | N_Shelf | 0.22 | 0.60 | 4.02E−08 | 0.0013 |
| cg13458803 | CD80 | 5'UTR | | 0.36 | 0.16 | 4.86E−08 | 0.0014 |
| cg01668352 | SRGAP1 | Body | | 0.32 | 0.62 | 4.97E−08 | 0.0014 |
| cg04402828 | KIAA1026 | Body | | 0.47 | 0.35 | 6.69E−08 | 0.0018 |
| cg07650681 | LOC100132354 | Body | | 0.66 | 0.40 | 7.19E−08 | 0.0018 |
| cg13610455 | LOC388796 | Body | | 0.29 | 0.44 | 7.37E−08 | 0.0018 |
| cg09127592 | TRIM35 | Body | N_Shelf | 0.33 | 0.73 | 8.72E−08 | 0.0019 |
| cg14223856 | | | | 0.43 | 0.81 | 9.60E−08 | 0.0019 |
| cg09006487 | RYBP | 3'UTR | | 0.35 | 0.50 | 9.69E−08 | 0.0019 |
| cg02233197 | TNFAIP8L3 | Body | S_Shelf | 0.29 | 0.72 | 9.85E−08 | 0.0019 |
| cg05317600 | | | | 0.34 | 0.65 | 9.86E−08 | 0.0019 |
| cg25466245 | SUSD4 | Body | | 0.36 | 0.57 | 1.09E−07 | 0.0020 |
| cg21418854 | C1orf113 | TSS1500 | N_Shore | 0.42 | 0.58 | 1.13E−07 | 0.0020 |

TABLE 25-continued

The Top 30 Most Significantly Differentially Methylated Probes in Alveolar Macrophage DNA

| Probe ID | GENE | Placement | Island Status | N-Smoker Avg | Smoker AVG | T-test | Corrected P-value |
|---|---|---|---|---|---|---|---|
| cg02341139 | | | S_Shelf | 0.34 | 0.60 | 1.17E−07 | 0.0020 |
| cg18030943 | LAMP3 | Body | N_Shelf | 0.23 | 0.38 | 1.20E−07 | 0.0020 |
| cg05337681 | LIPC | Body | | 0.23 | 0.47 | 1.25 −07 | 0.0020 |

All average methylation values are non-log transformed beta-values. Island status refers to the position of the probe relative to the island. Classes include: 1) Island, 2) N (north) shore, 3) S (south) shore, 4) N (north shelf), 5) S (south) shelf and 6) blank denoting that the probe does not map to an island.

TABLE 26

The Top 30 Most Significantly Differentially Methylated Regions in Alveolar Macrophage DNA

| Probe ID | GENE | Placement | Island Status | Average Methylation N-Smoker | Smoker | P value* | Corrected P-value |
|---|---|---|---|---|---|---|---|
| cg07965566 | | | | 0.60 | 0.30 | 2.40E−28 | 1.16E−22 |
| cg14310198 | RAPGEF1 | Body | | 0.70 | 0.48 | 4.83E−26 | 1.17E−20 |
| cg17574812 | ABHD6 | Body | | 0.49 | 0.26 | 9.83E−25 | 1.59E−19 |
| cg01668352 | SRGAP1 | Body | | 0.62 | 0.32 | 1.76E−24 | 2.14E−19 |
| cg17576603 | DAB2 | 5'UTR | | 0.62 | 0.39 | 2.52E−23 | 2.45E−18 |
| cg07457727 | | | | 0.60 | 0.22 | 3.98E−21 | 3.22E−16 |
| cg10169462 | | | | 0.13 | 0.06 | 1.30E−15 | 9.05E−11 |
| cg24790419 | KIAA1683 | TSS1500 | | 0.62 | 0.39 | 1.54E−15 | 9.38E−11 |
| cg04402828 | KIAA1026; | Body | | 0.35 | 0.47 | 3.16E−15 | 1.70E−10 |
| cg05951221 | | | | 0.42 | 0.28 | 4.80E−12 | 2.33E−07 |
| cg16039867 | MKNK1 | Body | | 0.58 | 0.78 | 2.50E−11 | 1.10E−06 |
| cg06634140 | | | | 0.54 | 0.30 | 9.81E−10 | 3.97E−05 |
| cg20485084 | FGR | Body | | 0.67 | 0.36 | 1.91E−09 | 7.16E−05 |
| cg02341139 | | | | 0.60 | 0.34 | 6.35E−09 | 0.0002 |
| cg22019569 | SMYD3 | Body | | 0.60 | 0.75 | 1.38E−08 | 0.0004 |
| cg14019523 | ASB2 | Body | | 0.37 | 0.24 | 2.11E−08 | 0.0006 |
| cg13675814 | CORO2A | 5'UTR | | 0.67 | 0.82 | 6.95E−08 | 0.0018 |
| cg04307274 | | | | 0.57 | 0.31 | 6.96E−08 | 0.0018 |
| cg15149645 | NUPR1 | TSS200 | | 0.59 | 0.75 | 9.66E−08 | 0.0024 |
| cg10192877 | ABCG1 | Body | | 0.61 | 0.74 | 1.20E−07 | 0.0028 |
| cg21566642 | | | | 0.56 | 0.33 | 1.24E−07 | 0.0028 |
| cg20568305 | GRAMD4 | Body | | 0.68 | 0.52 | 2.95E−07 | 0.0065 |
| cg01432692 | | | | 0.37 | 0.20 | 3.35E−07 | 0.0070 |
| cg24446429 | MBP | Body | | 0.60 | 0.39 | 3.88E−07 | 0.0075 |
| cg14414943 | CHI3L2 | Body | | 0.83 | 0.89 | 3.89E−07 | 0.0075 |
| cg16659773 | | | | 0.56 | 0.43 | 4.16E−07 | 0.0077 |
| cg04135110 | AHRR | Body | | 0.15 | 0.38 | 5.29E−07 | 0.0095 |
| cg00738897 | | | | 0.55 | 0.71 | 6.03E−07 | 0.0104 |
| cg13458803 | CD80 | 5'UTR | | 0.16 | 0.36 | 7.97E−07 | 0.0133 |
| cg11691844 | SYTL2 | Body | | 0.27 | 0.44 | 8.63E−07 | 0.0139 |

*Nominal P-value before Benjamini-Hochberg correction. Corrected value is per Benjamini-Hochberg method.

TABLE 27

The Top 30 Most Differentially Regulated Gene Ontology Pathways in Macrophage DNA

| GO Category | Category Name | Genes Total | Genes Changed | $\log^{10}$ P-Value | FDR |
|---|---|---|---|---|---|
| GO: 0005737 | cytoplasm | 7845 | 429 | −8.40 | 0 |
| GO: 0007165 | signal transduction | 2324 | 159 | −7.89 | 0 |
| GO: 0005515 | protein binding | 6815 | 378 | −7.62 | 0 |
| GO: 0023052 | signaling | 3788 | 233 | −7.56 | 0 |
| GO: 0023033 | signaling pathway | 2813 | 183 | −7.48 | 0 |
| GO: 0007264 | small GTPase mediated signal trans. | 566 | 54 | −6.90 | 0 |
| GO: 0023060 | signal transmission | 2728 | 173 | −6.29 | 0 |
| GO: 0023046 | signaling process | 2730 | 173 | −6.27 | 0 |
| GO: 0009611 | response to wounding | 828 | 68 | −6.06 | 0 |

TABLE 27-continued

The Top 30 Most Differentially Regulated Gene Ontology Pathways in Macrophage DNA

| | | Genes | | | |
|---|---|---|---|---|---|
| GO Category | Category Name | Total | Changed | $Log^{10}$ P-Value | FDR |
| GO: 0030234 | enzyme regulator activity | 880 | 71 | −6.02 | 0 |
| GO: 0030695 | GTPase regulator activity | 437 | 43 | −5.96 | 0.001 |
| GO: 0035466 | reg. of sig. pathway | 1158 | 87 | −5.96 | 0.001 |
| GO: 0051056 | reg. of GTPase mediated sig. trans. | 339 | 36 | −5.85 | 0.001 |
| GO: 0023034 | intracellular sig. pathway | 1708 | 117 | −5.81 | 0.001 |
| GO: 0060589 | nucleoside-triphosphatase reg. activity | 446 | 43 | −5.73 | 0.001 |
| GO: 0006928 | cellular component movement | 687 | 58 | −5.61 | 0.001 |
| GO: 0044444 | cytoplasmic part | 5629 | 311 | −5.60 | 0.001 |
| GO: 0007265 | Ras protein signal transduction | 335 | 35 | −5.54 | 0.001 |
| GO: 0016192 | vesicle-mediated transport | 743 | 61 | −5.48 | 0.001 |
| GO: 0010876 | lipid localization | 188 | 24 | −5.44 | 0.001 |
| GO: 0005085 | guanyl-nucleotide exchange factor act. | 152 | 21 | −5.38 | 0.001 |
| GO: 0035556 | intracellular signal transduction | 1454 | 101 | −5.31 | 0.001 |
| GO: 0006869 | lipid transport | 167 | 22 | −5.26 | 0.001 |
| GO: 0010885 | reg. of cholesterol storage | 12 | 6 | −5.24 | 0.001 |
| GO: 0016477 | cell migration | 564 | 49 | −5.16 | 0.001 |
| GO: 0042060 | wound healing | 470 | 43 | −5.15 | 0.001 |
| GO: 0007166 | cell surface receptor linked sig. path | 1745 | 116 | −5.14 | 0.001 |
| GO: 0005089 | Rho guanyl-nucleotide exchange act. | 68 | 13 | −5.08 | 0.001 |
| GO: 0051179 | localization | 3540 | 207 | −5.02 | 0.002 |
| GO: 0001816 | cytokine production | 240 | 27 | −4.99 | 0.002 | pos. reg. = positive reg.,
sig. = sig.,
trans. = transduction,
FDR = false discovery rate.

EXAMPLE 9

Summary of AHRR Methylation Patterns in Nicotine Dependence

In this example we demonstrate the general principle through which substance use status, in this case nicotine use, can be determined by the differential methylation signature. AHRR is a large gene localizing to Chromosome 5 that encodes a competitive antagonist of the aryl hydrocarbon receptor. This large gene (at least 125,000 base pairs) has at least 12 exons, expresses at least 10 different mRNA products and has a large number of CpG enriched regions. In Appendix A, we list the methylation levels at each of the 146 Illumina probes that interrogate this locus for lymphoblasts or pulmonary macrophages (which are derived from peripheral monocytes) derived from either smokers or non-smokers. As Appendix A shows, a number of the probes are differentially methylated in both DNA samples. But in particular, we call attention to the regions (which are in bold typeface) between Probes 58-59 (cg12806681 and cg03991871), Probes 67-78 (cg23576855 and cg05575921) and Probe 84 (cg14817490). As the data demonstrate, the CpG residues in DNA prepared from both smoker lymphoblast and macrophage DNA is significantly hypomethylated at these residues. For any blood derived cell type, it is therefore apparent that by comparing the obtained methylation value for these set of residues for a given patient to that of a non-smoking reference patient, it would be easy to decipher whether the subject is smoking or not. That is to say, if the methylation values at those loci are closer to that obtained from the smokers, then that patient is likely a smoker. Conversely, if the values at those loci are closer to that obtained from the non-smoking reference group, then that patient is likely a non-smoker.

By this principle, and any of the genes listed in the tables herein or the accompanying Appendices, a skilled practitioner can easily determine with the selected level of surety whether a subject is smoking or non-smoking. By applying the same principle to the differentially methylated genes listed for alcohol or cannabis use, it is also clear that similar determinations can be made for the use of those substances as well.

EXAMPLE 10

Summary of Illumina Probe Data

Appendix B is a listing of probes differentially methylated in lymphoblasts of smokers. In this table, a complete listing of all probes differentially methylated at a p-value of p<0.05 is provided. Abbreviations: Illumina ID refers to the probe identification according to the Illumina array. "Chrom" and "position" refer to the absolute chromosomal base pair position of the CG dinucleotide according to Build 37 of the human genome. "Methylation" difference indicates whether the methylation at this CpG residue was higher in smokers or lower in smokers.

Appendix C is a complete listing of all the genes which have at least one Illumina probe differentially methylated in smokers. All gene names are according to the Human Genome Organization (HUGO) convention.

Appendix D is a listing of probes differentially methylated in lymphoblasts of alcohol drinkers. In this table, a complete listing of all probes differentially methylated at a p-value of p<0.01 is provided. Abbreviations: Illumina ID refers to the probe identification according to the Illumina array. "Chrom" and "position" refer to the absolute chromosomal base pair position of the CG dinucleotide according to Build 37 of the human genome. "Methylation" difference indicates whether the methylation at this CpG residue was higher in drinkers or lower in drinkers.

Appendix E is a complete listing of all the genes which have at least one Illumina probe differentially methylated in drinkers. All gene names are according to the Human Genome Organization (HUGO) convention.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Appendix A. The position, average methylation and t-test comparisons for lymphoblast and macrophage DNA at all 146 probes localizing to AHRR.

| Probe Name | CHR 5 Position | Alveolar Smoker Avg | Alveolar Control Avg | Alveolar T-test | Lymphoblast smoker avg | Lymphoblast Non-Smoker | Lymphoblast T-test |
|---|---|---|---|---|---|---|---|
| cg04286878 | 306765 | 0.97 | 0.97 | 0.624545 | 0.97 | 0.97 | 0.604798 |
| cg08802770 | 306786 | 0.96 | 0.97 | 0.222237 | 0.96 | 0.96 | 0.591391 |
| cg22030839 | 306838 | 0.92 | 0.92 | 0.603344 | 0.92 | 0.92 | 0.652013 |
| cg03569073 | 307132 | 0.87 | 0.87 | 0.86966 | 0.86 | 0.85 | 0.298431 |
| cg09662430 | 307591 | 0.93 | 0.95 | 0.340503 | 0.92 | 0.93 | 0.128058 |
| cg17386114 | 307799 | 0.91 | 0.91 | 0.970548 | 0.90 | 0.91 | 0.637122 |
| cg13275321 | 307848 | 0.84 | 0.83 | 0.457095 | 0.67 | 0.66 | 0.80426 |
| cg06605558 | 307899 | 0.89 | 0.89 | 0.56154 | 0.88 | 0.87 | 0.384738 |
| cg16081854 | 308268 | 0.50 | 0.34 | 0.51573 | 0.31 | 0.28 | 0.556505 |
| cg17310215 | 308494 | 0.87 | 0.87 | 0.459839 | 0.87 | 0.86 | 0.153309 |
| cg13707777 | 308627 | 0.91 | 0.90 | 0.579318 | 0.89 | 0.87 | 0.132579 |
| cg03561637 | 309484 | 0.86 | 0.88 | 0.078128 | 0.57 | 0.60 | 0.345376 |
| cg08519949 | 309765 | 0.97 | 0.97 | 0.350582 | 0.97 | 0.97 | 0.555206 |
| cg04023872 | 310073 | 0.98 | 0.98 | 0.604565 | 0.97 | 0.97 | 0.27114 |
| cg09854184 | 310135 | 0.78 | 0.78 | 0.996981 | 0.81 | 0.84 | 0.339512 |
| cg12845747 | 310363 | 0.90 | 0.90 | 0.664301 | 0.88 | 0.88 | 0.151682 |
| cg11148817 | 312970 | 0.89 | 0.89 | 0.806362 | 0.85 | 0.85 | 0.640754 |
| cg18584368 | 314553 | 0.90 | 0.89 | 0.66428 | 0.87 | 0.85 | 0.541092 |
| cg02527419 | 314558 | 0.89 | 0.89 | 0.75369 | 0.88 | 0.87 | 0.256939 |
| cg17989581 | 314590 | 0.97 | 0.97 | 0.787608 | 0.97 | 0.97 | 0.918588 |
| cg14982043 | 314642 | 0.86 | 0.85 | 0.285232 | 0.75 | 0.70 | 0.217434 |
| cg13404472 | 317840 | 0.87 | 0.86 | 0.42483 | 0.75 | 0.73 | 0.436789 |
| cg00300637 | 319433 | 0.66 | 0.62 | 0.100203 | 0.55 | 0.53 | 0.548865 |
| cg14453201 | 320888 | 0.06 | 0.07 | 0.368797 | 0.07 | 0.07 | 0.769978 |
| cg11554391 | 321320 | 0.10 | 0.14 | 0.002229 | 0.10 | 0.12 | 0.046744 |
| cg09634134 | 321681 | 0.06 | 0.06 | 0.789724 | 0.05 | 0.05 | 0.702614 |
| cg09470163 | 322032 | 0.04 | 0.03 | 0.495053 | 0.04 | 0.04 | 0.696633 |
| cg16896326 | 322134 | 0.05 | 0.06 | 0.040329 | 0.05 | 0.05 | 0.969302 |
| cg07137034 | 322321 | 0.12 | 0.14 | 0.359457 | 0.06 | 0.07 | 0.301465 |
| cg06802630 | 322735 | 0.52 | 0.53 | 0.890734 | 0.45 | 0.41 | 0.434544 |
| cg12961784 | 322816 | 0.57 | 0.54 | 0.360065 | 0.54 | 0.49 | 0.143135 |
| cg01970407 | 323320 | 0.85 | 0.83 | 0.358345 | 0.75 | 0.73 | 0.357095 |
| cg17924476 | 323794 | 0.50 | 0.42 | 0.00791 | 0.47 | 0.45 | 0.410608 |
| cg23067299 | 323907 | 0.93 | 0.90 | 0.000456 | 0.92 | 0.91 | 0.51298 |
| cg08606254 | 323969 | 0.87 | 0.85 | 0.136883 | 0.88 | 0.86 | 0.040254 |
| cg25004427 | 326523 | 0.92 | 0.89 | 0.002754 | 0.68 | 0.70 | 0.588455 |
| cg02356223 | 336337 | 0.89 | 0.88 | 0.172075 | 0.86 | 0.87 | 0.132491 |
| cg16995193 | 339570 | 0.87 | 0.88 | 0.357861 | 0.86 | 0.85 | 0.353842 |
| cg03891523 | 342271 | 0.83 | 0.82 | 0.960094 | 0.80 | 0.80 | 0.603838 |

| | | | | | | | |
|---|---|---|---|---|---|---|---|
| cg09078014 | 343450 | 0.69 | 0.70 | 0.503465 | 0.67 | 0.66 | 0.788668 |
| cg14714797 | 343927 | 0.16 | 0.19 | 0.107809 | 0.29 | 0.31 | 0.625642 |
| cg09338136 | 344057 | 0.15 | 0.21 | 5.86E-05 | 0.23 | 0.26 | 0.155828 |
| cg16371648 | 344218 | 0.19 | 0.10 | 0.152155 | 0.13 | 0.16 | 0.113688 |
| cg24688690 | 345850 | 0.68 | 0.68 | 0.903469 | 0.46 | 0.52 | 0.00624 |
| cg08858540 | 346238 | 0.88 | 0.87 | 0.241232 | 0.88 | 0.88 | 0.952407 |
| cg09084391 | 346247 | 0.91 | 0.90 | 0.047342 | 0.90 | 0.91 | 0.158009 |
| cg04135110 | 346695 | 0.38 | 0.15 | 2.02E-07 | 0.15 | 0.15 | 0.850167 |
| cg24980413 | 346987 | 0.74 | 0.67 | 0.005255 | 0.46 | 0.48 | 0.468655 |
| cg05655106 | 353905 | 0.86 | 0.85 | 0.362743 | 0.83 | 0.83 | 0.569156 |
| cg02088390 | 355321 | 0.90 | 0.88 | 0.037867 | 0.85 | 0.84 | 0.541906 |
| cg02121612 | 356571 | 0.87 | 0.87 | 0.950207 | 0.86 | 0.86 | 0.462322 |
| cg00629928 | 358741 | 0.87 | 0.87 | 0.738601 | 0.87 | 0.87 | 0.598585 |
| cg17048538 | 359525 | 0.87 | 0.88 | 0.247056 | 0.88 | 0.86 | 0.122289 |
| cg23953254 | 359577 | 0.85 | 0.84 | 0.71444 | 0.83 | 0.83 | 0.929742 |
| cg15179499 | 362529 | 0.95 | 0.95 | 0.197677 | 0.92 | 0.92 | 0.332717 |
| cg19602050 | 367976 | 0.95 | 0.95 | 0.096555 | 0.95 | 0.95 | 0.221352 |
| cg05521499 | 368003 | 0.96 | 0.96 | 0.757039 | 0.95 | 0.95 | 0.229783 |
| cg12806681 | 368394 | 0.81 | 0.88 | 0.001413 | 0.83 | 0.87 | 0.006679 |
| cg03991871 | 368447 | 0.70 | 0.83 | 0.000158 | 0.67 | 0.78 | 4.97E-05 |
| cg23916896 | 368804 | 0.13 | 0.20 | 0.001429 | 0.12 | 0.12 | 0.466435 |
| cg11902777 | 368843 | 0.06 | 0.06 | 0.165683 | 0.05 | 0.05 | 0.837445 |
| cg12202185 | 369088 | 0.17 | 0.17 | 0.970997 | 0.16 | 0.16 | 0.803423 |
| cg01899089 | 369969 | 0.52 | 0.50 | 0.414089 | 0.22 | 0.27 | 0.007668 |
| cg04202140 | 370352 | 0.93 | 0.92 | 0.34155 | 0.91 | 0.91 | 0.888038 |
| cg20310920 | 370421 | 0.87 | 0.85 | 0.045594 | 0.86 | 0.85 | 0.70697 |
| cg14744022 | 371026 | 0.86 | 0.86 | 0.752098 | 0.81 | 0.79 | 0.323724 |
| cg23576855 | 373299 | 0.56 | 0.72 | 0.021524 | 0.41 | 0.49 | 0.039367 |
| cg05575921 | 373378 | 0.70 | 0.93 | 2.65E-05 | 0.70 | 0.85 | 1.34E-06 |
| cg22103736 | 373887 | 0.10 | 0.11 | 0.801294 | 0.10 | 0.11 | 0.081609 |
| cg08714121 | 374093 | 0.06 | 0.05 | 0.427103 | 0.05 | 0.05 | 0.504154 |
| cg04141806 | 374252 | 0.08 | 0.08 | 0.971247 | 0.10 | 0.09 | 0.566702 |
| cg22356527 | 374425 | 0.18 | 0.16 | 0.155374 | 0.11 | 0.11 | 0.892049 |
| cg24130459 | 375776 | 0.97 | 0.96 | 0.116385 | 0.96 | 0.96 | 0.433491 |
| cg26703534 | 377358 | 0.76 | 0.69 | 0.004971 | 0.80 | 0.79 | 0.488189 |
| cg01097768 | 378854 | 0.76 | 0.72 | 0.096793 | 0.23 | 0.24 | 0.674283 |
| cg18205372 | 386883 | 0.83 | 0.83 | 0.534198 | 0.84 | 0.83 | 0.3351 |
| cg17472786 | 389355 | 0.77 | 0.78 | 0.429916 | 0.55 | 0.52 | 0.330141 |
| cg05601199 | 389490 | 0.97 | 0.98 | 0.033299 | 0.97 | 0.97 | 0.919479 |
| cg04021706 | 389763 | 0.91 | 0.89 | 0.064828 | 0.78 | 0.79 | 0.626079 |
| cg06678548 | 390197 | 0.85 | 0.85 | 0.67458 | 0.85 | 0.85 | 0.691481 |
| cg26320890 | 390259 | 0.88 | 0.91 | 0.435 | 0.91 | 0.91 | 0.968128 |
| cg15168497 | 391455 | 0.88 | 0.90 | 0.560239 | 0.81 | 0.84 | 0.461628 |
| cg18615970 | 392364 | 0.92 | 0.93 | 0.909692 | 0.93 | 0.92 | 0.54447 |
| cg14817490 | 392920 | 0.22 | 0.41 | 0.000287 | 0.12 | 0.24 | 2.71E-08 |
| cg17287155 | 393347 | 0.93 | 0.92 | 0.543945 | 0.63 | 0.75 | 0.000912 |
| cg04551776 | 393366 | 0.87 | 0.86 | 0.307258 | 0.56 | 0.66 | 0.002581 |

| | | | | | | |
|---|---|---|---|---|---|---|
| cg25648203 | 395444 | 0.38 | 0.72 | 1.97E-09 | 0.78 | 0.77 | 0.492383 |
| cg12937950 | 398247 | 0.68 | 0.67 | 0.575906 | 0.64 | 0.63 | 0.504883 |
| cg19442702 | 398425 | 0.96 | 0.95 | 0.45953 | 0.94 | 0.95 | 0.416017 |
| cg11894422 | 398758 | 0.86 | 0.84 | 0.065762 | 0.76 | 0.78 | 0.499134 |
| cg16219322 | 399012 | 0.84 | 0.84 | 0.788587 | 0.72 | 0.72 | 0.995519 |
| cg21161138 | 399360 | 0.69 | 0.76 | 0.001499 | 0.57 | 0.62 | 0.137398 |
| cg14454127 | 399787 | 0.86 | 0.86 | 0.96515 | 0.31 | 0.44 | 2.73E-06 |
| cg17248487 | 399887 | 0.60 | 0.65 | 0.047118 | 0.10 | 0.12 | 0.007312 |
| cg03604011 | 400201 | 0.03 | 0.03 | 0.895767 | 0.02 | 0.02 | 0.733126 |
| cg22698028 | 400494 | 0.15 | 0.17 | 0.057884 | 0.14 | 0.15 | 0.11934 |
| cg17401179 | 400517 | 0.12 | 0.23 | 0.000113 | 0.11 | 0.15 | 0.005168 |
| cg24090911 | 400732 | 0.58 | 0.70 | 0.000177 | 0.56 | 0.58 | 0.305131 |
| cg14647125 | 403112 | 0.14 | 0.14 | 0.619221 | 0.12 | 0.13 | 0.068811 |
| cg05527650 | 403213 | 0.06 | 0.09 | 0.008686 | 0.05 | 0.06 | 0.071974 |
| cg19039843 | 404264 | 0.88 | 0.88 | 0.519304 | 0.85 | 0.84 | 0.417687 |
| cg05597431 | 404320 | 0.90 | 0.84 | 0.264903 | 0.87 | 0.89 | 0.249772 |
| cg08491376 | 404678 | 0.91 | 0.89 | 0.141045 | 0.87 | 0.85 | 0.085919 |
| cg08238319 | 404713 | 0.78 | 0.53 | 0.205809 | 0.46 | 0.36 | 0.178383 |
| cg02385153 | 404766 | 0.94 | 0.89 | 5.07E-05 | 0.76 | 0.74 | 0.600998 |
| cg24064903 | 404910 | 0.88 | 0.86 | 0.007162 | 0.87 | 0.85 | 0.126779 |
| cg11557553 | 404996 | 0.85 | 0.81 | 0.000629 | 0.80 | 0.80 | 0.830748 |
| cg12207033 | 405488 | 0.90 | 0.88 | 0.030954 | 0.88 | 0.86 | 0.074864 |
| cg01141993 | 405567 | 0.91 | 0.90 | 0.027368 | 0.88 | 0.87 | 0.360956 |
| cg22937882 | 405774 | 0.87 | 0.85 | 0.041958 | 0.80 | 0.81 | 0.784393 |
| cg00401753 | 405986 | 0.90 | 0.88 | 0.040707 | 0.86 | 0.86 | 0.806631 |
| cg19405895 | 407315 | 0.91 | 0.92 | 0.515513 | 0.90 | 0.90 | 0.406455 |
| cg08916839 | 415575 | 0.80 | 0.88 | 0.360383 | 0.85 | 0.87 | 0.277289 |
| cg24955955 | 415729 | 0.72 | 0.80 | 0.303817 | 0.77 | 0.80 | 0.249582 |
| cg07599136 | 415885 | 0.71 | 0.81 | 0.240683 | 0.79 | 0.76 | 0.440164 |
| cg09078081 | 416724 | 0.93 | 0.94 | 0.84301 | 0.93 | 0.92 | 0.216961 |
| cg08385200 | 417224 | 0.81 | 0.80 | 0.168557 | 0.78 | 0.77 | 0.373743 |
| cg16294152 | 418696 | 0.88 | 0.93 | 0.331678 | 0.91 | 0.89 | 0.400741 |
| cg26076054 | 421317 | 0.88 | 0.80 | 0.113456 | 0.91 | 0.89 | 0.412682 |
| cg09478603 | 421454 | 0.95 | 0.87 | 0.208813 | 0.86 | 0.86 | 0.988576 |
| cg12251573 | 421644 | 0.82 | 0.76 | 0.277591 | 0.76 | 0.73 | 0.36639 |
| cg00976097 | 421733 | 0.91 | 0.90 | 0.693497 | 0.93 | 0.90 | 0.518581 |
| cg22816059 | 422114 | 0.90 | 0.90 | 0.340522 | 0.89 | 0.90 | 0.066576 |
| cg14684960 | 422213 | 0.73 | 0.72 | 0.426781 | 0.71 | 0.72 | 0.496615 |
| cg24891125 | 422573 | 0.85 | 0.84 | 0.153089 | 0.81 | 0.79 | 0.305928 |
| cg16325394 | 422633 | 0.95 | 0.95 | 0.730455 | 0.94 | 0.95 | 0.256964 |
| cg14854287 | 423894 | 0.94 | 0.95 | 0.187436 | 0.94 | 0.95 | 0.253447 |
| cg21144161 | 423903 | 0.94 | 0.96 | 0.002047 | 0.94 | 0.94 | 0.770965 |
| cg26529655 | 424371 | 0.47 | 0.75 | 1.14E-06 | 0.40 | 0.42 | 0.41488 |
| cg09584122 | 427620 | 0.94 | 0.93 | 0.362872 | 0.93 | 0.92 | 0.708043 |
| cg07448928 | 427755 | 0.82 | 0.76 | 1.21E-05 | 0.65 | 0.58 | 0.05085 |
| cg05516328 | 427841 | 0.86 | 0.90 | 0.344007 | 0.89 | 0.87 | 0.472457 |
| cg16577724 | 428068 | 0.95 | 0.95 | 0.290655 | 0.95 | 0.95 | 0.679074 |

| | | | | | | | |
|---|---|---|---|---|---|---|---|
| cg16172278 | 428101 | 0.89 | 0.89 | 0.318761 | 0.88 | 0.87 | 0.386572 |
| cg26850624 | 429559 | 0.84 | 0.77 | 0.034435 | 0.71 | 0.68 | 0.236215 |
| cg08556107 | 429891 | 0.88 | 0.87 | 0.126172 | 0.79 | 0.81 | 0.153483 |
| cg18541609 | 430359 | 0.91 | 0.89 | 0.051402 | 0.88 | 0.87 | 0.864613 |
| cg11610050 | 430432 | 0.89 | 0.88 | 0.199423 | 0.86 | 0.86 | 0.66987 |
| cg10841124 | 433274 | 0.96 | 0.94 | 0.000633 | 0.86 | 0.85 | 0.739936 |
| cg16049691 | 434877 | 0.87 | 0.84 | 0.038989 | 0.76 | 0.78 | 0.352747 |
| cg22951524 | 434998 | 0.76 | 0.80 | 0.449564 | 0.77 | 0.71 | 0.205979 |
| cg14448919 | 435040 | 0.89 | 0.82 | 0.189639 | 0.79 | 0.74 | 0.236826 |
| cg16336872 | 435267 | 0.82 | 0.80 | 0.235485 | 0.77 | 0.75 | 0.118196 |
| cg14807090 | 435388 | 0.90 | 0.89 | 0.035081 | 0.82 | 0.77 | 0.097473 |
| cg21972741 | 435613 | 0.91 | 0.91 | 0.77633 | 0.89 | 0.89 | 0.577099 |
| cg26954197 | 436816 | 0.84 | 0.82 | 0.040678 | 0.74 | 0.70 | 0.385827 |

Appendix B

| Illumina ID | Chrom | Position | Methylation Difference |
|---|---|---|---|
| cg18685561 | 4 | 165305022 | Higher in Smoker |
| cg10390473 | 4 | 164775263 | Lower in Smoker |
| cg08748033 | 4 | 165111372 | Lower in Smoker |
| cg08897392 | 5 | 126332397 | Lower in Smoker |
| cg14435444 | 2 | 217236882 | Higher in Smoker |
| cg12288074 | 5 | 10354432 | Higher in Smoker |
| cg20126158 | 5 | 10353332 | Higher in Smoker |
| cg03705912 | 5 | 16179210 | Higher in Smoker |
| cg11284329 | 4 | 77870605 | Higher in Smoker |
| cg16382584 | 4 | 77935993 | Lower in Smoker |
| cg20062097 | 7 | 45808644 | Higher in Smoker |
| cg23643835 | 7 | 45809304 | Lower in Smoker |
| cg13918206 | 9 | 118159781 | Lower in Smoker |
| cg16682686 | 9 | 117903983 | Lower in Smoker |
| cg04056343 | 16 | 7137080 | Higher in Smoker |
| cg09683476 | 16 | 7420461 | Lower in Smoker |
| cg27623406 | 16 | 7382864 | Lower in Smoker |
| cg15688197 | 12 | 9265030 | Lower in Smoker |
| cg00134295 | 12 | 9269178 | Lower in Smoker |
| cg02427438 | 12 | 53715500 | Higher in Smoker |
| cg23032316 | 12 | 53715148 | Higher in Smoker |
| cg03625512 | 12 | 125569850 | Lower in Smoker |
| cg00522288 | 12 | 125625016 | Lower in Smoker |
| cg22940988 | 15 | 67538446 | Lower in Smoker |
| cg21174435 | 2 | 69871627 | Higher in Smoker |
| cg01773642 | 2 | 69748452 | Lower in Smoker |
| cg07992340 | 16 | 70320238 | Lower in Smoker |
| cg01439854 | 16 | 70323367 | Higher in Smoker |
| cg01122755 | 6 | 44281249 | Higher in Smoker |
| cg23649161 | 17 | 41132662 | Higher in Smoker |
| cg12578182 | 17 | 41132637 | Higher in Smoker |
| cg09999563 | 4 | 57253666 | Lower in Smoker |
| cg13939352 | 4 | 57253710 | Lower in Smoker |

| | | | |
|---|---|---|---|
| cg04893558 | 7 | 121783377 | Higher in Smoker |
| cg24133836 | 7 | 121784386 | Lower in Smoker |
| cg00591333 | 17 | 79109910 | Lower in Smoker |
| cg03698343 | 9 | 139921892 | Higher in Smoker |
| cg07301574 | 16 | 2338454 | Higher in Smoker |
| cg01491428 | 16 | 2334163 | Lower in Smoker |
| cg09168805 | 1 | 94514548 | Lower in Smoker |
| cg25174455 | 17 | 67260128 | Lower in Smoker |
| cg02817925 | 19 | 1046325 | Lower in Smoker |
| cg00874873 | 19 | 1051160 | Lower in Smoker |
| cg26576206 | 19 | 1064938 | Lower in Smoker |
| cg18542829 | 7 | 87257538 | Higher in Smoker |
| cg06869512 | 7 | 87093634 | Lower in Smoker |
| cg25823065 | 7 | 87105416 | Lower in Smoker |
| cg20966504 | 7 | 20654932 | Lower in Smoker |
| cg14878128 | 7 | 20655152 | Lower in Smoker |
| cg24775454 | 2 | 220083696 | Higher in Smoker |
| cg23279136 | X | 74375966 | Higher in Smoker |
| cg02615599 | 7 | 150725389 | Higher in Smoker |
| cg21964637 | 7 | 150729118 | Lower in Smoker |
| cg03831648 | 12 | 123430862 | Lower in Smoker |
| cg03212620 | 12 | 123414345 | Lower in Smoker |
| cg19189965 | 12 | 123459820 | Higher in Smoker |
| cg12162424 | 21 | 15646312 | Higher in Smoker |
| cg14652434 | 3 | 183674797 | Lower in Smoker |
| cg01324343 | 3 | 183735012 | Lower in Smoker |
| cg13851843 | 11 | 17498329 | Lower in Smoker |
| cg01713095 | 4 | 146050127 | Lower in Smoker |
| cg15595551 | 4 | 146019024 | Higher in Smoker |
| cg00678158 | 6 | 30538836 | Higher in Smoker |
| cg14793544 | 6 | 30538842 | Higher in Smoker |
| cg14141448 | 6 | 30538684 | Lower in Smoker |
| cg03413475 | 7 | 150925067 | Higher in Smoker |
| cg27147545 | 7 | 150920403 | Lower in Smoker |
| cg27220130 | 3 | 183903797 | Higher in Smoker |

| | | | |
|---|---|---|---|
| cg13465462 | 3 | 183903780 | Higher in Smoker |
| cg22574986 | 3 | 183904652 | Lower in Smoker |
| cg06500161 | 21 | 43656587 | Higher in Smoker |
| cg05639842 | 21 | 43639440 | Higher in Smoker |
| cg19844581 | 11 | 119020147 | Higher in Smoker |
| cg11467440 | 2 | 44065278 | Lower in Smoker |
| cg08109969 | 3 | 111697754 | Higher in Smoker |
| cg19714762 | 7 | 73153162 | Higher in Smoker |
| cg16651732 | 15 | 89631057 | Higher in Smoker |
| cg17860366 | 15 | 89634741 | Higher in Smoker |
| cg04645817 | 15 | 89693656 | Lower in Smoker |
| cg25680245 | 18 | 19284821 | Higher in Smoker |
| cg25890168 | 18 | 19262819 | Lower in Smoker |
| cg05766064 | 18 | 19262576 | Lower in Smoker |
| cg12153785 | 14 | 23067088 | Higher in Smoker |
| cg16014422 | 14 | 23067084 | Higher in Smoker |
| cg23239109 | 3 | 43732098 | Higher in Smoker |
| cg10572794 | 3 | 58223527 | Lower in Smoker |
| cg04614656 | 19 | 17414770 | Lower in Smoker |
| cg05462826 | 2 | 204193327 | Higher in Smoker |
| cg24521869 | 17 | 47296970 | Lower in Smoker |
| cg11164649 | 17 | 47297130 | Lower in Smoker |
| cg00980784 | 17 | 47287577 | Lower in Smoker |
| cg14205952 | 9 | 133588093 | Higher in Smoker |
| cg08417804 | 9 | 133588801 | Higher in Smoker |
| cg14483356 | 9 | 133706938 | Lower in Smoker |
| cg10228162 | 9 | 133589493 | Lower in Smoker |
| cg11243304 | 1 | 179074614 | Lower in Smoker |
| cg22688802 | 4 | 7980661 | Higher in Smoker |
| cg00130393 | 4 | 8098876 | Lower in Smoker |
| cg13130338 | 4 | 8091040 | Lower in Smoker |
| cg25326776 | 5 | 148520934 | Lower in Smoker |
| cg17680092 | 5 | 148523798 | Lower in Smoker |
| cg17259656 | 5 | 148521112 | Higher in Smoker |
| cg13850847 | 9 | 136131739 | Lower in Smoker |

| | | | |
|---|---|---|---|
| cg06767314 | 17 | 1035381 | Lower in Smoker |
| cg18468019 | 17 | 1040748 | Lower in Smoker |
| cg26013733 | 17 | 928851 | Lower in Smoker |
| cg24919342 | 3 | 127399204 | Lower in Smoker |
| cg04954111 | 11 | 34363786 | Higher in Smoker |
| cg04597004 | 11 | 34379532 | Higher in Smoker |
| cg10835651 | 11 | 34340108 | Lower in Smoker |
| cg24368167 | 3 | 38179936 | Higher in Smoker |
| cg00276752 | 17 | 35719639 | Lower in Smoker |
| cg26534468 | 17 | 35537229 | Lower in Smoker |
| cg01156990 | 17 | 35732801 | Lower in Smoker |
| cg06397845 | 17 | 35732737 | Lower in Smoker |
| cg06131338 | 12 | 109639461 | Lower in Smoker |
| cg25422937 | 12 | 112123904 | Higher in Smoker |
| cg08577424 | 12 | 112123256 | Higher in Smoker |
| cg05296856 | 3 | 132277407 | Lower in Smoker |
| cg00137606 | 3 | 123598469 | Higher in Smoker |
| cg24768164 | 12 | 121163261 | Lower in Smoker |
| cg12579196 | 17 | 7127302 | Lower in Smoker |
| cg02401352 | 15 | 89354338 | Lower in Smoker |
| cg20510724 | 15 | 89346795 | Higher in Smoker |
| cg19175364 | 17 | 7249511 | Lower in Smoker |
| cg05973813 | 11 | 107992235 | Higher in Smoker |
| cg25472589 | 11 | 107995927 | Lower in Smoker |
| cg00396407 | 1 | 226374726 | Higher in Smoker |
| cg15107987 | 1 | 180469147 | Lower in Smoker |
| cg09276982 | 10 | 15130648 | Lower in Smoker |
| cg23302998 | 17 | 31388899 | Lower in Smoker |
| cg09102690 | 17 | 31438995 | Lower in Smoker |
| cg25350252 | 2 | 220381129 | Lower in Smoker |
| cg02197228 | 2 | 220402771 | Lower in Smoker |
| cg24743778 | 2 | 220379058 | Higher in Smoker |
| cg09726982 | 2 | 220379016 | Higher in Smoker |
| cg17610929 | 2 | 220379044 | Higher in Smoker |
| cg09339476 | 11 | 44087396 | Higher in Smoker |

| | | | |
|---|---|---|---|
| cg08559914 | X | 15620240 | Lower in Smoker |
| cg04674056 | 9 | 19408789 | Higher in Smoker |
| cg14628274 | 9 | 19424228 | Lower in Smoker |
| cg08711063 | 11 | 76571529 | Higher in Smoker |
| cg09367198 | 14 | 23541523 | Lower in Smoker |
| cg24960563 | 17 | 40075304 | Higher in Smoker |
| cg03476105 | 7 | 96770912 | Lower in Smoker |
| cg16259069 | 9 | 32384421 | Lower in Smoker |
| cg13567378 | 9 | 32403106 | Lower in Smoker |
| cg10710218 | 1 | 55012989 | Lower in Smoker |
| cg11611950 | 6 | 24667276 | Lower in Smoker |
| cg09887323 | 1 | 6348460 | Higher in Smoker |
| cg16306654 | 1 | 6419767 | Lower in Smoker |
| cg16049283 | 1 | 6419606 | Lower in Smoker |
| cg08083689 | 4 | 8442326 | Higher in Smoker |
| cg06656551 | 4 | 8398737 | Lower in Smoker |
| cg18467339 | 4 | 8409328 | Lower in Smoker |
| cg18999185 | 4 | 8386198 | Lower in Smoker |
| cg08206079 | 4 | 8386188 | Lower in Smoker |
| cg25963412 | 4 | 8412369 | Lower in Smoker |
| cg16521213 | 2 | 277384 | Lower in Smoker |
| cg15144216 | 2 | 269218 | Lower in Smoker |
| cg19372772 | 2 | 264904 | Higher in Smoker |
| cg03719155 | 19 | 11689880 | Higher in Smoker |
| cg22402043 | 1 | 147138189 | Lower in Smoker |
| cg19941450 | 3 | 140950619 | Higher in Smoker |
| cg15782391 | 19 | 51293367 | Lower in Smoker |
| cg27130774 | X | 70821685 | Lower in Smoker |
| cg11896316 | X | 70800699 | Lower in Smoker |
| ch.11.261918CF | 11 | 125545646 | Higher in Smoker |
| cg12649208 | 17 | 48548533 | Lower in Smoker |
| cg00316478 | 16 | 89222027 | Lower in Smoker |
| cg07215234 | 16 | 89173837 | Lower in Smoker |
| cg06245181 | 16 | 89186403 | Lower in Smoker |
| cg00739608 | 16 | 89205832 | Lower in Smoker |

| | | | |
|---|---|---|---|
| cg09159004 | 16 | 89165752 | Lower in Smoker |
| cg07661835 | 16 | 89163578 | Lower in Smoker |
| cg09427016 | 16 | 89167018 | Lower in Smoker |
| cg09743596 | 16 | 89180843 | Lower in Smoker |
| cg06800849 | 16 | 89180587 | Lower in Smoker |
| cg06934654 | 16 | 89180742 | Lower in Smoker |
| cg02691035 | 16 | 89163300 | Lower in Smoker |
| cg20823481 | 4 | 185736247 | Higher in Smoker |
| cg03040554 | 2 | 223778280 | Lower in Smoker |
| cg20707765 | 10 | 114133700 | Lower in Smoker |
| cg25780389 | 10 | 114134915 | Higher in Smoker |
| cg07246873 | 16 | 20702422 | Lower in Smoker |
| cg10078415 | 16 | 20775011 | Higher in Smoker |
| cg05300045 | 16 | 20420663 | Higher in Smoker |
| cg27514874 | 16 | 20429506 | Lower in Smoker |
| cg05143887 | 12 | 81471938 | Higher in Smoker |
| cg17188567 | 12 | 81649347 | Lower in Smoker |
| cg26272220 | 12 | 81471884 | Higher in Smoker |
| cg10789281 | 12 | 81471882 | Higher in Smoker |
| cg05347845 | 1 | 229569892 | Higher in Smoker |
| cg02767613 | 1 | 229569894 | Higher in Smoker |
| cg25792990 | 1 | 229569965 | Higher in Smoker |
| cg23261233 | 7 | 5570489 | Higher in Smoker |
| cg26636061 | 7 | 5568044 | Lower in Smoker |
| cg14145074 | 7 | 5567891 | Lower in Smoker |
| cg26657920 | 5 | 56778977 | Lower in Smoker |
| cg03369957 | 7 | 100252863 | Lower in Smoker |
| cg16853982 | 1 | 236849389 | Higher in Smoker |
| cg18119735 | 1 | 236850308 | Higher in Smoker |
| cg00524169 | 19 | 39138063 | Higher in Smoker |
| cg27548256 | 19 | 39217070 | Lower in Smoker |
| cg12085852 | 14 | 58666262 | Higher in Smoker |
| cg04738270 | 10 | 104261507 | Higher in Smoker |
| cg07466585 | 10 | 104263680 | Higher in Smoker |
| cg27141863 | 2 | 98280310 | Higher in Smoker |

| | | | |
|---|---|---|---|
| cg03743214 | 2 | 98280713 | Higher in Smoker |
| cg22411710 | 2 | 98280854 | Higher in Smoker |
| cg21261105 | 2 | 65454636 | Higher in Smoker |
| cg15235832 | 2 | 65455536 | Higher in Smoker |
| cg16785387 | 12 | 100594386 | Higher in Smoker |
| cg26210255 | 12 | 100594894 | Higher in Smoker |
| cg25680916 | 3 | 53916015 | Lower in Smoker |
| cg08284207 | X | 127185519 | Higher in Smoker |
| cg01956267 | 2 | 159732380 | Higher in Smoker |
| cg08447934 | 12 | 52311706 | Higher in Smoker |
| cg00257303 | 4 | 123300294 | Lower in Smoker |
| cg15269541 | 15 | 43626905 | Lower in Smoker |
| cg25415508 | 15 | 43622652 | Higher in Smoker |
| cg15280358 | 10 | 127904472 | Lower in Smoker |
| cg11362955 | 2 | 9696126 | Higher in Smoker |
| cg05131524 | 7 | 87563251 | Higher in Smoker |
| cg06251395 | 20 | 3663186 | Higher in Smoker |
| cg07444323 | 20 | 3654504 | Higher in Smoker |
| cg17759443 | 20 | 3662724 | Higher in Smoker |
| cg07927909 | 8 | 39380592 | Higher in Smoker |
| cg03899706 | 14 | 106438465 | Lower in Smoker |
| cg05847038 | 8 | 24298771 | Lower in Smoker |
| cg23452957 | 10 | 135091431 | Higher in Smoker |
| cg23114262 | 10 | 135086817 | Higher in Smoker |
| cg18110015 | 10 | 135078252 | Lower in Smoker |
| cg24382527 | 10 | 135090367 | Higher in Smoker |
| cg13758712 | 21 | 28218959 | Higher in Smoker |
| cg11590772 | 19 | 8657916 | Higher in Smoker |
| cg12917072 | 5 | 33758285 | Lower in Smoker |
| cg16670809 | 5 | 5139797 | Higher in Smoker |
| cg04842157 | 5 | 123797456 | Higher in Smoker |
| cg07781332 | 5 | 123796696 | Higher in Smoker |
| cg25309017 | 5 | 123796266 | Higher in Smoker |
| cg21849875 | 5 | 173551628 | Higher in Smoker |
| cg03703637 | 5 | 173771776 | Higher in Smoker |

| | | | |
|---|---|---|---|
| cg11909340 | 5 | 178656491 | Lower in Smoker |
| cg03993109 | 5 | 178594649 | Lower in Smoker |
| cg21183664 | 5 | 178594526 | Lower in Smoker |
| cg01231141 | 5 | 178692691 | Lower in Smoker |
| cg13601496 | 21 | 28339487 | Higher in Smoker |
| cg20246113 | 15 | 79104481 | Higher in Smoker |
| cg00676660 | 3 | 64672609 | Higher in Smoker |
| cg14206717 | 9 | 136440350 | Lower in Smoker |
| cg00785522 | 1 | 150521766 | Higher in Smoker |
| cg11782479 | 19 | 1507932 | Higher in Smoker |
| cg00904258 | 7 | 968194 | Higher in Smoker |
| cg15392988 | 7 | 956642 | Higher in Smoker |
| cg06589239 | 7 | 961457 | Lower in Smoker |
| cg10211456 | 7 | 963471 | Lower in Smoker |
| cg09844687 | 1 | 154597547 | Lower in Smoker |
| cg27530370 | 1 | 154589288 | Lower in Smoker |
| cg08222185 | 21 | 46494823 | Lower in Smoker |
| cg05248655 | 10 | 1454265 | Higher in Smoker |
| cg00363080 | 10 | 1454292 | Higher in Smoker |
| cg02408697 | 10 | 1416920 | Higher in Smoker |
| cg24515131 | 10 | 1263207 | Higher in Smoker |
| cg27517502 | 10 | 1248770 | Lower in Smoker |
| cg02972640 | 10 | 1415977 | Lower in Smoker |
| cg13684379 | 10 | 1511173 | Lower in Smoker |
| cg06563471 | 10 | 1406508 | Lower in Smoker |
| cg12037550 | 10 | 1705054 | Lower in Smoker |
| cg05818501 | 10 | 1451648 | Lower in Smoker |
| cg16736679 | 10 | 1704969 | Lower in Smoker |
| cg03962411 | 1 | 33546533 | Lower in Smoker |
| cg05923595 | 1 | 33547713 | Lower in Smoker |
| cg11731031 | 14 | 78265516 | Lower in Smoker |
| cg04405332 | 1 | 167789609 | Lower in Smoker |
| cg15226348 | 5 | 7540955 | Lower in Smoker |
| cg26008260 | 2 | 25057298 | Lower in Smoker |
| cg19646112 | 14 | 24804342 | Higher in Smoker |

| | | | |
|---|---|---|---|
| cg20300093 | 3 | 123138250 | Lower in Smoker |
| cg26419941 | 12 | 49183133 | Higher in Smoker |
| cg22689690 | 12 | 49183468 | Higher in Smoker |
| cg23686556 | 6 | 131961316 | Higher in Smoker |
| cg05229355 | 6 | 132052702 | Higher in Smoker |
| cg09133979 | 16 | 4028440 | Lower in Smoker |
| cg09032423 | 16 | 4015231 | Lower in Smoker |
| cg01174786 | 16 | 4027541 | Lower in Smoker |
| cg13574337 | 16 | 4016720 | Lower in Smoker |
| cg06372303 | 18 | 907092 | Higher in Smoker |
| cg11218385 | 7 | 31092854 | Higher in Smoker |
| cg23921196 | 2 | 70978771 | Lower in Smoker |
| cg03801898 | 10 | 111767685 | Higher in Smoker |
| cg25073725 | 4 | 100010060 | Higher in Smoker |
| cg25705390 | 2 | 3522243 | Higher in Smoker |
| cg04392387 | 2 | 3502446 | Lower in Smoker |
| cg07990273 | 2 | 3524596 | Lower in Smoker |
| cg12132617 | 1 | 202928820 | Lower in Smoker |
| cg10314295 | 10 | 75936245 | Higher in Smoker |
| cg09639735 | 11 | 10326570 | Higher in Smoker |
| cg12662530 | 10 | 64564276 | Higher in Smoker |
| cg25103895 | 10 | 64565642 | Lower in Smoker |
| cg27381549 | 22 | 24824483 | Lower in Smoker |
| cg26001125 | 22 | 24823050 | Lower in Smoker |
| cg17716037 | 17 | 15878667 | Lower in Smoker |
| cg17580614 | 17 | 15849512 | Lower in Smoker |
| cg07833779 | 1 | 112050772 | Higher in Smoker |
| cg21550360 | 15 | 73075372 | Higher in Smoker |
| cg04002203 | 15 | 73072692 | Lower in Smoker |
| cg14322429 | 3 | 119298585 | Higher in Smoker |
| cg00945107 | 13 | 114090589 | Lower in Smoker |
| cg25745331 | 13 | 114083665 | Lower in Smoker |
| cg09506001 | 1 | 36559506 | Lower in Smoker |
| cg07572251 | 8 | 26688088 | Lower in Smoker |
| cg27606288 | 2 | 96783070 | Higher in Smoker |

| | | | |
|---|---|---|---|
| cg05394500 | 4 | 3768097 | Higher in Smoker |
| cg22646324 | 4 | 3768078 | Higher in Smoker |
| cg12094402 | 4 | 3767402 | Lower in Smoker |
| cg13648598 | 10 | 115804578 | Higher in Smoker |
| cg21580376 | 5 | 148206412 | Higher in Smoker |
| cg00432461 | 8 | 37825156 | Lower in Smoker |
| cg19363916 | 11 | 67034540 | Higher in Smoker |
| cg16061947 | 11 | 67032472 | Lower in Smoker |
| cg05882426 | 22 | 25961001 | Lower in Smoker |
| cg23656380 | 20 | 60877581 | Higher in Smoker |
| cg02290264 | 1 | 244616177 | Lower in Smoker |
| cg03992063 | 1 | 244615947 | Lower in Smoker |
| cg08161947 | 12 | 19592900 | Higher in Smoker |
| cg26259627 | 12 | 19592630 | Higher in Smoker |
| cg04572898 | 15 | 89164981 | Higher in Smoker |
| cg26544786 | 15 | 89164951 | Higher in Smoker |
| cg00251875 | 4 | 7801337 | Lower in Smoker |
| cg19601530 | 4 | 7788250 | Lower in Smoker |
| cg24358467 | 4 | 7812736 | Lower in Smoker |
| cg06346505 | 10 | 116164640 | Higher in Smoker |
| cg21687216 | 4 | 87857413 | Higher in Smoker |
| cg27185138 | 4 | 87928043 | Higher in Smoker |
| cg18880005 | 4 | 87927975 | Higher in Smoker |
| cg21571135 | 4 | 88038713 | Lower in Smoker |
| cg14151288 | 2 | 100322441 | Lower in Smoker |
| cg05506979 | 5 | 132295375 | Lower in Smoker |
| cg06048191 | 16 | 90039125 | Higher in Smoker |
| cg19066150 | 17 | 76183448 | Higher in Smoker |
| cg27436044 | 4 | 178360978 | Lower in Smoker |
| cg15981851 | 2 | 236773924 | Higher in Smoker |
| cg09317899 | 2 | 236404028 | Higher in Smoker |
| cg19761110 | 2 | 236774071 | Higher in Smoker |
| cg09726703 | 2 | 236441769 | Lower in Smoker |
| cg23337031 | 2 | 236416064 | Lower in Smoker |
| cg11377336 | 2 | 236721826 | Lower in Smoker |

| | | | |
|---|---|---|---|
| cg09589951 | 2 | 236897639 | Lower in Smoker |
| cg06342954 | 2 | 236757889 | Lower in Smoker |
| cg21195462 | 2 | 236481564 | Lower in Smoker |
| cg02746108 | 2 | 236672961 | Lower in Smoker |
| cg10376827 | 10 | 88730324 | Lower in Smoker |
| cg07159847 | 12 | 58122341 | Higher in Smoker |
| cg00769161 | 12 | 58130183 | Lower in Smoker |
| cg25582401 | 12 | 58133411 | Lower in Smoker |
| cg15539944 | 12 | 58129407 | Lower in Smoker |
| cg23286756 | 10 | 46344313 | Higher in Smoker |
| cg19653951 | 10 | 51748232 | Lower in Smoker |
| cg02907524 | 15 | 86683983 | Lower in Smoker |
| cg17840707 | 15 | 86951099 | Lower in Smoker |
| cg05547140 | 11 | 47736353 | Higher in Smoker |
| cg00588300 | 7 | 134671083 | Higher in Smoker |
| cg13424673 | 1 | 50489744 | Higher in Smoker |
| cg26249046 | 1 | 50489823 | Higher in Smoker |
| cg03038003 | 1 | 49242900 | Higher in Smoker |
| cg07790169 | 1 | 49242932 | Higher in Smoker |
| cg21429105 | 2 | 27290873 | Lower in Smoker |
| cg25126678 | 2 | 27274379 | Higher in Smoker |
| cg22003772 | 2 | 27273474 | Lower in Smoker |
| cg09199225 | 6 | 32149260 | Higher in Smoker |
| cg23104549 | 7 | 141254379 | Lower in Smoker |
| cg22353495 | 1 | 100326811 | Lower in Smoker |
| cg24794734 | 1 | 100316114 | Higher in Smoker |
| cg11418663 | 1 | 15910166 | Lower in Smoker |
| cg14750743 | 6 | 32137294 | Higher in Smoker |
| cg00689685 | 6 | 32139812 | Lower in Smoker |
| cg22261911 | 6 | 32143689 | Higher in Smoker |
| cg13422804 | 9 | 139582673 | Lower in Smoker |
| cg09731946 | 21 | 45336903 | Higher in Smoker |
| cg14209522 | 21 | 45381306 | Lower in Smoker |
| cg07912402 | 1 | 989305 | Lower in Smoker |
| cg16903000 | 1 | 990293 | Lower in Smoker |

| | | | |
|---|---|---|---|
| cg20594982 | 1 | 976707 | Lower in Smoker |
| cg04824673 | 9 | 88356442 | Higher in Smoker |
| cg15566448 | 1 | 11808230 | Lower in Smoker |
| cg16967583 | 2 | 241807859 | Lower in Smoker |
| cg15204036 | 4 | 109684526 | Higher in Smoker |
| cg23977063 | 5 | 177659926 | Lower in Smoker |
| cg20703240 | 5 | 177659585 | Higher in Smoker |
| cg16987804 | 1 | 247095607 | Higher in Smoker |
| cg23636941 | 20 | 32899839 | Higher in Smoker |
| cg15927257 | 7 | 128865654 | Higher in Smoker |
| cg06474646 | 7 | 128864675 | Higher in Smoker |
| cg16166368 | 7 | 128864205 | Lower in Smoker |
| cg17164905 | 1 | 27931310 | Lower in Smoker |
| cg14789828 | 11 | 62201168 | Higher in Smoker |
| cg14171514 | 11 | 62308492 | Lower in Smoker |
| cg09918450 | 11 | 62308513 | Lower in Smoker |
| cg18958585 | 14 | 105444904 | Higher in Smoker |
| cg13599499 | 14 | 105444874 | Higher in Smoker |
| cg11138227 | 14 | 105436973 | Lower in Smoker |
| cg05376485 | 14 | 105442241 | Lower in Smoker |
| cg08606254 | 5 | 323969 | Higher in Smoker |
| cg12806681 | 5 | 368394 | Lower in Smoker |
| cg24688690 | 5 | 345850 | Lower in Smoker |
| cg03991871 | 5 | 368447 | Lower in Smoker |
| cg04551776 | 5 | 393366 | Lower in Smoker |
| cg17287155 | 5 | 393347 | Lower in Smoker |
| cg23576855 | 5 | 373299 | Lower in Smoker |
| cg05575921 | 5 | 373378 | Lower in Smoker |
| cg17248487 | 5 | 399887 | Lower in Smoker |
| cg11554391 | 5 | 321320 | Lower in Smoker |
| cg01899089 | 5 | 369969 | Lower in Smoker |
| cg17401179 | 5 | 400517 | Lower in Smoker |
| cg14454127 | 5 | 399787 | Lower in Smoker |
| cg14481490 | 5 | 392920 | Lower in Smoker |
| cg03313140 | 2 | 61403611 | Lower in Smoker |

| | | | |
|---|---|---|---|
| cg25991028 | 6 | 143542226 | Lower in Smoker |
| cg24659501 | 1 | 159043551 | Lower in Smoker |
| cg09646028 | 4 | 107269030 | Lower in Smoker |
| cg03481658 | 7 | 6051355 | Lower in Smoker |
| cg21052656 | 11 | 67250046 | Lower in Smoker |
| cg21747271 | 11 | 67250052 | Lower in Smoker |
| cg13888445 | 9 | 130628947 | Lower in Smoker |
| cg19647301 | 1 | 33502579 | Higher in Smoker |
| cg06394897 | 1 | 33502464 | Higher in Smoker |
| cg06438056 | 1 | 33502433 | Higher in Smoker |
| cg21942430 | 1 | 65613385 | Higher in Smoker |
| cg26036018 | 1 | 65641680 | Lower in Smoker |
| cg20632208 | 1 | 77999560 | Higher in Smoker |
| cg23201883 | 14 | 96858394 | Lower in Smoker |
| cg08034643 | 17 | 55163474 | Higher in Smoker |
| cg17613373 | 17 | 55162322 | Lower in Smoker |
| cg13033898 | 6 | 151561055 | Lower in Smoker |
| cg06019170 | 6 | 151646957 | Higher in Smoker |
| cg16520955 | 15 | 85923272 | Higher in Smoker |
| cg07033880 | 15 | 85923739 | Higher in Smoker |
| cg26482757 | 15 | 85999002 | Lower in Smoker |
| cg17178777 | 15 | 85949116 | Lower in Smoker |
| cg03362667 | 15 | 85928046 | Lower in Smoker |
| cg15664701 | X | 119030658 | Lower in Smoker |
| cg15979172 | 19 | 15490570 | Higher in Smoker |
| cg20222376 | 19 | 15530606 | Lower in Smoker |
| cg17322935 | 7 | 91570297 | Higher in Smoker |
| cg23413068 | 6 | 109848677 | Lower in Smoker |
| cg26096107 | 6 | 110012386 | Higher in Smoker |
| cg14260530 | 9 | 117157871 | Lower in Smoker |
| cg13179880 | 1 | 46016123 | Higher in Smoker |
| cg11693019 | 7 | 134211620 | Lower in Smoker |
| cg15489301 | 7 | 134213038 | Lower in Smoker |
| cg00363716 | 10 | 5061094 | Lower in Smoker |
| cg17257469 | 7 | 137775104 | Lower in Smoker |

| | | | |
|---|---|---|---|
| cg24212267 | 7 | 137801780 | Lower in Smoker |
| cg12219123 | 1 | 19638411 | Higher in Smoker |
| cg20923444 | 14 | 105247170 | Lower in Smoker |
| cg00379836 | 19 | 50372937 | Higher in Smoker |
| cg12237272 | 19 | 50373379 | Higher in Smoker |
| cg10193733 | 16 | 53537223 | Higher in Smoker |
| cg10965432 | 16 | 53537025 | Higher in Smoker |
| cg02965178 | 16 | 53538660 | Lower in Smoker |
| cg14469290 | 9 | 116164446 | Lower in Smoker |
| cg16983541 | 3 | 52231347 | Lower in Smoker |
| cg13077930 | 4 | 74269525 | Lower in Smoker |
| cg17550268 | 3 | 105085597 | Higher in Smoker |
| cg12226306 | 3 | 105087718 | Higher in Smoker |
| cg02259284 | 3 | 105085701 | Higher in Smoker |
| cg08326933 | 19 | 49967537 | Lower in Smoker |
| cg12382153 | 15 | 58357204 | Higher in Smoker |
| cg14805347 | 15 | 58357879 | Higher in Smoker |
| cg03365437 | 15 | 58357874 | Higher in Smoker |
| cg13964005 | 9 | 38395561 | Lower in Smoker |
| cg11022432 | 3 | 125899878 | Higher in Smoker |
| cg14918927 | 12 | 105477694 | Lower in Smoker |
| cg06801483 | 12 | 112226133 | Lower in Smoker |
| cg18308351 | 17 | 79552182 | Higher in Smoker |
| cg01408871 | 11 | 67789045 | Lower in Smoker |
| cg12909523 | 1 | 19217472 | Lower in Smoker |
| cg19551232 | 5 | 125931001 | Higher in Smoker |
| cg13516796 | 16 | 5122251 | Higher in Smoker |
| cg23762105 | 12 | 34175262 | Higher in Smoker |
| cg26520232 | X | 110928236 | Lower in Smoker |
| cg10115827 | 1 | 95538375 | Higher in Smoker |
| cg13559495 | 1 | 95538467 | Higher in Smoker |
| cg11036189 | 3 | 183967354 | Higher in Smoker |
| cg09043750 | 13 | 37574610 | Higher in Smoker |
| cg14109335 | 1 | 63833820 | Higher in Smoker |
| cg15832574 | 1 | 63901727 | Lower in Smoker |

| | | | |
|---|---|---|---|
| cg05509800 | 12 | 109531564 | Lower in Smoker |
| cg06704539 | 7 | 102105256 | Higher in Smoker |
| cg00591342 | 17 | 18086559 | Higher in Smoker |
| cg05215272 | 17 | 6899095 | Higher in Smoker |
| cg20216752 | 17 | 6913521 | Lower in Smoker |
| cg27243389 | 10 | 45869702 | Higher in Smoker |
| cg07162257 | 1 | 21835692 | Higher in Smoker |
| cg13377965 | 1 | 21844799 | Lower in Smoker |
| cg24278695 | 3 | 46727805 | Lower in Smoker |
| cg00765312 | 12 | 85674694 | Higher in Smoker |
| cg03781931 | 12 | 85673200 | Higher in Smoker |
| cg06552356 | 12 | 85674531 | Higher in Smoker |
| cg25131551 | 1 | 110607342 | Lower in Smoker |
| cg26365854 | 11 | 44330903 | Higher in Smoker |
| cg01564033 | 11 | 44332216 | Higher in Smoker |
| cg23089549 | 11 | 44331905 | Higher in Smoker |
| cg11260848 | 11 | 44326260 | Higher in Smoker |
| cg00061629 | 11 | 44325258 | Higher in Smoker |
| cg21484512 | 8 | 11189650 | Lower in Smoker |
| cg14322040 | 4 | 71457880 | Lower in Smoker |
| cg16821385 | 11 | 46467232 | Lower in Smoker |
| cg27245817 | 11 | 46534980 | Lower in Smoker |
| cg21101750 | 11 | 46613652 | Lower in Smoker |
| cg19244380 | 11 | 46612744 | Lower in Smoker |
| cg27016906 | 6 | 111195967 | Lower in Smoker |
| cg07236190 | 12 | 96338038 | Lower in Smoker |
| cg18392482 | 12 | 96338011 | Lower in Smoker |
| cg03015899 | 16 | 2578331 | Lower in Smoker |
| cg09361751 | 16 | 56460156 | Lower in Smoker |
| cg02691360 | 16 | 56396075 | Lower in Smoker |
| cg00299047 | 19 | 2252069 | Higher in Smoker |
| cg05838358 | 12 | 47469754 | Lower in Smoker |
| cg18893793 | 12 | 47472810 | Higher in Smoker |
| cg24458009 | 12 | 47472775 | Higher in Smoker |
| cg15078681 | 3 | 49756571 | Higher in Smoker |

| | | | |
|---|---|---|---|
| cg16841389 | X | 109662275 | Lower in Smoker |
| cg25730281 | X | 109468667 | Lower in Smoker |
| cg07294263 | 2 | 128641893 | Lower in Smoker |
| cg08198187 | 12 | 31882596 | Lower in Smoker |
| cg24507210 | X | 112084814 | Higher in Smoker |
| cg24690818 | X | 112084127 | Higher in Smoker |
| cg01816615 | X | 112066190 | Lower in Smoker |
| cg20493960 | 11 | 94502524 | Higher in Smoker |
| cg18993847 | 11 | 94502349 | Higher in Smoker |
| cg04347820 | 1 | 110161002 | Lower in Smoker |
| cg15447512 | 1 | 110163209 | Higher in Smoker |
| cg03937605 | 1 | 110167976 | Lower in Smoker |
| cg21644334 | 1 | 110168049 | Lower in Smoker |
| cg02082273 | 11 | 10473038 | Lower in Smoker |
| cg26122980 | 7 | 38671001 | Higher in Smoker |
| cg10293925 | 7 | 38670985 | Higher in Smoker |
| cg07926691 | 7 | 38670987 | Higher in Smoker |
| cg20191453 | 3 | 49459855 | Higher in Smoker |
| cg01400750 | 4 | 145956168 | Higher in Smoker |
| cg07070583 | 4 | 146015419 | Lower in Smoker |
| cg01713505 | 4 | 146018691 | Higher in Smoker |
| cg01940055 | 4 | 146018582 | Lower in Smoker |
| cg02387854 | 17 | 79849442 | Higher in Smoker |
| cg15484384 | 3 | 134203672 | Lower in Smoker |
| cg24438954 | 12 | 110841535 | Higher in Smoker |
| cg11943753 | 12 | 110842879 | Lower in Smoker |
| cg04838709 | 14 | 21151782 | Higher in Smoker |
| cg26044428 | 14 | 77279408 | Higher in Smoker |
| cg12090942 | 14 | 77279508 | Lower in Smoker |
| cg23248351 | 8 | 108511700 | Higher in Smoker |
| cg02130329 | 8 | 108370910 | Lower in Smoker |
| cg15530351 | 8 | 6407676 | Lower in Smoker |
| cg17754742 | 8 | 6400956 | Lower in Smoker |
| cg20460488 | 8 | 6407812 | Lower in Smoker |
| cg06837791 | 19 | 8429491 | Higher in Smoker |

| | | | |
|---|---|---|---|
| cg00583328 | 8 | 41753348 | Higher in Smoker |
| cg21342785 | 8 | 41707516 | Higher in Smoker |
| cg14354820 | 8 | 41691767 | Lower in Smoker |
| cg05166490 | 8 | 41754172 | Higher in Smoker |
| cg17331296 | 8 | 41754181 | Higher in Smoker |
| cg11696388 | 8 | 41557540 | Higher in Smoker |
| cg23668222 | 8 | 41542092 | Higher in Smoker |
| cg27016366 | 8 | 41604672 | Lower in Smoker |
| cg15173741 | 8 | 41654618 | Lower in Smoker |
| cg16028169 | 4 | 113738957 | Lower in Smoker |
| cg07486252 | 4 | 114213914 | Lower in Smoker |
| cg25915539 | 4 | 114214080 | Lower in Smoker |
| cg17792419 | 10 | 61901305 | Lower in Smoker |
| cg00475235 | 17 | 54236118 | Lower in Smoker |
| cg03455107 | 17 | 54509207 | Lower in Smoker |
| cg08133013 | 17 | 4167205 | Higher in Smoker |
| cg01388015 | 17 | 4122618 | Lower in Smoker |
| cg21215929 | 5 | 14873039 | Higher in Smoker |
| cg08522087 | 5 | 14871910 | Higher in Smoker |
| cg16405454 | 11 | 113258223 | Lower in Smoker |
| cg16831471 | 12 | 133304233 | Higher in Smoker |
| cg20089935 | 12 | 133324714 | Lower in Smoker |
| cg06063464 | 12 | 133333850 | Lower in Smoker |
| cg21729214 | 12 | 133312061 | Lower in Smoker |
| cg13340065 | 2 | 241493941 | Lower in Smoker |
| cg13198503 | 2 | 241497583 | Lower in Smoker |
| cg13604246 | 2 | 241497412 | Lower in Smoker |
| cg03680250 | 13 | 111567502 | Higher in Smoker |
| cg23052366 | 13 | 111553101 | Lower in Smoker |
| cg25368566 | 13 | 111561016 | Lower in Smoker |
| cg07511934 | 16 | 89386912 | Higher in Smoker |
| cg05175606 | 16 | 89556089 | Higher in Smoker |
| cg05638739 | 16 | 89440324 | Higher in Smoker |
| cg03162666 | 16 | 89346269 | Higher in Smoker |
| cg03633073 | 16 | 89437513 | Lower in Smoker |

| | | | |
|---|---|---|---|
| cg08949854 | 16 | 89437501 | Lower in Smoker |
| cg01271982 | 16 | 89417545 | Lower in Smoker |
| cg08144444 | 16 | 89485322 | Lower in Smoker |
| cg21787369 | 16 | 89373297 | Lower in Smoker |
| cg16442258 | 16 | 89439288 | Lower in Smoker |
| cg09938469 | 16 | 89338688 | Lower in Smoker |
| cg08822215 | 16 | 89438651 | Lower in Smoker |
| cg07929642 | 16 | 89390685 | Lower in Smoker |
| cg09971549 | 16 | 89487322 | Lower in Smoker |
| cg05504729 | 16 | 89399490 | Lower in Smoker |
| cg14215472 | 17 | 27940404 | Lower in Smoker |
| cg19016062 | 10 | 5904561 | Lower in Smoker |
| cg17560720 | 10 | 5932700 | Higher in Smoker |
| cg27469738 | 10 | 99338074 | Lower in Smoker |
| cg13994504 | 10 | 99338056 | Lower in Smoker |
| cg13773678 | 9 | 67927392 | Higher in Smoker |
| cg14442939 | 10 | 27389572 | Higher in Smoker |
| cg13421439 | 18 | 21199515 | Higher in Smoker |
| cg22935653 | 5 | 74532268 | Lower in Smoker |
| cg06091475 | 5 | 79863923 | Lower in Smoker |
| cg26305827 | 5 | 79866869 | Lower in Smoker |
| cg21800232 | 5 | 79866368 | Lower in Smoker |
| cg25316339 | 5 | 79866379 | Lower in Smoker |
| cg03399905 | 15 | 79576060 | Higher in Smoker |
| cg01697989 | 15 | 79574209 | Lower in Smoker |
| cg18762736 | 1 | 145549283 | Higher in Smoker |
| cg00232805 | 2 | 97779565 | Higher in Smoker |
| cg21404851 | 2 | 97783139 | Lower in Smoker |
| cg20256403 | 2 | 97523850 | Higher in Smoker |
| cg23286353 | 2 | 97523832 | Lower in Smoker |
| cg04721602 | 11 | 82905091 | Higher in Smoker |
| cg12923585 | 5 | 132149015 | Higher in Smoker |
| cg07876862 | 5 | 132151047 | Lower in Smoker |
| cg26784000 | 2 | 197937755 | Lower in Smoker |
| cg11223184 | 2 | 198003295 | Lower in Smoker |

| | | | |
|---|---|---|---|
| cg07683388 | 2 | 198029332 | Lower in Smoker |
| cg22529184 | 1 | 173639712 | Lower in Smoker |
| cg03686887 | 8 | 101573204 | Lower in Smoker |
| cg01439488 | 20 | 10015909 | Lower in Smoker |
| cg26485563 | 12 | 56652449 | Higher in Smoker |
| cg03122372 | 12 | 56651912 | Higher in Smoker |
| cg06783668 | 2 | 71204585 | Higher in Smoker |
| cg12968987 | 5 | 55502758 | Lower in Smoker |
| cg24423515 | 4 | 77819003 | Higher in Smoker |
| cg09787909 | 6 | 90203426 | Lower in Smoker |
| cg20474699 | 14 | 102976161 | Higher in Smoker |
| cg00252594 | 14 | 102974737 | Lower in Smoker |
| cg12103197 | 14 | 102974365 | Lower in Smoker |
| cg03940243 | 6 | 34954030 | Lower in Smoker |
| cg24053343 | 6 | 34922135 | Lower in Smoker |
| cg25895490 | 12 | 99146745 | Lower in Smoker |
| cg01782711 | 12 | 99332500 | Lower in Smoker |
| cg03966669 | 16 | 4763799 | Lower in Smoker |
| cg01762626 | 16 | 4784081 | Higher in Smoker |
| cg08872617 | 16 | 4783947 | Higher in Smoker |
| cg11117896 | 2 | 220094984 | Higher in Smoker |
| cg23696210 | 11 | 69928942 | Lower in Smoker |
| cg25490527 | 11 | 69933927 | Lower in Smoker |
| cg23036678 | 11 | 70002831 | Lower in Smoker |
| cg24276624 | 11 | 69982941 | Lower in Smoker |
| cg26213458 | 12 | 5918191 | Lower in Smoker |
| cg20959403 | 12 | 101280484 | Lower in Smoker |
| cg20037773 | 12 | 45609616 | Higher in Smoker |
| cg22251879 | 2 | 242144684 | Lower in Smoker |
| cg10173475 | 2 | 242152697 | Lower in Smoker |
| cg04415689 | 2 | 242128250 | Lower in Smoker |
| cg24932241 | 11 | 442077 | Lower in Smoker |
| cg08200582 | 11 | 442649 | Lower in Smoker |
| cg25703361 | 15 | 69076089 | Higher in Smoker |
| cg08362102 | 15 | 69087774 | Higher in Smoker |

| | | | |
|---|---|---|---|
| cg12026394 | 9 | 100745975 | Higher in Smoker |
| cg19405555 | 15 | 90358483 | Lower in Smoker |
| cg15979937 | 2 | 69336567 | Lower in Smoker |
| cg16326777 | 4 | 80885735 | Lower in Smoker |
| cg07934068 | 4 | 80883595 | Lower in Smoker |
| cg09533293 | 15 | 60689670 | Higher in Smoker |
| cg16472060 | 15 | 60690385 | Lower in Smoker |
| cg09785377 | 15 | 60644157 | Lower in Smoker |
| cg17927583 | 4 | 79490198 | Lower in Smoker |
| cg13355704 | 2 | 69968414 | Higher in Smoker |
| cg21960922 | 2 | 69969227 | Higher in Smoker |
| cg00407659 | 5 | 150538414 | Lower in Smoker |
| cg15892650 | 5 | 150524635 | Lower in Smoker |
| cg14870539 | 5 | 150530752 | Lower in Smoker |
| cg18060909 | 5 | 150534782 | Lower in Smoker |
| cg15844154 | 10 | 75173990 | Higher in Smoker |
| cg25512683 | 17 | 41003399 | Lower in Smoker |
| cg03047098 | 16 | 71843015 | Lower in Smoker |
| cg10321766 | X | 15872216 | Higher in Smoker |
| cg03620623 | 19 | 50303257 | Lower in Smoker |
| cg27368423 | 11 | 926250 | Higher in Smoker |
| cg20946044 | 11 | 1010712 | Lower in Smoker |
| cg05998672 | 11 | 986408 | Lower in Smoker |
| cg17751065 | 17 | 33997547 | Lower in Smoker |
| cg17417198 | 5 | 77590955 | Lower in Smoker |
| cg03299454 | 8 | 42010433 | Higher in Smoker |
| cg13680246 | 8 | 42013960 | Lower in Smoker |
| cg02349866 | 15 | 90391877 | Higher in Smoker |
| cg08869031 | 15 | 90436841 | Higher in Smoker |
| cg04872610 | 1 | 114448489 | Lower in Smoker |
| cg21124552 | 15 | 51200363 | Higher in Smoker |
| cg27183811 | 15 | 51200847 | Higher in Smoker |
| cg08060512 | 15 | 51200672 | Higher in Smoker |
| cg01546046 | 14 | 31494849 | Lower in Smoker |
| cg12944944 | 12 | 99124716 | Lower in Smoker |

| | | | |
|---|---|---|---|
| cg14872956 | 12 | 99039015 | Higher in Smoker |
| cg15623573 | 9 | 72288098 | Higher in Smoker |
| cg22135269 | 15 | 29338250 | Lower in Smoker |
| cg18385440 | 15 | 29212889 | Lower in Smoker |
| cg05790451 | 15 | 29396200 | Lower in Smoker |
| cg03559682 | 11 | 6439864 | Higher in Smoker |
| cg03801030 | 11 | 6440781 | Higher in Smoker |
| cg15832405 | 4 | 41216869 | Higher in Smoker |
| cg11404380 | 4 | 41215359 | Lower in Smoker |
| cg05020685 | 4 | 40858965 | Higher in Smoker |
| cg05855008 | 5 | 139944351 | Higher in Smoker |
| cg11613015 | 5 | 112073406 | Higher in Smoker |
| cg01240931 | 5 | 112074043 | Lower in Smoker |
| cg19870717 | 19 | 1472936 | Higher in Smoker |
| cg21776993 | 19 | 1449424 | Higher in Smoker |
| cg23418591 | 20 | 57090317 | Higher in Smoker |
| cg00950473 | 20 | 57041294 | Lower in Smoker |
| cg13968061 | 1 | 159557257 | Lower in Smoker |
| cg03060546 | 3 | 49711283 | Higher in Smoker |
| cg16323843 | 3 | 49711263 | Higher in Smoker |
| cg20402382 | 3 | 49711530 | Higher in Smoker |
| cg06719487 | 1 | 10489962 | Higher in Smoker |
| cg19915020 | 1 | 10490985 | Higher in Smoker |
| cg11196904 | 1 | 10491304 | Lower in Smoker |
| cg09578353 | 1 | 10490236 | Lower in Smoker |
| cg22885367 | 2 | 68694660 | Higher in Smoker |
| cg16353361 | X | 128790057 | Lower in Smoker |
| cg25072179 | 11 | 57004934 | Higher in Smoker |
| cg15355388 | 11 | 57004919 | Higher in Smoker |
| cg26828119 | 19 | 36360834 | Higher in Smoker |
| cg23729763 | 11 | 129991544 | Higher in Smoker |
| cg03010018 | 11 | 116708299 | Lower in Smoker |
| cg13621464 | 11 | 116662643 | Lower in Smoker |
| cg08665930 | 22 | 39418130 | Lower in Smoker |
| cg09582545 | 22 | 39440294 | Higher in Smoker |

| | | | |
|---|---|---|---|
| cg13256546 | 22 | 39472544 | Lower in Smoker |
| cg23896816 | 22 | 39473253 | Higher in Smoker |
| cg17972162 | 22 | 39496387 | Lower in Smoker |
| cg16056272 | 1 | 183616968 | Lower in Smoker |
| cg00587465 | 19 | 45429910 | Lower in Smoker |
| cg20090143 | 19 | 45452003 | Lower in Smoker |
| cg03742763 | 11 | 116700049 | Lower in Smoker |
| cg20330126 | 22 | 36125053 | Lower in Smoker |
| cg05693982 | 12 | 12940390 | Higher in Smoker |
| cg04943927 | 12 | 12937632 | Lower in Smoker |
| cg02301528 | 12 | 12939519 | Lower in Smoker |
| cg08015776 | 21 | 27543229 | Higher in Smoker |
| cg24168308 | 21 | 27372387 | Lower in Smoker |
| cg18274664 | 21 | 27372461 | Lower in Smoker |
| cg11321156 | 21 | 27372396 | Lower in Smoker |
| cg23269692 | 21 | 27372446 | Lower in Smoker |
| cg09433780 | 3 | 57262354 | Higher in Smoker |
| cg22667787 | 9 | 33001657 | Higher in Smoker |
| cg15373767 | 7 | 30951328 | Higher in Smoker |
| cg03970961 | 1 | 154292240 | Higher in Smoker |
| cg24715106 | 11 | 77301139 | Higher in Smoker |
| cg26328335 | 12 | 50354840 | Lower in Smoker |
| cg05019001 | X | 66766334 | Higher in Smoker |
| cg27271368 | X | 66764411 | Higher in Smoker |
| cg00242341 | 11 | 72447419 | Lower in Smoker |
| cg01577292 | 8 | 143696144 | Higher in Smoker |
| cg03244277 | 4 | 75310450 | Higher in Smoker |
| cg18080937 | 12 | 49353479 | Lower in Smoker |
| cg00929050 | 14 | 50359216 | Higher in Smoker |
| cg13838074 | 14 | 50359978 | Higher in Smoker |
| cg18168672 | 20 | 61905223 | Lower in Smoker |
| cg19956078 | 4 | 153831380 | Lower in Smoker |
| cg09360748 | 14 | 68086507 | Higher in Smoker |
| cg11752250 | 14 | 68069471 | Lower in Smoker |
| cg04074001 | 4 | 148861409 | Lower in Smoker |

| | | | |
|---|---|---|---|
| cg07523098 | 10 | 32218391 | Higher in Smoker |
| cg05194545 | 10 | 32096116 | Lower in Smoker |
| cg25026949 | 2 | 144099197 | Lower in Smoker |
| cg17056048 | 2 | 144271431 | Lower in Smoker |
| cg17592268 | 2 | 144477916 | Lower in Smoker |
| cg13643376 | 11 | 110583543 | Higher in Smoker |
| cg21197233 | 11 | 110578533 | Lower in Smoker |
| cg07740574 | 10 | 24873784 | Lower in Smoker |
| cg21355487 | 10 | 49688693 | Higher in Smoker |
| cg12497224 | 10 | 49731965 | Higher in Smoker |
| cg10668121 | 2 | 68968418 | Lower in Smoker |
| cg07618462 | 5 | 142499847 | Lower in Smoker |
| cg00967294 | 5 | 142445604 | Lower in Smoker |
| cg00997251 | 5 | 142444988 | Lower in Smoker |
| cg12307314 | 5 | 142206724 | Lower in Smoker |
| cg20133129 | X | 153192433 | Lower in Smoker |
| cg26916470 | 14 | 32546448 | Higher in Smoker |
| cg07828380 | X | 11683977 | Higher in Smoker |
| cg24249486 | X | 11684119 | Lower in Smoker |
| cg13868987 | X | 11683131 | Higher in Smoker |
| cg18036967 | X | 11683625 | Higher in Smoker |
| cg06457408 | 17 | 79327882 | Lower in Smoker |
| cg11326429 | 17 | 79927632 | Lower in Smoker |
| cg26876334 | 16 | 329682 | Lower in Smoker |
| cg08062358 | 19 | 42386382 | Lower in Smoker |
| cg24138325 | 8 | 1898270 | Higher in Smoker |
| cg00783409 | 8 | 1789288 | Lower in Smoker |
| cg06463230 | 8 | 1779625 | Lower in Smoker |
| cg03726963 | 8 | 1808475 | Lower in Smoker |
| cg25063796 | 8 | 1857212 | Lower in Smoker |
| cg07298996 | 8 | 1809956 | Lower in Smoker |
| cg00030907 | 8 | 1796072 | Lower in Smoker |
| cg01824603 | 8 | 1878323 | Lower in Smoker |
| cg09076010 | 1 | 18022847 | Lower in Smoker |
| cg02239752 | 1 | 17998265 | Lower in Smoker |

| | | | |
|---|---|---|---|
| cg10493270 | 11 | 120251845 | Lower in Smoker |
| cg08711320 | 1 | 3387932 | Lower in Smoker |
| cg03916277 | 1 | 3380250 | Lower in Smoker |
| cg12097441 | 1 | 3395258 | Lower in Smoker |
| cg10020040 | 1 | 3397621 | Lower in Smoker |
| cg15902830 | 1 | 3387913 | Lower in Smoker |
| cg13621184 | 19 | 7459697 | Higher in Smoker |
| cg09353354 | 19 | 7460276 | Higher in Smoker |
| cg02859589 | 19 | 7463252 | Lower in Smoker |
| cg00068433 | 1 | 16540130 | Lower in Smoker |
| cg24406391 | 1 | 155938911 | Lower in Smoker |
| cg27537937 | 1 | 155948318 | Higher in Smoker |
| cg00383019 | 3 | 56797995 | Lower in Smoker |
| cg14633892 | 3 | 56810749 | Lower in Smoker |
| cg17336423 | 2 | 131749301 | Lower in Smoker |
| cg13602816 | 2 | 131674221 | Lower in Smoker |
| cg23841608 | 2 | 131676293 | Lower in Smoker |
| cg03461298 | 13 | 111805918 | Higher in Smoker |
| cg02672368 | 13 | 111805930 | Lower in Smoker |
| cg10130374 | 13 | 111935412 | Higher in Smoker |
| cg06787317 | 13 | 111885879 | Lower in Smoker |
| cg24542126 | 1 | 27022232 | Higher in Smoker |
| cg03123091 | 1 | 27080598 | Lower in Smoker |
| cg23721345 | 1 | 27043524 | Lower in Smoker |
| cg08614771 | 6 | 157100981 | Higher in Smoker |
| cg17475813 | 6 | 157430527 | Lower in Smoker |
| cg01484950 | 6 | 157322565 | Lower in Smoker |
| cg06785293 | 6 | 157187520 | Lower in Smoker |
| cg14659678 | 12 | 46243365 | Lower in Smoker |
| cg01774027 | 19 | 947712 | Lower in Smoker |
| cg17167278 | 19 | 950224 | Lower in Smoker |
| cg23599660 | 14 | 58839034 | Lower in Smoker |
| cg06318796 | 10 | 63796694 | Lower in Smoker |
| cg10502149 | 10 | 63746909 | Lower in Smoker |
| cg03969079 | 10 | 63759909 | Lower in Smoker |

| | | | |
|---|---|---|---|
| cg16240060 | 3 | 48956015 | Lower in Smoker |
| cg07352345 | 5 | 175793049 | Higher in Smoker |
| cg06525892 | 5 | 175792454 | Higher in Smoker |
| cg26929261 | 5 | 175792123 | Lower in Smoker |
| cg04658679 | 13 | 50202713 | Higher in Smoker |
| cg05112617 | 3 | 93698932 | Lower in Smoker |
| cg02386665 | 5 | 53432372 | Lower in Smoker |
| cg15610472 | 5 | 53510393 | Lower in Smoker |
| cg00421815 | 5 | 53345690 | Lower in Smoker |
| cg02624690 | 17 | 37323484 | Higher in Smoker |
| cg09173348 | 17 | 37322431 | Lower in Smoker |
| cg07330481 | 17 | 37322330 | Lower in Smoker |
| cg05098096 | 16 | 18809458 | Lower in Smoker |
| cg00023132 | 3 | 69133948 | Higher in Smoker |
| cg13174898 | 1 | 202104055 | Lower in Smoker |
| cg07330908 | 3 | 5163890 | Higher in Smoker |
| cg00217553 | 3 | 5208420 | Lower in Smoker |
| cg22799850 | 7 | 102714871 | Higher in Smoker |
| cg05748666 | 6 | 109169444 | Higher in Smoker |
| cg15193782 | 10 | 23217017 | Lower in Smoker |
| cg08555772 | 10 | 28287707 | Higher in Smoker |
| cg05826330 | 16 | 31470953 | Higher in Smoker |
| ch.2.4639917R | 2 | 232127891 | Higher in Smoker |
| cg03448840 | 2 | 232115234 | Lower in Smoker |
| cg23116589 | X | 100805503 | Higher in Smoker |
| cg03623097 | 10 | 124213466 | Lower in Smoker |
| cg03390636 | 15 | 80843452 | Higher in Smoker |
| cg15456414 | 15 | 80777126 | Lower in Smoker |
| cg13805518 | 15 | 80697783 | Lower in Smoker |
| cg08371852 | 15 | 80876744 | Lower in Smoker |
| cg14794298 | 11 | 13336674 | Lower in Smoker |
| cg07568015 | 11 | 13367266 | Lower in Smoker |
| cg15474407 | 12 | 27500572 | Lower in Smoker |
| cg08798295 | 7 | 98972169 | Higher in Smoker |
| cg05715492 | 7 | 98991138 | Lower in Smoker |

| | | | |
|---|---|---|---|
| cg13999774 | 2 | 219119034 | Lower in Smoker |
| cg24316949 | 1 | 183601017 | Lower in Smoker |
| cg18507362 | 3 | 169484810 | Lower in Smoker |
| cg02811712 | 15 | 52861446 | Higher in Smoker |
| cg05944271 | 3 | 35762844 | Lower in Smoker |
| cg21574316 | 11 | 75062600 | Higher in Smoker |
| cg22969079 | 11 | 75046350 | Lower in Smoker |
| cg20393975 | 9 | 140499623 | Higher in Smoker |
| cg18096253 | 19 | 18118079 | Higher in Smoker |
| cg00474840 | 19 | 18120819 | Lower in Smoker |
| cg11297817 | 22 | 51066761 | Higher in Smoker |
| cg13121490 | 5 | 78280331 | Higher in Smoker |
| cg22366897 | X | 2836235 | Lower in Smoker |
| cg17012513 | X | 2984799 | Lower in Smoker |
| cg27366162 | 17 | 66375195 | Higher in Smoker |
| cg05163093 | 17 | 66289930 | Lower in Smoker |
| cg14778914 | 17 | 66289482 | Lower in Smoker |
| cg26728709 | 4 | 114823338 | Higher in Smoker |
| cg01351300 | 4 | 114873079 | Lower in Smoker |
| cg06089269 | 4 | 114900720 | Higher in Smoker |
| cg13789363 | 4 | 77033759 | Lower in Smoker |
| cg20276103 | 1 | 44398868 | Higher in Smoker |
| cg00476814 | 22 | 19974536 | Higher in Smoker |
| cg19339932 | 22 | 20004356 | Higher in Smoker |
| cg20563534 | 22 | 20004369 | Higher in Smoker |
| cg06943593 | X | 25030643 | Higher in Smoker |
| cg02938958 | X | 25022847 | Higher in Smoker |
| cg16414561 | X | 25033893 | Higher in Smoker |
| cg25437947 | 8 | 17941982 | Higher in Smoker |
| ch.8.2599852F | 8 | 131171898 | Higher in Smoker |
| cg14019348 | 2 | 9504768 | Lower in Smoker |
| cg13414444 | 2 | 239344617 | Higher in Smoker |
| cg09841747 | 2 | 239336167 | Lower in Smoker |
| cg22812874 | 7 | 150872392 | Lower in Smoker |
| cg24654025 | 10 | 5685896 | Lower in Smoker |

| | | | |
|---|---|---|---|
| cg16988970 | 17 | 42248062 | Lower in Smoker |
| cg06258596 | 17 | 42254662 | Lower in Smoker |
| cg21998638 | 2 | 237145775 | Higher in Smoker |
| cg07486732 | 2 | 237150793 | Lower in Smoker |
| cg15817482 | 14 | 94423801 | Higher in Smoker |
| cg18485877 | 14 | 94402477 | Lower in Smoker |
| cg19949550 | 14 | 94423704 | Higher in Smoker |
| cg01956154 | 14 | 94423399 | Higher in Smoker |
| cg19100779 | 7 | 95115232 | Lower in Smoker |
| cg26847490 | 7 | 95115289 | Lower in Smoker |
| cg27016565 | 15 | 101168155 | Higher in Smoker |
| cg09355889 | 12 | 48550727 | Higher in Smoker |
| cg09386303 | 12 | 48551862 | Lower in Smoker |
| cg10200408 | 12 | 48551356 | Higher in Smoker |
| cg06285475 | 10 | 73885299 | Lower in Smoker |
| cg15013801 | 10 | 73976790 | Lower in Smoker |
| cg05517447 | 6 | 101211671 | Lower in Smoker |
| cg27569040 | 12 | 103351855 | Higher in Smoker |
| cg24057514 | 11 | 2293181 | Lower in Smoker |
| cg25813345 | 11 | 8964967 | Lower in Smoker |
| cg16741602 | 11 | 8965730 | Lower in Smoker |
| cg06969527 | 19 | 14248428 | Higher in Smoker |
| cg03513471 | X | 146993485 | Lower in Smoker |
| cg15340652 | 7 | 65540641 | Higher in Smoker |
| cg19709354 | 2 | 190526349 | Higher in Smoker |
| cg14969899 | 14 | 104569581 | Lower in Smoker |
| cg10606061 | 8 | 62534440 | Lower in Smoker |
| cg18006411 | 8 | 62415183 | Lower in Smoker |
| cg06068338 | 8 | 62494502 | Lower in Smoker |
| cg10584100 | 8 | 62604144 | Lower in Smoker |
| cg03961580 | 8 | 62589300 | Lower in Smoker |
| cg12700695 | 22 | 26833717 | Lower in Smoker |
| cg04597389 | 17 | 79935740 | Higher in Smoker |
| cg20901787 | 17 | 79936477 | Lower in Smoker |
| cg20538228 | 17 | 79941335 | Lower in Smoker |

| | | | |
|---|---|---|---|
| cg23135546 | 17 | 79953026 | Lower in Smoker |
| cg22693702 | 11 | 62105635 | Higher in Smoker |
| cg04728402 | 11 | 62104662 | Lower in Smoker |
| cg06239285 | 11 | 62104954 | Higher in Smoker |
| cg13597397 | 9 | 133320948 | Higher in Smoker |
| cg12268575 | 1 | 177133536 | Higher in Smoker |
| cg13480937 | 1 | 177112230 | Lower in Smoker |
| cg10886678 | 20 | 30946050 | Higher in Smoker |
| cg06443831 | 2 | 26052597 | Lower in Smoker |
| cg00844078 | 2 | 26098817 | Lower in Smoker |
| cg18608498 | 10 | 89577399 | Higher in Smoker |
| cg23735749 | 1 | 1417247 | Lower in Smoker |
| cg19621710 | 1 | 1404170 | Higher in Smoker |
| cg20951194 | 1 | 1396296 | Lower in Smoker |
| cg17282836 | 1 | 1397524 | Lower in Smoker |
| cg10522845 | 1 | 1397837 | Lower in Smoker |
| cg05655647 | 12 | 51157023 | Higher in Smoker |
| cg08740063 | 12 | 51180192 | Lower in Smoker |
| cg10315420 | 12 | 51213748 | Lower in Smoker |
| cg24043307 | 12 | 51157954 | Higher in Smoker |
| cg19447671 | 2 | 176032513 | Higher in Smoker |
| cg03970567 | 1 | 212761056 | Higher in Smoker |
| cg10309957 | 1 | 161735234 | Higher in Smoker |
| cg09175582 | 1 | 161736000 | Higher in Smoker |
| cg07376805 | 1 | 161833149 | Lower in Smoker |
| cg19816775 | 1 | 161916064 | Lower in Smoker |
| cg06609004 | 6 | 32086425 | Higher in Smoker |
| cg22986222 | 6 | 32095276 | Lower in Smoker |
| cg21755457 | 12 | 54020320 | Lower in Smoker |
| cg03846111 | 12 | 14547229 | Higher in Smoker |
| cg27147858 | 11 | 64662747 | Lower in Smoker |
| cg00170343 | 3 | 11313890 | Higher in Smoker |
| cg06592829 | 3 | 11519599 | Lower in Smoker |
| cg18531720 | 3 | 11526841 | Lower in Smoker |
| cg10411146 | 11 | 289966 | Higher in Smoker |

| | | | |
|---|---|---|---|
| cg11480797 | 11 | 288943 | Lower in Smoker |
| cg05734400 | 2 | 216176660 | Higher in Smoker |
| cg14036868 | 2 | 38604442 | Higher in Smoker |
| cg25400013 | 11 | 108093439 | Higher in Smoker |
| cg24399924 | 2 | 85980533 | Higher in Smoker |
| cg10674105 | 5 | 151134687 | Lower in Smoker |
| cg16389285 | 15 | 26108399 | Higher in Smoker |
| cg21951425 | 15 | 26108612 | Higher in Smoker |
| cg00602502 | 15 | 26089080 | Lower in Smoker |
| cg16988989 | 15 | 25925801 | Lower in Smoker |
| cg15531450 | 15 | 26047499 | Lower in Smoker |
| cg27087136 | 5 | 160061746 | Lower in Smoker |
| cg26757305 | 4 | 47487301 | Higher in Smoker |
| cg26666292 | 13 | 113540557 | Higher in Smoker |
| cg08464505 | 13 | 113425982 | Higher in Smoker |
| cg27326999 | 13 | 113521666 | Higher in Smoker |
| cg25457815 | 13 | 113427738 | Higher in Smoker |
| cg21456212 | 13 | 113359836 | Higher in Smoker |
| cg15495091 | 13 | 113491819 | Lower in Smoker |
| cg00239491 | 13 | 113405479 | Lower in Smoker |
| cg21570597 | 13 | 113495380 | Lower in Smoker |
| cg09815356 | 13 | 113359631 | Lower in Smoker |
| cg07156557 | 3 | 194185300 | Lower in Smoker |
| cg25013044 | 3 | 193096009 | Lower in Smoker |
| cg11342277 | 1 | 116915598 | Higher in Smoker |
| cg14841875 | 1 | 116916411 | Higher in Smoker |
| cg12034297 | 1 | 160137816 | Lower in Smoker |
| cg04792642 | 1 | 160140085 | Lower in Smoker |
| cg20364320 | 17 | 3867794 | Higher in Smoker |
| cg11608582 | 17 | 3843121 | Lower in Smoker |
| cg14808132 | 3 | 10547179 | Higher in Smoker |
| cg22810426 | X | 152801393 | Lower in Smoker |
| cg22226839 | 1 | 203596051 | Higher in Smoker |
| cg14565279 | 1 | 203698627 | Lower in Smoker |
| cg25611880 | 3 | 130612784 | Higher in Smoker |

| | | | |
|---|---|---|---|
| cg04481715 | 13 | 114303538 | Lower in Smoker |
| cg05201344 | 13 | 114304887 | Lower in Smoker |
| cg26446071 | 13 | 114311372 | Lower in Smoker |
| cg22283488 | 18 | 43678583 | Higher in Smoker |
| cg23376861 | 18 | 43678713 | Lower in Smoker |
| cg05244682 | 10 | 7839613 | Lower in Smoker |
| cg14103143 | 17 | 46969973 | Higher in Smoker |
| cg11715999 | 17 | 46970694 | Higher in Smoker |
| cg08995424 | 12 | 54070891 | Higher in Smoker |
| cg13784195 | 21 | 27104564 | Lower in Smoker |
| cg25694218 | 21 | 27106793 | Higher in Smoker |
| cg02734762 | 11 | 118272031 | Higher in Smoker |
| cg02053566 | 11 | 118272700 | Higher in Smoker |
| cg21018522 | 11 | 118272357 | Lower in Smoker |
| cg15996947 | 14 | 50780115 | Lower in Smoker |
| cg14054120 | 19 | 41945352 | Higher in Smoker |
| cg10645377 | X | 153659893 | Lower in Smoker |
| cg20530560 | 17 | 40610845 | Higher in Smoker |
| cg02062348 | 12 | 124196676 | Higher in Smoker |
| cg04211927 | 7 | 138435324 | Lower in Smoker |
| cg11799589 | 1 | 44443270 | Lower in Smoker |
| cg04619838 | 16 | 67515103 | Higher in Smoker |
| cg06120000 | 16 | 67480229 | Lower in Smoker |
| cg05966241 | 16 | 67515938 | Lower in Smoker |
| cg17784027 | 8 | 67109832 | Lower in Smoker |
| cg06689659 | 8 | 87110279 | Lower in Smoker |
| cg26316599 | 5 | 172456055 | Higher in Smoker |
| cg20225275 | 5 | 172410975 | Higher in Smoker |
| cg02433905 | 3 | 113465485 | Higher in Smoker |
| cg08924488 | 3 | 113464993 | Higher in Smoker |
| cg11856918 | 8 | 20054956 | Higher in Smoker |
| cg07762761 | 8 | 104033118 | Higher in Smoker |
| cg12090242 | 22 | 18111911 | Higher in Smoker |
| cg26688816 | 2 | 46740690 | Lower in Smoker |
| cg06463759 | 7 | 128502823 | Higher in Smoker |

| | | | |
|---|---|---|---|
| cg17140815 | 7 | 128502651 | Higher in Smoker |
| cg14421829 | 9 | 117350234 | Higher in Smoker |
| cg24926872 | 8 | 54755585 | Higher in Smoker |
| cg24533989 | 4 | 42659536 | Higher in Smoker |
| cg23886154 | 4 | 42659286 | Higher in Smoker |
| cg05510976 | 13 | 26477773 | Lower in Smoker |
| cg08368169 | 13 | 25949998 | Lower in Smoker |
| cg19599368 | 15 | 50180387 | Higher in Smoker |
| cg10823157 | 18 | 76829834 | Higher in Smoker |
| cg17928607 | 18 | 77082212 | Lower in Smoker |
| cg02771587 | 18 | 76910242 | Lower in Smoker |
| cg00215224 | 15 | 35839876 | Lower in Smoker |
| cg05349356 | 20 | 3451609 | Higher in Smoker |
| cg04335339 | 10 | 116853118 | Higher in Smoker |
| cg10082114 | X | 77041194 | Higher in Smoker |
| cg18440893 | 6 | 16760537 | Higher in Smoker |
| cg06076692 | 6 | 16736892 | Lower in Smoker |
| cg08635723 | 6 | 16399244 | Lower in Smoker |
| cg00464814 | 6 | 16758889 | Lower in Smoker |
| cg10487127 | 6 | 16761668 | Higher in Smoker |
| cg26673609 | 14 | 92572604 | Higher in Smoker |
| cg06793890 | X | 13338497 | Lower in Smoker |
| cg07186939 | X | 13336853 | Lower in Smoker |
| cg18411108 | 3 | 63955727 | Higher in Smoker |
| cg15226514 | 3 | 63856759 | Higher in Smoker |
| cg07753241 | 3 | 63849527 | Higher in Smoker |
| cg23105099 | 7 | 105339648 | Lower in Smoker |
| cg19053223 | 7 | 105359070 | Lower in Smoker |
| cg14427668 | 7 | 105319437 | Lower in Smoker |
| cg18982073 | 17 | 42275458 | Higher in Smoker |
| cg14542950 | 9 | 94123659 | Higher in Smoker |
| cg03139435 | 20 | 54966401 | Lower in Smoker |
| cg19603903 | 19 | 57742345 | Higher in Smoker |
| cg01471203 | 7 | 70255416 | Lower in Smoker |
| cg07915206 | 15 | 34260555 | Lower in Smoker |

| | | | |
|---|---|---|---|
| cg08181251 | 10 | 99443455 | Lower in Smoker |
| cg15677434 | 1 | 206226009 | Lower in Smoker |
| cg19351638 | X | 153170390 | Lower in Smoker |
| cg00432872 | 16 | 349062 | Lower in Smoker |
| cg01517185 | 16 | 358490 | Lower in Smoker |
| cg25554283 | 17 | 63558259 | Higher in Smoker |
| cg10965669 | 17 | 63533778 | Lower in Smoker |
| cg06234564 | 3 | 28389645 | Lower in Smoker |
| cg09767126 | 8 | 103877365 | Higher in Smoker |
| cg00837838 | 15 | 45003774 | Higher in Smoker |
| cg16039157 | 15 | 45007336 | Lower in Smoker |
| cg21146905 | 3 | 160822423 | Higher in Smoker |
| cg02633690 | 1 | 235667903 | Higher in Smoker |
| cg03108070 | 6 | 33245490 | Higher in Smoker |
| cg09349343 | 6 | 33245717 | Lower in Smoker |
| cg03721978 | 6 | 33245706 | Lower in Smoker |
| cg23950233 | 6 | 33245739 | Lower in Smoker |
| cg22878469 | 6 | 33245701 | Lower in Smoker |
| cg19268452 | 6 | 33246488 | Lower in Smoker |
| cg24391854 | 11 | 134254690 | Higher in Smoker |
| cg03275130 | 11 | 62389744 | Higher in Smoker |
| cg04058752 | 11 | 76751369 | Higher in Smoker |
| cg04286697 | 2 | 232259623 | Lower in Smoker |
| cg25658272 | 17 | 80971636 | Lower in Smoker |
| cg10820736 | 17 | 80970892 | Lower in Smoker |
| cg03657678 | 17 | 80960511 | Lower in Smoker |
| cg19934381 | 17 | 80944090 | Lower in Smoker |
| cg01723146 | 12 | 58021295 | Higher in Smoker |
| cg22929808 | 12 | 58027113 | Higher in Smoker |
| cg18874307 | 12 | 58027504 | Higher in Smoker |
| cg09855739 | 12 | 58027032 | Higher in Smoker |
| cg14546619 | 12 | 58019647 | Lower in Smoker |
| cg12366518 | 12 | 590469 | Lower in Smoker |
| cg20306062 | 11 | 369414 | Higher in Smoker |
| cg07556915 | 11 | 368683 | Lower in Smoker |

| | | | |
|---|---|---|---|
| cg17806952 | 1 | 161147426 | Higher in Smoker |
| cg15128876 | 1 | 161146073 | Lower in Smoker |
| cg21674153 | 18 | 29264051 | Higher in Smoker |
| cg11313997 | 5 | 177027589 | Higher in Smoker |
| cg03493123 | 5 | 177029444 | Lower in Smoker |
| cg21189099 | 17 | 19266143 | Higher in Smoker |
| cg21642926 | 8 | 104154149 | Lower in Smoker |
| cg03693762 | 21 | 30671158 | Lower in Smoker |
| cg27558594 | 6 | 91006613 | Higher in Smoker |
| cg16779839 | 17 | 79374327 | Higher in Smoker |
| cg17624073 | 17 | 79393583 | Lower in Smoker |
| cg13710969 | 17 | 79393463 | Lower in Smoker |
| cg07016556 | 17 | 79393532 | Lower in Smoker |
| cg19536407 | 17 | 79431331 | Lower in Smoker |
| cg13710595 | 15 | 40733110 | Higher in Smoker |
| cg15844895 | 8 | 143610829 | Lower in Smoker |
| cg11335323 | 8 | 143578616 | Lower in Smoker |
| cg01052614 | 8 | 143619583 | Lower in Smoker |
| cg00826603 | 1 | 32231019 | Higher in Smoker |
| cg20317521 | 17 | 79026312 | Higher in Smoker |
| cg22184944 | 17 | 79031091 | Lower in Smoker |
| cg10030684 | 17 | 79031643 | Lower in Smoker |
| cg19632565 | 17 | 79045765 | Lower in Smoker |
| cg14611816 | 17 | 79068961 | Lower in Smoker |
| cg00713204 | 16 | 88016632 | Higher in Smoker |
| cg08684535 | 16 | 88105596 | Higher in Smoker |
| cg07527105 | 16 | 88053339 | Higher in Smoker |
| cg08414605 | 16 | 88097766 | Higher in Smoker |
| cg01118653 | 16 | 88110441 | Lower in Smoker |
| cg08608042 | 16 | 88053104 | Lower in Smoker |
| cg16871520 | 3 | 52442033 | Higher in Smoker |
| cg03913989 | 3 | 52436356 | Higher in Smoker |
| cg09243735 | 2 | 215674664 | Higher in Smoker |
| cg16380885 | 5 | 17219936 | Lower in Smoker |
| cg21979559 | 5 | 17224135 | Lower in Smoker |

| | | | |
|---|---|---|---|
| cg23752963 | 6 | 31502336 | Lower in Smoker |
| cg17742434 | 6 | 31502944 | Lower in Smoker |
| cg05945401 | 6 | 31506990 | Lower in Smoker |
| cg04755523 | 6 | 31508665 | Lower in Smoker |
| cg04431990 | 6 | 31509496 | Higher in Smoker |
| cg10407266 | 6 | 31588727 | Higher in Smoker |
| cg11203714 | 6 | 31588231 | Higher in Smoker |
| cg10140190 | 6 | 31588707 | Higher in Smoker |
| cg09276739 | 6 | 31588427 | Higher in Smoker |
| cg03625897 | 6 | 31587864 | Higher in Smoker |
| cg20887391 | 6 | 31599520 | Lower in Smoker |
| cg08394355 | 6 | 31597565 | Lower in Smoker |
| cg22017797 | 6 | 31588526 | Lower in Smoker |
| cg17468317 | 6 | 31620788 | Higher in Smoker |
| cg12435665 | 6 | 31619951 | Higher in Smoker |
| cg20029156 | 6 | 31617604 | Lower in Smoker |
| cg16171137 | 6 | 31607634 | Lower in Smoker |
| cg20847496 | 6 | 31620262 | Higher in Smoker |
| cg10963893 | 6 | 31670957 | Higher in Smoker |
| cg06362354 | 6 | 31672483 | Lower in Smoker |
| cg00505979 | 1 | 212873626 | Higher in Smoker |
| cg15718594 | 1 | 212874742 | Lower in Smoker |
| cg20095680 | 19 | 49457927 | Higher in Smoker |
| cg06089712 | 14 | 35343862 | Higher in Smoker |
| cg14093363 | 7 | 72936880 | Higher in Smoker |
| cg25197388 | 11 | 66278006 | Higher in Smoker |
| cg26248486 | 12 | 76742361 | Higher in Smoker |
| cg24651966 | 4 | 123664110 | Lower in Smoker |
| cg05797533 | 16 | 56554066 | Higher in Smoker |
| cg18141365 | 7 | 33169015 | Higher in Smoker |
| cg09080746 | 7 | 33169470 | Higher in Smoker |
| cg18057559 | 3 | 107243151 | Higher in Smoker |
| cg20270188 | 1 | 156611963 | Higher in Smoker |
| cg06949837 | 16 | 75285637 | Higher in Smoker |
| cg08774694 | 16 | 75287019 | Lower in Smoker |

| | | | |
|---|---|---|---|
| cg02328807 | 16 | 75269564 | Lower in Smoker |
| cg22514229 | 1 | 94118054 | Lower in Smoker |
| cg06221222 | 1 | 94147831 | Lower in Smoker |
| cg03568039 | 20 | 52561293 | Higher in Smoker |
| cg12385032 | 17 | 59273979 | Lower in Smoker |
| cg08002981 | 17 | 59356720 | Lower in Smoker |
| cg11769476 | 20 | 49410810 | Higher in Smoker |
| cg11633557 | 20 | 49493097 | Lower in Smoker |
| cg15549231 | 20 | 49415761 | Lower in Smoker |
| cg20399616 | 12 | 25055967 | Higher in Smoker |
| cg23930313 | 12 | 25056083 | Higher in Smoker |
| cg17166103 | 19 | 49298422 | Higher in Smoker |
| cg07875848 | 12 | 50237045 | Higher in Smoker |
| cg16102247 | 3 | 165555160 | Lower in Smoker |
| cg05360949 | 19 | 41903737 | Higher in Smoker |
| cg01210372 | 16 | 31119640 | Higher in Smoker |
| cg01005605 | 2 | 60757902 | Higher in Smoker |
| cg16905255 | 2 | 60777906 | Lower in Smoker |
| cg08426369 | 2 | 60753602 | Lower in Smoker |
| cg13795805 | 14 | 99640604 | Lower in Smoker |
| cg19457263 | 2 | 111880964 | Higher in Smoker |
| cg11729679 | 2 | 111877065 | Higher in Smoker |
| cg25455438 | 2 | 111878453 | Higher in Smoker |
| cg04021674 | 2 | 111878760 | Higher in Smoker |
| cg20141578 | 12 | 12225262 | Higher in Smoker |
| cg27366072 | 12 | 12222913 | Higher in Smoker |
| cg16094954 | 19 | 45251180 | Higher in Smoker |
| cg03490711 | 3 | 187459194 | Higher in Smoker |
| cg00480331 | 3 | 187455371 | Higher in Smoker |
| cg18562663 | 3 | 187455516 | Higher in Smoker |
| cg19198148 | 3 | 187451818 | Lower in Smoker |
| cg06070445 | 3 | 187453772 | Lower in Smoker |
| cg05450995 | 12 | 12246C105 | Higher in Smoker |
| cg27616543 | 11 | 118773657 | Lower in Smoker |
| cg23737407 | X | 40029094 | Higher in Smoker |

| | | | |
|---|---|---|---|
| cg20197861 | X | 39964229 | Higher in Smoker |
| cg03527511 | X | 40006072 | Higher in Smoker |
| cg10169869 | X | 40033636 | Higher in Smoker |
| cg24208785 | X | 40013348 | Higher in Smoker |
| cg13723115 | X | 40030819 | Higher in Smoker |
| cg08614574 | X | 39961501 | Lower in Smoker |
| cg04886769 | X | 70435029 | Lower in Smoker |
| cg27553057 | X | 70712724 | Higher in Smoker |
| cg15012678 | 3 | 197285336 | Higher in Smoker |
| cg09363194 | 3 | 197282902 | Higher in Smoker |
| cg00003014 | 3 | 197279819 | Lower in Smoker |
| cg19005485 | 3 | 197272328 | Lower in Smoker |
| cg02214188 | 4 | 104020949 | Higher in Smoker |
| cg24980174 | 14 | 96671169 | Higher in Smoker |
| cg01583131 | 11 | 27744675 | Lower in Smoker |
| cg04106006 | 11 | 27742454 | Higher in Smoker |
| cg12448003 | 11 | 27742365 | Higher in Smoker |
| cg20144981 | 11 | 27527687 | Higher in Smoker |
| cg11237734 | 11 | 27528142 | Higher in Smoker |
| cg04067598 | 5 | 70751409 | Higher in Smoker |
| cg24731015 | 5 | 70751422 | Higher in Smoker |
| cg01164326 | 16 | 66460784 | Higher in Smoker |
| cg26279372 | 14 | 101036192 | Lower in Smoker |
| cg13521842 | 14 | 101036202 | Lower in Smoker |
| cg01991752 | 14 | 101014148 | Higher in Smoker |
| cg01044883 | 14 | 101035262 | Higher in Smoker |
| cg23997405 | 14 | 101033689 | Higher in Smoker |
| cg11820913 | 14 | 101021865 | Lower in Smoker |
| cg02781618 | 4 | 42153695 | Higher in Smoker |
| cg22097249 | 4 | 42122113 | Lower in Smoker |
| cg07033093 | 4 | 42154977 | Lower in Smoker |
| cg10309386 | 10 | 13515334 | Lower in Smoker |
| cg15110101 | 11 | 61717334 | Lower in Smoker |
| cg25331073 | 19 | 12868938 | Lower in Smoker |
| cg05493841 | 12 | 70083096 | Higher in Smoker |

| | | | |
|---|---|---|---|
| cg02072975 | 1 | 45249541 | Higher in Smoker |
| cg04108939 | 1 | 45250181 | Higher in Smoker |
| cg25350789 | 1 | 45253490 | Higher in Smoker |
| cg03078718 | 7 | 93621830 | Lower in Smoker |
| cg05152629 | 11 | 207881 | Higher in Smoker |
| cg15793196 | X | 102316054 | Lower in Smoker |
| cg01804836 | X | 102565738 | Higher in Smoker |
| cg20383064 | 3 | 133117420 | Lower in Smoker |
| cg02507167 | 3 | 133129182 | Lower in Smoker |
| cg12036877 | 1 | 156211896 | Lower in Smoker |
| cg27501878 | 20 | 61638588 | Higher in Smoker |
| cg16320419 | 3 | 5025570 | Lower in Smoker |
| cg18058747 | 5 | 78408253 | Higher in Smoker |
| cg09696939 | 10 | 60272079 | Higher in Smoker |
| cg07857251 | 10 | 60272754 | Higher in Smoker |
| cg17548395 | 10 | 60461164 | Lower in Smoker |
| cg00832457 | 12 | 32287236 | Lower in Smoker |
| cg05969697 | 9 | 95527975 | Higher in Smoker |
| cg14279997 | 9 | 95476582 | Lower in Smoker |
| cg02929681 | 9 | 95479924 | Lower in Smoker |
| cg01388022 | 22 | 18229010 | Lower in Smoker |
| cg10432177 | 22 | 43506591 | Higher in Smoker |
| cg12353452 | 12 | 5171865 | Higher in Smoker |
| cg08847737 | 11 | 102206714 | Lower in Smoker |
| cg12030369 | 2 | 32583264 | Lower in Smoker |
| cg14582983 | 20 | 61870691 | Lower in Smoker |
| cg14173599 | 20 | 61867137 | Lower in Smoker |
| cg00895528 | 20 | 61867349 | Lower in Smoker |
| cg25654957 | 20 | 36156668 | Higher in Smoker |
| cg21863334 | 20 | 36157405 | Lower in Smoker |
| cg15440392 | 20 | 36156634 | Lower in Smoker |
| cg14176575 | 20 | 36156574 | Lower in Smoker |
| cg11421182 | 20 | 36153479 | Lower in Smoker |
| cg14160807 | 20 | 36156231 | Higher in Smoker |
| cg21497594 | 8 | 11366745 | Lower in Smoker |

| | | | |
|---|---|---|---|
| cg20540372 | 10 | 98031961 | Lower in Smoker |
| cg08222053 | 12 | 56113434 | Lower in Smoker |
| cg14282612 | 10 | 102046509 | Higher in Smoker |
| cg05596149 | 1 | 169337205 | Higher in Smoker |
| cg26278858 | 15 | 40401256 | Higher in Smoker |
| cg17809595 | 15 | 40395913 | Lower in Smoker |
| cg07712904 | 15 | 40389891 | Lower in Smoker |
| cg09587957 | 15 | 40399101 | Lower in Smoker |
| cg12929983 | 15 | 40399004 | Lower in Smoker |
| cg19225068 | 10 | 22614933 | Higher in Smoker |
| cg12486533 | 8 | 22021530 | Lower in Smoker |
| cg10881615 | 2 | 69100119 | Lower in Smoker |
| cg26665274 | 20 | 6747409 | Lower in Smoker |
| cg08396974 | 20 | 55840416 | Higher in Smoker |
| cg25011475 | 10 | 88517608 | Higher in Smoker |
| cg18525126 | 10 | 88617460 | Higher in Smoker |
| cg19051661 | 10 | 88588785 | Higher in Smoker |
| cg04940109 | 2 | 203240432 | Higher in Smoker |
| cg04957730 | 10 | 43278700 | Higher in Smoker |
| cg00231099 | 10 | 46763197 | Higher in Smoker |
| cg17628040 | 10 | 46763211 | Higher in Smoker |
| cg21955534 | X | 15525514 | Lower in Smoker |
| cg15736165 | 15 | 83951732 | Higher in Smoker |
| cg18560204 | 15 | 83953709 | Higher in Smoker |
| cg07639720 | 15 | 83952875 | Higher in Smoker |
| cg14061067 | 9 | 16413736 | Lower in Smoker |
| cg10491368 | 5 | 172570703 | Lower in Smoker |
| cg21080251 | 5 | 172570776 | Lower in Smoker |
| cg25357589 | 5 | 172571536 | Higher in Smoker |
| cg11356398 | 10 | 133783182 | Lower in Smoker |
| cg15390444 | 10 | 133793442 | Lower in Smoker |
| cg18477674 | 10 | 133793527 | Lower in Smoker |
| cg23471067 | 10 | 133793477 | Lower in Smoker |
| cg03359468 | 8 | 26240463 | Higher in Smoker |
| cg11498079 | 5 | 173043766 | Higher in Smoker |

| | | | |
|---|---|---|---|
| cg17652741 | 4 | 13629432 | Higher in Smoker |
| cg07197374 | 1 | 149870687 | Lower in Smoker |
| cg07363880 | 16 | 29466740 | Lower in Smoker |
| cg08280159 | 8 | 145504568 | Lower in Smoker |
| cg04746089 | 8 | 145501862 | Lower in Smoker |
| cg09333580 | 20 | 31606541 | Higher in Smoker |
| cg22443205 | 17 | 65821133 | Higher in Smoker |
| cg00712547 | 17 | 65821745 | Higher in Smoker |
| cg04582861 | 17 | 41276606 | Lower in Smoker |
| cg11964474 | 17 | 41278655 | Higher in Smoker |
| cg15865175 | 13 | 32890215 | Higher in Smoker |
| cg16001355 | 22 | 50219912 | Lower in Smoker |
| cg05111146 | 6 | 32935025 | Higher in Smoker |
| cg17840326 | 6 | 32935853 | Higher in Smoker |
| cg17451945 | 6 | 32936363 | Lower in Smoker |
| cg15266497 | 6 | 32936347 | Lower in Smoker |
| cg26246658 | 6 | 32936741 | Higher in Smoker |
| cg10061292 | 6 | 32939335 | Higher in Smoker |
| cg03077751 | 6 | 32937207 | Higher in Smoker |
| cg17871437 | 6 | 32940801 | Higher in Smoker |
| cg04138346 | 6 | 32938946 | Higher in Smoker |
| cg14587902 | 9 | 136913560 | Lower in Smoker |
| cg12231068 | 9 | 136916357 | Lower in Smoker |
| cg02020879 | 5 | 887052 | Lower in Smoker |
| cg06922155 | 5 | 889617 | Lower in Smoker |
| cg03833993 | 2 | 28124698 | Lower in Smoker |
| cg27639613 | 2 | 28408263 | Lower in Smoker |
| cg04221355 | 2 | 28114116 | Higher in Smoker |
| cg04168939 | 14 | 105767399 | Higher in Smoker |
| cg22576489 | 14 | 105685732 | Lower in Smoker |
| cg19904653 | 8 | 37707692 | Lower in Smoker |
| cg11212038 | 17 | 59940826 | Higher in Smoker |
| cg06257227 | 17 | 59941132 | Higher in Smoker |
| cg00091162 | 1 | 167906284 | Higher in Smoker |
| cg17391474 | 6 | 166796744 | Higher in Smoker |

| | | | |
|---|---|---|---|
| cg14572581 | 3 | 9773022 | Higher in Smoker |
| cg20346912 | 18 | 35147165 | Higher in Smoker |
| cg14350197 | 18 | 35147162 | Higher in Smoker |
| cg17973164 | 18 | 35146591 | Higher in Smoker |
| cg18735473 | 18 | 35015946 | Higher in Smoker |
| cg02345961 | 18 | 34854574 | Higher in Smoker |
| cg11950360 | 18 | 34834690 | Higher in Smoker |
| cg06370528 | 18 | 34972877 | Lower in Smoker |
| cg06734812 | 19 | 3223915 | Lower in Smoker |
| cg16477190 | 15 | 72612653 | Higher in Smoker |
| cg13686331 | 21 | 40557788 | Lower in Smoker |
| ch.21.551062R | 21 | 40568843 | Higher in Smoker |
| cg26333513 | 11 | 62477082 | Higher in Smoker |
| cg10573476 | 11 | 62474118 | Lower in Smoker |
| cg22431486 | 19 | 572309 | Higher in Smoker |
| cg08510456 | 3 | 49591008 | Lower in Smoker |
| cg11843333 | 4 | 15719138 | Lower in Smoker |
| cg11558551 | 19 | 17516442 | Higher in Smoker |
| cg16958189 | 15 | 83736204 | Lower in Smoker |
| cg06815419 | 15 | 83735862 | Lower in Smoker |
| cg19557422 | 11 | 13484070 | Higher in Smoker |
| cg00170564 | 12 | 107714106 | Higher in Smoker |
| cg11417612 | 12 | 107779567 | Lower in Smoker |
| cg05058976 | 16 | 3637956 | Lower in Smoker |
| cg03211864 | 10 | 124060833 | Higher in Smoker |
| cg05087067 | 14 | 105715741 | Lower in Smoker |
| cg08160231 | 1 | 92545224 | Lower in Smoker |
| cg13024741 | 6 | 38605053 | Lower in Smoker |
| cg11617821 | 4 | 75672135 | Lower in Smoker |
| cg26084667 | 3 | 15673302 | Lower in Smoker |
| cg11494437 | 3 | 15678564 | Lower in Smoker |
| cg05586242 | 3 | 15642818 | Higher in Smoker |
| cg24239808 | 3 | 15641908 | Lower in Smoker |
| cg18204685 | 3 | 15641821 | Lower in Smoker |
| cg17561030 | 5 | 72794050 | Higher in Smoker |

| | | | |
|---|---|---|---|
| cg01665118 | 13 | 77502805 | Lower in Smoker |
| cg10566592 | 1 | 52521781 | Higher in Smoker |
| cg06373167 | 1 | 203278044 | Lower in Smoker |
| cg12414502 | 6 | 26468835 | Lower in Smoker |
| cg01221716 | 6 | 26421570 | Higher in Smoker |
| cg18807527 | 6 | 26415234 | Lower in Smoker |
| cg21432745 | 6 | 26375990 | Lower in Smoker |
| cg07535133 | 6 | 32363892 | Lower in Smoker |
| cg12966392 | 6 | 32364075 | Lower in Smoker |
| cg05381852 | 6 | 32368318 | Lower in Smoker |
| cg02448934 | 6 | 32367970 | Lower in Smoker |
| cg18104646 | 6 | 32371235 | Lower in Smoker |
| cg21171279 | 6 | 32372943 | Lower in Smoker |
| cg02136066 | 6 | 32363084 | Lower in Smoker |
| cg08726004 | 6 | 32363255 | Lower in Smoker |
| cg17385727 | 6 | 32370790 | Lower in Smoker |
| cg02158755 | 6 | 32375317 | Lower in Smoker |
| cg25391023 | 6 | 32374754 | Lower in Smoker |
| cg04970287 | 6 | 32362638 | Lower in Smoker |
| cg17961273 | 6 | 32370637 | Lower in Smoker |
| cg26657086 | 6 | 32373089 | Lower in Smoker |
| cg24359188 | 15 | 40509472 | Higher in Smoker |
| cg17954165 | 10 | 124913710 | Higher in Smoker |
| cg03020885 | 11 | 116643423 | Higher in Smoker |
| cg04337854 | 6 | 105585762 | Lower in Smoker |
| cg12117658 | 17 | 56406294 | Higher in Smoker |
| cg21557979 | 17 | 56381668 | Lower in Smoker |
| cg03193689 | 2 | 201677036 | Lower in Smoker |
| cg22294755 | 7 | 16685683 | Higher in Smoker |
| cg18515031 | 10 | 73988469 | Lower in Smoker |
| cg03641066 | 10 | 77542423 | Lower in Smoker |
| cg16072382 | 10 | 78096093 | Lower in Smoker |
| cg06894710 | 10 | 78142662 | Lower in Smoker |
| cg01045971 | 10 | 1083259 | Lower in Smoker |
| cg15011337 | 10 | 1071902 | Lower in Smoker |

| | | | |
|---|---|---|---|
| cg24024176 | 10 | 21784395 | Higher in Smoker |
| cg08551088 | 10 | 121631655 | Higher in Smoker |
| cg09859240 | 10 | 121633447 | Lower in Smoker |
| cg17180012 | 10 | 97666929 | Higher in Smoker |
| cg08890360 | 10 | 127407768 | Higher in Smoker |
| cg22569973 | 10 | 127408789 | Higher in Smoker |
| cg08452525 | 10 | 5727808 | Higher in Smoker |
| cg17502312 | 10 | 5794375 | Lower in Smoker |
| cg00899659 | 10 | 45495971 | Higher in Smoker |
| cg14015502 | 10 | 104535020 | Lower in Smoker |
| cg07550278 | 10 | 95462365 | Higher in Smoker |
| cg24799921 | 10 | 77168180 | Higher in Smoker |
| cg26740856 | 10 | 77163316 | Lower in Smoker |
| cg05088898 | 10 | 120489294 | Higher in Smoker |
| cg22962619 | 10 | 120466516 | Lower in Smoker |
| cg27264016 | 10 | 120442665 | Lower in Smoker |
| cg09233392 | 10 | 50887488 | Lower in Smoker |
| cg09402276 | 10 | 50887472 | Lower in Smoker |
| cg07016590 | 10 | 23633066 | Higher in Smoker |
| cg00828709 | 10 | 50507071 | Lower in Smoker |
| cg10775039 | 10 | 50507214 | Higher in Smoker |
| cg15741482 | 10 | 105880990 | Higher in Smoker |
| cg16750440 | 10 | 105992436 | Higher in Smoker |
| cg15749148 | 10 | 105992428 | Higher in Smoker |
| cg06740223 | 10 | 105953667 | Lower in Smoker |
| cg27327268 | 10 | 118428651 | Lower in Smoker |
| cg19716967 | 10 | 120101689 | Higher in Smoker |
| cg10477193 | 10 | 124714180 | Higher in Smoker |
| cg15834395 | 10 | 134261413 | Lower in Smoker |
| cg03666796 | 10 | 134746860 | Higher in Smoker |
| cg19799413 | 10 | 134746824 | Higher in Smoker |
| cg07421032 | 10 | 134756306 | Lower in Smoker |
| cg25091705 | 11 | 111752853 | Lower in Smoker |
| cg14196353 | 11 | 111750159 | Higher in Smoker |
| cg19535375 | 11 | 64068908 | Lower in Smoker |

| | | | |
|---|---|---|---|
| cg10276576 | 11 | 68039926 | Higher in Smoker |
| cg11197202 | 11 | 76155647 | Higher in Smoker |
| cg26945811 | 11 | 76155767 | Higher in Smoker |
| cg12820122 | 11 | 76156044 | Higher in Smoker |
| cg27217878 | 11 | 76155921 | Lower in Smoker |
| cg27398535 | 11 | 112131049 | Lower in Smoker |
| cg00716245 | 11 | 555724 | Higher in Smoker |
| cg06937829 | 11 | 554920 | Higher in Smoker |
| cg20073320 | 11 | 33677621 | Lower in Smoker |
| cg10334127 | 11 | 33656146 | Lower in Smoker |
| cg09443484 | 11 | 33673943 | Lower in Smoker |
| cg09600152 | 11 | 6232291 | Lower in Smoker |
| cg17632233 | 11 | 62439667 | Lower in Smoker |
| ch.11.975705R | 11 | 47080364 | Higher in Smoker |
| cg14990438 | 11 | 47130537 | Higher in Smoker |
| cg21146187 | 11 | 47077603 | Lower in Smoker |
| cg12076194 | 11 | 47125753 | Lower in Smoker |
| cg25129781 | 11 | 111156908 | Lower in Smoker |
| cg18423962 | 11 | 111945365 | Higher in Smoker |
| cg10353785 | 11 | 16759993 | Higher in Smoker |
| cg20876055 | 11 | 118436750 | Higher in Smoker |
| cg07931631 | 11 | 122753950 | Higher in Smoker |
| cg20058744 | 11 | 61257511 | Lower in Smoker |
| cg06081030 | 11 | 65687220 | Higher in Smoker |
| cg20346726 | 11 | 101918403 | Higher in Smoker |
| cg20303232 | 11 | 114270563 | Lower in Smoker |
| cg19630883 | 11 | 93275826 | Higher in Smoker |
| cg23979269 | 11 | 62439091 | Higher in Smoker |
| cg03505797 | 11 | 63579540 | Lower in Smoker |
| cg10454766 | 11 | 109293945 | Higher in Smoker |
| cg24731731 | 11 | 61545348 | Higher in Smoker |
| cg20583684 | 11 | 33722499 | Higher in Smoker |
| cg22077528 | 11 | 33722475 | Higher in Smoker |
| cg17247314 | 11 | 63528669 | Lower in Smoker |
| cg23461906 | 12 | 107349191 | Higher in Smoker |

| | | | |
|---|---|---|---|
| cg26011809 | 12 | 107351005 | Higher in Smoker |
| cg07545743 | 12 | 121409957 | Higher in Smoker |
| cg22727109 | 12 | 32112813 | Higher in Smoker |
| cg08766850 | 12 | 32112438 | Higher in Smoker |
| cg19952067 | 12 | 49062856 | Lower in Smoker |
| cg18798446 | 12 | 103862780 | Lower in Smoker |
| cg04422896 | 12 | 121454269 | Higher in Smoker |
| cg21805138 | 12 | 117155636 | Lower in Smoker |
| cg02416656 | 12 | 112625321 | Lower in Smoker |
| cg19642920 | 12 | 6810328 | Lower in Smoker |
| cg01031441 | 12 | 64784663 | Higher in Smoker |
| cg10296162 | 12 | 14956242 | Higher in Smoker |
| cg25217357 | 12 | 62997570 | Higher in Smoker |
| cg12375960 | 12 | 50505775 | Higher in Smoker |
| cg08142063 | 12 | 64616026 | Higher in Smoker |
| cg15968307 | 12 | 48577213 | Lower in Smoker |
| cg07454491 | 12 | 48578076 | Lower in Smoker |
| cg15476885 | 12 | 14968227 | Lower in Smoker |
| cg11915525 | 12 | 27622700 | Lower in Smoker |
| cg22022442 | 12 | 31811083 | Lower in Smoker |
| cg25484519 | 12 | 104351068 | Higher in Smoker |
| cg17417591 | 12 | 110485937 | Lower in Smoker |
| cg16484526 | 12 | 25150608 | Lower in Smoker |
| cg06099459 | 12 | 25150530 | Lower in Smoker |
| cg21368143 | 12 | 25150626 | Lower in Smoker |
| cg16877615 | 13 | 111973089 | Lower in Smoker |
| cg20864734 | 13 | 46953510 | Lower in Smoker |
| cg05926266 | 13 | 39612065 | Higher in Smoker |
| cg09179485 | 13 | 39612920 | Higher in Smoker |
| cg10664305 | 13 | 43360920 | Lower in Smoker |
| cg08535171 | 13 | 44458022 | Lower in Smoker |
| cg11126134 | 13 | 31480304 | Higher in Smoker |
| cg24717696 | 13 | 73302139 | Lower in Smoker |
| cg01713535 | 14 | 57046409 | Higher in Smoker |
| cg18151676 | 14 | 45722704 | Higher in Smoker |

| | | | |
|---|---|---|---|
| cg02273647 | 14 | 45722745 | Higher in Smoker |
| cg14171478 | 14 | 76618642 | Higher in Smoker |
| cg25803423 | 14 | 23563820 | Higher in Smoker |
| cg11819429 | 14 | 23565029 | Higher in Smoker |
| cg20513833 | 14 | 31926483 | Higher in Smoker |
| cg15998421 | 14 | 31926362 | Higher in Smoker |
| cg07057342 | 14 | 31915923 | Lower in Smoker |
| cg10006614 | 14 | 95877336 | Higher in Smoker |
| cg00712289 | 14 | 81130611 | Lower in Smoker |
| cg06907680 | 14 | 91580129 | Higher in Smoker |
| cg06607384 | 14 | 91579359 | Higher in Smoker |
| cg23296408 | 14 | 91580613 | Higher in Smoker |
| cg18633154 | 14 | 77296234 | Lower in Smoker |
| cg14464802 | 14 | 77846560 | Higher in Smoker |
| cg02101808 | 14 | 77843745 | Higher in Smoker |
| cg26398691 | 14 | 99176473 | Lower in Smoker |
| cg13438944 | 14 | 76452183 | Higher in Smoker |
| cg18313013 | 14 | 105052560 | Lower in Smoker |
| cg21846009 | 14 | 105053550 | Lower in Smoker |
| cg04269909 | 14 | 50473602 | Lower in Smoker |
| cg04991036 | 14 | 29243762 | Higher in Smoker |
| cg05733554 | 14 | 58618292 | Higher in Smoker |
| cg21028633 | 14 | 60043767 | Higher in Smoker |
| cg18240143 | 14 | 60952599 | Higher in Smoker |
| cg15528081 | 14 | 74486154 | Higher in Smoker |
| cg16413785 | 14 | 98445284 | Lower in Smoker |
| cg09959585 | 14 | 103570855 | Higher in Smoker |
| cg26286101 | 14 | 105452037 | Higher in Smoker |
| cg27066162 | 15 | 75199472 | Higher in Smoker |
| cg07719965 | 15 | 24919600 | Lower in Smoker |
| cg24094450 | 15 | 76429151 | Higher in Smoker |
| cg11163362 | 15 | 49688450 | Lower in Smoker |
| cg11709662 | 15 | 49913013 | Higher in Smoker |
| cg04468564 | 15 | 49913596 | Higher in Smoker |
| cg11520554 | 15 | 80216034 | Higher in Smoker |

| | | | |
|---|---|---|---|
| cg05361709 | 15 | 75494287 | Lower in Smoker |
| cg13175480 | 15 | 83680325 | Higher in Smoker |
| cg01048253 | 15 | 83679867 | Higher in Smoker |
| cg18558073 | 15 | 36872349 | Higher in Smoker |
| cg20038602 | 15 | 37071175 | Lower in Smoker |
| cg02278675 | 15 | 65903322 | Higher in Smoker |
| cg16119128 | 15 | 40630304 | Higher in Smoker |
| cg07344355 | 15 | 40633416 | Lower in Smoker |
| cg23969342 | 15 | 74045075 | Higher in Smoker |
| cg24133784 | 15 | 74045083 | Higher in Smoker |
| cg18564888 | 15 | 73734744 | Lower in Smoker |
| cg11154384 | 15 | 67814409 | Higher in Smoker |
| cg16452248 | 16 | 613526 | Lower in Smoker |
| cg06360784 | 16 | 15534699 | Lower in Smoker |
| cg04091712 | 16 | 4563767 | Higher in Smoker |
| cg08262496 | 16 | 22023163 | Lower in Smoker |
| cg07354129 | 16 | 29827367 | Lower in Smoker |
| cg26640110 | 16 | 89731161 | Lower in Smoker |
| cg10350251 | 16 | 89727194 | Lower in Smoker |
| cg04364504 | 16 | 58035198 | Lower in Smoker |
| cg05932648 | 16 | 15983341 | Lower in Smoker |
| cg08745197 | 16 | 15983315 | Lower in Smoker |
| cg09713758 | 16 | 31711160 | Lower in Smoker |
| cg01300778 | 16 | 9184995 | Higher in Smoker |
| cg00011122 | 16 | 11439027 | Higher in Smoker |
| cg05575046 | 16 | 58163367 | Higher in Smoker |
| cg18633178 | 16 | 58163203 | Higher in Smoker |
| cg08653945 | 16 | 89228636 | Higher in Smoker |
| cg01967564 | 16 | 27078517 | Lower in Smoker |
| cg03980541 | 16 | 67700924 | Higher in Smoker |
| cg02717630 | 16 | 46865118 | Higher in Smoker |
| cg04311355 | 16 | 1470717 | Higher in Smoker |
| cg08736072 | 16 | 1471543 | Lower in Smoker |
| cg08181402 | 16 | 1479446 | Lower in Smoker |
| cg03939612 | 17 | 21156707 | Higher in Smoker |

| | | | |
|---|---|---|---|
| cg04662250 | 17 | 21157499 | Lower in Smoker |
| cg08449860 | 17 | 72968988 | Higher in Smoker |
| cg17713161 | 17 | 72951370 | Lower in Smoker |
| cg12349832 | 17 | 72951240 | Lower in Smoker |
| cg13537156 | 17 | 72951218 | Lower in Smoker |
| cg01281078 | 17 | 37886864 | Higher in Smoker |
| cg24608385 | 17 | 37887009 | Higher in Smoker |
| cg03616195 | 17 | 29233260 | Higher in Smoker |
| cg06436508 | 17 | 56619769 | Lower in Smoker |
| cg12785122 | 17 | 10601181 | Higher in Smoker |
| cg22700039 | 17 | 21455065 | Lower in Smoker |
| cg17861836 | 17 | 79202505 | Lower in Smoker |
| cg05768005 | 17 | 8094486 | Lower in Smoker |
| cg12397252 | 17 | 80408797 | Higher in Smoker |
| cg20469991 | 17 | 27169893 | Higher in Smoker |
| cg25323554 | 17 | 27135257 | Lower in Smoker |
| cg09361941 | 17 | 8128471 | Higher in Smoker |
| cg01882395 | 17 | 43717810 | Higher in Smoker |
| cg06748584 | 17 | 79520919 | Higher in Smoker |
| cg03554335 | 17 | 62075151 | Higher in Smoker |
| cg05101846 | 17 | 72580962 | Lower in Smoker |
| cg06794038 | 17 | 72580515 | Lower in Smoker |
| cg08385173 | 17 | 71244894 | Lower in Smoker |
| cg24942343 | 17 | 7155773 | Higher in Smoker |
| cg13468084 | 17 | 7155896 | Higher in Smoker |
| cg07091842 | 17 | 7155530 | Higher in Smoker |
| cg08521655 | 17 | 3749512 | Higher in Smoker |
| cg16299813 | 17 | 79632380 | Lower in Smoker |
| cg02659149 | 17 | 1620008 | Higher in Smoker |
| cg12374721 | 17 | 46799640 | Higher in Smoker |
| cg23183568 | 17 | 74726642 | Lower in Smoker |
| cg25004679 | 17 | 74722398 | Lower in Smoker |
| cg26585845 | 17 | 36831195 | Higher in Smoker |
| cg19804182 | 18 | 13262750 | Higher in Smoker |
| cg20795680 | 18 | 13387658 | Lower in Smoker |

| | | | |
|---|---|---|---|
| cg14825976 | 18 | 13611370 | Higher in Smoker |
| cg15056105 | 18 | 13611489 | Higher in Smoker |
| cg22454011 | 18 | 13611439 | Higher in Smoker |
| cg14846965 | 18 | 13611481 | Higher in Smoker |
| cg25374649 | 18 | 13611400 | Higher in Smoker |
| cg00832308 | 18 | 13218884 | Higher in Smoker |
| cg00737978 | 18 | 13611807 | Higher in Smoker |
| cg25140190 | 18 | 13641529 | Lower in Smoker |
| cg07648207 | 18 | 34389670 | Higher in Smoker |
| cg21861644 | 18 | 13726504 | Higher in Smoker |
| cg25215885 | 18 | 77794317 | Higher in Smoker |
| cg00363486 | 18 | 77794302 | Higher in Smoker |
| cg27311476 | 18 | 77794419 | Higher in Smoker |
| cg27638057 | 18 | 20682779 | Higher in Smoker |
| cg15712413 | 18 | 652270 | Higher in Smoker |
| cg14976569 | 19 | 4667105 | Higher in Smoker |
| cg27304729 | 19 | 30205554 | Lower in Smoker |
| cg27042528 | 19 | 513536 | Lower in Smoker |
| cg14052044 | 19 | 751159 | Lower in Smoker |
| cg19301960 | 19 | 1271312 | Lower in Smoker |
| cg02644867 | 19 | 1271057 | Lower in Smoker |
| cg09400566 | 19 | 1271371 | Lower in Smoker |
| cg15226147 | 19 | 1275266 | Lower in Smoker |
| cg06914509 | 19 | 3626080 | Higher in Smoker |
| cg13603510 | 19 | 3626908 | Higher in Smoker |
| cg09268313 | 19 | 3613573 | Lower in Smoker |
| cg24199453 | 19 | 3612331 | Lower in Smoker |
| cg01985343 | 19 | 2278451 | Lower in Smoker |
| cg00372610 | 19 | 2096731 | Higher in Smoker |
| cg11995437 | 19 | 11484869 | Higher in Smoker |
| cg26495639 | 19 | 11484842 | Higher in Smoker |
| cg25368113 | 19 | 33462881 | Higher in Smoker |
| cg15196793 | 19 | 33462892 | Higher in Smoker |
| cg21912241 | 19 | 33462915 | Higher in Smoker |
| cg16174234 | 19 | 33463305 | Lower in Smoker |

| | | | |
|---|---|---|---|
| cg25903122 | 19 | 16765692 | Lower in Smoker |
| cg24941931 | 19 | 16607335 | Higher in Smoker |
| cg23158022 | 19 | 16605905 | Lower in Smoker |
| cg03743981 | 19 | 40850441 | Lower in Smoker |
| cg22306691 | 19 | 51306906 | Higher in Smoker |
| cg02714062 | 19 | 18668982 | Higher in Smoker |
| cg18326578 | 19 | 55677993 | Lower in Smoker |
| cg01397912 | 19 | 55670288 | Lower in Smoker |
| cg25654926 | 19 | 36249990 | Higher in Smoker |
| cg23792364 | 19 | 1021362 | Higher in Smoker |
| cg05700088 | 19 | 1017316 | Lower in Smoker |
| cg08172787 | 19 | 44258864 | Higher in Smoker |
| cg02324774 | 19 | 50980121 | Lower in Smoker |
| cg24862153 | 19 | 10196729 | Higher in Smoker |
| cg06795069 | 19 | 10197426 | Higher in Smoker |
| cg22642495 | 19 | 10197356 | Lower in Smoker |
| cg13109289 | 7 | 7274782 | Lower in Smoker |
| cg13015740 | X | 119760591 | Lower in Smoker |
| cg19780807 | X | 119763998 | Lower in Smoker |
| cg00806311 | 1 | 244625112 | Lower in Smoker |
| cg22109208 | 1 | 172414443 | Lower in Smoker |
| cg08587864 | 1 | 172413612 | Lower in Smoker |
| cg03978041 | 1 | 200862726 | Lower in Smoker |
| cg01930947 | 1 | 162343861 | Lower in Smoker |
| cg17960769 | 1 | 36772837 | Higher in Smoker |
| cg20738274 | 1 | 207201020 | Lower in Smoker |
| cg04299080 | 1 | 38274753 | Higher in Smoker |
| cg24234277 | 1 | 231473324 | Higher in Smoker |
| cg08648047 | 1 | 11028561 | Lower in Smoker |
| cg05352668 | 1 | 11023756 | Lower in Smoker |
| cg22341848 | 1 | 24106359 | Lower in Smoker |
| cg17273683 | 1 | 24921731 | Lower in Smoker |
| cg20270863 | 1 | 210407484 | Higher in Smoker |
| cg00224299 | 1 | 26185997 | Higher in Smoker |
| cg20845544 | 1 | 26185473 | Lower in Smoker |

| | | | |
|---|---|---|---|
| cg03525644 | 1 | 67562326 | Lower in Smoker |
| cg04017052 | 1 | 16694728 | Higher in Smoker |
| cg20433455 | 1 | 16699437 | Lower in Smoker |
| cg02052265 | 1 | 247712110 | Lower in Smoker |
| cg21789695 | 1 | 19945158 | Lower in Smoker |
| cg26023751 | 1 | 169763990 | Higher in Smoker |
| cg05035248 | 1 | 1020820 | Lower in Smoker |
| cg04315086 | 1 | 1023163 | Lower in Smoker |
| cg16679343 | 1 | 1052949 | Lower in Smoker |
| cg02079931 | 1 | 53164179 | Higher in Smoker |
| cg05505459 | 1 | 911995 | Higher in Smoker |
| cg13792780 | 1 | 156310970 | Lower in Smoker |
| cg13921387 | 1 | 109655348 | Higher in Smoker |
| cg11243995 | 1 | 231002232 | Lower in Smoker |
| cg13980834 | 1 | 24727850 | Lower in Smoker |
| cg22436963 | 1 | 24727829 | Lower in Smoker |
| cg20692896 | 1 | 184356555 | Higher in Smoker |
| cg06533042 | 1 | 184385917 | Lower in Smoker |
| cg13576682 | 1 | 35325800 | Higher in Smoker |
| cg05783676 | 1 | 23695730 | Higher in Smoker |
| cg20959676 | 1 | 23696021 | Higher in Smoker |
| cg15605235 | 1 | 45189743 | Higher in Smoker |
| cg12432038 | 1 | 247275735 | Lower in Smoker |
| cg11316386 | 1 | 247275803 | Lower in Smoker |
| cg23335946 | 1 | 185125966 | Higher in Smoker |
| cg15642292 | 1 | 150253842 | Higher in Smoker |
| cg16501235 | 1 | 150245983 | Lower in Smoker |
| cg01721149 | 1 | 156394727 | Lower in Smoker |
| cg00659035 | 1 | 25573464 | Higher in Smoker |
| cg04340510 | 1 | 156701346 | Lower in Smoker |
| cg11811409 | 1 | 1477025 | Lower in Smoker |
| cg13467169 | 1 | 153606345 | Higher in Smoker |
| cg06203364 | 1 | 2137307 | Lower in Smoker |
| cg05337761 | 1 | 2121349 | Higher in Smoker |
| cg08161158 | 1 | 2126151 | Lower in Smoker |

| | | | |
|---|---|---|---|
| cg06963192 | 1 | 172557938 | Lower in Smoker |
| cg22402053 | 1 | 156897540 | Higher in Smoker |
| cg26226879 | 1 | 34642305 | Lower in Smoker |
| cg16403299 | 1 | 211589678 | Lower in Smoker |
| cg11505417 | 1 | 22966051 | Higher in Smoker |
| cg14041976 | 1 | 22978981 | Lower in Smoker |
| cg25541078 | 17 | 43041623 | Lower in Smoker |
| cg03431544 | 17 | 77020867 | Higher in Smoker |
| cg18527716 | 17 | 77038216 | Lower in Smoker |
| cg07816439 | 5 | 159797845 | Higher in Smoker |
| cg05600864 | 5 | 159797914 | Higher in Smoker |
| cg20713525 | 5 | 34044727 | Lower in Smoker |
| cg19379102 | 22 | 37576698 | Lower in Smoker |
| cg14264901 | 22 | 37579522 | Lower in Smoker |
| cg06097727 | 4 | 15376119 | Lower in Smoker |
| cg22686240 | 4 | 15375625 | Lower in Smoker |
| cg01892977 | 16 | 1139733 | Higher in Smoker |
| cg10224476 | 16 | 1139166 | Lower in Smoker |
| cg02726898 | 16 | 1146545 | Lower in Smoker |
| cg20371401 | 6 | 31895493 | Higher in Smoker |
| cg15847272 | 6 | 31913250 | Lower in Smoker |
| cg03207439 | 20 | 9495199 | Higher in Smoker |
| cg20543869 | 20 | 55107839 | Lower in Smoker |
| cg07814359 | 20 | 42839582 | Higher in Smoker |
| cg21263890 | 20 | 42839731 | Higher in Smoker |
| cg12871687 | 20 | 31072777 | Higher in Smoker |
| cg22323786 | 20 | 35491355 | Lower in Smoker |
| cg14893639 | 20 | 35423080 | Lower in Smoker |
| cg19443292 | 20 | 35504064 | Higher in Smoker |
| cg24780445 | 20 | 35808365 | Higher in Smoker |
| cg01143454 | 20 | 2795601 | Higher in Smoker |
| cg27431396 | 20 | 32250213 | Higher in Smoker |
| cg06154311 | 20 | 61002657 | Lower in Smoker |
| cg00334976 | 20 | 61003303 | Lower in Smoker |
| cg03359095 | 20 | 61002866 | Lower in Smoker |

| | | | |
|---|---|---|---|
| cg23929284 | 20 | 30605916 | Higher in Smoker |
| cg00599463 | 20 | 30609716 | Lower in Smoker |
| cg12084436 | 20 | 30597664 | Lower in Smoker |
| cg05954273 | 20 | 61153997 | Lower in Smoker |
| cg04990378 | 20 | 61160996 | Lower in Smoker |
| cg02884024 | 20 | 58515388 | Higher in Smoker |
| cg11523191 | 20 | 62187126 | Higher in Smoker |
| cg25169338 | 20 | 35238351 | Lower in Smoker |
| cg03076771 | 20 | 35233484 | Lower in Smoker |
| cg21656428 | 20 | 20033533 | Higher in Smoker |
| cg05283538 | 20 | 1165228 | Higher in Smoker |
| cg06226567 | 20 | 22559676 | Higher in Smoker |
| cg11113534 | 20 | 31756024 | Lower in Smoker |
| cg06824795 | 20 | 31766130 | Lower in Smoker |
| cg07770857 | 20 | 17949703 | Higher in Smoker |
| cg09687966 | 20 | 10415809 | Higher in Smoker |
| cg04608177 | 20 | 37230389 | Lower in Smoker |
| cg17441724 | 20 | 271417 | Higher in Smoker |
| cg10865444 | 21 | 43136563 | Lower in Smoker |
| cg04837104 | 21 | 46129620 | Higher in Smoker |
| cg04677846 | 21 | 45560806 | Higher in Smoker |
| cg09441337 | 21 | 33650994 | Higher in Smoker |
| cg22550799 | 21 | 47721702 | Lower in Smoker |
| cg14442408 | 21 | 33785412 | Lower in Smoker |
| cg16334524 | 21 | 44898123 | Lower in Smoker |
| cg01284306 | 21 | 19190629 | Higher in Smoker |
| cg09045508 | 21 | 19191866 | Higher in Smoker |
| cg21703572 | 22 | 24951237 | Higher in Smoker |
| cg09255637 | 22 | 24951963 | Higher in Smoker |
| cg22250642 | 22 | 38349509 | Higher in Smoker |
| cg25983317 | 22 | 32340208 | Higher in Smoker |
| cg13780602 | 22 | 32145680 | Higher in Smoker |
| cg05233946 | 22 | 32078088 | Higher in Smoker |
| cg04237429 | 22 | 50051110 | Higher in Smoker |
| cg02477126 | 22 | 24988729 | Higher in Smoker |

| | | | |
|---|---|---|---|
| cg03259733 | 22 | 19435237 | Higher in Smoker |
| cg23149423 | 22 | 46646366 | Higher in Smoker |
| cg27023953 | 22 | 51001200 | Higher in Smoker |
| cg10613381 | 22 | 24890330 | Higher in Smoker |
| cg07795766 | 22 | 45608516 | Lower in Smoker |
| cg14696444 | 22 | 45596957 | Lower in Smoker |
| cg09428349 | 21 | 43346858 | Higher in Smoker |
| cg23884964 | 11 | 118977786 | Higher in Smoker |
| cg05159066 | 11 | 73767794 | Lower in Smoker |
| cg21618333 | 15 | 62359139 | Higher in Smoker |
| cg04569583 | 15 | 62358531 | Lower in Smoker |
| cg14002233 | 2 | 220041199 | Higher in Smoker |
| cg08095377 | 2 | 132511110 | Lower in Smoker |
| cg09947274 | 2 | 27439915 | Lower in Smoker |
| cg14242246 | 2 | 27434262 | Lower in Smoker |
| cg22016434 | 2 | 101869349 | Higher in Smoker |
| cg21423557 | 2 | 75935530 | Lower in Smoker |
| cg22653665 | 2 | 44999348 | Lower in Smoker |
| cg01169075 | 2 | 44915427 | Lower in Smoker |
| cg00230869 | 2 | 70418140 | Higher in Smoker |
| cg14757738 | 2 | 20928037 | Higher in Smoker |
| cg19188207 | 2 | 10340837 | Lower in Smoker |
| cg18856091 | 2 | 105956343 | Lower in Smoker |
| cg02527811 | 2 | 241834907 | Higher in Smoker |
| cg01588581 | 2 | 241832900 | Lower in Smoker |
| cg09236434 | 2 | 99553642 | Higher in Smoker |
| cg14122696 | 2 | 99553055 | Higher in Smoker |
| cg12832145 | 2 | 99442537 | Lower in Smoker |
| cg01310365 | 2 | 99443540 | Lower in Smoker |
| cg14663177 | 2 | 38373737 | Higher in Smoker |
| cg00306298 | 2 | 99225662 | Lower in Smoker |
| cg09414612 | 2 | 85838835 | Higher in Smoker |
| cg17644776 | 2 | 200775616 | Lower in Smoker |
| cg14649965 | 2 | 73456858 | Lower in Smoker |
| cg24478803 | 2 | 26786046 | Lower in Smoker |

| | | | |
|---|---|---|---|
| cg12542238 | 2 | 170550800 | Higher in Smoker |
| cg25406923 | 2 | 74010396 | Higher in Smoker |
| cg02313965 | 2 | 25016582 | Higher in Smoker |
| cg06532037 | 2 | 191045430 | Higher in Smoker |
| cg13581496 | 3 | 119470613 | Lower in Smoker |
| cg12741529 | 3 | 112723537 | Lower in Smoker |
| cg10779423 | 3 | 50604763 | Higher in Smoker |
| cg19233043 | 3 | 50605003 | Higher in Smoker |
| cg12793864 | 3 | 14693121 | Higher in Smoker |
| cg18443411 | 3 | 14814383 | Lower in Smoker |
| cg17057138 | 3 | 194992095 | Higher in Smoker |
| cg17362109 | 3 | 194981274 | Higher in Smoker |
| cg21445764 | 3 | 99752916 | Lower in Smoker |
| cg11732673 | 3 | 99782793 | Lower in Smoker |
| cg21419939 | 3 | 99598918 | Lower in Smoker |
| cg24828422 | 3 | 99646755 | Lower in Smoker |
| cg22372070 | 3 | 11861650 | Lower in Smoker |
| cg07781040 | 3 | 8664898 | Higher in Smoker |
| cg02219117 | 3 | 155523655 | Higher in Smoker |
| cg16969274 | 3 | 196435434 | Lower in Smoker |
| cg15849439 | 3 | 37456129 | Lower in Smoker |
| cg15685811 | 3 | 128998585 | Higher in Smoker |
| cg08230475 | 3 | 128997692 | Higher in Smoker |
| cg10297257 | 3 | 88198751 | Higher in Smoker |
| cg15993503 | 3 | 43133494 | Lower in Smoker |
| cg15038777 | 3 | 43147571 | Lower in Smoker |
| cg13452923 | 3 | 196243269 | Lower in Smoker |
| cg22605924 | 3 | 168526498 | Lower in Smoker |
| cg05756178 | 3 | 111805365 | Higher in Smoker |
| cg14018690 | 3 | 111804832 | Lower in Smoker |
| cg02461627 | 3 | 161089247 | Higher in Smoker |
| cg03327615 | 3 | 143690246 | Higher in Smoker |
| cg23344395 | 3 | 192634002 | Lower in Smoker |
| cg01881444 | 3 | 69061575 | Lower in Smoker |
| cg00084131 | 3 | 69025488 | Lower in Smoker |

| | | | |
|---|---|---|---|
| cg13916298 | 3 | 108896099 | Lower in Smoker |
| cg06028917 | 3 | 59035407 | Lower in Smoker |
| cg14317554 | 3 | 184870948 | Higher in Smoker |
| cg06158985 | 3 | 52099285 | Lower in Smoker |
| cg04068784 | 3 | 47537514 | Lower in Smoker |
| cg21131031 | 4 | 37455341 | Higher in Smoker |
| cg11002851 | 4 | 37455729 | Higher in Smoker |
| cg07790638 | 4 | 113508575 | Lower in Smoker |
| cg23692997 | 4 | 113554716 | Lower in Smoker |
| cg15299568 | 4 | 81449664 | Lower in Smoker |
| cg25269000 | 4 | 8468476 | Lower in Smoker |
| cg11528666 | 4 | 129886049 | Higher in Smoker |
| cg22103764 | 4 | 120222006 | Higher in Smoker |
| cg03870411 | 4 | 113070602 | Lower in Smoker |
| cg09107603 | 4 | 39560775 | Lower in Smoker |
| cg23151374 | 4 | 164415611 | Higher in Smoker |
| cg26125787 | 4 | 164415830 | Higher in Smoker |
| cg06533319 | 4 | 3265114 | Lower in Smoker |
| cg00497219 | 4 | 3253559 | Lower in Smoker |
| cg00178864 | 4 | 140201574 | Higher in Smoker |
| cg06329684 | 4 | 140187743 | Higher in Smoker |
| cg19391731 | 4 | 140201951 | Lower in Smoker |
| cg26278987 | 4 | 5960351 | Higher in Smoker |
| cg27193726 | 4 | 5990227 | Higher in Smoker |
| cg23355704 | 5 | 111313321 | Lower in Smoker |
| cg03348573 | 5 | 133304316 | Lower in Smoker |
| cg06953768 | 5 | 134181484 | Higher in Smoker |
| cg12852390 | 5 | 134180823 | Lower in Smoker |
| cg23004862 | 5 | 175669020 | Lower in Smoker |
| cg19768013 | 5 | 95194688 | Higher in Smoker |
| cg11403368 | 5 | 43484385 | Higher in Smoker |
| cg09671005 | 5 | 102594958 | Higher in Smoker |
| cg00287773 | 5 | 139594619 | Lower in Smoker |
| cg07866207 | 5 | 56206137 | Lower in Smoker |
| cg25236382 | 5 | 93732017 | Lower in Smoker |

| | | | |
|---|---|---|---|
| cg07256206 | 5 | 93732031 | Lower in Smoker |
| cg04297686 | 5 | 93643309 | Lower in Smoker |
| cg00563847 | 5 | 93530270 | Lower in Smoker |
| cg09639547 | 5 | 93954075 | Higher in Smoker |
| cg18426009 | 5 | 75013471 | Higher in Smoker |
| cg15552172 | 5 | 154231167 | Lower in Smoker |
| cg15656113 | 5 | 172482832 | Higher in Smoker |
| cg16658609 | 5 | 37206515 | Lower in Smoker |
| cg04657419 | 5 | 60454782 | Lower in Smoker |
| cg01395394 | 5 | 64921203 | Higher in Smoker |
| cg01038640 | 5 | 157097845 | Lower in Smoker |
| cg15157209 | 5 | 159936550 | Higher in Smoker |
| cg03653573 | 5 | 131762326 | Higher in Smoker |
| cg16716345 | 6 | 34216949 | Higher in Smoker |
| cg25145195 | 6 | 32340955 | Lower in Smoker |
| cg11196533 | 6 | 32303626 | Lower in Smoker |
| cg25605800 | 6 | 32333231 | Lower in Smoker |
| cg21293943 | 6 | 32337906 | Lower in Smoker |
| cg01858458 | 6 | 32296549 | Lower in Smoker |
| cg12898793 | 6 | 32288224 | Lower in Smoker |
| cg12989473 | 6 | 32286943 | Lower in Smoker |
| cg19721802 | 6 | 32301389 | Lower in Smoker |
| cg00738945 | 6 | 32340354 | Lower in Smoker |
| cg09177461 | 6 | 32280185 | Lower in Smoker |
| cg09452510 | 6 | 32330188 | Lower in Smoker |
| cg08484972 | 6 | 32282981 | Lower in Smoker |
| cg25924085 | 6 | 32324878 | Lower in Smoker |
| cg11748650 | 6 | 32279016 | Lower in Smoker |
| cg15744124 | 6 | 32306089 | Lower in Smoker |
| cg01937212 | 6 | 32295097 | Lower in Smoker |
| cg02808240 | 6 | 32304143 | Lower in Smoker |
| cg26263563 | 6 | 32306040 | Lower in Smoker |
| cg16905004 | 6 | 32317028 | Lower in Smoker |
| cg18698799 | 6 | 32301513 | Lower in Smoker |
| cg22863148 | 6 | 32339554 | Lower in Smoker |

| | | | |
|---|---|---|---|
| cg10197432 | 6 | 146920119 | Higher in Smoker |
| cg16526755 | 6 | 34569886 | Lower in Smoker |
| cg15653111 | 6 | 34574629 | Lower in Smoker |
| cg18878034 | 6 | 43197151 | Higher in Smoker |
| cg13891659 | 6 | 170190454 | Higher in Smoker |
| cg17247293 | 6 | 168197921 | Higher in Smoker |
| cg16492833 | 6 | 33679775 | Higher in Smoker |
| cg09082921 | 6 | 35744226 | Higher in Smoker |
| cg01820273 | 6 | 35754906 | Lower in Smoker |
| cg02776628 | 6 | 37465322 | Lower in Smoker |
| cg00885461 | 6 | 37465801 | Lower in Smoker |
| cg23653391 | 6 | 30614734 | Higher in Smoker |
| cg18674914 | 6 | 30616867 | Lower in Smoker |
| cg13527624 | 6 | 30614782 | Lower in Smoker |
| cg17160886 | 6 | 49518986 | Higher in Smoker |
| cg19670870 | 6 | 49518358 | Higher in Smoker |
| cg16554447 | 6 | 54058452 | Lower in Smoker |
| cg20867963 | 6 | 3743529 | Higher in Smoker |
| cg10185489 | 6 | 31079555 | Lower in Smoker |
| cg21757368 | 6 | 121656329 | Higher in Smoker |
| cg10245778 | 6 | 127837570 | Higher in Smoker |
| cg01747191 | 6 | 109449950 | Lower in Smoker |
| cg22229829 | 6 | 109449739 | Lower in Smoker |
| cg01451057 | 6 | 109450553 | Lower in Smoker |
| cg00239660 | 6 | 130182620 | Lower in Smoker |
| cg15368264 | 6 | 130182413 | Lower in Smoker |
| cg15415953 | 6 | 2636435 | Lower in Smoker |
| cg01285783 | 6 | 2623778 | Lower in Smoker |
| cg27250807 | 6 | 4079649 | Higher in Smoker |
| cg19688752 | 6 | 118909918 | Lower in Smoker |
| cg25726699 | 6 | 135826776 | Lower in Smoker |
| cg22301664 | 6 | 74072820 | Lower in Smoker |
| cg16039071 | 6 | 43968282 | Lower in Smoker |
| cg21730778 | 6 | 42858647 | Higher in Smoker |
| cg05991539 | 6 | 31692365 | Lower in Smoker |

| | | | |
|---|---|---|---|
| cg26656884 | 6 | 31743820 | Lower in Smoker |
| cg23287992 | 6 | 31734390 | Lower in Smoker |
| cg10047612 | 6 | 157713044 | Lower in Smoker |
| cg10993074 | 6 | 31627313 | Lower in Smoker |
| cg27409499 | 6 | 31628339 | Higher in Smoker |
| cg09673200 | 6 | 31803103 | Higher in Smoker |
| cg17794996 | 6 | 31806478 | Lower in Smoker |
| cg13541527 | 6 | 31804078 | Lower in Smoker |
| cg06320936 | 6 | 31803094 | Higher in Smoker |
| cg20900994 | 6 | 31803089 | Higher in Smoker |
| cg22988444 | 6 | 31802601 | Higher in Smoker |
| cg26754510 | 6 | 71276074 | Lower in Smoker |
| cg14186264 | 6 | 127898305 | Lower in Smoker |
| cg23659696 | 6 | 39083005 | Lower in Smoker |
| cg25513133 | 6 | 149887296 | Higher in Smoker |
| cg15896056 | 6 | 144187583 | Higher in Smoker |
| cg04134305 | 7 | 156433520 | Higher in Smoker |
| cg15179113 | 7 | 156433342 | Higher in Smoker |
| cg20964021 | 7 | 156434403 | Lower in Smoker |
| cg06707886 | 7 | 916393 | Higher in Smoker |
| cg17735131 | 7 | 86849176 | Higher in Smoker |
| cg20305142 | 7 | 86849011 | Higher in Smoker |
| cg22325059 | 7 | 6648166 | Lower in Smoker |
| cg08710987 | 7 | 5939791 | Lower in Smoker |
| cg03995966 | 7 | 25219874 | Higher in Smoker |
| cg04464504 | 7 | 148303238 | Lower in Smoker |
| cg23146534 | 7 | 99149191 | Higher in Smoker |
| cg02233849 | 7 | 99753892 | Lower in Smoker |
| cg20200811 | 7 | 23723014 | Lower in Smoker |
| cg22785556 | 7 | 1081061 | Higher in Smoker |
| cg09373282 | 7 | 1070111 | Higher in Smoker |
| cg01687997 | 7 | 1083072 | Higher in Smoker |
| cg01105362 | 7 | 1059627 | Lower in Smoker |
| cg12260801 | 7 | 1045157 | Lower in Smoker |
| cg00171290 | 7 | 1160746 | Lower in Smoker |

| | | | |
|---|---|---|---|
| cg21239511 | 7 | 1090845 | Lower in Smoker |
| cg00364696 | 7 | 1142433 | Lower in Smoker |
| cg23496178 | 7 | 1142861 | Lower in Smoker |
| cg19054158 | 7 | 1099421 | Lower in Smoker |
| cg06962782 | 7 | 100091575 | Higher in Smoker |
| cg00731958 | 7 | 48081031 | Lower in Smoker |
| cg07776698 | 7 | 120903952 | Lower in Smoker |
| cg01541773 | 7 | 120701117 | Lower in Smoker |
| cg21794767 | 7 | 120657213 | Lower in Smoker |
| cg17756530 | 7 | 120639815 | Lower in Smoker |
| cg25202791 | 7 | 120721606 | Lower in Smoker |
| cg25181490 | 7 | 99747129 | Lower in Smoker |
| cg03885022 | 7 | 92158293 | Higher in Smoker |
| cg27445709 | 7 | 47693946 | Lower in Smoker |
| cg27665018 | 7 | 47698707 | Lower in Smoker |
| cg04982193 | 8 | 146278795 | Lower in Smoker |
| cg12370643 | 8 | 96281700 | Higher in Smoker |
| cg08328324 | 8 | 33370759 | Higher in Smoker |
| cg03294066 | 8 | 494721 | Higher in Smoker |
| cg01434042 | 8 | 67782385 | Lower in Smoker |
| cg15070801 | 8 | 67417875 | Lower in Smoker |
| cg06390415 | 8 | 67405405 | Lower in Smoker |
| cg10918419 | 8 | 143808262 | Higher in Smoker |
| cg14304364 | 8 | 143807962 | Higher in Smoker |
| cg12137450 | 8 | 22458046 | Higher in Smoker |
| cg19455335 | 8 | 22457658 | Higher in Smoker |
| cg12799003 | 8 | 86132456 | Higher in Smoker |
| cg05313129 | 8 | 58192883 | Lower in Smoker |
| cg24351694 | 8 | 144655447 | Lower in Smoker |
| cg07297681 | 8 | 124254762 | Lower in Smoker |
| cg25515982 | 8 | 12860315 | Lower in Smoker |
| cg25626869 | 8 | 93978374 | Higher in Smoker |
| cg13311096 | 8 | 74005566 | Higher in Smoker |
| cg04367680 | 8 | 74005697 | Higher in Smoker |
| cg17661686 | 8 | 73986912 | Lower in Smoker |

| | | | |
|---|---|---|---|
| cg09975039 | 9 | 132082957 | Higher in Smoker |
| cg13687261 | 9 | 96082521 | Lower in Smoker |
| cg13599886 | 9 | 98637534 | Higher in Smoker |
| cg14394451 | 9 | 72514243 | Lower in Smoker |
| cg14205519 | 9 | 139925750 | Lower in Smoker |
| cg21241219 | 9 | 139965163 | Lower in Smoker |
| cg09642020 | 9 | 139379173 | Lower in Smoker |
| cg10735196 | 9 | 139377111 | Higher in Smoker |
| cg13977355 | 9 | 140171765 | Higher in Smoker |
| cg14558431 | 9 | 89763370 | Higher in Smoker |
| cg13499395 | 9 | 135361993 | Lower in Smoker |
| cg13725752 | 9 | 34453817 | Lower in Smoker |
| cg05208153 | 9 | 34398637 | Lower in Smoker |
| cg16771596 | 9 | 103188942 | Lower in Smoker |
| cg13723983 | 9 | 132383362 | Higher in Smoker |
| cg11953824 | 9 | 111697545 | Lower in Smoker |
| cg12975295 | 9 | 86571409 | Higher in Smoker |
| cg14059835 | 9 | 132598917 | Higher in Smoker |
| cg27495908 | 9 | 90498223 | Lower in Smoker |
| cg20684615 | 9 | 139726218 | Lower in Smoker |
| cg13723106 | 9 | 139704146 | Lower in Smoker |
| cg20216130 | 9 | 117374308 | Higher in Smoker |
| cg14075203 | 9 | 135677835 | Higher in Smoker |
| cg26925025 | 8 | 86291400 | Lower in Smoker |
| cg22289837 | 8 | 86350278 | Lower in Smoker |
| cg18743730 | 17 | 58226981 | Lower in Smoker |
| cg10019392 | 16 | 87934324 | Lower in Smoker |
| cg04352288 | 16 | 87958407 | Lower in Smoker |
| cg10444261 | X | 15693037 | Higher in Smoker |
| cg01532206 | 16 | 66878709 | Higher in Smoker |
| cg11258532 | 16 | 66877873 | Lower in Smoker |
| cg12538248 | 8 | 61194072 | Higher in Smoker |
| cg20910102 | 8 | 61194077 | Higher in Smoker |
| cg20550050 | 2 | 231683214 | Lower in Smoker |
| cg04687511 | 13 | 49917452 | Lower in Smoker |

| | | | |
|---|---|---|---|
| cg00786909 | 1 | 227163427 | Lower in Smoker |
| cg06661671 | 22 | 24407852 | Higher in Smoker |
| cg18793086 | 18 | 20735005 | Lower in Smoker |
| cg02577078 | 12 | 121092968 | Lower in Smoker |
| cg24339197 | 12 | 121093625 | Lower in Smoker |
| cg07954316 | 11 | 67287567 | Lower in Smoker |
| cg13576483 | 11 | 67290850 | Lower in Smoker |
| cg08479675 | 19 | 48537443 | Lower in Smoker |
| cg26955996 | 19 | 48547989 | Lower in Smoker |
| cg14416559 | 18 | 21719381 | Higher in Smoker |
| cg24639703 | 1 | 64986155 | Higher in Smoker |
| cg19304410 | 1 | 64971188 | Higher in Smoker |
| cg25210796 | 1 | 65089808 | Lower in Smoker |
| cg13960084 | 9 | 140773147 | Higher in Smoker |
| cg14241045 | 9 | 140778757 | Lower in Smoker |
| cg09436713 | 12 | 2323135 | Higher in Smoker |
| cg02959759 | 12 | 2801584 | Higher in Smoker |
| cg03626208 | 12 | 2443169 | Higher in Smoker |
| cg04006520 | 12 | 2660504 | Lower in Smoker |
| cg13371705 | 12 | 2452955 | Lower in Smoker |
| cg14337339 | 3 | 53529481 | Higher in Smoker |
| cg16241391 | 1 | 181470120 | Higher in Smoker |
| cg10573505 | 1 | 181454164 | Lower in Smoker |
| cg24106020 | 1 | 181452827 | Lower in Smoker |
| cg20433386 | 17 | 48702158 | Lower in Smoker |
| cg26915870 | 16 | 1227475 | Lower in Smoker |
| cg10233104 | 16 | 1212809 | Lower in Smoker |
| cg03825234 | 16 | 1213894 | Lower in Smoker |
| cg09238049 | 16 | 1205018 | Lower in Smoker |
| cg00592007 | 16 | 1226235 | Lower in Smoker |
| cg20683057 | 22 | 40054124 | Lower in Smoker |
| cg25244980 | 22 | 40042606 | Lower in Smoker |
| cg17810781 | 1 | 201082982 | Higher in Smoker |
| cg10369665 | 7 | 82071752 | Lower in Smoker |
| cg22670759 | 3 | 50487955 | Lower in Smoker |

| | | | |
|---|---|---|---|
| cg22211564 | 3 | 54988324 | Lower in Smoker |
| cg05523017 | 3 | 54153728 | Lower in Smoker |
| cg03364832 | 3 | 54659987 | Lower in Smoker |
| cg25214305 | 3 | 54970460 | Lower in Smoker |
| cg16618218 | 3 | 54950385 | Lower in Smoker |
| cg01347553 | 12 | 1906764 | Lower in Smoker |
| cg17737835 | 12 | 2027805 | Higher in Smoker |
| cg00476617 | 10 | 18492374 | Lower in Smoker |
| cg23029183 | 12 | 49211271 | Lower in Smoker |
| cg04766365 | 17 | 65040101 | Lower in Smoker |
| cg03366891 | 16 | 24372874 | Lower in Smoker |
| cg04543269 | 16 | 24267559 | Higher in Smoker |
| cg20410810 | 17 | 64962417 | Higher in Smoker |
| cg09840840 | 17 | 64961117 | Higher in Smoker |
| cg14055896 | 19 | 54481859 | Higher in Smoker |
| cg06116236 | 19 | 54466724 | Lower in Smoker |
| cg18055623 | 19 | 54485327 | Lower in Smoker |
| cg01730534 | 1 | 174968376 | Higher in Smoker |
| cg24338760 | 1 | 174968123 | Lower in Smoker |
| cg16743289 | 1 | 174968144 | Lower in Smoker |
| cg18281160 | 11 | 115375341 | Higher in Smoker |
| cg20541723 | 3 | 85007894 | Higher in Smoker |
| cg24621982 | 3 | 85008061 | Higher in Smoker |
| cg14312063 | 3 | 85010606 | Higher in Smoker |
| cg18458597 | 3 | 85544609 | Lower in Smoker |
| cg18480946 | 3 | 85054782 | Lower in Smoker |
| cg13331200 | 3 | 85008587 | Higher in Smoker |
| cg10544564 | 1 | 159141860 | Higher in Smoker |
| cg02719752 | 3 | 62861245 | Higher in Smoker |
| cg27111053 | 3 | 62524536 | Lower in Smoker |
| cg04245373 | 16 | 71392615 | Higher in Smoker |
| cg06796866 | 11 | 14994644 | Higher in Smoker |
| cg14110660 | 11 | 14994179 | Higher in Smoker |
| cg13491234 | 11 | 14994230 | Higher in Smoker |
| cg26393713 | 11 | 14995129 | Lower in Smoker |

| | | | |
|---|---|---|---|
| cg23558942 | 11 | 15005178 | Higher in Smoker |
| cg07503684 | 12 | 54121449 | Higher in Smoker |
| cg15022609 | 17 | 46908359 | Higher in Smoker |
| cg21044022 | 17 | 46907742 | Lower in Smoker |
| cg05384712 | 7 | 93203843 | Higher in Smoker |
| cg10902514 | 2 | 188211981 | Lower in Smoker |
| cg17231494 | 7 | 134633404 | Lower in Smoker |
| cg07625383 | 7 | 134626083 | Lower in Smoker |
| cg09247981 | 10 | 105215423 | Lower in Smoker |
| cg14099121 | 10 | 105215306 | Lower in Smoker |
| cg23753748 | 10 | 105212803 | Higher in Smoker |
| cg20250521 | 10 | 105240332 | Lower in Smoker |
| cg18079499 | 14 | 90868646 | Higher in Smoker |
| cg01755342 | 1 | 1845396 | Lower in Smoker |
| cg15102821 | 1 | 1844801 | Lower in Smoker |
| cg10780164 | 10 | 135149009 | Lower in Smoker |
| cg11716598 | 10 | 135139716 | Lower in Smoker |
| cg02415341 | 10 | 135146439 | Lower in Smoker |
| cg00115178 | 10 | 12648176 | Higher in Smoker |
| cg07639982 | 10 | 12555079 | Higher in Smoker |
| cg12708867 | 10 | 12610076 | Lower in Smoker |
| cg22211058 | 7 | 44259684 | Lower in Smoker |
| cg00528351 | 7 | 44348318 | Lower in Smoker |
| cg00447682 | 1 | 20813064 | Higher in Smoker |
| cg08398233 | 1 | 20811641 | Lower in Smoker |
| cg01781374 | 5 | 110777659 | Lower in Smoker |
| cg23668631 | 17 | 3796936 | Lower in Smoker |
| cg20239081 | 12 | 121687822 | Lower in Smoker |
| cg00500936 | 12 | 121735583 | Higher in Smoker |
| cg03098937 | 3 | 49907095 | Higher in Smoker |
| cg09543635 | 3 | 48266468 | Lower in Smoker |
| cg00539757 | 1 | 200772244 | Higher in Smoker |
| cg26152704 | 1 | 7024757 | Lower in Smoker |
| cg17973385 | 1 | 6958900 | Lower in Smoker |
| cg04874074 | 1 | 6355140 | Lower in Smoker |

| | | | |
|---|---|---|---|
| cg24628816 | 1 | 6649430 | Lower in Smoker |
| cg10521808 | 1 | 7313750 | Lower in Smoker |
| cg10176514 | 1 | 7688803 | Lower in Smoker |
| cg23021268 | 1 | 7534995 | Lower in Smoker |
| cg10536786 | 1 | 7550036 | Lower in Smoker |
| cg18993757 | 17 | 4889754 | Lower in Smoker |
| cg26968203 | 17 | 4671318 | Higher in Smoker |
| cg21255657 | 17 | 77006304 | Higher in Smoker |
| cg10008571 | 17 | 76987812 | Lower in Smoker |
| cg26055438 | 17 | 76993618 | Lower in Smoker |
| cg04999441 | 17 | 77005584 | Lower in Smoker |
| cg02998018 | 1 | 40505782 | Higher in Smoker |
| cg19627006 | 2 | 85637673 | Lower in Smoker |
| cg00686623 | 11 | 64949038 | Higher in Smoker |
| cg08439122 | 1 | 223899685 | Lower in Smoker |
| cg14511094 | 15 | 42703753 | Lower in Smoker |
| cg13545089 | 19 | 5915037 | Lower in Smoker |
| cg22716773 | 12 | 75723785 | Higher in Smoker |
| cg01084270 | 5 | 35904569 | Lower in Smoker |
| cg27409650 | 22 | 37915342 | Higher in Smoker |
| cg14549249 | 7 | 3083541 | Higher in Smoker |
| cg13775050 | 11 | 104916075 | Higher in Smoker |
| cg26818786 | 5 | 40841493 | Higher in Smoker |
| cg24793265 | 9 | 139269240 | Lower in Smoker |
| cg11017500 | 13 | 111290755 | Lower in Smoker |
| cg12317676 | 19 | 1098181C | Higher in Smoker |
| cg02159763 | 13 | 111358924 | Lower in Smoker |
| cg02372702 | 12 | 25304568 | Lower in Smoker |
| cg25653011 | 17 | 38296442 | Higher in Smoker |
| cg27426500 | 17 | 38327194 | Lower in Smoker |
| cg00443673 | 17 | 38296516 | Higher in Smoker |
| cg26295328 | 15 | 44581216 | Lower in Smoker |
| cg07106138 | 15 | 40954471 | Lower in Smoker |
| cg21977766 | 7 | 94138743 | Higher in Smoker |
| cg06831064 | 16 | 2229298 | Lower in Smoker |

| | | | |
|---|---|---|---|
| cg09457470 | 17 | 73499240 | Lower in Smoker |
| cg02021789 | 19 | 15162515 | Lower in Smoker |
| cg06003022 | 11 | 104814390 | Lower in Smoker |
| cg14758526 | 11 | 104879683 | Lower in Smoker |
| cg26532499 | 11 | 104876060 | Lower in Smoker |
| cg25116460 | 4 | 110624798 | Higher in Smoker |
| cg22906389 | 10 | 115438910 | Higher in Smoker |
| cg10981747 | 10 | 115438129 | Lower in Smoker |
| cg21449655 | 1 | 15851444 | Higher in Smoker |
| cg14770407 | 20 | 54987154 | Higher in Smoker |
| cg09187004 | 5 | 95999014 | Higher in Smoker |
| cg10874402 | 5 | 96037871 | Lower in Smoker |
| cg24705254 | 5 | 96098115 | Lower in Smoker |
| cg02396224 | 1 | 10693794 | Higher in Smoker |
| cg10491460 | 1 | 10854307 | Higher in Smoker |
| cg20462360 | 1 | 10753832 | Higher in Smoker |
| cg19253831 | 1 | 10795020 | Lower in Smoker |
| cg24661860 | 1 | 10784363 | Lower in Smoker |
| cg17944110 | 1 | 10856657 | Higher in Smoker |
| cg17034036 | 11 | 34461028 | Higher in Smoker |
| cg23685560 | 15 | 43940867 | Lower in Smoker |
| cg18346106 | 14 | 92199899 | Lower in Smoker |
| cg23924603 | 19 | 38826365 | Higher in Smoker |
| cg08526637 | 7 | 116166339 | Higher in Smoker |
| cg25274503 | 7 | 116140128 | Higher in Smoker |
| cg14893128 | 20 | 32077794 | Higher in Smoker |
| cg05021312 | 20 | 32078768 | Lower in Smoker |
| cg16678522 | 20 | 32149963 | Higher in Smoker |
| cg07569264 | 16 | 89020038 | Higher in Smoker |
| cg26956157 | 16 | 89036698 | Higher in Smoker |
| cg09910674 | 16 | 89028015 | Lower in Smoker |
| cg08047086 | 16 | 89044646 | Lower in Smoker |
| cg02003041 | 16 | 89008134 | Higher in Smoker |
| cg27434245 | 16 | 89007493 | Higher in Smoker |
| cg22414151 | 11 | 119080056 | Lower in Smoker |

| | | | |
|---|---|---|---|
| cg02696971 | 3 | 105377640 | Lower in Smoker |
| cg21211594 | 3 | 105387814 | Higher in Smoker |
| cg15056119 | 7 | 107384245 | Higher in Smoker |
| cg14590325 | 7 | 107385716 | Lower in Smoker |
| cg13105904 | 14 | 24900044 | Lower in Smoker |
| cg01856849 | 4 | 169931464 | Higher in Smoker |
| cg01775970 | 21 | 44486298 | Lower in Smoker |
| cg09257178 | 2 | 114197839 | Lower in Smoker |
| cg13606720 | 9 | 70490853 | Higher in Smoker |
| cg26932693 | 17 | 46152449 | Lower in Smoker |
| cg20440414 | 17 | 46178346 | Higher in Smoker |
| cg03711622 | 7 | 26240903 | Higher in Smoker |
| cg27487227 | 17 | 77813221 | Higher in Smoker |
| cg24725841 | 17 | 77811683 | Higher in Smoker |
| cg07097310 | 17 | 77808391 | Lower in Smoker |
| cg04398978 | 17 | 77814064 | Lower in Smoker |
| cg20687242 | 12 | 54653427 | Higher in Smoker |
| cg27408285 | 12 | 54653364 | Higher in Smoker |
| cg24858279 | 22 | 39267540 | Higher in Smoker |
| cg13639345 | 22 | 39052718 | Higher in Smoker |
| cg03947026 | 1 | 52832320 | Lower in Smoker |
| cg18993949 | 4 | 15481269 | Lower in Smoker |
| cg03627944 | 10 | 97760036 | Lower in Smoker |
| cg26685743 | 18 | 57108056 | Lower in Smoker |
| cg08096786 | 16 | 57571099 | Higher in Smoker |
| cg23192899 | 2 | 55746287 | Higher in Smoker |
| cg19300632 | 2 | 55746645 | Higher in Smoker |
| cg04768697 | 19 | 15122135 | Higher in Smoker |
| cg19631576 | 19 | 15132007 | Lower in Smoker |
| cg22312354 | 19 | 56158714 | Lower in Smoker |
| cg11326613 | 9 | 35657478 | Lower in Smoker |
| cg25116900 | 10 | 74452662 | Higher in Smoker |
| cg19709928 | 4 | 185595799 | Lower in Smoker |
| cg13330050 | 5 | 114632793 | Lower in Smoker |
| cg01323634 | 5 | 114631921 | Higher in Smoker |

| | | | |
|---|---|---|---|
| cg02845569 | 19 | 48800655 | Lower in Smoker |
| cg25533551 | 19 | 48823178 | Lower in Smoker |
| cg01886396 | 2 | 131099816 | Higher in Smoker |
| cg20111235 | 22 | 29168748 | Higher in Smoker |
| cg16306228 | 3 | 46985840 | Lower in Smoker |
| cg00006884 | 7 | 23637030 | Higher in Smoker |
| cg16224521 | 5 | 205606 | Lower in Smoker |
| cg04342821 | 3 | 42614752 | Higher in Smoker |
| cg26916117 | 22 | 42196600 | Higher in Smoker |
| cg11374884 | 7 | 128450375 | Lower in Smoker |
| cg20757348 | 2 | 109403120 | Higher in Smoker |
| cg20520273 | 2 | 109403139 | Higher in Smoker |
| cg08224051 | 3 | 123669383 | Lower in Smoker |
| cg17765952 | 2 | 179737173 | Lower in Smoker |
| cg20995835 | 17 | 18523589 | Higher in Smoker |
| cg08277486 | 17 | 20770315 | Lower in Smoker |
| cg00429706 | 7 | 76751736 | Higher in Smoker |
| cg24395241 | 7 | 76755312 | Lower in Smoker |
| cg21254135 | 7 | 76852292 | Lower in Smoker |
| cg08241295 | 7 | 76829979 | Higher in Smoker |
| cg01310473 | 7 | 76829168 | Higher in Smoker |
| cg19840387 | 2 | 159314016 | Higher in Smoker |
| cg07658771 | 4 | 24982060 | Lower in Smoker |
| cg02289038 | 4 | 24915774 | Lower in Smoker |
| cg01243246 | 11 | 124823843 | Higher in Smoker |
| cg12707723 | 11 | 119067057 | Lower in Smoker |
| cg14009451 | 19 | 49893460 | Lower in Smoker |
| cg14220678 | 1 | 46089024 | Higher in Smoker |
| cg03335125 | 1 | 46088541 | Higher in Smoker |
| cg14017991 | 1 | 26560780 | Higher in Smoker |
| cg26606552 | X | 49092437 | Lower in Smoker |
| cg14666006 | 8 | 27629879 | Higher in Smoker |
| cg24719086 | 1 | 3686349 | Lower in Smoker |
| cg07997596 | 1 | 3685319 | Lower in Smoker |
| cg00236261 | 10 | 12999618 | Lower in Smoker |

| | | | |
|---|---|---|---|
| cg18468796 | 15 | 74612177 | Lower in Smoker |
| cg26855812 | 12 | 96336499 | Higher in Smoker |
| cg07083543 | 12 | 96337410 | Higher in Smoker |
| cg04040925 | 17 | 78011083 | Higher in Smoker |
| cg27371984 | 17 | 78009155 | Higher in Smoker |
| cg05049646 | 12 | 94852090 | Lower in Smoker |
| cg11684889 | 12 | 94853499 | Higher in Smoker |
| cg02639007 | 12 | 94853345 | Higher in Smoker |
| cg12979921 | 12 | 113594302 | Lower in Smoker |
| cg15903404 | 17 | 62506925 | Lower in Smoker |
| cg06604625 | 17 | 64187838 | Higher in Smoker |
| cg25197194 | 3 | 128758787 | Lower in Smoker |
| cg26325444 | 3 | 19104058 | Lower in Smoker |
| cg19892944 | 3 | 113217290 | Lower in Smoker |
| cg05054006 | 17 | 28443555 | Higher in Smoker |
| cg01863613 | 17 | 28443583 | Higher in Smoker |
| cg20197093 | 17 | 80113085 | Lower in Smoker |
| cg24442978 | 12 | 119895394 | Lower in Smoker |
| cg01519345 | 12 | 123259107 | Higher in Smoker |
| cg03015758 | 16 | 3083902 | Higher in Smoker |
| cg13792233 | 3 | 56591045 | Higher in Smoker |
| cg26827247 | 11 | 93063208 | Lower in Smoker |
| cg12955441 | 18 | 52626524 | Higher in Smoker |
| cg03778029 | 18 | 52626773 | Higher in Smoker |
| cg12974637 | 18 | 52626668 | Higher in Smoker |
| cg25447549 | 5 | 150603693 | Higher in Smoker |
| cg14001165 | 5 | 150566089 | Lower in Smoker |
| cg11256290 | 10 | 32734912 | Higher in Smoker |
| cg25858682 | 3 | 48431793 | Higher in Smoker |
| cg10111831 | 11 | 32815365 | Lower in Smoker |
| cg14465237 | 11 | 32816254 | Lower in Smoker |
| cg04157726 | 2 | 132235131 | Lower in Smoker |
| cg04951819 | 12 | 551573 | Higher in Smoker |
| cg07594933 | 12 | 515355 | Lower in Smoker |
| cg15814980 | 12 | 535355 | Lower in Smoker |

| | | | |
|---|---|---|---|
| cg04419012 | 16 | 66835618 | Lower in Smoker |
| cg24051057 | 3 | 112358409 | Lower in Smoker |
| cg13790353 | 11 | 85565559 | Higher in Smoker |
| cg18801806 | 11 | 118869385 | Lower in Smoker |
| cg05991743 | 2 | 56412380 | Higher in Smoker |
| cg20348765 | 2 | 56415578 | Lower in Smoker |
| cg06054963 | 11 | 65657880 | Higher in Smoker |
| cg27621997 | 11 | 60608634 | Lower in Smoker |
| cg26736400 | 11 | 66360499 | Lower in Smoker |
| cg02776177 | 19 | 47774873 | Lower in Smoker |
| cg01945841 | 6 | 13813278 | Lower in Smoker |
| cg04558386 | 6 | 13815568 | Lower in Smoker |
| cg19941758 | 11 | 82997468 | Higher in Smoker |
| cg02658319 | 12 | 124434452 | Lower in Smoker |
| cg13355233 | 2 | 118771338 | Higher in Smoker |
| cg01587095 | 19 | 41815869 | Higher in Smoker |
| cg26738916 | 6 | 31126003 | Higher in Smoker |
| cg16864658 | 3 | 42306150 | Higher in Smoker |
| cg25531987 | 17 | 34346381 | Lower in Smoker |
| cg02901006 | 19 | 8117024 | Higher in Smoker |
| cg21743830 | 19 | 8117966 | Lower in Smoker |
| cg09722555 | 9 | 34662282 | Lower in Smoker |
| cg04187185 | 5 | 43396953 | Higher in Smoker |
| cg18199554 | 5 | 43397238 | Higher in Smoker |
| cg18407309 | 17 | 34417530 | Higher in Smoker |
| cg04850148 | 17 | 34539744 | Lower in Smoker |
| cg23235142 | 7 | 45066841 | Higher in Smoker |
| cg00156230 | 7 | 45073692 | Lower in Smoker |
| cg27375029 | 7 | 45039799 | Higher in Smoker |
| cg10002561 | 4 | 122744832 | Higher in Smoker |
| cg03950590 | 15 | 59397186 | Higher in Smoker |
| cg11113650 | X | 50028082 | Lower in Smoker |
| cg14513281 | 11 | 69455457 | Higher in Smoker |
| cg11802013 | 11 | 69469175 | Lower in Smoker |
| cg03801902 | 12 | 4381800 | Higher in Smoker |

| | | | |
|---|---|---|---|
| cg10091994 | 12 | 4381803 | Higher in Smoker |
| cg18584387 | 12 | 4384879 | Lower in Smoker |
| cg26989531 | 12 | 4383117 | Higher in Smoker |
| cg12151296 | 6 | 42013349 | Higher in Smoker |
| cg05191454 | 6 | 42016435 | Higher in Smoker |
| cg16836589 | 19 | 30303674 | Lower in Smoker |
| cg27475126 | 19 | 30303651 | Lower in Smoker |
| cg20527070 | 8 | 95906439 | Higher in Smoker |
| cg01459673 | 8 | 95907442 | Higher in Smoker |
| cg13963099 | 5 | 162364768 | Higher in Smoker |
| cg14452392 | 5 | 86708659 | Higher in Smoker |
| cg11299854 | 5 | 132083184 | Lower in Smoker |
| cg09323434 | 10 | 97802912 | Higher in Smoker |
| cg26268044 | 10 | 97802928 | Higher in Smoker |
| cg04590978 | 10 | 97802941 | Higher in Smoker |
| cg11444704 | 5 | 159738916 | Higher in Smoker |
| cg11965671 | 5 | 159739797 | Higher in Smoker |
| cg27143204 | 5 | 54530375 | Lower in Smoker |
| cg19073520 | 2 | 135676222 | Higher in Smoker |
| cg00869330 | 10 | 35621144 | Higher in Smoker |
| cg17615773 | 10 | 35535084 | Lower in Smoker |
| cg11953675 | 10 | 35618813 | Lower in Smoker |
| cg16894974 | 15 | 55700780 | Higher in Smoker |
| cg24341442 | 15 | 55699975 | Higher in Smoker |
| cg06026269 | 3 | 46245807 | Lower in Smoker |
| cg10499974 | 3 | 46244099 | Lower in Smoker |
| cg21759685 | 3 | 46400618 | Lower in Smoker |
| cg03050629 | 3 | 46307918 | Lower in Smoker |
| cg22022041 | 3 | 45928137 | Lower in Smoker |
| cg04702527 | 4 | 139940407 | Lower in Smoker |
| cg05062047 | 12 | 69979562 | Lower in Smoker |
| cg23097696 | 1 | 156308121 | Higher in Smoker |
| cg19716462 | 2 | 62115576 | Higher in Smoker |
| cg12289617 | 5 | 10259861 | Lower in Smoker |
| cg16890606 | 7 | 65216203 | Higher in Smoker |

| | | | |
|---|---|---|---|
| cg14421218 | 2 | 73461263 | Higher in Smoker |
| cg06642617 | 2 | 73461528 | Higher in Smoker |
| cg01112801 | 21 | 30443603 | Lower in Smoker |
| cg01474260 | 22 | 17073884 | Lower in Smoker |
| cg23004174 | 6 | 74404879 | Lower in Smoker |
| cg06987936 | 6 | 74406097 | Lower in Smoker |
| cg22009923 | 11 | 832065 | Higher in Smoker |
| cg05981394 | 16 | 28942152 | Lower in Smoker |
| cg02478603 | 1 | 158301451 | Lower in Smoker |
| cg00173005 | 1 | 158258366 | Lower in Smoker |
| cg10324825 | 1 | 158153227 | Lower in Smoker |
| cg03329165 | 3 | 112052218 | Higher in Smoker |
| cg26572165 | 1 | 160807694 | Lower in Smoker |
| cg12480903 | 1 | 167423965 | Higher in Smoker |
| cg13210595 | 1 | 167471264 | Lower in Smoker |
| cg12782654 | 11 | 66085299 | Higher in Smoker |
| cg22036538 | 12 | 6554051 | Lower in Smoker |
| cg11384427 | 12 | 6553585 | Lower in Smoker |
| cg13474877 | 9 | 5450724 | Higher in Smoker |
| cg00133909 | 15 | 73977201 | Higher in Smoker |
| cg17021265 | 6 | 47445121 | Higher in Smoker |
| cg20172563 | 6 | 47487173 | Lower in Smoker |
| cg23250715 | 6 | 47444224 | Lower in Smoker |
| cg05592035 | 17 | 72462984 | Higher in Smoker |
| cg10357151 | 17 | 41924123 | Higher in Smoker |
| cg27625491 | 7 | 80266930 | Lower in Smoker |
| cg02325411 | 7 | 80291794 | Lower in Smoker |
| cg02189760 | 19 | 49842655 | Lower in Smoker |
| cg15994026 | 4 | 15780306 | Higher in Smoker |
| cg23068731 | 4 | 15780849 | Higher in Smoker |
| cg16257086 | 1 | 207925400 | Higher in Smoker |
| cg22500738 | 1 | 207928706 | Lower in Smoker |
| cg25382848 | 3 | 107809996 | Higher in Smoker |
| cg21382749 | 3 | 107791034 | Lower in Smoker |
| cg19408145 | 1 | 160681530 | Higher in Smoker |

| | | | |
|---|---|---|---|
| cg00797651 | 1 | 207494336 | Higher in Smoker |
| cg07114444 | 1 | 117074498 | Lower in Smoker |
| cg23254918 | 11 | 33758121 | Higher in Smoker |
| cg19904031 | 1 | 157805906 | Lower in Smoker |
| cg03761113 | 1 | 157811724 | Lower in Smoker |
| cg21939215 | 11 | 60738995 | Higher in Smoker |
| cg00055617 | 17 | 80273685 | Higher in Smoker |
| cg14016344 | 9 | 35616726 | Lower in Smoker |
| cg22183016 | 5 | 149784443 | Lower in Smoker |
| cg04602992 | 17 | 62009628 | Lower in Smoker |
| cg13913728 | 3 | 119278596 | Higher in Smoker |
| cg06699519 | 11 | 2398327 | Lower in Smoker |
| cg04069951 | 11 | 2398336 | Lower in Smoker |
| cg02541231 | 11 | 2398776 | Lower in Smoker |
| cg21108085 | 11 | 44591098 | Higher in Smoker |
| cg22697239 | 11 | 44626706 | Lower in Smoker |
| cg01991582 | 11 | 44587154 | Higher in Smoker |
| cg25939861 | 2 | 37020937 | Lower in Smoker |
| cg24214168 | 3 | 111259879 | Lower in Smoker |
| cg18327855 | 19 | 14517401 | Lower in Smoker |
| cg16893618 | 19 | 14491899 | Lower in Smoker |
| cg00519069 | 19 | 14491737 | Lower in Smoker |
| cg07491702 | 15 | 43030817 | Lower in Smoker |
| cg23861715 | 9 | 99382235 | Higher in Smoker |
| cg24890222 | 13 | 115000162 | Higher in Smoker |
| cg23133153 | 13 | 115000275 | Higher in Smoker |
| cg05981896 | 13 | 115003939 | Higher in Smoker |
| cg16147196 | 1 | 43828680 | Lower in Smoker |
| cg05525368 | 1 | 43825904 | Lower in Smoker |
| cg14165142 | 20 | 3778655 | Lower in Smoker |
| cg05114625 | 17 | 45266880 | Higher in Smoker |
| cg17357984 | 19 | 532039 | Higher in Smoker |
| cg15124432 | 19 | 541031 | Lower in Smoker |
| cg14075496 | 9 | 4679516 | Higher in Smoker |
| cg16137285 | 6 | 110552097 | Lower in Smoker |

| | | | |
|---|---|---|---|
| cg21086153 | 14 | 103519032 | Higher in Smoker |
| cg08999486 | 14 | 103523305 | Higher in Smoker |
| cg27028800 | 14 | 103411330 | Higher in Smoker |
| cg04754454 | 14 | 103475666 | Higher in Smoker |
| cg13443768 | 11 | 65084386 | Lower in Smoker |
| cg07992500 | 2 | 37896583 | Lower in Smoker |
| cg13286582 | 2 | 37883934 | Lower in Smoker |
| cg20113012 | 17 | 71308660 | Lower in Smoker |
| cg13769548 | 19 | 54984708 | Higher in Smoker |
| cg00224508 | 1 | 151031323 | Higher in Smoker |
| cg02308795 | 5 | 130599504 | Higher in Smoker |
| cg05671347 | 6 | 44355199 | Higher in Smoker |
| cg11080379 | 8 | 25364185 | Lower in Smoker |
| cg20252016 | 11 | 64851499 | Lower in Smoker |
| cg22449745 | 1 | 38156939 | Lower in Smoker |
| cg02037573 | 3 | 45148056 | Lower in Smoker |
| cg24975222 | 3 | 45187717 | Higher in Smoker |
| cg19455306 | 3 | 45154734 | Lower in Smoker |
| cg25640619 | 3 | 119013031 | Higher in Smoker |
| cg18671784 | 3 | 119121029 | Lower in Smoker |
| cg21869219 | 3 | 119120865 | Lower in Smoker |
| cg09081994 | 3 | 119011925 | Lower in Smoker |
| cg12163490 | 16 | 65155841 | Higher in Smoker |
| cg27106290 | 5 | 22853901 | Lower in Smoker |
| cg18394953 | 5 | 22853703 | Higher in Smoker |
| cg26227411 | 5 | 22853464 | Higher in Smoker |
| cg16777782 | 16 | 82671333 | Higher in Smoker |
| cg16512311 | 16 | 83148892 | Lower in Smoker |
| cg16710278 | 5 | 19988366 | Higher in Smoker |
| cg16503924 | 5 | 19988368 | Higher in Smoker |
| cg11538311 | 5 | 19988838 | Higher in Smoker |
| cg12169536 | 18 | 25758430 | Higher in Smoker |
| cg25123102 | 20 | 44879723 | Higher in Smoker |
| cg01059768 | 20 | 44874567 | Lower in Smoker |
| cg00200803 | 20 | 44838776 | Lower in Smoker |

| | | | |
|---|---|---|---|
| cg06768251 | 10 | 73553035 | Higher in Smoker |
| cg24331301 | 10 | 73156377 | Lower in Smoker |
| cg19901116 | 10 | 73156858 | Higher in Smoker |
| cg12827632 | 10 | 73156838 | Higher in Smoker |
| cg02815102 | 20 | 60388903 | Lower in Smoker |
| cg05637351 | 18 | 63417669 | Higher in Smoker |
| cg00589371 | 18 | 63417783 | Higher in Smoker |
| cg02835467 | 18 | 63417385 | Higher in Smoker |
| cg02401235 | 10 | 62538861 | Higher in Smoker |
| cg13954297 | 10 | 62538113 | Lower in Smoker |
| cg03147900 | 16 | 89762721 | Lower in Smoker |
| cg11851198 | 1 | 1642075 | Lower in Smoker |
| cg18282011 | 1 | 1590447 | Higher in Smoker |
| cg24007552 | 7 | 39989862 | Higher in Smoker |
| cg12881278 | 7 | 39989090 | Higher in Smoker |
| cg25150238 | 7 | 90390136 | Lower in Smoker |
| cg07521988 | 7 | 90393740 | Lower in Smoker |
| cg00009750 | 2 | 202730892 | Lower in Smoker |
| cg17102411 | 12 | 96794611 | Higher in Smoker |
| cg17641104 | 12 | 96794247 | Higher in Smoker |
| cg24315209 | 1 | 205494299 | Lower in Smoker |
| cg14721531 | 6 | 111136912 | Higher in Smoker |
| cg03330747 | 12 | 56361238 | Higher in Smoker |
| cg22465824 | 12 | 123746176 | Lower in Smoker |
| cg02328113 | 7 | 150755601 | Higher in Smoker |
| cg02723617 | 7 | 150755897 | Lower in Smoker |
| cg04106785 | 17 | 30813145 | Lower in Smoker |
| cg15631337 | 17 | 46048070 | Higher in Smoker |
| cg25156198 | 7 | 92250996 | Lower in Smoker |
| cg01558324 | 5 | 68530482 | Higher in Smoker |
| cg10231862 | 6 | 20641512 | Lower in Smoker |
| cg12215484 | 6 | 21231537 | Lower in Smoker |
| cg25475839 | 6 | 20697104 | Lower in Smoker |
| cg23941211 | 6 | 20907817 | Lower in Smoker |
| cg23496562 | 14 | 50363094 | Higher in Smoker |

| | | | |
|---|---|---|---|
| cg10133125 | 14 | 50863783 | Higher in Smoker |
| cg03032677 | 6 | 36648794 | Lower in Smoker |
| cg17434043 | 11 | 2907123 | Higher in Smoker |
| cg01294058 | 11 | 2905554 | Lower in Smoker |
| cg05267118 | 11 | 2907884 | Lower in Smoker |
| cg03079681 | 9 | 21994223 | Lower in Smoker |
| cg20686432 | 4 | 184365613 | Higher in Smoker |
| cg09109880 | 4 | 184365620 | Higher in Smoker |
| cg04556418 | 4 | 184367379 | Lower in Smoker |
| cg14615680 | 5 | 133747782 | Lower in Smoker |
| cg07908422 | 1 | 51434354 | Higher in Smoker |
| cg03496289 | 19 | 10680229 | Higher in Smoker |
| cg20454620 | 14 | 54863806 | Higher in Smoker |
| cg00649500 | 14 | 54862622 | Lower in Smoker |
| cg12442803 | 11 | 125933698 | Lower in Smoker |
| cg17697105 | 20 | 5170968 | Lower in Smoker |
| cg16204700 | 3 | 133292376 | Higher in Smoker |
| cg17055934 | 3 | 133292432 | Lower in Smoker |
| cg06303875 | 13 | 28543515 | Higher in Smoker |
| cg13314694 | 6 | 4734661 | Lower in Smoker |
| cg13644646 | 6 | 4336018 | Higher in Smoker |
| cg03749198 | 19 | 51979766 | Lower in Smoker |
| cg03110722 | 19 | 51984816 | Lower in Smoker |
| cg19399653 | 19 | 43085416 | Lower in Smoker |
| cg19556438 | 19 | 33793146 | Higher in Smoker |
| cg21696089 | 19 | 33793095 | Higher in Smoker |
| cg09631309 | 2 | 37458880 | Higher in Smoker |
| cg09118555 | 22 | 17628168 | Lower in Smoker |
| cg07244980 | 22 | 17516125 | Higher in Smoker |
| cg01007894 | 9 | 135957353 | Lower in Smoker |
| cg22768487 | 22 | 46770253 | Higher in Smoker |
| cg27166033 | 22 | 46933090 | Higher in Smoker |
| cg17198147 | 3 | 48699373 | Higher in Smoker |
| cg21175642 | 3 | 48701770 | Lower in Smoker |
| cg10573386 | 3 | 48700375 | Lower in Smoker |

| | | | |
|---|---|---|---|
| cg11929643 | 3 | 48700391 | Lower in Smoker |
| cg26456021 | 16 | 2580073 | Lower in Smoker |
| cg00165888 | 4 | 68411268 | Higher in Smoker |
| cg08656504 | 4 | 104119605 | Lower in Smoker |
| cg22426789 | 1 | 214782654 | Lower in Smoker |
| cg13085338 | 1 | 214776475 | Lower in Smoker |
| cg21993406 | 5 | 68484783 | Lower in Smoker |
| cg16925970 | 13 | 25496605 | Higher in Smoker |
| cg13255538 | 13 | 25496950 | Higher in Smoker |
| cg18503711 | 5 | 64859377 | Higher in Smoker |
| cg23633679 | 1 | 173793655 | Higher in Smoker |
| cg12793502 | 1 | 173794210 | Higher in Smoker |
| cg02552097 | 22 | 42343915 | Lower in Smoker |
| cg27450867 | 22 | 42335021 | Lower in Smoker |
| cg15806457 | 16 | 81039895 | Higher in Smoker |
| cg26478992 | 9 | 95245965 | Lower in Smoker |
| cg13872739 | 9 | 95246206 | Lower in Smoker |
| cg08367673 | 6 | 49430596 | Higher in Smoker |
| cg07931783 | 6 | 49431133 | Higher in Smoker |
| cg09850601 | 16 | 67867788 | Higher in Smoker |
| cg02117197 | 16 | 67880355 | Higher in Smoker |
| cg05625024 | 16 | 67876020 | Higher in Smoker |
| cg07179821 | 15 | 49103270 | Higher in Smoker |
| cg24732465 | 15 | 49103565 | Higher in Smoker |
| cg13313467 | 15 | 49103283 | Higher in Smoker |
| cg06109529 | 3 | 134205091 | Lower in Smoker |
| cg08330572 | 5 | 620259 | Lower in Smoker |
| cg07001201 | 5 | 642380 | Lower in Smoker |
| cg10791930 | 3 | 101443444 | Higher in Smoker |
| cg20293582 | 3 | 101485366 | Lower in Smoker |
| cg02019072 | 2 | 182521926 | Higher in Smoker |
| cg08065101 | 2 | 182521918 | Higher in Smoker |
| cg05113709 | 2 | 182521874 | Higher in Smoker |
| cg25029669 | 2 | 182458107 | Lower in Smoker |
| cg02256576 | 16 | 66995192 | Lower in Smoker |

| | | | |
|---|---|---|---|
| cg07039362 | 16 | 55908870 | Lower in Smoker |
| cg08713858 | 16 | 67035388 | Lower in Smoker |
| cg01143314 | 6 | 31916711 | Lower in Smoker |
| cg02512559 | 16 | 75414554 | Higher in Smoker |
| cg25840094 | 1 | 196945530 | Lower in Smoker |
| cg05072552 | 11 | 65623512 | Lower in Smoker |
| cg16985113 | 11 | 65625714 | Higher in Smoker |
| cg24277705 | 10 | 89603720 | Lower in Smoker |
| cg04885315 | 15 | 57731648 | Lower in Smoker |
| cg07549406 | 2 | 27341896 | Higher in Smoker |
| cg07702830 | 15 | 41245597 | Higher in Smoker |
| cg00552318 | 22 | 41633632 | Lower in Smoker |
| cg21000447 | 22 | 41634226 | Lower in Smoker |
| cg18199666 | 10 | 50821031 | Lower in Smoker |
| cg26399411 | 7 | 56174390 | Higher in Smoker |
| cg16463573 | 3 | 14166336 | Higher in Smoker |
| cg14318370 | 2 | 113342262 | Higher in Smoker |
| cg00694512 | 3 | 126423063 | Higher in Smoker |
| cg24673769 | 3 | 126671985 | Lower in Smoker |
| cg09847753 | 11 | 73588532 | Higher in Smoker |
| cg13916266 | 17 | 7787653 | Higher in Smoker |
| cg00532411 | 1 | 6241506 | Higher in Smoker |
| cg09667775 | 1 | 6170013 | Higher in Smoker |
| cg01335566 | 1 | 6200312 | Lower in Smoker |
| cg01295264 | 1 | 6185999 | Lower in Smoker |
| cg05382282 | 1 | 6164735 | Lower in Smoker |
| cg01055025 | 1 | 6226998 | Lower in Smoker |
| cg18493314 | 14 | 21899075 | Higher in Smoker |
| cg01044580 | 14 | 21900820 | Lower in Smoker |
| cg08361399 | 16 | 53088769 | Higher in Smoker |
| cg05087309 | 16 | 53088738 | Higher in Smoker |
| cg27292417 | 3 | 53850724 | Lower in Smoker |
| cg10223066 | 12 | 133464665 | Higher in Smoker |
| cg27040423 | 12 | 133464462 | Higher in Smoker |
| cg20066677 | 12 | 133424420 | Lower in Smoker |

| | | | |
|---|---|---|---|
| cg17522601 | 12 | 133430387 | Lower in Smoker |
| cg11653336 | 12 | 133465188 | Lower in Smoker |
| cg17387870 | 12 | 133463607 | Lower in Smoker |
| cg07140797 | 20 | 5905708 | Higher in Smoker |
| cg07423149 | 1 | 203156246 | Higher in Smoker |
| cg05526099 | 1 | 203152295 | Lower in Smoker |
| cg25211348 | 1 | 111769665 | Lower in Smoker |
| cg02336323 | 4 | 54931210 | Higher in Smoker |
| cg19548539 | 11 | 910938 | Higher in Smoker |
| cg24533917 | 1 | 203200291 | Lower in Smoker |
| cg13150344 | 11 | 67889062 | Higher in Smoker |
| cg12065366 | 3 | 238618 | Higher in Smoker |
| cg03175049 | 19 | 59062999 | Lower in Smoker |
| cg23635812 | 3 | 87276149 | Higher in Smoker |
| cg18584012 | 8 | 82644373 | Lower in Smoker |
| cg19132701 | 17 | 78965457 | Higher in Smoker |
| cg06163904 | 17 | 78964779 | Lower in Smoker |
| cg07504288 | 2 | 175870204 | Higher in Smoker |
| cg07154063 | 2 | 175664535 | Lower in Smoker |
| cg00235460 | 2 | 175867417 | Lower in Smoker |
| cg17197489 | 7 | 29235180 | Higher in Smoker |
| cg24804652 | 7 | 29234082 | Higher in Smoker |
| cg11433319 | 21 | 19617873 | Higher in Smoker |
| cg21350575 | 21 | 19617439 | Higher in Smoker |
| cg00597055 | 15 | 41523239 | Higher in Smoker |
| cg11445122 | 15 | 41523093 | Higher in Smoker |
| cg27324993 | 15 | 41523362 | Higher in Smoker |
| cg24330386 | 2 | 220409543 | Lower in Smoker |
| cg02291466 | 7 | 150929492 | Higher in Smoker |
| cg13748552 | 7 | 150929513 | Higher in Smoker |
| cg05051957 | 8 | 141522459 | Higher in Smoker |
| cg22957206 | 3 | 184096500 | Lower in Smoker |
| cg25271892 | 11 | 62690462 | Lower in Smoker |
| cg14632899 | 11 | 62678618 | Lower in Smoker |
| cg25074066 | 11 | 62690043 | Lower in Smoker |

| | | | |
|---|---|---|---|
| cg23886662 | 7 | 136564429 | Lower in Smoker |
| cg01257383 | 11 | 46408399 | Lower in Smoker |
| cg10783584 | 11 | 3686892 | Lower in Smoker |
| cg26506779 | 8 | 27320982 | Lower in Smoker |
| cg02953306 | 8 | 27336626 | Lower in Smoker |
| cg04671614 | 15 | 78913820 | Lower in Smoker |
| cg22980306 | 20 | 61978175 | Higher in Smoker |
| cg01684256 | 20 | 61977221 | Lower in Smoker |
| cg16751781 | 15 | 78858589 | Higher in Smoker |
| cg20148796 | 8 | 42608060 | Lower in Smoker |
| cg25730356 | 1 | 154540159 | Higher in Smoker |
| cg21052164 | 1 | 154539977 | Lower in Smoker |
| cg11412248 | 15 | 78930962 | Higher in Smoker |
| cg14482741 | 17 | 4802906 | Higher in Smoker |
| cg20147389 | 2 | 101010037 | Lower in Smoker |
| cg05352754 | 2 | 101034825 | Lower in Smoker |
| cg03311459 | 12 | 104850321 | Higher in Smoker |
| cg12970542 | 12 | 104851909 | Higher in Smoker |
| cg16618104 | 12 | 104853100 | Higher in Smoker |
| cg04737991 | 12 | 105050768 | Lower in Smoker |
| cg06260964 | 7 | 2473003 | Higher in Smoker |
| cg20712058 | 3 | 126243125 | Higher in Smoker |
| cg26399662 | 3 | 142840837 | Lower in Smoker |
| cg18738190 | 10 | 73740291 | Higher in Smoker |
| cg10772263 | 10 | 73746656 | Higher in Smoker |
| cg11801857 | 10 | 73723920 | Higher in Smoker |
| cg10153214 | 16 | 71571146 | Lower in Smoker |
| cg04872051 | X | 46433447 | Higher in Smoker |
| cg09340741 | X | 46432858 | Lower in Smoker |
| cg25999442 | 19 | 34113398 | Higher in Smoker |
| cg21483110 | 19 | 34112288 | Higher in Smoker |
| cg10579818 | 19 | 34117242 | Lower in Smoker |
| cg24739326 | 19 | 34175354 | Higher in Smoker |
| cg13954131 | 19 | 34175007 | Lower in Smoker |
| cg16190732 | 19 | 34113010 | Higher in Smoker |

| | | | |
|---|---|---|---|
| cg13959523 | 19 | 34175481 | Higher in Smoker |
| ch.18.502248F | 18 | 24708090 | Higher in Smoker |
| cg06619066 | 18 | 24765154 | Higher in Smoker |
| cg18536607 | 15 | 101729526 | Lower in Smoker |
| cg18829263 | 5 | 129240272 | Higher in Smoker |
| cg15884411 | 2 | 96932403 | Higher in Smoker |
| cg08162257 | 15 | 90777190 | Higher in Smoker |
| cg19236454 | 19 | 42799926 | Lower in Smoker |
| cg18309817 | 18 | 12254153 | Higher in Smoker |
| cg18649459 | 18 | 12253749 | Higher in Smoker |
| cg01262948 | 18 | 12271803 | Higher in Smoker |
| cg23479742 | 19 | 19648939 | Lower in Smoker |
| cg07608290 | 14 | 102829271 | Higher in Smoker |
| cg00596521 | 2 | 175260560 | Higher in Smoker |
| cg14138171 | 2 | 175261646 | Lower in Smoker |
| cg03498888 | 3 | 50649296 | Higher in Smoker |
| cg11345172 | 12 | 120315133 | Higher in Smoker |
| cg18917399 | 1 | 41327272 | Lower in Smoker |
| cg13642260 | 9 | 130955380 | Higher in Smoker |
| cg14217552 | 9 | 130956057 | Higher in Smoker |
| cg10071929 | 9 | 130955135 | Higher in Smoker |
| cg17617387 | 9 | 130953234 | Higher in Smoker |
| cg24469095 | 13 | 53029211 | Higher in Smoker |
| cg11342366 | 12 | 106642001 | Higher in Smoker |
| cg23710492 | 11 | 46848442 | Higher in Smoker |
| cg14669500 | 11 | 46868024 | Lower in Smoker |
| cg03679734 | 15 | 73885090 | Lower in Smoker |
| cg13858136 | 2 | 122375210 | Lower in Smoker |
| cg07603794 | 2 | 122354626 | Lower in Smoker |
| cg09030852 | 4 | 170629768 | Lower in Smoker |
| cg01725297 | 1 | 11888644 | Lower in Smoker |
| cg23226134 | 1 | 11866389 | Higher in Smoker |
| cg18187189 | 1 | 11866930 | Higher in Smoker |
| cg00700436 | 16 | 1497766 | Higher in Smoker |
| cg13358262 | 1 | 16374167 | Lower in Smoker |

| | | | |
|---|---|---|---|
| cg06428163 | 13 | 96204856 | Higher in Smoker |
| cg00894757 | 3 | 170137240 | Higher in Smoker |
| cg06023994 | 3 | 170137871 | Higher in Smoker |
| cg06073141 | 3 | 190105762 | Lower in Smoker |
| cg08545416 | 1 | 43207302 | Higher in Smoker |
| cg06671706 | 8 | 8559999 | Lower in Smoker |
| cg15441831 | 7 | 73245178 | Lower in Smoker |
| cg09446908 | 22 | 19512320 | Lower in Smoker |
| cg14618624 | 16 | 3068382 | Higher in Smoker |
| cg26746482 | 16 | 3065427 | Lower in Smoker |
| cg03186999 | 17 | 7165420 | Higher in Smoker |
| cg05898907 | 3 | 98242685 | Lower in Smoker |
| cg22065498 | 19 | 51871891 | Higher in Smoker |
| cg13516928 | 17 | 6979505 | Lower in Smoker |
| cg02138992 | 12 | 10168905 | Lower in Smoker |
| cg15027563 | 16 | 11038165 | Higher in Smoker |
| cg07486170 | 16 | 11221455 | Lower in Smoker |
| cg03995533 | 16 | 11194243 | Lower in Smoker |
| cg01472075 | 16 | 69984927 | Lower in Smoker |
| cg13600716 | 12 | 10223804 | Lower in Smoker |
| cg08753403 | 12 | 10007156 | Lower in Smoker |
| cg13300689 | 12 | 9826503 | Lower in Smoker |
| cg18873914 | 7 | 139208223 | Higher in Smoker |
| cg04365980 | 16 | 78056736 | Lower in Smoker |
| cg02235659 | 3 | 45066530 | Higher in Smoker |
| cg12401842 | 12 | 8276175 | Higher in Smoker |
| cg03425731 | 12 | 8665044 | Lower in Smoker |
| cg12762799 | 12 | 8693542 | Higher in Smoker |
| cg21278129 | 19 | 7797355 | Lower in Smoker |
| cg21227085 | 19 | 7853851 | Higher in Smoker |
| cg19223467 | 12 | 10163267 | Lower in Smoker |
| cg15207826 | 4 | 141348043 | Higher in Smoker |
| cg02651961 | 4 | 141349016 | Higher in Smoker |
| cg00657529 | 6 | 31698687 | Lower in Smoker |
| cg03359503 | X | 154563952 | Higher in Smoker |

| | | | |
|---|---|---|---|
| cg18742464 | 6 | 45895069 | Lower in Smoker |
| cg18434367 | 6 | 45891455 | Lower in Smoker |
| cg12941675 | 12 | 122870630 | Lower in Smoker |
| cg07873779 | 7 | 73788420 | Higher in Smoker |
| cg24329710 | 19 | 36507075 | Lower in Smoker |
| cg03135351 | 2 | 29338258 | Higher in Smoker |
| cg13257636 | 2 | 29338109 | Lower in Smoker |
| cg16098332 | 2 | 201730594 | Higher in Smoker |
| cg11837713 | 15 | 74908863 | Higher in Smoker |
| cg05068951 | 14 | 95722106 | Lower in Smoker |
| cg09112682 | 16 | 28503005 | Higher in Smoker |
| cg26814565 | 16 | 28501491 | Lower in Smoker |
| cg02359899 | 16 | 28503490 | Higher in Smoker |
| cg23833896 | 8 | 1711046 | Higher in Smoker |
| cg13996619 | 8 | 1712271 | Higher in Smoker |
| cg05960806 | 11 | 77348884 | Higher in Smoker |
| cg25530661 | 4 | 56301576 | Higher in Smoker |
| cg07236904 | 4 | 56413229 | Lower in Smoker |
| cg06334611 | 11 | 57425136 | Higher in Smoker |
| cg06551161 | 11 | 57424534 | Lower in Smoker |
| cg17756392 | 19 | 6361455 | Higher in Smoker |
| cg02376650 | 19 | 6360197 | Lower in Smoker |
| cg25107791 | 6 | 35764958 | Lower in Smoker |
| cg26823505 | 6 | 35765589 | Lower in Smoker |
| cg21081097 | 19 | 45458610 | Higher in Smoker |
| cg07172091 | 19 | 45458812 | Higher in Smoker |
| cg16754747 | 5 | 1339235 | Lower in Smoker |
| cg09826697 | 5 | 1325156 | Lower in Smoker |
| cg14500614 | 5 | 1324645 | Lower in Smoker |
| cg13786165 | 15 | 65477609 | Higher in Smoker |
| cg02281821 | 10 | 129692341 | Lower in Smoker |
| cg11352256 | 10 | 129684500 | Lower in Smoker |
| cg01515806 | 1 | 36235799 | Higher in Smoker |
| cg00393247 | 1 | 36234276 | Lower in Smoker |
| cg08845510 | 1 | 9884029 | Higher in Smoker |

| | | | |
|---|---|---|---|
| cg16513416 | 3 | 139665283 | Higher in Smoker |
| cg01490772 | 12 | 7282593 | Higher in Smoker |
| cg06671621 | 12 | 7281629 | Lower in Smoker |
| cg18431408 | 5 | 175843141 | Higher in Smoker |
| cg24735937 | 5 | 175843923 | Lower in Smoker |
| cg12494208 | 17 | 57743594 | Lower in Smoker |
| cg00928580 | 8 | 27473612 | Lower in Smoker |
| cg08521777 | 16 | 3550080 | Higher in Smoker |
| cg23326228 | 8 | 62200498 | Higher in Smoker |
| cg26862247 | 13 | 100497665 | Lower in Smoker |
| cg04291704 | 12 | 22199588 | Higher in Smoker |
| cg26276530 | 12 | 22199522 | Higher in Smoker |
| cg02702107 | 12 | 22218253 | Lower in Smoker |
| cg05593349 | 5 | 10307744 | Higher in Smoker |
| cg13679679 | 3 | 28282245 | Higher in Smoker |
| cg03287566 | 16 | 81564527 | Lower in Smoker |
| cg02597246 | 16 | 81711959 | Lower in Smoker |
| cg15630394 | 12 | 108715244 | Lower in Smoker |
| cg06156157 | 1 | 47799348 | Higher in Smoker |
| cg14851742 | 2 | 7001591 | Lower in Smoker |
| cg19274871 | 2 | 6989510 | Lower in Smoker |
| cg08032924 | 16 | 66613096 | Higher in Smoker |
| cg09057050 | 16 | 66639160 | Higher in Smoker |
| cg00355909 | 16 | 66638320 | Lower in Smoker |
| cg26280526 | 3 | 32543926 | Higher in Smoker |
| cg19788308 | 3 | 32443454 | Higher in Smoker |
| cg07881061 | 3 | 32433393 | Lower in Smoker |
| cg01617750 | 3 | 32279261 | Higher in Smoker |
| cg15954792 | 2 | 93986971 | Lower in Smoker |
| cg08099570 | 16 | 57937637 | Lower in Smoker |
| cg21221571 | 8 | 87755644 | Lower in Smoker |
| cg13278441 | 14 | 54908213 | Higher in Smoker |
| cg25789216 | 11 | 66045486 | Higher in Smoker |
| cg23816049 | 1 | 224804081 | Higher in Smoker |
| cg07230107 | 1 | 224804396 | Higher in Smoker |

| | | | |
|---|---|---|---|
| cg01785339 | 1 | 224544456 | Higher in Smoker |
| cg09221951 | 1 | 224543865 | Lower in Smoker |
| cg21694843 | X | 21391817 | Higher in Smoker |
| cg10730425 | 19 | 1035093 | Lower in Smoker |
| cg27143070 | 10 | 101087766 | Lower in Smoker |
| cg02576296 | 10 | 104705597 | Lower in Smoker |
| cg18457491 | 10 | 104829517 | Lower in Smoker |
| cg01376245 | 2 | 97426602 | Higher in Smoker |
| cg02913511 | 2 | 97454042 | Lower in Smoker |
| cg07980242 | 4 | 6718548 | Higher in Smoker |
| cg23515892 | 4 | 6718196 | Lower in Smoker |
| cg06081371 | 3 | 32726639 | Higher in Smoker |
| cg10464585 | 12 | 70636491 | Higher in Smoker |
| cg26151740 | 19 | 54641525 | Higher in Smoker |
| cg01718788 | 4 | 78740310 | Higher in Smoker |
| cg11854259 | 7 | 155325815 | Higher in Smoker |
| cg07707875 | 7 | 155326102 | Higher in Smoker |
| cg07710211 | 6 | 42900123 | Lower in Smoker |
| cg14186641 | 6 | 38876741 | Higher in Smoker |
| cg23287243 | 1 | 24230384 | Lower in Smoker |
| cg24171907 | 2 | 68546579 | Higher in Smoker |
| cg10722426 | 19 | 40729157 | Higher in Smoker |
| cg14243778 | 12 | 41086879 | Higher in Smoker |
| cg23225103 | 1 | 205040765 | Lower in Smoker |
| cg02944123 | 3 | 2812875 | Lower in Smoker |
| cg16471850 | 11 | 98891811 | Higher in Smoker |
| cg04719537 | 11 | 98891797 | Higher in Smoker |
| cg16035520 | 11 | 98891820 | Higher in Smoker |
| cg18109530 | 11 | 99504688 | Lower in Smoker |
| cg26577454 | 16 | 76311266 | Higher in Smoker |
| cg24592194 | 2 | 125410491 | Lower in Smoker |
| cg05049825 | 2 | 124944568 | Lower in Smoker |
| cg21445398 | 2 | 125425654 | Lower in Smoker |
| cg14447152 | 9 | 140153393 | Lower in Smoker |
| cg02452435 | 17 | 71188192 | Higher in Smoker |

| | | | |
|---|---|---|---|
| cg18150300 | 17 | 71187853 | Higher in Smoker |
| cg03734401 | 17 | 71198198 | Lower in Smoker |
| cg18580551 | 13 | 46039771 | Higher in Smoker |
| cg10486909 | 13 | 46038825 | Higher in Smoker |
| cg03014495 | 13 | 46102390 | Lower in Smoker |
| cg24556660 | 7 | 106842632 | Lower in Smoker |
| cg10208294 | 16 | 23464607 | Higher in Smoker |
| cg14345524 | 17 | 55038516 | Higher in Smoker |
| cg17343201 | 17 | 55038735 | Lower in Smoker |
| cg18494192 | 6 | 116448231 | Lower in Smoker |
| cg20631997 | 6 | 33151512 | Higher in Smoker |
| cg11761176 | 6 | 33135298 | Lower in Smoker |
| cg00866054 | 6 | 33142284 | Lower in Smoker |
| cg16452067 | 6 | 33156293 | Lower in Smoker |
| cg01094192 | 6 | 33158597 | Lower in Smoker |
| cg01635061 | 6 | 33160234 | Higher in Smoker |
| cg00044107 | 6 | 75795067 | Higher in Smoker |
| cg20516176 | 10 | 71598949 | Lower in Smoker |
| cg14179150 | 10 | 71641786 | Lower in Smoker |
| cg08944476 | 10 | 71561505 | Lower in Smoker |
| cg13652445 | 10 | 71561999 | Higher in Smoker |
| cg12065840 | 8 | 121138133 | Higher in Smoker |
| cg19100596 | 1 | 32170361 | Lower in Smoker |
| cg24315840 | 10 | 105791156 | Lower in Smoker |
| cg27128560 | 10 | 105815443 | Lower in Smoker |
| cg25832305 | 21 | 46860683 | Lower in Smoker |
| cg11113589 | 21 | 46898764 | Higher in Smoker |
| cg25652516 | 21 | 46914628 | Lower in Smoker |
| cg21947116 | 21 | 46918189 | Lower in Smoker |
| cg07421341 | 6 | 70876404 | Higher in Smoker |
| cg03266780 | 6 | 70762024 | Higher in Smoker |
| cg03743861 | 17 | 48263173 | Lower in Smoker |
| cg00439089 | 17 | 48263150 | Lower in Smoker |
| cg25026926 | 17 | 48266268 | Lower in Smoker |
| cg14562086 | 17 | 48279265 | Lower in Smoker |

| | | | |
|---|---|---|---|
| cg05282437 | 20 | 61936520 | Higher in Smoker |
| cg00357971 | 20 | 61923848 | Lower in Smoker |
| cg13308187 | 20 | 61953801 | Lower in Smoker |
| cg21688209 | 20 | 61940917 | Lower in Smoker |
| cg20368283 | 6 | 56112592 | Higher in Smoker |
| cg17590710 | 5 | 177740069 | Higher in Smoker |
| cg18158172 | 5 | 177819485 | Lower in Smoker |
| cg08634511 | 5 | 177890047 | Lower in Smoker |
| cg19488785 | 5 | 177751557 | Lower in Smoker |
| cg13922901 | 5 | 177783729 | Lower in Smoker |
| cg24395801 | 1 | 86622624 | Higher in Smoker |
| cg01734045 | 4 | 109967535 | Higher in Smoker |
| cg14994944 | 4 | 110084469 | Lower in Smoker |
| cg22778014 | 4 | 109811985 | Lower in Smoker |
| cg21161568 | 9 | 117047688 | Lower in Smoker |
| cg13554901 | 12 | 48396630 | Higher in Smoker |
| cg13565575 | 12 | 48397568 | Lower in Smoker |
| cg15258722 | 13 | 110802573 | Lower in Smoker |
| cg25424029 | 13 | 110840177 | Lower in Smoker |
| cg04819250 | 13 | 111089384 | Higher in Smoker |
| cg10627737 | 13 | 111065189 | Lower in Smoker |
| cg07771477 | 13 | 111142065 | Lower in Smoker |
| cg21281201 | 13 | 111143644 | Lower in Smoker |
| cg13672379 | 13 | 111012914 | Lower in Smoker |
| cg20450058 | 13 | 111152708 | Lower in Smoker |
| cg01297370 | 2 | 228027969 | Lower in Smoker |
| cg10563352 | 2 | 228028774 | Higher in Smoker |
| cg04324308 | 2 | 228028741 | Lower in Smoker |
| cg08957039 | 5 | 74807535 | Higher in Smoker |
| cg01575816 | X | 107683385 | Higher in Smoker |
| cg13754661 | 9 | 137533360 | Higher in Smoker |
| cg13987700 | 9 | 137657798 | Higher in Smoker |
| cg14252519 | 9 | 137533851 | Higher in Smoker |
| cg18445715 | 2 | 189981405 | Lower in Smoker |
| cg09211763 | 2 | 190044504 | Higher in Smoker |

| | | | |
|---|---|---|---|
| cg25445612 | 21 | 47401277 | Higher in Smoker |
| cg11401293 | 21 | 47404268 | Higher in Smoker |
| cg24784350 | 21 | 47518998 | Higher in Smoker |
| cg03214640 | 21 | 47546211 | Lower in Smoker |
| cg12423553 | 21 | 47541643 | Lower in Smoker |
| cg15474435 | 3 | 130368058 | Lower in Smoker |
| cg15164782 | 3 | 99507048 | Lower in Smoker |
| cg00808579 | 1 | 40768026 | Lower in Smoker |
| cg06953252 | 1 | 40782906 | Lower in Smoker |
| cg14745622 | 20 | 61447636 | Higher in Smoker |
| cg27564579 | 20 | 61456564 | Higher in Smoker |
| cg18759061 | 20 | 61467939 | Lower in Smoker |
| cg10279872 | 8 | 120118684 | Lower in Smoker |
| cg04697946 | 2 | 3654582 | Lower in Smoker |
| cg02645778 | 2 | 3685207 | Lower in Smoker |
| cg07137336 | 18 | 501137 | Lower in Smoker |
| cg19382657 | 18 | 501234 | Lower in Smoker |
| cg15419820 | 3 | 15540973 | Lower in Smoker |
| cg14305711 | 2 | 62132430 | Higher in Smoker |
| cg16944159 | 2 | 62132759 | Higher in Smoker |
| cg23108291 | 5 | 115420582 | Higher in Smoker |
| cg11208656 | 10 | 22605201 | Higher in Smoker |
| cg26239085 | 20 | 31291155 | Lower in Smoker |
| cg24397995 | 11 | 36311334 | Higher in Smoker |
| cg02201071 | 19 | 18900568 | Higher in Smoker |
| cg23237097 | 1 | 160278129 | Lower in Smoker |
| cg13461710 | 1 | 160287986 | Lower in Smoker |
| cg01446576 | 1 | 160313037 | Higher in Smoker |
| cg09866659 | 1 | 160286315 | Lower in Smoker |
| cg12821290 | 3 | 128968351 | Lower in Smoker |
| cg11748880 | 15 | 49438392 | Lower in Smoker |
| cg21429409 | 4 | 83956251 | Higher in Smoker |
| cg18844850 | 12 | 6833560 | Higher in Smoker |
| cg01987515 | 2 | 232651086 | Higher in Smoker |
| cg22932215 | 2 | 232651635 | Lower in Smoker |

| | | | |
|---|---|---|---|
| cg10809094 | 2 | 238006557 | Lower in Smoker |
| cg15468909 | 12 | 54718899 | Higher in Smoker |
| cg24387347 | 12 | 56661247 | Higher in Smoker |
| cg19842065 | 12 | 56660480 | Higher in Smoker |
| cg26804944 | 12 | 56660921 | Lower in Smoker |
| cg15545222 | 12 | 120967037 | Higher in Smoker |
| cg07474051 | 12 | 120942642 | Lower in Smoker |
| cg08293930 | 16 | 57494706 | Higher in Smoker |
| cg01861389 | 16 | 57481027 | Higher in Smoker |
| cg16957463 | 4 | 47597617 | Lower in Smoker |
| cg03311252 | 11 | 67209355 | Lower in Smoker |
| cg23468927 | 11 | 67206263 | Lower in Smoker |
| cg12044599 | 11 | 67206308 | Lower in Smoker |
| cg16408081 | 11 | 67205869 | Lower in Smoker |
| cg25256924 | 11 | 67205739 | Lower in Smoker |
| cg23448432 | 12 | 109078342 | Lower in Smoker |
| cg26544459 | 12 | 109045006 | Lower in Smoker |
| cg18037808 | 12 | 109059679 | Lower in Smoker |
| cg23429240 | 12 | 109040983 | Lower in Smoker |
| cg04534872 | 12 | 109126397 | Lower in Smoker |
| cg02966574 | 15 | 68872082 | Higher in Smoker |
| cg02405503 | 15 | 68871738 | Lower in Smoker |
| cg19927100 | 15 | 68902085 | Lower in Smoker |
| cg27637363 | 17 | 27945387 | Higher in Smoker |
| cg05091796 | 16 | 4465799 | Higher in Smoker |
| cg07964754 | 16 | 84650202 | Lower in Smoker |
| cg11217004 | 10 | 101492579 | Higher in Smoker |
| cg03055888 | 14 | 70826472 | Higher in Smoker |
| cg02937776 | 14 | 70826572 | Higher in Smoker |
| cg01427290 | 3 | 119396225 | Higher in Smoker |
| cg07580418 | 4 | 73935807 | Higher in Smoker |
| cg11309342 | 7 | 1014982 | Higher in Smoker |
| cg22126965 | 7 | 1015501 | Higher in Smoker |
| cg24094675 | 7 | 1015382 | Higher in Smoker |
| cg04385420 | 16 | 85816991 | Lower in Smoker |

| | | | |
|---|---|---|---|
| cg02035565 | 15 | 75214453 | Lower in Smoker |
| cg24168378 | 8 | 100905427 | Higher in Smoker |
| cg06809298 | 6 | 75953853 | Lower in Smoker |
| cg18449462 | X | 77155144 | Higher in Smoker |
| cg27299949 | 4 | 46911333 | Lower in Smoker |
| cg10910685 | 4 | 46911519 | Lower in Smoker |
| cg04195581 | 5 | 85914155 | Higher in Smoker |
| cg18679324 | 5 | 85916067 | Lower in Smoker |
| cg00008493 | 14 | 93813777 | Lower in Smoker |
| cg00747859 | 16 | 19535170 | Higher in Smoker |
| cg27358006 | 16 | 19563474 | Lower in Smoker |
| cg15159987 | 19 | 17003890 | Lower in Smoker |
| cg08635242 | 17 | 28706081 | Higher in Smoker |
| cg26812418 | 4 | 166299976 | Higher in Smoker |
| cg23427348 | 4 | 166301256 | Lower in Smoker |
| cg15353821 | 4 | 166419173 | Lower in Smoker |
| cg26518884 | 4 | 166322679 | Lower in Smoker |
| cg18295838 | 4 | 15005434 | Higher in Smoker |
| cg21573345 | 4 | 15009110 | Lower in Smoker |
| cg22591889 | 10 | 93828960 | Lower in Smoker |
| cg05125693 | 10 | 94051830 | Higher in Smoker |
| cg24016044 | 5 | 173315549 | Higher in Smoker |
| cg23173307 | 4 | 786244 | Lower in Smoker |
| cg15622912 | 5 | 175225021 | Higher in Smoker |
| cg22988198 | 5 | 175305793 | Lower in Smoker |
| cg21013983 | 18 | 56987316 | Lower in Smoker |
| cg05209514 | 12 | 69353500 | Lower in Smoker |
| cg09100343 | 16 | 57147202 | Higher in Smoker |
| cg07999887 | 8 | 87526955 | Higher in Smoker |
| cg10459017 | 6 | 36737623 | Higher in Smoker |
| cg20626099 | 6 | 36807759 | Higher in Smoker |
| cg22082462 | 14 | 24540415 | Lower in Smoker |
| cg07690018 | 16 | 89642492 | Higher in Smoker |
| cg07551879 | 3 | 9745426 | Lower in Smoker |
| cg27318087 | 16 | 12896895 | Lower in Smoker |

| | | | |
|---|---|---|---|
| cg22996009 | 2 | 211457684 | Lower in Smoker |
| cg10257671 | 14 | 92629962 | Lower in Smoker |
| cg20071523 | 14 | 92587725 | Lower in Smoker |
| cg12046908 | 1 | 1258554 | Lower in Smoker |
| cg17709975 | 1 | 1248492 | Lower in Smoker |
| cg04926200 | 1 | 1254228 | Lower in Smoker |
| cg22397910 | 1 | 1259947 | Lower in Smoker |
| cg15145985 | 7 | 99051547 | Higher in Smoker |
| cg20629021 | 11 | 68580041 | Lower in Smoker |
| cg17641876 | 22 | 51017723 | Higher in Smoker |
| cg23448584 | 20 | 2781316 | Higher in Smoker |
| cg19373649 | 1 | 207817630 | Lower in Smoker |
| cg07573078 | 1 | 207626214 | Lower in Smoker |
| cg17165580 | 1 | 156676581 | Higher in Smoker |
| cg24251193 | 1 | 156676542 | Higher in Smoker |
| cg03861966 | 12 | 94136602 | Higher in Smoker |
| cg05059922 | 12 | 94244496 | Lower in Smoker |
| cg09220393 | 16 | 1703475 | Lower in Smoker |
| cg01258789 | 1 | 197237257 | Lower in Smoker |
| cg15919561 | 9 | 126129601 | Lower in Smoker |
| cg14782015 | 19 | 6464080 | Lower in Smoker |
| cg25637722 | 19 | 6464082 | Lower in Smoker |
| cg08253463 | 7 | 65579941 | Higher in Smoker |
| cg03352287 | 1 | 152488262 | Higher in Smoker |
| cg11750883 | 1 | 152486950 | Lower in Smoker |
| cg00711711 | 7 | 137687007 | Higher in Smoker |
| cg11831043 | 7 | 28449847 | Higher in Smoker |
| cg22396147 | 7 | 28450253 | Lower in Smoker |
| cg13545897 | 7 | 28450946 | Higher in Smoker |
| cg09832443 | 7 | 28612680 | Lower in Smoker |
| cg21840806 | 7 | 28772097 | Lower in Smoker |
| cg05151055 | 16 | 3777746 | Lower in Smoker |
| cg02578162 | 16 | 3927429 | Lower in Smoker |
| cg09269891 | 16 | 3843415 | Lower in Smoker |
| cg04979551 | 16 | 3784851 | Lower in Smoker |

| | | | |
|---|---|---|---|
| cg10203440 | 16 | 3776234 | Lower in Smoker |
| cg03761291 | 16 | 3868188 | Lower in Smoker |
| cg21637097 | 12 | 12764798 | Higher in Smoker |
| cg26037660 | 12 | 12796114 | Lower in Smoker |
| cg01510813 | 1 | 167523533 | Higher in Smoker |
| cg15612186 | 1 | 167523069 | Higher in Smoker |
| cg17824787 | 3 | 9979297 | Lower in Smoker |
| cg07778819 | 17 | 43862927 | Higher in Smoker |
| cg26656751 | 17 | 43910226 | Lower in Smoker |
| cg00068038 | 2 | 36688564 | Higher in Smoker |
| cg13138680 | 2 | 36689815 | Lower in Smoker |
| cg19145710 | 2 | 36756130 | Lower in Smoker |
| cg08182193 | 14 | 105942243 | Lower in Smoker |
| cg04704487 | 16 | 84876665 | Lower in Smoker |
| cg27088449 | 22 | 21272634 | Lower in Smoker |
| cg15136870 | 19 | 18717036 | Higher in Smoker |
| cg10617994 | 19 | 18716527 | Higher in Smoker |
| cg00166343 | 17 | 29150100 | Higher in Smoker |
| cg10616337 | 20 | 5986410 | Higher in Smoker |
| cg08376824 | 20 | 5987738 | Lower in Smoker |
| cg06932483 | 1 | 17292908 | Lower in Smoker |
| cg03785652 | 10 | 99786488 | Lower in Smoker |
| cg21473814 | 19 | 18873268 | Lower in Smoker |
| cg24085885 | 19 | 18879446 | Lower in Smoker |
| cg26260819 | 11 | 45869049 | Higher in Smoker |
| cg07326765 | 11 | 45866449 | Lower in Smoker |
| cg08668043 | 17 | 27581493 | Higher in Smoker |
| cg26577201 | 2 | 219857793 | Higher in Smoker |
| cg17182184 | 22 | 27014006 | Higher in Smoker |
| cg23035923 | 22 | 25615557 | Lower in Smoker |
| cg15349341 | 22 | 25595697 | Lower in Smoker |
| cg01358513 | 22 | 25595705 | Lower in Smoker |
| cg07068768 | 22 | 25595840 | Lower in Smoker |
| cg11942086 | 2 | 209012188 | Lower in Smoker |
| cg21035142 | 7 | 151136940 | Higher in Smoker |

| | | | |
|---|---|---|---|
| cg23666844 | 7 | 151137882 | Lower in Smoker |
| cg02402946 | 13 | 21035079 | Higher in Smoker |
| cg24572153 | 13 | 21047387 | Lower in Smoker |
| cg09282869 | 16 | 21289947 | Higher in Smoker |
| cg03114558 | 16 | 21289539 | Higher in Smoker |
| cg24580724 | 1 | 75180368 | Lower in Smoker |
| cg02709834 | 1 | 75198841 | Higher in Smoker |
| cg16268734 | 12 | 56690194 | Lower in Smoker |
| cg05242244 | 12 | 53553086 | Lower in Smoker |
| cg08980382 | 16 | 31580153 | Lower in Smoker |
| cg10243266 | 16 | 31579647 | Lower in Smoker |
| cg19374089 | 22 | 41970954 | Lower in Smoker |
| cg21250100 | 22 | 41956987 | Lower in Smoker |
| cg11095122 | 8 | 19540734 | Lower in Smoker |
| cg11303988 | 8 | 19266685 | Higher in Smoker |
| cg18741439 | 8 | 19310134 | Lower in Smoker |
| cg22619018 | 8 | 4852624 | Higher in Smoker |
| cg16593910 | 1 | 34098842 | Higher in Smoker |
| cg00087420 | 1 | 34090941 | Lower in Smoker |
| cg20314038 | 1 | 34629098 | Lower in Smoker |
| cg00171942 | 1 | 34088611 | Lower in Smoker |
| cg12164248 | 8 | 114445955 | Higher in Smoker |
| cg13334883 | 8 | 114447532 | Higher in Smoker |
| cg03334130 | 8 | 114447161 | Higher in Smoker |
| cg02292450 | 8 | 114389388 | Lower in Smoker |
| cg09096363 | 4 | 70796842 | Lower in Smoker |
| cg10343391 | 13 | 37679978 | Lower in Smoker |
| cg01668363 | 13 | 37679573 | Lower in Smoker |
| cg04428071 | 17 | 80225377 | Lower in Smoker |
| cg10929024 | 22 | 38713608 | Higher in Smoker |
| cg09197891 | 22 | 38713447 | Lower in Smoker |
| cg03228516 | 22 | 38710725 | Lower in Smoker |
| cg10898923 | 19 | 1940875 | Higher in Smoker |
| cg01335597 | 19 | 1944192 | Lower in Smoker |
| cg03694243 | 19 | 1978914 | Lower in Smoker |

| | | | |
|---|---|---|---|
| cg08184586 | 19 | 1940417 | Lower in Smoker |
| cg15508020 | 16 | 58232206 | Higher in Smoker |
| cg23893942 | 15 | 75980285 | Lower in Smoker |
| cg05208483 | 15 | 75975041 | Lower in Smoker |
| cg13532473 | 3 | 47620536 | Higher in Smoker |
| cg26114804 | 3 | 47616147 | Lower in Smoker |
| cg26572856 | 8 | 67976465 | Higher in Smoker |
| cg22433775 | 8 | 67976671 | Lower in Smoker |
| cg21320567 | 8 | 67975880 | Higher in Smoker |
| cg26035625 | 3 | 39195358 | Higher in Smoker |
| cg27172337 | 12 | 51477527 | Higher in Smoker |
| cg24993990 | 2 | 166428802 | Lower in Smoker |
| cg13561226 | 1 | 201476960 | Lower in Smoker |
| cg21777364 | 20 | 23807778 | Lower in Smoker |
| cg25965576 | 20 | 23670089 | Lower in Smoker |
| cg15249629 | 21 | 45196311 | Higher in Smoker |
| cg23597562 | 20 | 54976805 | Lower in Smoker |
| cg07998499 | X | 134847042 | Lower in Smoker |
| cg18976418 | 14 | 39735496 | Higher in Smoker |
| cg03092548 | 14 | 39736835 | Higher in Smoker |
| cg07944469 | 14 | 39736721 | Higher in Smoker |
| cg24726668 | 14 | 39736238 | Lower in Smoker |
| cg26125503 | 14 | 39792755 | Lower in Smoker |
| cg03867037 | 4 | 1234817 | Lower in Smoker |
| cg00917642 | 4 | 1208960 | Lower in Smoker |
| cg25965774 | 10 | 126841033 | Higher in Smoker |
| cg04764907 | 10 | 126842580 | Lower in Smoker |
| cg10491546 | 10 | 126752908 | Lower in Smoker |
| cg07752194 | 10 | 126686658 | Higher in Smoker |
| cg16692196 | 1 | 85040371 | Higher in Smoker |
| cg06070054 | 18 | 77475255 | Lower in Smoker |
| cg13909076 | 18 | 77468488 | Lower in Smoker |
| cg03609787 | 15 | 44719012 | Higher in Smoker |
| cg23690355 | 15 | 44719213 | Higher in Smoker |
| cg27312049 | 16 | 30910121 | Lower in Smoker |

| | | | |
|---|---|---|---|
| cg00261932 | 6 | 132270033 | Lower in Smoker |
| cg07874153 | 5 | 138089656 | Higher in Smoker |
| cg01146063 | 2 | 80549973 | Higher in Smoker |
| cg22350070 | 2 | 79738639 | Higher in Smoker |
| cg04048705 | 2 | 80534883 | Lower in Smoker |
| cg18690705 | 2 | 80547658 | Lower in Smoker |
| cg22980483 | 2 | 80023725 | Lower in Smoker |
| cg13753435 | 2 | 80527011 | Lower in Smoker |
| cg19707040 | 2 | 79740185 | Higher in Smoker |
| cg00132141 | 10 | 69456307 | Lower in Smoker |
| cg14452121 | 9 | 111776163 | Higher in Smoker |
| cg18276810 | 3 | 41239573 | Lower in Smoker |
| cg08127629 | 20 | 36322390 | Higher in Smoker |
| cg06554120 | 5 | 11385067 | Higher in Smoker |
| cg19576843 | 5 | 11385893 | Lower in Smoker |
| cg06830983 | 17 | 3564998 | Lower in Smoker |
| cg05719052 | 17 | 3561497 | Lower in Smoker |
| cg05705964 | 1 | 41453012 | Lower in Smoker |
| cg17045772 | 1 | 41444651 | Lower in Smoker |
| cg00328724 | 1 | 41444812 | Lower in Smoker |
| cg19092368 | 1 | 41444829 | Lower in Smoker |
| cg09801607 | 1 | 41444796 | Lower in Smoker |
| cg07356130 | 11 | 10772521 | Higher in Smoker |
| cg15657206 | 11 | 10772781 | Higher in Smoker |
| cg16863382 | 16 | 75252695 | Lower in Smoker |
| cg06389950 | 16 | 75240536 | Lower in Smoker |
| cg07277962 | 8 | 11701719 | Lower in Smoker |
| cg01936565 | 11 | 1785618 | Lower in Smoker |
| cg20059407 | 15 | 79234318 | Lower in Smoker |
| cg01930204 | 9 | 90387678 | Lower in Smoker |
| cg07464217 | 20 | 57583263 | Lower in Smoker |
| cg13096351 | 11 | 70282432 | Lower in Smoker |
| cg12127706 | 11 | 70261959 | Lower in Smoker |
| cg08076147 | 7 | 117513825 | Higher in Smoker |
| cg06643622 | 7 | 117437223 | Lower in Smoker |

| | | | |
|---|---|---|---|
| cg15626307 | 1 | 112938553 | Higher in Smoker |
| cg07157169 | 5 | 126984994 | Lower in Smoker |
| cg23309843 | 5 | 126987825 | Lower in Smoker |
| cg11298524 | 10 | 17118624 | Lower in Smoker |
| cg17779676 | 17 | 55982124 | Lower in Smoker |
| cg05230392 | 17 | 55976522 | Lower in Smoker |
| cg26033879 | 10 | 104192437 | Higher in Smoker |
| cg12477931 | 10 | 104193363 | Lower in Smoker |
| cg14232165 | 11 | 47571658 | Lower in Smoker |
| cg14099685 | 11 | 47546068 | Lower in Smoker |
| cg08698796 | 11 | 47561199 | Lower in Smoker |
| cg19368016 | 10 | 11187764 | Higher in Smoker |
| cg19191555 | 10 | 11167635 | Lower in Smoker |
| cg03789645 | 7 | 148394842 | Higher in Smoker |
| cg03010756 | 7 | 148480080 | Higher in Smoker |
| cg19709083 | 7 | 148497970 | Lower in Smoker |
| cg11229715 | 2 | 225441832 | Higher in Smoker |
| cg07226679 | 2 | 225450636 | Higher in Smoker |
| cg19305527 | 2 | 225434838 | Lower in Smoker |
| cg14151426 | 13 | 113864409 | Higher in Smoker |
| cg14528881 | 13 | 113864354 | Higher in Smoker |
| cg25698940 | X | 119695102 | Higher in Smoker |
| cg22131825 | 6 | 43021414 | Lower in Smoker |
| cg05413918 | 6 | 33387188 | Lower in Smoker |
| cg02652579 | 6 | 33386967 | Lower in Smoker |
| cg02611466 | 7 | 101901707 | Lower in Smoker |
| cg13393612 | 7 | 101560291 | Higher in Smoker |
| cg15600935 | 7 | 101556684 | Higher in Smoker |
| cg00387107 | 7 | 101845057 | Lower in Smoker |
| cg25355904 | 7 | 101517935 | Lower in Smoker |
| cg06404238 | 7 | 101586820 | Lower in Smoker |
| cg09437692 | 7 | 101842731 | Lower in Smoker |
| cg09951433 | 7 | 101843287 | Lower in Smoker |
| cg09712195 | 7 | 101590206 | Lower in Smoker |
| cg15673616 | 7 | 101870851 | Lower in Smoker |

| | | | |
|---|---|---|---|
| cg05005422 | 7 | 101650989 | Lower in Smoker |
| cg24257168 | 7 | 101559134 | Lower in Smoker |
| cg06866237 | 7 | 101846993 | Lower in Smoker |
| cg23602489 | 7 | 101508949 | Lower in Smoker |
| cg05577293 | 7 | 101848689 | Lower in Smoker |
| cg21291321 | 7 | 101566940 | Lower in Smoker |
| cg23686983 | 7 | 101880640 | Lower in Smoker |
| cg14466759 | 7 | 101518899 | Lower in Smoker |
| cg05469826 | 7 | 101844947 | Lower in Smoker |
| cg16241421 | 12 | 111473641 | Higher in Smoker |
| cg16721194 | 12 | 111537057 | Higher in Smoker |
| cg17420983 | 12 | 111471202 | Higher in Smoker |
| cg07366670 | 12 | 111619077 | Lower in Smoker |
| cg12301744 | 11 | 107328559 | Higher in Smoker |
| cg17008286 | 5 | 134906484 | Lower in Smoker |
| cg05205953 | 4 | 74965154 | Higher in Smoker |
| cg08017326 | 4 | 74965162 | Higher in Smoker |
| cg24774306 | 4 | 74702713 | Higher in Smoker |
| cg10819992 | 2 | 219001517 | Lower in Smoker |
| cg02937802 | 2 | 218999173 | Lower in Smoker |
| cg12311057 | 2 | 136875897 | Higher in Smoker |
| cg25982140 | 2 | 136875681 | Higher in Smoker |
| cg24342283 | 11 | 118758603 | Lower in Smoker |
| cg00594866 | 2 | 237478577 | Lower in Smoker |
| cg16776114 | X | 40507041 | Higher in Smoker |
| cg15322570 | X | 40506804 | Higher in Smoker |
| cg20112962 | X | 106449726 | Higher in Smoker |
| cg20649285 | X | 134302207 | Lower in Smoker |
| cg08147391 | X | 118699975 | Lower in Smoker |
| cg19887750 | 18 | 47813174 | Lower in Smoker |
| cg26807935 | 5 | 139028606 | Higher in Smoker |
| cg27018502 | 17 | 61516369 | Lower in Smoker |
| cg18275051 | 1 | 202937114 | Higher in Smoker |
| cg06876708 | 1 | 202936586 | Higher in Smoker |
| cg00859655 | 11 | 7694524 | Lower in Smoker |

| | | | |
|---|---|---|---|
| cg16400025 | 22 | 43045209 | Higher in Smoker |
| cg14284759 | 22 | 43037849 | Lower in Smoker |
| cg20619563 | 6 | 84621458 | Lower in Smoker |
| cg10527784 | 1 | 54665283 | Higher in Smoker |
| cg26537639 | 16 | 88717374 | Higher in Smoker |
| cg14363636 | 11 | 61129374 | Higher in Smoker |
| cg03576425 | 8 | 145151285 | Lower in Smoker |
| cg03441544 | 15 | 22991065 | Lower in Smoker |
| cg25996001 | 15 | 23003087 | Lower in Smoker |
| cg10171802 | 5 | 156693063 | Higher in Smoker |
| cg06645946 | 5 | 156693074 | Higher in Smoker |
| cg17746119 | 17 | 74533853 | Higher in Smoker |
| cg03678039 | 17 | 74525066 | Lower in Smoker |
| cg02108130 | 8 | 145637727 | Higher in Smoker |
| cg03630056 | 15 | 74645873 | Lower in Smoker |
| cg14349956 | 15 | 74637483 | Lower in Smoker |
| cg20073007 | 8 | 143958385 | Lower in Smoker |
| cg02226239 | 8 | 143999155 | Lower in Smoker |
| cg00136400 | 8 | 144000430 | Lower in Smoker |
| cg27051335 | 15 | 75019733 | Lower in Smoker |
| cg01359532 | 15 | 75045126 | Lower in Smoker |
| cg14577373 | 2 | 204102500 | Lower in Smoker |
| cg15583012 | 2 | 204103676 | Higher in Smoker |
| cg02712555 | 20 | 52790733 | Higher in Smoker |
| cg11310684 | 10 | 94832631 | Higher in Smoker |
| cg22979783 | 2 | 72371261 | Higher in Smoker |
| cg09984469 | 2 | 72372162 | Higher in Smoker |
| cg00790395 | 10 | 94822172 | Higher in Smoker |
| cg09233204 | 10 | 94819559 | Lower in Smoker |
| cg20322977 | 10 | 94821085 | Lower in Smoker |
| cg03460682 | 2 | 219646316 | Higher in Smoker |
| cg20601919 | 2 | 219646831 | Higher in Smoker |
| cg04176888 | 19 | 41596066 | Lower in Smoker |
| cg09508736 | 19 | 41385865 | Lower in Smoker |
| cg07641578 | 22 | 42537241 | Lower in Smoker |

| | | | |
|---|---|---|---|
| cg25054154 | 4 | 108852144 | Higher in Smoker |
| cg21363128 | 4 | 108852555 | Higher in Smoker |
| cg04353264 | 7 | 99355204 | Lower in Smoker |
| cg15923534 | 14 | 100150608 | Higher in Smoker |
| cg06633543 | 14 | 100151561 | Higher in Smoker |
| cg08670281 | 19 | 16023350 | Higher in Smoker |
| cg23232844 | 4 | 187111853 | Higher in Smoker |
| cg11969330 | 4 | 187125413 | Higher in Smoker |
| cg10387890 | 1 | 47489543 | Higher in Smoker |
| cg16689634 | 1 | 47489539 | Higher in Smoker |
| cg11421459 | 7 | 91763989 | Higher in Smoker |
| cg24990212 | 8 | 65710790 | Higher in Smoker |
| cg09430445 | 3 | 42918546 | Lower in Smoker |
| cg20365867 | 3 | 42917340 | Lower in Smoker |
| cg10091155 | X | 77584550 | Lower in Smoker |
| cg02977955 | 17 | 76760976 | Lower in Smoker |
| cg14134128 | 17 | 76774832 | Lower in Smoker |
| cg12871285 | 17 | 76713379 | Lower in Smoker |
| cg01532436 | 19 | 48983942 | Higher in Smoker |
| cg02590401 | 19 | 48984071 | Higher in Smoker |
| cg24452181 | 19 | 48984318 | Higher in Smoker |
| cg00512872 | 7 | 6268584 | Higher in Smoker |
| cg20492034 | 7 | 6313058 | Lower in Smoker |
| cg17832858 | 7 | 6210667 | Lower in Smoker |
| cg23723359 | 7 | 6290148 | Lower in Smoker |
| cg07945148 | 22 | 24666632 | Higher in Smoker |
| cg24566615 | 17 | 19989115 | Lower in Smoker |
| cg07103201 | 17 | 20171047 | Lower in Smoker |
| cg21039874 | 21 | 27945708 | Higher in Smoker |
| cg12235062 | 4 | 4386906 | Higher in Smoker |
| cg13432708 | 4 | 4383505 | Higher in Smoker |
| cg16321116 | 14 | 59655311 | Lower in Smoker |
| cg02265239 | 14 | 59746448 | Lower in Smoker |
| cg14436871 | 6 | 39759955 | Higher in Smoker |
| cg01985396 | 6 | 39760833 | Higher in Smoker |

| | | | |
|---|---|---|---|
| cg02774129 | 1 | 58712062 | Lower in Smoker |
| cg18264728 | 5 | 39421189 | Higher in Smoker |
| cg14136214 | 9 | 124545901 | Lower in Smoker |
| cg14582957 | 9 | 124517757 | Lower in Smoker |
| cg17571554 | X | 85403296 | Higher in Smoker |
| cg10656687 | 6 | 168707831 | Lower in Smoker |
| cg03439990 | 19 | 47164505 | Higher in Smoker |
| cg15602972 | 19 | 47151481 | Lower in Smoker |
| cg17862667 | 19 | 47163739 | Lower in Smoker |
| cg20620180 | 12 | 25072248 | Lower in Smoker |
| cg25362648 | 12 | 109273780 | Lower in Smoker |
| cg16362140 | 5 | 10708717 | Higher in Smoker |
| cg16002248 | 1 | 155699008 | Higher in Smoker |
| cg14250336 | 9 | 90195885 | Lower in Smoker |
| cg26924890 | 19 | 3971211 | Higher in Smoker |
| cg18226382 | 19 | 3964369 | Lower in Smoker |
| cg08103568 | 4 | 100737138 | Lower in Smoker |
| cg18110444 | 2 | 136743460 | Higher in Smoker |
| cg24513883 | 6 | 33290607 | Higher in Smoker |
| cg20672430 | 6 | 33287248 | Higher in Smoker |
| cg20849032 | 6 | 33289243 | Lower in Smoker |
| cg20818407 | 6 | 33289196 | Lower in Smoker |
| cg20552903 | 6 | 33289678 | Lower in Smoker |
| cg10285420 | 6 | 33289719 | Lower in Smoker |
| cg05431670 | 6 | 33290873 | Lower in Smoker |
| cg07607074 | 6 | 33289544 | Lower in Smoker |
| cg07811113 | 19 | 1408140 | Higher in Smoker |
| cg23311195 | 19 | 1434935 | Lower in Smoker |
| cg11288801 | 19 | 1406661 | Lower in Smoker |
| cg16467775 | 16 | 90085110 | Higher in Smoker |
| cg10076951 | 16 | 90072776 | Lower in Smoker |
| cg25096456 | 3 | 137893564 | Higher in Smoker |
| cg26309261 | 3 | 137880405 | Lower in Smoker |
| cg26188061 | 1 | 100681102 | Lower in Smoker |
| cg22737282 | 11 | 20183008 | Higher in Smoker |

| | | | |
|---|---|---|---|
| cg15985775 | 11 | 20183267 | Higher in Smoker |
| cg14777561 | 11 | 20180336 | Higher in Smoker |
| cg18242712 | 11 | 20182324 | Higher in Smoker |
| cg13754859 | 14 | 24584296 | Higher in Smoker |
| cg13950250 | 8 | 104430401 | Lower in Smoker |
| cg01870903 | 8 | 104427655 | Higher in Smoker |
| cg26650007 | 19 | 14065157 | Lower in Smoker |
| cg13089154 | 14 | 73392648 | Higher in Smoker |
| cg19948037 | 14 | 73392801 | Higher in Smoker |
| cg14331882 | 14 | 73393894 | Higher in Smoker |
| cg13198844 | 14 | 73392933 | Higher in Smoker |
| cg16042943 | 14 | 69574378 | Higher in Smoker |
| cg27661869 | 17 | 61627703 | Higher in Smoker |
| cg01429181 | 1 | 160231585 | Higher in Smoker |
| cg03915298 | 1 | 160231971 | Lower in Smoker |
| cg23516342 | X | 27764690 | Lower in Smoker |
| cg18827893 | X | 27765005 | Lower in Smoker |
| cg02853375 | 17 | 43129916 | Higher in Smoker |
| cg01839464 | 18 | 49868477 | Higher in Smoker |
| cg14222939 | 18 | 49866097 | Higher in Smoker |
| cg05416337 | 18 | 49865270 | Lower in Smoker |
| cg00868860 | 12 | 55041948 | Lower in Smoker |
| cg00293644 | 1 | 32674341 | Lower in Smoker |
| cg25639082 | 11 | 6655429 | Lower in Smoker |
| cg18463371 | 4 | 155334071 | Lower in Smoker |
| cg24494262 | 4 | 155339844 | Lower in Smoker |
| cg00554631 | 4 | 155340841 | Lower in Smoker |
| cg17807806 | 4 | 155257112 | Lower in Smoker |
| cg21578543 | 4 | 155312795 | Lower in Smoker |
| cg03842933 | 4 | 155244316 | Lower in Smoker |
| cg07786760 | 4 | 155412677 | Higher in Smoker |
| cg11325273 | 13 | 36642977 | Lower in Smoker |
| cg17169566 | 4 | 150999923 | Higher in Smoker |
| cg17954724 | 4 | 151177137 | Lower in Smoker |
| cg09308942 | 12 | 91573372 | Lower in Smoker |

| | | | |
|---|---|---|---|
| cg22671299 | 3 | 53380873 | Higher in Smoker |
| cg00166352 | 4 | 183836691 | Lower in Smoker |
| cg13622657 | 9 | 34620508 | Higher in Smoker |
| cg01907644 | 5 | 150138530 | Lower in Smoker |
| cg02733650 | 16 | 30441347 | Higher in Smoker |
| cg10958840 | 3 | 182686679 | Lower in Smoker |
| cg11357670 | 13 | 114143948 | Lower in Smoker |
| cg13677120 | 4 | 52709175 | Higher in Smoker |
| cg12209024 | 4 | 52710789 | Higher in Smoker |
| cg00394214 | 19 | 17420434 | Higher in Smoker |
| cg24724587 | 1 | 86044103 | Lower in Smoker |
| cg06493473 | 6 | 31696803 | Higher in Smoker |
| cg10709727 | 6 | 31698145 | Lower in Smoker |
| cg21286967 | 6 | 31696710 | Lower in Smoker |
| cg17825714 | 6 | 31695903 | Lower in Smoker |
| cg13051970 | 7 | 50628968 | Lower in Smoker |
| cg03546712 | 14 | 53619603 | Higher in Smoker |
| cg17703658 | 12 | 57914352 | Higher in Smoker |
| cg16323491 | 10 | 74032730 | Lower in Smoker |
| cg25071651 | 4 | 101112317 | Higher in Smoker |
| cg19215110 | 6 | 30850913 | Lower in Smoker |
| cg13329862 | 6 | 30850876 | Lower in Smoker |
| cg04510153 | 1 | 162660951 | Higher in Smoker |
| cg00457087 | 1 | 162602295 | Higher in Smoker |
| cg16397071 | 2 | 15731827 | Higher in Smoker |
| cg21693780 | 2 | 15731793 | Lower in Smoker |
| cg27936630 | 11 | 108535499 | Higher in Smoker |
| cg18944711 | 11 | 108535663 | Higher in Smoker |
| cg13225881 | 11 | 108777990 | Lower in Smoker |
| cg23074401 | 11 | 108535340 | Higher in Smoker |
| cg16864700 | 12 | 31226536 | Lower in Smoker |
| cg09336228 | 16 | 70380615 | Higher in Smoker |
| cg03966708 | 1 | 112302316 | Lower in Smoker |
| cg26240433 | 14 | 94547826 | Higher in Smoker |
| cg16051582 | 11 | 125778343 | Lower in Smoker |

| | | | |
|---|---|---|---|
| cg01736784 | 11 | 125774092 | Higher in Smoker |
| cg16819604 | 20 | 47836038 | Higher in Smoker |
| cg03601053 | Y | 15016101 | Lower in Smoker |
| cg22696214 | 5 | 55033753 | Lower in Smoker |
| cg02269094 | 5 | 55061610 | Lower in Smoker |
| cg19269661 | 17 | 61850865 | Higher in Smoker |
| cg12354594 | 17 | 61850856 | Lower in Smoker |
| cg05797656 | 17 | 61851352 | Higher in Smoker |
| cg01986757 | 17 | 61895456 | Lower in Smoker |
| cg27261494 | 6 | 74104097 | Lower in Smoker |
| cg07492251 | 5 | 134094363 | Higher in Smoker |
| cg16272868 | 5 | 134094170 | Higher in Smoker |
| cg00246980 | 12 | 12966231 | Higher in Smoker |
| cg09141038 | 17 | 62502266 | Higher in Smoker |
| cg06286604 | 12 | 132627456 | Lower in Smoker |
| cg09671242 | 12 | 124086660 | Higher in Smoker |
| cg16773563 | 7 | 44614475 | Lower in Smoker |
| cg20979296 | 4 | 169401717 | Higher in Smoker |
| cg04337611 | 4 | 169401687 | Higher in Smoker |
| cg20282429 | 11 | 679841 | Higher in Smoker |
| cg17005319 | 11 | 655579 | Lower in Smoker |
| cg27453301 | 16 | 451575 | Higher in Smoker |
| cg25672287 | 16 | 452092 | Lower in Smoker |
| cg22799212 | 1 | 161102325 | Higher in Smoker |
| cg25658385 | 6 | 35265341 | Lower in Smoker |
| cg00026455 | 16 | 90032736 | Lower in Smoker |
| cg05787038 | 8 | 6826392 | Lower in Smoker |
| cg20710667 | 8 | 6736922 | Lower in Smoker |
| cg23781075 | 20 | 170581 | Lower in Smoker |
| cg00545462 | 20 | 238452 | Lower in Smoker |
| cg20126775 | 6 | 49917145 | Lower in Smoker |
| cg11465442 | 8 | 11832261 | Lower in Smoker |
| cg04755365 | 14 | 100625253 | Higher in Smoker |
| cg13776158 | 9 | 126145211 | Lower in Smoker |
| cg13413792 | 9 | 126182794 | Lower in Smoker |

| | | | |
|---|---|---|---|
| cg14171944 | 9 | 126323477 | Lower in Smoker |
| cg08379738 | 19 | 6477033 | Lower in Smoker |
| cg02599912 | 19 | 6472086 | Lower in Smoker |
| cg02327894 | 19 | 6479667 | Lower in Smoker |
| cg18967180 | 7 | 140241567 | Higher in Smoker |
| cg13906069 | 1 | 115213259 | Higher in Smoker |
| cg05590442 | 1 | 115213174 | Higher in Smoker |
| cg26518580 | 1 | 111742515 | Lower in Smoker |
| cg19268695 | 1 | 111743411 | Lower in Smoker |
| cg23631538 | 1 | 111743537 | Lower in Smoker |
| cg08864105 | 1 | 111743020 | Lower in Smoker |
| cg19269039 | 1 | 111743200 | Lower in Smoker |
| cg20317872 | 1 | 111743202 | Lower in Smoker |
| cg24641737 | 1 | 111743271 | Lower in Smoker |
| cg15591513 | 8 | 142139310 | Higher in Smoker |
| cg12564151 | 8 | 142190640 | Lower in Smoker |
| cg18697026 | 8 | 142183179 | Lower in Smoker |
| cg08291539 | 15 | 66084447 | Higher in Smoker |
| cg07312954 | 1 | 153914453 | Lower in Smoker |
| cg22805813 | 12 | 123240082 | Lower in Smoker |
| cg18790814 | 12 | 123237467 | Higher in Smoker |
| cg19102575 | 22 | 32152158 | Lower in Smoker |
| cg21645572 | 8 | 120931649 | Higher in Smoker |
| cg07675337 | 11 | 33036574 | Higher in Smoker |
| cg01345517 | 12 | 16064533 | Higher in Smoker |
| cg17472736 | 12 | 16135031 | Lower in Smoker |
| cg10504436 | 22 | 24180492 | Lower in Smoker |
| cg21934588 | 1 | 10532847 | Higher in Smoker |
| cg09358618 | 1 | 3801728 | Lower in Smoker |
| cg00905725 | 1 | 3773312 | Higher in Smoker |
| cg01733570 | 7 | 24797656 | Lower in Smoker |
| cg25723149 | 7 | 24797680 | Lower in Smoker |
| cg22804000 | 7 | 24797691 | Lower in Smoker |
| cg14623754 | 9 | 117228122 | Lower in Smoker |
| cg13632058 | 9 | 117267392 | Lower in Smoker |

| | | | |
|---|---|---|---|
| cg16505237 | 8 | 145550609 | Higher in Smoker |
| cg07816271 | 22 | 19008649 | Lower in Smoker |
| cg02157633 | 22 | 19035933 | Lower in Smoker |
| cg00612502 | 22 | 19109875 | Higher in Smoker |
| cg18251360 | 22 | 20067313 | Higher in Smoker |
| cg22126047 | 22 | 19003887 | Lower in Smoker |
| cg10882179 | 22 | 19005524 | Lower in Smoker |
| cg21587469 | 12 | 56323816 | Lower in Smoker |
| cg25641269 | 3 | 185866557 | Lower in Smoker |
| cg02956372 | 4 | 967467 | Higher in Smoker |
| cg13704403 | 4 | 967460 | Higher in Smoker |
| cg24878090 | 11 | 46354005 | Higher in Smoker |
| cg15925492 | 11 | 46365893 | Lower in Smoker |
| cg07998213 | 11 | 46366813 | Lower in Smoker |
| cg18568067 | 11 | 46373641 | Higher in Smoker |
| cg18337963 | 11 | 46383209 | Higher in Smoker |
| cg02896696 | 1 | 55352717 | Higher in Smoker |
| cg08735549 | 1 | 55317306 | Lower in Smoker |
| cg03933646 | 1 | 55317098 | Lower in Smoker |
| cg17475467 | 1 | 55316769 | Lower in Smoker |
| cg05896371 | 11 | 71159218 | Higher in Smoker |
| cg21619547 | 3 | 93780328 | Lower in Smoker |
| cg18720580 | 14 | 24768914 | Higher in Smoker |
| cg26937389 | 1 | 12677975 | Higher in Smoker |
| cg10523319 | 1 | 12669600 | Lower in Smoker |
| cg13314614 | 1 | 12655992 | Lower in Smoker |
| cg04339937 | 1 | 12656114 | Lower in Smoker |
| cg07706067 | 17 | 21030370 | Higher in Smoker |
| cg00768195 | 2 | 169927922 | Lower in Smoker |
| cg08194384 | 6 | 30633353 | Lower in Smoker |
| cg15011596 | 6 | 30627459 | Lower in Smoker |
| cg04166546 | 6 | 30640826 | Higher in Smoker |
| cg04075035 | 5 | 54602880 | Higher in Smoker |
| cg14915620 | 3 | 47887956 | Lower in Smoker |
| cg08530760 | 3 | 47887839 | Lower in Smoker |

| | | | |
|---|---|---|---|
| cg04060888 | 10 | 127570400 | Lower in Smoker |
| cg14270556 | 17 | 5373138 | Lower in Smoker |
| cg07955828 | 20 | 37591298 | Higher in Smoker |
| cg22183849 | 3 | 154042356 | Higher in Smoker |
| cg15277914 | 3 | 154042611 | Lower in Smoker |
| cg24951396 | 12 | 125473687 | Higher in Smoker |
| cg11906173 | 12 | 125473388 | Lower in Smoker |
| cg10809441 | 17 | 41561461 | Lower in Smoker |
| cg04641648 | 1 | 182808313 | Higher in Smoker |
| cg13587802 | 12 | 122712381 | Lower in Smoker |
| cg17694877 | X | 95939631 | Higher in Smoker |
| cg02012821 | X | 95940519 | Higher in Smoker |
| cg02875834 | X | 95939848 | Higher in Smoker |
| cg12152167 | X | 95939864 | Higher in Smoker |
| cg01899581 | 13 | 60733965 | Lower in Smoker |
| cg23899649 | 14 | 95553486 | Lower in Smoker |
| cg11703637 | 20 | 61509768 | Lower in Smoker |
| cg03879251 | 20 | 6155700? | Higher in Smoker |
| cg07970734 | 20 | 61557028 | Higher in Smoker |
| cg04238096 | 5 | 61699834 | Higher in Smoker |
| cg25102759 | 1 | 54376557 | Lower in Smoker |
| cg20932440 | 1 | 54359778 | Lower in Smoker |
| cg00217795 | 14 | 80677688 | Higher in Smoker |
| cg01044961 | 14 | 102026525 | Higher in Smoker |
| cg07389144 | 21 | 47969887 | Lower in Smoker |
| cg05196905 | 21 | 47877665 | Lower in Smoker |
| cg05827208 | 12 | 50898684 | Higher in Smoker |
| cg12980886 | 12 | 50898622 | Higher in Smoker |
| cg10071690 | 10 | 666063 | Higher in Smoker |
| cg18503829 | 10 | 729956 | Higher in Smoker |
| cg24318365 | 10 | 392243 | Lower in Smoker |
| cg02514579 | 10 | 717091 | Lower in Smoker |
| cg13908149 | 10 | 630942 | Lower in Smoker |
| cg23502751 | 10 | 445130 | Lower in Smoker |
| cg26314512 | 10 | 629625 | Lower in Smoker |

| | | | |
|---|---|---|---|
| cg18467406 | 10 | 665510 | Lower in Smoker |
| cg11001780 | 10 | 623056 | Lower in Smoker |
| cg17333886 | 10 | 711676 | Lower in Smoker |
| cg17079987 | 10 | 557562 | Lower in Smoker |
| cg12070746 | 1 | 68516080 | Lower in Smoker |
| cg12442404 | 3 | 122512787 | Higher in Smoker |
| cg27539627 | 3 | 122513065 | Higher in Smoker |
| cg16629569 | 3 | 122513933 | Higher in Smoker |
| cg21898226 | 2 | 218231392 | Lower in Smoker |
| cg01821113 | 2 | 218277531 | Lower in Smoker |
| cg05502445 | 2 | 218332960 | Lower in Smoker |
| cg05511924 | 2 | 218418852 | Lower in Smoker |
| cg14538944 | 2 | 218340518 | Lower in Smoker |
| cg22245446 | 2 | 218316451 | Lower in Smoker |
| cg13384501 | 15 | 66584299 | Higher in Smoker |
| cg05197660 | 2 | 232824857 | Lower in Smoker |
| cg05985576 | 2 | 233001675 | Lower in Smoker |
| cg04948483 | 15 | 40650255 | Higher in Smoker |
| cg03416422 | 11 | 111807767 | Higher in Smoker |
| cg12507030 | 19 | 31640194 | Lower in Smoker |
| cg23418839 | 11 | 17375113 | Higher in Smoker |
| cg19909712 | 11 | 17374669 | Lower in Smoker |
| cg20900519 | 11 | 17379213 | Lower in Smoker |
| cg02162906 | 10 | 54073488 | Higher in Smoker |
| cg11931116 | 10 | 54074040 | Higher in Smoker |
| cg25262044 | 4 | 107958491 | Higher in Smoker |
| cg01471384 | 4 | 107957265 | Higher in Smoker |
| cg05038512 | 19 | 49866817 | Higher in Smoker |
| cg27191019 | 11 | 111895465 | Higher in Smoker |
| cg18792365 | 8 | 13132967 | Lower in Smoker |
| cg26326560 | 8 | 13349394 | Lower in Smoker |
| cg00933411 | 8 | 13373090 | Lower in Smoker |
| cg05748937 | 8 | 12991064 | Lower in Smoker |
| cg02609781 | 13 | 50656090 | Lower in Smoker |
| cg03778895 | 13 | 50699716 | Higher in Smoker |

| | | | |
|---|---|---|---|
| cg03722184 | 13 | 51353941 | Lower in Smoker |
| cg24376537 | X | 69665103 | Higher in Smoker |
| cg24776910 | 17 | 7117615 | Higher in Smoker |
| cg04153604 | 17 | 7099823 | Lower in Smoker |
| cg08860136 | 17 | 7111414 | Lower in Smoker |
| cg15029735 | 10 | 79681906 | Higher in Smoker |
| cg11063088 | 10 | 79622515 | Lower in Smoker |
| cg02664451 | 8 | 1497878 | Lower in Smoker |
| cg18803856 | 8 | 1495169 | Lower in Smoker |
| cg00672445 | 8 | 1616925 | Lower in Smoker |
| cg14887752 | 1 | 35370638 | Lower in Smoker |
| cg24626851 | 1 | 35350721 | Lower in Smoker |
| cg10113715 | 14 | 101192416 | Lower in Smoker |
| cg04815758 | 6 | 43423089 | Higher in Smoker |
| cg25565138 | 6 | 43422937 | Higher in Smoker |
| cg24236938 | 6 | 43424191 | Lower in Smoker |
| cg14497851 | 6 | 170599833 | Higher in Smoker |
| cg10918171 | 6 | 170601120 | Higher in Smoker |
| cg25627144 | 19 | 39989412 | Higher in Smoker |
| cg11680792 | 19 | 39989422 | Higher in Smoker |
| cg19183842 | 19 | 39993358 | Lower in Smoker |
| cg03807316 | 19 | 39998290 | Lower in Smoker |
| cg07873251 | 15 | 41220951 | Lower in Smoker |
| cg27084680 | 14 | 75349060 | Higher in Smoker |
| cg15941449 | 2 | 172949738 | Higher in Smoker |
| cg23288335 | 2 | 172965046 | Higher in Smoker |
| cg23763424 | 2 | 172967795 | Higher in Smoker |
| cg06864796 | 17 | 48072833 | Higher in Smoker |
| cg08756712 | 17 | 48049475 | Higher in Smoker |
| cg09359114 | 7 | 96650096 | Higher in Smoker |
| cg01448276 | 7 | 96654782 | Higher in Smoker |
| cg11997899 | 7 | 96654183 | Higher in Smoker |
| cg08835113 | 7 | 96650192 | Higher in Smoker |
| cg13344740 | 7 | 96654132 | Higher in Smoker |
| cg03121281 | 7 | 96627253 | Higher in Smoker |

| | | | |
|---|---|---|---|
| cg08711530 | X | 31282451 | Lower in Smoker |
| cg21561124 | 19 | 35994180 | Lower in Smoker |
| cg19375053 | 19 | 35991319 | Lower in Smoker |
| cg13418235 | 9 | 843748 | Higher in Smoker |
| cg13413955 | 9 | 842914 | Lower in Smoker |
| cg11530960 | 9 | 1052239 | Higher in Smoker |
| cg10005978 | 9 | 977818 | Higher in Smoker |
| cg13853186 | 9 | 975997 | Lower in Smoker |
| cg16809460 | 1 | 50885369 | Higher in Smoker |
| cg24872117 | 19 | 42356072 | Lower in Smoker |
| cg14681187 | 7 | 86784227 | Lower in Smoker |
| cg23207958 | 5 | 118406933 | Higher in Smoker |
| cg05596911 | 5 | 118502651 | Lower in Smoker |
| cg04856203 | 5 | 118407258 | Higher in Smoker |
| cg13501507 | 15 | 51915413 | Higher in Smoker |
| cg14296394 | 15 | 51910925 | Lower in Smoker |
| cg04451703 | 10 | 70231397 | Higher in Smoker |
| ch.10.1432102R | 10 | 70200132 | Higher in Smoker |
| cg26060971 | 3 | 52407402 | Higher in Smoker |
| cg15439202 | 3 | 52348951 | Higher in Smoker |
| cg03785426 | 12 | 124419970 | Lower in Smoker |
| cg14808040 | 12 | 124418532 | Lower in Smoker |
| cg03697024 | 7 | 21583438 | Higher in Smoker |
| cg16474297 | 7 | 21582745 | Higher in Smoker |
| cg01122187 | 7 | 21582758 | Higher in Smoker |
| cg08570341 | 7 | 21582749 | Higher in Smoker |
| cg16502522 | 17 | 76490379 | Higher in Smoker |
| cg00002309 | 17 | 76482353 | Higher in Smoker |
| cg11752357 | 17 | 76449599 | Higher in Smoker |
| cg18098769 | 17 | 76471562 | Lower in Smoker |
| cg26524256 | 17 | 7696167 | Lower in Smoker |
| cg18105529 | 17 | 7643190 | Lower in Smoker |
| cg02385411 | 17 | 7674264 | Lower in Smoker |
| cg06654079 | 16 | 21169179 | Lower in Smoker |
| cg20380465 | 5 | 13919497 | Lower in Smoker |

| | | | |
|---|---|---|---|
| cg05004705 | 5 | 13807296 | Lower in Smoker |
| cg04547220 | 2 | 84743558 | Higher in Smoker |
| cg23963153 | 2 | 196933266 | Higher in Smoker |
| cg07213065 | 2 | 196642873 | Lower in Smoker |
| cg24647724 | 17 | 11502254 | Higher in Smoker |
| cg11849461 | 17 | 11547756 | Higher in Smoker |
| cg13548543 | 9 | 34460044 | Higher in Smoker |
| cg06006130 | 16 | 47007832 | Lower in Smoker |
| cg05878098 | 16 | 47003209 | Lower in Smoker |
| cg06344270 | 16 | 4475679 | Higher in Smoker |
| cg01083584 | 19 | 14629193 | Higher in Smoker |
| cg20906767 | 3 | 186303239 | Lower in Smoker |
| cg15670924 | 11 | 73669256 | Higher in Smoker |
| cg25507226 | 7 | 157190734 | Higher in Smoker |
| cg13515783 | 7 | 157201622 | Lower in Smoker |
| cg27496299 | 7 | 157171202 | Lower in Smoker |
| cg08620789 | 7 | 157129638 | Lower in Smoker |
| cg15831653 | 10 | 22292874 | Higher in Smoker |
| cg19603966 | 10 | 22292833 | Higher in Smoker |
| cg07029854 | 10 | 69571138 | Lower in Smoker |
| cg26837766 | 15 | 41078599 | Lower in Smoker |
| cg18739392 | 5 | 138756226 | Lower in Smoker |
| cg26115449 | 3 | 180707572 | Higher in Smoker |
| cg13720278 | 3 | 180702012 | Lower in Smoker |
| cg01783706 | 12 | 49739991 | Higher in Smoker |
| cg22174355 | 9 | 114413582 | Lower in Smoker |
| cg13810332 | 9 | 114421433 | Lower in Smoker |
| cg21310499 | 21 | 34863825 | Higher in Smoker |
| cg04134859 | 7 | 73097692 | Higher in Smoker |
| cg04942564 | 20 | 62562232 | Lower in Smoker |
| cg14437606 | 8 | 66932975 | Lower in Smoker |
| cg14928319 | 8 | 67012327 | Lower in Smoker |
| cg07197831 | 2 | 27503157 | Lower in Smoker |
| cg26304237 | 1 | 65730384 | Higher in Smoker |
| cg08856601 | 1 | 65730351 | Higher in Smoker |

| | | | |
|---|---|---|---|
| cg23258152 | 1 | 65743415 | Lower in Smoker |
| cg21168982 | 1 | 28559030 | Higher in Smoker |
| cg17584296 | 10 | 75007026 | Higher in Smoker |
| cg08156120 | 14 | 74111075 | Lower in Smoker |
| cg17515744 | 22 | 39190301 | Higher in Smoker |
| cg05628436 | 22 | 39186607 | Lower in Smoker |
| cg20772512 | 1 | 38022359 | Lower in Smoker |
| cg16405946 | X | 153640960 | Lower in Smoker |
| cg06235653 | 16 | 2287161 | Lower in Smoker |
| cg10235741 | 3 | 58200326 | Lower in Smoker |
| cg16902156 | 1 | 94864089 | Lower in Smoker |
| cg04774103 | 2 | 230517179 | Lower in Smoker |
| cg08858201 | 9 | 131012953 | Higher in Smoker |
| cg11572381 | 19 | 10827337 | Lower in Smoker |
| cg04740198 | 19 | 10828629 | Higher in Smoker |
| cg20300956 | 1 | 171811477 | Higher in Smoker |
| cg16423650 | 10 | 101769971 | Higher in Smoker |
| cg14405603 | 10 | 101768701 | Lower in Smoker |
| cg18522740 | 10 | 101768580 | Lower in Smoker |
| cg02746110 | 2 | 25552398 | Lower in Smoker |
| cg17475857 | 20 | 31366466 | Lower in Smoker |
| cg24403338 | 20 | 31366437 | Lower in Smoker |
| cg00300969 | 20 | 31366486 | Lower in Smoker |
| cg27482168 | 2 | 220253963 | Lower in Smoker |
| cg23633626 | 1 | 94344791 | Higher in Smoker |
| cg16833230 | 1 | 94344337 | Higher in Smoker |
| cg05608777 | 10 | 128594144 | Higher in Smoker |
| cg18932726 | 10 | 128594141 | Higher in Smoker |
| cg17547524 | X | 117629324 | Lower in Smoker |
| cg25959131 | 3 | 50855436 | Lower in Smoker |
| cg07635854 | 19 | 11374482 | Lower in Smoker |
| cg11595059 | 19 | 11314087 | Lower in Smoker |
| cg21409833 | 1 | 63062724 | Lower in Smoker |
| cg02218214 | 1 | 63062489 | Lower in Smoker |
| cg03953257 | 13 | 99738468 | Higher in Smoker |

| | | | |
|---|---|---|---|
| cg13690241 | 2 | 74784248 | Lower in Smoker |
| cg08288130 | 3 | 21771540 | Higher in Smoker |
| cg21031128 | 3 | 21771278 | Higher in Smoker |
| cg09314421 | 3 | 21771252 | Higher in Smoker |
| cg13292636 | 3 | 21771258 | Higher in Smoker |
| cg16476235 | 3 | 21771668 | Higher in Smoker |
| cg03732056 | 3 | 21771059 | Higher in Smoker |
| cg03089940 | 3 | 21767146 | Lower in Smoker |
| cg17200320 | 5 | 176931422 | Lower in Smoker |
| cg01540102 | 16 | 57506038 | Lower in Smoker |
| cg08557393 | 16 | 57521521 | Lower in Smoker |
| cg12799689 | 18 | 67067893 | Higher in Smoker |
| cg27708897 | 18 | 67136810 | Lower in Smoker |
| cg06943431 | 4 | 3475041 | Lower in Smoker |
| cg15307169 | 4 | 3465064 | Higher in Smoker |
| cg05455825 | 6 | 31939840 | Lower in Smoker |
| cg13709054 | 6 | 31940004 | Lower in Smoker |
| cg02181369 | 6 | 83877953 | Lower in Smoker |
| cg12787836 | 21 | 37536685 | Lower in Smoker |
| cg02776867 | 19 | 2210438 | Lower in Smoker |
| cg13643356 | 19 | 2202660 | Lower in Smoker |
| cg13978352 | 6 | 30903706 | Lower in Smoker |
| cg08984500 | 16 | 89692422 | Lower in Smoker |
| cg02893490 | 16 | 68014110 | Lower in Smoker |
| cg03698539 | 16 | 68012273 | Lower in Smoker |
| cg13917712 | 19 | 38714681 | Higher in Smoker |
| cg06942742 | 19 | 38713242 | Lower in Smoker |
| cg15072680 | 19 | 38713292 | Lower in Smoker |
| cg20526548 | 17 | 1941774 | Lower in Smoker |
| cg21433329 | 20 | 49574938 | Lower in Smoker |
| cg14586500 | 9 | 130697656 | Lower in Smoker |
| cg01205831 | 9 | 130699236 | Lower in Smoker |
| cg15487600 | 1 | 155113158 | Higher in Smoker |
| cg23260456 | 2 | 116474615 | Lower in Smoker |
| cg06434874 | 11 | 66243366 | Lower in Smoker |

| | | | |
|---|---|---|---|
| cg18892517 | 2 | 162930244 | Higher in Smoker |
| cg10160539 | 2 | 162875880 | Lower in Smoker |
| cg20539283 | 2 | 162932048 | Lower in Smoker |
| cg08318371 | 2 | 162881135 | Lower in Smoker |
| cg25912827 | 2 | 162930805 | Higher in Smoker |
| cg10507402 | 2 | 162930666 | Higher in Smoker |
| cg05751344 | 7 | 153641267 | Higher in Smoker |
| cg18940047 | 7 | 153749736 | Higher in Smoker |
| cg27520905 | 7 | 153999655 | Lower in Smoker |
| cg27411746 | 7 | 154454882 | Lower in Smoker |
| cg00252418 | 7 | 154540325 | Lower in Smoker |
| cg18202577 | 15 | 65809771 | Higher in Smoker |
| cg08484839 | 15 | 65810117 | Lower in Smoker |
| cg13513411 | 19 | 4676202 | Lower in Smoker |
| cg22561727 | 19 | 4719848 | Lower in Smoker |
| cg11437223 | 7 | 35078097 | Higher in Smoker |
| cg18347153 | 7 | 89747970 | Higher in Smoker |
| cg16015966 | 19 | 32896872 | Higher in Smoker |
| cg16792347 | 8 | 95802202 | Lower in Smoker |
| cg24155937 | 1 | 97833212 | Lower in Smoker |
| cg16320208 | 1 | 98036695 | Lower in Smoker |
| cg18645035 | 1 | 97559808 | Lower in Smoker |
| cg14072140 | 1 | 98031839 | Lower in Smoker |
| cg18269457 | 1 | 98383686 | Lower in Smoker |
| cg07142723 | 8 | 105431269 | Lower in Smoker |
| cg22544144 | 8 | 26435318 | Higher in Smoker |
| cg03245229 | 8 | 26436527 | Higher in Smoker |
| cg02399645 | 5 | 146833937 | Higher in Smoker |
| cg02099233 | 5 | 146832387 | Higher in Smoker |
| cg00106565 | 5 | 146784171 | Lower in Smoker |
| cg20564764 | 5 | 146833171 | Higher in Smoker |
| cg02034222 | 2 | 74753281 | Lower in Smoker |
| cg08675262 | 5 | 174871399 | Higher in Smoker |
| cg00698685 | 5 | 174871341 | Higher in Smoker |
| cg09133032 | 11 | 640094 | Lower in Smoker |

| | | | |
|---|---|---|---|
| cg21279601 | 4 | 9782931 | Higher in Smoker |
| cg25545182 | 22 | 31795303 | Higher in Smoker |
| cg17227358 | 10 | 50599882 | Lower in Smoker |
| cg15538809 | 18 | 28658043 | Lower in Smoker |
| cg27648075 | 18 | 28622876 | Higher in Smoker |
| cg01078582 | 21 | 42212601 | Lower in Smoker |
| cg09880551 | 21 | 42218932 | Higher in Smoker |
| cg18585693 | 11 | 117668161 | Higher in Smoker |
| cg19703610 | 11 | 117667737 | Higher in Smoker |
| cg25816610 | 21 | 39494547 | Lower in Smoker |
| cg18220168 | 6 | 116688224 | Lower in Smoker |
| cg24407607 | 6 | 116753994 | Lower in Smoker |
| cg15056247 | 6 | 116601073 | Higher in Smoker |
| cg11740152 | 20 | 35402426 | Higher in Smoker |
| cg07992052 | 20 | 35402295 | Higher in Smoker |
| cg26090554 | 20 | 35402449 | Lower in Smoker |
| cg20448717 | 6 | 7542126 | Higher in Smoker |
| cg15230849 | 6 | 56608324 | Lower in Smoker |
| cg19768311 | 6 | 56323702 | Lower in Smoker |
| cg26350987 | 6 | 56509042 | Lower in Smoker |
| cg05789608 | 1 | 205180302 | Higher in Smoker |
| cg20414749 | 1 | 205181261 | Higher in Smoker |
| cg23406451 | 18 | 32171998 | Lower in Smoker |
| cg11360819 | 6 | 15663360 | Higher in Smoker |
| cg05356998 | 6 | 15547383 | Lower in Smoker |
| cg15210999 | 6 | 15663538 | Lower in Smoker |
| cg14542802 | 6 | 15663170 | Higher in Smoker |
| cg10338571 | 15 | 49920878 | Lower in Smoker |
| cg07125541 | 12 | 113534668 | Higher in Smoker |
| cg00231239 | 12 | 113534615 | Lower in Smoker |
| cg04562491 | 12 | 113495386 | Lower in Smoker |
| cg19217692 | 12 | 57998656 | Higher in Smoker |
| cg17044529 | 11 | 58944103 | Lower in Smoker |
| cg08031485 | 2 | 242617771 | Lower in Smoker |
| cg13855384 | 17 | 7151975 | Lower in Smoker |

| | | | |
|---|---|---|---|
| cg07470322 | 17 | 7149217 | Lower in Smoker |
| cg00471903 | 15 | 45444918 | Lower in Smoker |
| cg15105703 | 15 | 45421860 | Higher in Smoker |
| cg07320850 | 15 | 45422371 | Lower in Smoker |
| cg04222582 | 15 | 45405103 | Higher in Smoker |
| cg23899628 | 15 | 45406506 | Higher in Smoker |
| cg13665184 | 16 | 68057062 | Lower in Smoker |
| cg09211336 | 19 | 5790808 | Higher in Smoker |
| cg24870476 | 1 | 221910211 | Lower in Smoker |
| cg14874678 | 2 | 74008401 | Lower in Smoker |
| cg11132352 | 1 | 161719642 | Lower in Smoker |
| cg26105766 | 10 | 76869969 | Lower in Smoker |
| cg06619580 | 17 | 35870477 | Lower in Smoker |
| cg21497602 | 12 | 12715811 | Higher in Smoker |
| cg14853597 | 12 | 12714548 | Higher in Smoker |
| cg04927360 | 1 | 159752179 | Lower in Smoker |
| cg20203041 | 17 | 41857647 | Higher in Smoker |
| cg04221400 | 17 | 41856489 | Higher in Smoker |
| cg27130302 | 8 | 29209604 | Higher in Smoker |
| cg07151117 | 8 | 29204954 | Lower in Smoker |
| cg24379915 | 8 | 29202958 | Lower in Smoker |
| cg01865118 | 8 | 29204221 | Lower in Smoker |
| cg18432895 | 8 | 29205555 | Lower in Smoker |
| cg03784956 | 1 | 228785238 | Higher in Smoker |
| cg01814191 | 12 | 89744524 | Higher in Smoker |
| cg05769889 | 12 | 89744701 | Higher in Smoker |
| cg02248763 | 11 | 1580098 | Lower in Smoker |
| cg23221544 | X | 152907546 | Lower in Smoker |
| cg06646682 | 1 | 1273442 | Lower in Smoker |
| cg07862129 | 10 | 82122651 | Lower in Smoker |
| cg26932586 | 14 | 102514382 | Lower in Smoker |
| cg15973528 | 14 | 102482817 | Lower in Smoker |
| cg15441556 | 14 | 102483164 | Lower in Smoker |
| cg13460297 | 2 | 172581104 | Lower in Smoker |
| cg07070019 | 3 | 32611876 | Higher in Smoker |

| | | | |
|---|---|---|---|
| cg23563507 | 2 | 44001149 | Higher in Smoker |
| cg01989857 | 2 | 44001018 | Higher in Smoker |
| cg19009761 | 17 | 56160829 | Higher in Smoker |
| cg05789476 | 6 | 159065051 | Higher in Smoker |
| cg15319206 | 6 | 159065938 | Higher in Smoker |
| cg17245862 | 6 | 159065192 | Higher in Smoker |
| cg15248353 | 21 | 38738865 | Higher in Smoker |
| cg16320339 | 21 | 38740894 | Higher in Smoker |
| cg09224523 | 1 | 206808529 | Higher in Smoker |
| cg03812320 | 1 | 206808936 | Higher in Smoker |
| cg00477086 | 2 | 71785920 | Lower in Smoker |
| cg23901409 | 15 | 55790571 | Higher in Smoker |
| cg18344452 | 15 | 55790608 | Higher in Smoker |
| cg16593081 | 15 | 55799927 | Lower in Smoker |
| cg14215625 | 15 | 55800831 | Lower in Smoker |
| cg19400179 | 3 | 108321607 | Higher in Smoker |
| cg04779640 | 3 | 108307951 | Higher in Smoker |
| cg19593285 | 20 | 32267661 | Lower in Smoker |
| cg21211746 | 1 | 23858035 | Higher in Smoker |
| cg11798959 | 1 | 23857321 | Higher in Smoker |
| cg02992252 | 1 | 23857546 | Lower in Smoker |
| cg11195034 | 6 | 20493106 | Lower in Smoker |
| cg13654085 | 6 | 20416519 | Lower in Smoker |
| cg07679219 | 12 | 77417738 | Higher in Smoker |
| cg25144696 | 12 | 77459591 | Lower in Smoker |
| cg23812361 | 11 | 19262624 | Higher in Smoker |
| cg26690592 | 11 | 19261879 | Higher in Smoker |
| cg07036730 | 16 | 2273332 | Higher in Smoker |
| cg05319934 | 16 | 2284375 | Lower in Smoker |
| cg19590858 | 14 | 35009852 | Lower in Smoker |
| cg26530971 | 8 | 110552297 | Higher in Smoker |
| cg07710020 | 8 | 110551799 | Higher in Smoker |
| cg18533313 | 8 | 110553825 | Lower in Smoker |
| cg05474370 | 5 | 158360366 | Lower in Smoker |
| cg11286669 | 5 | 158456317 | Lower in Smoker |

| | | | |
|---|---|---|---|
| cg11891579 | 5 | 158478533 | Lower in Smoker |
| cg00251610 | 5 | 158527817 | Lower in Smoker |
| cg23210478 | 5 | 158437811 | Lower in Smoker |
| cg22987487 | 8 | 25868076 | Higher in Smoker |
| cg10905495 | 8 | 25868109 | Higher in Smoker |
| cg22883472 | 8 | 25868045 | Higher in Smoker |
| cg24295381 | 8 | 25902594 | Higher in Smoker |
| cg16895719 | 8 | 25899257 | Higher in Smoker |
| cg09953520 | 8 | 25812278 | Lower in Smoker |
| cg22655696 | 10 | 131757191 | Higher in Smoker |
| cg00416409 | 10 | 131682862 | Lower in Smoker |
| cg10827854 | 10 | 131713829 | Lower in Smoker |
| cg07554626 | 10 | 131653285 | Lower in Smoker |
| cg19273683 | 1 | 21656047 | Lower in Smoker |
| cg00960509 | 1 | 21671908 | Higher in Smoker |
| cg11834658 | 1 | 21611224 | Lower in Smoker |
| cg07864323 | 3 | 183978878 | Higher in Smoker |
| cg08770580 | 3 | 183979197 | Higher in Smoker |
| cg12942257 | 3 | 183997855 | Lower in Smoker |
| cg00706683 | 2 | 233251030 | Higher in Smoker |
| cg23446375 | 19 | 39322544 | Higher in Smoker |
| cg13659813 | 19 | 39322968 | Lower in Smoker |
| cg20822052 | 1 | 236643871 | Lower in Smoker |
| cg12585162 | 1 | 236592400 | Lower in Smoker |
| cg01714418 | 15 | 74986709 | Higher in Smoker |
| cg06812099 | 15 | 74984455 | Lower in Smoker |
| cg09999650 | 16 | 67907176 | Higher in Smoker |
| cg06084313 | 3 | 5228974 | Higher in Smoker |
| cg22250390 | 3 | 5246986 | Lower in Smoker |
| cg01332827 | 20 | 33735167 | Higher in Smoker |
| cg10789151 | 20 | 33735143 | Lower in Smoker |
| cg09875087 | 1 | 184724775 | Higher in Smoker |
| cg05336561 | 1 | 184724800 | Higher in Smoker |
| cg22468975 | 1 | 184724009 | Higher in Smoker |
| cg15716405 | 5 | 83680690 | Higher in Smoker |

| | | | |
|---|---|---|---|
| cg05179846 | 5 | 83678235 | Higher in Smoker |
| cg22920665 | 5 | 83680719 | Higher in Smoker |
| cg22022671 | 5 | 83253023 | Lower in Smoker |
| cg27565517 | 6 | 12292676 | Higher in Smoker |
| cg06823651 | 6 | 12290395 | Higher in Smoker |
| cg16203262 | 13 | 78495961 | Lower in Smoker |
| cg04390523 | 13 | 78493100 | Higher in Smoker |
| cg24236409 | 13 | 78493282 | Higher in Smoker |
| cg06971129 | 13 | 78493066 | Higher in Smoker |
| cg19650157 | 13 | 78493297 | Higher in Smoker |
| cg15836660 | 13 | 78493128 | Higher in Smoker |
| cg12602112 | 13 | 78493294 | Higher in Smoker |
| cg25717994 | 13 | 78493631 | Higher in Smoker |
| cg15699226 | 13 | 78492678 | Higher in Smoker |
| cg13434989 | 13 | 78493305 | Higher in Smoker |
| cg13818654 | 13 | 78493126 | Higher in Smoker |
| cg06179060 | 13 | 78493012 | Higher in Smoker |
| cg07974719 | 13 | 78494064 | Higher in Smoker |
| cg19742055 | 13 | 78493365 | Higher in Smoker |
| cg07219710 | 6 | 74230925 | Higher in Smoker |
| cg01915951 | 20 | 62130500 | Lower in Smoker |
| cg09113420 | 2 | 207027298 | Higher in Smoker |
| cg04782072 | 6 | 8102505 | Higher in Smoker |
| cg18474153 | 19 | 3984323 | Lower in Smoker |
| cg20738733 | 19 | 3983041 | Lower in Smoker |
| cg01180236 | 16 | 22218483 | Higher in Smoker |
| cg23039837 | 3 | 127872427 | Higher in Smoker |
| cg27394987 | 3 | 128118189 | Lower in Smoker |
| cg04266474 | 7 | 36318491 | Lower in Smoker |
| cg17094624 | 1 | 245254667 | Lower in Smoker |
| cg05790237 | 1 | 245268112 | Lower in Smoker |
| cg24524470 | 1 | 245273257 | Lower in Smoker |
| cg13093989 | 1 | 245254391 | Lower in Smoker |
| cg16570157 | 11 | 829783 | Higher in Smoker |
| cg22773555 | 11 | 830233 | Higher in Smoker |

| | | | |
|---|---|---|---|
| cg10759769 | 12 | 3749671 | Lower in Smoker |
| cg24433095 | 12 | 3858471 | Lower in Smoker |
| cg10917293 | 12 | 3841539 | Lower in Smoker |
| cg12864903 | 17 | 28267374 | Lower in Smoker |
| cg26525008 | 17 | 28256777 | Higher in Smoker |
| cg25711779 | 2 | 56149825 | Lower in Smoker |
| cg26096599 | 11 | 65641445 | Higher in Smoker |
| cg26348939 | 11 | 65641335 | Higher in Smoker |
| cg04143750 | 2 | 233497656 | Higher in Smoker |
| cg26667821 | 1 | 155099774 | Higher in Smoker |
| cg21199495 | 1 | 155059162 | Lower in Smoker |
| cg08218206 | 5 | 106722289 | Lower in Smoker |
| cg22991477 | 5 | 106969956 | Lower in Smoker |
| cg24728949 | 5 | 106820169 | Lower in Smoker |
| cg20259518 | X | 68048749 | Higher in Smoker |
| cg26410404 | X | 68050206 | Lower in Smoker |
| cg12240515 | 8 | 132944153 | Lower in Smoker |
| cg08271180 | 8 | 132997218 | Lower in Smoker |
| cg14370314 | 14 | 23834891 | Higher in Smoker |
| cg22435300 | 15 | 82555336 | Higher in Smoker |
| cg27227909 | 4 | 110932718 | Lower in Smoker |
| cg07810164 | X | 13588174 | Higher in Smoker |
| cg17443080 | 9 | 139557460 | Lower in Smoker |
| cg16468631 | 6 | 32134865 | Higher in Smoker |
| cg26687830 | 6 | 32135326 | Lower in Smoker |
| cg17208278 | 6 | 32135231 | Lower in Smoker |
| cg10262770 | 6 | 32135370 | Lower in Smoker |
| cg11356387 | 6 | 32135776 | Lower in Smoker |
| cg11475323 | 5 | 38262316 | Lower in Smoker |
| cg12476044 | 5 | 38403758 | Lower in Smoker |
| cg17389149 | 7 | 55227884 | Lower in Smoker |
| ch.7.1264585R | 7 | 55212640 | Higher in Smoker |
| cg25923056 | 19 | 41306455 | Lower in Smoker |
| cg14219290 | 14 | 34420499 | Higher in Smoker |
| cg13009654 | 5 | 137802252 | Lower in Smoker |

| | | | |
|---|---|---|---|
| cg06190380 | 10 | 64576262 | Higher in Smoker |
| cg19355190 | 10 | 64575798 | Lower in Smoker |
| cg26834504 | 2 | 63198779 | Lower in Smoker |
| cg19446589 | 2 | 63268631 | Lower in Smoker |
| cg10142520 | 11 | 65344604 | Higher in Smoker |
| cg18765439 | 11 | 65343343 | Higher in Smoker |
| cg14043527 | 11 | 64642516 | Lower in Smoker |
| cg06154903 | 11 | 64642558 | Lower in Smoker |
| cg01151584 | 11 | 64627528 | Lower in Smoker |
| cg01559302 | 19 | 48246266 | Lower in Smoker |
| cg09204108 | 15 | 42211679 | Lower in Smoker |
| cg13879937 | 15 | 42265413 | Lower in Smoker |
| cg02586712 | 15 | 42249569 | Lower in Smoker |
| cg14168941 | 9 | 140716770 | Lower in Smoker |
| cg01756374 | 9 | 140712932 | Lower in Smoker |
| cg13394060 | 9 | 140704065 | Lower in Smoker |
| cg03523203 | 9 | 140726863 | Lower in Smoker |
| cg14050824 | 9 | 140683797 | Lower in Smoker |
| cg17942750 | 9 | 140683527 | Lower in Smoker |
| cg21230387 | 9 | 140673936 | Lower in Smoker |
| cg00210002 | 6 | 31866208 | Higher in Smoker |
| cg21786114 | 6 | 31866072 | Higher in Smoker |
| cg23739027 | 6 | 31850912 | Higher in Smoker |
| cg16414425 | 6 | 31865522 | Higher in Smoker |
| cg11203797 | 6 | 31856381 | Lower in Smoker |
| cg20208853 | 6 | 31862943 | Lower in Smoker |
| cg19669701 | 6 | 31855914 | Lower in Smoker |
| cg22048274 | 6 | 31853428 | Lower in Smoker |
| cg22810281 | 6 | 31863252 | Lower in Smoker |
| cg00866667 | 19 | 40031046 | Higher in Smoker |
| cg15055808 | 19 | 40030247 | Higher in Smoker |
| cg16619662 | 19 | 40030871 | Higher in Smoker |
| cg16010664 | 19 | 40023715 | Higher in Smoker |
| cg25543604 | 19 | 40023503 | Higher in Smoker |
| cg05057777 | 12 | 104697631 | Higher in Smoker |

| | | | |
|---|---|---|---|
| cg00586621 | 12 | 104697620 | Higher in Smoker |
| cg01848457 | 12 | 104697983 | Higher in Smoker |
| cg22156456 | 17 | 39844239 | Higher in Smoker |
| cg26622502 | 11 | 65769931 | Higher in Smoker |
| cg11225091 | Y | 22737663 | Lower in Smoker |
| cg05332270 | 2 | 37384401 | Higher in Smoker |
| cg24022829 | 2 | 37384227 | Higher in Smoker |
| cg16587158 | 14 | 75469461 | Higher in Smoker |
| cg19882377 | 8 | 141646205 | Higher in Smoker |
| cg18044585 | 8 | 141619425 | Lower in Smoker |
| cg03172341 | 8 | 141577150 | Lower in Smoker |
| cg24492446 | 8 | 141572291 | Lower in Smoker |
| cg06007675 | 8 | 141542162 | Lower in Smoker |
| cg24262486 | 8 | 141556397 | Lower in Smoker |
| cg23731089 | 8 | 141599208 | Lower in Smoker |
| cg19352830 | 8 | 141599356 | Lower in Smoker |
| cg10952591 | 14 | 67827467 | Higher in Smoker |
| cg03948139 | 10 | 120804863 | Lower in Smoker |
| cg16729899 | 7 | 2414985 | Lower in Smoker |
| cg18044723 | 8 | 109261011 | Higher in Smoker |
| cg02164407 | 11 | 8008755 | Higher in Smoker |
| cg10693065 | 11 | 8008448 | Lower in Smoker |
| cg22753376 | 6 | 117768031 | Higher in Smoker |
| cg21336288 | 6 | 117742444 | Lower in Smoker |
| cg08749362 | 15 | 44829310 | Higher in Smoker |
| cg15594284 | 22 | 38245605 | Higher in Smoker |
| cg01108316 | 11 | 32605196 | Lower in Smoker |
| cg01623657 | 17 | 7477935 | Lower in Smoker |
| cg24502904 | 12 | 53399544 | Lower in Smoker |
| cg11037477 | 4 | 99851008 | Lower in Smoker |
| cg14972143 | 4 | 99851003 | Lower in Smoker |
| cg14696254 | 5 | 176057813 | Higher in Smoker |
| ch.2.4679874R | 2 | 233430461 | Higher in Smoker |
| cg18350458 | 8 | 37887952 | Higher in Smoker |
| cg26084484 | 5 | 139927167 | Higher in Smoker |

| | | | |
|---|---|---|---|
| cg10731022 | 5 | 139927252 | Higher in Smoker |
| cg07810961 | 5 | 139927271 | Higher in Smoker |
| cg26782787 | 22 | 31835691 | Higher in Smoker |
| cg00969153 | 22 | 31884264 | Lower in Smoker |
| cg23504634 | 3 | 184032286 | Higher in Smoker |
| cg01817714 | 3 | 184032711 | Lower in Smoker |
| cg08681689 | 3 | 184034132 | Lower in Smoker |
| cg06294803 | 3 | 184033282 | Lower in Smoker |
| cg08506841 | 11 | 10830655 | Lower in Smoker |
| cg08463298 | 1 | 21503432 | Higher in Smoker |
| cg22600610 | 1 | 21500625 | Lower in Smoker |
| cg23138682 | 14 | 103801128 | Lower in Smoker |
| cg06749174 | 3 | 170627029 | Lower in Smoker |
| cg19391583 | 2 | 99997497 | Lower in Smoker |
| cg11911418 | 16 | 48493759 | Lower in Smoker |
| cg19001809 | 17 | 12921385 | Higher in Smoker |
| cg23254346 | 17 | 12899395 | Lower in Smoker |
| cg19055217 | 17 | 12921270 | Higher in Smoker |
| cg16860587 | 19 | 8069925 | Higher in Smoker |
| cg27296944 | 19 | 11563628 | Lower in Smoker |
| cg17478228 | 19 | 11591593 | Higher in Smoker |
| cg22932804 | 1 | 50513451 | Lower in Smoker |
| cg04538760 | 4 | 140040594 | Lower in Smoker |
| cg03940407 | 4 | 140029922 | Lower in Smoker |
| cg20103938 | 4 | 140005223 | Higher in Smoker |
| cg25918359 | X | 129244732 | Higher in Smoker |
| cg06428055 | X | 129243872 | Higher in Smoker |
| cg22731981 | 11 | 34535579 | Lower in Smoker |
| cg08410691 | 7 | 1753909 | Lower in Smoker |
| cg17390940 | 7 | 1782346 | Lower in Smoker |
| cg26911787 | 12 | 96587734 | Higher in Smoker |
| cg09501305 | 19 | 18572599 | Lower in Smoker |
| cg11571761 | 5 | 95298041 | Higher in Smoker |
| cg19753607 | 5 | 95231593 | Lower in Smoker |
| cg00159100 | 7 | 37487633 | Higher in Smoker |

| | | | |
|---|---|---|---|
| cg23208271 | 7 | 37148793 | Lower in Smoker |
| cg14261863 | 20 | 45035638 | Higher in Smoker |
| cg00488260 | 11 | 107461894 | Higher in Smoker |
| cg09422220 | 4 | 141445306 | Higher in Smoker |
| cg12291509 | 4 | 141444910 | Lower in Smoker |
| cg18109289 | 7 | 73457810 | Lower in Smoker |
| cg25130728 | 7 | 73483053 | Lower in Smoker |
| cg17314888 | 7 | 73442282 | Lower in Smoker |
| cg23129573 | 7 | 73442487 | Lower in Smoker |
| cg08680689 | 19 | 11670216 | Higher in Smoker |
| cg07637183 | 19 | 11667661 | Lower in Smoker |
| cg05846476 | 6 | 80655418 | Lower in Smoker |
| cg10410213 | 6 | 53214258 | Higher in Smoker |
| cg11748354 | 6 | 53200697 | Higher in Smoker |
| cg07959837 | 4 | 111026731 | Lower in Smoker |
| cg00460260 | 4 | 111119726 | Higher in Smoker |
| cg15134801 | 5 | 60138838 | Lower in Smoker |
| cg00164542 | 18 | 33709842 | Higher in Smoker |
| cg20820438 | 17 | 655625 | Higher in Smoker |
| cg18155211 | 17 | 655491 | Higher in Smoker |
| cg15950743 | 5 | 49708521 | Lower in Smoker |
| cg02327123 | 7 | 101006363 | Higher in Smoker |
| cg13267931 | 7 | 101006308 | Higher in Smoker |
| cg14133708 | 18 | 2846834 | Higher in Smoker |
| cg25501902 | 18 | 2913220 | Lower in Smoker |
| cg07012770 | 18 | 2847301 | Lower in Smoker |
| cg06746017 | 14 | 100357086 | Higher in Smoker |
| cg05312964 | 2 | 42442880 | Lower in Smoker |
| cg18223896 | 14 | 89081931 | Lower in Smoker |
| cg10236687 | 16 | 10626884 | Lower in Smoker |
| cg05093711 | 16 | 10674008 | Lower in Smoker |
| cg06350544 | 19 | 48833535 | Higher in Smoker |
| cg05707704 | 2 | 73144283 | Lower in Smoker |
| cg15921587 | 2 | 73144353 | Lower in Smoker |
| cg20038591 | 10 | 119306659 | Higher in Smoker |

| | | | |
|---|---|---|---|
| cg17276590 | 10 | 119930487 | Higher in Smoker |
| cg20804050 | 2 | 119605441 | Higher in Smoker |
| cg12034383 | 7 | 155250299 | Higher in Smoker |
| cg19256125 | 7 | 155249528 | Higher in Smoker |
| cg20547407 | 7 | 155255369 | Higher in Smoker |
| cg06385227 | 7 | 155252201 | Higher in Smoker |
| cg26368942 | 1 | 225841650 | Higher in Smoker |
| cg07371373 | 1 | 225821245 | Lower in Smoker |
| cg16528926 | 11 | 94823603 | Higher in Smoker |
| cg06414941 | 11 | 94864238 | Lower in Smoker |
| cg24630593 | 17 | 77082929 | Lower in Smoker |
| cg17099445 | 17 | 77078091 | Lower in Smoker |
| cg12902497 | 1 | 8938815 | Higher in Smoker |
| cg05106804 | 4 | 83381983 | Lower in Smoker |
| cg01118451 | 13 | 44361220 | Higher in Smoker |
| cg03677003 | 13 | 44359996 | Higher in Smoker |
| cg26023939 | 13 | 43964225 | Lower in Smoker |
| cg25544384 | 13 | 44000493 | Lower in Smoker |
| cg04365696 | 13 | 43834391 | Lower in Smoker |
| cg10861555 | X | 130036945 | Lower in Smoker |
| cg01372992 | X | 130037175 | Higher in Smoker |
| cg26002634 | 4 | 111396631 | Lower in Smoker |
| cg08733482 | 4 | 111395729 | Lower in Smoker |
| cg04296147 | 6 | 132129423 | Higher in Smoker |
| cg21975007 | 6 | 132128965 | Lower in Smoker |
| cg25681688 | 6 | 46097468 | Higher in Smoker |
| cg10779656 | 6 | 46138787 | Higher in Smoker |
| cg23889391 | 6 | 46138699 | Higher in Smoker |
| cg10203211 | 4 | 185018682 | Higher in Smoker |
| cg13874759 | 17 | 77704250 | Higher in Smoker |
| cg15965583 | 1 | 150601949 | Lower in Smoker |
| cg12179661 | 9 | 140333805 | Lower in Smoker |
| cg12858460 | 3 | 27763737 | Higher in Smoker |
| cg23705060 | 12 | 132443404 | Lower in Smoker |
| cg26627511 | 2 | 46525649 | Higher in Smoker |

| | | | |
|---|---|---|---|
| cg21276379 | 2 | 46523790 | Higher in Smoker |
| cg01313320 | 2 | 46526265 | Higher in Smoker |
| cg05049980 | 2 | 46612798 | Lower in Smoker |
| cg22488486 | 2 | 46612964 | Lower in Smoker |
| cg07901411 | 2 | 46527523 | Lower in Smoker |
| cg12731400 | 1 | 29213810 | Higher in Smoker |
| cg02446871 | 1 | 29241833 | Higher in Smoker |
| cg01834027 | 1 | 29240256 | Lower in Smoker |
| cg19692318 | 6 | 131384600 | Higher in Smoker |
| cg27355739 | 6 | 131383432 | Higher in Smoker |
| cg19712745 | 6 | 131275789 | Lower in Smoker |
| cg16622495 | 18 | 5544099 | Higher in Smoker |
| cg18543270 | 18 | 5543271 | Higher in Smoker |
| cg15536663 | 5 | 111665548 | Higher in Smoker |
| cg14071612 | 9 | 112081275 | Lower in Smoker |
| cg23896874 | 8 | 21924512 | Higher in Smoker |
| cg17560136 | 8 | 21915510 | Lower in Smoker |
| cg10711996 | 10 | 32635917 | Lower in Smoker |
| cg05692819 | 2 | 149432332 | Lower in Smoker |
| cg07658533 | 2 | 47596136 | Higher in Smoker |
| cg04105479 | 1 | 38225577 | Lower in Smoker |
| cg20510207 | 1 | 38230779 | Higher in Smoker |
| cg23237801 | 1 | 16476620 | Lower in Smoker |
| cg26371327 | 1 | 16473143 | Lower in Smoker |
| cg00081574 | 2 | 222437836 | Higher in Smoker |
| cg03776464 | 2 | 222436947 | Higher in Smoker |
| cg01101647 | 4 | 66535732 | Higher in Smoker |
| cg14386496 | 4 | 66536463 | Higher in Smoker |
| cg02463413 | 4 | 66535575 | Higher in Smoker |
| cg15093079 | 3 | 96533290 | Higher in Smoker |
| cg24337235 | 3 | 97463425 | Lower in Smoker |
| cg05266226 | 1 | 22920119 | Lower in Smoker |
| cg10938091 | 1 | 22889780 | Higher in Smoker |
| cg27573841 | 1 | 23038177 | Higher in Smoker |
| cg09463984 | 1 | 23111484 | Lower in Smoker |

| | | | |
|---|---|---|---|
| cg26554265 | 1 | 23206348 | Lower in Smoker |
| cg17292583 | 3 | 184287196 | Higher in Smoker |
| cg02565842 | 3 | 184278268 | Lower in Smoker |
| cg03867377 | 3 | 184289145 | Lower in Smoker |
| cg06221861 | 7 | 100425075 | Higher in Smoker |
| cg27628312 | 7 | 142552171 | Higher in Smoker |
| cg25399743 | 8 | 27348177 | Lower in Smoker |
| cg16184495 | 19 | 15343350 | Higher in Smoker |
| cg24607398 | 3 | 37033625 | Lower in Smoker |
| cg21490561 | 3 | 37034825 | Higher in Smoker |
| cg27573549 | 19 | 56189952 | Lower in Smoker |
| cg09368046 | 17 | 19140629 | Higher in Smoker |
| cg17742418 | 17 | 19188816 | Lower in Smoker |
| cg10567637 | 17 | 48609923 | Higher in Smoker |
| cg17100761 | 7 | 100318080 | Lower in Smoker |
| cg08538175 | 19 | 11491391 | Lower in Smoker |
| cg19593732 | 8 | 144941479 | Lower in Smoker |
| cg21366602 | 1 | 51887613 | Lower in Smoker |
| cg23272305 | 19 | 16582048 | Lower in Smoker |
| cg09761310 | 12 | 15942665 | Higher in Smoker |
| cg12544020 | 12 | 15941292 | Higher in Smoker |
| cg03652390 | 12 | 15873565 | Lower in Smoker |
| cg13582001 | 11 | 706533 | Lower in Smoker |
| cg03478249 | 13 | 43566547 | Higher in Smoker |
| cg06146977 | 13 | 43469464 | Lower in Smoker |
| cg25232719 | 5 | 96131793 | Lower in Smoker |
| cg04492048 | X | 48686119 | Higher in Smoker |
| cg08535669 | 17 | 37853032 | Lower in Smoker |
| cg13263114 | 17 | 37857070 | Higher in Smoker |
| cg25300234 | 2 | 212938740 | Lower in Smoker |
| cg07550819 | 12 | 1482931 | Lower in Smoker |
| cg14574951 | 3 | 55861102 | Lower in Smoker |
| cg09783209 | 19 | 45873853 | Lower in Smoker |
| cg13057891 | 13 | 103498411 | Higher in Smoker |
| cg10232140 | 10 | 50747652 | Higher in Smoker |

| | | | |
|---|---|---|---|
| cg12590548 | 10 | 50747167 | Higher in Smoker |
| cg15490694 | 10 | 50747084 | Higher in Smoker |
| cg01982597 | 10 | 50733420 | Lower in Smoker |
| cg04163967 | 21 | 39870627 | Lower in Smoker |
| cg03321829 | 5 | 172295653 | Lower in Smoker |
| cg01560676 | 5 | 172260799 | Lower in Smoker |
| cg13010299 | 20 | 34129465 | Higher in Smoker |
| cg14969015 | 1 | 44687687 | Lower in Smoker |
| cg01782059 | 1 | 44715942 | Lower in Smoker |
| cg13974084 | 8 | 681354 | Higher in Smoker |
| cg02668261 | 8 | 660158 | Lower in Smoker |
| cg22811350 | 8 | 655845 | Lower in Smoker |
| cg02209998 | 8 | 649235 | Lower in Smoker |
| cg17932911 | 10 | 101942982 | Lower in Smoker |
| cg26432044 | 8 | 37593919 | Higher in Smoker |
| cg10063512 | 8 | 37594142 | Lower in Smoker |
| cg20998539 | 17 | 62208374 | Lower in Smoker |
| cg03596167 | 16 | 23724821 | Higher in Smoker |
| cg15393565 | 14 | 53162558 | Higher in Smoker |
| cg21321768 | 18 | 19176371 | Lower in Smoker |
| cg23453420 | 18 | 19180773 | Lower in Smoker |
| cg13517398 | 18 | 19180670 | Lower in Smoker |
| cg18221891 | 8 | 27632578 | Higher in Smoker |
| cg20451680 | 5 | 54281336 | Higher in Smoker |
| cg12143651 | 1 | 6515748 | Higher in Smoker |
| cg24153044 | 1 | 6485201 | Higher in Smoker |
| cg13356427 | 1 | 6520354 | Higher in Smoker |
| cg17430636 | 1 | 6500410 | Higher in Smoker |
| cg13068963 | 1 | 6485317 | Lower in Smoker |
| cg26624031 | 1 | 17034476 | Higher in Smoker |
| cg05208572 | 1 | 17027941 | Lower in Smoker |
| cg22190721 | 16 | 68269295 | Lower in Smoker |
| cg27160968 | 11 | 64081545 | Lower in Smoker |
| cg19843226 | 14 | 76836781 | Lower in Smoker |
| cg07490447 | 14 | 76869993 | Lower in Smoker |

| | | | |
|---|---|---|---|
| cg10526223 | 14 | 76957697 | Lower in Smoker |
| cg07170252 | 14 | 76870544 | Lower in Smoker |
| cg04732303 | 14 | 76848081 | Lower in Smoker |
| cg02998463 | 14 | 76874418 | Lower in Smoker |
| cg07029665 | 1 | 217170675 | Lower in Smoker |
| cg01432520 | 1 | 217068243 | Lower in Smoker |
| cg13490235 | 1 | 217004524 | Lower in Smoker |
| cg17279365 | 1 | 217168635 | Lower in Smoker |
| cg23637314 | 1 | 216774226 | Higher in Smoker |
| cg10108237 | 1 | 216896863 | Higher in Smoker |
| cg17231418 | X | 103499335 | Higher in Smoker |
| cg00455738 | X | 103498075 | Higher in Smoker |
| cg18395615 | X | 103499807 | Higher in Smoker |
| cg03447800 | X | 103499585 | Higher in Smoker |
| cg23588713 | 12 | 56523270 | Higher in Smoker |
| cg04574046 | 7 | 158551048 | Higher in Smoker |
| cg08016138 | 7 | 158524693 | Lower in Smoker |
| cg16802792 | 3 | 138153278 | Higher in Smoker |
| cg07421368 | 2 | 67624930 | Higher in Smoker |
| cg12203416 | 5 | 137845907 | Lower in Smoker |
| cg12734386 | 15 | 76531223 | Lower in Smoker |
| cg16792062 | 11 | 128458153 | Lower in Smoker |
| cg24662823 | 11 | 128350635 | Lower in Smoker |
| cg23110422 | 21 | 40182073 | Lower in Smoker |
| cg10336045 | 7 | 14029680 | Higher in Smoker |
| cg26986937 | 7 | 14029421 | Higher in Smoker |
| cg12421032 | 1 | 157108028 | Higher in Smoker |
| cg16655375 | 3 | 185827035 | Higher in Smoker |
| cg12760110 | 12 | 11802609 | Higher in Smoker |
| cg21168444 | 12 | 11896095 | Lower in Smoker |
| cg26249450 | 6 | 36355732 | Higher in Smoker |
| cg01442064 | 4 | 5713450 | Lower in Smoker |
| cg15128562 | 19 | 7895127 | Higher in Smoker |
| cg17666539 | 19 | 7927207 | Lower in Smoker |
| cg04172795 | 14 | 100578523 | Lower in Smoker |

| | | | |
|---|---|---|---|
| cg07104209 | 7 | 27281872 | Higher in Smoker |
| cg12550866 | 7 | 27281315 | Higher in Smoker |
| cg05467160 | 2 | 176945526 | Higher in Smoker |
| cg13942186 | 9 | 140305942 | Higher in Smoker |
| cg01596854 | 9 | 140310081 | Lower in Smoker |
| cg13434688 | 9 | 140270145 | Lower in Smoker |
| cg03292648 | 1 | 242010305 | Lower in Smoker |
| cg07639959 | 1 | 242011162 | Higher in Smoker |
| cg03116938 | 1 | 242030232 | Lower in Smoker |
| cg13578062 | 4 | 56719681 | Higher in Smoker |
| cg27149530 | 6 | 692947 | Higher in Smoker |
| cg20949502 | 6 | 503807 | Higher in Smoker |
| cg18134577 | 5 | 456502 | Lower in Smoker |
| cg21643731 | 7 | 133545053 | Lower in Smoker |
| cg14305382 | 7 | 133198736 | Lower in Smoker |
| cg18321423 | 7 | 133084947 | Lower in Smoker |
| cg22295389 | 7 | 132937102 | Lower in Smoker |
| cg12332526 | 10 | 94792635 | Lower in Smoker |
| cg14375121 | 10 | 94749516 | Lower in Smoker |
| cg25533547 | 2 | 73053217 | Higher in Smoker |
| cg16986851 | 2 | 73052567 | Higher in Smoker |
| cg16721449 | 2 | 73052964 | Higher in Smoker |
| cg17560967 | 2 | 73053226 | Higher in Smoker |
| cg16429080 | 2 | 72431433 | Lower in Smoker |
| cg04906603 | 2 | 73048869 | Lower in Smoker |
| cg02066144 | 2 | 73052126 | Lower in Smoker |
| cg15617699 | 3 | 38538063 | Lower in Smoker |
| cg07190630 | 1 | 11160325 | Lower in Smoker |
| cg22228043 | 1 | 11159903 | Lower in Smoker |
| cg14462758 | 9 | 133576487 | Lower in Smoker |
| cg13441107 | 9 | 37730478 | Lower in Smoker |
| cg20577535 | 11 | 108464736 | Higher in Smoker |
| cg10022155 | 11 | 108464931 | Lower in Smoker |
| cg08545463 | 11 | 108459708 | Lower in Smoker |
| cg16934235 | 11 | 108423124 | Lower in Smoker |

| | | | |
|---|---|---|---|
| cg22271457 | 8 | 116939185 | Lower in Smoker |
| cg20389847 | 8 | 119043482 | Lower in Smoker |
| cg11170956 | 8 | 119038325 | Lower in Smoker |
| cg01664039 | 8 | 118941962 | Lower in Smoker |
| cg10090158 | 8 | 119083946 | Lower in Smoker |
| cg08305378 | 8 | 118953376 | Lower in Smoker |
| cg05495611 | 11 | 44243314 | Lower in Smoker |
| cg04440597 | 8 | 28573618 | Lower in Smoker |
| cg17048233 | 8 | 28560467 | Lower in Smoker |
| cg08994982 | 20 | 45522855 | Lower in Smoker |
| cg26501369 | 6 | 133561814 | Higher in Smoker |
| cg07327468 | 6 | 133561765 | Higher in Smoker |
| cg13912545 | 6 | 133561649 | Higher in Smoker |
| cg02965931 | 6 | 133672385 | Lower in Smoker |
| cg04548096 | 6 | 133691357 | Lower in Smoker |
| cg09649901 | 6 | 133851460 | Lower in Smoker |
| cg10782703 | 6 | 133851542 | Lower in Smoker |
| cg10105684 | 6 | 133753539 | Lower in Smoker |
| cg07224291 | 6 | 133777802 | Lower in Smoker |
| cg26092564 | 6 | 66207286 | Lower in Smoker |
| cg27088844 | 17 | 40897149 | Higher in Smoker |
| cg12893852 | 17 | 40893415 | Lower in Smoker |
| cg20617661 | 6 | 6321364 | Higher in Smoker |
| cg14773260 | 5 | 76011323 | Higher in Smoker |
| cg03636183 | 19 | 17000585 | Lower in Smoker |
| cg01185754 | 1 | 95006729 | Lower in Smoker |
| cg01953591 | 1 | 169555805 | Lower in Smoker |
| cg10654280 | 13 | 113763122 | Lower in Smoker |
| cg20329620 | 13 | 113759894 | Lower in Smoker |
| cg07200650 | 16 | 74608755 | Higher in Smoker |
| cg08699631 | 16 | 74782152 | Lower in Smoker |
| cg07670227 | 16 | 74755435 | Lower in Smoker |
| cg19921581 | 1 | 46859680 | Lower in Smoker |
| cg25330232 | 3 | 82193704 | Higher in Smoker |
| cg03625952 | 5 | 159625457 | Lower in Smoker |

| | | | |
|---|---|---|---|
| cg03952543 | 6 | 123101437 | Lower in Smoker |
| cg07886701 | 8 | 82375121 | Lower in Smoker |
| cg07999042 | 11 | 61598930 | Lower in Smoker |
| cg07930313 | 17 | 72889714 | Higher in Smoker |
| cg01202197 | 17 | 72889973 | Higher in Smoker |
| cg05002512 | 1 | 51425990 | Higher in Smoker |
| cg20739726 | 1 | 50907107 | Lower in Smoker |
| cg06856840 | 15 | 80446451 | Lower in Smoker |
| cg08818385 | 2 | 96067685 | Lower in Smoker |
| cg04090027 | 2 | 97760622 | Higher in Smoker |
| cg25762974 | 12 | 50293815 | Lower in Smoker |
| cg07870378 | 16 | 4665298 | Lower in Smoker |
| cg16429214 | 17 | 74266574 | Lower in Smoker |
| cg14474520 | 12 | 124781038 | Higher in Smoker |
| cg23981320 | 12 | 124780274 | Higher in Smoker |
| cg04433201 | 17 | 296265 | Lower in Smoker |
| cg06096805 | 9 | 130743943 | Lower in Smoker |
| cg17308606 | 9 | 130706144 | Lower in Smoker |
| cg25976094 | 1 | 109177782 | Lower in Smoker |
| cg17174180 | 15 | 83654701 | Higher in Smoker |
| cg05669100 | 15 | 83655128 | Higher in Smoker |
| cg01809941 | 5 | 14581404 | Higher in Smoker |
| cg23827531 | 3 | 58563097 | Higher in Smoker |
| cg19585312 | 10 | 14818216 | Lower in Smoker |
| cg17510987 | 19 | 1883657 | Lower in Smoker |
| cg12292492 | 15 | 80992262 | Higher in Smoker |
| cg07781158 | 15 | 80987797 | Higher in Smoker |
| cg02073928 | 12 | 111807059 | Higher in Smoker |
| cg17456749 | 12 | 111807011 | Lower in Smoker |
| cg03962458 | 13 | 50745832 | Lower in Smoker |
| cg08042538 | 20 | 821854 | Lower in Smoker |
| cg14304515 | 20 | 822499 | Lower in Smoker |
| cg20353496 | 20 | 825268 | Higher in Smoker |
| cg12219325 | 8 | 59058585 | Higher in Smoker |
| cg23548885 | 2 | 47150 | Higher in Smoker |

| | | | |
|---|---|---|---|
| cg27109163 | 11 | 58910237 | Higher in Smoker |
| cg15474378 | 11 | 58921817 | Lower in Smoker |
| cg10011647 | 11 | 58892585 | Lower in Smoker |
| cg14859464 | 11 | 58874723 | Lower in Smoker |
| cg10221014 | 12 | 47618577 | Lower in Smoker |
| cg15393461 | 4 | 38880766 | Lower in Smoker |
| cg01030534 | 7 | 143579698 | Higher in Smoker |
| cg04662015 | 7 | 143318041 | Higher in Smoker |
| cg05846642 | 7 | 143318036 | Higher in Smoker |
| cg18999165 | 7 | 143318047 | Higher in Smoker |
| cg00113554 | 17 | 47840835 | Higher in Smoker |
| cg26394624 | 17 | 47841537 | Higher in Smoker |
| cg06315390 | 22 | 45704914 | Higher in Smoker |
| cg03837677 | 22 | 45705688 | Higher in Smoker |
| cg21383720 | 9 | 96214543 | Higher in Smoker |
| cg14516552 | 9 | 96213518 | Lower in Smoker |
| cg14097855 | 9 | 96215483 | Higher in Smoker |
| cg21219785 | 9 | 96215191 | Lower in Smoker |
| cg04922606 | 6 | 170703742 | Higher in Smoker |
| cg08601570 | 6 | 170619241 | Lower in Smoker |
| cg05184394 | 2 | 131512773 | Higher in Smoker |
| cg09971591 | 2 | 131525196 | Lower in Smoker |
| cg18428563 | 13 | 51796223 | Higher in Smoker |
| cg25522046 | 13 | 51855413 | Lower in Smoker |
| cg18890556 | 2 | 225266580 | Higher in Smoker |
| cg00695561 | 19 | 17531239 | Higher in Smoker |
| cg26034150 | 2 | 201936608 | Higher in Smoker |
| cg01099541 | X | 134166046 | Lower in Smoker |
| cg20230419 | 2 | 130944171 | Lower in Smoker |
| cg17739181 | 9 | 130271384 | Lower in Smoker |
| cg11888381 | 3 | 184053532 | Lower in Smoker |
| cg07449620 | X | 92929446 | Higher in Smoker |
| cg26425555 | 5 | 16616459 | Higher in Smoker |
| cg25671686 | 5 | 16617290 | Higher in Smoker |
| cg01862523 | 6 | 71123290 | Higher in Smoker |

| | | | |
|---|---|---|---|
| cg11244648 | 12 | 149495 | Lower in Smoker |
| cg13640730 | 4 | 89679571 | Lower in Smoker |
| cg23191485 | 4 | 89645788 | Lower in Smoker |
| cg05254221 | 10 | 61050062 | Lower in Smoker |
| cg08571229 | 10 | 74927769 | Higher in Smoker |
| cg16424196 | 8 | 53452398 | Lower in Smoker |
| cg19588432 | 2 | 284640 | Lower in Smoker |
| cg26413355 | 5 | 79783674 | Higher in Smoker |
| cg17885260 | 15 | 82558555 | Lower in Smoker |
| cg17673237 | 13 | 108518419 | Higher in Smoker |
| cg23782866 | 13 | 107928782 | Lower in Smoker |
| cg23511851 | 13 | 108087589 | Lower in Smoker |
| cg19639798 | 13 | 108519318 | Higher in Smoker |
| cg08265889 | 5 | 63990800 | Lower in Smoker |
| cg05786548 | 4 | 152330215 | Higher in Smoker |
| cg19183248 | 4 | 152364959 | Lower in Smoker |
| cg01123541 | 11 | 6256799 | Higher in Smoker |
| cg12479696 | 11 | 6240462 | Lower in Smoker |
| cg26860703 | 11 | 6255872 | Higher in Smoker |
| cg07733920 | 10 | 116636356 | Higher in Smoker |
| cg03682117 | 10 | 116581829 | Lower in Smoker |
| cg00008036 | 1 | 179712091 | Lower in Smoker |
| cg13814351 | 9 | 136446836 | Lower in Smoker |
| cg14584407 | 9 | 136445244 | Lower in Smoker |
| cg25741567 | 21 | 35747810 | Higher in Smoker |
| cg08013227 | 9 | 140142392 | Higher in Smoker |
| cg21212076 | 9 | 35564052 | Higher in Smoker |
| cg10220992 | 8 | 11324327 | Higher in Smoker |
| cg05147714 | 11 | 73239682 | Higher in Smoker |
| cg10580715 | 11 | 73149993 | Lower in Smoker |
| cg12771178 | 10 | 50342081 | Lower in Smoker |
| cg13905757 | 10 | 15411709 | Higher in Smoker |
| cg15393936 | 10 | 15354631 | Lower in Smoker |
| cg17408185 | 10 | 15364093 | Lower in Smoker |
| cg19935040 | 17 | 42432165 | Lower in Smoker |

| | | | |
|---|---|---|---|
| cg23766254 | 17 | 42431859 | Lower in Smoker |
| cg06359394 | 2 | 187559328 | Higher in Smoker |
| cg24789487 | 2 | 187558797 | Higher in Smoker |
| cg18430156 | 2 | 187558795 | Higher in Smoker |
| cg19375969 | 5 | 92956676 | Lower in Smoker |
| cg16485800 | 5 | 93076260 | Lower in Smoker |
| cg25015043 | 5 | 93077859 | Higher in Smoker |
| cg07617175 | 5 | 99871683 | Higher in Smoker |
| cg18252731 | 15 | 93198700 | Higher in Smoker |
| cg23257697 | 2 | 75784752 | Higher in Smoker |
| cg24405470 | 2 | 75767666 | Lower in Smoker |
| cg14128890 | 1 | 36788627 | Higher in Smoker |
| cg10586751 | 1 | 222916779 | Lower in Smoker |
| cg27585533 | 10 | 102676881 | Lower in Smoker |
| cg19828537 | 2 | 97563889 | Lower in Smoker |
| cg14659978 | 2 | 97563966 | Lower in Smoker |
| cg09001591 | 2 | 29236577 | Lower in Smoker |
| cg11675630 | 2 | 29255881 | Lower in Smoker |
| cg05707236 | 2 | 29204695 | Lower in Smoker |
| cg23167594 | 2 | 29204200 | Lower in Smoker |
| cg09935440 | 7 | 135429446 | Lower in Smoker |
| cg03219493 | 14 | 94392406 | Lower in Smoker |
| cg13737408 | 14 | 94393654 | Lower in Smoker |
| cg03465157 | 7 | 38725962 | Lower in Smoker |
| cg02918166 | 6 | 119471046 | Lower in Smoker |
| cg01386556 | 4 | 17783205 | Higher in Smoker |
| cg24000693 | 4 | 17778675 | Lower in Smoker |
| cg13197733 | 7 | 102389205 | Higher in Smoker |
| cg05771132 | 7 | 102389239 | Higher in Smoker |
| cg18966140 | 10 | 15898349 | Lower in Smoker |
| cg03475190 | 7 | 30919932 | Lower in Smoker |
| cg08904058 | 15 | 29859427 | Lower in Smoker |
| cg21908287 | 1 | 155225385 | Higher in Smoker |
| cg12801917 | 17 | 15417503 | Lower in Smoker |
| cg25234170 | 17 | 15467188 | Higher in Smoker |

| | | | |
|---|---|---|---|
| cg04795638 | 17 | 15468098 | Lower in Smoker |
| cg03584879 | 10 | 86224508 | Lower in Smoker |
| cg01471006 | 10 | 86087566 | Lower in Smoker |
| ch.4.1114693 | 4 | 2705309 | Higher in Smoker |
| cg05083414 | 4 | 2627039 | Lower in Smoker |
| cg00097088 | 4 | 2627246 | Lower in Smoker |
| cg17393458 | 5 | 176982009 | Lower in Smoker |
| cg05700348 | 5 | 176948150 | Lower in Smoker |
| cg13683440 | 3 | 150421878 | Higher in Smoker |
| cg00318796 | 3 | 68057025 | Higher in Smoker |
| cg03858703 | 3 | 68316096 | Lower in Smoker |
| cg02922094 | 7 | 113262512 | Lower in Smoker |
| cg09868336 | 3 | 68981866 | Higher in Smoker |
| cg12417685 | 3 | 68981852 | Higher in Smoker |
| cg12412079 | 3 | 68961877 | Higher in Smoker |
| cg12219082 | 3 | 68981854 | Higher in Smoker |
| cg01616797 | 22 | 48959190 | Lower in Smoker |
| cg02805639 | 22 | 48970993 | Higher in Smoker |
| cg18406700 | 6 | 116833441 | Lower in Smoker |
| cg02389323 | 16 | 88786976 | Higher in Smoker |
| cg09786329 | 16 | 88821445 | Lower in Smoker |
| cg01011276 | 16 | 88816022 | Lower in Smoker |
| cg06261925 | 16 | 88786114 | Lower in Smoker |
| cg20431676 | 16 | 88815953 | Lower in Smoker |
| cg03895784 | 16 | 88822883 | Lower in Smoker |
| cg02167678 | 16 | 88815867 | Lower in Smoker |
| cg02823132 | 16 | 88805054 | Lower in Smoker |
| cg02603662 | 16 | 88800103 | Lower in Smoker |
| cg04602696 | 16 | 88846723 | Lower in Smoker |
| cg15822387 | 1 | 110577200 | Higher in Smoker |
| cg04241844 | 1 | 20878380 | Lower in Smoker |
| cg23922819 | 1 | 27335739 | Lower in Smoker |
| cg25894334 | 4 | 77172836 | Higher in Smoker |
| cg20077155 | 4 | 77172699 | Higher in Smoker |
| cg19337295 | 13 | 37633341 | Higher in Smoker |

| | | | |
|---|---|---|---|
| cg21744973 | X | 24332146 | Higher in Smoker |
| cg19482842 | 2 | 16790314 | Higher in Smoker |
| cg05786381 | 4 | 1677882 | Higher in Smoker |
| cg04330884 | 10 | 126339578 | Lower in Smoker |
| cg15044573 | 10 | 126434204 | Lower in Smoker |
| cg17879101 | 10 | 126329354 | Lower in Smoker |
| cg06561892 | 5 | 137679726 | Lower in Smoker |
| cg09682190 | 6 | 136571455 | Higher in Smoker |
| cg14280627 | 1 | 26146449 | Higher in Smoker |
| cg09404911 | 3 | 101498279 | Higher in Smoker |
| cg15554898 | 3 | 101498198 | Higher in Smoker |
| cg06073471 | 3 | 101497857 | Higher in Smoker |
| cg12103453 | 17 | 635598 | Higher in Smoker |
| cg26173420 | 17 | 639409 | Lower in Smoker |
| cg07245700 | 16 | 30041013 | Lower in Smoker |
| cg14385280 | 18 | 30051183 | Higher in Smoker |
| cg14482684 | 18 | 30051176 | Higher in Smoker |
| cg01931994 | 1 | 177225850 | Higher in Smoker |
| cg03184588 | 12 | 31480300 | Higher in Smoker |
| cg16285215 | 12 | 31477228 | Higher in Smoker |
| cg21937128 | 1 | 150971889 | Higher in Smoker |
| cg05156742 | 15 | 59063176 | Higher in Smoker |
| cg08354309 | 15 | 59065586 | Higher in Smoker |
| cg06636971 | 6 | 24911553 | Higher in Smoker |
| cg23973566 | 6 | 24877729 | Lower in Smoker |
| cg19623429 | 12 | 8332737 | Higher in Smoker |
| cg15495124 | 1 | 93427847 | Higher in Smoker |
| cg25179170 | 1 | 93427589 | Higher in Smoker |
| cg11993230 | 18 | 72123607 | Higher in Smoker |
| cg10635722 | 12 | 100041844 | Lower in Smoker |
| cg19619331 | 7 | 128311783 | Lower in Smoker |
| cg10439914 | 1 | 206137759 | Higher in Smoker |
| cg15723641 | 1 | 78245331 | Higher in Smoker |
| cg09823721 | 1 | 28052398 | Higher in Smoker |
| cg18936052 | 1 | 28051702 | Lower in Smoker |

| | | | |
|---|---|---|---|
| cg03412097 | 11 | 95524327 | Higher in Smoker |
| cg02178585 | 2 | 38155457 | Lower in Smoker |
| cg18852899 | 2 | 38154797 | Lower in Smoker |
| cg26914927 | 2 | 38156004 | Lower in Smoker |
| cg10246038 | 2 | 38244725 | Lower in Smoker |
| cg05761971 | 2 | 38177677 | Lower in Smoker |
| cg25225841 | 15 | 41039134 | Lower in Smoker |
| cg05427907 | 8 | 124216259 | Lower in Smoker |
| cg16922340 | 20 | 33873526 | Lower in Smoker |
| cg15195292 | 20 | 37554840 | Higher in Smoker |
| cg05458609 | 22 | 40417760 | Lower in Smoker |
| cg13911690 | 8 | 144810854 | Higher in Smoker |
| cg01854491 | 8 | 144815021 | Lower in Smoker |
| cg13015300 | 16 | 5147952 | Higher in Smoker |
| cg10694761 | 8 | 12052206 | Higher in Smoker |
| cg03258364 | 8 | 12295064 | Higher in Smoker |
| cg11371122 | 8 | 12294468 | Higher in Smoker |
| cg04682787 | 11 | 65339779 | Higher in Smoker |
| cg05528131 | 6 | 17599948 | Lower in Smoker |
| cg05954614 | 12 | 8380785 | Lower in Smoker |
| cg02854515 | 12 | 8380360 | Lower in Smoker |
| cg16734947 | 8 | 124780351 | Higher in Smoker |
| cg26785230 | 16 | 66969735 | Higher in Smoker |
| cg04039667 | 16 | 66968153 | Higher in Smoker |
| cg04677537 | 19 | 38893516 | Higher in Smoker |
| cg01666573 | X | 8769701 | Lower in Smoker |
| cg06116593 | X | 13058358 | Lower in Smoker |
| cg07648498 | 16 | 89883185 | Higher in Smoker |
| cg13791971 | 9 | 97945584 | Lower in Smoker |
| cg24104099 | 3 | 10068264 | Higher in Smoker |
| cg05576539 | 9 | 35080212 | Higher in Smoker |
| cg13933729 | 9 | 35076434 | Lower in Smoker |
| cg10856972 | 2 | 163040992 | Lower in Smoker |
| cg04981208 | 2 | 163077401 | Lower in Smoker |
| cg00347673 | 2 | 163033514 | Lower in Smoker |

| | | | |
|---|---|---|---|
| cg14222432 | 12 | 29376421 | Lower in Smoker |
| cg24684709 | 2 | 242298761 | Lower in Smoker |
| cg02306493 | 19 | 13044967 | Lower in Smoker |
| cg06450397 | 10 | 90749255 | Higher in Smoker |
| cg23621652 | 2 | 207630148 | Higher in Smoker |
| cg20931060 | 4 | 187557879 | Lower in Smoker |
| cg02018180 | 5 | 150910600 | Lower in Smoker |
| cg01119912 | 5 | 150911450 | Lower in Smoker |
| cg13677577 | 5 | 150911349 | Lower in Smoker |
| cg00599601 | 5 | 150912396 | Lower in Smoker |
| cg04907084 | 11 | 92498796 | Lower in Smoker |
| cg16691477 | 11 | 64889790 | Lower in Smoker |
| cg07572592 | 17 | 73937177 | Higher in Smoker |
| cg20012089 | 17 | 73936804 | Higher in Smoker |
| cg12068257 | 1 | 16091149 | Higher in Smoker |
| cg02099543 | 22 | 45899186 | Higher in Smoker |
| cg16818414 | 22 | 45898966 | Higher in Smoker |
| cg11229230 | 2 | 112944829 | Higher in Smoker |
| cg00930628 | 2 | 112895793 | Lower in Smoker |
| cg23000950 | 15 | 48785738 | Lower in Smoker |
| cg13740339 | 9 | 97400757 | Higher in Smoker |
| cg24333422 | 9 | 97402058 | Higher in Smoker |
| cg27013931 | 16 | 30674490 | Lower in Smoker |
| cg24906420 | 12 | 133133512 | Higher in Smoker |
| cg16038107 | 12 | 133066646 | Higher in Smoker |
| cg19026573 | 12 | 133137360 | Higher in Smoker |
| cg15473325 | 12 | 133137087 | Higher in Smoker |
| cg24462656 | 12 | 133156510 | Lower in Smoker |
| cg03700001 | 12 | 133073220 | Lower in Smoker |
| cg00638311 | 12 | 133100714 | Lower in Smoker |
| cg27655716 | 12 | 133100670 | Lower in Smoker |
| cg08500417 | 7 | 102574445 | Lower in Smoker |
| cg22151768 | 12 | 1702874 | Higher in Smoker |
| cg17824906 | 12 | 1700011 | Lower in Smoker |
| cg02334987 | 16 | 751450 | Lower in Smoker |

| | | | |
|---|---|---|---|
| cg03349020 | 16 | 744861 | Lower in Smoker |
| cg07482202 | 16 | 745687 | Lower in Smoker |
| cg19918145 | 5 | 107271174 | Lower in Smoker |
| cg26246796 | 5 | 107292051 | Lower in Smoker |
| cg02086523 | 5 | 107717630 | Higher in Smoker |
| cg09004351 | 7 | 5515555 | Lower in Smoker |
| cg08236912 | 17 | 37557587 | Higher in Smoker |
| cg01305981 | 5 | 135266673 | Higher in Smoker |
| cg14827778 | 5 | 135266896 | Higher in Smoker |
| cg05674466 | 15 | 63893895 | Higher in Smoker |
| cg00494066 | 13 | 77601485 | Higher in Smoker |
| cg12604490 | 6 | 99373813 | Higher in Smoker |
| cg19290902 | 6 | 99396345 | Lower in Smoker |
| cg16628918 | 8 | 145580818 | Lower in Smoker |
| cg01149929 | 5 | 15750836 | Lower in Smoker |
| cg11918372 | 2 | 48132755 | Higher in Smoker |
| cg00895070 | 18 | 71812699 | Lower in Smoker |
| cg24372565 | 18 | 71815078 | Higher in Smoker |
| cg18792022 | 1 | 11709271 | Higher in Smoker |
| cg25430671 | 1 | 11714784 | Higher in Smoker |
| cg18466965 | 12 | 117628589 | Higher in Smoker |
| cg06609997 | 12 | 117628469 | Higher in Smoker |
| cg00088026 | 12 | 117628347 | Higher in Smoker |
| cg26035463 | 12 | 117627651 | Higher in Smoker |
| cg02197293 | 19 | 39523158 | Lower in Smoker |
| cg09318521 | 1 | 224301995 | Higher in Smoker |
| cg26043391 | 1 | 224302174 | Higher in Smoker |
| cg20998770 | 6 | 146136106 | Higher in Smoker |
| cg05196076 | 16 | 87404139 | Higher in Smoker |
| cg27548450 | 16 | 87387229 | Higher in Smoker |
| cg15998800 | 14 | 55738852 | Higher in Smoker |
| cg24787443 | 5 | 147781634 | Higher in Smoker |
| cg15335117 | 5 | 41925216 | Higher in Smoker |
| cg13491192 | 1 | 16679149 | Higher in Smoker |
| cg03978675 | 1 | 16679500 | Lower in Smoker |

| | | | |
|---|---|---|---|
| cg04290747 | 1 | 11715197 | Higher in Smoker |
| cg12119068 | 19 | 46230553 | Lower in Smoker |
| cg14765172 | 6 | 153304972 | Higher in Smoker |
| cg25401754 | 6 | 153304305 | Higher in Smoker |
| cg00220769 | 6 | 153305382 | Lower in Smoker |
| cg04708391 | 4 | 175177265 | Lower in Smoker |
| cg07640645 | 4 | 175204879 | Higher in Smoker |
| cg04739134 | 6 | 52930747 | Higher in Smoker |
| cg04487714 | 6 | 52929660 | Higher in Smoker |
| cg16076651 | 6 | 52930071 | Lower in Smoker |
| cg01411725 | 17 | 18646832 | Lower in Smoker |
| cg24676969 | 5 | 171408783 | Lower in Smoker |
| cg11409572 | 10 | 103453901 | Higher in Smoker |
| cg05656770 | 9 | 139838089 | Lower in Smoker |
| cg18222235 | 12 | 117348646 | Higher in Smoker |
| cg02973792 | 12 | 117408122 | Lower in Smoker |
| cg10065736 | 12 | 117440120 | Lower in Smoker |
| cg18412326 | 19 | 1280767 | Higher in Smoker |
| cg21415060 | 1 | 159277295 | Lower in Smoker |
| cg24465943 | 1 | 161185061 | Higher in Smoker |
| cg09965679 | 14 | 75179859 | Higher in Smoker |
| cg26649232 | 19 | 40430595 | Lower in Smoker |
| cg17784516 | 19 | 40380853 | Lower in Smoker |
| cg00586700 | 19 | 50015178 | Higher in Smoker |
| cg08358907 | 19 | 17877508 | Lower in Smoker |
| cg17372738 | 5 | 72252437 | Lower in Smoker |
| cg02889437 | 11 | 72614724 | Lower in Smoker |
| cg16816400 | 9 | 137809991 | Higher in Smoker |
| cg00394221 | 1 | 157772525 | Lower in Smoker |
| cg11810135 | 1 | 157771971 | Lower in Smoker |
| cg05784088 | 1 | 157738458 | Lower in Smoker |
| cg12282588 | 1 | 157737828 | Lower in Smoker |
| cg05777583 | 1 | 157716415 | Lower in Smoker |
| cg24881910 | 1 | 157672074 | Lower in Smoker |
| cg07184316 | 1 | 157669111 | Lower in Smoker |

| | | | |
|---|---|---|---|
| cg15202552 | 1 | 157671759 | Lower in Smoker |
| cg13380622 | 1 | 157557578 | Lower in Smoker |
| cg12903648 | 1 | 157522570 | Higher in Smoker |
| cg00248302 | 1 | 157490756 | Lower in Smoker |
| cg10313167 | 1 | 157485456 | Lower in Smoker |
| cg18884942 | 1 | 161679921 | Lower in Smoker |
| cg15836394 | 8 | 11659832 | Higher in Smoker |
| cg14026927 | 1 | 155278455 | Higher in Smoker |
| cg10414747 | 11 | 110299159 | Lower in Smoker |
| cg02239377 | 11 | 110334097 | Lower in Smoker |
| cg02764611 | 19 | 10426516 | Higher in Smoker |
| cg21592158 | 11 | 111750640 | Lower in Smoker |
| cg15075985 | 19 | 4791566 | Higher in Smoker |
| cg17617946 | 5 | 114879806 | Higher in Smoker |
| cg08873353 | 11 | 61560534 | Higher in Smoker |
| cg15870379 | 5 | 108099747 | Lower in Smoker |
| cg22433521 | 20 | 34191237 | Lower in Smoker |
| cg23242649 | 20 | 34196465 | Lower in Smoker |
| cg02503874 | 7 | 19184427 | Higher in Smoker |
| cg10334927 | 14 | 53418112 | Lower in Smoker |
| cg07682037 | 11 | 63974153 | Higher in Smoker |
| cg00021256 | 2 | 219848373 | Higher in Smoker |
| cg20031656 | 11 | 125366267 | Higher in Smoker |
| cg11324054 | 2 | 36825448 | Higher in Smoker |
| cg03981954 | 7 | 121942010 | Higher in Smoker |
| cg18633561 | 7 | 121943354 | Higher in Smoker |
| cg18902742 | 3 | 62358610 | Higher in Smoker |
| cg23170483 | X | 54508656 | Lower in Smoker |
| cg08507806 | 6 | 36996068 | Lower in Smoker |
| cg16373643 | 3 | 14889308 | Lower in Smoker |
| cg04943612 | 3 | 14860482 | Lower in Smoker |
| cg05173159 | 12 | 95491799 | Lower in Smoker |
| cg21182715 | 12 | 95567919 | Lower in Smoker |
| cg19683675 | 5 | 142077712 | Lower in Smoker |
| cg19056772 | 17 | 7341616 | Higher in Smoker |

| | | | |
|---|---|---|---|
| cg05513300 | 17 | 7345301 | Lower in Smoker |
| cg11201710 | 3 | 192232468 | Higher in Smoker |
| cg22830694 | 3 | 192417927 | Lower in Smoker |
| cg24172416 | 13 | 102572252 | Higher in Smoker |
| cg22809871 | 13 | 102572229 | Higher in Smoker |
| cg06313119 | 13 | 103046736 | Higher in Smoker |
| cg10069736 | 13 | 102929516 | Lower in Smoker |
| cg16654732 | 5 | 170846517 | Higher in Smoker |
| cg03737760 | 11 | 69517841 | Higher in Smoker |
| cg03941587 | 4 | 123747634 | Lower in Smoker |
| cg11327857 | 4 | 123747558 | Lower in Smoker |
| cg02775417 | 19 | 643457 | Lower in Smoker |
| cg14119236 | 12 | 4489075 | Lower in Smoker |
| cg23219570 | 12 | 4488893 | Higher in Smoker |
| cg15119027 | 11 | 69634363 | Higher in Smoker |
| cg00043379 | 11 | 69634240 | Higher in Smoker |
| cg00022558 | 11 | 69590287 | Higher in Smoker |
| cg23964057 | 11 | 69590113 | Lower in Smoker |
| cg02583247 | 12 | 4555311 | Lower in Smoker |
| cg10155026 | 12 | 4553029 | Lower in Smoker |
| cg12052250 | 10 | 103530237 | Higher in Smoker |
| cg17530673 | 10 | 93667938 | Higher in Smoker |
| cg15321288 | 8 | 38326400 | Higher in Smoker |
| cg17643699 | 12 | 27091484 | Higher in Smoker |
| cg00907756 | 4 | 1803077 | Lower in Smoker |
| cg08145949 | 4 | 1798209 | Lower in Smoker |
| cg13131329 | 4 | 1801148 | Lower in Smoker |
| cg17386911 | 5 | 176523180 | Higher in Smoker |
| cg27002826 | 5 | 176520024 | Lower in Smoker |
| cg17105609 | 4 | 1006237 | Higher in Smoker |
| cg06839424 | 4 | 1007283 | Lower in Smoker |
| cg02851034 | 1 | 59937877 | Higher in Smoker |
| cg22866068 | 1 | 59842365 | Lower in Smoker |
| cg16922167 | 1 | 27961746 | Higher in Smoker |
| cg12465678 | 1 | 27953336 | Higher in Smoker |

| | | | |
|---|---|---|---|
| cg26586917 | 4 | 153899740 | Lower in Smoker |
| cg11158760 | 3 | 61237270 | Higher in Smoker |
| cg25921543 | 3 | 59980762 | Lower in Smoker |
| cg19282443 | 3 | 60541935 | Lower in Smoker |
| cg21374587 | X | 135278952 | Lower in Smoker |
| cg02092708 | 6 | 97063714 | Lower in Smoker |
| cg14675869 | 18 | 34340941 | Lower in Smoker |
| cg14532376 | 9 | 133799686 | Lower in Smoker |
| cg02530222 | 9 | 133794590 | Lower in Smoker |
| cg13718100 | 9 | 133796449 | Lower in Smoker |
| cg13033853 | 9 | 133814399 | Lower in Smoker |
| cg07777008 | 11 | 27015808 | Higher in Smoker |
| cg14783074 | 11 | 65652435 | Lower in Smoker |
| cg16019558 | 6 | 110104633 | Lower in Smoker |
| cg13358623 | X | 15402593 | Lower in Smoker |
| cg22573003 | X | 15402648 | Lower in Smoker |
| cg04760602 | 4 | 54243733 | Higher in Smoker |
| cg24466109 | 4 | 54244549 | Higher in Smoker |
| cg02987906 | 4 | 54243303 | Lower in Smoker |
| cg17603857 | 19 | 56111499 | Higher in Smoker |
| cg08361684 | 11 | 35641255 | Higher in Smoker |
| cg26750927 | 17 | 39977959 | Lower in Smoker |
| cg09471280 | 17 | 39968804 | Higher in Smoker |
| cg03466032 | 17 | 39968802 | Higher in Smoker |
| cg14688751 | 7 | 30066350 | Higher in Smoker |
| cg00284173 | 2 | 24273093 | Higher in Smoker |
| cg24177057 | 11 | 64009406 | Higher in Smoker |
| cg23801475 | 11 | 64009419 | Higher in Smoker |
| cg09217565 | 14 | 45605027 | Higher in Smoker |
| cg08501815 | 12 | 2903984 | Higher in Smoker |
| cg01044331 | 12 | 2904352 | Higher in Smoker |
| cg04915277 | 12 | 2904111 | Higher in Smoker |
| cg00502241 | 19 | 18642658 | Lower in Smoker |
| cg26686415 | 7 | 32996816 | Higher in Smoker |
| cg02953960 | 7 | 53756785 | Higher in Smoker |

| | | | |
|---|---|---|---|
| cg20822606 | 6 | 32098077 | Higher in Smoker |
| cg14751180 | 6 | 32097774 | Higher in Smoker |
| cg07968979 | 6 | 27291363 | Lower in Smoker |
| cg17603500 | 1 | 154955711 | Higher in Smoker |
| cg02975142 | 17 | 17140597 | Higher in Smoker |
| cg03465714 | 1 | 152285911 | Lower in Smoker |
| cg11017065 | 11 | 128564874 | Higher in Smoker |
| cg20707279 | 17 | 18162086 | Higher in Smoker |
| cg03916694 | 17 | 18150707 | Lower in Smoker |
| cg18575809 | 14 | 21540329 | Higher in Smoker |
| cg26066597 | 14 | 21540022 | Higher in Smoker |
| cg11603241 | 8 | 3085544 | Higher in Smoker |
| cg00015319 | 12 | 54500832 | Higher in Smoker |
| cg23295636 | 12 | 54494573 | Lower in Smoker |
| cg06216090 | 4 | 38615922 | Lower in Smoker |
| cg18412834 | 20 | 61885291 | Higher in Smoker |
| cg21258057 | 20 | 61885262 | Higher in Smoker |
| cg15571277 | 20 | 61885249 | Higher in Smoker |
| cg08970682 | 4 | 106472990 | Lower in Smoker |
| cg05309399 | 4 | 106552544 | Lower in Smoker |
| cg08233811 | 6 | 21667333 | Higher in Smoker |
| cg16804603 | 6 | 21856613 | Lower in Smoker |
| cg25420132 | 6 | 21762391 | Lower in Smoker |
| cg15943139 | 6 | 22061708 | Lower in Smoker |
| cg25302087 | 6 | 21668049 | Lower in Smoker |
| cg26715571 | 19 | 50554280 | Higher in Smoker |
| cg26257814 | 19 | 50553708 | Lower in Smoker |
| cg26429530 | 14 | 58765206 | Higher in Smoker |
| cg06550057 | 2 | 200336200 | Higher in Smoker |
| cg08373323 | 11 | 100624415 | Lower in Smoker |
| cg02328035 | 5 | 6338017 | Lower in Smoker |
| cg06100461 | 13 | 52419380 | Higher in Smoker |
| cg07363130 | 1 | 16161673 | Higher in Smoker |
| cg14793291 | 1 | 16176059 | Higher in Smoker |
| cg11553591 | 22 | 21356472 | Higher in Smoker |

| | | | |
|---|---|---|---|
| cg14577840 | 4 | 16257979 | Lower in Smoker |
| cg15475840 | 10 | 102995719 | Higher in Smoker |
| cg18153816 | 10 | 102998117 | Higher in Smoker |
| cg23645302 | 4 | 69084723 | Lower in Smoker |
| cg24045574 | 5 | 148961311 | Higher in Smoker |
| cg22179015 | 5 | 148960866 | Higher in Smoker |
| cg10876003 | 22 | 18512005 | Lower in Smoker |
| cg19046697 | 5 | 92915581 | Higher in Smoker |
| cg11853830 | 5 | 92914036 | Higher in Smoker |
| cg01779765 | 14 | 62583795 | Higher in Smoker |
| cg18655384 | 14 | 62583787 | Higher in Smoker |
| cg17437088 | 7 | 130698670 | Lower in Smoker |
| cg25697881 | 8 | 142517341 | Lower in Smoker |
| cg14415066 | 14 | 69950574 | Higher in Smoker |
| cg04990472 | 14 | 69950043 | Lower in Smoker |
| cg11610614 | 17 | 75877811 | Higher in Smoker |
| cg19315863 | 10 | 8096597 | Higher in Smoker |
| cg05071898 | 10 | 8095723 | Higher in Smoker |
| cg20314737 | 10 | 8096579 | Higher in Smoker |
| cg14773858 | X | 153603488 | Lower in Smoker |
| cg01698523 | X | 153583936 | Lower in Smoker |
| cg13605542 | 3 | 58110814 | Lower in Smoker |
| cg01940964 | 7 | 128471600 | Higher in Smoker |
| cg11590760 | 7 | 128470419 | Higher in Smoker |
| cg15904623 | 7 | 128488744 | Lower in Smoker |
| cg02182754 | 6 | 30699363 | Lower in Smoker |
| cg16717099 | 6 | 30710901 | Lower in Smoker |
| cg17568035 | 17 | 27224811 | Higher in Smoker |
| cg18845692 | 14 | 85996274 | Higher in Smoker |
| cg21571339 | 14 | 86001111 | Higher in Smoker |
| cg04862347 | 14 | 86001058 | Higher in Smoker |
| cg18919660 | 14 | 86032626 | Lower in Smoker |
| cg02188358 | 13 | 29068150 | Higher in Smoker |
| cg03247926 | 13 | 29069623 | Higher in Smoker |
| cg22708853 | 19 | 49977670 | Higher in Smoker |

| | | | |
|---|---|---|---|
| cg03730027 | 5 | 180041908 | Higher in Smoker |
| cg23297812 | 5 | 180046901 | Lower in Smoker |
| cg05940146 | 14 | 76097639 | Lower in Smoker |
| cg16412228 | 16 | 2941920 | Lower in Smoker |
| cg01245965 | 15 | 33278159 | Lower in Smoker |
| cg16146288 | 15 | 33148913 | Lower in Smoker |
| cg13736722 | 15 | 33066894 | Lower in Smoker |
| cg21617353 | 17 | 43319371 | Lower in Smoker |
| cg19332832 | 2 | 153191675 | Higher in Smoker |
| cg19529604 | 2 | 153246184 | Lower in Smoker |
| cg05880452 | 2 | 153191031 | Lower in Smoker |
| cg12226948 | 2 | 153504453 | Lower in Smoker |
| cg25880810 | 2 | 153428373 | Lower in Smoker |
| cg22923154 | 2 | 153266693 | Lower in Smoker |
| cg11172396 | 2 | 153295007 | Lower in Smoker |
| cg26207245 | 2 | 153347526 | Lower in Smoker |
| cg26676845 | 2 | 153280733 | Lower in Smoker |
| cg14261271 | 2 | 153268704 | Lower in Smoker |
| cg04215359 | 2 | 153381623 | Lower in Smoker |
| cg05935184 | 2 | 153350189 | Lower in Smoker |
| cg08268047 | 1 | 171156996 | Lower in Smoker |
| cg09040552 | 2 | 216298121 | Lower in Smoker |
| cg26950867 | 2 | 216299856 | Lower in Smoker |
| cg04587829 | 17 | 80692947 | Higher in Smoker |
| cg20053493 | 11 | 47776175 | Lower in Smoker |
| cg16316344 | 11 | 47738494 | Lower in Smoker |
| cg07264814 | 5 | 131129382 | Lower in Smoker |
| cg05615763 | 4 | 159689701 | Higher in Smoker |
| cg11484283 | 4 | 159816181 | Lower in Smoker |
| cg25542244 | 8 | 42910303 | Lower in Smoker |
| cg26750747 | 11 | 71899966 | Lower in Smoker |
| cg11872076 | 14 | 75744010 | Higher in Smoker |
| cg10232345 | 14 | 75745634 | Higher in Smoker |
| cg24397007 | 2 | 28619094 | Higher in Smoker |
| cg09538961 | 2 | 28616570 | Higher in Smoker |

| | | | |
|---|---|---|---|
| cg22777952 | 15 | 60296425 | Higher in Smoker |
| cg08451957 | 2 | 114256406 | Higher in Smoker |
| cg02157015 | 9 | 100615244 | Higher in Smoker |
| cg27175287 | 1 | 47883234 | Lower in Smoker |
| cg00314966 | 16 | 86544346 | Higher in Smoker |
| cg07769121 | 16 | 86543519 | Higher in Smoker |
| cg05555338 | 16 | 86542964 | Higher in Smoker |
| cg03492747 | 16 | 86543308 | Higher in Smoker |
| cg26174583 | 6 | 1392624 | Lower in Smoker |
| cg17525102 | 14 | 29236221 | Higher in Smoker |
| cg16804284 | 14 | 29237480 | Higher in Smoker |
| cg10828337 | 14 | 29236476 | Higher in Smoker |
| cg27111463 | 2 | 88751405 | Higher in Smoker |
| cg23511613 | 2 | 88752322 | Higher in Smoker |
| cg23638801 | 17 | 74137520 | Higher in Smoker |
| cg13443843 | 1 | 42797239 | Lower in Smoker |
| cg24377558 | 1 | 42801138 | Lower in Smoker |
| cg06660057 | 7 | 4762371 | Higher in Smoker |
| cg04160501 | 7 | 4723667 | Higher in Smoker |
| cg25350986 | 7 | 4762844 | Higher in Smoker |
| cg07180538 | 7 | 4786899 | Lower in Smoker |
| cg05308424 | 7 | 4800594 | Lower in Smoker |
| cg10626959 | 7 | 4800797 | Lower in Smoker |
| cg01541347 | 7 | 4729920 | Lower in Smoker |
| cg26176014 | 17 | 80491645 | Lower in Smoker |
| cg05945266 | 17 | 80545020 | Lower in Smoker |
| cg02796939 | 17 | 80545125 | Lower in Smoker |
| cg11293699 | 3 | 138666473 | Higher in Smoker |
| cg20461912 | 3 | 138664350 | Higher in Smoker |
| cg08971724 | 12 | 2983426 | Lower in Smoker |
| cg24412006 | 12 | 109728152 | Lower in Smoker |
| cg03278811 | 6 | 108883330 | Higher in Smoker |
| cg07580479 | 6 | 108913822 | Lower in Smoker |
| cg03583643 | 3 | 71114116 | Higher in Smoker |
| cg13726313 | 3 | 71201264 | Lower in Smoker |

| | | | |
|---|---|---|---|
| cg21379733 | 3 | 71136296 | Lower in Smoker |
| cg07516697 | 3 | 71631212 | Higher in Smoker |
| cg25457604 | 3 | 71332437 | Lower in Smoker |
| cg09459774 | 3 | 71457237 | Lower in Smoker |
| cg05734456 | 6 | 41516035 | Lower in Smoker |
| cg19405941 | 11 | 118841080 | Lower in Smoker |
| cg27066155 | 11 | 126139048 | Higher in Smoker |
| cg01402409 | 4 | 78978133 | Lower in Smoker |
| cg18929663 | 4 | 79102707 | Lower in Smoker |
| cg19418525 | 4 | 79077191 | Lower in Smoker |
| cg24399830 | 13 | 39260633 | Higher in Smoker |
| cg08141612 | 20 | 29611676 | Higher in Smoker |
| cg07525313 | 6 | 116262856 | Lower in Smoker |
| cg25996663 | 6 | 116290520 | Lower in Smoker |
| cg05888872 | 10 | 14050479 | Higher in Smoker |
| cg20130213 | 10 | 13934169 | Higher in Smoker |
| cg00296121 | 10 | 13933247 | Higher in Smoker |
| cg15658978 | 10 | 13736020 | Higher in Smoker |
| cg18698819 | 10 | 13736003 | Higher in Smoker |
| cg23016080 | 15 | 44486450 | Lower in Smoker |
| cg15434023 | 14 | 52066950 | Lower in Smoker |
| cg16074393 | 14 | 52116710 | Lower in Smoker |
| cg23549641 | 14 | 51994091 | Lower in Smoker |
| cg00820637 | 14 | 51955005 | Lower in Smoker |
| cg07612928 | 14 | 51956044 | Lower in Smoker |
| cg06647694 | X | 131261385 | Higher in Smoker |
| cg23085281 | 10 | 49459949 | Lower in Smoker |
| cg22670503 | 10 | 49482695 | Lower in Smoker |
| cg04913666 | 12 | 69908322 | Lower in Smoker |
| cg04937857 | 12 | 69863677 | Lower in Smoker |
| cg24346858 | 6 | 41738686 | Lower in Smoker |
| cg19878568 | 6 | 41741219 | Lower in Smoker |
| cg22219254 | 13 | 32605406 | Higher in Smoker |
| cg07317641 | 2 | 183731944 | Higher in Smoker |
| cg09084279 | 17 | 79495006 | Lower in Smoker |

| | | | |
|---|---|---|---|
| cg05424970 | 7 | 127233574 | Lower in Smoker |
| cg13990129 | 9 | 108311111 | Lower in Smoker |
| cg13794553 | 9 | 108210689 | Higher in Smoker |
| cg18822411 | 15 | 40075102 | Higher in Smoker |
| cg17744835 | 15 | 40064068 | Lower in Smoker |
| cg04582364 | 5 | 52778441 | Higher in Smoker |
| cg07368396 | 5 | 132945815 | Lower in Smoker |
| cg01734786 | 4 | 163085663 | Higher in Smoker |
| cg21230535 | 21 | 47556290 | Lower in Smoker |
| cg10394047 | 21 | 47575416 | Lower in Smoker |
| cg14341051 | 21 | 47562057 | Lower in Smoker |
| cg18090198 | X | 51090374 | Lower in Smoker |
| cg09441819 | 5 | 121186479 | Lower in Smoker |
| cg26746331 | 16 | 53737506 | Higher in Smoker |
| cg02172222 | 7 | 2274545 | Lower in Smoker |
| cg20631595 | 7 | 2282104 | Higher in Smoker |
| cg04398916 | 16 | 71323367 | Higher in Smoker |
| cg22814740 | 1 | 78442554 | Lower in Smoker |
| cg16906859 | 1 | 24191987 | Lower in Smoker |
| cg08896387 | 1 | 24191740 | Lower in Smoker |
| cg12306853 | 6 | 143833173 | Lower in Smoker |
| cg12980185 | X | 154255174 | Higher in Smoker |
| cg22654949 | 19 | 49198516 | Lower in Smoker |
| cg18062651 | 19 | 5841170 | Lower in Smoker |
| cg21967545 | 19 | 5833807 | Higher in Smoker |
| cg18266771 | 14 | 66026095 | Lower in Smoker |
| cg14621161 | 6 | 96573489 | Lower in Smoker |
| cg11006156 | 11 | 6502714 | Higher in Smoker |
| cg05529097 | 17 | 7518511 | Higher in Smoker |
| cg07780528 | 19 | 35630334 | Lower in Smoker |
| cg15929395 | 11 | 117695828 | Higher in Smoker |
| cg18232841 | 19 | 35615103 | Lower in Smoker |
| cg22524864 | 19 | 35561900 | Higher in Smoker |
| cg04619627 | 3 | 46037496 | Higher in Smoker |
| cg04222917 | 6 | 112021676 | Lower in Smoker |

| | | | |
|---|---|---|---|
| cg23191380 | 7 | 90393747 | Lower in Smoker |
| cg20301962 | 17 | 42636006 | Higher in Smoker |
| cg14011663 | 2 | 208634169 | Higher in Smoker |
| cg25727306 | 2 | 208634186 | Higher in Smoker |
| cg05774672 | 2 | 208631916 | Lower in Smoker |
| cg01445942 | 7 | 72847976 | Higher in Smoker |
| cg19224938 | 19 | 3530957 | Lower in Smoker |
| cg00316677 | 5 | 151151425 | Higher in Smoker |
| cg06808983 | 17 | 42148292 | Higher in Smoker |
| cg04780294 | 17 | 78075547 | Higher in Smoker |
| cg05754631 | 4 | 144258809 | Higher in Smoker |
| cg10227830 | 4 | 144332828 | Lower in Smoker |
| cg10042298 | 11 | 78024311 | Lower in Smoker |
| cg06625174 | X | 153979792 | Lower in Smoker |
| cg00294149 | 16 | 75604552 | Higher in Smoker |
| cg01453816 | 6 | 29600108 | Higher in Smoker |
| cg03063957 | 6 | 29585617 | Lower in Smoker |
| cg12055610 | 6 | 29585658 | Lower in Smoker |
| cg20486977 | 6 | 29594481 | Lower in Smoker |
| cg21026120 | 6 | 29581121 | Lower in Smoker |
| cg18004110 | 6 | 29589729 | Lower in Smoker |
| cg02014853 | 6 | 29595335 | Lower in Smoker |
| cg01777786 | 21 | 27120614 | Lower in Smoker |
| cg17813475 | 15 | 50589763 | Lower in Smoker |
| cg25176742 | 15 | 50647253 | Higher in Smoker |
| cg24860775 | 5 | 161275745 | Higher in Smoker |
| cg02065387 | 5 | 161274307 | Higher in Smoker |
| cg21757920 | 5 | 161285320 | Lower in Smoker |
| cg02620694 | 4 | 46391436 | Higher in Smoker |
| cg14778074 | 4 | 46391448 | Higher in Smoker |
| cg14411873 | 4 | 46391532 | Higher in Smoker |
| cg00452958 | 4 | 46391259 | Higher in Smoker |
| cg24995836 | X | 151619390 | Higher in Smoker |
| cg22345214 | 4 | 46995509 | Higher in Smoker |
| cg02912913 | 15 | 27128279 | Lower in Smoker |

| | | | |
|---|---|---|---|
| cg18724037 | 15 | 27127627 | Lower in Smoker |
| cg01101742 | 5 | 160974552 | Higher in Smoker |
| cg02583228 | 15 | 26885279 | Lower in Smoker |
| cg24105782 | 1 | 1957385 | Higher in Smoker |
| cg23283755 | 1 | 1957320 | Higher in Smoker |
| cg00400948 | 1 | 1959442 | Lower in Smoker |
| cg08460080 | 15 | 27215448 | Lower in Smoker |
| cg13132884 | 6 | 90025136 | Lower in Smoker |
| cg00782607 | 2 | 171672156 | Higher in Smoker |
| cg00733780 | 10 | 26505127 | Higher in Smoker |
| cg01485266 | 19 | 2476132 | Higher in Smoker |
| cg21210124 | 9 | 92219187 | Higher in Smoker |
| cg20070077 | 9 | 92219995 | Higher in Smoker |
| cg26361892 | 19 | 13067683 | Higher in Smoker |
| cg06175036 | 4 | 846732 | Higher in Smoker |
| cg08604785 | 4 | 899970 | Lower in Smoker |
| cg24840182 | 4 | 843344 | Lower in Smoker |
| cg24780007 | 4 | 851935 | Lower in Smoker |
| cg22140614 | 4 | 867730 | Lower in Smoker |
| cg22051586 | 4 | 881820 | Lower in Smoker |
| cg19800605 | 4 | 903531 | Lower in Smoker |
| cg09151583 | 4 | 881283 | Lower in Smoker |
| cg11308921 | 4 | 867560 | Lower in Smoker |
| cg09022808 | 22 | 30960857 | Lower in Smoker |
| cg03462699 | 2 | 242743214 | Higher in Smoker |
| cg17518962 | 7 | 99766552 | Higher in Smoker |
| cg14084312 | 14 | 86459488 | Higher in Smoker |
| cg13789423 | 14 | 86455546 | Lower in Smoker |
| cg04975205 | 1 | 24127260 | Higher in Smoker |
| cg06476228 | 15 | 49447928 | Higher in Smoker |
| cg04551282 | 16 | 88884836 | Higher in Smoker |
| cg16582469 | 16 | 88910141 | Lower in Smoker |
| cg05256999 | 16 | 88902466 | Lower in Smoker |
| cg19031384 | 5 | 153756247 | Lower in Smoker |
| cg01126095 | 5 | 153665707 | Lower in Smoker |

| | | | |
|---|---|---|---|
| cg07835283 | 5 | 153783496 | Lower in Smoker |
| cg13789443 | 7 | 151723607 | Lower in Smoker |
| cg22447839 | 9 | 101569843 | Higher in Smoker |
| cg02593932 | 2 | 154728308 | Higher in Smoker |
| cg03279535 | 2 | 31360817 | Higher in Smoker |
| cg24401487 | 1 | 230416880 | Higher in Smoker |
| cg12526197 | 1 | 230416938 | Higher in Smoker |
| cg12840261 | 1 | 230204191 | Higher in Smoker |
| cg16698674 | 1 | 230272358 | Lower in Smoker |
| cg22811817 | 1 | 230404249 | Lower in Smoker |
| cg17100751 | 1 | 230414293 | Lower in Smoker |
| cg24537836 | 12 | 51782159 | Higher in Smoker |
| cg11369235 | 4 | 174091422 | Higher in Smoker |
| cg09254264 | 12 | 132891706 | Lower in Smoker |
| cg17811894 | 12 | 132897506 | Lower in Smoker |
| cg19598571 | 12 | 132690384 | Lower in Smoker |
| cg15159017 | 12 | 132854526 | Lower in Smoker |
| cg05049361 | 14 | 69726536 | Higher in Smoker |
| cg09068031 | 11 | 11500492 | Lower in Smoker |
| cg21565299 | 7 | 151664071 | Lower in Smoker |
| cg26814276 | 4 | 172734266 | Higher in Smoker |
| cg03304610 | 4 | 172734276 | Higher in Smoker |
| cg20343859 | 4 | 173747801 | Lower in Smoker |
| cg03413465 | 4 | 172734776 | Higher in Smoker |
| cg21574244 | 15 | 42568411 | Lower in Smoker |
| cg19676835 | 3 | 115377773 | Higher in Smoker |
| cg13592373 | 3 | 115396096 | Lower in Smoker |
| cg11508669 | 12 | 6643545 | Higher in Smoker |
| cg17810176 | 19 | 36035831 | Lower in Smoker |
| cg27088473 | 4 | 110739437 | Lower in Smoker |
| cg00342530 | 9 | 130027020 | Higher in Smoker |
| cg00940212 | 7 | 30633751 | Higher in Smoker |
| cg20960443 | 7 | 30634175 | Higher in Smoker |
| cg00543658 | 7 | 30634387 | Higher in Smoker |
| cg08475931 | 7 | 30634393 | Higher in Smoker |

| | | | |
|---|---|---|---|
| cg22542663 | 21 | 34915757 | Higher in Smoker |
| cg12343881 | 22 | 29708647 | Lower in Smoker |
| cg03584783 | 1 | 173836803 | Lower in Smoker |
| cg11851411 | 17 | 10096767 | Lower in Smoker |
| cg11734841 | 17 | 9963861 | Lower in Smoker |
| cg02605292 | 17 | 9936735 | Higher in Smoker |
| cg17479840 | 17 | 9863061 | Higher in Smoker |
| cg23010077 | 17 | 39868441 | Lower in Smoker |
| cg12030231 | X | 48650312 | Lower in Smoker |
| cg23520930 | 3 | 128206967 | Higher in Smoker |
| cg12567615 | 3 | 11609706 | Lower in Smoker |
| cg25793191 | 20 | 61038971 | Lower in Smoker |
| cg09864990 | 20 | 61041274 | Lower in Smoker |
| cg03777459 | 20 | 61051302 | Lower in Smoker |
| cg18632712 | 18 | 19748135 | Higher in Smoker |
| cg08505228 | 19 | 19495962 | Higher in Smoker |
| cg22153745 | 1 | 153894579 | Lower in Smoker |
| cg15272908 | 22 | 30685756 | Higher in Smoker |
| cg19293995 | 22 | 30685271 | Higher in Smoker |
| cg12728516 | 1 | 155197152 | Higher in Smoker |
| cg15011721 | 7 | 56032604 | Higher in Smoker |
| cg16472210 | 3 | 81810621 | Higher in Smoker |
| cg07356753 | 3 | 81810745 | Lower in Smoker |
| cg14653977 | 9 | 136038692 | Higher in Smoker |
| cg15765724 | 2 | 237077151 | Higher in Smoker |
| cg08767286 | 2 | 237077265 | Higher in Smoker |
| cg13387677 | 22 | 38203902 | Higher in Smoker |
| cg00022492 | 15 | 41055530 | Higher in Smoker |
| cg23381646 | 7 | 44187310 | Lower in Smoker |
| cg19144949 | 6 | 53375437 | Lower in Smoker |
| cg14104172 | 9 | 79074807 | Higher in Smoker |
| cg16337108 | 6 | 10584655 | Lower in Smoker |
| cg17658084 | 8 | 75262759 | Higher in Smoker |
| cg00534295 | 1 | 118472370 | Higher in Smoker |
| cg14213160 | 19 | 18496259 | Lower in Smoker |

| | | | |
|---|---|---|---|
| cg10314572 | 20 | 34027000 | Higher in Smoker |
| cg15277906 | 8 | 97170364 | Higher in Smoker |
| cg00535714 | 8 | 97156859 | Higher in Smoker |
| cg02246426 | 8 | 97162431 | Higher in Smoker |
| cg13211683 | 8 | 97171827 | Lower in Smoker |
| cg27141850 | 2 | 20869434 | Higher in Smoker |
| cg07755735 | 2 | 20870362 | Higher in Smoker |
| cg12266953 | 2 | 20866261 | Higher in Smoker |
| cg18946478 | 2 | 20866414 | Higher in Smoker |
| cg07966910 | 2 | 20866399 | Higher in Smoker |
| cg24552128 | 5 | 132200516 | Lower in Smoker |
| cg01043865 | 5 | 37837978 | Higher in Smoker |
| cg20936892 | 17 | 57297306 | Higher in Smoker |
| cg06655504 | 17 | 57297718 | Higher in Smoker |
| cg06598597 | 17 | 57297622 | Lower in Smoker |
| cg13545850 | X | 69650994 | Lower in Smoker |
| cg02364642 | 12 | 58005758 | Higher in Smoker |
| cg26018827 | 2 | 17935443 | Higher in Smoker |
| cg04695436 | 2 | 17934493 | Higher in Smoker |
| cg25061061 | 1 | 92941433 | Lower in Smoker |
| cg09935388 | 1 | 92947588 | Lower in Smoker |
| cg14179389 | 1 | 92947961 | Lower in Smoker |
| cg03802272 | 3 | 158361750 | Lower in Smoker |
| cg07252851 | 5 | 74063056 | Lower in Smoker |
| cg18489719 | 5 | 74063690 | Higher in Smoker |
| cg16090192 | 5 | 74063324 | Higher in Smoker |
| cg18671057 | 6 | 13489248 | Lower in Smoker |
| cg06277588 | 6 | 13489246 | Lower in Smoker |
| cg23939865 | 6 | 13422581 | Lower in Smoker |
| cg10946816 | 6 | 13466329 | Lower in Smoker |
| cg25640176 | 16 | 67752877 | Higher in Smoker |
| cg15899800 | 2 | 69586350 | Lower in Smoker |
| cg26918954 | 5 | 179728553 | Lower in Smoker |
| cg17256532 | 10 | 118031950 | Higher in Smoker |
| cg13890706 | 10 | 118033115 | Higher in Smoker |

| | | | |
|---|---|---|---|
| cg22987590 | 8 | 21645524 | Higher in Smoker |
| cg20521389 | 8 | 21645509 | Higher in Smoker |
| cg05021638 | 8 | 21647026 | Higher in Smoker |
| cg16294000 | 8 | 21638355 | Lower in Smoker |
| cg00902636 | 8 | 21645807 | Higher in Smoker |
| cg21597152 | 20 | 3644719 | Lower in Smoker |
| cg27365823 | 6 | 55263110 | Lower in Smoker |
| cg15756928 | 6 | 55267138 | Lower in Smoker |
| cg23978358 | 6 | 55192049 | Lower in Smoker |
| cg00647403 | 16 | 23521932 | Higher in Smoker |
| cg14427694 | 7 | 30544570 | Higher in Smoker |
| cg10506212 | 2 | 85788810 | Higher in Smoker |
| cg27177195 | 17 | 34945903 | Lower in Smoker |
| cg07814876 | 1 | 235492429 | Higher in Smoker |
| cg03478533 | 22 | 24989059 | Higher in Smoker |
| cg01120527 | 22 | 25003400 | Lower in Smoker |
| cg25706358 | 22 | 18766635 | Lower in Smoker |
| cg00145141 | 17 | 4464022 | Higher in Smoker |
| cg13514050 | 20 | 33460585 | Higher in Smoker |
| cg20594433 | 22 | 22987563 | Lower in Smoker |
| cg12706330 | 10 | 85898700 | Lower in Smoker |
| cg12042587 | 5 | 42423947 | Higher in Smoker |
| cg00837832 | 7 | 31007724 | Lower in Smoker |
| cg00497796 | 3 | 10335844 | Lower in Smoker |
| cg03751527 | 3 | 10335375 | Lower in Smoker |
| cg04924511 | 3 | 10334731 | Lower in Smoker |
| cg09876440 | 3 | 10325981 | Lower in Smoker |
| cg07852825 | 3 | 172166182 | Higher in Smoker |
| cg01361449 | 7 | 100288046 | Lower in Smoker |
| cg13982505 | 2 | 233642094 | Lower in Smoker |
| cg23018117 | 7 | 150413687 | Higher in Smoker |
| cg20990694 | 7 | 150417431 | Higher in Smoker |
| cg00051483 | 7 | 150211811 | Higher in Smoker |
| cg01827098 | 7 | 150211152 | Higher in Smoker |
| cg19063768 | 20 | 25392112 | Lower in Smoker |

| | | | |
|---|---|---|---|
| cg04164838 | 19 | 14591148 | Lower in Smoker |
| cg22336107 | 19 | 14606894 | Higher in Smoker |
| cg03879902 | 19 | 46171872 | Lower in Smoker |
| cg02103822 | 1 | 147246329 | Lower in Smoker |
| cg23486142 | 13 | 20767607 | Higher in Smoker |
| cg15936439 | 13 | 20767183 | Higher in Smoker |
| cg18262616 | 1 | 35247397 | Higher in Smoker |
| cg00259249 | 1 | 35246726 | Lower in Smoker |
| cg06088858 | 1 | 35224726 | Lower in Smoker |
| cg02255892 | 17 | 42908915 | Lower in Smoker |
| cg18212720 | 17 | 42884655 | Lower in Smoker |
| cg27532847 | 15 | 35047401 | Higher in Smoker |
| cg05347914 | 17 | 38521067 | Lower in Smoker |
| cg04239009 | 3 | 141944519 | Higher in Smoker |
| cg03323292 | 11 | 134146132 | Higher in Smoker |
| cg12635263 | 15 | 51636552 | Lower in Smoker |
| cg05620814 | 16 | 74640948 | Higher in Smoker |
| cg05550612 | 16 | 74641310 | Higher in Smoker |
| cg13335447 | 12 | 57853735 | Lower in Smoker |
| cg14270760 | 2 | 121578165 | Lower in Smoker |
| cg23367392 | 7 | 42267337 | Higher in Smoker |
| cg17347386 | 7 | 42192975 | Lower in Smoker |
| cg10055593 | 7 | 42265817 | Lower in Smoker |
| cg19430489 | 12 | 75728104 | Higher in Smoker |
| cg13168314 | 1 | 54051041 | Higher in Smoker |
| cg10959408 | 1 | 54017944 | Lower in Smoker |
| cg13555519 | 9 | 4224635 | Lower in Smoker |
| cg14047387 | 9 | 4080919 | Lower in Smoker |
| cg19968631 | 4 | 175750792 | Higher in Smoker |
| cg22045888 | 4 | 175750802 | Higher in Smoker |
| cg16592586 | 4 | 175751001 | Higher in Smoker |
| cg27517702 | 4 | 175750280 | Higher in Smoker |
| cg04985324 | 14 | 96000921 | Higher in Smoker |
| cg24684394 | 14 | 96000032 | Higher in Smoker |
| cg12096759 | 14 | 96002581 | Lower in Smoker |

| | | | |
|---|---|---|---|
| cg06552369 | 2 | 191746552 | Higher in Smoker |
| cg25350416 | 2 | 191746073 | Higher in Smoker |
| cg18151275 | 12 | 56873616 | Lower in Smoker |
| cg18073970 | 1 | 184006765 | Higher in Smoker |
| cg04922803 | 12 | 104444418 | Higher in Smoker |
| cg15747733 | 10 | 88850398 | Lower in Smoker |
| cg10593994 | 6 | 49467064 | Lower in Smoker |
| cg17336185 | 3 | 52321266 | Higher in Smoker |
| cg00636946 | 16 | 4898667 | Lower in Smoker |
| cg20394898 | 6 | 1625111 | Higher in Smoker |
| cg22994582 | 6 | 1774548 | Lower in Smoker |
| cg09510246 | 6 | 1684515 | Lower in Smoker |
| cg18434348 | 6 | 1720088 | Lower in Smoker |
| cg10927510 | 20 | 62259125 | Higher in Smoker |
| cg01190919 | 20 | 62221766 | Lower in Smoker |
| cg02247823 | 14 | 54955826 | Higher in Smoker |
| cg06916012 | 2 | 220363862 | Higher in Smoker |
| cg26652666 | 19 | 3121109 | Lower in Smoker |
| ch.7.1416978 | 7 | 2825048 | Higher in Smoker |
| cg15302705 | 7 | 2884276 | Higher in Smoker |
| cg03084158 | 7 | 2859672 | Lower in Smoker |
| cg09658497 | 7 | 2847517 | Lower in Smoker |
| cg24524634 | 7 | 2800976 | Lower in Smoker |
| cg19717773 | 7 | 2847554 | Lower in Smoker |
| cg09070201 | 17 | 63049758 | Lower in Smoker |
| cg13840089 | 9 | 80201784 | Lower in Smoker |
| cg07865607 | 19 | 3136076 | Higher in Smoker |
| cg24055461 | 19 | 3135489 | Higher in Smoker |
| cg24401199 | 19 | 3159786 | Lower in Smoker |
| cg18760587 | 7 | 79764886 | Higher in Smoker |
| cg25418001 | 7 | 79780310 | Higher in Smoker |
| cg03451029 | 7 | 79764387 | Higher in Smoker |
| cg12996903 | 3 | 50275575 | Higher in Smoker |
| cg15877314 | 3 | 50273895 | Higher in Smoker |
| cg11118235 | 3 | 50284010 | Higher in Smoker |

| | | | |
|---|---|---|---|
| cg08644463 | 1 | 110106962 | Lower in Smoker |
| cg15653282 | 18 | 11639218 | Higher in Smoker |
| cg20059140 | 18 | 11751516 | Higher in Smoker |
| cg27449777 | 18 | 11851347 | Higher in Smoker |
| cg09965996 | 16 | 56390429 | Higher in Smoker |
| cg16475558 | 16 | 56388945 | Lower in Smoker |
| cg20435370 | 9 | 80646370 | Higher in Smoker |
| cg22885821 | 20 | 57465921 | Higher in Smoker |
| cg03908391 | 20 | 57427170 | Lower in Smoker |
| cg11669839 | 20 | 57426322 | Lower in Smoker |
| cg20582984 | 20 | 57417233 | Higher in Smoker |
| cg01042877 | 3 | 50228220 | Lower in Smoker |
| cg06803253 | 3 | 50229604 | Lower in Smoker |
| cg05049280 | 1 | 110155535 | Lower in Smoker |
| cg00845219 | 22 | 19842449 | Higher in Smoker |
| cg25392362 | 7 | 100271250 | Higher in Smoker |
| cg07982057 | 7 | 100270964 | Higher in Smoker |
| cg27369641 | 7 | 100274361 | Lower in Smoker |
| cg27591053 | 5 | 180671165 | Higher in Smoker |
| cg11692021 | 12 | 6949472 | Lower in Smoker |
| cg14120436 | 15 | 52433498 | Higher in Smoker |
| cg20550536 | 15 | 52481261 | Lower in Smoker |
| cg17191518 | 15 | 52468850 | Lower in Smoker |
| cg07232612 | 7 | 93551012 | Lower in Smoker |
| cg00536924 | 7 | 93551004 | Lower in Smoker |
| cg17931620 | 1 | 68297703 | Higher in Smoker |
| cg01865825 | 16 | 850240 | Lower in Smoker |
| cg04576607 | 1 | 235787279 | Lower in Smoker |
| cg00043510 | 1 | 235814134 | Lower in Smoker |
| cg25217317 | 1 | 235811994 | Lower in Smoker |
| cg09575871 | 19 | 2702929 | Higher in Smoker |
| cg03969219 | 19 | 2611456 | Higher in Smoker |
| cg21340148 | 19 | 2702986 | Higher in Smoker |
| cg15436476 | 19 | 2626283 | Lower in Smoker |
| cg01871907 | 19 | 2703055 | Lower in Smoker |

| | | | |
|---|---|---|---|
| cg06371583 | 19 | 2581343 | Lower in Smoker |
| cg19477361 | 19 | 2607903 | Lower in Smoker |
| cg17617491 | 19 | 2607726 | Lower in Smoker |
| cg23463608 | 19 | 2607757 | Lower in Smoker |
| cg22459924 | 19 | 2607850 | Lower in Smoker |
| cg04968197 | 6 | 30509595 | Higher in Smoker |
| cg02247514 | 6 | 30520623 | Lower in Smoker |
| cg12576073 | 6 | 30521242 | Lower in Smoker |
| cg21899138 | 3 | 52720056 | Higher in Smoker |
| cg11041457 | 3 | 52719354 | Higher in Smoker |
| cg10056627 | 6 | 42928773 | Higher in Smoker |
| cg02077977 | 1 | 231376624 | Higher in Smoker |
| cg02014416 | 1 | 231376203 | Lower in Smoker |
| cg12374003 | 5 | 141380315 | Lower in Smoker |
| cg18214930 | 14 | 53254659 | Lower in Smoker |
| cg00136105 | 12 | 102224911 | Higher in Smoker |
| cg08157318 | 12 | 102224140 | Higher in Smoker |
| cg18135853 | 16 | 1402335 | Higher in Smoker |
| cg08473533 | 16 | 1402333 | Higher in Smoker |
| cg26636835 | 12 | 133391157 | Higher in Smoker |
| cg10666906 | 3 | 37284460 | Higher in Smoker |
| cg04831495 | 15 | 85060580 | Lower in Smoker |
| cg14892222 | 15 | 34671426 | Lower in Smoker |
| cg01338957 | 15 | 34875117 | Lower in Smoker |
| cg20247523 | 15 | 34817982 | Lower in Smoker |
| cg01893100 | 3 | 167799377 | Lower in Smoker |
| cg11075718 | 8 | 110701184 | Lower in Smoker |
| cg05807885 | 1 | 204183355 | Lower in Smoker |
| cg00504075 | 1 | 155827556 | Lower in Smoker |
| cg06212631 | 2 | 171785547 | Higher in Smoker |
| cg23666278 | 2 | 171785822 | Higher in Smoker |
| cg14825683 | 8 | 37797789 | Lower in Smoker |
| cg21934015 | 17 | 4834179 | Higher in Smoker |
| cg19238840 | 16 | 20339175 | Lower in Smoker |
| cg05323324 | 3 | 194120023 | Higher in Smoker |

| | | | |
|---|---|---|---|
| cg07280097 | 3 | 128779601 | Higher in Smoker |
| cg19977179 | 3 | 128779500 | Higher in Smoker |
| cg02726291 | 3 | 128779596 | Higher in Smoker |
| cg15011026 | 1 | 217604611 | Lower in Smoker |
| cg16370856 | 5 | 56470520 | Higher in Smoker |
| cg09865339 | 7 | 99774935 | Higher in Smoker |
| cg05037863 | 13 | 92305086 | Lower in Smoker |
| cg24847541 | 13 | 92051154 | Higher in Smoker |
| cg07529657 | 13 | 93878969 | Higher in Smoker |
| cg14778311 | 13 | 93380942 | Higher in Smoker |
| cg20095609 | 13 | 94979759 | Higher in Smoker |
| cg24149455 | 13 | 94214495 | Lower in Smoker |
| cg06149212 | 13 | 93932639 | Lower in Smoker |
| cg18880946 | 13 | 94422696 | Lower in Smoker |
| cg17465462 | 3 | 32148028 | Higher in Smoker |
| cg24066516 | 2 | 157353685 | Lower in Smoker |
| cg03230175 | 2 | 157291462 | Lower in Smoker |
| cg21100690 | 11 | 64703818 | Lower in Smoker |
| cg13489987 | 14 | 67292468 | Lower in Smoker |
| cg08056903 | 14 | 66974163 | Higher in Smoker |
| cg23283667 | 8 | 144293742 | Lower in Smoker |
| cg00152340 | 8 | 144297019 | Lower in Smoker |
| cg09012091 | 6 | 24431322 | Lower in Smoker |
| cg02346062 | 6 | 24491168 | Lower in Smoker |
| cg17588373 | X | 13957417 | Higher in Smoker |
| cg13867326 | X | 13821440 | Higher in Smoker |
| cg24367850 | 1 | 27217401 | Higher in Smoker |
| cg19666600 | 12 | 110907609 | Lower in Smoker |
| cg26517004 | 12 | 110903494 | Lower in Smoker |
| cg05712507 | 12 | 110905729 | Higher in Smoker |
| cg21459215 | 7 | 23314138 | Lower in Smoker |
| cg14633820 | 9 | 132874557 | Lower in Smoker |
| cg12148898 | 6 | 47010823 | Higher in Smoker |
| cg07779444 | 10 | 134902278 | Higher in Smoker |
| cg14922775 | 8 | 37688296 | Lower in Smoker |

| | | | |
|---|---|---|---|
| cg05552035 | 8 | 37699239 | Lower in Smoker |
| cg07704151 | 3 | 100327897 | Lower in Smoker |
| cg25558761 | 14 | 105522902 | Lower in Smoker |
| cg27648006 | 12 | 131526535 | Lower in Smoker |
| cg25130831 | 12 | 131497012 | Lower in Smoker |
| cg13240326 | 12 | 131496071 | Lower in Smoker |
| cg21726551 | 12 | 131590460 | Lower in Smoker |
| cg14211097 | 14 | 59930456 | Lower in Smoker |
| cg02792333 | 11 | 64051402 | Higher in Smoker |
| cg25400358 | 11 | 64054159 | Lower in Smoker |
| cg16505687 | 1 | 236305169 | Higher in Smoker |
| cg09169938 | 1 | 236306000 | Lower in Smoker |
| cg00938050 | 16 | 20084944 | Higher in Smoker |
| cg11592852 | 17 | 72363447 | Lower in Smoker |
| cg16415834 | X | 9733668 | Higher in Smoker |
| cg04037952 | 2 | 131486950 | Higher in Smoker |
| cg26385013 | 3 | 98249859 | Lower in Smoker |
| cg19859270 | 3 | 98251294 | Lower in Smoker |
| cg03916104 | 1 | 6314748 | Lower in Smoker |
| cg00581848 | 1 | 9189367 | Higher in Smoker |
| cg20284891 | 1 | 9182171 | Lower in Smoker |
| cg01006048 | 10 | 25620462 | Lower in Smoker |
| cg20137461 | 3 | 169782135 | Lower in Smoker |
| cg01159288 | 1 | 168105875 | Higher in Smoker |
| cg08349804 | 12 | 6929591 | Lower in Smoker |
| cg14136810 | 15 | 40213326 | Lower in Smoker |
| cg06232205 | 15 | 40120808 | Lower in Smoker |
| cg06872176 | 1 | 68697386 | Higher in Smoker |
| cg11661263 | 13 | 95253900 | Higher in Smoker |
| cg10736330 | 13 | 99960957 | Lower in Smoker |
| cg19825182 | 13 | 99948367 | Lower in Smoker |
| cg03574723 | 10 | 125425994 | Higher in Smoker |
| cg17185817 | 1 | 27719012 | Higher in Smoker |
| cg00921097 | 1 | 202090980 | Lower in Smoker |
| cg19404354 | 1 | 202093479 | Lower in Smoker |

| | | | |
|---|---|---|---|
| cg20814312 | 2 | 133339746 | Higher in Smoker |
| cg15173319 | 19 | 46094030 | Lower in Smoker |
| cg11962524 | 11 | 60619624 | Lower in Smoker |
| cg27229823 | 2 | 105858015 | Lower in Smoker |
| cg02858997 | 2 | 105858314 | Lower in Smoker |
| cg03032770 | 16 | 57669519 | Lower in Smoker |
| cg15499402 | 6 | 97282253 | Higher in Smoker |
| cg13810673 | 14 | 88473038 | Lower in Smoker |
| cg00357958 | 12 | 123215010 | Lower in Smoker |
| cg03345037 | 11 | 94134446 | Higher in Smoker |
| cg24310431 | 7 | 112726396 | Higher in Smoker |
| cg06223162 | 1 | 101003688 | Lower in Smoker |
| cg07174053 | 1 | 145827038 | Lower in Smoker |
| cg08811815 | 16 | 57723044 | Higher in Smoker |
| cg05948710 | 16 | 19888977 | Lower in Smoker |
| cg05072547 | 16 | 19883549 | Lower in Smoker |
| cg02144954 | 17 | 72439205 | Higher in Smoker |
| cg04387597 | 17 | 72443179 | Higher in Smoker |
| cg02734358 | 4 | 90227074 | Higher in Smoker |
| cg21722775 | 17 | 80014694 | Lower in Smoker |
| cg14471084 | 9 | 139236663 | Lower in Smoker |
| cg13957175 | 9 | 139233849 | Lower in Smoker |
| cg24685167 | 6 | 32162755 | Lower in Smoker |
| cg07710971 | 16 | 46920836 | Lower in Smoker |
| cg05380921 | 16 | 46921663 | Lower in Smoker |
| cg16238523 | 3 | 49395303 | Higher in Smoker |
| cg25187648 | 3 | 49395165 | Lower in Smoker |
| cg13612480 | 19 | 1103771 | Higher in Smoker |
| cg07790947 | 6 | 28474513 | Lower in Smoker |
| cg03330022 | 1 | 53072410 | Lower in Smoker |
| cg01400822 | 1 | 53067365 | Lower in Smoker |
| cg06797734 | 11 | 123448381 | Lower in Smoker |
| cg06174296 | 11 | 123396593 | Lower in Smoker |
| cg22088645 | 3 | 113557409 | Lower in Smoker |
| cg03224126 | 15 | 72491032 | Lower in Smoker |

| | | | |
|---|---|---|---|
| cg26107055 | 5 | 125695687 | Lower in Smoker |
| cg03594790 | 5 | 125706443 | Lower in Smoker |
| cg02730804 | 5 | 125799820 | Lower in Smoker |
| cg26492175 | 22 | 47022658 | Higher in Smoker |
| cg03840259 | 22 | 40297036 | Higher in Smoker |
| cg00817367 | 12 | 52401214 | Higher in Smoker |
| cg15774495 | 7 | 50861549 | Higher in Smoker |
| cg23104539 | 7 | 50861535 | Higher in Smoker |
| cg12903177 | 7 | 50850564 | Higher in Smoker |
| cg17739152 | 7 | 50727547 | Lower in Smoker |
| cg23987548 | 17 | 73401912 | Lower in Smoker |
| cg00200289 | 17 | 73401734 | Higher in Smoker |
| cg11183072 | 17 | 37894397 | Higher in Smoker |
| cg13761998 | 17 | 37894403 | Higher in Smoker |
| cg17740645 | 17 | 37894413 | Higher in Smoker |
| cg25676215 | 17 | 37902268 | Lower in Smoker |
| cg00697095 | 17 | 37897076 | Lower in Smoker |
| cg09923456 | 17 | 37903448 | Lower in Smoker |
| cg11598054 | 2 | 11752960 | Lower in Smoker |
| cg01655831 | 18 | 18822994 | Higher in Smoker |
| cg03780851 | 8 | 102504564 | Higher in Smoker |
| cg01236933 | 8 | 102520514 | Lower in Smoker |
| cg21239280 | 1 | 24645885 | Higher in Smoker |
| cg26365938 | 1 | 24645953 | Higher in Smoker |
| cg12405265 | 1 | 24655961 | Higher in Smoker |
| cg19752602 | 5 | 153039227 | Higher in Smoker |
| cg07633435 | 5 | 152869009 | Lower in Smoker |
| cg12754421 | 11 | 105480790 | Higher in Smoker |
| cg08230483 | 10 | 88123453 | Higher in Smoker |
| cg07712541 | 10 | 88072732 | Lower in Smoker |
| cg05873487 | 4 | 93225360 | Higher in Smoker |
| cg19745314 | 4 | 94124971 | Lower in Smoker |
| cg11976671 | 6 | 102166512 | Lower in Smoker |
| cg17952046 | 1 | 37379413 | Higher in Smoker |
| cg13052954 | 1 | 37467416 | Lower in Smoker |

| | | | |
|---|---|---|---|
| cg04913851 | 11 | 120545098 | Higher in Smoker |
| cg11281320 | 11 | 120553251 | Lower in Smoker |
| cg09434500 | 19 | 42502897 | Lower in Smoker |
| cg01049121 | 9 | 140055180 | Lower in Smoker |
| cg06880615 | 16 | 10051500 | Lower in Smoker |
| cg07561162 | 16 | 10174417 | Lower in Smoker |
| cg24226973 | 12 | 14133336 | Higher in Smoker |
| cg20684528 | 12 | 14133667 | Higher in Smoker |
| cg12536809 | 17 | 72852514 | Lower in Smoker |
| cg22175779 | 15 | 57993734 | Higher in Smoker |
| cg25019961 | 12 | 66996175 | Lower in Smoker |
| cg26485003 | 12 | 66742565 | Lower in Smoker |
| cg10504573 | 12 | 66876894 | Lower in Smoker |
| cg06064636 | 13 | 114324615 | Lower in Smoker |
| cg08968034 | 4 | 3022836 | Higher in Smoker |
| cg10515982 | 10 | 120966350 | Higher in Smoker |
| cg03907390 | 10 | 121066392 | Higher in Smoker |
| cg09205599 | 10 | 121214780 | Lower in Smoker |
| cg09395855 | 10 | 120967408 | Lower in Smoker |
| cg01577865 | 5 | 176854009 | Higher in Smoker |
| cg00636527 | 5 | 176859356 | Lower in Smoker |
| cg25423647 | 3 | 51746723 | Lower in Smoker |
| cg04062190 | 7 | 86413438 | Lower in Smoker |
| cg20103018 | 6 | 33996522 | Lower in Smoker |
| cg12008034 | 6 | 33996580 | Lower in Smoker |
| cg15834992 | 6 | 34023192 | Lower in Smoker |
| cg10083824 | 6 | 34102147 | Lower in Smoker |
| cg04023483 | 3 | 6904134 | Higher in Smoker |
| cg07751325 | 3 | 7340242 | Lower in Smoker |
| cg13054613 | 3 | 7742036 | Lower in Smoker |
| cg16899265 | 18 | 56887002 | Higher in Smoker |
| cg04280647 | 1 | 26488129 | Higher in Smoker |
| cg13930683 | 13 | 114000009 | Lower in Smoker |
| cg14184077 | 4 | 42895607 | Lower in Smoker |
| cg01533258 | 14 | 95235489 | Higher in Smoker |

| | | | |
|---|---|---|---|
| cg18687675 | 14 | 95234965 | Higher in Smoker |
| cg04756853 | 17 | 38118787 | Lower in Smoker |
| cg12686110 | 8 | 144635478 | Higher in Smoker |
| cg14721632 | 8 | 144635430 | Higher in Smoker |
| cg01117621 | 16 | 28073818 | Higher in Smoker |
| cg00843236 | 16 | 28074980 | Higher in Smoker |
| cg01469715 | 16 | 27900716 | Lower in Smoker |
| cg05038804 | 3 | 119813689 | Higher in Smoker |
| cg06230599 | 16 | 12011342 | Lower in Smoker |
| cg17325073 | 8 | 30585433 | Higher in Smoker |
| cg19701087 | 6 | 52859008 | Higher in Smoker |
| cg15925365 | 6 | 52858998 | Higher in Smoker |
| cg08830754 | 6 | 52860234 | Higher in Smoker |
| cg24493367 | 4 | 106635507 | Higher in Smoker |
| cg06970744 | 1 | 110210439 | Higher in Smoker |
| cg08142344 | 1 | 110210699 | Higher in Smoker |
| cg03070194 | 1 | 110210684 | Higher in Smoker |
| cg15955341 | 1 | 110198890 | Higher in Smoker |
| cg03390723 | 10 | 106028329 | Lower in Smoker |
| cg26609631 | 13 | 28366814 | Higher in Smoker |
| cg05196820 | 4 | 54967018 | Higher in Smoker |
| cg08516463 | 2 | 145052759 | Lower in Smoker |
| cg27559097 | 2 | 144987743 | Lower in Smoker |
| cg08687485 | 2 | 144869361 | Lower in Smoker |
| cg14422338 | 15 | 59945426 | Lower in Smoker |
| cg05306956 | 1 | 89357390 | Higher in Smoker |
| cg22607980 | 1 | 89357197 | Higher in Smoker |
| cg02667880 | 8 | 30436207 | Lower in Smoker |
| cg05378535 | 13 | 45831942 | Lower in Smoker |
| cg08690812 | 11 | 18343758 | Higher in Smoker |
| cg11063328 | 11 | 18343203 | Higher in Smoker |
| cg22459990 | 6 | 30877246 | Lower in Smoker |
| cg22025250 | 6 | 30876152 | Higher in Smoker |
| cg23612142 | 6 | 158589101 | Higher in Smoker |
| cg07358745 | 7 | 74072514 | Higher in Smoker |

| | | | |
|---|---|---|---|
| cg22647092 | 7 | 74122902 | Lower in Smoker |
| cg23166765 | 7 | 73867948 | Higher in Smoker |
| cg09756225 | 7 | 73894999 | Higher in Smoker |
| cg24860938 | 13 | 27998603 | Higher in Smoker |
| cg04070771 | 13 | 27998621 | Lower in Smoker |
| cg27372015 | 16 | 27526259 | Lower in Smoker |
| cg19364957 | 2 | 27579796 | Higher in Smoker |
| cg21939635 | 2 | 197665460 | Lower in Smoker |
| cg11457044 | 2 | 197664369 | Higher in Smoker |
| cg14229207 | 9 | 135929747 | Lower in Smoker |
| cg14283710 | 9 | 135913241 | Lower in Smoker |
| cg00894869 | 6 | 111280279 | Higher in Smoker |
| cg15034267 | 22 | 39106452 | Lower in Smoker |
| cg10519155 | 20 | 60757898 | Higher in Smoker |
| cg12151328 | 3 | 112709521 | Lower in Smoker |
| cg24981181 | 22 | 46724065 | Lower in Smoker |
| cg06049111 | 6 | 42145539 | Lower in Smoker |
| cg18557215 | 3 | 108633926 | Higher in Smoker |
| cg15847198 | 11 | 106889318 | Higher in Smoker |
| cg02649987 | 11 | 106888392 | Lower in Smoker |
| cg01651499 | 4 | 156646379 | Lower in Smoker |
| cg17714276 | 4 | 156588619 | Higher in Smoker |
| cg25616573 | 4 | 156684300 | Lower in Smoker |
| cg06848060 | 17 | 7907755 | Lower in Smoker |
| cg08071904 | 11 | 76401495 | Lower in Smoker |
| cg24818183 | 4 | 44680862 | Higher in Smoker |
| cg27275133 | 6 | 26860451 | Higher in Smoker |
| cg06375580 | 12 | 42538820 | Higher in Smoker |
| cg01285164 | 3 | 72936145 | Higher in Smoker |
| cg17946284 | 3 | 72937052 | Higher in Smoker |
| cg06368369 | 3 | 148709353 | Higher in Smoker |
| cg13669804 | 3 | 148712659 | Lower in Smoker |
| cg05017821 | 20 | 23346586 | Lower in Smoker |
| cg12493107 | 20 | 23344079 | Lower in Smoker |
| cg18338021 | 19 | 544349 | Lower in Smoker |

| | | | |
|---|---|---|---|
| cg21083709 | 3 | 129035520 | Higher in Smoker |
| cg14194708 | 11 | 118967322 | Lower in Smoker |
| cg02735204 | 10 | 71871463 | Lower in Smoker |
| cg13626863 | 10 | 71813912 | Lower in Smoker |
| cg00190642 | X | 103268431 | Higher in Smoker |
| cg15624314 | 1 | 226251003 | Higher in Smoker |
| cg18243159 | 17 | 73775296 | Higher in Smoker |
| cg00226143 | 3 | 15643039 | Higher in Smoker |
| cg12860909 | 4 | 108910804 | Higher in Smoker |
| cg11079189 | 4 | 108910929 | Higher in Smoker |
| cg00674415 | 16 | 1859330 | Lower in Smoker |
| cg01834210 | 5 | 153858967 | Higher in Smoker |
| cg15376615 | 5 | 153858822 | Higher in Smoker |
| cg04846307 | 5 | 153858585 | Higher in Smoker |
| cg03158581 | 5 | 153858816 | Higher in Smoker |
| cg01566965 | 4 | 174447847 | Lower in Smoker |
| cg13063101 | 1 | 119914432 | Lower in Smoker |
| cg03762535 | 1 | 119911480 | Lower in Smoker |
| cg12518734 | 17 | 39891458 | Higher in Smoker |
| cg12320221 | 17 | 39890581 | Higher in Smoker |
| cg13420004 | 15 | 89421300 | Lower in Smoker |
| cg01156302 | 15 | 89422783 | Lower in Smoker |
| cg01647632 | 15 | 89438905 | Lower in Smoker |
| cg16661000 | 15 | 89437710 | Lower in Smoker |
| cg01367393 | 15 | 89438731 | Higher in Smoker |
| cg03719032 | 19 | 19374710 | Lower in Smoker |
| cg13904348 | 5 | 140070172 | Lower in Smoker |
| cg13300756 | 19 | 52228038 | Lower in Smoker |
| cg25922341 | 8 | 122654566 | Higher in Smoker |
| cg03046946 | X | 152735584 | Higher in Smoker |
| cg17572791 | 1 | 154245185 | Higher in Smoker |
| cg18234280 | 11 | 5257248 | Lower in Smoker |
| cg27105634 | 11 | 5255241 | Lower in Smoker |
| cg05940881 | 5 | 139726074 | Higher in Smoker |
| cg18768582 | 11 | 5270556 | Lower in Smoker |

| | | | |
|---|---|---|---|
| cg07893512 | 16 | 214776 | Higher in Smoker |
| cg05057452 | 16 | 214970 | Higher in Smoker |
| cg23293999 | 7 | 106826042 | Lower in Smoker |
| cg05933901 | 16 | 229407 | Lower in Smoker |
| cg21035511 | 6 | 135318509 | Lower in Smoker |
| cg16255804 | 6 | 135334527 | Lower in Smoker |
| cg17164863 | 1 | 110951258 | Lower in Smoker |
| cg09262729 | 11 | 1567941 | Higher in Smoker |
| cg26745757 | 11 | 1715454 | Higher in Smoker |
| cg03836507 | 11 | 1520312 | Higher in Smoker |
| cg03784994 | 11 | 1556050 | Lower in Smoker |
| cg26066887 | 11 | 1693962 | Lower in Smoker |
| cg08437403 | 11 | 1669832 | Lower in Smoker |
| cg19547124 | 11 | 1669376 | Lower in Smoker |
| cg03450829 | 11 | 1772468 | Lower in Smoker |
| cg23121547 | 11 | 1593657 | Lower in Smoker |
| cg04651621 | 6 | 30292292 | Lower in Smoker |
| cg01842890 | 6 | 30292264 | Lower in Smoker |
| cg00355447 | 6 | 30292220 | Lower in Smoker |
| cg13818708 | 6 | 30291314 | Lower in Smoker |
| cg18286060 | 6 | 30291349 | Lower in Smoker |
| cg17553885 | 6 | 31165290 | Higher in Smoker |
| cg12555879 | 6 | 31165601 | Higher in Smoker |
| cg10773928 | 6 | 31165850 | Lower in Smoker |
| cg17394649 | 6 | 29760164 | Higher in Smoker |
| cg22025232 | 6 | 29894874 | Higher in Smoker |
| cg19349217 | 6 | 29894903 | Lower in Smoker |
| cg24091270 | 6 | 29894908 | Lower in Smoker |
| cg04109898 | 6 | 29943455 | Higher in Smoker |
| cg07466983 | 6 | 29944982 | Higher in Smoker |
| cg23244913 | 6 | 29943401 | Higher in Smoker |
| cg13115683 | 6 | 29943460 | Higher in Smoker |
| cg10432093 | 6 | 29945155 | Higher in Smoker |
| cg22407123 | 6 | 29944524 | Higher in Smoker |
| cg06614284 | 20 | 30689432 | Lower in Smoker |

| | | | |
|---|---|---|---|
| cg04259977 | 5 | 45696491 | Higher in Smoker |
| cg21148923 | 5 | 45553518 | Lower in Smoker |
| cg02468728 | 19 | 611107 | Higher in Smoker |
| cg19865472 | 19 | 617133 | Lower in Smoker |
| cg12033273 | 1 | 155247785 | Higher in Smoker |
| cg07581823 | 1 | 155252506 | Lower in Smoker |
| cg19559628 | 15 | 73636424 | Lower in Smoker |
| cg23232773 | 6 | 31431902 | Lower in Smoker |
| cg19965511 | 17 | 40336475 | Higher in Smoker |
| cg20372821 | 17 | 40337892 | Lower in Smoker |
| cg02309594 | 1 | 32084329 | Lower in Smoker |
| cg22753888 | 6 | 55038900 | Higher in Smoker |
| cg14975122 | 1 | 32761824 | Higher in Smoker |
| cg12464820 | 22 | 50690166 | Higher in Smoker |
| cg13706066 | 3 | 13521223 | Higher in Smoker |
| cg20922324 | 3 | 13521744 | Higher in Smoker |
| cg10094994 | 2 | 240162323 | Higher in Smoker |
| cg03169059 | 2 | 240145022 | Higher in Smoker |
| cg00360072 | 2 | 240322717 | Higher in Smoker |
| cg04724190 | 2 | 240029740 | Lower in Smoker |
| cg18988412 | 2 | 240308765 | Lower in Smoker |
| cg12082681 | 2 | 240099656 | Lower in Smoker |
| cg21649361 | 2 | 240090040 | Lower in Smoker |
| cg26627327 | 2 | 240131751 | Lower in Smoker |
| cg01114124 | 2 | 240171748 | Lower in Smoker |
| cg13090969 | 2 | 240043331 | Lower in Smoker |
| cg15656521 | 2 | 239970617 | Lower in Smoker |
| cg00166368 | 2 | 240001910 | Lower in Smoker |
| cg15964153 | 2 | 239974232 | Lower in Smoker |
| cg21184951 | 2 | 240168413 | Lower in Smoker |
| cg14414903 | 2 | 240171712 | Lower in Smoker |
| cg19774624 | 17 | 42201019 | Higher in Smoker |
| cg05154234 | 12 | 48204680 | Lower in Smoker |
| cg27337857 | 7 | 18628714 | Lower in Smoker |
| cg06230668 | 7 | 18652971 | Lower in Smoker |

| | | | |
|---|---|---|---|
| cg24458314 | 7 | 18679329 | Lower in Smoker |
| cg25620356 | 7 | 18535407 | Lower in Smoker |
| cg25680145 | 6 | 125623414 | Higher in Smoker |
| cg02880877 | 6 | 125623484 | Lower in Smoker |
| cg24227984 | 19 | 4474970 | Higher in Smoker |
| cg05247799 | 19 | 4483319 | Lower in Smoker |
| cg11075227 | X | 7066076 | Higher in Smoker |
| cg20957739 | 18 | 44676672 | Higher in Smoker |
| cg05848120 | 18 | 44676992 | Higher in Smoker |
| cg05830870 | 18 | 44677236 | Higher in Smoker |
| cg19125081 | 2 | 242219370 | Lower in Smoker |
| cg09861631 | 1 | 236767555 | Higher in Smoker |
| cg07700062 | 1 | 236767390 | Higher in Smoker |
| cg11464436 | 7 | 792090 | Lower in Smoker |
| cg07763142 | 7 | 817218 | Lower in Smoker |
| cg01652476 | 7 | 809048 | Lower in Smoker |
| cg13353244 | 16 | 50099780 | Higher in Smoker |
| cg04331694 | 16 | 50104184 | Lower in Smoker |
| cg07567107 | 17 | 58156231 | Higher in Smoker |
| cg11397541 | 8 | 145215694 | Lower in Smoker |
| cg24349555 | 6 | 139456526 | Higher in Smoker |
| cg08125824 | 14 | 31607371 | Lower in Smoker |
| cg19753255 | 1 | 45476701 | Higher in Smoker |
| cg04442388 | 7 | 43151168 | Higher in Smoker |
| cg01124575 | 7 | 43288039 | Higher in Smoker |
| cg10835986 | 7 | 43577361 | Lower in Smoker |
| cg01311222 | 3 | 124776153 | Lower in Smoker |
| cg10469553 | 12 | 66696092 | Higher in Smoker |
| cg01570069 | 10 | 96305623 | Higher in Smoker |
| cg14526579 | 17 | 65237654 | Lower in Smoker |
| cg24962545 | 3 | 50606606 | Higher in Smoker |
| cg20725239 | 11 | 124805963 | Lower in Smoker |
| cg12280150 | 11 | 93819150 | Lower in Smoker |
| cg23507834 | 11 | 93824553 | Lower in Smoker |
| cg16923991 | 15 | 64011253 | Lower in Smoker |

| | | | |
|---|---|---|---|
| cg12364786 | 15 | 64056664 | Lower in Smoker |
| cg00067684 | 15 | 63970198 | Lower in Smoker |
| cg00855398 | 15 | 28362491 | Lower in Smoker |
| cg14684716 | 4 | 89520253 | Lower in Smoker |
| cg06217267 | 4 | 89582323 | Lower in Smoker |
| cg24804970 | 4 | 89299314 | Lower in Smoker |
| cg08684066 | 4 | 89299173 | Lower in Smoker |
| cg09067465 | 16 | 56965519 | Higher in Smoker |
| cg12665951 | 7 | 35734808 | Higher in Smoker |
| cg21428647 | 3 | 193852690 | Higher in Smoker |
| cg25544231 | 3 | 193852935 | Higher in Smoker |
| cg12031182 | 3 | 193855352 | Higher in Smoker |
| cg07104732 | 1 | 6478615 | Higher in Smoker |
| cg10976661 | 2 | 239149937 | Lower in Smoker |
| cg27248455 | 17 | 8024759 | Higher in Smoker |
| cg22107986 | 5 | 73980935 | Higher in Smoker |
| cg07696658 | 5 | 73980914 | Higher in Smoker |
| cg18735724 | 17 | 43225229 | Higher in Smoker |
| cg22236687 | 17 | 43238757 | Higher in Smoker |
| cg04737993 | 17 | 43246622 | Lower in Smoker |
| cg20607417 | 6 | 168377744 | Lower in Smoker |
| cg16033274 | 7 | 81391327 | Lower in Smoker |
| cg18944653 | 7 | 81381353 | Lower in Smoker |
| cg22543992 | 7 | 81399680 | Lower in Smoker |
| cg26900875 | 4 | 3443608 | Higher in Smoker |
| cg01815074 | 17 | 79657406 | Lower in Smoker |
| cg24464927 | 8 | 42996206 | Higher in Smoker |
| cg00903041 | 1 | 210708987 | Lower in Smoker |
| cg08776619 | 3 | 42743921 | Lower in Smoker |
| cg14851485 | 14 | 100126685 | Lower in Smoker |
| cg18678107 | 14 | 100130465 | Lower in Smoker |
| cg16753180 | 8 | 133093593 | Lower in Smoker |
| cg19746906 | 1 | 70820072 | Higher in Smoker |
| ch.1.2435132F | 1 | 100543910 | Higher in Smoker |
| cg19058189 | 17 | 1958090 | Lower in Smoker |

| | | | |
|---|---|---|---|
| cg04948941 | 14 | 62161878 | Lower in Smoker |
| cg16674323 | 3 | 42846108 | Higher in Smoker |
| cg20354502 | 15 | 72978361 | Higher in Smoker |
| cg05145297 | 7 | 75264568 | Higher in Smoker |
| cg23657377 | 7 | 75368420 | Higher in Smoker |
| cg22605936 | 7 | 75296038 | Lower in Smoker |
| cg02358858 | 12 | 123335357 | Lower in Smoker |
| cg14277677 | 12 | 123336568 | Lower in Smoker |
| cg12491302 | 12 | 123339291 | Lower in Smoker |
| cg27405626 | 12 | 123340936 | Lower in Smoker |
| cg26682900 | 12 | 123344689 | Lower in Smoker |
| cg23999318 | 7 | 139333352 | Higher in Smoker |
| cg00995324 | 7 | 139446195 | Higher in Smoker |
| cg12246945 | 7 | 139257086 | Lower in Smoker |
| cg01824172 | 7 | 139475138 | Lower in Smoker |
| cg06079564 | 7 | 139468310 | Lower in Smoker |
| cg02815320 | 7 | 139462359 | Lower in Smoker |
| cg14646457 | 11 | 33280348 | Higher in Smoker |
| cg26400421 | 11 | 33334443 | Lower in Smoker |
| cg13658962 | 19 | 40886898 | Lower in Smoker |
| cg01644518 | 19 | 40889848 | Lower in Smoker |
| cg15018694 | 5 | 102463772 | Lower in Smoker |
| cg05770626 | 5 | 102465432 | Lower in Smoker |
| cg15267532 | 15 | 43879335 | Lower in Smoker |
| cg07138603 | 6 | 27835385 | Higher in Smoker |
| cg23460835 | 6 | 27835403 | Higher in Smoker |
| cg10717387 | 6 | 26057256 | Higher in Smoker |
| cg22213149 | 6 | 26107687 | Lower in Smoker |
| cg10985452 | 6 | 26199562 | Higher in Smoker |
| cg27133864 | 6 | 26216541 | Higher in Smoker |
| cg06926499 | 6 | 27775877 | Higher in Smoker |
| cg14752990 | 6 | 27783059 | Lower in Smoker |
| cg14754637 | 6 | 27861800 | Higher in Smoker |
| cg17767596 | 6 | 27861570 | Lower in Smoker |
| cg04492267 | 6 | 26169666 | Lower in Smoker |

| | | | |
|---|---|---|---|
| cg21316379 | 6 | 26156157 | Higher in Smoker |
| cg03007571 | 6 | 26157673 | Higher in Smoker |
| cg25938227 | 6 | 26157227 | Higher in Smoker |
| cg15019694 | 6 | 26217890 | Higher in Smoker |
| cg14064694 | 6 | 26273556 | Higher in Smoker |
| cg15479139 | 6 | 26032472 | Higher in Smoker |
| cg25438963 | 6 | 26045663 | Higher in Smoker |
| cg00247599 | 6 | 27777649 | Higher in Smoker |
| cg05071577 | 6 | 27840147 | Higher in Smoker |
| cg25529393 | 6 | 27858380 | Lower in Smoker |
| cg02841227 | 6 | 26021843 | Higher in Smoker |
| cg12474759 | 6 | 26027625 | Higher in Smoker |
| cg13637913 | 6 | 26189410 | Higher in Smoker |
| cg16706631 | 6 | 26204623 | Higher in Smoker |
| cg05868516 | 6 | 26286170 | Higher in Smoker |
| cg19183932 | 6 | 27791712 | Higher in Smoker |
| cg11744777 | 6 | 27799370 | Lower in Smoker |
| cg01247537 | 6 | 27842098 | Higher in Smoker |
| cg15692279 | 1 | 149821905 | Higher in Smoker |
| cg09697416 | 1 | 149859252 | Higher in Smoker |
| cg01081836 | 1 | 149858341 | Higher in Smoker |
| ch.1.2799699R | 1 | 120906506 | Higher in Smoker |
| cg11378619 | 6 | 12164359 | Lower in Smoker |
| cg19245228 | 6 | 12012242 | Lower in Smoker |
| cg11276388 | 6 | 12064975 | Lower in Smoker |
| cg00109300 | 6 | 14326586 | Higher in Smoker |
| cg09606421 | 6 | 14315407 | Lower in Smoker |
| cg02031397 | 1 | 42383598 | Higher in Smoker |
| cg27143307 | 2 | 234763110 | Higher in Smoker |
| cg06310422 | 2 | 234763532 | Higher in Smoker |
| ch.10.1464434F | 10 | 71133003 | Higher in Smoker |
| cg23177739 | 10 | 71067364 | Lower in Smoker |
| cg20142377 | 6 | 29910206 | Higher in Smoker |
| cg15633609 | 6 | 31324621 | Higher in Smoker |
| cg14651305 | 6 | 31325003 | Higher in Smoker |

| | | | |
|---|---|---|---|
| cg03500977 | 6 | 31325314 | Higher in Smoker |
| cg11255427 | 6 | 31324500 | Higher in Smoker |
| cg14998329 | 6 | 31324252 | Lower in Smoker |
| cg26392102 | 6 | 31238751 | Lower in Smoker |
| cg18511546 | 6 | 31238388 | Lower in Smoker |
| cg26128383 | 6 | 31239158 | Lower in Smoker |
| cg17096269 | 6 | 31238788 | Lower in Smoker |
| cg12682872 | 6 | 32919427 | Lower in Smoker |
| cg25285720 | 6 | 32919433 | Lower in Smoker |
| cg15418419 | 6 | 32916606 | Lower in Smoker |
| cg14851271 | 6 | 32919431 | Lower in Smoker |
| cg00575744 | 6 | 32908642 | Lower in Smoker |
| cg15737554 | 6 | 32974897 | Lower in Smoker |
| cg06954660 | 6 | 32975336 | Lower in Smoker |
| cg22016094 | 6 | 32781261 | Lower in Smoker |
| cg10294956 | 6 | 32782845 | Lower in Smoker |
| cg03477130 | 6 | 32782796 | Lower in Smoker |
| cg11469594 | 6 | 32783046 | Lower in Smoker |
| cg19350197 | 6 | 32782988 | Lower in Smoker |
| cg12391576 | 6 | 33037662 | Lower in Smoker |
| cg06437840 | 6 | 33048529 | Higher in Smoker |
| cg09059466 | 6 | 33048086 | Higher in Smoker |
| cg19990651 | 6 | 33048555 | Higher in Smoker |
| cg02692313 | 6 | 33048444 | Higher in Smoker |
| cg01132696 | 6 | 33048558 | Higher in Smoker |
| cg19053046 | 6 | 33048254 | Higher in Smoker |
| cg00570906 | 6 | 33048809 | Higher in Smoker |
| cg25511667 | 6 | 33048732 | Higher in Smoker |
| cg12893780 | 6 | 33048752 | Higher in Smoker |
| cg20223237 | 6 | 33048735 | Higher in Smoker |
| cg26645432 | 6 | 33048502 | Higher in Smoker |
| cg03636880 | 6 | 33048687 | Higher in Smoker |
| cg09234582 | 6 | 33048286 | Higher in Smoker |
| cg10850215 | 6 | 33048469 | Higher in Smoker |
| cg13581859 | 6 | 33048706 | Higher in Smoker |

| | | | |
|---|---|---|---|
| cg14870156 | 6 | 33048540 | Higher in Smoker |
| cg15829535 | 6 | 33048760 | Higher in Smoker |
| cg13349035 | 6 | 33048310 | Higher in Smoker |
| cg17588455 | 6 | 33048485 | Higher in Smoker |
| cg25045942 | 6 | 33048291 | Higher in Smoker |
| cg02197634 | 6 | 33048875 | Higher in Smoker |
| cg03229061 | 6 | 33048483 | Higher in Smoker |
| cg14801692 | 6 | 33048592 | Higher in Smoker |
| cg14428733 | 6 | 33049505 | Higher in Smoker |
| cg25491704 | 6 | 33048879 | Higher in Smoker |
| cg23750365 | 6 | 33043072 | Lower in Smoker |
| cg10665390 | 6 | 33085521 | Higher in Smoker |
| cg20212304 | 6 | 33083808 | Lower in Smoker |
| cg23376071 | 6 | 33087989 | Lower in Smoker |
| cg23917817 | 6 | 33089397 | Lower in Smoker |
| cg01541565 | 6 | 32606385 | Lower in Smoker |
| cg12715811 | 6 | 32609130 | Lower in Smoker |
| cg24143305 | 6 | 32604865 | Lower in Smoker |
| cg10217052 | 6 | 32607174 | Lower in Smoker |
| cg13009819 | 6 | 32609094 | Lower in Smoker |
| cg23221363 | 6 | 32710933 | Lower in Smoker |
| cg06598146 | 6 | 32711632 | Lower in Smoker |
| cg26489369 | 6 | 32709909 | Lower in Smoker |
| cg23117647 | 6 | 32712930 | Lower in Smoker |
| cg17776207 | 6 | 32714066 | Lower in Smoker |
| cg10846853 | 6 | 32632859 | Higher in Smoker |
| cg16577979 | 6 | 32630856 | Lower in Smoker |
| cg18902440 | 6 | 32632036 | Lower in Smoker |
| cg24298476 | 6 | 32729808 | Lower in Smoker |
| cg10218546 | 6 | 32729823 | Lower in Smoker |
| cg23418102 | 6 | 32729847 | Lower in Smoker |
| cg16794061 | 6 | 32407430 | Higher in Smoker |
| cg25258233 | 6 | 32407570 | Higher in Smoker |
| cg19330213 | 6 | 32410443 | Lower in Smoker |
| cg06968241 | 6 | 32411144 | Lower in Smoker |

| | | | |
|---|---|---|---|
| cg10765922 | 6 | 32552022 | Higher in Smoker |
| cg01815645 | 6 | 32548627 | Lower in Smoker |
| cg09086151 | 6 | 32550067 | Lower in Smoker |
| cg10385522 | 6 | 32558175 | Lower in Smoker |
| cg27362989 | 6 | 32492198 | Lower in Smoker |
| cg22901297 | 6 | 32522795 | Lower in Smoker |
| cg20649689 | 6 | 30455885 | Higher in Smoker |
| cg13036546 | 6 | 30460576 | Lower in Smoker |
| cg16535080 | 6 | 30460600 | Lower in Smoker |
| cg27486565 | 6 | 30459595 | Lower in Smoker |
| cg26069562 | 6 | 29691981 | Lower in Smoker |
| cg17213462 | 6 | 29795411 | Higher in Smoker |
| cg09708750 | 6 | 29794008 | Lower in Smoker |
| cg18031134 | 6 | 29796402 | Lower in Smoker |
| cg03298800 | 6 | 29796770 | Lower in Smoker |
| cg00157477 | 6 | 29855473 | Higher in Smoker |
| cg23273834 | 6 | 29855252 | Lower in Smoker |
| cg15327477 | 6 | 29856182 | Lower in Smoker |
| cg22550397 | 6 | 29856632 | Lower in Smoker |
| cg24828683 | 6 | 29856210 | Lower in Smoker |
| cg11867546 | 6 | 29974810 | Higher in Smoker |
| cg08879910 | 6 | 29974319 | Higher in Smoker |
| cg03163199 | 6 | 29974858 | Higher in Smoker |
| cg15788639 | 6 | 29974251 | Higher in Smoker |
| cg25720815 | 6 | 29974692 | Higher in Smoker |
| cg01814945 | 6 | 29974723 | Higher in Smoker |
| cg24725574 | 6 | 29974717 | Higher in Smoker |
| cg16722947 | 6 | 30228431 | Lower in Smoker |
| cg12109566 | 6 | 30227986 | Lower in Smoker |
| cg25643819 | 6 | 30227942 | Lower in Smoker |
| cg03912051 | 6 | 30227733 | Lower in Smoker |
| cg25298725 | 6 | 30228047 | Lower in Smoker |
| cg11456756 | 6 | 30228069 | Lower in Smoker |
| cg12007166 | 6 | 30228058 | Lower in Smoker |
| cg13445593 | 6 | 30228076 | Lower in Smoker |

| | | | |
|---|---|---|---|
| cg07723510 | 6 | 30228063 | Lower in Smoker |
| cg01655658 | 6 | 30227583 | Lower in Smoker |
| cg21871091 | 21 | 38349937 | Lower in Smoker |
| cg04219321 | 17 | 53341659 | Higher in Smoker |
| cg25534244 | 17 | 53341098 | Higher in Smoker |
| cg07275648 | 3 | 148804790 | Lower in Smoker |
| cg18549036 | 3 | 148804541 | Lower in Smoker |
| cg01411220 | 20 | 30134188 | Lower in Smoker |
| cg19984199 | 11 | 118955550 | Higher in Smoker |
| cg04490478 | 11 | 118957635 | Lower in Smoker |
| cg09996240 | 19 | 3574625 | Lower in Smoker |
| cg24776736 | 12 | 66356357 | Lower in Smoker |
| cg11095632 | 20 | 56063618 | Higher in Smoker |
| cg19091677 | 4 | 174255518 | Higher in Smoker |
| cg09026481 | 5 | 74633022 | Higher in Smoker |
| cg01777187 | 21 | 40721343 | Higher in Smoker |
| cg02189121 | 6 | 79943796 | Higher in Smoker |
| cg21612666 | 6 | 26537797 | Higher in Smoker |
| cg21896142 | X | 80457315 | Higher in Smoker |
| cg21545248 | 5 | 149402498 | Lower in Smoker |
| cg03070533 | 22 | 35653394 | Higher in Smoker |
| cg20781212 | 22 | 35653362 | Higher in Smoker |
| cg06625062 | 22 | 35653265 | Higher in Smoker |
| cg13347784 | 19 | 1086437 | Lower in Smoker |
| cg18644543 | 19 | 1067356 | Lower in Smoker |
| cg14461752 | 5 | 143191194 | Lower in Smoker |
| cg15122828 | 5 | 162887362 | Higher in Smoker |
| cg22001924 | 5 | 162887193 | Higher in Smoker |
| cg14733672 | 22 | 35777245 | Higher in Smoker |
| cg05973832 | 16 | 4526445 | Higher in Smoker |
| cg24186750 | 5 | 173472732 | Higher in Smoker |
| cg04594452 | 10 | 124906685 | Higher in Smoker |
| cg15396686 | 10 | 124897043 | Higher in Smoker |
| cg07819944 | 10 | 124897153 | Higher in Smoker |
| cg18920754 | 17 | 73150420 | Higher in Smoker |

| | | | |
|---|---|---|---|
| cg24084359 | 20 | 42934276 | Higher in Smoker |
| cg09653879 | 12 | 54673490 | Higher in Smoker |
| cg22125717 | 5 | 177638023 | Lower in Smoker |
| cg10038259 | 5 | 177631514 | Higher in Smoker |
| cg03699765 | 10 | 43882723 | Lower in Smoker |
| cg24635157 | 5 | 179050864 | Higher in Smoker |
| cg12518259 | X | 100668953 | Lower in Smoker |
| cg05424366 | X | 100663101 | Higher in Smoker |
| cg09352155 | 19 | 39340066 | Higher in Smoker |
| cg15007646 | 19 | 8550758 | Lower in Smoker |
| cg23037798 | 1 | 23650159 | Lower in Smoker |
| cg24517768 | 1 | 245028012 | Lower in Smoker |
| cg00781658 | 19 | 41805850 | Higher in Smoker |
| cg06621757 | 12 | 54674353 | Higher in Smoker |
| cg08002795 | 4 | 83351453 | Higher in Smoker |
| cg14738493 | 2 | 38818738 | Lower in Smoker |
| cg08942894 | 15 | 83563792 | Lower in Smoker |
| cg08886546 | 19 | 19051335 | Lower in Smoker |
| cg13617534 | 14 | 23755418 | Higher in Smoker |
| cg08127876 | 14 | 23755478 | Higher in Smoker |
| cg16378352 | 1 | 60230106 | Higher in Smoker |
| cg11824172 | 1 | 60230096 | Higher in Smoker |
| cg26254792 | 1 | 60230088 | Higher in Smoker |
| cg00072407 | 19 | 12887524 | Lower in Smoker |
| cg09125779 | 4 | 57547999 | Higher in Smoker |
| cg06771126 | 4 | 57547699 | Higher in Smoker |
| cg00935819 | 1 | 150672619 | Lower in Smoker |
| cg11328436 | 12 | 54360511 | Higher in Smoker |
| cg01215762 | 7 | 27214126 | Higher in Smoker |
| cg12997720 | 7 | 27225058 | Higher in Smoker |
| cg05977669 | 7 | 27225070 | Higher in Smoker |
| cg14922886 | 7 | 27239701 | Higher in Smoker |
| cg09798023 | 7 | 27161624 | Lower in Smoker |
| cg24469729 | 7 | 27160520 | Lower in Smoker |
| cg09865454 | 7 | 27149139 | Lower in Smoker |

| | | | |
|---|---|---|---|
| cg08203294 | 7 | 27171528 | Lower in Smoker |
| cg23204968 | 7 | 27183816 | Lower in Smoker |
| cg02646423 | 7 | 27183794 | Lower in Smoker |
| cg20517050 | 7 | 27183806 | Lower in Smoker |
| cg04863892 | 7 | 27183375 | Lower in Smoker |
| cg01748892 | 7 | 27184667 | Lower in Smoker |
| cg19759481 | 7 | 27183401 | Lower in Smoker |
| cg17569124 | 7 | 27183643 | Lower in Smoker |
| cg13694927 | 7 | 27184712 | Lower in Smoker |
| cg09549073 | 7 | 27183274 | Lower in Smoker |
| cg00599770 | 7 | 27198825 | Higher in Smoker |
| cg24948406 | 17 | 46608268 | Lower in Smoker |
| cg26101366 | 17 | 46805563 | Higher in Smoker |
| cg15786837 | 17 | 46806935 | Higher in Smoker |
| cg02873421 | 17 | 46629306 | Higher in Smoker |
| cg27656658 | 17 | 46628224 | Lower in Smoker |
| cg23551720 | 17 | 46633726 | Lower in Smoker |
| cg07438617 | 17 | 46655289 | Higher in Smoker |
| cg09194159 | 17 | 46655588 | Higher in Smoker |
| cg02422694 | 17 | 46655790 | Higher in Smoker |
| cg04609859 | 17 | 46655736 | Higher in Smoker |
| cg17584085 | 17 | 46688329 | Higher in Smoker |
| cg16305379 | 12 | 54347702 | Lower in Smoker |
| cg18054172 | 12 | 54424902 | Higher in Smoker |
| cg18843682 | 12 | 54425156 | Higher in Smoker |
| cg07545037 | 12 | 54423920 | Higher in Smoker |
| cg04576672 | 12 | 54422239 | Higher in Smoker |
| cg21487207 | 12 | 54410576 | Higher in Smoker |
| cg02150988 | 2 | 177053283 | Higher in Smoker |
| cg22455694 | 2 | 176974001 | Higher in Smoker |
| cg03371669 | 2 | 176965435 | Higher in Smoker |
| cg11754318 | 2 | 176964506 | Higher in Smoker |
| cg11523712 | 2 | 176957055 | Higher in Smoker |
| cg17495130 | 2 | 176960255 | Higher in Smoker |
| cg21128569 | 2 | 176956396 | Lower in Smoker |

| | | | |
|---|---|---|---|
| cg23981871 | 2 | 177028714 | Lower in Smoker |
| cg02347773 | 2 | 176994142 | Higher in Smoker |
| cg06172871 | 16 | 72088244 | Higher in Smoker |
| cg05232061 | 2 | 10567526 | Lower in Smoker |
| cg11074834 | 2 | 10559952 | Lower in Smoker |
| cg17466636 | 2 | 10456284 | Lower in Smoker |
| cg11915812 | 2 | 10554240 | Lower in Smoker |
| cg03578662 | 1 | 40157289 | Higher in Smoker |
| cg24715735 | 19 | 35531403 | Higher in Smoker |
| cg24139898 | 19 | 35531817 | Higher in Smoker |
| cg25195477 | 3 | 148847134 | Higher in Smoker |
| cg10148280 | 3 | 148846750 | Lower in Smoker |
| cg08927006 | 10 | 100993556 | Higher in Smoker |
| cg18499443 | 10 | 100993553 | Higher in Smoker |
| cg09511126 | 10 | 100993597 | Higher in Smoker |
| cg16401360 | 10 | 100993589 | Higher in Smoker |
| cg17863743 | 10 | 100993587 | Higher in Smoker |
| cg13737332 | 10 | 100993583 | Higher in Smoker |
| cg24638235 | 8 | 21988805 | Lower in Smoker |
| cg25903363 | 8 | 21972479 | Lower in Smoker |
| cg26702929 | 8 | 21988147 | Higher in Smoker |
| cg02606081 | 11 | 536182 | Higher in Smoker |
| cg24078905 | 19 | 49655323 | Lower in Smoker |
| cg02253201 | 9 | 35906148 | Lower in Smoker |
| cg03737442 | 3 | 11177295 | Lower in Smoker |
| cg09575258 | 5 | 175084718 | Higher in Smoker |
| cg25599573 | 5 | 175108429 | Lower in Smoker |
| cg17613924 | 17 | 77245327 | Higher in Smoker |
| cg19481531 | 17 | 77100818 | Lower in Smoker |
| cg08587737 | 17 | 77388152 | Lower in Smoker |
| cg01328806 | 2 | 20851404 | Lower in Smoker |
| cg16401890 | 1 | 87484460 | Lower in Smoker |
| cg26610681 | 1 | 87380186 | Higher in Smoker |
| cg24093763 | 4 | 11431253 | Higher in Smoker |
| cg01555981 | 16 | 22926347 | Lower in Smoker |

| | | | |
|---|---|---|---|
| cg05037662 | 16 | 25704296 | Higher in Smoker |
| cg09070371 | 16 | 1968598 | Higher in Smoker |
| cg23425970 | 2 | 129076394 | Higher in Smoker |
| cg13525428 | 2 | 129076361 | Higher in Smoker |
| cg17032602 | 2 | 129076392 | Higher in Smoker |
| cg25180075 | 2 | 129076367 | Higher in Smoker |
| cg02447370 | X | 132092772 | Higher in Smoker |
| cg13534205 | X | 131762213 | Lower in Smoker |
| cg08612100 | 13 | 96742421 | Higher in Smoker |
| cg23680480 | 22 | 29139549 | Lower in Smoker |
| cg12065670 | 1 | 209858339 | Lower in Smoker |
| cg20941184 | 1 | 209878178 | Lower in Smoker |
| cg27492874 | 19 | 5680956 | Higher in Smoker |
| cg07724674 | 16 | 67465455 | Higher in Smoker |
| cg04241572 | X | 53461213 | Higher in Smoker |
| cg14874121 | 5 | 118788291 | Higher in Smoker |
| cg11375622 | 8 | 145516294 | Higher in Smoker |
| cg00603428 | 6 | 122721289 | Higher in Smoker |
| cg03811260 | 16 | 67198215 | Higher in Smoker |
| cg07188665 | 16 | 67200492 | Lower in Smoker |
| cg06621126 | 16 | 67198243 | Lower in Smoker |
| cg00545916 | 17 | 56565440 | Higher in Smoker |
| cg25148282 | 17 | 56561060 | Lower in Smoker |
| cg08357436 | 17 | 56565641 | Higher in Smoker |
| cg00878163 | 17 | 56565644 | Higher in Smoker |
| cg14893857 | 14 | 102554969 | Higher in Smoker |
| cg19615102 | 12 | 104335436 | Lower in Smoker |
| cg16925499 | 10 | 118502705 | Lower in Smoker |
| cg17064051 | 20 | 3713345 | Higher in Smoker |
| cg01662102 | 21 | 15755986 | Higher in Smoker |
| cg05192974 | 6 | 31795436 | Lower in Smoker |
| cg21080034 | 6 | 31797874 | Higher in Smoker |
| cg06128358 | 6 | 31777883 | Lower in Smoker |
| cg06928312 | 6 | 31781480 | Lower in Smoker |
| cg05494073 | 6 | 31781411 | Lower in Smoker |

| | | | |
|---|---|---|---|
| cg12873692 | 14 | 65006875 | Higher in Smoker |
| cg19619721 | 14 | 65007061 | Higher in Smoker |
| cg01141043 | 14 | 65007050 | Higher in Smoker |
| cg25598086 | 14 | 65006720 | Lower in Smoker |
| cg13146426 | 11 | 122932858 | Higher in Smoker |
| cg21217886 | 7 | 75932562 | Higher in Smoker |
| cg27376817 | 7 | 75931888 | Higher in Smoker |
| cg07681419 | 7 | 75932007 | Higher in Smoker |
| cg20713852 | 19 | 36248996 | Lower in Smoker |
| cg05910615 | 19 | 36248877 | Lower in Smoker |
| cg16425829 | 12 | 119632544 | Lower in Smoker |
| cg01501896 | 17 | 40274670 | Lower in Smoker |
| cg01642168 | 19 | 55791471 | Higher in Smoker |
| cg05348535 | 20 | 18774637 | Higher in Smoker |
| cg00442256 | 20 | 18775549 | Lower in Smoker |
| cg17592565 | 1 | 22355055 | Lower in Smoker |
| cg08602604 | 2 | 198364282 | Higher in Smoker |
| cg22827827 | 2 | 198367525 | Lower in Smoker |
| cg07636088 | 13 | 31734946 | Higher in Smoker |
| cg01397325 | 11 | 20386022 | Higher in Smoker |
| cg06045408 | 11 | 20385389 | Higher in Smoker |
| cg23424273 | 6 | 78173227 | Higher in Smoker |
| cg13077519 | 6 | 78174007 | Higher in Smoker |
| cg10644575 | 6 | 87725675 | Lower in Smoker |
| cg06476131 | 13 | 47471052 | Higher in Smoker |
| cg26383972 | X | 113817409 | Higher in Smoker |
| cg05942508 | 11 | 113846922 | Higher in Smoker |
| cg04091563 | 5 | 148034045 | Higher in Smoker |
| cg01406506 | 5 | 147938667 | Lower in Smoker |
| cg27551227 | 7 | 154877217 | Lower in Smoker |
| cg05360158 | 12 | 13153430 | Higher in Smoker |
| cg22701672 | 10 | 124258577 | Lower in Smoker |
| cg07304526 | 10 | 124221058 | Lower in Smoker |
| cg02197303 | 4 | 3240621 | Higher in Smoker |
| cg22597340 | 4 | 3208678 | Lower in Smoker |

| | | | |
|---|---|---|---|
| cg25060525 | 4 | 3235295 | Lower in Smoker |
| cg25354617 | 4 | 3241813 | Lower in Smoker |
| cg11324953 | 4 | 3077939 | Lower in Smoker |
| cg02203922 | 6 | 657011 | Higher in Smoker |
| cg23771329 | X | 53713697 | Higher in Smoker |
| cg02734755 | X | 53710671 | Higher in Smoker |
| cg08796898 | X | 53713664 | Higher in Smoker |
| cg10435123 | 12 | 111127010 | Higher in Smoker |
| cg14943722 | 3 | 50341009 | Lower in Smoker |
| cg03655330 | 3 | 50337494 | Lower in Smoker |
| cg09369490 | 3 | 50336841 | Higher in Smoker |
| cg02616906 | 16 | 71265770 | Lower in Smoker |
| cg05396731 | 1 | 43920161 | Higher in Smoker |
| cg24731678 | 1 | 43919862 | Higher in Smoker |
| cg23714454 | 11 | 125756760 | Lower in Smoker |
| cg24758816 | 11 | 125756762 | Lower in Smoker |
| cg05326984 | 6 | 144329766 | Higher in Smoker |
| cg13660600 | 2 | 9628525 | Lower in Smoker |
| cg12127290 | 12 | 21531643 | Lower in Smoker |
| cg27631248 | 1 | 220267790 | Lower in Smoker |
| cg14459960 | 6 | 82957569 | Higher in Smoker |
| cg17076789 | 6 | 82957751 | Higher in Smoker |
| cg24512794 | 2 | 203640233 | Lower in Smoker |
| cg10962407 | 2 | 203736738 | Higher in Smoker |
| cg04754916 | 19 | 10381498 | Higher in Smoker |
| cg26972937 | 19 | 10450862 | Lower in Smoker |
| cg00389463 | 19 | 10397620 | Higher in Smoker |
| cg03740216 | 19 | 10397561 | Higher in Smoker |
| cg18902930 | 19 | 10400308 | Higher in Smoker |
| cg26316885 | 19 | 10407317 | Lower in Smoker |
| cg21098990 | 19 | 10399845 | Lower in Smoker |
| cg27541349 | 1 | 6296337 | Higher in Smoker |
| cg17992056 | 1 | 6296335 | Higher in Smoker |
| cg00518190 | 1 | 6294768 | Lower in Smoker |
| cg15344028 | 2 | 204801510 | Lower in Smoker |

| | | | |
|---|---|---|---|
| cg18561976 | 2 | 204801508 | Lower in Smoker |
| cg21626886 | 20 | 30193307 | Higher in Smoker |
| cg06818804 | 15 | 78441680 | Higher in Smoker |
| cg22501608 | 15 | 78449129 | Lower in Smoker |
| cg08020381 | 10 | 1095554 | Higher in Smoker |
| cg21542308 | 8 | 39853778 | Lower in Smoker |
| cg11363097 | 8 | 39792086 | Lower in Smoker |
| cg02264182 | X | 148586734 | Higher in Smoker |
| cg15750461 | 4 | 991553 | Higher in Smoker |
| cg21616051 | 4 | 987303 | Lower in Smoker |
| cg08823577 | 4 | 985606 | Lower in Smoker |
| cg24797471 | 19 | 13262633 | Higher in Smoker |
| cg14567593 | 19 | 13265338 | Higher in Smoker |
| cg02937051 | 18 | 44702545 | Higher in Smoker |
| cg12128262 | 18 | 44703596 | Lower in Smoker |
| cg06237647 | 12 | 6666539 | Lower in Smoker |
| cg17601658 | 1 | 158979647 | Higher in Smoker |
| cg07463059 | 1 | 158979310 | Higher in Smoker |
| cg12177001 | 14 | 94576148 | Lower in Smoker |
| cg20227766 | 1 | 27998703 | Higher in Smoker |
| cg26974214 | 10 | 91151885 | Higher in Smoker |
| cg10552523 | 11 | 313478 | Higher in Smoker |
| cg22963452 | 11 | 312766 | Lower in Smoker |
| cg08843492 | 11 | 308231 | Lower in Smoker |
| cg06046490 | 11 | 320940 | Higher in Smoker |
| cg08596817 | 11 | 320929 | Higher in Smoker |
| cg14402017 | 11 | 300490 | Higher in Smoker |
| cg02480602 | 6 | 137518909 | Higher in Smoker |
| cg07587746 | 3 | 129180151 | Lower in Smoker |
| cg23064060 | 3 | 129159190 | Higher in Smoker |
| cg01389088 | 16 | 1644692 | Lower in Smoker |
| cg17706173 | 16 | 1582581 | Lower in Smoker |
| cg01042641 | 16 | 1575979 | Lower in Smoker |
| cg05977523 | 16 | 1586043 | Lower in Smoker |
| cg16460816 | 16 | 1601884 | Lower in Smoker |

| | | | |
|---|---|---|---|
| cg23401251 | 2 | 27683905 | Higher in Smoker |
| cg08787988 | 2 | 27713044 | Lower in Smoker |
| cg03559340 | 20 | 42218758 | Higher in Smoker |
| cg00511405 | 20 | 42219387 | Higher in Smoker |
| cg08618693 | 20 | 42222986 | Lower in Smoker |
| cg26723237 | 15 | 65643176 | Lower in Smoker |
| cg19012170 | 15 | 65715664 | Higher in Smoker |
| cg25560775 | 15 | 65707468 | Lower in Smoker |
| cg12742178 | 12 | 102815929 | Higher in Smoker |
| cg22375192 | 15 | 99193466 | Higher in Smoker |
| cg01631855 | 15 | 99194172 | Higher in Smoker |
| cg08315825 | 15 | 99337389 | Lower in Smoker |
| cg25574024 | 11 | 2161894 | Higher in Smoker |
| cg13791131 | 11 | 2161892 | Higher in Smoker |
| cg21237591 | 11 | 2162510 | Higher in Smoker |
| cg22896991 | 17 | 47073994 | Higher in Smoker |
| cg01384163 | 17 | 47073969 | Higher in Smoker |
| cg02782889 | 17 | 47074637 | Higher in Smoker |
| ch.17.1283089F | 17 | 47117551 | Higher in Smoker |
| cg11783901 | 17 | 47102000 | Lower in Smoker |
| cg08797864 | 3 | 185531258 | Lower in Smoker |
| cg03078488 | 7 | 23506648 | Higher in Smoker |
| cg00122683 | 6 | 160510345 | Lower in Smoker |
| cg08569322 | 6 | 160388967 | Lower in Smoker |
| cg00629117 | 16 | 1844932 | Lower in Smoker |
| cg05982504 | 16 | 1844962 | Lower in Smoker |
| cg10325224 | 16 | 1843751 | Lower in Smoker |
| cg25316969 | 2 | 217498388 | Higher in Smoker |
| cg13977557 | 7 | 45957390 | Higher in Smoker |
| cg15898840 | 7 | 45960834 | Higher in Smoker |
| cg13448906 | 2 | 217557710 | Higher in Smoker |
| cg01959562 | 4 | 57976561 | Higher in Smoker |
| cg21921384 | 4 | 57976556 | Higher in Smoker |
| cg03876618 | 4 | 57976034 | Higher in Smoker |
| cg25246031 | 19 | 46732864 | Lower in Smoker |

| | | | |
|---|---|---|---|
| cg05666713 | 1 | 201181883 | Lower in Smoker |
| cg22489583 | 19 | 51814765 | Higher in Smoker |
| cg25728174 | 19 | 51814782 | Higher in Smoker |
| cg01962676 | 1 | 18436969 | Higher in Smoker |
| cg11232944 | 1 | 18433572 | Higher in Smoker |
| cg23264776 | 1 | 18636650 | Lower in Smoker |
| cg08885927 | 1 | 18625743 | Lower in Smoker |
| cg08279194 | 1 | 18536457 | Lower in Smoker |
| cg23010629 | 1 | 18700603 | Lower in Smoker |
| cg05032399 | 11 | 18743376 | Higher in Smoker |
| cg17032184 | 1 | 117117195 | Lower in Smoker |
| cg13774792 | 11 | 133825997 | Higher in Smoker |
| cg05955566 | 12 | 99038273 | Higher in Smoker |
| cg13659268 | 9 | 111693331 | Lower in Smoker |
| cg16345559 | 2 | 213933386 | Lower in Smoker |
| cg26346104 | 10 | 124768792 | Higher in Smoker |
| cg26661481 | 11 | 117855870 | Higher in Smoker |
| cg11751927 | 11 | 117857137 | Higher in Smoker |
| cg14607407 | 21 | 34638535 | Higher in Smoker |
| cg03153360 | 19 | 55882504 | Higher in Smoker |
| cg21226253 | 9 | 34661706 | Lower in Smoker |
| cg00993824 | 1 | 67773175 | Higher in Smoker |
| cg03975876 | 1 | 67773073 | Higher in Smoker |
| cg09010346 | 4 | 142557655 | Higher in Smoker |
| cg25580782 | 10 | 6003621 | Lower in Smoker |
| cg05042034 | 15 | 81509050 | Lower in Smoker |
| cg23969506 | 13 | 21287304 | Lower in Smoker |
| cg11322251 | 13 | 21277362 | Lower in Smoker |
| cg13595439 | 22 | 17564750 | Lower in Smoker |
| cg12487088 | 3 | 9953686 | Higher in Smoker |
| cg22352371 | 3 | 57184624 | Lower in Smoker |
| cg13563334 | 22 | 50448833 | Lower in Smoker |
| cg16385335 | 11 | 71710614 | Lower in Smoker |
| cg00111978 | 2 | 102978529 | Lower in Smoker |
| cg27361520 | 2 | 103038171 | Lower in Smoker |

| | | | |
|---|---|---|---|
| cg02073054 | 1 | 207000757 | Lower in Smoker |
| cg27606396 | 2 | 113542117 | Higher in Smoker |
| cg01290568 | 2 | 113593859 | Higher in Smoker |
| cg06383401 | 2 | 113825234 | Lower in Smoker |
| cg00706302 | 2 | 113832957 | Lower in Smoker |
| cg13298167 | 2 | 113735451 | Lower in Smoker |
| cg25091458 | 3 | 190232250 | Higher in Smoker |
| cg17664443 | 3 | 190264104 | Lower in Smoker |
| cg23334620 | X | 103810458 | Higher in Smoker |
| cg01076217 | 6 | 137364811 | Higher in Smoker |
| cg27656754 | 6 | 137366492 | Lower in Smoker |
| cg13714540 | 6 | 137366432 | Lower in Smoker |
| cg06448442 | 6 | 137494919 | Lower in Smoker |
| cg16317713 | 1 | 67631342 | Lower in Smoker |
| cg09933279 | 1 | 207075400 | Lower in Smoker |
| cg19510472 | 19 | 14142205 | Lower in Smoker |
| cg18317474 | 19 | 14142577 | Higher in Smoker |
| cg11781854 | 19 | 39736690 | Lower in Smoker |
| cg26105232 | 10 | 6105656 | Higher in Smoker |
| cg09558975 | 3 | 3135232 | Lower in Smoker |
| cg06980173 | 1 | 154376344 | Lower in Smoker |
| cg23512958 | 8 | 79717776 | Higher in Smoker |
| cg01819306 | 8 | 79716458 | Higher in Smoker |
| cg11854227 | 3 | 121714109 | Lower in Smoker |
| cg26037239 | 1 | 153643678 | Higher in Smoker |
| cg26496705 | 19 | 10792843 | Higher in Smoker |
| cg07918736 | 19 | 10793775 | Lower in Smoker |
| cg03221702 | 19 | 10792991 | Lower in Smoker |
| cg24731756 | 11 | 6625293 | Higher in Smoker |
| cg01763057 | 2 | 239112731 | Lower in Smoker |
| cg14145049 | 7 | 111202457 | Higher in Smoker |
| cg11879096 | 7 | 110496797 | Lower in Smoker |
| cg13931356 | 18 | 22006370 | Higher in Smoker |
| cg22061809 | 18 | 22033229 | Lower in Smoker |
| cg19083143 | 18 | 22006626 | Lower in Smoker |

| | | | |
|---|---|---|---|
| cg14234680 | 3 | 57905925 | Higher in Smoker |
| cg24641027 | 7 | 128050275 | Higher in Smoker |
| cg03454397 | 6 | 76644790 | Higher in Smoker |
| cg10139846 | 1 | 62207966 | Higher in Smoker |
| cg26122413 | 14 | 105185236 | Lower in Smoker |
| cg03573445 | 14 | 105154858 | Lower in Smoker |
| cg02656441 | 13 | 111367915 | Higher in Smoker |
| cg20524211 | 13 | 111366070 | Higher in Smoker |
| cg05867960 | 13 | 111366057 | Higher in Smoker |
| cg10348863 | 4 | 184425226 | Higher in Smoker |
| cg21940830 | 4 | 184425975 | Lower in Smoker |
| cg00994876 | 2 | 242663243 | Lower in Smoker |
| cg09138133 | 7 | 41741428 | Lower in Smoker |
| cg00421221 | 2 | 121106091 | Lower in Smoker |
| cg03399971 | 12 | 57828847 | Lower in Smoker |
| cg05685435 | 12 | 57851749 | Lower in Smoker |
| cg03230769 | 7 | 30791030 | Lower in Smoker |
| cg03490115 | 2 | 74681972 | Higher in Smoker |
| cg18267330 | 2 | 99095277 | Lower in Smoker |
| cg11555067 | 2 | 99081350 | Lower in Smoker |
| cg04135372 | 2 | 99061383 | Lower in Smoker |
| cg00183107 | 4 | 143767118 | Higher in Smoker |
| cg00091953 | 4 | 143326541 | Higher in Smoker |
| cg17087414 | 4 | 143768275 | Higher in Smoker |
| cg15874062 | 4 | 143767647 | Lower in Smoker |
| cg16123421 | 10 | 134473552 | Lower in Smoker |
| cg17496877 | 10 | 134476628 | Lower in Smoker |
| cg17859552 | 10 | 134564260 | Lower in Smoker |
| cg05536439 | 10 | 134540511 | Lower in Smoker |
| cg14546128 | 10 | 134491509 | Lower in Smoker |
| cg10494449 | 10 | 134596049 | Lower in Smoker |
| cg12499572 | 10 | 134462831 | Lower in Smoker |
| cg06381135 | 10 | 134505548 | Lower in Smoker |
| cg24517875 | 10 | 134538559 | Lower in Smoker |
| cg09311690 | 10 | 134506448 | Lower in Smoker |

| | | | |
|---|---|---|---|
| cg12608975 | 10 | 134404873 | Lower in Smoker |
| cg06788249 | 10 | 134566575 | Lower in Smoker |
| cg04708830 | 10 | 134373018 | Lower in Smoker |
| cg04391569 | 10 | 134595301 | Lower in Smoker |
| cg02201479 | 10 | 134563815 | Lower in Smoker |
| cg14275445 | 10 | 134560047 | Lower in Smoker |
| cg08719605 | 1 | 38327818 | Lower in Smoker |
| cg03904674 | 10 | 121587426 | Lower in Smoker |
| cg11613559 | 10 | 121577971 | Lower in Smoker |
| cg23930945 | 11 | 15136376 | Higher in Smoker |
| cg14702589 | 11 | 15135669 | Lower in Smoker |
| cg17927917 | 7 | 155089006 | Higher in Smoker |
| cg14705142 | 2 | 118845915 | Higher in Smoker |
| cg05226506 | 2 | 118845797 | Higher in Smoker |
| cg20322299 | 2 | 118849751 | Lower in Smoker |
| cg08686462 | 11 | 2171184 | Lower in Smoker |
| cg08983259 | 1 | 67267855 | Lower in Smoker |
| cg11521979 | 1 | 67266410 | Lower in Smoker |
| cg11830061 | 9 | 5185415 | Lower in Smoker |
| cg06033738 | 20 | 20350367 | Higher in Smoker |
| cg14900579 | 19 | 7294137 | Higher in Smoker |
| cg00428638 | 19 | 7224713 | Higher in Smoker |
| cg00554421 | 7 | 1513368 | Higher in Smoker |
| cg17390817 | 7 | 1525085 | Higher in Smoker |
| cg14576951 | 7 | 1514568 | Lower in Smoker |
| cg06640728 | 7 | 1512940 | Lower in Smoker |
| cg05674406 | 7 | 1541901 | Lower in Smoker |
| cg07005770 | 7 | 1530051 | Lower in Smoker |
| cg12552676 | 4 | 106613852 | Lower in Smoker |
| cg05092885 | 4 | 106629795 | Higher in Smoker |
| cg15865788 | 17 | 60005843 | Lower in Smoker |
| cg23692497 | 11 | 77706182 | Higher in Smoker |
| cg04383038 | 7 | 64671875 | Higher in Smoker |
| cg03193454 | 11 | 62420599 | Higher in Smoker |
| cg00530199 | 13 | 52027382 | Higher in Smoker |

| | | | |
|---|---|---|---|
| cg14091473 | 9 | 103062981 | Lower in Smoker |
| cg07900624 | 3 | 49761894 | Higher in Smoker |
| cg13219625 | 3 | 49823913 | Higher in Smoker |
| cg16180552 | 3 | 48725646 | Lower in Smoker |
| cg09695647 | 3 | 48754612 | Higher in Smoker |
| cg00871019 | 10 | 60028461 | Higher in Smoker |
| cg11332336 | 1 | 44412331 | Higher in Smoker |
| cg13577655 | 1 | 44432363 | Lower in Smoker |
| cg09127005 | 1 | 44416390 | Lower in Smoker |
| cg16985259 | 1 | 44412491 | Higher in Smoker |
| cg25151295 | 13 | 98605857 | Lower in Smoker |
| cg27246280 | 11 | 9406063 | Higher in Smoker |
| cg23560715 | 11 | 9406072 | Higher in Smoker |
| ch.12.679484R | 12 | 30831546 | Higher in Smoker |
| cg19722847 | 12 | 30849114 | Lower in Smoker |
| cg27171890 | 1 | 46216671 | Higher in Smoker |
| cg22187826 | 3 | 121554169 | Higher in Smoker |
| cg04400980 | 3 | 121553992 | Higher in Smoker |
| cg03241971 | 7 | 2638278 | Higher in Smoker |
| cg22745355 | 7 | 2623374 | Lower in Smoker |
| cg17543469 | 7 | 2634897 | Lower in Smoker |
| cg08703857 | 7 | 2653651 | Lower in Smoker |
| cg12919294 | 3 | 158962196 | Lower in Smoker |
| cg04911307 | 16 | 19726462 | Lower in Smoker |
| cg23480821 | 15 | 90931228 | Higher in Smoker |
| cg08595501 | 5 | 75878300 | Lower in Smoker |
| cg27271732 | 3 | 13029200 | Lower in Smoker |
| cg21924571 | 3 | 13114441 | Lower in Smoker |
| cg03926815 | 3 | 13114681 | Lower in Smoker |
| cg23336797 | 3 | 13114570 | Lower in Smoker |
| cg19115941 | 12 | 187284 | Higher in Smoker |
| cg02412810 | 12 | 217788 | Lower in Smoker |
| cg24385675 | 7 | 123174539 | Higher in Smoker |
| cg19572242 | X | 153285790 | Higher in Smoker |
| cg19518265 | 3 | 10277547 | Lower in Smoker |

| | | | |
|---|---|---|---|
| cg13807985 | 12 | 66583255 | Higher in Smoker |
| cg09308829 | 4 | 185395352 | Higher in Smoker |
| cg09029046 | 4 | 185377241 | Lower in Smoker |
| cg21533544 | 4 | 185309524 | Lower in Smoker |
| cg05501617 | 4 | 185339075 | Lower in Smoker |
| cg03177708 | 19 | 46389676 | Higher in Smoker |
| cg24319508 | 6 | 394966 | Lower in Smoker |
| cg00140447 | 7 | 128580709 | Lower in Smoker |
| cg21007190 | 7 | 128578297 | Lower in Smoker |
| cg07660635 | 16 | 85936147 | Lower in Smoker |
| cg11065693 | 14 | 24630380 | Higher in Smoker |
| cg08834602 | 19 | 44220122 | Lower in Smoker |
| cg10501621 | 5 | 150227345 | Lower in Smoker |
| cg05340042 | 5 | 150224636 | Lower in Smoker |
| cg27141915 | 19 | 44094007 | Higher in Smoker |
| cg19382545 | 2 | 227663669 | Higher in Smoker |
| cg05514401 | 13 | 110436111 | Lower in Smoker |
| cg02320481 | 13 | 110438578 | Higher in Smoker |
| cg17700139 | X | 107980270 | Higher in Smoker |
| cg24035953 | X | 107976034 | Higher in Smoker |
| cg24754154 | X | 107979584 | Higher in Smoker |
| cg07881405 | 5 | 3597487 | Higher in Smoker |
| cg06060135 | 5 | 3596704 | Higher in Smoker |
| cg08492173 | 5 | 3597311 | Higher in Smoker |
| cg15505412 | 5 | 3596996 | Higher in Smoker |
| cg06259881 | 16 | 54321165 | Higher in Smoker |
| cg27228168 | 16 | 54320674 | Higher in Smoker |
| cg24662961 | 16 | 54320670 | Higher in Smoker |
| cg00243313 | 5 | 1883413 | Higher in Smoker |
| cg09662325 | 16 | 55363601 | Lower in Smoker |
| cg07541744 | 16 | 55363277 | Lower in Smoker |
| cg13381718 | 12 | 108955348 | Higher in Smoker |
| cg08469540 | 1 | 948627 | Higher in Smoker |
| cg03778780 | 15 | 74466910 | Lower in Smoker |
| cg20314548 | 15 | 74426273 | Higher in Smoker |

| | | | |
|---|---|---|---|
| cg05505745 | 15 | 74422330 | Higher in Smoker |
| cg23152885 | 15 | 74422282 | Higher in Smoker |
| cg15577927 | 20 | 13201328 | Higher in Smoker |
| cg23504092 | 20 | 13201342 | Higher in Smoker |
| cg25384906 | 20 | 13201349 | Higher in Smoker |
| cg19118558 | 20 | 13201353 | Higher in Smoker |
| cg06567525 | 20 | 13201551 | Higher in Smoker |
| cg10378364 | 20 | 13202437 | Higher in Smoker |
| cg06469542 | 14 | 77965869 | Lower in Smoker |
| cg21192621 | 3 | 128880118 | Higher in Smoker |
| cg11287475 | 3 | 128876291 | Lower in Smoker |
| cg15907699 | 3 | 128879836 | Higher in Smoker |
| cg21638053 | 5 | 52127619 | Lower in Smoker |
| cg16619991 | 5 | 52096811 | Lower in Smoker |
| cg02454536 | 15 | 68713677 | Lower in Smoker |
| cg11222053 | 17 | 48132102 | Higher in Smoker |
| cg23292453 | 17 | 48133402 | Higher in Smoker |
| cg06262280 | 2 | 173330296 | Lower in Smoker |
| cg27553745 | 12 | 56101649 | Higher in Smoker |
| cg08821998 | 3 | 37562371 | Lower in Smoker |
| cg05772218 | 17 | 3658684 | Lower in Smoker |
| cg13254286 | 17 | 3658044 | Lower in Smoker |
| cg04716530 | 16 | 30485684 | Lower in Smoker |
| cg16391678 | 16 | 30485597 | Lower in Smoker |
| cg24033122 | 16 | 30485383 | Lower in Smoker |
| cg09099830 | 16 | 30485485 | Lower in Smoker |
| cg17340492 | 19 | 3932951 | Lower in Smoker |
| cg18464559 | 1 | 63989278 | Higher in Smoker |
| cg24079672 | 17 | 73739840 | Lower in Smoker |
| cg17646499 | 3 | 124601778 | Higher in Smoker |
| cg00589181 | 3 | 124560306 | Lower in Smoker |
| cg07896068 | 2 | 161056600 | Lower in Smoker |
| cg15889057 | 12 | 53602179 | Lower in Smoker |
| cg21690450 | 13 | 102276634 | Higher in Smoker |
| cg01664065 | 13 | 102249040 | Lower in Smoker |

| | | | |
|---|---|---|---|
| cg07095346 | 3 | 52864812 | Lower in Smoker |
| cg19422218 | 10 | 7670701 | Lower in Smoker |
| cg13340899 | 10 | 7670827 | Lower in Smoker |
| cg10894453 | X | 78622859 | Higher in Smoker |
| cg06580891 | 20 | 3189935 | Higher in Smoker |
| cg22808839 | 14 | 93415226 | Higher in Smoker |
| cg02039485 | 14 | 93570854 | Lower in Smoker |
| cg10040594 | 14 | 93556554 | Lower in Smoker |
| cg22444124 | 1 | 226867960 | Higher in Smoker |
| cg19160520 | 1 | 226927217 | Higher in Smoker |
| cg23717186 | 1 | 226924311 | Lower in Smoker |
| cg05306109 | 1 | 226924257 | Lower in Smoker |
| cg21142512 | 3 | 4791251 | Lower in Smoker |
| cg14708401 | 3 | 4715031 | Lower in Smoker |
| cg05795849 | 3 | 4794082 | Higher in Smoker |
| cg23202253 | 12 | 26902211 | Higher in Smoker |
| cg09257092 | 12 | 26986805 | Higher in Smoker |
| cg23425324 | 12 | 26986193 | Higher in Smoker |
| cg15828915 | 12 | 26801163 | Lower in Smoker |
| cg03078593 | 12 | 26789311 | Lower in Smoker |
| cg16301004 | 10 | 106082537 | Lower in Smoker |
| cg05497345 | 2 | 96990914 | Higher in Smoker |
| cg06777352 | 16 | 19124984 | Higher in Smoker |
| cg13786429 | 21 | 35210094 | Lower in Smoker |
| cg15099273 | 21 | 35014195 | Lower in Smoker |
| cg24921022 | 2 | 24426374 | Lower in Smoker |
| cg26886850 | 15 | 70697719 | Lower in Smoker |
| cg19563513 | 2 | 128283341 | Higher in Smoker |
| cg08213351 | 2 | 128283535 | Higher in Smoker |
| cg16385448 | 14 | 105612130 | Lower in Smoker |
| cg00420347 | 1 | 65362428 | Lower in Smoker |
| cg18227442 | 1 | 65352699 | Lower in Smoker |
| cg00153395 | 1 | 65327523 | Lower in Smoker |
| cg03390472 | 9 | 5043263 | Higher in Smoker |
| cg04777091 | 4 | 6050440 | Higher in Smoker |

| | | | |
|---|---|---|---|
| cg22328396 | 4 | 6116698 | Higher in Smoker |
| cg01929855 | 4 | 6107649 | Lower in Smoker |
| cg15158859 | 10 | 133978304 | Higher in Smoker |
| cg18936304 | 10 | 133949163 | Lower in Smoker |
| cg00960857 | 10 | 133938631 | Lower in Smoker |
| cg27316068 | 10 | 133955986 | Lower in Smoker |
| cg20627988 | 10 | 133946881 | Lower in Smoker |
| cg06416097 | 10 | 133989312 | Lower in Smoker |
| cg14044216 | 10 | 133921075 | Lower in Smoker |
| cg14634826 | 11 | 133982272 | Lower in Smoker |
| cg15046123 | 6 | 15421581 | Higher in Smoker |
| cg12104547 | 6 | 15328030 | Lower in Smoker |
| cg06984176 | 6 | 15501652 | Lower in Smoker |
| cg14632031 | 6 | 15307677 | Lower in Smoker |
| cg06487194 | 6 | 15345097 | Lower in Smoker |
| cg04020066 | 7 | 28220514 | Lower in Smoker |
| cg23620719 | 7 | 28220237 | Lower in Smoker |
| cg10959498 | 10 | 65000809 | Lower in Smoker |
| cg01667332 | 10 | 65225630 | Higher in Smoker |
| cg03572679 | 16 | 27214731 | Higher in Smoker |
| cg13533061 | 17 | 74712429 | Lower in Smoker |
| cg16542977 | 17 | 74719994 | Lower in Smoker |
| cg09087897 | 17 | 74714618 | Lower in Smoker |
| cg06646636 | 16 | 734766 | Lower in Smoker |
| cg24856658 | 5 | 78533917 | Lower in Smoker |
| cg06711259 | 22 | 39095898 | Lower in Smoker |
| cg00751253 | 8 | 75233613 | Higher in Smoker |
| cg09552213 | 16 | 87636782 | Higher in Smoker |
| cg25938042 | 16 | 87637283 | Higher in Smoker |
| cg07873172 | 16 | 87712631 | Higher in Smoker |
| cg14220764 | 14 | 23452408 | Higher in Smoker |
| cg22971594 | 14 | 23442770 | Lower in Smoker |
| cg00543485 | 1 | 59249218 | Higher in Smoker |
| cg12899673 | 17 | 39913952 | Lower in Smoker |
| cg25149475 | 17 | 39928107 | Lower in Smoker |

| | | | |
|---|---|---|---|
| cg04084455 | X | 8700315 | Higher in Smoker |
| cg22109064 | X | 8699687 | Higher in Smoker |
| cg20130098 | 3 | 123984695 | Higher in Smoker |
| cg15001930 | 3 | 124306820 | Lower in Smoker |
| cg04516112 | 3 | 124303404 | Lower in Smoker |
| cg12144803 | 3 | 123813383 | Lower in Smoker |
| cg11148677 | 3 | 123876715 | Lower in Smoker |
| cg14274665 | 9 | 507411 | Lower in Smoker |
| cg03358592 | 9 | 707410 | Lower in Smoker |
| cg07888912 | 19 | 11305913 | Higher in Smoker |
| cg09934056 | 19 | 8400203 | Higher in Smoker |
| cg08271996 | 1 | 62739132 | Higher in Smoker |
| cg09588271 | 1 | 62784651 | Lower in Smoker |
| cg18053505 | 3 | 20081161 | Higher in Smoker |
| cg06133722 | 11 | 65485453 | Higher in Smoker |
| cg25748121 | 18 | 44541383 | Lower in Smoker |
| cg19804570 | 18 | 44618587 | Lower in Smoker |
| cg01656750 | 16 | 57771195 | Lower in Smoker |
| cg00439196 | 16 | 57769757 | Higher in Smoker |
| cg26366480 | 10 | 102820327 | Higher in Smoker |
| cg03168249 | 10 | 102822423 | Lower in Smoker |
| cg12060422 | 10 | 102821684 | Higher in Smoker |
| cg10740880 | 2 | 170365212 | Lower in Smoker |
| cg26775644 | 8 | 1921369 | Higher in Smoker |
| cg09618998 | 8 | 1950965 | Higher in Smoker |
| cg21825526 | 3 | 127642355 | Lower in Smoker |
| cg05731021 | 7 | 32930798 | Higher in Smoker |
| cg03915167 | 11 | 105947676 | Lower in Smoker |
| cg09602562 | 11 | 105948187 | Higher in Smoker |
| cg02407032 | 11 | 47600271 | Higher in Smoker |
| cg03053285 | 2 | 85197235 | Higher in Smoker |
| cg00791468 | 1 | 111148984 | Higher in Smoker |
| cg07808555 | 1 | 111217712 | Higher in Smoker |
| cg07903677 | 1 | 111218079 | Lower in Smoker |
| cg11595545 | 1 | 111217497 | Higher in Smoker |

| | | | |
|---|---|---|---|
| cg08490115 | 11 | 30038675 | Higher in Smoker |
| cg15044957 | 11 | 30038672 | Higher in Smoker |
| cg15310492 | 11 | 30038677 | Higher in Smoker |
| cg05756220 | 11 | 30038685 | Higher in Smoker |
| cg10141352 | 3 | 155859344 | Lower in Smoker |
| cg23158419 | 3 | 155838399 | Lower in Smoker |
| cg13736068 | 3 | 156009398 | Higher in Smoker |
| cg20814688 | 1 | 6132879 | Lower in Smoker |
| cg00813560 | 1 | 6106358 | Lower in Smoker |
| cg22235088 | 1 | 6111835 | Lower in Smoker |
| cg19814116 | 1 | 6086448 | Higher in Smoker |
| cg27162435 | 17 | 7833163 | Lower in Smoker |
| cg14918082 | 17 | 7833237 | Lower in Smoker |
| cg01323777 | 17 | 7832943 | Lower in Smoker |
| cg23365801 | 17 | 7832909 | Lower in Smoker |
| cg16513459 | 17 | 7832932 | Lower in Smoker |
| cg10536151 | 11 | 17758285 | Lower in Smoker |
| cg17203063 | 12 | 75601711 | Higher in Smoker |
| cg10148473 | 12 | 75601824 | Higher in Smoker |
| cg04144226 | 7 | 119912636 | Higher in Smoker |
| cg17454942 | 1 | 112422473 | Lower in Smoker |
| cg15211908 | 1 | 112531263 | Lower in Smoker |
| cg20240715 | 21 | 35828503 | Lower in Smoker |
| cg05437059 | X | 108968775 | Higher in Smoker |
| cg03027241 | 20 | 49620453 | Lower in Smoker |
| cg06998507 | 16 | 84275740 | Higher in Smoker |
| cg27435498 | 7 | 150655387 | Higher in Smoker |
| cg10454121 | 7 | 150675859 | Higher in Smoker |
| cg17564354 | 7 | 150675025 | Higher in Smoker |
| cg22566355 | 12 | 49943340 | Lower in Smoker |
| cg16656196 | 17 | 40321577 | Higher in Smoker |
| cg06514003 | 17 | 40330907 | Lower in Smoker |
| cg26846781 | 17 | 61620942 | Lower in Smoker |
| cg07486085 | 2 | 163625066 | Lower in Smoker |
| cg25849262 | 3 | 19189070 | Lower in Smoker |

| | | | |
|---|---|---|---|
| cg11953015 | 5 | 170163538 | Lower in Smoker |
| cg01585372 | 5 | 169931363 | Higher in Smoker |
| cg18364678 | 10 | 103586829 | Lower in Smoker |
| cg14739214 | 10 | 103589138 | Lower in Smoker |
| cg03595348 | 2 | 95999906 | Lower in Smoker |
| cg16178141 | 2 | 96016283 | Lower in Smoker |
| cg26279668 | 4 | 21949853 | Higher in Smoker |
| cg06482428 | 4 | 21950173 | Higher in Smoker |
| cg18347642 | 4 | 21950766 | Higher in Smoker |
| cg03271761 | 4 | 21699209 | Lower in Smoker |
| cg15127791 | 11 | 128729883 | Higher in Smoker |
| cg12408998 | 11 | 128737463 | Lower in Smoker |
| cg12204555 | 11 | 128712645 | Lower in Smoker |
| cg06995869 | 11 | 128712697 | Lower in Smoker |
| cg20962532 | 11 | 128712462 | Lower in Smoker |
| cg05768141 | 1 | 160039847 | Lower in Smoker |
| cg03928539 | 17 | 21279613 | Higher in Smoker |
| cg10222534 | 19 | 48958894 | Lower in Smoker |
| cg18248112 | 21 | 39629123 | Higher in Smoker |
| cg08773640 | 17 | 68125102 | Lower in Smoker |
| cg18432768 | 17 | 68100565 | Lower in Smoker |
| cg12204395 | 17 | 68171750 | Lower in Smoker |
| cg23649004 | 22 | 38851332 | Lower in Smoker |
| cg04452906 | 11 | 128760609 | Lower in Smoker |
| cg25312594 | 1 | 233749381 | Higher in Smoker |
| cg02581587 | 1 | 233765350 | Higher in Smoker |
| cg11382055 | 1 | 233749410 | Higher in Smoker |
| cg16676775 | 1 | 233771806 | Lower in Smoker |
| cg05052893 | 14 | 88789655 | Higher in Smoker |
| cg16730078 | 14 | 88788422 | Lower in Smoker |
| cg00932251 | 14 | 88789516 | Higher in Smoker |
| cg00364611 | 14 | 90528870 | Higher in Smoker |
| cg12212555 | 14 | 90528722 | Higher in Smoker |
| cg21191365 | 14 | 90529014 | Higher in Smoker |
| cg00029521 | 6 | 39272634 | Lower in Smoker |

| | | | |
|---|---|---|---|
| cg18193242 | 6 | 39277547 | Lower in Smoker |
| cg26547924 | 1 | 215256870 | Higher in Smoker |
| cg17130063 | 1 | 215256448 | Higher in Smoker |
| cg01805869 | 2 | 26915772 | Higher in Smoker |
| cg25444821 | 2 | 26952869 | Lower in Smoker |
| cg23847700 | 11 | 64066766 | Higher in Smoker |
| cg13654525 | 11 | 65360509 | Higher in Smoker |
| cg13179915 | 11 | 65362949 | Lower in Smoker |
| cg05479582 | 10 | 79396624 | Lower in Smoker |
| cg16738985 | 10 | 79264178 | Lower in Smoker |
| cg08252303 | 10 | 79399007 | Lower in Smoker |
| cg07802909 | 5 | 169817797 | Lower in Smoker |
| cg25465483 | 3 | 178432932 | Lower in Smoker |
| cg23096553 | 12 | 70759870 | Higher in Smoker |
| cg11249835 | 12 | 70824419 | Lower in Smoker |
| cg23541257 | 19 | 18096662 | Lower in Smoker |
| cg20733663 | 19 | 18109226 | Lower in Smoker |
| cg14558673 | 5 | 113785032 | Lower in Smoker |
| cg25201998 | 1 | 154821946 | Lower in Smoker |
| cg12058501 | 1 | 154690385 | Lower in Smoker |
| cg22732644 | 1 | 154745124 | Lower in Smoker |
| cg02289321 | 1 | 154746968 | Lower in Smoker |
| cg26890181 | 19 | 44285940 | Lower in Smoker |
| cg14066757 | 19 | 44285568 | Lower in Smoker |
| cg24900654 | 19 | 44285594 | Lower in Smoker |
| cg06533200 | 11 | 2466138 | Higher in Smoker |
| cg11363972 | 11 | 2465249 | Lower in Smoker |
| cg07618453 | 11 | 2502181 | Higher in Smoker |
| cg17494446 | 11 | 2569380 | Lower in Smoker |
| cg24039935 | 11 | 2554295 | Lower in Smoker |
| cg02219360 | 11 | 2721409 | Higher in Smoker |
| cg18438187 | 20 | 62059392 | Lower in Smoker |
| cg12401793 | 20 | 62098002 | Higher in Smoker |
| cg20650029 | 8 | 133204098 | Higher in Smoker |
| cg03461431 | 1 | 41285096 | Lower in Smoker |

| | | | |
|---|---|---|---|
| cg06626599 | 1 | 41284135 | Lower in Smoker |
| cg11168433 | 1 | 41283979 | Lower in Smoker |
| cg11008243 | 6 | 73331238 | Higher in Smoker |
| cg24687051 | 6 | 73332073 | Higher in Smoker |
| cg25353142 | 20 | 43729869 | Higher in Smoker |
| cg11999255 | 2 | 18058717 | Higher in Smoker |
| cg25420747 | 2 | 18112176 | Lower in Smoker |
| cg13537226 | 9 | 136660643 | Lower in Smoker |
| cg09177518 | 1 | 196578010 | Higher in Smoker |
| cg13846960 | 9 | 2718456 | Higher in Smoker |
| cg17511168 | 7 | 128516960 | Lower in Smoker |
| cg01861634 | 7 | 128530369 | Lower in Smoker |
| cg14798754 | 18 | 24221245 | Lower in Smoker |
| cg02901177 | 18 | 24128506 | Higher in Smoker |
| cg00742557 | 18 | 24128623 | Higher in Smoker |
| cg16650292 | 13 | 77460719 | Higher in Smoker |
| cg15901783 | 13 | 77461426 | Lower in Smoker |
| cg04474731 | 5 | 143585107 | Higher in Smoker |
| cg22444610 | 2 | 201375087 | Higher in Smoker |
| cg07158797 | 1 | 215740701 | Higher in Smoker |
| cg03424058 | 1 | 215791864 | Lower in Smoker |
| cg19910763 | 1 | 215773070 | Lower in Smoker |
| cg06581357 | 16 | 2736874 | Lower in Smoker |
| cg05244581 | 8 | 25315002 | Higher in Smoker |
| cg04794299 | 11 | 106368512 | Higher in Smoker |
| cg06320126 | 11 | 66886141 | Higher in Smoker |
| cg03389662 | 11 | 67007586 | Higher in Smoker |
| cg04085336 | 11 | 67007785 | Higher in Smoker |
| cg05067991 | 12 | 122018586 | Higher in Smoker |
| cg26975807 | 12 | 122000960 | Lower in Smoker |
| cg01236774 | 12 | 122007814 | Lower in Smoker |
| cg08520742 | 12 | 121882033 | Lower in Smoker |
| cg03241244 | 12 | 122017052 | Lower in Smoker |
| cg08461425 | 12 | 121971790 | Lower in Smoker |
| cg13708645 | 12 | 121974305 | Lower in Smoker |

| | | | |
|---|---|---|---|
| cg15695155 | 12 | 121973871 | Lower in Smoker |
| cg26995224 | 12 | 121974146 | Lower in Smoker |
| cg17737314 | 1 | 44114355 | Lower in Smoker |
| cg00946598 | 1 | 44117093 | Lower in Smoker |
| cg16886828 | 19 | 5032663 | Higher in Smoker |
| cg23839891 | 19 | 5094994 | Lower in Smoker |
| cg04592958 | 19 | 5138093 | Lower in Smoker |
| cg02659867 | 19 | 5033098 | Lower in Smoker |
| cg25637520 | 19 | 5043247 | Lower in Smoker |
| cg22646782 | 19 | 5152272 | Lower in Smoker |
| cg09547226 | 19 | 5058863 | Lower in Smoker |
| cg20098875 | 19 | 5093370 | Lower in Smoker |
| cg11782515 | 19 | 4986183 | Lower in Smoker |
| cg13844787 | 9 | 6731623 | Lower in Smoker |
| cg23023599 | 11 | 94732500 | Lower in Smoker |
| cg05745632 | 11 | 94706668 | Higher in Smoker |
| cg20024259 | 12 | 392537 | Lower in Smoker |
| cg27461800 | 12 | 498354 | Higher in Smoker |
| cg00528052 | 1 | 202777295 | Higher in Smoker |
| cg01101782 | 1 | 202778711 | Lower in Smoker |
| cg23390745 | 1 | 202778061 | Lower in Smoker |
| cg19903753 | X | 53254678 | Higher in Smoker |
| cg25815185 | Y | 21906868 | Lower in Smoker |
| cg21126573 | 17 | 7755257 | Higher in Smoker |
| cg03538808 | 17 | 7746830 | Higher in Smoker |
| cg09911083 | 17 | 7754956 | Lower in Smoker |
| cg05754435 | 4 | 55992155 | Higher in Smoker |
| cg19759864 | 18 | 61034945 | Higher in Smoker |
| cg14776016 | 18 | 61034565 | Higher in Smoker |
| cg16172657 | 6 | 73973008 | Lower in Smoker |
| cg22014661 | 6 | 62996130 | Higher in Smoker |
| cg26719995 | 2 | 27309153 | Higher in Smoker |
| cg19826802 | 17 | 2697212 | Higher in Smoker |
| cg17792876 | 5 | 141303293 | Higher in Smoker |
| cg10200608 | 5 | 141302906 | Lower in Smoker |

| | | | |
|---|---|---|---|
| ch.8.1073630F | 8 | 48637817 | Higher in Smoker |
| cg08506869 | 8 | 48572447 | Higher in Smoker |
| cg16826795 | 8 | 48173930 | Higher in Smoker |
| cg12846837 | 8 | 48172889 | Lower in Smoker |
| cg08165361 | 8 | 48474400 | Lower in Smoker |
| cg04246999 | 16 | 71930048 | Lower in Smoker |
| cg09205083 | 16 | 85674320 | Higher in Smoker |
| cg04317076 | 16 | 85682219 | Lower in Smoker |
| cg27201775 | 16 | 85674895 | Lower in Smoker |
| cg04148089 | 16 | 85673599 | Lower in Smoker |
| cg26771832 | 16 | 85656125 | Lower in Smoker |
| cg02678638 | 16 | 85671115 | Lower in Smoker |
| cg01397513 | 16 | 85670135 | Lower in Smoker |
| cg13441891 | 16 | 85648370 | Lower in Smoker |
| cg19440670 | 3 | 197464091 | Higher in Smoker |
| cg25194415 | 4 | 6784170 | Higher in Smoker |
| cg04555107 | 14 | 70130327 | Lower in Smoker |
| cg19739432 | 14 | 105344718 | Lower in Smoker |
| cg14772955 | 1 | 36024404 | Higher in Smoker |
| cg00183804 | 19 | 34746203 | Higher in Smoker |
| cg05001598 | 9 | 114246158 | Higher in Smoker |
| cg21410293 | 18 | 46386361 | Lower in Smoker |
| cg21602842 | 18 | 46291908 | Lower in Smoker |
| cg00307276 | 16 | 15689899 | Higher in Smoker |
| cg15501359 | 1 | 47185051 | Higher in Smoker |
| cg03342366 | 1 | 47184735 | Higher in Smoker |
| cg23666378 | 1 | 3663164 | Lower in Smoker |
| cg07450021 | 16 | 85097151 | Lower in Smoker |
| cg08048517 | 12 | 22697480 | Higher in Smoker |
| cg04274990 | 16 | 27611319 | Lower in Smoker |
| cg19634774 | 13 | 42179326 | Lower in Smoker |
| cg24046884 | 13 | 42224923 | Lower in Smoker |
| cg05179396 | 13 | 42206323 | Lower in Smoker |
| cg16122145 | 13 | 42218760 | Lower in Smoker |
| cg02995055 | 13 | 42535448 | Higher in Smoker |

| | | | |
|---|---|---|---|
| cg10333333 | 13 | 42535460 | Higher in Smoker |
| cg07645461 | 13 | 42535296 | Higher in Smoker |
| cg06505703 | 13 | 42531447 | Lower in Smoker |
| cg13132016 | 14 | 58893740 | Higher in Smoker |
| cg11178136 | 11 | 46637717 | Lower in Smoker |
| cg10533255 | 11 | 46679301 | Lower in Smoker |
| cg01132515 | 17 | 2601803 | Higher in Smoker |
| cg01401336 | 17 | 2606734 | Lower in Smoker |
| cg19219778 | 12 | 55378638 | Higher in Smoker |
| cg25486399 | 12 | 55376897 | Higher in Smoker |
| ch.17.254251R | 17 | 6533972 | Higher in Smoker |
| ch.19.820881F | 19 | 19440400 | Higher in Smoker |
| cg18607470 | 7 | 36407067 | Higher in Smoker |
| cg10031648 | 16 | 67210632 | Higher in Smoker |
| cg06361057 | 16 | 67219207 | Higher in Smoker |
| cg18088056 | 10 | 75551723 | Lower in Smoker |
| cg06465196 | 4 | 154387603 | Higher in Smoker |
| cg26055899 | 4 | 154462759 | Lower in Smoker |
| cg03054600 | 18 | 29523728 | Higher in Smoker |
| cg01320648 | 4 | 123091375 | Lower in Smoker |
| cg13986870 | 9 | 34376534 | Higher in Smoker |
| cg20241254 | 9 | 34372821 | Lower in Smoker |
| cg24796627 | 15 | 81071708 | Higher in Smoker |
| cg23895729 | 15 | 81073931 | Lower in Smoker |
| cg19359966 | 4 | 57180029 | Lower in Smoker |
| cg08704681 | 10 | 23983534 | Higher in Smoker |
| cg22539706 | 10 | 24646727 | Lower in Smoker |
| cg06651311 | 4 | 37246230 | Higher in Smoker |
| cg25205699 | 4 | 37246280 | Higher in Smoker |
| cg08320879 | 4 | 37450181 | Lower in Smoker |
| cg07113870 | 6 | 138661029 | Lower in Smoker |
| cg18521796 | 3 | 128713631 | Lower in Smoker |
| cg13740709 | 3 | 128712555 | Lower in Smoker |
| cg13587449 | 10 | 72240883 | Higher in Smoker |
| cg08928321 | 10 | 70748447 | Higher in Smoker |

| | | | |
|---|---|---|---|
| cg22692790 | 10 | 70748415 | Higher in Smoker |
| cg16797931 | 1 | 109657035 | Lower in Smoker |
| cg27038198 | 7 | 86686461 | Lower in Smoker |
| cg23171636 | 15 | 52954695 | Lower in Smoker |
| cg18295923 | 14 | 94004416 | Lower in Smoker |
| cg07158312 | 8 | 95565682 | Lower in Smoker |
| cg00801798 | 9 | 5628280 | Higher in Smoker |
| cg19826211 | 10 | 30348638 | Higher in Smoker |
| cg01062834 | 10 | 30348632 | Higher in Smoker |
| cg24350475 | 10 | 30316933 | Lower in Smoker |
| cg05912082 | 12 | 13197550 | Higher in Smoker |
| cg19262476 | 1 | 33232579 | Lower in Smoker |
| cg25825204 | 4 | 1339874 | Higher in Smoker |
| cg05657564 | 4 | 1352290 | Higher in Smoker |
| cg21499685 | 4 | 1362252 | Lower in Smoker |
| cg09820011 | 10 | 118765125 | Higher in Smoker |
| cg03968911 | 10 | 118734132 | Lower in Smoker |
| cg02156380 | 1 | 180882591 | Higher in Smoker |
| cg27128322 | 18 | 43547338 | Lower in Smoker |
| cg19296405 | 19 | 18368483 | Lower in Smoker |
| cg25667997 | 8 | 145758486 | Lower in Smoker |
| cg04236901 | 4 | 175204805 | Higher in Smoker |
| cg24930774 | 4 | 175205098 | Lower in Smoker |
| cg09290497 | 11 | 93394826 | Higher in Smoker |
| cg05757448 | 1 | 1895206 | Lower in Smoker |
| cg03771099 | 1 | 1917911 | Lower in Smoker |
| cg05035260 | 1 | 1909092 | Lower in Smoker |
| cg15100231 | 11 | 105880578 | Higher in Smoker |
| cg26683639 | 6 | 30653755 | Lower in Smoker |
| cg10426318 | 6 | 30647588 | Lower in Smoker |
| cg10145196 | 6 | 30647849 | Lower in Smoker |
| cg11554650 | 6 | 30653191 | Lower in Smoker |
| cg23672659 | 6 | 30648020 | Lower in Smoker |
| cg17438419 | 6 | 30654622 | Higher in Smoker |
| cg08052856 | 6 | 30654693 | Higher in Smoker |

| | | | |
|---|---|---|---|
| cg19504658 | 6 | 30655197 | Higher in Smoker |
| cg24261270 | 8 | 22462105 | Higher in Smoker |
| cg25591036 | 9 | 139694867 | Higher in Smoker |
| cg13934792 | 9 | 139694739 | Higher in Smoker |
| cg06707403 | 1 | 11985681 | Lower in Smoker |
| cg17812951 | 3 | 113415923 | Higher in Smoker |
| cg23977002 | 2 | 8945049 | Lower in Smoker |
| cg26426395 | 2 | 8870227 | Lower in Smoker |
| ch.10.1963761R | 10 | 94373483 | Higher in Smoker |
| cg16144590 | 8 | 28926051 | Higher in Smoker |
| cg19780614 | 8 | 28932339 | Lower in Smoker |
| cg22561384 | 8 | 28932160 | Lower in Smoker |
| cg26151597 | 3 | 44802853 | Higher in Smoker |
| cg10530135 | 1 | 21022984 | Higher in Smoker |
| cg18955698 | 17 | 43025023 | Higher in Smoker |
| cg27211088 | 17 | 72345476 | Lower in Smoker |
| cg17033457 | 2 | 241721504 | Lower in Smoker |
| cg15023006 | 2 | 241760782 | Lower in Smoker |
| cg11399195 | 1 | 10364025 | Lower in Smoker |
| cg16612511 | 17 | 4927006 | Higher in Smoker |
| cg06381661 | 10 | 91461385 | Higher in Smoker |
| cg05717833 | 15 | 69706383 | Higher in Smoker |
| cg01787565 | 1 | 245318209 | Higher in Smoker |
| cg16591381 | 1 | 245499719 | Lower in Smoker |
| cg05816786 | 1 | 245375925 | Lower in Smoker |
| cg25143359 | 1 | 245533949 | Lower in Smoker |
| cg25471644 | 1 | 245704602 | Lower in Smoker |
| cg09974780 | 5 | 61601128 | Higher in Smoker |
| cg00251536 | 1 | 45205438 | Higher in Smoker |
| cg12269116 | 1 | 45205193 | Higher in Smoker |
| cg27300397 | 5 | 132073308 | Lower in Smoker |
| cg22507535 | 5 | 132073257 | Higher in Smoker |
| cg07518170 | 20 | 30865285 | Lower in Smoker |
| cg24772167 | 2 | 26205606 | Higher in Smoker |
| cg24826355 | 10 | 32344604 | Higher in Smoker |

| | | | |
|---|---|---|---|
| cg00686595 | 10 | 32345476 | Higher in Smoker |
| cg11489602 | 10 | 32345426 | Higher in Smoker |
| cg19240233 | 6 | 39399816 | Lower in Smoker |
| cg20169734 | 3 | 47307826 | Lower in Smoker |
| cg13469180 | 3 | 47324151 | Higher in Smoker |
| cg10681256 | 3 | 47324572 | Higher in Smoker |
| cg10483461 | 1 | 170043670 | Lower in Smoker |
| cg18049541 | 6 | 33374619 | Lower in Smoker |
| cg00188321 | 6 | 33358615 | Lower in Smoker |
| cg25474873 | 6 | 33358798 | Lower in Smoker |
| cg26908388 | 6 | 33358785 | Lower in Smoker |
| cg20400383 | 6 | 33359642 | Higher in Smoker |
| cg04794268 | 8 | 145690383 | Lower in Smoker |
| cg26927427 | 16 | 57832230 | Lower in Smoker |
| cg07479337 | 16 | 57822386 | Lower in Smoker |
| cg20337093 | 10 | 89621678 | Lower in Smoker |
| cg25033144 | 19 | 55048290 | Higher in Smoker |
| cg01449341 | 19 | 55044295 | Lower in Smoker |
| cg24301250 | 11 | 126626136 | Lower in Smoker |
| cg16592378 | 11 | 126498687 | Lower in Smoker |
| cg01308409 | 13 | 33591937 | Higher in Smoker |
| cg21496948 | 14 | 104153614 | Lower in Smoker |
| cg05321721 | 14 | 104094918 | Lower in Smoker |
| cg25736830 | 11 | 66023582 | Lower in Smoker |
| cg13306893 | 11 | 66024688 | Higher in Smoker |
| cg18046087 | 11 | 66035276 | Higher in Smoker |
| cg03622002 | 11 | 66035105 | Higher in Smoker |
| cg10498476 | 11 | 66035147 | Higher in Smoker |
| cg25967419 | 6 | 43027303 | Higher in Smoker |
| cg10194341 | 6 | 43027125 | Higher in Smoker |
| cg18825594 | 2 | 10184650 | Lower in Smoker |
| cg24966735 | 13 | 74708143 | Higher in Smoker |
| cg13897833 | 13 | 74562744 | Higher in Smoker |
| cg16792560 | 15 | 31625860 | Lower in Smoker |
| cg05368038 | 15 | 31621727 | Lower in Smoker |

| | | | |
|---|---|---|---|
| cg04528819 | 7 | 130418315 | Higher in Smoker |
| cg12608881 | 1 | 44584111 | Lower in Smoker |
| cg25266327 | 19 | 16435660 | Lower in Smoker |
| cg17074863 | 4 | 38668754 | Higher in Smoker |
| cg13152856 | 4 | 38691626 | Lower in Smoker |
| cg27283993 | 10 | 3826051 | Higher in Smoker |
| cg12570716 | 10 | 3822379 | Lower in Smoker |
| cg25749254 | 10 | 3823907 | Lower in Smoker |
| cg06048750 | 10 | 3823844 | Lower in Smoker |
| cg08614871 | 10 | 3824555 | Lower in Smoker |
| cg15474859 | 2 | 208030304 | Lower in Smoker |
| cg06774787 | X | 56258973 | Lower in Smoker |
| cg17916407 | 14 | 50234392 | Higher in Smoker |
| cg25974764 | 14 | 50234454 | Higher in Smoker |
| cg11888757 | 16 | 87799687 | Higher in Smoker |
| cg09254049 | 16 | 87799191 | Higher in Smoker |
| cg04196691 | 16 | 87759493 | Lower in Smoker |
| cg09821701 | 16 | 87769432 | Lower in Smoker |
| cg27451581 | 1 | 18806517 | Lower in Smoker |
| cg24692170 | 1 | 205327054 | Lower in Smoker |
| cg02157802 | 13 | 70431522 | Lower in Smoker |
| cg12917718 | 13 | 70682019 | Higher in Smoker |
| cg00978248 | 17 | 39996374 | Lower in Smoker |
| cg02645977 | 17 | 40021718 | Higher in Smoker |
| cg11231849 | 1 | 202897531 | Lower in Smoker |
| cg11084308 | 1 | 898397 | Lower in Smoker |
| cg02315113 | 1 | 173684045 | Higher in Smoker |
| cg10055231 | 1 | 6651358 | Higher in Smoker |
| cg03030002 | 3 | 183354815 | Higher in Smoker |
| cg00892804 | 3 | 183353372 | Higher in Smoker |
| cg06135755 | 15 | 86338090 | Higher in Smoker |
| cg24873414 | 19 | 18746981 | Higher in Smoker |
| cg03228222 | 19 | 18747721 | Higher in Smoker |
| cg25102449 | 19 | 18761273 | Lower in Smoker |
| cg15873908 | 14 | 45415114 | Lower in Smoker |

| | | | |
|---|---|---|---|
| cg03445244 | 2 | 23721722 | Lower in Smoker |
| cg13774015 | 2 | 23743468 | Lower in Smoker |
| cg15073625 | 2 | 23862014 | Lower in Smoker |
| cg03880733 | 2 | 23784893 | Lower in Smoker |
| cg14826211 | 2 | 23747197 | Lower in Smoker |
| cg14551881 | 2 | 23788592 | Lower in Smoker |
| cg26202529 | 2 | 23865356 | Lower in Smoker |
| cg00854172 | 2 | 23748104 | Lower in Smoker |
| cg11985987 | 2 | 23676430 | Lower in Smoker |
| cg04681095 | 2 | 23870823 | Lower in Smoker |
| cg18988938 | 2 | 23849671 | Lower in Smoker |
| cg10663628 | 2 | 23798452 | Lower in Smoker |
| cg08748913 | 5 | 137071788 | Higher in Smoker |
| cg16277405 | 5 | 137042224 | Lower in Smoker |
| cg05995361 | 2 | 239056683 | Lower in Smoker |
| cg15367150 | 2 | 239046275 | Lower in Smoker |
| cg01143222 | 6 | 53514567 | Lower in Smoker |
| cg01653446 | 14 | 20904169 | Lower in Smoker |
| cg14162144 | 14 | 20903913 | Lower in Smoker |
| cg01399477 | 16 | 84681940 | Higher in Smoker |
| cg05767633 | 4 | 88140994 | Higher in Smoker |
| cg16713292 | 4 | 88110161 | Lower in Smoker |
| cg21869055 | 19 | 51522454 | Higher in Smoker |
| cg20104456 | 19 | 51568523 | Higher in Smoker |
| cg24425175 | 19 | 51587945 | Lower in Smoker |
| cg07592136 | 19 | 51473480 | Lower in Smoker |
| cg04516952 | 19 | 51472042 | Higher in Smoker |
| cg03946012 | 16 | 58328209 | Lower in Smoker |
| cg09668716 | 12 | 9760326 | Lower in Smoker |
| cg09261289 | 12 | 10459923 | Lower in Smoker |
| cg02233518 | 10 | 135005330 | Lower in Smoker |
| cg27089219 | 3 | 122234258 | Lower in Smoker |
| cg16366059 | 13 | 50366559 | Higher in Smoker |
| cg14105736 | 6 | 117002217 | Higher in Smoker |
| cg06795980 | 7 | 98805289 | Lower in Smoker |

| | | | |
|---|---|---|---|
| cg07918846 | 12 | 25405226 | Lower in Smoker |
| cg05997116 | 7 | 149416913 | Lower in Smoker |
| cg08456281 | 17 | 8275997 | Lower in Smoker |
| cg24719912 | 12 | 75893116 | Lower in Smoker |
| cg12253845 | 17 | 39675198 | Lower in Smoker |
| cg00463848 | 12 | 53046105 | Lower in Smoker |
| cg04219544 | 17 | 39860042 | Lower in Smoker |
| cg04576298 | 17 | 39550152 | Lower in Smoker |
| cg25929399 | 17 | 39597601 | Higher in Smoker |
| cg16353632 | 12 | 52914330 | Lower in Smoker |
| cg00028929 | 12 | 52908478 | Lower in Smoker |
| cg07653640 | 12 | 52868602 | Lower in Smoker |
| cg03806752 | 12 | 53098326 | Lower in Smoker |
| cg03327403 | 12 | 53298911 | Higher in Smoker |
| cg24773412 | 12 | 53293549 | Lower in Smoker |
| cg21185271 | 12 | 52569410 | Lower in Smoker |
| cg04472592 | 12 | 52585786 | Lower in Smoker |
| cg11057082 | 12 | 52789556 | Lower in Smoker |
| cg17903229 | 21 | 45959142 | Lower in Smoker |
| cg24062909 | 21 | 46020461 | Lower in Smoker |
| cg16692258 | 21 | 31655822 | Lower in Smoker |
| cg21319411 | 17 | 39340925 | Lower in Smoker |
| cg20663846 | 17 | 39254439 | Lower in Smoker |
| cg00688125 | 2 | 27664399 | Lower in Smoker |
| cg16115072 | 17 | 25938812 | Higher in Smoker |
| cg19781309 | 17 | 25830583 | Lower in Smoker |
| cg16300531 | 12 | 118405988 | Higher in Smoker |
| cg12338273 | 2 | 143753686 | Lower in Smoker |
| cg06300944 | X | 153141270 | Higher in Smoker |
| cg27177954 | 22 | 41601126 | Higher in Smoker |
| cg24516147 | 6 | 130339725 | Higher in Smoker |
| cg06855336 | 18 | 6284379 | Lower in Smoker |
| cg04213089 | 18 | 6284382 | Lower in Smoker |
| cg12090105 | 18 | 6287052 | Lower in Smoker |
| cg18194597 | 6 | 108616203 | Lower in Smoker |

| | | | |
|---|---|---|---|
| cg20033557 | 15 | 63414489 | Higher in Smoker |
| cg15338603 | 15 | 63414256 | Higher in Smoker |
| cg03092550 | 15 | 63417207 | Lower in Smoker |
| cg26539023 | 1 | 201369031 | Lower in Smoker |
| cg10500147 | 12 | 6881601 | Higher in Smoker |
| cg02695343 | 12 | 6881595 | Higher in Smoker |
| cg16352923 | 12 | 6881590 | Higher in Smoker |
| cg25410279 | X | 153707517 | Higher in Smoker |
| cg19547155 | 19 | 55013954 | Lower in Smoker |
| cg25588792 | 19 | 55013946 | Lower in Smoker |
| cg14950072 | 18 | 7118122 | Higher in Smoker |
| cg10264354 | 6 | 129505619 | Lower in Smoker |
| cg14894144 | 18 | 21270554 | Higher in Smoker |
| cg17048240 | 20 | 60889183 | Lower in Smoker |
| cg19674797 | 20 | 60886077 | Lower in Smoker |
| cg18417634 | 20 | 60884328 | Lower in Smoker |
| cg26236922 | 20 | 60912673 | Lower in Smoker |
| cg10064162 | 7 | 107644249 | Higher in Smoker |
| cg24937126 | 7 | 107643285 | Higher in Smoker |
| cg10002668 | 7 | 107665708 | Lower in Smoker |
| cg12552165 | 1 | 183154981 | Lower in Smoker |
| cg14091920 | 9 | 133903136 | Lower in Smoker |
| cg14447608 | 9 | 133886309 | Lower in Smoker |
| cg27300804 | 13 | 113976054 | Lower in Smoker |
| cg14713118 | 8 | 98787351 | Lower in Smoker |
| cg18411043 | 1 | 31221135 | Lower in Smoker |
| cg22787311 | 5 | 154173503 | Lower in Smoker |
| cg03547017 | 17 | 37031281 | Lower in Smoker |
| cg08553913 | 17 | 37028977 | Lower in Smoker |
| cg02459569 | 1 | 150944634 | Lower in Smoker |
| cg22012583 | 1 | 150947949 | Lower in Smoker |
| cg14204255 | 19 | 8274062 | Higher in Smoker |
| cg08698605 | 19 | 8273643 | Lower in Smoker |
| cg23095680 | 12 | 50561308 | Higher in Smoker |
| cg25038572 | 12 | 50561295 | Higher in Smoker |

| | | | |
|---|---|---|---|
| cg15701842 | 2 | 169609566 | Lower in Smoker |
| cg23663476 | 16 | 28996449 | Lower in Smoker |
| cg11295301 | 6 | 150039190 | Higher in Smoker |
| cg12022621 | 1 | 203734505 | Lower in Smoker |
| cg06958535 | 1 | 203734478 | Lower in Smoker |
| cg17711527 | 1 | 203734396 | Lower in Smoker |
| cg21060796 | 11 | 111411979 | Higher in Smoker |
| cg17250262 | 2 | 30457110 | Lower in Smoker |
| cg05823218 | 2 | 74725810 | Higher in Smoker |
| cg00656860 | 15 | 68116607 | Higher in Smoker |
| cg11067224 | 1 | 152780139 | Lower in Smoker |
| cg22616525 | 1 | 152669985 | Lower in Smoker |
| cg18116418 | 1 | 152553244 | Lower in Smoker |
| cg04221650 | 1 | 152681887 | Lower in Smoker |
| cg22124859 | 1 | 152813850 | Lower in Smoker |
| cg20269797 | 2 | 30796122 | Lower in Smoker |
| cg04240491 | 2 | 30827623 | Lower in Smoker |
| cg03437924 | 16 | 25123326 | Lower in Smoker |
| cg13764516 | 9 | 139648911 | Higher in Smoker |
| cg13918042 | 10 | 98596430 | Higher in Smoker |
| cg01089331 | 4 | 18024929 | Higher in Smoker |
| cg20358902 | 4 | 18019937 | Lower in Smoker |
| cg05762700 | 4 | 18023779 | Lower in Smoker |
| cg19060371 | 13 | 46742722 | Higher in Smoker |
| cg08670465 | 5 | 169725100 | Higher in Smoker |
| cg14667406 | 2 | 136577303 | Lower in Smoker |
| cg17106419 | 10 | 103880236 | Higher in Smoker |
| cg19861824 | 4 | 16901058 | Lower in Smoker |
| cg24813857 | 4 | 16859428 | Lower in Smoker |
| cg07187103 | 11 | 18415850 | Higher in Smoker |
| cg10640764 | 19 | 11216364 | Lower in Smoker |
| cg17992670 | 19 | 11216306 | Lower in Smoker |
| cg06830981 | 1 | 22142491 | Higher in Smoker |
| cg13403586 | 1 | 22141170 | Higher in Smoker |
| cg22025064 | 1 | 22141400 | Lower in Smoker |

| | | | |
|---|---|---|---|
| cg24334174 | 1 | 22141341 | Lower in Smoker |
| cg03551456 | 11 | 35965708 | Higher in Smoker |
| cg26597485 | 11 | 36244771 | Lower in Smoker |
| cg04583074 | 11 | 36164090 | Lower in Smoker |
| cg09261020 | 1 | 25869937 | Higher in Smoker |
| cg10176185 | 1 | 25894479 | Lower in Smoker |
| cg27440002 | 5 | 132208244 | Higher in Smoker |
| cg02081065 | 5 | 132209139 | Lower in Smoker |
| cg16301924 | 13 | 53314226 | Lower in Smoker |
| cg06037943 | 4 | 109088038 | Higher in Smoker |
| cg01002317 | 3 | 156559505 | Lower in Smoker |
| cg19514961 | 19 | 54960460 | Higher in Smoker |
| cg18603538 | 7 | 127894591 | Lower in Smoker |
| cg04118124 | 1 | 43231249 | Lower in Smoker |
| cg22250605 | 3 | 189804187 | Lower in Smoker |
| cg13434714 | 12 | 6936787 | Higher in Smoker |
| cg13202122 | 1 | 65886182 | Higher in Smoker |
| cg06246552 | 8 | 29952761 | Higher in Smoker |
| cg18986713 | 8 | 29953064 | Higher in Smoker |
| cg20544675 | 8 | 38243945 | Higher in Smoker |
| cg15649346 | 12 | 51444293 | Lower in Smoker |
| cg06822952 | 22 | 38073178 | Higher in Smoker |
| cg21064451 | 22 | 38071534 | Lower in Smoker |
| cg19855760 | 22 | 38071677 | Lower in Smoker |
| cg13439241 | 11 | 63273507 | Lower in Smoker |
| cg04420917 | 19 | 39303993 | Lower in Smoker |
| cg09334514 | 1 | 236686671 | Higher in Smoker |
| cg01030476 | 1 | 236686564 | Higher in Smoker |
| cg01796143 | 1 | 236687575 | Lower in Smoker |
| cg03909504 | 17 | 25959847 | Higher in Smoker |
| cg22840852 | 14 | 93215209 | Higher in Smoker |
| cg23327070 | 14 | 93214896 | Higher in Smoker |
| cg05670290 | 12 | 71833070 | Higher in Smoker |
| cg27166993 | 12 | 71833031 | Higher in Smoker |
| cg13435381 | 12 | 71833017 | Higher in Smoker |

| | | | |
|---|---|---|---|
| cg01103590 | 12 | 71833534 | Higher in Smoker |
| cg01622344 | 12 | 71833515 | Higher in Smoker |
| cg27555099 | 1 | 202163186 | Higher in Smoker |
| cg09854088 | 1 | 202183279 | Higher in Smoker |
| cg21284380 | 13 | 40177740 | Higher in Smoker |
| cg19859781 | 13 | 40174685 | Lower in Smoker |
| cg07463400 | 13 | 40058357 | Lower in Smoker |
| cg16684811 | 5 | 77944851 | Higher in Smoker |
| cg18281939 | 5 | 77783895 | Higher in Smoker |
| cg26601559 | 5 | 77837019 | Lower in Smoker |
| cg17462560 | 5 | 77814551 | Lower in Smoker |
| cg23029236 | 5 | 77894196 | Lower in Smoker |
| cg26951839 | 5 | 77801011 | Lower in Smoker |
| cg12141457 | 10 | 126182012 | Higher in Smoker |
| cg07596401 | 10 | 126150086 | Lower in Smoker |
| cg20938699 | 17 | 35296966 | Higher in Smoker |
| cg01520571 | 17 | 35296481 | Higher in Smoker |
| cg14608020 | 9 | 126782556 | Higher in Smoker |
| cg13585776 | 9 | 126783547 | Lower in Smoker |
| cg09671258 | 1 | 180202530 | Higher in Smoker |
| cg17836735 | 1 | 180198325 | Higher in Smoker |
| cg21172814 | 1 | 180199001 | Higher in Smoker |
| cg00003298 | 12 | 113901210 | Higher in Smoker |
| cg11213520 | 12 | 113901529 | Higher in Smoker |
| cg00802728 | 12 | 113906079 | Lower in Smoker |
| cg13571460 | 9 | 124989337 | Lower in Smoker |
| cg02342594 | 9 | 124976596 | Lower in Smoker |
| cg13364881 | 1 | 197880513 | Higher in Smoker |
| cg00783748 | 1 | 197884134 | Higher in Smoker |
| cg00795248 | 1 | 197888305 | Higher in Smoker |
| cg01369082 | 5 | 38557465 | Higher in Smoker |
| cg26465295 | 19 | 54851740 | Lower in Smoker |
| cg13535489 | 19 | 54761827 | Lower in Smoker |
| cg12197557 | 19 | 54760833 | Lower in Smoker |
| cg22222644 | 19 | 51883242 | Lower in Smoker |

| | | | |
|---|---|---|---|
| cg21150049 | 12 | 50677498 | Lower in Smoker |
| cg07338958 | 12 | 50677279 | Higher in Smoker |
| cg04609245 | 4 | 41646293 | Higher in Smoker |
| cg08062273 | 3 | 45641120 | Lower in Smoker |
| cg09121543 | 17 | 61774794 | Lower in Smoker |
| cg00446123 | 20 | 62367888 | Lower in Smoker |
| cg21201401 | 20 | 62367884 | Lower in Smoker |
| cg20513976 | 20 | 62367893 | Lower in Smoker |
| cg01606027 | 22 | 31607212 | Higher in Smoker |
| cg00520380 | 22 | 31643997 | Higher in Smoker |
| cg10075819 | 2 | 109229337 | Lower in Smoker |
| cg22490845 | 2 | 128429716 | Lower in Smoker |
| cg05768558 | 1 | 26737005 | Higher in Smoker |
| cg02388865 | 1 | 26737318 | Higher in Smoker |
| cg17119521 | 6 | 105404769 | Higher in Smoker |
| cg13629345 | 11 | 27528465 | Higher in Smoker |
| cg04208928 | 1 | 226498038 | Lower in Smoker |
| cg24008435 | 15 | 101137976 | Lower in Smoker |
| cg10715640 | 10 | 90983690 | Lower in Smoker |
| cg07020025 | 15 | 58840678 | Lower in Smoker |
| cg02647247 | 19 | 42909519 | Higher in Smoker |
| cg12537688 | 10 | 90346479 | Lower in Smoker |
| cg06213287 | 5 | 96478495 | Higher in Smoker |
| cg21332946 | 1 | 145476871 | Lower in Smoker |
| cg20131685 | 17 | 18128578 | Higher in Smoker |
| cg14612068 | 18 | 57026693 | Higher in Smoker |
| cg12901498 | 15 | 75117033 | Lower in Smoker |
| cg22219278 | 5 | 176779063 | Higher in Smoker |
| cg24952358 | 7 | 156561790 | Lower in Smoker |
| cg10063233 | 7 | 156685824 | Higher in Smoker |
| cg06334495 | 16 | 1020046 | Higher in Smoker |
| cg08336687 | 16 | 907744 | Lower in Smoker |
| cg27622515 | 16 | 1004929 | Lower in Smoker |
| cg05095057 | 16 | 959445 | Lower in Smoker |
| cg09616608 | 16 | 949331 | Lower in Smoker |

| | | | |
|---|---|---|---|
| cg06835404 | 16 | 988973 | Lower in Smoker |
| cg02200944 | 16 | 968024 | Lower in Smoker |
| cg07527909 | 16 | 966593 | Lower in Smoker |
| cg26812486 | 16 | 928778 | Lower in Smoker |
| cg03836831 | 16 | 969069 | Lower in Smoker |
| cg08531623 | 16 | 969293 | Lower in Smoker |
| cg02842158 | 22 | 50943720 | Higher in Smoker |
| cg03946955 | 1 | 156096301 | Lower in Smoker |
| cg08881019 | 1 | 156096178 | Lower in Smoker |
| cg10835230 | 19 | 2457145 | Higher in Smoker |
| cg13572309 | 12 | 16758267 | Higher in Smoker |
| cg02325300 | 12 | 16758836 | Higher in Smoker |
| cg14172412 | 1 | 87797008 | Higher in Smoker |
| cg24394990 | 1 | 87793364 | Lower in Smoker |
| ch.13.111173417 | 13 | 76263533 | Higher in Smoker |
| cg05078075 | 13 | 76250138 | Lower in Smoker |
| cg04757411 | 13 | 76259545 | Lower in Smoker |
| cg11959007 | 13 | 76432094 | Lower in Smoker |
| cg16409306 | 13 | 76195284 | Lower in Smoker |
| cg13060233 | 13 | 76361354 | Lower in Smoker |
| cg09161542 | 13 | 76430188 | Lower in Smoker |
| cg02958194 | 7 | 97736036 | Higher in Smoker |
| cg14993964 | 7 | 97824766 | Lower in Smoker |
| cg26070020 | 1 | 165201385 | Lower in Smoker |
| cg22852353 | 1 | 165171672 | Lower in Smoker |
| cg14204784 | 9 | 129387231 | Higher in Smoker |
| cg13466694 | 9 | 129380728 | Higher in Smoker |
| cg21156006 | 9 | 129455121 | Lower in Smoker |
| cg01127608 | 9 | 129377854 | Lower in Smoker |
| cg01180046 | 5 | 96271324 | Higher in Smoker |
| cg26392545 | 13 | 28187379 | Lower in Smoker |
| cg12822286 | 3 | 101394951 | Higher in Smoker |
| cg08801017 | 13 | 19918525 | Higher in Smoker |
| cg14966074 | 20 | 61299190 | Lower in Smoker |
| cg12064008 | 1 | 32827730 | Higher in Smoker |

| | | | |
|---|---|---|---|
| cg03987786 | 17 | 8264387 | Lower in Smoker |
| cg19036007 | 3 | 38496311 | Higher in Smoker |
| cg08360738 | 19 | 35597447 | Lower in Smoker |
| cg01740367 | 2 | 27294264 | Higher in Smoker |
| cg04484916 | 16 | 2801730 | Lower in Smoker |
| cg16792312 | 16 | 2801668 | Lower in Smoker |
| cg17612147 | 17 | 43922356 | Lower in Smoker |
| cg00270654 | 16 | 87735724 | Lower in Smoker |
| cg09816756 | 4 | 69047758 | Lower in Smoker |
| cg00719400 | 1 | 227915962 | Higher in Smoker |
| cg02694925 | 18 | 77904435 | Lower in Smoker |
| cg04627186 | 2 | 178257342 | Lower in Smoker |
| cg11907662 | 2 | 178257407 | Lower in Smoker |
| cg20569034 | 12 | 58121550 | Lower in Smoker |
| cg01638225 | 4 | 1202930 | Lower in Smoker |
| cg25119654 | 11 | 67085309 | Higher in Smoker |
| cg09093409 | 11 | 67113285 | Lower in Smoker |
| cg00036347 | 1 | 151811923 | Higher in Smoker |
| cg19177627 | 2 | 63274709 | Higher in Smoker |
| cg17397364 | 2 | 63273436 | Lower in Smoker |
| cg06713116 | 7 | 154720452 | Higher in Smoker |
| cg01227815 | 11 | 71597184 | Lower in Smoker |
| cg26550938 | 1 | 3827428 | Lower in Smoker |
| cg09362969 | 1 | 3827065 | Lower in Smoker |
| cg13716787 | 2 | 70351227 | Higher in Smoker |
| cg17600863 | 10 | 93372507 | Lower in Smoker |
| cg14131834 | 13 | 45914250 | Lower in Smoker |
| cg05709578 | 8 | 77591132 | Higher in Smoker |
| cg07516483 | 8 | 77586264 | Higher in Smoker |
| cg07475151 | 5 | 172382825 | Higher in Smoker |
| cg12963237 | 17 | 45501697 | Higher in Smoker |
| cg09941176 | 12 | 50222608 | Higher in Smoker |
| cg02294055 | 2 | 109746170 | Higher in Smoker |
| cg12518410 | 2 | 109745312 | Higher in Smoker |
| cg18756557 | 12 | 1609369 | Lower in Smoker |

| | | | |
|---|---|---|---|
| cg25265234 | 3 | 106955668 | Lower in Smoker |
| cg17363084 | X | 118603274 | Higher in Smoker |
| cg03056525 | 16 | 81130036 | Higher in Smoker |
| cg26785823 | 1 | 2482001 | Lower in Smoker |
| cg20183756 | 12 | 131649195 | Lower in Smoker |
| cg06795216 | 13 | 44596456 | Lower in Smoker |
| cg22955140 | 13 | 44604007 | Lower in Smoker |
| cg24330793 | 13 | 103532159 | Lower in Smoker |
| cg00009871 | 13 | 103532260 | Lower in Smoker |
| cg20271330 | 1 | 204338515 | Higher in Smoker |
| cg23758703 | 10 | 114610508 | Lower in Smoker |
| cg12469954 | 11 | 576084 | Higher in Smoker |
| cg18527764 | 12 | 49083894 | Lower in Smoker |
| cg16754378 | 15 | 57179394 | Higher in Smoker |
| cg27042266 | 15 | 37175007 | Higher in Smoker |
| cg06451900 | 15 | 37172274 | Higher in Smoker |
| cg00216138 | 15 | 37171175 | Higher in Smoker |
| cg19791043 | 16 | 1116361 | Lower in Smoker |
| cg01953240 | 16 | 1129666 | Lower in Smoker |
| cg07739927 | 17 | 62778162 | Higher in Smoker |
| cg17783086 | 17 | 62775188 | Lower in Smoker |
| cg10578996 | 19 | 29455873 | Lower in Smoker |
| cg17155612 | 19 | 28284698 | Higher in Smoker |
| cg15888663 | 1 | 207992084 | Lower in Smoker |
| cg00819949 | 22 | 20193391 | Lower in Smoker |
| cg10930290 | 2 | 219840349 | Lower in Smoker |
| cg01731777 | 3 | 107597099 | Lower in Smoker |
| cg11276189 | 7 | 158815080 | Higher in Smoker |
| cg03749915 | 7 | 158817176 | Lower in Smoker |
| cg26906258 | 7 | 158809804 | Lower in Smoker |
| cg09654116 | 7 | 158816213 | Lower in Smoker |
| cg27307810 | 7 | 158813888 | Lower in Smoker |
| cg27598956 | 8 | 9758788 | Lower in Smoker |
| cg15248835 | 8 | 9761171 | Higher in Smoker |
| cg27416261 | 9 | 35406590 | Higher in Smoker |

| | | | |
|---|---|---|---|
| cg01125381 | X | 49644706 | Lower in Smoker |
| cg17165841 | 2 | 207507001 | Higher in Smoker |
| cg25146557 | 2 | 207507421 | Higher in Smoker |
| cg12110911 | 2 | 207506991 | Higher in Smoker |
| cg03143697 | 5 | 177099378 | Higher in Smoker |
| cg06079468 | 10 | 81839181 | Higher in Smoker |
| cg01026898 | 11 | 44995262 | Lower in Smoker |
| cg19931206 | 6 | 11138650 | Lower in Smoker |
| cg11938951 | 6 | 28186923 | Higher in Smoker |
| cg00414398 | 12 | 104323367 | Higher in Smoker |
| cg16009167 | 5 | 6587105 | Lower in Smoker |
| cg25213547 | 5 | 6587293 | Lower in Smoker |
| cg25186140 | 11 | 133771378 | Lower in Smoker |
| cg26656163 | 11 | 33096673 | Lower in Smoker |
| cg04317051 | 15 | 57599596 | Lower in Smoker |
| cg13936125 | 16 | 56225599 | Higher in Smoker |
| cg02951765 | 16 | 65341412 | Higher in Smoker |
| cg00754896 | 17 | 76227255 | Lower in Smoker |
| cg22284422 | 18 | 74240476 | Lower in Smoker |
| cg14146249 | 1 | 205525378 | Lower in Smoker |
| cg04307594 | 1 | 205525860 | Lower in Smoker |
| cg15571353 | 1 | 24528833 | Lower in Smoker |
| cg13760683 | 20 | 46968477 | Lower in Smoker |
| cg05908371 | 20 | 25129529 | Higher in Smoker |
| cg07934732 | 21 | 45233508 | Lower in Smoker |
| cg00293631 | 22 | 28315337 | Higher in Smoker |
| cg04150583 | 3 | 107602013 | Lower in Smoker |
| cg05146399 | 3 | 107602260 | Lower in Smoker |
| cg23217527 | 3 | 107639884 | Lower in Smoker |
| cg22488719 | 3 | 107601033 | Lower in Smoker |
| cg09839177 | 4 | 124791563 | Lower in Smoker |
| cg08993690 | 4 | 124621338 | Lower in Smoker |
| cg16525761 | 4 | 109541525 | Higher in Smoker |
| cg07829289 | 5 | 158894390 | Higher in Smoker |
| cg08335854 | 5 | 17216368 | Higher in Smoker |

| | | | |
|---|---|---|---|
| cg25407410 | 6 | 143891975 | Lower in Smoker |
| cg20298778 | 6 | 143891455 | Lower in Smoker |
| cg17449769 | 6 | 143877635 | Lower in Smoker |
| cg15922678 | 6 | 29694484 | Lower in Smoker |
| cg00089464 | 6 | 29717223 | Higher in Smoker |
| cg18371410 | 6 | 29699406 | Lower in Smoker |
| cg04892672 | 6 | 29695164 | Lower in Smoker |
| cg25456960 | 6 | 29717019 | Lower in Smoker |
| cg02068996 | 7 | 41817771 | Lower in Smoker |
| cg24488001 | 1 | 238644629 | Lower in Smoker |
| cg09471204 | 22 | 42347991 | Lower in Smoker |
| cg16575530 | 2 | 8118404 | Lower in Smoker |
| cg25344508 | 2 | 8112652 | Lower in Smoker |
| cg05691383 | 9 | 99839414 | Higher in Smoker |
| cg04729592 | 3 | 106967365 | Lower in Smoker |
| cg23921854 | 4 | 40059010 | Higher in Smoker |
| cg01786216 | 12 | 7917888 | Lower in Smoker |
| cg11484543 | 13 | 25159916 | Lower in Smoker |
| cg02400509 | 17 | 41052130 | Lower in Smoker |
| cg06336578 | 17 | 41052107 | Lower in Smoker |
| cg16466065 | 17 | 79146774 | Lower in Smoker |
| cg07624915 | 1 | 3689151 | Higher in Smoker |
| cg05198938 | 1 | 149278358 | Lower in Smoker |
| cg24963147 | 5 | 135529341 | Higher in Smoker |
| cg25234732 | 7 | 56183885 | Higher in Smoker |
| cg03896432 | 7 | 56184866 | Lower in Smoker |
| cg06961473 | 15 | 65369801 | Lower in Smoker |
| cg07754143 | 15 | 65395040 | Lower in Smoker |
| cg27212940 | 11 | 122074089 | Lower in Smoker |
| cg17658568 | 11 | 122033987 | Lower in Smoker |
| cg14654629 | 12 | 46121631 | Higher in Smoker |
| cg27518240 | 1 | 221510354 | Lower in Smoker |
| cg02403294 | 22 | 38795347 | Higher in Smoker |
| cg21472198 | 22 | 38792966 | Lower in Smoker |
| cg24731441 | 22 | 46481822 | Higher in Smoker |

| | | | |
|---|---|---|---|
| cg20967343 | 22 | 46509534 | Lower in Smoker |
| cg10788262 | 2 | 132201777 | Lower in Smoker |
| cg22771332 | 2 | 132202004 | Lower in Smoker |
| cg24869475 | 3 | 10052793 | Higher in Smoker |
| cg13036361 | 3 | 159942495 | Higher in Smoker |
| cg09827440 | 7 | 112758744 | Higher in Smoker |
| cg12767726 | 7 | 112758502 | Higher in Smoker |
| cg00805116 | X | 46404864 | Higher in Smoker |
| cg17475505 | X | 46404859 | Higher in Smoker |
| cg24889708 | 17 | 46678719 | Lower in Smoker |
| cg09176539 | 11 | 49580074 | Higher in Smoker |
| cg20689647 | 17 | 66194695 | Higher in Smoker |
| cg05288475 | 17 | 66195804 | Higher in Smoker |
| cg20645729 | 17 | 66194433 | Higher in Smoker |
| cg15773338 | 2 | 111160867 | Lower in Smoker |
| cg24643594 | 2 | 171571797 | Higher in Smoker |
| cg21789326 | 7 | 26487456 | Lower in Smoker |
| cg21161069 | 7 | 32768311 | Lower in Smoker |
| cg27395922 | 11 | 50257633 | Higher in Smoker |
| cg25886479 | 11 | 50257625 | Higher in Smoker |
| cg09667753 | 11 | 50239550 | Lower in Smoker |
| cg24555071 | 1 | 1358016 | Lower in Smoker |
| cg25721369 | 7 | 35808698 | Lower in Smoker |
| cg03897851 | X | 56764293 | Lower in Smoker |
| cg09511963 | 11 | 18230625 | Higher in Smoker |
| cg07233469 | 16 | 30346368 | Higher in Smoker |
| cg13520532 | 10 | 135273122 | Higher in Smoker |
| cg20783133 | 1 | 765028 | Lower in Smoker |
| cg07498168 | 11 | 107462941 | Higher in Smoker |
| cg07570113 | 16 | 59790180 | Lower in Smoker |
| cg04142323 | 5 | 87981449 | Higher in Smoker |
| cg01080998 | 5 | 87981177 | Higher in Smoker |
| cg27529225 | 5 | 87898489 | Lower in Smoker |
| cg17499941 | 5 | 87975812 | Lower in Smoker |
| cg16730596 | 11 | 67573103 | Higher in Smoker |

| | | | |
|---|---|---|---|
| cg10325253 | 17 | 58166296 | Lower in Smoker |
| cg22821677 | 15 | 21941178 | Lower in Smoker |
| cg04881008 | 7 | 29726226 | Lower in Smoker |
| cg00393435 | 22 | 39052596 | Higher in Smoker |
| cg17042715 | 13 | 75814730 | Lower in Smoker |
| cg19587779 | 20 | 34638023 | Higher in Smoker |
| cg15730213 | 20 | 34639058 | Higher in Smoker |
| cg16900618 | 1 | 104113039 | Lower in Smoker |
| cg02402948 | 11 | 3430206 | Higher in Smoker |
| cg02367709 | 17 | 66097352 | Lower in Smoker |
| cg10318359 | 16 | 22587853 | Lower in Smoker |
| cg00552822 | 15 | 22368443 | Lower in Smoker |
| cg02529358 | 5 | 148786302 | Lower in Smoker |
| cg15754901 | 17 | 5402972 | Lower in Smoker |
| cg23502639 | 17 | 5402883 | Lower in Smoker |
| cg23017753 | 5 | 21459475 | Higher in Smoker |
| cg26078137 | 5 | 21461903 | Lower in Smoker |
| cg05972376 | 1 | 1624399 | Higher in Smoker |
| cg06528340 | 1 | 1602685 | Lower in Smoker |
| cg19782173 | 5 | 76383047 | Higher in Smoker |
| cg18002437 | 1 | 144522237 | Lower in Smoker |
| cg24735611 | 1 | 146494928 | Lower in Smoker |
| cg19504089 | 1 | 146495202 | Lower in Smoker |
| cg14833810 | 15 | 41575924 | Higher in Smoker |
| cg26618210 | 15 | 41576042 | Higher in Smoker |
| cg06061069 | 7 | 66309966 | Higher in Smoker |
| cg07733441 | 4 | 123653918 | Higher in Smoker |
| cg12959106 | 3 | 129830318 | Higher in Smoker |
| cg03068446 | 11 | 89656189 | Lower in Smoker |
| cg26246897 | 1 | 59612710 | Higher in Smoker |
| cg11238352 | 1 | 59609170 | Lower in Smoker |
| cg22755296 | 11 | 43918825 | Lower in Smoker |
| cg26152485 | 19 | 19281474 | Lower in Smoker |
| cg02927821 | 17 | 39216677 | Lower in Smoker |
| cg10194295 | 17 | 39216457 | Lower in Smoker |

| | | | |
|---|---|---|---|
| cg21308011 | 8 | 142350506 | Lower in Smoker |
| cg11788447 | 8 | 142350581 | Lower in Smoker |
| cg14780482 | 8 | 142349774 | Lower in Smoker |
| cg03330223 | 16 | 86371363 | Higher in Smoker |
| cg06066596 | 15 | 83166174 | Higher in Smoker |
| cg04395798 | 10 | 42971732 | Lower in Smoker |
| cg07800806 | 22 | 24059925 | Lower in Smoker |
| cg00489795 | 22 | 24041104 | Lower in Smoker |
| cg06617335 | 15 | 78286905 | Lower in Smoker |
| cg03741419 | X | 62781690 | Higher in Smoker |
| cg24721777 | 17 | 79885593 | Higher in Smoker |
| cg12283822 | 4 | 6675756 | Higher in Smoker |
| cg10445599 | 12 | 12558857 | Higher in Smoker |
| cg26652079 | 19 | 5707316 | Lower in Smoker |
| cg01048904 | 19 | 5712068 | Lower in Smoker |
| cg01756115 | 16 | 48357692 | Lower in Smoker |
| cg20450712 | 8 | 12580385 | Lower in Smoker |
| cg12232463 | 2 | 100926650 | Lower in Smoker |
| cg06944050 | X | 118109068 | Higher in Smoker |
| cg21205654 | X | 118110766 | Lower in Smoker |
| cg26429169 | 1 | 153230941 | Lower in Smoker |
| cg26422022 | 5 | 121414137 | Higher in Smoker |
| cg12934788 | 18 | 44099028 | Lower in Smoker |
| cg10372921 | 15 | 74218733 | Higher in Smoker |
| cg06372668 | 15 | 74221840 | Lower in Smoker |
| cg26510500 | 2 | 74778482 | Lower in Smoker |
| cg15989091 | 2 | 74780172 | Lower in Smoker |
| cg00831247 | 2 | 74780268 | Lower in Smoker |
| cg19148731 | 2 | 74780229 | Lower in Smoker |
| cg23674882 | 2 | 74780272 | Lower in Smoker |
| cg12962355 | 2 | 74781907 | Higher in Smoker |
| cg08940570 | 2 | 74780617 | Lower in Smoker |
| cg11067786 | 2 | 74780467 | Lower in Smoker |
| cg10674511 | X | 78003091 | Higher in Smoker |
| cg15844109 | X | 78003205 | Higher in Smoker |

| | | | |
|---|---|---|---|
| cg04249993 | 13 | 49019949 | Lower in Smoker |
| cg21131054 | 5 | 1466799 | Lower in Smoker |
| cg23312151 | 5 | 1466132 | Lower in Smoker |
| cg13042527 | 5 | 1492873 | Lower in Smoker |
| cg02531924 | 5 | 1522816 | Lower in Smoker |
| cg07902156 | 5 | 1495284 | Lower in Smoker |
| cg22394329 | 5 | 1495356 | Lower in Smoker |
| cg05661533 | 5 | 1495043 | Lower in Smoker |
| cg00857851 | 5 | 1493973 | Lower in Smoker |
| cg00256485 | 5 | 1494980 | Lower in Smoker |
| cg09849319 | 5 | 1494983 | Lower in Smoker |
| cg07627639 | 16 | 55544136 | Higher in Smoker |
| cg01751134 | 16 | 55543166 | Lower in Smoker |
| cg16176379 | 16 | 55543049 | Higher in Smoker |
| cg24359375 | 12 | 7121914 | Lower in Smoker |
| cg24530000 | 19 | 14274172 | Lower in Smoker |
| cg14529474 | 1 | 82269526 | Lower in Smoker |
| cg22794376 | 2 | 11921850 | Lower in Smoker |
| cg18110535 | 18 | 3012413 | Higher in Smoker |
| cg22846611 | 20 | 39969379 | Higher in Smoker |
| cg22108175 | 8 | 19796591 | Higher in Smoker |
| cg21909391 | 3 | 187896222 | Lower in Smoker |
| cg07757358 | 3 | 187897193 | Lower in Smoker |
| cg02716749 | 3 | 187871801 | Higher in Smoker |
| cg02391906 | 9 | 103792059 | Higher in Smoker |
| cg15728779 | 1 | 99729504 | Lower in Smoker |
| cg05657427 | 1 | 99470895 | Higher in Smoker |
| cg24899209 | 11 | 58346540 | Higher in Smoker |
| cg23344338 | 4 | 151231429 | Lower in Smoker |
| cg06215107 | 4 | 151504725 | Lower in Smoker |
| cg06457149 | X | 114468096 | Higher in Smoker |
| cg17628894 | 11 | 804452 | Lower in Smoker |
| cg15496866 | 6 | 40491590 | Lower in Smoker |
| cg26131019 | 3 | 66550735 | Higher in Smoker |
| cg24150385 | 3 | 66543263 | Lower in Smoker |

| | | | |
|---|---|---|---|
| cg10983720 | 1 | 113615878 | Higher in Smoker |
| cg26947450 | 12 | 59314400 | Higher in Smoker |
| cg12342451 | 10 | 66001509 | Lower in Smoker |
| cg17965159 | 12 | 25246439 | Lower in Smoker |
| cg19258868 | 12 | 57585184 | Lower in Smoker |
| cg08699270 | 12 | 57607029 | Lower in Smoker |
| cg16079358 | 14 | 23340577 | Higher in Smoker |
| cg27032353 | 14 | 23343818 | Lower in Smoker |
| cg24638722 | 8 | 105509494 | Lower in Smoker |
| cg25554917 | 2 | 170220129 | Higher in Smoker |
| cg01400477 | 2 | 170218258 | Lower in Smoker |
| cg23238677 | 2 | 170157334 | Lower in Smoker |
| cg07992044 | 11 | 68096049 | Higher in Smoker |
| cg02891082 | 11 | 68118671 | Higher in Smoker |
| cg03533590 | 11 | 68188824 | Higher in Smoker |
| cg27101654 | 11 | 68214299 | Lower in Smoker |
| cg25027522 | 11 | 68207228 | Lower in Smoker |
| cg17651317 | 11 | 68080928 | Lower in Smoker |
| cg14624207 | 11 | 68142198 | Lower in Smoker |
| cg13738327 | 11 | 68139233 | Lower in Smoker |
| cg00464927 | 11 | 68139121 | Lower in Smoker |
| cg12623695 | 1 | 53744325 | Lower in Smoker |
| cg27318418 | 4 | 3520389 | Lower in Smoker |
| cg10407935 | 4 | 3524288 | Lower in Smoker |
| cg00356499 | 4 | 3516065 | Lower in Smoker |
| cg20494878 | 4 | 3517779 | Lower in Smoker |
| cg00919567 | 4 | 3520016 | Lower in Smoker |
| cg11475305 | 6 | 53663860 | Lower in Smoker |
| cg19167755 | 6 | 53667257 | Lower in Smoker |
| cg12174175 | 6 | 53693227 | Lower in Smoker |
| cg15693248 | 12 | 70004787 | Lower in Smoker |
| cg15351009 | 5 | 191486 | Lower in Smoker |
| cg23257561 | 6 | 25359959 | Lower in Smoker |
| cg03509329 | 14 | 24520788 | Lower in Smoker |
| cg07253870 | 12 | 7013813 | Higher in Smoker |

| | | | |
|---|---|---|---|
| cg08872590 | 8 | 145748059 | Higher in Smoker |
| cg13994897 | 10 | 134162016 | Lower in Smoker |
| cg25717182 | 11 | 76382149 | Higher in Smoker |
| cg10788371 | 11 | 76381040 | Lower in Smoker |
| cg02909711 | 16 | 67360805 | Higher in Smoker |
| cg04603928 | 17 | 62912201 | Higher in Smoker |
| cg00897863 | 17 | 30347422 | Higher in Smoker |
| ch.17.828578F | 17 | 30349190 | Higher in Smoker |
| cg08111035 | 17 | 30347411 | Higher in Smoker |
| cg02386875 | 17 | 28927378 | Lower in Smoker |
| cg07532245 | 17 | 28927093 | Lower in Smoker |
| cg26035366 | 3 | 26664621 | Higher in Smoker |
| cg03979582 | 1 | 46769114 | Higher in Smoker |
| cg09747578 | 1 | 46769076 | Higher in Smoker |
| cg12511929 | 12 | 122652175 | Lower in Smoker |
| cg00184240 | 12 | 122666660 | Lower in Smoker |
| cg04052606 | 12 | 122666575 | Lower in Smoker |
| cg11430783 | 1 | 3703792 | Lower in Smoker |
| cg13695956 | 17 | 17912592 | Lower in Smoker |
| cg19003389 | 17 | 17876154 | Higher in Smoker |
| cg15089487 | 15 | 71185252 | Higher in Smoker |
| cg25075015 | 11 | 40138552 | Lower in Smoker |
| cg03097336 | 16 | 84178939 | Higher in Smoker |
| cg23928963 | 11 | 56956428 | Lower in Smoker |
| cg25512791 | 11 | 56949074 | Lower in Smoker |
| cg25273160 | 11 | 56955011 | Lower in Smoker |
| cg19171175 | 11 | 542109 | Lower in Smoker |
| cg02837194 | 11 | 542226 | Lower in Smoker |
| cg16418258 | 15 | 42840397 | Higher in Smoker |
| cg18006085 | 17 | 48474872 | Higher in Smoker |
| cg22678977 | 8 | 133689006 | Lower in Smoker |
| cg08479976 | 1 | 90286333 | Higher in Smoker |
| cg11839020 | 1 | 90309998 | Lower in Smoker |
| cg10101470 | 1 | 90286633 | Higher in Smoker |
| cg03504039 | 2 | 238578435 | Lower in Smoker |

| | | | |
|---|---|---|---|
| cg22734058 | 2 | 238857491 | Lower in Smoker |
| cg15819128 | 2 | 238604020 | Higher in Smoker |
| cg06853609 | 3 | 37218771 | Higher in Smoker |
| cg05433805 | 3 | 37204814 | Lower in Smoker |
| cg21634555 | 3 | 169538417 | Lower in Smoker |
| cg12064201 | 15 | 101606006 | Lower in Smoker |
| cg12648213 | 15 | 101538805 | Lower in Smoker |
| cg18185006 | 1 | 204589407 | Lower in Smoker |
| cg11820840 | 1 | 204586547 | Lower in Smoker |
| cg11588889 | 20 | 6021584 | Lower in Smoker |
| cg16577593 | 5 | 138210550 | Lower in Smoker |
| cg04092699 | 2 | 76975220 | Lower in Smoker |
| cg04980928 | 12 | 1940618 | Lower in Smoker |
| cg08097973 | 11 | 71793051 | Lower in Smoker |
| cg16581075 | 7 | 102113508 | Lower in Smoker |
| cg26033586 | 3 | 116163858 | Higher in Smoker |
| cg22372951 | 3 | 115632345 | Lower in Smoker |
| cg15502430 | 3 | 115529503 | Lower in Smoker |
| cg27309905 | 3 | 115556374 | Lower in Smoker |
| cg20364183 | 3 | 115758614 | Lower in Smoker |
| cg08417006 | 3 | 194392839 | Higher in Smoker |
| cg04088137 | 3 | 194392978 | Higher in Smoker |
| cg26386464 | 8 | 38033970 | Higher in Smoker |
| cg16895057 | 1 | 36859417 | Lower in Smoker |
| cg18295152 | 5 | 157170440 | Higher in Smoker |
| cg04057051 | 5 | 157182396 | Lower in Smoker |
| cg23355000 | 17 | 42120896 | Higher in Smoker |
| cg15800722 | 17 | 42144929 | Lower in Smoker |
| cg01002634 | 20 | 60697705 | Higher in Smoker |
| cg15155672 | 3 | 14220327 | Higher in Smoker |
| cg09245582 | 19 | 18419467 | Lower in Smoker |
| cg19419739 | 11 | 1902923 | Higher in Smoker |
| cg02597644 | 11 | 1898970 | Lower in Smoker |
| cg22043296 | 11 | 1892139 | Lower in Smoker |
| cg20229931 | 21 | 47647656 | Lower in Smoker |

| | | | |
|---|---|---|---|
| cg14089945 | 6 | 31538984 | Higher in Smoker |
| cg00501919 | 6 | 31540750 | Lower in Smoker |
| cg21029447 | 6 | 31548572 | Higher in Smoker |
| cg03316030 | 6 | 31551526 | Lower in Smoker |
| cg26822501 | 2 | 33171334 | Lower in Smoker |
| cg04007841 | 11 | 65307006 | Lower in Smoker |
| cg00475131 | 19 | 41117096 | Higher in Smoker |
| cg21944491 | 19 | 41119829 | Lower in Smoker |
| cg06679319 | 15 | 41806867 | Lower in Smoker |
| cg25683535 | 6 | 144164400 | Higher in Smoker |
| cg01687051 | 16 | 278852 | Higher in Smoker |
| cg27362010 | 16 | 279746 | Lower in Smoker |
| cg04553810 | 1 | 23495527 | Higher in Smoker |
| cg12483005 | 1 | 23474871 | Lower in Smoker |
| cg21784305 | 11 | 24727469 | Lower in Smoker |
| cg11015348 | 11 | 25070714 | Lower in Smoker |
| cg05988698 | 11 | 24665557 | Lower in Smoker |
| cg05114100 | X | 114524286 | Higher in Smoker |
| cg14260465 | X | 114524264 | Higher in Smoker |
| cg22125214 | 7 | 135612081 | Lower in Smoker |
| cg19108435 | 5 | 115337401 | Lower in Smoker |
| cg09964873 | 8 | 143868136 | Lower in Smoker |
| cg10140583 | 8 | 143868110 | Lower in Smoker |
| cg14489570 | 8 | 144099280 | Lower in Smoker |
| cg02733847 | 6 | 31649519 | Higher in Smoker |
| cg25136988 | 6 | 31649623 | Lower in Smoker |
| cg21813187 | 6 | 31674553 | Lower in Smoker |
| cg03807391 | 6 | 31674897 | Lower in Smoker |
| cg10100256 | 8 | 143780576 | Higher in Smoker |
| cg01367992 | 1 | 160766535 | Lower in Smoker |
| cg10816700 | 4 | 4291837 | Lower in Smoker |
| cg23761936 | 2 | 133405937 | Lower in Smoker |
| cg00937742 | 2 | 133429299 | Lower in Smoker |
| cg15380115 | 2 | 133430560 | Lower in Smoker |
| cg16900980 | 19 | 44303058 | Higher in Smoker |

| | | | |
|---|---|---|---|
| cg05660611 | 1 | 24117493 | Higher in Smoker |
| cg07395436 | 1 | 219383604 | Lower in Smoker |
| cg11240327 | 6 | 90348503 | Higher in Smoker |
| cg09611852 | 6 | 5241236 | Lower in Smoker |
| cg02724404 | 15 | 100274248 | Lower in Smoker |
| cg19857151 | 1 | 235985454 | Lower in Smoker |
| cg06713769 | 11 | 10589810 | Lower in Smoker |
| cg04496081 | 17 | 34261810 | Lower in Smoker |
| cg08186124 | 3 | 45883676 | Higher in Smoker |
| cg26917999 | 8 | 20112890 | Lower in Smoker |
| cg18313342 | 10 | 102762626 | Lower in Smoker |
| cg24370375 | 1 | 39624920 | Lower in Smoker |
| cg22367631 | 1 | 39569079 | Lower in Smoker |
| cg08238444 | 1 | 39952373 | Lower in Smoker |
| cg10198749 | 1 | 39920707 | Lower in Smoker |
| cg18669654 | 11 | 63803839 | Higher in Smoker |
| cg11838384 | 11 | 63803845 | Higher in Smoker |
| cg18403673 | 11 | 63828569 | Higher in Smoker |
| cg04140971 | 11 | 63916691 | Lower in Smoker |
| cg01804278 | 11 | 63894802 | Lower in Smoker |
| cg11033686 | 7 | 1902804 | Higher in Smoker |
| cg12404837 | 7 | 2130633 | Lower in Smoker |
| cg23001930 | 7 | 2094477 | Lower in Smoker |
| cg24077588 | 7 | 2169152 | Lower in Smoker |
| cg12356249 | 7 | 1969874 | Lower in Smoker |
| cg11457582 | 7 | 2107102 | Lower in Smoker |
| cg27162392 | 7 | 2208908 | Lower in Smoker |
| cg07268571 | 7 | 1989028 | Lower in Smoker |
| cg26066560 | 7 | 2086333 | Lower in Smoker |
| cg07167778 | 7 | 2024828 | Lower in Smoker |
| cg11130530 | 7 | 2261506 | Lower in Smoker |
| cg17803235 | 7 | 2165689 | Lower in Smoker |
| cg25352924 | 7 | 2063583 | Lower in Smoker |
| cg16026522 | 7 | 2137679 | Lower in Smoker |
| cg01648996 | 7 | 2054385 | Lower in Smoker |

| | | | |
|---|---|---|---|
| cg07156006 | 7 | 2195321 | Lower in Smoker |
| cg07095637 | 7 | 2079008 | Lower in Smoker |
| cg06417831 | 6 | 43596987 | Higher in Smoker |
| cg02685901 | 6 | 43597772 | Higher in Smoker |
| cg01719832 | 1 | 11752772 | Higher in Smoker |
| cg13030908 | 1 | 11741533 | Higher in Smoker |
| cg16479173 | 11 | 47290859 | Lower in Smoker |
| cg17580616 | 11 | 47350136 | Lower in Smoker |
| cg21110844 | 4 | 1331987 | Higher in Smoker |
| cg15985344 | 4 | 1299155 | Lower in Smoker |
| cg22914057 | 4 | 1331882 | Lower in Smoker |
| cg04277993 | 4 | 1331546 | Lower in Smoker |
| cg06976589 | 4 | 1304048 | Lower in Smoker |
| cg12902062 | 20 | 39316218 | Higher in Smoker |
| cg18884555 | 22 | 38610234 | Lower in Smoker |
| cg21805791 | 7 | 1581258 | Higher in Smoker |
| cg19964192 | X | 151307053 | Higher in Smoker |
| cg19992083 | X | 151904268 | Lower in Smoker |
| cg01331780 | X | 30265202 | Higher in Smoker |
| cg20319903 | X | 30259964 | Lower in Smoker |
| cg17928317 | X | 140982278 | Lower in Smoker |
| cg03742148 | X | 51636629 | Higher in Smoker |
| cg06232789 | X | 54833768 | Lower in Smoker |
| cg07767690 | X | 54834292 | Lower in Smoker |
| cg20858239 | X | 54834222 | Lower in Smoker |
| cg22072691 | X | 54839625 | Higher in Smoker |
| cg07397399 | 3 | 66025220 | Higher in Smoker |
| cg00303026 | 3 | 65601500 | Lower in Smoker |
| cg23080908 | 3 | 65580091 | Lower in Smoker |
| cg16328079 | 3 | 65706740 | Lower in Smoker |
| cg20119101 | 3 | 65541167 | Lower in Smoker |
| cg03009871 | 7 | 79082038 | Higher in Smoker |
| cg04976780 | 7 | 77649540 | Higher in Smoker |
| cg11208322 | 7 | 77788546 | Lower in Smoker |
| cg13691428 | 7 | 78093472 | Lower in Smoker |

| | | | |
|---|---|---|---|
| cg02097144 | 7 | 78280216 | Lower in Smoker |
| cg16554933 | 16 | 4401344 | Lower in Smoker |
| cg20071498 | 8 | 33342594 | Higher in Smoker |
| cg06822816 | 8 | 120220882 | Higher in Smoker |
| cg15574972 | 11 | 65265134 | Higher in Smoker |
| cg02894944 | 2 | 110859091 | Higher in Smoker |
| cg20460697 | 18 | 56338298 | Higher in Smoker |
| cg21396956 | 18 | 56340167 | Lower in Smoker |
| cg25930340 | 5 | 179160251 | Higher in Smoker |
| cg22390023 | 11 | 95997732 | Lower in Smoker |
| cg05900538 | 11 | 95756907 | Lower in Smoker |
| cg18727239 | 11 | 96076269 | Higher in Smoker |
| cg05302350 | 4 | 141013724 | Higher in Smoker |
| cg16218705 | 4 | 140941031 | Lower in Smoker |
| cg20054111 | 4 | 140829046 | Lower in Smoker |
| cg12546665 | X | 149675952 | Lower in Smoker |
| cg07512231 | 19 | 49221389 | Higher in Smoker |
| cg22403971 | 6 | 119671423 | Higher in Smoker |
| cg14604489 | 9 | 139982149 | Higher in Smoker |
| cg13937012 | 1 | 26053121 | Lower in Smoker |
| cg21480660 | 5 | 109024966 | Lower in Smoker |
| cg10986814 | 5 | 109025713 | Higher in Smoker |
| cg13579205 | 15 | 91447540 | Higher in Smoker |
| cg27361250 | 4 | 103682344 | Higher in Smoker |
| cg14802355 | 4 | 103683140 | Lower in Smoker |
| cg24768163 | 4 | 103655432 | Lower in Smoker |
| cg12810720 | 20 | 35917127 | Lower in Smoker |
| cg01044394 | 3 | 51422497 | Higher in Smoker |
| cg02264238 | 3 | 51426377 | Lower in Smoker |
| cg05443523 | X | 43515213 | Higher in Smoker |
| cg16792302 | 2 | 172945058 | Higher in Smoker |
| cg08402365 | 2 | 172945274 | Higher in Smoker |
| cg16760971 | 2 | 172912454 | Lower in Smoker |
| cg03157700 | 2 | 172916330 | Lower in Smoker |
| cg26335048 | 19 | 17830116 | Higher in Smoker |

| | | | |
|---|---|---|---|
| cg16261923 | 19 | 17840970 | Lower in Smoker |
| cg01441622 | 2 | 210292579 | Lower in Smoker |
| cg13193848 | 15 | 66678964 | Higher in Smoker |
| cg08161449 | 15 | 66679676 | Lower in Smoker |
| cg25990678 | 19 | 4101212 | Higher in Smoker |
| cg08644106 | 19 | 4102601 | Lower in Smoker |
| cg09419402 | 17 | 21187779 | Higher in Smoker |
| cg08891406 | 17 | 11924092 | Higher in Smoker |
| cg02746232 | 17 | 11923262 | Lower in Smoker |
| cg27578458 | 19 | 7968585 | Higher in Smoker |
| cg11938120 | 5 | 56110761 | Higher in Smoker |
| cg04462534 | 5 | 56133370 | Lower in Smoker |
| cg25244628 | 11 | 65381814 | Higher in Smoker |
| cg02856565 | 11 | 65366953 | Lower in Smoker |
| cg19418951 | 3 | 185080816 | Higher in Smoker |
| cg21574349 | 3 | 185080951 | Higher in Smoker |
| cg10535017 | 17 | 61699755 | Higher in Smoker |
| cg11913894 | 6 | 161412392 | Higher in Smoker |
| cg07537655 | 6 | 161415612 | Lower in Smoker |
| cg02023154 | 6 | 136912404 | Lower in Smoker |
| cg24897291 | 6 | 136910199 | Lower in Smoker |
| cg18914962 | 6 | 136914796 | Lower in Smoker |
| cg04862314 | 1 | 27692533 | Higher in Smoker |
| cg21475375 | 6 | 149674055 | Lower in Smoker |
| cg04081651 | 10 | 30722660 | Higher in Smoker |
| cg14937784 | 3 | 48129311 | Higher in Smoker |
| cg05242416 | 3 | 48128669 | Lower in Smoker |
| cg04292549 | 19 | 39108723 | Higher in Smoker |
| cg02306730 | 19 | 39109456 | Lower in Smoker |
| cg05258935 | 19 | 39086923 | Lower in Smoker |
| cg19109909 | 11 | 64570509 | Higher in Smoker |
| cg11491749 | 2 | 39665186 | Higher in Smoker |
| cg06095752 | 2 | 102313242 | Lower in Smoker |
| ch.14.564806R | 14 | 50890364 | Higher in Smoker |
| cg10684802 | 11 | 75379491 | Higher in Smoker |

| | | | |
|---|---|---|---|
| cg12727374 | 3 | 183542914 | Higher in Smoker |
| cg19555986 | 6 | 136872119 | Lower in Smoker |
| cg18872215 | 6 | 136872115 | Lower in Smoker |
| cg08724517 | 4 | 156298204 | Higher in Smoker |
| cg10467997 | 4 | 156298145 | Lower in Smoker |
| cg08328535 | 22 | 22222169 | Higher in Smoker |
| cg00578437 | 22 | 22217249 | Lower in Smoker |
| cg15554007 | 22 | 50703936 | Higher in Smoker |
| cg26790091 | 22 | 50702460 | Lower in Smoker |
| cg06595275 | 6 | 35995676 | Higher in Smoker |
| cg06614469 | 18 | 48086302 | Lower in Smoker |
| cg21948591 | 15 | 52311380 | Higher in Smoker |
| cg00083937 | 22 | 51039805 | Lower in Smoker |
| cg02295856 | 16 | 1758935 | Higher in Smoker |
| cg02952494 | 16 | 1818699 | Higher in Smoker |
| cg05821771 | 16 | 1795420 | Lower in Smoker |
| cg06650246 | 1 | 206897270 | Higher in Smoker |
| cg02859319 | 3 | 50674664 | Lower in Smoker |
| cg25348927 | 12 | 112306624 | Lower in Smoker |
| cg16718327 | 15 | 42066260 | Higher in Smoker |
| cg27302645 | 15 | 42089208 | Lower in Smoker |
| cg05202483 | 4 | 100801612 | Lower in Smoker |
| cg11663824 | 18 | 32621083 | Higher in Smoker |
| cg04400587 | 2 | 27193588 | Higher in Smoker |
| cg10780632 | 17 | 43973522 | Higher in Smoker |
| cg03836283 | 17 | 44058856 | Higher in Smoker |
| cg13149767 | 4 | 164448333 | Lower in Smoker |
| cg25518707 | 17 | 60801924 | Higher in Smoker |
| cg14042879 | 19 | 8478143 | Higher in Smoker |
| cg17139369 | 19 | 8478169 | Higher in Smoker |
| cg11280390 | 19 | 8478043 | Higher in Smoker |
| cg02543075 | 2 | 217236425 | Higher in Smoker |
| cg04749646 | 2 | 217236630 | Higher in Smoker |
| cg11322936 | 10 | 46065860 | Lower in Smoker |
| cg05956132 | 10 | 46091449 | Lower in Smoker |

| | | | |
|---|---|---|---|
| cg27092808 | 10 | 46089769 | Higher in Smoker |
| cg02446434 | 6 | 114178220 | Higher in Smoker |
| cg02004337 | 6 | 114181482 | Lower in Smoker |
| cg10474881 | 6 | 114181686 | Lower in Smoker |
| cg19203457 | 6 | 114181798 | Lower in Smoker |
| cg06221946 | 1 | 32802312 | Lower in Smoker |
| cg11940773 | 11 | 63606512 | Higher in Smoker |
| cg12968701 | 12 | 57881178 | Lower in Smoker |
| cg27165884 | 10 | 99473085 | Higher in Smoker |
| cg14475854 | 1 | 11104980 | Higher in Smoker |
| cg21491176 | 19 | 12958399 | Higher in Smoker |
| cg22693772 | 19 | 12953481 | Lower in Smoker |
| cg26870725 | 19 | 12978805 | Lower in Smoker |
| cg25362169 | 19 | 18237920 | Higher in Smoker |
| cg18310205 | 19 | 18258254 | Lower in Smoker |
| cg03594868 | 19 | 18234829 | Lower in Smoker |
| cg24689196 | 5 | 65893165 | Higher in Smoker |
| cg27116842 | 5 | 66300503 | Higher in Smoker |
| cg14546471 | 5 | 65892027 | Higher in Smoker |
| ch.5.1264897R | 5 | 66306121 | Higher in Smoker |
| cg02625902 | 5 | 65892575 | Higher in Smoker |
| cg06003834 | 5 | 66354967 | Lower in Smoker |
| cg20691612 | 5 | 66392514 | Lower in Smoker |
| cg11590213 | 5 | 66331682 | Lower in Smoker |
| cg26159395 | 2 | 85765084 | Higher in Smoker |
| cg05842036 | 2 | 85771606 | Higher in Smoker |
| cg16417447 | 5 | 162931633 | Higher in Smoker |
| cg08625094 | 5 | 162931829 | Higher in Smoker |
| cg09023820 | 8 | 98881129 | Higher in Smoker |
| cg14088921 | 8 | 98944936 | Higher in Smoker |
| cg07333924 | 8 | 98881254 | Higher in Smoker |
| cg03293015 | 8 | 98881351 | Higher in Smoker |
| cg18705408 | 2 | 20212524 | Higher in Smoker |
| cg00261781 | 2 | 20212517 | Higher in Smoker |
| cg16837441 | 20 | 43935222 | Lower in Smoker |

| | | | |
|---|---|---|---|
| cg07534843 | 20 | 43935283 | Lower in Smoker |
| cg27227742 | 20 | 43935291 | Lower in Smoker |
| cg02759765 | 5 | 138629210 | Lower in Smoker |
| cg14717906 | 5 | 138641864 | Lower in Smoker |
| cg04318212 | 14 | 65569343 | Higher in Smoker |
| cg27254601 | 16 | 29817104 | Higher in Smoker |
| cg08877257 | 16 | 29820592 | Lower in Smoker |
| cg22358797 | 18 | 51750188 | Higher in Smoker |
| cg15438404 | 12 | 57916622 | Higher in Smoker |
| cg03516318 | 14 | 36790242 | Lower in Smoker |
| cg24109116 | 7 | 99725975 | Higher in Smoker |
| cg01685644 | 7 | 99724788 | Higher in Smoker |
| cg12360736 | 3 | 151985869 | Higher in Smoker |
| cg23207280 | 3 | 152147674 | Lower in Smoker |
| cg18850264 | 3 | 152038549 | Lower in Smoker |
| cg00085438 | 3 | 152049980 | Lower in Smoker |
| cg05796845 | 3 | 152053795 | Lower in Smoker |
| cg01001472 | 13 | 97947958 | Lower in Smoker |
| cg15690853 | 13 | 97928270 | Lower in Smoker |
| cg24097238 | 13 | 97975043 | Lower in Smoker |
| cg17188384 | 13 | 97874279 | Lower in Smoker |
| cg24434274 | 19 | 54695002 | Higher in Smoker |
| cg18206567 | 18 | 74828771 | Lower in Smoker |
| cg14298244 | 18 | 74729074 | Lower in Smoker |
| cg01991530 | X | 21857632 | Higher in Smoker |
| cg19992190 | X | 21857624 | Higher in Smoker |
| cg20494779 | 18 | 13916113 | Lower in Smoker |
| cg06407053 | 20 | 54823194 | Higher in Smoker |
| cg24298684 | 20 | 54823878 | Lower in Smoker |
| cg25367647 | X | 103401960 | Lower in Smoker |
| cg07344288 | 22 | 43540248 | Lower in Smoker |
| cg17846100 | 22 | 43538986 | Lower in Smoker |
| cg13531667 | 5 | 112825132 | Higher in Smoker |
| cg04614008 | 5 | 112630677 | Higher in Smoker |
| cg11341213 | 3 | 182786070 | Lower in Smoker |

| | | | |
|---|---|---|---|
| cg08476890 | X | 138774601 | Higher in Smoker |
| cg13450266 | 13 | 113625160 | Lower in Smoker |
| cg11668844 | 13 | 113655622 | Higher in Smoker |
| cg08584230 | 13 | 113666091 | Lower in Smoker |
| cg16351318 | 13 | 113642709 | Lower in Smoker |
| cg14783051 | 13 | 113663538 | Lower in Smoker |
| cg04789409 | 13 | 113717064 | Lower in Smoker |
| cg25983594 | 13 | 113650922 | Lower in Smoker |
| cg27269148 | 13 | 113735331 | Lower in Smoker |
| cg03870188 | 13 | 113717830 | Lower in Smoker |
| cg25947845 | 13 | 113718045 | Lower in Smoker |
| cg17831440 | 13 | 113699526 | Lower in Smoker |
| cg17962866 | 13 | 113637695 | Lower in Smoker |
| cg08248134 | 13 | 113659597 | Lower in Smoker |
| cg11158441 | 13 | 113702004 | Lower in Smoker |
| cg13108304 | 13 | 113634805 | Lower in Smoker |
| cg19658665 | 13 | 113652296 | Lower in Smoker |
| cg20696912 | 3 | 183146011 | Higher in Smoker |
| cg05502478 | 3 | 182911560 | Lower in Smoker |
| cg20585088 | 3 | 182970927 | Higher in Smoker |
| cg27324128 | 3 | 182970728 | Higher in Smoker |
| cg12988725 | 2 | 47142883 | Higher in Smoker |
| cg20326580 | 22 | 41078015 | Lower in Smoker |
| cg26797238 | 3 | 127323818 | Lower in Smoker |
| cg14550653 | 6 | 52149695 | Higher in Smoker |
| cg25420070 | 6 | 52149649 | Higher in Smoker |
| cg25703567 | 6 | 52128822 | Lower in Smoker |
| cg07418892 | 6 | 52150456 | Lower in Smoker |
| cg07608496 | 21 | 47649218 | Higher in Smoker |
| cg04903157 | 22 | 35795952 | Lower in Smoker |
| cg21593860 | 22 | 35796189 | Higher in Smoker |
| cg16284168 | 7 | 99698217 | Higher in Smoker |
| cg03239514 | 20 | 5931190 | Higher in Smoker |
| cg06000050 | 6 | 119256092 | Higher in Smoker |
| cg13331559 | 1 | 85514554 | Higher in Smoker |

| | | | |
|---|---|---|---|
| cg14833805 | 8 | 6470667 | Higher in Smoker |
| cg17642576 | 8 | 6424726 | Lower in Smoker |
| cg16451879 | 8 | 6430718 | Lower in Smoker |
| cg15447610 | 8 | 6328807 | Lower in Smoker |
| cg06452647 | 12 | 49961750 | Higher in Smoker |
| cg01860328 | 5 | 94620959 | Higher in Smoker |
| cg27086758 | 15 | 94840112 | Lower in Smoker |
| cg12047536 | X | 119737620 | Higher in Smoker |
| cg10536534 | X | 119737767 | Higher in Smoker |
| cg05317081 | 6 | 30685534 | Higher in Smoker |
| cg26568546 | 6 | 30682678 | Lower in Smoker |
| cg09232906 | 6 | 30684280 | Lower in Smoker |
| cg10925640 | 6 | 30684572 | Lower in Smoker |
| cg21105955 | 6 | 30684478 | Lower in Smoker |
| cg24700494 | 6 | 30684284 | Lower in Smoker |
| cg14029839 | 6 | 30685271 | Higher in Smoker |
| cg21045502 | 6 | 37620936 | Lower in Smoker |
| cg02180424 | 14 | 48095779 | Lower in Smoker |
| cg19503462 | 14 | 47872288 | Lower in Smoker |
| cg21443773 | 2 | 207630406 | Lower in Smoker |
| cg12339003 | 6 | 90528821 | Higher in Smoker |
| cg08582827 | 6 | 90529665 | Higher in Smoker |
| cg03716245 | 6 | 90509463 | Lower in Smoker |
| cg07797367 | 6 | 84136471 | Lower in Smoker |
| cg20151452 | 11 | 86290281 | Lower in Smoker |
| cg19918734 | 11 | 86343931 | Lower in Smoker |
| cg00857557 | 6 | 42982050 | Higher in Smoker |
| cg13806793 | 1 | 37980734 | Lower in Smoker |
| cg03679456 | 3 | 169377946 | Higher in Smoker |
| cg11123595 | 3 | 169376618 | Higher in Smoker |
| cg03330522 | 3 | 168830776 | Lower in Smoker |
| cg00742240 | X | 153287830 | Lower in Smoker |
| cg20965255 | 17 | 37607625 | Higher in Smoker |
| cg00283284 | 5 | 6378638 | Higher in Smoker |
| cg21401219 | 3 | 150803669 | Higher in Smoker |

| | | | |
|---|---|---|---|
| cg21895319 | 3 | 150874026 | Lower in Smoker |
| cg19010441 | 3 | 150917888 | Lower in Smoker |
| cg13229867 | 3 | 151058783 | Lower in Smoker |
| cg17795586 | 3 | 151047735 | Lower in Smoker |
| cg00091349 | 3 | 151048406 | Lower in Smoker |
| cg03841081 | 3 | 150967799 | Lower in Smoker |
| cg24305685 | 12 | 116715986 | Higher in Smoker |
| cg04677508 | X | 40595724 | Higher in Smoker |
| cg05662582 | 11 | 93517353 | Higher in Smoker |
| cg27497687 | 11 | 57479637 | Higher in Smoker |
| cg16776574 | 11 | 57479604 | Higher in Smoker |
| cg11976929 | 6 | 41888945 | Higher in Smoker |
| cg19606431 | 6 | 131949205 | Lower in Smoker |
| cg26628907 | 17 | 38195238 | Higher in Smoker |
| cg03671276 | 17 | 38183370 | Lower in Smoker |
| cg25468554 | 19 | 16739491 | Higher in Smoker |
| cg13606800 | 19 | 16687076 | Lower in Smoker |
| cg14287546 | 9 | 134919163 | Lower in Smoker |
| cg24184221 | 17 | 6555443 | Higher in Smoker |
| cg22723209 | 5 | 156570043 | Higher in Smoker |
| cg06754923 | 5 | 156571045 | Lower in Smoker |
| cg11972721 | 17 | 17394732 | Higher in Smoker |
| cg25782563 | 17 | 17380313 | Higher in Smoker |
| cg00062736 | 15 | 100171683 | Higher in Smoker |
| cg13690989 | 5 | 88180146 | Higher in Smoker |
| cg14034270 | 14 | 101291100 | Higher in Smoker |
| cg27142093 | 14 | 101302507 | Lower in Smoker |
| cg07886142 | 5 | 126793022 | Lower in Smoker |
| cg08095985 | 15 | 66544325 | Higher in Smoker |
| cg13702629 | 15 | 66546648 | Higher in Smoker |
| cg19648612 | 15 | 66274894 | Higher in Smoker |
| cg10941254 | 15 | 66406406 | Lower in Smoker |
| cg06278108 | 15 | 66274343 | Lower in Smoker |
| cg08719577 | 1 | 3528355 | Higher in Smoker |
| cg14521408 | 1 | 3500451 | Lower in Smoker |

| | | | |
|---|---|---|---|
| cg23686029 | 1 | 3435989 | Lower in Smoker |
| cg22226131 | 1 | 3496027 | Lower in Smoker |
| cg21811896 | 1 | 3465381 | Lower in Smoker |
| cg09018862 | 19 | 42882644 | Lower in Smoker |
| cg13777150 | 19 | 42830328 | Lower in Smoker |
| cg14180030 | 9 | 123475675 | Higher in Smoker |
| cg19329225 | 22 | 42192720 | Lower in Smoker |
| cg23497016 | 2 | 66666684 | Higher in Smoker |
| cg24421216 | 2 | 66782331 | Higher in Smoker |
| cg09550063 | 2 | 66672337 | Higher in Smoker |
| cg04367866 | 2 | 66695875 | Lower in Smoker |
| cg12055515 | 2 | 66735203 | Lower in Smoker |
| cg13051302 | 15 | 37384042 | Lower in Smoker |
| cg10451116 | 15 | 37350381 | Lower in Smoker |
| cg13378934 | 19 | 47910580 | Higher in Smoker |
| cg21145624 | 19 | 47922899 | Lower in Smoker |
| cg04569660 | 19 | 47922909 | Lower in Smoker |
| cg15825417 | 17 | 15689957 | Higher in Smoker |
| cg11500390 | 11 | 64572185 | Lower in Smoker |
| cg19904522 | 11 | 64574610 | Lower in Smoker |
| cg10928294 | 17 | 41739326 | Lower in Smoker |
| cg20040772 | 7 | 100026353 | Higher in Smoker |
| cg16333401 | 2 | 112656153 | Higher in Smoker |
| cg11865119 | 7 | 130125932 | Higher in Smoker |
| cg12347392 | 7 | 130131676 | Lower in Smoker |
| cg07829809 | 4 | 99957216 | Lower in Smoker |
| cg19636411 | 12 | 95909538 | Lower in Smoker |
| cg13005859 | 17 | 81036778 | Higher in Smoker |
| cg19563574 | 17 | 81050693 | Lower in Smoker |
| cg22946776 | 17 | 2324861 | Lower in Smoker |
| cg10128557 | 14 | 21461556 | Lower in Smoker |
| cg00604539 | 4 | 119606524 | Higher in Smoker |
| cg05567435 | 12 | 56074329 | Lower in Smoker |
| cg04518477 | 16 | 21610459 | Higher in Smoker |
| cg17866680 | 15 | 82338403 | Higher in Smoker |

| | | | |
|---|---|---|---|
| cg27511678 | 18 | 48721148 | Lower in Smoker |
| cg00009970 | 18 | 48723811 | Higher in Smoker |
| cg02614657 | 19 | 1568833 | Higher in Smoker |
| cg10592521 | 19 | 1560658 | Higher in Smoker |
| cg15119221 | 17 | 19290755 | Higher in Smoker |
| cg20431135 | 17 | 19290762 | Higher in Smoker |
| cg18574995 | 12 | 8815634 | Lower in Smoker |
| cg13406768 | 2 | 228192416 | Lower in Smoker |
| cg26894288 | 15 | 89447626 | Lower in Smoker |
| cg26967453 | 8 | 8652379 | Lower in Smoker |
| cg22239952 | 3 | 196758083 | Lower in Smoker |
| cg14637144 | 3 | 196750506 | Lower in Smoker |
| cg13726633 | 3 | 179064405 | Higher in Smoker |
| cg11628282 | 3 | 179065624 | Higher in Smoker |
| cg14973995 | 4 | 2935692 | Lower in Smoker |
| cg15978014 | 1 | 40420635 | Lower in Smoker |
| cg15405397 | 2 | 24232161 | Lower in Smoker |
| cg19273694 | 2 | 24233923 | Lower in Smoker |
| cg09372546 | 8 | 145733659 | Lower in Smoker |
| cg25600410 | 1 | 205550669 | Lower in Smoker |
| cg12586596 | 12 | 53645731 | Higher in Smoker |
| cg15332241 | 12 | 53645477 | Higher in Smoker |
| cg05827190 | 4 | 681440 | Higher in Smoker |
| cg04212021 | 5 | 180231084 | Higher in Smoker |
| cg09615860 | 2 | 99262816 | Lower in Smoker |
| cg18344063 | 12 | 87232511 | Lower in Smoker |
| cg07319315 | 2 | 135149599 | Lower in Smoker |
| cg11088706 | 17 | 74941572 | Lower in Smoker |
| cg24931632 | 1 | 47899667 | Higher in Smoker |
| cg17340166 | 12 | 110177689 | Lower in Smoker |
| cg17093877 | 17 | 72206412 | Lower in Smoker |
| cg08033845 | 14 | 105286102 | Higher in Smoker |
| cg00010046 | 16 | 88729480 | Higher in Smoker |
| cg05566591 | 16 | 88753099 | Higher in Smoker |
| cg01005517 | 16 | 88752439 | Higher in Smoker |

| | | | |
|---|---|---|---|
| cg06975633 | 1 | 78694398 | Lower in Smoker |
| cg13681940 | 6 | 134159412 | Higher in Smoker |
| cg04007151 | 5 | 43193035 | Higher in Smoker |
| cg11111460 | 4 | 183063637 | Higher in Smoker |
| cg09795809 | 4 | 183062729 | Higher in Smoker |
| cg24620592 | 7 | 97601903 | Lower in Smoker |
| cg22928405 | 3 | 127523174 | Lower in Smoker |
| cg13050716 | 3 | 127416580 | Lower in Smoker |
| cg26201213 | 10 | 131265796 | Lower in Smoker |
| cg10090769 | 16 | 4740791 | Lower in Smoker |
| cg09250423 | 16 | 4717752 | Lower in Smoker |
| cg23292259 | 14 | 39702965 | Lower in Smoker |
| cg21568317 | 1 | 222792261 | Higher in Smoker |
| cg08133669 | 1 | 222790218 | Lower in Smoker |
| cg03612722 | 22 | 27053402 | Higher in Smoker |
| cg09436871 | 18 | 19321130 | Higher in Smoker |
| cg15558634 | 1 | 1553405 | Lower in Smoker |
| cg00499399 | 6 | 31371550 | Higher in Smoker |
| cg18007127 | 6 | 31379971 | Higher in Smoker |
| cg25285646 | 6 | 31380432 | Lower in Smoker |
| cg05949660 | 6 | 109777642 | Lower in Smoker |
| cg23390397 | 6 | 109777103 | Higher in Smoker |
| cg25108382 | 7 | 1499184 | Higher in Smoker |
| cg15857635 | 7 | 1482527 | Higher in Smoker |
| cg15018486 | 7 | 1477191 | Lower in Smoker |
| cg25095587 | 6 | 31465685 | Higher in Smoker |
| cg16034423 | 6 | 31476690 | Lower in Smoker |
| cg03162819 | 6 | 31475392 | Lower in Smoker |
| cg25787812 | 6 | 31478830 | Lower in Smoker |
| cg03693925 | 6 | 31475055 | Lower in Smoker |
| cg20113277 | 6 | 31465901 | Higher in Smoker |
| cg12071142 | X | 10588311 | Higher in Smoker |
| cg01954531 | X | 38660667 | Higher in Smoker |
| cg11941526 | X | 38660299 | Higher in Smoker |
| cg19771541 | X | 107069417 | Higher in Smoker |

| | | | |
|---|---|---|---|
| cg02986494 | 19 | 1248287 | Higher in Smoker |
| cg26831409 | 19 | 1257077 | Lower in Smoker |
| cg22855438 | 1 | 67395917 | Higher in Smoker |
| cg07059151 | 22 | 24236617 | Higher in Smoker |
| cg05906777 | 17 | 73268160 | Lower in Smoker |
| cg15059389 | 1 | 12079390 | Higher in Smoker |
| cg04434568 | 17 | 4736365 | Lower in Smoker |
| cg17463508 | 17 | 4737022 | Lower in Smoker |
| cg18418479 | 17 | 4735500 | Lower in Smoker |
| cg25905815 | 13 | 24408063 | Lower in Smoker |
| cg10271981 | 19 | 10514432 | Higher in Smoker |
| cg01569295 | 1 | 231155862 | Lower in Smoker |
| cg01534125 | 1 | 231155818 | Lower in Smoker |
| cg02464665 | 1 | 231156359 | Lower in Smoker |
| cg00571033 | 8 | 9760957 | Higher in Smoker |
| cg25900085 | 8 | 65291513 | Higher in Smoker |
| cg05637686 | 2 | 180726697 | Higher in Smoker |
| cg06749053 | 11 | 121971219 | Higher in Smoker |
| cg18007341 | 6 | 33967924 | Lower in Smoker |
| cg12798274 | 10 | 105154067 | Lower in Smoker |
| cg10734581 | 14 | 101520078 | Lower in Smoker |
| cg02961808 | 16 | 56891173 | Lower in Smoker |
| cg22413603 | 12 | 7072765 | Higher in Smoker |
| cg07513914 | 2 | 232758224 | Lower in Smoker |
| cg12035782 | 2 | 232757030 | Lower in Smoker |
| cg19477205 | 14 | 101525106 | Lower in Smoker |
| cg17297071 | 21 | 26934424 | Higher in Smoker |
| cg02219476 | 15 | 63115816 | Lower in Smoker |
| cg21536086 | 1 | 154166546 | Lower in Smoker |
| cg14764512 | 3 | 49058575 | Lower in Smoker |
| cg04018325 | 16 | 14397685 | Lower in Smoker |
| cg03295417 | 16 | 14397892 | Lower in Smoker |
| cg06273075 | 16 | 14397688 | Lower in Smoker |
| cg07665535 | 16 | 14397756 | Lower in Smoker |
| cg05250768 | 7 | 27209270 | Higher in Smoker |

| | | | |
|---|---|---|---|
| cg23426816 | 10 | 115934681 | Higher in Smoker |
| cg25135143 | 10 | 115934548 | Higher in Smoker |
| cg14467654 | 9 | 131155819 | Higher in Smoker |
| cg19127840 | X | 65233616 | Higher in Smoker |
| cg15787712 | 19 | 13948243 | Lower in Smoker |
| cg10758022 | 7 | 130561592 | Lower in Smoker |
| cg20632224 | 1 | 117214228 | Lower in Smoker |
| cg20454429 | X | 133303524 | Lower in Smoker |
| cg00218620 | 2 | 219866460 | Higher in Smoker |
| cg19892668 | 14 | 101487503 | Lower in Smoker |
| cg18440069 | 14 | 101488391 | Lower in Smoker |
| cg07918453 | 14 | 101531403 | Lower in Smoker |
| cg03528302 | 1 | 1104399 | Lower in Smoker |
| cg11212178 | 12 | 95226807 | Lower in Smoker |
| cg06789392 | X | 49774388 | Lower in Smoker |
| cg09721969 | X | 146313275 | Lower in Smoker |
| cg05865548 | 14 | 101498206 | Lower in Smoker |
| cg09411231 | 1 | 186159350 | Lower in Smoker |
| cg16621560 | 13 | 36495173 | Lower in Smoker |
| cg02558362 | 13 | 36052605 | Higher in Smoker |
| cg13757194 | 15 | 69223774 | Higher in Smoker |
| cg10443315 | 8 | 7947282 | Lower in Smoker |
| cg00074313 | 2 | 179371342 | Lower in Smoker |
| cg14284588 | 2 | 179341804 | Lower in Smoker |
| cg05205299 | 9 | 109848356 | Lower in Smoker |
| cg10857203 | 4 | 166307422 | Lower in Smoker |
| cg09753632 | 5 | 95413861 | Higher in Smoker |
| cg01459030 | 7 | 73605490 | Lower in Smoker |
| cg14158769 | 7 | 126698156 | Lower in Smoker |
| cg02090654 | 7 | 126698344 | Lower in Smoker |
| cg16193245 | 7 | 158325503 | Higher in Smoker |
| cg25673948 | 8 | 1765296 | Higher in Smoker |
| cg25804357 | 10 | 29834263 | Higher in Smoker |
| cg16150798 | 11 | 61560092 | Lower in Smoker |
| cg20017464 | 17 | 30677219 | Higher in Smoker |

| | | | |
|---|---|---|---|
| cg23263051 | 17 | 74733425 | Higher in Smoker |
| cg06905901 | 19 | 14639450 | Lower in Smoker |
| cg01200264 | 14 | 101505523 | Lower in Smoker |
| cg18702576 | 22 | 38243855 | Lower in Smoker |
| cg26775123 | 16 | 819440 | Lower in Smoker |
| cg07616094 | 11 | 43581175 | Lower in Smoker |
| cg21501241 | 14 | 101491839 | Lower in Smoker |
| cg12530503 | 15 | 89911148 | Higher in Smoker |
| cg10581281 | 3 | 69788259 | Higher in Smoker |
| cg07499607 | 3 | 69789199 | Higher in Smoker |
| cg12466700 | 3 | 69789955 | Lower in Smoker |
| cg17445875 | 3 | 69859618 | Lower in Smoker |
| cg15449049 | 3 | 69812125 | Lower in Smoker |
| cg01113900 | 3 | 69925279 | Lower in Smoker |
| cg13151171 | 3 | 69915189 | Lower in Smoker |
| cg18691055 | 10 | 129924607 | Higher in Smoker |
| cg03286467 | 22 | 41032802 | Higher in Smoker |
| cg09449449 | 16 | 14357888 | Lower in Smoker |
| cg00808545 | 16 | 14219324 | Lower in Smoker |
| cg02559410 | 16 | 14169732 | Lower in Smoker |
| cg04851652 | 7 | 130798757 | Lower in Smoker |
| cg18272456 | 7 | 131037705 | Lower in Smoker |
| cg08713474 | 7 | 131068678 | Lower in Smoker |
| cg22858630 | 1 | 47060645 | Higher in Smoker |
| cg18418335 | 19 | 2042088 | Higher in Smoker |
| cg02976323 | 7 | 140156225 | Lower in Smoker |
| cg06840042 | 3 | 12598618 | Higher in Smoker |
| cg09437135 | 15 | 23810163 | Lower in Smoker |
| cg19488213 | 10 | 28033338 | Higher in Smoker |
| cg11821702 | 9 | 5891258 | Lower in Smoker |
| cg10854441 | 22 | 50524691 | Higher in Smoker |
| cg01776495 | 12 | 6858115 | Lower in Smoker |
| cg26645069 | 12 | 6861493 | Lower in Smoker |
| cg07101782 | 3 | 37034495 | Higher in Smoker |
| cg23407670 | 14 | 75518217 | Higher in Smoker |

| | | | |
|---|---|---|---|
| cg00011350 | 12 | 49444296 | Higher in Smoker |
| cg07546102 | 7 | 151873302 | Lower in Smoker |
| cg24471867 | 19 | 36207871 | Higher in Smoker |
| cg10488185 | 7 | 104654258 | Higher in Smoker |
| cg13842305 | 1 | 151033007 | Higher in Smoker |
| cg17811167 | 17 | 36861499 | Higher in Smoker |
| cg17337668 | 17 | 36863216 | Lower in Smoker |
| cg08992911 | 2 | 238395768 | Higher in Smoker |
| cg03343262 | 16 | 2255396 | Higher in Smoker |
| cg11395975 | 16 | 2255950 | Higher in Smoker |
| cg20724073 | 17 | 40719654 | Higher in Smoker |
| cg14408505 | 17 | 40719291 | Lower in Smoker |
| cg16497413 | 12 | 109992779 | Lower in Smoker |
| cg00008971 | 1 | 45966925 | Lower in Smoker |
| cg01992081 | 17 | 53498958 | Higher in Smoker |
| cg26435501 | 7 | 4998094 | Higher in Smoker |
| cg18932078 | 1 | 2524107 | Lower in Smoker |
| cg17740752 | 1 | 2529902 | Lower in Smoker |
| cg16159491 | 22 | 24115290 | Higher in Smoker |
| cg01612337 | 16 | 58059149 | Higher in Smoker |
| cg20722590 | 16 | 58061473 | Higher in Smoker |
| cg20531808 | 8 | 89231006 | Lower in Smoker |
| cg10632507 | 12 | 132317390 | Lower in Smoker |
| cg01821058 | 16 | 55512870 | Higher in Smoker |
| cg02458945 | 16 | 55514470 | Higher in Smoker |
| cg00355286 | 16 | 55525729 | Lower in Smoker |
| cg08231710 | 1 | 1566687 | Higher in Smoker |
| cg11648594 | 1 | 1566860 | Lower in Smoker |
| cg07957458 | 20 | 33862215 | Lower in Smoker |
| cg09758894 | 11 | 102576508 | Lower in Smoker |
| cg04059146 | 11 | 102402233 | Lower in Smoker |
| cg22545356 | 10 | 88716659 | Lower in Smoker |
| cg07052063 | 10 | 99255236 | Higher in Smoker |
| cg27045447 | 22 | 28198218 | Higher in Smoker |
| cg13184270 | 15 | 56757290 | Higher in Smoker |

| | | | |
|---|---|---|---|
| cg22441074 | 17 | 2304393 | Higher in Smoker |
| cg12164596 | 7 | 156799224 | Lower in Smoker |
| cg05940971 | 14 | 93651131 | Higher in Smoker |
| cg10477385 | 2 | 74401583 | Lower in Smoker |
| cg01518398 | 2 | 74406523 | Lower in Smoker |
| cg15187398 | 19 | 2093896 | Lower in Smoker |
| cg05376185 | 1 | 47082869 | Higher in Smoker |
| cg06760830 | 1 | 47079672 | Higher in Smoker |
| cg09655253 | 6 | 39895417 | Lower in Smoker |
| cg25017994 | 6 | 29627296 | Lower in Smoker |
| cg01479031 | 6 | 29632349 | Lower in Smoker |
| cg22306344 | 3 | 49966773 | Higher in Smoker |
| cg22470056 | 3 | 49947811 | Lower in Smoker |
| cg08283408 | 3 | 49949060 | Lower in Smoker |
| cg06752914 | 16 | 77224636 | Higher in Smoker |
| cg25092670 | 3 | 109837620 | Lower in Smoker |
| cg02551882 | 22 | 31365455 | Lower in Smoker |
| cg12279734 | 4 | 174538350 | Lower in Smoker |
| cg04661436 | 15 | 79169207 | Lower in Smoker |
| cg18813010 | X | 102931660 | Lower in Smoker |
| cg16399855 | 1 | 2318621 | Higher in Smoker |
| cg22349332 | 1 | 2252794 | Lower in Smoker |
| cg12700755 | 1 | 2258373 | Lower in Smoker |
| cg18155888 | 1 | 2266591 | Lower in Smoker |
| cg14098223 | 1 | 2262333 | Lower in Smoker |
| cg17453416 | 1 | 2263665 | Lower in Smoker |
| cg19084427 | 1 | 2284530 | Lower in Smoker |
| cg03533858 | 1 | 2324396 | Lower in Smoker |
| cg17444015 | 1 | 2322981 | Higher in Smoker |
| cg20824876 | 2 | 39109167 | Lower in Smoker |
| cg07479988 | 2 | 39103277 | Lower in Smoker |
| cg03138064 | 12 | 122096667 | Higher in Smoker |
| cg00162751 | 1 | 220921532 | Higher in Smoker |
| cg01731096 | 7 | 100208950 | Lower in Smoker |
| cg15848628 | 7 | 100210192 | Higher in Smoker |

| | | | |
|---|---|---|---|
| cg11257300 | 1 | 113229103 | Lower in Smoker |
| cg06462666 | 22 | 50528312 | Lower in Smoker |
| cg15768556 | 16 | 128630 | Higher in Smoker |
| cg27005181 | 13 | 20208413 | Higher in Smoker |
| cg21805179 | 12 | 123707825 | Lower in Smoker |
| cg07732037 | 12 | 123707827 | Lower in Smoker |
| cg07977713 | 1 | 43814169 | Lower in Smoker |
| cg18856478 | 1 | 43814358 | Lower in Smoker |
| cg17552029 | 17 | 41985222 | Higher in Smoker |
| cg14567414 | 17 | 41910795 | Higher in Smoker |
| cg16860267 | 18 | 11908803 | Higher in Smoker |
| cg17320698 | 11 | 30510489 | Lower in Smoker |
| cg23944405 | 11 | 30602030 | Lower in Smoker |
| cg16455894 | 17 | 16966893 | Higher in Smoker |
| cg05308895 | 1 | 167691710 | Higher in Smoker |
| cg08882650 | 1 | 167691462 | Lower in Smoker |
| cg16594165 | 11 | 118135105 | Higher in Smoker |
| cg25640892 | 6 | 84743294 | Higher in Smoker |
| cg08932381 | 3 | 138078989 | Lower in Smoker |
| cg11701250 | 11 | 94227183 | Higher in Smoker |
| cg26262057 | 11 | 94227038 | Higher in Smoker |
| cg27081634 | 11 | 68778745 | Lower in Smoker |
| cg05304057 | 11 | 18141625 | Lower in Smoker |
| cg06978737 | 11 | 18194514 | Higher in Smoker |
| cg22583444 | 19 | 13879660 | Lower in Smoker |
| cg07207937 | 4 | 78783799 | Higher in Smoker |
| cg18450378 | 4 | 78783746 | Higher in Smoker |
| cg16785953 | 4 | 78787669 | Lower in Smoker |
| cg12996171 | 17 | 79674399 | Higher in Smoker |
| cg06171787 | 11 | 59578490 | Higher in Smoker |
| cg03776775 | 11 | 1971502 | Lower in Smoker |
| cg25371088 | 1 | 156710915 | Higher in Smoker |
| cg09339907 | 17 | 48448140 | Lower in Smoker |
| cg00150737 | 3 | 131221845 | Higher in Smoker |
| cg14073058 | 2 | 99797500 | Higher in Smoker |

| | | | |
|---|---|---|---|
| cg00365680 | 7 | 42972339 | Higher in Smoker |
| cg15251939 | 7 | 42972457 | Lower in Smoker |
| cg10535847 | 1 | 54665846 | Higher in Smoker |
| cg16069236 | 21 | 26980353 | Higher in Smoker |
| cg00221788 | 12 | 93859987 | Lower in Smoker |
| cg03872267 | 15 | 89011204 | Higher in Smoker |
| cg01815934 | 3 | 179308888 | Lower in Smoker |
| cg18552020 | 11 | 73498113 | Lower in Smoker |
| cg01231620 | 14 | 23298884 | Higher in Smoker |
| cg11854791 | 19 | 3761509 | Higher in Smoker |
| cg01342085 | 15 | 89010689 | Higher in Smoker |
| cg09961571 | 19 | 39421871 | Higher in Smoker |
| cg03122164 | 19 | 39421160 | Lower in Smoker |
| cg00705668 | 19 | 39421403 | Higher in Smoker |
| cg00248935 | 1 | 36930185 | Higher in Smoker |
| cg25977101 | 6 | 43655599 | Higher in Smoker |
| cg16210397 | 6 | 30585548 | Higher in Smoker |
| cg26813794 | 6 | 30584952 | Higher in Smoker |
| cg18207141 | 6 | 30585871 | Higher in Smoker |
| cg26365668 | 4 | 84375973 | Higher in Smoker |
| cg22587514 | 9 | 138392051 | Higher in Smoker |
| cg25373063 | 1 | 150266194 | Higher in Smoker |
| cg22047672 | 1 | 150275877 | Lower in Smoker |
| cg07843065 | 1 | 150265600 | Lower in Smoker |
| cg09808343 | 1 | 150266643 | Lower in Smoker |
| cg14879736 | 3 | 139062602 | Lower in Smoker |
| cg21817750 | 5 | 71543106 | Lower in Smoker |
| cg27326661 | 8 | 30922579 | Lower in Smoker |
| cg20669710 | 5 | 44809829 | Higher in Smoker |
| cg04762397 | 13 | 41344949 | Higher in Smoker |
| cg07735777 | 7 | 140715095 | Higher in Smoker |
| cg15556672 | 5 | 68513082 | Lower in Smoker |
| cg10599571 | 21 | 35445161 | Lower in Smoker |
| cg04686354 | 17 | 73261880 | Higher in Smoker |
| cg14185808 | 2 | 105653693 | Higher in Smoker |

| | | | |
|---|---|---|---|
| cg24328054 | 1 | 19586547 | Lower in Smoker |
| cg05704942 | 1 | 19581542 | Lower in Smoker |
| cg08298091 | 11 | 10645996 | Lower in Smoker |
| cg20285761 | 11 | 60551437 | Lower in Smoker |
| cg23754934 | 11 | 60047483 | Higher in Smoker |
| cg25827490 | 8 | 72756839 | Lower in Smoker |
| cg22762189 | 2 | 17996994 | Higher in Smoker |
| cg25746226 | 2 | 47629792 | Lower in Smoker |
| cg22350709 | 5 | 80023352 | Lower in Smoker |
| cg01207734 | 5 | 79950934 | Lower in Smoker |
| cg23634079 | 6 | 31712195 | Higher in Smoker |
| cg10435003 | 6 | 31707602 | Higher in Smoker |
| cg22430861 | 17 | 55584079 | Higher in Smoker |
| cg04643513 | 17 | 55335758 | Higher in Smoker |
| cg18783374 | 17 | 55474945 | Higher in Smoker |
| cg08322234 | 17 | 55663284 | Higher in Smoker |
| cg03818193 | 17 | 55623656 | Lower in Smoker |
| cg01796800 | 17 | 55595732 | Lower in Smoker |
| cg15782604 | 3 | 135915004 | Higher in Smoker |
| cg17177318 | 3 | 135913615 | Higher in Smoker |
| cg13369210 | X | 11775766 | Higher in Smoker |
| cg16569147 | 16 | 816088 | Lower in Smoker |
| cg02421962 | 16 | 815975 | Lower in Smoker |
| cg06943437 | X | 64387365 | Higher in Smoker |
| cg07998290 | 8 | 9912305 | Higher in Smoker |
| cg07355157 | 10 | 23385780 | Lower in Smoker |
| cg07834396 | 10 | 23385979 | Lower in Smoker |
| cg04254693 | 3 | 49727222 | Higher in Smoker |
| cg08687163 | 3 | 49940853 | Lower in Smoker |
| cg08063891 | 2 | 190923520 | Lower in Smoker |
| cg13207326 | 4 | 4860190 | Higher in Smoker |
| cg09748975 | 4 | 4864532 | Higher in Smoker |
| cg13882284 | 4 | 4859996 | Higher in Smoker |
| cg07462756 | 4 | 4859985 | Higher in Smoker |
| cg21689228 | 4 | 4860547 | Lower in Smoker |

| | | | |
|---|---|---|---|
| cg20588069 | 4 | 4860439 | Lower in Smoker |
| cg00519002 | 16 | 56659338 | Higher in Smoker |
| cg15134649 | 16 | 56659336 | Higher in Smoker |
| cg00178359 | 16 | 56659460 | Lower in Smoker |
| cg00916884 | 16 | 56666334 | Higher in Smoker |
| cg08917795 | 16 | 56716597 | Higher in Smoker |
| cg07395075 | 16 | 56642428 | Higher in Smoker |
| cg08409642 | 16 | 56641373 | Higher in Smoker |
| cg08270206 | 16 | 56623390 | Higher in Smoker |
| cg20300135 | 14 | 105909472 | Lower in Smoker |
| cg01538998 | 11 | 62361266 | Higher in Smoker |
| cg00230302 | 9 | 21802598 | Higher in Smoker |
| cg26117622 | 2 | 242042254 | Lower in Smoker |
| cg13567986 | 1 | 38310056 | Higher in Smoker |
| cg10599479 | 15 | 65321629 | Higher in Smoker |
| cg22020155 | 8 | 66557012 | Higher in Smoker |
| cg23419813 | 14 | 64860750 | Lower in Smoker |
| ch.6.2925136R | 6 | 151283923 | Higher in Smoker |
| cg13602242 | 6 | 151186614 | Higher in Smoker |
| cg00067414 | 6 | 151183081 | Higher in Smoker |
| cg11579907 | 6 | 151412213 | Higher in Smoker |
| cg15331693 | 6 | 151373267 | Lower in Smoker |
| cg01887435 | 6 | 151402973 | Lower in Smoker |
| ch.2.1685112F | 2 | 74436960 | Higher in Smoker |
| cg03893307 | 4 | 75023849 | Higher in Smoker |
| cg18276943 | 1 | 11853610 | Lower in Smoker |
| cg12364461 | 15 | 80185399 | Lower in Smoker |
| cg00608860 | 16 | 86588622 | Higher in Smoker |
| cg20147645 | 13 | 28023563 | Lower in Smoker |
| cg06026817 | 11 | 68518826 | Higher in Smoker |
| cg12774559 | 11 | 68519071 | Higher in Smoker |
| cg25149391 | 11 | 68520448 | Lower in Smoker |
| cg17254405 | 11 | 68514089 | Lower in Smoker |
| cg00180631 | X | 149736640 | Higher in Smoker |
| cg00881203 | X | 149930926 | Lower in Smoker |

| | | | |
|---|---|---|---|
| cg22957339 | 15 | 31246272 | Lower in Smoker |
| cg16348820 | 1 | 149909080 | Lower in Smoker |
| cg21747617 | 3 | 9691076 | Higher in Smoker |
| cg24401310 | 15 | 31195869 | Higher in Smoker |
| cg25314817 | 11 | 95647661 | Lower in Smoker |
| cg04100434 | 17 | 56595363 | Higher in Smoker |
| cg16718054 | X | 63615366 | Higher in Smoker |
| cg05306193 | 8 | 11144705 | Lower in Smoker |
| cg15411402 | 8 | 11142072 | Lower in Smoker |
| cg09942999 | 1 | 32707389 | Higher in Smoker |
| cg26238041 | 4 | 187476543 | Higher in Smoker |
| cg01722932 | 11 | 92702653 | Higher in Smoker |
| cg19977866 | 11 | 92705264 | Lower in Smoker |
| cg13435101 | 6 | 74171350 | Higher in Smoker |
| cg07122170 | 1 | 11248185 | Lower in Smoker |
| cg21232129 | 22 | 30821704 | Higher in Smoker |
| cg03296761 | 22 | 30822510 | Lower in Smoker |
| cg19921439 | 13 | 41837776 | Higher in Smoker |
| cg10300154 | 5 | 7870577 | Lower in Smoker |
| cg26069068 | 8 | 125741265 | Lower in Smoker |
| cg19523819 | 8 | 125741259 | Lower in Smoker |
| cg12716367 | 8 | 17625476 | Lower in Smoker |
| cg25809502 | 13 | 29933441 | Lower in Smoker |
| cg07790085 | 13 | 29597447 | Lower in Smoker |
| cg07149992 | 13 | 30056422 | Lower in Smoker |
| cg25319237 | 13 | 30057464 | Lower in Smoker |
| cg07780517 | 13 | 30077489 | Lower in Smoker |
| cg07062476 | 5 | 79286648 | Lower in Smoker |
| cg06216400 | 1 | 155161161 | Lower in Smoker |
| cg06420088 | 1 | 155163590 | Higher in Smoker |
| cg04735437 | 7 | 100647879 | Lower in Smoker |
| cg03455418 | 7 | 100612725 | Lower in Smoker |
| cg14497879 | 3 | 124654885 | Lower in Smoker |
| cg00435098 | 11 | 1092171 | Lower in Smoker |
| cg05877661 | 11 | 1095156 | Lower in Smoker |

| | | | |
|---|---|---|---|
| cg27020953 | 11 | 1096455 | Lower in Smoker |
| cg27483767 | 11 | 1098080 | Lower in Smoker |
| cg05012239 | 3 | 195447691 | Lower in Smoker |
| cg11042373 | 6 | 30956585 | Lower in Smoker |
| cg27567922 | 3 | 195480636 | Lower in Smoker |
| cg26090359 | 11 | 1268962 | Higher in Smoker |
| cg06582806 | 11 | 1275741 | Lower in Smoker |
| cg27661209 | 11 | 1252192 | Lower in Smoker |
| cg03609102 | 11 | 1244533 | Lower in Smoker |
| cg20839554 | 11 | 1012937 | Lower in Smoker |
| cg05997730 | 11 | 1036727 | Lower in Smoker |
| cg26226988 | 11 | 1037923 | Lower in Smoker |
| cg16517186 | 14 | 57735545 | Higher in Smoker |
| cg11094161 | 14 | 57736037 | Higher in Smoker |
| cg22862384 | 14 | 57738063 | Lower in Smoker |
| cg15749157 | 19 | 1366829 | Lower in Smoker |
| cg03765980 | 19 | 1369515 | Lower in Smoker |
| cg09539256 | 11 | 65626522 | Higher in Smoker |
| cg21547371 | 3 | 52869521 | Lower in Smoker |
| cg13234997 | 12 | 110011138 | Higher in Smoker |
| cg03856401 | 16 | 29853262 | Higher in Smoker |
| cg10933439 | 21 | 42793818 | Lower in Smoker |
| cg21135483 | 21 | 42830710 | Lower in Smoker |
| cg15281283 | 21 | 42733894 | Higher in Smoker |
| cg02381521 | 21 | 42775934 | Lower in Smoker |
| cg20935156 | 4 | 2252845 | Lower in Smoker |
| cg09293286 | X | 3235329 | Higher in Smoker |
| cg22691336 | 1 | 1292638 | Lower in Smoker |
| cg15720926 | 19 | 54371050 | Lower in Smoker |
| cg19717326 | 19 | 54370016 | Lower in Smoker |
| cg10574148 | 6 | 135504383 | Higher in Smoker |
| cg18905962 | 17 | 4456069 | Lower in Smoker |
| cg00655982 | 19 | 50936038 | Lower in Smoker |
| cg09332784 | 1 | 109850837 | Lower in Smoker |
| cg15465092 | 8 | 128747754 | Higher in Smoker |

| | | | |
|---|---|---|---|
| cg19690410 | 1 | 39340248 | Lower in Smoker |
| cg23269605 | 13 | 77675444 | Higher in Smoker |
| cg08063724 | 1 | 40367097 | Higher in Smoker |
| cg21353292 | 2 | 16079983 | Higher in Smoker |
| cg06520300 | 2 | 16081824 | Higher in Smoker |
| cg08462247 | 2 | 241075202 | Higher in Smoker |
| cg18256790 | 17 | 8532950 | Higher in Smoker |
| cg04753668 | 17 | 8534404 | Higher in Smoker |
| cg10940874 | 17 | 8380417 | Lower in Smoker |
| cg22249386 | 17 | 10212450 | Lower in Smoker |
| cg16252322 | 19 | 50789296 | Lower in Smoker |
| cg16467929 | 3 | 108204398 | Lower in Smoker |
| cg25631723 | 17 | 10533122 | Lower in Smoker |
| cg26958741 | 12 | 111358470 | Lower in Smoker |
| cg08555912 | 4 | 674399 | Lower in Smoker |
| cg00723338 | 4 | 674590 | Lower in Smoker |
| cg03867607 | 12 | 56554439 | Lower in Smoker |
| cg08716553 | 12 | 56549960 | Lower in Smoker |
| cg20376421 | 12 | 56546193 | Lower in Smoker |
| cg23370883 | 7 | 44180604 | Lower in Smoker |
| cg05820491 | 20 | 35169594 | Higher in Smoker |
| cg01817204 | 3 | 123602957 | Higher in Smoker |
| cg03387092 | 3 | 123493248 | Lower in Smoker |
| cg23184556 | 3 | 123600215 | Lower in Smoker |
| cg24980700 | 20 | 30410739 | Lower in Smoker |
| cg05813616 | 16 | 46781713 | Lower in Smoker |
| cg08860143 | 16 | 30385767 | Lower in Smoker |
| cg18676803 | 3 | 169490697 | Higher in Smoker |
| cg26742770 | 17 | 18026502 | Lower in Smoker |
| cg16055132 | 13 | 109538794 | Lower in Smoker |
| cg20371573 | 13 | 109780516 | Lower in Smoker |
| cg09966204 | 13 | 109741117 | Lower in Smoker |
| cg24965356 | 13 | 109796642 | Lower in Smoker |
| cg16886468 | 17 | 27507505 | Higher in Smoker |
| cg02376256 | 17 | 27401160 | Lower in Smoker |

| | | | |
|---|---|---|---|
| cg05920725 | 17 | 1389108 | Higher in Smoker |
| cg12989085 | 17 | 1367637 | Lower in Smoker |
| cg20771846 | 17 | 1372516 | Lower in Smoker |
| cg26183265 | 17 | 1374597 | Lower in Smoker |
| cg21839984 | 17 | 30846986 | Higher in Smoker |
| cg22334879 | 19 | 8642370 | Higher in Smoker |
| cg22568423 | 19 | 8590567 | Lower in Smoker |
| cg01703884 | 12 | 109878174 | Lower in Smoker |
| cg15031351 | 10 | 26222922 | Higher in Smoker |
| cg03876032 | 10 | 26501065 | Lower in Smoker |
| cg04807567 | 2 | 171381284 | Lower in Smoker |
| cg22033823 | 15 | 52640656 | Lower in Smoker |
| cg01567656 | 11 | 76895869 | Lower in Smoker |
| cg12793160 | 2 | 128395196 | Lower in Smoker |
| cg05414026 | 15 | 72410439 | Higher in Smoker |
| cg11538903 | 19 | 17208493 | Lower in Smoker |
| cg12085226 | 10 | 95157742 | Lower in Smoker |
| cg13734710 | 10 | 95242014 | Higher in Smoker |
| cg10901806 | 1 | 203055422 | Lower in Smoker |
| cg24128316 | 18 | 3219966 | Lower in Smoker |
| cg02243278 | 8 | 2076984 | Higher in Smoker |
| cg02133140 | 8 | 2078250 | Lower in Smoker |
| cg06440275 | 8 | 2005701 | Lower in Smoker |
| cg01295646 | 8 | 2075820 | Lower in Smoker |
| cg07510346 | 8 | 2035751 | Lower in Smoker |
| cg05891136 | 8 | 2014195 | Lower in Smoker |
| cg11424828 | 8 | 2075469 | Lower in Smoker |
| cg09127607 | 10 | 69914213 | Higher in Smoker |
| cg03824275 | 3 | 40004565 | Lower in Smoker |
| cg02515103 | 1 | 59165868 | Higher in Smoker |
| cg13828871 | 16 | 31128860 | Higher in Smoker |
| cg15251374 | 3 | 41910035 | Higher in Smoker |
| cg14111928 | 10 | 76602391 | Lower in Smoker |
| cg15912797 | 10 | 76586332 | Higher in Smoker |
| cg12250197 | 20 | 62815606 | Lower in Smoker |

| | | | |
|---|---|---|---|
| cg20720697 | 2 | 1858583 | Higher in Smoker |
| cg04485956 | 2 | 1859071 | Higher in Smoker |
| cg18807003 | 2 | 1822412 | Lower in Smoker |
| cg22946562 | 2 | 1880012 | Lower in Smoker |
| cg12989104 | 16 | 48645051 | Lower in Smoker |
| cg05079544 | 16 | 48644408 | Lower in Smoker |
| cg08898622 | 4 | 40062021 | Lower in Smoker |
| cg16860991 | 4 | 40059040 | Higher in Smoker |
| cg05666130 | 13 | 33083560 | Lower in Smoker |
| cg27035514 | 5 | 177539998 | Lower in Smoker |
| cg12953095 | 13 | 21347486 | Higher in Smoker |
| cg27078455 | 4 | 140225613 | Lower in Smoker |
| cg03321912 | 13 | 41950907 | Lower in Smoker |
| cg26301777 | 13 | 41884544 | Lower in Smoker |
| cg14182682 | 14 | 57857589 | Higher in Smoker |
| cg10823546 | 9 | 88555702 | Higher in Smoker |
| cg02084325 | 11 | 63706275 | Lower in Smoker |
| cg24439307 | 11 | 89925406 | Lower in Smoker |
| cg24575651 | 3 | 174764477 | Lower in Smoker |
| cg09890077 | 3 | 175056652 | Lower in Smoker |
| cg07315006 | 3 | 174812890 | Lower in Smoker |
| cg27093645 | 12 | 57482538 | Higher in Smoker |
| cg01756730 | 12 | 57483513 | Higher in Smoker |
| cg12080431 | 12 | 57482774 | Higher in Smoker |
| cg02954252 | 12 | 57119365 | Higher in Smoker |
| cg04413986 | 12 | 57119373 | Higher in Smoker |
| cg08088948 | 12 | 57113463 | Lower in Smoker |
| cg13329981 | 12 | 57119060 | Higher in Smoker |
| cg15578948 | 1 | 1689012 | Lower in Smoker |
| cg18763089 | 1 | 1683738 | Lower in Smoker |
| cg12552303 | 1 | 1691617 | Lower in Smoker |
| cg06146607 | 11 | 71167505 | Higher in Smoker |
| cg20006855 | 11 | 71209518 | Lower in Smoker |
| cg07072878 | 4 | 164047991 | Lower in Smoker |
| cg15586945 | 4 | 164068095 | Higher in Smoker |

| | | | |
|---|---|---|---|
| cg05380008 | 22 | 42466865 | Lower in Smoker |
| cg08134518 | 22 | 42466753 | Higher in Smoker |
| cg03766027 | 2 | 71296001 | Higher in Smoker |
| cg02889450 | 16 | 5084885 | Lower in Smoker |
| cg09300856 | 17 | 42083686 | Lower in Smoker |
| cg01373473 | 7 | 105925859 | Higher in Smoker |
| cg13849525 | 19 | 46418069 | Lower in Smoker |
| cg17105689 | 11 | 3013942 | Higher in Smoker |
| cg13409589 | 11 | 3013777 | Higher in Smoker |
| cg07442639 | 11 | 3014225 | Lower in Smoker |
| cg26886572 | 11 | 3009206 | Lower in Smoker |
| cg18317022 | 19 | 48017995 | Higher in Smoker |
| cg07392482 | 18 | 10524910 | Higher in Smoker |
| cg08508337 | 8 | 144660607 | Higher in Smoker |
| cg00713939 | 8 | 144660590 | Higher in Smoker |
| cg08017634 | 8 | 144659831 | Lower in Smoker |
| cg09673444 | 17 | 80417290 | Higher in Smoker |
| cg13749424 | 17 | 80416444 | Higher in Smoker |
| cg14556515 | 17 | 80416454 | Higher in Smoker |
| cg03541381 | 16 | 790595 | Higher in Smoker |
| cg10034642 | 16 | 791241 | Higher in Smoker |
| cg00881372 | 16 | 780555 | Lower in Smoker |
| cg22384801 | 15 | 60767308 | Higher in Smoker |
| cg19895051 | 15 | 60771505 | Higher in Smoker |
| cg02041869 | 6 | 18028071 | Lower in Smoker |
| cg15267303 | 11 | 34127610 | Higher in Smoker |
| cg14884197 | 19 | 55996438 | Higher in Smoker |
| cg19820609 | 19 | 55998931 | Higher in Smoker |
| cg23258940 | 19 | 55995851 | Lower in Smoker |
| cg20912205 | 3 | 50337305 | Lower in Smoker |
| cg16417840 | 4 | 2069925 | Lower in Smoker |
| cg12575325 | 17 | 72772745 | Higher in Smoker |
| cg25167447 | 1 | 201617042 | Lower in Smoker |
| ch.1.3897073R | 1 | 201780598 | Higher in Smoker |
| cg00491064 | 11 | 19681786 | Lower in Smoker |

| | | | |
|---|---|---|---|
| cg08153755 | 11 | 19792080 | Lower in Smoker |
| cg18009574 | 11 | 19744280 | Lower in Smoker |
| cg18451529 | 2 | 15696011 | Lower in Smoker |
| cg17187705 | 13 | 35735300 | Lower in Smoker |
| cg00729885 | 13 | 36046056 | Lower in Smoker |
| cg27643099 | 2 | 203879262 | Higher in Smoker |
| cg09860653 | 1 | 19970708 | Lower in Smoker |
| cg13384150 | 1 | 16939173 | Higher in Smoker |
| cg26885858 | 1 | 21766368 | Higher in Smoker |
| cg00349071 | 1 | 21786740 | Lower in Smoker |
| cg26081003 | 17 | 41323112 | Higher in Smoker |
| cg08393117 | 17 | 41327244 | Lower in Smoker |
| cg05368731 | 17 | 41323189 | Lower in Smoker |
| cg10938478 | 8 | 103035373 | Lower in Smoker |
| cg14355482 | 21 | 22373039 | Lower in Smoker |
| cg15976079 | 19 | 19323330 | Higher in Smoker |
| cg17767542 | 19 | 19322902 | Lower in Smoker |
| cg18755698 | 11 | 134046415 | Lower in Smoker |
| cg18159393 | 11 | 134094510 | Lower in Smoker |
| cg15910994 | 2 | 97001734 | Higher in Smoker |
| cg26625319 | 2 | 97001960 | Higher in Smoker |
| cg19524049 | 1 | 36023720 | Higher in Smoker |
| cg00589895 | 3 | 172429056 | Higher in Smoker |
| cg02802062 | 3 | 172428840 | Higher in Smoker |
| cg09624565 | 22 | 37256900 | Lower in Smoker |
| cg16717867 | 3 | 136601982 | Lower in Smoker |
| cg15793456 | 2 | 183888544 | Lower in Smoker |
| cg26606682 | 2 | 133868449 | Lower in Smoker |
| cg01290856 | 2 | 134324896 | Lower in Smoker |
| cg22491320 | 2 | 133998732 | Lower in Smoker |
| cg05012457 | 2 | 133672682 | Lower in Smoker |
| cg15354803 | 2 | 133934804 | Lower in Smoker |
| cg14405137 | 12 | 50219283 | Higher in Smoker |
| cg03323444 | 12 | 50188704 | Lower in Smoker |
| cg00010789 | 2 | 232321341 | Lower in Smoker |

| | | | |
|---|---|---|---|
| cg12131620 | 19 | 3188985 | Higher in Smoker |
| cg26842089 | 19 | 3185763 | Higher in Smoker |
| cg14849556 | 2 | 24991672 | Lower in Smoker |
| cg07020398 | 8 | 71314049 | Higher in Smoker |
| cg08325898 | 8 | 71096899 | Lower in Smoker |
| cg09560912 | 20 | 46130354 | Higher in Smoker |
| cg24856420 | 20 | 46130460 | Lower in Smoker |
| cg06298701 | 10 | 51566673 | Lower in Smoker |
| cg23359810 | 10 | 51572113 | Higher in Smoker |
| cg08125503 | 17 | 16119344 | Lower in Smoker |
| cg09825309 | 12 | 124990897 | Higher in Smoker |
| cg17387577 | 12 | 124864657 | Higher in Smoker |
| cg22700848 | 12 | 124990942 | Higher in Smoker |
| cg21052873 | 12 | 124933573 | Higher in Smoker |
| cg11018432 | 12 | 124332427 | Lower in Smoker |
| cg27103591 | 12 | 124309023 | Lower in Smoker |
| cg22813019 | 12 | 124331272 | Lower in Smoker |
| cg16350126 | 12 | 124993754 | Lower in Smoker |
| cg00528779 | 12 | 124926062 | Lower in Smoker |
| cg06217303 | 6 | 31560670 | Lower in Smoker |
| cg06557776 | 10 | 112679649 | Higher in Smoker |
| cg14018731 | 9 | 98784336 | Higher in Smoker |
| cg27434467 | 10 | 101686326 | Lower in Smoker |
| cg03938110 | 21 | 31120485 | Lower in Smoker |
| cg13299324 | 21 | 40145949 | Lower in Smoker |
| cg06595162 | 21 | 40141040 | Lower in Smoker |
| cg04912523 | 3 | 132441916 | Higher in Smoker |
| cg27561949 | 6 | 88411006 | Higher in Smoker |
| cg02366959 | 2 | 133012353 | Lower in Smoker |
| cg03876030 | 11 | 129372826 | Higher in Smoker |
| cg09732027 | 6 | 29984811 | Lower in Smoker |
| cg05819860 | 6 | 30027209 | Lower in Smoker |
| cg02776080 | 6 | 29999615 | Lower in Smoker |
| cg22966673 | 6 | 30011664 | Lower in Smoker |
| cg02424995 | 6 | 30015848 | Lower in Smoker |

| | | | |
|---|---|---|---|
| cg10575170 | X | 73513412 | Higher in Smoker |
| cg17674548 | X | 73507186 | Lower in Smoker |
| cg04892600 | 17 | 16357027 | Higher in Smoker |
| cg08270477 | 17 | 16342776 | Higher in Smoker |
| cg16659583 | 10 | 1209455 | Higher in Smoker |
| cg06891538 | 10 | 1205229 | Lower in Smoker |
| cg02158199 | 5 | 111495974 | Lower in Smoker |
| cg08635395 | 16 | 15747286 | Lower in Smoker |
| cg01512180 | 17 | 8339091 | Higher in Smoker |
| cg12173651 | 17 | 8338822 | Higher in Smoker |
| cg21912653 | 13 | 80055180 | Higher in Smoker |
| cg15762399 | 13 | 80109047 | Lower in Smoker |
| cg24137567 | 15 | 23930952 | Lower in Smoker |
| cg18942213 | 8 | 134309101 | Higher in Smoker |
| cg04808179 | 16 | 58529306 | Higher in Smoker |
| cg19836174 | 5 | 149921140 | Higher in Smoker |
| cg06677890 | 5 | 149887486 | Lower in Smoker |
| cg14204430 | 4 | 116035217 | Lower in Smoker |
| cg00607036 | X | 119005506 | Higher in Smoker |
| ch.2.4917873F | 2 | 240940206 | Higher in Smoker |
| cg18976852 | 2 | 240927122 | Lower in Smoker |
| cg05715003 | 7 | 10979913 | Higher in Smoker |
| cg15607664 | 12 | 57630422 | Higher in Smoker |
| cg19062108 | 12 | 57630834 | Higher in Smoker |
| cg09053611 | 7 | 123196675 | Higher in Smoker |
| cg22406012 | 12 | 4753217 | Higher in Smoker |
| cg13719771 | 12 | 4762206 | Lower in Smoker |
| cg12482260 | 6 | 97345915 | Higher in Smoker |
| cg23429981 | 6 | 97345948 | Lower in Smoker |
| cg20350165 | 7 | 140405191 | Lower in Smoker |
| cg16859555 | 3 | 120314641 | Higher in Smoker |
| cg03734035 | 10 | 102289529 | Higher in Smoker |
| cg25349900 | 10 | 102290114 | Lower in Smoker |
| cg03344043 | 4 | 140217675 | Lower in Smoker |
| cg05201673 | 11 | 47600596 | Higher in Smoker |

| | | | |
|---|---|---|---|
| cg04996251 | 5 | 52856497 | Higher in Smoker |
| cg06476337 | 5 | 52856530 | Higher in Smoker |
| cg07388493 | 1 | 39491459 | Higher in Smoker |
| cg11396951 | 1 | 39492095 | Higher in Smoker |
| cg06603851 | 5 | 1813772 | Lower in Smoker |
| cg15095922 | 5 | 1800542 | Lower in Smoker |
| cg11925103 | 19 | 1393208 | Lower in Smoker |
| cg06264592 | 19 | 1393156 | Lower in Smoker |
| cg05278822 | 19 | 1387755 | Lower in Smoker |
| cg21384827 | 11 | 67798041 | Higher in Smoker |
| cg17583008 | 11 | 67797931 | Higher in Smoker |
| cg16906595 | 11 | 67798128 | Higher in Smoker |
| cg06312776 | 11 | 67374151 | Higher in Smoker |
| cg06853331 | 18 | 9132487 | Lower in Smoker |
| cg15383847 | 21 | 44329750 | Lower in Smoker |
| cg17254273 | 2 | 152591967 | Lower in Smoker |
| cg12208353 | 2 | 152527013 | Lower in Smoker |
| cg11787785 | 10 | 21463243 | Higher in Smoker |
| cg12715741 | 10 | 21313531 | Lower in Smoker |
| cg20040743 | 8 | 91803792 | Higher in Smoker |
| cg00151250 | 8 | 91803412 | Higher in Smoker |
| cg07939567 | 16 | 84036179 | Lower in Smoker |
| cg06563686 | 12 | 8234806 | Lower in Smoker |
| cg03136512 | 1 | 16767024 | Higher in Smoker |
| cg07549630 | 12 | 97300822 | Higher in Smoker |
| cg09887667 | 15 | 56285261 | Higher in Smoker |
| cg12876333 | 18 | 55710995 | Higher in Smoker |
| cg13009302 | 18 | 55863675 | Lower in Smoker |
| cg19737468 | 14 | 24701538 | Higher in Smoker |
| cg24705551 | 8 | 24774647 | Lower in Smoker |
| cg17517900 | 1 | 72748607 | Higher in Smoker |
| cg20281583 | 4 | 178233531 | Lower in Smoker |
| cg07701716 | 4 | 170533879 | Higher in Smoker |
| cg26036067 | 1 | 211849175 | Higher in Smoker |
| cg05246775 | 13 | 52733382 | Lower in Smoker |

| | | | |
|---|---|---|---|
| cg13745957 | 13 | 52702845 | Higher in Smoker |
| cg05546034 | 13 | 52702856 | Higher in Smoker |
| cg15721359 | 13 | 52699305 | Lower in Smoker |
| cg13974765 | 9 | 127036024 | Lower in Smoker |
| cg13487666 | 9 | 127021157 | Lower in Smoker |
| cg14036069 | 9 | 127047671 | Lower in Smoker |
| cg03667871 | 1 | 198125222 | Lower in Smoker |
| cg12075586 | 12 | 45088477 | Lower in Smoker |
| cg02901139 | 1 | 212605929 | Higher in Smoker |
| cg20285128 | 1 | 156646746 | Higher in Smoker |
| cg08032665 | 1 | 156642838 | Lower in Smoker |
| cg05558578 | 10 | 5487785 | Lower in Smoker |
| cg23883696 | 18 | 70534298 | Higher in Smoker |
| cg15745385 | 6 | 31830364 | Higher in Smoker |
| cg14119437 | 6 | 31830721 | Higher in Smoker |
| cg23641315 | 6 | 31828373 | Lower in Smoker |
| cg03832040 | 6 | 31829292 | Lower in Smoker |
| cg00890041 | 6 | 31830570 | Lower in Smoker |
| cg21904654 | 6 | 31831890 | Lower in Smoker |
| cg24198840 | 2 | 233897561 | Lower in Smoker |
| cg20386580 | 10 | 105344807 | Higher in Smoker |
| cg26550162 | 10 | 105344798 | Higher in Smoker |
| cg18178432 | 20 | 44517288 | Lower in Smoker |
| cg25567448 | 2 | 97175065 | Lower in Smoker |
| cg02836529 | 2 | 182544413 | Higher in Smoker |
| cg20153196 | 17 | 37760359 | Higher in Smoker |
| cg00574530 | 5 | 134872064 | Higher in Smoker |
| cg04330449 | 5 | 134871166 | Higher in Smoker |
| cg11260904 | 5 | 134872029 | Higher in Smoker |
| cg13336665 | 5 | 134872610 | Higher in Smoker |
| cg24899138 | 5 | 134872639 | Higher in Smoker |
| cg10511618 | 4 | 113436232 | Higher in Smoker |
| cg23206325 | 1 | 78353422 | Lower in Smoker |
| cg24359358 | 1 | 78353425 | Lower in Smoker |
| cg06560836 | 17 | 29697553 | Higher in Smoker |

| | | | |
|---|---|---|---|
| cg02750234 | 17 | 29422717 | Higher in Smoker |
| cg15400766 | 15 | 21131137 | Lower in Smoker |
| cg14926439 | 22 | 29999402 | Higher in Smoker |
| cg08108155 | 22 | 29999444 | Lower in Smoker |
| cg22571530 | 1 | 204797929 | Higher in Smoker |
| cg02673901 | 1 | 204828056 | Lower in Smoker |
| cg24488344 | 18 | 77258837 | Lower in Smoker |
| cg26910047 | 18 | 77234438 | Lower in Smoker |
| cg06784563 | 18 | 77284509 | Lower in Smoker |
| cg15260951 | 18 | 77165150 | Lower in Smoker |
| cg18092363 | 18 | 77202678 | Lower in Smoker |
| cg10049070 | 16 | 68128205 | Lower in Smoker |
| cg08279757 | 12 | 54694795 | Higher in Smoker |
| cg20732027 | 12 | 54694878 | Lower in Smoker |
| cg10369888 | 17 | 46136081 | Lower in Smoker |
| cg10536999 | 7 | 26193109 | Higher in Smoker |
| cg22803724 | 1 | 61542917 | Higher in Smoker |
| cg21414842 | 1 | 61545075 | Lower in Smoker |
| cg19726852 | 1 | 61715231 | Lower in Smoker |
| cg04535176 | 19 | 3359655 | Higher in Smoker |
| cg04251208 | 19 | 3458194 | Lower in Smoker |
| cg18385371 | 19 | 3432415 | Lower in Smoker |
| cg13465946 | 19 | 13208349 | Higher in Smoker |
| cg03675258 | 19 | 13124691 | Higher in Smoker |
| cg14925616 | 19 | 13125726 | Lower in Smoker |
| cg22966302 | 19 | 13196617 | Lower in Smoker |
| cg23256466 | 10 | 104159199 | Lower in Smoker |
| cg01177642 | 10 | 104154212 | Lower in Smoker |
| cg21996586 | 6 | 31515136 | Higher in Smoker |
| cg23249667 | 6 | 31515309 | Higher in Smoker |
| cg16517196 | 6 | 41040614 | Higher in Smoker |
| cg27013360 | 6 | 41040518 | Lower in Smoker |
| cg05229723 | 12 | 104526470 | Lower in Smoker |
| cg20539430 | 2 | 233762570 | Lower in Smoker |
| cg18446159 | 17 | 47574285 | Higher in Smoker |

| | | | |
|---|---|---|---|
| cg13888838 | 2 | 220025712 | Higher in Smoker |
| cg02537221 | 2 | 220025448 | Higher in Smoker |
| cg24106636 | 1 | 116381475 | Higher in Smoker |
| cg17900495 | 1 | 116382363 | Higher in Smoker |
| cg14640736 | 13 | 39612797 | Higher in Smoker |
| cg24546426 | 5 | 177581771 | Lower in Smoker |
| cg18239702 | X | 17393016 | Higher in Smoker |
| cg00111239 | X | 71238329 | Lower in Smoker |
| cg24569746 | X | 71352089 | Higher in Smoker |
| cg02487422 | 3 | 49467188 | Higher in Smoker |
| cg23028178 | 1 | 236229267 | Lower in Smoker |
| cg11706717 | 1 | 236203668 | Lower in Smoker |
| cg18905461 | 14 | 52534596 | Higher in Smoker |
| cg12812165 | 14 | 51296728 | Higher in Smoker |
| cg25134134 | 14 | 51271666 | Lower in Smoker |
| cg26945413 | 9 | 95896008 | Higher in Smoker |
| cg03854262 | 9 | 95896872 | Lower in Smoker |
| cg26549831 | 12 | 773616 | Lower in Smoker |
| cg15001687 | 20 | 25566336 | Lower in Smoker |
| cg27332399 | 15 | 23044980 | Lower in Smoker |
| cg26959990 | 15 | 23034449 | Higher in Smoker |
| cg25351036 | 4 | 48018582 | Higher in Smoker |
| cg06034202 | 5 | 36985656 | Lower in Smoker |
| cg02303067 | 5 | 36882196 | Lower in Smoker |
| cg27649295 | 6 | 124125227 | Higher in Smoker |
| cg26859878 | 8 | 63307589 | Lower in Smoker |
| cg12300018 | 8 | 63903574 | Lower in Smoker |
| cg23093450 | 17 | 40172452 | Higher in Smoker |
| cg03711854 | 19 | 45663488 | Higher in Smoker |
| cg13723766 | X | 113739835 | Higher in Smoker |
| cg08266027 | X | 113736960 | Lower in Smoker |
| cg19265364 | 3 | 42672763 | Lower in Smoker |
| cg13600489 | 14 | 36988217 | Higher in Smoker |
| cg02090569 | 14 | 36989583 | Higher in Smoker |
| cg06178563 | 20 | 21494712 | Higher in Smoker |

| | | | |
|---|---|---|---|
| cg07070391 | 20 | 21494748 | Higher in Smoker |
| cg23408114 | 20 | 21378278 | Lower in Smoker |
| cg21165027 | 5 | 172663784 | Lower in Smoker |
| cg13944084 | 4 | 85419350 | Higher in Smoker |
| cg10539507 | 4 | 85420782 | Higher in Smoker |
| cg00709110 | 4 | 85419151 | Higher in Smoker |
| cg11114873 | 4 | 85419975 | Lower in Smoker |
| cg04436469 | 10 | 134598496 | Higher in Smoker |
| cg25883020 | 8 | 41504993 | Higher in Smoker |
| cg22282038 | 8 | 41505495 | Lower in Smoker |
| cg16950726 | 17 | 7317514 | Lower in Smoker |
| cg04021548 | Y | 16634027 | Lower in Smoker |
| cg09804407 | Y | 16733251 | Lower in Smoker |
| cg13666659 | 17 | 26487538 | Lower in Smoker |
| cg01059818 | 17 | 26370690 | Lower in Smoker |
| cg22171142 | 16 | 3627546 | Higher in Smoker |
| cg03146649 | 16 | 57094643 | Higher in Smoker |
| cg08553449 | 16 | 57023715 | Higher in Smoker |
| cg06754565 | 16 | 57023317 | Higher in Smoker |
| cg02493440 | 16 | 57023485 | Higher in Smoker |
| cg19972788 | 17 | 5405118 | Lower in Smoker |
| cg20311730 | 11 | 7985183 | Lower in Smoker |
| cg04695373 | 19 | 54327995 | Higher in Smoker |
| cg02347487 | 11 | 7059103 | Lower in Smoker |
| cg24639969 | 1 | 247580565 | Higher in Smoker |
| cg18126557 | 1 | 247611842 | Lower in Smoker |
| cg06328831 | 11 | 278912 | Higher in Smoker |
| cg25022915 | 17 | 49243257 | Lower in Smoker |
| cg26508844 | 17 | 49244169 | Higher in Smoker |
| cg09317772 | 17 | 49242784 | Lower in Smoker |
| cg16799998 | 3 | 48343164 | Higher in Smoker |
| cg24356977 | 3 | 48339943 | Lower in Smoker |
| cg02481619 | 1 | 10003298 | Higher in Smoker |
| cg06853505 | 1 | 10003752 | Higher in Smoker |
| cg19422030 | 4 | 56501718 | Higher in Smoker |

| | | | |
|---|---|---|---|
| cg00886554 | 4 | 56502598 | Higher in Smoker |
| cg01649597 | 2 | 232395061 | Higher in Smoker |
| cg03164561 | 2 | 232396386 | Lower in Smoker |
| cg24430754 | 2 | 232396241 | Lower in Smoker |
| cg09489281 | 5 | 43604149 | Higher in Smoker |
| cg09617747 | 16 | 69788565 | Higher in Smoker |
| cg11564268 | 16 | 69789107 | Higher in Smoker |
| cg21830050 | 1 | 891193 | Higher in Smoker |
| cg20322444 | 1 | 886441 | Lower in Smoker |
| cg04598251 | 12 | 132628930 | Higher in Smoker |
| cg02486161 | 16 | 50766599 | Lower in Smoker |
| cg10850838 | 10 | 72201600 | Higher in Smoker |
| cg15002214 | 17 | 54670370 | Higher in Smoker |
| cg10551356 | 2 | 10774704 | Lower in Smoker |
| cg19533957 | 17 | 65713589 | Higher in Smoker |
| cg02896073 | 18 | 31799784 | Lower in Smoker |
| cg10530492 | 6 | 13615477 | Higher in Smoker |
| cg13749703 | 6 | 13615411 | Higher in Smoker |
| cg20373634 | 10 | 103911536 | Lower in Smoker |
| cg17827650 | 7 | 156741514 | Higher in Smoker |
| cg07626700 | 7 | 156741534 | Higher in Smoker |
| cg02413092 | 7 | 156741538 | Higher in Smoker |
| cg17324160 | 7 | 156757919 | Lower in Smoker |
| cg02528112 | 7 | 156754734 | Lower in Smoker |
| cg04271677 | 7 | 156754681 | Lower in Smoker |
| cg00789394 | 16 | 14927564 | Higher in Smoker |
| cg16115249 | X | 70520305 | Lower in Smoker |
| cg22686731 | 15 | 34635452 | Higher in Smoker |
| cg12390237 | 15 | 34634263 | Higher in Smoker |
| cg02435498 | 4 | 2957353 | Lower in Smoker |
| cg24524044 | 4 | 2939903 | Lower in Smoker |
| cg01252586 | 5 | 175815479 | Higher in Smoker |
| cg01629329 | 20 | 2633258 | Higher in Smoker |
| cg05205351 | 20 | 2634775 | Lower in Smoker |
| cg21028182 | 20 | 2635586 | Lower in Smoker |

| | | | |
|---|---|---|---|
| ch.2.4034195R | 2 | 203140804 | Higher in Smoker |
| cg19681610 | 1 | 162148501 | Lower in Smoker |
| cg09008080 | 1 | 162041072 | Lower in Smoker |
| cg07150830 | 17 | 26127542 | Lower in Smoker |
| cg25025646 | 7 | 150711449 | Lower in Smoker |
| cg21292909 | 19 | 50059937 | Lower in Smoker |
| cg03665287 | 19 | 15311886 | Higher in Smoker |
| cg22309798 | 19 | 15284353 | Lower in Smoker |
| cg01978236 | 6 | 32191479 | Lower in Smoker |
| cg07516450 | 6 | 32167900 | Lower in Smoker |
| cg12106346 | 6 | 32178991 | Lower in Smoker |
| cg15318627 | 6 | 32181764 | Lower in Smoker |
| cg18244508 | 6 | 32172371 | Lower in Smoker |
| cg25995397 | 2 | 73432912 | Lower in Smoker |
| cg02884775 | 2 | 73429333 | Lower in Smoker |
| cg15241582 | 11 | 89323227 | Lower in Smoker |
| cg13709882 | 9 | 140327546 | Lower in Smoker |
| cg27297033 | 16 | 2031217 | Lower in Smoker |
| cg16868994 | 19 | 47523585 | Higher in Smoker |
| cg20625074 | 19 | 47545905 | Lower in Smoker |
| cg12737833 | 2 | 101500543 | Lower in Smoker |
| cg04895360 | 14 | 34150408 | Lower in Smoker |
| cg23605547 | 14 | 33408460 | Higher in Smoker |
| cg18755296 | 8 | 53852446 | Higher in Smoker |
| cg21001487 | 8 | 53853112 | Higher in Smoker |
| cg07778080 | 18 | 21166698 | Higher in Smoker |
| cg19385725 | 18 | 21166173 | Higher in Smoker |
| cg05076775 | 14 | 74960176 | Higher in Smoker |
| cg12611723 | 9 | 139940867 | Higher in Smoker |
| cg10073706 | 20 | 57268419 | Higher in Smoker |
| cg06782849 | 3 | 132440859 | Higher in Smoker |
| cg21470600 | 1 | 6040824 | Higher in Smoker |
| cg00385956 | 1 | 5948600 | Lower in Smoker |
| cg15503971 | 1 | 6037314 | Lower in Smoker |
| cg09231416 | 1 | 5940136 | Lower in Smoker |

| | | | |
|---|---|---|---|
| cg15596789 | 1 | 5955929 | Lower in Smoker |
| cg23968579 | 1 | 5975890 | Lower in Smoker |
| cg18117393 | 1 | 182761262 | Lower in Smoker |
| cg08039322 | 17 | 79604097 | Higher in Smoker |
| cg16813552 | 10 | 103544649 | Lower in Smoker |
| cg06193043 | 1 | 11908199 | Higher in Smoker |
| cg07935340 | 2 | 232791964 | Lower in Smoker |
| cg14178748 | 1 | 153652247 | Higher in Smoker |
| cg05511392 | 1 | 153651938 | Higher in Smoker |
| cg12604435 | 1 | 153653559 | Lower in Smoker |
| cg17886303 | 1 | 153656052 | Lower in Smoker |
| cg10832005 | 5 | 32710658 | Higher in Smoker |
| cg06094707 | 17 | 78445867 | Higher in Smoker |
| cg02368096 | 7 | 98248993 | Higher in Smoker |
| cg15750986 | 7 | 98249103 | Lower in Smoker |
| cg11398081 | 7 | 25268513 | Lower in Smoker |
| cg25660890 | 16 | 2069394 | Lower in Smoker |
| cg18119803 | 7 | 24330680 | Lower in Smoker |
| cg20271517 | 4 | 156129862 | Higher in Smoker |
| cg01002253 | 4 | 164264914 | Higher in Smoker |
| cg20618622 | 4 | 164265004 | Higher in Smoker |
| cg13969273 | 16 | 69760564 | Higher in Smoker |
| cg09516362 | 16 | 69760459 | Higher in Smoker |
| cg20807872 | 6 | 2999964 | Higher in Smoker |
| cg00040455 | X | 30326676 | Higher in Smoker |
| cg01059731 | 17 | 38255663 | Higher in Smoker |
| cg22640452 | 17 | 38256967 | Higher in Smoker |
| cg06237717 | 12 | 95467511 | Higher in Smoker |
| cg11876979 | 3 | 14988829 | Higher in Smoker |
| ch.3.344014F | 3 | 15074400 | Higher in Smoker |
| cg08124330 | 19 | 19314918 | Higher in Smoker |
| cg17386213 | 6 | 108488335 | Higher in Smoker |
| cg06433023 | 6 | 108488544 | Higher in Smoker |
| cg23676151 | 6 | 108491372 | Higher in Smoker |
| cg00017003 | 6 | 108490371 | Lower in Smoker |

| | | | |
|---|---|---|---|
| cg25449484 | 5 | 92929372 | Higher in Smoker |
| cg24528447 | 5 | 92918517 | Higher in Smoker |
| cg14205663 | 15 | 96872827 | Higher in Smoker |
| cg10847032 | 5 | 142784522 | Higher in Smoker |
| cg18484679 | 5 | 142740314 | Lower in Smoker |
| cg13373360 | 4 | 149364681 | Higher in Smoker |
| cg23329208 | 4 | 149360981 | Lower in Smoker |
| cg03339537 | 2 | 157184816 | Higher in Smoker |
| cg20945253 | 2 | 157189510 | Higher in Smoker |
| cg07646377 | 2 | 157189969 | Higher in Smoker |
| cg15699971 | 2 | 157189241 | Higher in Smoker |
| cg13639936 | 9 | 102586628 | Higher in Smoker |
| cg01786973 | 9 | 127249749 | Higher in Smoker |
| cg13476077 | 1 | 200009373 | Higher in Smoker |
| cg21625944 | 1 | 200113062 | Lower in Smoker |
| cg13539372 | 9 | 127353894 | Lower in Smoker |
| cg14171636 | 9 | 127361263 | Lower in Smoker |
| cg24884887 | 1 | 115247411 | Higher in Smoker |
| cg09041916 | 10 | 64892889 | Higher in Smoker |
| cg10781704 | 10 | 64905996 | Lower in Smoker |
| cg08242000 | 6 | 144922888 | Higher in Smoker |
| cg15919396 | 7 | 108097187 | Higher in Smoker |
| cg06269204 | 7 | 107885906 | Lower in Smoker |
| cg16073236 | 7 | 107789943 | Lower in Smoker |
| cg00280235 | 7 | 107797076 | Lower in Smoker |
| cg21819024 | 1 | 52344978 | Higher in Smoker |
| cg06342283 | 1 | 52344726 | Higher in Smoker |
| cg01523285 | 1 | 52301876 | Lower in Smoker |
| cg19678561 | 7 | 129252859 | Higher in Smoker |
| cg19478057 | 7 | 129251173 | Higher in Smoker |
| cg03896273 | 7 | 129269304 | Higher in Smoker |
| cg08122307 | 6 | 32311756 | Lower in Smoker |
| cg14315805 | 6 | 31498947 | Lower in Smoker |
| cg03349819 | 6 | 32404691 | Higher in Smoker |
| cg10302781 | 10 | 83801048 | Lower in Smoker |

| | | | |
|---|---|---|---|
| cg15339688 | 10 | 84002713 | Lower in Smoker |
| cg18938560 | 10 | 83636072 | Lower in Smoker |
| cg04817908 | 11 | 124608371 | Lower in Smoker |
| cg00712106 | 21 | 16340625 | Lower in Smoker |
| cg00945547 | 21 | 16337172 | Lower in Smoker |
| cg03666741 | 11 | 9025298 | Higher in Smoker |
| cg02864070 | 11 | 9021859 | Lower in Smoker |
| cg08252855 | 14 | 24550926 | Higher in Smoker |
| cg04778192 | 6 | 30658551 | Higher in Smoker |
| cg13494704 | 6 | 30653635 | Lower in Smoker |
| ch.10.844982F | 10 | 33469591 | Higher in Smoker |
| cg14157435 | 2 | 206628692 | Lower in Smoker |
| cg19795793 | 2 | 206551844 | Higher in Smoker |
| cg04471779 | 2 | 206593298 | Higher in Smoker |
| cg09911521 | 19 | 5828301 | Higher in Smoker |
| cg13361749 | 19 | 5824196 | Lower in Smoker |
| cg10917619 | 2 | 51255627 | Lower in Smoker |
| cg19395706 | 11 | 64412079 | Lower in Smoker |
| cg23907108 | 11 | 64405993 | Lower in Smoker |
| cg00685573 | 14 | 79742823 | Lower in Smoker |
| cg16443633 | 14 | 79529179 | Lower in Smoker |
| cg21113554 | 14 | 79080416 | Lower in Smoker |
| cg15572745 | 14 | 78870232 | Lower in Smoker |
| cg19753609 | 14 | 80324276 | Lower in Smoker |
| cg07177395 | 14 | 79963686 | Lower in Smoker |
| cg08881067 | 5 | 74062846 | Higher in Smoker |
| cg19027636 | 5 | 176558658 | Lower in Smoker |
| cg03829491 | X | 152002367 | Lower in Smoker |
| cg20242129 | 17 | 44785029 | Lower in Smoker |
| cg01244043 | 20 | 1448437 | Higher in Smoker |
| cg05054149 | 20 | 1448577 | Higher in Smoker |
| ch.1.4146056R | 1 | 212905998 | Higher in Smoker |
| cg03349118 | 8 | 59572480 | Higher in Smoker |
| cg06388418 | 16 | 27237190 | Higher in Smoker |
| cg06364293 | 16 | 27270361 | Lower in Smoker |

| | | | |
|---|---|---|---|
| cg10453541 | 8 | 126353972 | Lower in Smoker |
| cg20739904 | 5 | 6629638 | Lower in Smoker |
| cg01541629 | 5 | 6633111 | Higher in Smoker |
| cg23242142 | 5 | 6633531 | Lower in Smoker |
| cg26301639 | 3 | 93781795 | Higher in Smoker |
| cg15305343 | 1 | 46806357 | Lower in Smoker |
| cg27330627 | 7 | 72722760 | Higher in Smoker |
| cg01088455 | 7 | 72723873 | Lower in Smoker |
| cg15779702 | 7 | 72722304 | Lower in Smoker |
| cg07617147 | 10 | 18940625 | Higher in Smoker |
| cg04840761 | 10 | 18940291 | Higher in Smoker |
| cg19847638 | 17 | 73128079 | Higher in Smoker |
| cg24159547 | 17 | 73128072 | Higher in Smoker |
| cg11409350 | 17 | 73126499 | Lower in Smoker |
| cg20946056 | 7 | 33102435 | Higher in Smoker |
| cg05065372 | 7 | 33102794 | Higher in Smoker |
| cg06734816 | 6 | 116422381 | Higher in Smoker |
| cg25495311 | 6 | 116454307 | Lower in Smoker |
| cg16288099 | 6 | 116441056 | Lower in Smoker |
| cg08346232 | 12 | 104235326 | Higher in Smoker |
| cg14592468 | 12 | 5603180 | Lower in Smoker |
| cg01377911 | 19 | 49568036 | Lower in Smoker |
| cg03393889 | 16 | 2094700 | Higher in Smoker |
| cg04119529 | 16 | 2094667 | Higher in Smoker |
| cg17510003 | 11 | 131737914 | Higher in Smoker |
| cg26367736 | 11 | 131758433 | Higher in Smoker |
| cg06962970 | 11 | 131761763 | Lower in Smoker |
| cg08566882 | 11 | 131348843 | Lower in Smoker |
| cg26808144 | 11 | 131779228 | Lower in Smoker |
| cg24953078 | 11 | 131878924 | Lower in Smoker |
| cg13148126 | 17 | 3924759 | Higher in Smoker |
| cg17280134 | 17 | 3960047 | Lower in Smoker |
| cg22349229 | 12 | 96115707 | Lower in Smoker |
| cg10964388 | 12 | 96069024 | Lower in Smoker |
| cg03045699 | 1 | 107737854 | Lower in Smoker |

| | | | |
|---|---|---|---|
| cg25572459 | 12 | 106501248 | Lower in Smoker |
| cg08712572 | 1 | 205291974 | Lower in Smoker |
| cg18873037 | 7 | 151038660 | Higher in Smoker |
| cg03287527 | 16 | 10843654 | Lower in Smoker |
| cg04704414 | 16 | 1836662 | Lower in Smoker |
| cg13165928 | 14 | 32180736 | Lower in Smoker |
| cg09821112 | 1 | 205719462 | Higher in Smoker |
| cg16417937 | 1 | 27248012 | Higher in Smoker |
| cg01204535 | 5 | 162888518 | Higher in Smoker |
| cg01632311 | 7 | 2281785 | Higher in Smoker |
| cg11071591 | 13 | 48611662 | Higher in Smoker |
| cg01596986 | 13 | 48611463 | Higher in Smoker |
| cg00472748 | 3 | 131104907 | Lower in Smoker |
| cg17207815 | 8 | 21966362 | Higher in Smoker |
| cg15248132 | 19 | 33182730 | Higher in Smoker |
| cg22928329 | 19 | 33183273 | Higher in Smoker |
| cg06291266 | 16 | 56481617 | Lower in Smoker |
| cg01553981 | 11 | 63993358 | Higher in Smoker |
| cg26624726 | 12 | 93772485 | Lower in Smoker |
| cg26456506 | 4 | 88344004 | Higher in Smoker |
| cg26991812 | 17 | 27621123 | Higher in Smoker |
| cg14701554 | 11 | 71751833 | Higher in Smoker |
| cg27269899 | 11 | 71752230 | Higher in Smoker |
| cg26632909 | 11 | 71752722 | Higher in Smoker |
| cg04462378 | 11 | 71749760 | Lower in Smoker |
| cg08147389 | 14 | 73756251 | Lower in Smoker |
| cg13285447 | 19 | 41196734 | Higher in Smoker |
| cg08450982 | 19 | 41195910 | Lower in Smoker |
| cg00036115 | 12 | 69080592 | Higher in Smoker |
| cg16918263 | 1 | 229644277 | Higher in Smoker |
| cg05187833 | 6 | 17706939 | Lower in Smoker |
| cg04534122 | 5 | 37371047 | Higher in Smoker |
| cg14105018 | 9 | 131711353 | Lower in Smoker |
| cg26005146 | 7 | 135242312 | Higher in Smoker |
| cg07383972 | 7 | 135242951 | Higher in Smoker |

| | | | |
|---|---|---|---|
| cg18357291 | 3 | 13461086 | Higher in Smoker |
| cg06143615 | 3 | 13462903 | Lower in Smoker |
| cg08085165 | 12 | 102511411 | Lower in Smoker |
| cg24737639 | 12 | 102513781 | Higher in Smoker |
| cg04630823 | 22 | 45575276 | Lower in Smoker |
| cg04315771 | 19 | 50433949 | Lower in Smoker |
| cg06477444 | 19 | 50411521 | Lower in Smoker |
| cg07203573 | 17 | 73201765 | Higher in Smoker |
| cg19065650 | 16 | 56763929 | Higher in Smoker |
| cg06576192 | 16 | 56782670 | Lower in Smoker |
| cg19941686 | 7 | 23221979 | Higher in Smoker |
| ch.15.430474R | 15 | 41664933 | Higher in Smoker |
| cg08782897 | 15 | 41624872 | Higher in Smoker |
| cg12740087 | 1 | 224445738 | Lower in Smoker |
| cg26527655 | 19 | 16918606 | Lower in Smoker |
| cg15581842 | 11 | 62572759 | Higher in Smoker |
| cg05865567 | 11 | 62572907 | Higher in Smoker |
| cg00950385 | 17 | 745746 | Lower in Smoker |
| cg24780883 | 19 | 17566941 | Higher in Smoker |
| cg26170604 | 7 | 8482614 | Higher in Smoker |
| cg03099208 | 7 | 8474544 | Higher in Smoker |
| cg01354961 | 7 | 8473462 | Higher in Smoker |
| cg00852549 | 7 | 8473457 | Higher in Smoker |
| cg21586412 | 17 | 47653212 | Higher in Smoker |
| cg27125631 | 17 | 47654653 | Lower in Smoker |
| cg16451431 | 12 | 57616956 | Higher in Smoker |
| cg08711175 | 12 | 57614182 | Higher in Smoker |
| cg22957228 | 12 | 57610482 | Higher in Smoker |
| cg10773670 | 20 | 23331356 | Lower in Smoker |
| cg08111832 | 14 | 24868082 | Higher in Smoker |
| cg13948230 | 10 | 126106957 | Lower in Smoker |
| cg07274998 | 10 | 126107781 | Lower in Smoker |
| cg18152871 | 10 | 126107471 | Higher in Smoker |
| cg13437554 | 19 | 2272716 | Lower in Smoker |
| cg05379882 | 1 | 151735684 | Higher in Smoker |

| | | | |
|---|---|---|---|
| cg12582028 | 1 | 151736699 | Lower in Smoker |
| cg12095968 | 1 | 151739679 | Lower in Smoker |
| cg04902826 | 10 | 105677453 | Higher in Smoker |
| cg06293931 | 10 | 105674300 | Lower in Smoker |
| cg20011116 | 2 | 192542603 | Higher in Smoker |
| cg26761226 | 12 | 56617996 | Higher in Smoker |
| cg08262088 | 1 | 228465491 | Higher in Smoker |
| cg21683105 | 1 | 228494821 | Lower in Smoker |
| cg07382039 | 1 | 228494830 | Lower in Smoker |
| cg26575914 | 1 | 228397977 | Lower in Smoker |
| cg00452266 | 2 | 220431399 | Lower in Smoker |
| cg04414095 | 2 | 220425951 | Lower in Smoker |
| cg23399286 | 8 | 133072873 | Lower in Smoker |
| cg10762626 | 15 | 28344715 | Higher in Smoker |
| cg15885628 | 15 | 28344718 | Higher in Smoker |
| cg20698924 | 15 | 28344730 | Higher in Smoker |
| cg14494623 | 15 | 28340459 | Higher in Smoker |
| cg14546500 | 15 | 28248727 | Lower in Smoker |
| cg15194100 | 15 | 28014040 | Lower in Smoker |
| cg25247615 | 19 | 17336996 | Higher in Smoker |
| cg04422289 | 4 | 48833305 | Higher in Smoker |
| cg23545105 | 4 | 48908833 | Higher in Smoker |
| cg23762633 | 2 | 10589242 | Lower in Smoker |
| cg07168392 | 1 | 86861658 | Higher in Smoker |
| cg19495614 | 15 | 76016056 | Lower in Smoker |
| cg15380508 | 5 | 166874870 | Higher in Smoker |
| cg19913582 | 5 | 167567540 | Higher in Smoker |
| cg19234412 | 11 | 78638670 | Lower in Smoker |
| cg27643190 | 11 | 79140447 | Lower in Smoker |
| cg21094613 | 11 | 78900687 | Lower in Smoker |
| cg18224993 | 11 | 78521705 | Lower in Smoker |
| cg23361764 | 11 | 78542948 | Lower in Smoker |
| cg02593517 | 16 | 56486336 | Lower in Smoker |
| cg03070473 | 20 | 61436002 | Higher in Smoker |
| cg10167233 | 6 | 72004311 | Lower in Smoker |

| | | | |
|---|---|---|---|
| cg20124547 | 2 | 175062978 | Lower in Smoker |
| cg05392169 | 9 | 138011814 | Lower in Smoker |
| cg14549951 | 9 | 137998970 | Lower in Smoker |
| cg00948900 | 9 | 137997205 | Lower in Smoker |
| cg13914893 | 9 | 137980958 | Higher in Smoker |
| cg11587925 | 19 | 10046956 | Higher in Smoker |
| cg06159220 | 19 | 10025176 | Higher in Smoker |
| cg21809447 | 1 | 102462682 | Higher in Smoker |
| cg19130550 | 1 | 161994277 | Higher in Smoker |
| cg20172280 | 1 | 161993542 | Higher in Smoker |
| cg22855923 | 1 | 114521157 | Lower in Smoker |
| cg27280904 | 21 | 34443601 | Higher in Smoker |
| cg13560452 | 6 | 137813584 | Higher in Smoker |
| cg13877670 | 15 | 53083532 | Higher in Smoker |
| cg00473031 | 19 | 1752325 | Higher in Smoker |
| cg02677946 | 11 | 132864357 | Higher in Smoker |
| cg23522601 | 11 | 132934377 | Higher in Smoker |
| cg16483737 | 11 | 132934224 | Higher in Smoker |
| cg17242596 | 11 | 132527296 | Lower in Smoker |
| cg12584551 | X | 67653401 | Lower in Smoker |
| cg23839682 | X | 67653496 | Lower in Smoker |
| cg01042334 | 8 | 145114994 | Lower in Smoker |
| cg18276235 | 6 | 47749839 | Lower in Smoker |
| cg20336122 | 8 | 54165371 | Lower in Smoker |
| cg05027549 | 8 | 54159889 | Lower in Smoker |
| cg17454746 | 20 | 62716485 | Lower in Smoker |
| cg10143581 | 6 | 154359967 | Lower in Smoker |
| cg16907766 | 10 | 13143470 | Lower in Smoker |
| cg04456892 | 11 | 6898245 | Lower in Smoker |
| cg08276752 | 11 | 7951221 | Lower in Smoker |
| cg12142869 | 12 | 48597881 | Lower in Smoker |
| cg22724854 | 11 | 55737072 | Lower in Smoker |
| cg18099058 | 11 | 55737045 | Lower in Smoker |
| cg07817928 | 6 | 29407979 | Lower in Smoker |
| cg25076881 | 1 | 159409836 | Lower in Smoker |

| | | | |
|---|---|---|---|
| cg01733284 | 1 | 158391119 | Lower in Smoker |
| cg23900936 | 11 | 57996699 | Lower in Smoker |
| cg19074437 | 6 | 29396270 | Lower in Smoker |
| cg25786333 | 6 | 29364799 | Lower in Smoker |
| cg17807683 | 17 | 2996801 | Lower in Smoker |
| cg14043602 | 17 | 3301340 | Lower in Smoker |
| cg14386668 | 17 | 3337334 | Lower in Smoker |
| cg25206451 | 7 | 143805315 | Lower in Smoker |
| cg26690138 | 9 | 35958306 | Lower in Smoker |
| cg13053563 | 1 | 248569331 | Lower in Smoker |
| cg22931151 | 5 | 180581761 | Lower in Smoker |
| cg13561817 | 17 | 3213102 | Higher in Smoker |
| cg15141401 | 11 | 55371077 | Higher in Smoker |
| cg03851956 | 11 | 48346680 | Lower in Smoker |
| cg21577365 | 15 | 22367858 | Lower in Smoker |
| cg22827986 | 11 | 48284249 | Lower in Smoker |
| cg00467296 | 11 | 4928760 | Lower in Smoker |
| cg02408311 | 11 | 5364676 | Lower in Smoker |
| cg07568203 | 11 | 5365377 | Lower in Smoker |
| cg20201128 | 11 | 4716867 | Lower in Smoker |
| cg18352935 | 11 | 4843021 | Lower in Smoker |
| cg12687069 | 11 | 5474001 | Lower in Smoker |
| cg25310592 | 11 | 5174413 | Lower in Smoker |
| cg12593634 | 11 | 5143555 | Lower in Smoker |
| cg25100880 | 11 | 5878019 | Lower in Smoker |
| cg05117324 | 11 | 4469604 | Lower in Smoker |
| cg05703009 | 11 | 5841698 | Lower in Smoker |
| cg13816428 | 14 | 21625173 | Lower in Smoker |
| cg25384000 | 11 | 55605161 | Lower in Smoker |
| cg23438598 | 11 | 55587764 | Lower in Smoker |
| cg03274368 | 11 | 55586293 | Lower in Smoker |
| cg05957546 | 11 | 7819874 | Lower in Smoker |
| cg03774040 | 2 | 240985345 | Lower in Smoker |
| cg01094310 | 12 | 55714602 | Lower in Smoker |
| cg03002968 | 1 | 158670397 | Lower in Smoker |

| | | | |
|---|---|---|---|
| cg20410409 | 1 | 158724057 | Lower in Smoker |
| cg27104671 | 12 | 48919471 | Lower in Smoker |
| cg01881778 | 12 | 48919444 | Lower in Smoker |
| cg09323906 | 7 | 141617279 | Lower in Smoker |
| cg00385194 | 11 | 57957102 | Lower in Smoker |
| cg26440361 | 12 | 122064389 | Higher in Smoker |
| cg02827278 | 12 | 122063043 | Lower in Smoker |
| cg21131149 | 11 | 69490108 | Higher in Smoker |
| cg04407474 | 1 | 52869986 | Higher in Smoker |
| cg16173229 | 6 | 98302428 | Lower in Smoker |
| cg18708365 | 7 | 103848079 | Higher in Smoker |
| cg04322298 | 2 | 190635899 | Lower in Smoker |
| cg03260790 | 12 | 56211718 | Higher in Smoker |
| cg19511844 | 17 | 38084119 | Higher in Smoker |
| cg06208615 | 12 | 58115115 | Lower in Smoker |
| cg18357645 | 12 | 58087776 | Higher in Smoker |
| cg20782215 | 11 | 59342127 | Lower in Smoker |
| cg08170140 | 22 | 31090747 | Higher in Smoker |
| cg13234088 | 3 | 125311137 | Lower in Smoker |
| cg00027037 | 18 | 21977708 | Higher in Smoker |
| cg23878101 | 20 | 60813426 | Higher in Smoker |
| cg12327130 | 20 | 60813777 | Higher in Smoker |
| cg06683288 | 20 | 60813424 | Lower in Smoker |
| cg09396895 | 7 | 25021067 | Higher in Smoker |
| cg13494951 | 7 | 24981816 | Lower in Smoker |
| cg18897335 | 11 | 3187790 | Lower in Smoker |
| cg24129458 | 12 | 76953543 | Higher in Smoker |
| cg25035360 | 1 | 36886443 | Higher in Smoker |
| cg12809031 | 1 | 36915704 | Lower in Smoker |
| cg03178320 | 2 | 190627986 | Higher in Smoker |
| cg09082480 | 16 | 83997636 | Lower in Smoker |
| cg06098963 | 16 | 83995163 | Lower in Smoker |
| cg21336181 | 8 | 90938815 | Lower in Smoker |
| cg17226575 | 8 | 90914282 | Higher in Smoker |
| cg10467217 | 22 | 30662874 | Lower in Smoker |

| | | | |
|---|---|---|---|
| cg04478991 | 3 | 195943198 | Lower in Smoker |
| cg03296935 | 3 | 195946851 | Lower in Smoker |
| cg13580008 | 15 | 65341868 | Higher in Smoker |
| cg01797652 | 16 | 21740820 | Lower in Smoker |
| cg05531689 | 2 | 26729139 | Lower in Smoker |
| cg14882700 | 4 | 4228571 | Higher in Smoker |
| cg01737415 | 17 | 72919525 | Higher in Smoker |
| cg12280050 | 17 | 72919355 | Lower in Smoker |
| cg06722121 | 17 | 72934409 | Lower in Smoker |
| cg19697911 | 2 | 241080057 | Lower in Smoker |
| cg04117688 | 11 | 63764217 | Lower in Smoker |
| cg20778582 | 11 | 63753376 | Higher in Smoker |
| cg16136338 | 1 | 20208717 | Higher in Smoker |
| cg11719836 | 1 | 20209026 | Higher in Smoker |
| cg03120789 | 1 | 20208808 | Higher in Smoker |
| cg00786939 | 1 | 20211659 | Lower in Smoker |
| cg02423323 | 4 | 146100633 | Higher in Smoker |
| cg18888595 | 8 | 92082609 | Higher in Smoker |
| cg03822622 | 15 | 31776450 | Higher in Smoker |
| cg20363192 | 15 | 31780722 | Lower in Smoker |
| cg14792350 | 1 | 149983257 | Lower in Smoker |
| cg24748769 | 14 | 57271015 | Higher in Smoker |
| cg25198275 | 12 | 29650692 | Lower in Smoker |
| cg20718083 | 11 | 65554410 | Lower in Smoker |
| cg02113429 | 20 | 18036013 | Lower in Smoker |
| cg12587960 | 20 | 18033564 | Lower in Smoker |
| ch.5.884579R | 5 | 41837108 | Higher in Smoker |
| cg22230912 | 3 | 16331335 | Lower in Smoker |
| cg01637244 | 3 | 25833304 | Lower in Smoker |
| cg11589699 | 3 | 8806317 | Higher in Smoker |
| cg18394557 | 17 | 3805136 | Lower in Smoker |
| cg04737916 | 12 | 133196028 | Higher in Smoker |
| cg04811534 | 11 | 57115016 | Lower in Smoker |
| cg24632597 | 12 | 121648093 | Lower in Smoker |
| cg26182497 | 3 | 151055545 | Lower in Smoker |

| | | | |
|---|---|---|---|
| cg01550445 | 11 | 72929983 | Higher in Smoker |
| cg26343510 | 11 | 72975668 | Higher in Smoker |
| cg17729859 | 10 | 74856286 | Higher in Smoker |
| cg11586658 | 5 | 131563581 | Higher in Smoker |
| cg24117468 | 5 | 131562848 | Lower in Smoker |
| cg09610987 | 3 | 49028278 | Higher in Smoker |
| cg17527142 | 3 | 49027225 | Higher in Smoker |
| cg08455380 | 3 | 49044317 | Lower in Smoker |
| cg05743086 | 8 | 101734283 | Higher in Smoker |
| cg21480165 | 13 | 25670170 | Higher in Smoker |
| cg18474108 | 13 | 25670319 | Higher in Smoker |
| cg18236571 | 4 | 135122410 | Higher in Smoker |
| cg17819538 | 14 | 23789234 | Lower in Smoker |
| cg22901337 | 14 | 23790498 | Higher in Smoker |
| cg09293792 | 6 | 163602881 | Lower in Smoker |
| cg15832436 | 6 | 163148290 | Higher in Smoker |
| cg06582575 | 6 | 163149167 | Higher in Smoker |
| cg26245302 | 6 | 163148501 | Higher in Smoker |
| cg27097962 | 14 | 105730695 | Higher in Smoker |
| cg24040299 | 14 | 105834764 | Lower in Smoker |
| cg21903221 | 14 | 105851981 | Lower in Smoker |
| cg06937357 | 14 | 105837270 | Lower in Smoker |
| cg05106897 | 6 | 34433775 | Higher in Smoker |
| cg00444847 | 6 | 34433789 | Higher in Smoker |
| cg17674042 | 6 | 34482479 | Lower in Smoker |
| cg13734410 | 11 | 47207390 | Lower in Smoker |
| cg12654045 | 1 | 17559606 | Lower in Smoker |
| cg18333690 | 1 | 17634716 | Higher in Smoker |
| cg14595462 | 9 | 138453863 | Lower in Smoker |
| cg02406092 | 19 | 39876337 | Lower in Smoker |
| cg02621988 | 17 | 2498631 | Lower in Smoker |
| cg12364755 | 17 | 2498642 | Lower in Smoker |
| cg05090835 | 11 | 117015971 | Higher in Smoker |
| cg10398005 | 11 | 117014868 | Higher in Smoker |
| cg15181396 | 19 | 42806958 | Higher in Smoker |

| | | | |
|---|---|---|---|
| cg19632574 | 7 | 26324332 | Higher in Smoker |
| cg16974308 | 8 | 81974381 | Lower in Smoker |
| cg19744943 | X | 55101639 | Higher in Smoker |
| cg09739904 | 12 | 103310839 | Lower in Smoker |
| cg12679980 | 5 | 43557583 | Lower in Smoker |
| cg06241044 | 2 | 71451310 | Higher in Smoker |
| cg07350210 | 11 | 77180550 | Lower in Smoker |
| cg20018767 | X | 110339465 | Higher in Smoker |
| cg10373030 | 15 | 40528967 | Lower in Smoker |
| cg14525688 | 15 | 40544855 | Higher in Smoker |
| cg12423123 | 15 | 40545511 | Higher in Smoker |
| cg21966319 | 4 | 169543126 | Lower in Smoker |
| cg20607169 | 4 | 169750834 | Lower in Smoker |
| cg22911687 | 5 | 102211822 | Lower in Smoker |
| cg10516204 | 12 | 56710362 | Lower in Smoker |
| cg15417900 | 12 | 56710096 | Higher in Smoker |
| cg00007981 | 11 | 93862594 | Higher in Smoker |
| cg07178896 | 16 | 50238554 | Lower in Smoker |
| cg02598642 | 19 | 39574483 | Higher in Smoker |
| cg17099683 | 14 | 96969243 | Higher in Smoker |
| cg12180123 | 2 | 60983194 | Higher in Smoker |
| cg10826053 | 4 | 108641834 | Higher in Smoker |
| cg17916473 | 10 | 89419373 | Higher in Smoker |
| cg05628107 | 10 | 89419384 | Higher in Smoker |
| cg07248455 | 15 | 69591753 | Higher in Smoker |
| cg15593298 | 3 | 142681996 | Higher in Smoker |
| cg18560144 | 15 | 25230200 | Lower in Smoker |
| cg24138862 | 10 | 35105401 | Higher in Smoker |
| cg18351448 | 10 | 34408586 | Lower in Smoker |
| cg03310691 | 10 | 34505321 | Lower in Smoker |
| cg25212025 | 10 | 34602937 | Lower in Smoker |
| cg15471177 | 2 | 205410786 | Higher in Smoker |
| ch.2.4104651R | 2 | 206156946 | Higher in Smoker |
| cg11924572 | 20 | 49347934 | Higher in Smoker |
| cg08228115 | 20 | 49347917 | Higher in Smoker |

| | | | |
|---|---|---|---|
| cg16238918 | 16 | 78004303 | Higher in Smoker |
| cg23642929 | 16 | 78002832 | Lower in Smoker |
| cg20989899 | 16 | 77921368 | Lower in Smoker |
| ch.6.3213513F | 6 | 162851709 | Higher in Smoker |
| cg16534579 | 6 | 162064339 | Lower in Smoker |
| cg20223211 | 3 | 183547296 | Lower in Smoker |
| cg15871647 | 4 | 75859930 | Higher in Smoker |
| cg09043569 | 16 | 14704596 | Lower in Smoker |
| cg04464523 | 12 | 3948619 | Higher in Smoker |
| cg05338969 | 12 | 3919438 | Lower in Smoker |
| cg03873220 | 7 | 139760375 | Lower in Smoker |
| cg07184411 | 3 | 122400006 | Higher in Smoker |
| cg23478105 | 15 | 65579253 | Higher in Smoker |
| cg07377586 | 3 | 122283313 | Lower in Smoker |
| cg07312661 | 3 | 122279522 | Lower in Smoker |
| cg06221218 | 1 | 55230625 | Higher in Smoker |
| cg17429631 | 1 | 55230368 | Higher in Smoker |
| cg22693570 | 1 | 55224579 | Lower in Smoker |
| cg26320696 | 11 | 12399109 | Higher in Smoker |
| cg19172497 | 22 | 44394856 | Lower in Smoker |
| cg12555844 | 22 | 44568337 | Higher in Smoker |
| cg10648547 | 2 | 242051808 | Lower in Smoker |
| cg01647795 | 15 | 44969244 | Lower in Smoker |
| cg09189428 | 22 | 31743558 | Higher in Smoker |
| cg17621054 | 12 | 80084980 | Higher in Smoker |
| cg20472745 | 12 | 80084972 | Higher in Smoker |
| cg07213060 | 20 | 21694827 | Higher in Smoker |
| cg26463200 | 20 | 21685401 | Higher in Smoker |
| cg17620199 | 20 | 21685925 | Higher in Smoker |
| cg26156687 | 10 | 102586168 | Lower in Smoker |
| cg09424526 | 2 | 223163809 | Higher in Smoker |
| cg15133719 | 2 | 223163804 | Higher in Smoker |
| cg27480727 | 2 | 223164831 | Higher in Smoker |
| cg02120658 | 2 | 223160297 | Higher in Smoker |
| cg01879473 | 2 | 223160102 | Higher in Smoker |

| | | | |
|---|---|---|---|
| cg14283649 | 9 | 36843876 | Lower in Smoker |
| cg10059959 | 9 | 37035381 | Lower in Smoker |
| cg00318543 | 9 | 37001111 | Lower in Smoker |
| cg13028700 | 11 | 31836254 | Lower in Smoker |
| cg25949958 | 11 | 31833007 | Higher in Smoker |
| cg21856670 | 1 | 19041952 | Lower in Smoker |
| cg26530301 | 1 | 19000726 | Lower in Smoker |
| cg23564664 | 2 | 113997917 | Higher in Smoker |
| cg09234973 | 2 | 113975820 | Lower in Smoker |
| cg23156509 | 2 | 114033830 | Higher in Smoker |
| cg21482265 | 2 | 113992762 | Lower in Smoker |
| cg12889195 | 2 | 113992843 | Lower in Smoker |
| cg17445212 | 2 | 113993313 | Lower in Smoker |
| cg07772999 | 2 | 113993052 | Lower in Smoker |
| cg19083407 | 2 | 113993142 | Lower in Smoker |
| cg07594247 | 2 | 113993304 | Lower in Smoker |
| cg11763394 | 2 | 113992921 | Lower in Smoker |
| cg21550016 | 2 | 113992930 | Lower in Smoker |
| cg04243401 | 14 | 37128378 | Lower in Smoker |
| cg05917460 | 14 | 37126902 | Higher in Smoker |
| cg10640731 | 10 | 70092995 | Higher in Smoker |
| cg06424719 | 10 | 70093223 | Higher in Smoker |
| cg05923681 | 3 | 52580707 | Lower in Smoker |
| cg25031777 | 1 | 164528501 | Higher in Smoker |
| cg14635654 | 6 | 32154447 | Lower in Smoker |
| cg03422527 | 6 | 32154568 | Lower in Smoker |
| cg24676384 | 1 | 154929455 | Lower in Smoker |
| cg11862081 | 11 | 66625106 | Lower in Smoker |
| cg06431702 | 11 | 66624841 | Higher in Smoker |
| cg05330472 | 11 | 66636291 | Lower in Smoker |
| cg23756143 | 11 | 66643501 | Lower in Smoker |
| cg22078869 | 5 | 134241244 | Higher in Smoker |
| cg03803211 | 2 | 70313772 | Lower in Smoker |
| cg12891177 | 2 | 70313597 | Lower in Smoker |
| cg19787841 | 12 | 53845606 | Higher in Smoker |

| | | | |
|---|---|---|---|
| cg05131707 | 12 | 53859512 | Lower in Smoker |
| cg04494562 | 13 | 101173774 | Higher in Smoker |
| cg21805940 | 13 | 101174420 | Higher in Smoker |
| cg24978725 | 13 | 101173617 | Higher in Smoker |
| cg18970151 | 13 | 101174130 | Higher in Smoker |
| cg12436019 | 13 | 101174364 | Higher in Smoker |
| cg08985968 | 13 | 101174096 | Higher in Smoker |
| cg05563033 | 13 | 101174060 | Higher in Smoker |
| cg25221774 | 13 | 101173669 | Higher in Smoker |
| cg23235217 | 13 | 100741026 | Higher in Smoker |
| cg18834544 | 13 | 101182535 | Lower in Smoker |
| cg13431811 | 13 | 101108790 | Lower in Smoker |
| cg19947501 | 13 | 101056411 | Lower in Smoker |
| cg02771673 | 13 | 101137103 | Lower in Smoker |
| cg15555995 | 5 | 141258138 | Higher in Smoker |
| cg23713176 | 4 | 134074369 | Higher in Smoker |
| cg12474452 | X | 91033945 | Higher in Smoker |
| cg09703571 | Y | 4867908 | Higher in Smoker |
| cg02453726 | 5 | 141339766 | Higher in Smoker |
| cg26837730 | 5 | 141324726 | Lower in Smoker |
| cg04913004 | 10 | 56057923 | Lower in Smoker |
| cg25891355 | 13 | 58205111 | Higher in Smoker |
| cg14427009 | 13 | 58207058 | Higher in Smoker |
| cg12614912 | X | 99664089 | Higher in Smoker |
| cg18671854 | 13 | 61989597 | Higher in Smoker |
| cg23076299 | 10 | 85954312 | Lower in Smoker |
| cg13727641 | 5 | 176006188 | Lower in Smoker |
| cg23972904 | 5 | 175991468 | Lower in Smoker |
| cg07562487 | 4 | 30759432 | Lower in Smoker |
| cg17535595 | 13 | 53422808 | Higher in Smoker |
| cg10484958 | 13 | 53424127 | Lower in Smoker |
| cg09985739 | 13 | 67621714 | Lower in Smoker |
| cg25155679 | 13 | 67479146 | Lower in Smoker |
| cg20666533 | 13 | 67714028 | Lower in Smoker |
| cg18815539 | 13 | 66981290 | Lower in Smoker |

| | | | |
|---|---|---|---|
| cg12150457 | 5 | 140165687 | Higher in Smoker |
| cg10645317 | 5 | 140167483 | Higher in Smoker |
| cg12314121 | 5 | 140167213 | Higher in Smoker |
| cg07555125 | 5 | 140175691 | Lower in Smoker |
| cg16607635 | 5 | 140181889 | Higher in Smoker |
| cg02047330 | 5 | 140208201 | Higher in Smoker |
| cg01416563 | 5 | 140237151 | Higher in Smoker |
| cg26618441 | 5 | 140213825 | Higher in Smoker |
| cg07745166 | 5 | 140213838 | Higher in Smoker |
| cg01029635 | 5 | 140226474 | Lower in Smoker |
| cg19596110 | 5 | 140221364 | Higher in Smoker |
| cg00504705 | 5 | 140221357 | Higher in Smoker |
| cg24648119 | 5 | 140242639 | Higher in Smoker |
| cg00617867 | 5 | 140242373 | Higher in Smoker |
| cg16014030 | 5 | 140305713 | Higher in Smoker |
| cg09088965 | 5 | 140573438 | Higher in Smoker |
| cg20475035 | 5 | 140573574 | Higher in Smoker |
| cg05852276 | 5 | 140579470 | Higher in Smoker |
| cg14522441 | 5 | 140582125 | Higher in Smoker |
| cg17007628 | 5 | 140588424 | Higher in Smoker |
| cg18313790 | 5 | 140595722 | Higher in Smoker |
| cg06327515 | 5 | 140603261 | Higher in Smoker |
| cg03572772 | 5 | 140624869 | Higher in Smoker |
| cg18664869 | 5 | 140625004 | Higher in Smoker |
| cg26569309 | 5 | 140563400 | Higher in Smoker |
| cg01248745 | 5 | 140563213 | Higher in Smoker |
| cg06048354 | 5 | 140501812 | Higher in Smoker |
| cg08493776 | 5 | 140529738 | Higher in Smoker |
| cg27069422 | 5 | 140531474 | Higher in Smoker |
| cg13283199 | 5 | 140552992 | Higher in Smoker |
| cg17785250 | 5 | 140554081 | Higher in Smoker |
| cg05941060 | 5 | 140568856 | Higher in Smoker |
| cg16263180 | 5 | 140710509 | Higher in Smoker |
| cg22056102 | 5 | 140709983 | Higher in Smoker |
| cg05580809 | 5 | 140711852 | Higher in Smoker |

| | | | |
|---|---|---|---|
| cg23383590 | 5 | 140717961 | Higher in Smoker |
| cg03617826 | 5 | 140718405 | Higher in Smoker |
| cg25657261 | 5 | 140723858 | Higher in Smoker |
| cg21073350 | 5 | 140729813 | Higher in Smoker |
| cg05197036 | 5 | 140824037 | Lower in Smoker |
| cg07448606 | 5 | 140855857 | Higher in Smoker |
| cg16621364 | 5 | 140745340 | Higher in Smoker |
| cg22604188 | 5 | 140774054 | Higher in Smoker |
| cg27665767 | 5 | 140764485 | Higher in Smoker |
| cg13972793 | 5 | 140751454 | Higher in Smoker |
| cg17048610 | 5 | 140731399 | Higher in Smoker |
| cg09833789 | 2 | 120301866 | Higher in Smoker |
| cg27140474 | 11 | 82868555 | Higher in Smoker |
| cg18396448 | 17 | 36905135 | Higher in Smoker |
| cg16754522 | 4 | 734600 | Lower in Smoker |
| cg15645804 | 4 | 754410 | Lower in Smoker |
| cg26131879 | 4 | 714341 | Lower in Smoker |
| cg02595378 | 4 | 763997 | Lower in Smoker |
| cg00864568 | 4 | 742377 | Lower in Smoker |
| cg01474840 | 10 | 105085296 | Lower in Smoker |
| cg11987853 | 13 | 113832521 | Lower in Smoker |
| ch.21.825836R | 21 | 47810293 | Higher in Smoker |
| cg17237181 | 21 | 47830619 | Lower in Smoker |
| cg13599649 | 21 | 47851742 | Lower in Smoker |
| cg11967727 | 21 | 47743836 | Lower in Smoker |
| cg15332261 | 14 | 71375349 | Higher in Smoker |
| cg09887634 | 1 | 233122135 | Lower in Smoker |
| cg24681612 | 1 | 233356952 | Lower in Smoker |
| cg22712403 | 11 | 65384321 | Lower in Smoker |
| cg20588618 | 11 | 65383161 | Higher in Smoker |
| cg25680486 | 7 | 100203114 | Higher in Smoker |
| cg18178595 | 7 | 100198429 | Lower in Smoker |
| cg06402330 | 7 | 100199982 | Lower in Smoker |
| cg07045199 | 13 | 24463743 | Higher in Smoker |
| cg17377054 | X | 48693397 | Higher in Smoker |

| | | | |
|---|---|---|---|
| cg13130271 | X | 48694012 | Higher in Smoker |
| cg09501006 | 9 | 78505549 | Higher in Smoker |
| cg21172497 | 9 | 78510119 | Lower in Smoker |
| cg04009860 | 15 | 101853297 | Lower in Smoker |
| cg03798986 | 15 | 101979368 | Lower in Smoker |
| cg27370471 | 15 | 101932559 | Lower in Smoker |
| cg20700977 | 11 | 117076344 | Lower in Smoker |
| cg02697902 | 11 | 117103610 | Higher in Smoker |
| cg08920610 | 1 | 55505343 | Higher in Smoker |
| cg13191808 | 1 | 55505327 | Higher in Smoker |
| cg08386490 | 17 | 53828930 | Higher in Smoker |
| cg12744185 | 17 | 53828387 | Higher in Smoker |
| cg18954037 | 2 | 70485171 | Higher in Smoker |
| cg08493904 | 2 | 70507416 | Lower in Smoker |
| cg18155062 | X | 24665469 | Higher in Smoker |
| cg22147539 | 17 | 79869413 | Higher in Smoker |
| cg02308097 | 17 | 79868996 | Higher in Smoker |
| cg24584890 | 17 | 79869441 | Lower in Smoker |
| cg02122525 | 2 | 242801252 | Higher in Smoker |
| cg25890838 | 2 | 242801046 | Lower in Smoker |
| cg24249075 | 3 | 187452484 | Higher in Smoker |
| cg26719024 | 10 | 105156444 | Higher in Smoker |
| cg14133084 | 9 | 5530115 | Higher in Smoker |
| cg10006515 | 19 | 34895882 | Lower in Smoker |
| cg05031034 | 15 | 65411022 | Lower in Smoker |
| cg23660999 | 11 | 777775 | Higher in Smoker |
| cg08447044 | 6 | 165902024 | Lower in Smoker |
| cg06860371 | 12 | 54942782 | Lower in Smoker |
| cg16643603 | 12 | 54954941 | Higher in Smoker |
| cg14378727 | 11 | 72369758 | Lower in Smoker |
| cg09877173 | 11 | 72380291 | Lower in Smoker |
| cg26534807 | 11 | 72381235 | Higher in Smoker |
| cg19341656 | 11 | 72350651 | Lower in Smoker |
| cg26571814 | 12 | 20589672 | Lower in Smoker |
| cg17242144 | 19 | 10531498 | Higher in Smoker |

| | | | |
|---|---|---|---|
| cg26912671 | 1 | 66458803 | Lower in Smoker |
| cg03435439 | 1 | 66458361 | Lower in Smoker |
| cg17834637 | 19 | 18340849 | Lower in Smoker |
| cg03401312 | 19 | 18338283 | Lower in Smoker |
| cg04326562 | 19 | 18320186 | Lower in Smoker |
| cg10010376 | 1 | 144932311 | Higher in Smoker |
| cg05453071 | 4 | 120472195 | Lower in Smoker |
| cg09381022 | 4 | 120465302 | Lower in Smoker |
| cg05264454 | 4 | 120549640 | Higher in Smoker |
| cg26397250 | 4 | 642765 | Lower in Smoker |
| cg18702278 | 4 | 650632 | Lower in Smoker |
| cg00465686 | 8 | 66701377 | Lower in Smoker |
| cg26772386 | 21 | 44110482 | Lower in Smoker |
| cg24450112 | 21 | 44103949 | Lower in Smoker |
| cg12225979 | 21 | 44103900 | Lower in Smoker |
| cg11265749 | 7 | 560499 | Higher in Smoker |
| cg13957198 | 7 | 559649 | Higher in Smoker |
| cg25661961 | 4 | 157862518 | Lower in Smoker |
| cg23852348 | 11 | 104030857 | Lower in Smoker |
| cg24249778 | 4 | 55095226 | Higher in Smoker |
| cg23550826 | 4 | 55095282 | Higher in Smoker |
| cg00917893 | 3 | 58419781 | Higher in Smoker |
| cg02474183 | 11 | 34937484 | Lower in Smoker |
| cg25383261 | 11 | 34937992 | Higher in Smoker |
| cg25364573 | 1 | 146649022 | Lower in Smoker |
| cg26084141 | 3 | 122786895 | Lower in Smoker |
| cg14465207 | 2 | 10951250 | Higher in Smoker |
| cg22004443 | 2 | 10953237 | Higher in Smoker |
| cg20821314 | 2 | 10950732 | Lower in Smoker |
| cg07919493 | 16 | 20417094 | Lower in Smoker |
| cg23845806 | 17 | 48172644 | Higher in Smoker |
| cg25581330 | 4 | 186434993 | Higher in Smoker |
| cg16592149 | 4 | 95409312 | Lower in Smoker |
| cg27650985 | 5 | 176911797 | Lower in Smoker |
| cg07413150 | 5 | 176918920 | Lower in Smoker |

| | | | |
|---|---|---|---|
| cg06991732 | 8 | 94934036 | Lower in Smoker |
| cg06567195 | 8 | 94937996 | Lower in Smoker |
| cg00547444 | 16 | 2587590 | Higher in Smoker |
| cg01222216 | 16 | 2648276 | Higher in Smoker |
| cg02801007 | 16 | 2645870 | Lower in Smoker |
| cg23954416 | 1 | 13909161 | Lower in Smoker |
| ch.16.1562336F | 16 | 70172531 | Higher in Smoker |
| cg07624639 | 13 | 28494002 | Higher in Smoker |
| cg25685262 | 13 | 28493316 | Higher in Smoker |
| cg26793256 | 13 | 28494004 | Higher in Smoker |
| cg18064631 | 13 | 28496413 | Lower in Smoker |
| cg00323916 | 22 | 38057185 | Lower in Smoker |
| cg25916188 | X | 153087306 | Lower in Smoker |
| cg03350932 | X | 153085101 | Lower in Smoker |
| cg00390049 | X | 153082274 | Lower in Smoker |
| cg10532290 | 10 | 119133434 | Higher in Smoker |
| cg05803361 | 1 | 145727320 | Lower in Smoker |
| cg06619077 | 1 | 47656003 | Lower in Smoker |
| cg23337650 | 3 | 73620925 | Higher in Smoker |
| cg02838088 | 3 | 73432452 | Lower in Smoker |
| cg14753334 | 3 | 73674702 | Lower in Smoker |
| cg12897782 | 12 | 116573868 | Higher in Smoker |
| cg24639902 | 8 | 22774971 | Lower in Smoker |
| cg24135112 | 6 | 4135877 | Higher in Smoker |
| cg09439093 | 6 | 4135575 | Higher in Smoker |
| cg21785847 | 2 | 216946279 | Higher in Smoker |
| cg02288777 | 1 | 32110861 | Higher in Smoker |
| cg01488147 | 7 | 94294080 | Lower in Smoker |
| cg25458871 | 19 | 57352584 | Lower in Smoker |
| cg11121623 | 14 | 56586572 | Higher in Smoker |
| cg19929409 | 14 | 56755226 | Lower in Smoker |
| cg04631728 | 17 | 4607671 | Higher in Smoker |
| cg14389924 | 17 | 4606729 | Lower in Smoker |
| cg22848150 | 8 | 57358165 | Higher in Smoker |
| cg24645221 | 8 | 57358928 | Lower in Smoker |

| | | | |
|---|---|---|---|
| cg23919308 | 19 | 34012901 | Higher in Smoker |
| cg19274401 | 19 | 33878161 | Lower in Smoker |
| cg21253188 | 19 | 33878798 | Lower in Smoker |
| cg07862575 | 19 | 33878938 | Lower in Smoker |
| cg14790638 | 19 | 34010091 | Lower in Smoker |
| cg10010386 | 19 | 34012747 | Higher in Smoker |
| cg25693525 | 19 | 34012759 | Higher in Smoker |
| cg23363911 | 17 | 8055756 | Higher in Smoker |
| cg17314998 | 17 | 8045615 | Lower in Smoker |
| cg23905308 | 2 | 239196947 | Higher in Smoker |
| cg03004097 | 2 | 239197782 | Higher in Smoker |
| cg21315421 | 2 | 239161191 | Lower in Smoker |
| cg22879834 | 2 | 239169591 | Lower in Smoker |
| cg06487986 | 1 | 7843564 | Higher in Smoker |
| cg08134286 | 1 | 7845798 | Lower in Smoker |
| cg09327610 | 1 | 7847797 | Lower in Smoker |
| cg09019803 | 6 | 138428736 | Higher in Smoker |
| cg08315187 | 6 | 138428131 | Higher in Smoker |
| cg24884985 | 6 | 138426136 | Lower in Smoker |
| cg06057952 | 4 | 152682178 | Lower in Smoker |
| cg19881481 | 20 | 18118358 | Higher in Smoker |
| cg05813650 | 1 | 2339995 | Lower in Smoker |
| cg15827505 | 19 | 7553721 | Higher in Smoker |
| cg25710854 | 17 | 33902444 | Lower in Smoker |
| cg08327903 | 2 | 61244727 | Higher in Smoker |
| cg16100063 | 1 | 10690011 | Lower in Smoker |
| cg27182133 | 1 | 10658147 | Lower in Smoker |
| cg16057915 | 1 | 10690564 | Lower in Smoker |
| cg07357157 | 1 | 10690588 | Lower in Smoker |
| cg01834541 | 1 | 10651801 | Lower in Smoker |
| cg22715764 | 1 | 10556294 | Lower in Smoker |
| cg18198545 | 1 | 160255804 | Lower in Smoker |
| cg02580626 | 22 | 18572133 | Lower in Smoker |
| cg10289305 | 3 | 179604962 | Lower in Smoker |
| cg18889437 | 6 | 42947671 | Higher in Smoker |

| | | | |
|---|---|---|---|
| cg15632659 | 6 | 42931860 | Lower in Smoker |
| cg01125463 | 6 | 42946178 | Lower in Smoker |
| cg19747945 | 6 | 42946146 | Lower in Smoker |
| cg06125930 | 6 | 137143662 | Higher in Smoker |
| cg16504641 | 6 | 137143711 | Higher in Smoker |
| cg15158783 | 4 | 74847646 | Higher in Smoker |
| cg15831212 | 5 | 139672796 | Lower in Smoker |
| cg06182359 | 1 | 161088957 | Lower in Smoker |
| cg20408175 | 12 | 53693169 | Lower in Smoker |
| cg24678243 | X | 55021561 | Lower in Smoker |
| cg07142068 | 10 | 6262870 | Higher in Smoker |
| cg24397108 | 10 | 6263474 | Lower in Smoker |
| cg01467100 | 10 | 6246406 | Lower in Smoker |
| cg21141812 | 3 | 48556323 | Higher in Smoker |
| cg18558420 | 21 | 45734417 | Higher in Smoker |
| cg14148108 | 21 | 45744314 | Lower in Smoker |
| cg10636490 | 3 | 149687315 | Lower in Smoker |
| cg24914077 | 11 | 60997852 | Lower in Smoker |
| cg02660350 | 10 | 99136001 | Higher in Smoker |
| cg17507888 | X | 77225299 | Lower in Smoker |
| cg19386169 | 12 | 133296477 | Lower in Smoker |
| cg16095660 | 11 | 3822594 | Lower in Smoker |
| cg10580903 | 11 | 3832691 | Lower in Smoker |
| cg12871376 | 6 | 41716240 | Lower in Smoker |
| cg22546818 | 19 | 17626408 | Higher in Smoker |
| cg11912570 | 19 | 17630670 | Lower in Smoker |
| cg08693172 | 19 | 46526333 | Higher in Smoker |
| cg07978145 | 11 | 74109510 | Higher in Smoker |
| cg07964958 | 6 | 83899760 | Lower in Smoker |
| cg18674899 | 6 | 83904319 | Higher in Smoker |
| cg02384122 | 19 | 18451192 | Higher in Smoker |
| cg13906669 | 11 | 100999399 | Higher in Smoker |
| cg22299741 | 11 | 101000164 | Higher in Smoker |
| cg17280624 | 4 | 129208725 | Higher in Smoker |
| cg18328477 | 17 | 76374570 | Higher in Smoker |

| | | | |
|---|---|---|---|
| cg00134843 | 17 | 76374495 | Lower in Smoker |
| cg20827128 | 6 | 13274284 | Higher in Smoker |
| cg11908041 | 6 | 13194027 | Lower in Smoker |
| cg09510202 | 6 | 13014671 | Lower in Smoker |
| cg13401235 | 6 | 13175441 | Lower in Smoker |
| cg02913194 | 6 | 143926514 | Lower in Smoker |
| cg10683775 | 6 | 143958167 | Lower in Smoker |
| cg01192112 | 6 | 144009131 | Lower in Smoker |
| cg02105346 | 6 | 144021172 | Lower in Smoker |
| cg05341786 | 6 | 144150174 | Lower in Smoker |
| cg13227551 | 6 | 144011222 | Lower in Smoker |
| cg10999598 | 5 | 125936257 | Lower in Smoker |
| cg03603669 | 3 | 169896616 | Higher in Smoker |
| cg23474801 | 7 | 11034330 | Lower in Smoker |
| cg01053196 | 5 | 133914579 | Lower in Smoker |
| cg18812977 | X | 46919898 | Lower in Smoker |
| cg04482257 | 4 | 129732056 | Higher in Smoker |
| cg00244317 | 4 | 129785576 | Lower in Smoker |
| cg11054680 | 9 | 123639935 | Higher in Smoker |
| cg16220788 | 11 | 46005268 | Lower in Smoker |
| cg18887228 | 6 | 64356606 | Lower in Smoker |
| cg16452396 | X | 133507394 | Higher in Smoker |
| cg05272837 | X | 54071268 | Higher in Smoker |
| cg12699599 | 15 | 40643142 | Lower in Smoker |
| cg26363168 | 6 | 79788481 | Higher in Smoker |
| cg03465562 | X | 19001031 | Lower in Smoker |
| cg25936168 | X | 18910803 | Higher in Smoker |
| cg24916116 | 12 | 7642497 | Higher in Smoker |
| cg05167973 | 11 | 2949546 | Higher in Smoker |
| cg02011054 | 11 | 2950754 | Lower in Smoker |
| cg16112844 | 11 | 2950638 | Higher in Smoker |
| cg00962755 | 1 | 201439001 | Higher in Smoker |
| cg18263988 | 3 | 111582491 | Lower in Smoker |
| cg17470227 | 3 | 111579551 | Lower in Smoker |
| cg23960922 | 3 | 111656555 | Lower in Smoker |

| | | | |
|---|---|---|---|
| cg25799073 | 3 | 111145690 | Lower in Smoker |
| cg22975160 | 19 | 43979614 | Higher in Smoker |
| cg02247591 | 19 | 43979372 | Higher in Smoker |
| cg05048372 | 18 | 60382543 | Higher in Smoker |
| cg02543960 | 18 | 60383467 | Higher in Smoker |
| cg00732059 | 16 | 71740210 | Lower in Smoker |
| cg02910180 | 11 | 71955299 | Higher in Smoker |
| cg03610629 | 11 | 611114 | Lower in Smoker |
| cg15376229 | 11 | 592496 | Lower in Smoker |
| cg17126941 | 7 | 77427790 | Higher in Smoker |
| cg02788195 | 10 | 60966072 | Lower in Smoker |
| cg13503413 | 10 | 60937257 | Lower in Smoker |
| cg00531789 | 6 | 36927248 | Higher in Smoker |
| cg01722343 | 4 | 25235437 | Higher in Smoker |
| cg18379859 | 4 | 25236431 | Higher in Smoker |
| cg08456334 | 1 | 151299699 | Lower in Smoker |
| cg17293363 | 2 | 229889859 | Lower in Smoker |
| cg06372249 | 4 | 515734 | Lower in Smoker |
| cg22375502 | 4 | 518315 | Lower in Smoker |
| cg17196244 | 4 | 518237 | Lower in Smoker |
| cg12194493 | 4 | 493061 | Higher in Smoker |
| cg12036741 | 1 | 160001633 | Higher in Smoker |
| cg15069926 | 1 | 160001653 | Higher in Smoker |
| cg05732725 | 18 | 59712034 | Lower in Smoker |
| cg18661731 | 18 | 59854239 | Higher in Smoker |
| cg14220272 | 21 | 39445791 | Higher in Smoker |
| cg06486124 | 16 | 619677 | Higher in Smoker |
| cg02085612 | 16 | 629464 | Lower in Smoker |
| cg04003920 | 20 | 44054623 | Higher in Smoker |
| cg18346038 | 20 | 33264828 | Higher in Smoker |
| cg18916626 | 20 | 33265164 | Lower in Smoker |
| cg14037036 | 1 | 27113573 | Higher in Smoker |
| cg09728506 | 3 | 196439567 | Lower in Smoker |
| cg12382864 | 10 | 98480463 | Higher in Smoker |
| cg06631766 | 10 | 98469437 | Lower in Smoker |

| | | | |
|---|---|---|---|
| cg17172681 | 10 | 98443500 | Lower in Smoker |
| cg13927938 | 1 | 204459584 | Higher in Smoker |
| cg14069622 | 12 | 18608819 | Lower in Smoker |
| cg00521887 | 18 | 39535162 | Higher in Smoker |
| cg22384366 | 3 | 178867004 | Higher in Smoker |
| cg17325959 | 1 | 9711961 | Higher in Smoker |
| cg04162034 | 1 | 9710821 | Lower in Smoker |
| cg14089636 | 1 | 9760357 | Lower in Smoker |
| cg07969918 | 22 | 31682909 | Lower in Smoker |
| cg02429595 | 19 | 18279515 | Lower in Smoker |
| cg18568116 | 19 | 18280177 | Lower in Smoker |
| cg12492496 | 19 | 18271859 | Lower in Smoker |
| cg27584146 | 1 | 46599915 | Lower in Smoker |
| cg19857071 | 1 | 46599010 | Higher in Smoker |
| cg21875080 | 1 | 46598774 | Higher in Smoker |
| cg24519598 | 1 | 46598275 | Higher in Smoker |
| cg04907571 | 17 | 8783908 | Lower in Smoker |
| cg22748815 | 7 | 99965437 | Lower in Smoker |
| cg07547730 | 7 | 99933501 | Higher in Smoker |
| cg14385482 | 7 | 99933530 | Higher in Smoker |
| cg21364723 | 22 | 50353623 | Lower in Smoker |
| cg22728790 | 19 | 9945653 | Higher in Smoker |
| cg10462174 | X | 71462220 | Lower in Smoker |
| cg12446953 | 1 | 20960867 | Higher in Smoker |
| cg26594488 | 7 | 77035648 | Lower in Smoker |
| cg14067425 | 7 | 77016535 | Lower in Smoker |
| cg17609282 | 7 | 77032864 | Lower in Smoker |
| cg05715123 | 7 | 76940422 | Lower in Smoker |
| cg02407048 | 7 | 77046134 | Lower in Smoker |
| cg02179239 | 10 | 23002514 | Higher in Smoker |
| cg26044171 | 12 | 57985301 | Higher in Smoker |
| cg24720336 | 1 | 151170427 | Lower in Smoker |
| cg08397339 | 19 | 3700613 | Higher in Smoker |
| cg23654206 | 19 | 3683811 | Lower in Smoker |
| cg19113603 | 9 | 130692917 | Higher in Smoker |

| | | | |
|---|---|---|---|
| cg14507088 | 9 | 130690399 | Higher in Smoker |
| cg19910327 | 10 | 95723024 | Lower in Smoker |
| cg19144013 | X | 15511746 | Higher in Smoker |
| cg01303008 | 17 | 10742003 | Lower in Smoker |
| cg12500632 | 22 | 32015384 | Lower in Smoker |
| cg00719899 | 3 | 138952852 | Lower in Smoker |
| cg03783110 | 17 | 1463739 | Lower in Smoker |
| cg07284476 | 17 | 65546480 | Lower in Smoker |
| cg15601195 | 17 | 65498589 | Lower in Smoker |
| cg10853830 | 11 | 67266176 | Lower in Smoker |
| cg04578677 | 11 | 67270800 | Lower in Smoker |
| cg01972009 | 11 | 67273431 | Lower in Smoker |
| cg17616646 | 11 | 67271660 | Lower in Smoker |
| cg05908960 | 12 | 123472150 | Higher in Smoker |
| cg13037550 | 12 | 123477107 | Lower in Smoker |
| cg27350398 | 10 | 3214550 | Higher in Smoker |
| cg03326990 | 10 | 3193421 | Lower in Smoker |
| cg12818481 | 10 | 3187667 | Lower in Smoker |
| cg11586382 | 10 | 3215966 | Lower in Smoker |
| cg02899903 | 10 | 3216063 | Lower in Smoker |
| cg19304088 | 4 | 111547790 | Higher in Smoker |
| cg12020444 | 12 | 130821456 | Lower in Smoker |
| cg07216348 | 8 | 22213245 | Lower in Smoker |
| cg24872692 | 22 | 25156026 | Lower in Smoker |
| ch.5.1992431R | 5 | 108685182 | Higher in Smoker |
| cg19049696 | 7 | 47989183 | Lower in Smoker |
| cg12350157 | 7 | 47986530 | Lower in Smoker |
| cg20360285 | 7 | 47989345 | Lower in Smoker |
| cg00701571 | 16 | 81134712 | Lower in Smoker |
| cg08272559 | 16 | 81208471 | Lower in Smoker |
| cg03266576 | 4 | 88929070 | Higher in Smoker |
| cg26621805 | 8 | 110373460 | Lower in Smoker |
| cg15433297 | 8 | 110374792 | Lower in Smoker |
| cg17686936 | 8 | 79428117 | Higher in Smoker |
| cg20583060 | 8 | 79429818 | Lower in Smoker |

| | | | |
|---|---|---|---|
| cg03946731 | 16 | 3028109 | Lower in Smoker |
| cg14005217 | 16 | 3029753 | Lower in Smoker |
| cg04164023 | 11 | 125106101 | Lower in Smoker |
| cg21611112 | 11 | 125253048 | Lower in Smoker |
| cg13026772 | 11 | 125398532 | Lower in Smoker |
| cg07972385 | 1 | 201301947 | Lower in Smoker |
| cg04904030 | 1 | 201263971 | Lower in Smoker |
| cg01851399 | 12 | 33050217 | Higher in Smoker |
| cg16785912 | 12 | 33048913 | Higher in Smoker |
| cg18308516 | 11 | 393648 | Lower in Smoker |
| cg20438915 | 2 | 159317294 | Lower in Smoker |
| cg19897172 | 7 | 135347071 | Lower in Smoker |
| cg16014987 | 3 | 119346741 | Lower in Smoker |
| cg13666341 | 3 | 119348585 | Lower in Smoker |
| cg06647218 | 16 | 68279240 | Higher in Smoker |
| cg15219506 | 11 | 63382047 | Higher in Smoker |
| cg19068218 | 1 | 20248753 | Higher in Smoker |
| cg02760164 | 15 | 42371967 | Lower in Smoker |
| cg06222062 | 1 | 20396690 | Higher in Smoker |
| cg17852424 | 22 | 38574118 | Lower in Smoker |
| cg24235037 | 2 | 160919532 | Higher in Smoker |
| cg13901694 | 5 | 145484536 | Lower in Smoker |
| cg07136641 | 8 | 57079634 | Lower in Smoker |
| cg20909773 | 8 | 57084179 | Lower in Smoker |
| cg27577583 | 6 | 144294847 | Lower in Smoker |
| cg18316621 | 6 | 144283348 | Lower in Smoker |
| cg12054981 | 8 | 42037387 | Higher in Smoker |
| cg17828057 | 8 | 42037527 | Higher in Smoker |
| cg19725903 | 12 | 14721020 | Higher in Smoker |
| cg27488348 | 12 | 14720834 | Higher in Smoker |
| cg27178677 | 20 | 8834803 | Lower in Smoker |
| cg24691182 | 11 | 64019217 | Higher in Smoker |
| cg12647801 | 11 | 64028732 | Lower in Smoker |
| cg20484832 | 20 | 9075810 | Lower in Smoker |
| cg25341131 | 3 | 38068777 | Higher in Smoker |

| | | | |
|---|---|---|---|
| cg06493829 | 20 | 39766765 | Lower in Smoker |
| cg00145596 | 16 | 81813706 | Higher in Smoker |
| cg05684569 | 16 | 81929465 | Lower in Smoker |
| cg16574934 | 16 | 81931759 | Lower in Smoker |
| cg09058650 | 16 | 81812565 | Lower in Smoker |
| cg23541926 | 3 | 155422092 | Higher in Smoker |
| cg11854493 | 1 | 2429996 | Higher in Smoker |
| cg24902038 | 1 | 2428882 | Lower in Smoker |
| cg00314892 | 1 | 2428080 | Lower in Smoker |
| cg19040667 | 2 | 198669333 | Higher in Smoker |
| cg12600692 | 2 | 198809390 | Lower in Smoker |
| cg10656016 | 3 | 111448206 | Lower in Smoker |
| cg06989693 | 5 | 41409354 | Lower in Smoker |
| cg26312814 | 5 | 41310595 | Lower in Smoker |
| cg22466012 | 3 | 171466200 | Higher in Smoker |
| cg25067877 | 17 | 17106312 | Lower in Smoker |
| cg23155717 | 8 | 145033622 | Lower in Smoker |
| cg00575153 | 8 | 145047469 | Lower in Smoker |
| cg08718031 | 8 | 145017243 | Lower in Smoker |
| cg09550697 | 8 | 145012068 | Lower in Smoker |
| cg03008241 | 8 | 144992234 | Lower in Smoker |
| cg11147309 | 8 | 145011888 | Lower in Smoker |
| cg07531549 | 8 | 145011406 | Lower in Smoker |
| cg13389508 | 8 | 145012644 | Lower in Smoker |
| cg24891660 | 8 | 145003653 | Lower in Smoker |
| cg25325005 | 8 | 145012748 | Lower in Smoker |
| cg00881417 | 10 | 124134372 | Higher in Smoker |
| cg24141036 | 8 | 38758705 | Higher in Smoker |
| cg15717617 | 8 | 38782090 | Lower in Smoker |
| cg01093065 | 19 | 49372101 | Lower in Smoker |
| cg17304713 | 12 | 19383622 | Higher in Smoker |
| cg11802843 | 12 | 19441930 | Lower in Smoker |
| cg05620648 | 12 | 19308364 | Lower in Smoker |
| cg26895569 | 1 | 204329222 | Higher in Smoker |
| cg11131599 | 1 | 204224211 | Lower in Smoker |

| | | | |
|---|---|---|---|
| cg14707162 | 11 | 17036581 | Higher in Smoker |
| cg14464464 | 11 | 17036337 | Higher in Smoker |
| cg01419967 | 11 | 16934961 | Lower in Smoker |
| cg08427305 | 19 | 30165133 | Lower in Smoker |
| cg22309568 | 19 | 30155122 | Lower in Smoker |
| cg16151082 | 8 | 96145483 | Lower in Smoker |
| cg10418114 | 6 | 151125848 | Lower in Smoker |
| cg08631890 | 19 | 39902969 | Higher in Smoker |
| cg21927177 | 14 | 65172436 | Higher in Smoker |
| cg13502346 | 14 | 65170209 | Higher in Smoker |
| cg06349754 | 16 | 67311653 | Lower in Smoker |
| cg26389819 | 5 | 142851 | Lower in Smoker |
| cg09290082 | 12 | 93129809 | Lower in Smoker |
| cg20829550 | 12 | 93129447 | Lower in Smoker |
| cg11524454 | 12 | 93129167 | Lower in Smoker |
| cg10044111 | 14 | 68000301 | Higher in Smoker |
| cg03862414 | 17 | 40824241 | Lower in Smoker |
| cg07589081 | 19 | 2236313 | Higher in Smoker |
| cg01365117 | 2 | 208761957 | Lower in Smoker |
| cg11671771 | 15 | 65133392 | Higher in Smoker |
| cg14334810 | 9 | 19126294 | Lower in Smoker |
| cg14227460 | 19 | 4518743 | Lower in Smoker |
| cg10020883 | 19 | 4517722 | Lower in Smoker |
| cg05657488 | 16 | 23689988 | Lower in Smoker |
| cg07753711 | 4 | 128801645 | Higher in Smoker |
| cg11734112 | 3 | 145809092 | Lower in Smoker |
| cg22366498 | X | 49027884 | Higher in Smoker |
| cg10542519 | X | 49029384 | Lower in Smoker |
| cg22069588 | 4 | 155471681 | Higher in Smoker |
| cg14225926 | 4 | 155471827 | Higher in Smoker |
| cg20824294 | 3 | 142316082 | Higher in Smoker |
| cg08990057 | X | 114795604 | Higher in Smoker |
| cg12289482 | X | 114794350 | Lower in Smoker |
| cg18778727 | 3 | 146249003 | Lower in Smoker |
| cg01024009 | 3 | 145968696 | Higher in Smoker |

| | | | |
|---|---|---|---|
| cg15701047 | 10 | 20106873 | Higher in Smoker |
| cg03959945 | 1 | 208326650 | Lower in Smoker |
| cg09244601 | 7 | 131864510 | Lower in Smoker |
| cg19887462 | 3 | 48456716 | Lower in Smoker |
| cg23391060 | X | 153029535 | Higher in Smoker |
| cg12503473 | 12 | 94580426 | Lower in Smoker |
| cg02757998 | 12 | 94546933 | Lower in Smoker |
| cg27560120 | 3 | 129293125 | Lower in Smoker |
| cg15629311 | 3 | 129295896 | Lower in Smoker |
| cg20631654 | 20 | 56285704 | Higher in Smoker |
| cg11075509 | 1 | 156182236 | Higher in Smoker |
| cg08066123 | 15 | 74287179 | Higher in Smoker |
| cg07345510 | 15 | 74317259 | Higher in Smoker |
| cg21950208 | 15 | 74294468 | Lower in Smoker |
| cg20795891 | 22 | 41935901 | Higher in Smoker |
| cg08260763 | 16 | 8891593 | Higher in Smoker |
| cg27281765 | 8 | 82358608 | Lower in Smoker |
| cg19301273 | 8 | 82361115 | Lower in Smoker |
| cg08794157 | 17 | 15164627 | Higher in Smoker |
| cg20140398 | 17 | 15164292 | Higher in Smoker |
| cg07710335 | 17 | 15151869 | Lower in Smoker |
| cg09987408 | 9 | 139311141 | Lower in Smoker |
| cg06224732 | 7 | 102936381 | Lower in Smoker |
| cg23004082 | 2 | 190649483 | Higher in Smoker |
| cg26381592 | 2 | 190649278 | Higher in Smoker |
| cg19116668 | 7 | 99932089 | Higher in Smoker |
| cg25990230 | 7 | 75157345 | Higher in Smoker |
| cg22899380 | 7 | 74306484 | Higher in Smoker |
| cg20977411 | 1 | 154909454 | Higher in Smoker |
| cg03627290 | 2 | 219155248 | Lower in Smoker |
| cg15758783 | 6 | 160221183 | Higher in Smoker |
| cg00444261 | 8 | 26371564 | Higher in Smoker |
| cg11277148 | 8 | 26371569 | Higher in Smoker |
| cg11809658 | 19 | 46971373 | Higher in Smoker |
| cg14569776 | 19 | 46974275 | Lower in Smoker |

| | | | |
|---|---|---|---|
| cg06851207 | 19 | 46975138 | Lower in Smoker |
| cg03283031 | 17 | 37824238 | Higher in Smoker |
| cg06596543 | 17 | 37823905 | Higher in Smoker |
| cg24049451 | 17 | 37826163 | Lower in Smoker |
| cg27336360 | 8 | 26174350 | Higher in Smoker |
| cg01293050 | 14 | 20937714 | Lower in Smoker |
| cg15000232 | 22 | 44319424 | Higher in Smoker |
| cg05508067 | X | 7895590 | Higher in Smoker |
| cg08841552 | 9 | 140444378 | Higher in Smoker |
| cg11128045 | 9 | 140395219 | Higher in Smoker |
| cg21177880 | 9 | 140377789 | Lower in Smoker |
| cg12689055 | 1 | 53541670 | Lower in Smoker |
| cg26969888 | 19 | 14064254 | Lower in Smoker |
| cg18547299 | 19 | 14049578 | Higher in Smoker |
| cg00040427 | 19 | 14044197 | Lower in Smoker |
| cg01986605 | 3 | 127348155 | Higher in Smoker |
| cg06365177 | 20 | 30798589 | Lower in Smoker |
| cg20607513 | 21 | 46708029 | Higher in Smoker |
| cg17217575 | 21 | 46697067 | Lower in Smoker |
| cg17021527 | 1 | 151432386 | Lower in Smoker |
| cg13326840 | X | 25014481 | Lower in Smoker |
| cg17124779 | 11 | 65046602 | Lower in Smoker |
| cg20250908 | 11 | 65032183 | Lower in Smoker |
| cg02849924 | 19 | 50887530 | Higher in Smoker |
| cg03033930 | 19 | 50905585 | Lower in Smoker |
| cg10864501 | 22 | 43011545 | Higher in Smoker |
| cg23791442 | 22 | 43010704 | Higher in Smoker |
| cg15388430 | 22 | 43010952 | Higher in Smoker |
| cg23545458 | 12 | 133239966 | Higher in Smoker |
| cg07306676 | 12 | 133220579 | Lower in Smoker |
| cg13505011 | 12 | 133264131 | Higher in Smoker |
| cg23716101 | 14 | 50155118 | Higher in Smoker |
| cg15091337 | 2 | 75185439 | Lower in Smoker |
| cg01877814 | 15 | 89879097 | Lower in Smoker |
| cg03173714 | 10 | 103341227 | Lower in Smoker |

| | | | |
|---|---|---|---|
| cg06103218 | 4 | 2073751 | Lower in Smoker |
| cg05147763 | 4 | 2078818 | Lower in Smoker |
| cg08279008 | 2 | 86263224 | Higher in Smoker |
| cg02285477 | 13 | 28196059 | Higher in Smoker |
| cg03034407 | 16 | 57496971 | Higher in Smoker |
| cg21850239 | 11 | 62528988 | Lower in Smoker |
| cg22459051 | 7 | 44058729 | Higher in Smoker |
| cg05983883 | 8 | 101162533 | Higher in Smoker |
| cg00188547 | 8 | 101162809 | Higher in Smoker |
| cg17326144 | 1 | 145608565 | Lower in Smoker |
| cg27001893 | 8 | 22136571 | Lower in Smoker |
| cg04303976 | 16 | 22309637 | Higher in Smoker |
| cg05712542 | 16 | 22337575 | Higher in Smoker |
| cg10669597 | 5 | 89771460 | Lower in Smoker |
| cg19913118 | 1 | 145471701 | Lower in Smoker |
| cg15739543 | 5 | 6713426 | Higher in Smoker |
| cg06481076 | 5 | 6745560 | Lower in Smoker |
| cg11036032 | 5 | 6747615 | Lower in Smoker |
| cg25011763 | 5 | 6727354 | Lower in Smoker |
| cg17835614 | 7 | 72409374 | Lower in Smoker |
| cg16961080 | 7 | 75115640 | Higher in Smoker |
| cg18371636 | 7 | 75067510 | Higher in Smoker |
| cg23610064 | 7 | 75070040 | Lower in Smoker |
| cg07608671 | 7 | 75115567 | Higher in Smoker |
| cg11738634 | 22 | 22980403 | Lower in Smoker |
| cg02652760 | 6 | 27278678 | Lower in Smoker |
| cg06297155 | 22 | 21043440 | Lower in Smoker |
| cg04036898 | 1 | 46664598 | Lower in Smoker |
| cg04821933 | 13 | 29232799 | Higher in Smoker |
| cg14403594 | 9 | 134377516 | Lower in Smoker |
| cg10136168 | 14 | 77783447 | Lower in Smoker |
| cg14137698 | 14 | 77741448 | Lower in Smoker |
| cg02315508 | 14 | 77787366 | Higher in Smoker |
| cg22599769 | 7 | 95064738 | Higher in Smoker |
| cg13236881 | 7 | 95064691 | Higher in Smoker |

| | | | |
|---|---|---|---|
| cg26776175 | 7 | 95064464 | Higher in Smoker |
| cg06126815 | 7 | 95065139 | Higher in Smoker |
| cg08698155 | 7 | 95026097 | Higher in Smoker |
| cg11713008 | 8 | 99129222 | Higher in Smoker |
| cg14377816 | 8 | 99129780 | Higher in Smoker |
| cg15399561 | 8 | 99129939 | Higher in Smoker |
| cg02362450 | 8 | 99129674 | Higher in Smoker |
| cg25291941 | 8 | 99129319 | Higher in Smoker |
| cg01232410 | 19 | 30097075 | Higher in Smoker |
| cg26963285 | 19 | 30100831 | Higher in Smoker |
| cg05874450 | 6 | 105627246 | Higher in Smoker |
| cg02909890 | 6 | 105607395 | Lower in Smoker |
| cg22580625 | 6 | 105627791 | Lower in Smoker |
| cg01737421 | X | 48367069 | Higher in Smoker |
| cg14340114 | 7 | 124570081 | Lower in Smoker |
| cg26969150 | 8 | 43147397 | Lower in Smoker |
| cg22630663 | 2 | 131975750 | Lower in Smoker |
| cg06178887 | 19 | 42599631 | Lower in Smoker |
| cg23181035 | 19 | 42593016 | Lower in Smoker |
| cg07716663 | 19 | 42636625 | Lower in Smoker |
| cg20663364 | 11 | 120110627 | Higher in Smoker |
| cg03356778 | 11 | 120110544 | Higher in Smoker |
| cg03840594 | 6 | 99283553 | Higher in Smoker |
| cg09626131 | X | 82764537 | Higher in Smoker |
| cg19497031 | 13 | 79176272 | Higher in Smoker |
| cg01819137 | 5 | 145719938 | Higher in Smoker |
| cg15278102 | 6 | 31138982 | Lower in Smoker |
| cg22994781 | 6 | 31139359 | Lower in Smoker |
| cg19777318 | 6 | 31134163 | Lower in Smoker |
| cg22493172 | 12 | 51611826 | Higher in Smoker |
| cg11752100 | 7 | 39446909 | Higher in Smoker |
| cg27443265 | 7 | 39298343 | Lower in Smoker |
| cg16114007 | 7 | 39500223 | Lower in Smoker |
| cg22460204 | 7 | 39332836 | Lower in Smoker |
| cg19704451 | 7 | 39373423 | Lower in Smoker |

| | | | |
|---|---|---|---|
| cg14878988 | 2 | 241393351 | Higher in Smoker |
| cg06713830 | 19 | 10220342 | Lower in Smoker |
| cg22386884 | 5 | 54632140 | Lower in Smoker |
| cg02707593 | 5 | 54823369 | Lower in Smoker |
| cg04141141 | 5 | 54777774 | Lower in Smoker |
| cg01789160 | 5 | 54830506 | Lower in Smoker |
| cg02723863 | 19 | 291239 | Higher in Smoker |
| cg24452451 | 19 | 292102 | Higher in Smoker |
| cg11101911 | 6 | 35360713 | Higher in Smoker |
| cg23903774 | 6 | 35370123 | Lower in Smoker |
| cg18887186 | 3 | 12330332 | Higher in Smoker |
| cg02896941 | 4 | 23890669 | Higher in Smoker |
| cg15809868 | 5 | 149111017 | Higher in Smoker |
| cg21184132 | 5 | 149109631 | Higher in Smoker |
| cg00966557 | 5 | 149219027 | Higher in Smoker |
| cg26623478 | 4 | 74863333 | Lower in Smoker |
| cg27341046 | 15 | 75315928 | Higher in Smoker |
| cg01631431 | 20 | 62160863 | Lower in Smoker |
| cg25987417 | 4 | 76823448 | Lower in Smoker |
| cg03928247 | 11 | 70229575 | Lower in Smoker |
| cg08092930 | 11 | 70117714 | Higher in Smoker |
| cg06384026 | 11 | 70117429 | Higher in Smoker |
| cg21231944 | 12 | 82153410 | Higher in Smoker |
| cg21665903 | 12 | 82121138 | Lower in Smoker |
| cg00461901 | 19 | 49653797 | Higher in Smoker |
| cg18169013 | 1 | 203030768 | Lower in Smoker |
| cg11656175 | 1 | 203040823 | Lower in Smoker |
| cg23032229 | 12 | 42720167 | Higher in Smoker |
| cg08300117 | 7 | 44842568 | Lower in Smoker |
| cg12326299 | 5 | 122369268 | Lower in Smoker |
| cg18399510 | 4 | 159644561 | Higher in Smoker |
| cg06261296 | 4 | 159644725 | Higher in Smoker |
| cg24920358 | 1 | 40204285 | Lower in Smoker |
| cg16876636 | 2 | 170494239 | Lower in Smoker |
| cg20988549 | 1 | 43123748 | Higher in Smoker |

| | | | |
|---|---|---|---|
| cg11273834 | 6 | 149863603 | Lower in Smoker |
| cg23978557 | 6 | 109760819 | Lower in Smoker |
| cg04964845 | 14 | 60761524 | Lower in Smoker |
| cg09980195 | 14 | 60715506 | Higher in Smoker |
| cg02703198 | 17 | 58678170 | Higher in Smoker |
| cg11704751 | 12 | 63329118 | Higher in Smoker |
| cg00066512 | 12 | 63199712 | Lower in Smoker |
| cg21417510 | 1 | 113257283 | Lower in Smoker |
| cg06340276 | 4 | 89204787 | Higher in Smoker |
| cg24398318 | 4 | 89205684 | Higher in Smoker |
| cg04132452 | 3 | 160475035 | Lower in Smoker |
| cg06970668 | 11 | 73882184 | Lower in Smoker |
| cg20803370 | 1 | 161136162 | Higher in Smoker |
| cg26938203 | 11 | 67168321 | Higher in Smoker |
| cg04075024 | 11 | 67167826 | Lower in Smoker |
| cg00374596 | 11 | 67169070 | Lower in Smoker |
| cg10717082 | 2 | 28978297 | Lower in Smoker |
| cg24766816 | 6 | 30568535 | Lower in Smoker |
| cg03596877 | 6 | 30568668 | Lower in Smoker |
| cg08677140 | 6 | 30582241 | Lower in Smoker |
| cg04862321 | 6 | 30580928 | Lower in Smoker |
| cg23056979 | 6 | 30034518 | Higher in Smoker |
| cg12817423 | 12 | 80329258 | Higher in Smoker |
| cg24734184 | 12 | 80321176 | Lower in Smoker |
| cg01576496 | 12 | 80269188 | Lower in Smoker |
| cg05798608 | 1 | 202317770 | Higher in Smoker |
| cg23250906 | 1 | 202543017 | Lower in Smoker |
| cg02474116 | 19 | 55625184 | Lower in Smoker |
| cg11378319 | 14 | 104313870 | Higher in Smoker |
| cg19802133 | 19 | 45884900 | Lower in Smoker |
| cg11236879 | 19 | 49375524 | Higher in Smoker |
| cg05702633 | 1 | 204381220 | Higher in Smoker |
| cg21656726 | 20 | 37434262 | Higher in Smoker |
| cg03288217 | 20 | 37464179 | Higher in Smoker |
| cg15735129 | 2 | 182850269 | Lower in Smoker |

| | | | |
|---|---|---|---|
| cg27230534 | 3 | 195267087 | Lower in Smoker |
| cg10317098 | 8 | 9008406 | Lower in Smoker |
| cg14037652 | 10 | 93390387 | Lower in Smoker |
| cg01248445 | 20 | 58513509 | Lower in Smoker |
| cg15707455 | 1 | 28157011 | Higher in Smoker |
| cg12479630 | 1 | 28157569 | Higher in Smoker |
| cg05492605 | 1 | 28157672 | Higher in Smoker |
| cg04951204 | 7 | 94537584 | Higher in Smoker |
| cg16801720 | 7 | 94537744 | Higher in Smoker |
| cg09643313 | 7 | 94537893 | Higher in Smoker |
| cg26884973 | 17 | 48228073 | Higher in Smoker |
| cg25426776 | 17 | 48226898 | Lower in Smoker |
| cg26218835 | 11 | 111617422 | Lower in Smoker |
| cg06876710 | 8 | 26148870 | Higher in Smoker |
| cg13877285 | 8 | 26148873 | Higher in Smoker |
| cg27319536 | 5 | 146260901 | Lower in Smoker |
| cg20560075 | 5 | 146257484 | Higher in Smoker |
| cg10926851 | 5 | 146253830 | Lower in Smoker |
| cg21938261 | 5 | 146257862 | Higher in Smoker |
| cg25542878 | 4 | 6474782 | Higher in Smoker |
| cg02556634 | 4 | 6449000 | Higher in Smoker |
| cg20689476 | 4 | 6385854 | Lower in Smoker |
| cg10516057 | 4 | 6323954 | Lower in Smoker |
| cg01118750 | 10 | 153767507 | Lower in Smoker |
| cg23909343 | 1 | 212457915 | Lower in Smoker |
| cg08285383 | 11 | 64692064 | Higher in Smoker |
| cg14542196 | 14 | 102227915 | Higher in Smoker |
| cg15321108 | 14 | 102227943 | Higher in Smoker |
| cg27663587 | 14 | 102360736 | Lower in Smoker |
| cg04219510 | 14 | 64010574 | Higher in Smoker |
| cg03875433 | 14 | 64010215 | Higher in Smoker |
| cg01943657 | 4 | 102268799 | Higher in Smoker |
| cg15916804 | 10 | 75255500 | Higher in Smoker |
| cg23941268 | 3 | 73046492 | Higher in Smoker |
| cg18777311 | 3 | 73093685 | Lower in Smoker |

| | | | |
|---|---|---|---|
| cg03005685 | 14 | 94640029 | Higher in Smoker |
| cg07126183 | 14 | 94642235 | Higher in Smoker |
| cg12250307 | 19 | 46849103 | Lower in Smoker |
| cg19312935 | 22 | 42017417 | Higher in Smoker |
| cg26971710 | 22 | 42016207 | Lower in Smoker |
| cg10477754 | 10 | 103892376 | Higher in Smoker |
| cg03995156 | 6 | 32122864 | Higher in Smoker |
| cg10369585 | 6 | 32122509 | Higher in Smoker |
| cg24535352 | 6 | 32130570 | Lower in Smoker |
| cg01138671 | 6 | 32130636 | Lower in Smoker |
| cg04264374 | 6 | 32121837 | Higher in Smoker |
| cg18235088 | 6 | 32120623 | Lower in Smoker |
| cg20703320 | 12 | 111021296 | Higher in Smoker |
| cg20383230 | 12 | 111021183 | Higher in Smoker |
| cg10282845 | 12 | 110974698 | Lower in Smoker |
| cg08870741 | 5 | 64858999 | Higher in Smoker |
| cg15368769 | 18 | 77711201 | Higher in Smoker |
| cg26560656 | 18 | 77711462 | Higher in Smoker |
| ch.8.214077F | 8 | 8179546 | Higher in Smoker |
| cg02903059 | 8 | 8235458 | Lower in Smoker |
| cg23015041 | 8 | 8176714 | Lower in Smoker |
| cg01639796 | 1 | 12946833 | Lower in Smoker |
| cg25705255 | 12 | 11422920 | Lower in Smoker |
| cg12467864 | 15 | 91537971 | Higher in Smoker |
| cg06324021 | 1 | 156770381 | Lower in Smoker |
| cg19733740 | 11 | 82609924 | Higher in Smoker |
| cg01761420 | 6 | 106534239 | Lower in Smoker |
| cg14359052 | 6 | 106546744 | Lower in Smoker |
| cg24874254 | 6 | 106546747 | Lower in Smoker |
| cg08742502 | 6 | 106546754 | Lower in Smoker |
| cg17521665 | 6 | 106546704 | Lower in Smoker |
| cg17143179 | 6 | 106546824 | Lower in Smoker |
| cg09036621 | 11 | 129870265 | Lower in Smoker |
| cg20227165 | 11 | 45115819 | Lower in Smoker |
| cg12539975 | 9 | 133539583 | Higher in Smoker |

| | | | |
|---|---|---|---|
| cg21789674 | 6 | 100056686 | Higher in Smoker |
| cg25273233 | 6 | 100054518 | Higher in Smoker |
| cg23758305 | 8 | 70982867 | Higher in Smoker |
| cg14774755 | 8 | 70980603 | Higher in Smoker |
| cg17014849 | 21 | 43299412 | Higher in Smoker |
| cg02286662 | 21 | 43242467 | Lower in Smoker |
| cg08541612 | 1 | 2985720 | Higher in Smoker |
| cg26435254 | 1 | 3087999 | Higher in Smoker |
| cg26762347 | 1 | 2990031 | Higher in Smoker |
| cg13907655 | 1 | 3037712 | Lower in Smoker |
| cg25783497 | 1 | 3307070 | Lower in Smoker |
| cg08739115 | 1 | 3139650 | Lower in Smoker |
| cg24629455 | 1 | 3163970 | Lower in Smoker |
| cg08947445 | 1 | 3328996 | Lower in Smoker |
| cg23818827 | 1 | 3044768 | Lower in Smoker |
| cg00049709 | 1 | 3057810 | Lower in Smoker |
| cg06521247 | 1 | 3209787 | Lower in Smoker |
| cg23999080 | 1 | 3319264 | Lower in Smoker |
| cg16694785 | 1 | 3163710 | Lower in Smoker |
| cg01713250 | 1 | 3289915 | Lower in Smoker |
| cg01900445 | 1 | 3129115 | Lower in Smoker |
| cg22688535 | 1 | 3223973 | Lower in Smoker |
| cg22862319 | 1 | 3289994 | Lower in Smoker |
| cg11837181 | 1 | 3001002 | Lower in Smoker |
| cg00922376 | 1 | 14026584 | Higher in Smoker |
| cg09826587 | 1 | 14026817 | Higher in Smoker |
| cg16680547 | 1 | 14027567 | Lower in Smoker |
| cg20464068 | 1 | 14026054 | Lower in Smoker |
| cg12379145 | 1 | 14030611 | Lower in Smoker |
| cg19359071 | 1 | 14030010 | Lower in Smoker |
| cg25450806 | 1 | 14031383 | Lower in Smoker |
| cg25116709 | 5 | 122426797 | Higher in Smoker |
| cg27087956 | 5 | 122430153 | Higher in Smoker |
| cg19157243 | 5 | 122424706 | Higher in Smoker |
| cg07622748 | 5 | 122425425 | Higher in Smoker |

| | | | |
|---|---|---|---|
| cg27111250 | 4 | 81111177 | Lower in Smoker |
| cg14326413 | 4 | 81123380 | Higher in Smoker |
| cg15627031 | 1 | 45987517 | Higher in Smoker |
| cg23252861 | 10 | 120939391 | Higher in Smoker |
| cg18397310 | X | 23685473 | Lower in Smoker |
| cg03716231 | X | 23684892 | Lower in Smoker |
| cg10718809 | 11 | 64087106 | Higher in Smoker |
| cg25944898 | 11 | 64085532 | Higher in Smoker |
| cg03945538 | 1 | 173447427 | Higher in Smoker |
| cg18824775 | 5 | 176731107 | Higher in Smoker |
| cg08293303 | 5 | 176731731 | Lower in Smoker |
| cg04233747 | 5 | 145214971 | Higher in Smoker |
| cg18338925 | 6 | 105752150 | Lower in Smoker |
| cg02374912 | 2 | 44589161 | Higher in Smoker |
| cg27343216 | 2 | 44588835 | Higher in Smoker |
| cg07914629 | 2 | 44589600 | Higher in Smoker |
| cg01101355 | 20 | 47422326 | Lower in Smoker |
| cg23300368 | 8 | 68664908 | Lower in Smoker |
| cg15971518 | 11 | 57159174 | Lower in Smoker |
| cg10801670 | 1 | 186264674 | Lower in Smoker |
| cg03590051 | 20 | 62200285 | Lower in Smoker |
| cg06695286 | 12 | 42880445 | Lower in Smoker |
| cg15655366 | 12 | 42919987 | Lower in Smoker |
| cg25078081 | 12 | 42878192 | Higher in Smoker |
| cg16720847 | 12 | 42854129 | Lower in Smoker |
| cg17393041 | 3 | 64136333 | Lower in Smoker |
| cg24269846 | 12 | 57146087 | Higher in Smoker |
| cg16398944 | 6 | 57182319 | Higher in Smoker |
| cg20059249 | 6 | 57245939 | Lower in Smoker |
| cg14836636 | 12 | 120106292 | Higher in Smoker |
| cg19302295 | 19 | 14228590 | Higher in Smoker |
| cg24603152 | 1 | 84543539 | Lower in Smoker |
| cg16374471 | 1 | 84543951 | Higher in Smoker |
| cg14547599 | 12 | 49410248 | Lower in Smoker |
| cg10902667 | 7 | 151423739 | Higher in Smoker |

| | | | |
|---|---|---|---|
| cg13439339 | 7 | 151441268 | Higher in Smoker |
| cg15787544 | 7 | 151489862 | Higher in Smoker |
| cg01246802 | 7 | 151421620 | Higher in Smoker |
| cg08151809 | 7 | 151480352 | Lower in Smoker |
| cg13334211 | 7 | 151328924 | Higher in Smoker |
| cg12889558 | 7 | 151330217 | Higher in Smoker |
| cg26033657 | 17 | 66507816 | Higher in Smoker |
| cg04987827 | 17 | 66508605 | Higher in Smoker |
| cg26559509 | 7 | 766384 | Higher in Smoker |
| cg10396616 | 7 | 768364 | Lower in Smoker |
| cg00992090 | 7 | 613222 | Higher in Smoker |
| cg18847089 | 7 | 676060 | Lower in Smoker |
| cg15589939 | 7 | 624495 | Lower in Smoker |
| cg00795927 | 7 | 640603 | Lower in Smoker |
| cg17593625 | 7 | 752800 | Higher in Smoker |
| cg17126250 | 7 | 106759732 | Lower in Smoker |
| cg17921248 | 17 | 64298993 | Higher in Smoker |
| cg05845533 | 17 | 64672205 | Lower in Smoker |
| cg25228562 | 17 | 64718121 | Lower in Smoker |
| cg26780231 | 17 | 64468338 | Lower in Smoker |
| cg01477379 | 17 | 64444522 | Lower in Smoker |
| cg10486865 | 17 | 64355892 | Lower in Smoker |
| cg15093766 | 17 | 64408569 | Lower in Smoker |
| cg24171047 | 17 | 64765921 | Lower in Smoker |
| cg13920858 | 17 | 64617748 | Lower in Smoker |
| cg01895374 | 17 | 64536954 | Lower in Smoker |
| cg20152362 | 17 | 64783099 | Lower in Smoker |
| cg24250393 | 16 | 23846838 | Higher in Smoker |
| cg00795205 | 16 | 23916466 | Lower in Smoker |
| cg05248742 | 16 | 24142386 | Lower in Smoker |
| cg05632631 | 16 | 24099614 | Lower in Smoker |
| cg26555733 | 16 | 23846279 | Lower in Smoker |
| cg06485596 | 16 | 24112658 | Lower in Smoker |
| cg03973705 | 16 | 24174850 | Lower in Smoker |
| cg04086239 | 16 | 24067174 | Lower in Smoker |

| | | | |
|---|---|---|---|
| cg09031790 | 16 | 24129948 | Lower in Smoker |
| cg06401532 | 16 | 24220008 | Lower in Smoker |
| cg12598524 | 2 | 46088325 | Higher in Smoker |
| cg02544394 | 2 | 45878759 | Higher in Smoker |
| cg20227627 | 2 | 46010726 | Lower in Smoker |
| cg12165758 | 14 | 61789593 | Higher in Smoker |
| cg25562834 | 14 | 61789603 | Higher in Smoker |
| cg13120108 | 14 | 61790037 | Higher in Smoker |
| cg10855746 | 14 | 61938004 | Lower in Smoker |
| cg12457611 | 3 | 169941221 | Higher in Smoker |
| cg20695805 | 3 | 169940192 | Higher in Smoker |
| cg21847584 | 3 | 169939805 | Higher in Smoker |
| cg24295479 | 3 | 169940196 | Higher in Smoker |
| cg12670756 | 3 | 169940172 | Higher in Smoker |
| cg08532220 | 3 | 169942945 | Lower in Smoker |
| ch.10.202299R | 10 | 6548100 | Higher in Smoker |
| cg23434428 | 10 | 6557129 | Lower in Smoker |
| cg20269544 | 1 | 2025441 | Lower in Smoker |
| cg15481172 | 1 | 2059086 | Higher in Smoker |
| cg12541626 | 19 | 47217900 | Higher in Smoker |
| cg11882144 | 8 | 48872560 | Higher in Smoker |
| cg05603630 | 10 | 52751341 | Higher in Smoker |
| cg05199084 | 10 | 53493554 | Lower in Smoker |
| cg27125304 | 10 | 52963388 | Lower in Smoker |
| cg13792641 | 10 | 53817201 | Lower in Smoker |
| cg25102782 | 2 | 179316089 | Higher in Smoker |
| cg21030559 | X | 3522732 | Lower in Smoker |
| cg15493780 | 10 | 120355201 | Higher in Smoker |
| cg24070673 | 5 | 35062210 | Lower in Smoker |
| cg03940074 | 16 | 11376154 | Lower in Smoker |
| cg14209854 | 16 | 11370349 | Higher in Smoker |
| cg24200426 | 19 | 50184585 | Lower in Smoker |
| cg05164514 | 4 | 148605397 | Higher in Smoker |
| cg11373980 | 21 | 48081066 | Lower in Smoker |
| cg22528358 | 1 | 107598549 | Lower in Smoker |

| | | | |
|---|---|---|---|
| cg01162920 | 16 | 68362700 | Higher in Smoker |
| cg06092312 | 16 | 68345214 | Lower in Smoker |
| cg23538195 | 12 | 3603811 | Lower in Smoker |
| cg09629675 | 12 | 3701350 | Lower in Smoker |
| cg24344011 | 20 | 39666465 | Lower in Smoker |
| cg07585069 | 17 | 27039120 | Higher in Smoker |
| cg18713809 | 22 | 18923876 | Higher in Smoker |
| cg11438552 | 22 | 18919803 | Lower in Smoker |
| cg03407228 | 22 | 18921705 | Lower in Smoker |
| cg19822518 | 3 | 71834840 | Higher in Smoker |
| cg22867816 | 4 | 16081205 | Lower in Smoker |
| cg05007022 | 14 | 75330462 | Lower in Smoker |
| cg10165162 | 14 | 75330792 | Lower in Smoker |
| cg04212235 | 1 | 150293070 | Higher in Smoker |
| cg26786623 | 1 | 150297760 | Lower in Smoker |
| cg26115927 | 1 | 52869501 | Higher in Smoker |
| cg13689156 | 12 | 50017412 | Higher in Smoker |
| cg26734215 | 20 | 62616301 | Lower in Smoker |
| cg04520396 | 17 | 1585312 | Higher in Smoker |
| cg15324340 | X | 106871509 | Higher in Smoker |
| cg03344806 | 7 | 18067282 | Lower in Smoker |
| cg20842040 | X | 12809608 | Higher in Smoker |
| cg24146586 | 17 | 74349090 | Higher in Smoker |
| cg24838305 | 19 | 50097747 | Lower in Smoker |
| cg26257869 | 19 | 50119332 | Lower in Smoker |
| cg17444904 | 7 | 29603253 | Higher in Smoker |
| cg16532606 | 17 | 46036419 | Higher in Smoker |
| cg17204213 | 5 | 119800403 | Higher in Smoker |
| cg11613229 | 5 | 119800742 | Higher in Smoker |
| cg05089968 | 6 | 166722773 | Lower in Smoker |
| cg27369401 | 6 | 166722053 | Lower in Smoker |
| cg09424870 | 19 | 5784792 | Lower in Smoker |
| cg07452777 | 3 | 138725214 | Lower in Smoker |
| cg25253217 | 19 | 47776728 | Higher in Smoker |
| cg23841361 | 6 | 30524010 | Higher in Smoker |

| | | | |
|---|---|---|---|
| cg12163646 | 6 | 30529027 | Lower in Smoker |
| cg13413789 | 6 | 30524755 | Higher in Smoker |
| cg26381878 | 22 | 45071340 | Lower in Smoker |
| cg16326073 | 22 | 45125218 | Higher in Smoker |
| cg16829924 | 11 | 36383991 | Lower in Smoker |
| cg03730492 | 11 | 36398442 | Higher in Smoker |
| cg24369746 | 11 | 36398236 | Higher in Smoker |
| cg00085029 | 11 | 36398393 | Higher in Smoker |
| cg14850730 | 11 | 36476232 | Lower in Smoker |
| cg06677913 | 5 | 176874720 | Higher in Smoker |
| cg17491117 | 5 | 176877512 | Lower in Smoker |
| cg13590816 | 5 | 126853178 | Higher in Smoker |
| cg05443326 | 5 | 126853169 | Higher in Smoker |
| cg23846114 | X | 150867161 | Lower in Smoker |
| cg06972381 | 11 | 32951378 | Higher in Smoker |
| cg14644001 | 6 | 32116653 | Higher in Smoker |
| cg27068095 | 6 | 32119016 | Higher in Smoker |
| cg11515873 | 6 | 32117401 | Lower in Smoker |
| cg21037008 | 6 | 32119939 | Higher in Smoker |
| cg00403498 | 6 | 32119923 | Higher in Smoker |
| cg19769182 | 16 | 29823868 | Higher in Smoker |
| cg02725398 | 3 | 9988144 | Lower in Smoker |
| cg21784396 | 7 | 127991421 | Lower in Smoker |
| cg17632579 | 4 | 119274013 | Higher in Smoker |
| cg17658733 | 6 | 27219385 | Higher in Smoker |
| cg27174822 | 16 | 2902830 | Higher in Smoker |
| cg05233310 | 16 | 2765900 | Lower in Smoker |
| cg15996051 | 19 | 690661 | Lower in Smoker |
| cg26931334 | 19 | 690763 | Lower in Smoker |
| cg03337218 | 10 | 25189866 | Higher in Smoker |
| cg24618739 | 10 | 25154684 | Lower in Smoker |
| cg09556178 | 10 | 25139517 | Lower in Smoker |
| cg14580287 | 10 | 25173338 | Lower in Smoker |
| cg23418510 | 10 | 25240660 | Lower in Smoker |
| cg15760529 | 19 | 843307 | Higher in Smoker |

| | | | |
|---|---|---|---|
| cg03251852 | 19 | 40917184 | Lower in Smoker |
| cg12548454 | 9 | 80911457 | Higher in Smoker |
| cg07684019 | 5 | 139174529 | Lower in Smoker |
| cg20918069 | 8 | 18870348 | Higher in Smoker |
| cg12082271 | 8 | 18541556 | Lower in Smoker |
| cg23927744 | 19 | 43423176 | Lower in Smoker |
| cg26186954 | 8 | 87082008 | Higher in Smoker |
| cg12352359 | 11 | 14542136 | Higher in Smoker |
| cg03324947 | 7 | 42971765 | Higher in Smoker |
| cg12800803 | 20 | 60717299 | Lower in Smoker |
| cg08627380 | 6 | 170858811 | Lower in Smoker |
| cg19692996 | 6 | 170862576 | Higher in Smoker |
| cg18978476 | 6 | 170862245 | Higher in Smoker |
| cg05184917 | 16 | 67970212 | Lower in Smoker |
| cg00808132 | 14 | 23511306 | Lower in Smoker |
| cg18955704 | 17 | 36909029 | Higher in Smoker |
| cg18034041 | 6 | 32811884 | Higher in Smoker |
| cg20060630 | 6 | 32809657 | Higher in Smoker |
| cg16009764 | 6 | 32809494 | Lower in Smoker |
| cg21764921 | 6 | 32825040 | Lower in Smoker |
| cg00045690 | 6 | 32825897 | Lower in Smoker |
| cg16853860 | 6 | 32823116 | Higher in Smoker |
| cg13403689 | 6 | 32820641 | Higher in Smoker |
| cg15993458 | 6 | 32820691 | Lower in Smoker |
| cg05912466 | 14 | 90725299 | Lower in Smoker |
| cg15517875 | 14 | 90724250 | Lower in Smoker |
| cg13942016 | 11 | 47447463 | Lower in Smoker |
| cg03701005 | 17 | 40729832 | Higher in Smoker |
| cg10372372 | 17 | 40729705 | Higher in Smoker |
| cg17757000 | 19 | 40476423 | Lower in Smoker |
| cg01544733 | 2 | 231920892 | Lower in Smoker |
| cg12353549 | 17 | 30771552 | Higher in Smoker |
| cg04134394 | 17 | 30805387 | Lower in Smoker |
| cg02197938 | 17 | 65363257 | Lower in Smoker |
| cg13706041 | 17 | 65362673 | Higher in Smoker |

| | | | |
|---|---|---|---|
| cg00345965 | 1 | 151226992 | Lower in Smoker |
| cg13959647 | 9 | 123605229 | Lower in Smoker |
| cg27418402 | 3 | 64008161 | Lower in Smoker |
| cg07773642 | 16 | 74330896 | Higher in Smoker |
| cg04504001 | 16 | 74340046 | Lower in Smoker |
| cg21824620 | 17 | 40986379 | Lower in Smoker |
| cg04218520 | 2 | 54092167 | Lower in Smoker |
| cg13620615 | 21 | 40555724 | Lower in Smoker |
| cg24558132 | 21 | 40555414 | Higher in Smoker |
| cg07632694 | 21 | 40555409 | Higher in Smoker |
| cg26070636 | 18 | 12703072 | Lower in Smoker |
| cg23903588 | 7 | 1607663 | Lower in Smoker |
| cg01966425 | 6 | 31093913 | Lower in Smoker |
| cg26965877 | 6 | 31107240 | Higher in Smoker |
| cg25380351 | 6 | 31106181 | Lower in Smoker |
| cg20823137 | 7 | 56097042 | Lower in Smoker |
| cg27339143 | 1 | 109825518 | Higher in Smoker |
| cg18351607 | 10 | 124739543 | Lower in Smoker |
| cg26227523 | 15 | 77287243 | Lower in Smoker |
| cg02086742 | 19 | 804311 | Lower in Smoker |
| cg06879406 | 19 | 797398 | Higher in Smoker |
| cg08462292 | 1 | 97188168 | Higher in Smoker |
| cg20228788 | 7 | 99032619 | Lower in Smoker |
| cg15656181 | 5 | 71654404 | Higher in Smoker |
| cg13754720 | 9 | 98274853 | Higher in Smoker |
| cg16626387 | 9 | 98268788 | Higher in Smoker |
| cg13461049 | 9 | 98213755 | Lower in Smoker |
| cg04145643 | 1 | 45288012 | Lower in Smoker |
| cg20692414 | 1 | 11539744 | Higher in Smoker |
| cg22002075 | 1 | 11538793 | Higher in Smoker |
| cg25287708 | 1 | 11596434 | Lower in Smoker |
| cg21296749 | 1 | 11538865 | Lower in Smoker |
| cg22138393 | 8 | 97340270 | Lower in Smoker |
| cg11921952 | 11 | 449622 | Lower in Smoker |
| cg21075020 | 11 | 488555 | Lower in Smoker |

| | | | |
|---|---|---|---|
| cg22352122 | 11 | 453757 | Lower in Smoker |
| cg10798225 | 11 | 448822 | Lower in Smoker |
| cg22761205 | 11 | 457256 | Lower in Smoker |
| cg03588460 | 10 | 89623442 | Higher in Smoker |
| cg18920423 | 10 | 23481389 | Higher in Smoker |
| cg20014049 | 10 | 23481385 | Higher in Smoker |
| cg06550984 | 10 | 23480002 | Higher in Smoker |
| cg17076890 | 10 | 23481421 | Higher in Smoker |
| cg23022053 | 14 | 52733243 | Lower in Smoker |
| cg03971521 | 19 | 14583389 | Lower in Smoker |
| cg06738602 | 14 | 52780634 | Higher in Smoker |
| cg00915178 | 1 | 71513733 | Higher in Smoker |
| cg22366350 | 12 | 57082604 | Higher in Smoker |
| cg24022301 | 1 | 78956570 | Higher in Smoker |
| cg03495868 | 1 | 78956905 | Higher in Smoker |
| cg13100218 | 1 | 117487539 | Lower in Smoker |
| cg15937641 | 1 | 117529619 | Lower in Smoker |
| cg15038938 | 9 | 114361411 | Higher in Smoker |
| cg14275693 | 9 | 114363076 | Lower in Smoker |
| cg13397260 | 9 | 114358399 | Lower in Smoker |
| cg09461185 | 1 | 186649631 | Higher in Smoker |
| cg24716125 | 3 | 46933808 | Higher in Smoker |
| cg07805345 | 3 | 46922486 | Lower in Smoker |
| cg11398680 | 8 | 142011853 | Higher in Smoker |
| cg06944982 | 8 | 141779353 | Lower in Smoker |
| cg00641828 | 8 | 141715451 | Lower in Smoker |
| cg17957094 | 8 | 141976433 | Lower in Smoker |
| cg20637223 | 8 | 141735573 | Lower in Smoker |
| cg03268399 | 8 | 141965597 | Lower in Smoker |
| cg24143495 | 8 | 141890871 | Lower in Smoker |
| cg24411870 | 8 | 141908312 | Lower in Smoker |
| cg06931405 | 8 | 141668936 | Lower in Smoker |
| cg24383305 | 8 | 141929688 | Lower in Smoker |
| cg14774290 | 8 | 141934252 | Lower in Smoker |
| cg12743031 | 8 | 27219512 | Lower in Smoker |

| | | | |
|---|---|---|---|
| cg18734877 | 8 | 27297419 | Lower in Smoker |
| cg18976893 | 8 | 27168292 | Higher in Smoker |
| cg00158934 | 20 | 62165160 | Higher in Smoker |
| cg21484834 | 20 | 62168579 | Lower in Smoker |
| cg13520525 | 20 | 62168463 | Lower in Smoker |
| cg21578195 | 20 | 62168727 | Lower in Smoker |
| cg01302136 | 6 | 43118059 | Lower in Smoker |
| cg24679411 | 12 | 6876188 | Higher in Smoker |
| cg15932738 | 12 | 6875631 | Higher in Smoker |
| cg22979093 | 7 | 137028410 | Higher in Smoker |
| cg26570040 | 19 | 50361827 | Lower in Smoker |
| cg21545720 | 1 | 32405093 | Lower in Smoker |
| cg21234162 | 9 | 96858147 | Lower in Smoker |
| ch.15.97966CF | 15 | 65855109 | Higher in Smoker |
| cg14498666 | 9 | 21031822 | Higher in Smoker |
| cg01152729 | 11 | 47593274 | Lower in Smoker |
| cg04776231 | 7 | 77168113 | Higher in Smoker |
| cg01015416 | 7 | 77166650 | Higher in Smoker |
| cg18291085 | 7 | 77236596 | Lower in Smoker |
| cg22162757 | 1 | 214699233 | Higher in Smoker |
| cg11504081 | 1 | 214725300 | Higher in Smoker |
| cg06768385 | 1 | 214557399 | Higher in Smoker |
| cg18816474 | 1 | 214687737 | Lower in Smoker |
| cg16318728 | 1 | 214679247 | Lower in Smoker |
| cg23073032 | 1 | 214724414 | Lower in Smoker |
| cg07157506 | 18 | 12883603 | Higher in Smoker |
| cg16491233 | 18 | 12794178 | Lower in Smoker |
| cg21548772 | 3 | 47422338 | Higher in Smoker |
| cg16928313 | 2 | 120578956 | Higher in Smoker |
| cg20707066 | 11 | 18809866 | Lower in Smoker |
| cg26363363 | 12 | 7060386 | Higher in Smoker |
| cg26004710 | 12 | 7066825 | Lower in Smoker |
| cg11700959 | 12 | 7066664 | Lower in Smoker |
| cg25936670 | 20 | 2854063 | Lower in Smoker |
| cg04214459 | 1 | 198637612 | Lower in Smoker |

| | | | |
|---|---|---|---|
| cg09247619 | 1 | 198648849 | Lower in Smoker |
| cg05353099 | 11 | 67203544 | Lower in Smoker |
| cg02685484 | 11 | 67203360 | Lower in Smoker |
| cg23456595 | 11 | 67203434 | Lower in Smoker |
| cg14621763 | 9 | 8856695 | Lower in Smoker |
| cg06967784 | 10 | 129809827 | Lower in Smoker |
| cg07832354 | 10 | 129709517 | Lower in Smoker |
| cg14731462 | 10 | 129789429 | Lower in Smoker |
| cg14933807 | 10 | 129883528 | Lower in Smoker |
| cg26606542 | 1 | 44069535 | Lower in Smoker |
| cg05110828 | 3 | 61570099 | Lower in Smoker |
| cg11921411 | 3 | 61950990 | Lower in Smoker |
| cg07336740 | 3 | 61608199 | Lower in Smoker |
| cg27525626 | 3 | 61726357 | Lower in Smoker |
| cg16836853 | 3 | 61896452 | Lower in Smoker |
| cg11261264 | 19 | 55720737 | Lower in Smoker |
| cg11545521 | 11 | 48019467 | Higher in Smoker |
| cg13759676 | 6 | 128799557 | Lower in Smoker |
| cg01946574 | 18 | 7568186 | Higher in Smoker |
| cg10225197 | 2 | 220159976 | Higher in Smoker |
| cg26308704 | 7 | 158325586 | Higher in Smoker |
| cg18407955 | 7 | 158110685 | Higher in Smoker |
| cg11053171 | 7 | 157890968 | Lower in Smoker |
| cg08576518 | 7 | 157711612 | Lower in Smoker |
| cg00904407 | 7 | 158364526 | Lower in Smoker |
| cg17022244 | 7 | 157566015 | Lower in Smoker |
| cg24154853 | 7 | 158122151 | Lower in Smoker |
| cg17376415 | 7 | 157914479 | Lower in Smoker |
| cg06779232 | 7 | 157579277 | Lower in Smoker |
| cg26389638 | 7 | 158264915 | Lower in Smoker |
| cg16016583 | 7 | 158246795 | Lower in Smoker |
| cg10257673 | 7 | 157573278 | Lower in Smoker |
| cg19212465 | 7 | 157765170 | Lower in Smoker |
| cg20983647 | 7 | 158252289 | Lower in Smoker |
| cg06423822 | 7 | 157701024 | Lower in Smoker |

| | | | |
|---|---|---|---|
| cg23455837 | 7 | 157809325 | Lower in Smoker |
| cg08452870 | 7 | 158264935 | Lower in Smoker |
| cg24646841 | 7 | 157818696 | Lower in Smoker |
| cg20956114 | 7 | 157451363 | Lower in Smoker |
| cg01818715 | 7 | 157493445 | Lower in Smoker |
| cg20519944 | 7 | 157412886 | Lower in Smoker |
| cg12144100 | 7 | 157890277 | Lower in Smoker |
| cg00449390 | 7 | 158379223 | Lower in Smoker |
| cg17701146 | 7 | 157387361 | Lower in Smoker |
| cg06649856 | 7 | 158355003 | Lower in Smoker |
| cg11072645 | 7 | 157754746 | Lower in Smoker |
| cg27196745 | 12 | 15475319 | Higher in Smoker |
| cg22374861 | 12 | 15475342 | Higher in Smoker |
| cg11643457 | 12 | 80904153 | Lower in Smoker |
| cg09816096 | 19 | 5223343 | Lower in Smoker |
| cg10948929 | 7 | 121513695 | Higher in Smoker |
| cg07757861 | 7 | 121513704 | Higher in Smoker |
| cg22410750 | 7 | 121513944 | Higher in Smoker |
| cg06527154 | 7 | 121566048 | Lower in Smoker |
| cg14305239 | 9 | 130477845 | Higher in Smoker |
| cg24615831 | 11 | 112097290 | Higher in Smoker |
| cg26925614 | 11 | 112097290 | Higher in Smoker |
| cg16370389 | 4 | 37962041 | Lower in Smoker |
| cg18431951 | 8 | 144906507 | Higher in Smoker |
| cg08862452 | 8 | 144903025 | Lower in Smoker |
| cg05359099 | 8 | 144906449 | Lower in Smoker |
| cg06537625 | 1 | 31538931 | Higher in Smoker |
| cg09261992 | 1 | 31510529 | Higher in Smoker |
| cg08659707 | 2 | 20527677 | Lower in Smoker |
| cg19311679 | 8 | 30891583 | Higher in Smoker |
| cg20533040 | 8 | 30891671 | Higher in Smoker |
| cg05585129 | 12 | 132413935 | Higher in Smoker |
| cg25011530 | 7 | 105162470 | Lower in Smoker |
| cg08265288 | 12 | 44131313 | Lower in Smoker |
| cg26545584 | 12 | 44150219 | Lower in Smoker |

| | | | |
|---|---|---|---|
| cg19136704 | 22 | 37215611 | Lower in Smoker |
| cg05878558 | 19 | 45147316 | Higher in Smoker |
| cg22845901 | 3 | 110791439 | Higher in Smoker |
| cg07832203 | 1 | 161050227 | Lower in Smoker |
| cg06547490 | 10 | 134222053 | Higher in Smoker |
| cg00259755 | 10 | 134209763 | Higher in Smoker |
| cg13750441 | 3 | 58316267 | Lower in Smoker |
| cg04686980 | 8 | 77893158 | Lower in Smoker |
| cg16785344 | 12 | 120703817 | Higher in Smoker |
| cg20153322 | 12 | 120703977 | Higher in Smoker |
| cg22564731 | 12 | 120668744 | Lower in Smoker |
| cg24873872 | 6 | 36391494 | Higher in Smoker |
| cg22897198 | 6 | 36391250 | Higher in Smoker |
| cg01059100 | 16 | 31214607 | Higher in Smoker |
| cg09866102 | 16 | 31214134 | Higher in Smoker |
| cg00130693 | 1 | 226110727 | Lower in Smoker |
| cg21458840 | 8 | 144691748 | Higher in Smoker |
| cg04267284 | 20 | 25227488 | Lower in Smoker |
| cg26884581 | 11 | 64527414 | Lower in Smoker |
| cg15575700 | 17 | 42072622 | Higher in Smoker |
| cg08729600 | 12 | 9360986 | Lower in Smoker |
| cg05522415 | 3 | 49135801 | Lower in Smoker |
| cg24273028 | 4 | 17513991 | Higher in Smoker |
| cg15923042 | 4 | 17513528 | Higher in Smoker |
| cg08169901 | 6 | 163834872 | Higher in Smoker |
| cg24310785 | 6 | 163965223 | Lower in Smoker |
| cg22629987 | 2 | 37571677 | Higher in Smoker |
| cg09386458 | 2 | 37571178 | Lower in Smoker |
| cg03488456 | 16 | 29706275 | Lower in Smoker |
| cg00097384 | 16 | 29703459 | Lower in Smoker |
| cg13643914 | 4 | 122302226 | Higher in Smoker |
| cg24727399 | 4 | 122302265 | Higher in Smoker |
| cg05604079 | 4 | 122302268 | Higher in Smoker |
| cg14847983 | 3 | 49130482 | Higher in Smoker |
| cg26475097 | 3 | 49130805 | Higher in Smoker |

| | | | |
|---|---|---|---|
| cg07451141 | 11 | 32914648 | Higher in Smoker |
| cg24354730 | 19 | 10815588 | Lower in Smoker |
| cg04522896 | 2 | 136292219 | Lower in Smoker |
| cg13588645 | 2 | 136289118 | Higher in Smoker |
| cg17689206 | 2 | 136288817 | Higher in Smoker |
| cg25203036 | 12 | 57704522 | Lower in Smoker |
| cg04535340 | 19 | 8454867 | Higher in Smoker |
| cg26744332 | 19 | 8469281 | Lower in Smoker |
| cg21346533 | 8 | 37757250 | Higher in Smoker |
| cg08385995 | 16 | 513010 | Lower in Smoker |
| cg05692420 | 16 | 523818 | Lower in Smoker |
| cg04166554 | 16 | 572062 | Lower in Smoker |
| cg08936549 | 16 | 560666 | Lower in Smoker |
| cg03419051 | 17 | 29814382 | Lower in Smoker |
| cg24873743 | 2 | 73340489 | Higher in Smoker |
| cg04943085 | 2 | 73340257 | Lower in Smoker |
| cg08364860 | 10 | 27827130 | Lower in Smoker |
| cg24614854 | 2 | 65356625 | Higher in Smoker |
| cg19071367 | 11 | 66036015 | Higher in Smoker |
| cg14538055 | 11 | 66035834 | Higher in Smoker |
| cg21531702 | 11 | 66035773 | Higher in Smoker |
| cg16728323 | 13 | 111212174 | Lower in Smoker |
| cg05932702 | 12 | 72148251 | Lower in Smoker |
| cg25490585 | 15 | 55581420 | Higher in Smoker |
| cg19853516 | 18 | 52495981 | Higher in Smoker |
| cg06958567 | 18 | 52495541 | Lower in Smoker |
| cg12914096 | 4 | 13485897 | Lower in Smoker |
| cg23934503 | 14 | 21945053 | Higher in Smoker |
| cg24214386 | 11 | 82782984 | Higher in Smoker |
| cg24227371 | 11 | 82718527 | Lower in Smoker |
| cg03452174 | 17 | 27045113 | Higher in Smoker |
| cg19998230 | 17 | 27045302 | Higher in Smoker |
| cg18761745 | 12 | 120540895 | Lower in Smoker |
| cg23832237 | 17 | 72667208 | Higher in Smoker |
| cg19801556 | 17 | 72733450 | Higher in Smoker |

| | | | |
|---|---|---|---|
| cg10817887 | 17 | 72732964 | Higher in Smoker |
| cg16208507 | 11 | 107798913 | Lower in Smoker |
| cg17498773 | 11 | 107799532 | Lower in Smoker |
| cg10487770 | 5 | 57879443 | Higher in Smoker |
| cg21180793 | 5 | 58096519 | Lower in Smoker |
| cg23123909 | 5 | 57878953 | Higher in Smoker |
| cg18312807 | 2 | 135809693 | Higher in Smoker |
| cg19857977 | 1 | 220408360 | Lower in Smoker |
| cg03349407 | 1 | 220441256 | Lower in Smoker |
| cg12564108 | 17 | 80624966 | Lower in Smoker |
| cg16167485 | 12 | 56367262 | Higher in Smoker |
| cg00172967 | 12 | 56367901 | Higher in Smoker |
| cg02235760 | 17 | 40307236 | Higher in Smoker |
| cg00435173 | 17 | 40284046 | Lower in Smoker |
| cg13547803 | 3 | 133614782 | Higher in Smoker |
| cg12319221 | 3 | 128498694 | Lower in Smoker |
| cg19205850 | 3 | 128446370 | Lower in Smoker |
| cg10098464 | 1 | 205745560 | Lower in Smoker |
| cg04591308 | 19 | 16224280 | Lower in Smoker |
| cg17556578 | 15 | 63481415 | Higher in Smoker |
| cg02547323 | X | 103087380 | Higher in Smoker |
| cg03363466 | 19 | 42463690 | Higher in Smoker |
| cg15209169 | 9 | 125702779 | Lower in Smoker |
| cg23441030 | 1 | 174909464 | Lower in Smoker |
| cg18978324 | 14 | 24740937 | Higher in Smoker |
| cg11138679 | 14 | 24740526 | Lower in Smoker |
| cg18279670 | 22 | 37172204 | Higher in Smoker |
| cg06225154 | 22 | 37640364 | Higher in Smoker |
| cg15575222 | 20 | 1206255 | Higher in Smoker |
| cg21337296 | 20 | 1207118 | Higher in Smoker |
| cg07683873 | 20 | 1206739 | Higher in Smoker |
| cg24134071 | 19 | 13059556 | Lower in Smoker |
| cg13717532 | 14 | 68972555 | Lower in Smoker |
| cg04179571 | 14 | 68444789 | Lower in Smoker |
| cg10333051 | 14 | 68541391 | Lower in Smoker |

| | | | |
|---|---|---|---|
| cg18403754 | 14 | 68721274 | Lower in Smoker |
| cg13539397 | 14 | 68785498 | Lower in Smoker |
| cg14983684 | 14 | 68822877 | Lower in Smoker |
| cg01989902 | 14 | 68807524 | Lower in Smoker |
| cg07112884 | 14 | 68548136 | Lower in Smoker |
| cg04994980 | 7 | 4882608 | Lower in Smoker |
| cg11594299 | 7 | 4924002 | Lower in Smoker |
| cg05045383 | 20 | 55926193 | Higher in Smoker |
| cg12070911 | 6 | 150209640 | Lower in Smoker |
| cg18926786 | 6 | 150244388 | Lower in Smoker |
| cg07579404 | 6 | 150346721 | Higher in Smoker |
| cg08119607 | 6 | 150347053 | Higher in Smoker |
| cg12173506 | 3 | 12705805 | Lower in Smoker |
| cg08285589 | 11 | 36599110 | Lower in Smoker |
| cg24704182 | 1 | 155108583 | Higher in Smoker |
| cg26189283 | 1 | 155109378 | Lower in Smoker |
| cg26821327 | 11 | 36616048 | Lower in Smoker |
| cg11778749 | 14 | 102772430 | Lower in Smoker |
| cg00096956 | 5 | 34691477 | Higher in Smoker |
| cg13182391 | X | 17878832 | Higher in Smoker |
| cg19865182 | 7 | 39663054 | Higher in Smoker |
| cg21200923 | 18 | 9481257 | Higher in Smoker |
| cg23873398 | 14 | 36278529 | Higher in Smoker |
| cg11015424 | 14 | 36157803 | Lower in Smoker |
| ch.20.437154R | 20 | 20495441 | Higher in Smoker |
| cg23465989 | 20 | 37101470 | Higher in Smoker |
| cg20073376 | 20 | 37146256 | Lower in Smoker |
| cg16872071 | 9 | 135997155 | Higher in Smoker |
| cg21295827 | 1 | 176708719 | Lower in Smoker |
| cg04842146 | 8 | 85097056 | Higher in Smoker |
| cg23649708 | 8 | 85097049 | Higher in Smoker |
| cg21671806 | 8 | 85097031 | Higher in Smoker |
| cg26723492 | 8 | 85538646 | Higher in Smoker |
| cg26669044 | 8 | 85095697 | Higher in Smoker |
| cg10846682 | 2 | 238805257 | Higher in Smoker |

| | | | |
|---|---|---|---|
| cg14999001 | 7 | 45197441 | Higher in Smoker |
| cg03284870 | 7 | 45197346 | Higher in Smoker |
| cg17930878 | 7 | 45197251 | Lower in Smoker |
| cg25201101 | 12 | 131355465 | Lower in Smoker |
| cg05742691 | 5 | 170238255 | Lower in Smoker |
| cg03118417 | 19 | 5974092 | Lower in Smoker |
| cg05511815 | 19 | 5978281 | Higher in Smoker |
| cg03127656 | 5 | 36303314 | Lower in Smoker |
| cg20894246 | 22 | 41682263 | Higher in Smoker |
| cg07745941 | 22 | 41679810 | Lower in Smoker |
| cg24879327 | 17 | 8191305 | Higher in Smoker |
| cg11178443 | 17 | 8192024 | Higher in Smoker |
| cg25277553 | 1 | 112162387 | Higher in Smoker |
| cg04907505 | 12 | 69004265 | Higher in Smoker |
| cg10497692 | 1 | 21996199 | Higher in Smoker |
| cg10038867 | 1 | 21982511 | Lower in Smoker |
| cg03132729 | 1 | 21947437 | Higher in Smoker |
| cg08118344 | 1 | 21974525 | Lower in Smoker |
| cg11869193 | 17 | 2839187 | Higher in Smoker |
| cg25373595 | 17 | 2699718 | Higher in Smoker |
| cg25871594 | 17 | 2795775 | Lower in Smoker |
| cg18394567 | 17 | 2758375 | Lower in Smoker |
| cg01770333 | 4 | 99182328 | Higher in Smoker |
| cg07285276 | 9 | 134613015 | Lower in Smoker |
| cg14162011 | 9 | 134571649 | Lower in Smoker |
| cg14485643 | 9 | 134484581 | Lower in Smoker |
| cg05924733 | 4 | 160277162 | Lower in Smoker |
| cg03351976 | 4 | 160230280 | Lower in Smoker |
| cg14854517 | 12 | 48152428 | Higher in Smoker |
| cg09114799 | 12 | 48152515 | Higher in Smoker |
| cg22104578 | 2 | 173601360 | Higher in Smoker |
| cg10202638 | 2 | 173754319 | Lower in Smoker |
| cg18892722 | 2 | 173693800 | Lower in Smoker |
| cg26443443 | 7 | 22396974 | Higher in Smoker |
| cg02088422 | 5 | 130970812 | Higher in Smoker |

| | | | |
|---|---|---|---|
| cg19572487 | 17 | 38476024 | Lower in Smoker |
| cg24957657 | 17 | 38497631 | Higher in Smoker |
| cg21554501 | 17 | 38474539 | Lower in Smoker |
| cg09265000 | 12 | 53614270 | Higher in Smoker |
| cg21746001 | 12 | 53610772 | Lower in Smoker |
| cg15664067 | 5 | 86564490 | Higher in Smoker |
| cg17596359 | 13 | 114844124 | Higher in Smoker |
| cg00054352 | 13 | 114891672 | Higher in Smoker |
| cg07981273 | 13 | 114881361 | Lower in Smoker |
| cg26181840 | 13 | 114869338 | Lower in Smoker |
| cg16127043 | 13 | 114861905 | Lower in Smoker |
| cg24226219 | 13 | 114887369 | Lower in Smoker |
| cg20691608 | 13 | 114843624 | Lower in Smoker |
| cg06834127 | 13 | 114813509 | Lower in Smoker |
| cg20483719 | 13 | 114799652 | Lower in Smoker |
| cg18021101 | 13 | 114800911 | Lower in Smoker |
| cg21747549 | 13 | 114804483 | Lower in Smoker |
| cg02745494 | 13 | 114771098 | Lower in Smoker |
| cg04155954 | 13 | 114776890 | Lower in Smoker |
| cg01289343 | 13 | 114814401 | Lower in Smoker |
| cg16087432 | 13 | 114883769 | Lower in Smoker |
| cg09033472 | 13 | 114890305 | Lower in Smoker |
| cg10002066 | 13 | 114896192 | Lower in Smoker |
| cg01616876 | 12 | 113544928 | Higher in Smoker |
| cg23736843 | 12 | 113541915 | Higher in Smoker |
| cg08865522 | 12 | 113574276 | Lower in Smoker |
| cg02939139 | 12 | 113574204 | Lower in Smoker |
| cg14508237 | 1 | 178263527 | Lower in Smoker |
| cg10319505 | 9 | 85678251 | Higher in Smoker |
| cg08980697 | 4 | 82362415 | Lower in Smoker |
| cg19924989 | 5 | 179563896 | Lower in Smoker |
| cg00471059 | 5 | 179562620 | Lower in Smoker |
| cg08323067 | 5 | 179553589 | Lower in Smoker |
| cg20946369 | 5 | 179635540 | Lower in Smoker |
| cg27147114 | 15 | 79358128 | Lower in Smoker |

| | | | |
|---|---|---|---|
| cg14091372 | 5 | 80339751 | Lower in Smoker |
| cg17350720 | 15 | 38857252 | Higher in Smoker |
| cg26726490 | 15 | 38781997 | Lower in Smoker |
| cg14170423 | 11 | 64513809 | Higher in Smoker |
| cg00156756 | 11 | 64510843 | Higher in Smoker |
| cg06464781 | 11 | 64509084 | Lower in Smoker |
| cg10701232 | 11 | 64507260 | Lower in Smoker |
| cg17598334 | 2 | 33700917 | Higher in Smoker |
| cg04707603 | 2 | 33735868 | Lower in Smoker |
| cg07876733 | 19 | 38909239 | Lower in Smoker |
| cg10347828 | 19 | 49244040 | Higher in Smoker |
| cg26260408 | 4 | 53727979 | Higher in Smoker |
| cg13872931 | 3 | 50377988 | Lower in Smoker |
| cg27569446 | 3 | 50378431 | Lower in Smoker |
| cg04743654 | 3 | 50378292 | Higher in Smoker |
| cg04540383 | 3 | 50378611 | Higher in Smoker |
| cg26005578 | 11 | 13030676 | Higher in Smoker |
| cg22831238 | 12 | 65076073 | Lower in Smoker |
| cg00771490 | 12 | 65008851 | Lower in Smoker |
| cg11770664 | 10 | 45470023 | Lower in Smoker |
| cg20595457 | 1 | 206753308 | Lower in Smoker |
| cg07469792 | 12 | 26112121 | Higher in Smoker |
| cg21917295 | 12 | 26126393 | Lower in Smoker |
| cg08646051 | 12 | 26205524 | Lower in Smoker |
| cg27035734 | 12 | 36230557 | Lower in Smoker |
| cg25279553 | 19 | 10444815 | Higher in Smoker |
| cg02978927 | 13 | 48877687 | Higher in Smoker |
| cg24463320 | 1 | 33121236 | Higher in Smoker |
| cg13641837 | 1 | 33116556 | Higher in Smoker |
| cg03048084 | X | 16888622 | Higher in Smoker |
| cg16978043 | X | 16888606 | Higher in Smoker |
| cg23169605 | 20 | 18478465 | Lower in Smoker |
| ch.20.750973F | 20 | 35650572 | Higher in Smoker |
| cg17113158 | 20 | 35724900 | Lower in Smoker |
| cg02931907 | 8 | 94753245 | Higher in Smoker |

| | | | |
|---|---|---|---|
| cg24341556 | 1 | 110881868 | Higher in Smoker |
| cg05072457 | 3 | 51428372 | Lower in Smoker |
| cg18842598 | 12 | 114273539 | Lower in Smoker |
| cg06328855 | 10 | 112404346 | Higher in Smoker |
| cg06143897 | 10 | 112404754 | Higher in Smoker |
| cg18961388 | 14 | 23374340 | Lower in Smoker |
| cg18691800 | 6 | 17281015 | Higher in Smoker |
| cg20034983 | 14 | 73525089 | Higher in Smoker |
| cg19243409 | 7 | 127963545 | Lower in Smoker |
| cg13639901 | 7 | 155556590 | Higher in Smoker |
| cg16433462 | 7 | 155461344 | Higher in Smoker |
| cg02499281 | 7 | 155573752 | Lower in Smoker |
| cg22860233 | 1 | 235324437 | Higher in Smoker |
| cg11772577 | 20 | 34330224 | Higher in Smoker |
| cg17201900 | 20 | 34330562 | Higher in Smoker |
| cg08161081 | 20 | 34327466 | Lower in Smoker |
| cg13965276 | 11 | 66405911 | Higher in Smoker |
| cg08442334 | 11 | 66411384 | Lower in Smoker |
| cg25272645 | 19 | 36119790 | Higher in Smoker |
| cg19793905 | 2 | 152118704 | Higher in Smoker |
| cg03761885 | 2 | 238707879 | Lower in Smoker |
| cg10316270 | 4 | 155702266 | Lower in Smoker |
| cg10019467 | 4 | 40632788 | Higher in Smoker |
| cg27076223 | 4 | 40632858 | Higher in Smoker |
| cg24116072 | 4 | 40631919 | Higher in Smoker |
| cg17409876 | 11 | 66436470 | Lower in Smoker |
| cg16165370 | 3 | 50155956 | Lower in Smoker |
| cg26343910 | 3 | 50127982 | Lower in Smoker |
| cg23625931 | 3 | 49977418 | Higher in Smoker |
| cg12418985 | 1 | 145507397 | Higher in Smoker |
| cg14019672 | 1 | 145507353 | Higher in Smoker |
| cg02772995 | 2 | 161348781 | Lower in Smoker |
| cg25310081 | 12 | 56959642 | Higher in Smoker |
| cg19142043 | 3 | 29724842 | Lower in Smoker |
| cg01347786 | 3 | 29517179 | Lower in Smoker |

| | | | |
|---|---|---|---|
| cg24912560 | 11 | 7110561 | Higher in Smoker |
| cg06176750 | 11 | 7112356 | Lower in Smoker |
| cg02925229 | 3 | 139258948 | Lower in Smoker |
| cg12331389 | 10 | 95360736 | Higher in Smoker |
| cg08950537 | 10 | 95361933 | Higher in Smoker |
| cg20413202 | 1 | 10056853 | Lower in Smoker |
| cg21008671 | 4 | 26322419 | Lower in Smoker |
| cg01398529 | 4 | 26322459 | Higher in Smoker |
| cg00760439 | 20 | 43940872 | Lower in Smoker |
| cg17221758 | 8 | 30243241 | Higher in Smoker |
| cg02619478 | 8 | 30248018 | Lower in Smoker |
| cg06705997 | 8 | 30248467 | Lower in Smoker |
| cg16625218 | 8 | 30272502 | Lower in Smoker |
| cg05265071 | 15 | 65032946 | Lower in Smoker |
| cg14500628 | 9 | 125646295 | Lower in Smoker |
| cg26153578 | 21 | 35987854 | Higher in Smoker |
| cg19278165 | 21 | 35986624 | Higher in Smoker |
| cg26677394 | 6 | 46258880 | Lower in Smoker |
| cg26692749 | 1 | 24861919 | Lower in Smoker |
| cg02665154 | 13 | 50159387 | Higher in Smoker |
| cg17533550 | 13 | 49104302 | Lower in Smoker |
| cg02506043 | 1 | 17765068 | Higher in Smoker |
| cg21932513 | 1 | 17751974 | Lower in Smoker |
| cg25660961 | 1 | 17764073 | Lower in Smoker |
| cg00794400 | 1 | 17774510 | Lower in Smoker |
| cg13439596 | 1 | 17746491 | Lower in Smoker |
| cg13170728 | 15 | 91503707 | Lower in Smoker |
| cg21184111 | 9 | 4792285 | Higher in Smoker |
| cg19777001 | 14 | 103150180 | Lower in Smoker |
| cg12527260 | 11 | 63683744 | Higher in Smoker |
| cg23957915 | 11 | 63684911 | Higher in Smoker |
| cg13802364 | 11 | 63684106 | Higher in Smoker |
| cg08549026 | 1 | 167656457 | Lower in Smoker |
| cg00695656 | 17 | 9808690 | Lower in Smoker |
| cg18744482 | 6 | 31920110 | Lower in Smoker |

| | | | |
|---|---|---|---|
| cg18626323 | 6 | 31919944 | Lower in Smoker |
| cg17680902 | 6 | 31927069 | Higher in Smoker |
| cg27331607 | 6 | 31926801 | Higher in Smoker |
| cg15463746 | 14 | 68167893 | Lower in Smoker |
| cg02167986 | 14 | 68201122 | Lower in Smoker |
| cg07598936 | 19 | 55574719 | Higher in Smoker |
| cg18393904 | 2 | 18741879 | Higher in Smoker |
| cg06143012 | 17 | 34258076 | Higher in Smoker |
| cg06481786 | 17 | 34257936 | Higher in Smoker |
| cg07981475 | 11 | 110167594 | Higher in Smoker |
| cg05212664 | 14 | 24639769 | Lower in Smoker |
| cg27536708 | 12 | 21654836 | Higher in Smoker |
| cg05389560 | 12 | 21654664 | Higher in Smoker |
| cg18822414 | 8 | 145738751 | Lower in Smoker |
| cg20176285 | 2 | 86564436 | Higher in Smoker |
| cg01824401 | 5 | 137774650 | Higher in Smoker |
| cg17863076 | 2 | 70312664 | Lower in Smoker |
| cg15090002 | 1 | 120351373 | Lower in Smoker |
| cg15139570 | 1 | 120354772 | Lower in Smoker |
| cg13255035 | 11 | 65423457 | Lower in Smoker |
| cg25203561 | 19 | 45541192 | Lower in Smoker |
| cg06562964 | 4 | 37686268 | Lower in Smoker |
| cg03203223 | 7 | 103630549 | Higher in Smoker |
| cg07426784 | 7 | 103279088 | Lower in Smoker |
| cg24777762 | 11 | 73087230 | Higher in Smoker |
| cg04313173 | 11 | 73087233 | Higher in Smoker |
| cg02658488 | 20 | 30063030 | Higher in Smoker |
| cg07809176 | 12 | 27849452 | Lower in Smoker |
| cg05950094 | X | 16964965 | Higher in Smoker |
| cg22526705 | 1 | 2335890 | Lower in Smoker |
| cg24352878 | 1 | 8772712 | Higher in Smoker |
| ch.1.315878R | 1 | 8617167 | Higher in Smoker |
| cg17442683 | 1 | 8664311 | Higher in Smoker |
| cg23042612 | 1 | 8613264 | Lower in Smoker |
| cg09635768 | 1 | 8601318 | Lower in Smoker |

| | | | |
|---|---|---|---|
| cg13084560 | 1 | 8418823 | Lower in Smoker |
| cg26915618 | 1 | 8427379 | Lower in Smoker |
| cg05045335 | 1 | 8457417 | Lower in Smoker |
| cg05531317 | 2 | 220194899 | Lower in Smoker |
| cg06559368 | 10 | 43573319 | Higher in Smoker |
| cg09848445 | 10 | 43601862 | Lower in Smoker |
| cg22322184 | 19 | 7734203 | Higher in Smoker |
| cg07868195 | 2 | 85581697 | Higher in Smoker |
| cg10370574 | 19 | 1840461 | Higher in Smoker |
| cg18751958 | 19 | 1827498 | Lower in Smoker |
| cg25538450 | 19 | 1847778 | Lower in Smoker |
| cg11579407 | 19 | 1847575 | Lower in Smoker |
| cg16714752 | 4 | 39368184 | Higher in Smoker |
| cg20227860 | 4 | 39368720 | Higher in Smoker |
| cg16910047 | 4 | 39368611 | Higher in Smoker |
| cg21828319 | 7 | 73645966 | Lower in Smoker |
| cg03312124 | 17 | 33416003 | Higher in Smoker |
| cg13789236 | 9 | 79009433 | Higher in Smoker |
| cg19650920 | 22 | 29834697 | Lower in Smoker |
| cg22623967 | 3 | 16554910 | Higher in Smoker |
| cg00506299 | 3 | 16469127 | Lower in Smoker |
| cg16875864 | 3 | 16441008 | Lower in Smoker |
| cg19399514 | 3 | 16545582 | Lower in Smoker |
| cg20832722 | 2 | 198523055 | Lower in Smoker |
| cg11851207 | 1 | 176176462 | Higher in Smoker |
| cg01002233 | 1 | 175931664 | Lower in Smoker |
| cg07297322 | 16 | 74661825 | Lower in Smoker |
| cg04558278 | 19 | 14074823 | Lower in Smoker |
| cg17977474 | 19 | 14073064 | Lower in Smoker |
| cg05659223 | 19 | 14117082 | Higher in Smoker |
| cg01516466 | 9 | 3526944 | Higher in Smoker |
| cg18075315 | 12 | 106988393 | Higher in Smoker |
| cg01899676 | 12 | 106988413 | Higher in Smoker |
| cg08285141 | 12 | 106976811 | Higher in Smoker |
| cg18446520 | 12 | 106981513 | Higher in Smoker |

| | | | |
|---|---|---|---|
| cg11797228 | 1 | 151319782 | Higher in Smoker |
| cg04555097 | 15 | 56535484 | Higher in Smoker |
| cg10507762 | 3 | 101284875 | Lower in Smoker |
| cg01754162 | 4 | 100484628 | Higher in Smoker |
| cg24750920 | 6 | 33267354 | Higher in Smoker |
| cg04823168 | 15 | 93632617 | Higher in Smoker |
| cg00925557 | 15 | 93631919 | Higher in Smoker |
| cg23754924 | 15 | 93616943 | Higher in Smoker |
| cg01019874 | 15 | 93588328 | Lower in Smoker |
| cg04646205 | 5 | 98109366 | Higher in Smoker |
| cg26096338 | 5 | 98129982 | Higher in Smoker |
| cg21221899 | 5 | 72921439 | Higher in Smoker |
| cg11781564 | 5 | 73016764 | Lower in Smoker |
| cg03167368 | 10 | 121285199 | Higher in Smoker |
| cg17675386 | 10 | 121260443 | Lower in Smoker |
| cg01344518 | 16 | 326728 | Lower in Smoker |
| cg01008894 | 4 | 3363509 | Lower in Smoker |
| cg04073934 | 4 | 3372272 | Lower in Smoker |
| cg07229767 | 4 | 3372206 | Lower in Smoker |
| cg26785604 | 4 | 3409168 | Lower in Smoker |
| cg22655196 | 4 | 3374909 | Lower in Smoker |
| cg18194426 | 1 | 192604056 | Lower in Smoker |
| cg11302624 | 5 | 176788169 | Lower in Smoker |
| cg01567482 | 5 | 176784318 | Lower in Smoker |
| cg17654660 | 5 | 176784965 | Higher in Smoker |
| cg17264670 | 6 | 153452732 | Higher in Smoker |
| cg16924337 | 6 | 153452724 | Higher in Smoker |
| cg27106513 | 8 | 54790372 | Lower in Smoker |
| cg20051292 | 8 | 101118512 | Higher in Smoker |
| cg08590069 | 8 | 101118899 | Higher in Smoker |
| cg19944367 | 9 | 116223775 | Lower in Smoker |
| cg26354398 | 9 | 116224036 | Lower in Smoker |
| cg14327394 | 9 | 116337285 | Lower in Smoker |
| cg06536874 | 1 | 163041039 | Lower in Smoker |
| cg03892631 | 1 | 163039184 | Lower in Smoker |

| | | | |
|---|---|---|---|
| cg02062816 | 1 | 163166949 | Lower in Smoker |
| cg18515872 | 14 | 72943461 | Higher in Smoker |
| cg01577850 | 14 | 72925867 | Higher in Smoker |
| cg02132051 | 14 | 73020007 | Lower in Smoker |
| cg16412573 | 14 | 72757840 | Lower in Smoker |
| cg17876456 | 1 | 182638158 | Lower in Smoker |
| cg24362123 | 1 | 182634861 | Lower in Smoker |
| cg04420141 | 17 | 63133231 | Higher in Smoker |
| cg19278232 | 6 | 49576124 | Lower in Smoker |
| cg09860047 | 2 | 227734267 | Lower in Smoker |
| cg09157320 | 2 | 227850069 | Lower in Smoker |
| cg07379557 | 16 | 725416 | Lower in Smoker |
| cg01934709 | 1 | 39357454 | Lower in Smoker |
| cg11604426 | 17 | 30592406 | Higher in Smoker |
| cg16954280 | 17 | 30593009 | Higher in Smoker |
| cg18459257 | 17 | 30593018 | Higher in Smoker |
| cg15836639 | 17 | 30595595 | Lower in Smoker |
| cg12412775 | 1 | 25698385 | Lower in Smoker |
| cg01366698 | 3 | 49397613 | Lower in Smoker |
| cg00174179 | 3 | 49450293 | Lower in Smoker |
| cg10996014 | 3 | 49449848 | Higher in Smoker |
| cg23720494 | 10 | 62735291 | Lower in Smoker |
| cg24853299 | 10 | 62674969 | Lower in Smoker |
| cg20642630 | 8 | 22846006 | Lower in Smoker |
| cg21799053 | 8 | 22856801 | Higher in Smoker |
| cg19861842 | 8 | 22855745 | Lower in Smoker |
| cg14668516 | 5 | 95108583 | Lower in Smoker |
| cg24965308 | 5 | 95067311 | Higher in Smoker |
| cg24497361 | 11 | 3858493 | Lower in Smoker |
| cg02210123 | 14 | 63670835 | Higher in Smoker |
| cg18824840 | 14 | 63742947 | Lower in Smoker |
| cg26944981 | 17 | 30469748 | Higher in Smoker |
| cg02057833 | 1 | 228872246 | Higher in Smoker |
| cg22914595 | 8 | 144462127 | Lower in Smoker |
| ch.19.1079710R | 19 | 33483456 | Higher in Smoker |

| | | | |
|---|---|---|---|
| cg23259289 | 17 | 12886154 | Lower in Smoker |
| cg09857830 | 17 | 12692900 | Higher in Smoker |
| cg18393905 | 5 | 39062214 | Lower in Smoker |
| cg07580652 | 2 | 152266582 | Higher in Smoker |
| cg00426193 | 2 | 152267492 | Higher in Smoker |
| cg06191203 | 2 | 152266755 | Lower in Smoker |
| cg19502936 | 17 | 1553591 | Lower in Smoker |
| cg04313875 | 17 | 1553202 | Higher in Smoker |
| cg04781075 | 12 | 123921371 | Higher in Smoker |
| cg21618040 | 12 | 123921306 | Lower in Smoker |
| cg09694527 | 12 | 123918498 | Lower in Smoker |
| cg10577257 | 12 | 130929193 | Higher in Smoker |
| cg07433411 | 12 | 130953785 | Lower in Smoker |
| cg01163340 | 12 | 130953962 | Lower in Smoker |
| cg19599226 | 12 | 130910731 | Lower in Smoker |
| cg00922522 | 12 | 130918862 | Lower in Smoker |
| cg02126688 | 12 | 130932128 | Lower in Smoker |
| cg04062767 | 12 | 130958162 | Lower in Smoker |
| cg11813246 | 1 | 42846740 | Higher in Smoker |
| cg08962682 | 12 | 8850939 | Higher in Smoker |
| cg27608224 | 6 | 72922399 | Lower in Smoker |
| cg26552233 | 6 | 72967959 | Lower in Smoker |
| cg01553434 | 6 | 73075887 | Lower in Smoker |
| cg19100772 | 6 | 72926485 | Lower in Smoker |
| cg26099432 | 6 | 73103615 | Lower in Smoker |
| cg20129213 | 8 | 104512317 | Lower in Smoker |
| cg09637757 | 8 | 104831516 | Lower in Smoker |
| cg17066238 | 11 | 66103823 | Lower in Smoker |
| cg14550985 | 11 | 66104159 | Lower in Smoker |
| cg23220439 | 11 | 66104481 | Lower in Smoker |
| cg12201988 | 20 | 19982870 | Lower in Smoker |
| cg16070279 | 6 | 33179725 | Lower in Smoker |
| cg19486707 | 6 | 33175225 | Higher in Smoker |
| cg03231163 | 19 | 39360465 | Higher in Smoker |
| cg25675800 | 19 | 39360961 | Lower in Smoker |

| | | | |
|---|---|---|---|
| cg18177659 | 18 | 21032322 | Lower in Smoker |
| cg23632791 | 8 | 90794647 | Higher in Smoker |
| cg01714342 | 14 | 24809593 | Lower in Smoker |
| cg16528511 | 6 | 84562892 | Higher in Smoker |
| cg00575005 | 6 | 84562838 | Higher in Smoker |
| cg14936188 | 18 | 40647794 | Lower in Smoker |
| cg01918888 | 1 | 40627050 | Higher in Smoker |
| cg10883421 | 6 | 151773342 | Higher in Smoker |
| cg15920202 | 2 | 86946868 | Higher in Smoker |
| cg14513923 | 5 | 177575216 | Lower in Smoker |
| cg09842118 | 14 | 21359737 | Lower in Smoker |
| cg01048203 | 14 | 21027321 | Lower in Smoker |
| cg01449715 | 13 | 51491406 | Higher in Smoker |
| cg12175143 | 13 | 51486384 | Higher in Smoker |
| cg11301670 | 6 | 167363345 | Lower in Smoker |
| cg24928378 | 12 | 49259415 | Higher in Smoker |
| cg16879222 | 17 | 41176744 | Higher in Smoker |
| cg11626656 | 2 | 151343868 | Higher in Smoker |
| cg27640988 | 2 | 86850406 | Higher in Smoker |
| cg13193757 | 20 | 48552853 | Higher in Smoker |
| cg08659621 | 20 | 48552817 | Higher in Smoker |
| cg26364766 | 20 | 48570238 | Lower in Smoker |
| cg27471092 | 19 | 663361 | Higher in Smoker |
| cg01476179 | 19 | 652016 | Lower in Smoker |
| cg22529541 | 3 | 149536976 | Lower in Smoker |
| cg06664874 | 5 | 179499304 | Higher in Smoker |
| cg02702477 | 5 | 179499311 | Higher in Smoker |
| cg17854747 | 18 | 29672535 | Higher in Smoker |
| cg09657348 | 11 | 10562473 | Higher in Smoker |
| cg18004068 | 11 | 10562070 | Higher in Smoker |
| cg23669896 | 11 | 10562165 | Higher in Smoker |
| cg10133630 | 11 | 10563302 | Lower in Smoker |
| cg20995753 | 2 | 7164586 | Higher in Smoker |
| cg08182975 | 2 | 7164527 | Lower in Smoker |
| cg12638576 | 6 | 18387407 | Higher in Smoker |

| | | | |
|---|---|---|---|
| cg22019980 | 6 | 127588323 | Higher in Smoker |
| cg11962007 | 2 | 101922922 | Lower in Smoker |
| cg01202265 | 4 | 142053146 | Higher in Smoker |
| cg24705668 | 4 | 141949314 | Lower in Smoker |
| cg18120376 | 4 | 142054254 | Higher in Smoker |
| cg10180052 | 16 | 2018558 | Lower in Smoker |
| cg14360865 | 18 | 59560371 | Higher in Smoker |
| cg19423014 | 18 | 59560091 | Higher in Smoker |
| cg24692254 | 21 | 30365293 | Higher in Smoker |
| cg08807101 | 21 | 30365312 | Higher in Smoker |
| cg01550828 | 3 | 196227453 | Lower in Smoker |
| cg02400751 | 11 | 74459640 | Higher in Smoker |
| cg25921194 | 11 | 74492567 | Lower in Smoker |
| cg21831927 | 13 | 25337649 | Higher in Smoker |
| cg23906264 | 8 | 42705540 | Lower in Smoker |
| cg15956738 | 2 | 85822773 | Higher in Smoker |
| cg09134314 | 6 | 13924570 | Higher in Smoker |
| cg24245352 | 22 | 31601170 | Higher in Smoker |
| cg01806258 | 1 | 228682590 | Lower in Smoker |
| cg04680037 | 1 | 33430483 | Higher in Smoker |
| cg22802759 | 1 | 185015193 | Higher in Smoker |
| cg17515966 | 1 | 6265894 | Lower in Smoker |
| cg19180828 | 1 | 6265220 | Lower in Smoker |
| cg04790147 | 4 | 1108671 | Lower in Smoker |
| cg04686953 | 4 | 1107512 | Higher in Smoker |
| cg08579465 | 17 | 78319089 | Lower in Smoker |
| cg18902820 | 17 | 78323643 | Lower in Smoker |
| cg25405318 | 17 | 78354680 | Higher in Smoker |
| cg24626411 | 17 | 78291020 | Lower in Smoker |
| cg22357164 | 17 | 78237117 | Lower in Smoker |
| cg05714094 | 11 | 117102988 | Lower in Smoker |
| cg12512856 | 22 | 30783074 | Higher in Smoker |
| cg18617808 | 7 | 5717675 | Lower in Smoker |
| cg12548634 | 1 | 44884109 | Higher in Smoker |
| cg17526060 | 2 | 219535843 | Lower in Smoker |

| | | | |
|---|---|---|---|
| cg19051225 | 12 | 121837829 | Higher in Smoker |
| cg13884344 | 9 | 36338497 | Lower in Smoker |
| cg11562284 | 6 | 30042960 | Higher in Smoker |
| cg27532187 | 6 | 30043354 | Higher in Smoker |
| cg06357743 | 6 | 30041727 | Lower in Smoker |
| cg22184136 | 6 | 30038720 | Lower in Smoker |
| cg24842142 | 6 | 30041178 | Lower in Smoker |
| cg27578637 | 16 | 30775658 | Lower in Smoker |
| cg27151980 | 16 | 30772821 | Higher in Smoker |
| cg03941744 | 16 | 30773383 | Lower in Smoker |
| cg25991937 | 5 | 175964864 | Higher in Smoker |
| cg10082991 | 5 | 175964280 | Higher in Smoker |
| cg17032533 | 5 | 175964269 | Higher in Smoker |
| cg25415650 | 13 | 26795862 | Higher in Smoker |
| cg17850880 | 13 | 26795990 | Higher in Smoker |
| cg14425796 | 6 | 37321643 | Higher in Smoker |
| cg25018208 | 6 | 37338607 | Lower in Smoker |
| cg07533488 | 12 | 117287121 | Lower in Smoker |
| cg15210314 | 11 | 498943 | Lower in Smoker |
| cg11382794 | 11 | 497754 | Lower in Smoker |
| cg19584341 | 11 | 506908 | Lower in Smoker |
| cg19223782 | 11 | 503807 | Lower in Smoker |
| cg10450899 | 17 | 685900 | Lower in Smoker |
| cg00876678 | 16 | 2319586 | Higher in Smoker |
| cg02612045 | 5 | 80529943 | Lower in Smoker |
| cg13216331 | 1 | 156025757 | Lower in Smoker |
| cg13934005 | 1 | 156025002 | Higher in Smoker |
| cg04894671 | 1 | 156024577 | Higher in Smoker |
| cg21743712 | 3 | 79817125 | Higher in Smoker |
| cg07997035 | 3 | 79816949 | Higher in Smoker |
| cg08233594 | 3 | 79066857 | Higher in Smoker |
| cg13514824 | 3 | 79067085 | Higher in Smoker |
| cg15645784 | 16 | 4852962 | Higher in Smoker |
| cg11933464 | 11 | 62379787 | Higher in Smoker |
| cg20629316 | 1 | 64413782 | Lower in Smoker |

| | | | |
|---|---|---|---|
| cg00463746 | 1 | 64434320 | Lower in Smoker |
| cg14044388 | 9 | 94579826 | Lower in Smoker |
| cg14014590 | 9 | 94540286 | Lower in Smoker |
| cg13577292 | 9 | 94485188 | Lower in Smoker |
| cg10298557 | 15 | 61519655 | Higher in Smoker |
| cg13146553 | 15 | 61343563 | Lower in Smoker |
| cg07017175 | 15 | 60884093 | Higher in Smoker |
| cg27395839 | 15 | 60812923 | Lower in Smoker |
| cg17423423 | 7 | 33149143 | Higher in Smoker |
| cg19655826 | 7 | 33150037 | Higher in Smoker |
| cg19228665 | 17 | 1787078 | Lower in Smoker |
| cg06176410 | 17 | 1733445 | Higher in Smoker |
| cg11754343 | 17 | 5322575 | Higher in Smoker |
| cg17239140 | 15 | 41836578 | Higher in Smoker |
| cg17683632 | 2 | 210883371 | Lower in Smoker |
| cg23851205 | X | 38186919 | Higher in Smoker |
| cg01752898 | X | 38186917 | Higher in Smoker |
| cg10328157 | 14 | 21769240 | Higher in Smoker |
| cg10201388 | 16 | 53737753 | Lower in Smoker |
| cg05967001 | 12 | 113229647 | Higher in Smoker |
| cg21335187 | 2 | 88990994 | Higher in Smoker |
| cg10103235 | 2 | 89012861 | Lower in Smoker |
| cg03464416 | X | 153626979 | Higher in Smoker |
| cg20148285 | 1 | 24018143 | Higher in Smoker |
| cg11252261 | 1 | 24018063 | Lower in Smoker |
| cg02589949 | 12 | 13027685 | Lower in Smoker |
| cg24082526 | 19 | 49993125 | Lower in Smoker |
| cg15531369 | 19 | 49993157 | Lower in Smoker |
| cg17679864 | 3 | 40498818 | Higher in Smoker |
| cg01274752 | 19 | 49120447 | Lower in Smoker |
| cg23972869 | 19 | 49123742 | Lower in Smoker |
| cg26940725 | 13 | 27825886 | Higher in Smoker |
| cg22433398 | 13 | 27825486 | Lower in Smoker |
| cg04025728 | 1 | 6259688 | Higher in Smoker |
| cg06744003 | 1 | 6255635 | Lower in Smoker |

| | | | |
|---|---|---|---|
| cg00182421 | 3 | 170586396 | Lower in Smoker |
| cg27592126 | 17 | 37010652 | Lower in Smoker |
| cg15036326 | 17 | 27048708 | Lower in Smoker |
| cg17015234 | 2 | 114384633 | Higher in Smoker |
| cg09243147 | 3 | 101399998 | Lower in Smoker |
| cg25565099 | 17 | 8286577 | Higher in Smoker |
| cg07633851 | 5 | 172387101 | Higher in Smoker |
| cg24876683 | 5 | 172386517 | Higher in Smoker |
| cg16805816 | 17 | 41150871 | Higher in Smoker |
| cg17308151 | 11 | 8703888 | Higher in Smoker |
| cg09769958 | 19 | 55896622 | Higher in Smoker |
| cg14529754 | 3 | 52030206 | Lower in Smoker |
| cg07047046 | 8 | 99058293 | Lower in Smoker |
| cg10446401 | 2 | 101619230 | Higher in Smoker |
| cg14513781 | 2 | 101618883 | Lower in Smoker |
| cg06150369 | 3 | 129118661 | Higher in Smoker |
| cg08798701 | 3 | 129118382 | Higher in Smoker |
| cg17514226 | 4 | 109541573 | Higher in Smoker |
| cg03131214 | X | 100646162 | Higher in Smoker |
| cg01485704 | 14 | 50087384 | Higher in Smoker |
| cg00090787 | 15 | 66795345 | Lower in Smoker |
| cg10957733 | 6 | 42847646 | Higher in Smoker |
| cg00517855 | 8 | 146016408 | Lower in Smoker |
| cg17499981 | 11 | 809742 | Higher in Smoker |
| cg26161170 | 6 | 30313174 | Higher in Smoker |
| cg26859557 | 6 | 30314164 | Lower in Smoker |
| cg27519140 | 6 | 30312645 | Lower in Smoker |
| cg13920624 | 10 | 92631648 | Higher in Smoker |
| cg14675513 | 6 | 5004368 | Higher in Smoker |
| cg13578932 | 18 | 33647664 | Higher in Smoker |
| cg12982440 | 20 | 36661586 | Higher in Smoker |
| cg17155610 | 1 | 150382400 | Lower in Smoker |
| cg04490108 | 1 | 150337032 | Higher in Smoker |
| cg00341742 | 2 | 154335698 | Lower in Smoker |
| cg13665025 | 17 | 45056837 | Higher in Smoker |

| | | | |
|---|---|---|---|
| cg22674412 | 17 | 45056008 | Lower in Smoker |
| cg09795081 | 6 | 34392105 | Lower in Smoker |
| cg04081324 | 5 | 149829376 | Higher in Smoker |
| cg06603828 | 5 | 149829668 | Higher in Smoker |
| cg06734429 | 19 | 39926689 | Higher in Smoker |
| cg05560494 | 6 | 33241974 | Lower in Smoker |
| cg15152201 | 20 | 60962045 | Higher in Smoker |
| cg11491770 | 20 | 60961646 | Lower in Smoker |
| cg01556715 | 5 | 81574292 | Higher in Smoker |
| cg08951005 | 10 | 79803774 | Lower in Smoker |
| cg05028089 | 10 | 79793366 | Higher in Smoker |
| cg05730301 | 10 | 79793430 | Higher in Smoker |
| cg14459420 | 2 | 55459779 | Higher in Smoker |
| cg26210447 | 15 | 63449535 | Higher in Smoker |
| cg24530510 | 11 | 75115385 | Lower in Smoker |
| cg01714671 | X | 71496701 | Higher in Smoker |
| cg16313903 | X | 71497113 | Higher in Smoker |
| cg11701312 | 19 | 58697497 | Lower in Smoker |
| cg10800585 | 1 | 26856574 | Higher in Smoker |
| cg15592062 | 6 | 167189543 | Higher in Smoker |
| cg12539053 | 6 | 167178830 | Lower in Smoker |
| cg20486651 | 6 | 167070296 | Lower in Smoker |
| cg23869232 | 6 | 167175937 | Lower in Smoker |
| cg03120116 | 6 | 167276567 | Lower in Smoker |
| cg02588532 | 6 | 166922931 | Higher in Smoker |
| cg07253384 | 6 | 166877002 | Higher in Smoker |
| cg15579816 | 6 | 166892438 | Higher in Smoker |
| cg01056358 | 6 | 166858118 | Higher in Smoker |
| cg14718836 | 6 | 167031273 | Lower in Smoker |
| cg04618331 | 11 | 64136263 | Lower in Smoker |
| cg19358195 | X | 83443518 | Lower in Smoker |
| cg26068595 | 14 | 75386651 | Higher in Smoker |
| cg06637938 | 14 | 75390232 | Lower in Smoker |
| cg11569329 | 19 | 54705747 | Lower in Smoker |
| cg23633526 | 3 | 39448019 | Higher in Smoker |

| | | | |
|---|---|---|---|
| cg14929116 | 3 | 39451211 | Lower in Smoker |
| cg05605052 | 19 | 23945659 | Higher in Smoker |
| cg24163448 | 9 | 79013444 | Lower in Smoker |
| cg00523683 | 17 | 78748471 | Higher in Smoker |
| cg08129331 | 17 | 78560478 | Higher in Smoker |
| cg01767927 | 17 | 78821024 | Higher in Smoker |
| cg17144164 | 17 | 78896700 | Lower in Smoker |
| cg23210522 | 17 | 78803474 | Lower in Smoker |
| cg07584637 | 17 | 78911577 | Lower in Smoker |
| cg04162316 | 17 | 78786355 | Lower in Smoker |
| cg11188237 | 17 | 78902396 | Lower in Smoker |
| cg21879029 | 17 | 78935175 | Lower in Smoker |
| cg12785535 | 17 | 78795392 | Lower in Smoker |
| cg26932839 | 17 | 78926130 | Lower in Smoker |
| cg23625086 | 17 | 78836339 | Lower in Smoker |
| cg22161269 | 17 | 78836513 | Lower in Smoker |
| cg19185574 | 17 | 78857631 | Lower in Smoker |
| cg05707492 | 17 | 78833484 | Lower in Smoker |
| cg16027727 | 17 | 78586328 | Lower in Smoker |
| cg06418238 | 17 | 78755442 | Lower in Smoker |
| cg04662369 | 17 | 78754318 | Lower in Smoker |
| cg14780427 | 17 | 78754372 | Lower in Smoker |
| cg22106051 | 15 | 40862171 | Higher in Smoker |
| cg09257101 | 15 | 40865840 | Lower in Smoker |
| cg02070354 | 2 | 219433199 | Higher in Smoker |
| cg13452904 | 9 | 19048088 | Lower in Smoker |
| cg23495059 | 1 | 39324743 | Higher in Smoker |
| cg01475538 | 11 | 14381234 | Lower in Smoker |
| cg00990977 | 20 | 17659317 | Lower in Smoker |
| cg07597892 | 20 | 17663972 | Lower in Smoker |
| cg12399162 | 6 | 7141575 | Higher in Smoker |
| cg24361357 | 6 | 7141246 | Higher in Smoker |
| cg03551454 | 6 | 7245704 | Lower in Smoker |
| cg18533466 | 6 | 7107952 | Higher in Smoker |
| cg09972864 | 16 | 15187975 | Higher in Smoker |

| | | | |
|---|---|---|---|
| cg03662014 | 16 | 29086271 | Higher in Smoker |
| cg21573476 | 21 | 45109991 | Lower in Smoker |
| cg20556598 | X | 18691243 | Lower in Smoker |
| cg10549986 | 2 | 7018153 | Higher in Smoker |
| cg13958304 | 1 | 114354463 | Higher in Smoker |
| cg20492436 | 7 | 77325562 | Higher in Smoker |
| cg03042802 | 1 | 15984979 | Lower in Smoker |
| cg01932125 | 11 | 77377926 | Lower in Smoker |
| cg18120111 | 21 | 43917047 | Lower in Smoker |
| cg14070647 | 8 | 109095264 | Higher in Smoker |
| cg06437464 | 6 | 127441704 | Higher in Smoker |
| cg08719139 | 16 | 57223804 | Lower in Smoker |
| cg03104758 | 16 | 57219801 | Higher in Smoker |
| cg08423269 | 3 | 157827682 | Higher in Smoker |
| cg14832954 | 1 | 100731266 | Higher in Smoker |
| cg11820522 | 1 | 100731476 | Higher in Smoker |
| cg14986832 | 22 | 23412408 | Higher in Smoker |
| cg11443786 | 20 | 62290395 | Higher in Smoker |
| cg05710299 | 14 | 101352549 | Lower in Smoker |
| cg06520812 | 19 | 46000742 | Higher in Smoker |
| cg10253465 | 19 | 45996944 | Higher in Smoker |
| cg18226166 | 19 | 45996901 | Higher in Smoker |
| cg19038042 | 19 | 45997888 | Lower in Smoker |
| cg23454082 | 2 | 55266232 | Lower in Smoker |
| cg16759976 | 3 | 186914720 | Lower in Smoker |
| cg03963008 | 5 | 179002268 | Lower in Smoker |
| cg24751538 | 10 | 70167018 | Higher in Smoker |
| cg26190225 | 4 | 71570509 | Higher in Smoker |
| cg12405833 | 16 | 12070719 | Higher in Smoker |
| cg03412557 | 16 | 12096923 | Lower in Smoker |
| cg02115818 | 17 | 42393931 | Lower in Smoker |
| cg00031165 | 7 | 87258360 | Higher in Smoker |
| cg08443845 | 21 | 36421955 | Higher in Smoker |
| cg00291213 | 21 | 36398056 | Higher in Smoker |
| cg26360861 | 21 | 36265744 | Lower in Smoker |

| | | | |
|---|---|---|---|
| cg13030790 | 21 | 36421503 | Higher in Smoker |
| cg04212846 | 21 | 36168008 | Lower in Smoker |
| cg17487050 | 3 | 93107627 | Higher in Smoker |
| cg16457433 | 3 | 93075534 | Lower in Smoker |
| cg00045118 | 3 | 93076177 | Lower in Smoker |
| cg16323984 | 6 | 45386802 | Lower in Smoker |
| cg23376821 | 6 | 45391365 | Higher in Smoker |
| cg12477370 | 6 | 45391852 | Lower in Smoker |
| cg26864395 | 1 | 25259106 | Lower in Smoker |
| cg14425908 | 1 | 25291991 | Lower in Smoker |
| cg16529592 | 1 | 25292215 | Lower in Smoker |
| cg11585280 | 1 | 25292059 | Lower in Smoker |
| cg14182690 | 1 | 25290947 | Lower in Smoker |
| cg16574073 | 1 | 25261746 | Lower in Smoker |
| cg19774846 | 1 | 25292225 | Lower in Smoker |
| cg26256263 | 1 | 25258146 | Lower in Smoker |
| cg18087266 | 1 | 25257629 | Lower in Smoker |
| cg02970551 | 1 | 25257191 | Lower in Smoker |
| cg03769939 | 1 | 25254129 | Lower in Smoker |
| cg24547565 | 1 | 155290236 | Higher in Smoker |
| cg13235288 | 1 | 155293343 | Higher in Smoker |
| cg12476242 | 3 | 127813395 | Lower in Smoker |
| cg18421592 | 6 | 83903012 | Higher in Smoker |
| cg12061021 | 1 | 95699574 | Higher in Smoker |
| cg07538248 | 1 | 95699815 | Higher in Smoker |
| cg13674088 | 4 | 184562216 | Lower in Smoker |
| cg14472716 | 9 | 137236548 | Higher in Smoker |
| ch.3.2658749R | 3 | 133915637 | Higher in Smoker |
| cg19710971 | 3 | 133966275 | Lower in Smoker |
| cg22647970 | 19 | 38993309 | Higher in Smoker |
| cg05471297 | 19 | 38924349 | Higher in Smoker |
| cg16532185 | 1 | 237251552 | Lower in Smoker |
| cg13373703 | 1 | 237346809 | Lower in Smoker |
| cg21413325 | 15 | 53602758 | Higher in Smoker |
| cg25848158 | 1 | 151966808 | Higher in Smoker |

| | | | |
|---|---|---|---|
| cg15559456 | 1 | 153600790 | Lower in Smoker |
| cg17421062 | 1 | 153432054 | Lower in Smoker |
| cg22933439 | 1 | 153387609 | Lower in Smoker |
| cg05848175 | 1 | 153330257 | Higher in Smoker |
| cg23978968 | 1 | 101704656 | Lower in Smoker |
| cg27125093 | 19 | 3179828 | Lower in Smoker |
| cg24807354 | 19 | 10629035 | Higher in Smoker |
| cg24893891 | 19 | 10629027 | Higher in Smoker |
| cg15484375 | 11 | 18287647 | Lower in Smoker |
| cg10266336 | 11 | 18270324 | Higher in Smoker |
| cg00442802 | 11 | 18138394 | Lower in Smoker |
| cg22288982 | 11 | 18258055 | Lower in Smoker |
| cg04189988 | 11 | 18127292 | Higher in Smoker |
| cg00256745 | 11 | 64808437 | Higher in Smoker |
| cg15060177 | 3 | 45731018 | Higher in Smoker |
| cg16923290 | 13 | 23949747 | Higher in Smoker |
| cg08391848 | 19 | 5661611 | Lower in Smoker |
| cg11928000 | 19 | 5622739 | Higher in Smoker |
| cg19149789 | 2 | 234225955 | Lower in Smoker |
| cg27423760 | 16 | 51186463 | Higher in Smoker |
| cg06724588 | 16 | 51185459 | Higher in Smoker |
| cg07502439 | 16 | 51185461 | Higher in Smoker |
| cg02417084 | 16 | 51183533 | Higher in Smoker |
| cg07498275 | 16 | 51184836 | Higher in Smoker |
| cg06099646 | 16 | 51174768 | Lower in Smoker |
| cg01679108 | 16 | 51174069 | Lower in Smoker |
| cg00800229 | 14 | 22004993 | Higher in Smoker |
| cg02507869 | 18 | 76754902 | Lower in Smoker |
| cg00169792 | 20 | 50418554 | Higher in Smoker |
| cg23440862 | 1 | 875880 | Higher in Smoker |
| cg24362661 | 1 | 871546 | Higher in Smoker |
| cg25206690 | 8 | 119302728 | Lower in Smoker |
| cg18001844 | 8 | 119220574 | Lower in Smoker |
| cg21500126 | 8 | 119372394 | Lower in Smoker |
| cg23925111 | 1 | 84815929 | Lower in Smoker |

| | | | |
|---|---|---|---|
| cg05193449 | 14 | 55034533 | Higher in Smoker |
| cg13706079 | 14 | 55179960 | Lower in Smoker |
| cg16398105 | 14 | 55103649 | Lower in Smoker |
| cg06914133 | 14 | 55067550 | Lower in Smoker |
| cg09399131 | 14 | 55227064 | Lower in Smoker |
| cg21687240 | 14 | 55220829 | Lower in Smoker |
| cg18474742 | 6 | 147830055 | Higher in Smoker |
| cg07520752 | 6 | 147830046 | Higher in Smoker |
| cg15960036 | 3 | 169633215 | Lower in Smoker |
| cg09454892 | 10 | 76870850 | Higher in Smoker |
| cg11094122 | 20 | 35579338 | Higher in Smoker |
| cg14766148 | 2 | 123786246 | Higher in Smoker |
| cg14772639 | 2 | 123711564 | Lower in Smoker |
| cg21067709 | 13 | 21714627 | Higher in Smoker |
| cg25495394 | 13 | 21714725 | Higher in Smoker |
| cg06708315 | 17 | 73689641 | Lower in Smoker |
| cg07661904 | 10 | 71930999 | Lower in Smoker |
| cg13826666 | 9 | 136600241 | Lower in Smoker |
| cg16937245 | 12 | 108936740 | Lower in Smoker |
| cg20407365 | 12 | 108953539 | Lower in Smoker |
| cg06492708 | 6 | 148664322 | Higher in Smoker |
| cg06081609 | 6 | 148663571 | Higher in Smoker |
| cg00380172 | 6 | 148663585 | Higher in Smoker |
| cg12355586 | 6 | 148869895 | Lower in Smoker |
| cg22685901 | 6 | 148668023 | Lower in Smoker |
| cg10583736 | 6 | 148663964 | Higher in Smoker |
| cg02616489 | 3 | 18404925 | Lower in Smoker |
| cg14520829 | 3 | 18390388 | Lower in Smoker |
| cg21902966 | 3 | 18391029 | Lower in Smoker |
| cg13014623 | 3 | 18465519 | Higher in Smoker |
| cg23994043 | 2 | 200326725 | Higher in Smoker |
| cg25928603 | 2 | 200323017 | Higher in Smoker |
| cg20785796 | 2 | 200326721 | Higher in Smoker |
| cg05358815 | 2 | 200324281 | Higher in Smoker |
| cg03139053 | 2 | 200320455 | Higher in Smoker |

| | | | |
|---|---|---|---|
| cg21879272 | 14 | 51135303 | Higher in Smoker |
| ch.14.569218R | 14 | 51107454 | Higher in Smoker |
| cg04730355 | 14 | 51134070 | Higher in Smoker |
| cg13800540 | 14 | 51135366 | Higher in Smoker |
| cg00498438 | 7 | 66460676 | Higher in Smoker |
| cg01781850 | 22 | 50884509 | Higher in Smoker |
| cg06729723 | 22 | 50885475 | Higher in Smoker |
| cg07016730 | 22 | 50912306 | Lower in Smoker |
| cg15376996 | 22 | 50912555 | Lower in Smoker |
| cg01453529 | 11 | 10209919 | Lower in Smoker |
| cg09087191 | 11 | 9907493 | Lower in Smoker |
| cg26007766 | 11 | 10253819 | Lower in Smoker |
| cg23014664 | 11 | 9995602 | Lower in Smoker |
| cg26701545 | 16 | 28331026 | Lower in Smoker |
| cg06415304 | 16 | 28304303 | Higher in Smoker |
| cg09364245 | 19 | 56047543 | Lower in Smoker |
| cg08889843 | 19 | 56048518 | Lower in Smoker |
| cg08121792 | 12 | 123804559 | Lower in Smoker |
| cg07076091 | 4 | 166259531 | Lower in Smoker |
| cg13421924 | 11 | 121163141 | Higher in Smoker |
| cg14138506 | 5 | 77656095 | Higher in Smoker |
| cg13410390 | 1 | 155232677 | Lower in Smoker |
| cg07189204 | 1 | 155225808 | Higher in Smoker |
| cg16186938 | 6 | 28555324 | Higher in Smoker |
| cg25049387 | 6 | 28555353 | Higher in Smoker |
| cg06217314 | 6 | 28543693 | Higher in Smoker |
| cg00571434 | 6 | 28550427 | Lower in Smoker |
| cg04664126 | 6 | 28554262 | Lower in Smoker |
| cg00337181 | 6 | 28548673 | Lower in Smoker |
| cg10875257 | 6 | 28554274 | Lower in Smoker |
| cg26529239 | 6 | 28550343 | Lower in Smoker |
| cg04264299 | 8 | 27491209 | Higher in Smoker |
| cg20263156 | 8 | 27850215 | Higher in Smoker |
| cg16004055 | 8 | 27850319 | Higher in Smoker |
| cg05270752 | 8 | 27846563 | Lower in Smoker |

| | | | |
|---|---|---|---|
| cg11198639 | 12 | 125287476 | Higher in Smoker |
| cg17878881 | 12 | 125349072 | Lower in Smoker |
| cg11659747 | 4 | 77134585 | Higher in Smoker |
| cg17465343 | 4 | 77126252 | Lower in Smoker |
| cg23214985 | 17 | 1537690 | Lower in Smoker |
| cg09783874 | 22 | 20791553 | Higher in Smoker |
| cg03448766 | 22 | 20792243 | Higher in Smoker |
| cg14998335 | 22 | 20792255 | Higher in Smoker |
| cg03952331 | 22 | 20792222 | Higher in Smoker |
| cg15243570 | 22 | 20792217 | Higher in Smoker |
| cg14785479 | 22 | 20792535 | Higher in Smoker |
| cg01251835 | 22 | 20783963 | Higher in Smoker |
| cg12895179 | 22 | 20779482 | Higher in Smoker |
| cg02050613 | 12 | 6618003 | Lower in Smoker |
| cg20478514 | 1 | 246887464 | Lower in Smoker |
| cg03440556 | 10 | 102107757 | Higher in Smoker |
| cg24503796 | 10 | 102107676 | Higher in Smoker |
| cg18328965 | 10 | 102107584 | Higher in Smoker |
| cg07161848 | 10 | 102123573 | Lower in Smoker |
| cg19746194 | 4 | 83720039 | Higher in Smoker |
| cg16425726 | 4 | 83680145 | Lower in Smoker |
| cg18833329 | 4 | 54232530 | Higher in Smoker |
| cg20601329 | 4 | 54231411 | Higher in Smoker |
| cg00112056 | 4 | 54232415 | Higher in Smoker |
| cg19303728 | 4 | 53759295 | Lower in Smoker |
| cg05172394 | 4 | 54233429 | Lower in Smoker |
| cg11944076 | 15 | 51997390 | Lower in Smoker |
| cg27302576 | 15 | 32964759 | Lower in Smoker |
| cg04011620 | 11 | 61956390 | Lower in Smoker |
| cg08298827 | 11 | 62009585 | Lower in Smoker |
| cg16936846 | 11 | 61976174 | Lower in Smoker |
| cg06334737 | 11 | 61976195 | Lower in Smoker |
| cg19697330 | 5 | 160018201 | Higher in Smoker |
| cg13834623 | 6 | 25652407 | Lower in Smoker |
| cg23553912 | 3 | 159558031 | Higher in Smoker |

| | | | |
|---|---|---|---|
| cg01364862 | 3 | 159364474 | Lower in Smoker |
| cg20728105 | 7 | 12610689 | Higher in Smoker |
| cg07551952 | 7 | 12613522 | Lower in Smoker |
| cg14498674 | 1 | 41707653 | Higher in Smoker |
| cg02187432 | X | 18371852 | Higher in Smoker |
| cg03500965 | 6 | 108145777 | Lower in Smoker |
| cg11749828 | 19 | 35531150 | Higher in Smoker |
| cg16631432 | 2 | 165998136 | Lower in Smoker |
| cg12527384 | 11 | 123525060 | Higher in Smoker |
| cg24069602 | 17 | 62045522 | Lower in Smoker |
| cg20341535 | 11 | 118017101 | Lower in Smoker |
| cg23473910 | 3 | 38597540 | Lower in Smoker |
| cg11410859 | 3 | 38687164 | Lower in Smoker |
| cg08253824 | 12 | 52088855 | Lower in Smoker |
| cg19760651 | 12 | 52201104 | Lower in Smoker |
| cg20059682 | 12 | 52201821 | Lower in Smoker |
| cg02901431 | 4 | 141207852 | Lower in Smoker |
| cg07444408 | 4 | 141218466 | Lower in Smoker |
| cg20424311 | 4 | 141221527 | Lower in Smoker |
| cg04761746 | 4 | 141177756 | Lower in Smoker |
| cg02945007 | 4 | 141294667 | Higher in Smoker |
| cg08859206 | 1 | 53392774 | Lower in Smoker |
| cg01802117 | 1 | 53393560 | Lower in Smoker |
| cg09901201 | 1 | 53515142 | Lower in Smoker |
| cg13685833 | 1 | 53393034 | Lower in Smoker |
| cg06438385 | 8 | 144886159 | Lower in Smoker |
| cg14234176 | 8 | 144887661 | Lower in Smoker |
| cg00659559 | 7 | 29961120 | Higher in Smoker |
| cg05073843 | 20 | 645199 | Higher in Smoker |
| cg07636295 | 20 | 656446 | Higher in Smoker |
| cg26736232 | 11 | 628603 | Lower in Smoker |
| cg04965050 | 22 | 43739790 | Lower in Smoker |
| cg13515585 | 11 | 9113190 | Higher in Smoker |
| cg04396314 | 11 | 65292474 | Higher in Smoker |
| cg26957012 | 11 | 65305575 | Higher in Smoker |

| | | | |
|---|---|---|---|
| cg11911934 | 12 | 100660633 | Higher in Smoker |
| cg23051655 | 1 | 169862721 | Higher in Smoker |
| cg09549329 | 1 | 169854522 | Lower in Smoker |
| cg12982277 | 2 | 20423114 | Higher in Smoker |
| cg26842303 | 8 | 97564627 | Lower in Smoker |
| cg27440965 | 20 | 43954866 | Lower in Smoker |
| ch.5.1225211R | 5 | 64300829 | Higher in Smoker |
| cg08610986 | 5 | 64064533 | Higher in Smoker |
| cg00295780 | 1 | 243635800 | Lower in Smoker |
| cg08916050 | 1 | 243419132 | Higher in Smoker |
| cg10824491 | 17 | 26989063 | Higher in Smoker |
| cg00656410 | 1 | 1157541 | Lower in Smoker |
| cg00062072 | 1 | 1157684 | Lower in Smoker |
| cg02691002 | 5 | 233697 | Lower in Smoker |
| cg24069048 | 5 | 256469 | Lower in Smoker |
| cg20965017 | 5 | 231967 | Lower in Smoker |
| cg02505535 | 3 | 195703920 | Lower in Smoker |
| cg13915730 | 7 | 7380506 | Higher in Smoker |
| cg09461837 | 7 | 3341524 | Higher in Smoker |
| cg16250868 | 7 | 3710628 | Higher in Smoker |
| cg15466606 | 7 | 3340860 | Higher in Smoker |
| cg08019384 | 7 | 3920439 | Lower in Smoker |
| cg14414971 | 7 | 3340979 | Lower in Smoker |
| cg01982837 | 7 | 3588642 | Lower in Smoker |
| cg01506471 | 7 | 3990479 | Lower in Smoker |
| cg03393322 | 7 | 4260883 | Lower in Smoker |
| cg11170896 | 7 | 4266872 | Lower in Smoker |
| cg16866485 | 7 | 4276220 | Lower in Smoker |
| cg23474811 | 7 | 4183807 | Lower in Smoker |
| cg19691505 | 7 | 4175336 | Lower in Smoker |
| cg23781810 | 17 | 71640253 | Higher in Smoker |
| cg19776515 | 8 | 57232395 | Lower in Smoker |
| cg27083414 | 19 | 49149933 | Higher in Smoker |
| cg26571142 | 19 | 49140646 | Higher in Smoker |
| cg05899224 | 18 | 56806647 | Higher in Smoker |

| | | | |
|---|---|---|---|
| cg14416747 | 17 | 75136725 | Higher in Smoker |
| cg00618183 | 17 | 75143600 | Lower in Smoker |
| cg09232069 | 17 | 75143118 | Lower in Smoker |
| cg03673688 | 22 | 30818470 | Lower in Smoker |
| cg01245880 | 22 | 30899870 | Lower in Smoker |
| cg07770360 | 16 | 5039472 | Lower in Smoker |
| cg13879547 | 9 | 139358536 | Lower in Smoker |
| cg01019496 | 1 | 145095965 | Lower in Smoker |
| cg06068373 | 3 | 42594510 | Lower in Smoker |
| cg27265637 | 10 | 75504303 | Higher in Smoker |
| cg19864851 | 10 | 75503847 | Higher in Smoker |
| cg21607141 | 4 | 119722917 | Lower in Smoker |
| cg03843493 | 4 | 119695822 | Lower in Smoker |
| cg20852788 | 4 | 119676722 | Lower in Smoker |
| cg08074962 | 4 | 83812797 | Higher in Smoker |
| cg12825059 | 10 | 12172258 | Higher in Smoker |
| cg03322752 | 7 | 54824520 | Lower in Smoker |
| cg08908843 | 15 | 49283846 | Lower in Smoker |
| cg16357287 | 18 | 12947517 | Higher in Smoker |
| cg10636044 | 14 | 82000026 | Higher in Smoker |
| cg08086809 | 14 | 82000312 | Higher in Smoker |
| cg06255670 | 4 | 25864318 | Lower in Smoker |
| cg26065909 | 1 | 151345173 | Lower in Smoker |
| cg00978415 | 1 | 151345771 | Lower in Smoker |
| cg06458732 | 2 | 26568464 | Higher in Smoker |
| cg00584995 | 2 | 26568855 | Higher in Smoker |
| cg25118511 | 3 | 53926156 | Higher in Smoker |
| cg13470658 | 3 | 150321009 | Higher in Smoker |
| cg12562967 | 19 | 40006192 | Higher in Smoker |
| cg08620606 | 19 | 40005611 | Higher in Smoker |
| cg02271707 | 7 | 83813729 | Lower in Smoker |
| cg07629965 | 3 | 50312389 | Higher in Smoker |
| cg06192381 | 3 | 50305066 | Higher in Smoker |
| cg16216311 | 3 | 50305083 | Higher in Smoker |
| cg19815904 | 7 | 80548307 | Higher in Smoker |

| | | | |
|---|---|---|---|
| cg04624362 | 15 | 90730573 | Lower in Smoker |
| cg14434745 | 15 | 90756012 | Lower in Smoker |
| cg05044706 | 2 | 97526613 | Higher in Smoker |
| cg17818613 | 2 | 97527586 | Higher in Smoker |
| cg18762104 | 2 | 97535692 | Higher in Smoker |
| cg13474090 | 9 | 92027541 | Lower in Smoker |
| cg06118588 | 2 | 74882001 | Higher in Smoker |
| cg05645002 | 5 | 9156800 | Lower in Smoker |
| cg05593589 | 5 | 9234356 | Lower in Smoker |
| cg17807777 | 5 | 9374198 | Lower in Smoker |
| cg18073906 | 3 | 122641029 | Lower in Smoker |
| cg07453683 | 5 | 115783283 | Lower in Smoker |
| cg26423542 | 5 | 115835345 | Lower in Smoker |
| cg27072247 | 5 | 115901296 | Lower in Smoker |
| cg21578050 | 5 | 115896354 | Lower in Smoker |
| cg24026146 | 5 | 115786403 | Lower in Smoker |
| cg06650664 | 5 | 115870174 | Lower in Smoker |
| cg15557084 | 5 | 115853116 | Lower in Smoker |
| cg09573435 | 5 | 115910259 | Higher in Smoker |
| cg04065086 | 1 | 151104186 | Lower in Smoker |
| cg26169213 | 15 | 74704423 | Higher in Smoker |
| cg27157619 | 15 | 74714463 | Lower in Smoker |
| cg00033304 | 3 | 185302692 | Lower in Smoker |
| cg17274771 | 17 | 7465072 | Lower in Smoker |
| cg27538497 | 15 | 72412574 | Lower in Smoker |
| cg02257172 | 10 | 13380770 | Lower in Smoker |
| cg02462818 | 2 | 110367141 | Higher in Smoker |
| cg16454349 | 16 | 4837889 | Lower in Smoker |
| cg07791671 | 2 | 242255336 | Higher in Smoker |
| cg13105709 | 17 | 56598862 | Lower in Smoker |
| cg23716141 | 17 | 75360477 | Higher in Smoker |
| cg18271897 | 17 | 75316784 | Lower in Smoker |
| cg10755077 | 17 | 75318882 | Lower in Smoker |
| cg20305489 | 17 | 75316480 | Lower in Smoker |
| cg15661536 | 17 | 75317185 | Lower in Smoker |

| | | | |
|---|---|---|---|
| cg03236137 | 17 | 75401367 | Higher in Smoker |
| cg12859577 | 17 | 75385278 | Higher in Smoker |
| cg23120541 | 17 | 75422456 | Higher in Smoker |
| cg27627381 | 17 | 75452100 | Lower in Smoker |
| cg14843920 | 17 | 75451932 | Lower in Smoker |
| cg20030711 | 17 | 75471308 | Higher in Smoker |
| cg22056755 | 6 | 158570952 | Lower in Smoker |
| cg14029994 | 6 | 158589857 | Higher in Smoker |
| cg16308101 | 1 | 67895914 | Lower in Smoker |
| cg20047447 | 15 | 44084326 | Higher in Smoker |
| cg18997990 | 15 | 44084145 | Higher in Smoker |
| cg10102256 | 11 | 18034688 | Higher in Smoker |
| cg11047973 | 11 | 18034355 | Higher in Smoker |
| cg06021522 | 11 | 17898125 | Lower in Smoker |
| cg23509077 | 11 | 17982058 | Lower in Smoker |
| cg08849813 | 11 | 17825098 | Lower in Smoker |
| cg00932007 | 6 | 122792946 | Higher in Smoker |
| cg20185863 | 6 | 122792938 | Higher in Smoker |
| cg13208584 | 20 | 43128003 | Lower in Smoker |
| cg09938490 | 15 | 44088809 | Lower in Smoker |
| cg14372171 | 15 | 44093010 | Lower in Smoker |
| cg10609043 | 5 | 79408024 | Higher in Smoker |
| cg14939475 | 18 | 61653588 | Lower in Smoker |
| cg07844977 | 6 | 2903699 | Higher in Smoker |
| cg11169461 | 2 | 224904347 | Higher in Smoker |
| cg20343375 | 2 | 224866411 | Lower in Smoker |
| cg05453373 | 13 | 51914201 | Lower in Smoker |
| cg18278729 | 17 | 1657676 | Higher in Smoker |
| cg13542022 | 19 | 40932276 | Higher in Smoker |
| cg00063909 | 2 | 64877006 | Lower in Smoker |
| cg12460075 | 6 | 109330005 | Higher in Smoker |
| cg26242302 | 11 | 94926302 | Lower in Smoker |
| cg10136773 | 11 | 94906134 | Lower in Smoker |
| cg17701168 | 9 | 131445948 | Higher in Smoker |
| cg00801360 | 9 | 131450106 | Lower in Smoker |

| | | | |
|---|---|---|---|
| cg02779164 | 18 | 42531099 | Lower in Smoker |
| cg20038204 | 18 | 42530828 | Lower in Smoker |
| cg03527663 | 18 | 42531132 | Lower in Smoker |
| cg15309045 | 18 | 42530935 | Lower in Smoker |
| cg25162568 | 18 | 42530893 | Lower in Smoker |
| cg13849552 | 18 | 42260056 | Higher in Smoker |
| cg20090762 | 18 | 42323716 | Lower in Smoker |
| cg02153299 | 16 | 30968484 | Lower in Smoker |
| cg00386008 | 12 | 122269623 | Lower in Smoker |
| cg11343534 | 12 | 122242517 | Lower in Smoker |
| cg05023903 | 14 | 99920322 | Lower in Smoker |
| cg24999883 | 14 | 99880641 | Lower in Smoker |
| cg14232552 | 14 | 99880406 | Lower in Smoker |
| cg13049261 | 14 | 99879199 | Lower in Smoker |
| cg06798460 | 3 | 9439221 | Higher in Smoker |
| cg05890285 | 3 | 9439271 | Higher in Smoker |
| cg05191824 | 12 | 123868698 | Higher in Smoker |
| cg06548892 | 13 | 50021335 | Lower in Smoker |
| cg15232450 | 3 | 4345438 | Lower in Smoker |
| cg17477442 | 17 | 27331600 | Higher in Smoker |
| cg16723002 | 17 | 27285150 | Lower in Smoker |
| cg26527105 | 11 | 64533113 | Lower in Smoker |
| cg11957798 | 19 | 2246864 | Lower in Smoker |
| cg27662093 | 19 | 2248302 | Lower in Smoker |
| cg22863204 | 6 | 144416746 | Higher in Smoker |
| cg08112740 | 19 | 19416944 | Lower in Smoker |
| cg12737971 | 22 | 31892148 | Higher in Smoker |
| cg11435225 | 22 | 32014422 | Higher in Smoker |
| cg00184864 | 22 | 31892343 | Higher in Smoker |
| cg02980650 | 10 | 7446012 | Lower in Smoker |
| cg12615100 | 1 | 35659060 | Higher in Smoker |
| cg01425479 | 1 | 35658293 | Higher in Smoker |
| cg00930833 | 8 | 41168264 | Higher in Smoker |
| cg14824366 | 8 | 41167923 | Higher in Smoker |
| cg13398291 | 8 | 41166169 | Higher in Smoker |

| | | | |
|---|---|---|---|
| cg10406295 | 8 | 41167113 | Higher in Smoker |
| cg22418909 | 8 | 41166738 | Higher in Smoker |
| cg25775322 | 4 | 154710373 | Higher in Smoker |
| cg14063488 | 4 | 154709878 | Higher in Smoker |
| cg09594069 | 7 | 37956906 | Higher in Smoker |
| cg06692050 | 10 | 99532398 | Lower in Smoker |
| cg05699018 | 10 | 99531747 | Higher in Smoker |
| cg00239061 | 17 | 56083898 | Higher in Smoker |
| cg23960707 | 17 | 56083289 | Lower in Smoker |
| cg22390894 | 1 | 70671645 | Higher in Smoker |
| cg16666456 | 1 | 70671441 | Higher in Smoker |
| cg22358068 | 1 | 24296851 | Lower in Smoker |
| cg23356850 | 6 | 89827912 | Higher in Smoker |
| cg22363327 | 6 | 89828097 | Higher in Smoker |
| cg27383468 | 6 | 99873554 | Higher in Smoker |
| cg08669361 | 6 | 99872792 | Higher in Smoker |
| cg01242602 | 6 | 99871510 | Lower in Smoker |
| cg20157484 | 12 | 46385525 | Higher in Smoker |
| cg24481441 | 1 | 29509511 | Lower in Smoker |
| cg18277960 | 14 | 70233819 | Lower in Smoker |
| cg20011543 | 20 | 42086465 | Higher in Smoker |
| cg14022523 | 6 | 166756177 | Higher in Smoker |
| cg13049997 | 6 | 166744404 | Lower in Smoker |
| cg05393023 | 1 | 168194826 | Lower in Smoker |
| cg24925163 | 2 | 128458248 | Lower in Smoker |
| cg20154206 | 2 | 128458240 | Lower in Smoker |
| cg20054157 | 10 | 10837080 | Higher in Smoker |
| cg12207120 | 14 | 36974523 | Higher in Smoker |
| cg04926361 | 14 | 36982447 | Lower in Smoker |
| cg00327383 | 8 | 22019275 | Lower in Smoker |
| cg10872209 | 10 | 104475308 | Lower in Smoker |
| cg27224392 | 10 | 104474430 | Higher in Smoker |
| cg24948792 | 10 | 102789961 | Lower in Smoker |
| cg20584546 | 2 | 73248097 | Lower in Smoker |
| cg01566785 | 7 | 94285745 | Higher in Smoker |

| | | | |
|---|---|---|---|
| cg05819130 | 7 | 94285759 | Higher in Smoker |
| cg17701373 | 7 | 94285343 | Higher in Smoker |
| cg26912242 | 7 | 94285352 | Higher in Smoker |
| cg14388858 | 7 | 94285520 | Higher in Smoker |
| cg04366249 | 7 | 94285501 | Higher in Smoker |
| cg23498273 | 7 | 94284526 | Higher in Smoker |
| cg02444961 | 7 | 94284539 | Higher in Smoker |
| cg14937059 | 7 | 94248343 | Lower in Smoker |
| cg13168042 | 13 | 23755059 | Lower in Smoker |
| cg04517343 | 3 | 153875979 | Lower in Smoker |
| cg14610403 | 1 | 66998812 | Higher in Smoker |
| ch.6.2574971F | 6 | 134493128 | Higher in Smoker |
| cg21676440 | 6 | 134493324 | Lower in Smoker |
| cg05183646 | 6 | 134491143 | Lower in Smoker |
| cg00345314 | 8 | 67624394 | Higher in Smoker |
| cg15969314 | 8 | 67624648 | Higher in Smoker |
| cg27622722 | 8 | 67624757 | Higher in Smoker |
| cg23158475 | 8 | 67683529 | Lower in Smoker |
| cg13971096 | 8 | 67690752 | Lower in Smoker |
| cg02127234 | 8 | 67688534 | Lower in Smoker |
| cg13382516 | 10 | 52336353 | Higher in Smoker |
| cg19876232 | 10 | 52174504 | Lower in Smoker |
| cg24037270 | 10 | 52066867 | Lower in Smoker |
| cg05977109 | 10 | 52178181 | Lower in Smoker |
| cg02114449 | 3 | 20227940 | Higher in Smoker |
| cg00043095 | 2 | 223289277 | Higher in Smoker |
| cg09097345 | 22 | 25202086 | Higher in Smoker |
| cg16155122 | 22 | 25201958 | Higher in Smoker |
| cg21287519 | 17 | 2251062 | Lower in Smoker |
| cg02628470 | 17 | 2279569 | Lower in Smoker |
| cg14045725 | 17 | 2240967 | Higher in Smoker |
| cg06228413 | 22 | 40766527 | Higher in Smoker |
| cg22758067 | 19 | 2783381 | Higher in Smoker |
| cg01356824 | 12 | 111849884 | Higher in Smoker |
| cg07821354 | 19 | 6768010 | Higher in Smoker |

| | | | |
|---|---|---|---|
| cg03138955 | 8 | 19170250 | Higher in Smoker |
| cg04097312 | 10 | 82345955 | Lower in Smoker |
| cg27210863 | 10 | 82299606 | Lower in Smoker |
| cg04421348 | 10 | 82299737 | Lower in Smoker |
| cg12064626 | 21 | 40817896 | Higher in Smoker |
| cg22945302 | 1 | 26606601 | Higher in Smoker |
| cg11392855 | 4 | 2795155 | Higher in Smoker |
| cg26759036 | 4 | 2828170 | Lower in Smoker |
| cg11236296 | 2 | 235961622 | Lower in Smoker |
| cg04088932 | 2 | 235953856 | Lower in Smoker |
| cg03495084 | 3 | 15311154 | Lower in Smoker |
| cg24170085 | 3 | 15311269 | Lower in Smoker |
| cg13620028 | 1 | 249120883 | Higher in Smoker |
| cg03612577 | 1 | 249115007 | Lower in Smoker |
| cg15232319 | 19 | 4376459 | Lower in Smoker |
| cg19005281 | 15 | 84116935 | Higher in Smoker |
| cg09201151 | 15 | 84116151 | Higher in Smoker |
| cg23538844 | 1 | 87170109 | Higher in Smoker |
| cg03958163 | 10 | 105615502 | Higher in Smoker |
| cg02722808 | 10 | 105595043 | Higher in Smoker |
| cg24904925 | 5 | 171881564 | Higher in Smoker |
| cg26528541 | 5 | 171881553 | Higher in Smoker |
| cg18629270 | 5 | 171881583 | Higher in Smoker |
| cg13383775 | 4 | 170038355 | Lower in Smoker |
| cg12257055 | 4 | 170086985 | Lower in Smoker |
| cg09124703 | 5 | 145316063 | Higher in Smoker |
| cg25707877 | 2 | 109889899 | Lower in Smoker |
| cg16268848 | 2 | 109744586 | Higher in Smoker |
| cg04332454 | 4 | 8221472 | Lower in Smoker |
| cg21586243 | 2 | 264756 | Higher in Smoker |
| cg22598669 | 19 | 51186978 | Higher in Smoker |
| cg26025487 | 11 | 70674245 | Lower in Smoker |
| cg21202716 | 11 | 70508022 | Higher in Smoker |
| cg06622135 | 11 | 70474416 | Lower in Smoker |
| cg16944941 | 11 | 70391346 | Lower in Smoker |

| | | | |
|---|---|---|---|
| cg16753846 | 11 | 70318894 | Lower in Smoker |
| cg19892433 | 11 | 70331861 | Lower in Smoker |
| cg11070176 | 11 | 70489806 | Lower in Smoker |
| cg26567213 | 22 | 51112165 | Higher in Smoker |
| cg04537738 | 22 | 51143999 | Lower in Smoker |
| cg23637124 | 15 | 49255455 | Higher in Smoker |
| cg03693601 | 16 | 46655349 | Higher in Smoker |
| cg09459280 | 16 | 46615086 | Lower in Smoker |
| cg02710224 | 15 | 45491210 | Higher in Smoker |
| cg19006841 | 15 | 45491101 | Higher in Smoker |
| cg06238944 | 7 | 155596996 | Higher in Smoker |
| cg14866200 | 4 | 42399843 | Higher in Smoker |
| cg00721603 | 4 | 42400738 | Higher in Smoker |
| cg18568657 | 3 | 48517026 | Lower in Smoker |
| cg26940328 | 17 | 11146412 | Higher in Smoker |
| cg13752254 | 19 | 55940813 | Lower in Smoker |
| cg00541002 | 10 | 112696816 | Higher in Smoker |
| cg05401764 | 3 | 157815808 | Higher in Smoker |
| cg17906146 | 3 | 72897762 | Higher in Smoker |
| cg15835805 | 5 | 132162441 | Lower in Smoker |
| cg22666517 | X | 9916563 | Lower in Smoker |
| cg24175289 | 4 | 77457089 | Lower in Smoker |
| cg27230396 | 4 | 77662896 | Lower in Smoker |
| cg19591902 | 4 | 77653343 | Lower in Smoker |
| cg06216640 | 4 | 77640141 | Lower in Smoker |
| cg19522262 | 4 | 77512495 | Lower in Smoker |
| cg24137322 | 4 | 77484566 | Lower in Smoker |
| cg15642468 | 4 | 77433177 | Lower in Smoker |
| cg10026495 | 4 | 77631215 | Lower in Smoker |
| cg01477861 | 4 | 77609841 | Lower in Smoker |
| cg10764785 | 16 | 48419812 | Higher in Smoker |
| cg02631622 | 16 | 48416433 | Higher in Smoker |
| cg00676042 | 3 | 150461287 | Higher in Smoker |
| cg05752393 | 18 | 43418829 | Higher in Smoker |
| cg00425636 | 18 | 43404545 | Higher in Smoker |

| | | | |
|---|---|---|---|
| cg16293105 | 19 | 52034970 | Higher in Smoker |
| cg11344533 | 11 | 111475393 | Higher in Smoker |
| cg25777073 | 11 | 111472741 | Higher in Smoker |
| cg23684410 | 11 | 116897558 | Lower in Smoker |
| cg04439458 | 5 | 138467593 | Lower in Smoker |
| cg21063722 | 6 | 100911709 | Higher in Smoker |
| cg24211504 | 6 | 100903575 | Higher in Smoker |
| cg12347554 | 6 | 100909443 | Higher in Smoker |
| cg05100070 | 6 | 100896760 | Higher in Smoker |
| cg11540692 | 6 | 100912072 | Higher in Smoker |
| cg11391393 | 6 | 100911727 | Higher in Smoker |
| cg14993283 | 6 | 100906182 | Higher in Smoker |
| cg22976224 | 21 | 38070639 | Higher in Smoker |
| cg01664094 | 15 | 75748568 | Higher in Smoker |
| cg15769256 | 15 | 75746558 | Higher in Smoker |
| cg15851274 | 15 | 75748063 | Higher in Smoker |
| cg08179428 | 15 | 75745131 | Higher in Smoker |
| cg01758634 | 15 | 75744504 | Higher in Smoker |
| cg11803771 | 11 | 65408566 | Higher in Smoker |
| cg24420726 | 19 | 38684319 | Lower in Smoker |
| cg03119618 | 19 | 38572401 | Lower in Smoker |
| cg13408605 | 20 | 1639816 | Lower in Smoker |
| cg23988827 | 10 | 69676715 | Lower in Smoker |
| cg07909422 | 6 | 13574371 | Higher in Smoker |
| cg09936839 | 19 | 4181854 | Lower in Smoker |
| cg10157936 | 14 | 105220767 | Lower in Smoker |
| cg05296818 | 14 | 61117162 | Higher in Smoker |
| cg10165331 | 14 | 61116900 | Lower in Smoker |
| cg20318845 | 2 | 45237781 | Higher in Smoker |
| cg03646261 | 2 | 45235408 | Higher in Smoker |
| cg02147764 | 2 | 45169681 | Higher in Smoker |
| cg02372786 | 2 | 45167549 | Higher in Smoker |
| cg16509777 | 2 | 45172265 | Higher in Smoker |
| cg02120584 | 2 | 45171340 | Higher in Smoker |
| cg06726207 | 14 | 61190550 | Higher in Smoker |

| | | | |
|---|---|---|---|
| cg20283449 | 14 | 61190829 | Higher in Smoker |
| cg26392828 | 14 | 61191075 | Higher in Smoker |
| cg02656609 | 17 | 57228618 | Lower in Smoker |
| cg20009499 | 17 | 57232567 | Higher in Smoker |
| cg16789104 | 17 | 46507777 | Higher in Smoker |
| cg06382459 | 1 | 2159373 | Higher in Smoker |
| cg27536187 | 1 | 2159365 | Higher in Smoker |
| cg19757330 | 1 | 2212997 | Lower in Smoker |
| cg01852476 | 1 | 2232063 | Lower in Smoker |
| cg16417118 | 1 | 2162931 | Lower in Smoker |
| cg08468599 | 1 | 2182126 | Lower in Smoker |
| cg15627834 | 3 | 170078469 | Lower in Smoker |
| cg18516595 | 5 | 133493247 | Lower in Smoker |
| cg24773493 | 5 | 36154983 | Lower in Smoker |
| cg09144905 | 13 | 78280893 | Lower in Smoker |
| cg07590721 | 1 | 159795518 | Lower in Smoker |
| cg06954855 | 1 | 159801570 | Lower in Smoker |
| cg09964575 | 4 | 1695311 | Higher in Smoker |
| cg18312429 | 13 | 103718930 | Lower in Smoker |
| cg05424879 | X | 153719176 | Higher in Smoker |
| cg06266461 | X | 153719192 | Higher in Smoker |
| cg14444103 | 4 | 147367017 | Lower in Smoker |
| cg20424486 | 4 | 147439128 | Lower in Smoker |
| cg20910303 | 4 | 147443095 | Higher in Smoker |
| cg15099037 | 2 | 219246468 | Lower in Smoker |
| cg20872692 | 12 | 51381135 | Lower in Smoker |
| cg03478448 | 16 | 56945735 | Lower in Smoker |
| cg01160557 | 20 | 44651777 | Higher in Smoker |
| cg03682073 | 20 | 44685203 | Lower in Smoker |
| cg00678890 | 20 | 44660599 | Lower in Smoker |
| cg10439765 | 20 | 44657838 | Higher in Smoker |
| cg03541369 | 15 | 34630435 | Lower in Smoker |
| cg13051058 | 15 | 34629706 | Higher in Smoker |
| cg12146829 | 5 | 1107855 | Higher in Smoker |
| cg11235297 | 5 | 1108315 | Higher in Smoker |

| | | | |
|---|---|---|---|
| cg19773466 | 5 | 1108374 | Higher in Smoker |
| cg11713480 | 5 | 1081913 | Higher in Smoker |
| cg23221540 | 5 | 1092417 | Lower in Smoker |
| cg04226648 | 5 | 1087829 | Lower in Smoker |
| cg21334510 | 5 | 1093580 | Lower in Smoker |
| cg04213775 | 5 | 1063087 | Lower in Smoker |
| cg16399589 | 17 | 26824423 | Lower in Smoker |
| cg15066489 | 3 | 121613396 | Lower in Smoker |
| cg16300317 | 6 | 111409547 | Higher in Smoker |
| cg07011163 | 17 | 6947325 | Higher in Smoker |
| cg25241322 | 17 | 6939304 | Higher in Smoker |
| cg09941770 | 17 | 6938926 | Higher in Smoker |
| cg03705718 | 2 | 230953322 | Lower in Smoker |
| cg24663315 | X | 73640043 | Higher in Smoker |
| cg10937494 | 17 | 80195101 | Higher in Smoker |
| cg07012687 | 17 | 80195180 | Higher in Smoker |
| cg10812247 | 12 | 60174815 | Lower in Smoker |
| cg06885175 | 6 | 25788879 | Lower in Smoker |
| cg09546929 | 6 | 25930894 | Lower in Smoker |
| cg09750510 | 6 | 25761690 | Lower in Smoker |
| cg22865713 | 6 | 25779897 | Lower in Smoker |
| cg00648153 | 6 | 74364149 | Higher in Smoker |
| cg16909495 | 19 | 49940062 | Higher in Smoker |
| cg08374499 | 19 | 49941241 | Lower in Smoker |
| cg00740822 | 19 | 49939611 | Lower in Smoker |
| cg17243364 | 21 | 46962793 | Higher in Smoker |
| cg00714531 | 21 | 46955647 | Lower in Smoker |
| cg04091914 | 2 | 228551538 | Lower in Smoker |
| cg24611631 | 9 | 4490288 | Higher in Smoker |
| cg25010361 | 5 | 36607377 | Higher in Smoker |
| cg21245981 | 5 | 36607390 | Higher in Smoker |
| cg24100705 | 19 | 47290674 | Higher in Smoker |
| cg03359362 | 19 | 47289611 | Higher in Smoker |
| cg21766592 | 19 | 47288066 | Lower in Smoker |
| cg10385290 | 19 | 15083818 | Lower in Smoker |

| | | | |
|---|---|---|---|
| cg12171675 | 19 | 15083795 | Lower in Smoker |
| cg00532936 | 1 | 53588449 | Lower in Smoker |
| cg01808968 | 1 | 53574533 | Lower in Smoker |
| cg15936066 | 8 | 42356637 | Higher in Smoker |
| cg19504179 | 8 | 42373715 | Lower in Smoker |
| cg26275110 | 11 | 64329426 | Lower in Smoker |
| cg22353097 | 1 | 116521539 | Lower in Smoker |
| cg08999895 | 11 | 2925869 | Higher in Smoker |
| cg23912877 | 11 | 2926337 | Lower in Smoker |
| cg02390725 | 11 | 2925768 | Lower in Smoker |
| cg26874323 | 11 | 2909709 | Higher in Smoker |
| cg05752118 | 11 | 2920564 | Higher in Smoker |
| cg14449910 | 11 | 2919689 | Higher in Smoker |
| cg14373018 | 11 | 64981297 | Lower in Smoker |
| cg21348565 | 11 | 62997285 | Lower in Smoker |
| cg07354253 | 5 | 131629923 | Lower in Smoker |
| cg07538946 | 5 | 131705188 | Higher in Smoker |
| cg07037963 | 6 | 43265846 | Lower in Smoker |
| cg11007296 | 5 | 138711261 | Lower in Smoker |
| cg24241057 | 20 | 4982241 | Higher in Smoker |
| cg12262395 | 20 | 4983435 | Lower in Smoker |
| cg14601251 | 15 | 65913984 | Lower in Smoker |
| cg26849077 | 15 | 65914281 | Lower in Smoker |
| cg14512346 | 14 | 92788914 | Higher in Smoker |
| cg12119780 | 12 | 113772592 | Higher in Smoker |
| cg00179532 | 17 | 79684775 | Lower in Smoker |
| cg07535928 | 14 | 37641436 | Higher in Smoker |
| cg17100943 | 19 | 6459300 | Lower in Smoker |
| cg03438742 | 6 | 46620708 | Higher in Smoker |
| cg13631913 | 1 | 9600345 | Higher in Smoker |
| cg06927343 | 1 | 9635799 | Lower in Smoker |
| cg21821674 | 1 | 16063471 | Higher in Smoker |
| cg00825497 | 17 | 8198725 | Higher in Smoker |
| cg19697725 | 17 | 8198295 | Lower in Smoker |
| cg26053771 | 17 | 8192194 | Higher in Smoker |

| | | | |
|---|---|---|---|
| cg01351041 | 3 | 140660569 | Higher in Smoker |
| cg10649384 | 7 | 87505489 | Higher in Smoker |
| cg19547236 | 19 | 19175039 | Higher in Smoker |
| cg25768103 | 19 | 19174831 | Higher in Smoker |
| cg03974275 | 1 | 156162316 | Higher in Smoker |
| cg22368545 | 11 | 65142946 | Lower in Smoker |
| cg10994292 | 5 | 110074295 | Higher in Smoker |
| cg26660316 | 5 | 110077272 | Lower in Smoker |
| cg16520288 | 12 | 58014857 | Higher in Smoker |
| cg12883767 | 12 | 58013109 | Higher in Smoker |
| cg07675682 | 17 | 78195515 | Lower in Smoker |
| cg25863369 | 17 | 78194236 | Lower in Smoker |
| cg04473302 | 7 | 107301217 | Higher in Smoker |
| cg23461615 | 7 | 103086074 | Higher in Smoker |
| cg23924438 | 7 | 103014771 | Lower in Smoker |
| cg17214676 | 8 | 92260467 | Lower in Smoker |
| cg06442162 | 8 | 92406857 | Lower in Smoker |
| cg02576503 | 19 | 17581430 | Higher in Smoker |
| cg09325679 | 19 | 17597534 | Lower in Smoker |
| cg06012269 | 19 | 17608374 | Lower in Smoker |
| cg16897014 | 15 | 50474230 | Lower in Smoker |
| cg14920199 | 15 | 50474232 | Lower in Smoker |
| cg18163252 | 1 | 153748120 | Higher in Smoker |
| cg15930240 | 1 | 153749015 | Lower in Smoker |
| cg12076344 | 9 | 131102607 | Higher in Smoker |
| cg23758765 | 11 | 66138996 | Higher in Smoker |
| cg24151204 | 11 | 66130871 | Lower in Smoker |
| cg19347288 | 11 | 66135554 | Lower in Smoker |
| cg08181642 | 11 | 66135624 | Lower in Smoker |
| cg13313036 | 11 | 66139196 | Higher in Smoker |
| cg08874645 | 10 | 73093425 | Higher in Smoker |
| cg23698832 | 7 | 5330336 | Lower in Smoker |
| cg05101809 | 7 | 5338832 | Lower in Smoker |
| cg03128534 | 1 | 43423976 | Higher in Smoker |
| cg06094523 | 1 | 43398103 | Lower in Smoker |

| | | | |
|---|---|---|---|
| cg21474257 | 1 | 43399327 | Lower in Smoker |
| cg05942022 | 1 | 43402591 | Lower in Smoker |
| cg05034603 | 1 | 43396871 | Lower in Smoker |
| cg00737593 | 1 | 43422337 | Lower in Smoker |
| cg09502149 | 1 | 43406792 | Lower in Smoker |
| cg05802386 | 1 | 43422920 | Lower in Smoker |
| cg01924561 | 1 | 43416103 | Lower in Smoker |
| cg20282814 | 1 | 43423072 | Lower in Smoker |
| cg02936854 | 22 | 24199972 | Higher in Smoker |
| cg11599694 | 6 | 134374934 | Lower in Smoker |
| cg04626413 | 12 | 40364819 | Lower in Smoker |
| cg07287345 | 12 | 40415007 | Lower in Smoker |
| cg14061497 | 12 | 40496213 | Lower in Smoker |
| cg16190510 | 12 | 40197081 | Lower in Smoker |
| cg19016972 | 12 | 8012926 | Higher in Smoker |
| cg07649206 | 3 | 170742094 | Lower in Smoker |
| cg02289343 | 1 | 9131622 | Lower in Smoker |
| cg00155732 | 1 | 9103309 | Lower in Smoker |
| cg00690929 | 1 | 9118237 | Lower in Smoker |
| cg00411595 | 9 | 136339349 | Higher in Smoker |
| cg20822540 | 1 | 9070127 | Lower in Smoker |
| cg00398500 | 4 | 10041776 | Lower in Smoker |
| cg02387843 | 4 | 9892887 | Lower in Smoker |
| cg04976746 | 1 | 211751127 | Higher in Smoker |
| cg01143423 | 1 | 211750967 | Higher in Smoker |
| cg02397727 | 1 | 26372300 | Higher in Smoker |
| cg03987192 | 1 | 26373407 | Higher in Smoker |
| cg09874052 | 1 | 101361842 | Higher in Smoker |
| cg10652277 | 4 | 41992362 | Higher in Smoker |
| cg14536921 | 4 | 41992485 | Higher in Smoker |
| cg19303434 | 4 | 41992264 | Higher in Smoker |
| cg03574651 | 4 | 41992907 | Lower in Smoker |
| cg13915754 | 20 | 37355965 | Higher in Smoker |
| cg02635677 | 5 | 176823320 | Lower in Smoker |
| cg07620167 | 9 | 140128686 | Lower in Smoker |

| | | | |
|---|---|---|---|
| cg06426831 | 1 | 100435258 | Lower in Smoker |
| cg25707238 | 3 | 112302060 | Lower in Smoker |
| cg20144576 | 6 | 44225102 | Higher in Smoker |
| cg06440160 | 6 | 44222046 | Lower in Smoker |
| cg20246548 | 6 | 8435978 | Lower in Smoker |
| cg01815076 | 6 | 8435968 | Lower in Smoker |
| cg24404943 | 7 | 134001981 | Higher in Smoker |
| cg00101729 | 6 | 137243228 | Higher in Smoker |
| cg08221064 | 12 | 69139738 | Higher in Smoker |
| cg20662988 | 6 | 118241243 | Higher in Smoker |
| cg14669345 | 6 | 118603516 | Lower in Smoker |
| cg15244223 | 6 | 118228493 | Lower in Smoker |
| cg04913974 | 14 | 58063811 | Lower in Smoker |
| cg08312083 | 2 | 114514236 | Higher in Smoker |
| cg24131671 | 5 | 150706354 | Lower in Smoker |
| cg22505977 | 5 | 150727459 | Lower in Smoker |
| cg01678321 | 5 | 150683530 | Lower in Smoker |
| cg11125805 | 5 | 150678162 | Lower in Smoker |
| cg11926764 | 11 | 92930916 | Higher in Smoker |
| cg24141725 | 21 | 44000964 | Lower in Smoker |
| cg01086404 | 11 | 124932906 | Higher in Smoker |
| cg03868193 | 11 | 124958746 | Lower in Smoker |
| cg06838869 | 7 | 140098259 | Higher in Smoker |
| cg23347835 | 12 | 46599935 | Lower in Smoker |
| cg24948499 | 17 | 79224065 | Lower in Smoker |
| cg03971338 | 17 | 79224178 | Lower in Smoker |
| cg22462714 | 17 | 79224306 | Lower in Smoker |
| cg06090161 | 17 | 79244943 | Higher in Smoker |
| cg04930733 | 17 | 79253479 | Lower in Smoker |
| cg02467899 | 17 | 79236161 | Lower in Smoker |
| cg07656922 | 17 | 79225309 | Lower in Smoker |
| cg27529668 | 17 | 79224770 | Lower in Smoker |
| cg02339793 | 17 | 79225573 | Lower in Smoker |
| cg26726230 | 17 | 79225857 | Lower in Smoker |
| cg23939642 | 17 | 79225757 | Lower in Smoker |

| | | | |
|---|---|---|---|
| cg19776793 | 17 | 79225974 | Lower in Smoker |
| cg18064171 | 12 | 47219956 | Higher in Smoker |
| cg06250214 | 16 | 58714489 | Lower in Smoker |
| cg04229059 | 16 | 58718971 | Lower in Smoker |
| cg08854094 | 16 | 84059158 | Lower in Smoker |
| cg01119072 | 16 | 84076582 | Lower in Smoker |
| cg03329536 | 5 | 55008469 | Higher in Smoker |
| cg13046296 | 2 | 196523030 | Higher in Smoker |
| cg01174096 | 2 | 196521556 | Higher in Smoker |
| cg19805748 | 17 | 71003041 | Lower in Smoker |
| cg27219182 | 17 | 70680294 | Lower in Smoker |
| cg23335976 | 10 | 18240598 | Lower in Smoker |
| cg23308107 | 11 | 47429939 | Higher in Smoker |
| cg26954671 | 8 | 22223465 | Lower in Smoker |
| cg01250699 | 8 | 22225185 | Higher in Smoker |
| cg22266764 | 19 | 2740123 | Higher in Smoker |
| cg23643568 | 6 | 33170779 | Lower in Smoker |
| cg08133228 | 6 | 33170832 | Lower in Smoker |
| cg24996709 | 6 | 33170838 | Lower in Smoker |
| cg12836424 | 6 | 33168439 | Higher in Smoker |
| cg23846145 | 4 | 103266423 | Higher in Smoker |
| cg12670371 | 4 | 103266563 | Lower in Smoker |
| cg16699382 | 11 | 62648149 | Higher in Smoker |
| cg27629023 | 11 | 62648823 | Lower in Smoker |
| cg22784260 | 12 | 105239832 | Lower in Smoker |
| cg24572577 | 3 | 125903249 | Higher in Smoker |
| cg02037518 | 11 | 57283212 | Higher in Smoker |
| cg23409370 | 11 | 57283278 | Higher in Smoker |
| cg10032131 | 11 | 57283055 | Lower in Smoker |
| cg02703843 | 17 | 1533176 | Higher in Smoker |
| cg18405360 | 17 | 1531863 | Lower in Smoker |
| cg23691006 | 17 | 1510666 | Lower in Smoker |
| cg21949830 | 17 | 1510041 | Lower in Smoker |
| cg00522883 | 11 | 57194120 | Higher in Smoker |
| cg00354381 | 11 | 57195187 | Lower in Smoker |

| | | | |
|---|---|---|---|
| cg07067982 | 11 | 57194370 | Higher in Smoker |
| cg19287114 | 9 | 108006611 | Higher in Smoker |
| cg16197528 | 19 | 10740327 | Lower in Smoker |
| cg10017105 | 6 | 31832428 | Higher in Smoker |
| cg07438099 | 6 | 31834178 | Lower in Smoker |
| cg15821546 | 6 | 31843465 | Lower in Smoker |
| cg20370184 | 6 | 31838544 | Lower in Smoker |
| cg04972669 | 1 | 75808730 | Lower in Smoker |
| cg23430771 | 5 | 33984781 | Lower in Smoker |
| cg12048674 | 1 | 205649805 | Higher in Smoker |
| cg00966749 | 8 | 142236124 | Lower in Smoker |
| cg21732977 | 17 | 26732836 | Higher in Smoker |
| cg10923085 | 17 | 26733302 | Higher in Smoker |
| cg13696535 | 9 | 115650839 | Lower in Smoker |
| cg21789898 | 13 | 29293245 | Higher in Smoker |
| cg12775884 | 13 | 29293133 | Lower in Smoker |
| cg24321030 | 13 | 29292888 | Lower in Smoker |
| cg24151087 | 17 | 19450271 | Higher in Smoker |
| cg15012572 | 12 | 48167095 | Higher in Smoker |
| cg16902190 | 20 | 3214756 | Higher in Smoker |
| cg01606538 | 20 | 3214849 | Higher in Smoker |
| cg15621697 | 4 | 72166462 | Lower in Smoker |
| cg25811526 | 2 | 74570564 | Lower in Smoker |
| cg01627492 | 17 | 18916400 | Lower in Smoker |
| cg13363904 | 11 | 26710632 | Lower in Smoker |
| cg22179256 | 19 | 17986728 | Lower in Smoker |
| cg23156781 | 2 | 27435514 | Higher in Smoker |
| cg03047508 | 3 | 11059480 | Lower in Smoker |
| cg21771682 | 3 | 11036537 | Lower in Smoker |
| cg24744557 | 12 | 322649 | Lower in Smoker |
| cg11145776 | 12 | 322514 | Lower in Smoker |
| cg03139377 | 12 | 323242 | Higher in Smoker |
| cg08143343 | 12 | 65307152 | Lower in Smoker |
| cg15989525 | 5 | 1234976 | Higher in Smoker |
| cg26197930 | 5 | 1222775 | Lower in Smoker |

| | | | |
|---|---|---|---|
| cg04135385 | 5 | 1218916 | Lower in Smoker |
| cg10035234 | 5 | 1212554 | Lower in Smoker |
| cg22165524 | 5 | 1213187 | Lower in Smoker |
| cg19619756 | 5 | 1219499 | Lower in Smoker |
| cg04248937 | 5 | 1222847 | Lower in Smoker |
| cg00472281 | 5 | 1205496 | Lower in Smoker |
| cg02693870 | 16 | 55689324 | Higher in Smoker |
| cg27047406 | 16 | 55689534 | Higher in Smoker |
| cg04450501 | 16 | 55718994 | Lower in Smoker |
| cg02929434 | 5 | 1415533 | Lower in Smoker |
| cg02688422 | 5 | 1409937 | Lower in Smoker |
| cg03479705 | 11 | 20668525 | Lower in Smoker |
| cg13496041 | 3 | 14494726 | Lower in Smoker |
| cg08631357 | 5 | 149589210 | Higher in Smoker |
| cg14349378 | X | 152954303 | Higher in Smoker |
| cg10574944 | X | 152953773 | Higher in Smoker |
| cg11207893 | 1 | 44494733 | Lower in Smoker |
| cg21302562 | 1 | 44497012 | Higher in Smoker |
| ch.13.268523R | 13 | 30087543 | Higher in Smoker |
| cg19928703 | 13 | 30143971 | Higher in Smoker |
| cg07754117 | 3 | 170183336 | Lower in Smoker |
| cg03861633 | 3 | 170300709 | Lower in Smoker |
| cg15536845 | 3 | 170304045 | Lower in Smoker |
| cg01758418 | X | 70151160 | Higher in Smoker |
| cg11859529 | X | 70150922 | Lower in Smoker |
| cg02114946 | 22 | 21386494 | Higher in Smoker |
| cg05834639 | 16 | 87885208 | Lower in Smoker |
| cg24734575 | 19 | 33360626 | Lower in Smoker |
| cg11720686 | 2 | 40440949 | Lower in Smoker |
| cg22409100 | 2 | 40658918 | Lower in Smoker |
| cg27060355 | 2 | 40590871 | Lower in Smoker |
| cg08245249 | 2 | 40342248 | Lower in Smoker |
| cg27052113 | 19 | 47951305 | Higher in Smoker |
| cg06399135 | 19 | 47951565 | Lower in Smoker |
| cg12192686 | 19 | 47938620 | Lower in Smoker |

| | | | |
|---|---|---|---|
| cg12858895 | 14 | 70654824 | Higher in Smoker |
| cg07945433 | 14 | 70657045 | Lower in Smoker |
| cg15823642 | 14 | 70516416 | Lower in Smoker |
| cg16799926 | 14 | 70546695 | Lower in Smoker |
| cg15907372 | 3 | 111904806 | Lower in Smoker |
| cg00902674 | 3 | 111904703 | Lower in Smoker |
| cg26829418 | 2 | 103238066 | Lower in Smoker |
| cg01050423 | 2 | 103236078 | Lower in Smoker |
| cg12628145 | 5 | 524679 | Higher in Smoker |
| cg21271026 | 5 | 508185 | Lower in Smoker |
| cg10555297 | 5 | 473380 | Higher in Smoker |
| cg10829342 | 17 | 72744524 | Higher in Smoker |
| cg03366251 | 16 | 2076810 | Higher in Smoker |
| cg05751189 | 2 | 103089678 | Higher in Smoker |
| cg14574489 | 3 | 143021680 | Lower in Smoker |
| cg02496728 | 3 | 133748505 | Higher in Smoker |
| cg19591206 | 3 | 133748809 | Higher in Smoker |
| cg27118876 | 15 | 92397541 | Higher in Smoker |
| cg25508605 | 15 | 92706125 | Higher in Smoker |
| cg03756778 | 15 | 92407388 | Lower in Smoker |
| cg11330307 | 15 | 92628595 | Lower in Smoker |
| cg06479426 | 20 | 61274286 | Higher in Smoker |
| cg00630480 | 5 | 101570551 | Lower in Smoker |
| cg11642652 | 8 | 70650320 | Lower in Smoker |
| cg03451212 | 8 | 70745466 | Lower in Smoker |
| cg09479694 | 8 | 70744954 | Lower in Smoker |
| cg10911913 | 17 | 33700817 | Higher in Smoker |
| cg04373379 | 17 | 33810868 | Lower in Smoker |
| cg01565438 | 17 | 33776554 | Higher in Smoker |
| cg17143565 | 17 | 33569990 | Higher in Smoker |
| cg00960373 | 1 | 41488301 | Lower in Smoker |
| cg18669388 | 5 | 168729015 | Higher in Smoker |
| cg27648808 | 5 | 168439973 | Lower in Smoker |
| cg19696317 | 13 | 84456171 | Higher in Smoker |
| cg27584469 | X | 144899412 | Higher in Smoker |

| | | | |
|---|---|---|---|
| cg24880787 | X | 144903661 | Higher in Smoker |
| cg19332075 | X | 144903691 | Higher in Smoker |
| cg06312254 | 3 | 164911348 | Higher in Smoker |
| cg10868293 | X | 142716477 | Lower in Smoker |
| cg09083627 | 13 | 88324597 | Higher in Smoker |
| cg15778745 | 13 | 88324570 | Higher in Smoker |
| cg26110710 | 13 | 88323607 | Higher in Smoker |
| cg06143522 | 13 | 88330200 | Higher in Smoker |
| cg19577779 | 13 | 88326635 | Higher in Smoker |
| cg26168643 | 13 | 88328009 | Lower in Smoker |
| cg00002426 | 3 | 57743543 | Lower in Smoker |
| cg00873919 | 3 | 57743599 | Lower in Smoker |
| cg24026757 | 18 | 12407806 | Higher in Smoker |
| cg08363339 | 20 | 57618487 | Lower in Smoker |
| cg27664390 | 15 | 59171928 | Lower in Smoker |
| cg20563447 | 15 | 67359289 | Higher in Smoker |
| cg15723784 | 15 | 67441067 | Higher in Smoker |
| cg26909431 | 18 | 48556216 | Higher in Smoker |
| cg04543131 | 15 | 67073942 | Lower in Smoker |
| cg16553757 | 15 | 67007131 | Lower in Smoker |
| cg06203649 | 18 | 46447634 | Lower in Smoker |
| cg14168755 | 13 | 37456407 | Lower in Smoker |
| cg18167349 | 12 | 51664410 | Higher in Smoker |
| cg21039196 | 6 | 71435620 | Lower in Smoker |
| cg27264437 | 1 | 40843940 | Lower in Smoker |
| cg24447042 | X | 128657893 | Higher in Smoker |
| cg07662247 | 9 | 2047800 | Lower in Smoker |
| cg13837335 | 9 | 2191798 | Lower in Smoker |
| cg13910439 | 9 | 2022036 | Lower in Smoker |
| cg14046463 | 19 | 11145635 | Lower in Smoker |
| cg10987071 | 2 | 217276744 | Lower in Smoker |
| cg14655732 | 2 | 217277275 | Higher in Smoker |
| cg04184623 | 2 | 217277352 | Lower in Smoker |
| cg25107077 | 12 | 50479197 | Higher in Smoker |
| cg01291336 | 7 | 150949495 | Higher in Smoker |

| | | | |
|---|---|---|---|
| cg26061357 | 7 | 150969275 | Higher in Smoker |
| cg07874329 | 7 | 150942352 | Higher in Smoker |
| cg08259454 | 3 | 160118302 | Higher in Smoker |
| cg14289863 | 9 | 72872391 | Lower in Smoker |
| cg11878476 | 22 | 39898238 | Higher in Smoker |
| cg07953385 | 14 | 91976755 | Higher in Smoker |
| cg20964023 | 14 | 91976739 | Lower in Smoker |
| cg03859395 | 2 | 55845619 | Higher in Smoker |
| cg18349258 | 2 | 55844203 | Higher in Smoker |
| cg02696763 | 1 | 156252642 | Higher in Smoker |
| cg02853512 | 17 | 1992954 | Lower in Smoker |
| cg13916835 | 17 | 2078431 | Lower in Smoker |
| cg22024931 | 5 | 69371421 | Lower in Smoker |
| cg04281426 | 5 | 69345099 | Higher in Smoker |
| cg17981675 | 10 | 112064886 | Higher in Smoker |
| ch.7.2667284R | 7 | 128843678 | Higher in Smoker |
| cg06217803 | 7 | 128830440 | Lower in Smoker |
| cg19741688 | 14 | 70346849 | Higher in Smoker |
| cg02873263 | 14 | 70476756 | Lower in Smoker |
| cg05415931 | 14 | 70368685 | Lower in Smoker |
| cg00664792 | 6 | 168957184 | Higher in Smoker |
| cg01310118 | 6 | 168855168 | Lower in Smoker |
| cg03873826 | 16 | 68407311 | Lower in Smoker |
| cg10992590 | 2 | 130940487 | Lower in Smoker |
| cg08722115 | 2 | 130938276 | Lower in Smoker |
| cg22655038 | 22 | 31477112 | Higher in Smoker |
| cg06894032 | 22 | 31477091 | Higher in Smoker |
| cg17402397 | 22 | 31477754 | Lower in Smoker |
| cg17039830 | 11 | 57308952 | Lower in Smoker |
| cg25585129 | 17 | 4486580 | Lower in Smoker |
| cg18564971 | 7 | 98633387 | Lower in Smoker |
| cg04108811 | 1 | 246670728 | Higher in Smoker |
| cg12648193 | 1 | 246669975 | Higher in Smoker |
| cg09413723 | 1 | 246670359 | Lower in Smoker |
| cg13053734 | 1 | 246670933 | Lower in Smoker |

| | | | |
|---|---|---|---|
| cg05403071 | 20 | 48599682 | Higher in Smoker |
| cg23100428 | 20 | 48600203 | Lower in Smoker |
| cg16786007 | 20 | 10200383 | Higher in Smoker |
| cg18383594 | 14 | 62263120 | Lower in Smoker |
| cg02772682 | 19 | 7985923 | Higher in Smoker |
| cg19478072 | 9 | 15423182 | Higher in Smoker |
| cg21211036 | 9 | 15422769 | Lower in Smoker |
| cg06023039 | 15 | 66790240 | Higher in Smoker |
| cg22468733 | 15 | 66790247 | Higher in Smoker |
| cg10731794 | 4 | 90759057 | Higher in Smoker |
| cg04684516 | 5 | 121647858 | Higher in Smoker |
| cg05028467 | 5 | 176057097 | Higher in Smoker |
| cg00967885 | 5 | 176054480 | Higher in Smoker |
| cg05986781 | 7 | 127291658 | Lower in Smoker |
| cg25747190 | 7 | 127295153 | Lower in Smoker |
| cg07304760 | 7 | 127514192 | Lower in Smoker |
| cg00872676 | 7 | 127721954 | Lower in Smoker |
| cg17257554 | 2 | 242004824 | Lower in Smoker |
| cg01121603 | 2 | 242005101 | Lower in Smoker |
| cg19322479 | 2 | 241967099 | Lower in Smoker |
| cg00452755 | 1 | 28864993 | Lower in Smoker |
| cg24348442 | 4 | 119199731 | Higher in Smoker |
| cg11106506 | 4 | 119200017 | Higher in Smoker |
| cg14702007 | 4 | 119200372 | Higher in Smoker |
| cg04386149 | 16 | 2015049 | Higher in Smoker |
| cg21871735 | 16 | 2015157 | Lower in Smoker |
| cg25597055 | 1 | 38002922 | Lower in Smoker |
| cg09571603 | 7 | 56126814 | Higher in Smoker |
| cg14305943 | 10 | 120820318 | Lower in Smoker |
| cg21121943 | 7 | 65220346 | Lower in Smoker |
| cg11075099 | 13 | 27829087 | Lower in Smoker |
| cg11218434 | 13 | 45911764 | Lower in Smoker |
| cg27314046 | 20 | 37076661 | Lower in Smoker |
| cg04474366 | 3 | 186505347 | Lower in Smoker |
| cg08970330 | 11 | 62432645 | Higher in Smoker |

| | | | |
|---|---|---|---|
| cg18139406 | 1 | 12565983 | Lower in Smoker |
| cg12977686 | 17 | 62223379 | Higher in Smoker |
| cg00530918 | 11 | 93466913 | Lower in Smoker |
| cg09516696 | 21 | 33749986 | Lower in Smoker |
| cg22907692 | 14 | 101455506 | Lower in Smoker |
| cg10046893 | 14 | 101456920 | Lower in Smoker |
| cg23331837 | 14 | 101419227 | Lower in Smoker |
| cg15479427 | 15 | 25436173 | Lower in Smoker |
| cg02705035 | 15 | 25457690 | Lower in Smoker |
| cg10610244 | 15 | 25455664 | Lower in Smoker |
| cg24524414 | 15 | 25463385 | Lower in Smoker |
| cg06127174 | 15 | 25472950 | Lower in Smoker |
| cg12910936 | 15 | 25473120 | Lower in Smoker |
| cg12629254 | 15 | 25484940 | Lower in Smoker |
| cg00078513 | 15 | 25486114 | Lower in Smoker |
| cg27513586 | 15 | 25513654 | Higher in Smoker |
| cg23841760 | 15 | 25427435 | Lower in Smoker |
| cg12019705 | 15 | 25307364 | Lower in Smoker |
| cg04866357 | 15 | 66794398 | Lower in Smoker |
| cg19439071 | 17 | 74557625 | Lower in Smoker |
| cg05727573 | 17 | 74557104 | Lower in Smoker |
| cg08608144 | 3 | 186502430 | Higher in Smoker |
| cg15345437 | 11 | 62620843 | Lower in Smoker |
| cg18159646 | 11 | 62621178 | Lower in Smoker |
| cg23385854 | 11 | 62623264 | Higher in Smoker |
| cg18039643 | 11 | 62622929 | Higher in Smoker |
| cg15172739 | 11 | 62621258 | Lower in Smoker |
| cg20858323 | 6 | 29549759 | Lower in Smoker |
| cg13595191 | 22 | 39715747 | Higher in Smoker |
| cg09642749 | 22 | 39715759 | Higher in Smoker |
| cg04940515 | 1 | 76251865 | Higher in Smoker |
| cg11245233 | 1 | 76251899 | Higher in Smoker |
| cg08585380 | 6 | 86386840 | Higher in Smoker |
| cg03051598 | 2 | 29148591 | Lower in Smoker |
| cg12768770 | 1 | 45240981 | Higher in Smoker |

| | | | |
|---|---|---|---|
| cg16556679 | 17 | 33900025 | Lower in Smoker |
| cg05708656 | 16 | 71792305 | Lower in Smoker |
| cg25883402 | 1 | 173837173 | Higher in Smoker |
| cg22060153 | 2 | 101889653 | Lower in Smoker |
| cg09577417 | 2 | 101890372 | Lower in Smoker |
| cg21595175 | 5 | 180670701 | Higher in Smoker |
| cg02556067 | 2 | 96970985 | Higher in Smoker |
| cg09962502 | 2 | 96971189 | Higher in Smoker |
| cg00953578 | 16 | 103715 | Higher in Smoker |
| cg01062126 | 16 | 104639 | Lower in Smoker |
| cg19795502 | 2 | 70121034 | Higher in Smoker |
| cg25332238 | 2 | 70122333 | Lower in Smoker |
| cg00134611 | 6 | 7589469 | Lower in Smoker |
| cg11455291 | 19 | 49611011 | Lower in Smoker |
| cg11023815 | 6 | 34725573 | Higher in Smoker |
| cg22215678 | 18 | 19191718 | Lower in Smoker |
| cg08253651 | 12 | 96252105 | Higher in Smoker |
| cg15712226 | 12 | 96252066 | Higher in Smoker |
| cg25657700 | 15 | 25123491 | Higher in Smoker |
| cg12298755 | 15 | 25199713 | Higher in Smoker |
| cg18305480 | 20 | 32031707 | Higher in Smoker |
| cg08155953 | 20 | 32031801 | Lower in Smoker |
| cg16770243 | 8 | 121719537 | Lower in Smoker |
| cg08846112 | 8 | 121598484 | Lower in Smoker |
| cg12637911 | 8 | 121628381 | Lower in Smoker |
| cg27039420 | 8 | 121768955 | Lower in Smoker |
| cg07175848 | 16 | 69327197 | Lower in Smoker |
| cg07739205 | 8 | 50823541 | Higher in Smoker |
| cg12074541 | 2 | 1286641 | Higher in Smoker |
| cg05472059 | 2 | 1054787 | Lower in Smoker |
| cg19906760 | 14 | 78227687 | Higher in Smoker |
| cg26163719 | 15 | 64388076 | Higher in Smoker |
| cg12965553 | 7 | 26403802 | Lower in Smoker |
| cg08413153 | 17 | 46185283 | Higher in Smoker |
| cg03312572 | 7 | 17979929 | Lower in Smoker |

| | | | |
|---|---|---|---|
| cg17019204 | 6 | 86303781 | Higher in Smoker |
| cg04270414 | 11 | 64807235 | Lower in Smoker |
| cg17516635 | 8 | 82712467 | Lower in Smoker |
| cg01582396 | 5 | 53817963 | Lower in Smoker |
| cg18373318 | 5 | 53813164 | Higher in Smoker |
| cg09159602 | 5 | 53813531 | Higher in Smoker |
| cg26346197 | 5 | 53813541 | Lower in Smoker |
| cg14556808 | 11 | 130752510 | Lower in Smoker |
| cg00458607 | 11 | 130763724 | Lower in Smoker |
| cg22201537 | 11 | 130779517 | Lower in Smoker |
| cg23642342 | 11 | 130786350 | Lower in Smoker |
| cg10699064 | 5 | 122110553 | Higher in Smoker |
| cg25624596 | 15 | 64443873 | Higher in Smoker |
| cg23071107 | 15 | 64445802 | Higher in Smoker |
| cg07245011 | 5 | 122181023 | Higher in Smoker |
| cg18639228 | 5 | 122232684 | Higher in Smoker |
| cg13832772 | 4 | 186283900 | Lower in Smoker |
| cg20461310 | 4 | 186253454 | Lower in Smoker |
| cg10989879 | 4 | 186131280 | Lower in Smoker |
| cg13206363 | 4 | 186131247 | Lower in Smoker |
| cg06416883 | 4 | 186131285 | Lower in Smoker |
| cg02225054 | 16 | 12210834 | Lower in Smoker |
| cg03204907 | 16 | 12272324 | Lower in Smoker |
| cg19133466 | 16 | 12355834 | Lower in Smoker |
| cg17199658 | 8 | 101661478 | Higher in Smoker |
| cg22959820 | 11 | 65601167 | Higher in Smoker |
| cg18762620 | 15 | 75940301 | Higher in Smoker |
| cg21830066 | 3 | 125239063 | Higher in Smoker |
| cg18374702 | 20 | 17949715 | Higher in Smoker |
| cg20478089 | 14 | 35099711 | Higher in Smoker |
| cg18396865 | 14 | 35098784 | Higher in Smoker |
| cg23973538 | 7 | 2318990 | Lower in Smoker |
| cg05516271 | 7 | 2339170 | Lower in Smoker |
| cg14789351 | 6 | 158244268 | Higher in Smoker |
| cg22510970 | 6 | 158327096 | Lower in Smoker |

| | | | |
|---|---|---|---|
| cg04062576 | 12 | 53496842 | Higher in Smoker |
| cg04953535 | 12 | 53517924 | Lower in Smoker |
| cg05181221 | 16 | 11351158 | Higher in Smoker |
| cg09741588 | 12 | 93963324 | Higher in Smoker |
| cg27619149 | 12 | 93963520 | Higher in Smoker |
| cg21500342 | 17 | 76356814 | Higher in Smoker |
| cg00474194 | 18 | 67955861 | Higher in Smoker |
| cg11890453 | 18 | 67959378 | Lower in Smoker |
| cg02533120 | 21 | 33031840 | Lower in Smoker |
| cg26893544 | 21 | 33032007 | Higher in Smoker |
| cg10766585 | 4 | 24801110 | Higher in Smoker |
| cg00332421 | 9 | 133590995 | Lower in Smoker |
| cg27558820 | 16 | 590094 | Higher in Smoker |
| cg07131540 | 16 | 587568 | Lower in Smoker |
| cg16081992 | 21 | 34932447 | Lower in Smoker |
| cg15608943 | 10 | 97243752 | Lower in Smoker |
| cg03190891 | 10 | 97201172 | Lower in Smoker |
| cg02764250 | 10 | 97145217 | Lower in Smoker |
| cg02572796 | 4 | 186732124 | Lower in Smoker |
| cg17006136 | 4 | 186559412 | Higher in Smoker |
| cg24132991 | 4 | 186560360 | Higher in Smoker |
| cg23836747 | 4 | 186559629 | Higher in Smoker |
| cg15658824 | 8 | 22423026 | Higher in Smoker |
| cg08273995 | 4 | 7526521 | Higher in Smoker |
| cg26349869 | 4 | 7528468 | Higher in Smoker |
| cg10356260 | 4 | 7593437 | Lower in Smoker |
| cg13423235 | 4 | 7486195 | Lower in Smoker |
| cg19420930 | 4 | 7667618 | Lower in Smoker |
| cg16571794 | 4 | 7648627 | Lower in Smoker |
| cg24378940 | 4 | 7742291 | Lower in Smoker |
| cg09551147 | 10 | 106399957 | Higher in Smoker |
| cg07908498 | 10 | 106425960 | Lower in Smoker |
| cg16026550 | 11 | 121323544 | Higher in Smoker |
| cg10107783 | 11 | 121474197 | Lower in Smoker |
| cg10087399 | 1 | 109940029 | Higher in Smoker |

| | | | |
|---|---|---|---|
| cg09764697 | 1 | 109940754 | Higher in Smoker |
| cg22346081 | 1 | 109937191 | Lower in Smoker |
| cg24153199 | 14 | 50698328 | Higher in Smoker |
| cg11417025 | 7 | 16505589 | Higher in Smoker |
| cg06126713 | 7 | 16505617 | Higher in Smoker |
| cg15653173 | 13 | 112723034 | Higher in Smoker |
| cg24604013 | 13 | 112721325 | Higher in Smoker |
| cg06488256 | 13 | 112725903 | Higher in Smoker |
| cg15034345 | 2 | 5836111 | Higher in Smoker |
| cg23922081 | 20 | 306359 | Higher in Smoker |
| cg16921083 | 3 | 137483063 | Higher in Smoker |
| cg14824495 | 17 | 7492801 | Higher in Smoker |
| cg15136181 | 8 | 55370434 | Higher in Smoker |
| cg04672706 | 8 | 55370423 | Higher in Smoker |
| cg15710198 | 8 | 55370334 | Higher in Smoker |
| cg13564289 | 20 | 62680977 | Higher in Smoker |
| cg11699435 | 13 | 95365673 | Higher in Smoker |
| cg11362010 | 3 | 181442713 | Higher in Smoker |
| cg12930100 | 3 | 181428697 | Higher in Smoker |
| cg25638997 | 17 | 70118162 | Lower in Smoker |
| cg26652092 | 12 | 53773602 | Higher in Smoker |
| cg13731387 | 17 | 45973624 | Higher in Smoker |
| cg20441701 | 7 | 21466380 | Higher in Smoker |
| cg10365563 | 7 | 21469772 | Lower in Smoker |
| cg00858840 | 2 | 171573839 | Higher in Smoker |
| cg13230424 | 17 | 45930033 | Lower in Smoker |
| cg23391107 | 17 | 45924227 | Lower in Smoker |
| cg07937786 | 12 | 53729629 | Lower in Smoker |
| cg11067736 | 8 | 101225252 | Higher in Smoker |
| cg13687825 | 8 | 101225344 | Higher in Smoker |
| cg05800758 | 8 | 101225800 | Higher in Smoker |
| cg07518837 | 8 | 101225078 | Higher in Smoker |
| cg20270320 | 8 | 101225902 | Higher in Smoker |
| cg17103929 | 8 | 101225361 | Higher in Smoker |
| cg05730975 | 2 | 214992482 | Lower in Smoker |

| | | | |
|---|---|---|---|
| cg00570000 | 1 | 118728226 | Higher in Smoker |
| cg16240368 | 1 | 118728086 | Higher in Smoker |
| cg11927951 | 10 | 22638314 | Lower in Smoker |
| cg11864574 | 10 | 22635028 | Lower in Smoker |
| cg12523109 | X | 52825220 | Lower in Smoker |
| cg15552249 | 4 | 68450824 | Lower in Smoker |
| cg21317524 | 2 | 32288526 | Higher in Smoker |
| cg04477202 | 2 | 32289458 | Higher in Smoker |
| cg07220032 | 13 | 24742701 | Lower in Smoker |
| cg17741814 | 1 | 217804517 | Higher in Smoker |
| cg18608389 | 4 | 52917561 | Higher in Smoker |
| cg18191605 | 20 | 48530082 | Lower in Smoker |
| cg02850941 | 16 | 89767921 | Higher in Smoker |
| cg10612096 | 2 | 231865097 | Higher in Smoker |
| cg07667367 | 4 | 177116832 | Higher in Smoker |
| cg01710865 | 1 | 48937404 | Higher in Smoker |
| cg21583160 | 1 | 48938137 | Higher in Smoker |
| cg12051027 | 1 | 48931095 | Lower in Smoker |
| cg26136325 | 14 | 68655259 | Lower in Smoker |
| cg03340244 | 5 | 95005831 | Lower in Smoker |
| cg07948472 | 5 | 95018471 | Lower in Smoker |
| cg25619549 | 12 | 49779016 | Lower in Smoker |
| cg26015513 | 2 | 201218948 | Lower in Smoker |
| cg07905049 | 19 | 11266334 | Higher in Smoker |
| cg08056863 | 19 | 11266458 | Higher in Smoker |
| cg18145911 | 11 | 74660517 | Higher in Smoker |
| cg00293599 | 6 | 34505610 | Lower in Smoker |
| cg11951692 | 20 | 3761938 | Higher in Smoker |
| cg02869459 | 2 | 220349208 | Higher in Smoker |
| cg25423755 | 2 | 220306636 | Higher in Smoker |
| cg21347733 | 2 | 220306674 | Lower in Smoker |
| cg22126505 | 2 | 220293547 | Lower in Smoker |
| cg18131810 | 2 | 220348515 | Lower in Smoker |
| cg10006419 | 17 | 7323660 | Lower in Smoker |
| cg08892464 | 1 | 16176383 | Higher in Smoker |

| | | | |
|---|---|---|---|
| cg10558887 | 13 | 36919409 | Higher in Smoker |
| cg00947032 | 13 | 36919960 | Higher in Smoker |
| cg05123138 | 13 | 36920987 | Higher in Smoker |
| cg10207553 | 15 | 65277977 | Higher in Smoker |
| cg03568793 | 16 | 89620236 | Lower in Smoker |
| cg16475925 | 16 | 89574613 | Higher in Smoker |
| cg01320507 | 1 | 229440351 | Lower in Smoker |
| cg12001304 | 2 | 229045020 | Higher in Smoker |
| cg08201854 | 19 | 50922128 | Higher in Smoker |
| cg02293258 | X | 57147872 | Higher in Smoker |
| cg09302010 | X | 57021502 | Lower in Smoker |
| cg17496990 | 5 | 147552209 | Lower in Smoker |
| cg23461926 | 5 | 147691991 | Lower in Smoker |
| cg08533268 | 3 | 48369177 | Lower in Smoker |
| cg12787209 | 15 | 41139786 | Higher in Smoker |
| cg04519327 | 15 | 41149780 | Lower in Smoker |
| cg27046604 | 15 | 41135869 | Lower in Smoker |
| cg20961591 | 19 | 38755588 | Higher in Smoker |
| cg07097041 | 18 | 12658644 | Higher in Smoker |
| cg06204638 | 18 | 12656910 | Higher in Smoker |
| cg07897354 | 18 | 12657909 | Lower in Smoker |
| cg01681367 | 16 | 29676071 | Higher in Smoker |
| cg23083984 | 16 | 29675846 | Higher in Smoker |
| cg11432797 | 16 | 29674487 | Higher in Smoker |
| cg10329001 | 16 | 28986645 | Higher in Smoker |
| cg08835403 | 17 | 4436580 | Lower in Smoker |
| cg21100638 | 17 | 4337082 | Higher in Smoker |
| cg20802515 | 20 | 55904768 | Higher in Smoker |
| cg23416994 | 20 | 55917535 | Lower in Smoker |
| cg14650610 | 5 | 136834492 | Higher in Smoker |
| cg26968544 | 5 | 136481972 | Lower in Smoker |
| cg10983208 | 10 | 73848320 | Higher in Smoker |
| cg12696488 | 11 | 14128237 | Lower in Smoker |
| cg00816515 | 11 | 13986348 | Lower in Smoker |
| cg07806421 | 2 | 139259153 | Higher in Smoker |

| | | | |
|---|---|---|---|
| cg23998381 | 2 | 73114610 | Higher in Smoker |
| cg11877270 | 2 | 65658583 | Higher in Smoker |
| cg06395028 | 2 | 65633100 | Lower in Smoker |
| cg18962288 | 2 | 65541060 | Lower in Smoker |
| cg08651590 | 2 | 65543410 | Lower in Smoker |
| cg26376241 | 2 | 65594021 | Lower in Smoker |
| cg23606417 | 1 | 153115333 | Lower in Smoker |
| cg22423979 | 4 | 124318670 | Higher in Smoker |
| cg06974483 | 4 | 124317831 | Higher in Smoker |
| cg15629719 | 13 | 80914158 | Higher in Smoker |
| cg06125576 | 13 | 80913340 | Higher in Smoker |
| cg22871548 | 12 | 56862240 | Higher in Smoker |
| cg02511531 | 11 | 55652114 | Lower in Smoker |
| cg02447606 | 1 | 9353862 | Higher in Smoker |
| cg09730123 | 16 | 1827948 | Lower in Smoker |
| cg27583037 | 2 | 54682530 | Higher in Smoker |
| cg23402524 | 2 | 54885027 | Higher in Smoker |
| cg07921436 | 2 | 54856099 | Lower in Smoker |
| cg03401297 | 19 | 41025959 | Higher in Smoker |
| cg17654091 | 19 | 41073716 | Lower in Smoker |
| cg07063351 | 19 | 41060190 | Higher in Smoker |
| cg09201001 | 11 | 18656081 | Higher in Smoker |
| cg13041269 | 5 | 179248748 | Higher in Smoker |
| cg03864338 | 3 | 142720134 | Higher in Smoker |
| cg04074137 | 3 | 142720408 | Lower in Smoker |
| cg10912634 | 5 | 139929838 | Lower in Smoker |
| cg02462761 | 5 | 139937169 | Lower in Smoker |
| cg25590579 | 2 | 45838450 | Higher in Smoker |
| cg18940723 | 2 | 45837923 | Higher in Smoker |
| cg08826468 | 16 | 30724604 | Lower in Smoker |
| cg16772533 | 7 | 76026556 | Lower in Smoker |
| cg05879499 | 5 | 6668385 | Lower in Smoker |
| cg24057680 | 5 | 6633496 | Higher in Smoker |
| cg21827969 | 4 | 56212299 | Higher in Smoker |
| cg07746918 | 22 | 42229324 | Higher in Smoker |

| | | | |
|---|---|---|---|
| cg09092344 | 5 | 121317684 | Lower in Smoker |
| cg01099855 | 12 | 64271616 | Lower in Smoker |
| cg11803077 | 1 | 11120633 | Higher in Smoker |
| cg21099221 | 1 | 11120574 | Higher in Smoker |
| cg02628374 | 15 | 40330739 | Higher in Smoker |
| cg16472356 | 5 | 112197930 | Higher in Smoker |
| cg04114590 | 5 | 112197864 | Lower in Smoker |
| cg12352315 | 17 | 74069707 | Lower in Smoker |
| cg25748794 | 6 | 35888709 | Higher in Smoker |
| cg00082656 | 7 | 104943515 | Lower in Smoker |
| cg02170577 | 7 | 104939331 | Lower in Smoker |
| cg15857470 | 7 | 104945248 | Lower in Smoker |
| cg21021145 | 7 | 104758224 | Lower in Smoker |
| cg11941507 | 3 | 133524510 | Higher in Smoker |
| cg09080030 | 16 | 2820366 | Lower in Smoker |
| cg16443009 | 7 | 75864075 | Higher in Smoker |
| cg23221651 | 7 | 75834378 | Lower in Smoker |
| cg08425070 | 7 | 75864319 | Lower in Smoker |
| cg27010159 | 12 | 119591747 | Higher in Smoker |
| cg09442740 | 7 | 100482960 | Higher in Smoker |
| cg09990401 | 20 | 633783 | Higher in Smoker |
| cg22748452 | 20 | 634604 | Lower in Smoker |
| cg13654344 | Y | 2654978 | Lower in Smoker |
| cg18538675 | 20 | 60740466 | Lower in Smoker |
| cg03554006 | 20 | 60745114 | Lower in Smoker |
| cg00767846 | 2 | 170655407 | Lower in Smoker |
| cg09036505 | 1 | 54872792 | Higher in Smoker |
| cg00758217 | 1 | 54818707 | Lower in Smoker |
| cg16321030 | 1 | 54694532 | Lower in Smoker |
| cg20433447 | 1 | 54868559 | Lower in Smoker |
| cg09820244 | 1 | 54790722 | Lower in Smoker |
| cg02832224 | 1 | 54825291 | Lower in Smoker |
| cg02927682 | 1 | 54844424 | Lower in Smoker |
| cg07527607 | 19 | 18542171 | Higher in Smoker |
| cg11557492 | 19 | 56002240 | Higher in Smoker |

| | | | |
|---|---|---|---|
| cg13757859 | 2 | 182757706 | Higher in Smoker |
| cg16972309 | 12 | 109251715 | Lower in Smoker |
| cg02059930 | 12 | 109204756 | Lower in Smoker |
| cg10733115 | 12 | 109222160 | Lower in Smoker |
| cg06376598 | 17 | 28049938 | Higher in Smoker |
| cg19192120 | 11 | 67070517 | Lower in Smoker |
| cg13909661 | 12 | 26386833 | Lower in Smoker |
| cg07860992 | 3 | 156273081 | Lower in Smoker |
| cg27590397 | 14 | 38677218 | Higher in Smoker |
| cg21173317 | 1 | 1478665 | Lower in Smoker |
| cg12292034 | X | 46242838 | Lower in Smoker |
| cg04103418 | 11 | 130076148 | Higher in Smoker |
| cg18753337 | 15 | 80206998 | Lower in Smoker |
| cg02986801 | 8 | 134501675 | Lower in Smoker |
| cg11958827 | 1 | 44252126 | Lower in Smoker |
| cg25600823 | 11 | 126266488 | Lower in Smoker |
| cg16685832 | 11 | 126284163 | Lower in Smoker |
| cg24969820 | 3 | 98497864 | Lower in Smoker |
| cg25080973 | 11 | 8743670 | Lower in Smoker |
| cg22593953 | 3 | 186781783 | Lower in Smoker |
| cg25372568 | 3 | 186648544 | Higher in Smoker |
| cg16935065 | 2 | 107503233 | Higher in Smoker |
| cg19825856 | 2 | 107501733 | Higher in Smoker |
| cg19302831 | 2 | 107502251 | Higher in Smoker |
| cg17277248 | 2 | 107458180 | Lower in Smoker |
| cg04490113 | 1 | 76704467 | Lower in Smoker |
| cg17517997 | 1 | 76607010 | Lower in Smoker |
| cg06211837 | 1 | 76540438 | Higher in Smoker |
| cg13944939 | 9 | 130679246 | Lower in Smoker |
| cg13463054 | 1 | 77333159 | Higher in Smoker |
| cg00294096 | 1 | 77333749 | Higher in Smoker |
| cg20707126 | 7 | 116750996 | Lower in Smoker |
| cg16937057 | 7 | 116593336 | Higher in Smoker |
| cg09728578 | 7 | 116593359 | Higher in Smoker |
| cg01629744 | 7 | 116758099 | Lower in Smoker |

| | | | |
|---|---|---|---|
| cg08625416 | 7 | 116593772 | Higher in Smoker |
| cg15573040 | 15 | 92938295 | Higher in Smoker |
| cg08769966 | 15 | 92937735 | Higher in Smoker |
| cg22965432 | 5 | 100240059 | Higher in Smoker |
| cg03975797 | 5 | 100238977 | Higher in Smoker |
| cg01466017 | 10 | 17496720 | Higher in Smoker |
| cg21445366 | 3 | 52529195 | Higher in Smoker |
| cg19055231 | 3 | 36422397 | Higher in Smoker |
| cg14328457 | 17 | 37381475 | Lower in Smoker |
| cg20584198 | 12 | 57637690 | Higher in Smoker |
| cg12622938 | 7 | 74306997 | Higher in Smoker |
| cg09342417 | 10 | 17715813 | Lower in Smoker |
| cg19058865 | 19 | 4327350 | Higher in Smoker |
| cg05517572 | 19 | 4338769 | Higher in Smoker |
| cg07092525 | 8 | 38008386 | Higher in Smoker |
| cg18101314 | 11 | 72504857 | Higher in Smoker |
| cg26049501 | 13 | 33860056 | Higher in Smoker |
| cg23022450 | 13 | 33728743 | Lower in Smoker |
| cg27643919 | 7 | 38217582 | Lower in Smoker |
| cg11787780 | 5 | 110844727 | Lower in Smoker |
| cg12871124 | 5 | 110848106 | Higher in Smoker |
| cg25269276 | 15 | 81612653 | Lower in Smoker |
| cg06522219 | X | 67879834 | Lower in Smoker |
| cg04965389 | 15 | 42911770 | Lower in Smoker |
| cg06856984 | 15 | 43008690 | Lower in Smoker |
| cg12693595 | 12 | 57304318 | Higher in Smoker |
| cg18993626 | 8 | 74463939 | Lower in Smoker |
| cg06464452 | 4 | 77227879 | Higher in Smoker |
| cg20977312 | 5 | 172748917 | Higher in Smoker |
| cg09450020 | 7 | 89841435 | Higher in Smoker |
| cg13577744 | 7 | 89840814 | Higher in Smoker |
| cg03441409 | 7 | 89840824 | Higher in Smoker |
| cg25380021 | 5 | 171601682 | Higher in Smoker |
| cg25645199 | 5 | 171533681 | Lower in Smoker |
| cg19782271 | 5 | 171616253 | Lower in Smoker |

| | | | |
|---|---|---|---|
| cg02764370 | 19 | 1205706 | Higher in Smoker |
| cg07202368 | 2 | 220462342 | Higher in Smoker |
| cg03345106 | 7 | 43622578 | Higher in Smoker |
| cg12708735 | 7 | 43640979 | Lower in Smoker |
| cg21830223 | 6 | 31943267 | Lower in Smoker |
| cg17439357 | 6 | 31943512 | Lower in Smoker |
| cg27483072 | 13 | 99186801 | Lower in Smoker |
| cg10914815 | 13 | 99148667 | Higher in Smoker |
| cg14573356 | 13 | 99174341 | Lower in Smoker |
| cg11535954 | 13 | 99174609 | Lower in Smoker |
| cg18252924 | 13 | 99129256 | Lower in Smoker |
| cg10806209 | 8 | 99834971 | Lower in Smoker |
| cg20673075 | 8 | 99838489 | Lower in Smoker |
| cg16420798 | 5 | 146614386 | Higher in Smoker |
| cg13850354 | 5 | 146614543 | Higher in Smoker |
| cg00604209 | 5 | 146614596 | Higher in Smoker |
| cg18162059 | 4 | 5405706 | Lower in Smoker |
| cg21186966 | 4 | 5401430 | Lower in Smoker |
| cg21077330 | 10 | 134121709 | Higher in Smoker |
| cg23740417 | 10 | 134093274 | Lower in Smoker |
| cg04967200 | 10 | 134115376 | Lower in Smoker |
| cg15922176 | 10 | 134096798 | Lower in Smoker |
| cg04680759 | 2 | 219536638 | Higher in Smoker |
| cg13644807 | 6 | 36515380 | Higher in Smoker |
| cg23092844 | 2 | 169103738 | Higher in Smoker |
| cg06067477 | 2 | 168844818 | Lower in Smoker |
| cg07857142 | 2 | 169103971 | Higher in Smoker |
| cg03113502 | 6 | 125282870 | Higher in Smoker |
| cg21216015 | 1 | 26230906 | Lower in Smoker |
| cg17337106 | 8 | 80577176 | Lower in Smoker |
| cg02462661 | 15 | 74275622 | Higher in Smoker |
| cg21166380 | 13 | 39565478 | Lower in Smoker |
| cg26451735 | 15 | 74494900 | Higher in Smoker |
| cg10085741 | 15 | 74487890 | Lower in Smoker |
| cg20308335 | 7 | 134927207 | Lower in Smoker |

| | | | |
|---|---|---|---|
| cg13332064 | 15 | 43912221 | Lower in Smoker |
| cg14987922 | 2 | 37194071 | Higher in Smoker |
| cg19975543 | 11 | 125462536 | Higher in Smoker |
| cg20449283 | 11 | 125466652 | Lower in Smoker |
| cg16538496 | 3 | 31574062 | Higher in Smoker |
| cg09826339 | 3 | 31578651 | Lower in Smoker |
| cg12427264 | 6 | 144508349 | Lower in Smoker |
| cg04990056 | 1 | 28099876 | Higher in Smoker |
| cg02391432 | 1 | 28099570 | Lower in Smoker |
| cg06529134 | 20 | 57226134 | Higher in Smoker |
| cg14153061 | 9 | 102669613 | Lower in Smoker |
| cg01920494 | 4 | 4543764 | Higher in Smoker |
| cg14471975 | 7 | 73134079 | Higher in Smoker |
| cg16680451 | 7 | 73121744 | Lower in Smoker |
| cg15932980 | 12 | 131276353 | Lower in Smoker |
| cg09812406 | 12 | 131303993 | Lower in Smoker |
| cg12977171 | 11 | 59521791 | Higher in Smoker |
| cg02437368 | 16 | 31044759 | Higher in Smoker |
| cg16540079 | 6 | 132786034 | Lower in Smoker |
| cg03258142 | 9 | 130454499 | Lower in Smoker |
| cg15258033 | 12 | 10826753 | Higher in Smoker |
| cg03592824 | 7 | 75666768 | Lower in Smoker |
| cg21494445 | 7 | 75677431 | Higher in Smoker |
| cg01170069 | 5 | 32599084 | Lower in Smoker |
| cg23344412 | 5 | 32602844 | Lower in Smoker |
| cg26366813 | 5 | 32585549 | Lower in Smoker |
| cg03976667 | 2 | 84686045 | Higher in Smoker |
| cg07341365 | 12 | 118854318 | Lower in Smoker |
| cg17537009 | 12 | 118814304 | Lower in Smoker |
| cg21520002 | 12 | 118814505 | Lower in Smoker |
| cg14203838 | 9 | 33390835 | Lower in Smoker |
| cg08134301 | 20 | 46415506 | Higher in Smoker |
| cg19754861 | 20 | 46414999 | Higher in Smoker |
| cg10407847 | 16 | 28607531 | Higher in Smoker |
| cg06795125 | 2 | 108905320 | Lower in Smoker |

| | | | |
|---|---|---|---|
| cg08151612 | 19 | 49055438 | Higher in Smoker |
| cg00698688 | 19 | 49055432 | Higher in Smoker |
| cg07543967 | 19 | 49055443 | Higher in Smoker |
| cg02571944 | 2 | 37416022 | Lower in Smoker |
| cg16643090 | 3 | 4509008 | Lower in Smoker |
| cg17215666 | 7 | 56131930 | Higher in Smoker |
| cg27066319 | 12 | 56392003 | Lower in Smoker |
| cg15701419 | 17 | 26991826 | Lower in Smoker |
| cg01859360 | 17 | 26990453 | Lower in Smoker |
| cg19051195 | 17 | 26989222 | Higher in Smoker |
| cg06376599 | 10 | 70939989 | Higher in Smoker |
| cg19494000 | 9 | 136203137 | Higher in Smoker |
| cg03004599 | 9 | 114937770 | Higher in Smoker |
| cg13601427 | 3 | 33260752 | Lower in Smoker |
| cg23675214 | X | 48554935 | Lower in Smoker |
| cg12042678 | 10 | 14920910 | Higher in Smoker |
| cg11287039 | 11 | 67980200 | Higher in Smoker |
| cg14834466 | 11 | 67981677 | Higher in Smoker |
| cg07448771 | 11 | 67980776 | Higher in Smoker |
| cg23037111 | 19 | 55857159 | Lower in Smoker |
| cg04927502 | 1 | 149889361 | Higher in Smoker |
| cg25742540 | 15 | 91643000 | Higher in Smoker |
| cg07342559 | 15 | 91670784 | Lower in Smoker |
| cg25025437 | 5 | 75377968 | Higher in Smoker |
| cg02989828 | 5 | 75469904 | Higher in Smoker |
| cg06705526 | 5 | 75379336 | Higher in Smoker |
| cg25577670 | 10 | 29804970 | Lower in Smoker |
| cg01616474 | 11 | 22850970 | Higher in Smoker |
| cg05719902 | 7 | 138348774 | Lower in Smoker |
| cg13673009 | 11 | 9684886 | Lower in Smoker |
| cg08813886 | X | 16737692 | Higher in Smoker |
| cg01753188 | 16 | 77233325 | Lower in Smoker |
| cg15204945 | 19 | 39694177 | Lower in Smoker |
| cg18396987 | 1 | 115398073 | Higher in Smoker |
| cg12813768 | 1 | 115398123 | Higher in Smoker |

| | | | |
|---|---|---|---|
| cg17269137 | 1 | 85666874 | Higher in Smoker |
| cg14005120 | 9 | 93652538 | Lower in Smoker |
| cg03310376 | 3 | 12229001 | Higher in Smoker |
| cg13523468 | 3 | 12047002 | Lower in Smoker |
| cg10110335 | 3 | 12197630 | Lower in Smoker |
| cg05206984 | 22 | 33454324 | Higher in Smoker |
| cg23817297 | 22 | 33195688 | Lower in Smoker |
| ch.1.1073856R | 1 | 33147899 | Higher in Smoker |
| cg04551500 | 1 | 33169558 | Lower in Smoker |
| cg22710398 | 6 | 86349279 | Lower in Smoker |
| cg01844274 | 6 | 152792267 | Lower in Smoker |
| cg19696227 | 6 | 152689441 | Lower in Smoker |
| cg15413940 | 6 | 152655593 | Lower in Smoker |
| cg19827346 | 6 | 152702387 | Lower in Smoker |
| cg23609375 | 14 | 64319306 | Higher in Smoker |
| cg05050958 | 14 | 64676831 | Lower in Smoker |
| cg25056332 | 14 | 64682466 | Lower in Smoker |
| cg18902579 | 6 | 33419353 | Higher in Smoker |
| cg00106093 | 6 | 33391341 | Lower in Smoker |
| cg27051937 | 6 | 33419580 | Lower in Smoker |
| cg26535273 | 6 | 33419140 | Lower in Smoker |
| cg15264710 | 6 | 33396168 | Lower in Smoker |
| cg05003791 | 22 | 39746550 | Higher in Smoker |
| cg05006092 | 17 | 76166303 | Lower in Smoker |
| cg03682972 | 6 | 158402912 | Higher in Smoker |
| cg13735013 | 6 | 158404121 | Lower in Smoker |
| cg09948076 | 15 | 99645088 | Higher in Smoker |
| cg13897374 | 5 | 150004783 | Lower in Smoker |
| cg01590948 | 5 | 150004773 | Lower in Smoker |
| cg00607609 | 4 | 119962922 | Lower in Smoker |
| cg25736617 | 10 | 75411098 | Lower in Smoker |
| cg12291247 | 10 | 75411501 | Lower in Smoker |
| cg06185146 | 3 | 63428305 | Lower in Smoker |
| cg27218536 | 17 | 35969412 | Higher in Smoker |
| cg09382850 | 7 | 105753147 | Higher in Smoker |

| | | | |
|---|---|---|---|
| cg18970346 | 20 | 43990951 | Lower in Smoker |
| cg22268341 | 12 | 79811775 | Lower in Smoker |
| cg25193867 | 12 | 79668119 | Lower in Smoker |
| cg00020191 | 12 | 79258083 | Lower in Smoker |
| cg06721860 | 12 | 33589594 | Lower in Smoker |
| cg10374493 | 12 | 33593913 | Lower in Smoker |
| cg10858542 | 12 | 33592642 | Higher in Smoker |
| cg26521129 | 1 | 155830797 | Lower in Smoker |
| cg16548261 | 11 | 66790373 | Lower in Smoker |
| cg09584118 | 11 | 45273975 | Lower in Smoker |
| cg25133706 | 14 | 62522891 | Lower in Smoker |
| cg01976076 | 16 | 19196646 | Lower in Smoker |
| cg00776252 | 16 | 19178699 | Lower in Smoker |
| cg00982214 | 1 | 202614080 | Lower in Smoker |
| cg24592621 | 1 | 202569587 | Lower in Smoker |
| cg13674662 | 19 | 51132637 | Higher in Smoker |
| cg07721458 | 19 | 55685292 | Higher in Smoker |
| cg10280412 | 11 | 61314117 | Higher in Smoker |
| cg00009053 | 11 | 61283865 | Lower in Smoker |
| cg26473272 | 11 | 1856268 | Lower in Smoker |
| cg09597390 | 11 | 7436013 | Lower in Smoker |
| cg25471443 | 1 | 27668058 | Lower in Smoker |
| cg21565368 | 11 | 85437579 | Lower in Smoker |
| cg18609248 | 6 | 159119898 | Lower in Smoker |
| cg01537968 | X | 99987037 | Higher in Smoker |
| cg02282849 | 11 | 64902154 | Higher in Smoker |
| cg05300538 | 11 | 64898766 | Lower in Smoker |
| cg24871596 | 6 | 166572045 | Higher in Smoker |
| cg07805642 | 6 | 132890602 | Lower in Smoker |
| cg12546981 | 6 | 132891738 | Lower in Smoker |
| cg14047911 | 6 | 132858546 | Lower in Smoker |
| cg04461311 | 17 | 47926783 | Lower in Smoker |
| cg11241541 | 8 | 38586066 | Lower in Smoker |
| cg04839259 | 10 | 123873277 | Higher in Smoker |
| cg12239557 | 10 | 123778187 | Higher in Smoker |

| | | | |
|---|---|---|---|
| cg24181174 | 10 | 123900861 | Lower in Smoker |
| cg26111575 | 10 | 123886914 | Lower in Smoker |
| cg09637367 | 17 | 61676756 | Lower in Smoker |
| cg05403555 | 2 | 75427088 | Higher in Smoker |
| cg23210365 | 2 | 75426841 | Higher in Smoker |
| cg22277431 | 2 | 75426726 | Higher in Smoker |
| cg20689228 | 2 | 75427489 | Higher in Smoker |
| cg15278682 | 10 | 71175852 | Higher in Smoker |
| cg06971773 | 10 | 71169083 | Lower in Smoker |
| cg04535008 | 4 | 104641033 | Higher in Smoker |
| cg27301328 | 1 | 166845490 | Higher in Smoker |
| cg01035900 | 17 | 35767301 | Higher in Smoker |
| cg24709285 | 4 | 7052788 | Lower in Smoker |
| ch.X.1083956F | X | 70645135 | Higher in Smoker |
| ch.X.1084407R | X | 70661061 | Higher in Smoker |
| cg11651904 | 1 | 28969799 | Higher in Smoker |
| cg18222891 | 1 | 28969288 | Higher in Smoker |
| cg21125452 | 8 | 120846352 | Lower in Smoker |
| cg04234156 | 10 | 7860746 | Higher in Smoker |
| cg07526974 | 10 | 7899001 | Lower in Smoker |
| cg07342845 | 20 | 60555591 | Lower in Smoker |
| ch.18.486455F | 18 | 23949690 | Higher in Smoker |
| cg25713684 | 10 | 105127687 | Higher in Smoker |
| cg20684973 | 10 | 105127632 | Higher in Smoker |
| cg20690916 | 5 | 140700301 | Higher in Smoker |
| cg00695046 | X | 100545995 | Lower in Smoker |
| cg24123479 | 5 | 68664773 | Higher in Smoker |
| cg00192980 | X | 77394971 | Lower in Smoker |
| cg27084622 | 6 | 159462964 | Lower in Smoker |
| cg16107628 | 1 | 159894061 | Higher in Smoker |
| cg19266779 | 1 | 47685463 | Lower in Smoker |
| cg08472449 | 2 | 160009677 | Higher in Smoker |
| cg10514237 | 2 | 162064025 | Lower in Smoker |
| cg25058462 | 2 | 161993315 | Higher in Smoker |
| cg07351059 | 16 | 29999179 | Lower in Smoker |

| | | | |
|---|---|---|---|
| cg10934821 | 12 | 118809648 | Higher in Smoker |
| cg17627898 | 12 | 118782453 | Lower in Smoker |
| cg14530528 | 6 | 32821814 | Higher in Smoker |
| cg14272068 | 6 | 32821742 | Higher in Smoker |
| cg18511153 | 6 | 32798182 | Lower in Smoker |
| cg19455396 | 6 | 32796056 | Lower in Smoker |
| cg17018201 | 6 | 33269769 | Higher in Smoker |
| cg05105110 | 6 | 33270914 | Lower in Smoker |
| cg05003685 | 6 | 33267721 | Higher in Smoker |
| cg14039343 | 6 | 33267684 | Lower in Smoker |
| cg26293201 | 6 | 33281517 | Lower in Smoker |
| cg18353226 | 6 | 33280390 | Lower in Smoker |
| cg16205375 | 6 | 33273460 | Lower in Smoker |
| cg24131538 | 12 | 6571347 | Higher in Smoker |
| cg03954861 | 12 | 6561352 | Higher in Smoker |
| cg20296524 | 1 | 234614614 | Higher in Smoker |
| cg10252600 | 12 | 53897344 | Lower in Smoker |
| cg22559639 | 12 | 53895182 | Higher in Smoker |
| cg24948372 | 5 | 33448253 | Lower in Smoker |
| cg20975713 | 15 | 102264772 | Higher in Smoker |
| cg07019009 | 15 | 102265803 | Lower in Smoker |
| cg09132215 | 1 | 6615264 | Lower in Smoker |
| cg15743657 | 1 | 19186787 | Lower in Smoker |
| cg06395167 | 1 | 1268243 | Lower in Smoker |
| cg24252805 | 1 | 1266548 | Lower in Smoker |
| cg03138863 | 12 | 10978947 | Lower in Smoker |
| cg21874193 | 12 | 11174898 | Lower in Smoker |
| cg12986639 | 7 | 141673903 | Lower in Smoker |
| cg10411339 | 8 | 125550661 | Higher in Smoker |
| cg03813905 | 8 | 125551074 | Higher in Smoker |
| cg26120756 | 8 | 125551131 | Higher in Smoker |
| cg21376738 | 3 | 10289910 | Higher in Smoker |
| cg23615248 | 1 | 212965701 | Higher in Smoker |
| cg18272543 | 7 | 27779524 | Higher in Smoker |
| cg00113623 | X | 153640221 | Higher in Smoker |

| | | | |
|---|---|---|---|
| cg24826020 | 4 | 38070998 | Higher in Smoker |
| cg07775292 | 22 | 30720496 | Higher in Smoker |
| cg18776876 | 11 | 67176946 | Lower in Smoker |
| cg05498905 | 4 | 6955698 | Lower in Smoker |
| ch.4.255198F | 4 | 7007709 | Higher in Smoker |
| cg27089072 | 4 | 6988367 | Higher in Smoker |
| cg09859456 | 12 | 72234313 | Higher in Smoker |
| cg02837432 | 12 | 72232889 | Lower in Smoker |
| cg14026788 | 12 | 72233266 | Lower in Smoker |
| cg11565911 | 12 | 72233249 | Lower in Smoker |
| cg20667480 | 17 | 77916768 | Higher in Smoker |
| cg14234302 | 19 | 50391354 | Lower in Smoker |
| cg22726760 | 19 | 50380763 | Higher in Smoker |
| cg18562923 | 20 | 442381 | Higher in Smoker |
| cg25141264 | 22 | 47560578 | Lower in Smoker |
| cg07397612 | 22 | 47423986 | Lower in Smoker |
| cg17157894 | 22 | 47187343 | Lower in Smoker |
| cg06294470 | 6 | 37276086 | Lower in Smoker |
| cg16524193 | 3 | 99979582 | Higher in Smoker |
| cg06935199 | 16 | 2524534 | Higher in Smoker |
| cg27383203 | 17 | 15646415 | Lower in Smoker |
| cg03336458 | 15 | 78324479 | Higher in Smoker |
| cg07023915 | 15 | 78370148 | Lower in Smoker |
| cg18597434 | 13 | 76055871 | Higher in Smoker |
| cg22375856 | 3 | 17301676 | Lower in Smoker |
| cg25468928 | 3 | 17680687 | Lower in Smoker |
| cg18398007 | 6 | 13328969 | Lower in Smoker |
| cg09285418 | 2 | 101768973 | Higher in Smoker |
| cg03584646 | 2 | 101676513 | Lower in Smoker |
| cg11446617 | 6 | 42713405 | Higher in Smoker |
| cg14506751 | 3 | 186289443 | Lower in Smoker |
| cg07893149 | 3 | 186285238 | Lower in Smoker |
| cg19467964 | 17 | 80806135 | Higher in Smoker |
| cg06969177 | 17 | 80763047 | Higher in Smoker |
| cg22043788 | 17 | 80879483 | Lower in Smoker |

| | | | |
|---|---|---|---|
| cg23549774 | 17 | 80859139 | Lower in Smoker |
| cg25339368 | 17 | 80819400 | Lower in Smoker |
| cg09036312 | 17 | 80766090 | Lower in Smoker |
| cg16344650 | 17 | 80884898 | Lower in Smoker |
| cg11520030 | 17 | 80710877 | Lower in Smoker |
| cg07114009 | 17 | 80797948 | Lower in Smoker |
| cg27345111 | 17 | 80796743 | Lower in Smoker |
| cg26385993 | 17 | 80788710 | Lower in Smoker |
| cg00492269 | 17 | 80798706 | Lower in Smoker |
| cg13305585 | 1 | 235530624 | Higher in Smoker |
| cg02366479 | 1 | 235530811 | Higher in Smoker |
| cg06747745 | 11 | 120894801 | Higher in Smoker |
| cg15709784 | 12 | 64845926 | Higher in Smoker |
| cg25613170 | 17 | 45772523 | Higher in Smoker |
| cg16892191 | X | 9431305 | Higher in Smoker |
| cg14105781 | X | 9433597 | Higher in Smoker |
| cg01975591 | X | 9432530 | Higher in Smoker |
| cg21024388 | 3 | 176794214 | Lower in Smoker |
| cg13072186 | 3 | 176904010 | Lower in Smoker |
| cg03930153 | 3 | 176868896 | Lower in Smoker |
| cg11250247 | 6 | 170864036 | Higher in Smoker |
| cg24710073 | 6 | 170864351 | Lower in Smoker |
| cg10373887 | 6 | 134274107 | Higher in Smoker |
| cg07687349 | 2 | 162273152 | Higher in Smoker |
| cg07419021 | 2 | 162274436 | Higher in Smoker |
| cg09876845 | 11 | 124492568 | Higher in Smoker |
| cg11299624 | 7 | 45151356 | Higher in Smoker |
| cg10726355 | 7 | 45151589 | Higher in Smoker |
| cg16113681 | 22 | 19748925 | Higher in Smoker |
| cg19092981 | 22 | 19751654 | Higher in Smoker |
| cg13655674 | 1 | 119522386 | Higher in Smoker |
| cg03989260 | 1 | 119529360 | Higher in Smoker |
| cg03942051 | 1 | 119532655 | Higher in Smoker |
| cg19730691 | 1 | 119526437 | Higher in Smoker |
| cg02862748 | 1 | 119426493 | Lower in Smoker |

| | | | |
|---|---|---|---|
| cg15513743 | 1 | 119528688 | Lower in Smoker |
| cg02177231 | 1 | 119529930 | Lower in Smoker |
| cg24884142 | 1 | 119532056 | Higher in Smoker |
| cg19021197 | 17 | 59476212 | Higher in Smoker |
| cg21977256 | 17 | 59477112 | Higher in Smoker |
| cg09365557 | 17 | 59477364 | Higher in Smoker |
| cg11117878 | 7 | 35294949 | Higher in Smoker |
| cg09775582 | 17 | 45810865 | Higher in Smoker |
| cg06365535 | 17 | 59534102 | Higher in Smoker |
| cg03866607 | 17 | 59532826 | Higher in Smoker |
| cg03936495 | 17 | 59539251 | Lower in Smoker |
| cg08985029 | 12 | 114843296 | Higher in Smoker |
| cg02011607 | 12 | 114792545 | Lower in Smoker |
| cg14214262 | 12 | 114843188 | Higher in Smoker |
| cg11357746 | 12 | 114837887 | Higher in Smoker |
| cg09233651 | 12 | 114838567 | Higher in Smoker |
| cg25556579 | 12 | 114829194 | Higher in Smoker |
| cg15861540 | 19 | 3606463 | Higher in Smoker |
| cg08069088 | 19 | 3606835 | Higher in Smoker |
| cg26407309 | 7 | 139479119 | Lower in Smoker |
| cg12521813 | 7 | 139477841 | Higher in Smoker |
| cg20667964 | 7 | 139553002 | Lower in Smoker |
| cg02082887 | 17 | 37820361 | Higher in Smoker |
| cg01677098 | 8 | 54935025 | Higher in Smoker |
| cg18813881 | 20 | 62691175 | Lower in Smoker |
| cg07820742 | 1 | 23751517 | Higher in Smoker |
| cg13538773 | X | 13671128 | Higher in Smoker |
| cg13568559 | X | 13671098 | Higher in Smoker |
| cg17964575 | X | 13680281 | Lower in Smoker |
| cg07059052 | 16 | 2828302 | Higher in Smoker |
| cg17512748 | 5 | 145826735 | Higher in Smoker |
| cg26714517 | 5 | 145827211 | Lower in Smoker |
| cg18138206 | 10 | 133110731 | Higher in Smoker |
| cg24783019 | 15 | 57251471 | Lower in Smoker |
| cg17140034 | 15 | 57220527 | Lower in Smoker |

| | | | |
|---|---|---|---|
| cg23713768 | 22 | 42575631 | Lower in Smoker |
| cg07571531 | 6 | 134216081 | Higher in Smoker |
| cg14801038 | 6 | 134214307 | Lower in Smoker |
| cg12209937 | 2 | 27371628 | Lower in Smoker |
| cg08831324 | 16 | 89940582 | Higher in Smoker |
| cg03293350 | 18 | 52891017 | Lower in Smoker |
| cg08063911 | 5 | 133451474 | Lower in Smoker |
| cg22834443 | 2 | 85382880 | Lower in Smoker |
| cg15624624 | 10 | 114819357 | Lower in Smoker |
| cg06978021 | 20 | 61493312 | Higher in Smoker |
| cg09194650 | 12 | 110337899 | Higher in Smoker |
| cg08932343 | 11 | 67815010 | Lower in Smoker |
| cg23860321 | 6 | 160211010 | Higher in Smoker |
| cg26839252 | 6 | 160211577 | Higher in Smoker |
| cg26296969 | 6 | 160206205 | Lower in Smoker |
| cg24749362 | 6 | 167589370 | Higher in Smoker |
| cg16214245 | 6 | 167584201 | Lower in Smoker |
| cg04435320 | 11 | 33083021 | Lower in Smoker |
| cg02476566 | 12 | 106696527 | Higher in Smoker |
| cg16872172 | 3 | 49449542 | Higher in Smoker |
| cg21322636 | 3 | 49449687 | Higher in Smoker |
| cg10921983 | 12 | 124155712 | Higher in Smoker |
| cg14967745 | 12 | 104360022 | Higher in Smoker |
| cg20471612 | X | 109763373 | Lower in Smoker |
| cg08121954 | 4 | 156825203 | Lower in Smoker |
| cg27280296 | 14 | 90422339 | Higher in Smoker |
| cg02190211 | 14 | 90423352 | Lower in Smoker |
| cg00006198 | 1 | 154476306 | Lower in Smoker |
| cg16683920 | 1 | 154474344 | Lower in Smoker |
| cg02457680 | 1 | 154475139 | Higher in Smoker |
| cg07668623 | 13 | 60971344 | Higher in Smoker |
| cg06884495 | 14 | 104394621 | Higher in Smoker |
| cg18669082 | 14 | 104395429 | Lower in Smoker |
| cg20488157 | 14 | 104394430 | Lower in Smoker |
| cg04904561 | 14 | 104394831 | Higher in Smoker |

| | | | |
|---|---|---|---|
| cg18019451 | 1 | 151746047 | Lower in Smoker |
| cg08537660 | 11 | 12699661 | Lower in Smoker |
| cg01546820 | 6 | 35453639 | Lower in Smoker |
| cg26888836 | 4 | 48272120 | Higher in Smoker |
| cg15412778 | 7 | 97881167 | Higher in Smoker |
| cg06819357 | 14 | 102928437 | Higher in Smoker |
| cg03132518 | 4 | 65275045 | Lower in Smoker |
| cg11310693 | 11 | 121023592 | Higher in Smoker |
| cg13751188 | 11 | 121023720 | Lower in Smoker |
| cg18972666 | 17 | 15245185 | Lower in Smoker |
| cg06383022 | 2 | 95537049 | Lower in Smoker |
| cg04402122 | 16 | 1544648 | Lower in Smoker |
| cg10624583 | 12 | 53440492 | Higher in Smoker |
| cg08699646 | 16 | 58019359 | Higher in Smoker |
| cg24350612 | 8 | 73921026 | Higher in Smoker |
| cg08885201 | 16 | 69419692 | Higher in Smoker |
| cg03669394 | 16 | 75685254 | Higher in Smoker |
| cg16671301 | 5 | 1289283 | Lower in Smoker |
| cg26336790 | 5 | 1264568 | Lower in Smoker |
| cg12324353 | 5 | 1269197 | Lower in Smoker |
| cg09278623 | 7 | 115892473 | Higher in Smoker |
| cg04964669 | 12 | 117536182 | Lower in Smoker |
| cg13948707 | 10 | 70321243 | Higher in Smoker |
| cg23602092 | 10 | 70319645 | Higher in Smoker |
| cg02952701 | 10 | 70319783 | Higher in Smoker |
| cg09183181 | 10 | 70320734 | Higher in Smoker |
| cg19127638 | 10 | 70322442 | Higher in Smoker |
| cg06795971 | 4 | 106067365 | Higher in Smoker |
| cg08167097 | X | 70128670 | Higher in Smoker |
| cg22399458 | 11 | 112038039 | Lower in Smoker |
| cg22650178 | 17 | 56767431 | Lower in Smoker |
| cg15602217 | 17 | 80319589 | Lower in Smoker |
| cg03019000 | 3 | 51704351 | Lower in Smoker |
| cg02621528 | 3 | 133464047 | Lower in Smoker |
| cg05831083 | 10 | 60147307 | Lower in Smoker |

| | | | |
|---|---|---|---|
| cg17673897 | 6 | 10418121 | Higher in Smoker |
| cg13298147 | 6 | 10416508 | Higher in Smoker |
| cg08401657 | 6 | 10399046 | Lower in Smoker |
| cg20432960 | 6 | 50804174 | Higher in Smoker |
| cg04606210 | 20 | 55205571 | Higher in Smoker |
| cg09364688 | 1 | 36038877 | Lower in Smoker |
| cg14844118 | 16 | 4311941 | Lower in Smoker |
| cg03514977 | 16 | 4313709 | Lower in Smoker |
| cg22151587 | 16 | 4322750 | Higher in Smoker |
| cg17825989 | 6 | 155635201 | Higher in Smoker |
| cg25028406 | 13 | 114277434 | Lower in Smoker |
| cg00916831 | 13 | 114260424 | Lower in Smoker |
| cg18109716 | 13 | 114291977 | Lower in Smoker |
| cg16829640 | X | 132352420 | Lower in Smoker |
| cg11901680 | X | 48901069 | Lower in Smoker |
| cg09490007 | 6 | 41704003 | Lower in Smoker |
| cg06493963 | 7 | 115608503 | Lower in Smoker |
| cg00927226 | 7 | 115608801 | Lower in Smoker |
| cg15198739 | 22 | 26908541 | Higher in Smoker |
| cg11665583 | 22 | 26893201 | Lower in Smoker |
| cg16628205 | 7 | 100240094 | Lower in Smoker |
| cg26126750 | 3 | 195809198 | Lower in Smoker |
| cg07349217 | 8 | 133878997 | Lower in Smoker |
| cg26180126 | 2 | 70779764 | Higher in Smoker |
| cg18418457 | 5 | 135364328 | Higher in Smoker |
| cg21550219 | 5 | 135394043 | Lower in Smoker |
| cg24719910 | 3 | 30691493 | Lower in Smoker |
| cg13724812 | 3 | 30689635 | Lower in Smoker |
| cg16299428 | 3 | 30648098 | Higher in Smoker |
| cg24879809 | 1 | 92351641 | Lower in Smoker |
| cg25385819 | 19 | 3445098 | Lower in Smoker |
| cg05128992 | 19 | 3450160 | Higher in Smoker |
| cg20443635 | 20 | 35200590 | Higher in Smoker |
| cg19262130 | 20 | 36766480 | Lower in Smoker |
| cg20726804 | 2 | 85553966 | Higher in Smoker |

| | | | |
|---|---|---|---|
| cg10216498 | 20 | 57556470 | Higher in Smoker |
| cg06678594 | 2 | 43573198 | Lower in Smoker |
| cg27300967 | 1 | 6685162 | Higher in Smoker |
| cg20285559 | 1 | 6688542 | Lower in Smoker |
| cg00513781 | 2 | 242571652 | Lower in Smoker |
| cg10570405 | 7 | 103210304 | Higher in Smoker |
| cg18176887 | 7 | 103210328 | Higher in Smoker |
| cg02833116 | 7 | 103210556 | Higher in Smoker |
| cg08470742 | 6 | 169653905 | Higher in Smoker |
| cg03535284 | 6 | 169653959 | Higher in Smoker |
| cg24407096 | 6 | 169653618 | Higher in Smoker |
| cg10784386 | 5 | 79330943 | Higher in Smoker |
| cg21985690 | 5 | 79330669 | Higher in Smoker |
| cg01194371 | 5 | 79331477 | Higher in Smoker |
| cg10590095 | 1 | 151879636 | Lower in Smoker |
| cg25823934 | 10 | 25313929 | Lower in Smoker |
| cg22974158 | 10 | 25305096 | Higher in Smoker |
| cg16019782 | 10 | 25305105 | Higher in Smoker |
| cg18634296 | 10 | 25305078 | Higher in Smoker |
| cg04689409 | 10 | 25305075 | Higher in Smoker |
| cg10323490 | 2 | 88469007 | Lower in Smoker |
| cg23315422 | 18 | 268381 | Higher in Smoker |
| cg01610915 | 22 | 29950274 | Lower in Smoker |
| cg04483623 | 22 | 29949575 | Higher in Smoker |
| cg22134162 | 3 | 63841271 | Lower in Smoker |
| cg25659677 | 19 | 2785212 | Higher in Smoker |
| cg02007638 | 19 | 2785672 | Lower in Smoker |
| cg08292058 | 19 | 2807172 | Lower in Smoker |
| cg10858898 | 17 | 38245607 | Lower in Smoker |
| cg15359321 | 3 | 24203479 | Lower in Smoker |
| cg16505204 | 11 | 77774337 | Lower in Smoker |
| cg04054012 | 13 | 52980262 | Lower in Smoker |
| cg18570369 | 15 | 71509830 | Lower in Smoker |
| cg26877508 | 15 | 71495324 | Lower in Smoker |
| cg09084967 | 2 | 137747719 | Lower in Smoker |

| | | | |
|---|---|---|---|
| cg16375179 | 16 | 20753272 | Higher in Smoker |
| cg10265472 | 16 | 20753215 | Lower in Smoker |
| cg06720048 | 2 | 39964566 | Lower in Smoker |
| cg19936885 | 3 | 9404556 | Higher in Smoker |
| cg10601287 | 11 | 119293861 | Lower in Smoker |
| cg16435808 | 2 | 70475954 | Higher in Smoker |
| cg23698271 | 10 | 121346762 | Lower in Smoker |
| cg06485447 | 10 | 121357400 | Lower in Smoker |
| cg27118059 | 21 | 32931471 | Higher in Smoker |
| cg06913744 | 1 | 43774711 | Lower in Smoker |
| cg08940762 | 2 | 233415810 | Lower in Smoker |
| cg02504457 | 12 | 56843332 | Higher in Smoker |
| cg27163440 | 12 | 56840065 | Lower in Smoker |
| cg07593415 | 19 | 2426333 | Lower in Smoker |
| cg09571097 | 17 | 899782 | Higher in Smoker |
| cg10180481 | 17 | 900238 | Higher in Smoker |
| cg08281515 | 11 | 111956885 | Higher in Smoker |
| cg03768106 | 11 | 111957237 | Higher in Smoker |
| cg15756407 | 11 | 111956086 | Higher in Smoker |
| cg22962425 | 14 | 58891595 | Lower in Smoker |
| cg07895499 | 3 | 156409317 | Lower in Smoker |
| cg11625262 | 3 | 156393772 | Higher in Smoker |
| cg13362147 | 15 | 66649138 | Higher in Smoker |
| cg02298012 | 15 | 66639594 | Lower in Smoker |
| cg04788575 | 1 | 168170646 | Lower in Smoker |
| cg17113809 | 1 | 168148080 | Higher in Smoker |
| cg15573846 | 11 | 126152723 | Higher in Smoker |
| cg08757191 | 11 | 126163050 | Lower in Smoker |
| cg18587484 | 6 | 43449436 | Lower in Smoker |
| cg14276120 | 9 | 71792936 | Lower in Smoker |
| cg18767057 | 17 | 76175611 | Higher in Smoker |
| cg06371723 | 4 | 164396333 | Lower in Smoker |
| cg23210938 | 4 | 164395039 | Higher in Smoker |
| cg02662840 | 17 | 27054111 | Higher in Smoker |
| cg14438399 | 17 | 27053147 | Higher in Smoker |

| | | | |
|---|---|---|---|
| cg02852421 | 15 | 70372614 | Lower in Smoker |
| cg07020846 | 15 | 70390363 | Higher in Smoker |
| cg17235610 | 9 | 82187209 | Higher in Smoker |
| cg13882835 | 2 | 172017928 | Higher in Smoker |
| cg21493633 | 4 | 166795596 | Higher in Smoker |
| cg26529911 | 4 | 166795773 | Higher in Smoker |
| cg19898128 | 4 | 166794971 | Higher in Smoker |
| cg23868720 | 10 | 98273719 | Higher in Smoker |
| cg18065177 | 15 | 63116127 | Lower in Smoker |
| cg20054786 | 4 | 38799406 | Lower in Smoker |
| cg07538512 | 1 | 223316757 | Higher in Smoker |
| cg12275981 | 1 | 223316272 | Lower in Smoker |
| cg13380109 | 3 | 52255762 | Higher in Smoker |
| cg07416656 | 10 | 102894441 | Higher in Smoker |
| cg23340017 | 10 | 102895133 | Higher in Smoker |
| cg00299972 | 10 | 102892528 | Higher in Smoker |
| cg18668780 | 10 | 102883165 | Higher in Smoker |
| cg24735307 | 10 | 102881114 | Lower in Smoker |
| cg24881420 | 5 | 170735754 | Higher in Smoker |
| cg10445046 | 1 | 62191186 | Higher in Smoker |
| cg13495118 | 3 | 149051523 | Lower in Smoker |
| cg01883662 | 3 | 196065289 | Lower in Smoker |
| cg01437803 | 17 | 4674220 | Lower in Smoker |
| cg02245485 | 15 | 83789735 | Higher in Smoker |
| cg26470696 | 19 | 19383613 | Lower in Smoker |
| cg05136452 | 11 | 64879891 | Higher in Smoker |
| cg04567600 | 14 | 24658841 | Lower in Smoker |
| cg14849559 | 2 | 219157356 | Higher in Smoker |
| cg08963669 | 12 | 66563719 | Higher in Smoker |
| cg13531802 | 9 | 75136701 | Lower in Smoker |
| cg07313882 | 17 | 76121348 | Lower in Smoker |
| cg04741689 | 17 | 76124828 | Higher in Smoker |
| cg06428742 | 16 | 18994943 | Lower in Smoker |
| cg18443748 | 17 | 76130305 | Lower in Smoker |
| cg02911077 | 17 | 76128621 | Higher in Smoker |

| | | | |
|---|---|---|---|
| cg05637296 | 17 | 76129475 | Lower in Smoker |
| cg19653282 | 12 | 95009858 | Lower in Smoker |
| cg24241129 | 1 | 165738348 | Higher in Smoker |
| cg14970096 | 1 | 165738563 | Higher in Smoker |
| cg18174222 | 1 | 165696598 | Lower in Smoker |
| cg01786075 | 1 | 165738056 | Higher in Smoker |
| cg20539175 | 13 | 114188051 | Lower in Smoker |
| cg01017780 | 13 | 114195030 | Lower in Smoker |
| cg19326100 | 13 | 114194084 | Lower in Smoker |
| cg16540036 | 5 | 140018942 | Higher in Smoker |
| cg08277382 | 16 | 68877317 | Higher in Smoker |
| cg27322863 | 16 | 69106629 | Lower in Smoker |
| cg05051316 | 19 | 10946973 | Higher in Smoker |
| cg11074549 | 14 | 75642944 | Lower in Smoker |
| cg18553939 | 12 | 124069758 | Higher in Smoker |
| cg13529907 | 7 | 44621997 | Higher in Smoker |
| cg23929381 | 1 | 93645855 | Higher in Smoker |
| cg06756473 | 16 | 69386847 | Lower in Smoker |
| cg14200954 | 9 | 103239817 | Lower in Smoker |
| cg02533035 | 2 | 192993904 | Lower in Smoker |
| cg04174777 | 2 | 192955734 | Lower in Smoker |
| cg19015897 | 17 | 53798372 | Higher in Smoker |
| cg00739770 | 17 | 42092631 | Lower in Smoker |
| cg27555365 | 17 | 7338618 | Higher in Smoker |
| cg25918947 | 17 | 41365094 | Higher in Smoker |
| cg23660014 | 17 | 8077884 | Lower in Smoker |
| cg12668122 | 3 | 133094221 | Lower in Smoker |
| cg04723601 | 11 | 60681193 | Higher in Smoker |
| cg13582446 | 11 | 60682267 | Higher in Smoker |
| cg08141245 | 17 | 21117936 | Higher in Smoker |
| cg16947394 | 3 | 52930628 | Lower in Smoker |
| cg14583999 | 3 | 10019040 | Higher in Smoker |
| cg03850113 | 16 | 8622884 | Lower in Smoker |
| cg22836470 | 12 | 108991777 | Lower in Smoker |
| cg04131734 | 11 | 102323536 | Higher in Smoker |

| | | | |
|---|---|---|---|
| cg25756617 | 1 | 43734917 | Higher in Smoker |
| cg08386165 | 11 | 85345554 | Lower in Smoker |
| cg13711609 | 11 | 85339258 | Higher in Smoker |
| cg17565299 | 4 | 1717835 | Lower in Smoker |
| cg09540957 | 2 | 98414154 | Lower in Smoker |
| cg11494616 | 2 | 98561179 | Lower in Smoker |
| cg15553522 | 11 | 60692329 | Higher in Smoker |
| cg10541517 | 12 | 128753103 | Higher in Smoker |
| cg07067993 | 12 | 130322378 | Higher in Smoker |
| cg20470734 | 12 | 130185016 | Lower in Smoker |
| cg23753415 | 17 | 32909292 | Higher in Smoker |
| cg21718627 | 11 | 87035156 | Lower in Smoker |
| cg20445883 | 11 | 61129875 | Higher in Smoker |
| cg22882201 | 9 | 139685724 | Higher in Smoker |
| cg01482620 | 19 | 48835971 | Higher in Smoker |
| cg04164538 | 19 | 48867262 | Higher in Smoker |
| cg18655958 | 19 | 48867355 | Higher in Smoker |
| cg13850625 | 4 | 159131690 | Higher in Smoker |
| cg11957331 | 19 | 42828156 | Higher in Smoker |
| cg08480906 | 19 | 36036175 | Higher in Smoker |
| cg23010258 | 6 | 10722915 | Higher in Smoker |
| cg25942178 | 2 | 85829333 | Higher in Smoker |
| cg03990588 | 2 | 85826175 | Lower in Smoker |
| cg12755397 | 4 | 83483204 | Higher in Smoker |
| cg11400333 | 11 | 66059695 | Lower in Smoker |
| cg21427017 | 4 | 153554923 | Lower in Smoker |
| cg25652781 | 4 | 153586344 | Lower in Smoker |
| cg04476764 | 4 | 122682720 | Lower in Smoker |
| cg05396967 | 4 | 122686269 | Higher in Smoker |
| cg10032387 | 4 | 38988166 | Lower in Smoker |
| cg07303856 | 3 | 45268633 | Lower in Smoker |
| cg00285026 | 16 | 21169867 | Lower in Smoker |
| cg17604407 | 5 | 87564800 | Higher in Smoker |
| cg11292593 | 2 | 135475699 | Higher in Smoker |
| cg17518512 | 2 | 135472934 | Lower in Smoker |

| | | | |
|---|---|---|---|
| cg16641190 | X | 109246250 | Higher in Smoker |
| cg20589243 | X | 109246229 | Higher in Smoker |
| cg21209948 | X | 109245514 | Higher in Smoker |
| cg01776012 | 4 | 56262702 | Higher in Smoker |
| cg19035457 | 4 | 56262833 | Higher in Smoker |
| cg01336729 | 1 | 109633224 | Higher in Smoker |
| cg26157248 | 1 | 109633052 | Higher in Smoker |
| cg13391638 | 7 | 112430772 | Higher in Smoker |
| cg25177452 | 5 | 72416677 | Higher in Smoker |
| cg10795659 | 5 | 72415998 | Higher in Smoker |
| cg23255964 | 5 | 138862353 | Higher in Smoker |
| cg02070118 | 4 | 952128 | Lower in Smoker |
| cg15974183 | 2 | 120436664 | Higher in Smoker |
| cg00049286 | 2 | 120436657 | Higher in Smoker |
| cg10539167 | 2 | 677574 | Higher in Smoker |
| cg18911943 | 2 | 677677 | Lower in Smoker |
| cg03417317 | 10 | 104221000 | Lower in Smoker |
| cg06555155 | 6 | 158981441 | Higher in Smoker |
| cg24918798 | 2 | 103432687 | Lower in Smoker |
| cg05868365 | 7 | 1584479 | Lower in Smoker |
| cg10633906 | 7 | 1595602 | Lower in Smoker |
| cg18683782 | 7 | 1582001 | Lower in Smoker |
| cg15303472 | 22 | 38668914 | Higher in Smoker |
| cg21030483 | X | 148713678 | Higher in Smoker |
| cg08138475 | 16 | 50059422 | Higher in Smoker |
| cg21432322 | 12 | 72079550 | Higher in Smoker |
| cg07452654 | 4 | 166034211 | Lower in Smoker |
| cg18505401 | 7 | 19812570 | Higher in Smoker |
| cg07679695 | 9 | 74384615 | Higher in Smoker |
| cg08468371 | 10 | 95653400 | Higher in Smoker |
| cg13361703 | 10 | 95653447 | Higher in Smoker |
| cg18176336 | 1 | 9648587 | Higher in Smoker |
| cg07147063 | 16 | 67260764 | Higher in Smoker |
| cg18946437 | 22 | 25335346 | Lower in Smoker |
| cg22855876 | 2 | 27256034 | Higher in Smoker |

| | | | |
|---|---|---|---|
| cg01435137 | 2 | 27255443 | Lower in Smoker |
| cg04010666 | 11 | 61158618 | Lower in Smoker |
| cg07485541 | 11 | 61166051 | Lower in Smoker |
| cg15890292 | 6 | 37226214 | Higher in Smoker |
| cg25007572 | 11 | 62559380 | Lower in Smoker |
| cg14107644 | 7 | 123673390 | Higher in Smoker |
| cg20454158 | 14 | 67982430 | Lower in Smoker |
| cg25898092 | 12 | 120033862 | Lower in Smoker |
| cg02853012 | 10 | 63213192 | Higher in Smoker |
| cg26062907 | X | 15683192 | Lower in Smoker |
| cg05779963 | X | 15683204 | Lower in Smoker |
| cg05580931 | X | 15683218 | Lower in Smoker |
| cg04373359 | 14 | 61746974 | Higher in Smoker |
| cg05119504 | 3 | 99905910 | Lower in Smoker |
| cg07207957 | 4 | 41937031 | Higher in Smoker |
| cg13652653 | 4 | 41937034 | Higher in Smoker |
| cg13028038 | 4 | 41941508 | Lower in Smoker |
| cg13601855 | 2 | 120190297 | Higher in Smoker |
| cg16650530 | 1 | 32538413 | Higher in Smoker |
| cg07258715 | 3 | 12801785 | Higher in Smoker |
| cg20070536 | 11 | 9335581 | Higher in Smoker |
| cg00315487 | 3 | 44906755 | Lower in Smoker |
| cg13740840 | 3 | 44903191 | Higher in Smoker |
| cg08843513 | 3 | 14164955 | Lower in Smoker |
| cg03263229 | 3 | 194349037 | Lower in Smoker |
| cg26671554 | 17 | 57784674 | Higher in Smoker |
| cg07177011 | 1 | 1849305 | Lower in Smoker |
| cg03385270 | 1 | 45140266 | Higher in Smoker |
| cg15626665 | 1 | 33366803 | Higher in Smoker |
| cg17906267 | 1 | 95582329 | Higher in Smoker |
| cg17014627 | 1 | 95582825 | Higher in Smoker |
| cg17221348 | 1 | 95582822 | Higher in Smoker |
| cg14838433 | 1 | 55446303 | Higher in Smoker |
| cg01189112 | 1 | 55446577 | Higher in Smoker |
| cg20082904 | 1 | 55446640 | Higher in Smoker |

| cg11184154 | 15 | 43425644 | Lower in Smoker |
| cg06779847 | 14 | 77687015 | Lower in Smoker |
| cg24030920 | 8 | 91637884 | Lower in Smoker |
| cg04002885 | 8 | 29940921 | Higher in Smoker |
| cg03463818 | 8 | 94766468 | Higher in Smoker |
| cg03190702 | 8 | 94766888 | Higher in Smoker |
| cg10944437 | 8 | 55686135 | Lower in Smoker |
| cg12156167 | 8 | 133760274 | Lower in Smoker |
| cg05187965 | 10 | 45406764 | Lower in Smoker |
| cg01103209 | 1 | 205053265 | Lower in Smoker |
| cg24670497 | 1 | 16068127 | Higher in Smoker |
| cg26049379 | 1 | 16071339 | Lower in Smoker |
| cg05180717 | 15 | 34516488 | Lower in Smoker |
| cg14847483 | 15 | 34516640 | Lower in Smoker |
| cg02414648 | 2 | 112812756 | Higher in Smoker |
| cg04669470 | 16 | 428475 | Lower in Smoker |
| cg08472243 | 16 | 427912 | Lower in Smoker |
| cg07530022 | 16 | 431628 | Higher in Smoker |
| cg13728834 | 9 | 35846324 | Higher in Smoker |
| cg01263574 | 9 | 136390861 | Lower in Smoker |
| cg05843944 | 14 | 74873358 | Lower in Smoker |
| cg24598087 | 20 | 24452091 | Higher in Smoker |
| cg12004730 | 17 | 3572336 | Higher in Smoker |
| cg25988106 | 17 | 7258481 | Higher in Smoker |
| cg06692120 | 17 | 26646884 | Higher in Smoker |
| cg19026207 | 17 | 26645466 | Lower in Smoker |
| cg03353971 | 17 | 31254616 | Lower in Smoker |
| cg14205126 | 11 | 8985648 | Higher in Smoker |
| cg00468740 | 19 | 4292274 | Lower in Smoker |
| cg14081631 | 9 | 100264289 | Lower in Smoker |
| cg00190321 | 15 | 52121780 | Higher in Smoker |
| cg12402318 | 15 | 52135487 | Lower in Smoker |
| cg03476529 | 11 | 117789847 | Lower in Smoker |
| cg00689211 | 21 | 42880107 | Higher in Smoker |
| cg18156003 | 21 | 42836963 | Lower in Smoker |

| | | | |
|---|---|---|---|
| cg26309194 | 21 | 42880557 | Lower in Smoker |
| cg14567985 | 21 | 43792734 | Lower in Smoker |
| cg27300950 | 11 | 117947628 | Lower in Smoker |
| cg22997974 | 11 | 117965421 | Lower in Smoker |
| cg21188731 | 22 | 37467720 | Lower in Smoker |
| cg17235415 | 3 | 111758050 | Lower in Smoker |
| cg21998505 | 2 | 85133728 | Higher in Smoker |
| cg25781258 | X | 103217712 | Lower in Smoker |
| cg26734249 | X | 12994598 | Higher in Smoker |
| ch.12.1667570F | 12 | 83498291 | Higher in Smoker |
| cg02850602 | 12 | 83150597 | Lower in Smoker |
| cg19598375 | 13 | 101326192 | Higher in Smoker |
| cg26151510 | 13 | 101327190 | Higher in Smoker |
| cg00367438 | 7 | 150780797 | Higher in Smoker |
| cg13827173 | 9 | 117873227 | Lower in Smoker |
| cg10650821 | 6 | 31543686 | Lower in Smoker |
| cg23384708 | 6 | 31544934 | Lower in Smoker |
| cg15989608 | 6 | 31545321 | Lower in Smoker |
| cg01360627 | 6 | 31544931 | Lower in Smoker |
| cg24120357 | 5 | 118691415 | Higher in Smoker |
| cg16565154 | 1 | 151129062 | Higher in Smoker |
| cg20642189 | 15 | 51387571 | Higher in Smoker |
| cg01058070 | 15 | 51398144 | Lower in Smoker |
| cg16174779 | 18 | 59993903 | Lower in Smoker |
| cg09879734 | 17 | 16842469 | Higher in Smoker |
| cg10193304 | 17 | 16876525 | Higher in Smoker |
| cg10583942 | 1 | 1142892 | Lower in Smoker |
| cg16977570 | 13 | 24152974 | Higher in Smoker |
| cg12217560 | 13 | 24144900 | Lower in Smoker |
| cg23773946 | 20 | 62327968 | Higher in Smoker |
| cg08715226 | 20 | 62327732 | Higher in Smoker |
| cg07166679 | 1 | 12123735 | Lower in Smoker |
| cg22882684 | 3 | 172233778 | Lower in Smoker |
| cg19987800 | 13 | 43181173 | Lower in Smoker |
| cg18879481 | 1 | 173012051 | Lower in Smoker |

| | | | |
|---|---|---|---|
| cg19589427 | 1 | 173019720 | Lower in Smoker |
| cg05335876 | 1 | 173018989 | Lower in Smoker |
| cg19343707 | 9 | 117692954 | Higher in Smoker |
| cg27631256 | 9 | 117692745 | Higher in Smoker |
| cg01186777 | 19 | 6531016 | Higher in Smoker |
| cg20532972 | 3 | 171179043 | Higher in Smoker |
| cg18471687 | 4 | 2743860 | Lower in Smoker |
| cg02132728 | 4 | 2755777 | Lower in Smoker |
| cg05802478 | 3 | 195634844 | Higher in Smoker |
| cg21438160 | 3 | 195615726 | Lower in Smoker |
| cg04228628 | 8 | 9413457 | Higher in Smoker |
| cg23320011 | 8 | 9485228 | Lower in Smoker |
| cg10976481 | 8 | 9415355 | Lower in Smoker |
| cg12603560 | 11 | 57090070 | Higher in Smoker |
| cg13526040 | 11 | 57093322 | Lower in Smoker |
| cg25628989 | 11 | 57093345 | Lower in Smoker |
| cg05643339 | 1 | 175036687 | Lower in Smoker |
| cg09704054 | 20 | 44453161 | Lower in Smoker |
| cg04045009 | 19 | 55667663 | Lower in Smoker |
| cg06478143 | 19 | 55669059 | Lower in Smoker |
| cg23594208 | 1 | 201347479 | Lower in Smoker |
| cg04734576 | 19 | 12811544 | Lower in Smoker |
| cg07107171 | 1 | 175712382 | Lower in Smoker |
| cg05605135 | 7 | 5462667 | Higher in Smoker |
| cg16238796 | 7 | 5461480 | Higher in Smoker |
| cg08460153 | 7 | 5461852 | Higher in Smoker |
| cg16718902 | 7 | 5352187 | Higher in Smoker |
| cg06420129 | 16 | 24831018 | Higher in Smoker |
| cg05736847 | 17 | 76100510 | Lower in Smoker |
| cg10029130 | 2 | 218808814 | Higher in Smoker |
| cg23830185 | 2 | 218771607 | Higher in Smoker |
| cg20697464 | 2 | 218793716 | Lower in Smoker |
| cg02057716 | 2 | 218807759 | Lower in Smoker |
| cg01103207 | 7 | 47535640 | Higher in Smoker |
| cg04879211 | 7 | 47576144 | Lower in Smoker |

| | | | |
|---|---|---|---|
| cg24499411 | 7 | 47580247 | Lower in Smoker |
| cg20468081 | 17 | 38657934 | Higher in Smoker |
| cg24882324 | 6 | 32064508 | Higher in Smoker |
| cg15196197 | 6 | 32064573 | Higher in Smoker |
| cg03556669 | 6 | 32064497 | Higher in Smoker |
| cg23257604 | 6 | 32076144 | Higher in Smoker |
| cg18419045 | 6 | 32076147 | Higher in Smoker |
| cg10783204 | 6 | 32065011 | Higher in Smoker |
| cg14620908 | 6 | 32078614 | Higher in Smoker |
| cg18055557 | 6 | 32073358 | Higher in Smoker |
| cg07609381 | 6 | 32056606 | Higher in Smoker |
| cg00592944 | 6 | 32032716 | Lower in Smoker |
| cg15773251 | 6 | 32073602 | Lower in Smoker |
| cg04754615 | 6 | 32032723 | Lower in Smoker |
| cg02553302 | 6 | 32019840 | Lower in Smoker |
| cg11032077 | 6 | 32032728 | Lower in Smoker |
| cg16673412 | 6 | 32062885 | Lower in Smoker |
| cg18331619 | 6 | 32058396 | Lower in Smoker |
| cg07654762 | 6 | 32030226 | Lower in Smoker |
| cg25270367 | 6 | 32022898 | Lower in Smoker |
| cg05298224 | 6 | 32016360 | Lower in Smoker |
| cg15398152 | 6 | 32016535 | Lower in Smoker |
| cg06580770 | 6 | 32054790 | Lower in Smoker |
| cg15595918 | 6 | 32047410 | Lower in Smoker |
| cg21722170 | 6 | 31977443 | Lower in Smoker |
| cg13720581 | 6 | 32077017 | Higher in Smoker |
| cg17484510 | 6 | 32015326 | Higher in Smoker |
| cg26571759 | 6 | 32011583 | Lower in Smoker |
| cg11431261 | 6 | 32015297 | Lower in Smoker |
| cg17205877 | 22 | 41842716 | Higher in Smoker |
| cg12353589 | 11 | 1309892 | Lower in Smoker |
| cg14091677 | 11 | 1310098 | Lower in Smoker |
| cg27234109 | 11 | 1308428 | Lower in Smoker |
| cg22050611 | 11 | 1321954 | Lower in Smoker |
| cg25751690 | 22 | 35695799 | Lower in Smoker |

| | | | |
|---|---|---|---|
| cg00365569 | 17 | 17876108 | Higher in Smoker |
| cg00757262 | 17 | 17747898 | Lower in Smoker |
| cg11681219 | 1 | 235291909 | Lower in Smoker |
| cg23481221 | 20 | 43589229 | Higher in Smoker |
| cg06336324 | 6 | 41755399 | Higher in Smoker |
| cg23691518 | 7 | 22863322 | Lower in Smoker |
| cg23629150 | 8 | 144416404 | Lower in Smoker |
| cg22897224 | 22 | 25160406 | Lower in Smoker |
| cg20491223 | 22 | 22337369 | Higher in Smoker |
| cg05732876 | 22 | 22337374 | Higher in Smoker |
| cg14242091 | 22 | 22337171 | Higher in Smoker |
| cg10716607 | 9 | 32552648 | Higher in Smoker |
| cg13448402 | 9 | 132586535 | Higher in Smoker |
| cg03427171 | 1 | 179053297 | Lower in Smoker |
| cg19003304 | 8 | 60029914 | Higher in Smoker |
| cg05901852 | 8 | 59757290 | Lower in Smoker |
| cg09643139 | 8 | 59746288 | Lower in Smoker |
| cg23920047 | 8 | 59791317 | Lower in Smoker |
| cg07211044 | 8 | 60032983 | Lower in Smoker |
| cg01427849 | 8 | 59826463 | Lower in Smoker |
| cg11559731 | 8 | 60032745 | Lower in Smoker |
| cg26745222 | 20 | 42543878 | Higher in Smoker |
| cg26817217 | 16 | 52580987 | Higher in Smoker |
| cg01883578 | 16 | 52579244 | Higher in Smoker |
| cg01200905 | 16 | 52480264 | Lower in Smoker |
| cg12041429 | 17 | 7585875 | Lower in Smoker |
| cg07760161 | 17 | 7588378 | Lower in Smoker |
| cg03388409 | 1 | 224014120 | Lower in Smoker |
| cg07619142 | 11 | 44971049 | Higher in Smoker |
| cg19808323 | 11 | 44972971 | Lower in Smoker |
| cg04745100 | 11 | 44973110 | Lower in Smoker |
| cg22623062 | 11 | 44972293 | Higher in Smoker |
| cg00605408 | 2 | 24307515 | Lower in Smoker |
| cg08755736 | 8 | 95957926 | Lower in Smoker |
| cg26204638 | 20 | 33297218 | Higher in Smoker |

| | | | |
|---|---|---|---|
| cg23530972 | 20 | 45313266 | Higher in Smoker |
| cg14001567 | 7 | 86974838 | Higher in Smoker |
| cg25708695 | 3 | 189353419 | Lower in Smoker |
| cg11729413 | 1 | 3568692 | Higher in Smoker |
| cg12268562 | 1 | 3625409 | Lower in Smoker |
| cg22039909 | 1 | 3635100 | Lower in Smoker |
| cg02529490 | 11 | 68616232 | Higher in Smoker |
| cg16651583 | 11 | 68850875 | Lower in Smoker |
| cg03472453 | 11 | 68846042 | Lower in Smoker |
| cg27413032 | 8 | 80997524 | Higher in Smoker |
| cg00953096 | 6 | 125475363 | Higher in Smoker |
| cg13520736 | 6 | 125543048 | Lower in Smoker |
| cg02807882 | 6 | 125534847 | Lower in Smoker |
| cg10797920 | 20 | 62495449 | Higher in Smoker |
| cg22332321 | 20 | 62510260 | Lower in Smoker |
| cg01345827 | 7 | 144532382 | Higher in Smoker |
| cg12203230 | 1 | 154164951 | Lower in Smoker |
| cg25107608 | 1 | 154155675 | Higher in Smoker |
| cg07810884 | 19 | 16178099 | Higher in Smoker |
| cg11905624 | 19 | 16186848 | Lower in Smoker |
| cg13618979 | 19 | 16186840 | Lower in Smoker |
| cg13978367 | 19 | 16186244 | Lower in Smoker |
| cg13661012 | 2 | 1516352 | Lower in Smoker |
| cg19502932 | 11 | 6640663 | Lower in Smoker |
| cg26564606 | 5 | 660180 | Lower in Smoker |
| cg00762659 | 2 | 73964772 | Higher in Smoker |
| cg22338307 | 2 | 73964768 | Higher in Smoker |
| cg08470892 | 16 | 1308233 | Lower in Smoker |
| cg01375871 | 16 | 1305420 | Lower in Smoker |
| cg27107150 | 16 | 1272275 | Lower in Smoker |
| cg02194908 | 16 | 1276278 | Lower in Smoker |
| cg05114334 | 7 | 65705962 | Lower in Smoker |
| cg22524346 | 7 | 65767274 | Lower in Smoker |
| cg13657092 | 22 | 26986419 | Higher in Smoker |
| cg15130481 | 22 | 26937502 | Higher in Smoker |

| | | | |
|---|---|---|---|
| cg24059033 | 21 | 10991334 | Higher in Smoker |
| cg08538752 | 21 | 10990890 | Higher in Smoker |
| cg22804499 | 3 | 185632943 | Lower in Smoker |
| cg05297854 | 22 | 50623687 | Higher in Smoker |
| cg10563131 | 22 | 50636443 | Lower in Smoker |
| cg01376469 | 22 | 50634745 | Lower in Smoker |
| cg01604539 | 16 | 67189134 | Higher in Smoker |
| cg12766106 | 9 | 139803690 | Lower in Smoker |
| cg01999046 | 9 | 139779708 | Lower in Smoker |
| cg18469747 | 14 | 103315426 | Lower in Smoker |
| cg05893542 | 14 | 103371620 | Lower in Smoker |
| cg04846720 | 14 | 103295640 | Lower in Smoker |
| cg27118298 | 14 | 103272938 | Lower in Smoker |
| cg13907363 | 2 | 239229182 | Higher in Smoker |
| cg24203562 | 2 | 239241869 | Lower in Smoker |
| cg24634333 | 6 | 11188784 | Higher in Smoker |
| cg17222992 | 1 | 211500296 | Higher in Smoker |
| cg06813419 | 1 | 211502171 | Lower in Smoker |
| cg03517024 | 16 | 2221057 | Higher in Smoker |
| cg26875902 | 16 | 2223324 | Lower in Smoker |
| cg06896044 | 16 | 2222637 | Lower in Smoker |
| cg27166767 | 16 | 2218945 | Lower in Smoker |
| cg00812236 | 16 | 2210434 | Lower in Smoker |
| cg26536800 | 8 | 71513741 | Lower in Smoker |
| cg00593404 | 6 | 52377740 | Higher in Smoker |
| cg08966889 | 6 | 52440429 | Lower in Smoker |
| cg11870261 | 3 | 36986679 | Higher in Smoker |
| cg10333520 | 3 | 36987040 | Higher in Smoker |
| cg11014921 | 3 | 36974725 | Lower in Smoker |
| cg14888255 | 3 | 36902745 | Lower in Smoker |
| cg21833841 | 3 | 36868879 | Lower in Smoker |
| cg10609615 | 16 | 3766942 | Higher in Smoker |
| cg04439028 | 16 | 3722002 | Lower in Smoker |
| cg06723414 | 16 | 3763022 | Lower in Smoker |
| cg21619287 | 16 | 3767727 | Lower in Smoker |

| | | | |
|---|---|---|---|
| cg14282407 | 17 | 7835499 | Higher in Smoker |
| cg22385817 | 17 | 7835249 | Higher in Smoker |
| cg07767789 | 16 | 88923709 | Higher in Smoker |
| cg08435079 | 1 | 36615170 | Higher in Smoker |
| cg19225031 | 1 | 36602646 | Lower in Smoker |
| cg26101560 | 11 | 118889209 | Higher in Smoker |
| cg02233890 | 14 | 39639503 | Higher in Smoker |
| cg11256152 | 8 | 141359736 | Higher in Smoker |
| cg06732667 | 8 | 141312916 | Lower in Smoker |
| cg23401796 | 8 | 141248667 | Lower in Smoker |
| cg16118491 | 8 | 141046707 | Lower in Smoker |
| cg07482692 | 8 | 140743036 | Lower in Smoker |
| cg13601615 | 8 | 141461241 | Lower in Smoker |
| cg11152943 | 8 | 141248938 | Lower in Smoker |
| cg04259001 | 8 | 141097242 | Lower in Smoker |
| cg24337701 | 8 | 141275191 | Lower in Smoker |
| cg15293750 | 10 | 17243266 | Higher in Smoker |
| cg22695245 | 10 | 17244393 | Lower in Smoker |
| cg19579782 | 10 | 17243880 | Lower in Smoker |
| cg19478478 | 6 | 123957927 | Lower in Smoker |
| cg05475010 | 6 | 41176577 | Lower in Smoker |
| cg21788755 | 3 | 48508391 | Lower in Smoker |
| cg19091784 | 3 | 48507618 | Higher in Smoker |
| cg14699869 | X | 152710205 | Lower in Smoker |
| cg02198544 | X | 152711731 | Lower in Smoker |
| cg14839014 | 8 | 110100005 | Lower in Smoker |
| cg25053891 | 12 | 120883986 | Higher in Smoker |
| cg02700454 | 8 | 126441997 | Higher in Smoker |
| cg24797493 | 8 | 126441753 | Higher in Smoker |
| cg21113923 | 20 | 360750 | Higher in Smoker |
| cg18824043 | 20 | 373122 | Lower in Smoker |
| cg24847621 | 6 | 30122565 | Lower in Smoker |
| cg16912957 | 6 | 30124214 | Lower in Smoker |
| cg12149881 | 6 | 30130149 | Lower in Smoker |
| cg22825979 | 13 | 50571203 | Lower in Smoker |

| | | | |
|---|---|---|---|
| cg21225548 | 9 | 100864335 | Higher in Smoker |
| cg03588007 | 9 | 100849274 | Lower in Smoker |
| cg05664039 | 6 | 30131755 | Lower in Smoker |
| cg23784132 | 6 | 30132471 | Lower in Smoker |
| cg08977390 | 6 | 30139594 | Lower in Smoker |
| cg17628867 | 17 | 15555115 | Higher in Smoker |
| cg20939768 | 1 | 228604953 | Higher in Smoker |
| cg02832697 | 4 | 154126481 | Lower in Smoker |
| cg10344698 | 7 | 138270134 | Lower in Smoker |
| cg00905858 | 6 | 30171614 | Lower in Smoker |
| cg04110164 | 6 | 30158249 | Lower in Smoker |
| cg19321263 | 6 | 30160045 | Lower in Smoker |
| cg16709517 | 6 | 30166031 | Lower in Smoker |
| cg24636541 | 6 | 30152802 | Lower in Smoker |
| cg03782662 | 6 | 30169120 | Lower in Smoker |
| cg04281416 | 6 | 30178180 | Lower in Smoker |
| cg06186900 | 6 | 30182518 | Lower in Smoker |
| cg14971718 | 6 | 30175327 | Lower in Smoker |
| cg00266604 | 6 | 30178343 | Lower in Smoker |
| cg10526841 | 6 | 30182507 | Lower in Smoker |
| cg16723189 | 6 | 28890556 | Higher in Smoker |
| cg03671443 | 6 | 28891045 | Lower in Smoker |
| cg13907859 | 11 | 120009124 | Lower in Smoker |
| cg13652887 | 11 | 6495452 | Higher in Smoker |
| cg04012857 | 6 | 30080405 | Higher in Smoker |
| cg15601071 | 6 | 30078080 | Lower in Smoker |
| cg09816018 | 6 | 30080295 | Lower in Smoker |
| cg12908665 | 5 | 114499431 | Lower in Smoker |
| cg04209766 | 5 | 114512608 | Lower in Smoker |
| cg12005950 | 6 | 30302816 | Lower in Smoker |
| cg23438945 | 7 | 99517277 | Lower in Smoker |
| cg10897223 | 6 | 30113774 | Lower in Smoker |
| cg13961318 | 6 | 30107614 | Lower in Smoker |
| cg11068217 | 6 | 30108946 | Lower in Smoker |
| cg10641368 | 5 | 180650158 | Higher in Smoker |

| | | | |
|---|---|---|---|
| cg24177093 | 5 | 180650516 | Higher in Smoker |
| cg05374129 | 2 | 27505530 | Lower in Smoker |
| cg05401447 | 7 | 100728731 | Higher in Smoker |
| cg04878813 | 4 | 165953028 | Lower in Smoker |
| cg12819144 | 4 | 165953018 | Lower in Smoker |
| cg19724522 | 4 | 165881424 | Lower in Smoker |
| cg13421133 | 17 | 73889100 | Lower in Smoker |
| cg01505275 | 11 | 4628823 | Higher in Smoker |
| cg05439368 | 15 | 45028098 | Lower in Smoker |
| cg22107533 | 15 | 45028083 | Lower in Smoker |
| cg14596312 | 11 | 5640527 | Lower in Smoker |
| cg00375457 | 11 | 5617273 | Higher in Smoker |
| cg19412791 | 5 | 180633063 | Lower in Smoker |
| ch.3.680450R | 3 | 32927740 | Higher in Smoker |
| cg02406098 | 3 | 32911355 | Lower in Smoker |
| cg23574924 | 14 | 51443494 | Lower in Smoker |
| cg15353061 | 14 | 51562486 | Higher in Smoker |
| cg09822136 | 5 | 14144123 | Higher in Smoker |
| cg10069238 | 5 | 14488532 | Lower in Smoker |
| cg17687981 | 5 | 14475938 | Lower in Smoker |
| cg07768372 | 5 | 14509008 | Lower in Smoker |
| cg00537351 | 5 | 14339109 | Lower in Smoker |
| cg07748253 | 5 | 14306269 | Lower in Smoker |
| cg05649906 | 5 | 14283950 | Lower in Smoker |
| cg01138673 | 5 | 14159230 | Lower in Smoker |
| cg06997707 | 5 | 14167188 | Lower in Smoker |
| cg11540735 | 22 | 38092771 | Higher in Smoker |
| cg03313666 | 22 | 38142162 | Higher in Smoker |
| cg19749445 | 14 | 92493378 | Lower in Smoker |
| cg20079193 | 5 | 892529 | Higher in Smoker |
| cg09497020 | 5 | 893046 | Higher in Smoker |
| cg19566658 | 7 | 100466241 | Lower in Smoker |
| cg10530613 | 1 | 40346530 | Lower in Smoker |
| cg02385661 | 19 | 13215729 | Higher in Smoker |
| cg15815206 | 19 | 13227474 | Higher in Smoker |

| | | | |
|---|---|---|---|
| cg26547947 | 8 | 125463066 | Higher in Smoker |
| cg25375711 | 8 | 125463057 | Higher in Smoker |
| cg25161283 | 22 | 20103922 | Lower in Smoker |
| cg17345036 | X | 100306958 | Higher in Smoker |
| cg18555206 | 14 | 61448125 | Higher in Smoker |
| cg26105310 | 1 | 23878155 | Lower in Smoker |
| cg21767135 | 3 | 3169141 | Lower in Smoker |
| cg12208691 | 1 | 193052736 | Lower in Smoker |
| cg08913815 | 1 | 193028592 | Higher in Smoker |
| cg10503359 | 3 | 142468059 | Lower in Smoker |
| cg17129833 | 11 | 3647695 | Higher in Smoker |
| cg05422957 | 4 | 122873181 | Higher in Smoker |
| cg13549719 | 13 | 38444052 | Higher in Smoker |
| cg01764020 | 13 | 38444087 | Higher in Smoker |
| cg18052042 | 13 | 38440839 | Lower in Smoker |
| cg12361311 | 20 | 33680752 | Higher in Smoker |
| cg08423054 | 20 | 33596700 | Lower in Smoker |
| cg17275074 | 5 | 135701422 | Higher in Smoker |
| cg09465288 | 15 | 31370762 | Lower in Smoker |
| cg03330762 | 19 | 49686116 | Lower in Smoker |
| cg19007908 | 19 | 49686020 | Lower in Smoker |
| cg09554406 | 19 | 49714044 | Lower in Smoker |
| cg09511741 | 19 | 49668729 | Lower in Smoker |
| cg21520111 | 19 | 49713645 | Lower in Smoker |
| cg18225577 | 19 | 49713901 | Lower in Smoker |
| cg10951975 | 19 | 49713828 | Lower in Smoker |
| cg26623224 | 19 | 49661080 | Lower in Smoker |
| cg26767083 | 11 | 2445047 | Higher in Smoker |
| cg17543973 | 11 | 2442163 | Higher in Smoker |
| cg26917665 | 11 | 2444465 | Lower in Smoker |
| cg04189705 | 9 | 77502517 | Higher in Smoker |
| cg03776087 | 2 | 234848156 | Lower in Smoker |
| cg06363590 | 8 | 116679763 | Higher in Smoker |
| cg12396523 | 8 | 116680127 | Higher in Smoker |
| cg11730559 | 8 | 116506662 | Lower in Smoker |

| | | | |
|---|---|---|---|
| cg05711842 | 8 | 116440901 | Lower in Smoker |
| cg01356948 | 8 | 116652764 | Lower in Smoker |
| cg18430465 | 8 | 116422845 | Lower in Smoker |
| cg17825770 | 8 | 116573953 | Lower in Smoker |
| cg13633262 | 17 | 3461398 | Lower in Smoker |
| cg09199598 | 17 | 3461480 | Lower in Smoker |
| cg11475555 | 17 | 3461450 | Lower in Smoker |
| cg10137010 | 17 | 3462438 | Lower in Smoker |
| cg05790038 | 17 | 3461143 | Lower in Smoker |
| cg16390380 | 17 | 3461140 | Lower in Smoker |
| cg16312954 | 7 | 142632296 | Lower in Smoker |
| cg13570487 | 7 | 142574509 | Lower in Smoker |
| cg12527998 | 7 | 93476069 | Higher in Smoker |
| cg24207108 | 7 | 93600653 | Higher in Smoker |
| cg15134482 | 7 | 93581089 | Lower in Smoker |
| cg23876131 | 7 | 93509496 | Lower in Smoker |
| cg07213487 | 7 | 93603561 | Lower in Smoker |
| cg10154880 | 7 | 93603502 | Lower in Smoker |
| cg03934681 | 10 | 116697604 | Higher in Smoker |
| cg14153740 | 7 | 141957702 | Lower in Smoker |
| cg01850110 | 16 | 2098113 | Higher in Smoker |
| cg08936056 | 16 | 2135250 | Higher in Smoker |
| cg02851047 | 16 | 2132723 | Lower in Smoker |
| cg26954928 | X | 106978259 | Lower in Smoker |
| cg03915527 | X | 106957793 | Lower in Smoker |
| cg05175020 | 7 | 130075402 | Lower in Smoker |
| cg00376553 | 7 | 130073281 | Lower in Smoker |
| cg07470396 | 19 | 54697539 | Higher in Smoker |
| cg04631757 | 12 | 58176492 | Higher in Smoker |
| cg11952239 | 6 | 94432258 | Lower in Smoker |
| cg05151496 | 11 | 65711834 | Lower in Smoker |
| cg27135917 | 7 | 130353961 | Higher in Smoker |
| cg09618387 | 19 | 50267850 | Lower in Smoker |
| cg20886049 | 11 | 76493545 | Lower in Smoker |
| cg15739437 | 5 | 110407538 | Lower in Smoker |

| | | | |
|---|---|---|---|
| cg13208492 | 2 | 122513376 | Higher in Smoker |
| cg06622267 | 8 | 143404298 | Lower in Smoker |
| cg02230133 | 8 | 143424799 | Lower in Smoker |
| cg02851167 | 8 | 143378153 | Lower in Smoker |
| cg20980299 | 8 | 143356985 | Lower in Smoker |
| cg21194021 | 8 | 143319259 | Lower in Smoker |
| cg09895514 | 1 | 231907041 | Lower in Smoker |
| cg04792727 | 1 | 231664260 | Higher in Smoker |
| cg04676715 | 16 | 67840712 | Higher in Smoker |
| cg04155026 | 16 | 67841269 | Higher in Smoker |
| cg10657228 | 8 | 10386222 | Lower in Smoker |
| cg23627038 | 7 | 120499546 | Lower in Smoker |
| cg06196828 | 7 | 120495037 | Lower in Smoker |
| cg24756756 | 7 | 16793323 | Lower in Smoker |
| cg14388049 | 10 | 71211838 | Higher in Smoker |
| cg01566955 | 10 | 71211468 | Higher in Smoker |
| cg25719876 | 11 | 44785348 | Lower in Smoker |
| cg03236627 | 11 | 44786104 | Lower in Smoker |
| cg17162355 | 11 | 44951492 | Lower in Smoker |
| cg22871870 | 15 | 77348431 | Lower in Smoker |
| cg06633889 | 12 | 58138676 | Higher in Smoker |
| cg01636582 | 11 | 844593 | Higher in Smoker |
| cg22031466 | 4 | 99504122 | Lower in Smoker |
| cg02015219 | 4 | 99450728 | Lower in Smoker |
| cg25569203 | X | 99384821 | Lower in Smoker |
| cg23065927 | 12 | 3309816 | Higher in Smoker |
| cg08965656 | 12 | 3186504 | Higher in Smoker |
| cg22132193 | 12 | 3334540 | Higher in Smoker |
| cg24409870 | 12 | 3190480 | Lower in Smoker |
| cg25705492 | Y | 9307448 | Lower in Smoker |
| cg09119244 | X | 53111239 | Higher in Smoker |
| cg13109482 | 2 | 3381345 | Higher in Smoker |
| cg09538006 | 2 | 3337909 | Lower in Smoker |
| cg11296774 | 11 | 2423847 | Lower in Smoker |
| cg02157755 | 11 | 2422654 | Lower in Smoker |

| | | | |
|---|---|---|---|
| cg02485697 | 11 | 2424015 | Lower in Smoker |
| cg08470031 | 11 | 2423043 | Lower in Smoker |
| cg02328278 | 5 | 112769927 | Lower in Smoker |
| cg14707431 | 9 | 100395413 | Higher in Smoker |
| cg01883159 | 6 | 43243461 | Higher in Smoker |
| cg25521461 | 6 | 43214396 | Lower in Smoker |
| cg15904908 | 15 | 43213022 | Higher in Smoker |
| cg05127217 | 11 | 113185802 | Lower in Smoker |
| cg16302655 | 11 | 113185879 | Lower in Smoker |
| cg14930059 | 3 | 180319824 | Lower in Smoker |
| cg23137128 | 2 | 3383975 | Higher in Smoker |
| cg22182287 | 2 | 3452347 | Lower in Smoker |
| cg01143247 | 2 | 3469390 | Lower in Smoker |
| cg00864770 | 9 | 130484472 | Lower in Smoker |
| cg06331271 | 11 | 43380295 | Lower in Smoker |
| cg05714926 | 2 | 166810417 | Higher in Smoker |
| ch.2.3376566R | 2 | 166772260 | Higher in Smoker |
| cg19757253 | 2 | 32853039 | Higher in Smoker |
| cg05300230 | 2 | 32853069 | Higher in Smoker |
| cg04196808 | 2 | 32956589 | Lower in Smoker |
| cg12565055 | 22 | 29076175 | Lower in Smoker |
| cg12269905 | 21 | 38574668 | Lower in Smoker |
| cg04939749 | 2 | 178417898 | Higher in Smoker |
| cg15837166 | 2 | 20101919 | Higher in Smoker |
| cg22293416 | 8 | 109493386 | Lower in Smoker |
| cg19909613 | 8 | 109487153 | Lower in Smoker |
| cg18932348 | 5 | 94844511 | Lower in Smoker |
| cg21191737 | 9 | 15306337 | Higher in Smoker |
| cg12639429 | 18 | 21572622 | Lower in Smoker |
| cg06586496 | 18 | 21715307 | Lower in Smoker |
| cg22041988 | 1 | 55181385 | Lower in Smoker |
| cg04574282 | 14 | 89315467 | Lower in Smoker |
| cg12742796 | 1 | 117602840 | Higher in Smoker |
| cg04910062 | 22 | 43463123 | Lower in Smoker |
| cg18770446 | 1 | 1109983 | Lower in Smoker |

| | | | |
|---|---|---|---|
| cg03278726 | 1 | 1109832 | Lower in Smoker |
| cg05706898 | 1 | 1115920 | Higher in Smoker |
| cg09976981 | 22 | 43564007 | Lower in Smoker |
| cg06870118 | 3 | 9850429 | Higher in Smoker |
| cg14611830 | 2 | 219575449 | Higher in Smoker |
| cg13824665 | 14 | 76183993 | Lower in Smoker |
| cg10866623 | 17 | 46895019 | Higher in Smoker |
| cg16757248 | 17 | 46872263 | Lower in Smoker |
| cg27475076 | 20 | 30458103 | Higher in Smoker |
| cg19906284 | 2 | 179395912 | Lower in Smoker |
| cg15609237 | 2 | 179395885 | Lower in Smoker |
| cg14626792 | 8 | 63998649 | Higher in Smoker |
| cg07002711 | 8 | 63998640 | Higher in Smoker |
| cg14817143 | 8 | 63998778 | Higher in Smoker |
| cg04945608 | 20 | 43118723 | Lower in Smoker |
| cg06412323 | 20 | 43108009 | Lower in Smoker |
| cg11802583 | 18 | 29178454 | Lower in Smoker |
| cg14778208 | Y | 7569246 | Lower in Smoker |
| cg12253634 | 17 | 72245470 | Lower in Smoker |
| cg16184737 | 7 | 2679971 | Lower in Smoker |
| cg02154914 | 7 | 2678208 | Lower in Smoker |
| cg00798876 | 7 | 2670978 | Lower in Smoker |
| cg26282283 | 7 | 2704368 | Lower in Smoker |
| cg10481202 | 12 | 49581272 | Lower in Smoker |
| cg22274414 | 13 | 19756318 | Lower in Smoker |
| cg08790550 | 2 | 130955686 | Lower in Smoker |
| cg19074496 | 2 | 220117868 | Higher in Smoker |
| cg05675032 | 22 | 18593364 | Higher in Smoker |
| cg27007110 | 6 | 30691699 | Lower in Smoker |
| cg20172858 | 6 | 30690757 | Lower in Smoker |
| cg12275289 | 6 | 30691665 | Lower in Smoker |
| cg08630415 | 6 | 30686922 | Lower in Smoker |
| cg08442217 | 16 | 89989115 | Higher in Smoker |
| cg10274682 | 19 | 6496041 | Higher in Smoker |
| cg03537241 | 18 | 12307649 | Higher in Smoker |

| | | | |
|---|---|---|---|
| cg16808455 | 18 | 12309071 | Lower in Smoker |
| cg17752083 | 10 | 135101849 | Lower in Smoker |
| cg01747036 | 13 | 113140125 | Higher in Smoker |
| cg20298978 | 13 | 113160167 | Higher in Smoker |
| cg03702675 | 13 | 113174184 | Lower in Smoker |
| cg10622024 | 13 | 113201972 | Lower in Smoker |
| cg07590584 | 13 | 113140145 | Lower in Smoker |
| cg22709985 | 13 | 113199725 | Lower in Smoker |
| cg27063932 | 15 | 22872668 | Lower in Smoker |
| cg10545682 | 1 | 151512625 | Higher in Smoker |
| cg22681721 | 6 | 35477358 | Lower in Smoker |
| cg21660964 | 3 | 50365740 | Higher in Smoker |
| cg09545109 | 3 | 50388910 | Lower in Smoker |
| cg08207395 | 3 | 50388901 | Lower in Smoker |
| cg18730023 | 12 | 44199730 | Higher in Smoker |
| cg04633409 | 12 | 44195947 | Lower in Smoker |
| cg04043591 | 7 | 19155806 | Higher in Smoker |
| cg10420952 | 7 | 19157420 | Higher in Smoker |
| cg02400740 | 7 | 19157938 | Lower in Smoker |
| cg05791153 | 7 | 19748676 | Higher in Smoker |
| cg16469426 | 7 | 19748791 | Higher in Smoker |
| cg25189836 | 7 | 19748663 | Lower in Smoker |
| cg07358372 | 18 | 9334693 | Higher in Smoker |
| cg03745493 | 18 | 9380358 | Lower in Smoker |
| cg01290843 | 5 | 134208721 | Higher in Smoker |
| cg14069412 | 5 | 134209415 | Lower in Smoker |
| ch.6.215100R | 6 | 7903714 | Higher in Smoker |
| cg23640757 | 6 | 7889014 | Lower in Smoker |
| cg09130402 | 18 | 54306120 | Higher in Smoker |
| cg26501139 | 18 | 77733105 | Higher in Smoker |
| cg17260058 | 18 | 77744646 | Lower in Smoker |
| cg17395064 | 12 | 104609476 | Higher in Smoker |
| cg25027799 | 12 | 104659306 | Higher in Smoker |
| cg20324369 | 12 | 104662681 | Lower in Smoker |
| cg15775217 | 12 | 104676774 | Lower in Smoker |

| | | | |
|---|---|---|---|
| cg03817911 | 12 | 104697389 | Higher in Smoker |
| cg27205904 | 12 | 104697514 | Higher in Smoker |
| cg09477407 | 12 | 104697545 | Higher in Smoker |
| cg26614916 | 12 | 104697532 | Higher in Smoker |
| cg21234561 | 12 | 104697526 | Higher in Smoker |
| cg20923245 | 12 | 104697419 | Higher in Smoker |
| cg18633684 | 12 | 104697387 | Higher in Smoker |
| cg02403412 | 22 | 19894638 | Lower in Smoker |
| cg15662184 | 19 | 10464842 | Lower in Smoker |
| cg02555513 | 22 | 50964653 | Higher in Smoker |
| cg10416593 | 22 | 50966123 | Lower in Smoker |
| cg17208363 | 15 | 41851964 | Higher in Smoker |
| cg25906537 | 15 | 41860668 | Lower in Smoker |
| cg19169023 | 15 | 41953346 | Lower in Smoker |
| cg10778415 | 7 | 66462276 | Higher in Smoker |
| cg09502221 | 1 | 75198599 | Higher in Smoker |
| cg05564340 | 21 | 44518156 | Lower in Smoker |
| cg26744362 | 19 | 56168861 | Lower in Smoker |
| cg15103675 | 1 | 162531519 | Higher in Smoker |
| cg13367381 | 19 | 34919148 | Higher in Smoker |
| cg11695030 | 19 | 34919128 | Higher in Smoker |
| cg16275883 | 3 | 69129409 | Higher in Smoker |
| cg20296673 | 3 | 132372730 | Lower in Smoker |
| cg21828998 | 3 | 132379245 | Higher in Smoker |
| cg02037349 | 3 | 49842702 | Higher in Smoker |
| cg13883063 | 9 | 138836839 | Lower in Smoker |
| cg09855140 | 13 | 100004097 | Lower in Smoker |
| cg10091709 | 13 | 100003011 | Lower in Smoker |
| cg05239163 | 1 | 154191266 | Lower in Smoker |
| cg26808167 | 1 | 154192205 | Lower in Smoker |
| cg26684673 | 11 | 122543428 | Lower in Smoker |
| cg12883617 | 11 | 122648094 | Lower in Smoker |
| cg12984369 | 12 | 125398157 | Lower in Smoker |
| cg06477632 | 6 | 29526338 | Lower in Smoker |
| cg21288364 | 6 | 29524117 | Lower in Smoker |

| | | | |
|---|---|---|---|
| cg20720118 | 6 | 29523976 | Lower in Smoker |
| cg05206294 | X | 118708375 | Higher in Smoker |
| cg09514527 | 5 | 133706677 | Higher in Smoker |
| cg10942898 | 5 | 133708361 | Higher in Smoker |
| cg17317548 | 5 | 133727746 | Lower in Smoker |
| cg19136718 | 20 | 44441187 | Higher in Smoker |
| cg12354270 | 20 | 44441124 | Higher in Smoker |
| cg22103183 | 6 | 83667130 | Lower in Smoker |
| cg01745629 | 6 | 83775548 | Lower in Smoker |
| cg06430387 | 10 | 60094511 | Lower in Smoker |
| cg09134154 | 10 | 60094858 | Lower in Smoker |
| cg08951000 | 4 | 103749375 | Lower in Smoker |
| cg01523860 | 4 | 103747967 | Lower in Smoker |
| cg02733728 | 3 | 23847990 | Higher in Smoker |
| cg09560953 | 3 | 23846810 | Lower in Smoker |
| cg16652937 | 3 | 23243625 | Higher in Smoker |
| cg15288845 | 3 | 23448023 | Lower in Smoker |
| cg12302983 | 3 | 23247317 | Lower in Smoker |
| cg08266852 | 2 | 181923138 | Lower in Smoker |
| cg19367991 | 7 | 129564637 | Higher in Smoker |
| cg02203513 | 16 | 1369140 | Lower in Smoker |
| cg03698668 | 16 | 1370559 | Lower in Smoker |
| cg03420791 | 16 | 1366380 | Lower in Smoker |
| cg24658349 | 1 | 1203450 | Lower in Smoker |
| cg23676538 | 19 | 59070579 | Higher in Smoker |
| cg01298284 | 16 | 34404774 | Lower in Smoker |
| cg08336604 | 12 | 93809819 | Lower in Smoker |
| cg04561571 | 12 | 93834146 | Lower in Smoker |
| ch.17.1996417R | 17 | 74403525 | Higher in Smoker |
| cg21334075 | 15 | 76135284 | Higher in Smoker |
| cg15460387 | 15 | 76135744 | Higher in Smoker |
| cg07895206 | 5 | 6492253 | Lower in Smoker |
| cg10935612 | 5 | 6450051 | Lower in Smoker |
| cg13150977 | 15 | 85114131 | Higher in Smoker |
| cg15739997 | 20 | 48729771 | Higher in Smoker |

| cg05637945 | 17 | 46985753 | Higher in Smoker |
| cg12177023 | 15 | 25683251 | Higher in Smoker |
| cg12060334 | 15 | 25680714 | Lower in Smoker |
| cg04231958 | 12 | 109915151 | Higher in Smoker |
| cg02065274 | 12 | 109951614 | Higher in Smoker |
| cg11990795 | 12 | 109913807 | Lower in Smoker |
| cg10203317 | 7 | 157058282 | Lower in Smoker |
| cg11230343 | 7 | 156932163 | Lower in Smoker |
| cg13699657 | 7 | 156931944 | Lower in Smoker |
| cg20492912 | 11 | 118230053 | Higher in Smoker |
| cg11651430 | 13 | 30426106 | Lower in Smoker |
| cg05803370 | X | 153715241 | Higher in Smoker |
| cg24493115 | 1 | 110655091 | Lower in Smoker |
| cg00964109 | 15 | 74753785 | Higher in Smoker |
| cg16391973 | 5 | 158689566 | Lower in Smoker |
| cg02864181 | 5 | 158689508 | Lower in Smoker |
| cg07117660 | 7 | 138916021 | Higher in Smoker |
| cg13930643 | 9 | 86323646 | Higher in Smoker |
| cg09013091 | X | 56589946 | Higher in Smoker |
| cg22796458 | 1 | 156022836 | Higher in Smoker |
| cg02376269 | 15 | 43398346 | Higher in Smoker |
| cg07607462 | 15 | 43398173 | Higher in Smoker |
| cg06721031 | 15 | 43398435 | Higher in Smoker |
| cg19448829 | 6 | 42531521 | Higher in Smoker |
| cg22164577 | 2 | 170685661 | Lower in Smoker |
| cg25354848 | 2 | 170773793 | Lower in Smoker |
| cg05787043 | 1 | 19537347 | Lower in Smoker |
| cg04571604 | 3 | 103424826 | Higher in Smoker |
| cg09509410 | 3 | 103413592 | Lower in Smoker |
| cg10029789 | 14 | 93690358 | Lower in Smoker |
| cg25247692 | 10 | 99313390 | Lower in Smoker |
| cg14175593 | 10 | 99257444 | Higher in Smoker |
| cg26992634 | 5 | 171709304 | Lower in Smoker |
| cg25118678 | 17 | 42297604 | Higher in Smoker |
| cg00386581 | 11 | 62446121 | Higher in Smoker |

| | | | |
|---|---|---|---|
| cg19696441 | 1 | 20512463 | Higher in Smoker |
| cg00813993 | 1 | 26644493 | Lower in Smoker |
| cg04990556 | 1 | 26633338 | Higher in Smoker |
| cg07780777 | 8 | 59323842 | Higher in Smoker |
| cg01266543 | 2 | 136499099 | Higher in Smoker |
| cg21393986 | 3 | 196159244 | Higher in Smoker |
| cg13629999 | 9 | 134407002 | Higher in Smoker |
| cg19551539 | 20 | 62579792 | Higher in Smoker |
| cg03482411 | 20 | 62572509 | Lower in Smoker |
| cg01337797 | 10 | 5406543 | Lower in Smoker |
| cg26004759 | 4 | 141489018 | Higher in Smoker |
| cg02268229 | 4 | 141490037 | Higher in Smoker |
| cg25599538 | 4 | 141490075 | Higher in Smoker |
| cg22274395 | 4 | 141490067 | Higher in Smoker |
| cg25793521 | 4 | 141489963 | Higher in Smoker |
| cg13219007 | 11 | 73691269 | Higher in Smoker |
| cg00039057 | 22 | 30162510 | Lower in Smoker |
| cg12352006 | 22 | 30163351 | Higher in Smoker |
| cg07571046 | 13 | 38924407 | Higher in Smoker |
| cg00621899 | 7 | 100486423 | Lower in Smoker |
| cg07427577 | 4 | 186344302 | Lower in Smoker |
| cg05026753 | 9 | 114659030 | Higher in Smoker |
| cg05120715 | 9 | 114659593 | Higher in Smoker |
| cg25117976 | 4 | 39529365 | Higher in Smoker |
| cg17713309 | 4 | 39512402 | Lower in Smoker |
| cg08693082 | 2 | 128851969 | Lower in Smoker |
| cg21475834 | 13 | 96706104 | Lower in Smoker |
| cg21846159 | 4 | 69522639 | Lower in Smoker |
| cg23455602 | 4 | 115519578 | Higher in Smoker |
| cg04492932 | 4 | 115571489 | Lower in Smoker |
| cg01991861 | 4 | 115576003 | Lower in Smoker |
| cg25683069 | 1 | 162467499 | Higher in Smoker |
| cg02763540 | 19 | 4914183 | Higher in Smoker |
| cg16034060 | 19 | 4953233 | Lower in Smoker |
| cg13961127 | 6 | 34759622 | Higher in Smoker |

| | | | |
|---|---|---|---|
| cg19355881 | 6 | 34759549 | Lower in Smoker |
| cg02927448 | 12 | 100532162 | Higher in Smoker |
| cg08890976 | 12 | 100538115 | Higher in Smoker |
| cg13428749 | 9 | 6412991 | Higher in Smoker |
| cg14078101 | 9 | 6412886 | Lower in Smoker |
| cg00126498 | 6 | 150286838 | Higher in Smoker |
| cg08413026 | 12 | 132380000 | Higher in Smoker |
| cg06838096 | 12 | 132400449 | Lower in Smoker |
| cg04568592 | 17 | 19771360 | Lower in Smoker |
| cg26917540 | 17 | 19771364 | Lower in Smoker |
| cg21272473 | 15 | 75128881 | Lower in Smoker |
| cg13055199 | 15 | 75136278 | Lower in Smoker |
| cg02648746 | 3 | 42004678 | Lower in Smoker |
| cg13144004 | 3 | 124449104 | Higher in Smoker |
| cg09634370 | 12 | 121154647 | Lower in Smoker |
| cg15404276 | 12 | 121148009 | Higher in Smoker |
| cg19027852 | 19 | 17717301 | Higher in Smoker |
| cg17952467 | 19 | 17758336 | Lower in Smoker |
| cg19095988 | 19 | 17728637 | Lower in Smoker |
| cg00379619 | 19 | 17793480 | Lower in Smoker |
| cg21333665 | 17 | 73840659 | Higher in Smoker |
| cg24374996 | 15 | 91478185 | Higher in Smoker |
| cg05675205 | 5 | 176305017 | Higher in Smoker |
| cg16457351 | 5 | 176297315 | Lower in Smoker |
| cg03320873 | 5 | 176238375 | Lower in Smoker |
| cg23542495 | 4 | 96469343 | Higher in Smoker |
| cg01788994 | 4 | 96469264 | Higher in Smoker |
| cg10528218 | 4 | 96361328 | Lower in Smoker |
| cg20776920 | 8 | 35091548 | Lower in Smoker |
| cg00948124 | 8 | 35452334 | Lower in Smoker |
| cg01311313 | 8 | 35252359 | Lower in Smoker |
| cg01792182 | 7 | 856023 | Higher in Smoker |
| cg03834919 | 7 | 862427 | Lower in Smoker |
| cg23669504 | 7 | 891106 | Lower in Smoker |
| cg14391362 | 7 | 866102 | Lower in Smoker |

| | | | |
|---|---|---|---|
| cg20221381 | 7 | 857981 | Lower in Smoker |
| cg10054262 | 7 | 856283 | Lower in Smoker |
| cg09682183 | 6 | 167705253 | Higher in Smoker |
| cg11263074 | 6 | 167727700 | Higher in Smoker |
| cg20272935 | 11 | 67765720 | Higher in Smoker |
| cg17066594 | 11 | 67764654 | Lower in Smoker |
| cg01711344 | 11 | 67770404 | Lower in Smoker |
| cg17294725 | 7 | 1272559 | Higher in Smoker |
| cg03092191 | 7 | 1272710 | Lower in Smoker |
| cg20184405 | 17 | 73780661 | Higher in Smoker |
| cg13162581 | 17 | 73805962 | Lower in Smoker |
| cg02906377 | 16 | 1448489 | Lower in Smoker |
| cg08063051 | 16 | 1428706 | Lower in Smoker |
| cg17587492 | 1 | 84857501 | Lower in Smoker |
| cg27647661 | 19 | 18942575 | Higher in Smoker |
| cg08395899 | 10 | 12085052 | Higher in Smoker |
| cg13016553 | X | 118987015 | Higher in Smoker |
| cg08104999 | 3 | 118906821 | Lower in Smoker |
| cg12839654 | 7 | 48147956 | Lower in Smoker |
| cg07493097 | 2 | 158957632 | Lower in Smoker |
| cg17889103 | 8 | 97247634 | Higher in Smoker |
| cg03536664 | 3 | 48636487 | Lower in Smoker |
| cg19056700 | 19 | 29702436 | Lower in Smoker |
| cg04898518 | 1 | 16133715 | Lower in Smoker |
| cg27648095 | 21 | 33762341 | Lower in Smoker |
| cg18220284 | 1 | 229762532 | Higher in Smoker |
| cg13088374 | 7 | 43965618 | Higher in Smoker |
| cg15262984 | 7 | 43965648 | Higher in Smoker |
| cg04887663 | 7 | 43966399 | Higher in Smoker |
| cg13860627 | 7 | 43965935 | Higher in Smoker |
| cg03490567 | 7 | 43944817 | Lower in Smoker |
| cg00577527 | 3 | 126237462 | Lower in Smoker |
| cg05620036 | 3 | 126236769 | Lower in Smoker |
| cg10701110 | 1 | 161017007 | Lower in Smoker |
| cg19985030 | 17 | 72917940 | Lower in Smoker |

| | | | |
|---|---|---|---|
| cg14524956 | 1 | 215804508 | Lower in Smoker |
| cg15251242 | 1 | 62900629 | Lower in Smoker |
| cg10950050 | 1 | 62902319 | Lower in Smoker |
| cg12559913 | 18 | 158463 | Higher in Smoker |
| cg01846352 | 18 | 159265 | Higher in Smoker |
| cg21280914 | 18 | 213653 | Lower in Smoker |
| cg12823746 | 12 | 62654080 | Higher in Smoker |
| cg10685559 | 22 | 18633123 | Higher in Smoker |
| cg24111059 | 3 | 49158491 | Higher in Smoker |
| cg13272256 | 11 | 119252474 | Higher in Smoker |
| cg14359435 | 11 | 119227592 | Higher in Smoker |
| cg27092752 | 11 | 119227298 | Higher in Smoker |
| cg13442428 | 11 | 119234736 | Lower in Smoker |
| cg14262490 | 9 | 132630396 | Lower in Smoker |
| cg13808594 | 9 | 132637059 | Lower in Smoker |
| cg04299990 | 17 | 20943806 | Higher in Smoker |
| cg19174165 | 11 | 113719236 | Lower in Smoker |
| cg18094999 | 11 | 113746795 | Lower in Smoker |
| cg22770592 | 15 | 63797403 | Higher in Smoker |
| cg07512971 | 15 | 63798022 | Higher in Smoker |
| ch.17.1542746R | 17 | 58268439 | Higher in Smoker |
| cg19611786 | 2 | 61698739 | Lower in Smoker |
| cg25473794 | 11 | 77921181 | Lower in Smoker |
| cg27340269 | 11 | 77921422 | Lower in Smoker |
| cg08989921 | 17 | 76836740 | Lower in Smoker |
| cg04947024 | 4 | 144105592 | Higher in Smoker |
| cg18886444 | 3 | 49378032 | Higher in Smoker |
| cg16719865 | 2 | 234394478 | Lower in Smoker |
| cg05638347 | 7 | 6188723 | Lower in Smoker |
| cg04086327 | 7 | 6200886 | Lower in Smoker |
| cg17924520 | 7 | 6188871 | Lower in Smoker |
| cg22777670 | 17 | 9548120 | Higher in Smoker |
| cg14686309 | 17 | 9548019 | Higher in Smoker |
| cg13879483 | 12 | 95942907 | Higher in Smoker |
| cg07783282 | 12 | 95942964 | Higher in Smoker |

| | | | |
|---|---|---|---|
| cg23065561 | 4 | 53522876 | Lower in Smoker |
| cg09683730 | 1 | 22013127 | Lower in Smoker |
| cg01289140 | 6 | 41862737 | Lower in Smoker |
| cg26573335 | 6 | 41863096 | Higher in Smoker |
| cg02712401 | 12 | 6961946 | Higher in Smoker |
| cg11808677 | 12 | 6960079 | Lower in Smoker |
| cg27181013 | 12 | 6960042 | Lower in Smoker |
| cg12064531 | X | 55515952 | Lower in Smoker |
| cg19175314 | 4 | 120162316 | Lower in Smoker |
| cg08971769 | 10 | 75258327 | Lower in Smoker |
| cg13701327 | 17 | 5030311 | Lower in Smoker |
| cg13610622 | 10 | 11504551 | Lower in Smoker |
| cg16766900 | 10 | 11574616 | Lower in Smoker |
| cg14026602 | 16 | 9056723 | Higher in Smoker |
| cg08313128 | 16 | 8987215 | Lower in Smoker |
| cg01601926 | 16 | 8986308 | Lower in Smoker |
| cg06806679 | X | 40943654 | Higher in Smoker |
| cg26039926 | X | 40945750 | Higher in Smoker |
| cg05967389 | X | 40948142 | Lower in Smoker |
| cg15545871 | 13 | 31191737 | Higher in Smoker |
| cg08646372 | 13 | 31191727 | Higher in Smoker |
| cg16374953 | 13 | 31191680 | Higher in Smoker |
| cg25089231 | 6 | 149067742 | Higher in Smoker |
| cg10832589 | 6 | 149287662 | Lower in Smoker |
| cg23982392 | 6 | 149140574 | Lower in Smoker |
| cg14332552 | 6 | 149245768 | Lower in Smoker |
| cg23828170 | 6 | 149099724 | Lower in Smoker |
| cg02201836 | X | 129039832 | Higher in Smoker |
| cg14084888 | 8 | 117777782 | Lower in Smoker |
| cg23415712 | 8 | 117778786 | Higher in Smoker |
| cg13382000 | 4 | 71553885 | Higher in Smoker |
| cg15131629 | 6 | 144935578 | Lower in Smoker |
| cg16689609 | 6 | 144682208 | Lower in Smoker |
| cg19184160 | 6 | 144611885 | Lower in Smoker |
| cg00591949 | 3 | 191048439 | Lower in Smoker |

| | | | |
|---|---|---|---|
| cg16374830 | 11 | 75525835 | Higher in Smoker |
| cg04768488 | 16 | 70808233 | Higher in Smoker |
| cg07221103 | 16 | 70796464 | Lower in Smoker |
| cg09654861 | 16 | 70802516 | Lower in Smoker |
| cg05794310 | 16 | 70783744 | Lower in Smoker |
| cg08274538 | 17 | 8066483 | Higher in Smoker |
| cg01421695 | 1 | 116183362 | Lower in Smoker |
| cg25388404 | 1 | 160370113 | Higher in Smoker |
| cg17755581 | 20 | 56964015 | Higher in Smoker |
| cg02581909 | 20 | 56964033 | Higher in Smoker |
| cg25841114 | 6 | 31762901 | Higher in Smoker |
| cg05797367 | 6 | 31759806 | Lower in Smoker |
| cg00051590 | 6 | 31759486 | Lower in Smoker |
| cg14003039 | 6 | 31759513 | Lower in Smoker |
| cg25843346 | 6 | 31762555 | Lower in Smoker |
| cg02932780 | 6 | 31762353 | Lower in Smoker |
| cg17365386 | 6 | 31763551 | Higher in Smoker |
| cg26784891 | 6 | 30884124 | Lower in Smoker |
| cg12457901 | 6 | 30882671 | Lower in Smoker |
| cg16008609 | 1 | 213123675 | Higher in Smoker |
| cg22440431 | 1 | 213122829 | Lower in Smoker |
| cg11666017 | 19 | 46013919 | Lower in Smoker |
| cg07857243 | 16 | 77822441 | Higher in Smoker |
| cg14405625 | 9 | 136855902 | Lower in Smoker |
| cg05667348 | 10 | 118892581 | Higher in Smoker |
| cg03048654 | 10 | 118893138 | Higher in Smoker |
| cg26263263 | 10 | 118893430 | Higher in Smoker |
| cg18709545 | 10 | 118892892 | Higher in Smoker |
| cg02187231 | 2 | 71132993 | Higher in Smoker |
| cg18150120 | 2 | 71134936 | Higher in Smoker |
| cg00731411 | 2 | 71127576 | Higher in Smoker |
| cg07478641 | 5 | 82768488 | Higher in Smoker |
| cg05176349 | 5 | 82767617 | Higher in Smoker |
| cg27119412 | 10 | 75830501 | Lower in Smoker |
| cg09565657 | 8 | 67579891 | Higher in Smoker |

| | | | |
|---|---|---|---|
| cg09018040 | X | 7810253 | Lower in Smoker |
| cg10037049 | 12 | 48276633 | Higher in Smoker |
| cg18022921 | 6 | 43736973 | Lower in Smoker |
| cg18872604 | 11 | 64002754 | Lower in Smoker |
| cg05982597 | 4 | 177654753 | Lower in Smoker |
| cg12500811 | 4 | 177648950 | Lower in Smoker |
| cg20472189 | 10 | 135051475 | Higher in Smoker |
| cg07370771 | 10 | 135050957 | Lower in Smoker |
| cg23502565 | 3 | 157156180 | Higher in Smoker |
| cg24825693 | 3 | 157122686 | Lower in Smoker |
| cg27376437 | 17 | 56064565 | Higher in Smoker |
| cg15339142 | 12 | 95651472 | Lower in Smoker |
| cg06391577 | 3 | 87039536 | Higher in Smoker |
| cg20109541 | 3 | 87040082 | Higher in Smoker |
| cg10669424 | 3 | 11763340 | Lower in Smoker |
| cg16131859 | 3 | 11684712 | Higher in Smoker |
| cg21396517 | 3 | 11655466 | Lower in Smoker |
| cg24340565 | 3 | 11686607 | Lower in Smoker |
| cg19778015 | 3 | 11625154 | Lower in Smoker |
| cg08815359 | 3 | 11606853 | Lower in Smoker |
| cg04814784 | 3 | 10182561 | Higher in Smoker |
| cg09836251 | 3 | 10187579 | Higher in Smoker |
| cg03619761 | 3 | 10182854 | Higher in Smoker |
| cg27313572 | 10 | 17271294 | Higher in Smoker |
| cg08479516 | 7 | 158905536 | Higher in Smoker |
| cg22240520 | 7 | 158855297 | Lower in Smoker |
| cg22055397 | 7 | 158923808 | Lower in Smoker |
| cg00852964 | 6 | 133035150 | Higher in Smoker |
| cg22498396 | 6 | 133036545 | Lower in Smoker |
| cg08337633 | 7 | 55602109 | Higher in Smoker |
| cg07459478 | 7 | 55589803 | Lower in Smoker |
| ch.3.1112380F | 3 | 51439951 | Higher in Smoker |
| cg02693238 | 8 | 100879336 | Lower in Smoker |
| cg10090866 | 1 | 12419262 | Lower in Smoker |
| cg04920869 | 1 | 12336515 | Lower in Smoker |

| | | | |
|---|---|---|---|
| cg03208707 | 1 | 12289388 | Lower in Smoker |
| cg22676023 | 1 | 12289220 | Lower in Smoker |
| cg00384847 | 1 | 12291339 | Lower in Smoker |
| cg18562023 | 8 | 145654087 | Higher in Smoker |
| cg00631230 | 12 | 122750916 | Higher in Smoker |
| cg14645546 | 13 | 53024934 | Higher in Smoker |
| cg12013777 | 13 | 53025762 | Lower in Smoker |
| cg26249100 | 12 | 123350969 | Lower in Smoker |
| cg10319073 | 12 | 123351548 | Lower in Smoker |
| cg02143067 | 7 | 73081771 | Higher in Smoker |
| cg21591848 | 15 | 42500463 | Higher in Smoker |
| cg05312688 | 7 | 38777574 | Lower in Smoker |
| cg07600548 | 7 | 38903039 | Lower in Smoker |
| cg04313758 | 1 | 150067911 | Lower in Smoker |
| cg15105901 | 16 | 69354863 | Lower in Smoker |
| cg23006805 | 6 | 33236857 | Lower in Smoker |
| cg17094160 | 6 | 33233157 | Lower in Smoker |
| cg15735018 | 6 | 33225455 | Lower in Smoker |
| cg21776572 | 6 | 33239236 | Higher in Smoker |
| cg01985412 | 17 | 618143 | Higher in Smoker |
| cg08856378 | 17 | 560590 | Lower in Smoker |
| cg27457290 | 2 | 64246845 | Higher in Smoker |
| cg08970020 | 2 | 64216731 | Lower in Smoker |
| cg14471727 | 14 | 97263643 | Higher in Smoker |
| cg22922810 | 14 | 97282535 | Lower in Smoker |
| cg01975338 | 14 | 97326473 | Lower in Smoker |
| cg10777679 | 14 | 97263710 | Higher in Smoker |
| cg14399369 | 2 | 58273683 | Higher in Smoker |
| cg13537276 | 19 | 50528986 | Higher in Smoker |
| cg08133930 | 12 | 118541851 | Higher in Smoker |
| cg13671890 | 12 | 118540222 | Lower in Smoker |
| cg24632139 | 1 | 159832353 | Lower in Smoker |
| cg11509669 | 2 | 17720758 | Higher in Smoker |
| cg23483069 | 2 | 17825778 | Lower in Smoker |
| cg21629006 | 7 | 54609680 | Higher in Smoker |

| | | | |
|---|---|---|---|
| cg03775422 | 7 | 54610192 | Higher in Smoker |
| cg12163925 | 20 | 36530296 | Higher in Smoker |
| cg22388634 | 20 | 25058429 | Higher in Smoker |
| cg13575339 | 14 | 74708313 | Higher in Smoker |
| cg02034669 | 14 | 74707360 | Higher in Smoker |
| cg15416329 | 14 | 74706016 | Lower in Smoker |
| cg12827555 | 14 | 74706031 | Lower in Smoker |
| cg09958560 | 10 | 114571695 | Lower in Smoker |
| cg24058852 | 10 | 114479162 | Lower in Smoker |
| cg07030336 | 10 | 114206784 | Higher in Smoker |
| cg00761861 | 14 | 68141669 | Higher in Smoker |
| cg18296956 | 5 | 140090936 | Higher in Smoker |
| cg16179182 | 5 | 140090404 | Higher in Smoker |
| cg02529723 | 5 | 140105629 | Lower in Smoker |
| cg21837069 | 1 | 1369466 | Higher in Smoker |
| cg17491622 | 1 | 1369616 | Higher in Smoker |
| cg03538326 | 1 | 1375845 | Lower in Smoker |
| cg22923514 | 10 | 115999708 | Higher in Smoker |
| cg02843201 | 16 | 22103596 | Lower in Smoker |
| cg20307292 | 2 | 98858595 | Lower in Smoker |
| cg11465363 | 2 | 98859136 | Lower in Smoker |
| cg06377106 | 1 | 20618331 | Higher in Smoker |
| cg09065654 | 3 | 183948302 | Higher in Smoker |
| cg12105765 | 3 | 183947332 | Higher in Smoker |
| cg04490945 | 3 | 183959465 | Higher in Smoker |
| cg03069122 | 7 | 49815751 | Lower in Smoker |
| cg03568957 | 12 | 6155761 | Lower in Smoker |
| cg02933984 | 6 | 110500337 | Higher in Smoker |
| cg20718170 | 7 | 123322268 | Lower in Smoker |
| cg14341030 | 12 | 14956580 | Higher in Smoker |
| cg10935138 | 17 | 73851978 | Higher in Smoker |
| cg24291845 | 17 | 73851885 | Higher in Smoker |
| cg11769382 | 17 | 73851439 | Higher in Smoker |
| cg24914313 | 13 | 41636195 | Higher in Smoker |
| cg13686622 | 13 | 41634589 | Higher in Smoker |

| | | | |
|---|---|---|---|
| cg16742763 | 7 | 74489750 | Higher in Smoker |
| cg11399535 | 7 | 70598282 | Higher in Smoker |
| cg09117643 | 7 | 73275265 | Lower in Smoker |
| cg19619807 | 13 | 52212570 | Lower in Smoker |
| cg14199148 | 13 | 52158669 | Higher in Smoker |
| cg23528488 | 4 | 85818121 | Lower in Smoker |
| cg09526135 | 4 | 85603757 | Lower in Smoker |
| cg05926837 | 10 | 50146991 | Lower in Smoker |
| cg06018666 | 4 | 10079364 | Lower in Smoker |
| cg12805593 | 2 | 203776981 | Higher in Smoker |
| cg23960468 | 17 | 9479939 | Higher in Smoker |
| cg03909602 | 4 | 176987577 | Higher in Smoker |
| cg25276412 | 4 | 176987453 | Higher in Smoker |
| cg16974909 | 4 | 176986856 | Higher in Smoker |
| cg03629777 | 4 | 39183982 | Higher in Smoker |
| cg13150061 | 14 | 102685953 | Lower in Smoker |
| cg25026981 | 14 | 100842523 | Lower in Smoker |
| cg04099562 | 1 | 224620034 | Higher in Smoker |
| cg19867517 | 1 | 224622813 | Higher in Smoker |
| cg13463984 | 1 | 224580455 | Lower in Smoker |
| cg00885506 | 9 | 116102792 | Higher in Smoker |
| cg00820664 | 2 | 128568918 | Higher in Smoker |
| cg19360930 | 2 | 20111778 | Lower in Smoker |
| cg14118424 | 5 | 110445104 | Lower in Smoker |
| cg23573822 | 10 | 1151180 | Lower in Smoker |
| cg27201679 | 10 | 1120794 | Lower in Smoker |
| cg09508432 | 21 | 44269937 | Lower in Smoker |
| cg18410494 | 5 | 76728190 | Lower in Smoker |
| cg01027498 | 5 | 76788287 | Higher in Smoker |
| cg03749630 | X | 117484304 | Higher in Smoker |
| cg12669314 | 6 | 33253607 | Higher in Smoker |
| cg16428857 | 6 | 33248616 | Lower in Smoker |
| cg27567953 | 1 | 109553055 | Lower in Smoker |
| cg00779858 | 3 | 167370529 | Lower in Smoker |
| cg03243700 | 9 | 137000940 | Higher in Smoker |

| | | | |
|---|---|---|---|
| cg27345282 | 3 | 196295526 | Higher in Smoker |
| cg20584918 | 3 | 196295759 | Higher in Smoker |
| cg02762393 | 16 | 75019140 | Higher in Smoker |
| cg02990814 | 16 | 75018816 | Higher in Smoker |
| cg13153740 | 7 | 158735104 | Lower in Smoker |
| cg11914216 | 7 | 158712291 | Lower in Smoker |
| cg26321613 | 7 | 158703554 | Lower in Smoker |
| cg01445689 | 7 | 158703106 | Lower in Smoker |
| cg05129591 | 1 | 43637803 | Higher in Smoker |
| cg03560652 | 12 | 122440709 | Lower in Smoker |
| cg06857900 | 12 | 122428377 | Lower in Smoker |
| cg15539901 | 8 | 124084814 | Higher in Smoker |
| cg26373411 | 8 | 124085620 | Higher in Smoker |
| cg21577049 | 2 | 228736449 | Higher in Smoker |
| cg23922867 | 18 | 54318612 | Higher in Smoker |
| cg13131111 | 15 | 54052305 | Lower in Smoker |
| cg24891986 | 2 | 190306355 | Higher in Smoker |
| cg00261688 | 2 | 190305566 | Higher in Smoker |
| cg22136124 | 15 | 44119091 | Higher in Smoker |
| cg26847753 | 15 | 44119241 | Higher in Smoker |
| cg21995800 | 1 | 111984376 | Lower in Smoker |
| cg09478268 | 1 | 111991669 | Lower in Smoker |
| cg06262497 | 1 | 3564676 | Lower in Smoker |
| cg09232289 | 1 | 3562654 | Lower in Smoker |
| cg06177107 | 1 | 3551901 | Lower in Smoker |
| cg19270286 | 1 | 3562445 | Lower in Smoker |
| cg02139951 | 17 | 1637339 | Lower in Smoker |
| cg13539115 | 3 | 52312860 | Lower in Smoker |
| cg21532325 | 7 | 151107400 | Higher in Smoker |
| cg26438167 | 7 | 151087979 | Lower in Smoker |
| cg04948503 | 14 | 64105073 | Lower in Smoker |
| cg06275028 | 16 | 707601 | Lower in Smoker |
| cg16968115 | 1 | 27560829 | Higher in Smoker |
| cg12646585 | 8 | 124429417 | Higher in Smoker |
| cg14018100 | 8 | 124428910 | Higher in Smoker |

| | | | |
|---|---|---|---|
| cg25222252 | 11 | 9595204 | Higher in Smoker |
| cg06664668 | 16 | 84328391 | Higher in Smoker |
| cg00751501 | 16 | 84342709 | Higher in Smoker |
| cg14780681 | 20 | 44420720 | Higher in Smoker |
| cg09659400 | 20 | 43744673 | Lower in Smoker |
| cg19427399 | 20 | 44209027 | Lower in Smoker |
| cg05113958 | 17 | 48918321 | Lower in Smoker |
| cg15558558 | 15 | 83477965 | Lower in Smoker |
| cg00225006 | 15 | 83477872 | Lower in Smoker |
| cg17463698 | 15 | 83477712 | Lower in Smoker |
| cg21386933 | 15 | 83477608 | Lower in Smoker |
| cg16542426 | 15 | 23205622 | Lower in Smoker |
| cg00249632 | 4 | 1872469 | Lower in Smoker |
| cg05284727 | 4 | 1874366 | Lower in Smoker |
| cg12901650 | 4 | 1980812 | Lower in Smoker |
| cg05080877 | 4 | 1957404 | Lower in Smoker |
| cg13883590 | 4 | 1952852 | Lower in Smoker |
| cg13112524 | 4 | 1983102 | Lower in Smoker |
| cg19445664 | 4 | 1894383 | Lower in Smoker |
| cg04477010 | 8 | 38175544 | Lower in Smoker |
| cg11360768 | 8 | 38239777 | Higher in Smoker |
| cg25548615 | 4 | 2011379 | Higher in Smoker |
| cg17169797 | 12 | 56321844 | Higher in Smoker |
| cg14032596 | 12 | 56321889 | Higher in Smoker |
| cg13937449 | 12 | 56320970 | Higher in Smoker |
| cg27635395 | 12 | 56295588 | Lower in Smoker |
| cg13821008 | 2 | 175499113 | Higher in Smoker |
| cg24891414 | 2 | 175436409 | Lower in Smoker |
| cg27305009 | 2 | 175471320 | Lower in Smoker |
| cg20687098 | 2 | 175480993 | Lower in Smoker |
| cg03931078 | 17 | 66453919 | Higher in Smoker |
| cg23783747 | 7 | 5229743 | Lower in Smoker |
| cg27152128 | 7 | 5269245 | Higher in Smoker |
| cg04193901 | 20 | 43343736 | Higher in Smoker |
| cg07709205 | 6 | 112375302 | Lower in Smoker |

| | | | |
|---|---|---|---|
| cg23845172 | 19 | 15550995 | Higher in Smoker |
| cg06553422 | 19 | 15560234 | Higher in Smoker |
| cg08269119 | 19 | 15560224 | Lower in Smoker |
| ch.12.28033R | 12 | 1013557 | Higher in Smoker |
| cg14220146 | 9 | 96068079 | Lower in Smoker |
| cg04154903 | 12 | 49374320 | Lower in Smoker |
| cg05164634 | 12 | 49366538 | Higher in Smoker |
| cg12345778 | 12 | 49364094 | Lower in Smoker |
| cg04106190 | 7 | 120964168 | Lower in Smoker |
| cg03721528 | 7 | 120967900 | Lower in Smoker |
| cg26690075 | 7 | 120968919 | Lower in Smoker |
| cg26575738 | 17 | 44896168 | Higher in Smoker |
| cg26332740 | 1 | 228196227 | Higher in Smoker |
| cg23633010 | 1 | 228225886 | Lower in Smoker |
| cg10606730 | 1 | 22456024 | Lower in Smoker |
| cg00828602 | 3 | 55520834 | Higher in Smoker |
| cg09774932 | 12 | 1725788 | Higher in Smoker |
| cg22587479 | 2 | 219738226 | Higher in Smoker |
| cg06862374 | 2 | 219736549 | Higher in Smoker |
| cg01166979 | 3 | 13921889 | Higher in Smoker |
| cg05475172 | 22 | 46371152 | Higher in Smoker |
| cg18386163 | 10 | 102242208 | Higher in Smoker |
| cg03456968 | 17 | 44929245 | Higher in Smoker |
| cg02855142 | 17 | 7591947 | Higher in Smoker |
| cg26315964 | 21 | 40752664 | Higher in Smoker |
| cg10477854 | 21 | 40760975 | Higher in Smoker |
| cg19910930 | 8 | 31031085 | Lower in Smoker |
| cg07010946 | 8 | 30891352 | Higher in Smoker |
| cg02754722 | 6 | 2766192 | Higher in Smoker |
| cg14116624 | 17 | 25621079 | Higher in Smoker |
| cg27112897 | 17 | 5974078 | Higher in Smoker |
| cg25573609 | 17 | 5974066 | Higher in Smoker |
| cg18893440 | 17 | 5974064 | Higher in Smoker |
| cg26132493 | 12 | 108634275 | Lower in Smoker |
| cg03391002 | 12 | 108566377 | Lower in Smoker |

| | | | |
|---|---|---|---|
| cg13066658 | 11 | 32449163 | Higher in Smoker |
| cg10698098 | 6 | 160148397 | Higher in Smoker |
| cg17395354 | 6 | 160148041 | Higher in Smoker |
| cg16802646 | 5 | 167718483 | Higher in Smoker |
| cg14412794 | 4 | 184094163 | Lower in Smoker |
| cg12229364 | 4 | 184075604 | Lower in Smoker |
| cg10716612 | 4 | 184113429 | Lower in Smoker |
| cg17964432 | 4 | 184020264 | Higher in Smoker |
| cg00909388 | X | 10085400 | Lower in Smoker |
| cg00253171 | 16 | 78291326 | Lower in Smoker |
| cg00854324 | 16 | 69941269 | Lower in Smoker |
| cg26832686 | 16 | 69958189 | Lower in Smoker |
| cg09419444 | 16 | 69958792 | Lower in Smoker |
| cg10723575 | 3 | 149422266 | Lower in Smoker |
| cg04925129 | 3 | 149247133 | Lower in Smoker |
| cg11566561 | 3 | 149259934 | Lower in Smoker |
| cg19483007 | 3 | 149327651 | Lower in Smoker |
| cg19005373 | 19 | 7690735 | Lower in Smoker |
| cg26502352 | 17 | 6659199 | Higher in Smoker |
| cg06085204 | 17 | 6659164 | Higher in Smoker |
| cg05513208 | 17 | 6659189 | Higher in Smoker |
| cg27386297 | X | 52897160 | Higher in Smoker |
| cg19195935 | 1 | 168544539 | Lower in Smoker |
| cg20948997 | 8 | 56014433 | Higher in Smoker |
| cg07241908 | 8 | 56284622 | Lower in Smoker |
| cg26923072 | 8 | 6671783 | Lower in Smoker |
| cg27487839 | 8 | 11058395 | Higher in Smoker |
| cg11434468 | 8 | 11059277 | Higher in Smoker |
| cg25396727 | 8 | 10756220 | Lower in Smoker |
| cg10519271 | 1 | 28286837 | Lower in Smoker |
| cg17288102 | 10 | 111683471 | Lower in Smoker |
| cg25131897 | X | 128893354 | Lower in Smoker |
| cg12638490 | 22 | 41252806 | Higher in Smoker |
| cg11607927 | 2 | 61765934 | Higher in Smoker |
| cg21827481 | 13 | 21440627 | Lower in Smoker |

| | | | |
|---|---|---|---|
| cg00468395 | 16 | 28193063 | Lower in Smoker |
| cg08260549 | 8 | 21777063 | Higher in Smoker |
| cg04249525 | 7 | 152373324 | Higher in Smoker |
| cg23861457 | 14 | 104173299 | Lower in Smoker |
| cg18597188 | 14 | 104178670 | Lower in Smoker |
| cg06826808 | 5 | 82373154 | Higher in Smoker |
| cg05424782 | 22 | 42017079 | Higher in Smoker |
| cg25508228 | 3 | 142166203 | Higher in Smoker |
| cg17764008 | 20 | 21283787 | Lower in Smoker |
| cg12340144 | 3 | 38388808 | Lower in Smoker |
| cg21608192 | 16 | 17563827 | Higher in Smoker |
| cg04165004 | 16 | 17299953 | Lower in Smoker |
| cg24804060 | 17 | 48425014 | Lower in Smoker |
| cg19980929 | 12 | 42632907 | Lower in Smoker |
| cg09612099 | 11 | 102096840 | Lower in Smoker |
| cg13722517 | 12 | 32908961 | Higher in Smoker |
| cg00650876 | 1 | 43148058 | Higher in Smoker |
| cg15557459 | 1 | 43152179 | Lower in Smoker |
| cg04190813 | 17 | 7199099 | Higher in Smoker |
| cg20976174 | 3 | 183415827 | Lower in Smoker |
| cg17193163 | 11 | 66056724 | Lower in Smoker |
| cg27106713 | 19 | 11033958 | Lower in Smoker |
| cg27194467 | 19 | 11039319 | Lower in Smoker |
| cg00243922 | 2 | 32502781 | Higher in Smoker |
| cg25812473 | 2 | 32503470 | Higher in Smoker |
| cg17317859 | 14 | 75231455 | Lower in Smoker |
| cg03667269 | 22 | 22090129 | Higher in Smoker |
| cg05898928 | 22 | 22090066 | Higher in Smoker |
| cg20821170 | 11 | 57418566 | Lower in Smoker |
| cg03773647 | 11 | 57417949 | Lower in Smoker |
| cg10285711 | 2 | 135762012 | Higher in Smoker |
| cg05693561 | 4 | 69215265 | Higher in Smoker |
| cg04094193 | 4 | 69216103 | Lower in Smoker |
| cg25604984 | 5 | 112849231 | Higher in Smoker |
| cg27657131 | 20 | 61847587 | Lower in Smoker |

| | | | |
|---|---|---|---|
| cg12451155 | 1 | 29065427 | Lower in Smoker |
| cg03922048 | 8 | 64085098 | Lower in Smoker |
| cg03385696 | 7 | 75988425 | Higher in Smoker |
| cg06186973 | 7 | 75988652 | Higher in Smoker |
| cg06464744 | 22 | 32340387 | Higher in Smoker |
| cg18861713 | 2 | 9766266 | Lower in Smoker |
| cg12965833 | 14 | 100744154 | Lower in Smoker |
| cg11870426 | 14 | 100709302 | Lower in Smoker |
| cg14161438 | 18 | 72920197 | Higher in Smoker |
| cg25292638 | 18 | 72917450 | Lower in Smoker |
| cg02750262 | 18 | 72916776 | Lower in Smoker |
| cg09288658 | 2 | 173940639 | Higher in Smoker |
| cg04567307 | 4 | 48492122 | Higher in Smoker |
| cg05815042 | 13 | 32886742 | Lower in Smoker |
| cg26941801 | 13 | 32882845 | Lower in Smoker |
| cg12845952 | 3 | 167098119 | Higher in Smoker |
| cg24935220 | 3 | 167095048 | Lower in Smoker |
| cg03163459 | 5 | 76373719 | Lower in Smoker |
| cg21793164 | 5 | 76376404 | Lower in Smoker |
| cg21139941 | 14 | 64992737 | Lower in Smoker |
| cg16600432 | 14 | 64970085 | Lower in Smoker |
| cg20200516 | 8 | 81400156 | Higher in Smoker |
| cg16560453 | 3 | 101395512 | Higher in Smoker |
| cg17761247 | 3 | 101395209 | Higher in Smoker |
| cg22306579 | 6 | 31869057 | Higher in Smoker |
| cg17766150 | 6 | 31868169 | Higher in Smoker |
| cg06169557 | 6 | 31868207 | Lower in Smoker |
| cg25861453 | 6 | 31867906 | Lower in Smoker |
| cg03541334 | 6 | 31870476 | Lower in Smoker |
| cg24051943 | 6 | 31870891 | Lower in Smoker |
| cg08844390 | 1 | 16298537 | Higher in Smoker |
| cg00338122 | 6 | 151711850 | Higher in Smoker |
| cg26152597 | 3 | 114865874 | Lower in Smoker |
| cg13484596 | 3 | 114575658 | Lower in Smoker |
| cg20387392 | 3 | 114378420 | Lower in Smoker |

| | | | |
|---|---|---|---|
| cg08996334 | 3 | 114270647 | Lower in Smoker |
| cg14258935 | 6 | 33283286 | Lower in Smoker |
| cg01199618 | 6 | 33283293 | Lower in Smoker |
| cg24221373 | 6 | 33283314 | Lower in Smoker |
| cg27368379 | 6 | 33283328 | Lower in Smoker |
| cg13387924 | 6 | 33284384 | Lower in Smoker |
| cg09005548 | 6 | 33283990 | Lower in Smoker |
| cg24511325 | 6 | 33285642 | Lower in Smoker |
| cg17896097 | 9 | 125693949 | Higher in Smoker |
| cg25278669 | 11 | 62521909 | Lower in Smoker |
| cg21062760 | 19 | 36205574 | Lower in Smoker |
| cg11142333 | 1 | 173840261 | Lower in Smoker |
| cg19825988 | 3 | 141146295 | Lower in Smoker |
| cg12690119 | 3 | 141043080 | Higher in Smoker |
| cg03403113 | 17 | 7338450 | Higher in Smoker |
| cg14314796 | 17 | 7370509 | Lower in Smoker |
| cg26681523 | 1 | 22854408 | Lower in Smoker |
| cg20118293 | 9 | 129595473 | Lower in Smoker |
| cg09078622 | 11 | 130115733 | Lower in Smoker |
| cg14212467 | 19 | 59030979 | Higher in Smoker |
| cg21517584 | 19 | 59026417 | Higher in Smoker |
| cg13301327 | 20 | 62387416 | Lower in Smoker |
| cg05791054 | 3 | 42696821 | Lower in Smoker |
| cg09022921 | 1 | 6649009 | Lower in Smoker |
| cg13625113 | 9 | 125675579 | Higher in Smoker |
| cg05574870 | 19 | 4054124 | Higher in Smoker |
| cg23237634 | 1 | 154976031 | Higher in Smoker |
| cg04432617 | 1 | 154976216 | Higher in Smoker |
| cg19233405 | 1 | 154988721 | Lower in Smoker |
| cg04752591 | 6 | 33422729 | Higher in Smoker |
| cg06865749 | 1 | 203764655 | Higher in Smoker |
| cg07348300 | 1 | 37949342 | Lower in Smoker |
| cg04064550 | 11 | 110036097 | Higher in Smoker |
| cg07828024 | 6 | 149772892 | Lower in Smoker |
| cg00632861 | 13 | 46626485 | Higher in Smoker |

| | | | |
|---|---|---|---|
| cg04570827 | 13 | 46627156 | Higher in Smoker |
| cg09598590 | 13 | 46563704 | Lower in Smoker |
| cg07967498 | 14 | 89059881 | Lower in Smoker |
| cg18902057 | 16 | 88636444 | Higher in Smoker |
| cg10039163 | 8 | 144593087 | Lower in Smoker |
| cg20490341 | 8 | 144549532 | Lower in Smoker |
| cg16490739 | 8 | 144569153 | Lower in Smoker |
| cg16292343 | 8 | 144545981 | Lower in Smoker |
| cg11210357 | 8 | 144543951 | Lower in Smoker |
| cg24010658 | 8 | 144544041 | Lower in Smoker |
| cg23931836 | 19 | 47615988 | Higher in Smoker |
| cg08647419 | 19 | 47614495 | Lower in Smoker |
| cg06338552 | 22 | 41742113 | Lower in Smoker |
| cg14341575 | 7 | 138794549 | Higher in Smoker |
| cg06850924 | 7 | 129691279 | Higher in Smoker |
| cg18233311 | 5 | 132362578 | Higher in Smoker |
| cg15037445 | 5 | 132360199 | Lower in Smoker |
| cg14422245 | 1 | 53017966 | Higher in Smoker |
| cg07205670 | 16 | 87442901 | Higher in Smoker |
| cg16590154 | 16 | 87443540 | Lower in Smoker |
| cg02854164 | 16 | 87474977 | Lower in Smoker |
| cg09981464 | 16 | 87441659 | Lower in Smoker |
| cg17748167 | 1 | 31769917 | Lower in Smoker |
| cg13506219 | 18 | 60193840 | Lower in Smoker |
| cg13834460 | 10 | 81142200 | Lower in Smoker |
| cg10789749 | 20 | 276888 | Lower in Smoker |
| cg23889780 | 7 | 100021830 | Lower in Smoker |
| cg08204402 | 5 | 851892 | Lower in Smoker |
| cg26223987 | 6 | 157802912 | Higher in Smoker |
| cg05373692 | X | 74743375 | Higher in Smoker |
| cg18296227 | 10 | 99205774 | Higher in Smoker |
| cg09192801 | 12 | 77156412 | Lower in Smoker |
| cg16562763 | 3 | 195939612 | Lower in Smoker |
| cg03356157 | 8 | 17013756 | Higher in Smoker |
| cg20576160 | 8 | 17016860 | Lower in Smoker |

| | | | |
|---|---|---|---|
| cg10501074 | 7 | 6616919 | Higher in Smoker |
| cg21212956 | 7 | 6617294 | Higher in Smoker |
| cg01876612 | 16 | 85045424 | Higher in Smoker |
| cg05529754 | 16 | 85045486 | Higher in Smoker |
| cg20289741 | X | 128977498 | Higher in Smoker |
| cg04623172 | 10 | 31607306 | Higher in Smoker |
| cg26365110 | 10 | 31709144 | Lower in Smoker |
| cg19465286 | 10 | 31609896 | Lower in Smoker |
| cg14827198 | 2 | 145147129 | Lower in Smoker |
| cg11432960 | 2 | 145143754 | Lower in Smoker |
| cg15345847 | 2 | 145146928 | Lower in Smoker |
| cg08187814 | 2 | 145202065 | Lower in Smoker |
| cg25296103 | 2 | 145268533 | Lower in Smoker |
| cg16321523 | 8 | 82633764 | Higher in Smoker |
| cg02322376 | 2 | 220071368 | Higher in Smoker |
| cg06185204 | 15 | 80351985 | Higher in Smoker |
| cg07965839 | 15 | 80351679 | Higher in Smoker |
| cg16795352 | 15 | 80368845 | Lower in Smoker |
| cg00267196 | 8 | 135710113 | Lower in Smoker |
| cg20007892 | 8 | 135614834 | Lower in Smoker |
| cg21672855 | 8 | 135614777 | Lower in Smoker |
| cg27495623 | 12 | 72058485 | Higher in Smoker |
| cg16397028 | 16 | 72884581 | Higher in Smoker |
| cg03045067 | 16 | 72819254 | Lower in Smoker |
| cg26609906 | 17 | 4981416 | Higher in Smoker |
| cg16656286 | 17 | 4981603 | Higher in Smoker |
| cg25739316 | 19 | 39897275 | Higher in Smoker |
| cg10780191 | 14 | 69261284 | Higher in Smoker |
| cg08739430 | 2 | 43452561 | Higher in Smoker |
| cg06169590 | 2 | 43455088 | Lower in Smoker |
| cg24641352 | 8 | 144326078 | Higher in Smoker |
| cg18209895 | 8 | 144326965 | Higher in Smoker |
| cg00019576 | 8 | 144337537 | Lower in Smoker |
| cg14843143 | 8 | 144331931 | Lower in Smoker |
| cg12736937 | 8 | 144329131 | Higher in Smoker |

| | | | |
|---|---|---|---|
| cg24519147 | 4 | 188916496 | Higher in Smoker |
| cg09357276 | 4 | 188917856 | Lower in Smoker |
| cg14189571 | 4 | 188916943 | Higher in Smoker |
| cg02991469 | 20 | 50720731 | Higher in Smoker |
| cg23604151 | 20 | 50766090 | Lower in Smoker |
| cg23916050 | 20 | 50808115 | Higher in Smoker |
| cg06885652 | 20 | 50768702 | Lower in Smoker |
| cg00639361 | 20 | 50772703 | Lower in Smoker |
| cg00449929 | 16 | 68573597 | Higher in Smoker |
| cg26151079 | 11 | 58345687 | Lower in Smoker |
| cg08592493 | 16 | 88563934 | Higher in Smoker |
| cg13302217 | 16 | 88601529 | Lower in Smoker |
| cg01704666 | 8 | 106799361 | Lower in Smoker |
| cg13963735 | 8 | 106810858 | Lower in Smoker |
| cg24001611 | 19 | 3804563 | Lower in Smoker |
| cg03417595 | 19 | 3811002 | Lower in Smoker |
| cg12007399 | 19 | 3868876 | Higher in Smoker |
| cg02715685 | 19 | 3867283 | Higher in Smoker |
| cg01114138 | X | 24169878 | Lower in Smoker |
| cg24837623 | Y | 2802900 | Higher in Smoker |
| cg14972466 | Y | 2802332 | Higher in Smoker |
| cg02577797 | Y | 2802968 | Lower in Smoker |
| cg11131351 | Y | 2802287 | Lower in Smoker |
| cg01245766 | 14 | 73494282 | Higher in Smoker |
| cg21907156 | 5 | 79703652 | Higher in Smoker |
| cg18376227 | 5 | 79707092 | Lower in Smoker |
| cg27033923 | 15 | 41106683 | Lower in Smoker |
| cg25234324 | 15 | 41099904 | Higher in Smoker |
| cg25092247 | 3 | 15140607 | Higher in Smoker |
| cg08330972 | 4 | 2403930 | Higher in Smoker |
| cg01601518 | 4 | 2404284 | Higher in Smoker |
| cg23151014 | 4 | 2418311 | Higher in Smoker |
| cg10797959 | 4 | 2420526 | Higher in Smoker |
| cg01161042 | 4 | 2322052 | Lower in Smoker |
| cg04835489 | 1 | 52624196 | Lower in Smoker |

| | | | |
|---|---|---|---|
| cg04616218 | 16 | 29789904 | Lower in Smoker |
| cg04125273 | 16 | 29790933 | Lower in Smoker |
| cg04220155 | 8 | 124287276 | Higher in Smoker |
| cg18956095 | 8 | 124287111 | Higher in Smoker |
| cg15396299 | 8 | 123793789 | Higher in Smoker |
| cg21008098 | 8 | 123793590 | Higher in Smoker |
| cg08789073 | 8 | 123964289 | Lower in Smoker |
| cg22043381 | 8 | 123850540 | Lower in Smoker |
| cg12091594 | 8 | 123964938 | Lower in Smoker |
| cg13935507 | 8 | 123793925 | Higher in Smoker |
| cg06424997 | 20 | 39929561 | Lower in Smoker |
| cg22294908 | 20 | 39928631 | Lower in Smoker |
| cg17280346 | 3 | 147126703 | Higher in Smoker |
| cg07291439 | 3 | 147125926 | Higher in Smoker |
| cg16756243 | 3 | 147132559 | Higher in Smoker |
| cg23449696 | 3 | 147125942 | Higher in Smoker |
| cg18383890 | 13 | 100636252 | Higher in Smoker |
| cg24714905 | 13 | 100637241 | Higher in Smoker |
| cg17740587 | X | 136651375 | Higher in Smoker |
| cg16870351 | X | 136651271 | Higher in Smoker |
| cg01063406 | X | 136652725 | Lower in Smoker |
| cg12907379 | 13 | 100624130 | Higher in Smoker |
| cg02600430 | 13 | 100623942 | Higher in Smoker |
| cg21911021 | 19 | 58095011 | Higher in Smoker |
| cg19098268 | 19 | 57352269 | Higher in Smoker |
| cg24841424 | 19 | 57657658 | Lower in Smoker |
| cg26670626 | 7 | 99613244 | Higher in Smoker |
| cg07782241 | 8 | 40731315 | Lower in Smoker |
| cg17823346 | 10 | 80848143 | Higher in Smoker |
| cg24983858 | 10 | 80887603 | Higher in Smoker |
| cg10313149 | 10 | 81075012 | Lower in Smoker |
| cg06308720 | 10 | 81006066 | Lower in Smoker |
| cg12660364 | 7 | 44788915 | Higher in Smoker |
| cg22736886 | 7 | 44808222 | Higher in Smoker |
| cg24615751 | 1 | 40723984 | Higher in Smoker |

| | | | |
|---|---|---|---|
| cg04867253 | X | 70472827 | Lower in Smoker |
| cg14878230 | 13 | 20437969 | Higher in Smoker |
| cg11800383 | 13 | 20437874 | Higher in Smoker |
| cg17434472 | 1 | 35496883 | Higher in Smoker |
| cg18153326 | 1 | 42922229 | Lower in Smoker |
| cg19841506 | 17 | 4642056 | Higher in Smoker |
| cg18056600 | 17 | 4642047 | Higher in Smoker |
| cg17900689 | 17 | 4649262 | Lower in Smoker |
| cg23599056 | 10 | 75194385 | Lower in Smoker |
| cg14411282 | 9 | 140476961 | Higher in Smoker |
| ch.20.1002962F | 20 | 45937282 | Higher in Smoker |
| cg23662675 | 20 | 45985596 | Higher in Smoker |
| cg18599129 | 20 | 45867857 | Lower in Smoker |
| cg25577680 | 12 | 133707579 | Higher in Smoker |
| cg08320014 | 12 | 133707169 | Higher in Smoker |
| cg20336222 | 7 | 64164903 | Lower in Smoker |
| cg09896999 | 7 | 6746977 | Higher in Smoker |
| cg13219008 | 19 | 9695776 | Higher in Smoker |
| cg17655978 | 19 | 58125659 | Higher in Smoker |
| cg02835214 | 19 | 58125672 | Higher in Smoker |
| cg15921240 | 4 | 331448 | Higher in Smoker |
| cg00075589 | 2 | 219524515 | Higher in Smoker |
| cg08652300 | 3 | 125094313 | Higher in Smoker |
| cg18107105 | 3 | 125094680 | Higher in Smoker |
| cg27209953 | 19 | 44488420 | Higher in Smoker |
| cg08699181 | 8 | 146176331 | Higher in Smoker |
| cg22524070 | 8 | 146174818 | Lower in Smoker |
| cg03415429 | 6 | 28048723 | Higher in Smoker |
| cg03646916 | 3 | 44596538 | Higher in Smoker |
| cg13212382 | 3 | 44597491 | Higher in Smoker |
| cg18708075 | 19 | 52074312 | Higher in Smoker |
| cg26915779 | 17 | 11897656 | Lower in Smoker |
| cg23596567 | 17 | 11901585 | Lower in Smoker |
| cg03752330 | 19 | 45004907 | Higher in Smoker |
| cg25994470 | 6 | 27441061 | Higher in Smoker |

| | | | |
|---|---|---|---|
| cg01086810 | 6 | 28234912 | Lower in Smoker |
| cg03592283 | 3 | 44666723 | Lower in Smoker |
| cg19006507 | 19 | 58144459 | Higher in Smoker |
| cg17327630 | 7 | 148937187 | Higher in Smoker |
| cg09936008 | 16 | 3188556 | Lower in Smoker |
| cg01762264 | 16 | 3192406 | Lower in Smoker |
| cg05883874 | 11 | 7041196 | Higher in Smoker |
| cg04063776 | 11 | 6947353 | Higher in Smoker |
| cg01885963 | 11 | 6947628 | Higher in Smoker |
| cg02595681 | 11 | 6947447 | Higher in Smoker |
| cg06872519 | 11 | 6947619 | Higher in Smoker |
| cg22096450 | 11 | 6947773 | Higher in Smoker |
| cg17098965 | 20 | 52199520 | Lower in Smoker |
| cg16074383 | 14 | 21561058 | Lower in Smoker |
| cg03227078 | 19 | 44455454 | Higher in Smoker |
| cg09757277 | 19 | 44529822 | Higher in Smoker |
| cg07737564 | 19 | 44556258 | Higher in Smoker |
| cg04323379 | 19 | 44617378 | Higher in Smoker |
| cg09556823 | 19 | 44675785 | Lower in Smoker |
| cg14298780 | 19 | 44506864 | Higher in Smoker |
| cg18700516 | 19 | 44507157 | Higher in Smoker |
| cg17858618 | 19 | 44507080 | Higher in Smoker |
| cg11360366 | 19 | 44645715 | Higher in Smoker |
| cg27585874 | 19 | 44809319 | Higher in Smoker |
| cg18025258 | 18 | 74607149 | Lower in Smoker |
| cg02704999 | 18 | 74636403 | Lower in Smoker |
| cg17093401 | 10 | 44070178 | Higher in Smoker |
| cg17187559 | 10 | 38146577 | Higher in Smoker |
| cg07640605 | 10 | 38146342 | Higher in Smoker |
| cg11042902 | 8 | 146126856 | Higher in Smoker |
| cg13592003 | 8 | 146126815 | Higher in Smoker |
| cg03485988 | 8 | 145978757 | Lower in Smoker |
| cg17514123 | 8 | 145981952 | Lower in Smoker |
| cg17739046 | 19 | 19977659 | Higher in Smoker |
| cg12048031 | 19 | 58459283 | Higher in Smoker |

| | | | |
|---|---|---|---|
| cg24175803 | 19 | 22235144 | Lower in Smoker |
| cg01592369 | 12 | 133564113 | Higher in Smoker |
| cg14467738 | 12 | 133562978 | Lower in Smoker |
| cg15048437 | 19 | 37019614 | Higher in Smoker |
| cg19990402 | 19 | 37019372 | Higher in Smoker |
| cg24909706 | 19 | 37020332 | Lower in Smoker |
| cg21116314 | 19 | 9546752 | Lower in Smoker |
| cg07403638 | 16 | 32870369 | Higher in Smoker |
| cg07268270 | 16 | 32870186 | Higher in Smoker |
| cg10770529 | 19 | 58695164 | Higher in Smoker |
| cg11208348 | 7 | 111849025 | Lower in Smoker |
| cg13459393 | 19 | 53326091 | Higher in Smoker |
| cg18520517 | 22 | 22875038 | Lower in Smoker |
| cg03559467 | 1 | 200379364 | Higher in Smoker |
| cg18097325 | 7 | 148904912 | Lower in Smoker |
| cg00576525 | 7 | 148902712 | Lower in Smoker |
| cg18514705 | 19 | 44330665 | Lower in Smoker |
| cg00835832 | 19 | 44575997 | Higher in Smoker |
| cg08483173 | 19 | 44583090 | Higher in Smoker |
| cg09775780 | 17 | 18585893 | Higher in Smoker |
| cg16927664 | 17 | 18575710 | Higher in Smoker |
| cg11291313 | 5 | 150284530 | Higher in Smoker |
| cg08390760 | 6 | 28973319 | Higher in Smoker |
| cg21310336 | 6 | 28973446 | Higher in Smoker |
| cg02781447 | 6 | 28967660 | Lower in Smoker |
| cg21757440 | 16 | 58031050 | Lower in Smoker |
| cg10819684 | 19 | 53445345 | Higher in Smoker |
| cg16489511 | 6 | 26659419 | Higher in Smoker |
| cg07267166 | 6 | 28324019 | Higher in Smoker |
| cg05605299 | 6 | 28304161 | Higher in Smoker |
| cg23473726 | 19 | 58978569 | Higher in Smoker |
| cg21877656 | 19 | 58662188 | Higher in Smoker |
| cg24884572 | 19 | 58661833 | Higher in Smoker |
| cg14884747 | 4 | 142141697 | Lower in Smoker |
| cg09918296 | 19 | 54024649 | Higher in Smoker |

| | | | |
|---|---|---|---|
| cg10140114 | 20 | 45142258 | Higher in Smoker |
| cg10705541 | 20 | 45141911 | Higher in Smoker |
| cg17591832 | 10 | 43134066 | Higher in Smoker |
| cg01755729 | 8 | 146012904 | Higher in Smoker |
| cg17660446 | 20 | 2489550 | Higher in Smoker |
| cg27327588 | 19 | 37341052 | Higher in Smoker |
| cg09181872 | 3 | 44690100 | Higher in Smoker |
| cg21962610 | 19 | 7580923 | Higher in Smoker |
| cg00007466 | 19 | 7585086 | Lower in Smoker |
| cg01137532 | 10 | 64133888 | Higher in Smoker |
| cg19127909 | 10 | 38383247 | Higher in Smoker |
| cg17272795 | 10 | 38382849 | Higher in Smoker |
| cg13531642 | 10 | 38383804 | Higher in Smoker |
| cg27137512 | 10 | 43048665 | Higher in Smoker |
| cg15872458 | 12 | 54784747 | Higher in Smoker |
| cg14557202 | 12 | 54764371 | Lower in Smoker |
| cg17970299 | 12 | 54772804 | Lower in Smoker |
| cg25173392 | 7 | 99094623 | Lower in Smoker |
| cg19586686 | 18 | 32957437 | Higher in Smoker |
| cg18885387 | 18 | 32820922 | Higher in Smoker |
| cg01768926 | 18 | 32820085 | Lower in Smoker |
| cg02699447 | 7 | 148845069 | Higher in Smoker |
| cg13525739 | X | 47337961 | Lower in Smoker |
| cg14945287 | 14 | 74398293 | Lower in Smoker |
| cg18236936 | 19 | 58419776 | Lower in Smoker |
| cg08140343 | 19 | 37569236 | Lower in Smoker |
| cg08692277 | 16 | 49730710 | Lower in Smoker |
| cg04505523 | 16 | 49810605 | Lower in Smoker |
| cg04208403 | 16 | 49525807 | Lower in Smoker |
| cg02478789 | 19 | 9649310 | Higher in Smoker |
| cg13604887 | 19 | 22018953 | Higher in Smoker |
| cg23466054 | 19 | 22018892 | Higher in Smoker |
| cg02729352 | 19 | 52552443 | Higher in Smoker |
| cg27344791 | 19 | 12145947 | Lower in Smoker |
| cg08764162 | 10 | 31147088 | Higher in Smoker |

| | | | |
|---|---|---|---|
| cg20692337 | 10 | 31191938 | Lower in Smoker |
| cg14137286 | 10 | 31288997 | Lower in Smoker |
| cg27506910 | 19 | 12406174 | Lower in Smoker |
| cg08040740 | 19 | 11925285 | Higher in Smoker |
| cg09791665 | 19 | 11878248 | Lower in Smoker |
| cg25591573 | 19 | 12476246 | Lower in Smoker |
| cg00788412 | 19 | 12551876 | Lower in Smoker |
| cg23679798 | 19 | 56654827 | Lower in Smoker |
| cg27154394 | 19 | 56671146 | Lower in Smoker |
| cg17935210 | 19 | 58987656 | Lower in Smoker |
| cg25029615 | 6 | 56954784 | Higher in Smoker |
| cg12292268 | 6 | 56982370 | Lower in Smoker |
| cg08516181 | 6 | 57005930 | Lower in Smoker |
| cg03355526 | 5 | 178368415 | Higher in Smoker |
| cg24018232 | 19 | 57795269 | Lower in Smoker |
| cg08066944 | 19 | 37157899 | Higher in Smoker |
| cg22282877 | 19 | 52800469 | Higher in Smoker |
| cg18435900 | 10 | 44101962 | Higher in Smoker |
| cg10610270 | 10 | 43932457 | Higher in Smoker |
| cg25890582 | 10 | 43951436 | Higher in Smoker |
| cg03238687 | 10 | 43941753 | Lower in Smoker |
| cg27438128 | 10 | 43951555 | Lower in Smoker |
| cg13417604 | 19 | 11910049 | Higher in Smoker |
| cg24404823 | 1 | 247496053 | Higher in Smoker |
| cg04020309 | 1 | 247496094 | Higher in Smoker |
| cg13911707 | 1 | 247496404 | Higher in Smoker |
| cg26553682 | 7 | 99214201 | Higher in Smoker |
| cg04771109 | 19 | 32865061 | Lower in Smoker |
| cg15525934 | 19 | 32836082 | Lower in Smoker |
| cg07908874 | 10 | 135123006 | Lower in Smoker |
| cg27089146 | 2 | 27309545 | Lower in Smoker |
| cg03710860 | 20 | 62592735 | Higher in Smoker |
| cg16839413 | 20 | 62594447 | Higher in Smoker |
| cg01018286 | 18 | 74150192 | Lower in Smoker |
| cg22444102 | 18 | 74175208 | Lower in Smoker |

| | | | |
|---|---|---|---|
| cg12270520 | 8 | 146023939 | Higher in Smoker |
| cg16289751 | 10 | 97889373 | Lower in Smoker |
| cg08749418 | 10 | 97893715 | Lower in Smoker |
| cg17303833 | 10 | 97889448 | Lower in Smoker |
| cg00123478 | 4 | 10458165 | Lower in Smoker |
| cg21183523 | 18 | 22929205 | Higher in Smoker |
| cg15743922 | 18 | 22930545 | Higher in Smoker |
| cg20214469 | 19 | 56114369 | Lower in Smoker |
| cg05020604 | 19 | 37096329 | Higher in Smoker |
| cg09500430 | 19 | 37064254 | Higher in Smoker |
| cg03036510 | 19 | 37037627 | Lower in Smoker |
| cg19406736 | 19 | 37096010 | Higher in Smoker |
| cg15681038 | 19 | 37064156 | Higher in Smoker |
| cg12476763 | 19 | 58111647 | Higher in Smoker |
| cg21867891 | 18 | 56529835 | Lower in Smoker |
| cg01936122 | 19 | 52933695 | Lower in Smoker |
| cg16043651 | 19 | 30865486 | Higher in Smoker |
| cg08180884 | 19 | 30939155 | Lower in Smoker |
| cg24788028 | 19 | 30869034 | Lower in Smoker |
| cg15708153 | 19 | 56879554 | Higher in Smoker |
| cg01325460 | 19 | 57831819 | Higher in Smoker |
| cg15568892 | 19 | 40522655 | Lower in Smoker |
| cg23961059 | 19 | 57874869 | Higher in Smoker |
| cg00496805 | 19 | 57901154 | Lower in Smoker |
| cg15721562 | 19 | 58199822 | Higher in Smoker |
| cg26986584 | 19 | 2819738 | Higher in Smoker |
| cg19038506 | 19 | 7069182 | Lower in Smoker |
| cg24818573 | 19 | 9609342 | Higher in Smoker |
| cg18712973 | 19 | 9609335 | Higher in Smoker |
| cg19484319 | 19 | 12444632 | Higher in Smoker |
| cg11979591 | 19 | 12444583 | Higher in Smoker |
| cg21775899 | 19 | 36980503 | Higher in Smoker |
| cg10661629 | 19 | 2900748 | Higher in Smoker |
| cg22380472 | 19 | 2900542 | Higher in Smoker |
| cg04215480 | 19 | 38270199 | Higher in Smoker |

| | | | |
|---|---|---|---|
| cg03338220 | 19 | 42580251 | Higher in Smoker |
| cg02350107 | 19 | 44037044 | Higher in Smoker |
| cg02683363 | 19 | 56092459 | Higher in Smoker |
| cg12162337 | 19 | 56152193 | Higher in Smoker |
| cg15248135 | 19 | 56154954 | Higher in Smoker |
| cg15689069 | 19 | 56154944 | Higher in Smoker |
| cg13445251 | 19 | 56156342 | Lower in Smoker |
| cg08692348 | 19 | 37642883 | Higher in Smoker |
| cg07515271 | 3 | 46282103 | Lower in Smoker |
| cg03396809 | 3 | 46282488 | Lower in Smoker |
| cg17204834 | 3 | 46282574 | Lower in Smoker |
| cg00409163 | 15 | 85291729 | Higher in Smoker |
| cg04852280 | 1 | 26496234 | Higher in Smoker |
| cg17047734 | 17 | 5095455 | Higher in Smoker |
| cg03444567 | 16 | 2054271 | Lower in Smoker |
| cg12019960 | 19 | 35264165 | Higher in Smoker |
| cg11807290 | 12 | 133512074 | Lower in Smoker |
| cg15999964 | 5 | 124065258 | Lower in Smoker |
| cg01154355 | 5 | 124043109 | Lower in Smoker |
| cg26878870 | 5 | 124080713 | Lower in Smoker |
| cg02966899 | 15 | 64793532 | Lower in Smoker |
| cg21748749 | 19 | 52838671 | Higher in Smoker |
| cg00844600 | 19 | 52839603 | Lower in Smoker |
| cg03382346 | 19 | 53233245 | Lower in Smoker |
| cg22067481 | 19 | 53234126 | Lower in Smoker |
| cg05930315 | 19 | 52430630 | Higher in Smoker |
| cg22383845 | 19 | 52430492 | Higher in Smoker |
| cg13735965 | 19 | 52643487 | Higher in Smoker |
| cg14598025 | 9 | 116740723 | Lower in Smoker |
| cg07863244 | 3 | 40547441 | Higher in Smoker |
| cg02329599 | 3 | 40547855 | Higher in Smoker |
| cg00875960 | 19 | 12267308 | Lower in Smoker |
| cg19591439 | 19 | 11708747 | Higher in Smoker |
| cg00167655 | 2 | 71559112 | Higher in Smoker |
| cg21843755 | 2 | 71558577 | Higher in Smoker |

| | | | |
|---|---|---|---|
| cg22024760 | 1 | 40942625 | Higher in Smoker |
| cg26401512 | 1 | 40922773 | Lower in Smoker |
| cg02939216 | X | 22290484 | Lower in Smoker |
| cg08918923 | 1 | 182027156 | Lower in Smoker |
| cg08052120 | 19 | 52409580 | Higher in Smoker |
| cg19864007 | 19 | 52408259 | Lower in Smoker |
| cg02838608 | 17 | 47438799 | Higher in Smoker |
| cg01139508 | 3 | 44626538 | Higher in Smoker |
| cg13871633 | 3 | 42947385 | Higher in Smoker |
| cg10380221 | 16 | 31075618 | Higher in Smoker |
| cg11824627 | 16 | 31075547 | Higher in Smoker |
| cg09324016 | 16 | 31085582 | Higher in Smoker |
| cg22710865 | 1 | 247268620 | Lower in Smoker |
| cg24016939 | 19 | 58239135 | Higher in Smoker |
| cg12657014 | 1 | 249137995 | Lower in Smoker |
| cg16703466 | 1 | 249137378 | Lower in Smoker |
| cg25441977 | X | 46405000 | Higher in Smoker |
| cg18717600 | X | 46404986 | Higher in Smoker |
| cg19062689 | 19 | 23871092 | Lower in Smoker |
| cg13915538 | 19 | 22379264 | Lower in Smoker |
| cg24114314 | 19 | 53758233 | Higher in Smoker |
| cg02962558 | 7 | 64023604 | Higher in Smoker |
| cg03942436 | 16 | 30583048 | Higher in Smoker |
| cg21819604 | 1 | 43312644 | Higher in Smoker |
| cg15161772 | 1 | 43311978 | Higher in Smoker |
| cg16314058 | 1 | 43312353 | Higher in Smoker |
| cg20156999 | 1 | 249154285 | Lower in Smoker |
| cg00611192 | 1 | 249151633 | Lower in Smoker |
| cg04120766 | 8 | 144373364 | Higher in Smoker |
| cg15045976 | 8 | 144378045 | Lower in Smoker |
| cg17035457 | 1 | 120190989 | Higher in Smoker |
| cg24680162 | 1 | 120170161 | Lower in Smoker |
| cg00862394 | 1 | 120167079 | Lower in Smoker |
| cg16901014 | 8 | 146051423 | Higher in Smoker |
| cg06658864 | 19 | 12036118 | Higher in Smoker |

| | | | |
|---|---|---|---|
| cg24371216 | 19 | 12034589 | Higher in Smoker |
| cg20125424 | 19 | 53073242 | Higher in Smoker |
| cg18765463 | 19 | 53073399 | Higher in Smoker |
| cg10782349 | 19 | 53073577 | Higher in Smoker |
| cg25487404 | 8 | 37551945 | Higher in Smoker |
| cg17816390 | 8 | 37553296 | Higher in Smoker |
| cg26695909 | 8 | 81639869 | Lower in Smoker |
| cg08187779 | 8 | 102217898 | Higher in Smoker |
| cg01795694 | 8 | 102217913 | Lower in Smoker |
| cg24312082 | 8 | 144775186 | Lower in Smoker |
| cg01559901 | 19 | 12624832 | Lower in Smoker |
| cg04181321 | 19 | 57106852 | Higher in Smoker |
| cg17863679 | X | 84499750 | Higher in Smoker |
| cg03668997 | 19 | 21264131 | Lower in Smoker |
| cg05856015 | 4 | 467047 | Lower in Smoker |
| cg22347355 | 4 | 291309 | Lower in Smoker |
| cg21771408 | 19 | 21540538 | Higher in Smoker |
| cg07841312 | 22 | 20748432 | Higher in Smoker |
| cg14052112 | 7 | 149194140 | Higher in Smoker |
| cg14222657 | 7 | 149172231 | Lower in Smoker |
| cg27089547 | 16 | 30546565 | Higher in Smoker |
| cg09835675 | 16 | 30546404 | Higher in Smoker |
| cg06656924 | 6 | 35228319 | Lower in Smoker |
| cg09325869 | 19 | 53956668 | Lower in Smoker |
| cg19342764 | 19 | 53935265 | Higher in Smoker |
| cg02690491 | 19 | 12075772 | Higher in Smoker |
| cg16849020 | 19 | 12075069 | Lower in Smoker |
| cg09438266 | 16 | 30569751 | Higher in Smoker |
| cg03356493 | 19 | 53898642 | Higher in Smoker |
| cg16588500 | 16 | 30538035 | Higher in Smoker |
| cg12228977 | 19 | 2945114 | Higher in Smoker |
| cg17456842 | 15 | 35280510 | Lower in Smoker |
| cg14166756 | 15 | 90894880 | Lower in Smoker |
| cg08398855 | 16 | 89283970 | Higher in Smoker |
| cg18606683 | 19 | 40596965 | Higher in Smoker |

| | | | |
|---|---|---|---|
| cg24916345 | 19 | 40593283 | Lower in Smoker |
| cg06940614 | 19 | 38182773 | Higher in Smoker |
| cg26591684 | 7 | 148981316 | Lower in Smoker |
| cg17661206 | 7 | 148979267 | Lower in Smoker |
| cg08355109 | 19 | 56599667 | Lower in Smoker |
| cg07642822 | 19 | 56608958 | Lower in Smoker |
| cg14576322 | 7 | 99085176 | Lower in Smoker |
| cg27486786 | 7 | 99074036 | Lower in Smoker |
| cg13412003 | 19 | 35455007 | Higher in Smoker |
| cg16254093 | 19 | 38022450 | Higher in Smoker |
| cg21137173 | 3 | 113953856 | Lower in Smoker |
| cg00047526 | 7 | 127031624 | Higher in Smoker |
| cg08137040 | 7 | 127033695 | Lower in Smoker |
| cg04622620 | 7 | 127032509 | Higher in Smoker |
| cg22455450 | 19 | 53038972 | Higher in Smoker |
| cg03662302 | 19 | 53466411 | Higher in Smoker |
| cg12984877 | 4 | 146856745 | Higher in Smoker |
| cg17271471 | 4 | 146859846 | Higher in Smoker |
| cg02405003 | 4 | 146850277 | Lower in Smoker |
| cg12181730 | 19 | 53194699 | Higher in Smoker |
| cg15008743 | 19 | 53142106 | Higher in Smoker |
| cg11221508 | 17 | 33288337 | Higher in Smoker |
| cg25170034 | 17 | 33288066 | Lower in Smoker |
| cg16473762 | 20 | 57797319 | Lower in Smoker |
| cg15516684 | 19 | 52675034 | Higher in Smoker |
| cg18678067 | 19 | 52674854 | Higher in Smoker |
| cg24052338 | 19 | 58879059 | Lower in Smoker |
| cg09594291 | 19 | 58879022 | Lower in Smoker |
| cg04333648 | 19 | 53836866 | Higher in Smoker |
| cg14223395 | 19 | 53837077 | Higher in Smoker |
| cg15690721 | 19 | 21106016 | Lower in Smoker |
| cg05015306 | 19 | 12163127 | Higher in Smoker |
| cg07538838 | 19 | 12167719 | Lower in Smoker |
| cg25396971 | 5 | 178450595 | Higher in Smoker |
| cg22632069 | 19 | 52873624 | Higher in Smoker |

| | | | |
|---|---|---|---|
| cg01436128 | 19 | 22605186 | Higher in Smoker |
| cg09768178 | 19 | 22605188 | Higher in Smoker |
| cg00806126 | 19 | 22604979 | Higher in Smoker |
| cg21781157 | 20 | 47874111 | Higher in Smoker |
| cg12625296 | 7 | 100861373 | Higher in Smoker |
| cg05374623 | 7 | 100861143 | Higher in Smoker |
| cg19039672 | 17 | 34845115 | Lower in Smoker |
| cg22481427 | 1 | 86171840 | Lower in Smoker |
| cg06833562 | 1 | 86174060 | Higher in Smoker |
| cg00956423 | 6 | 30029760 | Higher in Smoker |
| cg22394535 | 6 | 30028293 | Higher in Smoker |
| cg08549335 | 7 | 30387954 | Higher in Smoker |
| cg09470758 | 7 | 30341535 | Lower in Smoker |
| cg27662633 | 7 | 30395138 | Lower in Smoker |
| cg19963025 | 22 | 29426649 | Higher in Smoker |
| cg00032787 | 22 | 29424662 | Lower in Smoker |
| cg09434995 | 7 | 76040337 | Lower in Smoker |
| cg22468258 | 7 | 76029648 | Lower in Smoker |
| cg12361987 | 7 | 50109467 | Higher in Smoker |
| cg17162682 | 2 | 135960123 | Lower in Smoker |
| cg05633660 | 15 | 85147193 | Lower in Smoker |
| cg26805255 | 1 | 33961072 | Lower in Smoker |
| cg02487499 | 1 | 33937968 | Lower in Smoker |
| cg06078336 | 7 | 99647825 | Higher in Smoker |
| cg02801453 | 19 | 58838213 | Higher in Smoker |
| cg21486944 | 6 | 28411378 | Higher in Smoker |
| cg14621843 | 19 | 56739782 | Lower in Smoker |
| cg18755855 | 20 | 44509722 | Higher in Smoker |
| cg08003077 | 20 | 44485762 | Higher in Smoker |
| cg14023762 | 19 | 13920159 | Lower in Smoker |
| cg25321549 | 5 | 60629121 | Higher in Smoker |
| cg27335855 | 5 | 60787422 | Lower in Smoker |
| cg11023075 | 5 | 60633617 | Lower in Smoker |
| cg09615521 | 11 | 113664828 | Higher in Smoker |
| cg01106040 | 3 | 126194903 | Higher in Smoker |

| | | | |
|---|---|---|---|
| cg16325326 | 1 | 53192061 | Higher in Smoker |
| cg13081999 | 7 | 143078192 | Higher in Smoker |
| cg14497327 | 7 | 143078293 | Higher in Smoker |
| cg04718055 | 1 | 78149336 | Higher in Smoker |
| cg02253760 | 3 | 147077616 | Higher in Smoker |
| cg05467012 | 3 | 12595696 | Higher in Smoker |
| cg21064916 | 11 | 44340839 | Higher in Smoker |
| cg05475109 | 8 | 49427684 | Higher in Smoker |
| cg03635442 | 8 | 49427283 | Higher in Smoker |
| cg19578835 | 14 | 38067622 | Higher in Smoker |
| cg00108351 | 16 | 86529658 | Higher in Smoker |
| cg05222995 | 12 | 115124973 | Higher in Smoker |
| cg26389727 | 6 | 28510283 | Higher in Smoker |
| cg17213402 | 2 | 5813650 | Higher in Smoker |
| cg01268590 | 12 | 54346975 | Higher in Smoker |
| cg00592781 | 12 | 66122874 | Higher in Smoker |
| cg12974388 | 2 | 237072998 | Higher in Smoker |
| cg21707187 | 12 | 54345862 | Higher in Smoker |
| cg21802055 | 4 | 4868794 | Higher in Smoker |
| rs10796216 | | | Higher in Smoker |
| cg07313705 | 5 | 180600655 | Higher in Smoker |
| cg23697855 | 7 | 89950296 | Higher in Smoker |
| cg09939997 | 16 | 89325758 | Higher in Smoker |
| cg07101909 | 16 | 3202077 | Higher in Smoker |
| cg05960195 | 16 | 89324033 | Higher in Smoker |
| cg22459755 | 8 | 49293005 | Higher in Smoker |
| cg06765217 | 14 | 38091644 | Higher in Smoker |
| cg12744031 | 7 | 158751184 | Higher in Smoker |
| cg11400162 | 6 | 170455498 | Higher in Smoker |
| cg07458308 | 5 | 134827512 | Higher in Smoker |
| cg11390378 | 4 | 147576227 | Higher in Smoker |
| cg12243078 | 11 | 72388282 | Higher in Smoker |
| cg22225207 | 1 | 13840712 | Higher in Smoker |
| cg21229570 | 12 | 115124768 | Higher in Smoker |
| cg00980649 | 14 | 106366503 | Higher in Smoker |

| | | | |
|---|---|---|---|
| cg09491410 | 5 | 174178884 | Higher in Smoker |
| cg06377473 | 10 | 116528363 | Higher in Smoker |
| cg06759629 | 4 | 25090198 | Higher in Smoker |
| cg24413662 | 11 | 122311293 | Higher in Smoker |
| cg09263516 | 12 | 115107338 | Higher in Smoker |
| cg26678605 | 10 | 118925011 | Higher in Smoker |
| cg10799055 | 6 | 27725188 | Higher in Smoker |
| cg18075691 | 19 | 58566643 | Higher in Smoker |
| cg11353598 | 15 | 70740451 | Higher in Smoker |
| cg24740218 | 12 | 114075947 | Higher in Smoker |
| cg10811045 | 2 | 91635283 | Higher in Smoker |
| cg05723754 | 12 | 47225326 | Higher in Smoker |
| cg20442599 | 6 | 108479500 | Higher in Smoker |
| cg04011671 | 2 | 43202474 | Higher in Smoker |
| cg05625559 | 5 | 6775922 | Higher in Smoker |
| cg23244488 | 7 | 19146032 | Higher in Smoker |
| cg10320410 | 7 | 64343315 | Higher in Smoker |
| cg08371391 | 20 | 19739935 | Higher in Smoker |
| cg04493082 | 11 | 356222 | Higher in Smoker |
| cg13004182 | 5 | 172665707 | Higher in Smoker |
| cg06934774 | 7 | 27198025 | Higher in Smoker |
| cg22749589 | 20 | 21501710 | Higher in Smoker |
| cg01959730 | 1 | 119548825 | Higher in Smoker |
| cg20439030 | 19 | 34359847 | Higher in Smoker |
| cg12393645 | 5 | 174178693 | Higher in Smoker |
| cg27545205 | 1 | 63783070 | Higher in Smoker |
| cg02305377 | 12 | 103355958 | Higher in Smoker |
| cg11956442 | 4 | 39531927 | Higher in Smoker |
| cg04222358 | 3 | 2140256 | Higher in Smoker |
| cg21082028 | 17 | 46659993 | Higher in Smoker |
| cg08082810 | 14 | 61108391 | Higher in Smoker |
| cg08260658 | 5 | 132155330 | Higher in Smoker |
| cg26843648 | 16 | 3225401 | Higher in Smoker |
| cg11985220 | 4 | 30719706 | Higher in Smoker |
| cg01295994 | 19 | 51924572 | Higher in Smoker |

| | | | |
|---|---|---|---|
| cg06830665 | 1 | 20802818 | Higher in Smoker |
| cg20036791 | 13 | 112508324 | Higher in Smoker |
| cg04585694 | 6 | 125684860 | Higher in Smoker |
| cg25793051 | 7 | 149439005 | Higher in Smoker |
| cg23338516 | 10 | 134647225 | Higher in Smoker |
| cg22047350 | 5 | 54523532 | Higher in Smoker |
| cg21106407 | 14 | 57262177 | Higher in Smoker |
| cg16973098 | 13 | 95359203 | Higher in Smoker |
| cg16526416 | 11 | 20184487 | Higher in Smoker |
| cg21053831 | 18 | 4455512 | Higher in Smoker |
| cg07971089 | 8 | 144629702 | Higher in Smoker |
| cg09684233 | 2 | 175206966 | Higher in Smoker |
| cg16146177 | 4 | 41883608 | Higher in Smoker |
| cg10298052 | 10 | 57391055 | Higher in Smoker |
| cg14508358 | 9 | 6716417 | Higher in Smoker |
| cg09885505 | 16 | 73099184 | Higher in Smoker |
| cg04663842 | 7 | 73242001 | Higher in Smoker |
| cg14348741 | 9 | 139880223 | Higher in Smoker |
| cg05519187 | 17 | 35303387 | Higher in Smoker |
| cg04521510 | 7 | 27242044 | Higher in Smoker |
| cg16357224 | 16 | 86530053 | Higher in Smoker |
| cg18912209 | 4 | 170696239 | Higher in Smoker |
| cg05306472 | 16 | 73517129 | Higher in Smoker |
| cg24980653 | 4 | 1399235 | Higher in Smoker |
| cg09692129 | 4 | 58029962 | Higher in Smoker |
| cg24804948 | 5 | 87988507 | Higher in Smoker |
| cg03012170 | 18 | 73628366 | Higher in Smoker |
| cg21592327 | 6 | 41411051 | Higher in Smoker |
| cg19504702 | 5 | 153862394 | Higher in Smoker |
| cg07837260 | 9 | 19788564 | Higher in Smoker |
| cg04131583 | 16 | 86529961 | Higher in Smoker |
| cg16257051 | 5 | 153862183 | Higher in Smoker |
| cg18674643 | 4 | 154713748 | Higher in Smoker |
| cg26540559 | 10 | 102447443 | Higher in Smoker |
| cg08681904 | 8 | 49427415 | Higher in Smoker |

| | | | |
|---|---|---|---|
| cg23605843 | 1 | 26735630 | Higher in Smoker |
| cg12606409 | 2 | 27958270 | Higher in Smoker |
| cg00779065 | 14 | 61119218 | Higher in Smoker |
| cg05545777 | 5 | 101119128 | Higher in Smoker |
| cg01689438 | 3 | 147140930 | Higher in Smoker |
| cg26859365 | 12 | 52241186 | Higher in Smoker |
| cg04931256 | 3 | 147077636 | Higher in Smoker |
| cg04594598 | 8 | 145105319 | Higher in Smoker |
| cg26348487 | 19 | 2488560 | Higher in Smoker |
| cg06514855 | 17 | 21220141 | Higher in Smoker |
| cg00262132 | 4 | 113430381 | Higher in Smoker |
| cg05108031 | 11 | 17743840 | Higher in Smoker |
| cg26452868 | 10 | 57387715 | Higher in Smoker |
| cg05224741 | 6 | 10422322 | Higher in Smoker |
| cg12059112 | 1 | 181287684 | Higher in Smoker |
| cg25526930 | 19 | 48707029 | Higher in Smoker |
| cg08787622 | 6 | 42694995 | Higher in Smoker |
| cg00530925 | 10 | 23463094 | Higher in Smoker |
| cg20426959 | 5 | 134802501 | Higher in Smoker |
| cg06576532 | 10 | 3282437 | Higher in Smoker |
| cg15908152 | 8 | 23605561 | Higher in Smoker |
| cg26273211 | 5 | 139135269 | Higher in Smoker |
| cg14409414 | 17 | 77777649 | Higher in Smoker |
| cg14564616 | 5 | 1876337 | Higher in Smoker |
| cg22991512 | 3 | 14643854 | Higher in Smoker |
| cg25898784 | 7 | 100812136 | Higher in Smoker |
| cg18072629 | 10 | 8092036 | Higher in Smoker |
| cg05429527 | 6 | 1596122 | Higher in Smoker |
| cg01066472 | 1 | 75591029 | Higher in Smoker |
| cg22676401 | 20 | 21496507 | Higher in Smoker |
| cg12196853 | 22 | 27496930 | Higher in Smoker |
| cg14171486 | 1 | 155139557 | Higher in Smoker |
| cg14236735 | 9 | 133536345 | Higher in Smoker |
| cg23153227 | 6 | 27725408 | Higher in Smoker |
| cg20533952 | 21 | 43198601 | Higher in Smoker |

| | | | |
|---|---|---|---|
| cg19188855 | 12 | 54355476 | Higher in Smoker |
| cg03227037 | 20 | 62212228 | Higher in Smoker |
| cg26530061 | 7 | 27265522 | Higher in Smoker |
| cg22995692 | 5 | 141263164 | Higher in Smoker |
| cg07113199 | 12 | 52258163 | Higher in Smoker |
| cg27540865 | 1 | 243053934 | Higher in Smoker |
| cg06618356 | 16 | 73097364 | Higher in Smoker |
| cg04486019 | 6 | 28510281 | Higher in Smoker |
| cg06463708 | 6 | 3318187C | Higher in Smoker |
| cg04457792 | 10 | 102473207 | Higher in Smoker |
| cg17428242 | 5 | 54263 | Higher in Smoker |
| cg06351066 | 7 | 155246964 | Higher in Smoker |
| cg06846637 | 18 | 9017502 | Higher in Smoker |
| cg04707863 | 7 | 1706305 | Higher in Smoker |
| cg04215800 | 14 | 38068340 | Higher in Smoker |
| cg06765552 | 14 | 54430182 | Higher in Smoker |
| cg17568707 | 6 | 137818327 | Higher in Smoker |
| cg03584544 | 2 | 119067552 | Higher in Smoker |
| cg05495790 | 10 | 743286 | Higher in Smoker |
| cg21992238 | 2 | 66659590 | Higher in Smoker |
| cg19392754 | 10 | 83608473 | Higher in Smoker |
| cg05586304 | 3 | 75629039 | Higher in Smoker |
| cg09019154 | 8 | 19616290 | Higher in Smoker |
| cg25615184 | 5 | 180531373 | Higher in Smoker |
| cg08195512 | 17 | 71948430 | Higher in Smoker |
| cg06184647 | 16 | 88450241 | Higher in Smoker |
| cg17895608 | 15 | 68131410 | Higher in Smoker |
| cg17025620 | 3 | 193587939 | Higher in Smoker |
| cg01851782 | 16 | 49442215 | Higher in Smoker |
| cg10024876 | 3 | 69592049 | Higher in Smoker |
| cg07723459 | 8 | 144853338 | Higher in Smoker |
| cg14395298 | 13 | 23412250 | Higher in Smoker |
| cg19645221 | 14 | 38058284 | Higher in Smoker |
| cg06275859 | 4 | 1407694 | Higher in Smoker |
| cg02997061 | X | 40126573 | Higher in Smoker |

| | | | |
|---|---|---|---|
| cg00996758 | 3 | 137486536 | Higher in Smoker |
| cg13340765 | 8 | 142276287 | Higher in Smoker |
| cg25330343 | 8 | 49293457 | Higher in Smoker |
| cg14179944 | 14 | 35867515 | Higher in Smoker |
| cg06896987 | 2 | 177003735 | Higher in Smoker |
| cg25343618 | 1 | 156631235 | Higher in Smoker |
| cg00911123 | 14 | 29226326 | Higher in Smoker |
| cg03999934 | 6 | 30325790 | Higher in Smoker |
| cg20206984 | 6 | 1381511 | Higher in Smoker |
| cg01200640 | 8 | 687384 | Higher in Smoker |
| cg10269476 | 19 | 50651408 | Higher in Smoker |
| cg10924691 | 14 | 21439548 | Higher in Smoker |
| cg20647694 | 2 | 11496960 | Higher in Smoker |
| cg11248896 | 2 | 177003747 | Higher in Smoker |
| cg25741487 | 3 | 62363076 | Higher in Smoker |
| cg04496791 | 6 | 41395094 | Higher in Smoker |
| cg20485230 | X | 37765115 | Higher in Smoker |
| cg06030695 | 5 | 145714097 | Higher in Smoker |
| cg03655371 | 5 | 134827355 | Higher in Smoker |
| cg04998379 | 4 | 129491708 | Higher in Smoker |
| cg17741501 | 15 | 29077493 | Higher in Smoker |
| cg04103761 | 1 | 26735606 | Higher in Smoker |
| cg00919971 | 7 | 1286149 | Higher in Smoker |
| cg04201563 | 15 | 100466637 | Higher in Smoker |
| cg00025680 | 2 | 45180560 | Higher in Smoker |
| cg26070319 | 14 | 103687248 | Higher in Smoker |
| cg13535015 | 10 | 124893690 | Higher in Smoker |
| cg06650546 | X | 136633004 | Higher in Smoker |
| cg24871887 | 9 | 98111365 | Higher in Smoker |
| cg10397678 | 14 | 103655712 | Higher in Smoker |
| cg03325667 | 10 | 43447292 | Higher in Smoker |
| cg12485185 | 15 | 34782820 | Higher in Smoker |
| cg05059291 | 20 | 61703362 | Higher in Smoker |
| cg08914730 | 1 | 226297409 | Higher in Smoker |
| cg02116627 | 9 | 132500478 | Higher in Smoker |

| | | | |
|---|---|---|---|
| cg02856338 | 8 | 101822108 | Higher in Smoker |
| cg11622324 | 13 | 100630688 | Higher in Smoker |
| cg18237545 | 7 | 561071 | Higher in Smoker |
| cg04341730 | 4 | 175135312 | Higher in Smoker |
| cg10202835 | 5 | 25190672 | Higher in Smoker |
| cg25267863 | 7 | 1363124 | Higher in Smoker |
| cg01722423 | 1 | 111150133 | Higher in Smoker |
| cg06563066 | 17 | 44919303 | Higher in Smoker |
| cg04463386 | 11 | 75295186 | Higher in Smoker |
| cg21038785 | 15 | 53087068 | Higher in Smoker |
| cg25310310 | 2 | 229546364 | Higher in Smoker |
| cg10785793 | 1 | 207392261 | Higher in Smoker |
| cg01425666 | 7 | 5468436 | Higher in Smoker |
| cg14458932 | 20 | 45439805 | Higher in Smoker |
| cg24140666 | 5 | 72747302 | Higher in Smoker |
| cg12916710 | 15 | 84034253 | Higher in Smoker |
| cg21962423 | 12 | 113913887 | Higher in Smoker |
| cg10945079 | 2 | 162283856 | Higher in Smoker |
| cg14282221 | 14 | 101121016 | Higher in Smoker |
| cg09820150 | 5 | 87985219 | Higher in Smoker |
| cg01431063 | 10 | 115860903 | Higher in Smoker |
| cg07136646 | 12 | 114875637 | Higher in Smoker |
| cg18357048 | 6 | 125684780 | Higher in Smoker |
| cg03869928 | 2 | 3818142 | Higher in Smoker |
| cg07505018 | 16 | 54968831 | Higher in Smoker |
| cg23584332 | 10 | 54068462 | Higher in Smoker |
| cg09311630 | 17 | 79369841 | Higher in Smoker |
| cg02340083 | 1 | 50882006 | Higher in Smoker |
| cg08864645 | 6 | 33943929 | Higher in Smoker |
| cg25423416 | 22 | 46934860 | Higher in Smoker |
| cg25708328 | 2 | 177022056 | Higher in Smoker |
| cg01087008 | 14 | 38068590 | Higher in Smoker |
| cg10967023 | 12 | 115134886 | Higher in Smoker |
| cg01866955 | 6 | 19692217 | Higher in Smoker |
| cg08542016 | 6 | 28912084 | Higher in Smoker |

| | | | |
|---|---|---|---|
| cg17099568 | 8 | 65284438 | Higher in Smoker |
| cg09834794 | 3 | 147087702 | Higher in Smoker |
| cg00330492 | 15 | 28352558 | Higher in Smoker |
| cg13376120 | 2 | 208675738 | Higher in Smoker |
| cg07126525 | 6 | 166218519 | Higher in Smoker |
| cg07005113 | 5 | 134824754 | Higher in Smoker |
| cg02930107 | 14 | 97925164 | Higher in Smoker |
| cg21146184 | 22 | 46262436 | Higher in Smoker |
| cg03876413 | 7 | 32338240 | Higher in Smoker |
| cg11729934 | 6 | 1601693 | Higher in Smoker |
| cg19856593 | 21 | 38064236 | Higher in Smoker |
| cg22878441 | 3 | 159756648 | Higher in Smoker |
| cg06911277 | 4 | 9693312 | Higher in Smoker |
| cg18612627 | 12 | 14135203 | Higher in Smoker |
| cg10521147 | 13 | 45909283 | Higher in Smoker |
| cg01656244 | 8 | 65284080 | Higher in Smoker |
| cg17649385 | 8 | 91997985 | Higher in Smoker |
| cg08779783 | X | 136509907 | Higher in Smoker |
| cg09064304 | 4 | 141419169 | Higher in Smoker |
| cg13377264 | 6 | 30419135 | Higher in Smoker |
| cg07212852 | 20 | 21684348 | Higher in Smoker |
| cg14376917 | 14 | 21131367 | Higher in Smoker |
| cg17192322 | 8 | 26307416 | Higher in Smoker |
| cg00670111 | 7 | 128500474 | Higher in Smoker |
| cg19610750 | 2 | 231714995 | Higher in Smoker |
| cg03748503 | 17 | 19483554 | Higher in Smoker |
| cg16248756 | 7 | 127795594 | Higher in Smoker |
| cg05746523 | 6 | 108437684 | Higher in Smoker |
| cg02730303 | 11 | 103480630 | Higher in Smoker |
| cg15416735 | 14 | 38068858 | Higher in Smoker |
| cg23060047 | 12 | 130819504 | Higher in Smoker |
| cg17171215 | 2 | 237078223 | Higher in Smoker |
| cg08615070 | 16 | 53407013 | Higher in Smoker |
| cg19350360 | 15 | 100913948 | Higher in Smoker |
| cg07061260 | 16 | 68676557 | Higher in Smoker |

| | | | |
|---|---|---|---|
| cg04181528 | 15 | 89943836 | Higher in Smoker |
| cg25140419 | 1 | 221050742 | Higher in Smoker |
| cg13551117 | 2 | 111979398 | Higher in Smoker |
| cg00981795 | 10 | 50606683 | Higher in Smoker |
| cg05482956 | 11 | 16635016 | Higher in Smoker |
| cg11584690 | 19 | 42574196 | Higher in Smoker |
| cg26578049 | 5 | 87985911 | Higher in Smoker |
| cg06105694 | 17 | 36585340 | Higher in Smoker |
| cg20072118 | 12 | 52653637 | Higher in Smoker |
| cg04903789 | 18 | 59001676 | Higher in Smoker |
| cg13775306 | 6 | 33577711 | Higher in Smoker |
| cg23146172 | 1 | 230562701 | Higher in Smoker |
| cg05064297 | 16 | 10479966 | Higher in Smoker |
| cg03740167 | 10 | 23463746 | Higher in Smoker |
| cg13239348 | 10 | 131768533 | Higher in Smoker |
| cg08637438 | 17 | 70113856 | Higher in Smoker |
| cg07602980 | 19 | 50815719 | Higher in Smoker |
| cg07745596 | 10 | 54538682 | Higher in Smoker |
| cg00782355 | 16 | 85831502 | Higher in Smoker |
| cg14646055 | 13 | 25116491 | Higher in Smoker |
| cg22894301 | 3 | 147077665 | Higher in Smoker |
| cg12743976 | 10 | 31892154 | Higher in Smoker |
| cg20139336 | 6 | 10495435 | Higher in Smoker |
| cg14441153 | 9 | 4763200 | Higher in Smoker |
| cg11403708 | 20 | 62605086 | Higher in Smoker |
| cg09727277 | 7 | 155258828 | Higher in Smoker |
| cg20045394 | 17 | 36184576 | Higher in Smoker |
| cg11074232 | 2 | 173037800 | Higher in Smoker |
| cg19095600 | 5 | 155108933 | Higher in Smoker |
| cg04678392 | 15 | 68114548 | Higher in Smoker |
| cg25005112 | 6 | 28911938 | Higher in Smoker |
| cg15370180 | 10 | 23494326 | Higher in Smoker |
| cg05322837 | 17 | 70147783 | Higher in Smoker |
| cg00695177 | 6 | 8761750 | Higher in Smoker |
| cg05760402 | 18 | 20139913 | Higher in Smoker |

| | | | |
|---|---|---|---|
| cg22676075 | 6 | 135203613 | Higher in Smoker |
| cg24444521 | 6 | 28104462 | Higher in Smoker |
| cg11784990 | 12 | 103218665 | Higher in Smoker |
| cg04099180 | 17 | 46662651 | Higher in Smoker |
| cg21826606 | 1 | 25593055 | Higher in Smoker |
| cg11979303 | 6 | 1379795 | Higher in Smoker |
| cg21511816 | 14 | 76597824 | Higher in Smoker |
| cg16338365 | 6 | 167559913 | Higher in Smoker |
| cg19790352 | 8 | 318778 | Higher in Smoker |
| cg05976283 | 8 | 103140765 | Higher in Smoker |
| cg14633398 | 9 | 19789383 | Higher in Smoker |
| cg07893575 | 8 | 65289751 | Higher in Smoker |
| cg06871074 | 1 | 146551565 | Higher in Smoker |
| cg01791371 | 6 | 50817193 | Higher in Smoker |
| cg27112972 | 17 | 74378252 | Higher in Smoker |
| cg24565742 | 13 | 21650374 | Higher in Smoker |
| cg08443605 | 3 | 24872319 | Higher in Smoker |
| cg15711902 | 1 | 170630457 | Higher in Smoker |
| cg05124235 | X | 113816263 | Higher in Smoker |
| cg22961747 | 17 | 28973565 | Higher in Smoker |
| cg02044327 | 18 | 14450199 | Higher in Smoker |
| cg09155362 | 15 | 33487289 | Higher in Smoker |
| cg14983225 | 2 | 163879745 | Higher in Smoker |
| cg25391815 | 8 | 49292851 | Higher in Smoker |
| cg02391509 | 3 | 27766382 | Higher in Smoker |
| cg22855933 | 2 | 157179512 | Higher in Smoker |
| cg23237972 | 1 | 39281726 | Higher in Smoker |
| cg14784335 | 3 | 27770490 | Higher in Smoker |
| cg15462501 | 22 | 40437196 | Higher in Smoker |
| cg05162564 | 5 | 139491931 | Higher in Smoker |
| cg22772896 | 6 | 37752073 | Higher in Smoker |
| cg04647982 | 17 | 21220055 | Higher in Smoker |
| cg17033891 | 3 | 159852976 | Higher in Smoker |
| cg27624162 | 2 | 111876003 | Higher in Smoker |
| cg01176947 | 6 | 10385279 | Higher in Smoker |

| | | | |
|---|---|---|---|
| cg11168004 | 4 | 13537759 | Higher in Smoker |
| cg22168205 | 13 | 24477659 | Higher in Smoker |
| cg00012701 | 6 | 30434338 | Higher in Smoker |
| cg00337662 | 15 | 68113328 | Higher in Smoker |
| cg19816642 | 17 | 21220360 | Higher in Smoker |
| cg01382110 | 18 | 4454189 | Higher in Smoker |
| cg16196211 | 6 | 27261666 | Higher in Smoker |
| cg18107094 | 8 | 110020924 | Higher in Smoker |
| cg07446753 | 7 | 2527391 | Higher in Smoker |
| cg08730623 | 1 | 98515041 | Higher in Smoker |
| cg10428345 | 5 | 176170795 | Higher in Smoker |
| cg18907180 | 14 | 97499987 | Higher in Smoker |
| cg02524099 | 4 | 1037816 | Higher in Smoker |
| cg01638213 | 19 | 1776398 | Higher in Smoker |
| cg03377980 | 7 | 1363035 | Higher in Smoker |
| cg26307926 | 2 | 71116765 | Higher in Smoker |
| cg03468466 | 3 | 27771914 | Higher in Smoker |
| cg10261416 | 14 | 97925289 | Higher in Smoker |
| cg20866711 | 17 | 47647861 | Higher in Smoker |
| cg20978721 | 13 | 112761740 | Higher in Smoker |
| cg26006870 | 8 | 11559039 | Higher in Smoker |
| cg17643106 | 7 | 48915086 | Higher in Smoker |
| cg00513984 | 12 | 125039177 | Higher in Smoker |
| cg18713748 | 5 | 140706190 | Higher in Smoker |
| cg09354381 | 3 | 14851841 | Higher in Smoker |
| cg15752343 | 10 | 124904190 | Higher in Smoker |
| cg04932340 | 14 | 95239381 | Higher in Smoker |
| cg04804643 | 6 | 29932864 | Higher in Smoker |
| cg11346837 | 3 | 147077671 | Higher in Smoker |
| cg26343883 | 2 | 164205032 | Higher in Smoker |
| cg24964694 | 6 | 36308389 | Higher in Smoker |
| cg12042264 | 20 | 44443693 | Higher in Smoker |
| cg15552491 | 11 | 119037285 | Higher in Smoker |
| cg09000779 | 3 | 136867925 | Higher in Smoker |
| cg18420643 | 8 | 10590503 | Higher in Smoker |

| | | | |
|---|---|---|---|
| cg01558960 | 16 | 86963079 | Higher in Smoker |
| cg04245305 | 3 | 195940754 | Higher in Smoker |
| cg04326198 | 14 | 36994456 | Higher in Smoker |
| cg14570291 | 10 | 110672231 | Higher in Smoker |
| cg22708508 | 1 | 154325248 | Higher in Smoker |
| cg03171478 | 22 | 37572916 | Higher in Smoker |
| cg09295252 | 6 | 5026552 | Higher in Smoker |
| cg21576728 | 1 | 113683521 | Higher in Smoker |
| cg25285090 | 6 | 28510313 | Higher in Smoker |
| cg22317668 | 19 | 42772446 | Higher in Smoker |
| cg16195569 | 10 | 57390536 | Higher in Smoker |
| cg22267770 | 6 | 10422139 | Higher in Smoker |
| cg03417728 | 22 | 17850647 | Higher in Smoker |
| cg08910558 | 15 | 75471194 | Higher in Smoker |
| cg14203201 | 6 | 27258726 | Higher in Smoker |
| cg26564960 | 1 | 6082758 | Higher in Smoker |
| cg03019736 | 11 | 115529822 | Higher in Smoker |
| cg01676105 | 14 | 78447640 | Higher in Smoker |
| cg13422587 | 7 | 3134670 | Higher in Smoker |
| cg03444715 | 11 | 122855029 | Higher in Smoker |
| cg19978531 | 15 | 70403809 | Higher in Smoker |
| cg22864337 | 7 | 65509382 | Higher in Smoker |
| cg27096255 | 4 | 170712963 | Higher in Smoker |
| cg26219092 | 8 | 134388022 | Higher in Smoker |
| cg14631910 | 8 | 10590511 | Higher in Smoker |
| cg06118126 | 20 | 19738589 | Higher in Smoker |
| cg07376547 | 1 | 48058877 | Higher in Smoker |
| cg01311995 | 16 | 85205741 | Higher in Smoker |
| cg13117562 | 17 | 81025461 | Higher in Smoker |
| cg02628795 | 1 | 229543603 | Higher in Smoker |
| cg11179308 | 17 | 47987596 | Higher in Smoker |
| cg11532433 | 2 | 24735298 | Higher in Smoker |
| cg08672296 | 16 | 89632344 | Higher in Smoker |
| cg00450651 | 5 | 139485902 | Higher in Smoker |
| cg21841963 | 12 | 54388539 | Higher in Smoker |

| | | | |
|---|---|---|---|
| cg25519804 | 6 | 4647922 | Higher in Smoker |
| cg24717935 | 3 | 27756281 | Higher in Smoker |
| cg25342699 | 11 | 20184128 | Higher in Smoker |
| cg11064255 | 18 | 5629890 | Higher in Smoker |
| cg09595912 | 12 | 130819634 | Higher in Smoker |
| cg10339481 | 11 | 33850452 | Higher in Smoker |
| cg16215387 | 7 | 1407471 | Higher in Smoker |
| cg17480076 | 1 | 91190251 | Higher in Smoker |
| cg27077033 | 14 | 105311009 | Higher in Smoker |
| cg25233139 | 13 | 112187396 | Higher in Smoker |
| cg06760518 | 2 | 237087777 | Higher in Smoker |
| cg25879142 | 7 | 4671391 | Higher in Smoker |
| cg18098065 | 8 | 1765820 | Higher in Smoker |
| cg23588462 | 13 | 95357223 | Higher in Smoker |
| cg23867997 | 20 | 61810624 | Higher in Smoker |
| cg07040303 | 5 | 2915185 | Higher in Smoker |
| cg10851251 | 15 | 68131281 | Higher in Smoker |
| cg01366985 | 6 | 25167695 | Higher in Smoker |
| cg04522432 | 6 | 29618347 | Higher in Smoker |
| cg03555730 | 14 | 76796027 | Higher in Smoker |
| cg15543173 | 9 | 114434 | Higher in Smoker |
| cg13886354 | 9 | 17906113 | Higher in Smoker |
| cg07852231 | 2 | 71116638 | Higher in Smoker |
| cg16218241 | 6 | 90597591 | Higher in Smoker |
| cg13587477 | 10 | 102431136 | Higher in Smoker |
| cg12516686 | 12 | 90686217 | Higher in Smoker |
| cg03893446 | 1 | 41848436 | Higher in Smoker |
| cg22399790 | 20 | 21501378 | Higher in Smoker |
| cg07986943 | 2 | 176932579 | Higher in Smoker |
| cg11239823 | 1 | 226297335 | Higher in Smoker |
| cg10626744 | 1 | 63783466 | Higher in Smoker |
| cg05347736 | 1 | 6302164 | Higher in Smoker |
| cg15898874 | 15 | 96515411 | Higher in Smoker |
| cg11806488 | 19 | 295123 | Higher in Smoker |
| cg25386234 | 1 | 119542159 | Higher in Smoker |

| | | | |
|---|---|---|---|
| cg19518539 | 7 | 21301723 | Higher in Smoker |
| cg07034004 | 7 | 1250246 | Higher in Smoker |
| cg16175077 | 10 | 3282650 | Higher in Smoker |
| cg13575542 | 3 | 128326887 | Higher in Smoker |
| cg05285582 | 10 | 118923093 | Higher in Smoker |
| cg12348614 | 14 | 70193496 | Higher in Smoker |
| ch.2.1134293R | 2 | 47498499 | Higher in Smoker |
| cg08664412 | 6 | 26299939 | Higher in Smoker |
| cg05359130 | 14 | 29228970 | Higher in Smoker |
| cg21608600 | 2 | 45228716 | Higher in Smoker |
| cg21032292 | 21 | 34395093 | Higher in Smoker |
| cg18030587 | 10 | 124901495 | Higher in Smoker |
| cg23217025 | 2 | 128173482 | Higher in Smoker |
| cg04606367 | 7 | 121946213 | Higher in Smoker |
| cg26135397 | 11 | 10324126 | Higher in Smoker |
| cg08891110 | 15 | 96952425 | Higher in Smoker |
| cg20395698 | 22 | 38809016 | Higher in Smoker |
| cg04851505 | 1 | 37783871 | Higher in Smoker |
| cg24588339 | 5 | 2738626 | Higher in Smoker |
| cg05232694 | 20 | 48809539 | Higher in Smoker |
| cg12836280 | 5 | 50260240 | Higher in Smoker |
| cg17671005 | 5 | 113391774 | Higher in Smoker |
| cg22642485 | 5 | 139069846 | Higher in Smoker |
| cg18707489 | 14 | 104690151 | Higher in Smoker |
| cg08750554 | 1 | 1005100 | Higher in Smoker |
| cg03768175 | 18 | 76615402 | Higher in Smoker |
| cg23817169 | 12 | 113950659 | Higher in Smoker |
| cg00049595 | 6 | 41650636 | Higher in Smoker |
| cg09057863 | 16 | 30817168 | Higher in Smoker |
| cg21218082 | 22 | 37730886 | Higher in Smoker |
| cg15785898 | 6 | 144608500 | Higher in Smoker |
| cg00383384 | 10 | 57391271 | Higher in Smoker |
| cg04557452 | 11 | 62691251 | Higher in Smoker |
| cg22371653 | 1 | 119535817 | Higher in Smoker |
| cg17344516 | 5 | 154026930 | Higher in Smoker |

| | | | |
|---|---|---|---|
| cg04557197 | 17 | 77764992 | Higher in Smoker |
| cg13624988 | 5 | 173602861 | Higher in Smoker |
| cg11369761 | 2 | 168151051 | Higher in Smoker |
| cg02601475 | 5 | 121518272 | Higher in Smoker |
| cg13133387 | 17 | 43417272 | Higher in Smoker |
| cg26154268 | 14 | 22538783 | Higher in Smoker |
| cg06601071 | 16 | 85525842 | Higher in Smoker |
| cg15234946 | 6 | 116886349 | Higher in Smoker |
| cg01692639 | 6 | 99273568 | Higher in Smoker |
| cg26290926 | 15 | 89147965 | Higher in Smoker |
| cg02173289 | 14 | 101925020 | Higher in Smoker |
| cg08219438 | 19 | 47925480 | Higher in Smoker |
| cg09284066 | 7 | 25892407 | Higher in Smoker |
| cg16203491 | 13 | 112547459 | Higher in Smoker |
| cg10172675 | 8 | 104132683 | Higher in Smoker |
| cg12856114 | 7 | 73242028 | Higher in Smoker |
| cg15192750 | 16 | 69999425 | Higher in Smoker |
| cg12403132 | 12 | 17551396 | Higher in Smoker |
| cg22160472 | 5 | 42944494 | Higher in Smoker |
| cg19118751 | 17 | 26577636 | Higher in Smoker |
| cg06134410 | 7 | 1705349 | Higher in Smoker |
| cg01966816 | 3 | 131246020 | Higher in Smoker |
| cg03602898 | 1 | 223255040 | Higher in Smoker |
| cg10633931 | 6 | 34164263 | Higher in Smoker |
| cg06936564 | 19 | 40314927 | Higher in Smoker |
| ch.13.1677809R | 13 | 106622364 | Higher in Smoker |
| cg22977892 | 8 | 25907769 | Higher in Smoker |
| cg08434574 | 6 | 99292438 | Higher in Smoker |
| cg26110605 | 10 | 1981558 | Higher in Smoker |
| cg04636564 | 6 | 169335969 | Higher in Smoker |
| cg24460369 | 12 | 109549041 | Higher in Smoker |
| cg21231458 | 20 | 21485933 | Higher in Smoker |
| cg04674956 | 8 | 65499048 | Higher in Smoker |
| cg23594451 | 4 | 1035462 | Higher in Smoker |
| cg21640137 | 6 | 4282172 | Higher in Smoker |

| | | | |
|---|---|---|---|
| cg16586211 | 16 | 85296062 | Higher in Smoker |
| cg19279616 | 15 | 96894987 | Higher in Smoker |
| cg13768269 | 9 | 114140 | Higher in Smoker |
| cg00577449 | 3 | 127633887 | Higher in Smoker |
| cg04679384 | 15 | 54270661 | Higher in Smoker |
| cg12332863 | 11 | 113906781 | Higher in Smoker |
| cg26775176 | 6 | 27725308 | Higher in Smoker |
| cg26568372 | 1 | 91190173 | Higher in Smoker |
| cg00253658 | 16 | 54210496 | Higher in Smoker |
| cg23389808 | 17 | 80330638 | Higher in Smoker |
| cg05428701 | 11 | 129150329 | Higher in Smoker |
| cg18960629 | 17 | 36585452 | Higher in Smoker |
| cg20661138 | 8 | 145925314 | Higher in Smoker |
| cg25527494 | 13 | 100641243 | Higher in Smoker |
| cg12309360 | 5 | 177412636 | Higher in Smoker |
| cg20745457 | 6 | 170604676 | Higher in Smoker |
| cg05294936 | 12 | 115106212 | Higher in Smoker |
| cg01273232 | 15 | 93652756 | Higher in Smoker |
| cg27637617 | 8 | 49293600 | Higher in Smoker |
| cg24382686 | 17 | 35053756 | Higher in Smoker |
| cg12935434 | 4 | 4329441 | Higher in Smoker |
| cg18652346 | 6 | 28733673 | Higher in Smoker |
| cg00688681 | X | 53030043 | Higher in Smoker |
| cg16059978 | 11 | 2308487 | Higher in Smoker |
| cg24476540 | 10 | 102985714 | Higher in Smoker |
| cg09820101 | 1 | 162792092 | Higher in Smoker |
| cg01637404 | 16 | 86322358 | Higher in Smoker |
| cg03009158 | 1 | 106623546 | Higher in Smoker |
| cg24175823 | 10 | 118547670 | Higher in Smoker |
| cg16633901 | 7 | 140773736 | Higher in Smoker |
| cg14248553 | 1 | 201509308 | Higher in Smoker |
| cg03521044 | 7 | 20838564 | Higher in Smoker |
| cg18883897 | 9 | 95569697 | Higher in Smoker |
| cg17546366 | 5 | 145724443 | Higher in Smoker |
| cg07296447 | 7 | 1286023 | Higher in Smoker |

| | | | |
|---|---|---|---|
| cg23703060 | 6 | 168768172 | Higher in Smoker |
| ch.10.503573F | 10 | 17956857 | Higher in Smoker |
| cg19306368 | 1 | 59235016 | Higher in Smoker |
| cg14110884 | X | 25021203 | Higher in Smoker |
| cg00191102 | 8 | 1958171 | Higher in Smoker |
| cg06680243 | 14 | 103655242 | Higher in Smoker |
| cg03690187 | 15 | 41233838 | Higher in Smoker |
| cg26219540 | 5 | 92937739 | Higher in Smoker |
| cg15261730 | 7 | 55280797 | Higher in Smoker |
| cg15773794 | 2 | 172957583 | Higher in Smoker |
| cg04835811 | 4 | 174431922 | Higher in Smoker |
| cg15822656 | 7 | 30321030 | Higher in Smoker |
| cg09320662 | 12 | 133180698 | Higher in Smoker |
| cg09605164 | 7 | 152622787 | Higher in Smoker |
| cg19935945 | 11 | 44338782 | Higher in Smoker |
| cg02501365 | 5 | 131832805 | Higher in Smoker |
| cg13180315 | 2 | 177024294 | Higher in Smoker |
| cg06693487 | 3 | 174159416 | Higher in Smoker |
| cg09092280 | 6 | 62646214 | Higher in Smoker |
| cg19604496 | 9 | 69197696 | Higher in Smoker |
| cg15747825 | 6 | 28565626 | Higher in Smoker |
| cg18750738 | 5 | 72595322 | Higher in Smoker |
| cg24796261 | 12 | 7315351 | Higher in Smoker |
| cg09528275 | 15 | 99091811 | Higher in Smoker |
| cg11230940 | 5 | 3103774 | Higher in Smoker |
| cg07110860 | 7 | 156811655 | Higher in Smoker |
| cg19459332 | 15 | 98196247 | Higher in Smoker |
| cg20887073 | 6 | 10381764 | Higher in Smoker |
| cg00449812 | 16 | 3137690 | Higher in Smoker |
| cg01873311 | 16 | 89268689 | Higher in Smoker |
| cg11013415 | 14 | 78447545 | Higher in Smoker |
| cg00386940 | 20 | 43593364 | Higher in Smoker |
| cg16683746 | 8 | 93113829 | Higher in Smoker |
| cg04474277 | 7 | 134376946 | Higher in Smoker |
| cg13279244 | 7 | 20836581 | Higher in Smoker |

| | | | |
|---|---|---|---|
| cg18030960 | 4 | 13530948 | Higher in Smoker |
| cg24236591 | 20 | 21082729 | Higher in Smoker |
| cg08933615 | 1 | 149146618 | Higher in Smoker |
| cg09942546 | 13 | 28527119 | Higher in Smoker |
| cg24735210 | 7 | 38351468 | Higher in Smoker |
| cg03027244 | 15 | 66914883 | Higher in Smoker |
| cg20630647 | 19 | 41531805 | Higher in Smoker |
| cg17077639 | 6 | 31055492 | Higher in Smoker |
| cg18739950 | 15 | 95870440 | Higher in Smoker |
| cg21770300 | 6 | 5994982 | Higher in Smoker |
| cg22904048 | 4 | 6665672 | Higher in Smoker |
| cg15407505 | 11 | 119613061 | Higher in Smoker |
| cg16783186 | 2 | 30516374 | Higher in Smoker |
| cg06611910 | 19 | 41317067 | Higher in Smoker |
| cg23554686 | X | 40122371 | Higher in Smoker |
| cg07379167 | 10 | 131769074 | Higher in Smoker |
| cg02672530 | 20 | 34680964 | Higher in Smoker |
| cg03616189 | 7 | 139184911 | Higher in Smoker |
| cg05355757 | 12 | 16762831 | Higher in Smoker |
| cg09216650 | 12 | 115174051 | Higher in Smoker |
| cg02719359 | 16 | 30411426 | Higher in Smoker |
| cg22117825 | 4 | 174439478 | Higher in Smoker |
| cg16615154 | 6 | 40567553 | Higher in Smoker |
| cg08273957 | 14 | 29227941 | Higher in Smoker |
| cg08710841 | 6 | 30421107 | Higher in Smoker |
| cg10443195 | 6 | 114663570 | Higher in Smoker |
| cg10961186 | 3 | 127634298 | Higher in Smoker |
| cg24292235 | 12 | 8171463 | Higher in Smoker |
| cg23609027 | 6 | 40723038 | Higher in Smoker |
| cg17920186 | 3 | 72323154 | Higher in Smoker |
| cg22389949 | 6 | 152003038 | Higher in Smoker |
| cg11843799 | 3 | 50297388 | Higher in Smoker |
| cg18560936 | 7 | 1632620 | Higher in Smoker |
| cg04615460 | 12 | 115125098 | Higher in Smoker |
| cg08824847 | 11 | 35052388 | Higher in Smoker |

| | | | |
|---|---|---|---|
| cg00428214 | 1 | 147775496 | Higher in Smoker |
| cg20117256 | 15 | 78726576 | Higher in Smoker |
| cg07819575 | 15 | 60294517 | Higher in Smoker |
| cg24874350 | 20 | 45440346 | Higher in Smoker |
| cg09932636 | 12 | 58329862 | Higher in Smoker |
| cg26648203 | 2 | 45159457 | Higher in Smoker |
| cg20555772 | 6 | 137630455 | Higher in Smoker |
| cg18437319 | 22 | 43542604 | Higher in Smoker |
| cg15967278 | 8 | 29886272 | Higher in Smoker |
| cg06956232 | 14 | 78432436 | Higher in Smoker |
| cg11474864 | 18 | 60263588 | Higher in Smoker |
| cg19488804 | 5 | 176216823 | Higher in Smoker |
| cg10162019 | 5 | 146889701 | Higher in Smoker |
| cg08245317 | 11 | 16633070 | Higher in Smoker |
| cg08857159 | 3 | 2139690 | Higher in Smoker |
| cg13529733 | 2 | 1609194 | Higher in Smoker |
| cg23883058 | 2 | 5813866 | Higher in Smoker |
| cg11371883 | 19 | 4584187 | Higher in Smoker |
| cg06230664 | 9 | 68809732 | Higher in Smoker |
| cg26798879 | 12 | 131246468 | Higher in Smoker |
| cg13319698 | 11 | 66176589 | Higher in Smoker |
| cg22603450 | 19 | 551536 | Higher in Smoker |
| cg03541881 | 4 | 62068481 | Higher in Smoker |
| cg13208922 | 4 | 299022 | Higher in Smoker |
| cg13074866 | 1 | 232929753 | Higher in Smoker |
| cg12908187 | 16 | 88450261 | Higher in Smoker |
| cg22727304 | 6 | 108439520 | Higher in Smoker |
| cg20337384 | 7 | 39015705 | Higher in Smoker |
| cg26131026 | 17 | 63590120 | Higher in Smoker |
| cg14564793 | 9 | 98982105 | Higher in Smoker |
| cg17352975 | 20 | 5297429 | Higher in Smoker |
| ch.4.1616659F | 4 | 84178312 | Higher in Smoker |
| cg24543854 | 11 | 115860954 | Higher in Smoker |
| cg09101902 | 10 | 49863809 | Higher in Smoker |
| cg11407741 | 10 | 8079351 | Higher in Smoker |

| | | | |
|---|---|---|---|
| cg22509189 | 2 | 225307070 | Higher in Smoker |
| cg22779991 | 6 | 41341074 | Higher in Smoker |
| cg15847963 | 4 | 180979320 | Higher in Smoker |
| cg09185829 | 14 | 104603440 | Higher in Smoker |
| cg16178289 | 17 | 37309572 | Higher in Smoker |
| cg12840537 | 6 | 28831607 | Higher in Smoker |
| cg11762968 | 13 | 95354190 | Higher in Smoker |
| cg22729438 | 15 | 30260459 | Higher in Smoker |
| cg12537796 | X | 106515818 | Higher in Smoker |
| cg13629887 | 12 | 12876682 | Higher in Smoker |
| ch.6.2143967R | 6 | 109686530 | Higher in Smoker |
| cg10975000 | 13 | 28371375 | Higher in Smoker |
| cg00999865 | 14 | 77422934 | Higher in Smoker |
| cg19814934 | 5 | 42950152 | Higher in Smoker |
| cg15135617 | 1 | 17231562 | Higher in Smoker |
| cg11648662 | 10 | 69524272 | Higher in Smoker |
| cg14700524 | 10 | 3282231 | Higher in Smoker |
| cg05209518 | 2 | 227288518 | Higher in Smoker |
| cg00733786 | 14 | 54795898 | Higher in Smoker |
| cg04128499 | 1 | 112312243 | Higher in Smoker |
| cg27081103 | 16 | 3241159 | Higher in Smoker |
| cg17464350 | 17 | 47633750 | Higher in Smoker |
| cg16661209 | 13 | 29107069 | Higher in Smoker |
| cg22898814 | 14 | 37053331 | Higher in Smoker |
| cg06916315 | 5 | 174178587 | Higher in Smoker |
| cg15626405 | 5 | 536047 | Higher in Smoker |
| cg21772629 | X | 99668480 | Higher in Smoker |
| cg05226932 | 22 | 37720696 | Higher in Smoker |
| cg25663304 | 5 | 176172918 | Higher in Smoker |
| cg17183023 | 6 | 141474349 | Higher in Smoker |
| cg06087349 | 1 | 214154085 | Higher in Smoker |
| cg00344422 | 13 | 100149311 | Higher in Smoker |
| cg03303774 | 4 | 1407052 | Higher in Smoker |
| cg16394018 | 11 | 14927549 | Higher in Smoker |
| cg24809935 | 6 | 29720530 | Higher in Smoker |

| | | | |
|---|---|---|---|
| cg03151165 | 8 | 41107543 | Higher in Smoker |
| cg00237489 | 6 | 166511686 | Higher in Smoker |
| cg09361094 | 10 | 834503 | Higher in Smoker |
| ch.10.27873849F | 10 | 27833843 | Higher in Smoker |
| cg09649545 | 16 | 85155383 | Higher in Smoker |
| cg11551464 | 8 | 49595738 | Higher in Smoker |
| cg08780711 | 17 | 6560593 | Higher in Smoker |
| cg14058010 | 17 | 8029284 | Higher in Smoker |
| ch.10.2535095F | 10 | 120437770 | Higher in Smoker |
| cg09056677 | 5 | 88743831 | Higher in Smoker |
| cg00698771 | 1 | 113285940 | Higher in Smoker |
| cg09567311 | 17 | 53316197 | Higher in Smoker |
| cg06600135 | 14 | 81408086 | Higher in Smoker |
| cg05322217 | 17 | 36575655 | Higher in Smoker |
| cg14825633 | 11 | 69704700 | Higher in Smoker |
| cg19477977 | 2 | 235599692 | Higher in Smoker |
| cg24201964 | 19 | 6516520 | Higher in Smoker |
| cg15278262 | 10 | 36461679 | Higher in Smoker |
| cg08662620 | 10 | 34061705 | Higher in Smoker |
| cg04526658 | 16 | 66635626 | Higher in Smoker |
| cg27569863 | 18 | 73627887 | Higher in Smoker |
| cg14979301 | 5 | 42994123 | Higher in Smoker |
| cg25435917 | 3 | 12917884 | Higher in Smoker |
| cg00818198 | 7 | 55001045 | Higher in Smoker |
| cg23324048 | 14 | 60794590 | Higher in Smoker |
| cg19654869 | 6 | 27656290 | Higher in Smoker |
| cg01764904 | 15 | 60289326 | Higher in Smoker |
| cg02049949 | 2 | 7237580 | Higher in Smoker |
| cg12944343 | 14 | 93698416 | Higher in Smoker |
| cg21636911 | 5 | 155000366 | Higher in Smoker |
| cg25288068 | 6 | 28793681 | Higher in Smoker |
| cg25326048 | 7 | 153446106 | Higher in Smoker |
| cg23073974 | 2 | 8039990 | Higher in Smoker |
| cg10243301 | 19 | 20163542 | Higher in Smoker |
| cg13750949 | 14 | 105293957 | Higher in Smoker |

| | | | |
|---|---|---|---|
| cg04354671 | 6 | 116886211 | Higher in Smoker |
| cg07529608 | 14 | 70041661 | Higher in Smoker |
| cg16787365 | 14 | 77499911 | Higher in Smoker |
| cg10365597 | 2 | 30929997 | Higher in Smoker |
| cg05031741 | 16 | 89314419 | Higher in Smoker |
| cg15395148 | 6 | 29720485 | Higher in Smoker |
| cg06743588 | 17 | 8279694 | Higher in Smoker |
| cg00382463 | 19 | 30718424 | Higher in Smoker |
| cg02192300 | 6 | 114663564 | Higher in Smoker |
| cg04786043 | 15 | 40728263 | Higher in Smoker |
| cg00181834 | 10 | 23463015 | Higher in Smoker |
| cg23071120 | 1 | 13840480 | Higher in Smoker |
| cg01943692 | 1 | 26685715 | Higher in Smoker |
| cg08860607 | 10 | 8374293 | Higher in Smoker |
| cg09127406 | 1 | 144594107 | Higher in Smoker |
| cg02524205 | 6 | 167559851 | Higher in Smoker |
| cg02202141 | 3 | 35681158 | Higher in Smoker |
| cg20789378 | X | 102634244 | Higher in Smoker |
| cg15102827 | 6 | 28831739 | Higher in Smoker |
| cg11205072 | 6 | 28510306 | Higher in Smoker |
| cg00439630 | 15 | 25915520 | Higher in Smoker |
| cg05413988 | 16 | 231389 | Higher in Smoker |
| cg01977209 | 2 | 236293433 | Higher in Smoker |
| cg13762257 | 11 | 45864900 | Higher in Smoker |
| cg15553989 | 6 | 64346784 | Higher in Smoker |
| cg06308025 | 12 | 8179057 | Higher in Smoker |
| cg19586845 | 11 | 2211939 | Higher in Smoker |
| cg12593746 | 1 | 98789535 | Higher in Smoker |
| cg20954960 | 6 | 28602354 | Higher in Smoker |
| cg18434718 | 19 | 15090872 | Higher in Smoker |
| cg02788266 | 5 | 50694104 | Higher in Smoker |
| cg17029354 | 12 | 115134904 | Higher in Smoker |
| cg15190445 | 6 | 108442528 | Higher in Smoker |
| cg20559943 | 4 | 185820756 | Higher in Smoker |
| cg00077285 | 15 | 37427791 | Higher in Smoker |

| | | | |
|---|---|---|---|
| cg10915739 | 21 | 34405733 | Higher in Smoker |
| cg11799593 | 12 | 68845369 | Higher in Smoker |
| cg13176741 | X | 102809882 | Higher in Smoker |
| cg00388195 | 7 | 96647323 | Higher in Smoker |
| cg27495728 | 7 | 99067116 | Higher in Smoker |
| cg01144436 | 11 | 17743946 | Higher in Smoker |
| cg14580502 | 2 | 127977849 | Higher in Smoker |
| cg17504341 | 8 | 26724836 | Higher in Smoker |
| cg20148850 | 6 | 10422227 | Higher in Smoker |
| cg21712831 | 8 | 95003548 | Higher in Smoker |
| cg26899113 | 10 | 22625733 | Higher in Smoker |
| cg18660064 | 1 | 23504632 | Higher in Smoker |
| cg07152091 | 7 | 127807283 | Higher in Smoker |
| ch.9.25423502R | 9 | 25433502 | Higher in Smoker |
| cg21429615 | 6 | 16180388 | Higher in Smoker |
| cg12962078 | 2 | 119610113 | Higher in Smoker |
| cg23199886 | 2 | 107199044 | Higher in Smoker |
| cg02339891 | 7 | 1704031 | Higher in Smoker |
| cg07151445 | 8 | 19614946 | Higher in Smoker |
| cg21589191 | 15 | 100466592 | Higher in Smoker |
| cg27558387 | 3 | 156966620 | Higher in Smoker |
| cg10381455 | 12 | 52241317 | Higher in Smoker |
| cg18527119 | 7 | 66119851 | Higher in Smoker |
| cg23914849 | X | 52950051 | Higher in Smoker |
| cg04854226 | 15 | 96910513 | Higher in Smoker |
| cg03637906 | 16 | 2955295 | Higher in Smoker |
| cg21639387 | 3 | 143532922 | Higher in Smoker |
| cg16017303 | 5 | 149540235 | Higher in Smoker |
| cg01384158 | 2 | 61990829 | Higher in Smoker |
| cg13143525 | 6 | 3068570 | Higher in Smoker |
| cg07082267 | 16 | 85429035 | Higher in Smoker |
| cg27577023 | 18 | 24236500 | Higher in Smoker |
| cg01876978 | 2 | 11970145 | Higher in Smoker |
| cg26576657 | 4 | 30718510 | Higher in Smoker |
| cg21903378 | 14 | 104686811 | Higher in Smoker |

| | | | |
|---|---|---|---|
| cg05133370 | 14 | 32670611 | Higher in Smoker |
| cg22954052 | 10 | 743392 | Higher in Smoker |
| cg24085468 | 7 | 76009472 | Higher in Smoker |
| cg08748170 | 5 | 54518667 | Higher in Smoker |
| cg13345942 | 10 | 22625015 | Higher in Smoker |
| cg23051859 | 6 | 166298877 | Higher in Smoker |
| cg02909793 | 20 | 56324509 | Higher in Smoker |
| cg04623371 | 6 | 168768113 | Higher in Smoker |
| cg22020558 | 14 | 103590115 | Higher in Smoker |
| cg03983740 | 10 | 85049656 | Higher in Smoker |
| cg16872613 | 10 | 131260015 | Higher in Smoker |
| cg19031844 | 19 | 31210714 | Higher in Smoker |
| cg18244817 | 5 | 42949610 | Higher in Smoker |
| cg06905913 | 2 | 121102148 | Higher in Smoker |
| cg17730474 | 17 | 37729928 | Higher in Smoker |
| cg04398285 | 10 | 13424851 | Higher in Smoker |
| cg03442350 | 6 | 28641629 | Higher in Smoker |
| cg27017668 | 9 | 132099124 | Higher in Smoker |
| cg09452082 | 15 | 96886018 | Higher in Smoker |
| cg06183123 | 7 | 132340279 | Higher in Smoker |
| cg03599357 | 18 | 76737392 | Higher in Smoker |
| cg24496841 | 7 | 19152017 | Higher in Smoker |
| cg02560973 | 19 | 14444344 | Higher in Smoker |
| cg05086074 | 14 | 103557891 | Higher in Smoker |
| cg21785067 | 1 | 54587182 | Higher in Smoker |
| cg23258173 | 2 | 3506547 | Higher in Smoker |
| cg13755630 | 13 | 27949051 | Higher in Smoker |
| cg15919258 | 14 | 90849921 | Higher in Smoker |
| cg08090857 | 12 | 2861914 | Higher in Smoker |
| cg03209332 | 12 | 132670372 | Higher in Smoker |
| cg25102742 | 7 | 154688294 | Higher in Smoker |
| cg04459447 | 8 | 13548701 | Higher in Smoker |
| cg03010388 | X | 18693162 | Higher in Smoker |
| cg00914041 | 8 | 91997810 | Higher in Smoker |
| cg12522342 | 17 | 64831573 | Higher in Smoker |

| | | | |
|---|---|---|---|
| cg24403804 | 6 | 16805426 | Higher in Smoker |
| cg21230450 | 14 | 22320326 | Higher in Smoker |
| cg09671060 | 21 | 47062953 | Higher in Smoker |
| cg16817237 | 11 | 60793675 | Higher in Smoker |
| cg24116534 | 6 | 134176481 | Higher in Smoker |
| cg23031975 | 2 | 67601521 | Higher in Smoker |
| cg22768388 | 19 | 12388907 | Higher in Smoker |
| cg05167782 | 15 | 74392505 | Higher in Smoker |
| cg15552206 | 6 | 25710535 | Higher in Smoker |
| cg08636385 | 6 | 71816668 | Higher in Smoker |
| cg09478095 | 2 | 662887 | Higher in Smoker |
| cg16919567 | 17 | 19015961 | Higher in Smoker |
| cg03431079 | 12 | 54145474 | Higher in Smoker |
| cg16051651 | 11 | 75095765 | Higher in Smoker |
| cg17454263 | 15 | 96986397 | Higher in Smoker |
| cg04570149 | 6 | 5996893 | Higher in Smoker |
| cg11184748 | 3 | 36806179 | Higher in Smoker |
| cg14208057 | 9 | 137859623 | Higher in Smoker |
| cg00331101 | 4 | 184949987 | Higher in Smoker |
| cg04074404 | 10 | 3282585 | Higher in Smoker |
| cg16535144 | 7 | 155259524 | Higher in Smoker |
| cg11884030 | 7 | 4652822 | Higher in Smoker |
| cg19230501 | 10 | 35926227 | Higher in Smoker |
| cg05062820 | 16 | 1098546 | Higher in Smoker |
| cg18252515 | 7 | 66147081 | Higher in Smoker |
| cg03958041 | 12 | 65283867 | Higher in Smoker |
| ch.9.82095949F | 9 | 82906129 | Higher in Smoker |
| cg19129842 | 3 | 128565090 | Higher in Smoker |
| cg04244354 | 8 | 25908279 | Higher in Smoker |
| cg20156240 | 7 | 25891970 | Higher in Smoker |
| cg15900058 | 2 | 206666368 | Higher in Smoker |
| cg14363469 | 9 | 98790268 | Higher in Smoker |
| cg06466508 | 6 | 28641622 | Higher in Smoker |
| cg05639246 | 6 | 10393778 | Higher in Smoker |
| cg03223894 | 1 | 205410136 | Higher in Smoker |

| | | | |
|---|---|---|---|
| cg27272679 | 8 | 65294635 | Higher in Smoker |
| ch.8.80227880R | 8 | 80065325 | Higher in Smoker |
| cg18339598 | 2 | 238065252 | Higher in Smoker |
| cg17931890 | 2 | 176962423 | Higher in Smoker |
| cg08530064 | 7 | 150598393 | Higher in Smoker |
| cg24004238 | 17 | 7961098 | Higher in Smoker |
| cg15769424 | 17 | 46026892 | Higher in Smoker |
| cg11079989 | 1 | 17222715 | Higher in Smoker |
| cg11354349 | 12 | 53108165 | Higher in Smoker |
| cg07905965 | 19 | 39260460 | Higher in Smoker |
| cg14917395 | 11 | 123300849 | Higher in Smoker |
| cg08076807 | 17 | 80255910 | Higher in Smoker |
| cg19388739 | 19 | 3581993 | Higher in Smoker |
| cg04116270 | 2 | 88316557 | Higher in Smoker |
| cg20291855 | 4 | 13524143 | Higher in Smoker |
| cg01115070 | 11 | 43969000 | Higher in Smoker |
| cg25900995 | 7 | 127743962 | Higher in Smoker |
| ch.8.109472102F | 8 | 109402926 | Higher in Smoker |
| cg00861277 | 14 | 70721641 | Higher in Smoker |
| cg05481085 | 12 | 109549869 | Higher in Smoker |
| cg20983609 | 18 | 20143323 | Higher in Smoker |
| cg15779737 | 3 | 138654924 | Higher in Smoker |
| cg02822788 | 3 | 193587600 | Higher in Smoker |
| cg03347944 | 1 | 91317001 | Higher in Smoker |
| cg27168780 | 6 | 28521796 | Higher in Smoker |
| cg23427998 | 5 | 54522784 | Higher in Smoker |
| cg16032050 | 10 | 50605158 | Higher in Smoker |
| cg14170220 | 17 | 21220411 | Higher in Smoker |
| cg07957795 | 1 | 17231545 | Higher in Smoker |
| cg26229715 | 5 | 134071169 | Higher in Smoker |
| cg08005122 | 11 | 110779637 | Higher in Smoker |
| cg23139982 | 4 | 4763259 | Higher in Smoker |
| cg17819053 | 1 | 119549626 | Higher in Smoker |
| ch.8.145820133F | 8 | 145849325 | Higher in Smoker |
| ch.2.228034896R | 2 | 228326652 | Higher in Smoker |

| | | | |
|---|---|---|---|
| cg01202519 | 11 | 85645743 | Higher in Smoker |
| cg08910625 | 13 | 77903871 | Higher in Smoker |
| cg08412537 | 5 | 171720399 | Higher in Smoker |
| cg09512891 | 6 | 103780468 | Higher in Smoker |
| cg12346874 | 2 | 137523644 | Higher in Smoker |
| ch.18.1233013F | 18 | 62366632 | Higher in Smoker |
| cg18976457 | 1 | 160071037 | Higher in Smoker |
| cg22932808 | 7 | 41909842 | Higher in Smoker |
| cg06824382 | 7 | 47621332 | Higher in Smoker |
| cg11424456 | 17 | 1131878 | Higher in Smoker |
| ch.16.1348776F | 16 | 61357095 | Higher in Smoker |
| cg13144484 | 14 | 101543886 | Higher in Smoker |
| cg12364741 | 5 | 112846688 | Higher in Smoker |
| cg19232991 | 15 | 91063744 | Higher in Smoker |
| ch.17.49517645R | 17 | 52162646 | Higher in Smoker |
| cg02961004 | 10 | 57387702 | Higher in Smoker |
| cg03022732 | 13 | 42614748 | Higher in Smoker |
| cg04567466 | 1 | 23894902 | Higher in Smoker |
| cg16917654 | 3 | 39219249 | Higher in Smoker |
| cg12212829 | 22 | 37252652 | Higher in Smoker |
| cg14607660 | 9 | 36738765 | Higher in Smoker |
| cg25900631 | 15 | 97490760 | Higher in Smoker |
| cg22063434 | 4 | 174427529 | Higher in Smoker |
| ch.9.1059422R | 9 | 83693653 | Higher in Smoker |
| cg07313523 | 16 | 57450669 | Higher in Smoker |
| cg00493831 | 1 | 2472336 | Higher in Smoker |
| cg12082015 | 2 | 147789639 | Higher in Smoker |
| cg01025774 | 5 | 42944457 | Higher in Smoker |
| cg13985597 | 9 | 6704574 | Higher in Smoker |
| cg14030882 | 14 | 61655919 | Higher in Smoker |
| cg23642833 | 19 | 37262611 | Higher in Smoker |
| cg14871906 | 4 | 12634870 | Higher in Smoker |
| cg04258811 | 15 | 84976641 | Higher in Smoker |
| cg00059374 | 17 | 21477756 | Higher in Smoker |
| cg12192691 | 7 | 27291695 | Higher in Smoker |

| | | | |
|---|---|---|---|
| cg21915647 | 14 | 21439301 | Higher in Smoker |
| cg23173402 | 1 | 227635558 | Higher in Smoker |
| cg23856267 | 7 | 64030969 | Higher in Smoker |
| cg09760908 | 2 | 45028712 | Higher in Smoker |
| cg12882438 | X | 152782950 | Higher in Smoker |
| cg09509909 | 10 | 93672748 | Higher in Smoker |
| cg13622436 | 4 | 4341397 | Higher in Smoker |
| cg17558296 | 17 | 44344541 | Higher in Smoker |
| cg07107824 | 10 | 95633260 | Higher in Smoker |
| cg21348357 | 2 | 171574592 | Higher in Smoker |
| cg26607337 | 5 | 145758881 | Higher in Smoker |
| cg01993680 | 6 | 10837744 | Higher in Smoker |
| cg19768356 | 6 | 36547772 | Higher in Smoker |
| cg07628580 | 22 | 38819702 | Higher in Smoker |
| cg03547730 | 8 | 102138864 | Higher in Smoker |
| cg05904430 | 11 | 114691752 | Higher in Smoker |
| cg10326806 | 19 | 46991227 | Higher in Smoker |
| cg16405026 | 2 | 145281942 | Higher in Smoker |
| cg13826452 | 6 | 26758395 | Higher in Smoker |
| cg21358106 | 21 | 46974883 | Higher in Smoker |
| cg19778616 | 7 | 129425330 | Higher in Smoker |
| ch.6.78444873F | 6 | 78388154 | Higher in Smoker |
| cg26066512 | 3 | 27754049 | Higher in Smoker |
| cg02064267 | 10 | 112220471 | Higher in Smoker |
| cg24833739 | 5 | 174220754 | Higher in Smoker |
| cg12091936 | 11 | 70303534 | Higher in Smoker |
| ch.9.1930815F | 9 | 123981663 | Higher in Smoker |
| cg22646733 | 10 | 121446177 | Higher in Smoker |
| cg02311432 | 11 | 115530304 | Higher in Smoker |
| cg17052310 | 7 | 99588561 | Higher in Smoker |
| cg16584342 | 2 | 231276668 | Higher in Smoker |
| cg08911291 | 9 | 44119413 | Higher in Smoker |
| cg19304273 | 11 | 49070231 | Higher in Smoker |
| cg17656165 | 4 | 90031969 | Higher in Smoker |
| cg01347349 | 15 | 86383878 | Higher in Smoker |

| | | | |
|---|---|---|---|
| cg11991824 | 6 | 31651283 | Higher in Smoker |
| cg08202274 | 3 | 178800348 | Higher in Smoker |
| ch.14.44741640R | 14 | 45671890 | Higher in Smoker |
| cg00829269 | 20 | 44065852 | Higher in Smoker |
| cg03667862 | 12 | 8123463 | Higher in Smoker |
| cg10107434 | 2 | 177021899 | Higher in Smoker |
| cg23147574 | 3 | 147142102 | Higher in Smoker |
| cg26200118 | 14 | 98575729 | Higher in Smoker |
| cg15600422 | 16 | 88450381 | Higher in Smoker |
| cg09200260 | 21 | 36577539 | Higher in Smoker |
| cg14349549 | 7 | 84815156 | Higher in Smoker |
| cg02607683 | 3 | 72149807 | Higher in Smoker |
| cg10941255 | 6 | 100677004 | Higher in Smoker |
| cg06183872 | 12 | 133049993 | Higher in Smoker |
| cg06186820 | 6 | 28510514 | Higher in Smoker |
| cg09072408 | 11 | 118663568 | Higher in Smoker |
| cg03900474 | 12 | 115106786 | Higher in Smoker |
| cg10933494 | 6 | 28983143 | Higher in Smoker |
| cg05256504 | 7 | 121947072 | Higher in Smoker |
| cg22669787 | 2 | 127729597 | Higher in Smoker |
| cg08174387 | 15 | 22449510 | Higher in Smoker |
| cg03793066 | 7 | 113726654 | Higher in Smoker |
| cg11774399 | 19 | 7934559 | Higher in Smoker |
| cg22834172 | 17 | 37774349 | Higher in Smoker |
| cg07137955 | 5 | 42992774 | Higher in Smoker |
| cg03445151 | 2 | 23516881 | Higher in Smoker |
| cg00040013 | 1 | 249168473 | Higher in Smoker |
| cg06203207 | 19 | 42444781 | Higher in Smoker |
| ch.5.1161320F | 5 | 60527978 | Higher in Smoker |
| cg10135877 | 7 | 56246843 | Higher in Smoker |
| cg17736057 | 12 | 34372490 | Higher in Smoker |
| cg01129641 | 2 | 241561237 | Higher in Smoker |
| cg05849566 | 5 | 177503187 | Higher in Smoker |
| cg04822330 | 6 | 126069172 | Higher in Smoker |
| cg07337234 | 22 | 36851107 | Higher in Smoker |

| | | | |
|---|---|---|---|
| cg15427232 | 13 | 28550400 | Higher in Smoker |
| cg19544459 | 7 | 22123197 | Higher in Smoker |
| cg08076108 | 17 | 46026810 | Higher in Smoker |
| ch.14.53082129F | 14 | 54012379 | Higher in Smoker |
| ch.13.774712F | 13 | 54733675 | Higher in Smoker |
| cg25193323 | 8 | 125437986 | Higher in Smoker |
| cg04368076 | 2 | 3776067 | Higher in Smoker |
| cg10210909 | 8 | 11559488 | Higher in Smoker |
| ch.1.194404001R | 1 | 196137379 | Higher in Smoker |
| ch.9.98989607R | 9 | 99949786 | Higher in Smoker |
| ch.4.980419F | 4 | 43430790 | Higher in Smoker |
| cg09688773 | 3 | 172469100 | Higher in Smoker |
| cg23880631 | 2 | 167395901 | Higher in Smoker |
| cg04117972 | 1 | 227635322 | Higher in Smoker |
| cg02984092 | 15 | 89178874 | Higher in Smoker |
| cg12323884 | 15 | 70392862 | Higher in Smoker |
| cg04276524 | 7 | 64498472 | Higher in Smoker |
| cg17614974 | 3 | 44039919 | Higher in Smoker |
| ch.11.1215677R | 11 | 62479126 | Higher in Smoker |
| cg13519452 | 9 | 140122642 | Higher in Smoker |
| cg08450534 | 17 | 8030190 | Higher in Smoker |
| ch.6.1140072F | 6 | 46312258 | Higher in Smoker |
| cg03656770 | 6 | 116886276 | Higher in Smoker |
| cg12940104 | 6 | 108439511 | Higher in Smoker |
| cg17910899 | 13 | 100218552 | Higher in Smoker |
| cg05997655 | 16 | 53544321 | Higher in Smoker |
| cg13711457 | 5 | 5494990 | Higher in Smoker |
| cg02258246 | 5 | 55777117 | Higher in Smoker |
| cg14530304 | 17 | 77777792 | Higher in Smoker |
| cg13205528 | 1 | 2705849 | Higher in Smoker |
| cg01803461 | 16 | 86604522 | Higher in Smoker |
| cg14790630 | 1 | 84326462 | Higher in Smoker |
| cg13935108 | 11 | 113660932 | Higher in Smoker |
| cg06940720 | 5 | 1526929 | Higher in Smoker |
| cg00125414 | 20 | 58509242 | Higher in Smoker |

| | | | |
|---|---|---|---|
| cg14486894 | 15 | 89904767 | Higher in Smoker |
| cg13929270 | 6 | 99271709 | Higher in Smoker |
| cg01124922 | 5 | 92684412 | Higher in Smoker |
| ch.7.1839793F | 7 | 85740125 | Higher in Smoker |
| cg08600862 | 5 | 76939558 | Higher in Smoker |
| cg11741356 | 15 | 97490784 | Higher in Smoker |
| cg16293639 | 13 | 107568171 | Higher in Smoker |
| cg25342861 | 17 | 45177598 | Higher in Smoker |
| cg14792081 | 1 | 65468460 | Higher in Smoker |
| cg18974921 | 11 | 78131895 | Higher in Smoker |
| cg15698568 | 12 | 131200725 | Higher in Smoker |
| cg08625556 | 2 | 42068380 | Higher in Smoker |
| ch.15.865366R | 15 | 61630364 | Higher in Smoker |
| cg16257810 | 3 | 54121929 | Higher in Smoker |
| ch.3.5198520F | 3 | 5223520 | Higher in Smoker |
| cg14027385 | 10 | 32048204 | Higher in Smoker |
| cg18178715 | 1 | 43795999 | Higher in Smoker |
| cg23267450 | 10 | 47151484 | Higher in Smoker |
| cg17731209 | 21 | 38937316 | Higher in Smoker |
| cg10467371 | 6 | 167560347 | Higher in Smoker |
| cg07099553 | 15 | 89178856 | Higher in Smoker |
| ch.13.78755175F | 13 | 79857174 | Higher in Smoker |
| ch.X.57019131F | X | 57002406 | Higher in Smoker |
| cg15943851 | 7 | 25902573 | Higher in Smoker |
| cg05903289 | 2 | 130345205 | Higher in Smoker |
| cg14106909 | 9 | 138109322 | Higher in Smoker |
| cg23731184 | 20 | 49708799 | Higher in Smoker |
| cg04022555 | 17 | 8103571 | Higher in Smoker |
| cg11385338 | 7 | 63250817 | Higher in Smoker |
| cg07838270 | 16 | 86861522 | Higher in Smoker |
| cg03550129 | 2 | 1596054 | Higher in Smoker |
| cg02695873 | 7 | 127741520 | Higher in Smoker |
| cg26694028 | 1 | 244212908 | Higher in Smoker |
| cg19358307 | 12 | 128675426 | Higher in Smoker |
| cg18390181 | 10 | 102810139 | Higher in Smoker |

| | | | |
|---|---|---|---|
| cg00001261 | 16 | 3463964 | Higher in Smoker |
| cg26870745 | 19 | 3133503 | Higher in Smoker |
| cg22885407 | 2 | 132440298 | Higher in Smoker |
| cg11390905 | 9 | 139085102 | Higher in Smoker |
| cg06362543 | 20 | 42135794 | Higher in Smoker |
| cg24856756 | 6 | 68750267 | Higher in Smoker |
| cg26935391 | 12 | 50427095 | Higher in Smoker |
| cg16548613 | 17 | 40684064 | Higher in Smoker |
| cg13930261 | 5 | 42949882 | Higher in Smoker |
| cg14063182 | 7 | 4682116 | Higher in Smoker |
| cg06352730 | 7 | 47621692 | Higher in Smoker |
| cg00421846 | 6 | 41340293 | Higher in Smoker |
| cg27625887 | 8 | 11550841 | Higher in Smoker |
| cg04212922 | 4 | 141173867 | Higher in Smoker |
| cg14061378 | 9 | 139539092 | Higher in Smoker |
| cg01647561 | 2 | 238199815 | Higher in Smoker |
| cg05954192 | 11 | 57056613 | Higher in Smoker |
| ch.2.189510808F | 2 | 189802563 | Higher in Smoker |
| cg04456666 | 15 | 40615783 | Higher in Smoker |
| cg03203197 | 16 | 34587120 | Higher in Smoker |
| cg16748643 | 16 | 1336696 | Higher in Smoker |
| cg21868699 | 4 | 9534366 | Higher in Smoker |
| cg17933722 | 1 | 116711077 | Higher in Smoker |
| cg07590002 | 6 | 30449064 | Higher in Smoker |
| cg11100602 | 5 | 72497917 | Higher in Smoker |
| cg20610274 | 1 | 110745892 | Higher in Smoker |
| cg24877510 | 4 | 78742376 | Higher in Smoker |
| cg24951880 | 8 | 1960257 | Higher in Smoker |
| ch.7.54635456F | 7 | 54667962 | Higher in Smoker |
| cg02889777 | 17 | 37213271 | Higher in Smoker |
| cg02556042 | 12 | 117471086 | Higher in Smoker |
| cg15174393 | 12 | 125259081 | Higher in Smoker |
| cg10817554 | 2 | 231714705 | Higher in Smoker |
| cg05357107 | 7 | 63497623 | Higher in Smoker |
| cg12293204 | 3 | 39219562 | Higher in Smoker |

| | | | |
|---|---|---|---|
| cg25532925 | 17 | 47647473 | Higher in Smoker |
| cg01148786 | 3 | 97540262 | Higher in Smoker |
| cg14137279 | 6 | 150738947 | Higher in Smoker |
| cg26675097 | 20 | 21083737 | Higher in Smoker |
| cg11259446 | 19 | 3728250 | Higher in Smoker |
| cg25172604 | 17 | 41446521 | Higher in Smoker |
| cg06578342 | 16 | 4349215 | Higher in Smoker |
| ch.2.4251330R | 2 | 213799789 | Higher in Smoker |
| cg26874634 | 17 | 49022278 | Higher in Smoker |
| cg15240876 | 7 | 4926860 | Higher in Smoker |
| cg16270222 | 17 | 41446396 | Higher in Smoker |
| cg05650810 | 1 | 148902455 | Higher in Smoker |
| cg11166453 | 1 | 247681781 | Higher in Smoker |
| cg01156948 | 17 | 43662979 | Higher in Smoker |
| cg13953813 | 8 | 76319838 | Higher in Smoker |
| cg16650630 | 15 | 40364862 | Higher in Smoker |
| cg05236591 | 14 | 21082276 | Higher in Smoker |
| cg08121117 | 13 | 112575735 | Higher in Smoker |
| cg00510539 | 2 | 27958611 | Higher in Smoker |
| cg04291842 | 10 | 131767159 | Higher in Smoker |
| cg14458575 | 2 | 238380390 | Higher in Smoker |
| cg05929136 | 20 | 44941267 | Higher in Smoker |
| cg01589779 | 1 | 227975876 | Higher in Smoker |
| cg08662532 | 17 | 3641230 | Higher in Smoker |
| cg20467502 | 19 | 4593190 | Higher in Smoker |
| cg14214257 | 9 | 102058671 | Higher in Smoker |
| cg00188654 | 16 | 3696402 | Higher in Smoker |
| cg10900696 | 8 | 24858119 | Higher in Smoker |
| cg24025650 | 6 | 29720582 | Higher in Smoker |
| cg15959080 | 3 | 13939366 | Higher in Smoker |
| cg18401111 | 15 | 31773057 | Higher in Smoker |
| cg09943102 | 7 | 73157788 | Higher in Smoker |
| cg15779521 | 12 | 120729960 | Higher in Smoker |
| cg17076539 | 3 | 57204284 | Higher in Smoker |
| ch.2.226734209F | 2 | 227025965 | Higher in Smoker |

| | | | |
|---|---|---|---|
| ch.4.73985647R | 4 | 73766783 | Higher in Smoker |
| cg03466031 | 4 | 186050298 | Higher in Smoker |
| cg26053876 | 14 | 22991735 | Higher in Smoker |
| cg24997589 | 7 | 148680113 | Higher in Smoker |
| ch.17.33947170F | 17 | 36593644 | Higher in Smoker |
| cg26256401 | 3 | 44037543 | Higher in Smoker |
| ch.1.505031R | 1 | 14830428 | Higher in Smoker |
| cg07664454 | 17 | 27918580 | Higher in Smoker |
| cg21136544 | 6 | 3160547 | Higher in Smoker |
| cg17951850 | 4 | 99389164 | Higher in Smoker |
| cg07876340 | 5 | 143150957 | Higher in Smoker |
| cg25882579 | 8 | 24799414 | Higher in Smoker |
| ch.2.145029987F | 2 | 145313517 | Higher in Smoker |
| cg09275408 | 10 | 44500491 | Higher in Smoker |
| cg06907870 | 4 | 13655932 | Higher in Smoker |
| cg05132925 | 1 | 110438827 | Higher in Smoker |
| cg19403103 | 1 | 204347593 | Higher in Smoker |
| cg05349024 | 14 | 101471543 | Higher in Smoker |
| cg16740057 | 6 | 28908567 | Higher in Smoker |
| ch.3.2279603R | 3 | 116239686 | Higher in Smoker |
| cg11125883 | 12 | 68729045 | Higher in Smoker |
| cg02619116 | 17 | 40819808 | Higher in Smoker |
| cg12339131 | 15 | 90927959 | Higher in Smoker |
| ch.14.96436874F | 14 | 97367121 | Higher in Smoker |
| cg16748413 | 8 | 82543431 | Higher in Smoker |
| cg03517776 | 2 | 64834430 | Higher in Smoker |
| cg08671425 | 12 | 133050277 | Higher in Smoker |
| cg00903676 | 6 | 26172091 | Higher in Smoker |
| cg26978918 | 10 | 134836452 | Higher in Smoker |
| ch.2.147017622F | 2 | 147301152 | Higher in Smoker |
| cg19325791 | 17 | 46560683 | Higher in Smoker |
| cg22431861 | 8 | 103823181 | Higher in Smoker |
| cg00481216 | 2 | 181971175 | Higher in Smoker |
| cg05712271 | 12 | 130396377 | Higher in Smoker |
| cg23646888 | 3 | 112929672 | Higher in Smoker |

| | | | |
|---|---|---|---|
| ch.8.40958873F | 8 | 40839716 | Higher in Smoker |
| cg07199592 | 16 | 30817051 | Higher in Smoker |
| cg11816734 | 5 | 3962434 | Higher in Smoker |
| cg14510926 | 2 | 174877357 | Higher in Smoker |
| cg08042316 | 7 | 139930256 | Higher in Smoker |
| cg12934934 | 4 | 113445388 | Higher in Smoker |
| cg09915932 | 17 | 235713 | Higher in Smoker |
| cg00835429 | 15 | 89943283 | Higher in Smoker |
| cg11229864 | 11 | 58666068 | Higher in Smoker |
| cg17367816 | 10 | 42673902 | Higher in Smoker |
| ch.16.84131625R | 16 | 85574124 | Higher in Smoker |
| cg21881652 | 14 | 105033467 | Higher in Smoker |
| cg17844606 | 7 | 31174318 | Higher in Smoker |
| cg22508391 | 7 | 104624890 | Higher in Smoker |
| cg17671608 | 1 | 33593154 | Higher in Smoker |
| cg04983327 | 17 | 25289961 | Higher in Smoker |
| cg07937542 | 6 | 32765150 | Higher in Smoker |
| cg12451138 | 6 | 32862429 | Higher in Smoker |
| cg01955962 | 15 | 73089536 | Higher in Smoker |
| cg15627347 | 7 | 57472504 | Higher in Smoker |
| cg24118130 | 7 | 158793909 | Higher in Smoker |
| cg02029564 | 11 | 1354849 | Higher in Smoker |
| cg20128323 | 6 | 9503813 | Higher in Smoker |
| cg14772594 | 15 | 64752790 | Higher in Smoker |
| cg14851194 | 13 | 66501111 | Higher in Smoker |
| cg23723410 | 1 | 59486037 | Higher in Smoker |
| cg08626646 | X | 53123489 | Higher in Smoker |
| cg02707307 | 9 | 130370151 | Higher in Smoker |
| cg02674870 | 7 | 155356153 | Higher in Smoker |
| cg03558177 | 16 | 89307718 | Higher in Smoker |
| cg14212996 | 14 | 24020930 | Higher in Smoker |
| cg04388919 | 7 | 149119133 | Higher in Smoker |
| cg13923648 | 6 | 27173910 | Higher in Smoker |
| cg22037209 | X | 64627254 | Higher in Smoker |
| cg07679896 | 10 | 126605121 | Higher in Smoker |

| | | | |
|---|---|---|---|
| cg03894892 | 7 | 153445197 | Higher in Smoker |
| cg24919522 | 6 | 33313260 | Higher in Smoker |
| cg09628649 | 4 | 190944304 | Higher in Smoker |
| cg13743300 | 22 | 23908225 | Higher in Smoker |
| cg10107890 | 2 | 44314289 | Higher in Smoker |
| cg00338345 | 1 | 149224717 | Higher in Smoker |
| cg03830168 | 15 | 76050995 | Higher in Smoker |
| cg07117402 | 10 | 3448994 | Higher in Smoker |
| cg11844530 | 1 | 28576552 | Higher in Smoker |
| cg03002688 | 4 | 26152723 | Higher in Smoker |
| cg20522707 | 17 | 28995014 | Higher in Smoker |
| cg09860717 | 1 | 25566433 | Higher in Smoker |
| cg18815388 | 7 | 100291905 | Higher in Smoker |
| cg23036683 | 5 | 67512108 | Higher in Smoker |
| cg09432613 | 10 | 102497520 | Higher in Smoker |
| cg00833479 | 7 | 62528852 | Higher in Smoker |
| cg19747640 | 17 | 1812145 | Higher in Smoker |
| cg21593030 | 11 | 70952175 | Higher in Smoker |
| cg18906845 | 14 | 78121495 | Higher in Smoker |
| cg07614306 | 12 | 59990159 | Higher in Smoker |
| cg22322828 | 8 | 67025467 | Higher in Smoker |
| cg06890242 | 11 | 75250733 | Higher in Smoker |
| cg04889069 | 8 | 57030408 | Higher in Smoker |
| cg18090145 | 6 | 67741714 | Higher in Smoker |
| cg16512868 | 14 | 75760996 | Higher in Smoker |
| cg05947596 | 6 | 99969103 | Higher in Smoker |
| ch.7.226720508 | 7 | 22705525 | Higher in Smoker |
| cg18188392 | Y | 14649262 | Higher in Smoker |
| cg21292912 | 18 | 47863988 | Higher in Smoker |
| cg17621419 | 16 | 75550927 | Higher in Smoker |
| cg19092266 | 12 | 8179360 | Higher in Smoker |
| ch.8.157877763 | 8 | 15743405 | Higher in Smoker |
| cg07590215 | 4 | 1003440 | Higher in Smoker |
| cg14252954 | 1 | 114889371 | Higher in Smoker |
| cg12130984 | 14 | 76819168 | Higher in Smoker |

| | | | |
|---|---|---|---|
| ch.10.113099321F | 10 | 113109331 | Higher in Smoker |
| cg24996440 | 2 | 3583570 | Higher in Smoker |
| cg13907181 | 1 | 234736119 | Higher in Smoker |
| cg27551718 | 19 | 39572000 | Higher in Smoker |
| cg24607181 | 17 | 41446203 | Higher in Smoker |
| cg01857253 | X | 139014460 | Higher in Smoker |
| cg07067090 | 9 | 6680932 | Higher in Smoker |
| cg00206779 | 3 | 105341338 | Higher in Smoker |
| cg20636248 | 10 | 121439845 | Higher in Smoker |
| cg05536998 | 18 | 46500646 | Higher in Smoker |
| cg10163220 | 12 | 104776085 | Higher in Smoker |
| cg13703663 | 7 | 2765455 | Higher in Smoker |
| cg18319941 | 7 | 64894361 | Higher in Smoker |
| cg26573733 | 2 | 178013511 | Higher in Smoker |
| cg05006755 | 16 | 4233246 | Higher in Smoker |
| cg02438611 | 17 | 55828107 | Higher in Smoker |
| cg07613459 | 17 | 8090950 | Higher in Smoker |
| ch.7.109948253R | 7 | 110161017 | Higher in Smoker |
| cg20331612 | 10 | 3282311 | Higher in Smoker |
| cg15491911 | 6 | 167764620 | Higher in Smoker |
| cg06750566 | 4 | 88157084 | Higher in Smoker |
| ch.7.42519133R | 7 | 42552608 | Higher in Smoker |
| cg27615447 | 12 | 98791447 | Higher in Smoker |
| cg19846096 | 12 | 133049188 | Higher in Smoker |
| cg03010887 | 16 | 85600235 | Higher in Smoker |
| cg25201418 | 6 | 33217615 | Higher in Smoker |
| cg19435188 | 2 | 236293467 | Higher in Smoker |
| cg21475816 | 2 | 73404801 | Higher in Smoker |
| cg25236324 | 15 | 69755381 | Higher in Smoker |
| cg08900073 | 11 | 118796721 | Higher in Smoker |
| cg18063495 | 5 | 50262796 | Higher in Smoker |
| cg18664369 | 4 | 26030691 | Higher in Smoker |
| cg13870848 | 6 | 104973770 | Higher in Smoker |
| cg17481703 | 13 | 76444931 | Higher in Smoker |
| cg16669877 | 6 | 44041170 | Higher in Smoker |

| | | | |
|---|---|---|---|
| cg19978540 | 12 | 3409405 | Higher in Smoker |
| cg02146032 | 8 | 11559156 | Higher in Smoker |
| cg19562439 | 4 | 6540588 | Higher in Smoker |
| cg02716556 | 6 | 10838914 | Higher in Smoker |
| cg19106775 | 3 | 197391841 | Higher in Smoker |
| cg03991721 | 3 | 75704951 | Higher in Smoker |
| cg09574498 | 17 | 48944758 | Higher in Smoker |
| cg04696149 | 2 | 37552545 | Higher in Smoker |
| cg01600621 | 19 | 42681426 | Higher in Smoker |
| cg09821007 | X | 68348763 | Higher in Smoker |
| cg16516556 | 1 | 55008180 | Higher in Smoker |
| cg19459454 | 3 | 32509030 | Higher in Smoker |
| cg03709663 | 16 | 85731277 | Higher in Smoker |
| cg13976265 | X | 3732500 | Higher in Smoker |
| cg21815063 | 5 | 131800430 | Higher in Smoker |
| cg20482143 | 7 | 64340804 | Higher in Smoker |
| cg12611527 | 2 | 157257110 | Higher in Smoker |
| cg22652155 | 2 | 1554541 | Higher in Smoker |
| cg23684088 | 6 | 28510928 | Higher in Smoker |
| cg00868766 | 15 | 40364524 | Higher in Smoker |
| cg23239754 | 6 | 27760147 | Higher in Smoker |
| cg06450752 | 15 | 73611451 | Higher in Smoker |
| cg15898112 | 15 | 77988506 | Higher in Smoker |
| cg13117339 | 6 | 147178769 | Higher in Smoker |
| cg26685998 | 2 | 43334941 | Higher in Smoker |
| ch.6.1441955872 | 6 | 144153894 | Higher in Smoker |
| cg00914218 | X | 69654348 | Higher in Smoker |
| cg25102375 | 1 | 23946294 | Higher in Smoker |
| cg02420480 | 7 | 41919892 | Higher in Smoker |
| cg19783626 | 7 | 98311436 | Higher in Smoker |
| cg01106753 | 3 | 107150909 | Higher in Smoker |
| cg14469684 | 9 | 138997380 | Higher in Smoker |
| cg04848660 | 7 | 41174125 | Higher in Smoker |
| cg11079969 | 15 | 82339920 | Higher in Smoker |
| cg09681675 | 16 | 3481785 | Higher in Smoker |

| | | | |
|---|---|---|---|
| cg04027632 | 6 | 28908623 | Higher in Smoker |
| cg22464548 | 3 | 185000648 | Higher in Smoker |
| cg18323912 | 5 | 42994709 | Higher in Smoker |
| cg14962158 | 10 | 135138229 | Higher in Smoker |
| cg01329756 | 17 | 80346912 | Higher in Smoker |
| cg13750535 | 9 | 141042453 | Higher in Smoker |
| cg21393051 | 1 | 209585310 | Higher in Smoker |
| cg04540882 | 17 | 27703877 | Higher in Smoker |
| cg23398047 | 8 | 49783505 | Higher in Smoker |
| cg22027305 | 17 | 18759561 | Higher in Smoker |
| cg06899483 | 1 | 206037215 | Higher in Smoker |
| cg03846951 | 6 | 167764967 | Higher in Smoker |
| cg07099606 | 12 | 133051136 | Higher in Smoker |
| cg08983133 | 17 | 48944364 | Higher in Smoker |
| cg24530234 | 10 | 44224014 | Higher in Smoker |
| cg18610342 | 3 | 5019075 | Higher in Smoker |
| cg10502884 | 10 | 125852315 | Higher in Smoker |
| cg23572751 | 17 | 47270556 | Higher in Smoker |
| cg09096087 | 16 | 1338174 | Higher in Smoker |
| cg13352455 | 3 | 53230110 | Higher in Smoker |
| cg09601882 | 6 | 28634502 | Higher in Smoker |
| cg25969107 | 15 | 95128247 | Higher in Smoker |
| cg02395363 | 1 | 145395846 | Higher in Smoker |
| cg11254439 | 12 | 57335615 | Higher in Smoker |
| cg01557667 | 22 | 43411403 | Higher in Smoker |
| cg20677516 | 1 | 202781057 | Higher in Smoker |
| cg26518560 | X | 53123428 | Higher in Smoker |
| cg05085255 | 15 | 60298617 | Higher in Smoker |
| cg04464085 | 6 | 30923327 | Higher in Smoker |
| cg08507136 | 8 | 28515641 | Higher in Smoker |
| ch.3.638689R | 3 | 31240746 | Higher in Smoker |
| cg02201898 | 14 | 103376914 | Higher in Smoker |
| cg11989485 | 6 | 29815870 | Higher in Smoker |
| ch.11.1306362223 | 11 | 131131012 | Higher in Smoker |
| cg27441058 | 12 | 94498213 | Higher in Smoker |

| | | | |
|---|---|---|---|
| cg01001533 | 10 | 44184868 | Higher in Smoker |
| ch.2.71774667F | 2 | 71921159 | Higher in Smoker |
| cg19039340 | 19 | 34625816 | Higher in Smoker |
| cg15904764 | 14 | 21101308 | Higher in Smoker |
| cg16264722 | 12 | 108647479 | Higher in Smoker |
| cg12880602 | 6 | 91321150 | Higher in Smoker |
| cg01861574 | 7 | 104624590 | Higher in Smoker |
| cg10565662 | 8 | 2670187 | Higher in Smoker |
| cg15386877 | 6 | 161258456 | Higher in Smoker |
| cg20708061 | 12 | 131958981 | Higher in Smoker |
| cg05604874 | 17 | 80200785 | Higher in Smoker |
| cg07433923 | 6 | 147827800 | Higher in Smoker |
| cg05933623 | 1 | 223254899 | Higher in Smoker |
| cg20446824 | 12 | 125076771 | Higher in Smoker |
| cg02940101 | 3 | 138552891 | Higher in Smoker |
| cg02671126 | 9 | 34701735 | Higher in Smoker |
| cg03223659 | 1 | 23340833 | Higher in Smoker |
| cg02682052 | 19 | 3468058 | Higher in Smoker |
| cg03538169 | 6 | 150260156 | Higher in Smoker |
| cg03706086 | 8 | 71391216 | Higher in Smoker |
| cg05814027 | 1 | 2345894 | Higher in Smoker |
| cg26495867 | 5 | 131812112 | Higher in Smoker |
| cg11845426 | 10 | 31892464 | Higher in Smoker |
| ch.20.46106799F | 20 | 46673392 | Higher in Smoker |
| cg00286853 | 16 | 86528753 | Higher in Smoker |
| cg15325070 | 1 | 2792704 | Higher in Smoker |
| cg23991368 | 14 | 102414729 | Higher in Smoker |
| cg06841024 | 3 | 12933799 | Higher in Smoker |
| cg14094460 | 4 | 43900946 | Higher in Smoker |
| cg17940198 | 18 | 74204830 | Higher in Smoker |
| cg25808609 | 13 | 114917199 | Higher in Smoker |
| cg07492962 | 19 | 4173515 | Higher in Smoker |
| cg13891539 | 12 | 30322730 | Higher in Smoker |
| cg27353629 | 8 | 144309591 | Higher in Smoker |
| cg03112518 | 19 | 491572 | Higher in Smoker |

| | | | |
|---|---|---|---|
| cg09858655 | 2 | 132431334 | Higher in Smoker |
| cg27140441 | 4 | 184328596 | Higher in Smoker |
| cg19797930 | 2 | 242481817 | Higher in Smoker |
| cg22452543 | X | 149530926 | Higher in Smoker |
| cg15961693 | 6 | 139689053 | Higher in Smoker |
| cg20101110 | 11 | 16631939 | Higher in Smoker |
| cg12635937 | 4 | 61184925 | Higher in Smoker |
| cg22140793 | 8 | 95286745 | Higher in Smoker |
| cg00339687 | 1 | 161348895 | Higher in Smoker |
| cg18191540 | 14 | 107281437 | Higher in Smoker |
| cg27525185 | 19 | 36869526 | Higher in Smoker |
| cg05847075 | 12 | 76706337 | Higher in Smoker |
| cg00209037 | 22 | 46443395 | Higher in Smoker |
| cg22940953 | 21 | 15096426 | Higher in Smoker |
| cg13185745 | 14 | 104674793 | Higher in Smoker |
| cg12279688 | 4 | 189333449 | Higher in Smoker |
| cg07675285 | 16 | 27121267 | Higher in Smoker |
| cg09583921 | 3 | 87101925 | Higher in Smoker |
| cg10786279 | 9 | 139294812 | Higher in Smoker |
| cg13104880 | 7 | 155790512 | Higher in Smoker |
| cg20104126 | 12 | 46665816 | Higher in Smoker |
| cg00695049 | 5 | 180673395 | Higher in Smoker |
| cg27445281 | 6 | 6956307 | Higher in Smoker |
| cg14548259 | 12 | 116946214 | Higher in Smoker |
| cg01583134 | 8 | 67026111 | Higher in Smoker |
| cg09531019 | 5 | 159321157 | Higher in Smoker |
| cg02583163 | 10 | 132291878 | Higher in Smoker |
| ch.4.188979129F | 4 | 188742135 | Higher in Smoker |
| cg18457851 | X | 40104514 | Higher in Smoker |
| cg00965168 | 1 | 227974541 | Higher in Smoker |
| cg14523734 | 7 | 128020864 | Higher in Smoker |
| cg27637930 | 11 | 121297943 | Higher in Smoker |
| cg27431049 | 7 | 148638192 | Higher in Smoker |
| cg27537046 | 3 | 197387652 | Higher in Smoker |
| cg22698904 | 3 | 35680387 | Higher in Smoker |

| | | | |
|---|---|---|---|
| cg09088892 | 7 | 128170611 | Higher in Smoker |
| cg00163419 | 17 | 47270433 | Higher in Smoker |
| cg10384064 | 14 | 95156065 | Higher in Smoker |
| cg04675861 | 13 | 77903399 | Higher in Smoker |
| cg05533119 | 20 | 23343103 | Higher in Smoker |
| cg03631864 | 7 | 155260630 | Higher in Smoker |
| cg27387615 | X | 136627957 | Higher in Smoker |
| cg06739866 | 14 | 22314682 | Higher in Smoker |
| cg02666837 | 6 | 170578692 | Higher in Smoker |
| cg04494789 | 1 | 147807192 | Higher in Smoker |
| cg19204834 | 12 | 6281453 | Higher in Smoker |
| cg24609094 | 13 | 25319768 | Higher in Smoker |
| cg16508981 | X | 54669118 | Higher in Smoker |
| cg09015484 | 9 | 96929106 | Higher in Smoker |
| cg16206504 | 13 | 114917223 | Higher in Smoker |
| cg13962846 | 1 | 7973298 | Higher in Smoker |
| cg00242035 | 11 | 47416358 | Higher in Smoker |
| cg13022905 | 5 | 147699892 | Higher in Smoker |
| cg27171869 | 17 | 79451656 | Higher in Smoker |
| cg03914925 | 6 | 170405976 | Higher in Smoker |
| cg24893509 | 18 | 77547348 | Higher in Smoker |
| cg23407565 | X | 50024476 | Higher in Smoker |
| cg16669602 | 16 | 88385539 | Higher in Smoker |
| ch.2.39602547R | 2 | 39749043 | Higher in Smoker |
| cg27600449 | 12 | 107296829 | Higher in Smoker |
| cg21933197 | 19 | 3091923 | Higher in Smoker |
| cg24322366 | 4 | 190567721 | Higher in Smoker |
| cg04390734 | 11 | 120039366 | Higher in Smoker |
| cg01360115 | 22 | 50747878 | Higher in Smoker |
| cg01561878 | 7 | 27200681 | Higher in Smoker |
| cg15969768 | 3 | 75704573 | Higher in Smoker |
| cg26149658 | 4 | 2439423 | Higher in Smoker |
| cg18746037 | 9 | 68408734 | Higher in Smoker |
| cg17532444 | 15 | 40799368 | Higher in Smoker |
| ch.5.71339689R | 5 | 71303933 | Higher in Smoker |

| | | | |
|---|---|---|---|
| cg20592017 | 15 | 40364740 | Higher in Smoker |
| cg03279470 | 16 | 14379220 | Higher in Smoker |
| ch.8.1535391 | 8 | 5021898 | Higher in Smoker |
| cg19268708 | 1 | 2837518 | Higher in Smoker |
| cg08874067 | 13 | 19449177 | Higher in Smoker |
| cg03263247 | 17 | 20456385 | Higher in Smoker |
| cg08245147 | 7 | 151077624 | Higher in Smoker |
| cg02496447 | 16 | 15252838 | Higher in Smoker |
| cg17300333 | 17 | 13759255 | Higher in Smoker |
| cg26823466 | 5 | 90576256 | Higher in Smoker |
| cg11917780 | X | 49010944 | Higher in Smoker |
| cg14708893 | 7 | 36124863 | Higher in Smoker |
| cg10061805 | 10 | 111695004 | Higher in Smoker |
| cg19927373 | 8 | 429706 | Higher in Smoker |
| cg08089702 | 22 | 21822289 | Higher in Smoker |
| cg15078822 | 7 | 52341469 | Higher in Smoker |
| cg13808145 | 11 | 115024483 | Higher in Smoker |
| cg05677712 | 3 | 195586796 | Higher in Smoker |
| cg16149927 | 21 | 45198592 | Higher in Smoker |
| cg09526424 | 7 | 73270015 | Higher in Smoker |
| cg04181542 | 6 | 100584390 | Higher in Smoker |
| cg14927083 | 9 | 132175840 | Higher in Smoker |
| cg15783696 | 16 | 68564277 | Higher in Smoker |
| cg04358741 | 12 | 49739537 | Higher in Smoker |
| cg22785562 | 4 | 38184969 | Higher in Smoker |
| cg12515684 | 10 | 6203261 | Higher in Smoker |
| cg24958366 | 17 | 46952555 | Higher in Smoker |
| cg04697635 | 5 | 80181030 | Higher in Smoker |
| cg27108452 | 3 | 32822410 | Higher in Smoker |
| cg14278260 | 16 | 50280495 | Higher in Smoker |
| cg19523937 | 7 | 5060704 | Higher in Smoker |
| cg03672272 | 22 | 46470191 | Higher in Smoker |
| cg00949922 | 1 | 16514382 | Higher in Smoker |
| cg10096579 | 4 | 3572794 | Higher in Smoker |
| cg07700843 | 1 | 2391317 | Higher in Smoker |

| | | | |
|---|---|---|---|
| cg21864961 | 12 | 1656337 | Higher in Smoker |
| cg14643686 | 12 | 12264390 | Higher in Smoker |
| cg00800634 | 4 | 3882420 | Higher in Smoker |
| cg01978544 | 6 | 30418858 | Higher in Smoker |
| cg08704196 | 16 | 34787392 | Higher in Smoker |
| cg12144689 | 22 | 24820090 | Higher in Smoker |
| cg23967809 | 6 | 141647656 | Higher in Smoker |
| cg03376871 | 16 | 33938155 | Higher in Smoker |
| cg25986403 | 2 | 64978331 | Higher in Smoker |
| cg07633701 | 3 | 112021096 | Higher in Smoker |
| cg24901447 | 12 | 117036895 | Higher in Smoker |
| cg21335826 | 2 | 74981960 | Higher in Smoker |
| cg05295703 | 2 | 102895712 | Higher in Smoker |
| cg17839721 | 2 | 97193174 | Higher in Smoker |
| cg09234053 | 4 | 160024219 | Higher in Smoker |
| cg03505616 | 7 | 65958755 | Higher in Smoker |
| cg12647302 | 1 | 17201791 | Higher in Smoker |
| cg23234622 | 2 | 11621543 | Higher in Smoker |
| cg00639475 | 12 | 95228478 | Higher in Smoker |
| cg09238726 | 6 | 167315975 | Higher in Smoker |
| cg03202557 | 6 | 29617599 | Higher in Smoker |
| cg08658318 | 21 | 46351329 | Higher in Smoker |
| cg18654956 | 9 | 68377657 | Higher in Smoker |
| cg19670610 | 4 | 89455337 | Higher in Smoker |
| cg09605095 | 2 | 5847414 | Higher in Smoker |
| cg10117884 | 1 | 166955898 | Higher in Smoker |
| cg03672716 | 3 | 75708104 | Higher in Smoker |
| cg23203755 | 3 | 149182974 | Higher in Smoker |
| cg23575858 | 2 | 237712268 | Higher in Smoker |
| cg07526598 | 17 | 18295431 | Higher in Smoker |
| cg04246864 | 16 | 33357426 | Higher in Smoker |
| cg04305870 | 14 | 75725648 | Higher in Smoker |
| cg07967114 | 12 | 94915694 | Higher in Smoker |
| cg19839801 | 11 | 49913868 | Higher in Smoker |
| cg08104224 | 16 | 11588532 | Higher in Smoker |

| | | | |
|---|---|---|---|
| cg19367522 | 17 | 16492836 | Higher in Smoker |
| cg05266155 | 13 | 44544993 | Higher in Smoker |
| cg01536979 | 8 | 117840383 | Higher in Smoker |
| cg18221983 | 6 | 16198548 | Higher in Smoker |
| cg07154950 | 22 | 24370586 | Higher in Smoker |
| cg03259292 | 10 | 88162925 | Higher in Smoker |
| cg02535684 | 10 | 33339108 | Higher in Smoker |
| cg18100887 | 17 | 34611341 | Higher in Smoker |
| cg10480950 | 6 | 5067127 | Higher in Smoker |
| cg13424393 | 17 | 80569923 | Higher in Smoker |
| cg02600551 | 19 | 2950360 | Higher in Smoker |
| cg21428780 | 2 | 175582887 | Higher in Smoker |
| cg23180636 | 3 | 44140250 | Higher in Smoker |
| cg05970777 | 16 | 34490033 | Higher in Smoker |
| cg22874828 | X | 115004495 | Higher in Smoker |
| cg06758994 | 7 | 7034759 | Higher in Smoker |
| cg25575145 | 11 | 2233644 | Higher in Smoker |
| cg09225973 | 6 | 150232183 | Higher in Smoker |
| cg14284541 | 17 | 79998785 | Higher in Smoker |
| cg02980235 | 16 | 72258237 | Higher in Smoker |
| cg01762011 | X | 139173393 | Higher in Smoker |
| cg17978293 | 17 | 217614 | Higher in Smoker |
| cg11397149 | 1 | 19397963 | Higher in Smoker |
| cg05488217 | 11 | 58730897 | Higher in Smoker |
| cg23513183 | 19 | 2858944 | Higher in Smoker |
| cg01234379 | 16 | 88168314 | Higher in Smoker |
| cg08239426 | 1 | 244965954 | Higher in Smoker |
| cg05527416 | 7 | 55413168 | Higher in Smoker |
| cg07788167 | 7 | 57484272 | Higher in Smoker |
| cg15604170 | 13 | 19203463 | Higher in Smoker |
| cg05113078 | 3 | 12583485 | Higher in Smoker |
| cg13580862 | 1 | 55709508 | Higher in Smoker |
| cg07146984 | 6 | 109706151 | Higher in Smoker |
| cg10346475 | 10 | 29185822 | Higher in Smoker |
| cg24003020 | 10 | 72216624 | Higher in Smoker |

| | | | |
|---|---|---|---|
| cg16889350 | 10 | 2565606 | Higher in Smoker |
| cg04096697 | 6 | 37012867 | Higher in Smoker |
| cg07601148 | 13 | 20975917 | Higher in Smoker |
| cg12024160 | 4 | 1254474 | Higher in Smoker |
| cg27180412 | 1 | 143277743 | Higher in Smoker |
| cg00101287 | 5 | 956343 | Higher in Smoker |
| cg16085366 | 5 | 34188338 | Higher in Smoker |
| cg08792388 | 6 | 167560727 | Higher in Smoker |
| cg09264558 | 1 | 237144735 | Higher in Smoker |
| cg06601581 | 16 | 85404654 | Higher in Smoker |
| cg07415373 | 22 | 27153015 | Higher in Smoker |
| cg16434511 | 2 | 3151078 | Higher in Smoker |
| cg24507423 | 1 | 24275698 | Higher in Smoker |
| cg10533060 | 16 | 30430148 | Higher in Smoker |
| cg12978357 | 2 | 114426529 | Higher in Smoker |
| cg03299531 | 16 | 88476651 | Higher in Smoker |
| cg01259524 | 14 | 50055211 | Higher in Smoker |
| cg10021724 | 13 | 25562840 | Higher in Smoker |
| cg09394377 | 13 | 21676139 | Higher in Smoker |
| cg26623476 | 2 | 202988253 | Higher in Smoker |
| cg00920546 | 22 | 4159049 | Higher in Smoker |
| cg06606511 | 5 | 261389 | Higher in Smoker |
| cg22824450 | 7 | 75472763 | Higher in Smoker |
| cg20883195 | 2 | 241172262 | Higher in Smoker |
| cg07388711 | 12 | 1226417 | Higher in Smoker |
| cg17869339 | 1 | 148897999 | Higher in Smoker |
| cg00470192 | 16 | 28953867 | Higher in Smoker |
| cg03678938 | 5 | 50218876 | Higher in Smoker |
| cg02022519 | 11 | 115830067 | Higher in Smoker |
| cg27544384 | 6 | 170585971 | Higher in Smoker |
| cg22948085 | 3 | 155817341 | Higher in Smoker |
| cg06659875 | 5 | 149841965 | Higher in Smoker |
| cg21784781 | 1 | 26204593 | Higher in Smoker |
| cg03963784 | 7 | 144114242 | Higher in Smoker |
| cg08959585 | 11 | 130207562 | Higher in Smoker |

| | | | |
|---|---|---|---|
| cg09390022 | 8 | 53485670 | Higher in Smoker |
| cg04362716 | 2 | 128441417 | Higher in Smoker |
| cg15798163 | 13 | 113933520 | Higher in Smoker |
| cg26141807 | 5 | 62100540 | Higher in Smoker |
| cg07792320 | 1 | 39174721 | Higher in Smoker |
| cg26778317 | 16 | 33374028 | Higher in Smoker |
| cg08997193 | 6 | 132102258 | Higher in Smoker |
| cg09982321 | 7 | 54949472 | Higher in Smoker |
| cg20671781 | 10 | 43626471 | Higher in Smoker |
| cg09115837 | 10 | 79541592 | Higher in Smoker |
| cg23200818 | 12 | 133414294 | Higher in Smoker |
| cg15921012 | 3 | 15919793 | Higher in Smoker |
| cg23901896 | 1 | 201976446 | Higher in Smoker |
| cg18184147 | 14 | 19925080 | Higher in Smoker |
| cg22346032 | 8 | 1048841 | Higher in Smoker |
| cg18176509 | 1 | 94305707 | Higher in Smoker |
| cg13628325 | 7 | 149128236 | Higher in Smoker |
| cg22501690 | 5 | 125932790 | Higher in Smoker |
| cg23215275 | 13 | 19301347 | Higher in Smoker |
| cg09807446 | 16 | 1171603 | Higher in Smoker |
| cg17698584 | 3 | 127006287 | Higher in Smoker |
| cg21073776 | 6 | 7426189 | Higher in Smoker |
| cg05370471 | 2 | 118594649 | Higher in Smoker |
| cg21548464 | 13 | 50707937 | Higher in Smoker |
| cg20980303 | 6 | 435810 | Lower in Smoker |
| cg25223552 | 2 | 209225600 | Lower in Smoker |
| cg23139173 | 13 | 111589973 | Lower in Smoker |
| cg01048749 | 2 | 8724685 | Lower in Smoker |
| cg20490773 | 12 | 90313611 | Lower in Smoker |
| cg21757740 | 5 | 1538524 | Lower in Smoker |
| cg25581448 | 6 | 106582669 | Lower in Smoker |
| cg19707243 | 2 | 152042675 | Lower in Smoker |
| cg03664916 | 16 | 89674560 | Lower in Smoker |
| cg26601431 | 1 | 235054899 | Lower in Smoker |
| cg23674647 | 1 | 92001147 | Lower in Smoker |

| | | | |
|---|---|---|---|
| cg03311134 | 10 | 134807208 | Lower in Smoker |
| cg26160191 | 2 | 242853007 | Lower in Smoker |
| cg27159477 | 6 | 36641584 | Lower in Smoker |
| cg13005636 | 13 | 20392706 | Lower in Smoker |
| cg08902549 | 4 | 2540209 | Lower in Smoker |
| cg11960033 | 5 | 127323755 | Lower in Smoker |
| cg12342520 | 7 | 1393991 | Lower in Smoker |
| cg16907531 | 10 | 4194418 | Lower in Smoker |
| cg14023367 | 9 | 4744503 | Lower in Smoker |
| cg10030512 | 7 | 2656424 | Lower in Smoker |
| cg11113661 | 21 | 45622373 | Lower in Smoker |
| cg23245663 | 8 | 1298579 | Lower in Smoker |
| cg17106450 | 2 | 206954366 | Lower in Smoker |
| cg08539728 | 16 | 74326920 | Lower in Smoker |
| cg26174326 | 6 | 26016674 | Lower in Smoker |
| cg10023749 | 12 | 132303409 | Lower in Smoker |
| cg04216070 | 15 | 101712402 | Lower in Smoker |
| cg23667707 | 7 | 152569949 | Lower in Smoker |
| cg07013450 | 12 | 79198254 | Lower in Smoker |
| cg07873537 | 8 | 125316349 | Lower in Smoker |
| cg20119759 | 4 | 183794591 | Lower in Smoker |
| cg18755230 | 7 | 150100785 | Lower in Smoker |
| cg24739513 | 15 | 21905654 | Lower in Smoker |
| cg22154485 | 12 | 105153464 | Lower in Smoker |
| cg07618101 | 3 | 160879687 | Lower in Smoker |
| cg18953039 | 10 | 1031432 | Lower in Smoker |
| cg13814720 | 9 | 91193175 | Lower in Smoker |
| cg09993078 | 14 | 94448493 | Lower in Smoker |
| cg24823485 | 3 | 42626083 | Lower in Smoker |
| cg07855447 | 2 | 168401353 | Lower in Smoker |
| cg14135272 | 6 | 166799902 | Lower in Smoker |
| cg09946603 | 6 | 56297393 | Lower in Smoker |
| cg27535341 | 8 | 27449470 | Lower in Smoker |
| cg04304434 | 19 | 16305455 | Lower in Smoker |
| cg09447182 | 16 | 9277625 | Lower in Smoker |

| | | | |
|---|---|---|---|
| cg07209034 | 16 | 72459825 | Lower in Smoker |
| cg04849298 | 8 | 142309389 | Lower in Smoker |
| cg09483329 | 6 | 426770 | Lower in Smoker |
| cg13177453 | 6 | 111179373 | Lower in Smoker |
| cg03351580 | 6 | 166666210 | Lower in Smoker |
| cg05256967 | 3 | 81816600 | Lower in Smoker |
| cg05554592 | 3 | 107723149 | Lower in Smoker |
| cg12281325 | 19 | 32893668 | Lower in Smoker |
| cg01113401 | 6 | 146139656 | Lower in Smoker |
| cg16095411 | 17 | 55762444 | Lower in Smoker |
| cg03502001 | 13 | 29298122 | Lower in Smoker |
| cg05152568 | 15 | 70799556 | Lower in Smoker |
| cg08810419 | 16 | 84696447 | Lower in Smoker |
| cg25072359 | 17 | 41440525 | Lower in Smoker |
| cg02317534 | 7 | 22705333 | Lower in Smoker |
| cg17378509 | 4 | 4557712 | Lower in Smoker |
| cg18813177 | 15 | 93584909 | Lower in Smoker |
| cg18810797 | 2 | 144452920 | Lower in Smoker |
| cg03038061 | 16 | 47070186 | Lower in Smoker |
| cg20306821 | 10 | 32639458 | Lower in Smoker |
| cg02742996 | 10 | 70477819 | Lower in Smoker |
| cg07421245 | 4 | 89209240 | Lower in Smoker |
| cg26556624 | 18 | 9099862 | Lower in Smoker |
| cg24931017 | 20 | 59600990 | Lower in Smoker |
| cg16935567 | 6 | 32896516 | Lower in Smoker |
| cg04703318 | 11 | 95186117 | Lower in Smoker |
| cg07509464 | 2 | 106359129 | Lower in Smoker |
| cg27657685 | 20 | 5594689 | Lower in Smoker |
| cg01564165 | 13 | 114109526 | Lower in Smoker |
| cg11570843 | 10 | 27552270 | Lower in Smoker |
| cg01412379 | 2 | 38742665 | Lower in Smoker |
| cg00513941 | 19 | 42437245 | Lower in Smoker |
| cg03995102 | 3 | 39497808 | Lower in Smoker |
| cg11571868 | 19 | 53362925 | Lower in Smoker |
| cg15127705 | 10 | 31006017 | Lower in Smoker |

| | | | |
|---|---|---|---|
| cg01769749 | 2 | 68813121 | Lower in Smoker |
| cg10991955 | 12 | 1797536 | Lower in Smoker |
| cg08826066 | 8 | 30780259 | Lower in Smoker |
| cg08882084 | 7 | 65302258 | Lower in Smoker |
| cg16429105 | 16 | 30599761 | Lower in Smoker |
| cg02013918 | 12 | 131170584 | Lower in Smoker |
| cg04250681 | 14 | 71949117 | Lower in Smoker |
| cg24509919 | 1 | 168230886 | Lower in Smoker |
| cg03602886 | 2 | 48507243 | Lower in Smoker |
| cg19275220 | 7 | 108168721 | Lower in Smoker |
| cg17983632 | 6 | 1621930 | Lower in Smoker |
| cg20874668 | 6 | 7685285 | Lower in Smoker |
| cg18148620 | 12 | 68953689 | Lower in Smoker |
| cg04985032 | 1 | 944439 | Lower in Smoker |
| cg21663181 | 18 | 5889750 | Lower in Smoker |
| cg26722417 | 12 | 11326931 | Lower in Smoker |
| cg06917858 | 19 | 53403009 | Lower in Smoker |
| cg15716757 | 11 | 121104967 | Lower in Smoker |
| cg00947885 | 1 | 146521800 | Lower in Smoker |
| cg08155465 | 15 | 57176838 | Lower in Smoker |
| cg22486621 | 12 | 2049079 | Lower in Smoker |
| cg13972117 | 8 | 60844458 | Lower in Smoker |
| cg26474203 | 6 | 149547448 | Lower in Smoker |
| cg19365151 | 8 | 103254722 | Lower in Smoker |
| cg14774817 | 2 | 182183372 | Lower in Smoker |
| cg02227026 | 8 | 8173791 | Lower in Smoker |
| cg06645120 | 16 | 39868817 | Lower in Smoker |
| cg03130936 | 19 | 36795950 | Lower in Smoker |
| cg09711279 | 10 | 107711404 | Lower in Smoker |
| cg04108787 | 3 | 23650443 | Lower in Smoker |
| cg21432062 | 3 | 4908643 | Lower in Smoker |
| cg04939172 | 13 | 39179261 | Lower in Smoker |
| cg14740571 | 19 | 52107517 | Lower in Smoker |
| cg12815605 | 8 | 67384873 | Lower in Smoker |
| cg24791846 | 3 | 177000330 | Lower in Smoker |

| | | | |
|---|---|---|---|
| cg18638536 | 19 | 58298162 | Lower in Smoker |
| cg05302064 | 1 | 5922686 | Lower in Smoker |
| cg16975888 | 4 | 83722528 | Lower in Smoker |
| cg13048485 | 1 | 161586339 | Lower in Smoker |
| cg22903905 | 8 | 104012296 | Lower in Smoker |
| cg07593978 | 11 | 33400574 | Lower in Smoker |
| cg01162573 | 4 | 141715259 | Lower in Smoker |
| cg02279153 | 1 | 178507396 | Lower in Smoker |
| cg27241416 | 6 | 86392657 | Lower in Smoker |
| cg20977198 | 6 | 164061673 | Lower in Smoker |
| cg20198393 | 13 | 101194647 | Lower in Smoker |
| cg15327559 | 1 | 180925922 | Lower in Smoker |
| cg12621387 | 12 | 116731539 | Lower in Smoker |
| cg00177657 | 8 | 142278585 | Lower in Smoker |
| cg18116434 | 18 | 12097776 | Lower in Smoker |
| cg02131408 | 14 | 81702510 | Lower in Smoker |
| cg24699719 | 5 | 74913041 | Lower in Smoker |
| cg04056904 | 3 | 182399388 | Lower in Smoker |
| cg19489705 | 5 | 77146291 | Lower in Smoker |
| cg08660555 | 1 | 178508868 | Lower in Smoker |
| cg18899220 | 13 | 20392529 | Lower in Smoker |
| cg02355081 | 2 | 38150157 | Lower in Smoker |
| cg19302462 | 10 | 61669427 | Lower in Smoker |
| cg16997671 | 5 | 179121005 | Lower in Smoker |
| cg07033876 | 4 | 132686116 | Lower in Smoker |
| cg03932161 | 1 | 156848026 | Lower in Smoker |
| cg02145482 | 6 | 64342950 | Lower in Smoker |
| cg17969383 | 6 | 155197031 | Lower in Smoker |
| cg13760257 | 6 | 28832672 | Lower in Smoker |
| cg18820063 | 10 | 90814440 | Lower in Smoker |
| cg04184793 | 4 | 184244831 | Lower in Smoker |
| cg15950936 | 7 | 6914289 | Lower in Smoker |
| cg00105753 | 17 | 30437854 | Lower in Smoker |
| cg11338345 | 3 | 136052698 | Lower in Smoker |
| cg23105899 | 12 | 132611216 | Lower in Smoker |

| | | | |
|---|---|---|---|
| cg25036920 | 20 | 32577692 | Lower in Smoker |
| cg18089238 | 3 | 101493957 | Lower in Smoker |
| cg14380474 | 1 | 221975083 | Lower in Smoker |
| cg11307296 | 8 | 25373442 | Lower in Smoker |
| cg00022966 | 1 | 205747925 | Lower in Smoker |
| cg04251886 | 14 | 51414420 | Lower in Smoker |
| cg16379371 | 7 | 28275863 | Lower in Smoker |
| cg25129000 | 5 | 3325695 | Lower in Smoker |
| cg08996709 | 2 | 168525214 | Lower in Smoker |
| cg03254102 | 17 | 75237270 | Lower in Smoker |
| cg03211636 | 1 | 8354313 | Lower in Smoker |
| cg09164726 | 16 | 86121040 | Lower in Smoker |
| cg00334453 | 16 | 901023 | Lower in Smoker |
| cg02959966 | 2 | 26364971 | Lower in Smoker |
| cg06739333 | 13 | 41245484 | Lower in Smoker |
| cg09483967 | 12 | 109166645 | Lower in Smoker |
| cg20471241 | 18 | 47344134 | Lower in Smoker |
| cg03039519 | 14 | 93699218 | Lower in Smoker |
| cg18892424 | 10 | 131034796 | Lower in Smoker |
| cg15908953 | 4 | 163661836 | Lower in Smoker |
| cg01069459 | 5 | 173739739 | Lower in Smoker |
| cg25266533 | 10 | 90879549 | Lower in Smoker |
| cg16472945 | 2 | 86888210 | Lower in Smoker |
| cg08067030 | 11 | 10934109 | Lower in Smoker |
| cg16247733 | 1 | 62193198 | Lower in Smoker |
| cg09269276 | 4 | 140219912 | Lower in Smoker |
| cg18867202 | 19 | 6537434 | Lower in Smoker |
| cg13376438 | 7 | 108168711 | Lower in Smoker |
| cg01528913 | 2 | 118942638 | Lower in Smoker |
| cg02531614 | 6 | 131455450 | Lower in Smoker |
| cg10443159 | 7 | 7839258 | Lower in Smoker |
| cg01716527 | 3 | 170072769 | Lower in Smoker |
| cg00263326 | 7 | 35838357 | Lower in Smoker |
| cg20362689 | 8 | 112482677 | Lower in Smoker |
| cg11270005 | 2 | 58133858 | Lower in Smoker |

| | | | |
|---|---|---|---|
| cg05961962 | 16 | 72602838 | Lower in Smoker |
| cg23559165 | 12 | 8598739 | Lower in Smoker |
| cg19463193 | 15 | 68564546 | Lower in Smoker |
| cg13493091 | 6 | 28954762 | Lower in Smoker |
| cg02866996 | 6 | 33340235 | Lower in Smoker |
| cg26232346 | 2 | 27269613 | Lower in Smoker |
| cg07744536 | 3 | 25915549 | Lower in Smoker |
| cg18115969 | 1 | 169457855 | Lower in Smoker |
| cg06325996 | 3 | 10288127 | Lower in Smoker |
| cg20289531 | 6 | 89774872 | Lower in Smoker |
| cg17976731 | 17 | 46139285 | Lower in Smoker |
| cg22120373 | 7 | 131288554 | Lower in Smoker |
| cg00457720 | 12 | 76744781 | Lower in Smoker |
| cg01574912 | 7 | 585154 | Lower in Smoker |
| cg06794020 | 10 | 120963611 | Lower in Smoker |
| cg20380755 | 5 | 153546243 | Lower in Smoker |
| cg16630453 | 6 | 115562293 | Lower in Smoker |
| cg22240394 | 3 | 186211630 | Lower in Smoker |
| cg25626936 | 8 | 60531025 | Lower in Smoker |
| cg26119382 | 1 | 155561091 | Lower in Smoker |
| cg05380693 | 3 | 30535166 | Lower in Smoker |
| cg05565400 | 11 | 15963106 | Lower in Smoker |
| cg16774421 | 12 | 27481875 | Lower in Smoker |
| cg16207905 | 12 | 72231287 | Lower in Smoker |
| cg26640424 | 2 | 134956853 | Lower in Smoker |
| cg04038601 | 22 | 21059300 | Lower in Smoker |
| cg24683293 | 3 | 12517725 | Lower in Smoker |
| cg17778453 | 3 | 195724371 | Lower in Smoker |
| cg00894449 | 1 | 8280499 | Lower in Smoker |
| cg05269024 | 8 | 38085392 | Lower in Smoker |
| cg01654519 | 12 | 69631105 | Lower in Smoker |
| cg20591353 | 4 | 4171354 | Lower in Smoker |
| cg13601659 | 9 | 98979119 | Lower in Smoker |
| cg08090019 | 14 | 91886654 | Lower in Smoker |
| cg14953536 | 2 | 191188675 | Lower in Smoker |

| | | | |
|---|---|---|---|
| cg12292630 | 11 | 30386843 | Lower in Smoker |
| cg20434819 | 3 | 47145527 | Lower in Smoker |
| cg03186157 | 7 | 115321344 | Lower in Smoker |
| cg06182196 | 8 | 48049326 | Lower in Smoker |
| cg02455471 | 5 | 77146197 | Lower in Smoker |
| cg13976610 | 7 | 142970460 | Lower in Smoker |
| cg06676006 | 4 | 151179898 | Lower in Smoker |
| cg13453288 | 1 | 53166996 | Lower in Smoker |
| cg00008800 | 2 | 38710171 | Lower in Smoker |
| cg20095831 | 7 | 66332120 | Lower in Smoker |
| cg17450505 | 6 | 2515297 | Lower in Smoker |
| cg04636251 | 5 | 124537511 | Lower in Smoker |
| cg23531130 | 10 | 66125478 | Lower in Smoker |
| cg16396921 | 1 | 32753767 | Lower in Smoker |
| cg22144583 | 19 | 1307606 | Lower in Smoker |
| cg07712598 | 2 | 242165230 | Lower in Smoker |
| cg02963624 | 16 | 12012117 | Lower in Smoker |
| cg06435967 | 4 | 121471496 | Lower in Smoker |
| cg12033909 | 17 | 39797940 | Lower in Smoker |
| cg00347518 | 20 | 23337006 | Lower in Smoker |
| cg14607363 | 15 | 63366820 | Lower in Smoker |
| cg26523459 | 2 | 174146545 | Lower in Smoker |
| cg22739314 | 4 | 1334729 | Lower in Smoker |
| cg07575770 | 4 | 174081857 | Lower in Smoker |
| cg16295774 | 3 | 29157101 | Lower in Smoker |
| cg16901862 | 12 | 563019 | Lower in Smoker |
| cg05124242 | 4 | 47845589 | Lower in Smoker |
| cg18818267 | 8 | 142311072 | Lower in Smoker |
| cg01178772 | 16 | 77221668 | Lower in Smoker |
| cg00290039 | 3 | 197106029 | Lower in Smoker |
| cg26499089 | 10 | 30248887 | Lower in Smoker |
| cg26013796 | 12 | 46948457 | Lower in Smoker |
| cg05717473 | 6 | 387276 | Lower in Smoker |
| cg12667933 | 8 | 142261706 | Lower in Smoker |
| cg06973463 | 1 | 1002664 | Lower in Smoker |

| | | | |
|---|---|---|---|
| cg23980005 | 7 | 121040311 | Lower in Smoker |
| cg14296446 | 14 | 74683524 | Lower in Smoker |
| cg03765543 | 2 | 232543659 | Lower in Smoker |
| cg00341843 | 10 | 851265 | Lower in Smoker |
| cg26909864 | 16 | 21390421 | Lower in Smoker |
| cg17117651 | 12 | 121075585 | Lower in Smoker |
| cg24860345 | 6 | 144412862 | Lower in Smoker |
| cg11148483 | 3 | 28393736 | Lower in Smoker |
| cg03291430 | 3 | 186488698 | Lower in Smoker |
| cg18158524 | 14 | 46283172 | Lower in Smoker |
| cg22087953 | 7 | 4584700 | Lower in Smoker |
| cg09734033 | 7 | 30630200 | Lower in Smoker |
| cg22608996 | 8 | 99917762 | Lower in Smoker |
| cg22555741 | 7 | 48170072 | Lower in Smoker |
| cg17331781 | 11 | 33265440 | Lower in Smoker |
| cg03572664 | 14 | 61544141 | Lower in Smoker |
| cg13009965 | 4 | 184403403 | Lower in Smoker |
| cg27417031 | 15 | 59160318 | Lower in Smoker |
| cg01436665 | 10 | 176774 | Lower in Smoker |
| cg21408197 | 2 | 114534240 | Lower in Smoker |
| cg12802537 | 1 | 221870819 | Lower in Smoker |
| cg23657809 | 1 | 43847821 | Lower in Smoker |
| cg01986911 | 12 | 54612942 | Lower in Smoker |
| cg24354958 | 8 | 49954840 | Lower in Smoker |
| cg18146246 | 4 | 1554677 | Lower in Smoker |
| cg11201854 | 5 | 127148879 | Lower in Smoker |
| cg03680753 | 6 | 155169200 | Lower in Smoker |
| cg14945917 | 4 | 3814564 | Lower in Smoker |
| cg04458281 | 8 | 41433172 | Lower in Smoker |
| cg13962000 | 8 | 119138130 | Lower in Smoker |
| cg01276845 | 7 | 129467115 | Lower in Smoker |
| cg18691254 | 10 | 89969136 | Lower in Smoker |
| cg27547053 | 1 | 5665147 | Lower in Smoker |
| cg16392111 | 1 | 55218005 | Lower in Smoker |
| cg08631887 | 13 | 30692581 | Lower in Smoker |

| | | | |
|---|---|---|---|
| cg16768376 | 13 | 20392608 | Lower in Smoker |
| cg06600200 | 19 | 49455351 | Lower in Smoker |
| cg09023739 | 16 | 1858923 | Lower in Smoker |
| cg20207314 | 3 | 22112343 | Lower in Smoker |
| cg13750350 | 19 | 4004503 | Lower in Smoker |
| cg16669468 | 7 | 76588012 | Lower in Smoker |
| cg06536115 | 1 | 109417235 | Lower in Smoker |
| cg02739052 | 2 | 239332774 | Lower in Smoker |
| cg06894723 | 13 | 110393142 | Lower in Smoker |
| cg00190412 | 6 | 10836303 | Lower in Smoker |
| cg09437909 | 19 | 58975129 | Lower in Smoker |
| cg04170535 | 2 | 161127677 | Lower in Smoker |
| cg14067341 | 9 | 135232075 | Lower in Smoker |
| cg07783291 | 19 | 33178679 | Lower in Smoker |
| cg00868636 | 6 | 167511537 | Lower in Smoker |
| cg07185247 | 1 | 248097461 | Lower in Smoker |
| cg05406637 | 14 | 51332290 | Lower in Smoker |
| cg00442308 | 11 | 1488761 | Lower in Smoker |
| cg02195995 | 7 | 18425285 | Lower in Smoker |
| cg14593420 | 12 | 1708017 | Lower in Smoker |
| cg12416290 | 3 | 137432762 | Lower in Smoker |
| cg09894631 | 16 | 54542303 | Lower in Smoker |
| cg11911286 | 2 | 109177239 | Lower in Smoker |
| cg27305903 | 16 | 85320585 | Lower in Smoker |
| cg06832861 | 5 | 96146726 | Lower in Smoker |
| cg22389715 | 2 | 109062363 | Lower in Smoker |
| cg13740757 | 7 | 35746982 | Lower in Smoker |
| cg18150837 | 1 | 101763159 | Lower in Smoker |
| cg07668586 | 3 | 11772215 | Lower in Smoker |
| cg16338012 | 6 | 110850262 | Lower in Smoker |
| cg24971227 | 3 | 77890638 | Lower in Smoker |
| cg25115503 | 2 | 74678841 | Lower in Smoker |
| cg23283646 | 2 | 164999854 | Lower in Smoker |
| cg15562315 | 13 | 79693110 | Lower in Smoker |
| cg23630276 | 2 | 63290522 | Lower in Smoker |

| | | | |
|---|---|---|---|
| cg10058692 | 1 | 116690992 | Lower in Smoker |
| cg01316857 | 19 | 48685724 | Lower in Smoker |
| cg11941231 | 4 | 165928549 | Lower in Smoker |
| cg04921690 | 7 | 23244034 | Lower in Smoker |
| cg08599962 | 7 | 65508086 | Lower in Smoker |
| cg22120652 | 5 | 3932145 | Lower in Smoker |
| cg27513225 | 4 | 83997661 | Lower in Smoker |
| cg06396309 | 12 | 75268976 | Lower in Smoker |
| cg09914905 | 16 | 88458618 | Lower in Smoker |
| cg19200561 | 6 | 116615750 | Lower in Smoker |
| cg12929501 | 2 | 209124244 | Lower in Smoker |
| cg13820434 | 2 | 47828743 | Lower in Smoker |
| cg27278640 | 8 | 128520078 | Lower in Smoker |
| cg16422814 | 10 | 123691602 | Lower in Smoker |
| cg13748019 | 9 | 94192481 | Lower in Smoker |
| cg02441892 | 7 | 45159368 | Lower in Smoker |
| cg20009273 | 11 | 95340204 | Lower in Smoker |
| cg26413076 | 12 | 10515091 | Lower in Smoker |
| cg05876687 | 16 | 1467955 | Lower in Smoker |
| cg27215140 | 4 | 111797675 | Lower in Smoker |
| cg26780581 | 6 | 161549519 | Lower in Smoker |
| cg11213717 | 18 | 47866551 | Lower in Smoker |
| cg17873048 | 17 | 46697700 | Lower in Smoker |
| cg01457778 | 2 | 109158267 | Lower in Smoker |
| cg08206156 | 2 | 240658646 | Lower in Smoker |
| cg04138746 | 16 | 17034451 | Lower in Smoker |
| cg15003139 | 10 | 3679950 | Lower in Smoker |
| cg15932961 | 3 | 195869691 | Lower in Smoker |
| cg02401614 | 3 | 182509366 | Lower in Smoker |
| cg17420675 | 6 | 132766912 | Lower in Smoker |
| cg14504536 | 7 | 102792783 | Lower in Smoker |
| cg25832747 | 21 | 45581541 | Lower in Smoker |
| cg18451484 | 12 | 112760326 | Lower in Smoker |
| cg11695041 | 12 | 133035885 | Lower in Smoker |
| cg09664554 | 1 | 27988557 | Lower in Smoker |

| | | | |
|---|---|---|---|
| cg07804658 | 5 | 100108624 | Lower in Smoker |
| cg24057792 | 2 | 192539229 | Lower in Smoker |
| cg06486593 | 9 | 139318467 | Lower in Smoker |
| cg16765129 | 3 | 155026836 | Lower in Smoker |
| cg13307718 | 11 | 85995223 | Lower in Smoker |
| cg18742433 | 10 | 69622412 | Lower in Smoker |
| cg10615811 | 11 | 86619012 | Lower in Smoker |
| cg15370862 | 12 | 31270326 | Lower in Smoker |
| cg24703354 | 17 | 6936921 | Lower in Smoker |
| cg18827511 | X | 151652967 | Lower in Smoker |
| cg23465289 | 5 | 54909384 | Lower in Smoker |
| cg01137792 | 14 | 34971569 | Lower in Smoker |
| cg20816967 | 8 | 124166544 | Lower in Smoker |
| cg04622595 | 1 | 109232037 | Lower in Smoker |
| cg17298818 | 8 | 41420945 | Lower in Smoker |
| cg00579749 | 8 | 83290409 | Lower in Smoker |
| cg18745317 | 5 | 81063103 | Lower in Smoker |
| cg08002746 | 8 | 19961386 | Lower in Smoker |
| cg07811903 | 6 | 145568202 | Lower in Smoker |
| cg20749212 | 11 | 31262762 | Lower in Smoker |
| cg00854560 | 13 | 31002430 | Lower in Smoker |
| cg05010882 | 16 | 52297244 | Lower in Smoker |
| cg23519803 | 6 | 108845846 | Lower in Smoker |
| cg25215594 | 13 | 30981649 | Lower in Smoker |
| cg19471319 | 12 | 49480859 | Lower in Smoker |
| cg03749724 | 11 | 108467652 | Lower in Smoker |
| cg02648581 | 13 | 52381961 | Lower in Smoker |
| cg25369070 | 13 | 112907191 | Lower in Smoker |
| cg03010037 | 16 | 11430375 | Lower in Smoker |
| cg11477414 | 17 | 81052622 | Lower in Smoker |
| cg23923023 | 10 | 106011700 | Lower in Smoker |
| cg18468725 | 5 | 102193800 | Lower in Smoker |
| cg11289878 | 4 | 111121682 | Lower in Smoker |
| cg14260004 | 1 | 232692910 | Lower in Smoker |
| cg06824006 | 10 | 5523110 | Lower in Smoker |

| | | | |
|---|---|---|---|
| cg06621169 | 8 | 146075362 | Lower in Smoker |
| cg01409552 | 16 | 28830997 | Lower in Smoker |
| cg27654476 | 14 | 77503345 | Lower in Smoker |
| cg20825994 | 4 | 25448682 | Lower in Smoker |
| cg23008136 | 2 | 55743936 | Lower in Smoker |
| cg10216367 | 12 | 77463484 | Lower in Smoker |
| cg04130127 | 7 | 138088756 | Lower in Smoker |
| cg05516773 | 8 | 37643811 | Lower in Smoker |
| cg27320666 | 6 | 160885486 | Lower in Smoker |
| cg01813027 | 3 | 183164750 | Lower in Smoker |
| cg22009239 | 8 | 102221396 | Lower in Smoker |
| cg18569606 | 6 | 79624214 | Lower in Smoker |
| cg18606993 | 17 | 1168038 | Lower in Smoker |
| cg18169800 | 12 | 94916291 | Lower in Smoker |
| cg10131088 | 15 | 99979527 | Lower in Smoker |
| cg01979605 | 12 | 94534257 | Lower in Smoker |
| cg15402112 | 12 | 131163547 | Lower in Smoker |
| cg10456168 | 8 | 6924637 | Lower in Smoker |
| cg08323238 | 2 | 237496940 | Lower in Smoker |
| cg09137124 | 16 | 29166983 | Lower in Smoker |
| cg14190534 | 14 | 90848416 | Lower in Smoker |
| cg01746878 | 14 | 56236843 | Lower in Smoker |
| cg14189726 | 4 | 146974615 | Lower in Smoker |
| cg15574316 | 10 | 30071374 | Lower in Smoker |
| cg05892606 | 5 | 117098484 | Lower in Smoker |
| cg09773963 | 12 | 27032649 | Lower in Smoker |
| cg18813159 | 11 | 353762 | Lower in Smoker |
| cg25897891 | 12 | 26345227 | Lower in Smoker |
| cg22223441 | 6 | 11920499 | Lower in Smoker |
| cg03333188 | 16 | 49496733 | Lower in Smoker |
| cg08489228 | 4 | 9505764 | Lower in Smoker |
| cg26865274 | 12 | 50697206 | Lower in Smoker |
| cg02066441 | 1 | 17858588 | Lower in Smoker |
| cg02746640 | 7 | 145689965 | Lower in Smoker |
| cg27287593 | 4 | 139894898 | Lower in Smoker |

| | | | |
|---|---|---|---|
| cg10371042 | 16 | 71479409 | Lower in Smoker |
| cg17362593 | 5 | 115975463 | Lower in Smoker |
| cg11399974 | 4 | 95087436 | Lower in Smoker |
| cg17319097 | 7 | 127779130 | Lower in Smoker |
| cg01794405 | 1 | 198869002 | Lower in Smoker |
| cg01250001 | 8 | 103758088 | Lower in Smoker |
| cg04664628 | 10 | 6916491 | Lower in Smoker |
| cg03784170 | 17 | 8121849 | Lower in Smoker |
| cg13371627 | 1 | 199519142 | Lower in Smoker |
| cg01288748 | 22 | 22577105 | Lower in Smoker |
| cg01620911 | 8 | 785815 | Lower in Smoker |
| cg22295334 | 8 | 135835943 | Lower in Smoker |
| cg24527880 | 11 | 108906099 | Lower in Smoker |
| cg13906874 | 11 | 130089912 | Lower in Smoker |
| cg13263013 | 6 | 420130 | Lower in Smoker |
| cg04058305 | 2 | 104996109 | Lower in Smoker |
| cg00210839 | 7 | 70543490 | Lower in Smoker |
| cg21931263 | 5 | 67715050 | Lower in Smoker |
| cg00302979 | 4 | 124261320 | Lower in Smoker |
| cg26636398 | 5 | 31682503 | Lower in Smoker |
| cg23072921 | 13 | 27995121 | Lower in Smoker |
| cg25062197 | 8 | 90894030 | Lower in Smoker |
| cg25208740 | 15 | 42780090 | Lower in Smoker |
| cg06540578 | 15 | 78375824 | Lower in Smoker |
| cg08208899 | 2 | 181931215 | Lower in Smoker |
| cg00119364 | 3 | 138136952 | Lower in Smoker |
| cg19372063 | 2 | 11118387 | Lower in Smoker |
| cg11171466 | 11 | 1849486 | Lower in Smoker |
| cg23301378 | 7 | 3337443 | Lower in Smoker |
| cg17165585 | 4 | 82781063 | Lower in Smoker |
| cg01940102 | 12 | 1095972 | Lower in Smoker |
| cg22822779 | 13 | 84548755 | Lower in Smoker |
| cg24690924 | 17 | 27509976 | Lower in Smoker |
| cg07601598 | 6 | 14541800 | Lower in Smoker |
| cg08209549 | 10 | 134891011 | Lower in Smoker |

| | | | |
|---|---|---|---|
| cg02362017 | 9 | 131154347 | Lower in Smoker |
| cg24774627 | 5 | 52543882 | Lower in Smoker |
| cg01887633 | 7 | 89949631 | Lower in Smoker |
| cg01314597 | 4 | 4609712 | Lower in Smoker |
| cg27392395 | 8 | 23431014 | Lower in Smoker |
| cg08911237 | 12 | 104750418 | Lower in Smoker |
| cg25637042 | 12 | 4476809 | Lower in Smoker |
| cg15123572 | 13 | 114911570 | Lower in Smoker |
| cg00957505 | 17 | 81054294 | Lower in Smoker |
| cg25253207 | 8 | 61831678 | Lower in Smoker |
| cg08821561 | 12 | 127415035 | Lower in Smoker |
| cg22880475 | 6 | 24980543 | Lower in Smoker |
| cg15449560 | 1 | 17007531 | Lower in Smoker |
| cg08149747 | 6 | 33761600 | Lower in Smoker |
| cg15709435 | 5 | 180612719 | Lower in Smoker |
| cg07700847 | 17 | 80303083 | Lower in Smoker |
| cg00695265 | 7 | 98032586 | Lower in Smoker |
| cg01274753 | 16 | 605144 | Lower in Smoker |
| cg02848315 | 11 | 117045620 | Lower in Smoker |
| cg03872655 | 12 | 133168990 | Lower in Smoker |
| cg04575614 | 1 | 33773691 | Lower in Smoker |
| cg06847471 | 16 | 89315996 | Lower in Smoker |
| cg18902795 | 6 | 166124436 | Lower in Smoker |
| cg21679169 | 1 | 150518766 | Lower in Smoker |
| cg25921563 | 22 | 21993211 | Lower in Smoker |
| cg07186767 | 2 | 8788819 | Lower in Smoker |
| cg26155520 | 1 | 943647 | Lower in Smoker |
| cg27397114 | 8 | 60251872 | Lower in Smoker |
| cg09373875 | 4 | 159182779 | Lower in Smoker |
| cg07523089 | 15 | 21145758 | Lower in Smoker |
| cg07190903 | 11 | 8358374 | Lower in Smoker |
| cg27430444 | 2 | 194954642 | Lower in Smoker |
| cg19249042 | 7 | 108223218 | Lower in Smoker |
| cg26931296 | 7 | 150870852 | Lower in Smoker |
| cg07502454 | 6 | 116577801 | Lower in Smoker |

| | | | |
|---|---|---|---|
| cg09827353 | 2 | 221584360 | Lower in Smoker |
| cg26588398 | 16 | 22214346 | Lower in Smoker |
| cg19010166 | 5 | 1983799 | Lower in Smoker |
| cg17768635 | 10 | 85897036 | Lower in Smoker |
| cg11357079 | 3 | 197835815 | Lower in Smoker |
| cg24028260 | 6 | 139899284 | Lower in Smoker |
| cg16255334 | 13 | 100652448 | Lower in Smoker |
| cg25259815 | X | 134192119 | Lower in Smoker |
| cg18582979 | 7 | 65264459 | Lower in Smoker |
| cg09294136 | 14 | 52239813 | Lower in Smoker |
| cg03667033 | 4 | 25507416 | Lower in Smoker |
| cg04795044 | 3 | 129344706 | Lower in Smoker |
| cg15314588 | 7 | 129470730 | Lower in Smoker |
| cg05250380 | 9 | 140735359 | Lower in Smoker |
| cg02955262 | 12 | 39302027 | Lower in Smoker |
| cg10083258 | 15 | 93362731 | Lower in Smoker |
| cg00506862 | 5 | 176557982 | Lower in Smoker |
| cg10801238 | 3 | 149933002 | Lower in Smoker |
| cg27444609 | 1 | 55477113 | Lower in Smoker |
| cg08323135 | 7 | 53182844 | Lower in Smoker |
| cg02666070 | 5 | 153672690 | Lower in Smoker |
| cg08038741 | 14 | 104061870 | Lower in Smoker |
| cg00874691 | 4 | 77867684 | Lower in Smoker |
| cg06989739 | 1 | 235709461 | Lower in Smoker |
| cg12695487 | 3 | 151625374 | Lower in Smoker |
| cg27543672 | 1 | 84541035 | Lower in Smoker |
| cg22138219 | 8 | 117355748 | Lower in Smoker |
| cg01681290 | 4 | 159686146 | Lower in Smoker |
| cg14785303 | 1 | 4119624 | Lower in Smoker |
| cg19376127 | 6 | 170755891 | Lower in Smoker |
| cg27343660 | 5 | 116289441 | Lower in Smoker |
| cg07766916 | 16 | 88850845 | Lower in Smoker |
| cg22715697 | 13 | 22182258 | Lower in Smoker |
| cg10482532 | 10 | 96946522 | Lower in Smoker |
| cg11280108 | 3 | 51537627 | Lower in Smoker |

| | | | |
|---|---|---|---|
| cg19119609 | 20 | 57331394 | Lower in Smoker |
| cg12574416 | 6 | 55540484 | Lower in Smoker |
| cg01723163 | 8 | 126390552 | Lower in Smoker |
| cg09523601 | 16 | 66308269 | Lower in Smoker |
| cg00618087 | 17 | 16282382 | Lower in Smoker |
| cg05170582 | 12 | 48924228 | Lower in Smoker |
| cg10440989 | 6 | 144540635 | Lower in Smoker |
| cg01271726 | 6 | 26323586 | Lower in Smoker |
| cg12223009 | 17 | 68434585 | Lower in Smoker |
| cg25208142 | 10 | 134611553 | Lower in Smoker |
| cg10209068 | 6 | 106298492 | Lower in Smoker |
| cg06804334 | 1 | 192706599 | Lower in Smoker |
| cg23083229 | 5 | 54910575 | Lower in Smoker |
| cg01888395 | 9 | 132145105 | Lower in Smoker |
| cg02067994 | 5 | 148222894 | Lower in Smoker |
| cg26450044 | 16 | 21927746 | Lower in Smoker |
| cg21997182 | 8 | 7631923 | Lower in Smoker |
| cg06970082 | 2 | 15782968 | Lower in Smoker |
| cg03052431 | 7 | 135697576 | Lower in Smoker |
| cg13177860 | 6 | 79881191 | Lower in Smoker |
| cg13210581 | 11 | 29644815 | Lower in Smoker |
| cg09622691 | 6 | 108476189 | Lower in Smoker |
| cg06561458 | 7 | 5472241 | Lower in Smoker |
| cg19056537 | 2 | 132415749 | Lower in Smoker |
| cg06324719 | 15 | 70118762 | Lower in Smoker |
| cg21631904 | 7 | 1694569 | Lower in Smoker |
| cg15085431 | 3 | 138363566 | Lower in Smoker |
| cg11882601 | 8 | 103524861 | Lower in Smoker |
| cg14850653 | 3 | 49023660 | Lower in Smoker |
| cg24690069 | 8 | 55045121 | Lower in Smoker |
| cg04497786 | 13 | 21274956 | Lower in Smoker |
| cg02337277 | 6 | 52795627 | Lower in Smoker |
| cg14683317 | 4 | 27979369 | Lower in Smoker |
| cg18437099 | 5 | 154197936 | Lower in Smoker |
| cg10263003 | 2 | 235766844 | Lower in Smoker |

| | | | |
|---|---|---|---|
| cg22484614 | 6 | 107141695 | Lower in Smoker |
| cg17238970 | 1 | 81124441 | Lower in Smoker |
| cg24678148 | 1 | 193227662 | Lower in Smoker |
| cg15547241 | 7 | 66751257 | Lower in Smoker |
| cg04463863 | 5 | 173171737 | Lower in Smoker |
| cg24021343 | 3 | 170026743 | Lower in Smoker |
| cg08943393 | 2 | 166325622 | Lower in Smoker |
| cg27065729 | 14 | 99861110 | Lower in Smoker |
| cg24950506 | 12 | 95048009 | Lower in Smoker |
| cg12679725 | 22 | 42551834 | Lower in Smoker |
| cg05804047 | 4 | 77752568 | Lower in Smoker |
| cg24152554 | 14 | 58708762 | Lower in Smoker |
| cg00779551 | 3 | 39460981 | Lower in Smoker |
| cg10396713 | 8 | 602097 | Lower in Smoker |
| cg25195897 | 7 | 18447715 | Lower in Smoker |
| cg00574206 | 12 | 26262307 | Lower in Smoker |
| cg00102685 | 3 | 186645653 | Lower in Smoker |
| cg12237617 | 11 | 133916953 | Lower in Smoker |
| cg26622440 | 12 | 75980874 | Lower in Smoker |
| cg04385765 | 7 | 5122887 | Lower in Smoker |
| cg17474224 | 1 | 87760209 | Lower in Smoker |
| cg11312495 | 5 | 115697370 | Lower in Smoker |
| cg05779458 | 2 | 82756573 | Lower in Smoker |
| cg12516669 | 4 | 91045103 | Lower in Smoker |
| cg11117122 | 8 | 70042027 | Lower in Smoker |
| cg02350863 | X | 123466420 | Lower in Smoker |
| cg10350008 | X | 123466851 | Lower in Smoker |
| cg02776300 | 18 | 10415698 | Lower in Smoker |
| cg24943405 | 6 | 105936926 | Lower in Smoker |
| cg05768280 | 1 | 100728603 | Lower in Smoker |
| cg08721746 | 4 | 39175442 | Lower in Smoker |
| cg24345902 | 3 | 160414617 | Lower in Smoker |
| cg26843567 | 12 | 104846231 | Lower in Smoker |
| cg13879195 | 3 | 28886575 | Lower in Smoker |
| cg22394530 | 1 | 213193040 | Lower in Smoker |

| | | | |
|---|---|---|---|
| cg26106370 | 2 | 37554747 | Lower in Smoker |
| cg26312353 | 13 | 24580703 | Lower in Smoker |
| cg14725968 | 20 | 57763065 | Lower in Smoker |
| cg22506757 | 1 | 5919703 | Lower in Smoker |
| cg14592638 | 15 | 31749573 | Lower in Smoker |
| cg06328127 | 7 | 8469546 | Lower in Smoker |
| cg01343624 | 7 | 51842120 | Lower in Smoker |
| cg02597504 | 2 | 26364164 | Lower in Smoker |
| cg26790818 | 3 | 187786456 | Lower in Smoker |
| cg06040577 | 11 | 111322018 | Lower in Smoker |
| cg11233089 | 5 | 102395268 | Lower in Smoker |
| cg10495931 | 16 | 72232102 | Lower in Smoker |
| cg02002125 | 2 | 631818 | Lower in Smoker |
| cg01158161 | 6 | 26214630 | Lower in Smoker |
| cg17174370 | 2 | 153188845 | Lower in Smoker |
| cg10889502 | 1 | 200398670 | Lower in Smoker |
| cg04153563 | 16 | 61323411 | Lower in Smoker |
| cg08293548 | 5 | 112194422 | Lower in Smoker |
| cg08036333 | 12 | 116382986 | Lower in Smoker |
| cg26034145 | 1 | 116515695 | Lower in Smoker |
| cg27308445 | 5 | 149699675 | Lower in Smoker |
| cg21747072 | 12 | 3575076 | Lower in Smoker |
| cg04406229 | 1 | 94198787 | Lower in Smoker |
| cg13925235 | 11 | 118441064 | Lower in Smoker |
| cg24082384 | 2 | 145425403 | Lower in Smoker |
| cg20431441 | 8 | 82539527 | Lower in Smoker |
| cg17429842 | 1 | 179202149 | Lower in Smoker |
| cg11019629 | 14 | 106857655 | Lower in Smoker |
| cg00984540 | 7 | 155589293 | Lower in Smoker |
| cg02730299 | 5 | 95047004 | Lower in Smoker |
| cg03779213 | 7 | 106662131 | Lower in Smoker |
| cg22739440 | X | 68003612 | Lower in Smoker |
| cg24798153 | 5 | 38821875 | Lower in Smoker |
| cg02364855 | 6 | 53361893 | Lower in Smoker |
| cg00672414 | 3 | 43776590 | Lower in Smoker |

| | | | |
|---|---|---|---|
| cg02944840 | 3 | 72500152 | Lower in Smoker |
| cg12650565 | 13 | 79885536 | Lower in Smoker |
| cg00788354 | 6 | 168199725 | Lower in Smoker |
| cg11847442 | 15 | 41268170 | Lower in Smoker |
| cg16696727 | 14 | 103691932 | Lower in Smoker |
| cg21472050 | 12 | 92976320 | Lower in Smoker |
| cg14709234 | 1 | 55684023 | Lower in Smoker |
| cg15952586 | 7 | 18459971 | Lower in Smoker |
| cg09237562 | 4 | 137733853 | Lower in Smoker |
| cg23463685 | 7 | 155617333 | Lower in Smoker |
| cg12649087 | 11 | 94771318 | Lower in Smoker |
| cg26181316 | 11 | 67450544 | Lower in Smoker |
| cg25666830 | 13 | 50995080 | Lower in Smoker |
| cg18347903 | 2 | 427580 | Lower in Smoker |
| cg01974001 | 16 | 1297276 | Lower in Smoker |
| cg05854261 | 4 | 184297631 | Lower in Smoker |
| cg14297340 | 9 | 72871343 | Lower in Smoker |
| cg04423270 | 3 | 195771712 | Lower in Smoker |
| cg19364083 | 19 | 54701023 | Lower in Smoker |
| cg21045824 | 5 | 24169437 | Lower in Smoker |
| cg04214403 | 16 | 5479602 | Lower in Smoker |
| cg11173332 | 5 | 139117590 | Lower in Smoker |
| cg11218415 | 8 | 104030731 | Lower in Smoker |
| cg09346823 | 13 | 24528284 | Lower in Smoker |
| cg17218882 | 3 | 138641726 | Lower in Smoker |
| cg01021682 | 3 | 101926162 | Lower in Smoker |
| cg17374034 | 15 | 39000613 | Lower in Smoker |
| cg16610804 | 12 | 43685563 | Lower in Smoker |
| cg19584027 | 12 | 94529752 | Lower in Smoker |
| cg08104448 | 3 | 67125504 | Lower in Smoker |
| cg12636197 | 6 | 116998190 | Lower in Smoker |
| cg17653493 | X | 152742748 | Lower in Smoker |
| cg00349495 | 16 | 5290729 | Lower in Smoker |
| cg26396721 | 2 | 214171 | Lower in Smoker |
| cg26608982 | 16 | 89560068 | Lower in Smoker |

| | | | |
|---|---|---|---|
| cg09850161 | 3 | 149474138 | Lower in Smoker |
| cg13727085 | 10 | 134823902 | Lower in Smoker |
| cg02537826 | 5 | 54502896 | Lower in Smoker |
| cg00350931 | 4 | 1541867 | Lower in Smoker |
| cg21037935 | 19 | 58911965 | Lower in Smoker |
| cg26627760 | 16 | 48191219 | Lower in Smoker |
| cg14878302 | 18 | 18695624 | Lower in Smoker |
| cg10320265 | X | 45242887 | Lower in Smoker |
| cg08404725 | 5 | 156572785 | Lower in Smoker |
| cg21344200 | 12 | 45979553 | Lower in Smoker |
| cg14507016 | 12 | 132983814 | Lower in Smoker |
| cg03208893 | 6 | 170746098 | Lower in Smoker |
| cg26513854 | 5 | 141295517 | Lower in Smoker |
| cg15685514 | 19 | 13316043 | Lower in Smoker |
| cg24599790 | 5 | 18972260 | Lower in Smoker |
| cg02768998 | 6 | 24384627 | Lower in Smoker |
| cg02621481 | 13 | 50931836 | Lower in Smoker |
| cg16663747 | 8 | 103609603 | Lower in Smoker |
| cg07623839 | 16 | 767530 | Lower in Smoker |
| cg03905134 | 12 | 76146565 | Lower in Smoker |
| cg01227246 | 2 | 8988574 | Lower in Smoker |
| cg00634644 | 5 | 268995 | Lower in Smoker |
| cg12412598 | 12 | 132939165 | Lower in Smoker |
| cg13368042 | 11 | 103713957 | Lower in Smoker |
| cg22817748 | 11 | 94980075 | Lower in Smoker |
| cg01896432 | 4 | 68904160 | Lower in Smoker |
| cg21690675 | 7 | 129146078 | Lower in Smoker |
| cg25596486 | 8 | 1279421 | Lower in Smoker |
| cg04568264 | 8 | 54506557 | Lower in Smoker |
| cg16560313 | 14 | 103373122 | Lower in Smoker |
| cg23474036 | 6 | 29310293 | Lower in Smoker |
| cg17947765 | 7 | 117857964 | Lower in Smoker |
| cg06419093 | 8 | 144737766 | Lower in Smoker |
| cg00338529 | 2 | 134948022 | Lower in Smoker |
| cg03334307 | 16 | 58234168 | Lower in Smoker |

| | | | |
|---|---|---|---|
| cg13960894 | 15 | 83415633 | Lower in Smoker |
| cg22410262 | 11 | 64198213 | Lower in Smoker |
| cg00178562 | 1 | 16966354 | Lower in Smoker |
| cg10154973 | 4 | 114367529 | Lower in Smoker |
| cg21054194 | 5 | 124749655 | Lower in Smoker |
| cg01666716 | 8 | 29493005 | Lower in Smoker |
| cg24074783 | 3 | 43405624 | Lower in Smoker |
| cg07508304 | 16 | 85208316 | Lower in Smoker |
| cg17017394 | 1 | 43525160 | Lower in Smoker |
| cg07996580 | 1 | 2793928 | Lower in Smoker |
| cg01765623 | 17 | 75553783 | Lower in Smoker |
| cg02854902 | 11 | 111312361 | Lower in Smoker |
| cg03196666 | 1 | 247279205 | Lower in Smoker |
| cg01786362 | 1 | 90274359 | Lower in Smoker |
| cg11135937 | 14 | 24013847 | Lower in Smoker |
| cg08867549 | 17 | 29888620 | Lower in Smoker |
| cg10370687 | 16 | 89317353 | Lower in Smoker |
| cg11078040 | 17 | 5972001 | Lower in Smoker |
| cg25513230 | 17 | 16522406 | Lower in Smoker |
| cg05579037 | 7 | 27184853 | Lower in Smoker |
| cg14102556 | 5 | 171436197 | Lower in Smoker |
| cg13433891 | 12 | 26264492 | Lower in Smoker |
| cg01431873 | 16 | 85343657 | Lower in Smoker |
| cg09460999 | 7 | 123633258 | Lower in Smoker |
| cg04414446 | 1 | 92955118 | Lower in Smoker |
| cg09907439 | 12 | 109031953 | Lower in Smoker |
| cg07120031 | 2 | 102976268 | Lower in Smoker |
| cg00583731 | 17 | 66707367 | Lower in Smoker |
| cg23647410 | 1 | 221051066 | Lower in Smoker |
| cg20085265 | 8 | 22554827 | Lower in Smoker |
| cg07812380 | 2 | 239318100 | Lower in Smoker |
| cg08642138 | 17 | 7301657 | Lower in Smoker |
| cg15836231 | 6 | 91490663 | Lower in Smoker |
| cg08077354 | 17 | 40437010 | Lower in Smoker |
| cg22808564 | X | 102316174 | Lower in Smoker |

| | | | |
|---|---|---|---|
| cg19962052 | 2 | 241182704 | Lower in Smoker |
| cg02560642 | 13 | 110664301 | Lower in Smoker |
| cg16713321 | 11 | 73577813 | Lower in Smoker |
| cg16905211 | 19 | 1329131 | Lower in Smoker |
| cg00658440 | 12 | 91774944 | Lower in Smoker |
| cg04292660 | 4 | 155661234 | Lower in Smoker |
| cg24501299 | 6 | 108458569 | Lower in Smoker |
| cg08783558 | 13 | 65884020 | Lower in Smoker |
| cg17101611 | 8 | 144519203 | Lower in Smoker |
| cg26063962 | 5 | 60907320 | Lower in Smoker |
| cg00069969 | 13 | 33646763 | Lower in Smoker |
| cg02405128 | 6 | 29432580 | Lower in Smoker |
| cg10103036 | 8 | 92079649 | Lower in Smoker |
| cg02436602 | 6 | 26246270 | Lower in Smoker |
| cg23295491 | 7 | 47291414 | Lower in Smoker |
| cg06048766 | 2 | 64472941 | Lower in Smoker |
| cg14207326 | 4 | 100025015 | Lower in Smoker |
| cg00728029 | 8 | 99943905 | Lower in Smoker |
| cg06916514 | 15 | 81785576 | Lower in Smoker |
| cg02361881 | 1 | 143273345 | Lower in Smoker |
| cg26302986 | 7 | 90291360 | Lower in Smoker |
| cg06926343 | 8 | 94091210 | Lower in Smoker |
| cg24082880 | 2 | 119496616 | Lower in Smoker |
| cg09643027 | 3 | 50639263 | Lower in Smoker |
| cg25827102 | 15 | 89880727 | Lower in Smoker |
| cg27212917 | X | 57938975 | Lower in Smoker |
| cg07565150 | 14 | 69244243 | Lower in Smoker |
| cg20885910 | 11 | 48922741 | Lower in Smoker |
| cg26323746 | 19 | 58008348 | Lower in Smoker |
| cg13130022 | 6 | 44440494 | Lower in Smoker |
| cg11566520 | 5 | 3327977 | Lower in Smoker |
| cg20570030 | 1 | 236231282 | Lower in Smoker |
| cg20671790 | 7 | 63209243 | Lower in Smoker |
| cg03627678 | 16 | 607455 | Lower in Smoker |
| cg06211744 | 10 | 75389185 | Lower in Smoker |

| | | | |
|---|---|---|---|
| cg08204790 | 2 | 59522360 | Lower in Smoker |
| cg00396604 | 2 | 241065467 | Lower in Smoker |
| cg23517300 | 14 | 31929696 | Lower in Smoker |
| cg21153342 | 3 | 186144610 | Lower in Smoker |
| cg01968728 | 2 | 241609475 | Lower in Smoker |
| cg13984931 | 1 | 162783667 | Lower in Smoker |
| cg16485993 | 13 | 60205186 | Lower in Smoker |
| cg26818618 | 8 | 103616807 | Lower in Smoker |
| cg14595425 | 12 | 34363872 | Lower in Smoker |
| cg16555030 | 11 | 18065144 | Lower in Smoker |
| cg24794102 | 7 | 116132431 | Lower in Smoker |
| cg27034225 | 14 | 23757845 | Lower in Smoker |
| cg11192787 | 5 | 95580517 | Lower in Smoker |
| cg13604166 | 3 | 133811326 | Lower in Smoker |
| cg19343014 | 12 | 97611381 | Lower in Smoker |
| cg05452742 | 11 | 34070756 | Lower in Smoker |
| cg14423651 | 8 | 29302077 | Lower in Smoker |
| cg00849862 | 14 | 106096420 | Lower in Smoker |
| cg00014786 | 7 | 6614945 | Lower in Smoker |
| cg13797073 | 9 | 71199964 | Lower in Smoker |
| cg19306761 | 7 | 149732847 | Lower in Smoker |
| cg16371838 | 8 | 1108682 | Lower in Smoker |
| cg16969822 | 15 | 63613314 | Lower in Smoker |
| cg16392561 | 12 | 132653089 | Lower in Smoker |
| cg01899624 | 5 | 81082946 | Lower in Smoker |
| cg15441864 | 12 | 8549243 | Lower in Smoker |
| cg10838469 | 11 | 2211741 | Lower in Smoker |
| cg13396152 | 1 | 62005072 | Lower in Smoker |
| cg03460163 | 3 | 156532460 | Lower in Smoker |
| cg12799130 | 8 | 122454943 | Lower in Smoker |
| cg17968766 | 6 | 28960369 | Lower in Smoker |
| cg02269952 | 5 | 67811957 | Lower in Smoker |
| cg15196316 | 11 | 33399978 | Lower in Smoker |
| ch.2.238980020F | 2 | 239315281 | Lower in Smoker |
| cg24740632 | 5 | 134486678 | Lower in Smoker |

| | | | |
|---|---|---|---|
| cg11095011 | 6 | 3647175 | Lower in Smoker |
| cg09853206 | 6 | 12430810 | Lower in Smoker |
| cg16552959 | X | 149528296 | Lower in Smoker |
| cg25076678 | 4 | 4172379 | Lower in Smoker |
| cg26515389 | 16 | 89115544 | Lower in Smoker |
| cg20706621 | 7 | 61968148 | Lower in Smoker |
| cg09327778 | 6 | 363423 | Lower in Smoker |
| cg09766856 | 11 | 95232457 | Lower in Smoker |
| cg22730148 | 6 | 5979967 | Lower in Smoker |
| cg18963811 | 14 | 52210597 | Lower in Smoker |
| cg05056300 | 12 | 76257371 | Lower in Smoker |
| cg05196355 | 22 | 41484615 | Lower in Smoker |
| cg14559879 | 1 | 178902042 | Lower in Smoker |
| cg17033185 | 5 | 115294388 | Lower in Smoker |
| cg02265619 | 16 | 84963674 | Lower in Smoker |
| cg13940239 | 7 | 12810263 | Lower in Smoker |
| cg17675333 | 21 | 15451401 | Lower in Smoker |
| cg12315995 | 15 | 25920224 | Lower in Smoker |
| cg23640664 | 2 | 134882048 | Lower in Smoker |
| cg01463226 | 13 | 33640868 | Lower in Smoker |
| cg15146222 | 7 | 155206567 | Lower in Smoker |
| cg04663292 | 10 | 43275316 | Lower in Smoker |
| cg23687958 | 19 | 2954193 | Lower in Smoker |
| cg12395733 | 5 | 12795646 | Lower in Smoker |
| cg13961673 | 15 | 62910058 | Lower in Smoker |
| cg20178757 | 8 | 798432 | Lower in Smoker |
| cg19848529 | 6 | 170483067 | Lower in Smoker |
| cg18538499 | 5 | 27523974 | Lower in Smoker |
| cg10598868 | 15 | 93748065 | Lower in Smoker |
| cg24199724 | 3 | 194191570 | Lower in Smoker |
| cg19932993 | 14 | 59117221 | Lower in Smoker |
| cg21446514 | 12 | 132301886 | Lower in Smoker |
| cg21958457 | 11 | 325113 | Lower in Smoker |
| cg00345425 | 4 | 2070915 | Lower in Smoker |
| cg15542144 | 1 | 242221897 | Lower in Smoker |

| | | | |
|---|---|---|---|
| cg09333836 | 11 | 107732601 | Lower in Smoker |
| cg04852399 | 14 | 22362071 | Lower in Smoker |
| cg11450766 | 21 | 15309634 | Lower in Smoker |
| cg15582506 | 19 | 3583573 | Lower in Smoker |
| cg06832791 | 8 | 28256782 | Lower in Smoker |
| cg25221819 | 10 | 122605333 | Lower in Smoker |
| cg06509391 | 16 | 29266713 | Lower in Smoker |
| cg22380007 | 3 | 59718904 | Lower in Smoker |
| cg14796739 | 20 | 30437284 | Lower in Smoker |
| cg00622516 | 13 | 90015774 | Lower in Smoker |
| cg13188382 | 14 | 97091067 | Lower in Smoker |
| cg24669183 | 1 | 534242 | Lower in Smoker |
| cg00119053 | 6 | 159549723 | Lower in Smoker |
| cg09405334 | 6 | 8283067 | Lower in Smoker |
| cg25064274 | 1 | 116512673 | Lower in Smoker |
| cg21944219 | 1 | 67523185 | Lower in Smoker |
| cg05645634 | 10 | 118562797 | Lower in Smoker |
| cg07011538 | 2 | 47497026 | Lower in Smoker |
| cg03822217 | 3 | 186314464 | Lower in Smoker |
| cg10512779 | 13 | 30998440 | Lower in Smoker |
| cg21950780 | 4 | 122718592 | Lower in Smoker |
| cg06789340 | 6 | 26000384 | Lower in Smoker |
| cg17301930 | 5 | 56009405 | Lower in Smoker |
| cg02401524 | 10 | 134833335 | Lower in Smoker |
| cg24487991 | 2 | 84104579 | Lower in Smoker |
| cg03551378 | 6 | 36309528 | Lower in Smoker |
| cg02921923 | 11 | 92651425 | Lower in Smoker |
| cg26010028 | 1 | 178653297 | Lower in Smoker |
| cg19612004 | 5 | 13395163 | Lower in Smoker |
| cg15881795 | 12 | 106361273 | Lower in Smoker |
| cg09774022 | 2 | 200707417 | Lower in Smoker |
| cg05764121 | 6 | 5082456 | Lower in Smoker |
| cg13354930 | 12 | 55051924 | Lower in Smoker |
| cg09093035 | Y | 14074689 | Lower in Smoker |
| cg16296188 | 4 | 3270609 | Lower in Smoker |

| | | | |
|---|---|---|---|
| cg14889679 | 8 | 142277947 | Lower in Smoker |
| cg06769989 | 5 | 115929014 | Lower in Smoker |
| cg03048488 | 1 | 15733844 | Lower in Smoker |
| cg08087668 | 8 | 58116908 | Lower in Smoker |
| cg07709155 | 8 | 2186975 | Lower in Smoker |
| cg17661103 | 8 | 86154580 | Lower in Smoker |
| cg11643022 | 5 | 141589945 | Lower in Smoker |
| cg01641092 | 6 | 30094500 | Lower in Smoker |
| cg22482048 | 1 | 53023509 | Lower in Smoker |
| cg00966357 | 12 | 46945908 | Lower in Smoker |
| cg11349123 | 6 | 168390056 | Lower in Smoker |
| cg17249782 | 11 | 44488287 | Lower in Smoker |
| cg06850509 | 2 | 96314847 | Lower in Smoker |
| cg01901708 | 16 | 88308391 | Lower in Smoker |
| cg01156394 | 2 | 39714386 | Lower in Smoker |
| cg02128564 | 12 | 53642741 | Lower in Smoker |
| cg07701909 | 1 | 116099209 | Lower in Smoker |
| cg20265851 | 2 | 37567721 | Lower in Smoker |
| cg26858213 | 6 | 46455990 | Lower in Smoker |
| cg27047316 | 15 | 20567284 | Lower in Smoker |
| cg09659634 | 11 | 1159193 | Lower in Smoker |
| cg16279748 | 15 | 21145137 | Lower in Smoker |
| cg17126924 | 17 | 25773641 | Lower in Smoker |
| cg21541565 | 5 | 95976631 | Lower in Smoker |
| cg16977304 | 13 | 20134785 | Lower in Smoker |
| cg06501333 | 4 | 103419193 | Lower in Smoker |
| cg25920743 | 8 | 11907551 | Lower in Smoker |
| cg27260080 | 10 | 35958777 | Lower in Smoker |
| cg01061980 | 14 | 104854940 | Lower in Smoker |
| cg21012380 | 18 | 18519225 | Lower in Smoker |
| cg16051154 | 6 | 29758527 | Lower in Smoker |
| cg17943323 | 1 | 203876248 | Lower in Smoker |
| cg05520687 | 15 | 62516325 | Lower in Smoker |
| cg09469670 | 1 | 192808857 | Lower in Smoker |
| cg02536352 | 12 | 5142165 | Lower in Smoker |

| | | | |
|---|---|---|---|
| cg12370929 | 9 | 34701219 | Lower in Smoker |
| cg09875053 | 6 | 170918794 | Lower in Smoker |
| cg01167323 | 1 | 90284686 | Lower in Smoker |
| cg19224639 | 12 | 28186450 | Lower in Smoker |
| cg18697487 | 19 | 1502095 | Lower in Smoker |
| cg00355804 | 12 | 117103567 | Lower in Smoker |
| cg06439293 | 9 | 93956212 | Lower in Smoker |
| cg18489034 | 11 | 10531596 | Lower in Smoker |
| cg06006401 | 6 | 168482421 | Lower in Smoker |
| cg22700505 | 15 | 68257269 | Lower in Smoker |
| cg07871532 | 21 | 44816571 | Lower in Smoker |
| cg07489607 | 5 | 760048 | Lower in Smoker |
| cg05219051 | 10 | 18999228 | Lower in Smoker |
| cg21723150 | 6 | 467242 | Lower in Smoker |
| cg06047130 | 6 | 28980609 | Lower in Smoker |
| cg24764114 | 7 | 64412238 | Lower in Smoker |
| cg19601745 | 1 | 57048634 | Lower in Smoker |
| cg14969063 | 12 | 91015507 | Lower in Smoker |
| cg05042492 | 15 | 89899729 | Lower in Smoker |
| cg19970355 | 6 | 25277036 | Lower in Smoker |
| cg19311448 | 2 | 11797017 | Lower in Smoker |
| cg14620267 | 10 | 89349505 | Lower in Smoker |
| cg08574364 | 2 | 239847627 | Lower in Smoker |
| cg24997330 | 10 | 3419027 | Lower in Smoker |
| cg10577168 | 1 | 245039085 | Lower in Smoker |
| cg01603620 | 12 | 123898720 | Lower in Smoker |
| cg21576107 | 6 | 26243121 | Lower in Smoker |
| cg21083936 | 11 | 2295090 | Lower in Smoker |
| cg26102434 | 3 | 184975890 | Lower in Smoker |
| cg11236515 | 2 | 74213762 | Lower in Smoker |
| cg25198255 | 10 | 134878094 | Lower in Smoker |
| cg09140693 | 7 | 54794760 | Lower in Smoker |
| cg22861029 | 8 | 58128466 | Lower in Smoker |
| cg24827626 | 21 | 46169242 | Lower in Smoker |
| cg06095433 | 7 | 124422126 | Lower in Smoker |

| | | | |
|---|---|---|---|
| cg09491828 | 5 | 115367063 | Lower in Smoker |
| cg11413576 | 8 | 59650783 | Lower in Smoker |
| cg21723861 | 17 | 39686628 | Lower in Smoker |
| cg23791718 | 8 | 60034928 | Lower in Smoker |
| cg10483475 | 1 | 17212040 | Lower in Smoker |
| cg05288127 | 16 | 86102267 | Lower in Smoker |
| cg16581103 | 1 | 56293135 | Lower in Smoker |
| cg01868838 | 2 | 213590822 | Lower in Smoker |
| cg15397788 | 19 | 4560742 | Lower in Smoker |
| cg07013148 | 6 | 146233339 | Lower in Smoker |
| cg19251514 | 15 | 74729482 | Lower in Smoker |
| cg00930515 | 16 | 13646432 | Lower in Smoker |
| cg21182103 | 9 | 37798519 | Lower in Smoker |
| cg08724904 | 10 | 3343109 | Lower in Smoker |
| cg06119137 | 6 | 168617767 | Lower in Smoker |
| cg13614229 | 12 | 131217218 | Lower in Smoker |
| cg08014430 | 3 | 117453585 | Lower in Smoker |
| cg08610326 | 6 | 141540813 | Lower in Smoker |
| cg09845296 | 5 | 14094101 | Lower in Smoker |
| cg16354345 | 15 | 49012706 | Lower in Smoker |
| cg15513221 | 19 | 3975388 | Lower in Smoker |
| cg22677637 | 2 | 242636898 | Lower in Smoker |
| cg05291677 | 5 | 1744919 | Lower in Smoker |
| cg20409352 | 4 | 155838156 | Lower in Smoker |
| cg08167132 | 1 | 82063629 | Lower in Smoker |
| cg18389023 | X | 129086243 | Lower in Smoker |
| cg03081689 | 11 | 5408788 | Lower in Smoker |
| cg24073770 | 7 | 27734321 | Lower in Smoker |
| cg13180105 | 13 | 19968841 | Lower in Smoker |
| cg23920246 | 2 | 113398727 | Lower in Smoker |
| cg23614428 | 1 | 172498191 | Lower in Smoker |
| cg00894352 | 5 | 269864 | Lower in Smoker |
| cg25801742 | 11 | 58736104 | Lower in Smoker |
| cg07054564 | 18 | 12095187 | Lower in Smoker |
| cg22925888 | 2 | 623263 | Lower in Smoker |

| | | | |
|---|---|---|---|
| cg08808677 | 2 | 6911141 | Lower in Smoker |
| cg20208203 | 21 | 38932835 | Lower in Smoker |
| cg14478049 | 4 | 1537362 | Lower in Smoker |
| cg06716402 | 16 | 18494340 | Lower in Smoker |
| cg18034957 | 11 | 77012506 | Lower in Smoker |
| cg01281061 | 1 | 229541873 | Lower in Smoker |
| cg01741626 | 16 | 4364093 | Lower in Smoker |
| cg20640824 | 5 | 36246579 | Lower in Smoker |
| cg19673115 | 10 | 3105482 | Lower in Smoker |
| cg05055490 | 7 | 26284602 | Lower in Smoker |
| cg05834036 | 4 | 55063893 | Lower in Smoker |
| cg25977313 | 2 | 134844510 | Lower in Smoker |
| cg06308258 | 12 | 117069282 | Lower in Smoker |
| cg01432405 | 16 | 3205498 | Lower in Smoker |
| cg05029148 | 8 | 1321883 | Lower in Smoker |
| cg02106822 | 15 | 22474401 | Lower in Smoker |
| cg20047924 | 7 | 142334015 | Lower in Smoker |
| cg16918155 | 6 | 64275041 | Lower in Smoker |
| cg11487967 | 2 | 242968692 | Lower in Smoker |
| cg22606129 | 7 | 33714254 | Lower in Smoker |
| cg20018992 | X | 71948510 | Lower in Smoker |
| cg15551105 | 2 | 10260366 | Lower in Smoker |
| cg20902104 | 14 | 106307623 | Lower in Smoker |
| cg14565485 | 3 | 38504892 | Lower in Smoker |
| cg26568932 | 17 | 77666380 | Lower in Smoker |
| cg04646233 | 4 | 24481721 | Lower in Smoker |
| cg18986335 | 3 | 156846983 | Lower in Smoker |
| cg24317955 | 19 | 46438607 | Lower in Smoker |
| cg24087404 | 12 | 26266049 | Lower in Smoker |
| cg15972496 | 8 | 47130777 | Lower in Smoker |
| cg09888183 | 7 | 63020706 | Lower in Smoker |
| cg03513066 | 6 | 32586134 | Lower in Smoker |
| cg03342977 | 8 | 1311576 | Lower in Smoker |
| cg21680474 | 1 | 28463306 | Lower in Smoker |
| cg10766030 | 13 | 31408838 | Lower in Smoker |

| | | | |
|---|---|---|---|
| cg10464076 | 15 | 65099766 | Lower in Smoker |
| cg01566213 | 4 | 1579287 | Lower in Smoker |
| cg19207201 | 4 | 147043810 | Lower in Smoker |
| cg04828580 | 10 | 93639778 | Lower in Smoker |
| cg01622415 | 17 | 66028902 | Lower in Smoker |
| cg23188950 | 8 | 19095224 | Lower in Smoker |
| cg17839216 | 5 | 18504434 | Lower in Smoker |
| cg00787780 | 6 | 64151745 | Lower in Smoker |
| cg00702872 | 6 | 3524580 | Lower in Smoker |
| cg22141751 | 3 | 138766134 | Lower in Smoker |
| cg12567545 | 16 | 604948 | Lower in Smoker |
| cg15209710 | 1 | 182667173 | Lower in Smoker |
| cg18291151 | 3 | 39236594 | Lower in Smoker |
| cg02850416 | 11 | 1986266 | Lower in Smoker |
| cg15149205 | 8 | 126403700 | Lower in Smoker |
| cg02346342 | 8 | 74332435 | Lower in Smoker |
| cg02936679 | 2 | 60650136 | Lower in Smoker |
| cg27315773 | 10 | 134791549 | Lower in Smoker |
| cg18076831 | 12 | 88178340 | Lower in Smoker |
| cg10198943 | 5 | 75668478 | Lower in Smoker |
| cg00435752 | 15 | 98961417 | Lower in Smoker |
| cg24874173 | 1 | 145385677 | Lower in Smoker |
| cg03211626 | 16 | 58783679 | Lower in Smoker |
| cg21926038 | 19 | 44615062 | Lower in Smoker |
| cg04962865 | 8 | 117059957 | Lower in Smoker |
| cg21623115 | 12 | 126673890 | Lower in Smoker |
| cg05963082 | 7 | 18429033 | Lower in Smoker |
| cg26947579 | 12 | 113966153 | Lower in Smoker |
| cg02800013 | 21 | 45872301 | Lower in Smoker |
| cg19317226 | 10 | 130726701 | Lower in Smoker |
| cg11345909 | 1 | 22270751 | Lower in Smoker |
| cg22810515 | 4 | 4139646 | Lower in Smoker |
| cg11033697 | 4 | 177305431 | Lower in Smoker |
| cg01563858 | 7 | 26435415 | Lower in Smoker |
| cg04885333 | 17 | 80341642 | Lower in Smoker |

| | | | |
|---|---|---|---|
| cg16534483 | 3 | 32668281 | Lower in Smoker |
| cg12232146 | 12 | 76347937 | Lower in Smoker |
| cg11857567 | 13 | 100060513 | Lower in Smoker |
| cg16775110 | 16 | 35037569 | Lower in Smoker |
| cg12028326 | 19 | 523360 | Lower in Smoker |
| cg25180701 | 12 | 9391348 | Lower in Smoker |
| cg01710358 | 4 | 187880263 | Lower in Smoker |
| cg02737418 | 1 | 147384040 | Lower in Smoker |
| cg08617346 | 20 | 1716331 | Lower in Smoker |
| cg19517841 | 8 | 1337695 | Lower in Smoker |
| cg05482022 | 7 | 2476326 | Lower in Smoker |
| cg06723626 | 12 | 47699089 | Lower in Smoker |
| cg06617093 | 1 | 158110617 | Lower in Smoker |
| cg04649115 | 12 | 9210696 | Lower in Smoker |
| cg08215453 | 14 | 41623629 | Lower in Smoker |
| cg09973022 | 16 | 84717364 | Lower in Smoker |
| cg08729279 | 2 | 216708378 | Lower in Smoker |
| cg09755397 | 4 | 102341105 | Lower in Smoker |
| cg08506369 | 17 | 77610316 | Lower in Smoker |
| cg07054927 | 19 | 1300085 | Lower in Smoker |
| cg27421291 | 6 | 133873332 | Lower in Smoker |
| cg19037539 | 5 | 107011761 | Lower in Smoker |
| cg16181642 | 10 | 48491692 | Lower in Smoker |
| cg14114908 | 6 | 12246193 | Lower in Smoker |
| cg07023324 | 13 | 78435465 | Lower in Smoker |
| cg00303606 | 9 | 138302846 | Lower in Smoker |
| cg15697511 | 17 | 5972419 | Lower in Smoker |
| cg17836579 | 5 | 95310237 | Lower in Smoker |
| cg04733911 | 16 | 78082701 | Lower in Smoker |
| cg09120959 | 4 | 154684504 | Lower in Smoker |
| cg19159695 | 2 | 68923942 | Lower in Smoker |
| cg03715182 | 16 | 48088353 | Lower in Smoker |
| cg14711592 | 1 | 157839587 | Lower in Smoker |
| cg23222276 | 2 | 157202099 | Lower in Smoker |
| cg17579804 | 5 | 158533942 | Lower in Smoker |

| | | | |
|---|---|---|---|
| cg03387145 | 15 | 100465995 | Lower in Smoker |
| cg21496785 | 4 | 686870 | Lower in Smoker |
| cg06064725 | 11 | 17599715 | Lower in Smoker |
| cg02883604 | 4 | 24478362 | Lower in Smoker |
| cg22541038 | 4 | 1049653 | Lower in Smoker |
| cg26634403 | 12 | 56133575 | Lower in Smoker |
| cg14017444 | 4 | 138468381 | Lower in Smoker |
| cg15927465 | 1 | 197860832 | Lower in Smoker |
| cg07107427 | 1 | 16318931 | Lower in Smoker |
| cg02388446 | X | 64258522 | Lower in Smoker |
| cg26896754 | 5 | 180216985 | Lower in Smoker |
| cg08917821 | 12 | 59993762 | Lower in Smoker |
| cg22994849 | 7 | 149578441 | Lower in Smoker |
| cg02456602 | 15 | 20563473 | Lower in Smoker |
| cg25439867 | 13 | 30172641 | Lower in Smoker |
| cg13997640 | 8 | 67022776 | Lower in Smoker |
| cg09493284 | 7 | 8004848 | Lower in Smoker |
| cg08845235 | 1 | 85170253 | Lower in Smoker |
| cg17087741 | 2 | 233283010 | Lower in Smoker |
| cg08337060 | 19 | 1595421 | Lower in Smoker |
| cg14305659 | 9 | 138696500 | Lower in Smoker |
| cg27625401 | 16 | 3148536 | Lower in Smoker |
| cg14382249 | 2 | 816777 | Lower in Smoker |
| cg13642849 | 9 | 93957592 | Lower in Smoker |
| cg25274275 | 2 | 233217617 | Lower in Smoker |
| cg15886294 | 12 | 131767291 | Lower in Smoker |
| cg18162371 | 10 | 134621876 | Lower in Smoker |
| cg15899043 | 14 | 106066504 | Lower in Smoker |
| cg14233644 | 2 | 206790633 | Lower in Smoker |
| cg14887099 | 13 | 51060599 | Lower in Smoker |
| cg14477767 | 4 | 170195438 | Lower in Smoker |
| cg27094846 | 14 | 57548155 | Lower in Smoker |
| cg08493051 | 2 | 3487164 | Lower in Smoker |
| cg00578614 | 6 | 30070403 | Lower in Smoker |
| cg19583880 | 1 | 27143747 | Lower in Smoker |

| | | | |
|---|---|---|---|
| cg08708599 | 1 | 244893918 | Lower in Smoker |
| cg07625177 | 5 | 36001201 | Lower in Smoker |
| cg17074989 | 15 | 58880752 | Lower in Smoker |
| cg23066414 | 5 | 149337641 | Lower in Smoker |
| cg03022791 | X | 129090470 | Lower in Smoker |
| cg27111362 | 4 | 156895014 | Lower in Smoker |
| cg17280723 | 5 | 101634495 | Lower in Smoker |
| cg04962479 | 16 | 87575344 | Lower in Smoker |
| cg25248213 | 11 | 94888121 | Lower in Smoker |
| cg20238243 | 1 | 220998876 | Lower in Smoker |
| ch.10.72059822F | 10 | 72389816 | Lower in Smoker |
| cg16236688 | 10 | 9450208 | Lower in Smoker |
| cg01832665 | 7 | 154836613 | Lower in Smoker |
| cg02222761 | 4 | 142790226 | Lower in Smoker |
| cg07223090 | 2 | 240420604 | Lower in Smoker |
| cg26581165 | 15 | 39135589 | Lower in Smoker |
| cg23529856 | 13 | 30498683 | Lower in Smoker |
| cg06618740 | 1 | 1100126 | Lower in Smoker |
| cg21268256 | 1 | 25509521 | Lower in Smoker |
| cg11377464 | 1 | 2766719 | Lower in Smoker |
| cg06366792 | 12 | 121179966 | Lower in Smoker |
| cg00094158 | 10 | 126435795 | Lower in Smoker |
| cg14759494 | 6 | 166117676 | Lower in Smoker |
| cg04124201 | 5 | 113590940 | Lower in Smoker |
| cg12221927 | 7 | 57475905 | Lower in Smoker |
| cg00346320 | 16 | 88134589 | Lower in Smoker |
| cg09602251 | 10 | 25245759 | Lower in Smoker |
| cg12068734 | 2 | 132348567 | Lower in Smoker |
| cg16873780 | 19 | 44226149 | Lower in Smoker |
| cg02255242 | 15 | 33420912 | Lower in Smoker |
| cg14401614 | 15 | 74031640 | Lower in Smoker |
| cg06190759 | 16 | 71757240 | Lower in Smoker |
| cg10374248 | 10 | 99083645 | Lower in Smoker |
| cg11652668 | 18 | 13136899 | Lower in Smoker |
| cg12498326 | 12 | 130599682 | Lower in Smoker |

| | | | |
|---|---|---|---|
| cg21072567 | 14 | 62035431 | Lower in Smoker |
| cg03726377 | 5 | 132115709 | Lower in Smoker |
| cg08900511 | 1 | 843581 | Lower in Smoker |
| cg14354292 | 7 | 63353606 | Lower in Smoker |
| cg18512232 | 11 | 1365408 | Lower in Smoker |
| cg11796578 | 13 | 62931637 | Lower in Smoker |
| cg05306107 | 8 | 119918483 | Lower in Smoker |
| cg17450004 | 12 | 31370930 | Lower in Smoker |
| cg23647744 | 17 | 44334706 | Lower in Smoker |
| cg09268961 | 16 | 14400943 | Lower in Smoker |
| cg20368377 | 13 | 23499360 | Lower in Smoker |
| cg06009620 | 6 | 30904694 | Lower in Smoker |
| cg06532856 | 11 | 68762338 | Lower in Smoker |
| cg13997469 | 14 | 88608773 | Lower in Smoker |
| cg00386101 | 2 | 11621399 | Lower in Smoker |
| cg01925594 | 8 | 1320786 | Lower in Smoker |
| cg20534884 | 5 | 126429201 | Lower in Smoker |
| cg01977798 | 1 | 2886792 | Lower in Smoker |
| cg13400591 | 10 | 80165798 | Lower in Smoker |
| cg20134934 | 10 | 94456646 | Lower in Smoker |
| cg01611817 | 16 | 34610199 | Lower in Smoker |
| cg22461758 | 7 | 130612561 | Lower in Smoker |
| cg06439889 | 6 | 72077399 | Lower in Smoker |
| cg21958394 | 2 | 145425418 | Lower in Smoker |
| cg07615111 | 13 | 114965537 | Lower in Smoker |
| cg06783380 | 10 | 831947 | Lower in Smoker |
| cg22127848 | 17 | 64295986 | Lower in Smoker |
| cg13502545 | 15 | 26490045 | Lower in Smoker |
| cg21177063 | 4 | 4050335 | Lower in Smoker |
| cg07623058 | 5 | 2128976 | Lower in Smoker |
| cg05081144 | 11 | 66447739 | Lower in Smoker |
| cg23623214 | 18 | 6417130 | Lower in Smoker |
| cg16074271 | 22 | 13531028 | Lower in Smoker |
| cg15133265 | 2 | 198560904 | Lower in Smoker |
| cg26214055 | 5 | 27472029 | Lower in Smoker |

| | | | |
|---|---|---|---|
| cg10159460 | 14 | 59495933 | Lower in Smoker |
| cg19565382 | 10 | 82165193 | Lower in Smoker |
| cg09317239 | 10 | 21818060 | Lower in Smoker |
| cg17869647 | 3 | 109115491 | Lower in Smoker |
| cg21164813 | 4 | 43876927 | Lower in Smoker |
| cg10659680 | 3 | 8692466 | Lower in Smoker |
| cg01320748 | 4 | 105631962 | Lower in Smoker |
| cg18958286 | 6 | 56192811 | Lower in Smoker |
| cg02597454 | 20 | 60517090 | Lower in Smoker |
| cg24722070 | 1 | 222227490 | Lower in Smoker |
| cg20684375 | 8 | 38540652 | Lower in Smoker |
| cg03200890 | 10 | 113748431 | Lower in Smoker |
| cg26754071 | 7 | 35738132 | Lower in Smoker |
| cg03126765 | 16 | 3125838 | Lower in Smoker |
| cg27404897 | 2 | 152092933 | Lower in Smoker |
| cg16923164 | 7 | 17143745 | Lower in Smoker |
| cg01617520 | 14 | 59313765 | Lower in Smoker |
| cg04587176 | 10 | 128569222 | Lower in Smoker |
| cg18432954 | 10 | 134887227 | Lower in Smoker |
| cg17830921 | 1 | 224044382 | Lower in Smoker |
| cg00577969 | 11 | 122156457 | Lower in Smoker |
| cg26626729 | 8 | 61566439 | Lower in Smoker |
| cg21931298 | 11 | 1824157 | Lower in Smoker |
| cg23465295 | 5 | 20611854 | Lower in Smoker |
| cg23742314 | 12 | 5282086 | Lower in Smoker |
| cg17412654 | 6 | 30431579 | Lower in Smoker |
| cg11230363 | 10 | 72039764 | Lower in Smoker |
| cg16524570 | 13 | 77013618 | Lower in Smoker |
| cg26962609 | 15 | 20373540 | Lower in Smoker |
| cg10284755 | 14 | 97081899 | Lower in Smoker |
| cg06752365 | 13 | 33920491 | Lower in Smoker |
| cg06569437 | 6 | 130046710 | Lower in Smoker |
| cg13283845 | 8 | 144367265 | Lower in Smoker |
| cg24674302 | 2 | 26240871 | Lower in Smoker |
| cg13170468 | 11 | 10531665 | Lower in Smoker |

| | | | |
|---|---|---|---|
| cg26436579 | 7 | 112144923 | Lower in Smoker |
| cg13258195 | 17 | 80300821 | Lower in Smoker |
| cg08786112 | 7 | 81113240 | Lower in Smoker |
| cg22203628 | 11 | 69241075 | Lower in Smoker |
| cg17161130 | 10 | 113544977 | Lower in Smoker |
| cg10072464 | 13 | 114064536 | Lower in Smoker |
| cg02742969 | 5 | 172175604 | Lower in Smoker |
| cg01522525 | 11 | 10529706 | Lower in Smoker |
| cg16140714 | 14 | 41623577 | Lower in Smoker |
| cg12793753 | 6 | 75933274 | Lower in Smoker |
| cg03763457 | 1 | 158070317 | Lower in Smoker |
| cg05807698 | 11 | 118193562 | Lower in Smoker |
| cg23684502 | 22 | 41217753 | Lower in Smoker |
| cg16335566 | 5 | 128297215 | Lower in Smoker |
| cg26155338 | 5 | 61028899 | Lower in Smoker |
| cg11206526 | 20 | 44782126 | Lower in Smoker |
| cg04532707 | 8 | 145637525 | Lower in Smoker |
| cg12725782 | 6 | 167581988 | Lower in Smoker |
| cg02725013 | 4 | 5024327 | Lower in Smoker |
| cg07546446 | 10 | 15025245 | Lower in Smoker |
| cg10848564 | 5 | 20611845 | Lower in Smoker |
| cg27189533 | 16 | 87312115 | Lower in Smoker |
| cg23196630 | 8 | 144362100 | Lower in Smoker |
| cg14684854 | 2 | 241901865 | Lower in Smoker |
| cg27052418 | 5 | 66611496 | Lower in Smoker |
| cg11626582 | 10 | 3761802 | Lower in Smoker |
| cg06965590 | 16 | 77412466 | Lower in Smoker |
| cg23803709 | 10 | 54203646 | Lower in Smoker |
| cg07563725 | 11 | 95408124 | Lower in Smoker |
| cg18067236 | 5 | 536582 | Lower in Smoker |
| cg19758134 | 1 | 114829082 | Lower in Smoker |
| cg24931856 | 1 | 19104579 | Lower in Smoker |
| cg19821475 | 12 | 132076333 | Lower in Smoker |
| cg17945755 | 6 | 78362377 | Lower in Smoker |
| cg16039374 | 7 | 56875846 | Lower in Smoker |

| | | | |
|---|---|---|---|
| cg02068976 | X | 117972862 | Lower in Smoker |
| cg02455392 | 1 | 232514215 | Lower in Smoker |
| cg05521089 | 10 | 65733092 | Lower in Smoker |
| cg24843717 | 11 | 119352283 | Lower in Smoker |
| cg20747538 | 3 | 137838021 | Lower in Smoker |
| cg18527771 | 21 | 44629111 | Lower in Smoker |
| cg21532408 | 13 | 101241430 | Lower in Smoker |
| cg11537447 | 7 | 26283890 | Lower in Smoker |
| cg08388455 | 17 | 37081875 | Lower in Smoker |
| cg14832490 | 1 | 20957761 | Lower in Smoker |
| cg27582180 | 5 | 35652286 | Lower in Smoker |
| cg04804321 | 8 | 40065870 | Lower in Smoker |
| cg16616053 | 16 | 13924334 | Lower in Smoker |
| cg18027632 | 8 | 142278163 | Lower in Smoker |
| cg18774611 | 5 | 94623660 | Lower in Smoker |
| cg03861379 | 5 | 54128677 | Lower in Smoker |
| cg07102450 | 16 | 4355464 | Lower in Smoker |
| cg24022918 | 6 | 31047687 | Lower in Smoker |
| cg12161959 | 2 | 240868337 | Lower in Smoker |
| cg23428387 | 22 | 49814324 | Lower in Smoker |
| cg23000862 | 7 | 156819079 | Lower in Smoker |
| cg04399875 | 16 | 878162 | Lower in Smoker |
| cg16169833 | 5 | 87083582 | Lower in Smoker |
| cg14075881 | 12 | 65215090 | Lower in Smoker |
| cg13379208 | 6 | 142564220 | Lower in Smoker |
| cg06786335 | 13 | 112999147 | Lower in Smoker |
| cg17766651 | 12 | 76303552 | Lower in Smoker |
| cg21752340 | 12 | 127220617 | Lower in Smoker |
| cg03286535 | 15 | 90649835 | Lower in Smoker |
| cg22128071 | 3 | 93696108 | Lower in Smoker |
| cg22347686 | 19 | 1872806 | Lower in Smoker |
| cg15623339 | 6 | 88180175 | Lower in Smoker |
| cg12766777 | 6 | 42112884 | Lower in Smoker |
| cg03334701 | 11 | 128693801 | Lower in Smoker |
| cg00978901 | 1 | 22956280 | Lower in Smoker |

| | | | |
|---|---|---|---|
| cg03407184 | 3 | 70881475 | Lower in Smoker |
| cg13241659 | 12 | 132105972 | Lower in Smoker |
| cg24834165 | 5 | 95060853 | Lower in Smoker |
| cg08860639 | 4 | 828098 | Lower in Smoker |
| cg01256232 | 14 | 40337190 | Lower in Smoker |
| cg04191306 | 14 | 104854974 | Lower in Smoker |
| cg16409456 | 8 | 86551492 | Lower in Smoker |
| cg11691510 | 20 | 56800049 | Lower in Smoker |
| cg25353436 | 10 | 10839523 | Lower in Smoker |
| cg04719454 | 4 | 190232818 | Lower in Smoker |
| cg23440389 | 14 | 80440817 | Lower in Smoker |
| cg08073507 | 21 | 44861617 | Lower in Smoker |
| cg15841378 | 1 | 26535593 | Lower in Smoker |
| cg25210373 | 7 | 81301114 | Lower in Smoker |
| cg05262191 | 1 | 1714271 | Lower in Smoker |
| cg14130119 | 2 | 121341233 | Lower in Smoker |
| cg10071493 | 16 | 1179514 | Lower in Smoker |
| cg22687982 | 15 | 89900455 | Lower in Smoker |
| cg27090727 | 3 | 161884911 | Lower in Smoker |
| cg05641033 | 12 | 1639534 | Lower in Smoker |
| cg25127214 | 2 | 182525194 | Lower in Smoker |
| cg07022289 | 1 | 238226289 | Lower in Smoker |
| cg19477793 | 17 | 52027331 | Lower in Smoker |
| cg02058717 | 5 | 83776873 | Lower in Smoker |
| cg24239165 | 17 | 59496653 | Lower in Smoker |
| cg02659803 | 13 | 23409813 | Lower in Smoker |
| cg11307865 | 12 | 27587175 | Lower in Smoker |
| cg19382632 | 7 | 38344983 | Lower in Smoker |
| cg05800414 | 6 | 81348044 | Lower in Smoker |
| cg05678960 | Y | 6133838 | Lower in Smoker |
| cg20395789 | 11 | 107570881 | Lower in Smoker |
| cg19494252 | 4 | 105658912 | Lower in Smoker |
| cg09400607 | 17 | 76641712 | Lower in Smoker |
| cg00515814 | 11 | 115581955 | Lower in Smoker |
| cg18305853 | 2 | 2713323 | Lower in Smoker |

| | | | |
|---|---|---|---|
| cg13356709 | 5 | 35338762 | Lower in Smoker |
| cg22507887 | 1 | 157895500 | Lower in Smoker |
| cg01481251 | 11 | 32912719 | Lower in Smoker |
| cg08205714 | 13 | 90419012 | Lower in Smoker |
| cg19310365 | 19 | 47002878 | Lower in Smoker |
| cg05932024 | 2 | 42086889 | Lower in Smoker |
| cg11363444 | 2 | 153079618 | Lower in Smoker |
| cg19913199 | 8 | 60674791 | Lower in Smoker |
| cg10249506 | 22 | 42734458 | Lower in Smoker |
| cg14439150 | 6 | 1336193 | Lower in Smoker |
| cg21049397 | 12 | 25611175 | Lower in Smoker |
| cg18246107 | 13 | 23730771 | Lower in Smoker |
| cg26395513 | 7 | 1239908 | Lower in Smoker |
| cg00995220 | 6 | 56259582 | Lower in Smoker |
| cg27196081 | 10 | 103330144 | Lower in Smoker |
| cg17031739 | 1 | 67600172 | Lower in Smoker |
| cg00366836 | 2 | 53662766 | Lower in Smoker |
| cg19756885 | 14 | 105318494 | Lower in Smoker |
| cg17349760 | 12 | 10096794 | Lower in Smoker |
| cg14751431 | 12 | 133009355 | Lower in Smoker |
| cg16354452 | 12 | 131766931 | Lower in Smoker |
| cg08367069 | 2 | 36565096 | Lower in Smoker |
| cg01072550 | 1 | 21505969 | Lower in Smoker |
| cg17717052 | 12 | 74442868 | Lower in Smoker |
| cg06872709 | 16 | 86112085 | Lower in Smoker |
| cg05406381 | 4 | 1503917 | Lower in Smoker |
| cg00232160 | 9 | 129463157 | Lower in Smoker |
| cg20424036 | 8 | 32777053 | Lower in Smoker |
| cg07707479 | 1 | 47879840 | Lower in Smoker |
| cg15704004 | 11 | 92806448 | Lower in Smoker |
| cg24405248 | 15 | 62537146 | Lower in Smoker |
| cg26945894 | 10 | 974338 | Lower in Smoker |
| cg19241927 | 1 | 56333494 | Lower in Smoker |
| cg15646463 | 2 | 51446925 | Lower in Smoker |
| cg08878713 | 1 | 31325813 | Lower in Smoker |

| | | | |
|---|---|---|---|
| cg06361845 | 9 | 136074886 | Lower in Smoker |
| cg23782909 | 12 | 101945864 | Lower in Smoker |
| cg27494111 | 19 | 12369481 | Lower in Smoker |
| cg05097579 | 3 | 136750029 | Lower in Smoker |
| cg15905320 | 8 | 142661528 | Lower in Smoker |
| cg01547910 | 2 | 167629889 | Lower in Smoker |
| cg04842934 | 6 | 32757870 | Lower in Smoker |
| cg16522960 | 7 | 74493756 | Lower in Smoker |
| cg18451766 | 8 | 104492154 | Lower in Smoker |
| cg14633063 | 2 | 38101511 | Lower in Smoker |
| cg02505015 | 12 | 121197625 | Lower in Smoker |
| cg19535685 | 22 | 19845442 | Lower in Smoker |
| cg12903911 | 7 | 155170812 | Lower in Smoker |
| cg23632393 | 1 | 2145116 | Lower in Smoker |
| cg18034501 | 3 | 4043162 | Lower in Smoker |
| cg06580523 | 12 | 132908454 | Lower in Smoker |
| cg05026346 | 7 | 23057327 | Lower in Smoker |
| cg01110440 | 6 | 110707714 | Lower in Smoker |
| cg01518259 | 16 | 32323497 | Lower in Smoker |
| cg14766448 | 3 | 172171507 | Lower in Smoker |
| cg04713188 | 16 | 87634399 | Lower in Smoker |
| cg00590383 | 16 | 53410108 | Lower in Smoker |
| cg09580974 | 1 | 220006958 | Lower in Smoker |
| cg02599587 | 5 | 153275285 | Lower in Smoker |
| cg02615214 | 16 | 90002892 | Lower in Smoker |
| cg07410633 | 11 | 120397626 | Lower in Smoker |
| cg18516067 | 4 | 98239185 | Lower in Smoker |
| cg14645841 | 12 | 85945089 | Lower in Smoker |
| cg24839277 | 8 | 125311416 | Lower in Smoker |
| cg16475423 | 2 | 145106459 | Lower in Smoker |
| cg03665818 | 16 | 54724064 | Lower in Smoker |
| cg17938491 | 19 | 1875351 | Lower in Smoker |
| cg22623268 | 5 | 141886806 | Lower in Smoker |
| cg11380483 | 2 | 127933992 | Lower in Smoker |
| cg24798826 | 12 | 133055011 | Lower in Smoker |

| | | | |
|---|---|---|---|
| cg11855587 | 13 | 111746866 | Lower in Smoker |
| cg15410835 | 8 | 143125637 | Lower in Smoker |
| cg02436616 | 16 | 87219779 | Lower in Smoker |
| cg26358634 | 5 | 62365115 | Lower in Smoker |
| cg13452769 | 9 | 36726501 | Lower in Smoker |
| cg05861664 | 11 | 1140438 | Lower in Smoker |
| cg08581021 | 6 | 170590562 | Lower in Smoker |
| cg14471866 | 2 | 192734461 | Lower in Smoker |
| cg03622592 | 15 | 21145708 | Lower in Smoker |
| cg12214295 | 10 | 134835524 | Lower in Smoker |
| cg12421966 | 2 | 240649725 | Lower in Smoker |
| cg22388232 | 8 | 861072 | Lower in Smoker |
| cg02977790 | 1 | 16126356 | Lower in Smoker |
| cg27218993 | 6 | 73263351 | Lower in Smoker |
| cg18286498 | 5 | 1922911 | Lower in Smoker |
| cg14532344 | 3 | 186211530 | Lower in Smoker |
| cg13614103 | 5 | 141217652 | Lower in Smoker |
| cg10723146 | 14 | 65346721 | Lower in Smoker |
| cg13878023 | 12 | 43965985 | Lower in Smoker |
| cg01827805 | 1 | 240159816 | Lower in Smoker |
| cg18774154 | 2 | 126504079 | Lower in Smoker |
| cg00812839 | 1 | 146895247 | Lower in Smoker |
| cg00642740 | 6 | 19613221 | Lower in Smoker |
| cg02562387 | 10 | 134647457 | Lower in Smoker |
| cg12737285 | 2 | 192362155 | Lower in Smoker |
| cg02756168 | 10 | 15055005 | Lower in Smoker |
| cg11570082 | 7 | 116899446 | Lower in Smoker |
| cg00341906 | 9 | 2933229 | Lower in Smoker |
| cg03706109 | 17 | 43090472 | Lower in Smoker |
| cg10015974 | 1 | 199827580 | Lower in Smoker |
| cg16929850 | 10 | 18989097 | Lower in Smoker |
| cg15056803 | 10 | 33820120 | Lower in Smoker |
| cg23483799 | 11 | 18659383 | Lower in Smoker |
| cg17304457 | 12 | 115775889 | Lower in Smoker |
| cg13802736 | 1 | 157948536 | Lower in Smoker |

| | | | |
|---|---|---|---|
| cg10961439 | 2 | 137151911 | Lower in Smoker |
| cg14020037 | 9 | 131340763 | Lower in Smoker |
| cg13460168 | 1 | 16501540 | Lower in Smoker |
| cg21672401 | 12 | 43499608 | Lower in Smoker |
| cg19512604 | 19 | 10809044 | Lower in Smoker |
| cg01719904 | 3 | 26410290 | Lower in Smoker |
| cg04071440 | 6 | 29648275 | Lower in Smoker |
| cg26323924 | 14 | 106313769 | Lower in Smoker |
| cg19927058 | 4 | 27704430 | Lower in Smoker |
| cg02789045 | 3 | 142644867 | Lower in Smoker |
| cg06646218 | 3 | 59165920 | Lower in Smoker |
| cg05127995 | 4 | 2735245 | Lower in Smoker |
| cg18822951 | 5 | 141783822 | Lower in Smoker |
| cg08523756 | 11 | 41165407 | Lower in Smoker |
| cg07753366 | 5 | 52598132 | Lower in Smoker |
| cg10712884 | 4 | 186048269 | Lower in Smoker |
| cg00226689 | 7 | 41259421 | Lower in Smoker |
| cg08535779 | 1 | 2475961 | Lower in Smoker |
| cg24186459 | 3 | 181459418 | Lower in Smoker |
| cg01681688 | 8 | 145397116 | Lower in Smoker |
| cg21495366 | 5 | 1179159 | Lower in Smoker |
| cg13457741 | 10 | 3536731 | Lower in Smoker |
| cg20521963 | 3 | 154651783 | Lower in Smoker |
| cg11510938 | 7 | 1220897 | Lower in Smoker |
| cg13223182 | 1 | 227015944 | Lower in Smoker |
| cg10754341 | 2 | 113637962 | Lower in Smoker |
| cg19850275 | 10 | 75654257 | Lower in Smoker |
| cg07379508 | 2 | 171630114 | Lower in Smoker |
| cg04735598 | 2 | 76905622 | Lower in Smoker |
| cg01527164 | 13 | 114902156 | Lower in Smoker |
| cg09981999 | X | 53120031 | Lower in Smoker |
| cg13308080 | 6 | 26234061 | Lower in Smoker |
| cg12846203 | 22 | 39243970 | Lower in Smoker |
| cg23929072 | 1 | 222638937 | Lower in Smoker |
| cg03310594 | 7 | 22704316 | Lower in Smoker |

| | | | |
|---|---|---|---|
| cg18854004 | 2 | 8444004 | Lower in Smoker |
| cg08764465 | 8 | 15308417 | Lower in Smoker |
| cg27518483 | 15 | 80634135 | Lower in Smoker |
| cg10842008 | 1 | 24477838 | Lower in Smoker |
| cg10266455 | 2 | 174411207 | Lower in Smoker |
| cg25006509 | 14 | 19747134 | Lower in Smoker |
| cg06191536 | 17 | 78999725 | Lower in Smoker |
| cg06565377 | 21 | 37263529 | Lower in Smoker |
| cg26275841 | 14 | 103040826 | Lower in Smoker |
| cg22163972 | 17 | 77537086 | Lower in Smoker |
| cg09198601 | 6 | 10319180 | Lower in Smoker |
| cg14425888 | 9 | 74223055 | Lower in Smoker |
| cg01031312 | 3 | 195849513 | Lower in Smoker |
| cg24383344 | X | 25020570 | Lower in Smoker |
| cg18519837 | 19 | 49924582 | Lower in Smoker |
| cg16271833 | 10 | 21676880 | Lower in Smoker |
| cg05843312 | 7 | 76586131 | Lower in Smoker |
| cg17983053 | 10 | 73619524 | Lower in Smoker |
| cg01056615 | 5 | 1140096 | Lower in Smoker |
| cg14911204 | 22 | 41808989 | Lower in Smoker |
| cg20974659 | 11 | 1375304 | Lower in Smoker |
| cg15213081 | 19 | 523300 | Lower in Smoker |
| cg03367136 | 11 | 102638470 | Lower in Smoker |
| cg04258001 | 15 | 93909165 | Lower in Smoker |
| cg19683494 | 5 | 74908142 | Lower in Smoker |
| cg10984165 | 5 | 28809121 | Lower in Smoker |
| cg12322450 | X | 63263531 | Lower in Smoker |
| cg06092069 | 3 | 57992423 | Lower in Smoker |
| cg02981853 | 19 | 7445850 | Lower in Smoker |
| cg23558626 | 2 | 154400847 | Lower in Smoker |
| cg02417473 | 22 | 38434179 | Lower in Smoker |
| cg03147324 | 15 | 29928082 | Lower in Smoker |
| cg04729173 | 11 | 129613547 | Lower in Smoker |
| cg25747655 | 6 | 44440322 | Lower in Smoker |
| cg08368496 | 6 | 18522976 | Lower in Smoker |

| | | | |
|---|---|---|---|
| cg15075728 | 1 | 108026669 | Lower in Smoker |
| cg01097907 | 5 | 3608511 | Lower in Smoker |
| cg03957547 | 16 | 9524433 | Lower in Smoker |
| cg25338994 | 2 | 73168150 | Lower in Smoker |
| cg13175173 | 14 | 55914753 | Lower in Smoker |
| cg25762854 | 8 | 80048524 | Lower in Smoker |
| cg07882223 | 5 | 95651711 | Lower in Smoker |
| cg06174795 | 3 | 187755513 | Lower in Smoker |
| cg20040320 | 11 | 23191996 | Lower in Smoker |
| cg01727646 | 1 | 26337472 | Lower in Smoker |
| cg24228231 | 4 | 71557171 | Lower in Smoker |
| cg18076430 | 20 | 40325863 | Lower in Smoker |
| cg10534216 | 12 | 132661355 | Lower in Smoker |
| cg19787000 | 12 | 127220652 | Lower in Smoker |
| cg26954729 | 11 | 75950762 | Lower in Smoker |
| cg09408110 | 2 | 239888865 | Lower in Smoker |
| cg05565697 | 15 | 71100339 | Lower in Smoker |
| cg07125976 | 16 | 14499943 | Lower in Smoker |
| cg00112187 | 8 | 142653790 | Lower in Smoker |
| cg16029659 | 21 | 46241005 | Lower in Smoker |
| cg20811347 | 2 | 10619271 | Lower in Smoker |
| cg02080152 | 1 | 55967678 | Lower in Smoker |
| cg10281846 | 7 | 26156403 | Lower in Smoker |
| cg26068090 | 13 | 38518217 | Lower in Smoker |
| cg00933263 | 7 | 56434951 | Lower in Smoker |
| cg14690649 | 12 | 31884655 | Lower in Smoker |
| cg25388061 | 5 | 178215887 | Lower in Smoker |
| cg01328621 | 15 | 68567276 | Lower in Smoker |
| cg24535643 | 1 | 108029106 | Lower in Smoker |
| cg17840367 | 1 | 13886703 | Lower in Smoker |
| cg24125269 | 18 | 76825313 | Lower in Smoker |
| cg02856132 | 8 | 80695847 | Lower in Smoker |
| cg11193840 | 22 | 39742880 | Lower in Smoker |
| cg25162533 | 17 | 81032067 | Lower in Smoker |
| cg18174099 | 14 | 88200397 | Lower in Smoker |

| | | | |
|---|---|---|---|
| cg15296766 | 3 | 155817887 | Lower in Smoker |
| cg02570527 | 1 | 10970165 | Lower in Smoker |
| cg11523538 | 1 | 244013970 | Lower in Smoker |
| cg11570011 | 4 | 16362340 | Lower in Smoker |
| cg27126251 | 16 | 82161215 | Lower in Smoker |
| cg09955523 | 20 | 39948552 | Lower in Smoker |
| cg14261474 | 4 | 158555507 | Lower in Smoker |
| cg00252408 | 1 | 98389381 | Lower in Smoker |
| cg20459407 | 7 | 100895581 | Lower in Smoker |
| cg08607209 | 6 | 52610808 | Lower in Smoker |
| cg09448460 | 2 | 207129158 | Lower in Smoker |
| cg07213119 | 4 | 6359269 | Lower in Smoker |
| cg19982221 | 6 | 159316196 | Lower in Smoker |
| cg07426634 | 1 | 53943469 | Lower in Smoker |
| cg06486618 | 19 | 524262 | Lower in Smoker |
| cg02215899 | 16 | 83966922 | Lower in Smoker |
| cg20710603 | 17 | 1227932 | Lower in Smoker |
| cg23102514 | 2 | 241840339 | Lower in Smoker |
| cg05420143 | 2 | 210286628 | Lower in Smoker |
| cg17373759 | 11 | 76265321 | Lower in Smoker |
| cg00334941 | 3 | 146964907 | Lower in Smoker |
| cg00148558 | 22 | 20718691 | Lower in Smoker |
| cg18606619 | 4 | 38565294 | Lower in Smoker |
| cg21742071 | 12 | 76571364 | Lower in Smoker |
| cg12201625 | 5 | 160312279 | Lower in Smoker |
| cg19404692 | 2 | 129663717 | Lower in Smoker |
| cg10803767 | 2 | 231688923 | Lower in Smoker |
| cg26494337 | 11 | 127931200 | Lower in Smoker |
| cg05588271 | 16 | 1112257 | Lower in Smoker |
| cg18847904 | 5 | 1779178 | Lower in Smoker |
| cg01119145 | 20 | 706882 | Lower in Smoker |
| cg19679302 | 7 | 81239309 | Lower in Smoker |
| cg23798471 | 13 | 27834647 | Lower in Smoker |
| cg22913996 | 12 | 53542686 | Lower in Smoker |
| cg17425580 | 1 | 20521101 | Lower in Smoker |

| | | | |
|---|---|---|---|
| cg22399703 | 2 | 19456333 | Lower in Smoker |
| cg04265425 | 19 | 10411133 | Lower in Smoker |
| cg00113117 | 1 | 56946754 | Lower in Smoker |
| cg18845053 | 6 | 32769203 | Lower in Smoker |
| cg22867315 | 6 | 153476415 | Lower in Smoker |
| cg15893779 | 13 | 113753244 | Lower in Smoker |
| cg25405984 | 10 | 31074039 | Lower in Smoker |
| cg12367833 | 4 | 42764094 | Lower in Smoker |
| cg06702733 | 4 | 57397016 | Lower in Smoker |
| cg01969311 | 12 | 65350145 | Lower in Smoker |
| cg15650209 | 5 | 1866463 | Lower in Smoker |
| cg11875028 | 7 | 42742698 | Lower in Smoker |
| cg25014229 | 3 | 61785026 | Lower in Smoker |
| cg21205282 | 6 | 170553133 | Lower in Smoker |
| cg19083977 | 1 | 1712885 | Lower in Smoker |
| cg26105115 | 10 | 10099469 | Lower in Smoker |
| cg13036549 | 14 | 106092696 | Lower in Smoker |
| cg10190444 | 17 | 58213109 | Lower in Smoker |
| cg23246815 | 17 | 80336414 | Lower in Smoker |
| cg19811683 | 17 | 16587128 | Lower in Smoker |
| cg14447703 | 6 | 30846517 | Lower in Smoker |
| cg05996811 | 4 | 74808337 | Lower in Smoker |
| cg16623943 | 6 | 80251197 | Lower in Smoker |
| cg26050487 | 2 | 119825535 | Lower in Smoker |
| cg25078026 | 6 | 28829931 | Lower in Smoker |
| cg04203853 | 14 | 75770221 | Lower in Smoker |
| cg25741340 | 1 | 142672490 | Lower in Smoker |
| cg10604550 | 5 | 43001210 | Lower in Smoker |
| cg21932878 | 5 | 53179148 | Lower in Smoker |
| cg05150667 | 4 | 23994603 | Lower in Smoker |
| cg25211566 | 17 | 38808304 | Lower in Smoker |
| cg22021357 | 17 | 78483873 | Lower in Smoker |
| cg10127479 | 1 | 147624510 | Lower in Smoker |
| cg27624334 | 10 | 29018952 | Lower in Smoker |
| cg26856578 | 13 | 79360870 | Lower in Smoker |

| | | | |
|---|---|---|---|
| cg24598158 | 1 | 206788265 | Lower in Smoker |
| cg11906792 | 11 | 95160248 | Lower in Smoker |
| cg02025737 | 15 | 33384751 | Lower in Smoker |
| cg27634164 | 5 | 116751135 | Lower in Smoker |
| cg11225089 | 5 | 131430859 | Lower in Smoker |
| cg22699362 | 2 | 118775427 | Lower in Smoker |
| cg03024489 | 2 | 87040878 | Lower in Smoker |
| cg02158880 | 13 | 53174818 | Lower in Smoker |
| cg04785587 | 7 | 45154359 | Lower in Smoker |
| cg03114253 | 1 | 158122905 | Lower in Smoker |
| cg25601829 | 15 | 67355497 | Lower in Smoker |
| cg20288445 | 14 | 105871956 | Lower in Smoker |
| cg21413947 | 1 | 165329957 | Lower in Smoker |
| cg11192191 | 11 | 69291998 | Lower in Smoker |
| cg12199651 | 7 | 28329189 | Lower in Smoker |
| cg11829486 | 8 | 11772568 | Lower in Smoker |
| cg10233401 | 10 | 45192368 | Lower in Smoker |
| cg27582166 | 10 | 91187721 | Lower in Smoker |
| cg09880745 | 5 | 68316966 | Lower in Smoker |
| cg12342753 | 4 | 4329664 | Lower in Smoker |
| cg10092394 | 1 | 209408557 | Lower in Smoker |
| cg19394047 | 10 | 131223487 | Lower in Smoker |
| cg17335387 | 5 | 55828740 | Lower in Smoker |
| cg18583740 | 5 | 17490773 | Lower in Smoker |
| cg05444514 | 6 | 466935 | Lower in Smoker |
| cg03158063 | 2 | 10395333 | Lower in Smoker |
| cg23958464 | 1 | 30985690 | Lower in Smoker |
| cg07191839 | 1 | 149109519 | Lower in Smoker |
| cg07238058 | 12 | 19936611 | Lower in Smoker |
| cg16674047 | 15 | 68867577 | Lower in Smoker |
| cg02486364 | 7 | 13155344 | Lower in Smoker |
| cg10009827 | 2 | 81808933 | Lower in Smoker |
| cg13700939 | 2 | 128166166 | Lower in Smoker |
| cg27446442 | 1 | 36546899 | Lower in Smoker |
| cg01935731 | 12 | 128399269 | Lower in Smoker |

| | | | |
|---|---|---|---|
| cg11583041 | 6 | 169740781 | Lower in Smoker |
| cg27422857 | 2 | 105853526 | Lower in Smoker |
| cg18988861 | 7 | 51452804 | Lower in Smoker |
| cg03147592 | 12 | 133022955 | Lower in Smoker |
| cg19699056 | 7 | 73843743 | Lower in Smoker |
| cg04387820 | 10 | 18999425 | Lower in Smoker |
| cg26216724 | 5 | 1749217 | Lower in Smoker |
| cg22871227 | 5 | 173987519 | Lower in Smoker |
| cg17500962 | 16 | 73178951 | Lower in Smoker |
| cg03995615 | 5 | 36744219 | Lower in Smoker |
| cg00747618 | 1 | 247612701 | Lower in Smoker |
| cg21634818 | 4 | 49579904 | Lower in Smoker |
| cg04958337 | 12 | 6489206 | Lower in Smoker |
| cg05252153 | 10 | 80416410 | Lower in Smoker |
| cg18823849 | 8 | 19094722 | Lower in Smoker |
| cg19749361 | 4 | 124374860 | Lower in Smoker |
| cg16394952 | 16 | 88439457 | Lower in Smoker |
| cg14732789 | 20 | 29537189 | Lower in Smoker |
| cg27546911 | 16 | 1297816 | Lower in Smoker |
| cg13837857 | 9 | 38672315 | Lower in Smoker |
| cg23384960 | 11 | 12626570 | Lower in Smoker |
| cg15798823 | 7 | 22866267 | Lower in Smoker |
| cg02352401 | 3 | 128219629 | Lower in Smoker |
| cg11585952 | 5 | 2103437 | Lower in Smoker |
| cg02035061 | 10 | 124718071 | Lower in Smoker |
| cg04672762 | 11 | 94242884 | Lower in Smoker |
| cg05923350 | 6 | 29810094 | Lower in Smoker |
| cg09610792 | 11 | 94798056 | Lower in Smoker |
| cg12520996 | 13 | 45157755 | Lower in Smoker |
| cg13741263 | 9 | 68305914 | Lower in Smoker |
| cg04078644 | 3 | 155458975 | Lower in Smoker |
| cg07062747 | 3 | 28122982 | Lower in Smoker |
| cg20565082 | 5 | 60525509 | Lower in Smoker |
| cg09728333 | 3 | 177329038 | Lower in Smoker |
| cg27231292 | 6 | 50765846 | Lower in Smoker |

| | | | |
|---|---|---|---|
| cg17913570 | Y | 9382523 | Lower in Smoker |
| cg09063056 | 6 | 8155299 | Lower in Smoker |
| cg22112152 | 3 | 153501841 | Lower in Smoker |
| cg00175403 | 1 | 12223543 | Lower in Smoker |
| cg04832245 | 6 | 32829144 | Lower in Smoker |
| cg03451750 | 16 | 88294570 | Lower in Smoker |
| cg13537646 | 3 | 112143970 | Lower in Smoker |
| cg09098720 | 17 | 49412842 | Lower in Smoker |
| cg00242998 | 20 | 32807971 | Lower in Smoker |
| cg01106038 | 16 | 89112229 | Lower in Smoker |
| cg02264229 | 14 | 95240560 | Lower in Smoker |
| cg24588058 | 7 | 76591673 | Lower in Smoker |
| cg14465628 | 9 | 98125437 | Lower in Smoker |
| cg18537454 | 10 | 22623213 | Lower in Smoker |
| cg07209667 | 8 | 41425365 | Lower in Smoker |
| cg17333193 | 11 | 101664126 | Lower in Smoker |
| cg08294772 | 8 | 138135392 | Lower in Smoker |
| cg07789140 | 12 | 113921202 | Lower in Smoker |
| cg22015486 | 1 | 182925377 | Lower in Smoker |
| cg13554773 | 17 | 47340329 | Lower in Smoker |
| cg21484547 | 13 | 28319144 | Lower in Smoker |
| cg14930000 | X | 53028582 | Lower in Smoker |
| cg22993706 | 8 | 75542856 | Lower in Smoker |
| cg25026755 | 5 | 57702195 | Lower in Smoker |
| cg11282433 | 5 | 178463871 | Lower in Smoker |
| cg10223006 | X | 152590495 | Lower in Smoker |
| cg16533315 | 14 | 87621970 | Lower in Smoker |
| cg26513818 | 1 | 236555214 | Lower in Smoker |
| cg26235048 | 6 | 131132063 | Lower in Smoker |
| cg06628999 | 6 | 142129232 | Lower in Smoker |
| cg00953355 | 17 | 70114129 | Lower in Smoker |
| cg26565660 | 12 | 76176280 | Lower in Smoker |
| cg19185846 | 2 | 71123233 | Lower in Smoker |
| cg19439651 | 10 | 130299087 | Lower in Smoker |
| cg08687643 | 3 | 58569597 | Lower in Smoker |

| | | | |
|---|---|---|---|
| cg13065735 | 1 | 180868449 | Lower in Smoker |
| cg21041701 | 12 | 31942768 | Lower in Smoker |
| cg19720628 | 5 | 77986925 | Lower in Smoker |
| cg24919806 | 10 | 34189023 | Lower in Smoker |
| cg08667731 | X | 107023455 | Lower in Smoker |
| cg06422277 | 5 | 63458646 | Lower in Smoker |
| cg17341366 | 2 | 10148966 | Lower in Smoker |
| cg14700230 | 19 | 18719623 | Lower in Smoker |
| cg11040518 | 10 | 102331378 | Lower in Smoker |
| cg16382077 | 7 | 171543 | Lower in Smoker |
| cg00284179 | 2 | 155314028 | Lower in Smoker |
| cg27151303 | 7 | 27184821 | Lower in Smoker |
| cg09378105 | 7 | 100895380 | Lower in Smoker |
| cg15604241 | 11 | 35941235 | Lower in Smoker |
| cg04499646 | 6 | 133529701 | Lower in Smoker |
| cg00250761 | 1 | 31883323 | Lower in Smoker |
| cg00874589 | 3 | 112405614 | Lower in Smoker |
| cg17204337 | 15 | 91639877 | Lower in Smoker |
| cg23423163 | 11 | 45257480 | Lower in Smoker |
| cg19527084 | 2 | 74229775 | Lower in Smoker |
| cg10498585 | 3 | 155139702 | Lower in Smoker |
| cg01687389 | 16 | 53064480 | Lower in Smoker |
| cg26002568 | 4 | 74806905 | Lower in Smoker |
| cg15410441 | 8 | 143700158 | Lower in Smoker |
| cg17966227 | 1 | 113738233 | Lower in Smoker |
| cg11278749 | 5 | 127563986 | Lower in Smoker |
| cg23944588 | 4 | 14988786 | Lower in Smoker |
| cg15788369 | 19 | 15833777 | Lower in Smoker |
| cg05860371 | 4 | 152931291 | Lower in Smoker |
| cg04226138 | 8 | 107057242 | Lower in Smoker |
| cg25720825 | 1 | 2849682 | Lower in Smoker |
| cg23371507 | 6 | 44526765 | Lower in Smoker |
| cg17322044 | 12 | 125140105 | Lower in Smoker |
| cg21610556 | 4 | 181452599 | Lower in Smoker |
| cg05151709 | 1 | 846155 | Lower in Smoker |

| | | | |
|---|---|---|---|
| cg12789343 | 7 | 66056820 | Lower in Smoker |
| cg05877550 | 16 | 85369038 | Lower in Smoker |
| cg05668422 | 13 | 114026346 | Lower in Smoker |
| cg04147940 | 8 | 69781040 | Lower in Smoker |
| cg17525436 | 8 | 98552496 | Lower in Smoker |
| cg11123613 | 10 | 30643945 | Lower in Smoker |
| cg04134096 | 3 | 151643511 | Lower in Smoker |
| cg23794358 | 6 | 137690400 | Lower in Smoker |
| cg00829600 | 16 | 84678923 | Lower in Smoker |
| cg24153574 | 1 | 1296956 | Lower in Smoker |
| cg01916237 | 4 | 1558883 | Lower in Smoker |
| cg00555894 | 4 | 97182116 | Lower in Smoker |
| cg04778755 | 10 | 3235569 | Lower in Smoker |
| cg11419814 | 13 | 22056533 | Lower in Smoker |
| cg15026569 | 11 | 102860262 | Lower in Smoker |
| cg03328485 | 16 | 62267020 | Lower in Smoker |
| cg05196046 | 12 | 34756334 | Lower in Smoker |
| cg06931523 | 8 | 854757 | Lower in Smoker |
| cg13866688 | 4 | 188045495 | Lower in Smoker |
| cg12500300 | 10 | 133810178 | Lower in Smoker |
| cg20013942 | 6 | 160259178 | Lower in Smoker |
| cg19611612 | 15 | 67223583 | Lower in Smoker |
| cg21147063 | 21 | 34354927 | Lower in Smoker |
| cg13586794 | 10 | 20885882 | Lower in Smoker |
| cg07650271 | 12 | 82154719 | Lower in Smoker |
| cg22370710 | 4 | 128699484 | Lower in Smoker |
| cg07721042 | 8 | 127439142 | Lower in Smoker |
| cg11180316 | 14 | 53928144 | Lower in Smoker |
| cg16482878 | 15 | 37402488 | Lower in Smoker |
| cg07841831 | 17 | 41782011 | Lower in Smoker |
| cg21570843 | 1 | 2789896 | Lower in Smoker |
| cg15322455 | 7 | 1358274 | Lower in Smoker |
| cg03750034 | 8 | 94430696 | Lower in Smoker |
| cg19736047 | 4 | 177759864 | Lower in Smoker |
| cg20543968 | 12 | 72529102 | Lower in Smoker |

| | | | |
|---|---|---|---|
| cg14718995 | 3 | 3102321 | Lower in Smoker |
| cg03114584 | 4 | 1534311 | Lower in Smoker |
| cg26193468 | 2 | 6637936 | Lower in Smoker |
| cg24768167 | 14 | 21104434 | Lower in Smoker |
| cg06919519 | 5 | 1640077 | Lower in Smoker |
| cg20653032 | 11 | 7259254 | Lower in Smoker |
| cg24343594 | 13 | 33158569 | Lower in Smoker |
| cg09421361 | X | 65041584 | Lower in Smoker |
| cg05252143 | 4 | 9453010 | Lower in Smoker |
| cg14299508 | 8 | 105907690 | Lower in Smoker |
| cg14718065 | 2 | 131010763 | Lower in Smoker |
| cg07900344 | 2 | 6305776 | Lower in Smoker |
| cg07310677 | 13 | 113598558 | Lower in Smoker |
| cg09113939 | 16 | 89674844 | Lower in Smoker |
| cg04285194 | 2 | 187867339 | Lower in Smoker |
| cg05617678 | 15 | 81468859 | Lower in Smoker |
| cg26935330 | 17 | 54678114 | Lower in Smoker |
| cg05438719 | 16 | 81476518 | Lower in Smoker |
| cg26155674 | 2 | 86793873 | Lower in Smoker |
| cg23631133 | 2 | 240568824 | Lower in Smoker |
| cg24034715 | 1 | 142672461 | Lower in Smoker |
| cg12017221 | 12 | 22968563 | Lower in Smoker |
| cg15335988 | 15 | 63245400 | Lower in Smoker |
| cg13041894 | 22 | 47609321 | Lower in Smoker |
| cg26478205 | 16 | 25701385 | Lower in Smoker |
| cg23005102 | 14 | 56979854 | Lower in Smoker |
| cg09010707 | 12 | 26392567 | Lower in Smoker |
| cg01887388 | 2 | 81420861 | Lower in Smoker |
| cg18938313 | 1 | 214926740 | Lower in Smoker |
| cg27090073 | 14 | 104925368 | Lower in Smoker |
| cg05248004 | 8 | 74031115 | Lower in Smoker |
| cg24614200 | 13 | 19967206 | Lower in Smoker |
| cg15822328 | 1 | 1072197 | Lower in Smoker |
| cg02788637 | 7 | 853229 | Lower in Smoker |
| cg04319399 | 16 | 85497962 | Lower in Smoker |

| | | | |
|---|---|---|---|
| cg11081251 | 15 | 65375977 | Lower in Smoker |
| cg25772185 | 10 | 25371488 | Lower in Smoker |
| cg10746278 | 11 | 116061735 | Lower in Smoker |
| cg23145621 | 7 | 1406289 | Lower in Smoker |
| cg25040562 | 14 | 99850049 | Lower in Smoker |
| cg02270765 | 4 | 84843504 | Lower in Smoker |
| cg25028404 | 1 | 157896400 | Lower in Smoker |
| cg16801954 | 6 | 36916123 | Lower in Smoker |
| cg07744430 | 12 | 132345502 | Lower in Smoker |
| cg08262534 | 3 | 109072059 | Lower in Smoker |
| cg03005040 | 15 | 82119192 | Lower in Smoker |
| cg04981409 | 3 | 174093784 | Lower in Smoker |
| cg24932312 | 5 | 57232025 | Lower in Smoker |
| cg03386347 | 16 | 38261775 | Lower in Smoker |
| cg24485354 | 1 | 46797622 | Lower in Smoker |
| cg17388024 | 2 | 16673542 | Lower in Smoker |
| cg03174043 | 2 | 20548412 | Lower in Smoker |
| cg11721178 | 12 | 106010541 | Lower in Smoker |
| cg05617551 | 16 | 54209183 | Lower in Smoker |
| cg25629041 | 2 | 88817360 | Lower in Smoker |
| cg19867579 | 2 | 175643491 | Lower in Smoker |
| cg21899640 | 6 | 168609219 | Lower in Smoker |
| cg14477471 | 9 | 137107162 | Lower in Smoker |
| cg18591489 | 15 | 35475575 | Lower in Smoker |
| cg01586208 | 19 | 22806647 | Lower in Smoker |
| cg22593554 | 2 | 128990739 | Lower in Smoker |
| cg06118245 | 8 | 24293139 | Lower in Smoker |
| cg05316694 | 14 | 99786833 | Lower in Smoker |
| cg02367921 | 1 | 40504529 | Lower in Smoker |
| cg07991586 | 16 | 50279175 | Lower in Smoker |
| cg04171425 | 16 | 4654740 | Lower in Smoker |
| cg23513591 | 13 | 81229232 | Lower in Smoker |
| cg05514909 | 12 | 133022853 | Lower in Smoker |
| cg09807524 | 11 | 17569556 | Lower in Smoker |
| cg04628741 | 10 | 18425598 | Lower in Smoker |

| | | | |
|---|---|---|---|
| cg04964883 | 6 | 1410436 | Lower in Smoker |
| cg04216073 | 5 | 127878868 | Lower in Smoker |
| cg07822469 | 1 | 182585393 | Lower in Smoker |
| cg25977619 | 10 | 77054404 | Lower in Smoker |
| cg21888373 | 6 | 3175749 | Lower in Smoker |
| cg03780653 | 3 | 184788336 | Lower in Smoker |
| cg03192060 | 11 | 62674500 | Lower in Smoker |
| cg04568799 | 3 | 197840782 | Lower in Smoker |
| cg07939743 | 4 | 57507828 | Lower in Smoker |
| cg07144720 | 3 | 95038960 | Lower in Smoker |
| cg09768983 | 4 | 183935060 | Lower in Smoker |
| cg01468579 | 10 | 122102016 | Lower in Smoker |
| cg04727521 | 16 | 1154951 | Lower in Smoker |
| cg14536194 | 14 | 95157213 | Lower in Smoker |
| cg18063486 | 4 | 1512966 | Lower in Smoker |
| cg23619338 | 13 | 51753863 | Lower in Smoker |
| cg18841668 | 11 | 111077632 | Lower in Smoker |
| cg01674361 | 11 | 18213229 | Lower in Smoker |
| cg18900914 | 5 | 12230982 | Lower in Smoker |
| cg23136495 | 5 | 120248381 | Lower in Smoker |
| cg19618505 | X | 27882528 | Lower in Smoker |
| cg27586885 | 19 | 33726898 | Lower in Smoker |
| cg15883853 | 12 | 13080282 | Lower in Smoker |
| cg10521767 | 1 | 237116052 | Lower in Smoker |
| cg23253961 | 14 | 62394494 | Lower in Smoker |
| cg13835436 | 11 | 69809807 | Lower in Smoker |
| cg00543769 | 5 | 70749126 | Lower in Smoker |
| cg18291014 | 7 | 93658 | Lower in Smoker |
| cg01359236 | 8 | 11763828 | Lower in Smoker |
| cg10811961 | 12 | 54090346 | Lower in Smoker |
| cg02954324 | 3 | 67045043 | Lower in Smoker |
| cg22138597 | 11 | 82396872 | Lower in Smoker |
| cg26918577 | 17 | 75888026 | Lower in Smoker |
| cg16910908 | 11 | 89518310 | Lower in Smoker |
| cg08746591 | 7 | 5599905 | Lower in Smoker |

| | | | |
|---|---|---|---|
| cg23499133 | 3 | 50189428 | Lower in Smoker |
| cg10450005 | 6 | 164767056 | Lower in Smoker |
| cg13237147 | 3 | 188745304 | Lower in Smoker |
| cg23201265 | 12 | 23078236 | Lower in Smoker |
| cg19945931 | 12 | 133022760 | Lower in Smoker |
| cg10955744 | 8 | 119778490 | Lower in Smoker |
| cg26629715 | 8 | 89379430 | Lower in Smoker |
| cg02124499 | 20 | 61620257 | Lower in Smoker |
| cg24373608 | 3 | 103645997 | Lower in Smoker |
| cg11886405 | 11 | 133699751 | Lower in Smoker |
| cg05720721 | 3 | 123803128 | Lower in Smoker |
| cg26687318 | 10 | 20078731 | Lower in Smoker |
| cg09071407 | 5 | 115958234 | Lower in Smoker |
| cg04139007 | 8 | 124776493 | Lower in Smoker |
| cg07817648 | 10 | 79422355 | Lower in Smoker |
| cg09517766 | 10 | 44894102 | Lower in Smoker |
| cg08795149 | 7 | 49167921 | Lower in Smoker |
| cg14467690 | 9 | 135120707 | Lower in Smoker |
| cg22696982 | 2 | 177502905 | Lower in Smoker |
| cg07013698 | 17 | 80174780 | Lower in Smoker |
| cg20810675 | 4 | 171604188 | Lower in Smoker |
| cg23639120 | 8 | 55243106 | Lower in Smoker |
| cg18586262 | 13 | 69557960 | Lower in Smoker |
| cg21540530 | 2 | 188583082 | Lower in Smoker |
| cg12591622 | 6 | 126067118 | Lower in Smoker |
| cg19698348 | 15 | 40803733 | Lower in Smoker |
| cg03887906 | 1 | 208135621 | Lower in Smoker |
| cg18913924 | 7 | 82623 | Lower in Smoker |
| cg14165692 | 2 | 111367744 | Lower in Smoker |
| cg16906555 | 7 | 54728016 | Lower in Smoker |
| cg07441278 | 3 | 48256968 | Lower in Smoker |
| cg16759813 | 2 | 104988400 | Lower in Smoker |
| cg21253335 | 5 | 87835928 | Lower in Smoker |
| cg00366880 | 3 | 13244304 | Lower in Smoker |
| cg06669631 | 4 | 157227668 | Lower in Smoker |

| | | | |
|---|---|---|---|
| cg04570910 | 12 | 12122983 | Lower in Smoker |
| cg17628060 | 8 | 144367553 | Lower in Smoker |
| cg08162976 | 2 | 67032496 | Lower in Smoker |
| cg11908124 | 6 | 35756942 | Lower in Smoker |
| cg22330638 | 11 | 45732392 | Lower in Smoker |
| cg24196784 | 6 | 33866987 | Lower in Smoker |
| cg18022883 | 4 | 54972054 | Lower in Smoker |
| cg15835747 | 8 | 143523387 | Lower in Smoker |
| cg19941795 | 6 | 33216545 | Lower in Smoker |
| cg05096492 | 6 | 28828946 | Lower in Smoker |
| cg11827897 | 8 | 122234746 | Lower in Smoker |
| cg00955089 | 6 | 11878092 | Lower in Smoker |
| cg05142057 | 13 | 72971591 | Lower in Smoker |
| cg16999568 | 11 | 3601547 | Lower in Smoker |
| cg26264896 | 2 | 131655129 | Lower in Smoker |
| cg15914908 | 12 | 133012468 | Lower in Smoker |
| cg23728085 | 7 | 54359662 | Lower in Smoker |
| cg00903371 | 2 | 238360134 | Lower in Smoker |
| cg07525886 | 17 | 8227927 | Lower in Smoker |
| cg01980454 | 1 | 859173 | Lower in Smoker |
| cg08397456 | 16 | 79800489 | Lower in Smoker |
| cg22219379 | 3 | 140541355 | Lower in Smoker |
| cg20147285 | 19 | 22711958 | Lower in Smoker |
| cg05503062 | 15 | 90324339 | Lower in Smoker |
| cg05877048 | 15 | 47734755 | Lower in Smoker |
| cg14145896 | 14 | 84294194 | Lower in Smoker |
| cg15903032 | 10 | 101297605 | Lower in Smoker |
| cg08414643 | 5 | 153873149 | Lower in Smoker |
| cg27364244 | 12 | 132660955 | Lower in Smoker |
| cg17344598 | 3 | 131942442 | Lower in Smoker |
| cg13588355 | 5 | 126998388 | Lower in Smoker |
| cg03911745 | 8 | 49486641 | Lower in Smoker |
| cg24689119 | 4 | 56042287 | Lower in Smoker |
| cg04039177 | 8 | 8474738 | Lower in Smoker |
| cg08695418 | 4 | 6729199 | Lower in Smoker |

| | | | |
|---|---|---|---|
| cg11382203 | 11 | 76470635 | Lower in Smoker |
| cg18719158 | 10 | 80136983 | Lower in Smoker |
| cg12561945 | 8 | 64615707 | Lower in Smoker |
| cg27390627 | 1 | 242874219 | Lower in Smoker |
| cg21789008 | 8 | 118764818 | Lower in Smoker |
| cg14758065 | 17 | 81028496 | Lower in Smoker |
| cg13677785 | 22 | 42548868 | Lower in Smoker |
| cg18319612 | 1 | 203257946 | Lower in Smoker |
| cg24335273 | 3 | 117506059 | Lower in Smoker |
| cg01447344 | 1 | 159989137 | Lower in Smoker |
| cg22106280 | 5 | 141891754 | Lower in Smoker |
| cg14218629 | 1 | 204156575 | Lower in Smoker |
| cg21787873 | 1 | 2327611 | Lower in Smoker |
| cg02832905 | 18 | 75591983 | Lower in Smoker |
| cg21644660 | X | 108865686 | Lower in Smoker |
| cg15908324 | 11 | 119770117 | Lower in Smoker |
| cg11394820 | 2 | 107104579 | Lower in Smoker |
| cg12648671 | 18 | 77377538 | Lower in Smoker |
| cg14352298 | 13 | 112236639 | Lower in Smoker |
| cg25573480 | 5 | 2132239 | Lower in Smoker |
| cg20569369 | 22 | 51173646 | Lower in Smoker |
| cg16988072 | 17 | 41791475 | Lower in Smoker |
| cg26969197 | 8 | 6548570 | Lower in Smoker |
| cg14545305 | 2 | 171670978 | Lower in Smoker |
| cg19634252 | 4 | 38155144 | Lower in Smoker |
| cg19479744 | 6 | 156022315 | Lower in Smoker |
| cg11852796 | 21 | 44062183 | Lower in Smoker |
| cg14417372 | 11 | 119455230 | Lower in Smoker |
| cg15577516 | 7 | 12462597 | Lower in Smoker |
| cg10042132 | 14 | 81938575 | Lower in Smoker |
| cg17529041 | 6 | 108452210 | Lower in Smoker |
| cg10166609 | 2 | 71383612 | Lower in Smoker |
| cg09912512 | 22 | 42761285 | Lower in Smoker |
| cg03151294 | 4 | 189220624 | Lower in Smoker |
| cg22065604 | 4 | 98270564 | Lower in Smoker |

| | | | |
|---|---|---|---|
| cg16686279 | 1 | 4087226 | Lower in Smoker |
| cg11268585 | 5 | 1039552 | Lower in Smoker |
| cg06818582 | 15 | 67286903 | Lower in Smoker |
| cg21853568 | 1 | 16408902 | Lower in Smoker |
| cg15127879 | 8 | 69917477 | Lower in Smoker |
| cg05131175 | 1 | 193899449 | Lower in Smoker |
| cg21177494 | 15 | 33397692 | Lower in Smoker |
| cg27592568 | 16 | 29618499 | Lower in Smoker |
| cg02112621 | 3 | 78387362 | Lower in Smoker |
| cg03879594 | 16 | 85207569 | Lower in Smoker |
| cg14615268 | 6 | 27602081 | Lower in Smoker |
| cg27604672 | 11 | 97073773 | Lower in Smoker |
| cg18366169 | 5 | 1948875 | Lower in Smoker |
| cg02560364 | 16 | 63219709 | Lower in Smoker |
| cg16761097 | 2 | 68697545 | Lower in Smoker |
| cg11276506 | 19 | 14186130 | Lower in Smoker |
| cg14005025 | 11 | 56615879 | Lower in Smoker |
| cg17079556 | 7 | 57252146 | Lower in Smoker |
| cg10299128 | 4 | 82796846 | Lower in Smoker |
| cg15420395 | 17 | 58212421 | Lower in Smoker |
| cg14997321 | 6 | 134436460 | Lower in Smoker |
| cg17010905 | X | 153365806 | Lower in Smoker |
| cg08895590 | 1 | 91227319 | Lower in Smoker |
| cg02592403 | 19 | 51614910 | Lower in Smoker |
| cg05848884 | 8 | 74848047 | Lower in Smoker |
| cg03100509 | 12 | 49584947 | Lower in Smoker |
| cg16998186 | 6 | 27205956 | Lower in Smoker |
| cg01029637 | 20 | 4201164 | Lower in Smoker |
| cg05749642 | 16 | 89982268 | Lower in Smoker |
| cg07496687 | 22 | 22236176 | Lower in Smoker |
| cg16322269 | 8 | 49379533 | Lower in Smoker |
| cg08454015 | 1 | 240078452 | Lower in Smoker |
| cg13636952 | 7 | 142447956 | Lower in Smoker |
| cg11633264 | 8 | 102160417 | Lower in Smoker |
| cg12045999 | 12 | 23069755 | Lower in Smoker |

| | | | |
|---|---|---|---|
| cg27480427 | 7 | 35578510 | Lower in Smoker |
| cg10042554 | 15 | 40800292 | Lower in Smoker |
| cg06895675 | 10 | 88137553 | Lower in Smoker |
| cg04958528 | 16 | 28982197 | Lower in Smoker |
| cg26236972 | 2 | 237921310 | Lower in Smoker |
| cg13805793 | 10 | 54515952 | Lower in Smoker |
| cg16171105 | 1 | 18205396 | Lower in Smoker |
| cg23357209 | 13 | 51117881 | Lower in Smoker |
| cg14585907 | 11 | 94497474 | Lower in Smoker |
| cg26981966 | 7 | 152593597 | Lower in Smoker |
| cg12068833 | 4 | 132896266 | Lower in Smoker |
| cg19824055 | 6 | 114524946 | Lower in Smoker |
| cg14287311 | 13 | 77289721 | Lower in Smoker |
| cg00239171 | 4 | 136198747 | Lower in Smoker |
| cg06664486 | 6 | 170379377 | Lower in Smoker |
| cg26918808 | 1 | 67950349 | Lower in Smoker |
| cg21248287 | 20 | 47011259 | Lower in Smoker |
| cg27552406 | 16 | 11465792 | Lower in Smoker |
| cg10702770 | 1 | 39283780 | Lower in Smoker |
| cg24310711 | 17 | 70026605 | Lower in Smoker |
| cg05675331 | 7 | 152591459 | Lower in Smoker |
| cg18387985 | 11 | 15350125 | Lower in Smoker |
| cg09631769 | 22 | 49376986 | Lower in Smoker |
| cg20323874 | 14 | 100240804 | Lower in Smoker |
| cg16102024 | 12 | 127218981 | Lower in Smoker |
| cg25567054 | 14 | 104824020 | Lower in Smoker |
| cg07000643 | 12 | 133183142 | Lower in Smoker |
| cg01342968 | 9 | 38487169 | Lower in Smoker |
| cg25895971 | 17 | 77904396 | Lower in Smoker |
| cg18882486 | 12 | 115461557 | Lower in Smoker |
| cg11302293 | 4 | 3785772 | Lower in Smoker |
| cg27338202 | 3 | 187481967 | Lower in Smoker |
| cg05528623 | 1 | 2387670 | Lower in Smoker |
| cg08711059 | 5 | 139166290 | Lower in Smoker |
| cg07928232 | 1 | 218831506 | Lower in Smoker |

| | | | |
|---|---|---|---|
| cg17362483 | 4 | 177420127 | Lower in Smoker |
| cg19592732 | 3 | 120028889 | Lower in Smoker |
| cg22207405 | 2 | 70853907 | Lower in Smoker |
| cg12663490 | 15 | 47693183 | Lower in Smoker |
| cg14126093 | 6 | 128905086 | Lower in Smoker |
| cg11321092 | 5 | 144325284 | Lower in Smoker |
| cg08834573 | 10 | 77005666 | Lower in Smoker |
| cg11736524 | 8 | 128075224 | Lower in Smoker |
| cg21597304 | 15 | 27021321 | Lower in Smoker |
| cg07409153 | 2 | 76839078 | Lower in Smoker |
| cg08973688 | 17 | 47983990 | Lower in Smoker |
| cg25773223 | 10 | 3680061 | Lower in Smoker |
| cg06115388 | 11 | 70289855 | Lower in Smoker |
| cg08534443 | 12 | 133022550 | Lower in Smoker |
| cg12684999 | 2 | 161099777 | Lower in Smoker |
| cg02298220 | 20 | 35914908 | Lower in Smoker |
| cg10804254 | 1 | 218633247 | Lower in Smoker |
| cg13601957 | 6 | 60218373 | Lower in Smoker |
| cg16364066 | 10 | 6821184 | Lower in Smoker |
| cg10135682 | 10 | 20023014 | Lower in Smoker |
| cg17796982 | 8 | 143055406 | Lower in Smoker |
| cg06311879 | 12 | 93427724 | Lower in Smoker |
| cg24393009 | 12 | 94927093 | Lower in Smoker |
| cg24032056 | 12 | 75961704 | Lower in Smoker |
| cg09516210 | 1 | 2825189 | Lower in Smoker |
| cg26784929 | 1 | 178908942 | Lower in Smoker |
| cg03625515 | 16 | 1815708 | Lower in Smoker |
| cg10700019 | 8 | 145994882 | Lower in Smoker |
| cg24901488 | 3 | 41121968 | Lower in Smoker |
| cg24244695 | 11 | 2240683 | Lower in Smoker |
| cg04778125 | 14 | 104721657 | Lower in Smoker |
| cg03784113 | 13 | 112602492 | Lower in Smoker |
| cg13019844 | 6 | 170589897 | Lower in Smoker |
| cg18244362 | 8 | 21669615 | Lower in Smoker |
| cg09663081 | 5 | 8838602 | Lower in Smoker |

| | | | |
|---|---|---|---|
| cg03570577 | 6 | 29765324 | Lower in Smoker |
| cg19014749 | 17 | 35037101 | Lower in Smoker |
| cg26714693 | 5 | 172711094 | Lower in Smoker |
| cg01427471 | 11 | 134288416 | Lower in Smoker |
| cg09100373 | 8 | 127708756 | Lower in Smoker |
| cg16692507 | 13 | 36726031 | Lower in Smoker |
| cg00787013 | 10 | 125665208 | Lower in Smoker |
| cg20703997 | 1 | 4087676 | Lower in Smoker |
| cg01197411 | 5 | 87988624 | Lower in Smoker |
| cg27175112 | 2 | 11515031 | Lower in Smoker |
| cg07450292 | 3 | 76419070 | Lower in Smoker |
| cg17008160 | 1 | 232315535 | Lower in Smoker |
| cg11835955 | 14 | 40142517 | Lower in Smoker |
| cg14028769 | 7 | 38673294 | Lower in Smoker |
| cg16879895 | 13 | 79236684 | Lower in Smoker |
| cg19086905 | 15 | 102342791 | Lower in Smoker |
| cg12045443 | 12 | 89777963 | Lower in Smoker |
| cg02489189 | 2 | 157049585 | Lower in Smoker |
| cg01904216 | 16 | 85454460 | Lower in Smoker |
| cg21441211 | 17 | 71313862 | Lower in Smoker |
| cg14649424 | 9 | 98115754 | Lower in Smoker |
| cg26810230 | 10 | 134948300 | Lower in Smoker |
| cg17831277 | 7 | 131253722 | Lower in Smoker |
| cg10301767 | 12 | 59121643 | Lower in Smoker |
| cg17310256 | 11 | 31847173 | Lower in Smoker |
| cg16637458 | 13 | 113585948 | Lower in Smoker |
| cg18795277 | 5 | 131282379 | Lower in Smoker |
| cg19235974 | 12 | 1063197 | Lower in Smoker |
| cg10310751 | 11 | 1805969 | Lower in Smoker |
| cg21886541 | 7 | 155616422 | Lower in Smoker |
| cg02449564 | 4 | 8359247 | Lower in Smoker |
| cg13872898 | 2 | 121498194 | Lower in Smoker |
| cg03049501 | 16 | 55087225 | Lower in Smoker |
| cg16237594 | 18 | 14435120 | Lower in Smoker |
| cg22040631 | 2 | 129153820 | Lower in Smoker |

| | | | |
|---|---|---|---|
| cg23493018 | 8 | 37309823 | Lower in Smoker |
| cg10364905 | 3 | 50262408 | Lower in Smoker |
| cg22106273 | 5 | 117630841 | Lower in Smoker |
| cg25188760 | 20 | 5301547 | Lower in Smoker |
| cg23710960 | 4 | 4855629 | Lower in Smoker |
| cg26117369 | 13 | 113104975 | Lower in Smoker |
| cg10512769 | 1 | 211675356 | Lower in Smoker |
| cg14022105 | 11 | 78268793 | Lower in Smoker |
| cg25120513 | 17 | 58215290 | Lower in Smoker |
| cg16120196 | 1 | 2922569 | Lower in Smoker |
| cg13220723 | 18 | 6930452 | Lower in Smoker |
| cg00641579 | 10 | 88146442 | Lower in Smoker |
| cg24730705 | 10 | 119496382 | Lower in Smoker |
| cg00535994 | 2 | 165925489 | Lower in Smoker |
| cg23641319 | 8 | 143862739 | Lower in Smoker |
| cg22167763 | 13 | 95315772 | Lower in Smoker |
| cg06303706 | 5 | 1709413 | Lower in Smoker |
| cg06538709 | 8 | 48654011 | Lower in Smoker |
| cg05384646 | 15 | 30206862 | Lower in Smoker |
| cg21139935 | 13 | 25139847 | Lower in Smoker |
| cg20384231 | 10 | 131132572 | Lower in Smoker |
| cg10514207 | 13 | 49384181 | Lower in Smoker |
| cg07348845 | 1 | 227544540 | Lower in Smoker |
| cg06781213 | 8 | 22941370 | Lower in Smoker |
| cg10754002 | 2 | 121276805 | Lower in Smoker |
| cg17164513 | 19 | 2064075 | Lower in Smoker |
| cg14749802 | 10 | 133195108 | Lower in Smoker |
| cg01962405 | 6 | 63709255 | Lower in Smoker |
| cg22133973 | 6 | 170789640 | Lower in Smoker |
| cg21501167 | 4 | 84869222 | Lower in Smoker |
| cg06447614 | 16 | 1195491 | Lower in Smoker |
| cg09858951 | 10 | 132860218 | Lower in Smoker |
| cg01538605 | 6 | 169285957 | Lower in Smoker |
| cg09975044 | 14 | 104007538 | Lower in Smoker |
| cg08720250 | 12 | 107637226 | Lower in Smoker |

| | | | |
|---|---|---|---|
| cg09016994 | X | 5470075 | Lower in Smoker |
| cg21341134 | 20 | 3666877 | Lower in Smoker |
| cg02281854 | 2 | 217429125 | Lower in Smoker |
| cg09113505 | 1 | 246955186 | Lower in Smoker |
| cg07811262 | 16 | 50871285 | Lower in Smoker |
| cg22703113 | 4 | 7185164 | Lower in Smoker |
| cg01194279 | 12 | 114073142 | Lower in Smoker |
| cg16176378 | 3 | 34843233 | Lower in Smoker |
| cg25177692 | X | 129193893 | Lower in Smoker |
| cg21207730 | 9 | 86821905 | Lower in Smoker |
| cg19266329 | 1 | 145456128 | Lower in Smoker |
| cg12393374 | 5 | 95555970 | Lower in Smoker |
| cg16823976 | 1 | 247499595 | Lower in Smoker |
| cg08243931 | 5 | 34476633 | Lower in Smoker |
| cg19469722 | 14 | 105318459 | Lower in Smoker |
| cg00599530 | 6 | 170589809 | Lower in Smoker |
| cg11010432 | 2 | 239540451 | Lower in Smoker |
| cg00545702 | 5 | 1553167 | Lower in Smoker |
| cg04227079 | 5 | 3059042 | Lower in Smoker |
| cg13688783 | 9 | 138301441 | Lower in Smoker |
| cg02612650 | 6 | 26195910 | Lower in Smoker |
| cg22542222 | 10 | 132386640 | Lower in Smoker |
| cg27287357 | 15 | 39050013 | Lower in Smoker |
| cg14620039 | 9 | 21396107 | Lower in Smoker |
| cg14312323 | 17 | 47980310 | Lower in Smoker |
| cg01403655 | 13 | 43702940 | Lower in Smoker |
| cg05136724 | 2 | 65793962 | Lower in Smoker |
| cg24881334 | 17 | 69409104 | Lower in Smoker |
| cg14263518 | 9 | 134249904 | Lower in Smoker |
| cg07205823 | 3 | 49229620 | Lower in Smoker |
| cg22118250 | 6 | 27655512 | Lower in Smoker |
| cg16338011 | 3 | 137301727 | Lower in Smoker |
| cg03647927 | 17 | 36584240 | Lower in Smoker |
| cg27560132 | 2 | 65521323 | Lower in Smoker |
| cg06784691 | 1 | 2245988 | Lower in Smoker |

| | | | |
|---|---|---|---|
| cg08215169 | 13 | 112144901 | Lower in Smoker |
| cg16031270 | 15 | 63292560 | Lower in Smoker |
| cg09073443 | 8 | 329193 | Lower in Smoker |
| cg20578256 | 10 | 97732488 | Lower in Smoker |
| cg16790843 | 16 | 85212949 | Lower in Smoker |
| cg05056653 | 17 | 81023856 | Lower in Smoker |
| cg16749629 | 12 | 66459807 | Lower in Smoker |
| cg01299119 | 19 | 13070604 | Lower in Smoker |
| cg26181894 | 11 | 130274125 | Lower in Smoker |
| cg18396789 | 7 | 20346927 | Lower in Smoker |
| cg11826324 | 8 | 104278949 | Lower in Smoker |
| cg23539633 | 11 | 116228309 | Lower in Smoker |
| cg15235805 | 3 | 32941716 | Lower in Smoker |
| cg02530860 | 8 | 144371537 | Lower in Smoker |
| cg26373874 | 14 | 105323161 | Lower in Smoker |
| cg19607021 | 5 | 139104833 | Lower in Smoker |
| cg17933224 | 19 | 42774330 | Lower in Smoker |
| cg05595248 | 7 | 44183432 | Lower in Smoker |
| cg06998224 | 5 | 128113907 | Lower in Smoker |
| cg22368281 | 7 | 82270 | Lower in Smoker |
| cg00365481 | 19 | 46362237 | Lower in Smoker |
| cg08159033 | 4 | 139819191 | Lower in Smoker |
| cg20031032 | 14 | 104979378 | Lower in Smoker |
| cg02216535 | 4 | 85308929 | Lower in Smoker |
| cg15404971 | 5 | 7392579 | Lower in Smoker |
| cg01079019 | 16 | 21566602 | Lower in Smoker |
| cg25812683 | 10 | 6691515 | Lower in Smoker |
| cg17338299 | 7 | 155141719 | Lower in Smoker |
| cg05336997 | 11 | 1226873 | Lower in Smoker |
| cg10540573 | 2 | 218869684 | Lower in Smoker |
| cg21219525 | 9 | 98982897 | Lower in Smoker |
| cg17676618 | 10 | 80563421 | Lower in Smoker |
| cg17552471 | 7 | 4678661 | Lower in Smoker |
| cg15764067 | 13 | 28374053 | Lower in Smoker |
| cg20043649 | 2 | 47537239 | Lower in Smoker |

| | | | |
|---|---|---|---|
| cg18936502 | 7 | 35187811 | Lower in Smoker |
| cg08422054 | 3 | 100875565 | Lower in Smoker |
| cg00062437 | 22 | 23728539 | Lower in Smoker |
| cg13200482 | 21 | 47064462 | Lower in Smoker |
| cg24135923 | 4 | 124267807 | Lower in Smoker |
| cg13641690 | 15 | 78114888 | Lower in Smoker |
| cg05791544 | 4 | 129697855 | Lower in Smoker |
| cg21245718 | 9 | 93943683 | Lower in Smoker |
| cg22971600 | 6 | 169830859 | Lower in Smoker |
| cg11744631 | 6 | 55498560 | Lower in Smoker |
| cg23696214 | 7 | 141136170 | Lower in Smoker |
| cg11807280 | 2 | 66654644 | Lower in Smoker |
| cg17506621 | 6 | 160023581 | Lower in Smoker |
| cg27487959 | 8 | 40758947 | Lower in Smoker |
| cg24569257 | 5 | 155105708 | Lower in Smoker |
| cg02506275 | 12 | 130650643 | Lower in Smoker |
| cg04212450 | 7 | 90997889 | Lower in Smoker |
| cg02914112 | 6 | 99096390 | Lower in Smoker |
| cg01043845 | 2 | 177013071 | Lower in Smoker |
| cg09769755 | 17 | 43074945 | Lower in Smoker |
| cg08310088 | 16 | 28081556 | Lower in Smoker |
| cg19614643 | 2 | 19499118 | Lower in Smoker |
| cg19636627 | 6 | 29649084 | Lower in Smoker |
| cg07320883 | 15 | 81408453 | Lower in Smoker |
| cg16991316 | 10 | 54172718 | Lower in Smoker |
| cg04008056 | 3 | 52254842 | Lower in Smoker |
| cg07157117 | 4 | 109708677 | Lower in Smoker |
| cg01190800 | 4 | 1539702 | Lower in Smoker |
| cg20071203 | X | 150351493 | Lower in Smoker |
| cg18845960 | 2 | 37387350 | Lower in Smoker |
| cg20394141 | 7 | 157219787 | Lower in Smoker |
| cg04064160 | 8 | 26048065 | Lower in Smoker |
| cg04743510 | 17 | 39793142 | Lower in Smoker |
| cg02985871 | 8 | 135212805 | Lower in Smoker |
| cg26360924 | 1 | 118793005 | Lower in Smoker |

| | | | |
|---|---|---|---|
| cg10393508 | 13 | 50950265 | Lower in Smoker |
| cg01813327 | 16 | 883720 | Lower in Smoker |
| cg10238051 | 10 | 79399092 | Lower in Smoker |
| cg18846954 | 12 | 133028690 | Lower in Smoker |
| cg06463B1 | 17 | 77835854 | Lower in Smoker |
| cg07429804 | 17 | 39666961 | Lower in Smoker |
| cg11592230 | 2 | 26981306 | Lower in Smoker |
| cg14507845 | 9 | 137418069 | Lower in Smoker |
| cg00874073 | 17 | 73073329 | Lower in Smoker |
| cg20613432 | 1 | 2799579 | Lower in Smoker |
| cg06013833 | 11 | 123111851 | Lower in Smoker |
| cg03577128 | 3 | 148050624 | Lower in Smoker |
| cg13137032 | 4 | 5904897 | Lower in Smoker |
| cg05593707 | 11 | 30002836 | Lower in Smoker |
| cg23130369 | 2 | 129245177 | Lower in Smoker |
| cg21272919 | 15 | 25014966 | Lower in Smoker |
| cg23411529 | 14 | 106027044 | Lower in Smoker |
| cg12743419 | 10 | 33464523 | Lower in Smoker |
| cg18744822 | 2 | 91933576 | Lower in Smoker |
| cg07920381 | 12 | 132303685 | Lower in Smoker |
| cg12096762 | 15 | 88296044 | Lower in Smoker |
| cg10118557 | 8 | 142401373 | Lower in Smoker |
| cg17136073 | 13 | 23310675 | Lower in Smoker |
| cg01409693 | 4 | 1542171 | Lower in Smoker |
| cg08031492 | 2 | 469214 | Lower in Smoker |
| cg02164741 | 17 | 77537018 | Lower in Smoker |
| cg05620980 | 7 | 562844 | Lower in Smoker |
| cg00841988 | 14 | 100204153 | Lower in Smoker |
| cg11043993 | 10 | 50536966 | Lower in Smoker |
| cg09248276 | 1 | 160696468 | Lower in Smoker |
| cg19521610 | 22 | 49717457 | Lower in Smoker |
| cg26153182 | 7 | 154703374 | Lower in Smoker |
| cg03389926 | 2 | 42651266 | Lower in Smoker |
| cg11653948 | 11 | 2421970 | Lower in Smoker |
| cg17566325 | 12 | 133022423 | Lower in Smoker |

| | | | |
|---|---|---|---|
| cg26620314 | 16 | 66038809 | Lower in Smoker |
| cg10307894 | 12 | 125169804 | Lower in Smoker |
| cg22379463 | 3 | 45260330 | Lower in Smoker |
| cg26770890 | 8 | 16628810 | Lower in Smoker |
| cg00518276 | 11 | 106148020 | Lower in Smoker |
| cg12629796 | 7 | 74050146 | Lower in Smoker |
| cg06334005 | 10 | 22499738 | Lower in Smoker |
| cg04309849 | 10 | 131843517 | Lower in Smoker |
| cg05536692 | 11 | 41328069 | Lower in Smoker |
| cg05938624 | 8 | 1314612 | Lower in Smoker |
| cg14630993 | 9 | 7274452 | Lower in Smoker |
| cg20724168 | 12 | 130591337 | Lower in Smoker |
| cg06901307 | 13 | 66607275 | Lower in Smoker |
| cg24312610 | 6 | 153484006 | Lower in Smoker |
| cg19360937 | 2 | 76148284 | Lower in Smoker |
| cg23970546 | 5 | 87205266 | Lower in Smoker |
| cg10640004 | X | 25020238 | Lower in Smoker |
| cg02431531 | 16 | 59244939 | Lower in Smoker |
| cg24979203 | 2 | 206501294 | Lower in Smoker |
| cg26134692 | 2 | 101778863 | Lower in Smoker |
| cg00856850 | 14 | 107283452 | Lower in Smoker |
| cg25992016 | 13 | 77387018 | Lower in Smoker |
| cg06469455 | 5 | 127138134 | Lower in Smoker |
| cg18929842 | 17 | 39804040 | Lower in Smoker |
| cg09181015 | 5 | 158104558 | Lower in Smoker |
| cg09557543 | 6 | 27598947 | Lower in Smoker |
| cg16203594 | 3 | 58572394 | Lower in Smoker |
| cg14925328 | 2 | 207913718 | Lower in Smoker |
| cg22975791 | X | 55934874 | Lower in Smoker |
| cg19613915 | 5 | 170921824 | Lower in Smoker |
| cg18079355 | 5 | 74331325 | Lower in Smoker |
| cg16570669 | 11 | 126923106 | Lower in Smoker |
| cg17888259 | 1 | 179557662 | Lower in Smoker |
| cg14972827 | 6 | 17045947 | Lower in Smoker |
| cg04361749 | 2 | 240980455 | Lower in Smoker |

| | | | |
|---|---|---|---|
| cg13548452 | 14 | 22573606 | Lower in Smoker |
| cg06979726 | 16 | 84851070 | Lower in Smoker |
| cg15889793 | 6 | 37527311 | Lower in Smoker |
| cg13601565 | 10 | 1200124 | Lower in Smoker |
| cg13725826 | 14 | 100211213 | Lower in Smoker |
| cg00252472 | 6 | 150739173 | Lower in Smoker |
| cg05762488 | 1 | 64140332 | Lower in Smoker |
| cg10613706 | 17 | 19355650 | Lower in Smoker |
| cg22329776 | 12 | 76243294 | Lower in Smoker |
| cg25606969 | 1 | 110983728 | Lower in Smoker |
| cg11195363 | 12 | 61915276 | Lower in Smoker |
| cg08081424 | 2 | 159749591 | Lower in Smoker |
| cg11903206 | 3 | 70911187 | Lower in Smoker |
| cg07814541 | 5 | 71329680 | Lower in Smoker |
| cg23831517 | 8 | 34182528 | Lower in Smoker |
| cg04744156 | 2 | 102865140 | Lower in Smoker |
| cg12978232 | 12 | 89339873 | Lower in Smoker |
| cg18348086 | 1 | 1104526 | Lower in Smoker |
| cg07069742 | 3 | 59644285 | Lower in Smoker |
| cg11816081 | 17 | 47539827 | Lower in Smoker |
| cg12579684 | 14 | 101391505 | Lower in Smoker |
| cg05606878 | 5 | 126432189 | Lower in Smoker |
| cg24017555 | 6 | 131781271 | Lower in Smoker |
| cg01040585 | 17 | 36907054 | Lower in Smoker |
| cg02413104 | X | 150395248 | Lower in Smoker |
| cg24956176 | 17 | 33542219 | Lower in Smoker |
| cg13445067 | 7 | 131334527 | Lower in Smoker |
| cg19932515 | 2 | 98326480 | Lower in Smoker |
| cg16491739 | 14 | 105031052 | Lower in Smoker |
| cg03476212 | 16 | 85301902 | Lower in Smoker |
| cg25628898 | 8 | 49779136 | Lower in Smoker |
| cg10631854 | 3 | 197383170 | Lower in Smoker |
| cg25124045 | 5 | 52749655 | Lower in Smoker |
| cg05244013 | 15 | 94346066 | Lower in Smoker |
| cg09571762 | 12 | 39539558 | Lower in Smoker |

| | | | |
|---|---|---|---|
| cg02944312 | 7 | 3207719 | Lower in Smoker |
| cg26378984 | 11 | 116374243 | Lower in Smoker |
| cg11851804 | 1 | 848379 | Lower in Smoker |
| cg11863406 | 13 | 91825667 | Lower in Smoker |
| cg03394309 | 12 | 10544636 | Lower in Smoker |
| cg17870997 | 2 | 121498521 | Lower in Smoker |
| cg02208125 | 6 | 33866257 | Lower in Smoker |
| cg05839818 | 16 | 85634031 | Lower in Smoker |
| cg11073796 | 2 | 180748603 | Lower in Smoker |
| cg25525687 | 19 | 7982713 | Lower in Smoker |
| cg19415202 | 11 | 133706356 | Lower in Smoker |
| cg05223487 | 16 | 1080540 | Lower in Smoker |
| cg06779672 | 6 | 1378238 | Lower in Smoker |
| cg15444358 | 14 | 102051071 | Lower in Smoker |
| cg19595295 | 17 | 56019314 | Lower in Smoker |
| cg05473536 | 16 | 1131266 | Lower in Smoker |
| cg13170807 | 17 | 25708208 | Lower in Smoker |
| cg11310639 | 10 | 48623215 | Lower in Smoker |
| cg08770757 | 10 | 19993393 | Lower in Smoker |
| cg04895225 | 11 | 85862822 | Lower in Smoker |
| cg11013714 | 3 | 138128339 | Lower in Smoker |
| cg18358875 | 3 | 137476338 | Lower in Smoker |
| cg11263617 | 8 | 144852778 | Lower in Smoker |
| cg21678813 | 11 | 20229879 | Lower in Smoker |
| cg16450677 | 2 | 70312492 | Lower in Smoker |
| cg27303933 | 5 | 56029413 | Lower in Smoker |
| cg03108139 | 7 | 155165471 | Lower in Smoker |
| cg01874183 | 8 | 120548252 | Lower in Smoker |
| cg06955417 | 7 | 16890879 | Lower in Smoker |
| cg00423675 | 9 | 138067680 | Lower in Smoker |
| cg27492584 | 17 | 70599307 | Lower in Smoker |
| cg09142638 | 11 | 74394651 | Lower in Smoker |
| cg24843346 | 8 | 142736091 | Lower in Smoker |
| cg02716614 | 6 | 131101115 | Lower in Smoker |
| cg24704759 | 10 | 133446251 | Lower in Smoker |

| | | | |
|---|---|---|---|
| cg03495011 | 20 | 61757175 | Lower in Smoker |
| cg25731428 | 13 | 91830940 | Lower in Smoker |
| cg11202887 | 13 | 112076016 | Lower in Smoker |
| cg11615895 | X | 123465263 | Lower in Smoker |
| cg25547135 | 8 | 112691450 | Lower in Smoker |
| cg20274965 | 18 | 59989045 | Lower in Smoker |
| cg05865866 | 4 | 185205185 | Lower in Smoker |
| cg14397696 | 13 | 105792284 | Lower in Smoker |
| cg07245476 | 16 | 60448068 | Lower in Smoker |
| cg10961758 | 5 | 83222828 | Lower in Smoker |
| cg10468070 | 1 | 26551518 | Lower in Smoker |
| cg08899442 | 5 | 157398818 | Lower in Smoker |
| cg07653702 | 18 | 45612462 | Lower in Smoker |
| cg21211299 | 9 | 92982316 | Lower in Smoker |
| cg17298973 | 6 | 2876494 | Lower in Smoker |
| cg09300343 | X | 139521282 | Lower in Smoker |
| cg15896593 | 1 | 22975587 | Lower in Smoker |
| cg00886780 | 6 | 35149727 | Lower in Smoker |
| cg10114877 | 2 | 204427199 | Lower in Smoker |
| cg04606830 | 16 | 26999476 | Lower in Smoker |
| cg08003789 | 3 | 14630422 | Lower in Smoker |
| cg27058988 | 15 | 67200879 | Lower in Smoker |
| cg18904855 | 2 | 231693469 | Lower in Smoker |
| cg20342834 | 4 | 6013266 | Lower in Smoker |
| cg07352127 | 8 | 94442214 | Lower in Smoker |
| cg12929805 | 1 | 2399054 | Lower in Smoker |
| cg09324001 | 19 | 10049131 | Lower in Smoker |
| cg27311227 | 2 | 119769268 | Lower in Smoker |
| cg12458966 | 1 | 223674115 | Lower in Smoker |
| cg00272971 | 10 | 102419564 | Lower in Smoker |
| cg25575532 | 4 | 42270717 | Lower in Smoker |
| cg03344149 | 13 | 28535559 | Lower in Smoker |
| cg23867638 | 10 | 79459599 | Lower in Smoker |
| cg20559385 | 6 | 106049591 | Lower in Smoker |
| cg06195379 | 16 | 3124591 | Lower in Smoker |

| | | | |
|---|---|---|---|
| cg07270021 | 8 | 60627336 | Lower in Smoker |
| cg00270778 | 2 | 127977559 | Lower in Smoker |
| cg21566642 | 2 | 233284661 | Lower in Smoker |
| cg09313140 | 12 | 128309593 | Lower in Smoker |
| cg16691158 | 5 | 139140550 | Lower in Smoker |
| cg10868668 | 4 | 38606942 | Lower in Smoker |
| cg23261715 | 12 | 54144380 | Lower in Smoker |
| cg05170867 | 16 | 84375634 | Lower in Smoker |
| cg15587955 | 8 | 19026658 | Lower in Smoker |
| cg22950223 | 7 | 1403628 | Lower in Smoker |
| cg26781321 | 8 | 58131602 | Lower in Smoker |
| cg03230456 | 2 | 74939268 | Lower in Smoker |
| cg11746851 | 9 | 129988279 | Lower in Smoker |
| cg26684363 | 7 | 140135365 | Lower in Smoker |
| cg22494876 | 1 | 247618161 | Lower in Smoker |
| cg09696747 | 13 | 112053714 | Lower in Smoker |
| cg01207473 | 6 | 159359940 | Lower in Smoker |
| cg14097568 | 1 | 94792942 | Lower in Smoker |
| cg09682727 | 5 | 139953966 | Lower in Smoker |
| cg09374031 | 16 | 86548323 | Lower in Smoker |
| cg08901558 | 17 | 59472854 | Lower in Smoker |
| cg04002298 | 3 | 53230319 | Lower in Smoker |
| cg14901243 | 19 | 13951845 | Lower in Smoker |
| cg24306422 | 13 | 63084476 | Lower in Smoker |
| cg15801340 | 19 | 38345819 | Lower in Smoker |
| cg03662997 | 11 | 15963027 | Lower in Smoker |
| cg08294136 | 5 | 39760800 | Lower in Smoker |
| cg04871498 | 1 | 48450218 | Lower in Smoker |
| cg06638338 | 7 | 64712756 | Lower in Smoker |
| cg09546258 | 11 | 68444995 | Lower in Smoker |
| cg04896437 | 1 | 202076492 | Lower in Smoker |
| cg16660494 | 5 | 57073212 | Lower in Smoker |
| cg01643690 | 7 | 12228583 | Lower in Smoker |
| cg15473017 | 1 | 166853615 | Lower in Smoker |
| cg25744552 | 1 | 117368140 | Lower in Smoker |

| | | | |
|---|---|---|---|
| cg14741236 | 5 | 171985354 | Lower in Smoker |
| cg09342225 | 11 | 101668461 | Lower in Smoker |
| cg18033756 | 5 | 1660026 | Lower in Smoker |
| cg20944315 | 1 | 200839460 | Lower in Smoker |
| cg00064296 | 8 | 88712003 | Lower in Smoker |
| cg07879942 | 19 | 47013270 | Lower in Smoker |
| cg02846963 | 4 | 182430813 | Lower in Smoker |
| cg16290515 | 4 | 152246234 | Lower in Smoker |
| cg14484844 | 9 | 139590683 | Lower in Smoker |
| cg26028489 | 12 | 16674085 | Lower in Smoker |
| cg26147459 | 3 | 194592442 | Lower in Smoker |
| cg08670906 | 6 | 1604081 | Lower in Smoker |
| cg19309616 | 1 | 41851836 | Lower in Smoker |
| cg24555204 | 2 | 73334800 | Lower in Smoker |
| cg12804755 | 11 | 15796715 | Lower in Smoker |
| cg09251317 | 14 | 77393865 | Lower in Smoker |
| cg26985674 | 2 | 204980438 | Lower in Smoker |
| cg00189276 | 6 | 1410267 | Lower in Smoker |
| cg03774957 | 5 | 141227950 | Lower in Smoker |
| cg09185587 | 7 | 16890973 | Lower in Smoker |
| cg27123859 | 6 | 107230619 | Lower in Smoker |
| cg03339704 | 16 | 89050731 | Lower in Smoker |
| cg08628269 | 8 | 116073508 | Lower in Smoker |
| cg25469923 | 1 | 4087182 | Lower in Smoker |
| cg00883193 | 16 | 68485212 | Lower in Smoker |
| cg15885430 | 5 | 57069 | Lower in Smoker |
| cg25402228 | 15 | 47474134 | Lower in Smoker |
| cg00291366 | 7 | 12616550 | Lower in Smoker |
| cg00290023 | 5 | 174962968 | Lower in Smoker |
| cg06800658 | 5 | 134881970 | Lower in Smoker |
| cg06513974 | 1 | 117906338 | Lower in Smoker |
| cg09834729 | 11 | 35099055 | Lower in Smoker |
| cg22421804 | 5 | 54100067 | Lower in Smoker |
| cg15560801 | 1 | 46918254 | Lower in Smoker |
| cg09063663 | 1 | 16484811 | Lower in Smoker |

| | | | |
|---|---|---|---|
| cg02767177 | 10 | 102501755 | Lower in Smoker |
| cg25019503 | 11 | 44052211 | Lower in Smoker |
| cg04664968 | 2 | 118570237 | Lower in Smoker |
| cg15718555 | 2 | 239847497 | Lower in Smoker |
| cg06945807 | 1 | 95061616 | Lower in Smoker |
| cg25270089 | X | 153099097 | Lower in Smoker |
| cg02940003 | 3 | 186174294 | Lower in Smoker |
| cg16355945 | 12 | 132654742 | Lower in Smoker |
| cg05405483 | 7 | 120757 | Lower in Smoker |
| cg18712349 | 14 | 85214861 | Lower in Smoker |
| cg20902975 | 8 | 11138403 | Lower in Smoker |
| cg16398511 | 6 | 31010701 | Lower in Smoker |
| cg18664899 | 17 | 42278321 | Lower in Smoker |
| cg01365639 | 10 | 50975940 | Lower in Smoker |
| cg25520440 | 7 | 1734190 | Lower in Smoker |
| cg07084345 | 15 | 61972967 | Lower in Smoker |
| cg11324660 | 5 | 110199233 | Lower in Smoker |
| cg03068956 | 19 | 46990795 | Lower in Smoker |
| cg26290543 | 11 | 45377324 | Lower in Smoker |
| cg18144373 | 6 | 33736983 | Lower in Smoker |
| cg03305017 | 7 | 151036715 | Lower in Smoker |
| cg09085201 | 7 | 49708532 | Lower in Smoker |
| cg13087259 | 11 | 32193669 | Lower in Smoker |
| cg04150762 | 11 | 628677 | Lower in Smoker |
| cg05366050 | 4 | 164092065 | Lower in Smoker |
| cg21395577 | 1 | 221060851 | Lower in Smoker |
| cg19787448 | 17 | 69295698 | Lower in Smoker |
| cg23976431 | 11 | 102667025 | Lower in Smoker |
| cg16218715 | 2 | 63926253 | Lower in Smoker |
| cg03275375 | 8 | 28439379 | Lower in Smoker |
| cg04189591 | 22 | 42309398 | Lower in Smoker |
| cg16323034 | 6 | 37533807 | Lower in Smoker |
| cg06546183 | 21 | 44257072 | Lower in Smoker |
| cg04457114 | 5 | 174159705 | Lower in Smoker |
| cg17610889 | 3 | 177464075 | Lower in Smoker |

| | | | |
|---|---|---|---|
| cg14481124 | 10 | 71500729 | Lower in Smoker |
| cg24412662 | 1 | 2866667 | Lower in Smoker |
| cg12687617 | 15 | 89948930 | Lower in Smoker |
| cg14992768 | 2 | 209981979 | Lower in Smoker |
| cg14286256 | 9 | 98318448 | Lower in Smoker |
| cg08770034 | 5 | 1118757 | Lower in Smoker |
| cg01836906 | 2 | 192792315 | Lower in Smoker |
| cg13257690 | 14 | 101908752 | Lower in Smoker |
| cg17658266 | 6 | 74978996 | Lower in Smoker |
| cg02207386 | 7 | 25895834 | Lower in Smoker |
| cg05204532 | 2 | 8597177 | Lower in Smoker |
| cg02402882 | 5 | 56620429 | Lower in Smoker |
| cg02313986 | 15 | 40672041 | Lower in Smoker |
| cg20163689 | 2 | 13088414 | Lower in Smoker |
| cg10308610 | 10 | 49514273 | Lower in Smoker |
| cg02530834 | 3 | 14595849 | Lower in Smoker |
| cg05256483 | 2 | 119616242 | Lower in Smoker |
| cg24057775 | 1 | 2838930 | Lower in Smoker |
| cg14166209 | 1 | 117047015 | Lower in Smoker |
| cg07891120 | 4 | 171663610 | Lower in Smoker |
| cg08095522 | 16 | 83960312 | Lower in Smoker |
| cg07871633 | 19 | 41639260 | Lower in Smoker |
| cg06062187 | 5 | 5494730 | Lower in Smoker |
| cg10608476 | 5 | 50761067 | Lower in Smoker |
| cg06911613 | 16 | 85846184 | Lower in Smoker |
| cg12113851 | 10 | 65730093 | Lower in Smoker |
| cg21446772 | 2 | 222807796 | Lower in Smoker |
| cg09461792 | 7 | 17055230 | Lower in Smoker |
| cg00402417 | 13 | 100649423 | Lower in Smoker |
| cg05797224 | 1 | 94277532 | Lower in Smoker |
| cg05893353 | 3 | 115335126 | Lower in Smoker |
| cg14143504 | 9 | 132228647 | Lower in Smoker |
| cg01003211 | 7 | 1472830 | Lower in Smoker |
| cg26837773 | 1 | 947091 | Lower in Smoker |
| cg24943066 | 21 | 27009142 | Lower in Smoker |

| | | | |
|---|---|---|---|
| cg15282731 | 12 | 90177012 | Lower in Smoker |
| cg07468397 | 21 | 48090508 | Lower in Smoker |
| cg27365324 | 15 | 40727743 | Lower in Smoker |
| cg01810186 | 8 | 120058222 | Lower in Smoker |
| cg15418593 | 14 | 97492133 | Lower in Smoker |
| cg17811857 | 5 | 158529155 | Lower in Smoker |
| cg11596947 | 11 | 15966774 | Lower in Smoker |
| cg25051331 | 5 | 77253833 | Lower in Smoker |
| cg01612133 | 6 | 167317799 | Lower in Smoker |
| cg08122151 | 11 | 66764409 | Lower in Smoker |
| cg06061492 | 10 | 50221200 | Lower in Smoker |
| cg02067946 | 5 | 2149520 | Lower in Smoker |
| cg13705830 | 9 | 89518557 | Lower in Smoker |
| cg11639753 | 10 | 6821043 | Lower in Smoker |
| cg04349985 | 16 | 1107501 | Lower in Smoker |
| cg20402826 | 2 | 198077081 | Lower in Smoker |
| cg09858674 | 14 | 96965678 | Lower in Smoker |
| cg06793796 | 13 | 112705699 | Lower in Smoker |
| cg21179705 | 5 | 109392140 | Lower in Smoker |
| cg26371501 | 3 | 153003079 | Lower in Smoker |
| cg02550257 | 2 | 222147678 | Lower in Smoker |
| cg18902109 | 13 | 103821520 | Lower in Smoker |
| cg00698916 | 6 | 13767628 | Lower in Smoker |
| cg24060040 | 19 | 5802267 | Lower in Smoker |
| cg24485927 | 2 | 795989 | Lower in Smoker |
| cg17052041 | 3 | 144899243 | Lower in Smoker |
| cg22309696 | 2 | 172960993 | Lower in Smoker |
| cg01424263 | 10 | 77221564 | Lower in Smoker |
| cg11071155 | 6 | 157012049 | Lower in Smoker |
| cg04621944 | 1 | 5080448 | Lower in Smoker |
| cg25638602 | 11 | 68723743 | Lower in Smoker |
| cg20534732 | 15 | 42349694 | Lower in Smoker |
| cg19045700 | 4 | 69829409 | Lower in Smoker |
| cg25827670 | 17 | 15255513 | Lower in Smoker |
| cg06765475 | 10 | 128213438 | Lower in Smoker |

| | | | |
|---|---|---|---|
| cg06903103 | 15 | 34506071 | Lower in Smoker |
| cg23999454 | 7 | 1263031 | Lower in Smoker |
| cg01191058 | 16 | 89048433 | Lower in Smoker |
| cg09887251 | 4 | 1024735 | Lower in Smoker |
| cg20532925 | 3 | 17186314 | Lower in Smoker |
| cg01477933 | 12 | 122922107 | Lower in Smoker |
| cg01402347 | 4 | 96472269 | Lower in Smoker |
| cg11863863 | 17 | 75706410 | Lower in Smoker |
| cg25260543 | 7 | 100946792 | Lower in Smoker |
| cg24883219 | 18 | 14457820 | Lower in Smoker |
| cg03292069 | 3 | 126263781 | Lower in Smoker |
| cg05643464 | 8 | 25905134 | Lower in Smoker |
| cg26843498 | 19 | 2361574 | Lower in Smoker |
| cg20212364 | 4 | 101745102 | Lower in Smoker |
| cg06797156 | 8 | 124173733 | Lower in Smoker |
| cg26978064 | 17 | 70461791 | Lower in Smoker |
| cg23493260 | 11 | 23674834 | Lower in Smoker |
| cg10091335 | 10 | 43332443 | Lower in Smoker |
| cg03300596 | 17 | 53628947 | Lower in Smoker |
| cg26653990 | 5 | 72510846 | Lower in Smoker |
| cg14123750 | 13 | 114318492 | Lower in Smoker |
| cg18081498 | 1 | 14219312 | Lower in Smoker |
| cg15983072 | 2 | 146688047 | Lower in Smoker |
| cg15577126 | 2 | 218932178 | Lower in Smoker |
| cg18317788 | 4 | 185205197 | Lower in Smoker |
| cg21964928 | 5 | 153872958 | Lower in Smoker |
| cg22948201 | X | 106696043 | Lower in Smoker |
| cg19355929 | 11 | 20618001 | Lower in Smoker |
| cg24280819 | 10 | 71338046 | Lower in Smoker |
| cg17667592 | 11 | 123496000 | Lower in Smoker |
| cg06623935 | 1 | 214159131 | Lower in Smoker |
| cg10966830 | 4 | 115280987 | Lower in Smoker |
| cg11595135 | X | 136629694 | Lower in Smoker |
| cg02792740 | 6 | 2876395 | Lower in Smoker |
| cg09247170 | 14 | 87616490 | Lower in Smoker |

| | | | |
|---|---|---|---|
| cg05483125 | 16 | 75554060 | Lower in Smoker |
| cg04144973 | 2 | 105469001 | Lower in Smoker |
| cg03262802 | 2 | 234118754 | Lower in Smoker |
| cg05964950 | 6 | 1315685 | Lower in Smoker |
| cg05313910 | 8 | 98361938 | Lower in Smoker |
| cg04569313 | 5 | 1654452 | Lower in Smoker |
| cg26025169 | 13 | 112332591 | Lower in Smoker |
| cg11491998 | 6 | 30419493 | Lower in Smoker |
| cg07564291 | 17 | 77722518 | Lower in Smoker |
| cg05687174 | 5 | 31382507 | Lower in Smoker |
| cg00030005 | 7 | 155129409 | Lower in Smoker |
| cg00305993 | 15 | 76116615 | Lower in Smoker |
| cg03295107 | 7 | 151236292 | Lower in Smoker |
| cg01405242 | 8 | 131705773 | Lower in Smoker |
| cg07415423 | 11 | 120387622 | Lower in Smoker |
| cg06093152 | 1 | 212662017 | Lower in Smoker |
| cg27642784 | 3 | 157813670 | Lower in Smoker |
| cg19154467 | 3 | 177700638 | Lower in Smoker |
| cg24579604 | 10 | 1827639 | Lower in Smoker |
| cg12326965 | 17 | 76224587 | Lower in Smoker |
| cg07589899 | 2 | 62020677 | Lower in Smoker |
| cg09285851 | 6 | 10099656 | Lower in Smoker |
| cg18086868 | 1 | 220463627 | Lower in Smoker |
| cg02418072 | 10 | 104611004 | Lower in Smoker |
| cg00243040 | 7 | 127988331 | Lower in Smoker |
| cg12033615 | 6 | 157041546 | Lower in Smoker |
| cg19262315 | 11 | 67325980 | Lower in Smoker |
| cg13353152 | 1 | 158465963 | Lower in Smoker |
| cg01301660 | 5 | 110886711 | Lower in Smoker |
| cg07207043 | 6 | 7051497 | Lower in Smoker |
| cg24136431 | 19 | 47016623 | Lower in Smoker |
| cg05945290 | 17 | 39792147 | Lower in Smoker |
| cg10895682 | 1 | 22431609 | Lower in Smoker |
| cg21038291 | 17 | 70332630 | Lower in Smoker |
| cg14132620 | 9 | 100502742 | Lower in Smoker |

| | | | |
|---|---|---|---|
| cg19234738 | 3 | 134031551 | Lower in Smoker |
| cg26986629 | 2 | 37604081 | Lower in Smoker |
| cg25756406 | 10 | 134597884 | Lower in Smoker |
| cg24461194 | 10 | 113975156 | Lower in Smoker |
| cg18832738 | 12 | 95210053 | Lower in Smoker |
| cg09713684 | 5 | 134372398 | Lower in Smoker |
| cg23314514 | 14 | 104852775 | Lower in Smoker |
| cg18639495 | 10 | 70584876 | Lower in Smoker |
| cg04011474 | 2 | 28904455 | Lower in Smoker |
| cg05064683 | 17 | 20326541 | Lower in Smoker |
| cg07138399 | 1 | 200272215 | Lower in Smoker |
| cg23198815 | 11 | 87184120 | Lower in Smoker |
| cg23661466 | 10 | 63657173 | Lower in Smoker |
| cg10455321 | 11 | 46269315 | Lower in Smoker |
| cg20054309 | 2 | 237037176 | Lower in Smoker |
| cg11444332 | 10 | 8088904 | Lower in Smoker |
| cg01598371 | 2 | 37423428 | Lower in Smoker |
| cg02928935 | 17 | 17188379 | Lower in Smoker |
| cg22002034 | 1 | 119549948 | Lower in Smoker |
| cg09742555 | 17 | 35082656 | Lower in Smoker |
| cg02521457 | 22 | 20134463 | Lower in Smoker |
| cg05710411 | 3 | 62352633 | Lower in Smoker |
| cg10888902 | 10 | 134650312 | Lower in Smoker |
| cg02587993 | 12 | 92543184 | Lower in Smoker |
| cg11949262 | 7 | 20816184 | Lower in Smoker |
| cg20889322 | 11 | 65196622 | Lower in Smoker |
| cg10470368 | 11 | 64146517 | Lower in Smoker |
| cg09506029 | 19 | 18366283 | Lower in Smoker |
| cg16613240 | 6 | 10099623 | Lower in Smoker |
| cg09246878 | 4 | 160304826 | Lower in Smoker |
| cg24868150 | 2 | 20861653 | Lower in Smoker |
| cg14239655 | 12 | 46005115 | Lower in Smoker |
| cg03453916 | 7 | 31174468 | Lower in Smoker |
| cg14647190 | 11 | 67326023 | Lower in Smoker |
| cg15393490 | 1 | 207996459 | Lower in Smoker |

| | | | |
|---|---|---|---|
| cg18921980 | 2 | 175594943 | Lower in Smoker |
| cg17208748 | 3 | 197194394 | Lower in Smoker |
| cg23731501 | 1 | 1105317 | Lower in Smoker |
| cg10652583 | 11 | 44338186 | Lower in Smoker |
| cg07812589 | 16 | 49195595 | Lower in Smoker |
| cg12109883 | 15 | 70489053 | Lower in Smoker |
| cg21040775 | 6 | 10383669 | Lower in Smoker |
| cg25767154 | 8 | 145594413 | Lower in Smoker |
| cg12964420 | 13 | 50975679 | Lower in Smoker |
| cg17593342 | 6 | 14037614 | Lower in Smoker |
| cg01214012 | 14 | 30585046 | Lower in Smoker |
| cg27196974 | 17 | 80337729 | Lower in Smoker |
| cg08549806 | 16 | 49868530 | Lower in Smoker |
| cg07158065 | 8 | 96084821 | Lower in Smoker |
| cg05546763 | 14 | 95983383 | Lower in Smoker |
| cg05149097 | 11 | 59325534 | Lower in Smoker |
| cg01102307 | 1 | 9340416 | Lower in Smoker |
| cg00334274 | 22 | 30474915 | Lower in Smoker |
| cg07877987 | 10 | 133871444 | Lower in Smoker |
| cg01212215 | 8 | 49167054 | Lower in Smoker |
| cg11388673 | 8 | 144371779 | Lower in Smoker |
| cg12926341 | 2 | 70330714 | Lower in Smoker |
| cg26282047 | 7 | 142020101 | Lower in Smoker |
| cg20709203 | 13 | 53174588 | Lower in Smoker |
| cg06153623 | 12 | 130529849 | Lower in Smoker |
| cg02159489 | 17 | 79459563 | Lower in Smoker |
| cg05525812 | 2 | 177022646 | Lower in Smoker |
| cg05833067 | 7 | 43094396 | Lower in Smoker |
| cg08164151 | 12 | 131113432 | Lower in Smoker |
| cg15737302 | 11 | 118302063 | Lower in Smoker |
| cg09196346 | 13 | 23499332 | Lower in Smoker |
| cg23017741 | 12 | 110559276 | Lower in Smoker |
| cg06849778 | 1 | 16847214 | Lower in Smoker |
| cg06917772 | 11 | 126286370 | Lower in Smoker |
| cg19922871 | 1 | 46913532 | Lower in Smoker |

| | | | |
|---|---|---|---|
| cg03493146 | 7 | 69062082 | Lower in Smoker |
| cg08299521 | 5 | 179344619 | Lower in Smoker |
| cg25646708 | 3 | 134031685 | Lower in Smoker |
| cg06322403 | 11 | 70963994 | Lower in Smoker |
| cg13204977 | 7 | 66144066 | Lower in Smoker |
| cg24018321 | 4 | 148045888 | Lower in Smoker |
| cg08052546 | 7 | 50341210 | Lower in Smoker |
| cg26145487 | 10 | 3217355 | Lower in Smoker |
| cg12873476 | 8 | 142402728 | Lower in Smoker |
| cg11972534 | 2 | 11515164 | Lower in Smoker |
| cg26027576 | 8 | 27441373 | Lower in Smoker |
| cg00400964 | 22 | 42325444 | Lower in Smoker |
| cg27097542 | 16 | 11706435 | Lower in Smoker |
| cg04558115 | 17 | 45871717 | Lower in Smoker |
| cg03160883 | 6 | 36628713 | Lower in Smoker |
| cg19183252 | 4 | 120665941 | Lower in Smoker |
| cg16983723 | 3 | 182219752 | Lower in Smoker |
| cg08021945 | 12 | 9065639 | Lower in Smoker |
| cg08164191 | 14 | 65623632 | Lower in Smoker |
| cg21400170 | 17 | 78977614 | Lower in Smoker |
| cg19385090 | 7 | 27292614 | Lower in Smoker |
| cg13322849 | 17 | 37771901 | Lower in Smoker |
| cg11732226 | 6 | 20320376 | Lower in Smoker |
| cg13462890 | 11 | 74394411 | Lower in Smoker |
| cg21301805 | 1 | 119534644 | Lower in Smoker |
| cg01342115 | 3 | 134031663 | Lower in Smoker |
| cg20219891 | 2 | 121496875 | Lower in Smoker |
| cg27207756 | 4 | 1607291 | Lower in Smoker |
| cg06203476 | 7 | 121956302 | Lower in Smoker |
| cg05449190 | 17 | 74844962 | Lower in Smoker |
| cg27122441 | 22 | 18260411 | Lower in Smoker |
| cg14463412 | 9 | 96588830 | Lower in Smoker |
| cg11758283 | 6 | 7998697 | Lower in Smoker |
| cg03003752 | 16 | 86549962 | Lower in Smoker |
| cg26805720 | 5 | 1725285 | Lower in Smoker |

| | | | |
|---|---|---|---|
| cg11720896 | 17 | 29914487 | Lower in Smoker |
| cg08190125 | 14 | 106145435 | Lower in Smoker |
| cg11725972 | 7 | 155191845 | Lower in Smoker |
| cg13850695 | 9 | 131992409 | Lower in Smoker |
| cg01580340 | 7 | 16891079 | Lower in Smoker |
| cg17378803 | 2 | 242823275 | Lower in Smoker |
| cg12807237 | 10 | 134729045 | Lower in Smoker |
| cg21402748 | 1 | 2838849 | Lower in Smoker |
| cg25957301 | 15 | 79134331 | Lower in Smoker |
| cg20769856 | 13 | 31422123 | Lower in Smoker |
| cg10593047 | 2 | 232528667 | Lower in Smoker |
| cg04362790 | 14 | 100223811 | Lower in Smoker |
| cg23610453 | 10 | 79470966 | Lower in Smoker |
| cg17489750 | 6 | 54504774 | Lower in Smoker |
| cg13647973 | 19 | 56061337 | Lower in Smoker |
| cg25918827 | 2 | 62533140 | Lower in Smoker |
| cg02079700 | 22 | 43166347 | Lower in Smoker |
| cg27091422 | 4 | 30716343 | Lower in Smoker |
| cg08843064 | 6 | 126619805 | Lower in Smoker |
| cg00946921 | 14 | 106025021 | Lower in Smoker |
| cg08169827 | 1 | 32054766 | Lower in Smoker |
| cg15806569 | 2 | 1771408 | Lower in Smoker |
| cg25650964 | 13 | 33544014 | Lower in Smoker |
| cg11116758 | 19 | 7938601 | Lower in Smoker |
| cg19054360 | 10 | 133581904 | Lower in Smoker |
| cg01603079 | 10 | 102976327 | Lower in Smoker |
| cg16844941 | 8 | 11555178 | Lower in Smoker |
| cg08312412 | 5 | 141443781 | Lower in Smoker |
| cg17420058 | 12 | 132973450 | Lower in Smoker |
| cg06019763 | 6 | 25028080 | Lower in Smoker |
| cg24127310 | 10 | 102502104 | Lower in Smoker |
| cg21122225 | 2 | 238832508 | Lower in Smoker |
| cg17491368 | 1 | 211779938 | Lower in Smoker |
| cg24009861 | 8 | 29719552 | Lower in Smoker |
| cg26560699 | 5 | 171918659 | Lower in Smoker |

| | | | |
|---|---|---|---|
| cg11706177 | 7 | 155579794 | Lower in Smoker |
| cg02752932 | 2 | 38099030 | Lower in Smoker |
| cg24420534 | 8 | 143177785 | Lower in Smoker |
| cg17480077 | 1 | 10895517 | Lower in Smoker |
| cg18182981 | 6 | 1449399 | Lower in Smoker |
| cg04794690 | 1 | 17768059 | Lower in Smoker |
| cg16640008 | 6 | 159515404 | Lower in Smoker |
| cg09820318 | 22 | 39323648 | Lower in Smoker |
| cg03209412 | 4 | 183728196 | Lower in Smoker |
| cg20300764 | 2 | 64839958 | Lower in Smoker |
| cg24704287 | 19 | 13951481 | Lower in Smoker |
| cg03707634 | 13 | 107026178 | Lower in Smoker |
| cg24540810 | 6 | 14089148 | Lower in Smoker |
| cg12074024 | 1 | 209921577 | Lower in Smoker |
| cg01099150 | 2 | 8746519 | Lower in Smoker |
| cg13461447 | 1 | 1714001 | Lower in Smoker |
| cg15705813 | 2 | 70297499 | Lower in Smoker |
| cg03923265 | 16 | 412168 | Lower in Smoker |
| cg08668199 | 3 | 127795571 | Lower in Smoker |
| cg00478421 | 2 | 11515109 | Lower in Smoker |
| cg24014795 | 14 | 81893935 | Lower in Smoker |
| cg23758822 | 17 | 41437982 | Lower in Smoker |
| cg04480376 | 15 | 77896785 | Lower in Smoker |
| cg23468002 | 5 | 158532401 | Lower in Smoker |
| cg18496440 | 5 | 158532302 | Lower in Smoker |
| cg27535502 | 15 | 91395896 | Lower in Smoker |
| cg24659858 | 13 | 24270321 | Lower in Smoker |
| cg11024728 | 7 | 1425807 | Lower in Smoker |
| cg23919742 | 1 | 19832174 | Lower in Smoker |
| cg06394109 | 16 | 1152511 | Lower in Smoker |
| cg24126967 | 6 | 28945500 | Lower in Smoker |
| cg16090599 | 11 | 45105153 | Lower in Smoker |
| cg17490196 | 2 | 232507842 | Lower in Smoker |
| cg21354781 | 6 | 164029556 | Lower in Smoker |
| cg18872005 | 2 | 105275613 | Lower in Smoker |

| | | | |
|---|---|---|---|
| cg25238382 | 17 | 72981310 | Lower in Smoker |
| cg06288788 | 16 | 65158052 | Lower in Smoker |
| cg17845669 | 6 | 470823 | Lower in Smoker |
| cg17721879 | 5 | 158532473 | Lower in Smoker |
| cg21885251 | 8 | 64314339 | Lower in Smoker |
| cg26715559 | 6 | 30419491 | Lower in Smoker |
| cg03277049 | 3 | 156534076 | Lower in Smoker |
| cg14189141 | 9 | 1042605 | Lower in Smoker |
| cg06099431 | 20 | 44451667 | Lower in Smoker |
| cg04004158 | 16 | 1152474 | Lower in Smoker |
| cg01375075 | 15 | 66158565 | Lower in Smoker |
| cg08039560 | 21 | 45575832 | Lower in Smoker |
| cg22707397 | 19 | 49020528 | Lower in Smoker |
| cg26527263 | 1 | 53875972 | Lower in Smoker |
| cg23610041 | 20 | 39320926 | Lower in Smoker |
| cg00996827 | 1 | 2838805 | Lower in Smoker |
| cg06208288 | 1 | 58858074 | Lower in Smoker |

Appendix C

| | | | |
|---|---|---|---|
| A2BP1 | ABCB9 | ABLIM2 | ACE2 |
| A2M | ABCC13 | ABLIM3 | ACER2 |
| AAAS | ABCC5 | ABO | ACER3 |
| AACS | ABCC8 | ABR | ACIN1 |
| AAGAB | ABCE1 | ABTB1 | ACLY |
| AAK1 | ABCF1 | ABTB2 | ACN9 |
| AARS | ABCF2 | ACAA1 | ACO1 |
| AARS2 | ABCF3 | ACACA | ACOT11 |
| AARSD1 | ABCG1 | ACACB | ACOT13 |
| AASDH | ABCG4 | ACAD10 | ACOT7 |
| AASS | ABCG5 | ACAD11 | ACOX3 |
| AATK | ABHD10 | ACAD9 | ACP1 |
| ABCA2 | ABHD11 | ACADS | ACP5 |
| ABCA3 | ABHD2 | ACADVL | ACP6 |
| ABCA4 | ABHD3 | ACAN | ACPL2 |
| ABCA5 | ABHD4 | ACAP1 | ACPT |
| ABCA7 | ABHD5 | ACAT1 | ACRC |
| ABCB1 | ABHD6 | ACBD3 | ACRV1 |
| ABCB4 | ABHD8 | ACBD6 | ACSF2 |
| ABCB5 | ABI2 | ACBD7 | ACSF3 |
| ABCB6 | ABI3 | ACCN1 | ACSL1 |
| ABCB7 | ABL1 | ACCN4 | ACSL3 |
| ABCB8 | ABL2 | ACCS | ACSL5 |

| | | | |
|---|---|---|---|
| ACSM1 | ADAM3A | ADCY4 | ADRB1 |
| ACSM3 | ADAM6 | ADCY5 | ADRB2 |
| ACSM5 | ADAM7 | ADCY6 | ADRB3 |
| ACSS3 | ADAM8 | ADCY8 | ADRBK1 |
| ACTA1 | ADAMTS1 | ADCY9 | ADRBK2 |
| ACTB | ADAMTS10 | ADCYAP1 | ADRM1 |
| ACTBL2 | ADAMTS12 | ADCYAP1R1 | ADSS |
| ACTL6B | ADAMTS16 | ADD2 | AEBP2 |
| ACTN2 | ADAMTS19 | ADD3 | AEN |
| ACTN4 | ADAMTS2 | ADH5 | AFAP1 |
| ACTR10 | ADAMTS5 | ADI1 | AFAP1L2 |
| ACTR1A | ADAMTS7 | ADIPOR1 | AFF1 |
| ACTR1B | ADAMTS9 | ADK | AFF3 |
| ACTR2 | ADAMTSL2 | ADM | AFF4 |
| ACTR6 | ADAMTSL4 | ADO | AFG3L1 |
| ACTR8 | ADAMTSL5 | ADORA2A | AFMID |
| ACTRT1 | ADAP1 | ADORA2B | AGA |
| ACVR1 | ADAR | ADORA3 | AGAP1 |
| ACVRL1 | ADARB1 | ADPGK | AGAP11 |
| ADAD1 | ADARB2 | ADPRH | AGAP2 |
| ADAL | ADC | ADPRHL1 | AGAP4 |
| ADAM12 | ADCK1 | ADPRHL2 | AGAP6 |
| ADAM17 | ADCY10 | ADRA1A | AGBL1 |
| ADAM22 | ADCY2 | ADRA2B | AGBL2 |
| ADAM33 | ADCY3 | ADRA2C | AGBL3 |

| | | | |
|---|---|---|---|
| AGBL4 | AIMP1 | ALAD | ALOX5 |
| AGBL5 | AIMP2 | ALAS1 | ALPL |
| AGER | AIP | ALB | ALS2CL |
| AGK | AK1 | ALCAM | ALX1 |
| AGL | AK2 | ALDH16A1 | ALX3 |
| AGMAT | AK3L1 | ALDH1A2 | ALX4 |
| AGPAT1 | AK5 | ALDH1B1 | AMAC1L2 |
| AGPAT2 | AK7 | ALDH1L1 | AMBN |
| AGPAT3 | AKAP1 | ALDH1L2 | AMBRA1 |
| AGRN | AKAP12 | ALDH2 | AMD1 |
| AGTPBP1 | AKAP13 | ALDH3A2 | AMDHD1 |
| AGTRAP | AKAP14 | ALDH3B1 | AMDHD2 |
| AGXT | AKAP8 | ALDH4A1 | AMFR |
| AGXT2L1 | AKAP8L | ALDH7A1 | AMH |
| AGXT2L2 | AKAP9 | ALG1 | AMIGO2 |
| AHCTF1 | AKD1 | ALG10 | AMIGO3 |
| AHCY | AKNA | ALG13 | AMMECR1 |
| AHCYL2 | AKR1A1 | ALG14 | AMMECR1L |
| AHDC1 | AKR1B10 | ALG3 | AMN1 |
| AHNAK | AKR1C2 | ALG5 | AMOT |
| AHNAK2 | AKR1D1 | ALG6 | AMOTL1 |
| AHRR | AKR7A2 | ALKBH2 | AMPD2 |
| AHSA2 | AKT1 | ALKBH4 | AMPD3 |
| AIG1 | AKT1S1 | ALKBH5 | AMPH |
| AIM2 | AKTIP | ALOX12 | AMT |

| | | | |
|---|---|---|---|
| ANAPC10 | ANKRD29 | ANO4 | AP4S1 |
| ANAPC11 | ANKRD31 | ANO6 | APAF1 |
| ANAPC13 | ANKRD34B | ANO7 | APBA1 |
| ANAPC7 | ANKRD34C | ANO9 | APBA2 |
| ANG | ANKRD35 | ANP32A | APBB1 |
| ANGEL1 | ANKRD36 | ANP32B | APBB2 |
| ANGPT1 | ANKRD39 | ANPEP | APBB3 |
| ANGPT2 | ANKRD42 | ANTXR1 | APC |
| ANGPTL4 | ANKRD43 | ANTXR2 | APC2 |
| ANK1 | ANKRD44 | ANXA2 | APCDD1L |
| ANK2 | ANKRD45 | ANXA3 | APCS |
| ANK3 | ANKRD46 | ANXA4 | APEH |
| ANKFN1 | ANKRD5 | ANXA6 | APITD1 |
| ANKFY1 | ANKRD52 | ANXA7 | APLF |
| ANKH | ANKRD53 | AOC3 | APLN |
| ANKK1 | ANKRD55 | AP1G1 | APLNR |
| ANKLE2 | ANKRD56 | AP1S2 | APLP1 |
| ANKMY1 | ANKRD6 | AP2A1 | APLP2 |
| ANKRD10 | ANKRD9 | AP2A2 | APOA1 |
| ANKRD11 | ANKS1A | AP2B1 | APOA5 |
| ANKRD13B | ANKS1B | AP3B1 | APOBEC3D |
| ANKRD16 | ANKS3 | AP3M2 | APOBEC3F |
| ANKRD2 | ANKZF1 | AP3S2 | APOBEC3G |
| ANKRD20A3 | ANO1 | AP4B1 | APOBEC3H |
| ANKRD26 | ANO2 | AP4E1 | APOBEC4 |

| | | | |
|---|---|---|---|
| APOC1P1 | ARHGAP21 | ARID5B | ARPM1 |
| APOC2 | ARHGAP22 | ARIH2 | ARPP19 |
| APOC3 | ARHGAP25 | ARL10 | ARPP-21 |
| APOL5 | ARHGAP26 | ARL11 | ARRB1 |
| APOLD1 | ARHGAP4 | ARL13B | ARRDC1 |
| APP | ARHGAP5 | ARL15 | ARRDC2 |
| APPL1 | ARHGAP6 | ARL5C | ARSA |
| APTX | ARHGDIA | ARL6IP1 | ARSB |
| AQP1 | ARHGDIG | ARL6IP5 | ARSD |
| AQP10 | ARHGEF1 | ARL8A | ARSF |
| AQP11 | ARHGEF10 | ARL8B | ARSG |
| AQP5 | ARHGEF10L | ARMC10 | ARSJ |
| AR | ARHGEF12 | ARMC2 | ART3 |
| ARAP1 | ARHGEF16 | ARMC3 | ARTN |
| ARC | ARHGEF18 | ARMC4 | ARVCF |
| AREG | ARHGEF19 | ARMC5 | ARX |
| ARF3 | ARHGEF2 | ARMC9 | ASAH1 |
| ARF6 | ARHGEF3 | ARMCX1 | ASAP1 |
| ARFGAP1 | ARHGEF4 | ARMS2 | ASAP2 |
| ARFIP1 | ARHGEF7 | ARNT2 | ASB1 |
| ARG2 | ARID1A | ARNTL | ASB10 |
| ARHGAP10 | ARID1B | ARNTL2 | ASB13 |
| ARHGAP12 | ARID2 | ARPC1B | ASB16 |
| ARHGAP15 | ARID3A | ARPC2 | ASB18 |
| ARHGAP20 | ARID4A | ARPC5 | ASB2 |

| | | | |
|---|---|---|---|
| ASB4 | ATF2 | ATP2B4 | ATP6V1G1 |
| ASB7 | ATF3 | ATP2C1 | ATP6V1H |
| ASB8 | ATF6 | ATP4B | ATP8A1 |
| ASCC1 | ATF6B | ATP5A1 | ATP8A2 |
| ASCC3 | ATF7 | ATP5C1 | ATP8B4 |
| ASCL1 | ATF7IP | ATP5G1 | ATP9B |
| ASCL2 | ATG2A | ATP5G2 | ATPBD4 |
| ASCL3 | ATG7 | ATP5J | ATRN |
| ASF1B | ATHL1 | ATP5L | ATRNL1 |
| ASFMR1 | ATIC | ATP5S | ATRX |
| ASL | ATL2 | ATP5SL | ATXN1 |
| ASNSD1 | ATM | ATP6AP1 | ATXN3 |
| ASPG | ATOH8 | ATP6V0A1 | ATXN3L |
| ASPH | ATOX1 | ATP6V0A2 | ATXN7 |
| ASPHD2 | ATP10A | ATP6V0A4 | ATXN7L1 |
| ASPSCR1 | ATP10B | ATP6V0B | ATXN7L3 |
| ASRGL1 | ATP10D | ATP6V0D1 | AUH |
| ASS1 | ATP11A | ATP6V0D2 | AURKA |
| ASTN1 | ATP13A3 | ATP6V0E1 | AURKC |
| ASXL1 | ATP13A5 | ATP6V1A | AUTS2 |
| ASXL2 | ATP1A1 | ATP6V1B2 | AVEN |
| ATAD1 | ATP1A4 | ATP6V1C1 | AVPI1 |
| ATAD3B | ATP2A3 | ATP6V1E1 | AVPR1B |
| ATAD3C | ATP2B2 | ATP6V1E2 | AVPR2 |
| ATF1 | ATP2B3 | ATP6V1F | AXIN1 |

| | | | |
|---|---|---|---|
| AXIN2 | BAI2 | BCAS4 | BEND4 |
| AZI2 | BAIAP2 | BCAT1 | BEND7 |
| AZIN1 | BANP | BCAT2 | BEST1 |
| B2M | BAP1 | BCDIN3D | BEST2 |
| B3GALNT1 | BARD1 | BCHE | BEST3 |
| B3GALNT2 | BASP1 | BCKDHA | BEST4 |
| B3GALT4 | BAT1 | BCKDK | BET1 |
| B3GAT1 | BAT2 | BCL11A | BET1L |
| B3GAT3 | BAT3 | BCL11B | BEX1 |
| B3GNT6 | BAT5 | BCL2L11 | BEX2 |
| B3GNT7 | BATF3 | BCL2L14 | BFSP2 |
| B3GNTL1 | BAX | BCL3 | BGLAP |
| B4GALNT1 | BAZ1A | BCL6 | BHLHE23 |
| B4GALNT3 | BAZ1B | BCL7A | BHLHE40 |
| B4GALNT4 | BBS1 | BCL9L | BHMT |
| B4GALT3 | BBS10 | BCOR | BICC1 |
| B4GALT6 | BBS12 | BCYRN1 | BICD1 |
| B4GALT7 | BBS2 | BDH1 | BICD2 |
| B9D1 | BBS9 | BDH2 | BID |
| BAALC | BBX | BDKRB2 | BIK |
| BACH1 | BCAN | BDNF | BIN2 |
| BACH2 | BCAR1 | BDNFOS | BIRC3 |
| BAHCC1 | BCAR3 | BDP1 | BIRC6 |
| BAHD1 | BCAS1 | BEAN | BIRC7 |
| BAI1 | BCAS3 | BEGAIN | BLCAP |

| | | | |
|---|---|---|---|
| BLK | BOP1 | BTBD1 | BZW2 |
| BLNK | BPIL1 | BTBD10 | C10orf104 |
| BLOC1S1 | BPTF | BTBD11 | C10orf11 |
| BLOC1S2 | BRCA1 | BTBD12 | C10orf110 |
| BLZF1 | BRCA2 | BTBD16 | C10orf114 |
| BMF | BRD1 | BTBD6 | C10orf119 |
| BMI1 | BRD2 | BTBD8 | C10orf131 |
| BMP1 | BRD3 | BTBD9 | C10orf137 |
| BMP10 | BRD9 | BTC | C10orf18 |
| BMP2 | BRE | BTD | C10orf25 |
| BMP7 | BRF1 | BTF3 | C10orf26 |
| BMPR1A | BRF2 | BTF3L1 | C10orf4 |
| BMPR2 | BRIP1 | BTF3L4 | C10orf41 |
| BMS1 | BRP44 | BTG2 | C10orf46 |
| BMS1P1 | BRP44L | BTN2A1 | C10orf53 |
| BMX | BRPF1 | BTN2A3 | C10orf67 |
| BNC1 | BRUNOL4 | BTN3A1 | C10orf71 |
| BNC2 | BRUNOL5 | BTN3A2 | C10orf78 |
| BNIP1 | BRUNOL6 | BTNL2 | C10orf79 |
| BNIP3 | BRWD1 | BUB1B | C10orf82 |
| BNIP3L | BSCL2 | BUB3 | C10orf84 |
| BOD1 | BSG | BUD13 | C10orf88 |
| BOD1L | BSN | BVES | C10orf91 |
| BOLA1 | BST1 | BZRAP1 | C10orf93 |
| BOLA2 | BST2 | BZW1 | C11orf1 |

| | | | |
|---|---|---|---|
| C11orf20 | C12orf23 | C13orf31 | C15orf17 |
| C11orf24 | C12orf27 | C13orf33 | C15orf2 |
| C11orf30 | C12orf35 | C13orf34 | C15orf27 |
| C11orf34 | C12orf41 | C14orf101 | C15orf33 |
| C11orf35 | C12orf42 | C14orf106 | C15orf37 |
| C11orf41 | C12orf43 | C14orf118 | C15orf39 |
| C11orf42 | C12orf49 | C14orf119 | C15orf40 |
| C11orf48 | C12orf51 | C14orf126 | C15orf41 |
| C11orf49 | C12orf53 | C14orf139 | C15orf44 |
| C11orf53 | C12orf56 | C14orf145 | C15orf52 |
| C11orf57 | C12orf60 | C14orf159 | C15orf59 |
| C11orf58 | C12orf61 | C14orf166B | C15orf60 |
| C11orf60 | C12orf62 | C14orf174 | C15orf61 |
| C11orf63 | C12orf66 | C14orf177 | C16orf11 |
| C11orf66 | C12orf68 | C14orf179 | C16orf45 |
| C11orf68 | C12orf69 | C14orf180 | C16orf5 |
| C11orf70 | C12orf70 | C14orf182 | C16orf52 |
| C11orf71 | C12orf72 | C14orf23 | C16orf53 |
| C11orf75 | C12orf73 | C14orf37 | C16orf55 |
| C11orf83 | C12orf76 | C14orf38 | C16orf57 |
| C11orf84 | C12orf77 | C14orf39 | C16orf63 |
| C11orf87 | C13orf16 | C14orf45 | C16orf67 |
| C11orf9 | C13orf18 | C14orf64 | C16orf72 |
| C11orf91 | C13orf23 | C14orf73 | C16orf75 |
| C11orf95 | C13orf30 | C14orf79 | C16orf80 |

| | | | |
|---|---|---|---|
| C16orf81 | C17orf91 | C19orf50 | C1orf151 |
| C16orf82 | C17orf93 | C19orf51 | C1orf156 |
| C16orf86 | C17orf95 | C19orf55 | C1orf159 |
| C16orf87 | C17orf96 | C19orf6 | C1orf163 |
| C16orf91 | C18orf1 | C19orf61 | C1orf170 |
| C17orf103 | C18orf10 | C19orf63 | C1orf182 |
| C17orf28 | C18orf19 | C19orf66 | C1orf194 |
| C17orf37 | C18orf22 | C1GALT1 | C1orf198 |
| C17orf42 | C18orf45 | C1GALT1C1 | C1orf201 |
| C17orf47 | C18orf56 | C1orf101 | C1orf21 |
| C17orf48 | C19orf10 | C1orf105 | C1orf212 |
| C17orf51 | C19orf12 | C1orf106 | C1orf213 |
| C17orf56 | C19orf20 | C1orf111 | C1orf228 |
| C17orf59 | C19orf21 | C1orf113 | C1orf229 |
| C17orf62 | C19orf23 | C1orf116 | C1orf25 |
| C17orf63 | C19orf24 | C1orf122 | C1orf51 |
| C17orf68 | C19orf29 | C1orf124 | C1orf54 |
| C17orf69 | C19orf35 | C1orf127 | C1orf61 |
| C17orf70 | C19orf36 | C1orf128 | C1orf63 |
| C17orf72 | C19orf39 | C1orf130 | C1orf66 |
| C17orf77 | C19orf40 | C1orf133 | C1orf70 |
| C17orf80 | C19orf42 | C1orf135 | C1orf77 |
| C17orf81 | C19orf44 | C1orf141 | C1orf86 |
| C17orf85 | C19orf47 | C1orf144 | C1orf9 |
| C17orf90 | C19orf48 | C1orf150 | C1orf92 |

| | | | |
|---|---|---|---|
| C1orf94 | C20orf195 | C22orf40 | C2orf70 |
| C1orf97 | C20orf24 | C22orf41 | C2orf77 |
| C1QA | C20orf26 | C22orf45 | C2orf78 |
| C1QB | C20orf46 | C22orf9 | C2orf79 |
| C1QL1 | C20orf56 | C2CD2 | C2orf88 |
| C1QTNF1 | C20orf70 | C2CD2L | C3orf15 |
| C1QTNF2 | C20orf72 | C2CD3 | C3orf17 |
| C1QTNF3 | C20orf94 | C2CD4A | C3orf18 |
| C1QTNF6 | C20orf95 | C2orf24 | C3orf19 |
| C1QTNF7 | C20orf96 | C2orf27A | C3orf20 |
| C1QTNF8 | C21orf129 | C2orf28 | C3orf21 |
| C2 | C21orf29 | C2orf29 | C3orf26 |
| C20orf103 | C21orf33 | C2orf3 | C3orf31 |
| C20orf107 | C21orf45 | C2orf34 | C3orf32 |
| C20orf111 | C21orf58 | C2orf42 | C3orf33 |
| C20orf112 | C21orf63 | C2orf43 | C3orf34 |
| C20orf117 | C21orf84 | C2orf48 | C3orf35 |
| C20orf118 | C21orf91 | C2orf49 | C3orf37 |
| C20orf132 | C22orf13 | C2orf54 | C3orf38 |
| C20orf141 | C22orf23 | C2orf55 | C3orf39 |
| C20orf144 | C22orf24 | C2orf58 | C3orf43 |
| C20orf151 | C22orf30 | C2orf64 | C3orf50 |
| C20orf160 | C22orf34 | C2orf68 | C3orf52 |
| C20orf166 | C22orf36 | C2orf69 | C3orf57 |
| C20orf177 | C22orf39 | C2orf7 | C3orf58 |

| | | | |
|---|---|---|---|
| C3orf59 | C5orf30 | C6orf141 | C7orf13 |
| C3orf64 | C5orf32 | C6orf142 | C7orf20 |
| C3orf66 | C5orf35 | C6orf145 | C7orf23 |
| C3orf67 | C5orf36 | C6orf15 | C7orf26 |
| C3orf70 | C5orf37 | C6orf170 | C7orf28A |
| C3orf74 | C5orf4 | C6orf174 | C7orf31 |
| C3orf75 | C5orf41 | C6orf182 | C7orf33 |
| C4orf19 | C5orf42 | C6orf191 | C7orf38 |
| C4orf21 | C5orf43 | C6orf195 | C7orf43 |
| C4orf22 | C5orf44 | C6orf201 | C7orf46 |
| C4orf23 | C5orf52 | C6orf204 | C7orf50 |
| C4orf29 | C5orf54 | C6orf217 | C7orf51 |
| C4orf3 | C5orf56 | C6orf221 | C7orf57 |
| C4orf32 | C6orf1 | C6orf223 | C7orf58 |
| C4orf34 | C6orf10 | C6orf226 | C7orf59 |
| C4orf43 | C6orf103 | C6orf25 | C7orf64 |
| C4orf44 | C6orf106 | C6orf27 | C7orf65 |
| C4orf49 | C6orf108 | C6orf35 | C8orf33 |
| C4orf50 | C6orf122 | C6orf47 | C8orf37 |
| C5orf13 | C6orf123 | C6orf48 | C8orf41 |
| C5orf15 | C6orf125 | C6orf57 | C8orf42 |
| C5orf24 | C6orf126 | C6orf58 | C8orf45 |
| C5orf25 | C6orf127 | C6orf64 | C8orf46 |
| C5orf27 | C6orf129 | C6orf72 | C8orf55 |
| C5orf28 | C6orf136 | C6orf94 | C8orf58 |

| | | | |
|---|---|---|---|
| C8orf59 | C9orf91 | CACNA1I | CALHM1 |
| C8orf71 | C9orf98 | CACNA1S | CALHM2 |
| C8orf73 | CA1 | CACNA2D1 | CALHM3 |
| C8orf76 | CA3 | CACNA2D2 | CALM1 |
| C8orf79 | CA4 | CACNA2D3 | CALML6 |
| C8orf83 | CA5A | CACNA2D4 | CALY |
| C8orf84 | CA5BP | CACNB2 | CAMK1D |
| C9orf106 | CA7 | CACNB3 | CAMK2B |
| C9orf129 | CA8 | CACNG1 | CAMK2N1 |
| C9orf130 | CAB39 | CACNG3 | CAMK4 |
| C9orf135 | CAB39L | CACNG4 | CAMKK1 |
| C9orf139 | CABC1 | CACNG8 | CAMKK2 |
| C9orf140 | CABIN1 | CACYBP | CAMKV |
| C9orf163 | CABLES1 | CADM1 | CAMP |
| C9orf167 | CABP1 | CADM2 | CAMSAP1L1 |
| C9orf170 | CABP2 | CADM3 | CAMTA1 |
| C9orf171 | CABP5 | CADPS | CAMTA2 |
| C9orf25 | CABYR | CALB2 | CANT1 |
| C9orf30 | CACHD1 | CALCA | CAP1 |
| C9orf50 | CACNA1B | CALCB | CAPG |
| C9orf6 | CACNA1C | CALCOCO1 | CAPN1 |
| C9orf64 | CACNA1D | CALCOCO2 | CAPN2 |
| C9orf78 | CACNA1E | CALCR | CAPN3 |
| C9orf79 | CACNA1G | CALCRL | CAPS |
| C9orf86 | CACNA1H | CALD1 | CAPS2 |

| | | | |
|---|---|---|---|
| CAPSL | CAT | CCBE1 | CCDC149 |
| CARD10 | CATSPER2 | CCDC102A | CCDC15 |
| CARD11 | CATSPERB | CCDC104 | CCDC153 |
| CARD16 | CATSPERG | CCDC105 | CCDC155 |
| CARD6 | CAV1 | CCDC106 | CCDC17 |
| CARD9 | CAV2 | CCDC107 | CCDC21 |
| CARKD | CBFA2T2 | CCDC109A | CCDC22 |
| CARM1 | CBFA2T3 | CCDC111 | CCDC25 |
| CARS2 | CBL | CCDC112 | CCDC27 |
| CASC1 | CBLB | CCDC114 | CCDC3 |
| CASC3 | CBLL1 | CCDC115 | CCDC33 |
| CASC4 | CBLN3 | CCDC117 | CCDC38 |
| CASC5 | CBR4 | CCDC12 | CCDC40 |
| CASD1 | CBS | CCDC126 | CCDC41 |
| CASKIN1 | CBWD2 | CCDC127 | CCDC42B |
| CASKIN2 | CBWD3 | CCDC13 | CCDC45 |
| CASP14 | CBX1 | CCDC134 | CCDC46 |
| CASP4 | CBX3 | CCDC136 | CCDC48 |
| CASP5 | CBX4 | CCDC138 | CCDC50 |
| CASP6 | CBX5 | CCDC14 | CCDC52 |
| CASP7 | CBX6 | CCDC141 | CCDC55 |
| CASP9 | CBY1 | CCDC144B | CCDC57 |
| CASS4 | CC2D1B | CCDC144NL | CCDC60 |
| CAST | CC2D2A | CCDC146 | CCDC62 |
| CASZ1 | CC2D2B | CCDC148 | CCDC64B |

| | | | |
|---|---|---|---|
| CCDC66 | CCL23 | CCR2 | CD2AP |
| CCDC67 | CCL25 | CCR3 | CD300A |
| CCDC68 | CCL27 | CCR9 | CD300LG |
| CCDC69 | CCL28 | CCRN4L | CD36 |
| CCDC7 | CCL3 | CCT2 | CD37 |
| CCDC72 | CCL4L2 | CCT3 | CD38 |
| CCDC73 | CCM2 | CCT4 | CD46 |
| CCDC74A | CCNA2 | CCT5 | CD47 |
| CCDC77 | CCNB2 | CCT6P1 | CD48 |
| CCDC79 | CCNB3 | CCT7 | CD55 |
| CCDC80 | CCND1 | CCT8 | CD58 |
| CCDC83 | CCND2 | CCT8L2 | CD59 |
| CCDC84 | CCND3 | CD109 | CD5L |
| CCDC85A | CCNE1 | CD151 | CD6 |
| CCDC85B | CCNE2 | CD19 | CD7 |
| CCDC86 | CCNG1 | CD1B | CD72 |
| CCDC87 | CCNH | CD1C | CD74 |
| CCDC9 | CCNI2 | CD1D | CD79B |
| CCDC90A | CCNJ | CD200 | CD80 |
| CCDC90B | CCNJL | CD244 | CD81 |
| CCDC92 | CCNO | CD247 | CD82 |
| CCDC93 | CCNT2 | CD248 | CD8A |
| CCDC97 | CCNY | CD27 | CD96 |
| CCHCR1 | CCPG1 | CD274 | CD97 |
| CCK | CCR1 | CD276 | CDAN1 |

| | | | |
|---|---|---|---|
| CDC14B | CDH2 | CDKN1C | CENPH |
| CDC16 | CDH22 | CDKN2A | CENPJ |
| CDC20 | CDH23 | CDKN2AIP | CENPK |
| CDC25B | CDH4 | CDKN2AIPNL | CENPL |
| CDC27 | CDH7 | CDKN2C | CENPM |
| CDC34 | CDK1 | CDKN2D | CENPN |
| CDC37L1 | CDK10 | CDKN3 | CENPP |
| CDC40 | CDK11A | CDON | CENPQ |
| CDC42BPB | CDK11B | CDS2 | CENPT |
| CDC42EP2 | CDK13 | CDV3 | CEP152 |
| CDC42EP3 | CDK14 | CDX2 | CEP63 |
| CDC42EP4 | CDK15 | CDYL | CEP72 |
| CDC42EP5 | CDK17 | CEACAM18 | CEP97 |
| CDC42SE1 | CDK18 | CEACAM8 | CERKL |
| CDC42SE2 | CDK19 | CEBPA | CES3 |
| CDC5L | CDK2 | CEBPZ | CES7 |
| CDCA2 | CDK2AP1 | CECR5 | CES8 |
| CDCA5 | CDK5 | CECR7 | CFB |
| CDCA8 | CDK5R1 | CELP | CFDP1 |
| CDCP1 | CDK5RAP3 | CELSR1 | CFHR5 |
| CDGAP | CDK6 | CELSR3 | CFL1 |
| CDH11 | CDK7 | CEMP1 | CFLP1 |
| CDH12 | CDKAL1 | CENPC1 | CGNL1 |
| CDH13 | CDKL1 | CENPE | CGREF1 |
| CDH18 | CDKN1A | CENPF | CHAC1 |

| | | | |
|---|---|---|---|
| CHADL | CHN1 | CHST3 | CLCN7 |
| CHAT | CHN2 | CHST4 | CLCNKB |
| CHCHD2 | CHODL | CHST7 | CLDN10 |
| CHCHD4 | CHP | CHST8 | CLDN11 |
| CHCHD5 | CHPF | CHST9 | CLDN16 |
| CHCHD6 | CHPF2 | CHSY1 | CLDN19 |
| CHCHD8 | CHRAC1 | CHSY3 | CLDN23 |
| CHD3 | CHRD | CIAO1 | CLDN4 |
| CHD5 | CHRM1 | CIB1 | CLDN5 |
| CHD8 | CHRM2 | CIC | CLDN6 |
| CHD9 | CHRM4 | CIDEA | CLDN7 |
| CHDH | CHRNA10 | CILP2 | CLDND1 |
| CHFR | CHRNA2 | CINP | CLDND2 |
| CHGB | CHRNA3 | CIR1 | CLEC10A |
| CHI3L1 | CHRNA4 | CISH | CLEC12B |
| CHI3L2 | CHRNA5 | CIT | CLEC16A |
| CHIC2 | CHRNA6 | CITED4 | CLEC18A |
| CHID1 | CHRNB2 | CIZ1 | CLEC1A |
| CHIT1 | CHRNB4 | CKAP2 | CLEC2B |
| CHKA | CHRNE | CKAP4 | CLEC2D |
| CHL1 | CHST10 | CKAP5 | CLEC2L |
| CHMP2A | CHST11 | CKMT1B | CLEC3A |
| CHMP2B | CHST12 | CLASP1 | CLEC3B |
| CHMP4C | CHST13 | CLCN3 | CLEC4A |
| CHMP6 | CHST2 | CLCN6 | CLEC4D |

| | | | |
|---|---|---|---|
| CLEC4E | CLRN3 | CNGB3 | CNTNAP4 |
| CLEC4G | CLSPN | CNIH | CNTNAP5 |
| CLEC4GP1 | CLSTN1 | CNIH2 | COBRA1 |
| CLEC9A | CLSTN2 | CNIH3 | COG1 |
| CLGN | CLSTN3 | CNIH4 | COG3 |
| CLIC1 | CLTB | CNKSR2 | COG5 |
| CLIC2 | CLTC | CNN2 | COG7 |
| CLIC5 | CLU | CNNM1 | COIL |
| CLIP1 | CLUAP1 | CNNM2 | COL10A1 |
| CLIP2 | CLVS1 | CNNM4 | COL11A2 |
| CLIP3 | CLYBL | CNO | COL12A1 |
| CLIP4 | CMAS | CNOT10 | COL13A1 |
| CLK1 | CMBL | CNOT2 | COL14A1 |
| CLK3 | CMC1 | CNOT3 | COL16A1 |
| CLMN | CMIP | CNOT6L | COL17A1 |
| CLN3 | CMKLR1 | CNPY1 | COL18A1 |
| CLN8 | CMPK1 | CNPY3 | COL19A1 |
| CLNS1A | CMPK2 | CNR1 | COL1A1 |
| CLOCK | CMTM2 | CNR2 | COL20A1 |
| CLP1 | CMTM3 | CNRIP1 | COL21A1 |
| CLPP | CMTM6 | CNTD2 | COL23A1 |
| CLPS | CMTM7 | CNTN1 | COL24A1 |
| CLPTM1 | CMTM8 | CNTN2 | COL25A1 |
| CLPTM1L | CNGA3 | CNTN4 | COL27A1 |
| CLPX | CNGB1 | CNTN5 | COL2A1 |

| | | | |
|---|---|---|---|
| COL4A1 | COPS2 | COX7B | CPSF4 |
| COL4A2 | COPS4 | COX7B2 | CPT1A |
| COL4A3 | COPS7A | COX7C | CPT1B |
| COL4A3BP | COPS7B | COX8C | CPXM1 |
| COL4A5 | COPS8 | CP110 | CR1L |
| COL5A1 | COPZ1 | CPAMD8 | CR2 |
| COL5A2 | COQ10A | CPD | CRABP2 |
| COL6A1 | COQ5 | CPE | CRADD |
| COL6A2 | COQ9 | CPEB2 | CRAMP1L |
| COL6A6 | CORIN | CPEB3 | CRB1 |
| COL8A1 | CORO1B | CPEB4 | CRB2 |
| COL9A2 | CORO1C | CPLX1 | CRB3 |
| COL9A3 | CORO2B | CPLX2 | CRCP |
| COLEC10 | CORO6 | CPLX4 | CRCT1 |
| COLEC11 | CORO7 | CPM | CREB3L2 |
| COLEC12 | COTL1 | CPNE2 | CREB5 |
| COLQ | COX15 | CPNE3 | CREBBP |
| COMMD1 | COX16 | CPNE5 | CREBL2 |
| COMMD10 | COX17 | CPNE6 | CREG1 |
| COMMD3 | COX18 | CPNE7 | CRELD1 |
| COMMD7 | COX19 | CPNE9 | CRHR1 |
| COMMD9 | COX4NB | CPPED1 | CRIM1 |
| COMP | COX5A | CPS1 | CRIP2 |
| COPA | COX6C | CPSF2 | CRISPLD2 |
| COPG | COX7A2 | CPSF3L | CRKL |

| | | | |
|---|---|---|---|
| CRLF1 | CSN1S1 | CTGF | CUGBP1 |
| CRLF3 | CSNK1A1L | CTNNA1 | CUGBP2 |
| CRLS1 | CSNK1D | CTNNA2 | CUL1 |
| CROCC | CSNK1E | CTNNA3 | CUL3 |
| CRTAC1 | CSNK1G2 | CTNNAL1 | CUL4A |
| CRTC1 | CSNK2A2 | CTNNB1 | CUL4B |
| CRY2 | CSPG4 | CTNNBL1 | CUL7 |
| CRYBA1 | CSPG5 | CTNND2 | CUTA |
| CRYBA2 | CSPP1 | CTNS | CUX1 |
| CRYBB1 | CSRNP1 | CTPS | CUX2 |
| CRYBB2 | CSRNP2 | CTR9 | CWF19L2 |
| CRYBB3 | CSRNP3 | CTRB1 | CXCL14 |
| CRYGB | CSRP1 | CTRB2 | CXCL2 |
| CRYGN | CST2 | CTSB | CXCL6 |
| CRYL1 | CST4 | CTSD | CXCR2 |
| CRYM | CSTB | CTSH | CXCR4 |
| CRYZ | CSTF1 | CTSL3 | CXCR5 |
| CS | CT45A1 | CTSZ | CXCR7 |
| CSAD | CTAGE5 | CTTN | CXorf38 |
| CSDAP1 | CTBP1 | CTTNBP2 | CXorf41 |
| CSDC2 | CTBP2 | CTTNBP2NL | CXorf48 |
| CSGALNACT1 | CTBS | CTXN3 | CXorf56 |
| CSMD1 | CTDP1 | CUBN | CXXC1 |
| CSMD2 | CTDSPL2 | CUEDC1 | CXXC5 |
| CSMD3 | CTF1 | CUEDC2 | CYB561 |

| | | | |
|---|---|---|---|
| CYB5R1 | CYP2D7P1 | DACT3 | DCD |
| CYB5R2 | CYP2U1 | DAD1L | DCDC2B |
| CYB5R3 | CYP3A4 | DAO | DCHS1 |
| CYB5R4 | CYP46A1 | DAP | DCHS2 |
| CYB5RL | CYP4F11 | DAP3 | DCLK1 |
| CYBA | CYP4V2 | DAPK1 | DCLK2 |
| CYBASC3 | CYP4X1 | DAPK3 | DCN |
| CYC1 | CYP51A1 | DAPP1 | DCP1A |
| CYFIP1 | CYP7B1 | DARS | DCTD |
| CYFIP2 | CYP8B1 | DAXX | DCTN3 |
| CYGB | CYSLTR1 | DAZAP1 | DCTN4 |
| CYHR1 | CYTH1 | DBNDD1 | DCTPP1 |
| CYP11A1 | CYTH2 | DBR1 | DCUN1D1 |
| CYP11B1 | CYTH3 | DBT | DCUN1D2 |
| CYP11B2 | CYTSA | DBX1 | DCUN1D4 |
| CYP1A1 | CYTSB | DCAF11 | DDA1 |
| CYP1A2 | CYYR1 | DCAF13 | DDAH1 |
| CYP20A1 | D4S234E | DCAF15 | DDAH2 |
| CYP24A1 | DAAM1 | DCAF4 | DDC |
| CYP26A1 | DAAM2 | DCAF5 | DDHD1 |
| CYP26B1 | DAB1 | DCAF7 | DDIT3 |
| CYP26C1 | DAB2 | DCAF8 | DDIT4 |
| CYP27A1 | DAB2IP | DCAF8L2 | DDIT4L |
| CYP2A13 | DACH2 | DCAKD | DDR1 |
| CYP2A7 | DACT2 | DCC | DDR2 |

| | | | |
|---|---|---|---|
| DDX1 | DEFB1 | DGCR10 | DIABLO |
| DDX10 | DEFB128 | DGCR2 | DIAPH2 |
| DDX11 | DEFB132 | DGCR8 | DIAPH3 |
| DDX19A | DEFB133 | DGCR9 | DICER1 |
| DDX20 | DEFB136 | DGKA | DIDO1 |
| DDX24 | DEGS2 | DGKG | DIMT1L |
| DDX25 | DENND1A | DGKQ | DIO1 |
| DDX27 | DENND1C | DGKZ | DIO2 |
| DDX3Y | DENND2A | DHCR24 | DIO3 |
| DDX4 | DENND2C | DHCR7 | DIP2A |
| DDX42 | DENND2D | DHFRL1 | DIP2B |
| DDX43 | DENND3 | DHRS1 | DIP2C |
| DDX46 | DENND4A | DHRS3 | DIRAS3 |
| DDX47 | DENND4B | DHRS7B | DIRC2 |
| DDX5 | DENR | DHRS9 | DIRC3 |
| DDX51 | DEPDC5 | DHX16 | DIS3L |
| DDX55 | DEPDC6 | DHX29 | DIS3L2 |
| DDX56 | DEPDC7 | DHX30 | DISP2 |
| DDX60L | DERA | DHX32 | DIXDC1 |
| DEAF1 | DERL3 | DHX33 | DKFZp566F0947 |
| DECR2 | DFFA | DHX35 | DKFZp686O24166 |
| DEDD | DFFB | DHX36 | DKK1 |
| DEF6 | DFNA5 | DHX37 | DKK2 |
| DEF8 | DFNB31 | DHX8 | DKKL1 |
| DEFA10P | DGAT1 | DHX9 | DLAT |

| | | | |
|---|---|---|---|
| DLC1 | DMRT3 | DNAJC12 | DNM3 |
| DLEU1 | DMRTA2 | DNAJC17 | DNMBP |
| DLEU2 | DMRTC2 | DNAJC18 | DNMT3A |
| DLEU7 | DMTF1 | DNAJC19 | DNMT3B |
| DLG3 | DMXL1 | DNAJC22 | DNPEP |
| DLG4 | DMXL2 | DNAJC25 | DNTTIP2 |
| DLG5 | DNA2 | DNAJC25-GNG10 | DOCK1 |
| DLGAP2 | DNAH1 | DNAJC28 | DOCK11 |
| DLGAP3 | DNAH10 | DNAJC30 | DOCK3 |
| DLK1 | DNAH11 | DNAJC5 | DOCK6 |
| DLK2 | DNAH17 | DNAJC5B | DOCK7 |
| DLL1 | DNAH2 | DNAJC5G | DOCK9 |
| DLL3 | DNAH3 | DNAJC6 | DOK1 |
| DLL4 | DNAH5 | DNAJC8 | DOK2 |
| DLST | DNAH6 | DNAJC9 | DOK3 |
| DLX1 | DNAH7 | DNAL1 | DOK4 |
| DLX2 | DNAH9 | DNAL4 | DOK6 |
| DLX3 | DNAI1 | DNALI1 | DOK7 |
| DLX4 | DNAJA2 | DNASE1L1 | DOM3Z |
| DLX5 | DNAJA3 | DNASE1L2 | DOPEY1 |
| DLX6AS | DNAJB1 | DNASE1L3 | DOPEY2 |
| DMD | DNAJB11 | DNASE2B | DOT1L |
| DMKN | DNAJB13 | DNER | DPCR1 |
| DMRT1 | DNAJB6 | DNM1 | DPEP1 |
| DMRT2 | DNAJC1 | DNM2 | DPEP3 |

| | | | |
|---|---|---|---|
| DPF1 | DSC2 | DUSP13 | E2F3 |
| DPH1 | DSC3 | DUSP14 | E2F7 |
| DPM1 | DSCAM | DUSP16 | E2F8 |
| DPM2 | DSCAML1 | DUSP23 | E4F1 |
| DPM3 | DSCR8 | DUSP3 | EAPP |
| DPP10 | DSE | DUSP4 | EBAG9 |
| DPP3 | DSN1 | DUSP5P | EBF1 |
| DPP4 | DSP | DUSP6 | EBF2 |
| DPP6 | DST | DUSP8 | EBF3 |
| DPP8 | DSTYK | DUSP9 | ECE1 |
| DPP9 | DTNA | DVL1 | ECE2 |
| DPY19L1 | DTNBP1 | DYDC2 | ECEL1P2 |
| DPY19L2P4 | DTWD1 | DYNC1H1 | ECH1 |
| DPY19L3 | DTX1 | DYNC1I2 | EDARADD |
| DPY19L4 | DTX3 | DYNC1LI1 | EDC3 |
| DPYD | DTX4 | DYNC2LI1 | EDC4 |
| DPYS | DTYMK | DYNLL2 | EDEM1 |
| DPYSL2 | DULLARD | DYNLT1 | EDEM2 |
| DPYSL3 | DUOX1 | DYRK1A | EDEM3 |
| DQX1 | DUOX2 | DYRK3 | EDIL3 |
| DRD1 | DUS2L | DYSF | EDN1 |
| DRD4 | DUS3L | DYX1C1 | EDNRB |
| DRD5 | DUSP10 | DZIP3 | EEF1A1 |
| DRG1 | DUSP11 | E2F1 | EEF1A2 |
| DRGX | DUSP12 | E2F2 | EEF1B2 |

| | | | |
|---|---|---|---|
| EEF1E1 | EGLN2 | EIF3H | ELF5 |
| EEF2 | EGLN3 | EIF3J | ELFN1 |
| EEF2K | EGR1 | EIF3L | ELK3 |
| EEFSEC | EGR2 | EIF3M | ELL |
| EEPD1 | EHBP1 | EIF4A1 | ELL2 |
| EFCAB2 | EHBP1L1 | EIF4B | ELMO1 |
| EFCAB4A | EHD1 | EIF4E | ELMO2 |
| EFCAB4B | EHD2 | EIF4E1B | ELMOD1 |
| EFCAB5 | EHD4 | EIF4E2 | ELMOD2 |
| EFEMP1 | EHMT1 | EIF4EBP1 | ELN |
| EFEMP2 | EHMT2 | EIF4EBP3 | ELOF1 |
| EFHD1 | EID2 | EIF4ENIF1 | ELOVL4 |
| EFNA1 | EID2B | EIF4G1 | ELOVL5 |
| EFNA3 | EID3 | EIF4G2 | ELOVL6 |
| EFNA5 | EIF1 | EIF4G3 | ELOVL7 |
| EFNB1 | EIF1AD | EIF5 | ELP2 |
| EFR3A | EIF1AY | EIF5A2 | ELP2P |
| EFS | EIF2AK2 | EIF5B | EMB |
| EFTUD1 | EIF2B2 | ELAC1 | EMID2 |
| EGF | EIF2C2 | ELAC2 | EMILIN2 |
| EGFL6 | EIF2S1 | ELAVL1 | EML1 |
| EGFL7 | EIF3A | ELAVL3 | EML4 |
| EGFL8 | EIF3B | ELAVL4 | EML5 |
| EGFLAM | EIF3E | ELF2 | EMP2 |
| EGFR | EIF3F | ELF4 | EMP3 |

| | | | |
|---|---|---|---|
| EMX1 | EPB41L3 | EPPK1 | ESCO1 |
| EMX2 | EPB41L4A | EPS15 | ESCO2 |
| EMX2OS | EPB41L4B | EPS15L1 | ESM1 |
| EN1 | EPB49 | EPS8 | ESPN |
| EN2 | EPC1 | EPS8L2 | ESPNP |
| ENAH | EPC2 | EPSTI1 | ESRP2 |
| ENDOD1 | EPCAM | ERAP1 | ESRRA |
| ENGASE | EPHA10 | ERAS | ESRRB |
| ENO1 | EPHA2 | ERBB2 | ESRRG |
| ENOPH1 | EPHA4 | ERBB4 | ESX1 |
| ENOX1 | EPHA5 | ERC1 | ESYT1 |
| ENOX2 | EPHA6 | ERC2 | ESYT2 |
| ENPEP | EPHA8 | ERCC2 | ESYT3 |
| ENPP1 | EPHB2 | ERCC5 | ETAA1 |
| ENPP4 | EPHB3 | ERCC6 | ETF1 |
| ENPP5 | EPHB4 | ERG | ETFA |
| ENPP6 | EPHB6 | ERGIC1 | ETS1 |
| ENPP7 | EPHX2 | ERGIC3 | ETS2 |
| ENSA | EPHX3 | ERI3 | ETV1 |
| ENTPD8 | EPM2AIP1 | ERICH1 | ETV3 |
| EOMES | EPN1 | ERLIN1 | ETV5 |
| EP400 | EPN2 | ERLIN2 | ETV6 |
| EPAS1 | EPN3 | ERN1 | ETV7 |
| EPB41 | EPO | ERN2 | EVC |
| EPB41L2 | EPOR | ERO1L | EVI5L |

| | | | |
|---|---|---|---|
| EVL | F2RL3 | FAM107A | FAM128B |
| EVX1 | F3 | FAM107B | FAM129B |
| EVX2 | F5 | FAM108A1 | FAM131A |
| EXD3 | F7 | FAM108C1 | FAM133A |
| EXO1 | FA2H | FAM109A | FAM134B |
| EXOC1 | FAAH | FAM10A4 | FAM135A |
| EXOC2 | FABP5 | FAM110A | FAM138D |
| EXOC3 | FABP6 | FAM110B | FAM13A |
| EXOC4 | FABP7 | FAM110C | FAM13AOS |
| EXOC6 | FABP9 | FAM111A | FAM13C |
| EXOC6B | FADS2 | FAM111B | FAM149B1 |
| EXOG | FADS6 | FAM113B | FAM150A |
| EXOSC10 | FAF1 | FAM114A1 | FAM150B |
| EXOSC2 | FAH | FAM115A | FAM151B |
| EXOSC3 | FAHD2A | FAM115C | FAM154B |
| EXPH5 | FAHD2B | FAM117A | FAM155A |
| EXT1 | FAIM2 | FAM118A | FAM159B |
| EXT2 | FAM100A | FAM120AOS | FAM160A1 |
| EXTL3 | FAM100B | FAM120B | FAM160A2 |
| EYA2 | FAM101A | FAM123C | FAM160B1 |
| EYA4 | FAM101B | FAM124A | FAM163A |
| EYS | FAM102A | FAM124B | FAM163B |
| EZH1 | FAM102B | FAM125A | FAM165B |
| F13A1 | FAM103A1 | FAM126B | FAM166A |
| F2R | FAM105A | FAM127A | FAM166B |

| | | | |
|---|---|---|---|
| FAM167A | FAM18B2 | FAM57B | FAM86B2 |
| FAM168A | FAM190B | FAM59A | FAM89B |
| FAM170B | FAM193A | FAM5B | FAM8A1 |
| FAM171A1 | FAM193B | FAM60A | FAM90A1 |
| FAM171A2 | FAM194A | FAM63A | FAM91A1 |
| FAM171B | FAM19A1 | FAM63B | FAM96B |
| FAM172A | FAM19A3 | FAM65B | FAM98C |
| FAM174A | FAM19A4 | FAM66C | FAM9A |
| FAM174B | FAM19A5 | FAM69A | FAM9C |
| FAM176A | FAM26E | FAM69C | FANCA |
| FAM176B | FAM38A | FAM71C | FANCC |
| FAM177B | FAM40A | FAM71F2 | FANCD2 |
| FAM178A | FAM43B | FAM72A | FANCG |
| FAM178B | FAM46B | FAM73A | FAP |
| FAM179A | FAM47E | FAM76A | FAR2 |
| FAM180A | FAM48A | FAM76B | FARP2 |
| FAM181A | FAM48B2 | FAM82A1 | FARSA |
| FAM183B | FAM49A | FAM82A2 | FAS |
| FAM184A | FAM53A | FAM83A | FASTKD2 |
| FAM184B | FAM53B | FAM83C | FAT1 |
| FAM185A | FAM53C | FAM83D | FAT2 |
| FAM188A | FAM54A | FAM83F | FAT3 |
| FAM188B | FAM54B | FAM83H | FAU |
| FAM189A1 | FAM55C | FAM86A | FBF1 |
| FAM189B | FAM57A | FAM86B1 | FBLIM1 |

| | | | |
|---|---|---|---|
| FBLN1 | FBXO31 | FCRL1 | FGD2 |
| FBLN7 | FBXO34 | FCRL2 | FGD5 |
| FBN1 | FBXO38 | FCRL3 | FGD6 |
| FBP1 | FBXO4 | FCRL4 | FGF1 |
| FBRS | FBXO42 | FCRL5 | FGF11 |
| FBRSL1 | FBXO44 | FCRLA | FGF12 |
| FBXL13 | FBXO46 | FDFT1 | FGF14 |
| FBXL14 | FBXO5 | FDPS | FGF18 |
| FBXL16 | FBXO8 | FDX1 | FGF19 |
| FBXL17 | FBXO9 | FDX1L | FGF2 |
| FBXL18 | FBXW10 | FDXACB1 | FGF22 |
| FBXL20 | FBXW11 | FEM1A | FGF23 |
| FBXL21 | FBXW4 | FEM1C | FGF3 |
| FBXL22 | FBXW5 | FEN1 | FGF4 |
| FBXL3 | FBXW8 | FER | FGF6 |
| FBXL4 | FBXW9 | FER1L4 | FGF8 |
| FBXL6 | FCER1A | FERD3L | FGFBP3 |
| FBXL7 | FCER1G | FERMT2 | FGFR1 |
| FBXO11 | FCF1 | FERMT3 | FGFR1OP2 |
| FBXO15 | FCGBP | FEV | FGFR3 |
| FBXO2 | FCGRT | FEZ1 | FGFR4 |
| FBXO21 | FCHO1 | FEZ2 | FGFRL1 |
| FBXO27 | FCHO2 | FEZF1 | FGGY |
| FBXO28 | FCHSD2 | FEZF2 | FGR |
| FBXO30 | FCN1 | FGD1 | FHDC1 |

| | | | |
|---|---|---|---|
| FHIT | FLG | FLJ43663 | FNTA |
| FHL1 | FLI1 | FLJ43860 | FOLR1 |
| FHL5 | FLII | FLJ44817 | FOS |
| FHOD3 | FLJ10357 | FLJ45079 | FOSL2 |
| FIBCD1 | FLJ10661 | FLJ45983 | FOXB1 |
| FIBIN | FLJ12825 | FLNA | FOXD4L1 |
| FIBP | FLJ13197 | FLNB | FOXE1 |
| FIG4 | FLJ16779 | FLNC | FOXE3 |
| FIGF | FLJ20184 | FLOT1 | FOXF1 |
| FIP1L1 | FLJ22536 | FLOT2 | FOXF2 |
| FIZ1 | FLJ26850 | FLRT2 | FOXG1 |
| FJX1 | FLJ31306 | FLT1 | FOXI3 |
| FKBP10 | FLJ32063 | FLT3LG | FOXJ1 |
| FKBP14 | FLJ32810 | FLT4 | FOXJ3 |
| FKBP1B | FLJ33360 | FLVCR2 | FOXK1 |
| FKBP2 | FLJ37307 | FLYWCH2 | FOXK2 |
| FKBP3 | FLJ37453 | FMN1 | FOXL2 |
| FKBP4 | FLJ39582 | FMNL1 | FOXM1 |
| FKBP8 | FLJ39653 | FMNL2 | FOXN4 |
| FKBP9 | FLJ41350 | FMO2 | FOXO3 |
| FKBP9L | FLJ41562 | FN1 | FOXP1 |
| FKBPL | FLJ41603 | FN3K | FOXP4 |
| FKSG83 | FLJ41941 | FNBP4 | FOXR1 |
| FLAD1 | FLJ42709 | FNIP1 | FOXRED1 |
| FLCN | FLJ43390 | FNIP2 | FRAS1 |

| | | | |
|---|---|---|---|
| FREM2 | FUBP1 | GAB3 | GALE |
| FRG1B | FUCA1 | GABARAPL2 | GALK2 |
| FRK | FUCA2 | GABBR1 | GALNS |
| FRMD4A | FUNDC2 | GABPA | GALNT10 |
| FRMD5 | FUT2 | GABPB1 | GALNT11 |
| FRMD6 | FUT6 | GABRA1 | GALNT12 |
| FRMD7 | FUT8 | GABRA2 | GALNT13 |
| FRMPD2 | FUT9 | GABRA3 | GALNT14 |
| FRS2 | FXC1 | GABRA4 | GALNT2 |
| FRS3 | FXR2 | GABRA5 | GALNT6 |
| FRY | FXYD1 | GABRB2 | GALNT7 |
| FRZB | FXYD2 | GABRB3 | GALNT9 |
| FSCN2 | FXYD3 | GABRD | GALNTL1 |
| FSCN3 | FYCO1 | GABRG3 | GALNTL4 |
| FSD1L | FYN | GABRR2 | GALNTL5 |
| FSIP1 | FZD1 | GAD1 | GALNTL6 |
| FST | FZD2 | GAD2 | GANC |
| FSTL4 | FZD5 | GADD45B | GAP43 |
| FSTL5 | FZD9 | GADD45G | GAPDH |
| FTCD | FZR1 | GADD45GIP1 | GAPDHS |
| FTHL17 | G3BP1 | GAK | GAR1 |
| FTMT | G6PC3 | GAL3ST1 | GARNL3 |
| FTO | GAA | GAL3ST2 | GARS |
| FTSJ2 | GAB1 | GAL3ST4 | GART |
| FTSJD1 | GAB2 | GALC | GAS2L1 |

| | | | |
|---|---|---|---|
| GAS5 | GDF5 | GGT1 | GK5 |
| GAS7 | GDF6 | GGT3P | GLB1L3 |
| GAST | GDF7 | GGT6 | GLDN |
| GATA1 | GDF9 | GGT7 | GLG1 |
| GATA2 | GDNF | GGTLC2 | GLI1 |
| GATA4 | GDPD1 | GHITM | GLI2 |
| GATA5 | GDPD2 | GHR | GLI3 |
| GATA6 | GEFT | GHRHR | GLIPR1L1 |
| GATAD2A | GEN1 | GHRL | GLIS1 |
| GATAD2B | GFI1 | GHRLOS | GLIS3 |
| GATSL3 | GFM1 | GHSR | GLRA3 |
| GBAP1 | GFM2 | GIGYF1 | GLRX5 |
| GBAS | GFOD1 | GIGYF2 | GLS |
| GBE1 | GFOD2 | GIMAP1 | GLS2 |
| GBGT1 | GFPT1 | GIMAP7 | GLT25D2 |
| GBX2 | GFPT2 | GINS1 | GLT8D2 |
| GCAT | GFRA1 | GIPC1 | GLUD1 |
| GCHFR | GFRA2 | GIPR | GLYATL3 |
| GCK | GFRA4 | GJA5 | GLYCTK |
| GCLC | GFRAL | GJB2 | GLYR1 |
| GCNT1 | GGA2 | GJB3 | GMDS |
| GCNT2 | GGCT | GJB4 | GMEB2 |
| GDAP1 | GGCX | GJC1 | GMFB |
| GDAP2 | GGNBP2 | GJD2 | GMPPA |
| GDF15 | GGPS1 | GJD3 | GNA11 |

| | | | |
|---|---|---|---|
| GNA12 | GNL3 | GPC5 | GPR148 |
| GNA13 | GNMT | GPC6 | GPR15 |
| GNA14 | GNPAT | GPD1L | GPR153 |
| GNA15 | GNPDA1 | GPD2 | GPR157 |
| GNAI1 | GNPNAT1 | GPHA2 | GPR158 |
| GNAI2 | GNPTAB | GPHN | GPR160 |
| GNAI3 | GNPTG | GPIHBP1 | GPR161 |
| GNAL | GOLGA3 | GPLD1 | GPR162 |
| GNAO1 | GOLGA4 | GPM6B | GPR176 |
| GNAQ | GOLGA6L5 | GPN2 | GPR177 |
| GNAS | GOLGA8A | GPN3 | GPR180 |
| GNASAS | GOLGA8B | GPNMB | GPR183 |
| GNAT1 | GOLIM4 | GPR107 | GPR26 |
| GNAT2 | GOLSYN | GPR110 | GPR3 |
| GNB1L | GOLT1A | GPR123 | GPR37L1 |
| GNB2 | GON4L | GPR124 | GPR39 |
| GNB2L1 | GORASP2 | GPR128 | GPR4 |
| GNB3 | GOT1L1 | GPR132 | GPR44 |
| GNB5 | GP1BA | GPR133 | GPR45 |
| GNG11 | GP2 | GPR135 | GPR56 |
| GNG12 | GP5 | GPR137 | GPR63 |
| GNG13 | GP9 | GPR137B | GPR65 |
| GNG4 | GPATCH2 | GPR139 | GPR81 |
| GNG7 | GPBP1 | GPR142 | GPR83 |
| GNL1 | GPC2 | GPR143 | GPR85 |

| | | | |
|---|---|---|---|
| GPR88 | GREB1L | GRP | GTF2H5 |
| GPR89A | GRHL2 | GRRP1 | GTF2I |
| GPR97 | GRHL3 | GRTP1 | GTF2IRD1 |
| GPRC5B | GRIA1 | GRXCR1 | GTF3A |
| GPRC5C | GRIA4 | GSC | GTF3C1 |
| GPRIN3 | GRID1 | GSDMA | GTF3C2 |
| GPS1 | GRID2 | GSDMD | GTF3C3 |
| GPSM1 | GRIK2 | GSG1L | GTF3C5 |
| GPSM3 | GRIK3 | GSK3B | GTF3C6 |
| GPT2 | GRIK4 | GSPT1 | GTPBP1 |
| GPX1 | GRIK5 | GSR | GTPBP5 |
| GPX4 | GRIN1 | GSTA4 | GTPBP8 |
| GPX6 | GRIN2A | GSTCD | GTSE1 |
| GPX7 | GRIN2B | GSTM2 | GUCA1A |
| GRAMD1B | GRIN2C | GSTM4 | GUCA1C |
| GRAMD1C | GRINL1A | GSTO2 | GUCY1A2 |
| GRAMD2 | GRIP1 | GSX1 | GUCY1A3 |
| GRAMD3 | GRK1 | GSX2 | GUCY1B3 |
| GRAMD4 | GRK4 | GTDC1 | GUCY2D |
| GRAP2 | GRK5 | GTF2A2 | GUCY2E |
| GRASP | GRK6 | GTF2B | GUF1 |
| GRB10 | GRM2 | GTF2E2 | GUSBL1 |
| GRB2 | GRM3 | GTF2F2 | GXYLT1 |
| GRB7 | GRM4 | GTF2H1 | GXYLT2 |
| GREB1 | GRM7 | GTF2H4 | GYG1 |

| | | | |
|---|---|---|---|
| GZF1 | HBM | HDAC7 | HERC3 |
| GZMM | HBP1 | HDAC9 | HERC6 |
| H1FX | HBQ1 | HDDC2 | HERPUD1 |
| H2AFX | HBS1L | HDGF2 | HERPUD2 |
| H2AFY2 | HBXIP | HDHD1A | HES1 |
| H2BFWT | HCCA2 | HDHD2 | HES2 |
| H3F3A | HCG18 | HDLBP | HES6 |
| H3F3B | HCG27 | HEATR1 | HES7 |
| HACL1 | HCG4 | HEATR2 | HEXB |
| HADH | HCG4P6 | HEATR3 | HEXIM1 |
| HAGH | HCG9 | HEATR6 | HEXIM2 |
| HAND1 | HCK | HEATR7A | HGC6.3 |
| HAND2 | HCN1 | HECA | HGF |
| HAO2 | HCN2 | HECTD1 | HGFAC |
| HAP1 | HCN3 | HECTD3 | HGS |
| HAPLN3 | HCN4 | HECW1 | HGSNAT |
| HAPLN4 | HCP5 | HEG1 | HHAT |
| HARS2 | HCRT | HELB | HHATL |
| HAS1 | HCRTR1 | HELLS | HHIPL1 |
| HAS2 | HCRTR2 | HELZ | HHLA1 |
| HAUS7 | HDAC1 | HEMK1 | HHLA3 |
| HAX1 | HDAC10 | HEPACAM | HIAT1 |
| HBD | HDAC11 | HEPHL1 | HIC1 |
| HBEGF | HDAC4 | HERC1 | HIF1A |
| HBG1 | HDAC5 | HERC2 | HIGD1A |

| | | | |
|---|---|---|---|
| HIGD2B | HIST1H4B | HLA-DPB2 | HMGN1 |
| HIP1 | HIST1H4D | HLA-DQA1 | HMGN3 |
| HIP1R | HIST1H4E | HLA-DQA2 | HMGN4 |
| HIPK2 | HIST1H4H | HLA-DQB1 | HMGN5 |
| HIPK3 | HIST1H4J | HLA-DQB2 | HMGXB3 |
| HIPK4 | HIST1H4K | HLA-DRA | HMGXB4 |
| HISPPD1 | HIST1H4L | HLA-DRB1 | HMHA1 |
| HISPPD2A | HIST2H2AA4 | HLA-DRB5 | HMHB1 |
| HIST1H1B | HIST2H2AB | HLA-DRB6 | HMMR |
| HIST1H1C | HIST2H2AC | HLA-E | HMOX1 |
| HIST1H1T | HIST2H2BA | HLA-F | HMOX2 |
| HIST1H2AD | HIVEP1 | HLA-G | HMP19 |
| HIST1H2AE | HIVEP2 | HLA-H | HMX2 |
| HIST1H2AI | HIVEP3 | HLA-J | HMX3 |
| HIST1H2AJ | HJURP | HLA-L | HN1 |
| HIST1H2AM | HK1 | HLCS | HNF4A |
| HIST1H2BD | HLA-A | HLF | HNRNPA1 |
| HIST1H2BG | HLA-B | HLTF | HNRNPAB |
| HIST1H2BI | HLA-C | HM13 | HNRNPF |
| HIST1H3B | HLA-DMA | HMBS | HNRNPH1 |
| HIST1H3C | HLA-DMB | HMG20B | HNRNPH2 |
| HIST1H3H | HLA-DOA | HMGA2 | HNRNPL |
| HIST1H3I | HLA-DOB | HMGB1L1 | HNRNPM |
| HIST1H3J | HLA-DPA1 | HMGB2 | HNRNPR |
| HIST1H4A | HLA-DPB1 | HMGCR | HNRNPU |

| | | | |
|---|---|---|---|
| HNRNPUL1 | HOXC4 | HS3ST6 | HSPB8 |
| HNRPA1L-2 | HOXD1 | HS6ST1 | HSPB9 |
| HNRPDL | HOXD11 | HS6ST2 | HSPBP1 |
| HNRPLL | HOXD12 | HS6ST3 | HSPC072 |
| HOMER2 | HOXD13 | HSCB | HSPC157 |
| HOMER3 | HOXD3 | HSD11B1 | HSPD1 |
| HOMEZ | HOXD8 | HSD11B1L | HSPE1 |
| HOOK1 | HP | HSD11B2 | HSPH1 |
| HOOK2 | HPCAL1 | HSD17B10 | HTATIP2 |
| HOPX | HPCAL4 | HSD17B4 | HTR1B |
| HORMAD1 | HPN | HSF1 | HTR1E |
| HOTAIR | HPS3 | HSF2 | HTR2A |
| HOXA10 | HPSE2 | HSF4 | HTR2C |
| HOXA11AS | HR | HSF5 | HTR3A |
| HOXA13 | HRAS | HSP90AA1 | HTR4 |
| HOXA3 | HRC | HSP90B1 | HTR5A |
| HOXA4 | HRCT1 | HSPA12A | HTR7P |
| HOXA5 | HRH1 | HSPA12B | HTRA1 |
| HOXA7 | HRH2 | HSPA13 | HTT |
| HOXB1 | HRNBP3 | HSPA1B | HUS1B |
| HOXB13 | HS1BP3 | HSPA1L | HUWE1 |
| HOXB3 | HS2ST1 | HSPA2 | HVCN1 |
| HOXB4 | HS3ST1 | HSPA8 | HYAL1 |
| HOXB7 | HS3ST2 | HSPB1 | HYAL3 |
| HOXC12 | HS3ST4 | HSPB6 | HYDIN |

| | | | |
|---|---|---|---|
| HYI | IFI6 | IGFL1 | IL18R1 |
| HYLS1 | IFIT1 | IGFN1 | IL18RAP |
| HYMAI | IFITM1 | IGLON5 | IL19 |
| IAH1 | IFITM2 | IGSF21 | IL1A |
| IAPP | IFITM3 | IGSF22 | IL1B |
| IARS2 | IFITM5 | IGSF3 | IL1F10 |
| IBTK | IFNGR1 | IGSF9B | IL1F9 |
| ICA1L | IFT122 | IKBIP | IL1RAP |
| ICAM1 | IFT140 | IKBKAP | IL1RAPL2 |
| ICAM3 | IFT172 | IKZF2 | IL20RA |
| ICAM4 | IFT52 | IKZF5 | IL22RA2 |
| ICAM5 | IGDCC3 | IL10RA | IL23R |
| ICMT | IGDCC4 | IL10RB | IL24 |
| ICOS | IGF1 | IL11 | IL27RA |
| ID1 | IGF1R | IL11RA | IL28B |
| IDH3A | IGF2AS | IL12RB2 | IL2RA |
| IDI1 | IGF2BP1 | IL15 | IL5RA |
| IDO2 | IGF2BP2 | IL15RA | IL6R |
| IDS | IGF2BP3 | IL16 | IL7 |
| IDUA | IGF2R | IL17D | ILDR1 |
| IER2 | IGFALS | IL17RA | ILF2 |
| IER3IP1 | IGFBP2 | IL17RC | ILF3 |
| IFFO1 | IGFBP3 | IL17RD | ILK |
| IFI16 | IGFBP5 | IL17REL | ILKAP |
| IFI27 | IGFBP7 | IL18BP | IMMP2L |

| | | | |
|---|---|---|---|
| IMPACT | INSL6 | IQSEC1 | ISLR2 |
| IMPAD1 | INSM1 | IQSEC3 | ISM1 |
| IMPDH1 | INSR | IQUB | ISM2 |
| IMPG1 | INTS1 | IRAK1 | ISY1 |
| INADL | INTS12 | IRAK2 | ITGA1 |
| INF2 | INTS2 | IRAK3 | ITGA11 |
| ING1 | INTS4 | IRF2 | ITGA3 |
| ING2 | INTS4L1 | IRF2BP1 | ITGA6 |
| ING5 | INTS5 | IRF4 | ITGA7 |
| INHBA | INTS6 | IRF5 | ITGA9 |
| INHBB | INVS | IRF8 | ITGAE |
| INHBC | IP6K1 | IRF9 | ITGAL |
| INHBE | IP6K2 | IRGC | ITGB1BP3 |
| INMT | IPMK | IRGM | ITGB3BP |
| INO80B | IPO13 | IRGQ | ITGB4 |
| INPP4A | IPO5 | IRS1 | ITGB5 |
| INPP4B | IPO7 | IRS2 | ITGB6 |
| INPP5A | IPO8 | IRS4 | ITGB7 |
| INPP5B | IPP | IRX1 | ITGBL1 |
| INPP5F | IQCB1 | IRX3 | ITIH4 |
| INSC | IQCE | IRX4 | ITIH5 |
| INSIG1 | IQCJ | IRX6 | ITM2A |
| INSIG2 | IQCK | ISCU | ITPA |
| INS-IGF2 | IQGAP1 | ISG15 | ITPK1 |
| INSL5 | IQGAP2 | ISLR | ITPKB |

| | | | |
|---|---|---|---|
| ITPR1 | JUB | KCNAB2 | KCNJ16 |
| ITPR2 | JUN | KCNAB3 | KCNJ2 |
| ITPRIP | JUP | KCNC1 | KCNJ4 |
| ITPRIPL1 | KAL1 | KCNC2 | KCNJ5 |
| ITPRIPL2 | KALRN | KCND2 | KCNK1 |
| ITSN1 | KANK1 | KCND3 | KCNK10 |
| ITSN2 | KANK2 | KCNE1 | KCNK13 |
| IVD | KANK3 | KCNE1L | KCNK17 |
| IWS1 | KANK4 | KCNG1 | KCNK2 |
| JAG2 | KAT2B | KCNG4 | KCNK3 |
| JAK1 | KAT5 | KCNH2 | KCNK4 |
| JAK2 | KATNAL2 | KCNH3 | KCNK7 |
| JAKMIP1 | KATNB1 | KCNH4 | KCNMA1 |
| JAKMIP3 | KAZALD1 | KCNH6 | KCNMB1 |
| JAM3 | KBTBD10 | KCNH7 | KCNMB2 |
| JARID2 | KBTBD11 | KCNH8 | KCNMB4 |
| JAZF1 | KBTBD12 | KCNIP1 | KCNN1 |
| JMJD1C | KBTBD2 | KCNIP2 | KCNN2 |
| JMJD5 | KBTBD3 | KCNIP3 | KCNN3 |
| JMJD6 | KBTBD4 | KCNIP4 | KCNN4 |
| JMJD8 | KCMF1 | KCNJ1 | KCNQ1 |
| JMY | KCNA2 | KCNJ10 | KCNQ1OT1 |
| JOSD1 | KCNA3 | KCNJ12 | KCNQ2 |
| JPH1 | KCNA4 | KCNJ14 | KCNQ3 |
| JPH3 | KCNAB1 | KCNJ15 | KCNQ4 |

| | | | |
|---|---|---|---|
| KCNQ5 | KDM6B | KIAA0564 | KIAA1409 |
| KCNS1 | KDR | KIAA0586 | KIAA1429 |
| KCNS3 | KDSR | KIAA0652 | KIAA1432 |
| KCNT1 | KHDC1 | KIAA0664 | KIAA1462 |
| KCNT2 | KHDRBS2 | KIAA0748 | KIAA1467 |
| KCNV2 | KHK | KIAA0753 | KIAA1522 |
| KCP | KIAA0100 | KIAA0892 | KIAA1530 |
| KCTD1 | KIAA0141 | KIAA0895 | KIAA1598 |
| KCTD12 | KIAA0146 | KIAA0895L | KIAA1614 |
| KCTD16 | KIAA0174 | KIAA0913 | KIAA1632 |
| KCTD18 | KIAA0182 | KIAA0922 | KIAA1683 |
| KCTD3 | KIAA0226 | KIAA1012 | KIAA1688 |
| KCTD5 | KIAA0232 | KIAA1109 | KIAA1712 |
| KCTD9 | KIAA0247 | KIAA1161 | KIAA1731 |
| KDELC2 | KIAA0284 | KIAA1199 | KIAA1751 |
| KDM2A | KIAA0319L | KIAA1211 | KIAA1826 |
| KDM2B | KIAA0355 | KIAA1217 | KIAA1949 |
| KDM4A | KIAA0368 | KIAA1239 | KIAA1967 |
| KDM4B | KIAA0427 | KIAA1244 | KIAA1984 |
| KDM4C | KIAA0430 | KIAA1257 | KIAA2013 |
| KDM4D | KIAA0494 | KIAA1274 | KIAA2018 |
| KDM5A | KIAA0495 | KIAA1279 | KIDINS220 |
| KDM5B | KIAA0513 | KIAA1324 | KIF11 |
| KDM5C | KIAA0528 | KIAA1324L | KIF13B |
| KDM5D | KIAA0556 | KIAA1370 | KIF15 |

| | | | |
|---|---|---|---|
| KIF17 | KLC1 | KLHL25 | KRR1 |
| KIF18B | KLC2 | KLHL26 | KRT15 |
| KIF19 | KLC4 | KLHL28 | KRT2 |
| KIF1A | KLF11 | KLHL29 | KRT24 |
| KIF1B | KLF12 | KLHL3 | KRT31 |
| KIF1C | KLF13 | KLHL30 | KRT38 |
| KIF20B | KLF14 | KLHL31 | KRT5 |
| KIF23 | KLF17 | KLHL33 | KRT6C |
| KIF26B | KLF2 | KLHL36 | KRT77 |
| KIF2A | KLF3 | KLHL8 | KRT8 |
| KIF2C | KLF6 | KLK10 | KRT80 |
| KIF3A | KLF7 | KLK13 | KRT82 |
| KIF3B | KLF8 | KLK14 | KRTAP10-1 |
| KIF3C | KLHDC2 | KLK6 | KRTAP10-7 |
| KIF5B | KLHDC4 | KLKBL4 | KRTAP24-1 |
| KIF6 | KLHDC7A | KLRB1 | KRTAP4-1 |
| KIF9 | KLHDC8A | KLRD1 | KRTAP4-8 |
| KIFAP3 | KLHL1 | KNDC1 | KRTCAP3 |
| KIFC1 | KLHL10 | KPNA1 | KSR1 |
| KIFC2 | KLHL11 | KPNA3 | KSR2 |
| KIFC3 | KLHL12 | KPNA5 | KYNU |
| KILLIN | KLHL17 | KPNA7 | L1CAM |
| KIR3DX1 | KLHL20 | KRAS | L3MBTL2 |
| KIRREL3 | KLHL21 | KRBA1 | L3MBTL3 |
| KL | KLHL24 | KRBA2 | L3MBTL4 |

| | | | |
|---|---|---|---|
| LACE1 | LAX1 | LEAP2 | LHX2 |
| LACTB | LAYN | LECT1 | LHX4 |
| LAD1 | LBH | LEF1 | LHX5 |
| LAG3 | LBX2 | LEKR1 | LHX6 |
| LAGE3 | LBXCOR1 | LENG8 | LHX9 |
| LAIR2 | LCE1C | LEP | LIFR |
| LAMA1 | LCE2A | LEPRE1 | LILRA4 |
| LAMA2 | LCE3D | LEPREL1 | LILRB5 |
| LAMA3 | LCE4A | LEPREL2 | LIM2 |
| LAMA5 | LCE6A | LEPROT | LIMA1 |
| LAMB1 | LCLAT1 | LEPROTL1 | LIMCH1 |
| LAMB4 | LCMT1 | LETM2 | LIMD1 |
| LAMC2 | LCN8 | LETMD1 | LIMD2 |
| LAMC3 | LCOR | LGALS1 | LIME1 |
| LAMP1 | LCORL | LGALS12 | LIMK2 |
| LAPTM4B | LCP1 | LGALS4 | LIMS1 |
| LAPTM5 | LCP2 | LGALS8 | LIMS2 |
| LARP1 | LCT | LGALS9 | LIN28 |
| LASP1 | LDB1 | LGMN | LIN28B |
| LASS2 | LDB2 | LGR5 | LIN7C |
| LASS4 | LDHA | LGR6 | LIN9 |
| LASS5 | LDLR | LHFP | LINS1 |
| LASS6 | LDLRAD2 | LHFPL2 | LIPA |
| LAT | LDLRAD3 | LHPP | LIPC |
| LATS1 | LDLRAP1 | LHX1 | LIPE |

| | | | |
|---|---|---|---|
| LIPJ | LOC100128640 | LOC100287216 | LOC158381 |
| LIX1 | LOC100128675 | LOC100292680 | LOC158572 |
| LIX1L | LOC100128731 | LOC100302640 | LOC200726 |
| LLGL1 | LOC100128788 | LOC100303728 | LOC202181 |
| LMAN1 | LOC100128977 | LOC100329108 | LOC219347 |
| LMAN1L | LOC100129637 | LOC115110 | LOC221122 |
| LMAN2 | LOC100130017 | LOC116437 | LOC221710 |
| LMBR1 | LOC100130093 | LOC121838 | LOC222699 |
| LMF1 | LOC100130522 | LOC121952 | LOC253724 |
| LMF2 | LOC100130691 | LOC127841 | LOC255167 |
| LMNA | LOC100130776 | LOC143188 | LOC283174 |
| LMNB2 | LOC100130872 | LOC143666 | LOC283267 |
| LMO3 | LOC100130987 | LOC144438 | LOC283663 |
| LMO4 | LOC100132111 | LOC145783 | LOC283856 |
| LMO7 | LOC100132215 | LOC145845 | LOC283867 |
| LMTK2 | LOC100132707 | LOC146336 | LOC283999 |
| LMX1A | LOC100133315 | LOC146880 | LOC284276 |
| LMX1B | LOC100133612 | LOC148145 | LOC284578 |
| LNPEP | LOC100133985 | LOC148189 | LOC284632 |
| LNX2 | LOC100188947 | LOC148696 | LOC284749 |
| LOC100009676 | LOC100190939 | LOC150197 | LOC284798 |
| LOC100101938 | LOC100192378 | LOC151300 | LOC284837 |
| LOC100127888 | LOC100268168 | LOC151658 | LOC284900 |
| LOC100128071 | LOC100272146 | LOC154822 | LOC285205 |
| LOC100128288 | LOC100286844 | LOC157627 | LOC285419 |

| | | | |
|---|---|---|---|
| LOC285456 | LOC400927 | LOC645332 | LOC729799 |
| LOC285627 | LOC400931 | LOC645638 | LOC729991-MEF2B |
| LOC285696 | LOC401010 | LOC646214 | LOC730755 |
| LOC285740 | LOC401052 | LOC646762 | LOC731779 |
| LOC285830 | LOC401097 | LOC646851 | LOC732275 |
| LOC285954 | LOC401397 | LOC647288 | LOC80154 |
| LOC339535 | LOC401588 | LOC647979 | LOC84856 |
| LOC339674 | LOC404266 | LOC648740 | LOC91316 |
| LOC339788 | LOC440040 | LOC650368 | LOC91450 |
| LOC340508 | LOC440461 | LOC651250 | LOC92249 |
| LOC344595 | LOC440895 | LOC653786 | LOC92659 |
| LOC344967 | LOC440925 | LOC727924 | LOC93622 |
| LOC360030 | LOC441204 | LOC728264 | LOH12CR1 |
| LOC374491 | LOC441208 | LOC728392 | LONP1 |
| LOC388387 | LOC441601 | LOC728411 | LONP2 |
| LOC388428 | LOC441869 | LOC728661 | LONRF1 |
| LOC388588 | LOC442293 | LOC728723 | LONRF2 |
| LOC388692 | LOC442454 | LOC728875 | LONRF3 |
| LOC389332 | LOC494141 | LOC728989 | LOR |
| LOC389493 | LOC595101 | LOC729082 | LOX |
| LOC390594 | LOC619207 | LOC729156 | LOXHD1 |
| LOC390595 | LOC643837 | LOC729338 | LOXL1 |
| LOC399959 | LOC643923 | LOC729375 | LOXL3 |
| LOC400027 | LOC644649 | LOC729384 | LPAR4 |
| LOC400804 | LOC645323 | LOC729467 | LPAR6 |

| | | | |
|---|---|---|---|
| LPCAT1 | LRP12 | LRRC50 | LSM3 |
| LPCAT2 | LRP2 | LRRC55 | LSM4 |
| LPCAT3 | LRP5 | LRRC56 | LSP1 |
| LPHN1 | LRP8 | LRRC57 | LSS |
| LPHN2 | LRPAP1 | LRRC59 | LTA |
| LPIN1 | LRRC1 | LRRC6 | LTB |
| LPIN2 | LRRC10 | LRRC8D | LTBP1 |
| LPIN3 | LRRC14B | LRRFIP1 | LTBP3 |
| LPL | LRRC16A | LRRFIP2 | LTBP4 |
| LPP | LRRC16B | LRRIQ4 | LTK |
| LPPR1 | LRRC23 | LRRK1 | LTV1 |
| LPPR4 | LRRC24 | LRRN2 | LUC7L |
| LPPR5 | LRRC27 | LRRN4 | LUZP1 |
| LPXN | LRRC32 | LRRTM2 | LUZP2 |
| LRBA | LRRC36 | LRRTM4 | LUZP4 |
| LRCH2 | LRRC37A3 | LRTM2 | LUZP6 |
| LRDD | LRRC37B | LRTOMT | LVRN |
| LRFN2 | LRRC37B2 | LRWD1 | LY6D |
| LRIG1 | LRRC3B | LSAMP | LY6E |
| LRIG2 | LRRC41 | LSG1 | LY6G5C |
| LRIG3 | LRRC43 | LSM1 | LY6G6F |
| LRIT1 | LRRC47 | LSM10 | LY6K |
| LRMP | LRRC48 | LSM11 | LY9 |
| LRP1 | LRRC49 | LSM12 | LYAR |
| LRP10 | LRRC4C | LSM14B | LYPD1 |

| | | | |
|---|---|---|---|
| LYPD5 | MAGEB4 | MAOA | MAP6D1 |
| LYPLA2 | MAGEC3 | MAP1D | MAP7 |
| LYPLAL1 | MAGED1 | MAP1S | MAP9 |
| LYRM2 | MAGED2 | MAP2 | MAPK1 |
| LYRM4 | MAGI1 | MAP2K1 | MAPK11 |
| LYSMD4 | MAGI2 | MAP2K2 | MAPK14 |
| LYST | Magmas | MAP2K3 | MAPK4 |
| LYVE1 | MAK16 | MAP2K4 | MAPK6 |
| LYZL6 | MAL2 | MAP2K7 | MAPK8IP2 |
| LZTFL1 | MALAT1 | MAP3K1 | MAPK8IP3 |
| LZTS1 | MALL | MAP3K11 | MAPKAPK2 |
| LZTS2 | MALT1 | MAP3K13 | MAPKAPK3 |
| MACF1 | MAML1 | MAP3K3 | MAPKAPK5 |
| MACROD1 | MAML2 | MAP3K4 | MAPKBP1 |
| MAD1L1 | MAML3 | MAP3K5 | MAPKSP1 |
| MAD2L1BP | MAMLD1 | MAP3K6 | MAPRE2 |
| MAD2L2 | MAMSTR | MAP3K7IP2 | MAPRE3 |
| MADD | MAN1A1 | MAP3K8 | MAPT |
| MAEA | MAN1B1 | MAP4 | MARCKS |
| MAFB | MAN1C1 | MAP4K1 | MARCKSL1 |
| MAFF | MAN2A1 | MAP4K2 | MARK2 |
| MAFK | MAN2A2 | MAP4K3 | MARS |
| MAGEA10 | MANBA | MAP4K4 | MARVELD1 |
| MAGEA12 | MANBAL | MAP4K5 | MASP2 |
| MAGEB1 | MANF | MAP6 | MAST1 |

| | | | |
|---|---|---|---|
| MAST3 | MCF2 | MEA1 | MEGF8 |
| MAST4 | MCF2L | MEAF6 | MEGF9 |
| MAT2A | MCF2L2 | MECOM | MEI1 |
| MAT2B | MCFD2 | MECP2 | MEIS1 |
| MATN2 | MCHR1 | MED1 | MEIS2 |
| MATN3 | MCM2 | MED10 | MEIS3 |
| MATN4 | MCM3 | MED12L | MEIS3P1 |
| MATR3 | MCM3APAS | MED13L | MEN1 |
| MAX | MCM5 | MED14 | MEOX1 |
| MAZ | MCM7 | MED17 | MEPCE |
| MBD2 | MCM8 | MED19 | MERTK |
| MBD6 | MCM9 | MED20 | MEST |
| MBIP | MCOLN3 | MED23 | METAP1 |
| MBLAC1 | MCPH1 | MED24 | METAP2 |
| MBNL1 | MCRS1 | MED26 | METRNL |
| MBNL2 | MCTP1 | MED27 | METT10D |
| MBOAT7 | MCTP2 | MED31 | METT11D1 |
| MBP | MCTS1 | MED7 | METTL14 |
| MBTPS2 | MDC1 | MED9 | METTL7B |
| MC2R | MDGA1 | MEF2A | METTL9 |
| MC3R | MDGA2 | MEF2C | MEX3B |
| MCART6 | MDH1B | MEG3 | MEX3C |
| MCAT | MDN1 | MEGF10 | MEX3D |
| MCC | ME1 | MEGF11 | MFAP4 |
| MCCC1 | ME3 | MEGF6 | MFAP5 |

| | | | |
|---|---|---|---|
| MFF | MGC45800 | MIR1182 | MIR375 |
| MFGE8 | MGC72080 | MIR124-1 | MIR379 |
| MFHAS1 | MGLL | MIR124-2 | MIR411 |
| MFI2 | MGMT | MIR1258 | MIR412 |
| MFN1 | MGRN1 | MIR125B1 | MIR429 |
| MFSD10 | MIA2 | MIR1275 | MIR492 |
| MFSD2A | MIA3 | MIR1307 | MIR501 |
| MFSD2B | MIAT | MIR134 | MIR507 |
| MFSD3 | MIB1 | MIR138-2 | MIR543 |
| MFSD4 | MIB2 | MIR141 | MIR548F1 |
| MFSD5 | MICA | MIR1471 | MIR548F5 |
| MFSD7 | MICAL1 | MIR154 | MIR548H4 |
| MGAT1 | MICALL2 | MIR155HG | MIR548I3 |
| MGAT4A | MICB | MIR190 | MIR548N |
| MGAT4C | MID1 | MIR190B | MIR548Q |
| MGAT5 | MID1IP1 | MIR191 | MIR578 |
| MGAT5B | MID2 | MIR193B | MIR583 |
| MGC12982 | MIDN | MIR196B | MIR590 |
| MGC14436 | MIER1 | MIR2110 | MIR592 |
| MGC16275 | MIF | MIR219-2 | MIR595 |
| MGC23270 | MIF4GD | MIR223 | MIR596 |
| MGC23284 | MIIP | MIR24-2 | MIR604 |
| MGC27382 | MINK1 | MIR29A | MIR611 |
| MGC34034 | MIPEP | MIR320B1 | MIR632 |
| MGC42105 | MIR1181 | MIR363 | MIR636 |

| | | | |
|---|---|---|---|
| MIR639 | MLL4 | MNT | MPL |
| MIR654 | MLL5 | MNX1 | MPP2 |
| MIR659 | MLLT11 | MOAP1 | MPP3 |
| MIR662 | MLLT6 | MOBKL1B | MPPE1 |
| MIR670 | MLPH | MOBKL2A | MPPED2 |
| MIR758 | MLST8 | MOBKL2C | MPRIP |
| MIR9-3 | MLX | MOCS1 | MPZL1 |
| MITF | MMAB | MOG | MPZL2 |
| MKI67 | MMACHC | MON1A | MRAP2 |
| MKL1 | MMD | MON1B | MRAS |
| MKL2 | MMD2 | MORC1 | MRE11A |
| MKLN1 | MMEL1 | MORC2 | MRGPRF |
| MKNK1 | MMP11 | MORF4 | MRGPRX3 |
| MKNK2 | MMP15 | MORF4L1 | MRGPRX4 |
| MKRN1 | MMP16 | MORF4L2 | MRI1 |
| MKRN2 | MMP17 | MORN1 | MRPL1 |
| MKRN3 | MMP2 | MORN2 | MRPL12 |
| MKX | MMP23A | MORN3 | MRPL16 |
| MLANA | MMP24 | MOSC2 | MRPL23 |
| MLC1 | MMP27 | MOSPD3 | MRPL24 |
| MLF2 | MMP7 | MOV10 | MRPL27 |
| MLH1 | MMRN2 | MOV10L1 | MRPL3 |
| MLH3 | MMS19 | MPG | MRPL30 |
| MLL2 | MN1 | MPHOSPH8 | MRPL32 |
| MLL3 | MNS1 | MPHOSPH9 | MRPL37 |

| | | | |
|---|---|---|---|
| MRPL39 | MRTO4 | MTA1 | MTMR9 |
| MRPL42 | MRVI1 | MTA2 | MTMR9L |
| MRPL46 | MS4A10 | MTAP | MTNR1A |
| MRPL47 | MS4A4A | MTERFD2 | MTNR1B |
| MRPL48 | MSC | MTF1 | MTO1 |
| MRPL52 | MSGN1 | MTFMT | MTOR |
| MRPL54 | MSH2 | MTFR1 | MTP18 |
| MRPS11 | MSH3 | MTHFD1 | MTRF1 |
| MRPS12 | MSH5 | MTHFD1L | MTRR |
| MRPS15 | MSI2 | MTHFD2 | MTSS1 |
| MRPS18A | MSL2 | MTHFD2L | MTUS1 |
| MRPS18B | MSL3 | MTHFR | MTUS2 |
| MRPS18C | MSLN | MTHFS | MTX3 |
| MRPS2 | MSN | MTHFSD | MUC1 |
| MRPS21 | MSRA | MTIF3 | MUC12 |
| MRPS22 | MSRB2 | MTL5 | MUC13 |
| MRPS27 | MST1 | MTM1 | MUC2 |
| MRPS28 | MST1R | MTMR1 | MUC20 |
| MRPS30 | MSTN | MTMR10 | MUC21 |
| MRPS31 | MSX1 | MTMR11 | MUC4 |
| MRPS33 | MT1E | MTMR14 | MUC5B |
| MRPS36 | MT1M | MTMR15 | MUC6 |
| MRPS6 | MT1X | MTMR2 | MUDENG |
| MRPS7 | MT2A | MTMR4 | MUM1 |
| MRPS9 | MT3 | MTMR8 | MUS81 |

| | | | |
|---|---|---|---|
| MUSTN1 | MYL5 | MYOG | NADK |
| MVK | MYL6 | MYOM1 | NADSYN1 |
| MVP | MYL6B | MYOM2 | NAF1 |
| MX1 | MYL7 | MYPN | NAGA |
| MX2 | MYL9 | MYRIP | NAGK |
| MXD4 | MYLK | MYSM1 | NAGPA |
| MXRA5 | MYLK2 | MYST1 | NAGS |
| MXRA8 | MYLK3 | MYST3 | NAMPT |
| MYADM | MYLPF | MYST4 | NANOS2 |
| MYB | MYNN | MYT1 | NAP1L4 |
| MYBBP1A | MYO15A | MYT1L | NAPA |
| MYBPC2 | MYO16 | N4BP1 | NAPG |
| MYBPHL | MYO18A | N4BP2 | NAPRT1 |
| MYC | MYO1C | N4BP2L2 | NARF |
| MYCBP | MYO1D | N4BP3 | NARFL |
| MYCBP2 | MYO1F | N6AMT2 | NARG2 |
| MYCL1 | MYO1H | NAA15 | NAT1 |
| MYCN | MYO3A | NAA16 | NAT10 |
| MYEOV2 | MYO3B | NAA30 | NAT14 |
| MYH10 | MYO5A | NAA35 | NAT6 |
| MYH13 | MYO7A | NAA40 | NAT8L |
| MYH14 | MYO7B | NAALAD2 | NAT9 |
| MYH15 | MYO9A | NAALADL2 | NAV1 |
| MYH3 | MYO9B | NAB2 | NAV2 |
| MYL2 | MYOF | NACA | NBAS |

| | | | |
|---|---|---|---|
| NBEA | NCOR2 | NDUFA10 | NEDD1 |
| NBEAL1 | NCR3 | NDUFA4 | NEDD4 |
| NBL1 | NCRNA00081 | NDUFA4L2 | NEDD4L |
| NBPF1 | NCRNA00092 | NDUFA5 | NEDD8 |
| NBPF3 | NCRNA00093 | NDUFA9 | NEFM |
| NBR1 | NCRNA00110 | NDUFAF4 | NEGR1 |
| NCALD | NCRNA00114 | NDUFB2 | NEIL3 |
| NCAM2 | NCRNA00119 | NDUFB4 | NEK1 |
| NCAN | NCRNA00120 | NDUFB8 | NEK2 |
| NCAPD3 | NCRNA00164 | NDUFC1 | NEK3 |
| NCAPH | NCRNA00167 | NDUFS3 | NEK5 |
| NCDN | NCRNA00171 | NDUFS4 | NEK6 |
| NCEH1 | NCRNA00182 | NDUFS5 | NEK7 |
| NCF4 | NCRNA00188 | NDUFS6 | NELL2 |
| NCK1 | NCRNA00200 | NDUFS7 | NENF |
| NCKAP1 | NCRNA00219 | NDUFS8 | NES |
| NCKAP5 | NDE1 | NDUFV1 | NET1 |
| NCKAP5L | NDEL1 | NDUFV2 | NETO1 |
| NCL | NDFIP2 | NDUFV3 | NEU1 |
| NCLN | NDN | NEB | NEU2 |
| NCOA1 | NDRG1 | NEBL | NEURL |
| NCOA2 | NDRG4 | NECAB1 | NEURL2 |
| NCOA3 | NDST1 | NECAB2 | NEURL3 |
| NCOA4 | NDST4 | NECAP1 | NEUROD1 |
| NCOR1 | NDUFA1 | NECAP2 | NEUROD2 |

| | | | |
|---|---|---|---|
| NEUROG1 | NHS | NKX6-3 | NOL11 |
| NEUROG2 | NHSL2 | NLGN2 | NOL4 |
| NEXN | NICN1 | NLGN4Y | NOL7 |
| NF1 | NID1 | NLK | NOLC1 |
| NF1P1 | NID2 | NLRC3 | NOM1 |
| NF2 | NIN | NLRC5 | NOMO1 |
| NFASC | NINJ1 | NLRP1 | NONO |
| NFATC1 | NINJ2 | NLRP10 | NOP10 |
| NFATC3 | NINL | NLRP12 | NOP14 |
| NFE2 | NIPA1 | NLRP14 | NOP16 |
| NFE2L1 | NIPA2 | NLRP3 | NOP56 |
| NFE2L3 | NIPAL1 | NLRP6 | NOP58 |
| NFIA | NIPBL | NME2 | NOS1AP |
| NFIC | NKAIN2 | NME6 | NOS2 |
| NFIX | NKAIN3 | NMNAT1 | NOS3 |
| NFKB2 | NKIRAS2 | NMU | NOSIP |
| NFKBIL1 | NKPD1 | NMUR1 | NOTCH3 |
| NFYA | NKRF | NNT | NOTCH4 |
| NFYB | NKTR | NOB1 | NOTO |
| NGEF | NKX2-1 | NOC2L | NOX4 |
| NGFR | NKX2-2 | NOC4L | NOXA1 |
| NHEJ1 | NKX2-4 | NOD2 | NOXO1 |
| NHLH2 | NKX2-5 | NODAL | NPAS1 |
| NHLRC3 | NKX6-1 | NOG | NPAS2 |
| NHP2 | NKX6-2 | NOL10 | NPAS3 |

| | | | |
|---|---|---|---|
| NPBWR1 | NR2C1 | NRM | NTF3 |
| NPC1 | NR2C2 | NRP1 | NTF4 |
| NPC2 | NR2C2AP | NRP2 | NTHL1 |
| NPDC1 | NR2E1 | NRTN | NTM |
| NPEPL1 | NR2F1 | NRXN1 | NTN1 |
| NPHP3 | NR2F2 | NRXN2 | NTN4 |
| NPHP4 | NR3C1 | NRXN3 | NTNG1 |
| NPL | NR3C2 | NSA2 | NUAK1 |
| NPLOC4 | NR4A2 | NSD1 | NUAK2 |
| NPM3 | NR4A3 | NSDHL | NUB1 |
| NPPA | NR5A1 | NSF | NUBP1 |
| NPPC | NR5A2 | NSFL1C | NUBP2 |
| NPR1 | NR6A1 | NSL1 | NUBPL |
| NPR3 | NRAS | NSMAF | NUCKS1 |
| NPTX1 | NRBF2 | NSMCE1 | NUDC |
| NPTX2 | NRBP2 | NSMCE2 | NUDCD2 |
| NPVF | NRCAM | NSUN2 | NUDT1 |
| NPW | NRD1 | NSUN3 | NUDT15 |
| NPY | NRF1 | NSUN4 | NUDT16 |
| NPY2R | NRG1 | NSUN5 | NUDT18 |
| NPY5R | NRG3 | NSUN6 | NUDT19 |
| NQO1 | NRGN | NT5C | NUDT21 |
| NQO2 | NRIP1 | NT5C3 | NUDT22 |
| NR0B1 | NRIP3 | NT5DC1 | NUDT4 |
| NR1D1 | NRL | NT5DC3 | NUDT9 |

| | | | |
|---|---|---|---|
| NUFIP2 | NXPH4 | OLFM1 | OR11A1 |
| NUMA1 | NXT1 | OLFM2 | OR12D2 |
| NUMB | NYNRIN | OLFM3 | OR1D2 |
| NUMBL | OAT | OLFML2B | OR1E1 |
| NUP107 | OAZ1 | OLFML3 | OR1E2 |
| NUP133 | OAZ3 | OLIG1 | OR2A2 |
| NUP153 | OBFC1 | OLIG3 | OR2S2 |
| NUP155 | OBFC2A | ONECUT1 | OR2T1 |
| NUP188 | OBFC2B | ONECUT3 | OR2V2 |
| NUP205 | OBSCN | OPCML | OR3A4 |
| NUP210 | OBSL1 | OPHN1 | OR4C11 |
| NUP37 | OC90 | OPLAH | OR4C3 |
| NUP50 | OCA2 | OPN5 | OR4M2 |
| NUP62 | OCEL1 | OPRK1 | OR4X1 |
| NUP85 | OCIAD1 | OPRL1 | OR51A7 |
| NUP93 | OCIAD2 | OPRM1 | OR51B5 |
| NUPL2 | ODC1 | OPTN | OR51E2 |
| NUSAP1 | ODF2L | OR10A4 | OR51F2 |
| NVL | ODF3L1 | OR10A6 | OR51I2 |
| NWD1 | ODZ2 | OR10AD1 | OR52A1 |
| NXF1 | ODZ4 | OR10AG1 | OR52A4 |
| NXN | OGFOD1 | OR10C1 | OR52E8 |
| NXNL1 | OGFR | OR10J1 | OR52K2 |
| NXPH1 | OGFRL1 | OR10K2 | OR52N2 |
| NXPH3 | OLA1 | OR10Q1 | OR5AU1 |

| | | | |
|---|---|---|---|
| OR5D16 | OSBPL5 | OXCT1 | PAF1 |
| OR5D18 | OSBPL8 | OXNAD1 | PAFAH1B1 |
| OR5P2 | OSCP1 | OXSM | PAFAH1B2 |
| OR6B3 | OSGEPL1 | OXTR | PAFAH1B3 |
| OR6C1 | OSGIN1 | P2RX1 | PAFAH2 |
| OR6K2 | OSGIN2 | P2RX2 | PAG1 |
| OR6K6 | OSM | P2RX3 | PAGE2B |
| OR8S1 | OSTalpha | P2RX4 | PAH |
| OR9A4 | OSTBETA | P2RY12 | PAIP1 |
| OR9Q2 | OTOA | P2RY2 | PAIP2B |
| ORAI1 | OTOF | P2RY6 | PAK1 |
| ORAOV1 | OTOP1 | P4HA1 | PAK3 |
| ORC1L | OTOP2 | P4HA2 | PAK6 |
| ORC3L | OTOP3 | P4HTM | PALLD |
| ORC5L | OTOS | PABPC1 | PAM |
| ORMDL1 | OTUB1 | PABPC3 | PAN2 |
| ORMDL2 | OTUD3 | PABPC4L | PANX1 |
| ORMDL3 | OTUD4 | PABPN1 | PAPD5 |
| OS9 | OTUD6B | PACRG | PAPL |
| OSBP | OTUD7A | PACS2 | PAPOLA |
| OSBP2 | OTUD7B | PACSIN1 | PAPOLG |
| OSBPL11 | OTX2 | PACSIN3 | PAPSS1 |
| OSBPL1A | OVCH1 | PADI1 | PAPSS2 |
| OSBPL2 | OVOL1 | PADI4 | PAQR5 |
| OSBPL3 | OVOL2 | PAEP | PAQR9 |

| | | | |
|---|---|---|---|
| PAR5 | PAX5 | PCDH24 | PCGF2 |
| PARD3 | PAX6 | PCDH7 | PCGF3 |
| PARD3B | PAX7 | PCDH8 | PCGF6 |
| PARD6B | PAX8 | PCDH9 | PCID2 |
| PARD6G | PAX9 | PCDHA1 | PCNT |
| PARK2 | PBLD | PCDHA2 | PCNX |
| PARL | PBRM1 | PCDHA6 | PCNXL2 |
| PARM1 | PBX1 | PCDHA7 | PCNXL3 |
| PARN | PBX2 | PCDHB10 | PCOLCE |
| PARP11 | PBXIP1 | PCDHB11 | PCOTH |
| PARP12 | PC | PCDHB12 | PCSK1N |
| PARP14 | PCBD2 | PCDHB13 | PCSK5 |
| PARP16 | PCBP1 | PCDHB14 | PCSK6 |
| PARP9 | PCBP2 | PCDHB15 | PCSK7 |
| PARS2 | PCCA | PCDHB16 | PCSK9 |
| PARVA | PCDH1 | PCDHB4 | PCTP |
| PARVB | PCDH10 | PCDHB6 | PCYOX1 |
| PARVG | PCDH11X | PCDHB7 | PCYT1B |
| PASK | PCDH11Y | PCDHB9 | PCYT2 |
| PATL2 | PCDH12 | PCDHGA1 | PDCD1 |
| PATZ1 | PCDH15 | PCDHGA2 | PDCD10 |
| PAWR | PCDH17 | PCDHGA4 | PDCD11 |
| PAX1 | PCDH19 | PCDHGB1 | PDCD1LG2 |
| PAX2 | PCDH20 | PCDP1 | PDCD2L |
| PAX3 | PCDH21 | PCF11 | PDCD7 |

| | | | |
|---|---|---|---|
| PDDC1 | PDLIM5 | PER2 | PGAM1 |
| PDE10A | PDLIM7 | PER3 | PGAM4 |
| PDE1B | PDP1 | PERP | PGAM5 |
| PDE2A | PDPK1 | PET112L | PGAP2 |
| PDE3A | PDPN | PET117 | PGC |
| PDE4A | PDPR | PEX10 | PGLS |
| PDE4B | PDX1 | PEX11G | PGLYRP1 |
| PDE4C | PDXP | PEX12 | PGM2L1 |
| PDE4DIP | PDZD4 | PEX13 | PGM3 |
| PDE5A | PDZD8 | PEX14 | PGPEP1 |
| PDE6B | PDZK1 | PEX19 | PGR |
| PDE7A | PDZK1IP1 | PEX26 | PGRMC2 |
| PDE9A | PDZRN3 | PEX5L | PGS1 |
| PDGFA | PEBP1 | PEX6 | PHACTR1 |
| PDGFC | PEBP4 | PEX7 | PHACTR2 |
| PDGFD | PECI | PF4 | PHAX |
| PDGFRA | PECR | PFDN1 | PHC3 |
| PDHB | PEF1 | PFDN2 | PHF14 |
| PDHX | PEG10 | PFDN5 | PHF15 |
| PDIA3P | PEG3 | PFKFB1 | PHF16 |
| PDIA5 | PELI2 | PFKFB3 | PHF17 |
| PDIA6 | PELP1 | PFKFB4 | PHF19 |
| PDILT | PENK | PFKL | PHF21A |
| PDK2 | PEPD | PFN2 | PHF3 |
| PDLIM3 | PER1 | PGA4 | PHF6 |

| | | | |
|---|---|---|---|
| PHF8 | PIGU | PIR | PL-5283 |
| PHGR1 | PIGV | PIRT | PLA1A |
| PHIP | PIGX | PISD | PLA2G15 |
| PHKA2 | PIK3AP1 | PISRT1 | PLA2G16 |
| PHLDA1 | PIK3C2B | PITPNA | PLA2G2E |
| PHLDA2 | PIK3C2G | PITPNC1 | PLA2G4D |
| PHLDA3 | PIK3C3 | PITPNM1 | PLA2G5 |
| PHLDB2 | PIK3CA | PITPNM2 | PLA2G6 |
| PHLDB3 | PIK3CD | PITRM1 | PLA2R1 |
| PHLPP1 | PIK3IP1 | PITX2 | PLAC8L1 |
| PHLPP2 | PIK3R2 | PIWIL1 | PLAG1 |
| PHOX2A | PIK3R3 | PIWIL2 | PLAGL1 |
| PHRF1 | PIK3R5 | PIWIL3 | PLAT |
| PHTF2 | PILRB | PJA2 | PLBD1 |
| PHYHIPL | PIM3 | PKD1L1 | PLCB1 |
| PI16 | PIN1 | PKD1L2 | PLCB3 |
| PI4K2B | PIN4 | PKD2 | PLCB4 |
| PI4KB | PINK1 | PKHD1L1 | PLCD1 |
| PID1 | PION | PKIA | PLCG1 |
| PIGG | PIP4K2A | PKMYT1 | PLCG2 |
| PIGM | PIP4K2C | PKNOX2 | PLCH1 |
| PIGN | PIP5K1A | PKP1 | PLCH2 |
| PIGP | PIP5K1C | PKP2 | PLCL1 |
| PIGQ | PIP5KL1 | PKP3 | PLCXD2 |
| PIGT | PIPSL | PKP4 | PLCXD3 |

| | | | |
|---|---|---|---|
| PLD1 | PLK4 | PMS2L1 | POLE2 |
| PLD6 | PLOD2 | PMS2L3 | POLE4 |
| PLEC1 | PLP2 | PMS2L5 | POLG |
| PLEKHA1 | PLRG1 | PMVK | POLL |
| PLEKHA2 | PLS1 | PNKD | POLN |
| PLEKHA4 | PLS3 | PNLDC1 | POLR1A |
| PLEKHA5 | PLSCR1 | PNMA2 | POLR1D |
| PLEKHA6 | PLSCR4 | PNMAL1 | POLR2C |
| PLEKHA7 | PLXDC2 | PNMT | POLR2G |
| PLEKHF1 | PLXNA2 | PNOC | POLR2J4 |
| PLEKHF2 | PLXNA4 | PNP | POLR2K |
| PLEKHG1 | PLXNB1 | PNPLA3 | POLR3C |
| PLEKHG2 | PLXNB3 | PNPLA4 | POLR3D |
| PLEKHG3 | PLXNC1 | PNPLA7 | POLR3E |
| PLEKHG4 | PLXND1 | PODN | POLR3G |
| PLEKHG4B | PMEPA1 | PODNL1 | POLR3GL |
| PLEKHG7 | PMF1 | PODXL2 | POLS |
| PLEKHH1 | PML | POFUT1 | POM121 |
| PLEKHH3 | PMM1 | POFUT2 | POM121C |
| PLEKHJ1 | PMM2 | POGZ | POM121L1P |
| PLEKHM3 | PMP2 | POLA1 | POM121L2 |
| PLEKHO2 | PMP22 | POLA2 | POM121L4P |
| PLIN2 | PMPCA | POLD1 | POMGNT1 |
| PLIN4 | PMPCB | POLDIP3 | POMP |
| PLK1 | PMS1 | POLE | POMT1 |

| | | | |
|---|---|---|---|
| POMT2 | PPARGC1A | PPME1 | PPP2R2C |
| PON2 | PPARGC1B | PPOX | PPP2R2D |
| PON3 | PPBP | PPP1CA | PPP2R5A |
| POP1 | PPCDC | PPP1CB | PPP2R5B |
| POP4 | PPDPF | PPP1R10 | PPP2R5C |
| POPDC3 | PPEF2 | PPP1R11 | PPP2R5E |
| PORCN | PPFIA1 | PPP1R12A | PPP3CA |
| POT1 | PPFIA2 | PPP1R12B | PPP3CB |
| POTEA | PPFIA3 | PPP1R12C | PPP4R2 |
| POTEE | PPFIA4 | PPP1R13B | PPP4R4 |
| POU2F2 | PPHLN1 | PPP1R13L | PPP5C |
| POU2F3 | PPIA | PPP1R15A | PPPDE2 |
| POU3F2 | PPIC | PPP1R15B | PPRC1 |
| POU3F4 | PPID | PPP1R16B | PPT2 |
| POU4F1 | PPIE | PPP1R1C | PPTC7 |
| POU4F3 | PPIG | PPP1R2 | PPWD1 |
| POU5F1 | PPIH | PPP1R3B | PQLC1 |
| POU6F1 | PPIL4 | PPP1R3C | PRAGMIN |
| POU6F2 | PPIL6 | PPP1R3D | PRAMEF4 |
| PP14571 | PPM1A | PPP1R8 | PRB3 |
| PPAN-P2RY11 | PPM1D | PPP1R9A | PRC1 |
| PPAP2A | PPM1H | PPP1R9B | PRCC |
| PPAP2C | PPM1J | PPP2R1B | PRCP |
| PPARD | PPM1K | PPP2R2A | PRDM1 |
| PPARG | PPM1L | PPP2R2B | PRDM10 |

| | | | |
|---|---|---|---|
| PRDM11 | PRIM1 | PRM2 | PRR16 |
| PRDM12 | PRIM2 | PRMT1 | PRR18 |
| PRDM13 | PRKAB1 | PRMT10 | PRR22 |
| PRDM14 | PRKACA | PRMT2 | PRR23A |
| PRDM15 | PRKACB | PRMT6 | PRR24 |
| PRDM16 | PRKAG1 | PRMT7 | PRR3 |
| PRDM2 | PRKAG2 | PRMT8 | PRR5 |
| PRDM6 | PRKAR1A | PRO0628 | PRR5L |
| PRDM8 | PRKAR1B | PROCA1 | PRR7 |
| PRDX1 | PRKAR2B | PRODH | PRRC1 |
| PRDX3 | PRKCA | PROK2 | PRRG3 |
| PRDX4 | PRKCB | PROM1 | PRRG4 |
| PRDX5 | PRKCE | PROX2 | PRRT1 |
| PRDX6 | PRKCH | PRPF3 | PRRT2 |
| PRELID1 | PRKCI | PRPF38A | PRRT3 |
| PRELID2 | PRKCQ | PRPF40B | PRRT4 |
| PREP | PRKCZ | PRPF6 | PRSS12 |
| PREPL | PRKD2 | PRPF8 | PRSS16 |
| PREX1 | PRKDC | PRPS1 | PRSS22 |
| PREX2 | PRKG1 | PRPS1L1 | PRSS27 |
| PRG2 | PRKRA | PRPS2 | PRSSL1 |
| PRG4 | PRKX | PRPSAP1 | PRTFDC1 |
| PRIC285 | PRLHR | PRR12 | PRTN3 |
| PRICKLE1 | PRLR | PRR15 | PRX |
| PRICKLE2 | PRM1 | PRR15L | PSAT1 |

| | | | |
|---|---|---|---|
| PSD2 | PSME4 | PTGFR | PTPRC |
| PSD3 | PSMG1 | PTGFRN | PTPRCAP |
| PSG6 | PSMG2 | PTGR1 | PTPRD |
| PSKH2 | PSMG3 | PTGS2 | PTPRE |
| PSMA1 | PSORS1C1 | PTH1R | PTPRF |
| PSMA2 | PSPH | PTK2 | PTPRG |
| PSMA7 | PSRC1 | PTK2B | PTPRH |
| PSMB1 | PSTK | PTK6 | PTPRJ |
| PSMB10 | PSTPIP1 | PTK7 | PTPRK |
| PSMB11 | PTBP1 | PTMS | PTPRM |
| PSMB3 | PTBP2 | PTN | PTPRN |
| PSMB8 | PTCD1 | PTOV1 | PTPRN2 |
| PSMB9 | PTCD2 | PTP4A2 | PTPRO |
| PSMC1 | PTCH1 | PTPDC1 | PTPRQ |
| PSMC3 | PTCH2 | PTPLAD1 | PTPRS |
| PSMC3IP | PTCHD2 | PTPLAD2 | PTPRZ1 |
| PSMC4 | PTDSS1 | PTPMT1 | PTRH1 |
| PSMD1 | PTDSS2 | PTPN12 | PTS |
| PSMD11 | PTEN | PTPN14 | PTTG2 |
| PSMD12 | PTF1A | PTPN2 | PUF60 |
| PSMD4 | PTGDR | PTPN23 | PUM1 |
| PSMD5 | PTGER1 | PTPN4 | PUM2 |
| PSMD6 | PTGER2 | PTPN5 | PURG |
| PSMD7 | PTGER3 | PTPN6 | PUS1 |
| PSME3 | PTGES3 | PTPRA | PUS7 |

| | | | |
|---|---|---|---|
| PUS7L | QTRT1 | RAB40B | RAG1AP1 |
| PVALB | R3HDM1 | RAB5B | RAG2 |
| PVR | R3HDM2 | RAB5C | RAGE |
| PVRL3 | RAB11B | RAB6B | RAI14 |
| PVRL4 | RAB11FIP1 | RAB7A | RAI2 |
| PWWP2B | RAB11FIP3 | RAB7L1 | RALA |
| PXK | RAB11FIP4 | RAB8A | RALBP1 |
| PXMP3 | RAB11FIP5 | RAB8B | RALGAPA1 |
| PXN | RAB18 | RAB9B | RALGAPA2 |
| PXT1 | RAB1A | RABAC1 | RALGAPB |
| PYCARD | RAB1B | RABGAP1 | RALGDS |
| PYCR2 | RAB20 | RABGAP1L | RALGPS2 |
| PYCRL | RAB21 | RABGGTA | RALYL |
| PYGB | RAB27A | RABL4 | RAMP1 |
| PYGM | RAB27B | RAC2 | RAMP3 |
| PYY | RAB28 | RAD21L1 | RAN |
| PZP | RAB2B | RAD23A | RANBP17 |
| QARS | RAB30 | RAD51L1 | RANBP3 |
| QDPR | RAB34 | RADIL | RANBP3L |
| QKI | RAB35 | RAE1 | RANGAP1 |
| QPCT | RAB37 | RAET1E | RANGRF |
| QPRT | RAB39 | RAET1G | RAP1A |
| QRFPR | RAB3C | RAET1L | RAP1B |
| QRICH1 | RAB3GAP1 | RAF1 | RAP1GAP |
| QSER1 | RAB3GAP2 | RAG1 | RAP1GAP2 |

| | | | |
|---|---|---|---|
| RAP1GDS1 | RASSF10 | RBM42 | RCBTB2 |
| RAPGEF1 | RASSF3 | RBM43 | RCC2 |
| RAPGEF2 | RASSF4 | RBM44 | RCCD1 |
| RAPGEF3 | RASSF5 | RBM46 | RCL1 |
| RAPGEF4 | RASSF8 | RBM47 | RCOR1 |
| RAPGEF5 | RASSF9 | RBM4B | RCOR2 |
| RAPGEF6 | RAVER1 | RBM5 | RCSD1 |
| RARA | RB1 | RBM6 | RCVRN |
| RARG | RBBP4 | RBM8A | RDBP |
| RASA1 | RBBP7 | RBMS1 | RDH12 |
| RASA3 | RBBP9 | RBMS2 | RDH13 |
| RASAL1 | RBL1 | RBMS3 | RDH14 |
| RASAL2 | RBM12B | RBMXL2 | RDM1 |
| RASEF | RBM15 | RBP1 | RDX |
| RASGEF1B | RBM15B | RBP4 | REC8 |
| RASGEF1C | RBM19 | RBP7 | RECQL |
| RASGRF1 | RBM20 | RBPJ | RECQL4 |
| RASGRF2 | RBM23 | RBPJL | REEP1 |
| RASGRP1 | RBM24 | RBPMS | REEP2 |
| RASGRP2 | RBM25 | RBPMS2 | REG1B |
| RASGRP3 | RBM28 | RC3H2 | REG4 |
| RASGRP4 | RBM33 | RCAN1 | RELA |
| RASIP1 | RBM34 | RCAN2 | RELB |
| RASL11B | RBM39 | RCAN3 | RELL1 |
| RASSF1 | RBM4 | RCBTB1 | RELN |

| | | | |
|---|---|---|---|
| RELT | RG9MTD1 | RHCE | RIOK3 |
| REM1 | RG9MTD2 | RHOA | RIPK2 |
| REP15 | RGL2 | RHOBTB1 | RIPK3 |
| REPS2 | RGMA | RHOBTB2 | RIPPLY2 |
| RER1 | RGMB | RHOBTB3 | RIT2 |
| RERE | RGNEF | RHOG | RLF |
| RESP18 | RGS10 | RHOJ | RMND1 |
| RET | RGS11 | RHOT1 | RMND5A |
| RETN | RGS12 | RHOU | RMND5B |
| RETSAT | RGS13 | RHPN1 | RNASE3 |
| REXO1 | RGS14 | RHPN2 | RNASE9 |
| RFC1 | RGS17 | RICH2 | RNASEH2B |
| RFC2 | RGS20 | RICTOR | RNASET2 |
| RFFL | RGS22 | RIF1 | RND1 |
| RFK | RGS3 | RILP | RND2 |
| RFPL1S | RGS4 | RILPL2 | RND3 |
| RFTN1 | RGS5 | RIMBP2 | RNF103 |
| RFTN2 | RGS6 | RIMKLA | RNF114 |
| RFWD2 | RGS8 | RIMKLB | RNF126 |
| RFWD3 | RGS9 | RIMS1 | RNF13 |
| RFX1 | RHAG | RIMS2 | RNF130 |
| RFX3 | RHBDD1 | RIN1 | RNF138 |
| RFX4 | RHBDL1 | RIN2 | RNF141 |
| RFX5 | RHBDL2 | RING1 | RNF144A |
| RFX7 | RHBDL3 | RINL | RNF144B |

| | | | |
|---|---|---|---|
| RNF146 | RNF38 | RPGRIP1L | RPL34 |
| RNF149 | RNF39 | RPH3A | RPL36A |
| RNF150 | RNF40 | RPIA | RPL36AL |
| RNF151 | RNF44 | RPL10 | RPL4 |
| RNF152 | RNF6 | RPL11 | RPL7L1 |
| RNF160 | RNF8 | RPL13AP20 | RPL8 |
| RNF168 | RNFT2 | RPL13AP5 | RPLP2 |
| RNF169 | RNH1 | RPL14 | RPP21 |
| RNF17 | RNMTL1 | RPL18 | RPP30 |
| RNF170 | RNPS1 | RPL21 | RPP40 |
| RNF181 | RNU5E | RPL22 | RPRD1A |
| RNF182 | ROBLD3 | RPL22L1 | RPRD1B |
| RNF185 | ROBO1 | RPL23 | RPRD2 |
| RNF187 | ROGDI | RPL23A | RPRM |
| RNF19B | ROM1 | RPL23AP7 | RPRML |
| RNF2 | ROR1 | RPL24 | RPS10 |
| RNF207 | ROR2 | RPL26 | RPS14 |
| RNF212 | RORA | RPL26L1 | RPS16 |
| RNF213 | RP9 | RPL27 | RPS18 |
| RNF214 | RPA1 | RPL27A | RPS21 |
| RNF215 | RPAIN | RPL28 | RPS23 |
| RNF216 | RPAP1 | RPL29 | RPS24 |
| RNF220 | RPE | RPL30 | RPS27A |
| RNF25 | RPGR | RPL31 | RPS27L |
| RNF34 | RPGRIP1 | RPL32P3 | RPS3 |

| | | | |
|---|---|---|---|
| RPS4X | RSBN1L | RUSC1 | SACS |
| RPS5 | RSC1A1 | RUVBL1 | SAFB |
| RPS6KA1 | RSF1 | RWDD2A | SAFB2 |
| RPS6KA2 | RSPH1 | RWDD3 | SAG |
| RPS6KA4 | RSPO2 | RWDD4A | SALL1 |
| RPS6KA6 | RSPO3 | RXRA | SALL2 |
| RPS6KL1 | RSPRY1 | RYK | SALL3 |
| RPS9 | RSRC1 | RYR1 | SALL4 |
| RPSA | RTCD1 | RYR2 | SAMD11 |
| RPSAP58 | RTDR1 | RYR3 | SAMD12 |
| RPSAP9 | RTEL1 | S100A10 | SAMD13 |
| RPTOR | RTL1 | S100A13 | SAMD4A |
| RPUSD2 | RTN2 | S100A7 | SAMD5 |
| RQCD1 | RTN4 | S100A7A | SAMD7 |
| RRAGA | RTP1 | S100A9 | SAMD8 |
| RRAGC | RUFY1 | S1PR1 | SAMHD1 |
| RRAS2 | RUFY2 | S1PR4 | SAP130 |
| RRBP1 | RUFY3 | S1PR5 | SAP18 |
| RREB1 | RUNDC2A | SAA1 | SAP30BP |
| RRN3 | RUNDC3A | SAA2 | SAR1A |
| RRN3P2 | RUNDC3B | SAA3P | SARDH |
| RRP1B | RUNX1 | SAA4 | SART3 |
| RS1 | RUNX1T1 | SAAL1 | SASH1 |
| RSAD2 | RUNX2 | SAC3D1 | SATB1 |
| RSBN1 | RUNX3 | SACM1L | SATB2 |

| | | | |
|---|---|---|---|
| SAV1 | SCGB1D1 | SCYL1 | SEC24C |
| SBDS | SCGB1D2 | SCYL2 | SEC24D |
| SBF1 | SCGB2A1 | SCYL3 | SEC31A |
| SBF2 | SCGB3A1 | SDC1 | SEC61A2 |
| SBK1 | SCGN | SDC2 | SEC61G |
| SBK2 | SCHIP1 | SDC4 | SECISBP2L |
| SBNO1 | SCIN | SDCCAG10 | SEH1L |
| SC4MOL | SCMH1 | SDCCAG8 | SEL1L |
| SC5DL | SCML2 | SDF2 | SEL1L3 |
| SCAMP1 | SCML4 | SDF4 | SELENBP1 |
| SCAMP3 | SCN1B | SDHA | SELI |
| SCAND3 | SCN3A | SDHAP1 | SELK |
| SCARA3 | SCN3B | SDHB | SELT |
| SCARA5 | SCN4A | SDK1 | SELV |
| SCARB1 | SCN4B | SDK2 | SEMA3A |
| SCARB2 | SCN5A | SDR16C5 | SEMA3B |
| SCARF1 | SCN8A | SEC1 | SEMA3C |
| SCARF2 | SCOC | SEC11C | SEMA4B |
| SCARNA10 | SCP2 | SEC14L1 | SEMA4C |
| SCCPDH | SCRIB | SEC14L2 | SEMA4D |
| SCD | SCRN1 | SEC14L4 | SEMA4F |
| SCD5 | SCRT2 | SEC14L5 | SEMA5A |
| SCFD2 | SCT | SEC16A | SEMA5B |
| SCG3 | SCUBE1 | SEC22B | SEMA6A |
| SCG5 | SCUBE2 | SEC22C | SEMA6C |

| | | | |
|---|---|---|---|
| SEMA7A | SETD1B | SFRS5 | SH2D3A |
| SENP2 | SETD3 | SFRS6 | SH2D4A |
| SENP3 | SETD5 | SFT2D1 | SH2D4B |
| SENP8 | SETD8 | SFT2D2 | SH3BGR |
| SEPHS1 | SETDB2 | SFT2D3 | SH3BGRL3 |
| SERAC1 | SETMAR | SFTA1P | SH3BP2 |
| SERBP1 | SEZ6 | SFTA3 | SH3BP4 |
| SERF2 | SF1 | SFTPC | SH3BP5 |
| SERGEF | SF3A2 | SFXN2 | SH3BP5L |
| SERINC1 | SF3B5 | SFXN3 | SH3GL1 |
| SERINC3 | SF4 | SFXN5 | SH3GL3 |
| SERINC4 | SFI1 | SGCE | SH3GLB1 |
| SERINC5 | SFMBT2 | SGCG | SH3PXD2A |
| SERPINB8 | SFPQ | SGEF | SH3PXD2B |
| SERPINB9 | SFRP1 | SGIP1 | SH3RF1 |
| SERPINE2 | SFRP2 | SGK1 | SH3RF2 |
| SERPINE3 | SFRP4 | SGK3 | SH3RF3 |
| SERPINF2 | SFRP5 | SGMS1 | SH3TC1 |
| SERTAD1 | SFRS1 | SGOL1 | SH3YL1 |
| SERTAD2 | SFRS11 | SGPP2 | SHANK1 |
| SESN1 | SFRS13A | SGSM1 | SHANK2 |
| SESN3 | SFRS13B | SGSM2 | SHANK3 |
| SET | SFRS18 | SGSM3 | SHC4 |
| SETBP1 | SFRS2IP | SGTA | SHCBP1 |
| SETD1A | SFRS4 | SH2B3 | SHF |

| | | | |
|---|---|---|---|
| SHH | SIRT5 | SLC13A2 | SLC22A18AS |
| SHISA3 | SIRT6 | SLC15A2 | SLC22A20 |
| SHISA5 | SIVA1 | SLC16A10 | SLC22A25 |
| SHISA6 | SIX1 | SLC16A11 | SLC22A4 |
| SHISA7 | SIX2 | SLC16A13 | SLC22A5 |
| SHOC2 | SIX3 | SLC16A14 | SLC22A7 |
| SHOX2 | SIX4 | SLC16A2 | SLC23A1 |
| SHQ1 | SKA2 | SLC16A3 | SLC23A2 |
| SHROOM1 | SKAP1 | SLC16A7 | SLC24A1 |
| SHROOM2 | SKI | SLC17A1 | SLC24A4 |
| SHROOM3 | SKIL | SLC17A2 | SLC24A6 |
| SIAH1 | SKP1 | SLC17A4 | SLC25A10 |
| SIAH2 | SKP2 | SLC17A5 | SLC25A21 |
| SIGLEC15 | SLAIN1 | SLC17A7 | SLC25A23 |
| SIGLEC6 | SLAMF8 | SLC19A1 | SLC25A27 |
| SIK2 | SLBP | SLC19A3 | SLC25A33 |
| SIK3 | SLC10A2 | SLC1A1 | SLC25A34 |
| SIL1 | SLC10A3 | SLC1A3 | SLC25A35 |
| SIM1 | SLC10A7 | SLC1A5 | SLC25A36 |
| SIM2 | SLC11A1 | SLC1A6 | SLC25A40 |
| SIN3A | SLC11A2 | SLC1A7 | SLC25A42 |
| SIPA1 | SLC12A3 | SLC20A2 | SLC25A44 |
| SIPA1L3 | SLC12A5 | SLC22A11 | SLC25A45 |
| SIRPG | SLC12A6 | SLC22A15 | SLC25A46 |
| SIRT1 | SLC12A7 | SLC22A18 | SLC26A10 |

| | | | |
|---|---|---|---|
| SLC26A11 | SLC32A1 | SLC39A10 | SLC48A1 |
| SLC26A4 | SLC34A1 | SLC39A11 | SLC4A11 |
| SLC26A5 | SLC34A3 | SLC39A12 | SLC4A4 |
| SLC26A7 | SLC35A3 | SLC39A13 | SLC4A5 |
| SLC27A1 | SLC35A5 | SLC39A14 | SLC5A10 |
| SLC27A2 | SLC35B2 | SLC39A3 | SLC5A12 |
| SLC27A3 | SLC35B3 | SLC39A7 | SLC5A5 |
| SLC27A4 | SLC35B4 | SLC39A8 | SLC5A6 |
| SLC29A2 | SLC35D3 | SLC3A2 | SLC6A1 |
| SLC29A3 | SLC35E3 | SLC41A2 | SLC6A12 |
| SLC29A4 | SLC35F1 | SLC41A3 | SLC6A15 |
| SLC2A1 | SLC35F4 | SLC43A1 | SLC6A18 |
| SLC2A11 | SLC35F5 | SLC43A2 | SLC6A19 |
| SLC2A12 | SLC36A2 | SLC43A3 | SLC6A2 |
| SLC2A13 | SLC36A3 | SLC44A1 | SLC6A3 |
| SLC2A14 | SLC36A4 | SLC44A2 | SLC6A5 |
| SLC2A2 | SLC37A1 | SLC44A4 | SLC6A6 |
| SLC2A5 | SLC37A2 | SLC44A5 | SLC6A7 |
| SLC2A6 | SLC37A3 | SLC45A2 | SLC6A8 |
| SLC2A7 | SLC38A1 | SLC45A3 | SLC6A9 |
| SLC2A9 | SLC38A10 | SLC45A4 | SLC7A1 |
| SLC30A1 | SLC38A4 | SLC46A1 | SLC7A14 |
| SLC30A2 | SLC38A7 | SLC46A2 | SLC7A3 |
| SLC30A7 | SLC38A8 | SLC46A3 | SLC7A4 |
| SLC30A9 | SLC38A9 | SLC47A1 | SLC7A5 |

| 1389 | | 1390 | |
|---|---|---|---|
| SLC7A9 | SLITRK4 | SMG5 | SNED1 |
| SLC8A1 | SLITRK5 | SMG6 | SNHG3-RCC1 |
| SLC8A2 | SLMAP | SMN1 | SNHG8 |
| SLC8A3 | SLMO1 | SMN2 | SNHG9 |
| SLC9A10 | SLMO2 | SMNDC1 | SNIP1 |
| SLC9A2 | SLTM | SMO | SNORA15 |
| SLC9A3 | SMAD3 | SMOC1 | SNORA19 |
| SLC9A3R1 | SMAD4 | SMOC2 | SNORA22 |
| SLC9A3R2 | SMAD6 | SMPD3 | SNORA27 |
| SLC9A4 | SMAD7 | SMPD4 | SNORA31 |
| SLC9A9 | SMAD9 | SMTN | SNORA39 |
| SLCO2A1 | SMAGP | SMTNL1 | SNORA4 |
| SLCO3A1 | SMAP1 | SMTNL2 | SNORA57 |
| SLCO4A1 | SMAP2 | SMURF1 | SNORA59A |
| SLCO4C1 | SMARCA1 | SMYD3 | SNORA76 |
| SLCO5A1 | SMARCA2 | SNAI1 | SNORA8 |
| SLFN11 | SMARCA4 | SNAP25 | SNORA80 |
| SLFN12L | SMARCAL1 | SNAPC1 | SNORD114-29 |
| SLFN13 | SMARCD1 | SNAPC2 | SNORD114-30 |
| SLFN5 | SMARCD3 | SNAPC3 | SNORD114-4 |
| SLFNL1 | SMC4 | SNAPC5 | SNORD115-13 |
| SLIT3 | SMC5 | SNCA | SNORD115-15 |
| SLITRK1 | SMCR7L | SNCAIP | SNORD115-38 |
| SLITRK2 | SMEK1 | SNCB | SNORD115-40 |
| SLITRK3 | SMEK2 | SND1 | SNORD115-48 |

| | | | |
|---|---|---|---|
| SNORD115-7 | SNRPD1 | SNX33 | SOX1 |
| SNORD116-5 | SNRPF | SNX4 | SOX11 |
| SNORD18C | SNRPN | SNX5 | SOX12 |
| SNORD1A | SNTA1 | SNX6 | SOX14 |
| SNORD2 | SNTB1 | SNX8 | SOX15 |
| SNORD22 | SNTB2 | SNX9 | SOX17 |
| SNORD27 | SNTG1 | SOAT2 | SOX18 |
| SNORD30 | SNTG2 | SOCS1 | SOX21 |
| SNORD32B | SNW1 | SOCS2 | SOX2OT |
| SNORD43 | SNX1 | SOCS3 | SOX9 |
| SNORD45C | SNX10 | SOCS6 | SP1 |
| SNORD50B | SNX11 | SOD1 | SP2 |
| SNORD53 | SNX13 | SOD3 | SP4 |
| SNORD55 | SNX14 | SOHLH1 | SP5 |
| SNORD7 | SNX15 | SOLH | SP6 |
| SNORD71 | SNX16 | SON | SP7 |
| SNORD76 | SNX18 | SORBS1 | SPAG1 |
| SNORD89 | SNX19 | SORBS2 | SPAG16 |
| SNORD95 | SNX2 | SORBS3 | SPAG17 |
| SNRNP200 | SNX22 | SORCS2 | SPAG6 |
| SNRNP25 | SNX24 | SORCS3 | SPANXN5 |
| SNRNP27 | SNX25 | SORL1 | SPARCL1 |
| SNRNP48 | SNX29 | SORT1 | SPAST |
| SNRNP70 | SNX31 | SOS2 | SPATA13 |
| SNRPC | SNX32 | SOSTDC1 | SPATA17 |

| | | | |
|---|---|---|---|
| SPATA18 | SPINK5L2 | SPTBN4 | SRY |
| SPATA2 | SPINK7 | SPTY2D1 | SS18L1 |
| SPATA2L | SPINK8 | SQSTM1 | SSB |
| SPATA3 | SPINT1 | SR140 | SSBP3 |
| SPATA4 | SPINT2 | SRA1 | SSBP4 |
| SPATA6 | SPIRE1 | SRBD1 | SSC5D |
| SPATA7 | SPN | SRCAP | SSFA2 |
| SPATA9 | SPNS1 | SRCRB4D | SSH1 |
| SPATS2 | SPNS2 | SRD5A1 | SSH2 |
| SPATS2L | SPNS3 | SRD5A3 | SSH3 |
| SPC24 | SPO11 | SREBF2 | SSPN |
| SPCS2 | SPOCK1 | SRFBP1 | SSR3 |
| SPDEF | SPOCK2 | SRGAP1 | SSTR1 |
| SPEF1 | SPON1 | SRM | SSU72 |
| SPEG | SPOPL | SRP14 | SSX4B |
| SPEM1 | SPR | SRP19 | ST14 |
| SPEN | SPRED2 | SRP68 | ST20 |
| SPG20 | SPRR2C | SRPK1 | ST3GAL1 |
| SPG21 | SPRY1 | SRPK2 | ST3GAL3 |
| SPG7 | SPRY2 | SRPRB | ST3GAL4 |
| SPHAR | SPRYD4 | SRRM2 | ST3GAL6 |
| SPHKAP | SPRYD5 | SRRM3 | ST5 |
| SPIB | SPSB1 | SRRM4 | ST6GAL1 |
| SPIN2B | SPSB3 | SRRT | ST6GAL2 |
| SPIN3 | SPTBN1 | SRXN1 | ST6GALNAC3 |

| | | | |
|---|---|---|---|
| ST6GALNAC4 | STBD1 | STT3A | SUMF2 |
| ST6GALNAC5 | STC2 | STT3B | SUOX |
| ST7 | STEAP2 | STX11 | SUPT6H |
| ST7OT2 | STK10 | STX12 | SUPV3L1 |
| ST7OT4 | STK11 | STX16 | SURF6 |
| ST8SIA2 | STK11IP | STX17 | SUSD1 |
| ST8SIA4 | STK17A | STX18 | SUSD5 |
| ST8SIA6 | STK19 | STX1A | SUV39H1 |
| STAB1 | STK24 | STX2 | SUV39H2 |
| STAC | STK3 | STX3 | SUV420H1 |
| STAC2 | STK32A | STX4 | SUV420H2 |
| STAC3 | STK32B | STX7 | SV2A |
| STAG3L2 | STK32C | STXBP1 | SV2B |
| STAM | STK36 | STYK1 | SV2C |
| STAP2 | STK38 | STYXL1 | SVIL |
| STAR | STK39 | SUB1 | SVIP |
| STARD10 | STL | SUCLG1 | SVOPL |
| STARD13 | STMN1 | SUDS3 | SWAP70 |
| STARD3NL | STMN2 | SUGT1P1 | SYAP1 |
| STARD4 | STOML1 | SULF2 | SYCE1L |
| STARD5 | STOML3 | SULT1A2 | SYCN |
| STARD8 | STRA6 | SULT1C2 | SYCP1 |
| STARD9 | STRA8 | SULT2B1 | SYDE2 |
| STAT6 | STRC | SULT6B1 | SYK |
| STAU2 | STRN | SUMF1 | SYN2 |

| | | | |
|---|---|---|---|
| SYN3 | SYT3 | TAF2 | TAS1R2 |
| SYNC | SYT5 | TAF3 | TAS1R3 |
| SYNCRIP | SYT7 | TAF4 | TAS2R10 |
| SYNE1 | SYT8 | TAF4B | TAS2R19 |
| SYNE2 | SYT9 | TAF5 | TAS2R38 |
| SYNGAP1 | SYTL1 | TAF7 | TATDN1 |
| SYNGR1 | SYTL2 | TAF7L | TATDN2 |
| SYNGR2 | SYTL3 | TAF9 | TATDN3 |
| SYNJ2 | SYTL4 | TAF9B | TAX1BP1 |
| SYNM | SYVN1 | TAGAP | TAZ |
| SYNPO | T | TAGLN2 | TBC1D1 |
| SYNPO2 | TAAR6 | TAL1 | TBC1D10A |
| SYNPO2L | TAAR9 | TANC1 | TBC1D10C |
| SYNPR | TAC4 | TANK | TBC1D14 |
| SYNRG | TACC1 | TAOK2 | TBC1D15 |
| SYPL1 | TACC2 | TAOK3 | TBC1D16 |
| SYS1 | TACO1 | TAP1 | TBC1D17 |
| SYT1 | TACR1 | TAP2 | TBC1D20 |
| SYT10 | TACR2 | TAPBP | TBC1D22A |
| SYT11 | TACR3 | TAPBPL | TBC1D22B |
| SYT12 | TADA1 | TARBP1 | TBC1D23 |
| SYT13 | TADA2A | TARBP2 | TBC1D24 |
| SYT16 | TADA2B | TARS | TBC1D26 |
| SYT17 | TAF1 | TARSL2 | TBC1D2B |
| SYT2 | TAF12 | TAS1R1 | TBC1D4 |

| | | | |
|---|---|---|---|
| TBC1D5 | TBXAS1 | TCTA | TERT |
| TBC1D7 | TCAP | TCTN2 | TES |
| TBC1D8 | TCEA1 | TDG | TESC |
| TBCC | TCEA2 | TDGF3 | TET1 |
| TBCCD1 | TCEA3 | TDO2 | TET2 |
| TBCD | TCEANC | TDP1 | TEX11 |
| TBCE | TCEB2 | TDRD10 | TEX12 |
| TBCEL | TCERG1 | TDRD3 | TEX14 |
| TBK1 | TCERG1L | TDRD9 | TEX19 |
| TBKBP1 | TCF12 | TDRKH | TEX264 |
| TBL1X | TCF20 | TEAD1 | TF |
| TBL1XR1 | TCF21 | TEAD3 | TFAM |
| TBP | TCF23 | TEC | TFAP2A |
| TBPL1 | TCF25 | TECPR1 | TFAP2B |
| TBR1 | TCF4 | TECPR2 | TFAP2C |
| TBRG1 | TCF7 | TECRL | TFAP2E |
| TBRG4 | TCF7L1 | TECTA | TFAP4 |
| TBX1 | TCF7L2 | TEKT3 | TFB1M |
| TBX15 | TCFL5 | TEKT4 | TFDP1 |
| TBX2 | TCHP | TELO2 | TFDP3 |
| TBX20 | TCIRG1 | TENC1 | TFE3 |
| TBX21 | TCP1 | TEPP | TFEB |
| TBX4 | TCP10L2 | TERF1 | TFEC |
| TBX5 | TCP11L1 | TERF2 | TFIP11 |
| TBXA2R | TCP11L2 | TERF2IP | TFR2 |

| | | | |
|---|---|---|---|
| TFRC | THRB | TK1 | TMC1 |
| TG | THRSP | TKTL2 | TMC6 |
| TGFA | THSD1 | TLCD1 | TMC7 |
| TGFBI | THSD4 | TLE3 | TMC8 |
| TGFBR2 | THSD7B | TLE4 | TMCC3 |
| TGFBR3 | THUMPD1 | TLK1 | TMCO1 |
| TGIF1 | THUMPD2 | TLL1 | TMCO3 |
| TGIF2 | THUMPD3 | TLL2 | TMCO6 |
| TGM2 | THY1 | TLN2 | TMCO7 |
| TGOLN2 | TIA1 | TLR1 | TMED1 |
| TH1L | TIAL1 | TLR5 | TMED10 |
| THADA | TIAM1 | TLR9 | TMED2 |
| THAP3 | TIE1 | TLX1 | TMED4 |
| THAP4 | TIGD1 | TLX1NB | TMED5 |
| THAP5 | TIMELESS | TLX3 | TMED6 |
| THBS2 | TIMM13 | TM2D1 | TMEFF1 |
| THBS4 | TIMM22 | TM4SF18 | TMEFF2 |
| THEM4 | TIMM8B | TM4SF19 | TMEM100 |
| THNSL1 | TIMM9 | TM4SF5 | TMEM101 |
| THNSL2 | TIPARP | TM6SF1 | TMEM102 |
| THOC1 | TIPIN | TM6SF2 | TMEM106A |
| THOC5 | TIPRL | TM7SF2 | TMEM107 |
| THOC7 | TIRAP | TM9SF1 | TMEM108 |
| THOP1 | TJAP1 | TMBIM1 | TMEM109 |
| THRA | TJP2 | TMBIM4 | TMEM11 |

| | | | |
|---|---|---|---|
| TMEM110 | TMEM155 | TMEM2 | TMEM52 |
| TMEM111 | TMEM156 | TMEM20 | TMEM53 |
| TMEM114 | TMEM158 | TMEM201 | TMEM54 |
| TMEM119 | TMEM159 | TMEM208 | TMEM56 |
| TMEM123 | TMEM161B | TMEM211 | TMEM61 |
| TMEM125 | TMEM163 | TMEM214 | TMEM62 |
| TMEM126B | TMEM164 | TMEM216 | TMEM63C |
| TMEM129 | TMEM165 | TMEM217 | TMEM64 |
| TMEM131 | TMEM167B | TMEM223 | TMEM66 |
| TMEM132A | TMEM168 | TMEM229A | TMEM67 |
| TMEM132C | TMEM171 | TMEM229B | TMEM68 |
| TMEM132D | TMEM173 | TMEM233 | TMEM71 |
| TMEM132E | TMEM175 | TMEM26 | TMEM72 |
| TMEM135 | TMEM177 | TMEM27 | TMEM81 |
| TMEM138 | TMEM18 | TMEM30B | TMEM82 |
| TMEM141 | TMEM180 | TMEM30C | TMEM85 |
| TMEM143 | TMEM181 | TMEM33 | TMEM87B |
| TMEM144 | TMEM182 | TMEM37 | TMEM8A |
| TMEM145 | TMEM184A | TMEM39B | TMEM8B |
| TMEM147 | TMEM184B | TMEM40 | TMEM8C |
| TMEM14C | TMEM185A | TMEM41B | TMEM90A |
| TMEM150A | TMEM188 | TMEM42 | TMEM90B |
| TMEM150C | TMEM19 | TMEM43 | TMEM93 |
| TMEM151A | TMEM192 | TMEM44 | TMEM95 |
| TMEM154 | TMEM196 | TMEM49 | TMEM97 |

| | | | |
|---|---|---|---|
| TMEM98 | TNFRSF19 | TNXB | TP53TG1 |
| TMEM9B | TNFRSF6B | TOB2 | TP63 |
| TMIGD2 | TNFRSF8 | TOLLIP | TP73 |
| TMOD1 | TNFSF10 | TOM1 | TPCN2 |
| TMOD3 | TNFSF11 | TOM1L2 | TPD52 |
| TMPRSS13 | TNFSF18 | TOMM20 | TPD52L1 |
| TMPRSS2 | TNFSF8 | TOMM34 | TPD52L2 |
| TMPRSS3 | TNFSF9 | TOMM6 | TPK1 |
| TMPRSS4 | TNIK | TOMM7 | TPM3 |
| TMPRSS6 | TNIP2 | TOP1MT | TPM4 |
| TMPRSS7 | TNK2 | TOP1P2 | TPO |
| TMSB10 | TNKS | TOP3B | TPP1 |
| TMSB15B | TNKS1BP1 | TOPORS | TPPP |
| TMSL3 | TNN | TOR1A | TPRKB |
| TMTC2 | TNNC2 | TOR3A | TPSD1 |
| TMTC4 | TNNI3 | TOX | TPSG1 |
| TMUB1 | TNNT2 | TOX2 | TPST1 |
| TNC | TNPO2 | TOX3 | TPST2 |
| TNF | TNR | TP53 | TPTE |
| TNFAIP8 | TNRC18 | TP53BP2 | TRA2B |
| TNFAIP8L2 | TNRC6A | TP53I11 | TRABD |
| TNFAIP8L3 | TNRC6C | TP53I3 | TRADD |
| TNFRSF11A | TNS1 | TP53INP1 | TRAF2 |
| TNFRSF13B | TNS3 | TP53INP2 | TRAF3 |
| TNFRSF18 | TNS4 | TP53RK | TRAF3IP1 |

| | | | |
|---|---|---|---|
| TRAF3IP2 | TRIM15 | TRIM9 | TRPM8 |
| TRAF5 | TRIM16 | TRIO | TRPS1 |
| TRAF7 | TRIM17 | TRIOBP | TRPV3 |
| TRAM1 | TRIM2 | TRIP11 | TRPV5 |
| TRAM2 | TRIM24 | TRIP13 | TRPV6 |
| TRANK1 | TRIM26 | TRIP6 | TRRAP |
| TRAP1 | TRIM27 | TRIT1 | TRUB1 |
| TRAPPC1 | TRIM29 | TRMT1 | TRYX3 |
| TRAPPC2L | TRIM3 | TRMT12 | TSC2 |
| TRAPPC3 | TRIM31 | TRMT2A | TSC22D3 |
| TRAPPC4 | TRIM36 | TRMT2B | TSC22D4 |
| TRAPPC6B | TRIM39 | TRMT5 | TSEN34 |
| TRAPPC9 | TRIM4 | TRNAU1AP | TSFM |
| TRDMT1 | TRIM40 | TRNT1 | TSG1 |
| TRDN | TRIM41 | TROVE2 | TSGA10IP |
| TREML3 | TRIM54 | TRPC1 | TSGA13 |
| TREX1 | TRIM56 | TRPC2 | TSKS |
| TREX2 | TRIM60 | TRPC3 | TSKU |
| TRHR | TRIM61 | TRPC4 | TSLP |
| TRIAP1 | TRIM65 | TRPC4AP | TSN |
| TRIB1 | TRIM68 | TRPC7 | TSNARE1 |
| TRIB3 | TRIM69 | TRPM1 | TSNAX-DISC1 |
| TRIM10 | TRIM6-TRIM34 | TRPM4 | TSNAXIP1 |
| TRIM13 | TRIM7 | TRPM5 | T-SP1 |
| TRIM14 | TRIM71 | TRPM6 | TSPAN12 |

| | | | |
|---|---|---|---|
| TSPAN13 | TTC3 | TUBA1A | TXNRD2 |
| TSPAN15 | TTC30B | TUBA3C | TYK2 |
| TSPAN18 | TTC32 | TUBA3E | TYMP |
| TSPAN3 | TTC35 | TUBA4B | TYRO3 |
| TSPAN31 | TTC37 | TUBA8 | TYW1 |
| TSPAN4 | TTC39B | TUBB | TYW3 |
| TSPAN5 | TTC39C | TUBB3 | U2AF1 |
| TSPAN6 | TTC4 | TUBB4 | U2AF2 |
| TSPAN9 | TTC8 | TUBB6 | UAP1 |
| TSPY4 | TTF2 | TUBGCP2 | UBA2 |
| TSPYL2 | TTLL1 | TUBGCP3 | UBA3 |
| TSSC1 | TTLL10 | TUBGCP5 | UBA5 |
| TSSC4 | TTLL12 | TUFT1 | UBA7 |
| TSSK1B | TTLL3 | TULP1 | UBAC1 |
| TSTD2 | TTLL4 | TUSC2 | UBAC2 |
| TTBK1 | TTLL5 | TUSC4 | UBAP2L |
| TTBK2 | TTLL6 | TWF1 | UBASH3B |
| TTC12 | TTLL9 | TWIST1 | UBC |
| TTC14 | TTN | TWISTNB | UBD |
| TTC15 | TTPA | TWSG1 | UBE2A |
| TTC16 | TTPAL | TXNDC15 | UBE2B |
| TTC17 | TTR | TXNDC5 | UBE2C |
| TTC21B | TTTY16 | TXNL1 | UBE2CBP |
| TTC27 | TTYH2 | TXNL4A | UBE2D1 |
| TTC28 | TTYH3 | TXNRD1 | UBE2D3 |

| | | | |
|---|---|---|---|
| UBE2E1 | UBQLN1 | UFSP1 | UNC5D |
| UBE2E2 | UBQLN2 | UFSP2 | UNC84A |
| UBE2E3 | UBQLN4 | UGCG | UNC93A |
| UBE2H | UBR1 | UGDH | UNC93B1 |
| UBE2I | UBR2 | UGGT1 | UNCX |
| UBE2J2 | UBR3 | UGGT2 | UNK |
| UBE2M | UBR4 | UGT2B15 | UNKL |
| UBE2MP1 | UBR5 | UGT8 | UOX |
| UBE2N | UBR7 | UHMK1 | UPF1 |
| UBE2O | UBTD1 | UHRF1 | UPF2 |
| UBE2Q2 | UBTD2 | UHRF1BP1 | UPF3B |
| UBE2QL1 | UBTF | UHRF1BP1L | UPK1B |
| UBE2QP1 | UBXN1 | UHRF2 | UPP1 |
| UBE2V1 | UBXN10 | ULBP1 | UPP2 |
| UBE2Z | UBXN11 | ULK1 | UQCRB |
| UBE3A | UBXN2B | ULK2 | UQCRC1 |
| UBE3B | UBXN4 | ULK3 | UQCRFS1 |
| UBE3C | UBXN7 | ULK4 | UQCRHL |
| UBE4A | UCK1 | UMPS | URB1 |
| UBL3 | UCKL1 | UNC119B | URB2 |
| UBL4A | UCN3 | UNC13A | URGCP |
| UBL4B | UCP1 | UNC13D | UROC1 |
| UBL7 | UCP2 | UNC45A | USF1 |
| UBLCP1 | UCRC | UNC5A | USH1G |
| UBN2 | UFM1 | UNC5C | USH2A |

| | | | |
|---|---|---|---|
| USP1 | USP53 | VAX1 | VPS33A |
| USP14 | USP54 | VAX2 | VPS36 |
| USP15 | USP6 | VCAN | VPS37B |
| USP18 | USP6NL | VCL | VPS37D |
| USP19 | USP7 | VCPIP1 | VPS39 |
| USP2 | USP9X | VCX | VPS41 |
| USP20 | USPL1 | VDR | VPS45 |
| USP22 | UST | VEGFA | VPS4A |
| USP28 | UTP14A | VEGFB | VPS52 |
| USP3 | UTP23 | VEGFC | VPS53 |
| USP32 | UTP3 | VENTX | VPS54 |
| USP34 | UTRN | VEPH1 | VRK1 |
| USP35 | UTS2D | VEZF1 | VRK2 |
| USP36 | UVRAG | VEZT | VRK3 |
| USP38 | VAC14 | VGLL3 | VSIG10 |
| USP4 | VAMP2 | VGLL4 | VSIG8 |
| USP40 | VANGL1 | VHL | VSNL1 |
| USP42 | VANGL2 | VIM | VSTM2A |
| USP43 | VAPB | VIPR2 | VSTM2L |
| USP44 | VARS | VNN1 | VSX1 |
| USP46 | VARS2 | VOPP1 | VSX2 |
| USP48 | VASH2 | VPRBP | VTI1A |
| USP49 | VASP | VPS13B | VTI1B |
| USP5 | VAT1L | VPS13D | VTRNA1-1 |
| USP51 | VAV2 | VPS28 | VTRNA1-3 |

| | | | |
|---|---|---|---|
| VWA1 | WDR25 | WDR77 | WISP3 |
| VWA2 | WDR26 | WDR8 | WIZ |
| VWA3A | WDR31 | WDR81 | WNK1 |
| VWA3B | WDR33 | WDR82 | WNK2 |
| VWA5B1 | WDR35 | WDR86 | WNT1 |
| VWA5B2 | WDR36 | WDR89 | WNT10B |
| VWC2 | WDR37 | WDR90 | WNT16 |
| VWF | WDR4 | WDTC1 | WNT3 |
| WASF1 | WDR41 | WDYHV1 | WNT3A |
| WASL | WDR44 | WEE1 | WNT4 |
| WBP11 | WDR46 | WFDC1 | WNT5A |
| WBP2 | WDR47 | WFDC3 | WNT5B |
| WBP4 | WDR49 | WFDC5 | WNT6 |
| WBSCR16 | WDR5 | WFDC8 | WNT7A |
| WBSCR17 | WDR53 | WFIKKN2 | WNT7B |
| WBSCR28 | WDR59 | WHAMM | WNT8B |
| WDFY2 | WDR60 | WHAMML1 | WNT9B |
| WDFY3 | WDR65 | WHSC1 | WRAP53 |
| WDFY4 | WDR66 | WHSC1L1 | WRB |
| WDR1 | WDR67 | WHSC2 | WRN |
| WDR12 | WDR69 | WIBG | WRNIP1 |
| WDR16 | WDR7 | WIPF1 | WSB1 |
| WDR17 | WDR72 | WIPI1 | WSCD1 |
| WDR19 | WDR75 | WIPI2 | WSCD2 |
| WDR20 | WDR76 | WISP2 | WT1 |

| | | | |
|---|---|---|---|
| WTAP | XRCC6 | YWHAH | ZBTB44 |
| WWC1 | XRN1 | YWHAQ | ZBTB45 |
| WWC2 | XRN2 | YY1 | ZBTB46 |
| WWC3 | XYLB | ZADH2 | ZBTB47 |
| WWOX | XYLT1 | ZAK | ZBTB48 |
| WWP2 | XYLT2 | ZAR1 | ZBTB6 |
| WWTR1 | YAF2 | ZAR1L | ZBTB7A |
| XAB2 | YAP1 | ZBBX | ZBTB7B |
| XAF1 | YARS2 | ZBED3 | ZBTB9 |
| XAGE3 | YBX1 | ZBTB1 | ZC3H11A |
| XCL1 | YBX2 | ZBTB10 | ZC3H12A |
| XKR4 | YEATS2 | ZBTB11 | ZC3H12C |
| XKR5 | YIF1A | ZBTB12 | ZC3H12D |
| XKR6 | YIPF2 | ZBTB17 | ZC3H13 |
| XKR8 | YIPF4 | ZBTB2 | ZC3H14 |
| XPNPEP1 | YLPM1 | ZBTB20 | ZC3H18 |
| XPNPEP2 | YPEL1 | ZBTB22 | ZC3H3 |
| XPNPEP3 | YPEL4 | ZBTB26 | ZC3H4 |
| XPO1 | YSK4 | ZBTB3 | ZC3H7B |
| XPO4 | YTHDC1 | ZBTB32 | ZC3HAV1 |
| XPO6 | YTHDC2 | ZBTB37 | ZC3HC1 |
| XPO7 | YTHDF1 | ZBTB38 | ZCCHC10 |
| XRCC2 | YTHDF2 | ZBTB4 | ZCCHC11 |
| XRCC3 | YTHDF3 | ZBTB40 | ZCCHC14 |
| XRCC4 | YWHAG | ZBTB43 | ZCCHC17 |

| | | | |
|---|---|---|---|
| ZCCHC2 | ZFP36L2 | ZIK1 | ZNF16 |
| ZCCHC24 | ZFP41 | ZIM2 | ZNF165 |
| ZCCHC3 | ZFP42 | ZIM3 | ZNF167 |
| ZCWPW1 | ZFP64 | ZKSCAN1 | ZNF175 |
| ZDHHC11 | ZFP90 | ZMAT4 | ZNF18 |
| ZDHHC14 | ZFP91 | ZMIZ1 | ZNF180 |
| ZDHHC15 | ZFPM1 | ZMIZ2 | ZNF184 |
| ZDHHC16 | ZFPM2 | ZMPSTE24 | ZNF187 |
| ZDHHC17 | ZFR2 | ZMYM3 | ZNF197 |
| ZDHHC19 | ZFX | ZMYM5 | ZNF211 |
| ZDHHC2 | ZFY | ZMYM6 | ZNF212 |
| ZDHHC4 | ZFYVE1 | ZMYND12 | ZNF213 |
| ZDHHC7 | ZFYVE16 | ZMYND15 | ZNF214 |
| ZDHHC9 | ZFYVE19 | ZMYND17 | ZNF215 |
| ZEB1 | ZFYVE20 | ZMYND19 | ZNF217 |
| ZEB2 | ZFYVE28 | ZMYND8 | ZNF219 |
| ZFAND1 | ZFYVE9 | ZNF10 | ZNF221 |
| ZFAND2B | ZG16 | ZNF107 | ZNF222 |
| ZFAND6 | ZHX1 | ZNF12 | ZNF223 |
| ZFAT | ZHX2 | ZNF121 | ZNF225 |
| ZFC3H1 | ZHX3 | ZNF134 | ZNF226 |
| ZFHX3 | ZIC1 | ZNF141 | ZNF230 |
| ZFP3 | ZIC2 | ZNF142 | ZNF234 |
| ZFP36 | ZIC3 | ZNF148 | ZNF235 |
| ZFP36L1 | ZIC5 | ZNF155 | ZNF236 |

| | | | |
|---|---|---|---|
| ZNF239 | ZNF323 | ZNF426 | ZNF512B |
| ZNF248 | ZNF324 | ZNF43 | ZNF516 |
| ZNF250 | ZNF329 | ZNF432 | ZNF517 |
| ZNF251 | ZNF330 | ZNF433 | ZNF518A |
| ZNF253 | ZNF331 | ZNF438 | ZNF518B |
| ZNF256 | ZNF334 | ZNF44 | ZNF521 |
| ZNF257 | ZNF33B | ZNF440 | ZNF524 |
| ZNF26 | ZNF34 | ZNF441 | ZNF529 |
| ZNF260 | ZNF343 | ZNF442 | ZNF530 |
| ZNF266 | ZNF345 | ZNF443 | ZNF532 |
| ZNF271 | ZNF35 | ZNF444 | ZNF534 |
| ZNF274 | ZNF358 | ZNF446 | ZNF536 |
| ZNF277 | ZNF365 | ZNF451 | ZNF542 |
| ZNF28 | ZNF37A | ZNF454 | ZNF543 |
| ZNF280A | ZNF37B | ZNF460 | ZNF546 |
| ZNF281 | ZNF385A | ZNF461 | ZNF547 |
| ZNF282 | ZNF394 | ZNF480 | ZNF548 |
| ZNF283 | ZNF396 | ZNF485 | ZNF551 |
| ZNF284 | ZNF397 | ZNF487 | ZNF554 |
| ZNF286B | ZNF398 | ZNF491 | ZNF557 |
| ZNF300 | ZNF41 | ZNF496 | ZNF560 |
| ZNF311 | ZNF410 | ZNF498 | ZNF563 |
| ZNF319 | ZNF417 | ZNF507 | ZNF566 |
| ZNF321 | ZNF420 | ZNF511 | ZNF57 |
| ZNF322A | ZNF423 | ZNF512 | ZNF573 |

| | | | |
|---|---|---|---|
| ZNF574 | ZNF643 | ZNF704 | ZNF783 |
| ZNF575 | ZNF645 | ZNF706 | ZNF787 |
| ZNF579 | ZNF648 | ZNF707 | ZNF789 |
| ZNF580 | ZNF649 | ZNF709 | ZNF792 |
| ZNF581 | ZNF652 | ZNF71 | ZNF793 |
| ZNF585A | ZNF660 | ZNF711 | ZNF80 |
| ZNF589 | ZNF662 | ZNF714 | ZNF800 |
| ZNF592 | ZNF668 | ZNF721 | ZNF808 |
| ZNF593 | ZNF669 | ZNF732 | ZNF816A |
| ZNF594 | ZNF671 | ZNF738 | ZNF827 |
| ZNF598 | ZNF672 | ZNF74 | ZNF83 |
| ZNF599 | ZNF674 | ZNF746 | ZNF830 |
| ZNF605 | ZNF675 | ZNF747 | ZNF831 |
| ZNF608 | ZNF676 | ZNF76 | ZNF836 |
| ZNF609 | ZNF677 | ZNF761 | ZNF837 |
| ZNF610 | ZNF680 | ZNF763 | ZNF845 |
| ZNF611 | ZNF688 | ZNF764 | ZNF85 |
| ZNF613 | ZNF691 | ZNF765 | ZNF878 |
| ZNF616 | ZNF692 | ZNF768 | ZNF879 |
| ZNF618 | ZNF696 | ZNF77 | ZNF880 |
| ZNF620 | ZNF697 | ZNF770 | ZNF98 |
| ZNF625 | ZNF7 | ZNF774 | ZNFX1 |
| ZNF627 | ZNF700 | ZNF778 | ZNHIT1 |
| ZNF638 | ZNF701 | ZNF780A | ZNHIT3 |
| ZNF642 | ZNF703 | ZNF781 | ZNHIT6 |

ZNRD1

ZNRF2

ZNRF3

ZP3

ZPBP

ZRANB3

ZSCAN2

ZSCAN20

ZSCAN21

ZSCAN22

ZSCAN23

ZSCAN5A

ZSWIM1

ZSWIM3

ZSWIM4

ZSWIM6

ZW10

ZXDC

ZYG11B

ZYX

ZZZ3

Appendix D

| ILMNID | CHR | MAPINFO | Methylation Difference |
|---|---|---|---|
| cg00002591 | 3 | 52870543 | Higher in Drinkers |
| cg00003784 | 17 | 62503072 | Higher in Drinkers |
| cg00004055 | 16 | 66586745 | Higher in Drinkers |
| cg00004209 | 1 | 17004267 | Higher in Drinkers |
| cg00006884 | 7 | 23637030 | Higher in Drinkers |
| cg00007226 | 14 | 105781366 | Higher in Drinkers |
| cg00007300 | 14 | 24521434 | Higher in Drinkers |
| cg00009407 | 14 | 89290921 | Higher in Drinkers |
| cg00011284 | 16 | 53469344 | Higher in Drinkers |
| cg00012238 | 18 | 21718458 | Lower in Drinkers |
| cg00014285 | 2 | 200716175 | Higher in Drinkers |
| cg00016593 | 1 | 41483423 | Higher in Drinkers |
| cg00019880 | 17 | 53832578 | Lower in Drinkers |
| cg00020720 | 1 | 84972482 | Higher in Drinkers |
| cg00026104 | 16 | 85855299 | Higher in Drinkers |
| cg00028013 | 15 | 74218697 | Higher in Drinkers |
| cg00028829 | 16 | 58768411 | Higher in Drinkers |
| cg00031779 | 18 | 56296243 | Higher in Drinkers |
| cg00035452 | 16 | 88018556 | Higher in Drinkers |
| cg00038239 | 17 | 42090466 | Lower in Drinkers |
| cg00039794 | 2 | 109403368 | Higher in Drinkers |
| cg00041401 | 1 | 114414408 | Higher in Drinkers |
| cg00043095 | 2 | 223289277 | Higher in Drinkers |
| cg00045748 | 22 | 42908796 | Higher in Drinkers |
| cg00046105 | 1 | 233112527 | Higher in Drinkers |
| cg00047469 | 9 | 116172568 | Higher in Drinkers |
| cg00049253 | 1 | 231473541 | Higher in Drinkers |
| cg00054774 | 21 | 43373079 | Higher in Drinkers |
| cg00054890 | 7 | 98632054 | Higher in Drinkers |
| cg00055679 | 13 | 79170430 | Higher in Drinkers |
| cg00055848 | 2 | 62422984 | Higher in Drinkers |
| cg00056676 | 5 | 101631668 | Higher in Drinkers |

| | | | |
|---|---|---|---|
| cg00057114 | 1 | 6344362 | Higher in Drinkers |
| cg00057700 | 10 | 124768526 | Higher in Drinkers |
| cg00060800 | 5 | 141600994 | Higher in Drinkers |
| cg00063535 | 12 | 113729491 | Higher in Drinkers |
| cg00064950 | 17 | 7184216 | Higher in Drinkers |
| cg00065726 | 3 | 194406929 | Higher in Drinkers |
| cg00065921 | 2 | 37458357 | Higher in Drinkers |
| cg00067600 | 3 | 34109141 | Higher in Drinkers |
| cg00068038 | 2 | 36688564 | Higher in Drinkers |
| cg00070460 | 4 | 1227676 | Higher in Drinkers |
| cg00071274 | 7 | 2313925 | Lower in Drinkers |
| cg00071869 | 3 | 141599902 | Lower in Drinkers |
| cg00082426 | 2 | 61763737 | Higher in Drinkers |
| cg00082939 | 10 | 77165293 | Higher in Drinkers |
| cg00085029 | 11 | 36398393 | Higher in Drinkers |
| cg00087568 | 16 | 560280 | Higher in Drinkers |
| cg00087799 | 19 | 4831891 | Higher in Drinkers |
| cg00089353 | 3 | 160473693 | Higher in Drinkers |
| cg00090648 | 1 | 226187276 | Higher in Drinkers |
| cg00092273 | 8 | 124780287 | Higher in Drinkers |
| cg00093058 | 16 | 717932 | Higher in Drinkers |
| cg00097225 | 10 | 65389215 | Higher in Drinkers |
| cg00099129 | 2 | 114082718 | Higher in Drinkers |
| cg00101287 | 5 | 956343 | Higher in Drinkers |
| cg00101693 | 10 | 70715578 | Higher in Drinkers |
| cg00103685 | 14 | 75536130 | Higher in Drinkers |
| cg00106093 | 6 | 33391341 | Lower in Drinkers |
| cg00106211 | 6 | 36514552 | Higher in Drinkers |
| cg00106250 | 2 | 232329963 | Higher in Drinkers |
| cg00107632 | 4 | 37828500 | Higher in Drinkers |
| cg00109465 | 12 | 54121359 | Higher in Drinkers |
| cg00110578 | 6 | 25993015 | Higher in Drinkers |
| cg00110623 | 5 | 150461116 | Higher in Drinkers |
| cg00114963 | 11 | 120894690 | Higher in Drinkers |
| cg00115511 | X | 46404799 | Higher in Drinkers |

| | | | |
|---|---|---|---|
| cg00118712 | 10 | 131686819 | Lower in Drinkers |
| cg00120096 | 17 | 42404197 | Higher in Drinkers |
| cg00120948 | 1 | 8484417 | Higher in Drinkers |
| cg00123035 | 1 | 151319538 | Higher in Drinkers |
| cg00123652 | 7 | 5427647 | Higher in Drinkers |
| cg00124175 | 20 | 17950611 | Higher in Drinkers |
| cg00125048 | 5 | 176023439 | Higher in Drinkers |
| cg00127732 | 19 | 42757846 | Higher in Drinkers |
| cg00128732 | 5 | 141258637 | Higher in Drinkers |
| cg00128812 | 3 | 145019377 | Higher in Drinkers |
| cg00129461 | 9 | 35748386 | Higher in Drinkers |
| cg00137652 | 12 | 66696023 | Higher in Drinkers |
| cg00137696 | 7 | 127703101 | Higher in Drinkers |
| cg00138641 | 16 | 14397074 | Higher in Drinkers |
| cg00139244 | 10 | 31608402 | Higher in Drinkers |
| cg00141162 | 3 | 121379777 | Higher in Drinkers |
| cg00142759 | 4 | 37979166 | Higher in Drinkers |
| cg00143527 | 15 | 81292171 | Higher in Drinkers |
| cg00144161 | 6 | 31927018 | Higher in Drinkers |
| cg00145253 | 1 | 75602857 | Higher in Drinkers |
| cg00146695 | 13 | 44453858 | Higher in Drinkers |
| cg00146755 | 21 | 45551519 | Higher in Drinkers |
| cg00150231 | 2 | 234112793 | Higher in Drinkers |
| cg00152768 | 3 | 50397174 | Higher in Drinkers |
| cg00154443 | 16 | 71917454 | Higher in Drinkers |
| cg00154557 | 6 | 116763525 | Higher in Drinkers |
| cg00159100 | 7 | 37487633 | Higher in Drinkers |
| cg00161970 | 1 | 167684333 | Higher in Drinkers |
| cg00164894 | 1 | 55535598 | Higher in Drinkers |
| cg00166327 | 13 | 73356072 | Higher in Drinkers |
| cg00167941 | 11 | 70116446 | Higher in Drinkers |
| cg00168205 | 12 | 120524932 | Higher in Drinkers |
| cg00169633 | 3 | 134093551 | Higher in Drinkers |
| cg00169917 | 10 | 120514287 | Higher in Drinkers |
| cg00171203 | 1 | 35657571 | Higher in Drinkers |

| | | | |
|---|---|---|---|
| cg00172020 | 3 | 150264474 | Higher in Drinkers |
| cg00173435 | 12 | 106696525 | Higher in Drinkers |
| cg00178030 | 16 | 16162238 | Higher in Drinkers |
| cg00181419 | 16 | 4748987 | Higher in Drinkers |
| cg00183340 | 1 | 120838644 | Higher in Drinkers |
| cg00187614 | 1 | 42500967 | Higher in Drinkers |
| cg00193902 | 7 | 98579722 | Higher in Drinkers |
| cg00197641 | 14 | 23299461 | Higher in Drinkers |
| cg00201296 | 2 | 113954589 | Higher in Drinkers |
| cg00201670 | 21 | 46221900 | Higher in Drinkers |
| cg00202403 | 17 | 41624089 | Higher in Drinkers |
| cg00203291 | 15 | 37176035 | Higher in Drinkers |
| cg00203461 | 10 | 70287181 | Higher in Drinkers |
| cg00205485 | 1 | 153958871 | Higher in Drinkers |
| cg00207389 | 20 | 18569003 | Higher in Drinkers |
| cg00207973 | 16 | 84492862 | Higher in Drinkers |
| cg00208461 | 11 | 47664272 | Higher in Drinkers |
| cg00210842 | 12 | 99039578 | Higher in Drinkers |
| cg00211661 | 11 | 72433619 | Higher in Drinkers |
| cg00213853 | X | 154034091 | Higher in Drinkers |
| cg00213905 | 11 | 64684725 | Higher in Drinkers |
| cg00215744 | 16 | 57334530 | Higher in Drinkers |
| cg00216504 | 7 | 91763516 | Higher in Drinkers |
| cg00216931 | 16 | 4666438 | Higher in Drinkers |
| cg00218146 | 15 | 31619396 | Higher in Drinkers |
| cg00219543 | 6 | 170190519 | Higher in Drinkers |
| cg00220492 | 15 | 36871852 | Higher in Drinkers |
| cg00230183 | 16 | 88882565 | Lower in Drinkers |
| cg00230302 | 9 | 21802598 | Higher in Drinkers |
| cg00231521 | 19 | 52643038 | Higher in Drinkers |
| cg00231549 | X | 33744176 | Higher in Drinkers |
| cg00232059 | 22 | 45131501 | Higher in Drinkers |
| cg00234261 | 7 | 151106082 | Higher in Drinkers |
| cg00236766 | 2 | 219268000 | Higher in Drinkers |
| cg00238848 | 11 | 72408252 | Lower in Drinkers |

| | | | |
|---|---|---|---|
| cg00240378 | 2 | 8650020 | Lower in Drinkers |
| cg00241281 | 14 | 105779794 | Higher in Drinkers |
| cg00242035 | 11 | 47416358 | Higher in Drinkers |
| cg00242285 | 3 | 124480225 | Higher in Drinkers |
| cg00251271 | 16 | 1832493 | Higher in Drinkers |
| cg00257659 | 1 | 209800214 | Lower in Drinkers |
| cg00257786 | 1 | 173991688 | Higher in Drinkers |
| cg00258976 | 16 | 89283889 | Higher in Drinkers |
| cg00261144 | 9 | 139360435 | Higher in Drinkers |
| cg00261552 | 12 | 12764894 | Higher in Drinkers |
| cg00261900 | 6 | 44194802 | Higher in Drinkers |
| cg00262368 | 12 | 69081084 | Higher in Drinkers |
| cg00264236 | 16 | 89634049 | Higher in Drinkers |
| cg00265442 | 5 | 132113386 | Higher in Drinkers |
| cg00268338 | 10 | 93169495 | Higher in Drinkers |
| cg00269115 | 1 | 23695530 | Higher in Drinkers |
| cg00269996 | 6 | 42979961 | Higher in Drinkers |
| cg00272951 | 5 | 77590791 | Higher in Drinkers |
| cg00276797 | 10 | 105726614 | Higher in Drinkers |
| cg00279406 | 1 | 226924739 | Higher in Drinkers |
| cg00279797 | X | 109561919 | Higher in Drinkers |
| cg00280922 | 14 | 74226427 | Higher in Drinkers |
| cg00287541 | 16 | 74398168 | Higher in Drinkers |
| cg00291877 | 15 | 101835933 | Higher in Drinkers |
| cg00291981 | 3 | 49591748 | Higher in Drinkers |
| cg00292290 | 4 | 865852 | Higher in Drinkers |
| cg00292662 | 22 | 38071168 | Higher in Drinkers |
| cg00292851 | 21 | 44300012 | Higher in Drinkers |
| cg00294025 | 12 | 7276360 | Higher in Drinkers |
| cg00294419 | 3 | 23244681 | Higher in Drinkers |
| cg00294658 | 12 | 7126344 | Higher in Drinkers |
| cg00295887 | 8 | 146228807 | Higher in Drinkers |
| cg00296291 | 4 | 129733887 | Higher in Drinkers |
| cg00297660 | 19 | 36869860 | Higher in Drinkers |
| cg00299893 | 15 | 101609726 | Higher in Drinkers |

| | | | |
|---|---|---|---|
| cg00305281 | 22 | 42316176 | Higher in Drinkers |
| cg00306607 | 1 | 246729875 | Higher in Drinkers |
| cg00308344 | 12 | 117536531 | Higher in Drinkers |
| cg00308767 | 1 | 38155539 | Higher in Drinkers |
| cg00312921 | 4 | 113441703 | Higher in Drinkers |
| cg00315394 | 5 | 179232165 | Higher in Drinkers |
| cg00315487 | 3 | 44906755 | Higher in Drinkers |
| cg00320243 | 19 | 18314691 | Higher in Drinkers |
| cg00321150 | 11 | 62623587 | Higher in Drinkers |
| cg00321642 | 1 | 42501967 | Higher in Drinkers |
| cg00325866 | 15 | 62359130 | Higher in Drinkers |
| cg00326642 | 3 | 140949072 | Higher in Drinkers |
| cg00327524 | 8 | 144510753 | Higher in Drinkers |
| cg00329943 | 16 | 72127485 | Higher in Drinkers |
| cg00330888 | 2 | 46524148 | Higher in Drinkers |
| cg00332249 | 11 | 14995258 | Higher in Drinkers |
| cg00334542 | 7 | 100209784 | Higher in Drinkers |
| cg00335003 | 20 | 30697488 | Higher in Drinkers |
| cg00335633 | 19 | 51308339 | Higher in Drinkers |
| cg00337020 | 19 | 2241089 | Higher in Drinkers |
| cg00338329 | 20 | 398430 | Higher in Drinkers |
| cg00344358 | 12 | 56135693 | Higher in Drinkers |
| cg00346180 | 19 | 50189880 | Higher in Drinkers |
| cg00346716 | 20 | 11906616 | Lower in Drinkers |
| cg00346970 | 6 | 24499591 | Higher in Drinkers |
| cg00347280 | 1 | 45477834 | Higher in Drinkers |
| cg00347369 | 8 | 80523320 | Higher in Drinkers |
| cg00347863 | 7 | 94220697 | Higher in Drinkers |
| cg00350296 | 11 | 66084841 | Higher in Drinkers |
| cg00350371 | 20 | 2633524 | Higher in Drinkers |
| cg00350702 | 20 | 34129927 | Higher in Drinkers |
| cg00352349 | 2 | 179316347 | Higher in Drinkers |
| cg00353340 | 12 | 26112746 | Higher in Drinkers |
| cg00355794 | 4 | 63578633 | Higher in Drinkers |
| cg00357238 | 7 | 124570053 | Higher in Drinkers |

| | | | |
|---|---|---|---|
| cg00359604 | 21 | 38935977 | Higher in Drinkers |
| cg00359868 | 21 | 40752339 | Higher in Drinkers |
| cg00360362 | 5 | 74633527 | Higher in Drinkers |
| cg00360718 | 10 | 104192479 | Higher in Drinkers |
| cg00361696 | 5 | 139780805 | Higher in Drinkers |
| cg00362906 | 11 | 118305799 | Higher in Drinkers |
| cg00363465 | 16 | 30569976 | Higher in Drinkers |
| cg00365963 | 22 | 26895362 | Higher in Drinkers |
| cg00366814 | 2 | 75061219 | Higher in Drinkers |
| cg00367327 | 22 | 44419885 | Higher in Drinkers |
| cg00368415 | 1 | 151584398 | Higher in Drinkers |
| cg00372669 | 10 | 75571033 | Higher in Drinkers |
| cg00374078 | 16 | 87351569 | Higher in Drinkers |
| cg00374377 | 17 | 27038186 | Higher in Drinkers |
| cg00379836 | 19 | 50372937 | Higher in Drinkers |
| cg00381179 | 3 | 134093562 | Higher in Drinkers |
| cg00381391 | 3 | 33837694 | Higher in Drinkers |
| cg00382190 | 2 | 136742926 | Higher in Drinkers |
| cg00383977 | 3 | 183852781 | Higher in Drinkers |
| cg00385471 | 17 | 72733521 | Higher in Drinkers |
| cg00387964 | 4 | 7651935 | Higher in Drinkers |
| cg00388471 | 16 | 1475871 | Lower in Drinkers |
| cg00388987 | 16 | 72698624 | Higher in Drinkers |
| cg00389713 | 6 | 43138877 | Higher in Drinkers |
| cg00391696 | 11 | 65139500 | Higher in Drinkers |
| cg00392872 | 20 | 33104052 | Higher in Drinkers |
| cg00393470 | 3 | 120066154 | Higher in Drinkers |
| cg00394214 | 19 | 17420434 | Higher in Drinkers |
| cg00394793 | 15 | 70391374 | Higher in Drinkers |
| cg00395063 | 11 | 120210293 | Higher in Drinkers |
| cg00397575 | 15 | 65359932 | Higher in Drinkers |
| cg00400992 | 5 | 77923936 | Lower in Drinkers |
| cg00404025 | 10 | 49892741 | Higher in Drinkers |
| cg00407468 | 9 | 126692955 | Lower in Drinkers |
| cg00407938 | 13 | 114282230 | Higher in Drinkers |

| | | | |
|---|---|---|---|
| cg00409700 | 3 | 12941089 | Higher in Drinkers |
| cg00411741 | 19 | 18208476 | Higher in Drinkers |
| cg00417165 | 14 | 75079321 | Higher in Drinkers |
| cg00417963 | 7 | 1529251 | Higher in Drinkers |
| cg00418927 | 16 | 70380649 | Higher in Drinkers |
| cg00420568 | 9 | 91794904 | Higher in Drinkers |
| cg00420895 | 6 | 70577606 | Higher in Drinkers |
| cg00421624 | 1 | 153746588 | Higher in Drinkers |
| cg00423124 | 13 | 44453862 | Higher in Drinkers |
| cg00430895 | 18 | 13136340 | Higher in Drinkers |
| cg00432497 | 16 | 89438714 | Lower in Drinkers |
| cg00435408 | 16 | 57220662 | Higher in Drinkers |
| cg00436051 | 22 | 29663508 | Higher in Drinkers |
| cg00436301 | 6 | 116421736 | Higher in Drinkers |
| cg00436488 | 16 | 4743913 | Higher in Drinkers |
| cg00438775 | 2 | 97175311 | Higher in Drinkers |
| cg00440797 | 6 | 32493873 | Higher in Drinkers |
| cg00443869 | 5 | 114631994 | Higher in Drinkers |
| cg00449384 | 9 | 130515119 | Higher in Drinkers |
| cg00450164 | 1 | 209930127 | Higher in Drinkers |
| cg00454770 | 10 | 116286974 | Higher in Drinkers |
| cg00455164 | 2 | 230931922 | Higher in Drinkers |
| cg00456387 | 2 | 20101664 | Higher in Drinkers |
| cg00456395 | 12 | 96641089 | Higher in Drinkers |
| cg00456868 | 15 | 34331390 | Higher in Drinkers |
| cg00458016 | 19 | 50096876 | Higher in Drinkers |
| cg00459043 | 17 | 30771460 | Higher in Drinkers |
| cg00460286 | 15 | 77320261 | Higher in Drinkers |
| cg00461612 | 2 | 223158076 | Higher in Drinkers |
| cg00462202 | 11 | 67374668 | Higher in Drinkers |
| cg00462849 | 2 | 12853027 | Lower in Drinkers |
| cg00466301 | 20 | 56285388 | Higher in Drinkers |
| cg00466488 | 1 | 118148927 | Higher in Drinkers |
| cg00466544 | 14 | 57046243 | Higher in Drinkers |
| cg00467652 | 3 | 50357644 | Higher in Drinkers |

| | | | |
|---|---|---|---|
| cg00473044 | 13 | 37566862 | Higher in Drinkers |
| cg00473462 | 5 | 472545 | Higher in Drinkers |
| cg00474209 | 6 | 170600060 | Higher in Drinkers |
| cg00478326 | 15 | 78978136 | Higher in Drinkers |
| cg00480643 | 4 | 117702017 | Lower in Drinkers |
| cg00481605 | 19 | 14063031 | Higher in Drinkers |
| cg00489902 | 12 | 133260711 | Higher in Drinkers |
| cg00490075 | 13 | 27359547 | Higher in Drinkers |
| cg00490249 | 3 | 49058586 | Higher in Drinkers |
| cg00490431 | 17 | 48201664 | Lower in Drinkers |
| cg00492083 | 17 | 79164939 | Higher in Drinkers |
| cg00492233 | 7 | 135242493 | Higher in Drinkers |
| cg00492309 | 16 | 2221491 | Higher in Drinkers |
| cg00494949 | 7 | 5392379 | Higher in Drinkers |
| cg00495436 | 3 | 132441907 | Higher in Drinkers |
| cg00495462 | 1 | 226497359 | Higher in Drinkers |
| cg00496102 | 7 | 7605238 | Higher in Drinkers |
| cg00496455 | 2 | 220118770 | Higher in Drinkers |
| cg00497630 | 17 | 26733052 | Higher in Drinkers |
| cg00497967 | 16 | 77822438 | Higher in Drinkers |
| cg00499210 | 11 | 65190135 | Higher in Drinkers |
| cg00499819 | 20 | 62496386 | Higher in Drinkers |
| cg00500299 | 16 | 1501833 | Higher in Drinkers |
| cg00500602 | 16 | 2105310 | Higher in Drinkers |
| cg00502099 | 11 | 2322618 | Higher in Drinkers |
| cg00502952 | 1 | 2160666 | Higher in Drinkers |
| cg00505979 | 1 | 212873626 | Higher in Drinkers |
| cg00506343 | 12 | 54421033 | Higher in Drinkers |
| cg00508543 | 3 | 64672197 | Higher in Drinkers |
| cg00511596 | 10 | 16478834 | Higher in Drinkers |
| cg00513984 | 12 | 125039177 | Higher in Drinkers |
| cg00517072 | 1 | 145096849 | Higher in Drinkers |
| cg00519490 | 20 | 33734811 | Higher in Drinkers |
| cg00519553 | 11 | 119211047 | Higher in Drinkers |
| cg00520307 | 10 | 105881384 | Higher in Drinkers |

| | | | |
|---|---|---|---|
| cg00524220 | 19 | 3098963 | Higher in Drinkers |
| cg00524912 | 22 | 37172668 | Higher in Drinkers |
| cg00525508 | 10 | 1749360 | Higher in Drinkers |
| cg00528793 | 22 | 19842837 | Higher in Drinkers |
| cg00532998 | 13 | 41763820 | Higher in Drinkers |
| cg00540587 | 2 | 240184656 | Higher in Drinkers |
| cg00540850 | 5 | 1277126 | Higher in Drinkers |
| cg00541002 | 10 | 112696816 | Higher in Drinkers |
| cg00543073 | 2 | 60773386 | Lower in Drinkers |
| cg00544436 | 6 | 34203564 | Higher in Drinkers |
| cg00548173 | 10 | 135103296 | Higher in Drinkers |
| cg00549123 | 1 | 174025906 | Lower in Drinkers |
| cg00551140 | 20 | 60814142 | Higher in Drinkers |
| cg00552973 | 1 | 206137054 | Higher in Drinkers |
| cg00554442 | 16 | 1021074 | Higher in Drinkers |
| cg00554682 | 2 | 185463132 | Higher in Drinkers |
| cg00554858 | 5 | 95991891 | Lower in Drinkers |
| cg00556514 | 3 | 38066524 | Higher in Drinkers |
| cg00557308 | 15 | 66274821 | Higher in Drinkers |
| cg00559179 | 7 | 105925850 | Higher in Drinkers |
| cg00567536 | 3 | 47422272 | Higher in Drinkers |
| cg00567703 | 12 | 54413101 | Higher in Drinkers |
| cg00568027 | 1 | 229644024 | Higher in Drinkers |
| cg00568044 | 8 | 91658696 | Higher in Drinkers |
| cg00568741 | 7 | 92219338 | Higher in Drinkers |
| cg00568792 | 11 | 125462554 | Higher in Drinkers |
| cg00569953 | 11 | 66036020 | Higher in Drinkers |
| cg00571634 | 3 | 122134820 | Higher in Drinkers |
| cg00574424 | 14 | 50101902 | Higher in Drinkers |
| cg00576388 | 12 | 54718905 | Higher in Drinkers |
| cg00577070 | 3 | 47049880 | Higher in Drinkers |
| cg00577109 | 19 | 59074507 | Higher in Drinkers |
| cg00577623 | X | 57934090 | Lower in Drinkers |
| cg00577935 | 5 | 112073348 | Higher in Drinkers |
| cg00578174 | 1 | 93293275 | Higher in Drinkers |

| | | | |
|---|---|---|---|
| cgCC578414 | 12 | 133307618 | Higher in Drinkers |
| cgCC578828 | 5 | 131826934 | Higher in Drinkers |
| cgCC579036 | 6 | 25138551 | Higher in Drinkers |
| cgCC579105 | 6 | 31704587 | Higher in Drinkers |
| cgCC579481 | 22 | 21271797 | Higher in Drinkers |
| cgCC582583 | 16 | 88992178 | Lower in Drinkers |
| cgCC582820 | 3 | 125314599 | Higher in Drinkers |
| cgCC582881 | 5 | 148651359 | Higher in Drinkers |
| cgCC583492 | 11 | 66610708 | Higher in Drinkers |
| cgCC584995 | 2 | 26568855 | Higher in Drinkers |
| cgCC585572 | 22 | 41347381 | Higher in Drinkers |
| cgCC585790 | 2 | 109204845 | Higher in Drinkers |
| cgCC586700 | 19 | 50015178 | Higher in Drinkers |
| cgCC587628 | 6 | 111584033 | Higher in Drinkers |
| cgCC587941 | 13 | 114741241 | Lower in Drinkers |
| cgCC588920 | 8 | 72917147 | Higher in Drinkers |
| cgCC589895 | 3 | 172429056 | Higher in Drinkers |
| cgCC591489 | 1 | 24829151 | Higher in Drinkers |
| cgCC593404 | 6 | 52377740 | Higher in Drinkers |
| cgCC594191 | 10 | 11755103 | Higher in Drinkers |
| cgCC594561 | 17 | 48073423 | Higher in Drinkers |
| cgCC596643 | 12 | 75905429 | Higher in Drinkers |
| cgCC598858 | 19 | 11545966 | Higher in Drinkers |
| cgCC598985 | 2 | 242088379 | Higher in Drinkers |
| cgCC599252 | 11 | 64491089 | Higher in Drinkers |
| cgCC605063 | 7 | 27289128 | Higher in Drinkers |
| cgCC607725 | 16 | 70380558 | Higher in Drinkers |
| cgCC607919 | 2 | 109403071 | Higher in Drinkers |
| cgCC611397 | 20 | 60768026 | Higher in Drinkers |
| cgCC611429 | 11 | 64072922 | Higher in Drinkers |
| cgCC611674 | 5 | 138775742 | Lower in Drinkers |
| cgCC612107 | 16 | 85645923 | Higher in Drinkers |
| cgCC612467 | 4 | 108911077 | Higher in Drinkers |
| cgCC614081 | 4 | 1233439 | Higher in Drinkers |
| cgCC614641 | 11 | 61596405 | Higher in Drinkers |

| | | | |
|---|---|---|---|
| cg00614834 | 6 | 33172869 | Higher in Drinkers |
| cg00615550 | 6 | 109703901 | Higher in Drinkers |
| cg00619231 | 15 | 35279938 | Higher in Drinkers |
| cg00619630 | 17 | 79455201 | Higher in Drinkers |
| cg00621029 | 21 | 35747559 | Higher in Drinkers |
| cg00621258 | 20 | 60781288 | Higher in Drinkers |
| cg00622749 | 10 | 43689584 | Higher in Drinkers |
| cg00628228 | 1 | 167424562 | Higher in Drinkers |
| cg00630020 | 20 | 1306618 | Higher in Drinkers |
| cg00630080 | 16 | 67264248 | Higher in Drinkers |
| cg00631272 | 7 | 1654491 | Higher in Drinkers |
| cg00632607 | 12 | 4648052 | Higher in Drinkers |
| cg00634573 | 17 | 953069 | Higher in Drinkers |
| cg00638384 | 12 | 68052134 | Lower in Drinkers |
| cg00642494 | 5 | 76941749 | Higher in Drinkers |
| cg00647220 | 16 | 14013937 | Higher in Drinkers |
| cg00647769 | 1 | 227170663 | Higher in Drinkers |
| cg00648476 | 11 | 123525237 | Higher in Drinkers |
| cg00650006 | 17 | 18218974 | Higher in Drinkers |
| cg00651923 | 4 | 52904174 | Higher in Drinkers |
| cg00652942 | 5 | 170847313 | Higher in Drinkers |
| cg00654448 | 8 | 142365315 | Higher in Drinkers |
| cg00655412 | 16 | 21312069 | Higher in Drinkers |
| cg00657871 | 1 | 85156634 | Higher in Drinkers |
| cg00658427 | 14 | 102431823 | Higher in Drinkers |
| cg00659035 | 1 | 25573464 | Higher in Drinkers |
| cg00659667 | 1 | 24742110 | Higher in Drinkers |
| cg00660400 | 5 | 133562159 | Higher in Drinkers |
| cg00663986 | 17 | 80866232 | Higher in Drinkers |
| cg00664842 | 6 | 31939758 | Higher in Drinkers |
| cg00667026 | 14 | 69262265 | Higher in Drinkers |
| cg00667360 | 16 | 30076044 | Higher in Drinkers |
| cg00669119 | 18 | 6284570 | Lower in Drinkers |
| cg00673963 | 1 | 100731856 | Higher in Drinkers |
| cg00679546 | 17 | 60729882 | Higher in Drinkers |

| | | | |
|---|---|---|---|
| cg00679681 | 16 | 89346491 | Higher in Drinkers |
| cg00680003 | 6 | 30523449 | Higher in Drinkers |
| cg00687686 | 16 | 58497236 | Higher in Drinkers |
| cg00687766 | 8 | 38854579 | Higher in Drinkers |
| cg00687936 | 11 | 75526841 | Higher in Drinkers |
| cg00688979 | 6 | 31113017 | Higher in Drinkers |
| cg00691125 | 1 | 169455409 | Higher in Drinkers |
| cg00692677 | 17 | 46534756 | Higher in Drinkers |
| cg00693401 | 17 | 80655383 | Higher in Drinkers |
| cg00694968 | X | 113997817 | Lower in Drinkers |
| cg00695799 | 6 | 149803087 | Higher in Drinkers |
| cg00696158 | 6 | 37190552 | Higher in Drinkers |
| cg00696166 | 21 | 34863496 | Higher in Drinkers |
| cg00696540 | 6 | 112194776 | Higher in Drinkers |
| cg00696803 | 17 | 43394474 | Higher in Drinkers |
| cg00697668 | 14 | 105617575 | Lower in Drinkers |
| cg00698124 | 18 | 42259037 | Higher in Drinkers |
| cg00698228 | 12 | 120423883 | Lower in Drinkers |
| cg00698602 | 3 | 44481324 | Higher in Drinkers |
| cg00703273 | 17 | 61700589 | Higher in Drinkers |
| cg00704305 | 6 | 127664950 | Higher in Drinkers |
| cg00704310 | 19 | 34288103 | Higher in Drinkers |
| cg00706505 | 3 | 49142215 | Higher in Drinkers |
| cg00708642 | 14 | 103800518 | Higher in Drinkers |
| cg00709805 | 14 | 68236698 | Higher in Drinkers |
| cg00711351 | 22 | 50689941 | Higher in Drinkers |
| cg00711711 | 7 | 137687007 | Higher in Drinkers |
| cg00712547 | 17 | 65821745 | Higher in Drinkers |
| cg00713947 | 5 | 126365876 | Higher in Drinkers |
| cg00714377 | 20 | 35274715 | Higher in Drinkers |
| cg00715835 | 7 | 1584061 | Higher in Drinkers |
| cg00716254 | 2 | 122406912 | Higher in Drinkers |
| cg00716787 | 2 | 131100118 | Higher in Drinkers |
| cg00717297 | 12 | 122170156 | Higher in Drinkers |
| cg00718107 | 8 | 105537856 | Higher in Drinkers |

| | | | |
|---|---|---|---|
| cg00718440 | 9 | 21995312 | Higher in Drinkers |
| cg00718519 | 6 | 30689608 | Higher in Drinkers |
| cg00719502 | 3 | 11608329 | Higher in Drinkers |
| cg00720072 | 10 | 94051159 | Higher in Drinkers |
| cg00721771 | 3 | 59903821 | Lower in Drinkers |
| cg00722180 | 14 | 73525139 | Higher in Drinkers |
| cg00724098 | 7 | 40174410 | Higher in Drinkers |
| cg00724662 | 11 | 62573193 | Higher in Drinkers |
| cg00725244 | 10 | 86086681 | Higher in Drinkers |
| cg00726615 | 3 | 113252640 | Higher in Drinkers |
| cg00729475 | 16 | 19533549 | Higher in Drinkers |
| cg00729654 | 20 | 31123895 | Higher in Drinkers |
| cg00734724 | 15 | 41406630 | Higher in Drinkers |
| cg00737655 | 3 | 127340234 | Lower in Drinkers |
| cg00743068 | X | 77041832 | Higher in Drinkers |
| cg00743372 | 6 | 28109648 | Higher in Drinkers |
| cg00745248 | 2 | 20101788 | Higher in Drinkers |
| cg00746338 | 21 | 38763513 | Higher in Drinkers |
| cg00747065 | 2 | 26467663 | Higher in Drinkers |
| cg00747647 | 19 | 10045441 | Lower in Drinkers |
| cg00748218 | 11 | 19372553 | Higher in Drinkers |
| cg00750684 | 13 | 49107423 | Higher in Drinkers |
| cg00751253 | 8 | 75233613 | Higher in Drinkers |
| cg00752099 | 4 | 94748619 | Higher in Drinkers |
| cg00753739 | 10 | 11653489 | Higher in Drinkers |
| cg00753747 | 16 | 22201766 | Higher in Drinkers |
| cg00755751 | 14 | 64677007 | Lower in Drinkers |
| cg00757413 | 9 | 130160153 | Higher in Drinkers |
| cg00758584 | 1 | 40254741 | Higher in Drinkers |
| cg00759254 | 1 | 27679961 | Higher in Drinkers |
| cg00764619 | 2 | 242610529 | Higher in Drinkers |
| cg00765710 | 1 | 249200642 | Higher in Drinkers |
| cg00767560 | 19 | 19887256 | Higher in Drinkers |
| cg00768861 | 10 | 104005440 | Higher in Drinkers |
| cg00768999 | 2 | 133038669 | Higher in Drinkers |

| | | | |
|---|---|---|---|
| cg00770265 | 14 | 24912346 | Higher in Drinkers |
| cg00770636 | 13 | 77566064 | Higher in Drinkers |
| cg00771593 | 16 | 67472931 | Higher in Drinkers |
| cg00771642 | 19 | 48988436 | Lower in Drinkers |
| cg00774100 | 6 | 31465369 | Higher in Drinkers |
| cg00774435 | 12 | 7249439 | Higher in Drinkers |
| cg00774538 | 16 | 9056486 | Higher in Drinkers |
| cg00775906 | 8 | 144872060 | Lower in Drinkers |
| cg00777121 | 3 | 50378191 | Higher in Drinkers |
| cg00777341 | 1 | 3551978 | Higher in Drinkers |
| cg00782697 | 10 | 134454481 | Lower in Drinkers |
| cg00789034 | 6 | 158245090 | Higher in Drinkers |
| cg00790036 | X | 46696474 | Higher in Drinkers |
| cg00792172 | 1 | 150602446 | Higher in Drinkers |
| cg00793450 | 12 | 22697620 | Higher in Drinkers |
| cg00798836 | 5 | 54603441 | Higher in Drinkers |
| cg00800365 | 15 | 90318772 | Higher in Drinkers |
| cg00800634 | 4 | 3882420 | Higher in Drinkers |
| cg00801465 | 3 | 193852989 | Higher in Drinkers |
| cg00803873 | 21 | 33984631 | Higher in Drinkers |
| cg00806644 | 10 | 126889815 | Higher in Drinkers |
| cg00808740 | 12 | 46661305 | Higher in Drinkers |
| cg00808969 | 11 | 77898785 | Higher in Drinkers |
| cg00809614 | 11 | 75919862 | Higher in Drinkers |
| cg00810473 | 15 | 64443709 | Higher in Drinkers |
| cg00812861 | 9 | 35114699 | Higher in Drinkers |
| cg00813720 | 5 | 153989231 | Lower in Drinkers |
| cg00814244 | 2 | 16079687 | Higher in Drinkers |
| cg00814443 | 9 | 91003462 | Higher in Drinkers |
| cg00816548 | X | 77154821 | Higher in Drinkers |
| cg00817377 | 7 | 73441057 | Higher in Drinkers |
| cg00817749 | X | 37699631 | Higher in Drinkers |
| cg00818693 | 3 | 180319964 | Higher in Drinkers |
| cg00823995 | 19 | 46389577 | Higher in Drinkers |
| cg00825705 | 17 | 26593560 | Higher in Drinkers |

| | | | |
|---|---|---|---|
| cg00827369 | 7 | 73588253 | Higher in Drinkers |
| cg00827392 | 20 | 61436997 | Higher in Drinkers |
| cg00829575 | X | 38663062 | Higher in Drinkers |
| cg00830393 | 3 | 66552063 | Higher in Drinkers |
| cg00830621 | 16 | 18799106 | Lower in Drinkers |
| cg00830813 | 7 | 984874 | Higher in Drinkers |
| cg00833344 | 2 | 150426294 | Higher in Drinkers |
| cg00833552 | 10 | 46221282 | Higher in Drinkers |
| cg00834319 | 14 | 64970752 | Higher in Drinkers |
| cg00835612 | 16 | 72698400 | Higher in Drinkers |
| cg00836119 | 10 | 75634696 | Higher in Drinkers |
| cg00836571 | 15 | 75639825 | Higher in Drinkers |
| cg00838150 | 3 | 69788442 | Higher in Drinkers |
| cg00838250 | 3 | 186287958 | Higher in Drinkers |
| cg00840115 | 2 | 145282103 | Higher in Drinkers |
| cg00840926 | 19 | 58919549 | Higher in Drinkers |
| cg00845368 | 9 | 97572553 | Higher in Drinkers |
| cg00847309 | 19 | 51303252 | Higher in Drinkers |
| cg00848397 | 17 | 34948594 | Higher in Drinkers |
| cg00850039 | 19 | 12476508 | Higher in Drinkers |
| cg00850971 | 6 | 7052187 | Higher in Drinkers |
| cg00853811 | 2 | 241463429 | Higher in Drinkers |
| cg00853819 | 7 | 1877678 | Higher in Drinkers |
| cg00858599 | 20 | 3220929 | Lower in Drinkers |
| cg00860090 | 1 | 226832000 | Higher in Drinkers |
| cg00860570 | 2 | 86333337 | Higher in Drinkers |
| cg00861308 | 3 | 23852449 | Higher in Drinkers |
| cg00861635 | 16 | 3285425 | Higher in Drinkers |
| cg00863397 | 16 | 67215239 | Higher in Drinkers |
| cg00864261 | 14 | 52456074 | Higher in Drinkers |
| cg00864384 | 2 | 69871130 | Higher in Drinkers |
| cg00866936 | 17 | 17942403 | Higher in Drinkers |
| cg00869632 | 17 | 59940709 | Higher in Drinkers |
| cg00870837 | 16 | 1171361 | Lower in Drinkers |
| cg00871019 | 10 | 60028461 | Higher in Drinkers |

| | | | |
|---|---|---|---|
| cg00874320 | 12 | 133219044 | Higher in Drinkers |
| cg00877620 | 17 | 33905870 | Higher in Drinkers |
| cg00877837 | 9 | 131315495 | Higher in Drinkers |
| cg00878023 | X | 21392544 | Higher in Drinkers |
| cg00880074 | 3 | 124172962 | Higher in Drinkers |
| cg00883123 | 4 | 154373513 | Higher in Drinkers |
| cg00883854 | 14 | 50053110 | Higher in Drinkers |
| cg00885708 | 5 | 139167076 | Higher in Drinkers |
| cg00887700 | 12 | 124118360 | Higher in Drinkers |
| cg00889833 | 3 | 38388432 | Higher in Drinkers |
| cg00890916 | 20 | 30158833 | Higher in Drinkers |
| cg00892804 | 3 | 183353372 | Higher in Drinkers |
| cg00893636 | 3 | 37034640 | Higher in Drinkers |
| cg00893987 | 6 | 42847415 | Higher in Drinkers |
| cg00895099 | 11 | 111945153 | Higher in Drinkers |
| cg00897627 | 10 | 99447216 | Higher in Drinkers |
| cg00906973 | 6 | 10419835 | Higher in Drinkers |
| cg00909706 | 1 | 9211836 | Higher in Drinkers |
| cg00910419 | 2 | 60780754 | Higher in Drinkers |
| cg00912580 | 2 | 135169533 | Higher in Drinkers |
| cg00913289 | 2 | 232573281 | Higher in Drinkers |
| cg00914781 | 1 | 47902275 | Higher in Drinkers |
| cg00916454 | 4 | 156877765 | Lower in Drinkers |
| cg00918762 | 6 | 30585117 | Higher in Drinkers |
| cg00920043 | 1 | 11333412 | Higher in Drinkers |
| cg00921160 | 14 | 97129452 | Higher in Drinkers |
| cg00921934 | 16 | 1866946 | Higher in Drinkers |
| cg00925229 | 11 | 64052547 | Higher in Drinkers |
| cg00928191 | 16 | 419800 | Higher in Drinkers |
| cg00929860 | 10 | 73846448 | Lower in Drinkers |
| cg00934312 | 7 | 149570931 | Higher in Drinkers |
| cg00936146 | 8 | 29206333 | Higher in Drinkers |
| cg00936449 | 17 | 63119501 | Higher in Drinkers |
| cg00937135 | 7 | 127983655 | Higher in Drinkers |
| cg00940287 | X | 139332755 | Lower in Drinkers |

| | | | |
|---|---|---|---|
| cg00941203 | 10 | 31016591 | Lower in Drinkers |
| cg00944541 | 22 | 43045525 | Higher in Drinkers |
| cg00945719 | 19 | 39971230 | Higher in Drinkers |
| cg00949922 | 1 | 16514382 | Higher in Drinkers |
| cg00952145 | 20 | 57417152 | Higher in Drinkers |
| cg00952576 | 6 | 114175901 | Higher in Drinkers |
| cg00955089 | 6 | 11878092 | Lower in Drinkers |
| cg00958217 | 1 | 6681584 | Higher in Drinkers |
| cg00960197 | 1 | 16161098 | Higher in Drinkers |
| cg00964109 | 15 | 74753785 | Higher in Drinkers |
| cg00970015 | 12 | 2904419 | Higher in Drinkers |
| cg00972296 | 5 | 176450006 | Higher in Drinkers |
| cg00977690 | X | 24167334 | Higher in Drinkers |
| cg00977744 | 17 | 27139688 | Higher in Drinkers |
| cg00977805 | 1 | 205197845 | Higher in Drinkers |
| cg00979307 | 3 | 47889555 | Higher in Drinkers |
| cg00979634 | 1 | 16011290 | Higher in Drinkers |
| cg00980331 | 2 | 55746625 | Higher in Drinkers |
| cg00981267 | 22 | 46402486 | Higher in Drinkers |
| cg00981415 | 19 | 40502931 | Higher in Drinkers |
| cg00983485 | 15 | 31284262 | Higher in Drinkers |
| cg00984618 | 10 | 96122660 | Higher in Drinkers |
| cg00986762 | 1 | 36107072 | Higher in Drinkers |
| cg00991447 | 16 | 88072689 | Higher in Drinkers |
| cg00995047 | 5 | 1634460 | Higher in Drinkers |
| cg00995327 | 3 | 142838847 | Higher in Drinkers |
| cg00995584 | 10 | 75757877 | Higher in Drinkers |
| cg00997720 | 19 | 39616233 | Higher in Drinkers |
| cg01000365 | 8 | 124428803 | Higher in Drinkers |
| cg01002125 | 1 | 15853764 | Higher in Drinkers |
| cg01003815 | 9 | 5184060 | Lower in Drinkers |
| cg01009875 | 1 | 165738180 | Higher in Drinkers |
| cg01017344 | 1 | 225615852 | Higher in Drinkers |
| cg01019163 | 3 | 43663675 | Higher in Drinkers |
| cg01019362 | 1 | 53163908 | Higher in Drinkers |

| | | | |
|---|---|---|---|
| cg01020399 | 1 | 249153122 | Higher in Drinkers |
| cg01021975 | 22 | 43570314 | Higher in Drinkers |
| cg01022871 | 4 | 146654614 | Higher in Drinkers |
| cg01022951 | 4 | 100815818 | Higher in Drinkers |
| cg01023053 | 1 | 87797123 | Higher in Drinkers |
| cg01023668 | 1 | 114471714 | Higher in Drinkers |
| cg01023703 | 16 | 1393766 | Higher in Drinkers |
| cg01025838 | 12 | 132653430 | Higher in Drinkers |
| cg01025891 | 7 | 99717060 | Higher in Drinkers |
| cg01025954 | 8 | 144263025 | Lower in Drinkers |
| cg01026373 | 5 | 141071769 | Higher in Drinkers |
| cg01028142 | 2 | 7004578 | Higher in Drinkers |
| cg01028457 | 3 | 152878518 | Higher in Drinkers |
| cg01028869 | 1 | 46598456 | Higher in Drinkers |
| cg01029838 | 7 | 77428748 | Higher in Drinkers |
| cg01029867 | 8 | 145961147 | Higher in Drinkers |
| cg01030973 | 1 | 2574695 | Higher in Drinkers |
| cg01031100 | 19 | 16644066 | Lower in Drinkers |
| cg01033205 | 8 | 107876626 | Lower in Drinkers |
| cg01035038 | 14 | 88459686 | Higher in Drinkers |
| cg01035528 | 12 | 123460159 | Higher in Drinkers |
| cg01035945 | 6 | 28317393 | Higher in Drinkers |
| cg01036148 | 1 | 201951866 | Higher in Drinkers |
| cg01040759 | 2 | 86116384 | Higher in Drinkers |
| cg01044076 | 6 | 5261366 | Higher in Drinkers |
| cg01045118 | 17 | 33814163 | Higher in Drinkers |
| cg01048253 | 15 | 83679867 | Higher in Drinkers |
| cg01049188 | 1 | 151227128 | Higher in Drinkers |
| cg01049274 | 8 | 146228340 | Higher in Drinkers |
| cg01050433 | 15 | 41851042 | Higher in Drinkers |
| cg01050965 | 5 | 177650821 | Higher in Drinkers |
| cg01051318 | 2 | 27440764 | Higher in Drinkers |
| cg01053714 | 15 | 34631762 | Higher in Drinkers |
| cg01055281 | 16 | 50746052 | Higher in Drinkers |
| cg01057962 | 3 | 187463312 | Higher in Drinkers |

| | | | |
|---|---|---|---|
| cg01060952 | 17 | 48424106 | Higher in Drinkers |
| cg01061575 | 22 | 45098367 | Higher in Drinkers |
| cg01065592 | 7 | 157215172 | Higher in Drinkers |
| cg01066465 | 1 | 31191582 | Higher in Drinkers |
| cg01067963 | 22 | 22222305 | Higher in Drinkers |
| cg01068014 | 13 | 92000225 | Higher in Drinkers |
| cg01068240 | 1 | 43889011 | Higher in Drinkers |
| cg01069256 | 8 | 79577942 | Higher in Drinkers |
| cg01071644 | 9 | 139138751 | Higher in Drinkers |
| cg01073837 | 8 | 38757859 | Higher in Drinkers |
| cg01074305 | 12 | 132882872 | Higher in Drinkers |
| cg01074795 | 22 | 20940421 | Higher in Drinkers |
| cg01077616 | 6 | 42017945 | Lower in Drinkers |
| cg01077724 | 1 | 75590483 | Higher in Drinkers |
| cg01079126 | X | 149861641 | Higher in Drinkers |
| cg01083040 | 15 | 73973808 | Higher in Drinkers |
| cg01083434 | 7 | 40174191 | Higher in Drinkers |
| cg01084685 | 14 | 20923741 | Higher in Drinkers |
| cg01087382 | 6 | 91297190 | Higher in Drinkers |
| cg01087594 | 20 | 3762116 | Higher in Drinkers |
| cg01087645 | 16 | 28503407 | Higher in Drinkers |
| cg01087710 | 16 | 67144175 | Higher in Drinkers |
| cg01088404 | 12 | 48214523 | Higher in Drinkers |
| cg01088726 | 4 | 163124839 | Lower in Drinkers |
| cg01089838 | 16 | 88091471 | Lower in Drinkers |
| cg01091951 | 5 | 42993450 | Higher in Drinkers |
| cg01092528 | 4 | 76861103 | Higher in Drinkers |
| cg01094301 | 19 | 47745212 | Higher in Drinkers |
| cg01096752 | 19 | 49468454 | Higher in Drinkers |
| cg01097907 | 5 | 3608511 | Lower in Drinkers |
| cg01098812 | 14 | 77591726 | Higher in Drinkers |
| cg01099470 | 2 | 131103656 | Lower in Drinkers |
| cg01100525 | 7 | 44083715 | Higher in Drinkers |
| cg01101178 | 1 | 2198760 | Higher in Drinkers |
| cg01102197 | 9 | 135753538 | Higher in Drinkers |

| | | | |
|---|---|---|---|
| cg01104045 | 5 | 110560587 | Higher in Drinkers |
| cg01107741 | 17 | 77006080 | Higher in Drinkers |
| cg01107801 | 17 | 6938938 | Higher in Drinkers |
| cg01108112 | 9 | 139254189 | Higher in Drinkers |
| cg01110797 | 6 | 11093513 | Higher in Drinkers |
| cg01112452 | X | 117958532 | Higher in Drinkers |
| cg01116067 | 1 | 2461838 | Higher in Drinkers |
| cg01117627 | 14 | 100150713 | Higher in Drinkers |
| cg01118031 | 16 | 15149275 | Higher in Drinkers |
| cg01118451 | 13 | 44361220 | Higher in Drinkers |
| cg01118653 | 16 | 88110441 | Lower in Drinkers |
| cg01120898 | 3 | 190231382 | Higher in Drinkers |
| cg01121830 | X | 38186700 | Higher in Drinkers |
| cg01125329 | 15 | 30918328 | Higher in Drinkers |
| cg01128044 | 16 | 31470247 | Higher in Drinkers |
| cg01130771 | 5 | 159414197 | Higher in Drinkers |
| cg01134297 | 16 | 90014983 | Higher in Drinkers |
| cg01136191 | 2 | 97215100 | Higher in Drinkers |
| cg01137198 | 12 | 111020449 | Higher in Drinkers |
| cg01138972 | 6 | 31509891 | Higher in Drinkers |
| cg01139526 | 5 | 139682850 | Higher in Drinkers |
| cg01140006 | 16 | 57701999 | Higher in Drinkers |
| cg01141043 | 14 | 65007050 | Higher in Drinkers |
| cg01141973 | 5 | 102455888 | Higher in Drinkers |
| cg01145389 | 1 | 51433840 | Higher in Drinkers |
| cg01149192 | 5 | 180231058 | Higher in Drinkers |
| cg01151699 | 22 | 37099259 | Higher in Drinkers |
| cg01152408 | 6 | 41496060 | Higher in Drinkers |
| cg01153132 | 6 | 119400114 | Higher in Drinkers |
| cg01153817 | 11 | 17409509 | Lower in Drinkers |
| cg01155847 | 17 | 34948071 | Higher in Drinkers |
| cg01157304 | 4 | 39639723 | Higher in Drinkers |
| cg01158937 | 10 | 101190385 | Higher in Drinkers |
| cg01161597 | 8 | 120844978 | Higher in Drinkers |
| cg01161889 | 6 | 27145367 | Higher in Drinkers |

| | | | |
|---|---|---|---|
| cg01161936 | 11 | 57224878 | Higher in Drinkers |
| cg01163790 | 16 | 50582193 | Higher in Drinkers |
| cg01164291 | 10 | 13699426 | Higher in Drinkers |
| cg01165575 | 16 | 30075904 | Higher in Drinkers |
| cg01167496 | 9 | 74526070 | Higher in Drinkers |
| cg01170099 | 14 | 82000431 | Higher in Drinkers |
| cg01172049 | 12 | 132286526 | Higher in Drinkers |
| cg01174264 | 4 | 80992999 | Higher in Drinkers |
| cg01175876 | 4 | 1738760 | Higher in Drinkers |
| cg01177524 | 6 | 11232933 | Higher in Drinkers |
| cg01177907 | 16 | 3164694 | Lower in Drinkers |
| cg01179674 | 20 | 43150968 | Higher in Drinkers |
| cg01182159 | 16 | 89762169 | Higher in Drinkers |
| cg01184149 | 6 | 34498918 | Lower in Drinkers |
| cg01184522 | 1 | 247495818 | Higher in Drinkers |
| cg01185350 | 16 | 75681490 | Higher in Drinkers |
| cg01185801 | 11 | 65265397 | Higher in Drinkers |
| cg01188574 | 19 | 925914 | Higher in Drinkers |
| cg01190522 | 6 | 144606245 | Higher in Drinkers |
| cg01194468 | 9 | 33264774 | Higher in Drinkers |
| cg01195198 | 18 | 18692028 | Higher in Drinkers |
| cg01196712 | 3 | 167812510 | Higher in Drinkers |
| cg01202521 | 16 | 1360231 | Higher in Drinkers |
| cg01202751 | 6 | 143248085 | Higher in Drinkers |
| cg01208563 | 14 | 75746307 | Higher in Drinkers |
| cg01210264 | 4 | 114792378 | Higher in Drinkers |
| cg01211396 | 6 | 30624478 | Higher in Drinkers |
| cg01220033 | 9 | 131419100 | Higher in Drinkers |
| cg01220264 | 4 | 83956141 | Higher in Drinkers |
| cg01220822 | 9 | 139407979 | Higher in Drinkers |
| cg01221207 | 20 | 33680493 | Higher in Drinkers |
| cg01221637 | 20 | 31071944 | Higher in Drinkers |
| cg01222684 | 5 | 159435961 | Higher in Drinkers |
| cg01224063 | 15 | 99395633 | Higher in Drinkers |
| cg01225095 | 12 | 32909323 | Higher in Drinkers |

| | | | |
|---|---|---|---|
| cg01225298 | X | 132091287 | Higher in Drinkers |
| cg01225317 | 1 | 205473878 | Higher in Drinkers |
| cg01229873 | 16 | 69373940 | Higher in Drinkers |
| cg01230160 | 2 | 234263768 | Higher in Drinkers |
| cg01230254 | 16 | 87376350 | Higher in Drinkers |
| cg01231485 | 12 | 133140633 | Higher in Drinkers |
| cg01232492 | 3 | 172429000 | Higher in Drinkers |
| cg01232604 | 7 | 5632262 | Higher in Drinkers |
| cg01233518 | 21 | 44837158 | Lower in Drinkers |
| cg01233897 | 5 | 56060091 | Higher in Drinkers |
| cg01234645 | 3 | 111393543 | Higher in Drinkers |
| cg01234929 | 11 | 4115909 | Higher in Drinkers |
| cg01240483 | 11 | 93861934 | Higher in Drinkers |
| cg01241007 | 22 | 39953001 | Higher in Drinkers |
| cg01243586 | 11 | 18270548 | Higher in Drinkers |
| cg01244134 | 2 | 25426151 | Higher in Drinkers |
| cg01244877 | X | 153598902 | Higher in Drinkers |
| cg01246405 | 11 | 3876562 | Higher in Drinkers |
| cg01247273 | 6 | 112318395 | Higher in Drinkers |
| cg01248866 | 12 | 32260000 | Higher in Drinkers |
| cg01251714 | 20 | 56285394 | Higher in Drinkers |
| cg01253107 | 9 | 35102903 | Higher in Drinkers |
| cg01253826 | 2 | 202316104 | Higher in Drinkers |
| cg01254559 | 10 | 112254100 | Higher in Drinkers |
| cg01257601 | 16 | 4815648 | Higher in Drinkers |
| cg01258061 | 17 | 43275464 | Higher in Drinkers |
| cg01262913 | 21 | 38580486 | Higher in Drinkers |
| cg01263169 | 9 | 126031334 | Higher in Drinkers |
| cg01263901 | 20 | 37554897 | Higher in Drinkers |
| cg01265860 | 21 | 36256316 | Higher in Drinkers |
| cg01266790 | 14 | 105781312 | Higher in Drinkers |
| cg01269344 | 21 | 33246216 | Higher in Drinkers |
| cg01273287 | 14 | 62228901 | Higher in Drinkers |
| cg01273994 | 14 | 68286939 | Higher in Drinkers |
| cg01274826 | 19 | 12596128 | Higher in Drinkers |

| | | | |
|---|---|---|---|
| cg01274846 | X | 152683499 | Lower in Drinkers |
| cg01277763 | 12 | 123011700 | Higher in Drinkers |
| cg01278696 | 4 | 144434369 | Higher in Drinkers |
| cg01279709 | 13 | 28196083 | Higher in Drinkers |
| cg01281038 | 16 | 67966256 | Lower in Drinkers |
| cg01283863 | 20 | 33863759 | Higher in Drinkers |
| cg01284721 | 15 | 40780499 | Higher in Drinkers |
| cg01287788 | 2 | 86362935 | Higher in Drinkers |
| cg01288184 | 13 | 20811408 | Higher in Drinkers |
| cg01290580 | 14 | 103851502 | Higher in Drinkers |
| cg01291508 | 17 | 80040974 | Higher in Drinkers |
| cg01294023 | 19 | 41816151 | Higher in Drinkers |
| cg01295022 | 11 | 100558647 | Higher in Drinkers |
| cg01295518 | 3 | 238392 | Higher in Drinkers |
| cg01297367 | 17 | 54857860 | Higher in Drinkers |
| cg01297397 | 1 | 150206972 | Higher in Drinkers |
| cg01298356 | 11 | 64889837 | Higher in Drinkers |
| cg01299282 | 16 | 70323049 | Higher in Drinkers |
| cg01299496 | 15 | 34635504 | Higher in Drinkers |
| cg01299854 | 22 | 21867049 | Higher in Drinkers |
| cg01300778 | 16 | 9184995 | Higher in Drinkers |
| cg01306410 | 9 | 69147338 | Higher in Drinkers |
| cg01307507 | 17 | 77751480 | Higher in Drinkers |
| cg01308483 | 5 | 1770031 | Lower in Drinkers |
| cg01312039 | 7 | 6662789 | Higher in Drinkers |
| cg01312837 | 16 | 3923772 | Higher in Drinkers |
| cg01314003 | 19 | 36705648 | Higher in Drinkers |
| cg01316516 | 11 | 18415964 | Higher in Drinkers |
| cg01319727 | 5 | 14487268 | Higher in Drinkers |
| cg01321836 | 21 | 16436497 | Higher in Drinkers |
| cg01321872 | 6 | 30882269 | Higher in Drinkers |
| cg01324115 | 19 | 42722189 | Higher in Drinkers |
| cg01324883 | 3 | 23244690 | Higher in Drinkers |
| cg01330762 | 19 | 44030756 | Higher in Drinkers |
| cg01331191 | 7 | 107383827 | Higher in Drinkers |

| | | | |
|---|---|---|---|
| cg01333619 | 11 | 134094250 | Higher in Drinkers |
| cg01333713 | 19 | 506852 | Higher in Drinkers |
| cg01335042 | 19 | 3572516 | Higher in Drinkers |
| cg01337439 | 15 | 64995501 | Higher in Drinkers |
| cg01338474 | 19 | 41782099 | Higher in Drinkers |
| cg01338599 | 20 | 30697450 | Higher in Drinkers |
| cg01338658 | 1 | 182992728 | Higher in Drinkers |
| cg01340314 | 1 | 202114058 | Higher in Drinkers |
| cg01343084 | X | 54521658 | Higher in Drinkers |
| cg01344859 | 14 | 55518182 | Higher in Drinkers |
| cg01348873 | 3 | 52349823 | Higher in Drinkers |
| cg01349093 | 3 | 107241928 | Higher in Drinkers |
| cg01350440 | 11 | 63439155 | Higher in Drinkers |
| cg01351869 | 15 | 80215929 | Higher in Drinkers |
| cg01352076 | 6 | 168363221 | Higher in Drinkers |
| cg01352921 | 7 | 100210343 | Higher in Drinkers |
| cg01353524 | 17 | 43237975 | Higher in Drinkers |
| cg01354384 | 10 | 74057347 | Higher in Drinkers |
| cg01354656 | 6 | 151411710 | Higher in Drinkers |
| cg01355739 | 20 | 57416888 | Higher in Drinkers |
| cg01355875 | 4 | 10118935 | Higher in Drinkers |
| cg01357897 | 17 | 9246710 | Lower in Drinkers |
| cg01359895 | 17 | 3796066 | Higher in Drinkers |
| cg01360325 | 10 | 105127811 | Higher in Drinkers |
| cg01360605 | 20 | 58983676 | Higher in Drinkers |
| cg01361777 | 10 | 79629102 | Higher in Drinkers |
| cg01362115 | 15 | 68075218 | Higher in Drinkers |
| cg01366085 | 8 | 103668528 | Higher in Drinkers |
| cg01369233 | 11 | 1316833 | Higher in Drinkers |
| cg01371420 | 2 | 33327715 | Higher in Drinkers |
| cg01372898 | 6 | 31093165 | Higher in Drinkers |
| cg01373911 | 1 | 6269367 | Higher in Drinkers |
| cg01376245 | 2 | 97426602 | Higher in Drinkers |
| cg01380373 | 16 | 30010946 | Higher in Drinkers |
| cg01383668 | 15 | 52860841 | Higher in Drinkers |

| | | | |
|---|---|---|---|
| cg01386121 | 16 | 22012560 | Higher in Drinkers |
| cg01386868 | 19 | 1816383 | Higher in Drinkers |
| cg01394093 | 4 | 103266697 | Higher in Drinkers |
| cg01395659 | 5 | 6633232 | Higher in Drinkers |
| cg01396275 | 19 | 4961535 | Lower in Drinkers |
| cg01396580 | 1 | 52832012 | Higher in Drinkers |
| cg01398299 | 7 | 2761640 | Lower in Drinkers |
| cg01398912 | X | 147583273 | Higher in Drinkers |
| cg01400987 | 2 | 55844294 | Higher in Drinkers |
| cg01404182 | 6 | 170102495 | Higher in Drinkers |
| cg01405684 | 16 | 30369820 | Lower in Drinkers |
| cg01406075 | 11 | 58731104 | Higher in Drinkers |
| cg01406341 | 2 | 220042724 | Higher in Drinkers |
| cg01412321 | 7 | 36429799 | Higher in Drinkers |
| cg01412936 | 1 | 43637799 | Higher in Drinkers |
| cg01413405 | 17 | 36858329 | Higher in Drinkers |
| cg01414882 | 7 | 27192480 | Lower in Drinkers |
| cg01415527 | 19 | 1110591 | Lower in Drinkers |
| cg01419084 | 19 | 36236615 | Higher in Drinkers |
| cg01420215 | 2 | 224821720 | Higher in Drinkers |
| cg01423027 | X | 15873247 | Higher in Drinkers |
| cg01423077 | 20 | 60719442 | Higher in Drinkers |
| cg01423251 | 6 | 32765322 | Higher in Drinkers |
| cg01423563 | 3 | 9851850 | Higher in Drinkers |
| cg01427435 | 4 | 110355680 | Higher in Drinkers |
| cg01428115 | 11 | 46402506 | Higher in Drinkers |
| cg01428195 | 9 | 139349673 | Higher in Drinkers |
| cg01429256 | 17 | 17687834 | Higher in Drinkers |
| cg01431960 | 19 | 3806098 | Higher in Drinkers |
| cg01432010 | 19 | 8006001 | Higher in Drinkers |
| cg01433443 | 1 | 6673467 | Higher in Drinkers |
| cg01436705 | 5 | 171434426 | Higher in Drinkers |
| cg01438685 | 7 | 907934 | Higher in Drinkers |
| cg01439854 | 16 | 70323367 | Higher in Drinkers |
| cg01441172 | 17 | 7142946 | Higher in Drinkers |

| | | | |
|---|---|---|---|
| cg01443440 | 11 | 119252448 | Higher in Drinkers |
| cg01444801 | 10 | 135216882 | Lower in Drinkers |
| cg01446372 | 21 | 30365398 | Higher in Drinkers |
| cg01446477 | 1 | 28696170 | Higher in Drinkers |
| cg01449224 | 4 | 123073775 | Higher in Drinkers |
| cg01449415 | 16 | 3184811 | Higher in Drinkers |
| cg01453157 | 17 | 1639375 | Lower in Drinkers |
| cg01454148 | 17 | 7129155 | Higher in Drinkers |
| cg01456440 | 13 | 21714647 | Higher in Drinkers |
| cg01456691 | 6 | 11382556 | Higher in Drinkers |
| cg01456938 | 4 | 2470303 | Higher in Drinkers |
| cg01458961 | 4 | 102269425 | Higher in Drinkers |
| cg01459033 | 16 | 77228497 | Higher in Drinkers |
| cg01462040 | X | 147582071 | Higher in Drinkers |
| cg01465169 | 17 | 27944849 | Higher in Drinkers |
| cg01466035 | 7 | 139477480 | Higher in Drinkers |
| cg01466967 | 5 | 59995837 | Higher in Drinkers |
| cg01467739 | 8 | 37595333 | Higher in Drinkers |
| cg01468171 | 16 | 48278340 | Higher in Drinkers |
| cg01469549 | 7 | 157129690 | Higher in Drinkers |
| cg01470384 | 15 | 68155873 | Higher in Drinkers |
| cg01474600 | 16 | 315564 | Higher in Drinkers |
| cg01474603 | 12 | 100536694 | Higher in Drinkers |
| cg01476739 | 11 | 71146764 | Higher in Drinkers |
| cg01476820 | 2 | 86333266 | Higher in Drinkers |
| cg01477633 | 10 | 71078714 | Higher in Drinkers |
| cg01477963 | 13 | 22032863 | Higher in Drinkers |
| cg01478628 | 11 | 20614302 | Lower in Drinkers |
| cg01479818 | 10 | 103986012 | Higher in Drinkers |
| cg01481734 | 1 | 161369725 | Higher in Drinkers |
| cg01482279 | 17 | 38083788 | Higher in Drinkers |
| cg01482980 | 7 | 92861284 | Higher in Drinkers |
| cg01484320 | 1 | 109757057 | Higher in Drinkers |
| cg01485010 | 7 | 143106010 | Higher in Drinkers |
| cg01485326 | 16 | 88787689 | Lower in Drinkers |

| | | | |
|---|---|---|---|
| cg01486020 | X | 71131509 | Higher in Drinkers |
| cg01490535 | 11 | 71499006 | Higher in Drinkers |
| cg01490870 | 19 | 12722019 | Higher in Drinkers |
| cg01491540 | 17 | 28256424 | Higher in Drinkers |
| cg01498655 | 16 | 67694768 | Higher in Drinkers |
| cg01500001 | 17 | 7198087 | Higher in Drinkers |
| cg01500100 | 22 | 29168505 | Higher in Drinkers |
| cg01501461 | 19 | 54684477 | Higher in Drinkers |
| cg01503881 | 20 | 57607569 | Higher in Drinkers |
| cg01504424 | 11 | 27385006 | Higher in Drinkers |
| cg01504489 | 7 | 1131626 | Higher in Drinkers |
| cg01507044 | 13 | 23949294 | Higher in Drinkers |
| cg01507046 | 17 | 48637818 | Higher in Drinkers |
| cg01508380 | 14 | 23305585 | Higher in Drinkers |
| cg01508757 | 12 | 125450326 | Higher in Drinkers |
| cg01510332 | 19 | 59087201 | Higher in Drinkers |
| cg01513538 | 9 | 4804014 | Higher in Drinkers |
| cg01513611 | 19 | 5904233 | Higher in Drinkers |
| cg01515896 | 17 | 77290812 | Higher in Drinkers |
| cg01515913 | 1 | 39339553 | Higher in Drinkers |
| cg01516282 | 1 | 39492474 | Higher in Drinkers |
| cg01518357 | 15 | 65822686 | Higher in Drinkers |
| cg01519261 | 21 | 36421467 | Higher in Drinkers |
| cg01520443 | 3 | 50330026 | Higher in Drinkers |
| cg01520983 | 11 | 130184819 | Higher in Drinkers |
| cg01521250 | 11 | 62539321 | Higher in Drinkers |
| cg01523370 | 3 | 120068337 | Higher in Drinkers |
| cg01525597 | 12 | 1739061 | Higher in Drinkers |
| cg01527394 | 22 | 47368387 | Higher in Drinkers |
| cg01530687 | 16 | 85646973 | Higher in Drinkers |
| cg01532694 | 8 | 8243576 | Higher in Drinkers |
| cg01534273 | 19 | 1877553 | Higher in Drinkers |
| cg01538522 | 20 | 57463974 | Higher in Drinkers |
| cg01542644 | 6 | 26458326 | Higher in Drinkers |
| cg01545575 | 17 | 4700069 | Higher in Drinkers |

| | | | |
|---|---|---|---|
| cg01549227 | 9 | 124980074 | Higher in Drinkers |
| cg01549404 | 16 | 55358636 | Higher in Drinkers |
| cg01549820 | 15 | 67547218 | Higher in Drinkers |
| cg01553632 | 3 | 32509364 | Higher in Drinkers |
| cg01554437 | 14 | 21091422 | Higher in Drinkers |
| cg01555122 | 2 | 55276516 | Higher in Drinkers |
| cg01555791 | 17 | 1012288 | Higher in Drinkers |
| cg01556457 | 15 | 64443744 | Higher in Drinkers |
| cg01556979 | 22 | 50727524 | Higher in Drinkers |
| cg01559356 | 19 | 2282568 | Higher in Drinkers |
| cg01561271 | 1 | 146696779 | Higher in Drinkers |
| cg01561878 | 7 | 27200681 | Higher in Drinkers |
| cg01562552 | 3 | 127543493 | Higher in Drinkers |
| cg01566217 | 1 | 208084255 | Higher in Drinkers |
| cg01567615 | 13 | 114808107 | Lower in Drinkers |
| cg01572652 | 12 | 103695883 | Higher in Drinkers |
| cg01572979 | 8 | 27455004 | Higher in Drinkers |
| cg01574564 | 7 | 115851459 | Higher in Drinkers |
| cg01577187 | 2 | 106362832 | Higher in Drinkers |
| cg01578057 | 4 | 89618667 | Higher in Drinkers |
| cg01579322 | X | 54209148 | Higher in Drinkers |
| cg01580655 | 8 | 10649960 | Higher in Drinkers |
| cg01581050 | 7 | 139256124 | Lower in Drinkers |
| cg01584634 | 11 | 72525302 | Higher in Drinkers |
| cg01585069 | 8 | 70602467 | Higher in Drinkers |
| cg01585985 | 5 | 176730172 | Higher in Drinkers |
| cg01586524 | 8 | 67341819 | Higher in Drinkers |
| cg01592662 | 16 | 15150200 | Higher in Drinkers |
| cg01596892 | 20 | 54967413 | Higher in Drinkers |
| cg01601628 | 5 | 149792348 | Higher in Drinkers |
| cg01604430 | 17 | 75877899 | Higher in Drinkers |
| cg01605739 | 1 | 95500538 | Higher in Drinkers |
| cg01607369 | 11 | 7598673 | Higher in Drinkers |
| cg01607897 | 8 | 103667900 | Higher in Drinkers |
| cg01609705 | 8 | 38240669 | Higher in Drinkers |

| | | | |
|---|---|---|---|
| cg01610838 | 4 | 186131545 | Higher in Drinkers |
| cg01611428 | 5 | 666524 | Higher in Drinkers |
| cg01612883 | 12 | 125023115 | Higher in Drinkers |
| cg01614615 | 1 | 14075923 | Higher in Drinkers |
| cg01623663 | 11 | 66244423 | Higher in Drinkers |
| cg01627669 | 12 | 8068706 | Lower in Drinkers |
| cg01628253 | 1 | 154244960 | Higher in Drinkers |
| cg01628954 | 18 | 60190696 | Higher in Drinkers |
| cg01633858 | 22 | 43547540 | Higher in Drinkers |
| cg01636561 | 2 | 225906664 | Higher in Drinkers |
| cg01640443 | 14 | 102510281 | Higher in Drinkers |
| cg01640444 | 3 | 193311744 | Higher in Drinkers |
| cg01642415 | 14 | 32181048 | Higher in Drinkers |
| cg01644723 | 8 | 146228246 | Higher in Drinkers |
| cg01646147 | 11 | 46638831 | Higher in Drinkers |
| cg01647729 | 14 | 100594643 | Higher in Drinkers |
| cg01652532 | 20 | 32253007 | Higher in Drinkers |
| cg01655123 | 19 | 44008476 | Higher in Drinkers |
| cg01655341 | 19 | 41903697 | Higher in Drinkers |
| cg01656221 | 2 | 179278558 | Higher in Drinkers |
| cg01657408 | 5 | 158634989 | Higher in Drinkers |
| cg01657493 | 2 | 64681082 | Higher in Drinkers |
| cg01658259 | 14 | 24337143 | Higher in Drinkers |
| cg01658265 | 3 | 194406362 | Higher in Drinkers |
| cg01658908 | 12 | 56110396 | Higher in Drinkers |
| cg01663768 | 11 | 35160843 | Higher in Drinkers |
| cg01665846 | 22 | 40742083 | Higher in Drinkers |
| cg01669185 | 6 | 11430614 | Higher in Drinkers |
| cg01674009 | 19 | 45655294 | Higher in Drinkers |
| cg01678084 | 15 | 67022087 | Lower in Drinkers |
| cg01678313 | 3 | 13083892 | Higher in Drinkers |
| cg01678893 | 19 | 13049949 | Higher in Drinkers |
| cg01682021 | 4 | 144480376 | Higher in Drinkers |
| cg01684318 | 3 | 183415696 | Higher in Drinkers |
| cg01684528 | 16 | 4233614 | Higher in Drinkers |

| | | | |
|---|---|---|---|
| cg01685246 | 16 | 30538016 | Higher in Drinkers |
| cg01686044 | 19 | 45754802 | Higher in Drinkers |
| cg01686522 | 16 | 88905165 | Lower in Drinkers |
| cg01687051 | 16 | 278852 | Higher in Drinkers |
| cg01687680 | 16 | 49312238 | Higher in Drinkers |
| cg01687864 | 7 | 120591397 | Higher in Drinkers |
| cg01693157 | 2 | 220118273 | Higher in Drinkers |
| cg01694451 | 11 | 1854224 | Higher in Drinkers |
| cg01697743 | 11 | 82997076 | Higher in Drinkers |
| cg01698708 | 1 | 28100000 | Higher in Drinkers |
| cg01699028 | 15 | 25322897 | Higher in Drinkers |
| cg01704332 | 1 | 151020263 | Higher in Drinkers |
| cg01705566 | 16 | 19535184 | Higher in Drinkers |
| cg01710146 | 12 | 117348848 | Higher in Drinkers |
| cg01710897 | 15 | 91497902 | Higher in Drinkers |
| cg01712359 | 16 | 88783355 | Lower in Drinkers |
| cg01712700 | 2 | 241535695 | Higher in Drinkers |
| cg01713485 | 2 | 119613275 | Higher in Drinkers |
| cg01715551 | 20 | 57426789 | Higher in Drinkers |
| cg01716083 | 6 | 30029143 | Higher in Drinkers |
| cg01716316 | 17 | 40897182 | Higher in Drinkers |
| cg01717706 | 16 | 11349308 | Higher in Drinkers |
| cg01720920 | 14 | 104185151 | Higher in Drinkers |
| cg01720991 | 8 | 81399518 | Higher in Drinkers |
| cg01724336 | 1 | 111992067 | Higher in Drinkers |
| cg01725773 | 14 | 23475850 | Higher in Drinkers |
| cg01727434 | 2 | 152118530 | Higher in Drinkers |
| cg01728445 | 17 | 60559732 | Higher in Drinkers |
| cg01729862 | 16 | 1824041 | Higher in Drinkers |
| cg01730976 | 17 | 8076883 | Higher in Drinkers |
| cg01731360 | 5 | 49736671 | Higher in Drinkers |
| cg01733271 | 16 | 58521840 | Higher in Drinkers |
| cg01733673 | 4 | 113152850 | Higher in Drinkers |
| cg01733795 | 17 | 7465439 | Higher in Drinkers |
| cg01735318 | 2 | 24307664 | Higher in Drinkers |

| | | | |
|---|---|---|---|
| cg01736403 | 3 | 52312682 | Higher in Drinkers |
| cg01737828 | 15 | 75230659 | Higher in Drinkers |
| cg01739965 | 2 | 64246297 | Higher in Drinkers |
| cg01741878 | 17 | 79269038 | Higher in Drinkers |
| cg01744160 | 15 | 83680526 | Higher in Drinkers |
| cg01746522 | 15 | 20500830 | Higher in Drinkers |
| cg01750507 | 18 | 158229 | Higher in Drinkers |
| cg01751245 | 2 | 65593761 | Higher in Drinkers |
| cg01752898 | X | 38186917 | Higher in Drinkers |
| cg01754848 | 16 | 427756 | Higher in Drinkers |
| cg01755467 | 6 | 30890617 | Higher in Drinkers |
| cg01758167 | 12 | 131357429 | Higher in Drinkers |
| cg01759413 | 5 | 180650114 | Higher in Drinkers |
| cg01759437 | 7 | 44925080 | Higher in Drinkers |
| cg01760580 | 11 | 68700879 | Higher in Drinkers |
| cg01762070 | 14 | 21101007 | Higher in Drinkers |
| cg01765063 | 2 | 237994925 | Higher in Drinkers |
| cg01766534 | 2 | 224822249 | Higher in Drinkers |
| cg01766941 | 1 | 92953907 | Higher in Drinkers |
| cg01767927 | 17 | 78821024 | Higher in Drinkers |
| cg01768385 | 15 | 22960745 | Higher in Drinkers |
| cg01770236 | 1 | 53164152 | Higher in Drinkers |
| cg01771673 | X | 106361539 | Higher in Drinkers |
| cg01771737 | 2 | 240199147 | Higher in Drinkers |
| cg01772663 | 8 | 30027362 | Higher in Drinkers |
| cg01773061 | 1 | 36863007 | Higher in Drinkers |
| cg01774454 | 1 | 179262772 | Higher in Drinkers |
| cg01774471 | 2 | 86790641 | Higher in Drinkers |
| cg01780109 | 16 | 81812606 | Higher in Drinkers |
| cg01784852 | 1 | 94703167 | Higher in Drinkers |
| cg01786994 | 15 | 78556945 | Higher in Drinkers |
| cg01788996 | 2 | 109403045 | Higher in Drinkers |
| cg01789463 | 5 | 177031478 | Higher in Drinkers |
| cg01799681 | 6 | 11043368 | Higher in Drinkers |
| cg01799862 | 16 | 67143802 | Higher in Drinkers |

| | | | |
|---|---|---|---|
| cg01802009 | 2 | 68694860 | Higher in Drinkers |
| cg01802073 | 14 | 54976343 | Higher in Drinkers |
| cg01802219 | 3 | 15468933 | Higher in Drinkers |
| cg01803125 | 7 | 75157456 | Higher in Drinkers |
| cg01804284 | 1 | 41157659 | Higher in Drinkers |
| cg01804827 | 5 | 126853558 | Higher in Drinkers |
| cg01805124 | 17 | 30814031 | Higher in Drinkers |
| cg01806741 | 6 | 1527072 | Higher in Drinkers |
| cg01811037 | 8 | 6565846 | Higher in Drinkers |
| cg01811561 | 16 | 67753396 | Higher in Drinkers |
| cg01815035 | 1 | 180601046 | Higher in Drinkers |
| cg01815906 | 1 | 246622633 | Higher in Drinkers |
| cg01816515 | 2 | 21022699 | Higher in Drinkers |
| cg01817009 | 16 | 67978182 | Higher in Drinkers |
| cg01821993 | 17 | 7412449 | Higher in Drinkers |
| cg01823269 | 3 | 50397107 | Higher in Drinkers |
| cg01826322 | 11 | 82997446 | Higher in Drinkers |
| cg01826728 | 7 | 100170610 | Higher in Drinkers |
| cg01830644 | 10 | 12110754 | Higher in Drinkers |
| cg01831743 | 12 | 110352941 | Higher in Drinkers |
| cg01833234 | 11 | 6592585 | Higher in Drinkers |
| cg01835695 | 5 | 180230959 | Higher in Drinkers |
| cg01838317 | 14 | 55369861 | Higher in Drinkers |
| cg01838544 | 16 | 57576594 | Higher in Drinkers |
| cg01839430 | 2 | 216177098 | Higher in Drinkers |
| cg01840268 | 6 | 26402776 | Higher in Drinkers |
| cg01843058 | 22 | 26908119 | Higher in Drinkers |
| cg01846065 | 2 | 153032369 | Higher in Drinkers |
| cg01852180 | 14 | 64971105 | Higher in Drinkers |
| cg01854842 | 20 | 49547693 | Higher in Drinkers |
| cg01856349 | 4 | 169931464 | Higher in Drinkers |
| cg01859312 | 8 | 145618658 | Higher in Drinkers |
| cg01859586 | X | 53254818 | Higher in Drinkers |
| cg01861740 | 7 | 2764486 | Lower in Drinkers |
| cg01862418 | 14 | 105953145 | Higher in Drinkers |

| | | | |
|---|---|---|---|
| cg01863808 | 14 | 24020586 | Higher in Drinkers |
| cg01864100 | 2 | 98274988 | Higher in Drinkers |
| cg01866098 | 22 | 24059229 | Higher in Drinkers |
| cg01866521 | 11 | 64646436 | Higher in Drinkers |
| cg01869554 | 15 | 90772557 | Higher in Drinkers |
| cg01869661 | 20 | 524496 | Higher in Drinkers |
| cg01869698 | 8 | 144886651 | Higher in Drinkers |
| cg01869960 | 2 | 136289456 | Higher in Drinkers |
| cg01870625 | 12 | 6981935 | Higher in Drinkers |
| cg01870865 | 3 | 48507087 | Lower in Drinkers |
| cg01873619 | 2 | 3493623 | Higher in Drinkers |
| cg01877967 | 7 | 56148907 | Lower in Drinkers |
| cg01878839 | 17 | 8126381 | Higher in Drinkers |
| cg01879591 | 2 | 242954430 | Lower in Drinkers |
| cg01881322 | 6 | 53660654 | Higher in Drinkers |
| cg01881870 | 1 | 45240812 | Higher in Drinkers |
| cg01882150 | 11 | 63933998 | Higher in Drinkers |
| cg01885202 | X | 18443457 | Higher in Drinkers |
| cg01885859 | 5 | 153569823 | Higher in Drinkers |
| cg01886077 | 2 | 98612542 | Higher in Drinkers |
| cg01887995 | 8 | 54569999 | Lower in Drinkers |
| cg01888206 | 1 | 36850933 | Higher in Drinkers |
| cg01888592 | 5 | 6714537 | Higher in Drinkers |
| cg01889169 | 7 | 927986 | Lower in Drinkers |
| cg01889448 | 6 | 32635871 | Lower in Drinkers |
| cg01890546 | 7 | 884588 | Higher in Drinkers |
| cg01892727 | 3 | 3221728 | Higher in Drinkers |
| cg01892874 | 3 | 158288706 | Lower in Drinkers |
| cg01893176 | 11 | 2721952 | Higher in Drinkers |
| cg01896432 | 4 | 68904160 | Lower in Drinkers |
| cg01898370 | 4 | 1283560 | Higher in Drinkers |
| cg01899154 | 3 | 56689211 | Higher in Drinkers |
| cg01900759 | 9 | 77501693 | Higher in Drinkers |
| cg01907644 | 5 | 150138530 | Higher in Drinkers |
| cg01907837 | 6 | 37321337 | Higher in Drinkers |

| | | | |
|---|---|---|---|
| cg01915525 | 12 | 132599943 | Higher in Drinkers |
| cg01916610 | 15 | 75342802 | Higher in Drinkers |
| cg01917209 | 3 | 49938721 | Higher in Drinkers |
| cg01918043 | 15 | 71054667 | Lower in Drinkers |
| cg01918534 | X | 118828926 | Higher in Drinkers |
| cg01919429 | 13 | 100154415 | Higher in Drinkers |
| cg01921368 | 15 | 75746777 | Higher in Drinkers |
| cg01922936 | 5 | 100239017 | Higher in Drinkers |
| cg01926348 | 4 | 185393810 | Higher in Drinkers |
| cg01926972 | 6 | 168476576 | Lower in Drinkers |
| cg01928068 | 11 | 43941594 | Higher in Drinkers |
| cg01929065 | 12 | 56122634 | Higher in Drinkers |
| cg01929377 | 13 | 37634127 | Lower in Drinkers |
| cg01931678 | 3 | 50365687 | Higher in Drinkers |
| cg01935036 | 1 | 32674191 | Higher in Drinkers |
| cg01939477 | 11 | 43602879 | Higher in Drinkers |
| cg01941219 | 13 | 98795021 | Higher in Drinkers |
| cg01942003 | 8 | 144776547 | Higher in Drinkers |
| cg01942719 | 1 | 12079274 | Higher in Drinkers |
| cg01943029 | 16 | 31715088 | Higher in Drinkers |
| cg01944087 | 15 | 69110737 | Higher in Drinkers |
| cg01944444 | 6 | 30688681 | Higher in Drinkers |
| cg01946193 | 20 | 47895123 | Higher in Drinkers |
| cg01947036 | 16 | 2802311 | Higher in Drinkers |
| cg01948390 | 11 | 22850866 | Higher in Drinkers |
| cg01954107 | 1 | 100731633 | Higher in Drinkers |
| cg01959238 | 16 | 85200915 | Higher in Drinkers |
| cg01960789 | 16 | 3184957 | Higher in Drinkers |
| cg01962969 | 21 | 37442104 | Higher in Drinkers |
| cg01963061 | 14 | 65879906 | Higher in Drinkers |
| cg01963278 | 6 | 30457850 | Higher in Drinkers |
| cg01963870 | 16 | 3790368 | Higher in Drinkers |
| cg01964262 | 13 | 97874638 | Higher in Drinkers |
| cg01965475 | 16 | 23701459 | Higher in Drinkers |
| cg01965751 | 17 | 38218791 | Higher in Drinkers |

| | | | |
|---|---|---|---|
| cg01967774 | 2 | 43453449 | Higher in Drinkers |
| cg01968759 | 4 | 146101151 | Higher in Drinkers |
| cg01970017 | 17 | 36908303 | Higher in Drinkers |
| cg01971363 | 7 | 150768318 | Lower in Drinkers |
| cg01973164 | 16 | 89972593 | Higher in Drinkers |
| cg01973725 | 5 | 80608537 | Higher in Drinkers |
| cg01977486 | 11 | 2019736 | Higher in Drinkers |
| cg01978544 | 6 | 30418858 | Higher in Drinkers |
| cg01979511 | 1 | 185126431 | Higher in Drinkers |
| cg01979603 | 6 | 84937631 | Higher in Drinkers |
| cg01980456 | 17 | 16266204 | Higher in Drinkers |
| cg01984237 | 9 | 71682105 | Higher in Drinkers |
| cg01985090 | 22 | 20104996 | Higher in Drinkers |
| cg01992590 | 17 | 48277042 | Higher in Drinkers |
| cg01992890 | 3 | 72897260 | Higher in Drinkers |
| cg01992990 | 1 | 202780680 | Higher in Drinkers |
| cg01997182 | 20 | 43104450 | Higher in Drinkers |
| cg02002684 | 7 | 149128631 | Higher in Drinkers |
| cg02004621 | 6 | 43027301 | Higher in Drinkers |
| cg02004723 | 20 | 42574341 | Higher in Drinkers |
| cg02005385 | 1 | 157108616 | Higher in Drinkers |
| cg02007150 | 6 | 30293518 | Higher in Drinkers |
| cg02008175 | 3 | 120315613 | Higher in Drinkers |
| cg02008544 | 8 | 22926600 | Higher in Drinkers |
| cg02013035 | 14 | 92572273 | Higher in Drinkers |
| cg02014809 | 22 | 20861768 | Higher in Drinkers |
| cg02018101 | 14 | 64320521 | Higher in Drinkers |
| cg02020296 | 15 | 96900272 | Higher in Drinkers |
| cg02025407 | 20 | 5986831 | Higher in Drinkers |
| cg02026475 | 16 | 20912113 | Higher in Drinkers |
| cg02027010 | 9 | 116163386 | Higher in Drinkers |
| cg02028332 | 19 | 19335919 | Higher in Drinkers |
| cg02029478 | 20 | 16269068 | Higher in Drinkers |
| cg02030275 | 20 | 31169126 | Higher in Drinkers |
| cg02030628 | 11 | 62554067 | Higher in Drinkers |

| | | | |
|---|---|---|---|
| cg02031303 | 17 | 47305050 | Higher in Drinkers |
| cg02032125 | 14 | 101000186 | Lower in Drinkers |
| cg02033694 | 16 | 29296797 | Higher in Drinkers |
| cg02034085 | 14 | 69261594 | Higher in Drinkers |
| cg02034102 | 9 | 37026739 | Higher in Drinkers |
| cg02034497 | 15 | 76031293 | Higher in Drinkers |
| cg02038323 | 12 | 121477093 | Higher in Drinkers |
| cg02039022 | 5 | 72112005 | Higher in Drinkers |
| cg02042605 | 17 | 74382166 | Higher in Drinkers |
| cg02044051 | 11 | 9634970 | Higher in Drinkers |
| cg02044161 | 3 | 136675705 | Higher in Drinkers |
| cg02046226 | 10 | 121410475 | Higher in Drinkers |
| cg02048890 | 18 | 33877274 | Higher in Drinkers |
| cg02049041 | 17 | 27085579 | Lower in Drinkers |
| cg02053171 | 7 | 74489585 | Higher in Drinkers |
| cg02056550 | Y | 8552374 | Higher in Drinkers |
| cg02057598 | 16 | 87904547 | Higher in Drinkers |
| cg02058632 | X | 30906829 | Higher in Drinkers |
| cg02059813 | 3 | 148805294 | Higher in Drinkers |
| cg02061213 | X | 107068771 | Higher in Drinkers |
| cg02062404 | 1 | 228295382 | Higher in Drinkers |
| cg02062731 | 16 | 69139444 | Higher in Drinkers |
| cg02063458 | 16 | 48190773 | Higher in Drinkers |
| cg02064798 | 4 | 1021291 | Lower in Drinkers |
| cg02070289 | 5 | 43066798 | Higher in Drinkers |
| cg02070354 | 2 | 219433199 | Higher in Drinkers |
| cg02070564 | 13 | 46038973 | Higher in Drinkers |
| cg02071439 | 9 | 139377021 | Higher in Drinkers |
| cg02071957 | 16 | 19191409 | Higher in Drinkers |
| cg02072256 | 9 | 124922169 | Higher in Drinkers |
| cg02072366 | 12 | 54345056 | Higher in Drinkers |
| cg02073545 | 12 | 133324729 | Higher in Drinkers |
| cg02075378 | 12 | 1800071 | Higher in Drinkers |
| cg02076355 | 10 | 45474372 | Higher in Drinkers |
| cg02076804 | 7 | 10979997 | Higher in Drinkers |

| | | | |
|---|---|---|---|
| cg02077561 | 1 | 6270963 | Higher in Drinkers |
| cg02077638 | 12 | 127257703 | Higher in Drinkers |
| cg02077793 | 19 | 10983098 | Higher in Drinkers |
| cg02079831 | 12 | 58014709 | Higher in Drinkers |
| cg02080260 | 17 | 43238036 | Higher in Drinkers |
| cg02081905 | 3 | 14988669 | Higher in Drinkers |
| cg02083029 | 6 | 44280859 | Higher in Drinkers |
| cg02083139 | 1 | 100503813 | Higher in Drinkers |
| cg02083373 | 5 | 74807542 | Higher in Drinkers |
| cg02083536 | 1 | 2445356 | Higher in Drinkers |
| cg02085276 | 1 | 222763438 | Higher in Drinkers |
| cg02085805 | 1 | 110527112 | Higher in Drinkers |
| cg02092098 | 20 | 20032981 | Higher in Drinkers |
| cg02098156 | 3 | 197401134 | Higher in Drinkers |
| cg02099313 | 1 | 231114956 | Higher in Drinkers |
| cg02099814 | 1 | 77748190 | Higher in Drinkers |
| cg02100305 | 11 | 73308991 | Higher in Drinkers |
| cg02100543 | 11 | 64879991 | Higher in Drinkers |
| cg02101693 | 1 | 11994533 | Higher in Drinkers |
| cg02105393 | Y | 2804282 | Higher in Drinkers |
| cg02105423 | 11 | 108093095 | Higher in Drinkers |
| cg02107163 | 2 | 241500091 | Higher in Drinkers |
| cg02107718 | 20 | 57463713 | Higher in Drinkers |
| cg02109139 | 13 | 112611279 | Lower in Drinkers |
| cg02111504 | 5 | 93954110 | Higher in Drinkers |
| cg02113449 | 13 | 48877641 | Higher in Drinkers |
| cg02114082 | 10 | 12306459 | Higher in Drinkers |
| cg02114449 | 3 | 20227940 | Higher in Drinkers |
| cg02115142 | 2 | 61921868 | Higher in Drinkers |
| cg02119220 | 5 | 5492724 | Higher in Drinkers |
| cg02121118 | 3 | 53195029 | Higher in Drinkers |
| cg02122920 | 6 | 42883534 | Higher in Drinkers |
| cg02130453 | 4 | 2537789 | Higher in Drinkers |
| cg02131512 | 16 | 29882803 | Lower in Drinkers |
| cg02133936 | 12 | 6859148 | Higher in Drinkers |

| | | | |
|---|---|---|---|
| cg02134200 | 1 | 153895546 | Higher in Drinkers |
| cg02134594 | 1 | 3632713 | Higher in Drinkers |
| cg02135523 | 12 | 14956701 | Higher in Drinkers |
| cg02136635 | 12 | 111348709 | Higher in Drinkers |
| cg02140097 | 12 | 110719074 | Higher in Drinkers |
| cg02141716 | 11 | 74460474 | Higher in Drinkers |
| cg02145220 | 15 | 79223378 | Higher in Drinkers |
| cg02148360 | 14 | 50065270 | Higher in Drinkers |
| cg02148421 | 22 | 37595162 | Higher in Drinkers |
| cg02148711 | X | 77041559 | Higher in Drinkers |
| cg02149314 | 7 | 137686706 | Higher in Drinkers |
| cg02150714 | 8 | 1876715 | Lower in Drinkers |
| cg02151120 | 11 | 71724287 | Higher in Drinkers |
| cg02154997 | 11 | 46397426 | Higher in Drinkers |
| cg02155262 | 4 | 178363707 | Higher in Drinkers |
| cg02155627 | 7 | 56032821 | Higher in Drinkers |
| cg02159999 | 8 | 30085163 | Higher in Drinkers |
| cg02160419 | 7 | 75807660 | Higher in Drinkers |
| cg02161115 | 1 | 76262373 | Higher in Drinkers |
| cg02162202 | 13 | 101240654 | Higher in Drinkers |
| cg02166782 | 17 | 7591564 | Higher in Drinkers |
| cg02167021 | 3 | 121379791 | Higher in Drinkers |
| cg02168723 | 13 | 100258760 | Higher in Drinkers |
| cg02169203 | 16 | 3451144 | Higher in Drinkers |
| cg02169446 | 15 | 72410194 | Higher in Drinkers |
| cg02169734 | 6 | 80656973 | Higher in Drinkers |
| cg02170310 | 1 | 203296207 | Higher in Drinkers |
| cg02171008 | 11 | 8703884 | Higher in Drinkers |
| cg02171503 | 17 | 1588363 | Higher in Drinkers |
| cg02172790 | 2 | 61404147 | Higher in Drinkers |
| cg02172824 | 16 | 75467946 | Higher in Drinkers |
| cg02174225 | 11 | 133938941 | Higher in Drinkers |
| cg02175291 | 11 | 10329568 | Higher in Drinkers |
| cg02179112 | 5 | 10354198 | Higher in Drinkers |
| cg02181036 | 7 | 30328151 | Higher in Drinkers |

| | | | |
|---|---|---|---|
| cg02181247 | 11 | 10325567 | Higher in Drinkers |
| cg02181494 | 22 | 51066755 | Higher in Drinkers |
| cg02184918 | 16 | 75269222 | Higher in Drinkers |
| cg02186127 | 17 | 33914245 | Higher in Drinkers |
| cg02190454 | 8 | 11771345 | Higher in Drinkers |
| cg02191336 | 6 | 31789535 | Higher in Drinkers |
| cg02194129 | 14 | 104171313 | Higher in Drinkers |
| cg02195366 | X | 11776368 | Higher in Drinkers |
| cg02197330 | 4 | 89300321 | Higher in Drinkers |
| cg02197392 | 19 | 13049544 | Higher in Drinkers |
| cg02198017 | 14 | 103801143 | Higher in Drinkers |
| cg02198582 | 16 | 2099376 | Higher in Drinkers |
| cg02199239 | 17 | 39968091 | Higher in Drinkers |
| cg02201215 | 14 | 105714846 | Higher in Drinkers |
| cg02201836 | X | 129039832 | Higher in Drinkers |
| cg02208308 | 15 | 101592151 | Higher in Drinkers |
| cg02208529 | 5 | 176901781 | Higher in Drinkers |
| cg02211978 | 16 | 15068550 | Higher in Drinkers |
| cg02212389 | 7 | 151070905 | Higher in Drinkers |
| cg02212934 | 16 | 90072563 | Lower in Drinkers |
| cg02214096 | 16 | 77822350 | Higher in Drinkers |
| cg02215560 | 17 | 80791077 | Higher in Drinkers |
| cg02217842 | 10 | 65393556 | Higher in Drinkers |
| cg02217979 | 12 | 123868268 | Higher in Drinkers |
| cg02219071 | 6 | 29596540 | Higher in Drinkers |
| cg02222310 | 13 | 41363578 | Higher in Drinkers |
| cg02222250 | 1 | 182993172 | Higher in Drinkers |
| cg02222722 | 2 | 20101793 | Higher in Drinkers |
| cg02226192 | 16 | 89461734 | Higher in Drinkers |
| cg02226194 | 17 | 17398962 | Higher in Drinkers |
| cg02227867 | 8 | 22457446 | Higher in Drinkers |
| cg02228160 | 5 | 143192067 | Higher in Drinkers |
| cg02230085 | 17 | 900491 | Higher in Drinkers |
| cg02230180 | 1 | 245025960 | Higher in Drinkers |
| cg02233558 | 5 | 127418922 | Higher in Drinkers |

| | | | |
|---|---|---|---|
| cg02235760 | 17 | 40307236 | Higher in Drinkers |
| cg02235880 | 11 | 22647123 | Higher in Drinkers |
| cg02237493 | 19 | 21949978 | Higher in Drinkers |
| cg02238950 | 17 | 1505303 | Higher in Drinkers |
| cg02241358 | 4 | 99917544 | Higher in Drinkers |
| cg02242372 | 8 | 119963842 | Higher in Drinkers |
| cg02245743 | 17 | 8114003 | Higher in Drinkers |
| cg02246053 | 17 | 57184577 | Higher in Drinkers |
| cg02246180 | 14 | 21945391 | Higher in Drinkers |
| cg02249648 | 12 | 1703181 | Higher in Drinkers |
| cg02249930 | 10 | 70166207 | Higher in Drinkers |
| cg02250263 | 17 | 70117055 | Higher in Drinkers |
| cg02253230 | 22 | 22292638 | Higher in Drinkers |
| cg02254798 | 10 | 74856984 | Higher in Drinkers |
| cg02255054 | 14 | 19888629 | Higher in Drinkers |
| cg02255700 | 11 | 69455274 | Higher in Drinkers |
| cg02255914 | 17 | 8700574 | Higher in Drinkers |
| cg02257533 | 15 | 43425591 | Higher in Drinkers |
| cg02259877 | 6 | 33217421 | Higher in Drinkers |
| cg02260774 | 4 | 8228048 | Higher in Drinkers |
| cg02261118 | 12 | 123943000 | Higher in Drinkers |
| cg02263717 | X | 9431326 | Higher in Drinkers |
| cg02266689 | 16 | 88573448 | Higher in Drinkers |
| cg02273422 | 7 | 130353956 | Higher in Drinkers |
| cg02275878 | 17 | 72919391 | Higher in Drinkers |
| cg02277235 | 14 | 104192854 | Higher in Drinkers |
| cg02280023 | 12 | 68726324 | Higher in Drinkers |
| cg02280907 | 6 | 150326453 | Higher in Drinkers |
| cg02283775 | 2 | 162272202 | Higher in Drinkers |
| cg02285477 | 13 | 28196059 | Higher in Drinkers |
| cg02286589 | 16 | 1556286 | Lower in Drinkers |
| cg02286857 | 2 | 47297177 | Higher in Drinkers |
| cg02288341 | 5 | 137610226 | Higher in Drinkers |
| cg02289127 | 2 | 27357746 | Higher in Drinkers |
| cg02289754 | 1 | 47068636 | Higher in Drinkers |

| | | | |
|---|---|---|---|
| cg02291424 | 19 | 17448344 | Higher in Drinkers |
| cg02291855 | 16 | 30934439 | Higher in Drinkers |
| cg02292066 | 1 | 2518269 | Higher in Drinkers |
| cg02296128 | 13 | 45694882 | Higher in Drinkers |
| cg02296167 | 20 | 62363890 | Higher in Drinkers |
| cg02299542 | 1 | 45241296 | Higher in Drinkers |
| cg02301364 | X | 106871826 | Higher in Drinkers |
| cg02301718 | 22 | 39883966 | Higher in Drinkers |
| cg02303897 | 12 | 53268136 | Higher in Drinkers |
| cg02304070 | 12 | 44229711 | Higher in Drinkers |
| cg02309335 | 6 | 30227294 | Higher in Drinkers |
| cg02311152 | 14 | 71276396 | Higher in Drinkers |
| cg02313850 | 10 | 88516765 | Higher in Drinkers |
| cg02314348 | 15 | 91224043 | Higher in Drinkers |
| cg02315249 | 2 | 220118660 | Higher in Drinkers |
| cg02316156 | 12 | 132661639 | Higher in Drinkers |
| cg02322894 | 20 | 4721532 | Higher in Drinkers |
| cg02324021 | 5 | 86564119 | Higher in Drinkers |
| cg02326931 | 13 | 37572901 | Higher in Drinkers |
| cg02327604 | 7 | 808834 | Higher in Drinkers |
| cg02328295 | 6 | 33291002 | Higher in Drinkers |
| cg02328403 | 12 | 121790544 | Higher in Drinkers |
| cg02330432 | 8 | 7212941 | Higher in Drinkers |
| cg02330494 | 15 | 41786605 | Higher in Drinkers |
| cg02332537 | 3 | 46540019 | Higher in Drinkers |
| cg02333667 | 11 | 34934680 | Higher in Drinkers |
| cg02334126 | 12 | 121017209 | Higher in Drinkers |
| cg02337283 | 19 | 10599976 | Higher in Drinkers |
| cg02338191 | 15 | 51200825 | Higher in Drinkers |
| cg02338858 | 1 | 10002945 | Higher in Drinkers |
| cg02339542 | 12 | 92823161 | Higher in Drinkers |
| cg02342053 | 9 | 37592791 | Higher in Drinkers |
| cg02343814 | 11 | 28129122 | Higher in Drinkers |
| cg02344167 | 12 | 96252759 | Higher in Drinkers |
| cg02346492 | 17 | 9143174 | Higher in Drinkers |

| | | | |
|---|---|---|---|
| cg02347105 | 16 | 21557425 | Lower in Drinkers |
| cg02353148 | 19 | 11670241 | Higher in Drinkers |
| cg02357017 | 5 | 133512566 | Higher in Drinkers |
| cg02357877 | 7 | 56032049 | Higher in Drinkers |
| cg02358477 | 20 | 36156735 | Higher in Drinkers |
| cg02360337 | 11 | 65627185 | Higher in Drinkers |
| cg02360776 | 11 | 62521582 | Higher in Drinkers |
| cg02361363 | 1 | 44173578 | Higher in Drinkers |
| cg02361612 | 7 | 130353136 | Higher in Drinkers |
| cg02362450 | 8 | 99129674 | Higher in Drinkers |
| cg02365739 | 1 | 225662675 | Higher in Drinkers |
| cg02368820 | 1 | 3052501 | Lower in Drinkers |
| cg02372712 | 7 | 149470295 | Higher in Drinkers |
| cg02372745 | 13 | 50365574 | Higher in Drinkers |
| cg02373380 | 18 | 61603746 | Higher in Drinkers |
| cg02375201 | 1 | 27114675 | Higher in Drinkers |
| cg02376834 | 5 | 154134051 | Higher in Drinkers |
| cg02379052 | 14 | 105486781 | Higher in Drinkers |
| cg02383160 | 11 | 62496393 | Higher in Drinkers |
| cg02386723 | 1 | 1203167 | Higher in Drinkers |
| cg02387744 | 8 | 142138588 | Higher in Drinkers |
| cg02391387 | 7 | 111202222 | Higher in Drinkers |
| cg02393447 | 15 | 65117607 | Higher in Drinkers |
| cg02393684 | 1 | 149144161 | Higher in Drinkers |
| cg02394110 | 1 | 25573993 | Higher in Drinkers |
| cg02397499 | 11 | 61891354 | Higher in Drinkers |
| cg02399570 | 3 | 156877196 | Higher in Drinkers |
| cg02400128 | 5 | 114849010 | Higher in Drinkers |
| cg02401260 | 16 | 77224291 | Higher in Drinkers |
| cg02404933 | 17 | 79995793 | Higher in Drinkers |
| cg02405329 | 22 | 51063680 | Higher in Drinkers |
| cg02409878 | 8 | 99960498 | Higher in Drinkers |
| cg02414586 | 19 | 10335193 | Higher in Drinkers |
| cg02415297 | 1 | 3553416 | Higher in Drinkers |
| cg02417553 | 15 | 41186498 | Higher in Drinkers |

| | | | |
|---|---|---|---|
| cg02418294 | 1 | 14076293 | Higher in Drinkers |
| cg02419920 | 4 | 48486785 | Higher in Drinkers |
| cg02422639 | 19 | 45873808 | Higher in Drinkers |
| cg02422847 | 7 | 45026583 | Higher in Drinkers |
| cg02424007 | 6 | 110967726 | Higher in Drinkers |
| cg02424238 | 17 | 33905661 | Higher in Drinkers |
| cg02425595 | 13 | 101185600 | Higher in Drinkers |
| cg02426940 | 15 | 75647225 | Higher in Drinkers |
| cg02427042 | 22 | 40767032 | Higher in Drinkers |
| cg02429092 | 12 | 112546400 | Higher in Drinkers |
| cg02430305 | 4 | 183839170 | Higher in Drinkers |
| cg02431098 | 1 | 51425775 | Higher in Drinkers |
| cg02433807 | 16 | 11234924 | Higher in Drinkers |
| cg02434059 | 17 | 29248604 | Higher in Drinkers |
| cg02434316 | 16 | 15150255 | Higher in Drinkers |
| cg02435593 | 20 | 32399369 | Higher in Drinkers |
| cg02436004 | 3 | 128211540 | Higher in Drinkers |
| cg02436636 | 19 | 39826150 | Higher in Drinkers |
| cg02442900 | 2 | 234296642 | Higher in Drinkers |
| cg02443062 | 6 | 35436159 | Higher in Drinkers |
| cg02443306 | 11 | 268923 | Higher in Drinkers |
| cg02446225 | 19 | 10662782 | Higher in Drinkers |
| cg02447122 | 2 | 25142523 | Higher in Drinkers |
| cg02447185 | 17 | 71228623 | Higher in Drinkers |
| cg02447779 | 16 | 31505062 | Higher in Drinkers |
| cg02450981 | 1 | 32825803 | Higher in Drinkers |
| cg02451122 | 14 | 104096106 | Higher in Drinkers |
| cg02452838 | 17 | 4925570 | Higher in Drinkers |
| cg02454464 | 19 | 49957206 | Higher in Drinkers |
| cg02459555 | 1 | 46806155 | Higher in Drinkers |
| cg02460419 | 12 | 124198876 | Higher in Drinkers |
| cg02462374 | 1 | 86861923 | Higher in Drinkers |
| cg02466749 | 9 | 98054877 | Higher in Drinkers |
| cg02467794 | 17 | 55162598 | Higher in Drinkers |
| cg02468320 | 12 | 2404134 | Higher in Drinkers |

| | | | |
|---|---|---|---|
| cg02470373 | 11 | 555312 | Higher in Drinkers |
| cg02470871 | 3 | 119278637 | Higher in Drinkers |
| cg02470959 | 12 | 132196036 | Higher in Drinkers |
| cg02472998 | 13 | 45945362 | Higher in Drinkers |
| cg02473953 | 16 | 24550417 | Higher in Drinkers |
| cg02477456 | 1 | 226112258 | Higher in Drinkers |
| cg02478836 | 22 | 47510037 | Higher in Drinkers |
| cg02479196 | 2 | 160569048 | Higher in Drinkers |
| cg02481846 | 8 | 91942157 | Lower in Drinkers |
| cg02482460 | 1 | 89664338 | Higher in Drinkers |
| cg02486520 | 22 | 47256230 | Higher in Drinkers |
| cg02486845 | 6 | 88411799 | Higher in Drinkers |
| cg02488887 | 5 | 176830915 | Higher in Drinkers |
| cg02491754 | 12 | 53773040 | Lower in Drinkers |
| cg02493440 | 16 | 57023485 | Higher in Drinkers |
| cg02493846 | 1 | 151809534 | Higher in Drinkers |
| cg02494152 | 12 | 82752508 | Higher in Drinkers |
| cg02494664 | 3 | 57741837 | Higher in Drinkers |
| cg02497428 | 16 | 21665138 | Higher in Drinkers |
| cg02497504 | 3 | 182510964 | Higher in Drinkers |
| cg02497830 | 1 | 9099281 | Higher in Drinkers |
| cg02503257 | 21 | 47743914 | Higher in Drinkers |
| cg02504541 | 3 | 9437946 | Higher in Drinkers |
| cg02505296 | 8 | 63951123 | Higher in Drinkers |
| cg02506275 | 12 | 130650643 | Lower in Drinkers |
| cg02507578 | 2 | 178130284 | Higher in Drinkers |
| cg02509985 | 11 | 9483081 | Higher in Drinkers |
| cg02515103 | 1 | 59165868 | Higher in Drinkers |
| cg02515422 | 9 | 120466493 | Higher in Drinkers |
| cg02515445 | 2 | 191301880 | Higher in Drinkers |
| cg02517556 | 12 | 53473207 | Higher in Drinkers |
| cg02519222 | 13 | 79980793 | Higher in Drinkers |
| cg02521930 | 20 | 44600922 | Higher in Drinkers |
| cg02522681 | 16 | 69345610 | Higher in Drinkers |
| cg02523617 | 4 | 39699380 | Higher in Drinkers |

| | | | |
|---|---|---|---|
| cg02525232 | 11 | 63580619 | Higher in Drinkers |
| cg02525785 | 17 | 7117684 | Higher in Drinkers |
| cg02526331 | 14 | 59656312 | Higher in Drinkers |
| cg02526982 | 16 | 85309801 | Higher in Drinkers |
| cg02527419 | 5 | 314558 | Higher in Drinkers |
| cg02528908 | 10 | 11505056 | Lower in Drinkers |
| cg02530860 | 8 | 144371537 | Higher in Drinkers |
| cg02532488 | 11 | 65343341 | Higher in Drinkers |
| cg02533419 | 1 | 59249324 | Higher in Drinkers |
| cg02537913 | 17 | 37027030 | Higher in Drinkers |
| cg02538199 | 9 | 37034277 | Higher in Drinkers |
| cg02539714 | 12 | 122231866 | Higher in Drinkers |
| cg02542118 | 2 | 61245510 | Higher in Drinkers |
| cg02543249 | 2 | 176867176 | Higher in Drinkers |
| cg02544037 | 12 | 68759069 | Higher in Drinkers |
| cg02544257 | 16 | 70510663 | Higher in Drinkers |
| cg02544394 | 2 | 45878759 | Higher in Drinkers |
| cg02545393 | 11 | 70244902 | Higher in Drinkers |
| cg02546941 | 17 | 73030677 | Higher in Drinkers |
| cg02548606 | 15 | 77363299 | Higher in Drinkers |
| cg02552868 | 16 | 87380480 | Lower in Drinkers |
| cg02555393 | 1 | 226829707 | Higher in Drinkers |
| cg02558041 | 5 | 131133021 | Higher in Drinkers |
| cg02562122 | 7 | 150755221 | Higher in Drinkers |
| cg02562809 | 3 | 193311018 | Higher in Drinkers |
| cg02563952 | 6 | 31707803 | Higher in Drinkers |
| cg02568374 | 16 | 4586917 | Higher in Drinkers |
| cg02568834 | 20 | 34824352 | Higher in Drinkers |
| cg02569333 | 8 | 67625280 | Higher in Drinkers |
| cg02572796 | 4 | 186732124 | Lower in Drinkers |
| cg02573613 | X | 46814806 | Higher in Drinkers |
| cg02577909 | 9 | 136914463 | Higher in Drinkers |
| cg02580722 | 11 | 114309934 | Higher in Drinkers |
| cg02582997 | 4 | 866299 | Higher in Drinkers |
| cg02585483 | 5 | 61602105 | Higher in Drinkers |

| | | | |
|---|---|---|---|
| cg02586366 | 21 | 47804759 | Higher in Drinkers |
| cg02586637 | 2 | 198318130 | Higher in Drinkers |
| cg02592798 | 5 | 162886952 | Higher in Drinkers |
| cg02596331 | 3 | 69590955 | Higher in Drinkers |
| cg02596508 | 16 | 29604068 | Higher in Drinkers |
| cg02596779 | 5 | 179496893 | Higher in Drinkers |
| cg02598978 | 16 | 20817844 | Higher in Drinkers |
| cg02599551 | 9 | 100396302 | Higher in Drinkers |
| cg02603868 | 16 | 87799809 | Higher in Drinkers |
| cg02604121 | 19 | 19843707 | Higher in Drinkers |
| cg02605776 | 1 | 111507160 | Higher in Drinkers |
| cg02606081 | 11 | 536182 | Higher in Drinkers |
| cg02606327 | 12 | 31079406 | Higher in Drinkers |
| cg02606627 | 19 | 5047711 | Lower in Drinkers |
| cg02607330 | 4 | 3510935 | Higher in Drinkers |
| cg02615402 | 14 | 74227201 | Higher in Drinkers |
| cg02615599 | 7 | 150725389 | Higher in Drinkers |
| cg02621907 | 5 | 93954419 | Higher in Drinkers |
| cg02622835 | 17 | 34745068 | Higher in Drinkers |
| cg02624052 | 5 | 180673365 | Higher in Drinkers |
| cg02626656 | 3 | 13036375 | Higher in Drinkers |
| cg02627531 | 19 | 52873085 | Higher in Drinkers |
| cg02629156 | 6 | 31856193 | Higher in Drinkers |
| cg02630349 | 1 | 978667 | Lower in Drinkers |
| cg02630704 | 19 | 13260775 | Higher in Drinkers |
| cg02632643 | 19 | 8370165 | Lower in Drinkers |
| cg02633838 | 2 | 95787034 | Higher in Drinkers |
| cg02634501 | 3 | 130465382 | Higher in Drinkers |
| cg02634544 | 12 | 53689602 | Higher in Drinkers |
| cg02635324 | 8 | 26306648 | Higher in Drinkers |
| cg02635865 | 20 | 56885090 | Higher in Drinkers |
| cg02636596 | 8 | 91013176 | Higher in Drinkers |
| cg02636872 | 16 | 28510023 | Higher in Drinkers |
| cg02637978 | X | 3761067 | Higher in Drinkers |
| cg02639927 | 1 | 77334748 | Higher in Drinkers |

| | | | |
|---|---|---|---|
| cg02639929 | 14 | 54908227 | Higher in Drinkers |
| cg02640475 | 5 | 162932472 | Higher in Drinkers |
| cg02640691 | 16 | 87949690 | Lower in Drinkers |
| cg02641095 | 5 | 157170413 | Higher in Drinkers |
| cg02642117 | 6 | 21033836 | Higher in Drinkers |
| cg02642404 | 1 | 244998532 | Higher in Drinkers |
| cg02643835 | 3 | 44598699 | Higher in Drinkers |
| cg02644840 | 11 | 3876535 | Higher in Drinkers |
| cg02650828 | 10 | 102973602 | Higher in Drinkers |
| cg02650964 | 4 | 1222621 | Higher in Drinkers |
| cg02652260 | 21 | 13935383 | Higher in Drinkers |
| cg02657611 | 1 | 45814632 | Higher in Drinkers |
| cg02659009 | 5 | 140079941 | Higher in Drinkers |
| cg02659149 | 17 | 1620008 | Higher in Drinkers |
| cg02662441 | 10 | 104355824 | Higher in Drinkers |
| cg02666105 | 16 | 31724574 | Higher in Drinkers |
| cg02668051 | 1 | 43888546 | Higher in Drinkers |
| cg02668581 | 2 | 216878340 | Higher in Drinkers |
| cg02670096 | 5 | 172386299 | Higher in Drinkers |
| cg02672116 | 5 | 56205359 | Higher in Drinkers |
| cg02672146 | 6 | 32571122 | Higher in Drinkers |
| cg02672229 | 10 | 101594256 | Lower in Drinkers |
| cg02674789 | 2 | 37375119 | Lower in Drinkers |
| cg02678356 | X | 57937004 | Higher in Drinkers |
| cg02680629 | 5 | 147763595 | Higher in Drinkers |
| cg02682520 | 5 | 159989160 | Higher in Drinkers |
| cg02682789 | 6 | 19804855 | Higher in Drinkers |
| cg02683621 | 7 | 150100820 | Higher in Drinkers |
| cg02683985 | 7 | 559070 | Higher in Drinkers |
| cg02688760 | 1 | 182573731 | Higher in Drinkers |
| cg02688848 | 19 | 57922457 | Higher in Drinkers |
| cg02691192 | 17 | 59693501 | Higher in Drinkers |
| cg02691484 | 7 | 140714419 | Higher in Drinkers |
| cg02692808 | 11 | 121712639 | Lower in Drinkers |
| cg02692952 | 11 | 36531754 | Higher in Drinkers |

| | | | |
|---|---|---|---|
| cg02693818 | 12 | 97379556 | Higher in Drinkers |
| cg02693857 | 5 | 176738937 | Higher in Drinkers |
| cg02695219 | 16 | 9136852 | Higher in Drinkers |
| cg02698622 | 2 | 242698811 | Lower in Drinkers |
| cg02698731 | 17 | 79516420 | Higher in Drinkers |
| cg02699461 | 10 | 120925349 | Higher in Drinkers |
| cg02699540 | 16 | 31454170 | Higher in Drinkers |
| cg02701278 | 2 | 109648208 | Higher in Drinkers |
| cg02704895 | 6 | 28109581 | Higher in Drinkers |
| cg02704927 | 5 | 65440543 | Higher in Drinkers |
| cg02705752 | 11 | 64135650 | Higher in Drinkers |
| cg02705895 | 4 | 6642252 | Higher in Drinkers |
| cg02706910 | 19 | 24269975 | Higher in Drinkers |
| cg02707576 | 5 | 139682775 | Higher in Drinkers |
| cg02710132 | 1 | 119683330 | Higher in Drinkers |
| cg02710332 | 11 | 65222786 | Higher in Drinkers |
| cg02711188 | 15 | 34394260 | Higher in Drinkers |
| cg02713901 | 16 | 74640890 | Higher in Drinkers |
| cg02714192 | 18 | 77201972 | Lower in Drinkers |
| cg02714566 | 15 | 69706517 | Higher in Drinkers |
| cg02715531 | 17 | 77709027 | Higher in Drinkers |
| cg02716516 | 3 | 45838074 | Higher in Drinkers |
| cg02716556 | 6 | 10838914 | Higher in Drinkers |
| cg02721336 | 13 | 99853153 | Higher in Drinkers |
| cg02723142 | 19 | 12886624 | Higher in Drinkers |
| cg02725362 | 16 | 721101 | Higher in Drinkers |
| cg02725795 | 4 | 84405871 | Higher in Drinkers |
| cg02725900 | 11 | 118965121 | Higher in Drinkers |
| cg02728558 | 3 | 170626482 | Higher in Drinkers |
| cg02730139 | 8 | 847575 | Lower in Drinkers |
| cg02732202 | 6 | 100051635 | Higher in Drinkers |
| cg02733444 | 10 | 134536138 | Higher in Drinkers |
| cg02734472 | 16 | 699218 | Higher in Drinkers |
| cg02734527 | 16 | 4303413 | Higher in Drinkers |
| cg02737619 | 1 | 2222440 | Higher in Drinkers |

| | | | |
|---|---|---|---|
| cg02737801 | 1 | 43638006 | Higher in Drinkers |
| cg02738255 | 20 | 25231685 | Higher in Drinkers |
| cg02740861 | 16 | 71061931 | Lower in Drinkers |
| cg02741544 | 8 | 141567390 | Higher in Drinkers |
| cg02741854 | 5 | 52285176 | Higher in Drinkers |
| cg02743091 | 6 | 2999911 | Higher in Drinkers |
| cg02743522 | 6 | 111136488 | Higher in Drinkers |
| cg02745683 | 4 | 3513990 | Higher in Drinkers |
| cg02747298 | 18 | 814876 | Higher in Drinkers |
| cg02748316 | 3 | 50273710 | Higher in Drinkers |
| cg02749789 | 17 | 1303531 | Higher in Drinkers |
| cg02750435 | 12 | 133373625 | Higher in Drinkers |
| cg02750754 | 19 | 41869941 | Higher in Drinkers |
| cg02751449 | 3 | 142443340 | Higher in Drinkers |
| cg02751532 | 7 | 3041110 | Higher in Drinkers |
| cg02752267 | X | 69671886 | Higher in Drinkers |
| cg02753865 | 7 | 56119046 | Higher in Drinkers |
| cg02756106 | 12 | 45270707 | Higher in Drinkers |
| cg02756511 | X | 106693692 | Higher in Drinkers |
| cg02756835 | 19 | 19765944 | Higher in Drinkers |
| cg02756845 | 22 | 51038542 | Higher in Drinkers |
| cg02757696 | 20 | 33104113 | Higher in Drinkers |
| cg02758040 | 11 | 20384736 | Higher in Drinkers |
| cg02759005 | 3 | 53925912 | Higher in Drinkers |
| cg02759966 | 16 | 29139086 | Higher in Drinkers |
| cg02762561 | 7 | 154792046 | Higher in Drinkers |
| cg02763968 | 15 | 86338211 | Higher in Drinkers |
| cg02766846 | 19 | 1902475 | Higher in Drinkers |
| cg02767601 | 10 | 22614694 | Higher in Drinkers |
| cg02767841 | 20 | 40986173 | Higher in Drinkers |
| cg02768471 | 1 | 155231827 | Higher in Drinkers |
| cg02768694 | 2 | 74875536 | Higher in Drinkers |
| cg02774160 | 22 | 24979633 | Higher in Drinkers |
| cg02774855 | 2 | 29338636 | Higher in Drinkers |
| cg02775028 | 4 | 184580387 | Higher in Drinkers |

| | | | |
|---|---|---|---|
| cg02776251 | 12 | 62654319 | Higher in Drinkers |
| cg02777633 | 3 | 64009154 | Higher in Drinkers |
| cg02784350 | 1 | 3447721 | Higher in Drinkers |
| cg02788021 | 13 | 30882905 | Higher in Drinkers |
| cg02794589 | 11 | 70049600 | Higher in Drinkers |
| cg02796204 | 16 | 2499223 | Higher in Drinkers |
| cg02800384 | 16 | 88052309 | Higher in Drinkers |
| cg02801073 | 3 | 50388115 | Higher in Drinkers |
| cg02801645 | 22 | 24059735 | Higher in Drinkers |
| cg02806658 | 12 | 102513592 | Higher in Drinkers |
| cg02808110 | 17 | 34957846 | Higher in Drinkers |
| cg02813021 | 10 | 180599 | Higher in Drinkers |
| cg02814054 | 19 | 18234911 | Higher in Drinkers |
| cg02815249 | 6 | 30877746 | Higher in Drinkers |
| cg02820836 | 7 | 4652842 | Higher in Drinkers |
| cg02824291 | 7 | 154795251 | Higher in Drinkers |
| cg02829456 | 2 | 201982020 | Higher in Drinkers |
| cg02831821 | 17 | 7231188 | Higher in Drinkers |
| cg02832646 | 16 | 81040020 | Higher in Drinkers |
| cg02835214 | 19 | 58125672 | Higher in Drinkers |
| cg02836833 | 6 | 153308650 | Lower in Drinkers |
| cg02838499 | 19 | 4342461 | Higher in Drinkers |
| cg02840044 | 19 | 30299177 | Higher in Drinkers |
| cg02845591 | 2 | 74730523 | Higher in Drinkers |
| cg02848074 | 13 | 31306178 | Higher in Drinkers |
| cg02850812 | 13 | 46961666 | Higher in Drinkers |
| cg02852923 | 1 | 1132852 | Higher in Drinkers |
| cg02853152 | 4 | 6690702 | Higher in Drinkers |
| cg02855142 | 17 | 7591947 | Higher in Drinkers |
| cg02855924 | 3 | 50402563 | Higher in Drinkers |
| cg02856070 | 11 | 65686288 | Higher in Drinkers |
| cg02858512 | 17 | 1992954 | Higher in Drinkers |
| cg02862674 | 6 | 44238426 | Higher in Drinkers |
| cg02864690 | 11 | 2023450 | Higher in Drinkers |
| cg02865498 | 19 | 13043901 | Higher in Drinkers |

| | | | |
|---|---|---|---|
| cg02867162 | 16 | 1020843 | Higher in Drinkers |
| cg02867650 | 6 | 11094066 | Higher in Drinkers |
| cg02869547 | 11 | 14521079 | Higher in Drinkers |
| cg02875788 | 18 | 61603679 | Higher in Drinkers |
| cg02876672 | 12 | 107349508 | Higher in Drinkers |
| cg02877433 | 11 | 660680 | Higher in Drinkers |
| cg02878913 | 10 | 105417188 | Higher in Drinkers |
| cg02878987 | 1 | 222365407 | Higher in Drinkers |
| cg02879081 | 14 | 102500684 | Higher in Drinkers |
| cg02881419 | 6 | 52396472 | Higher in Drinkers |
| cg02881625 | 7 | 14030255 | Higher in Drinkers |
| cg02884239 | 17 | 75369228 | Higher in Drinkers |
| cg02886961 | 14 | 24679935 | Higher in Drinkers |
| cg02888146 | 6 | 143267449 | Higher in Drinkers |
| cg02889777 | 17 | 37213271 | Higher in Drinkers |
| cg02890030 | 14 | 102414739 | Higher in Drinkers |
| cg02890434 | 2 | 200819881 | Higher in Drinkers |
| cg02890457 | 1 | 45205198 | Higher in Drinkers |
| cg02890812 | X | 129114962 | Higher in Drinkers |
| cg02891495 | 16 | 30075969 | Higher in Drinkers |
| cg02891522 | 4 | 1976232 | Higher in Drinkers |
| cg02891579 | 10 | 102823812 | Higher in Drinkers |
| cg02893779 | 14 | 99876534 | Higher in Drinkers |
| cg02894810 | X | 118284617 | Lower in Drinkers |
| cg02899960 | 16 | 74641326 | Higher in Drinkers |
| cg02900213 | 11 | 20385756 | Higher in Drinkers |
| cg02900516 | 10 | 32667723 | Higher in Drinkers |
| cg02900669 | 19 | 12754736 | Higher in Drinkers |
| cg02901177 | 18 | 24128506 | Higher in Drinkers |
| cg02902489 | 6 | 33419510 | Higher in Drinkers |
| cg02903192 | 18 | 29027745 | Higher in Drinkers |
| cg02905066 | 7 | 141251439 | Higher in Drinkers |
| cg02912316 | 1 | 32527924 | Higher in Drinkers |
| cg02916459 | 12 | 2113756 | Higher in Drinkers |
| cg02916962 | 2 | 157180144 | Higher in Drinkers |

| | | | |
|---|---|---|---|
| cg02918101 | 6 | 31371497 | Higher in Drinkers |
| cg02923047 | 9 | 140342917 | Higher in Drinkers |
| cg02925464 | 2 | 62132897 | Higher in Drinkers |
| cg02928928 | 11 | 1975304 | Higher in Drinkers |
| cg02930078 | 6 | 17706856 | Higher in Drinkers |
| cg02936468 | 9 | 77642970 | Higher in Drinkers |
| cg02938863 | 2 | 3241469 | Higher in Drinkers |
| cg02941118 | 11 | 134201640 | Higher in Drinkers |
| cg02941859 | 7 | 99869835 | Higher in Drinkers |
| cg02943336 | 7 | 2959067 | Higher in Drinkers |
| cg02943497 | 13 | 25087090 | Higher in Drinkers |
| cg02944857 | 19 | 56098480 | Higher in Drinkers |
| cg02949992 | 14 | 105487248 | Higher in Drinkers |
| cg02952548 | 11 | 45848289 | Higher in Drinkers |
| cg02954359 | 1 | 45139975 | Higher in Drinkers |
| cg02956148 | 17 | 36762611 | Higher in Drinkers |
| cg02956499 | 2 | 74280825 | Higher in Drinkers |
| cg02957918 | 6 | 30180785 | Higher in Drinkers |
| cg02964602 | 2 | 203130213 | Higher in Drinkers |
| cg02967959 | 6 | 33168311 | Higher in Drinkers |
| cg02968844 | 1 | 884964 | Higher in Drinkers |
| cg02970830 | 14 | 24674242 | Higher in Drinkers |
| cg02971627 | 15 | 59042282 | Higher in Drinkers |
| cg02972188 | 12 | 58165945 | Higher in Drinkers |
| cg02972793 | 2 | 3322136 | Lower in Drinkers |
| cg02973971 | X | 149106460 | Higher in Drinkers |
| cg02975142 | 17 | 17140597 | Higher in Drinkers |
| cg02979120 | 16 | 67180466 | Higher in Drinkers |
| cg02982559 | 15 | 52971788 | Higher in Drinkers |
| cg02983835 | 19 | 42772892 | Higher in Drinkers |
| cg02986494 | 19 | 1248287 | Higher in Drinkers |
| cg02988255 | 11 | 60621110 | Higher in Drinkers |
| cg02990239 | 19 | 13947284 | Higher in Drinkers |
| cg02990439 | 17 | 4875527 | Higher in Drinkers |
| cg02993259 | 14 | 89493561 | Higher in Drinkers |

| | | | |
|---|---|---|---|
| cg02993943 | 7 | 39605861 | Higher in Drinkers |
| cg02994216 | 2 | 121010979 | Higher in Drinkers |
| cg02995290 | 1 | 225965777 | Higher in Drinkers |
| cg02996142 | 1 | 53168724 | Higher in Drinkers |
| cg02996397 | 6 | 29720477 | Higher in Drinkers |
| cg02998427 | 2 | 242955553 | Higher in Drinkers |
| cg03000156 | 6 | 79577260 | Higher in Drinkers |
| cg03003218 | 6 | 24495614 | Higher in Drinkers |
| cg03004860 | 16 | 85684468 | Lower in Drinkers |
| cg03008387 | 20 | 62089152 | Higher in Drinkers |
| cg03008634 | 22 | 43506528 | Higher in Drinkers |
| cg03012230 | 19 | 49589224 | Higher in Drinkers |
| cg03012674 | 2 | 27274208 | Higher in Drinkers |
| cg03016571 | 17 | 48844124 | Higher in Drinkers |
| cg03017195 | 1 | 1590941 | Higher in Drinkers |
| cg03018679 | 12 | 120241922 | Higher in Drinkers |
| cg03019024 | X | 75392955 | Higher in Drinkers |
| cg03020271 | 19 | 4867550 | Higher in Drinkers |
| cg03020885 | 11 | 116643423 | Higher in Drinkers |
| cg03021192 | 17 | 73043368 | Higher in Drinkers |
| cg03023867 | 1 | 109756414 | Higher in Drinkers |
| cg03024536 | 3 | 16555452 | Higher in Drinkers |
| cg03027244 | 15 | 66914883 | Higher in Drinkers |
| cg03031583 | 16 | 21964721 | Higher in Drinkers |
| cg03033398 | 7 | 149174757 | Higher in Drinkers |
| cg03034664 | 1 | 234509241 | Higher in Drinkers |
| cg03035248 | 3 | 50540699 | Higher in Drinkers |
| cg03036514 | 1 | 120255011 | Higher in Drinkers |
| cg03038395 | X | 25031600 | Higher in Drinkers |
| cg03039196 | 19 | 44506973 | Higher in Drinkers |
| cg03040420 | 15 | 78442296 | Higher in Drinkers |
| cg03041365 | 7 | 44836969 | Higher in Drinkers |
| cg03041860 | 2 | 208489911 | Higher in Drinkers |
| cg03044513 | 11 | 116706153 | Higher in Drinkers |
| cg03046705 | 5 | 131746062 | Higher in Drinkers |

| | | | |
|---|---|---|---|
| cg03046746 | 3 | 179322246 | Higher in Drinkers |
| cg03047114 | 1 | 169337131 | Higher in Drinkers |
| cg03050491 | X | 153285654 | Higher in Drinkers |
| cg03050907 | 1 | 28844869 | Higher in Drinkers |
| cg03052137 | 2 | 203500768 | Higher in Drinkers |
| cg03054491 | 12 | 101674203 | Higher in Drinkers |
| cg03055520 | 11 | 121460793 | Higher in Drinkers |
| cg03056849 | X | 149861683 | Higher in Drinkers |
| cg03058187 | 11 | 1785407 | Higher in Drinkers |
| cg03059528 | 6 | 127587721 | Higher in Drinkers |
| cg03063277 | 7 | 937827 | Lower in Drinkers |
| cg03065614 | 6 | 44096542 | Higher in Drinkers |
| cg03066323 | 7 | 99970779 | Higher in Drinkers |
| cg03066618 | 6 | 31929757 | Higher in Drinkers |
| cg03067660 | 6 | 43027575 | Higher in Drinkers |
| cg03069638 | 2 | 99346902 | Higher in Drinkers |
| cg03071098 | 2 | 19554237 | Higher in Drinkers |
| cg03074016 | 16 | 88698516 | Higher in Drinkers |
| cg03076047 | 8 | 128748337 | Higher in Drinkers |
| cg03077062 | 2 | 73299091 | Higher in Drinkers |
| cg03080377 | 15 | 63893412 | Higher in Drinkers |
| cg03081707 | 11 | 993756 | Higher in Drinkers |
| cg03087372 | 20 | 4803035 | Higher in Drinkers |
| cg03088756 | X | 40011385 | Higher in Drinkers |
| cg03092548 | 14 | 39736835 | Higher in Drinkers |
| cg03093786 | 16 | 27413786 | Higher in Drinkers |
| cg03097336 | 16 | 84178939 | Higher in Drinkers |
| cg03098047 | 12 | 19593584 | Higher in Drinkers |
| cg03100509 | 12 | 49584947 | Lower in Drinkers |
| cg03102087 | 6 | 167412320 | Higher in Drinkers |
| cg03102306 | 10 | 85899580 | Higher in Drinkers |
| cg03105756 | 16 | 4589127 | Higher in Drinkers |
| cg03110167 | 19 | 3964912 | Higher in Drinkers |
| cg03115072 | 11 | 207155 | Higher in Drinkers |
| cg03116466 | 7 | 2116512 | Higher in Drinkers |

| | | | |
|---|---|---|---|
| cgC3116579 | 19 | 922016 | Higher in Drinkers |
| cgC3116648 | 22 | 50192934 | Higher in Drinkers |
| cgC3116917 | 19 | 40324490 | Higher in Drinkers |
| cgC3118076 | 16 | 11770228 | Higher in Drinkers |
| cgC3120091 | 8 | 132052779 | Higher in Drinkers |
| cgC3121538 | 16 | 30017856 | Lower in Drinkers |
| cgC3122372 | 12 | 56651912 | Higher in Drinkers |
| cgC3124769 | 7 | 138793831 | Higher in Drinkers |
| cgC3125605 | 16 | 67236337 | Higher in Drinkers |
| cgC3125909 | 16 | 88725594 | Higher in Drinkers |
| cgC3126834 | 7 | 98632678 | Higher in Drinkers |
| cgC3127722 | 10 | 103051861 | Higher in Drinkers |
| cgC3129910 | 4 | 57333643 | Higher in Drinkers |
| cgC3131677 | 7 | 43965924 | Higher in Drinkers |
| cgC3132197 | 1 | 28696105 | Higher in Drinkers |
| cgC3133917 | 7 | 155436674 | Higher in Drinkers |
| cgC3137826 | 1 | 10720368 | Higher in Drinkers |
| cgC3138405 | 19 | 17666150 | Higher in Drinkers |
| cgC3139053 | 2 | 200320455 | Higher in Drinkers |
| cgC3141069 | 1 | 228463734 | Higher in Drinkers |
| cgC3142365 | 10 | 124134013 | Higher in Drinkers |
| cgC3142574 | 1 | 98386452 | Higher in Drinkers |
| cgC3142634 | 7 | 45151369 | Higher in Drinkers |
| cgC3142751 | 20 | 60775169 | Higher in Drinkers |
| cgC3145134 | 1 | 210502787 | Higher in Drinkers |
| cgC3149049 | X | 47053031 | Higher in Drinkers |
| cgC3149749 | 22 | 50741674 | Higher in Drinkers |
| cgC3149958 | 6 | 36326677 | Higher in Drinkers |
| cgC3150474 | 6 | 10695108 | Higher in Drinkers |
| cgC3151739 | 7 | 45115766 | Higher in Drinkers |
| cgC3152000 | 12 | 6696982 | Higher in Drinkers |
| cgC3154277 | 17 | 72968639 | Higher in Drinkers |
| cgC3159329 | 2 | 169103514 | Higher in Drinkers |
| cgC3161839 | 19 | 42387947 | Higher in Drinkers |
| cgC3162045 | 3 | 142443933 | Higher in Drinkers |

| | | | |
|---|---|---|---|
| cg03163734 | 2 | 65659863 | Higher in Drinkers |
| cg03166265 | 4 | 7512278 | Higher in Drinkers |
| cg03168184 | 14 | 100071186 | Higher in Drinkers |
| cg03169242 | 11 | 9638619 | Higher in Drinkers |
| cg03169527 | 3 | 11888582 | Higher in Drinkers |
| cg03169876 | 13 | 21750926 | Higher in Drinkers |
| cg03170670 | 3 | 194930312 | Higher in Drinkers |
| cg03178185 | 16 | 71758038 | Higher in Drinkers |
| cg03179043 | 5 | 49737178 | Higher in Drinkers |
| cg03181052 | 17 | 80691620 | Higher in Drinkers |
| cg03182504 | 7 | 144532459 | Higher in Drinkers |
| cg03182688 | 17 | 33825300 | Higher in Drinkers |
| cg03183257 | 2 | 101618566 | Higher in Drinkers |
| cg03193349 | 6 | 139309610 | Higher in Drinkers |
| cg03198116 | 1 | 55270945 | Higher in Drinkers |
| cg03200502 | 6 | 24403107 | Higher in Drinkers |
| cg03201604 | 4 | 76861293 | Higher in Drinkers |
| cg03202557 | 6 | 29617599 | Higher in Drinkers |
| cg03203114 | 11 | 118505622 | Higher in Drinkers |
| cg03208317 | 2 | 25599894 | Higher in Drinkers |
| cg03209557 | 6 | 26273611 | Higher in Drinkers |
| cg03209720 | 6 | 157727126 | Higher in Drinkers |
| cg03213967 | 1 | 227729463 | Higher in Drinkers |
| cg03216823 | 10 | 64892844 | Higher in Drinkers |
| cg03223126 | 12 | 111471192 | Higher in Drinkers |
| cg03226425 | 6 | 170151538 | Higher in Drinkers |
| cg03228760 | 20 | 60754003 | Higher in Drinkers |
| cg03233464 | 5 | 139938009 | Higher in Drinkers |
| cg03235119 | 5 | 176449645 | Higher in Drinkers |
| cg03237356 | 4 | 178230943 | Higher in Drinkers |
| cg03238516 | 7 | 1195630 | Higher in Drinkers |
| cg03238899 | 4 | 174166943 | Higher in Drinkers |
| cg03241897 | 11 | 2985112 | Higher in Drinkers |
| cg03243946 | 12 | 21811034 | Higher in Drinkers |
| cg03245962 | 3 | 142167057 | Higher in Drinkers |

| | | | |
|---|---|---|---|
| cg03248799 | 12 | 56510114 | Higher in Drinkers |
| cg03248820 | 10 | 102822873 | Higher in Drinkers |
| cg03254875 | 10 | 180361 | Higher in Drinkers |
| cg03255775 | 5 | 98265241 | Higher in Drinkers |
| cg03258011 | 17 | 54857409 | Higher in Drinkers |
| cg03263117 | 17 | 45798767 | Higher in Drinkers |
| cg03264960 | 2 | 187350743 | Higher in Drinkers |
| cg03270376 | 2 | 219536588 | Higher in Drinkers |
| cg03271893 | 10 | 102760970 | Higher in Drinkers |
| cg03279631 | 16 | 84553297 | Higher in Drinkers |
| cg03280113 | 2 | 24346267 | Higher in Drinkers |
| cg03280759 | 13 | 25386500 | Lower in Drinkers |
| cg03286467 | 22 | 41032802 | Higher in Drinkers |
| cg03289369 | 4 | 57253815 | Higher in Drinkers |
| cg03295098 | 1 | 46152002 | Higher in Drinkers |
| cg03297042 | 22 | 29468762 | Higher in Drinkers |
| cg03297783 | 3 | 50378664 | Higher in Drinkers |
| cg03298938 | 9 | 137533366 | Higher in Drinkers |
| cg03300898 | 17 | 18538782 | Higher in Drinkers |
| cg03301240 | 11 | 47400330 | Higher in Drinkers |
| cg03303025 | 16 | 85833081 | Higher in Drinkers |
| cg03309367 | 4 | 190123549 | Higher in Drinkers |
| cg03310517 | 2 | 109276121 | Higher in Drinkers |
| cg03312124 | 17 | 33416003 | Higher in Drinkers |
| cg03315562 | 1 | 154975574 | Higher in Drinkers |
| cg03316474 | 1 | 151139495 | Higher in Drinkers |
| cg03317280 | 1 | 228675123 | Higher in Drinkers |
| cg03319323 | 16 | 475643 | Higher in Drinkers |
| cg03322239 | 6 | 42531869 | Higher in Drinkers |
| cg03322548 | 4 | 331119 | Higher in Drinkers |
| cg03327899 | 2 | 88926246 | Higher in Drinkers |
| cg03329536 | 5 | 55008469 | Higher in Drinkers |
| cg03333776 | 1 | 52455146 | Higher in Drinkers |
| cg03341025 | 5 | 1290458 | Lower in Drinkers |
| cg03341985 | 5 | 179226186 | Higher in Drinkers |

| | | | |
|---|---|---|---|
| cg03343534 | 8 | 117778609 | Higher in Drinkers |
| cg03345925 | 8 | 144599347 | Higher in Drinkers |
| cg03346875 | 2 | 27546116 | Higher in Drinkers |
| cg03347287 | 11 | 693032 | Higher in Drinkers |
| cg03348902 | 1 | 569603 | Higher in Drinkers |
| cg03349241 | 8 | 145743334 | Higher in Drinkers |
| cg03350138 | 6 | 28446794 | Lower in Drinkers |
| cg03350814 | 8 | 104512423 | Higher in Drinkers |
| cg03351307 | 19 | 59087165 | Higher in Drinkers |
| cg03351618 | 2 | 170551124 | Higher in Drinkers |
| cg03352907 | 7 | 44058984 | Higher in Drinkers |
| cg03353885 | 13 | 113489392 | Lower in Drinkers |
| cg03355101 | 19 | 16449718 | Higher in Drinkers |
| cg03355327 | 16 | 86093344 | Higher in Drinkers |
| cg03357721 | 13 | 111956695 | Lower in Drinkers |
| cg03359285 | 17 | 38573817 | Higher in Drinkers |
| cg03361085 | 11 | 1324625 | Higher in Drinkers |
| cg03363242 | 8 | 28747738 | Higher in Drinkers |
| cg03363466 | 19 | 42463690 | Higher in Drinkers |
| cg03364683 | 4 | 169402298 | Higher in Drinkers |
| cg03366776 | 14 | 103851627 | Higher in Drinkers |
| cg03366896 | 10 | 135186866 | Higher in Drinkers |
| cg03371669 | 2 | 176965435 | Higher in Drinkers |
| cg03372654 | 17 | 79682032 | Higher in Drinkers |
| cg03374317 | 3 | 184043400 | Higher in Drinkers |
| cg03376565 | 6 | 26104165 | Higher in Drinkers |
| cg03376719 | 3 | 105086940 | Higher in Drinkers |
| cg03377355 | 22 | 39853885 | Higher in Drinkers |
| cg03380406 | 9 | 114393978 | Higher in Drinkers |
| cg03384094 | 8 | 19172048 | Higher in Drinkers |
| cg03385696 | 7 | 75988425 | Higher in Drinkers |
| cg03386722 | 17 | 80056517 | Higher in Drinkers |
| cg03387238 | 15 | 75647072 | Higher in Drinkers |
| cg03387256 | 10 | 90750898 | Higher in Drinkers |
| cg03393966 | 19 | 18548015 | Higher in Drinkers |

| | | | |
|---|---|---|---|
| cg03398966 | 3 | 48225680 | Lower in Drinkers |
| cg03399271 | 16 | 56228385 | Higher in Drinkers |
| cg03403386 | 16 | 69373069 | Higher in Drinkers |
| cg03404102 | 3 | 122103036 | Higher in Drinkers |
| cg03410576 | 4 | 119756869 | Higher in Drinkers |
| cg03412310 | 8 | 55014671 | Higher in Drinkers |
| cg03413303 | 1 | 9670134 | Higher in Drinkers |
| cg03421014 | 4 | 140586396 | Higher in Drinkers |
| cg03422651 | 16 | 2542324 | Higher in Drinkers |
| cg03429034 | 7 | 99613105 | Higher in Drinkers |
| cg03430067 | 19 | 14016927 | Higher in Drinkers |
| cg03432151 | 15 | 89745000 | Higher in Drinkers |
| cg03433785 | 11 | 69482043 | Higher in Drinkers |
| cg03436478 | 7 | 94286760 | Higher in Drinkers |
| cg03437326 | 17 | 40086856 | Higher in Drinkers |
| cg03437748 | 15 | 99193247 | Higher in Drinkers |
| cg03438515 | 3 | 9291212 | Higher in Drinkers |
| cg03438742 | 6 | 46620708 | Higher in Drinkers |
| cg03439145 | 22 | 19419477 | Higher in Drinkers |
| cg03440066 | 20 | 44420729 | Higher in Drinkers |
| cg03440588 | 1 | 47900320 | Higher in Drinkers |
| cg03442014 | 16 | 23607821 | Higher in Drinkers |
| cg03443205 | 2 | 43454133 | Higher in Drinkers |
| cg03448915 | 16 | 66583078 | Higher in Drinkers |
| cg03449631 | 4 | 1714019 | Higher in Drinkers |
| cg03451574 | 1 | 61542546 | Higher in Drinkers |
| cg03452174 | 17 | 27045113 | Higher in Drinkers |
| cg03454375 | 15 | 34660076 | Higher in Drinkers |
| cg03459008 | 2 | 160472720 | Higher in Drinkers |
| cg03460137 | 6 | 100051480 | Higher in Drinkers |
| cg03461296 | 20 | 60637948 | Higher in Drinkers |
| cg03462322 | 16 | 126397 | Higher in Drinkers |
| cg03464232 | 8 | 146278302 | Higher in Drinkers |
| cg03465891 | 6 | 45389953 | Higher in Drinkers |
| cg03465947 | 6 | 80487839 | Higher in Drinkers |

| | | | |
|---|---|---|---|
| cg03466237 | 11 | 1298256 | Lower in Drinkers |
| cg03467014 | 1 | 1158648 | Higher in Drinkers |
| cg03469086 | 4 | 141073908 | Higher in Drinkers |
| cg03469484 | 2 | 3456162 | Higher in Drinkers |
| cg03469793 | 1 | 180199269 | Higher in Drinkers |
| cg03472672 | 6 | 28762471 | Higher in Drinkers |
| cg03472695 | 7 | 154661095 | Higher in Drinkers |
| cg03472898 | 14 | 29240992 | Higher in Drinkers |
| cg03474795 | 5 | 176074466 | Higher in Drinkers |
| cg03476000 | 1 | 6480167 | Higher in Drinkers |
| cg03476862 | 7 | 98581334 | Higher in Drinkers |
| cg03477043 | 16 | 2812423 | Lower in Drinkers |
| cg03478533 | 22 | 24989059 | Higher in Drinkers |
| cg03478540 | X | 44732183 | Higher in Drinkers |
| cg03481488 | 10 | 81091172 | Higher in Drinkers |
| cg03481620 | 11 | 71715003 | Higher in Drinkers |
| cg03482029 | 4 | 6642442 | Higher in Drinkers |
| cg03483142 | 8 | 87521078 | Higher in Drinkers |
| cg03483426 | 7 | 134671876 | Higher in Drinkers |
| cg03486540 | 19 | 44598375 | Higher in Drinkers |
| cg03487430 | 9 | 35616244 | Higher in Drinkers |
| cg03491584 | 19 | 17958961 | Higher in Drinkers |
| cg03492136 | 12 | 111137054 | Higher in Drinkers |
| cg03493260 | 21 | 30389043 | Higher in Drinkers |
| cg03494797 | 8 | 95731991 | Higher in Drinkers |
| cg03495688 | 9 | 6007586 | Higher in Drinkers |
| cg03497297 | 18 | 2655452 | Higher in Drinkers |
| cg03499052 | 4 | 38869262 | Higher in Drinkers |
| cg03502001 | 13 | 29298122 | Lower in Drinkers |
| cg03503634 | 11 | 36531973 | Higher in Drinkers |
| cg03503905 | 20 | 60640758 | Higher in Drinkers |
| cg03506372 | 11 | 60897603 | Higher in Drinkers |
| cg03509024 | 3 | 10184013 | Higher in Drinkers |
| cg03510310 | 11 | 63331286 | Higher in Drinkers |
| cg03511957 | 1 | 167765211 | Higher in Drinkers |

| | | | |
|---|---|---|---|
| cg03512355 | 12 | 121837704 | Higher in Drinkers |
| cg03515380 | 2 | 242660724 | Higher in Drinkers |
| cg03515494 | 12 | 8068627 | Lower in Drinkers |
| cg03519451 | 7 | 150780317 | Higher in Drinkers |
| cg03519880 | 3 | 125321157 | Higher in Drinkers |
| cg03520342 | 6 | 32920784 | Higher in Drinkers |
| cg03521085 | 4 | 1219008 | Higher in Drinkers |
| cg03522132 | 2 | 74725040 | Higher in Drinkers |
| cg03523363 | 20 | 48532218 | Higher in Drinkers |
| cg03524308 | 19 | 37663414 | Higher in Drinkers |
| cg03525122 | 1 | 230203783 | Higher in Drinkers |
| cg03528353 | 17 | 61819722 | Higher in Drinkers |
| cg03529908 | 1 | 2478089 | Higher in Drinkers |
| cg03530925 | 1 | 59165848 | Higher in Drinkers |
| cg03532167 | 2 | 114341680 | Higher in Drinkers |
| cg03535284 | 6 | 169653959 | Higher in Drinkers |
| cg03535461 | 1 | 23885568 | Higher in Drinkers |
| cg03535663 | 15 | 48937856 | Higher in Drinkers |
| cg03535933 | 8 | 67974296 | Higher in Drinkers |
| cg03536488 | 19 | 3198970 | Higher in Drinkers |
| cg03536881 | 19 | 49496987 | Higher in Drinkers |
| cg03539511 | 20 | 57607061 | Higher in Drinkers |
| cg03539876 | 3 | 149688127 | Higher in Drinkers |
| cg03540028 | 21 | 43183977 | Higher in Drinkers |
| cg03540197 | 16 | 12894048 | Higher in Drinkers |
| cg03540622 | 3 | 42706066 | Lower in Drinkers |
| cg03540781 | 15 | 83680553 | Higher in Drinkers |
| cg03541056 | 16 | 4365718 | Higher in Drinkers |
| cg03544525 | 1 | 207226564 | Higher in Drinkers |
| cg03545047 | 7 | 149321876 | Higher in Drinkers |
| cg03547730 | 8 | 102138864 | Higher in Drinkers |
| cg03552327 | 12 | 50222455 | Higher in Drinkers |
| cg03552472 | 10 | 51623769 | Higher in Drinkers |
| cg03552992 | 17 | 3599635 | Higher in Drinkers |
| cg03553246 | 4 | 2827126 | Higher in Drinkers |

| | | | |
|---|---|---|---|
| cgC3563403 | 9 | 35079882 | Higher in Drinkers |
| cgC3564698 | 3 | 48889206 | Higher in Drinkers |
| cgC3565274 | 3 | 50629708 | Higher in Drinkers |
| cgC3565659 | 12 | 72332624 | Higher in Drinkers |
| cgC3565868 | 11 | 47400146 | Higher in Drinkers |
| cgC3566409 | 13 | 114253797 | Higher in Drinkers |
| cgC3566853 | 2 | 106810993 | Higher in Drinkers |
| cgC3569748 | 17 | 37764220 | Higher in Drinkers |
| cgC3572913 | 20 | 34287853 | Higher in Drinkers |
| cgC3573702 | 19 | 44669354 | Higher in Drinkers |
| cgC3574882 | 7 | 151574332 | Higher in Drinkers |
| cgC3576039 | X | 133306349 | Higher in Drinkers |
| cgC3577601 | 20 | 47663236 | Higher in Drinkers |
| cgC3579053 | 5 | 175936147 | Higher in Drinkers |
| cgC3586803 | 1 | 54587426 | Higher in Drinkers |
| cgC3589311 | 6 | 33220036 | Higher in Drinkers |
| cgC3591483 | 16 | 85663099 | Higher in Drinkers |
| cgC3591676 | 8 | 96281769 | Higher in Drinkers |
| cgC3591917 | 3 | 197476477 | Higher in Drinkers |
| cgC3595439 | 2 | 232574653 | Higher in Drinkers |
| cgC3596181 | 8 | 41686111 | Higher in Drinkers |
| cgC3597174 | 17 | 27359875 | Higher in Drinkers |
| cgC3598726 | 22 | 50246859 | Higher in Drinkers |
| cgC3603951 | 2 | 47797488 | Higher in Drinkers |
| cgC3603977 | 1 | 35332137 | Higher in Drinkers |
| cgC3604819 | 4 | 17813007 | Higher in Drinkers |
| cgC3607220 | 6 | 32526263 | Higher in Drinkers |
| cgC3608712 | 5 | 140777607 | Lower in Drinkers |
| cgC3610266 | 16 | 31471393 | Higher in Drinkers |
| cgC3613132 | 8 | 37888764 | Higher in Drinkers |
| cgC3614513 | 1 | 115632038 | Higher in Drinkers |
| cgC3615207 | 18 | 12702659 | Higher in Drinkers |
| cgC3615408 | 19 | 11032005 | Higher in Drinkers |
| cgC3616827 | 8 | 135697767 | Higher in Drinkers |
| cgC3617367 | 14 | 74226931 | Higher in Drinkers |

| | | | |
|---|---|---|---|
| cg03624415 | 15 | 64995499 | Higher in Drinkers |
| cg03625627 | 22 | 31687370 | Higher in Drinkers |
| cg03625951 | 6 | 149867442 | Higher in Drinkers |
| cg03626511 | 19 | 14548632 | Lower in Drinkers |
| cg03628719 | 15 | 89438964 | Higher in Drinkers |
| cg03629318 | 3 | 48481693 | Higher in Drinkers |
| cg03629926 | 19 | 8438839 | Lower in Drinkers |
| cg03630215 | 11 | 75236771 | Higher in Drinkers |
| cg03630615 | 8 | 97274052 | Higher in Drinkers |
| cg03630797 | 16 | 98753119 | Higher in Drinkers |
| cg03636215 | 1 | 38512601 | Higher in Drinkers |
| cg03641940 | 5 | 125712782 | Higher in Drinkers |
| cg03642224 | 10 | 27443433 | Higher in Drinkers |
| cg03643520 | 19 | 36119666 | Higher in Drinkers |
| cg03647944 | 16 | 2582597 | Higher in Drinkers |
| cg03648361 | 17 | 73893010 | Higher in Drinkers |
| cg03650119 | 1 | 228346014 | Lower in Drinkers |
| cg03652525 | 3 | 72149324 | Higher in Drinkers |
| cg03652611 | 5 | 138941366 | Higher in Drinkers |
| cg03653817 | 1 | 181065498 | Higher in Drinkers |
| cg03654668 | 10 | 14551049 | Higher in Drinkers |
| cg03655940 | 16 | 15737228 | Higher in Drinkers |
| cg03658471 | 10 | 52383438 | Higher in Drinkers |
| cg03660876 | X | 11284010 | Higher in Drinkers |
| cg03662467 | 18 | 43753538 | Higher in Drinkers |
| cg03663739 | 21 | 37432700 | Higher in Drinkers |
| cg03664772 | 7 | 786682 | Lower in Drinkers |
| cg03668033 | 3 | 101405211 | Higher in Drinkers |
| cg03669292 | 16 | 30087955 | Higher in Drinkers |
| cg03669590 | 12 | 113592619 | Higher in Drinkers |
| cg03670158 | 17 | 41323431 | Higher in Drinkers |
| cg03672716 | 3 | 75708104 | Higher in Drinkers |
| cg03673787 | 17 | 78079481 | Lower in Drinkers |
| cg03675884 | 16 | 67700743 | Higher in Drinkers |
| cg03677003 | 13 | 44359996 | Higher in Drinkers |

| | | | |
|---|---|---|---|
| cg03677952 | 22 | 50524541 | Higher in Drinkers |
| cg03679305 | 1 | 9129487 | Higher in Drinkers |
| cg03680790 | 12 | 131281661 | Lower in Drinkers |
| cg03681057 | 5 | 143172702 | Higher in Drinkers |
| cg03682823 | 7 | 94286953 | Higher in Drinkers |
| cg03682872 | 6 | 158402912 | Higher in Drinkers |
| cg03684513 | 1 | 24882451 | Higher in Drinkers |
| cg03687994 | 6 | 90538873 | Higher in Drinkers |
| cg03688139 | 7 | 152161695 | Higher in Drinkers |
| cg03688995 | 11 | 1086421 | Higher in Drinkers |
| cg03689568 | 16 | 2259923 | Lower in Drinkers |
| cg03691020 | 6 | 144416889 | Higher in Drinkers |
| cg03691312 | 16 | 30194416 | Higher in Drinkers |
| cg03692134 | X | 129116990 | Higher in Drinkers |
| cg03693434 | 17 | 80050880 | Higher in Drinkers |
| cg03694261 | 11 | 122753977 | Higher in Drinkers |
| cg03695699 | 6 | 111580364 | Higher in Drinkers |
| cg03697723 | 17 | 79451274 | Higher in Drinkers |
| cg03697918 | 16 | 86546628 | Lower in Drinkers |
| cg03700024 | 2 | 74666700 | Higher in Drinkers |
| cg03703940 | 11 | 93394809 | Higher in Drinkers |
| cg03707784 | 2 | 240965007 | Higher in Drinkers |
| cg03711046 | X | 48814205 | Higher in Drinkers |
| cg03712239 | 10 | 38265764 | Higher in Drinkers |
| cg03713996 | 12 | 132195583 | Higher in Drinkers |
| cg03714531 | 6 | 30923590 | Higher in Drinkers |
| cg03715846 | 9 | 126761062 | Higher in Drinkers |
| cg03719026 | 12 | 6619479 | Higher in Drinkers |
| cg03719128 | 10 | 31607150 | Higher in Drinkers |
| cg03719169 | 17 | 73285533 | Higher in Drinkers |
| cg03719236 | 10 | 115934698 | Higher in Drinkers |
| cg03720745 | 8 | 22561445 | Higher in Drinkers |
| cg03721017 | 19 | 18558309 | Higher in Drinkers |
| cg03727756 | 1 | 51425478 | Higher in Drinkers |
| cg03731056 | 17 | 47270386 | Higher in Drinkers |

| | | | |
|---|---|---|---|
| cg03731896 | 19 | 49474391 | Higher in Drinkers |
| cg03736058 | 19 | 4361801 | Lower in Drinkers |
| cg03737984 | 11 | 33280157 | Higher in Drinkers |
| cg03738959 | 9 | 37904295 | Higher in Drinkers |
| cg03741348 | 1 | 32712237 | Higher in Drinkers |
| cg03742890 | 19 | 13910592 | Lower in Drinkers |
| cg03742947 | 6 | 29856275 | Higher in Drinkers |
| cg03747695 | 19 | 44716642 | Higher in Drinkers |
| cg03750061 | 10 | 119131167 | Higher in Drinkers |
| cg03751030 | 8 | 56015576 | Higher in Drinkers |
| cg03752639 | 1 | 209953185 | Higher in Drinkers |
| cg03753191 | 13 | 43566902 | Higher in Drinkers |
| cg03753849 | 12 | 42877401 | Higher in Drinkers |
| cg03759077 | 2 | 153575599 | Higher in Drinkers |
| cg03760316 | 18 | 3594197 | Higher in Drinkers |
| cg03761091 | 15 | 21968339 | Higher in Drinkers |
| cg03761210 | 20 | 32251509 | Higher in Drinkers |
| cg03761810 | 2 | 10264850 | Higher in Drinkers |
| cg03765359 | X | 47479190 | Higher in Drinkers |
| cg03769523 | 10 | 104613934 | Higher in Drinkers |
| cg03771185 | 4 | 775700 | Higher in Drinkers |
| cg03771385 | 2 | 43454876 | Higher in Drinkers |
| cg03773146 | X | 129114634 | Higher in Drinkers |
| cg03774988 | 20 | 62715942 | Higher in Drinkers |
| cg03776042 | 22 | 45633117 | Higher in Drinkers |
| cg03777474 | 17 | 26132578 | Higher in Drinkers |
| cg03778895 | 13 | 50699716 | Higher in Drinkers |
| cg03779117 | 7 | 57271021 | Higher in Drinkers |
| cg03780078 | 10 | 70715529 | Higher in Drinkers |
| cg03780356 | 3 | 184032924 | Higher in Drinkers |
| cg03780905 | 11 | 10326565 | Higher in Drinkers |
| cg03782381 | 17 | 43450670 | Higher in Drinkers |
| cg03786424 | 4 | 1334139 | Higher in Drinkers |
| cg03788131 | 7 | 149412290 | Higher in Drinkers |
| cg03789276 | 3 | 160170225 | Higher in Drinkers |

| | | | |
|---|---|---|---|
| cg03790022 | 7 | 4797831 | Higher in Drinkers |
| cg03790236 | 11 | 67057248 | Higher in Drinkers |
| cg03790864 | 15 | 78731104 | Higher in Drinkers |
| cg03791955 | 15 | 65024147 | Lower in Drinkers |
| cg03793131 | 1 | 43833547 | Higher in Drinkers |
| cg03793407 | 5 | 141705077 | Higher in Drinkers |
| cg03795157 | 12 | 133531927 | Higher in Drinkers |
| cg03801128 | 16 | 77224772 | Lower in Drinkers |
| cg03801816 | 1 | 155214815 | Higher in Drinkers |
| cg03801871 | 2 | 30453395 | Higher in Drinkers |
| cg03801946 | 16 | 4303664 | Higher in Drinkers |
| cg03803325 | 5 | 271584 | Higher in Drinkers |
| cg03805410 | 22 | 42487359 | Higher in Drinkers |
| cg03807711 | 17 | 47492440 | Higher in Drinkers |
| cg03813688 | 2 | 74740991 | Higher in Drinkers |
| cg03814686 | 5 | 78533319 | Higher in Drinkers |
| cg03816593 | 20 | 30311703 | Higher in Drinkers |
| cg03816991 | 3 | 122135401 | Higher in Drinkers |
| cg03820936 | 19 | 58326375 | Higher in Drinkers |
| cg03823468 | 17 | 40557347 | Higher in Drinkers |
| cg03824868 | 16 | 50744353 | Higher in Drinkers |
| cg03827639 | 3 | 32501676 | Higher in Drinkers |
| cg03834394 | 5 | 179226172 | Higher in Drinkers |
| cg03835793 | 6 | 139094465 | Higher in Drinkers |
| cg03837963 | 16 | 15666930 | Lower in Drinkers |
| cg03839661 | 4 | 183066237 | Higher in Drinkers |
| cg03840259 | 22 | 40297036 | Higher in Drinkers |
| cg03840920 | 15 | 12321227 | Higher in Drinkers |
| cg03841832 | 4 | 9981202 | Higher in Drinkers |
| cg03848267 | 12 | 57506361 | Higher in Drinkers |
| cg03848637 | 14 | 34931577 | Higher in Drinkers |
| cg03848857 | 4 | 52861702 | Higher in Drinkers |
| cg03849851 | 6 | 166980629 | Higher in Drinkers |
| cg03852056 | 16 | 57769597 | Higher in Drinkers |
| cg03854543 | 4 | 154074127 | Higher in Drinkers |

| | | | |
|---|---|---|---|
| cg03857186 | 2 | 27255618 | Higher in Drinkers |
| cg03862781 | 11 | 14521235 | Higher in Drinkers |
| cg03863149 | 1 | 91487516 | Higher in Drinkers |
| cg03869253 | 6 | 88299900 | Higher in Drinkers |
| cg03870270 | 3 | 15643045 | Higher in Drinkers |
| cg03870856 | 12 | 58138780 | Higher in Drinkers |
| cg03871102 | 11 | 68024285 | Higher in Drinkers |
| cg03872267 | 15 | 89011204 | Higher in Drinkers |
| cg03873659 | 3 | 123304056 | Higher in Drinkers |
| cg03874358 | 19 | 17392384 | Higher in Drinkers |
| cg03876676 | 10 | 96162988 | Higher in Drinkers |
| cg03877960 | 16 | 5079023 | Lower in Drinkers |
| cg03878377 | 15 | 55489120 | Higher in Drinkers |
| cg03880724 | 16 | 21312085 | Higher in Drinkers |
| cg03881051 | 19 | 3036221 | Higher in Drinkers |
| cg03881294 | 2 | 11884333 | Higher in Drinkers |
| cg03881446 | 13 | 33002412 | Higher in Drinkers |
| cg03883491 | 1 | 46639752 | Higher in Drinkers |
| cg03884783 | 19 | 37957997 | Higher in Drinkers |
| cg03885270 | 10 | 22843938 | Higher in Drinkers |
| cg03885929 | 10 | 120513992 | Higher in Drinkers |
| cg03887008 | 16 | 1360923 | Higher in Drinkers |
| cg03887534 | 22 | 18121194 | Higher in Drinkers |
| cg03892543 | 16 | 84650330 | Higher in Drinkers |
| cg03894033 | 22 | 20850168 | Higher in Drinkers |
| cg03899737 | 1 | 3615390 | Lower in Drinkers |
| cg03900072 | 20 | 30060822 | Higher in Drinkers |
| cg03900664 | 4 | 99917553 | Higher in Drinkers |
| cg03901185 | 12 | 124087057 | Higher in Drinkers |
| cg03901532 | 2 | 36718460 | Lower in Drinkers |
| cg03902159 | 16 | 88051832 | Lower in Drinkers |
| cg03905094 | 5 | 59996421 | Higher in Drinkers |
| cg03907390 | 10 | 121066392 | Higher in Drinkers |
| cg03912740 | 9 | 136242381 | Higher in Drinkers |
| cg03915645 | 3 | 9344441 | Higher in Drinkers |

| | | | |
|---|---|---|---|
| cg03915648 | 12 | 115130124 | Higher in Drinkers |
| cg03918523 | 17 | 58041547 | Higher in Drinkers |
| cg03920003 | 1 | 154582007 | Higher in Drinkers |
| cg03927504 | 16 | 88843923 | Higher in Drinkers |
| cg03929575 | 12 | 29909122 | Lower in Drinkers |
| cg03930770 | 22 | 41253267 | Higher in Drinkers |
| cg03930948 | 17 | 5322888 | Higher in Drinkers |
| cg03932406 | 2 | 65657881 | Higher in Drinkers |
| cg03934150 | 1 | 244212074 | Higher in Drinkers |
| cg03934572 | 7 | 93633877 | Higher in Drinkers |
| cg03935116 | 12 | 31476565 | Higher in Drinkers |
| cg03935370 | 16 | 3054007 | Higher in Drinkers |
| cg03936193 | 10 | 105727425 | Higher in Drinkers |
| cg03936229 | 17 | 55392230 | Higher in Drinkers |
| cg03939087 | 16 | 2933515 | Higher in Drinkers |
| cg03939485 | 6 | 33266076 | Higher in Drinkers |
| cg03939820 | 1 | 155057257 | Higher in Drinkers |
| cg03941531 | 22 | 50170670 | Higher in Drinkers |
| cg03943025 | 6 | 33084549 | Higher in Drinkers |
| cg03945800 | 16 | 4165515 | Lower in Drinkers |
| cg03948048 | 10 | 91352963 | Higher in Drinkers |
| cg03950654 | 17 | 4613328 | Higher in Drinkers |
| cg03951132 | 20 | 5931305 | Higher in Drinkers |
| cg03953709 | 2 | 157189668 | Higher in Drinkers |
| cg03955927 | 2 | 63272232 | Higher in Drinkers |
| cg03956833 | 1 | 1051711 | Higher in Drinkers |
| cg03961086 | 15 | 77223867 | Higher in Drinkers |
| cg03962173 | 7 | 101930855 | Higher in Drinkers |
| cg03966045 | 2 | 202316319 | Higher in Drinkers |
| cg03969070 | 1 | 36851558 | Higher in Drinkers |
| cg03969997 | 7 | 73256865 | Higher in Drinkers |
| cg03971344 | 16 | 89349124 | Higher in Drinkers |
| cg03975948 | 12 | 123320751 | Higher in Drinkers |
| cg03978514 | 2 | 241494647 | Higher in Drinkers |
| cg03982443 | 3 | 128968543 | Higher in Drinkers |

| | | | |
|---|---|---|---|
| cg03983837 | 11 | 2323801 | Higher in Drinkers |
| cg03986968 | 15 | 34330894 | Higher in Drinkers |
| cg03987227 | 5 | 139494540 | Higher in Drinkers |
| cg03988778 | 11 | 22850391 | Higher in Drinkers |
| cg03989569 | 1 | 156471288 | Higher in Drinkers |
| cg03990551 | 4 | 122791477 | Higher in Drinkers |
| cg03996465 | 13 | 53226743 | Higher in Drinkers |
| cg03998476 | 20 | 56884536 | Higher in Drinkers |
| cg03999420 | 13 | 77901358 | Higher in Drinkers |
| cg04001090 | 8 | 77912693 | Higher in Drinkers |
| cg04002454 | 2 | 231191893 | Higher in Drinkers |
| cg04002758 | 16 | 28303471 | Higher in Drinkers |
| cg04005032 | 3 | 32022767 | Higher in Drinkers |
| cg04007858 | 20 | 18774820 | Higher in Drinkers |
| cg04010032 | X | 129244631 | Higher in Drinkers |
| cg04011872 | 11 | 1968980 | Higher in Drinkers |
| cg04017276 | 22 | 44577135 | Higher in Drinkers |
| cg04018023 | 7 | 47616088 | Higher in Drinkers |
| cg04021430 | 16 | 46723153 | Higher in Drinkers |
| cg04021674 | 2 | 111878760 | Higher in Drinkers |
| cg04022912 | 16 | 24864984 | Higher in Drinkers |
| cg04027632 | 6 | 28908623 | Higher in Drinkers |
| cg04027916 | 11 | 65686562 | Higher in Drinkers |
| cg04028224 | 17 | 72733172 | Higher in Drinkers |
| cg04028591 | 19 | 15529955 | Higher in Drinkers |
| cg04030492 | 4 | 184426817 | Higher in Drinkers |
| cg04033650 | 7 | 72722679 | Higher in Drinkers |
| cg04034539 | 11 | 62439802 | Higher in Drinkers |
| cg04034891 | 16 | 72128225 | Higher in Drinkers |
| cg04043571 | 9 | 127265989 | Lower in Drinkers |
| cg04044561 | 7 | 100303839 | Higher in Drinkers |
| cg04047127 | 2 | 203500074 | Higher in Drinkers |
| cg04048131 | 13 | 107031945 | Higher in Drinkers |
| cg04050020 | 6 | 4776995 | Higher in Drinkers |
| cg04052570 | 14 | 88459528 | Higher in Drinkers |

| | | | |
|---|---|---|---|
| cg04053045 | 2 | 96810531 | Higher in Drinkers |
| cg04054034 | 11 | 32113137 | Higher in Drinkers |
| cg04054303 | 6 | 32606445 | Lower in Drinkers |
| cg04054600 | 11 | 67121358 | Higher in Drinkers |
| cg04057288 | 9 | 130504189 | Higher in Drinkers |
| cg04060830 | 9 | 132316023 | Higher in Drinkers |
| cg04062135 | 5 | 114879581 | Higher in Drinkers |
| cg04064675 | 11 | 19139135 | Higher in Drinkers |
| cg04069277 | 16 | 30661984 | Higher in Drinkers |
| cg04071694 | 13 | 76056416 | Higher in Drinkers |
| cg04072691 | 16 | 5008272 | Higher in Drinkers |
| cg04075973 | 11 | 118781608 | Higher in Drinkers |
| cg04076682 | 11 | 32915823 | Higher in Drinkers |
| cg04078251 | 16 | 29802448 | Higher in Drinkers |
| cg04078921 | 6 | 26235441 | Higher in Drinkers |
| cg04080080 | 12 | 247459 | Higher in Drinkers |
| cg04081091 | 3 | 32726522 | Higher in Drinkers |
| cg04081651 | 10 | 30722660 | Higher in Drinkers |
| cg04086771 | 20 | 35724798 | Higher in Drinkers |
| cg04088137 | 3 | 194392978 | Higher in Drinkers |
| cg04089434 | 10 | 94516971 | Higher in Drinkers |
| cg04091768 | 5 | 149900791 | Higher in Drinkers |
| cg04094067 | 16 | 570658 | Higher in Drinkers |
| cg04098023 | 17 | 67410253 | Lower in Drinkers |
| cg04098052 | 7 | 24517414 | Higher in Drinkers |
| cg04100647 | 6 | 74229933 | Higher in Drinkers |
| cg04102510 | 1 | 226350741 | Higher in Drinkers |
| cg04105716 | 17 | 79094934 | Higher in Drinkers |
| cg04107773 | 20 | 62273555 | Higher in Drinkers |
| cg04113200 | 12 | 131303774 | Higher in Drinkers |
| cg04113895 | 3 | 197676776 | Higher in Drinkers |
| cg04115602 | 19 | 49552606 | Higher in Drinkers |
| cg04116858 | 1 | 159895664 | Higher in Drinkers |
| cg04117643 | 17 | 7476796 | Higher in Drinkers |
| cg04118242 | 8 | 28259409 | Higher in Drinkers |

| | | | |
|---|---|---|---|
| cg04119843 | 1 | 1284268 | Higher in Drinkers |
| cg04123260 | 1 | 249120154 | Higher in Drinkers |
| cg04126707 | 5 | 40680039 | Higher in Drinkers |
| cg04129736 | 22 | 37415199 | Higher in Drinkers |
| cg04129905 | 1 | 109642671 | Higher in Drinkers |
| cg04131494 | 5 | 176936862 | Higher in Drinkers |
| cg04132983 | 16 | 79632620 | Higher in Drinkers |
| cg04133572 | 1 | 161195810 | Higher in Drinkers |
| cg04134859 | 7 | 73097692 | Higher in Drinkers |
| cg04136290 | 17 | 80477136 | Higher in Drinkers |
| cg04136480 | 6 | 31510196 | Higher in Drinkers |
| cg04138571 | 15 | 99190795 | Higher in Drinkers |
| cg04139514 | 6 | 150335417 | Higher in Drinkers |
| cg04141459 | 3 | 183852329 | Higher in Drinkers |
| cg04141788 | 7 | 43731989 | Higher in Drinkers |
| cg04142692 | 11 | 67379534 | Higher in Drinkers |
| cg04143736 | 4 | 183066224 | Higher in Drinkers |
| cg04145287 | 1 | 26552102 | Higher in Drinkers |
| cg04145477 | 6 | 107077629 | Higher in Drinkers |
| cg04148720 | 16 | 67144419 | Higher in Drinkers |
| cg04151839 | 8 | 146126807 | Higher in Drinkers |
| cg04156970 | 19 | 1605618 | Higher in Drinkers |
| cg04157658 | 11 | 110243994 | Higher in Drinkers |
| cg04160653 | 11 | 3877315 | Higher in Drinkers |
| cg04162685 | 17 | 80207551 | Higher in Drinkers |
| cg04165030 | 5 | 175843293 | Higher in Drinkers |
| cg04165824 | 11 | 63580733 | Higher in Drinkers |
| cg04165910 | 11 | 208656 | Higher in Drinkers |
| cg04166544 | 2 | 230580574 | Higher in Drinkers |
| cg04166546 | 6 | 30640826 | Higher in Drinkers |
| cg04169021 | 17 | 35060451 | Higher in Drinkers |
| cg04169469 | 2 | 10588434 | Higher in Drinkers |
| cg04169534 | 17 | 507544 | Higher in Drinkers |
| cg04174125 | 16 | 23521756 | Higher in Drinkers |
| cg04174938 | X | 3733239 | Higher in Drinkers |

| | | | |
|---|---|---|---|
| cg04177705 | 3 | 88199274 | Higher in Drinkers |
| cg04180868 | 10 | 25241462 | Higher in Drinkers |
| cg04182114 | 15 | 63116019 | Lower in Drinkers |
| cg04182912 | 14 | 95157037 | Lower in Drinkers |
| cg04182927 | 17 | 80861959 | Higher in Drinkers |
| cg04183237 | 2 | 242165518 | Lower in Drinkers |
| cg04185037 | 6 | 159239164 | Higher in Drinkers |
| cg04188086 | 1 | 16175878 | Higher in Drinkers |
| cg04189768 | 16 | 89713915 | Higher in Drinkers |
| cg04190530 | 3 | 12598397 | Higher in Drinkers |
| cg04193635 | 16 | 28379378 | Lower in Drinkers |
| cg04194405 | 1 | 36622147 | Higher in Drinkers |
| cg04195161 | 17 | 36613704 | Higher in Drinkers |
| cg04197051 | 1 | 160001439 | Higher in Drinkers |
| cg04197452 | 1 | 208083913 | Higher in Drinkers |
| cg04199911 | 15 | 83419719 | Higher in Drinkers |
| cg04199943 | 6 | 30227732 | Higher in Drinkers |
| cg04203292 | 5 | 172124636 | Higher in Drinkers |
| cg04204002 | 21 | 43817086 | Higher in Drinkers |
| cg04207218 | 21 | 39878866 | Higher in Drinkers |
| cg04207741 | 12 | 57482553 | Higher in Drinkers |
| cg04210991 | 1 | 226374609 | Higher in Drinkers |
| cg04212021 | 5 | 180231084 | Higher in Drinkers |
| cg04213101 | 1 | 36690560 | Higher in Drinkers |
| cg04213235 | 1 | 145826932 | Higher in Drinkers |
| cg04216051 | 2 | 240172612 | Lower in Drinkers |
| cg04217650 | 3 | 66428294 | Higher in Drinkers |
| cg04217927 | 11 | 47737105 | Higher in Drinkers |
| cg04219287 | 22 | 31477504 | Higher in Drinkers |
| cg04219510 | 14 | 64010574 | Higher in Drinkers |
| cg04220088 | 4 | 141294522 | Higher in Drinkers |
| cg04220298 | 11 | 73587932 | Higher in Drinkers |
| cg04221305 | 14 | 75348497 | Higher in Drinkers |
| cg04221877 | 1 | 25257515 | Lower in Drinkers |
| cg04222027 | 5 | 64331794 | Higher in Drinkers |

| | | | |
|---|---|---|---|
| cg04226386 | 6 | 36853708 | Higher in Drinkers |
| cg04228628 | 8 | 9413457 | Higher in Drinkers |
| cg04229372 | 13 | 113477850 | Higher in Drinkers |
| cg04230662 | 1 | 1343134 | Higher in Drinkers |
| cg04230869 | 8 | 103251129 | Higher in Drinkers |
| cg04232128 | 5 | 138886241 | Higher in Drinkers |
| cg04232615 | 16 | 56998704 | Higher in Drinkers |
| cg04234318 | 5 | 176074477 | Higher in Drinkers |
| cg04236718 | 12 | 71834183 | Higher in Drinkers |
| cg04236901 | 4 | 175204805 | Higher in Drinkers |
| cg04237075 | 9 | 34637949 | Higher in Drinkers |
| cg04237127 | 17 | 38215109 | Lower in Drinkers |
| cg04237429 | 22 | 50051110 | Higher in Drinkers |
| cg04237436 | 11 | 35808688 | Higher in Drinkers |
| cg04238185 | 3 | 89164223 | Lower in Drinkers |
| cg04243582 | 1 | 1655942 | Higher in Drinkers |
| cg04243827 | 5 | 3103718 | Lower in Drinkers |
| cg04246357 | 6 | 158589294 | Higher in Drinkers |
| cg04246880 | 10 | 135150497 | Higher in Drinkers |
| cg04248573 | 6 | 37226124 | Higher in Drinkers |
| cg04249769 | 8 | 80680899 | Higher in Drinkers |
| cg04252145 | 5 | 67516319 | Higher in Drinkers |
| cg04252558 | 8 | 74884436 | Higher in Drinkers |
| cg04254693 | 3 | 49727222 | Higher in Drinkers |
| cg04257362 | 19 | 3585935 | Higher in Drinkers |
| cg04261248 | 19 | 1241559 | Higher in Drinkers |
| cg04262392 | 16 | 2136746 | Lower in Drinkers |
| cg04263740 | 7 | 65375514 | Higher in Drinkers |
| cg04265210 | 20 | 5931609 | Higher in Drinkers |
| cg04265957 | 14 | 65237663 | Lower in Drinkers |
| cg04270274 | 16 | 58662988 | Higher in Drinkers |
| cg04270867 | 19 | 2116807 | Higher in Drinkers |
| cg04273556 | 9 | 35096672 | Higher in Drinkers |
| cg04274800 | 18 | 72266094 | Higher in Drinkers |
| cg04276069 | 19 | 2061849 | Higher in Drinkers |

| | | | |
|---|---|---|---|
| cg04276536 | 16 | 57567813 | Higher in Drinkers |
| cg04279629 | 4 | 52710605 | Higher in Drinkers |
| cg04280480 | 22 | 46547117 | Higher in Drinkers |
| cg04280758 | 11 | 96076485 | Higher in Drinkers |
| cg04281649 | 2 | 98612676 | Higher in Drinkers |
| cg04282206 | 17 | 62833786 | Higher in Drinkers |
| cg04282419 | 11 | 110583662 | Higher in Drinkers |
| cg04285855 | 14 | 105794185 | Lower in Drinkers |
| cg04286697 | 2 | 232259623 | Lower in Drinkers |
| cg04287330 | 1 | 43423596 | Higher in Drinkers |
| cg04288012 | X | 53711065 | Higher in Drinkers |
| cg04290162 | 16 | 82204401 | Higher in Drinkers |
| cg04290510 | 14 | 54864231 | Higher in Drinkers |
| cg04291082 | 1 | 193028561 | Higher in Drinkers |
| cg04294952 | 20 | 36500432 | Higher in Drinkers |
| cg04295928 | 11 | 3829466 | Higher in Drinkers |
| cg04296434 | 20 | 48769996 | Higher in Drinkers |
| cg04300687 | 22 | 46727235 | Higher in Drinkers |
| cg04301857 | 19 | 56604827 | Higher in Drinkers |
| cg04304033 | 19 | 18547070 | Higher in Drinkers |
| cg04305858 | 6 | 30457182 | Higher in Drinkers |
| cg04310649 | 10 | 35416472 | Higher in Drinkers |
| cg04312406 | 1 | 226497240 | Higher in Drinkers |
| cg04313968 | 19 | 1821895 | Higher in Drinkers |
| cg04319276 | 19 | 42445244 | Higher in Drinkers |
| cg04321154 | 2 | 178417545 | Higher in Drinkers |
| cg04328842 | 19 | 11144151 | Higher in Drinkers |
| cg04330631 | 6 | 42016203 | Higher in Drinkers |
| cg04335102 | 3 | 123680028 | Higher in Drinkers |
| cg04337542 | 12 | 1704080 | Higher in Drinkers |
| cg04338022 | 1 | 20126560 | Higher in Drinkers |
| cg04338175 | 7 | 6646162 | Higher in Drinkers |
| cg04338428 | 19 | 42746319 | Higher in Drinkers |
| cg04340772 | 4 | 75023606 | Higher in Drinkers |
| cg04342895 | 12 | 112847041 | Higher in Drinkers |

| | | | |
|---|---|---|---|
| cg04343407 | 16 | 3015092 | Higher in Drinkers |
| cg04346968 | 11 | 3877179 | Higher in Drinkers |
| cg04347006 | 1 | 3688759 | Higher in Drinkers |
| cg04347379 | 7 | 794485 | Higher in Drinkers |
| cg04348816 | 7 | 5461417 | Higher in Drinkers |
| cg04349311 | 1 | 52521202 | Higher in Drinkers |
| cg04352115 | 16 | 29801967 | Higher in Drinkers |
| cg04352288 | 16 | 87958407 | Lower in Drinkers |
| cg04353469 | 3 | 50337070 | Higher in Drinkers |
| cg04354317 | 1 | 165667545 | Higher in Drinkers |
| cg04355250 | 12 | 113796401 | Higher in Drinkers |
| cg04358923 | 11 | 76091681 | Higher in Drinkers |
| cg04360147 | 1 | 27021709 | Higher in Drinkers |
| cg04360491 | 11 | 47600569 | Higher in Drinkers |
| cg04361053 | 19 | 38686253 | Higher in Drinkers |
| cg04362960 | 10 | 104952993 | Higher in Drinkers |
| cg04365617 | 1 | 101491640 | Higher in Drinkers |
| cg04366619 | 19 | 14544028 | Higher in Drinkers |
| cg04371633 | 14 | 65381025 | Higher in Drinkers |
| cg04371779 | 14 | 76618201 | Higher in Drinkers |
| cg04372321 | 4 | 967432 | Higher in Drinkers |
| cg04375083 | 1 | 167684280 | Higher in Drinkers |
| cg04376719 | 19 | 1028379 | Higher in Drinkers |
| cg04376747 | 19 | 36120543 | Lower in Drinkers |
| cg04378830 | 16 | 89965359 | Higher in Drinkers |
| cg04380513 | 5 | 100236983 | Higher in Drinkers |
| cg04381122 | 14 | 59655332 | Higher in Drinkers |
| cg04382063 | 6 | 35027226 | Higher in Drinkers |
| cg04392971 | 1 | 161369648 | Higher in Drinkers |
| cg04393897 | 1 | 171454518 | Higher in Drinkers |
| cg04393903 | 3 | 53381207 | Higher in Drinkers |
| cg04395498 | 7 | 2017437 | Higher in Drinkers |
| cg04396539 | 2 | 208030966 | Higher in Drinkers |
| cg04401710 | 4 | 141294570 | Higher in Drinkers |
| cg04403415 | 12 | 124991087 | Higher in Drinkers |

| | | | |
|---|---|---|---|
| cg04406441 | 4 | 109541957 | Higher in Drinkers |
| cg04407431 | 1 | 840618 | Higher in Drinkers |
| cg04407474 | 1 | 52869986 | Higher in Drinkers |
| cg04407762 | 4 | 113442791 | Higher in Drinkers |
| cg04410161 | 6 | 116892488 | Higher in Drinkers |
| cg04413680 | 6 | 71998398 | Higher in Drinkers |
| cg04414274 | 17 | 1957866 | Higher in Drinkers |
| cg04414860 | 6 | 116575894 | Higher in Drinkers |
| cg04417954 | 15 | 91073943 | Higher in Drinkers |
| cg04418576 | 14 | 103851554 | Higher in Drinkers |
| cg04419754 | 22 | 20044371 | Lower in Drinkers |
| cg04420749 | 6 | 21586358 | Higher in Drinkers |
| cg04420835 | 7 | 99724443 | Higher in Drinkers |
| cg04420878 | 8 | 56987290 | Higher in Drinkers |
| cg04421631 | 3 | 72495876 | Higher in Drinkers |
| cg04422742 | 6 | 32527793 | Higher in Drinkers |
| cg04423166 | 14 | 24702070 | Higher in Drinkers |
| cg04424385 | 7 | 129074328 | Higher in Drinkers |
| cg04425201 | 8 | 144335029 | Higher in Drinkers |
| cg04425419 | 17 | 42580524 | Higher in Drinkers |
| cg04425551 | 6 | 30297338 | Higher in Drinkers |
| cg04427462 | 19 | 47216031 | Higher in Drinkers |
| cg04428799 | 3 | 15116218 | Higher in Drinkers |
| cg04430835 | 4 | 52917409 | Higher in Drinkers |
| cg04430996 | 16 | 591437 | Higher in Drinkers |
| cg04431990 | 6 | 31509496 | Higher in Drinkers |
| cg04436449 | 3 | 185214835 | Higher in Drinkers |
| cg04437956 | 2 | 242869281 | Higher in Drinkers |
| cg04438064 | 2 | 240161619 | Higher in Drinkers |
| cg04438818 | 17 | 7737225 | Higher in Drinkers |
| cg04439584 | 15 | 64316219 | Higher in Drinkers |
| cg04440597 | 8 | 28573618 | Lower in Drinkers |
| cg04441780 | 15 | 83479272 | Higher in Drinkers |
| cg04446447 | 8 | 100905835 | Higher in Drinkers |
| cg04449126 | 13 | 99852558 | Higher in Drinkers |

| | | | |
|---|---|---|---|
| cg04450862 | 5 | 114516315 | Higher in Drinkers |
| cg04457481 | 20 | 57426835 | Higher in Drinkers |
| cg04458094 | 1 | 52831562 | Higher in Drinkers |
| cg04464062 | 16 | 88540349 | Higher in Drinkers |
| cg04464465 | 12 | 123755775 | Higher in Drinkers |
| cg04464559 | 6 | 107780641 | Higher in Drinkers |
| cg04465201 | 20 | 32699025 | Higher in Drinkers |
| cg04466696 | 16 | 66521191 | Higher in Drinkers |
| cg04467034 | 13 | 111567140 | Higher in Drinkers |
| cg04467611 | 11 | 64808285 | Higher in Drinkers |
| cg04467702 | 16 | 71320629 | Higher in Drinkers |
| cg04468608 | 2 | 74375168 | Higher in Drinkers |
| cg04473912 | 8 | 101920999 | Higher in Drinkers |
| cg04477741 | 1 | 11724884 | Higher in Drinkers |
| cg04476874 | 19 | 345778 | Higher in Drinkers |
| cg04478075 | 17 | 80753985 | Higher in Drinkers |
| cg04478698 | 4 | 26033992 | Higher in Drinkers |
| cg04478795 | 7 | 128828120 | Higher in Drinkers |
| cg04480285 | 11 | 61097029 | Higher in Drinkers |
| cg04489586 | 20 | 36148642 | Higher in Drinkers |
| cg04498032 | 1 | 155242826 | Higher in Drinkers |
| cg04498104 | 3 | 48573748 | Lower in Drinkers |
| cg04498580 | 4 | 140478204 | Higher in Drinkers |
| cg04500996 | 1 | 6526531 | Higher in Drinkers |
| cg04502927 | 5 | 60626960 | Higher in Drinkers |
| cg04503297 | 2 | 30597135 | Higher in Drinkers |
| cg04503743 | 7 | 142960869 | Higher in Drinkers |
| cg04506601 | 1 | 100435212 | Higher in Drinkers |
| cg04509940 | 21 | 45079326 | Higher in Drinkers |
| cg04516757 | 7 | 75599274 | Lower in Drinkers |
| cg04518342 | 5 | 131593106 | Lower in Drinkers |
| cg04521675 | 8 | 66556930 | Higher in Drinkers |
| cg04521724 | 2 | 2875964 | Higher in Drinkers |
| cg04523929 | 3 | 10168401 | Higher in Drinkers |
| cg04525476 | 5 | 172198714 | Higher in Drinkers |

| | | | |
|---|---|---|---|
| cg04525496 | 5 | 82767526 | Higher in Drinkers |
| cg04525773 | 7 | 87506040 | Higher in Drinkers |
| cg04526020 | 11 | 64948989 | Higher in Drinkers |
| cg04528024 | 13 | 111366565 | Higher in Drinkers |
| cg04529406 | X | 118897145 | Higher in Drinkers |
| cg04533699 | 4 | 175204644 | Higher in Drinkers |
| cg04534276 | 10 | 75255926 | Higher in Drinkers |
| cg04537374 | 6 | 31865753 | Higher in Drinkers |
| cg04542489 | 14 | 23775746 | Higher in Drinkers |
| cg04544093 | 9 | 140134707 | Higher in Drinkers |
| cg04549583 | 2 | 12146219 | Higher in Drinkers |
| cg04551011 | 8 | 17435008 | Higher in Drinkers |
| cg04551154 | 10 | 95462393 | Higher in Drinkers |
| cg04552346 | 5 | 133450238 | Higher in Drinkers |
| cg04556432 | 14 | 99880573 | Higher in Drinkers |
| cg04557057 | 7 | 12151638 | Higher in Drinkers |
| cg04559485 | 1 | 1159328 | Higher in Drinkers |
| cg04559896 | 17 | 10561738 | Higher in Drinkers |
| cg04561332 | 2 | 20550539 | Higher in Drinkers |
| cg04562396 | 14 | 55518417 | Higher in Drinkers |
| cg04563643 | 17 | 79995691 | Higher in Drinkers |
| cg04565490 | 6 | 29570607 | Higher in Drinkers |
| cg04568117 | 19 | 54695088 | Higher in Drinkers |
| cg04570283 | 14 | 82000256 | Higher in Drinkers |
| cg04571513 | 17 | 38716802 | Higher in Drinkers |
| cg04571604 | 8 | 103424826 | Higher in Drinkers |
| cg04574834 | 10 | 99891730 | Higher in Drinkers |
| cg04575325 | 6 | 160210070 | Higher in Drinkers |
| cg04575467 | 8 | 41997444 | Higher in Drinkers |
| cg04581073 | 6 | 37776593 | Lower in Drinkers |
| cg04585227 | 7 | 158671570 | Higher in Drinkers |
| cg04585679 | 19 | 5044863 | Higher in Drinkers |
| cg04585992 | 14 | 39639574 | Higher in Drinkers |
| cg04588257 | 19 | 45059935 | Lower in Drinkers |
| cg04590234 | 7 | 102105201 | Higher in Drinkers |

| | | | |
|---|---|---|---|
| cg04591119 | 6 | 111197245 | Higher in Drinkers |
| cg04591734 | 7 | 101630546 | Higher in Drinkers |
| cg04593445 | 16 | 2265125 | Higher in Drinkers |
| cg04595983 | 4 | 156298166 | Higher in Drinkers |
| cg04597831 | 1 | 45806086 | Higher in Drinkers |
| cg04598300 | 17 | 40531272 | Higher in Drinkers |
| cg04598683 | 11 | 129871924 | Higher in Drinkers |
| cg04599631 | 4 | 84256200 | Higher in Drinkers |
| cg04603176 | 11 | 118306465 | Higher in Drinkers |
| cg04604656 | 19 | 1356153 | Higher in Drinkers |
| cg04606265 | 12 | 112600525 | Higher in Drinkers |
| cg04609859 | 17 | 46655736 | Higher in Drinkers |
| cg04610628 | 7 | 7606396 | Higher in Drinkers |
| cg04612276 | 7 | 138554322 | Higher in Drinkers |
| cg04613133 | 7 | 142985809 | Higher in Drinkers |
| cg04614155 | 15 | 42209202 | Higher in Drinkers |
| cg04618230 | 4 | 54677002 | Higher in Drinkers |
| cg04619185 | 22 | 45706476 | Higher in Drinkers |
| cg04619710 | 22 | 41745221 | Higher in Drinkers |
| cg04619859 | 7 | 134855396 | Higher in Drinkers |
| cg04621020 | 5 | 101632341 | Higher in Drinkers |
| cg04621664 | 6 | 31802874 | Higher in Drinkers |
| cg04625536 | 6 | 42533006 | Higher in Drinkers |
| cg04625615 | 15 | 41788368 | Higher in Drinkers |
| cg04630748 | 7 | 100964998 | Higher in Drinkers |
| cg04631283 | 21 | 48068748 | Higher in Drinkers |
| cg04633021 | 1 | 150241625 | Higher in Drinkers |
| cg04634639 | 21 | 37757673 | Higher in Drinkers |
| cg04635917 | 6 | 35227381 | Higher in Drinkers |
| cg04643909 | 4 | 39640571 | Lower in Drinkers |
| cg04644833 | 4 | 141071988 | Higher in Drinkers |
| cg04648334 | 6 | 27236866 | Higher in Drinkers |
| cg04648440 | 9 | 136932424 | Higher in Drinkers |
| cg04653012 | 16 | 58163677 | Higher in Drinkers |
| cg04655431 | 9 | 125796809 | Higher in Drinkers |

| | | | |
|---|---|---|---|
| cg04655804 | 1 | 16302461 | Higher in Drinkers |
| cg04656070 | 8 | 116661063 | Higher in Drinkers |
| cg04658591 | 10 | 111971039 | Higher in Drinkers |
| cg04659396 | 5 | 131806593 | Higher in Drinkers |
| cg04659467 | 16 | 29822785 | Higher in Drinkers |
| cg04660357 | 12 | 53895291 | Higher in Drinkers |
| cg04660686 | 11 | 9635595 | Higher in Drinkers |
| cg04660698 | 16 | 29828145 | Higher in Drinkers |
| cg04661991 | 4 | 6989230 | Higher in Drinkers |
| cg04665180 | 9 | 132934972 | Higher in Drinkers |
| cg04665838 | 7 | 148936646 | Higher in Drinkers |
| cg04666029 | 11 | 2552843 | Higher in Drinkers |
| cg04667141 | 15 | 89089914 | Higher in Drinkers |
| cg04667719 | 15 | 59950097 | Lower in Drinkers |
| cg04671334 | 19 | 35224921 | Higher in Drinkers |
| cg04672450 | 1 | 860185 | Higher in Drinkers |
| cg04673590 | 7 | 27136191 | Higher in Drinkers |
| cg04673825 | 4 | 10459183 | Higher in Drinkers |
| cg04678315 | 12 | 125212010 | Higher in Drinkers |
| cg04680037 | 1 | 33430483 | Higher in Drinkers |
| cg04682916 | 7 | 42276848 | Higher in Drinkers |
| cg04685003 | 17 | 57696515 | Higher in Drinkers |
| cg04685459 | 3 | 52273525 | Higher in Drinkers |
| cg04689023 | 19 | 13266516 | Higher in Drinkers |
| cg04690289 | 3 | 45017999 | Higher in Drinkers |
| cg04691270 | 10 | 2371195 | Lower in Drinkers |
| cg04692942 | 20 | 3189896 | Higher in Drinkers |
| cg04693873 | 6 | 89855887 | Higher in Drinkers |
| cg04696494 | 2 | 234620385 | Higher in Drinkers |
| cg04697119 | 1 | 160068221 | Higher in Drinkers |
| cg04701182 | 10 | 69834353 | Higher in Drinkers |
| cg04703844 | 8 | 74207197 | Higher in Drinkers |
| cg04705238 | 11 | 126152868 | Higher in Drinkers |
| cg04708340 | 19 | 5622366 | Higher in Drinkers |
| cg04709655 | 2 | 122513098 | Higher in Drinkers |

| | | | |
|---|---|---|---|
| cg04709931 | 15 | 66679953 | Higher in Drinkers |
| cg04712004 | 6 | 71999105 | Higher in Drinkers |
| cg04714201 | 6 | 30538986 | Higher in Drinkers |
| cg04718055 | 1 | 78149336 | Higher in Drinkers |
| cg04718987 | 4 | 185355309 | Higher in Drinkers |
| cg04723723 | 1 | 67966270 | Higher in Drinkers |
| cg04724319 | 17 | 1009219 | Higher in Drinkers |
| cg04724489 | 7 | 127725176 | Higher in Drinkers |
| cg04724720 | 11 | 65640939 | Higher in Drinkers |
| cg04730635 | 13 | 95360278 | Higher in Drinkers |
| cg04730925 | 18 | 51795821 | Higher in Drinkers |
| cg04736401 | 3 | 183898712 | Higher in Drinkers |
| cg04737916 | 12 | 133196028 | Higher in Drinkers |
| cg04738309 | 5 | 111093624 | Higher in Drinkers |
| cg04738496 | 16 | 2021690 | Higher in Drinkers |
| cg04740028 | X | 47383436 | Higher in Drinkers |
| cg04740046 | 17 | 55330842 | Higher in Drinkers |
| cg04740258 | 3 | 138553760 | Higher in Drinkers |
| cg04740522 | 3 | 112738055 | Higher in Drinkers |
| cg04741636 | 3 | 122283583 | Higher in Drinkers |
| cg04742345 | 6 | 44186969 | Higher in Drinkers |
| cg04742977 | 14 | 91127460 | Higher in Drinkers |
| cg04746303 | 6 | 32163839 | Higher in Drinkers |
| cg04747510 | 6 | 31370923 | Higher in Drinkers |
| cg04752818 | 7 | 1536622 | Higher in Drinkers |
| cg04753107 | 20 | 31172130 | Higher in Drinkers |
| cg04761267 | 11 | 65621144 | Higher in Drinkers |
| cg04762347 | 4 | 87928590 | Higher in Drinkers |
| cg04764597 | 10 | 63510947 | Higher in Drinkers |
| cg04765955 | 11 | 67260414 | Higher in Drinkers |
| cg04769879 | 16 | 12145888 | Higher in Drinkers |
| cg04770731 | 6 | 160148267 | Higher in Drinkers |
| cg04780126 | 11 | 65029484 | Higher in Drinkers |
| cg04780431 | 19 | 16469350 | Higher in Drinkers |
| cg04783530 | 13 | 30163303 | Higher in Drinkers |

| | | | |
|---|---|---|---|
| cg04786564 | 16 | 2950686 | Higher in Drinkers |
| cg04790874 | 19 | 42381950 | Higher in Drinkers |
| cg04792644 | 6 | 157528094 | Higher in Drinkers |
| cg04792715 | 3 | 49058577 | Higher in Drinkers |
| cg04792777 | 14 | 106322429 | Lower in Drinkers |
| cg04796498 | 8 | 145509700 | Higher in Drinkers |
| cg04797985 | 16 | 58498190 | Higher in Drinkers |
| cg04798154 | 22 | 51020960 | Higher in Drinkers |
| cg04798929 | 17 | 8287246 | Higher in Drinkers |
| cg04799823 | 15 | 65810148 | Higher in Drinkers |
| cg04800168 | 12 | 56546068 | Higher in Drinkers |
| cg04802238 | 16 | 87873610 | Higher in Drinkers |
| cg04804616 | 16 | 30622014 | Higher in Drinkers |
| cg04807152 | 16 | 147558 | Higher in Drinkers |
| cg04808027 | 11 | 66102146 | Lower in Drinkers |
| cg04811556 | X | 133683331 | Higher in Drinkers |
| cg04815601 | 16 | 31092695 | Higher in Drinkers |
| cg04815707 | 20 | 61200716 | Higher in Drinkers |
| cg04818078 | 16 | 3929633 | Higher in Drinkers |
| cg04820195 | 11 | 110035921 | Higher in Drinkers |
| cg04820362 | 12 | 122651762 | Higher in Drinkers |
| cg04820387 | 20 | 62887534 | Higher in Drinkers |
| cg04822621 | 5 | 169724656 | Higher in Drinkers |
| cg04824535 | 7 | 150768477 | Higher in Drinkers |
| cg04826071 | 15 | 43213593 | Higher in Drinkers |
| cg04826336 | 7 | 157550279 | Lower in Drinkers |
| cg04826422 | 2 | 46667825 | Higher in Drinkers |
| cg04831728 | 16 | 1437752 | Lower in Drinkers |
| cg04832619 | 14 | 100574836 | Higher in Drinkers |
| cg04833630 | 11 | 1782593 | Higher in Drinkers |
| cg04837722 | 6 | 160463767 | Higher in Drinkers |
| cg04844016 | 2 | 65659148 | Higher in Drinkers |
| cg04845347 | 14 | 24731398 | Higher in Drinkers |
| cg04845821 | 16 | 89220554 | Higher in Drinkers |
| cg04850017 | 11 | 63683019 | Higher in Drinkers |

| | | | |
|---|---|---|---|
| cg04850254 | 2 | 8722072 | Higher in Drinkers |
| cg04853151 | 1 | 54519244 | Higher in Drinkers |
| cg04854342 | 8 | 67525436 | Higher in Drinkers |
| cg04858230 | 10 | 116581358 | Higher in Drinkers |
| cg04858776 | 11 | 59318494 | Higher in Drinkers |
| cg04859607 | 7 | 6647402 | Higher in Drinkers |
| cg04859719 | 13 | 111141854 | Higher in Drinkers |
| cg04864640 | 14 | 58711071 | Higher in Drinkers |
| cg04865929 | 17 | 42908410 | Higher in Drinkers |
| cg04866833 | 11 | 1968266 | Higher in Drinkers |
| cg04868296 | 2 | 122494691 | Higher in Drinkers |
| cg04870010 | 2 | 131099943 | Higher in Drinkers |
| cg04870415 | 8 | 7212954 | Higher in Drinkers |
| cg04872399 | 1 | 201346784 | Lower in Drinkers |
| cg04875007 | 16 | 2014871 | Higher in Drinkers |
| cg04877737 | 22 | 50155965 | Lower in Drinkers |
| cg04878072 | 12 | 53259474 | Higher in Drinkers |
| cg04878973 | 3 | 49057761 | Higher in Drinkers |
| cg04882394 | 1 | 1565931 | Higher in Drinkers |
| cg04882584 | 2 | 128389103 | Lower in Drinkers |
| cg04882937 | 2 | 96811058 | Higher in Drinkers |
| cg04884732 | 2 | 242042016 | Higher in Drinkers |
| cg04885614 | 16 | 72130881 | Higher in Drinkers |
| cg04886672 | 17 | 79215047 | Higher in Drinkers |
| cg04887663 | 7 | 43966399 | Higher in Drinkers |
| cg04890646 | 3 | 150480280 | Higher in Drinkers |
| cg04891094 | 22 | 38003202 | Higher in Drinkers |
| cg04892060 | 14 | 75643373 | Higher in Drinkers |
| cg04894993 | 7 | 129710370 | Higher in Drinkers |
| cg04899282 | 14 | 103523516 | Higher in Drinkers |
| cg04902542 | 17 | 77920130 | Higher in Drinkers |
| cg04905775 | 14 | 71109040 | Higher in Drinkers |
| cg04907664 | X | 68049805 | Higher in Drinkers |
| cg04910403 | 20 | 24973309 | Higher in Drinkers |
| cg04912466 | 11 | 63742028 | Higher in Drinkers |

| | | | |
|---|---|---|---|
| cg04912999 | 3 | 142682652 | Higher in Drinkers |
| cg04913815 | 16 | 60438 | Higher in Drinkers |
| cg04914105 | 15 | 75872043 | Higher in Drinkers |
| cg04915300 | 2 | 157314925 | Higher in Drinkers |
| cg04918265 | 1 | 228353294 | Higher in Drinkers |
| cg04918358 | 2 | 97405868 | Higher in Drinkers |
| cg04921619 | 12 | 7000534 | Higher in Drinkers |
| cg04922833 | 10 | 77161525 | Higher in Drinkers |
| cg04923620 | 10 | 28031330 | Higher in Drinkers |
| cg04924696 | X | 23925746 | Higher in Drinkers |
| cg04925196 | 12 | 51592141 | Lower in Drinkers |
| cg04925705 | 17 | 77813227 | Higher in Drinkers |
| cg04928129 | 16 | 1429051 | Higher in Drinkers |
| cg04930463 | 17 | 79234445 | Higher in Drinkers |
| cg04932691 | 22 | 50280375 | Higher in Drinkers |
| cg04940109 | 2 | 203240432 | Higher in Drinkers |
| cg04945248 | 7 | 1570369 | Higher in Drinkers |
| cg04945541 | 17 | 43299826 | Higher in Drinkers |
| cg04947024 | 4 | 144105592 | Higher in Drinkers |
| cg04948622 | 6 | 3647043 | Higher in Drinkers |
| cg04949346 | 2 | 169746998 | Higher in Drinkers |
| cg04949608 | 6 | 30314256 | Higher in Drinkers |
| cg04950789 | 8 | 86090224 | Higher in Drinkers |
| cg04951739 | 22 | 24093724 | Higher in Drinkers |
| cg04952324 | 7 | 73727108 | Higher in Drinkers |
| cg04955303 | 6 | 42952294 | Higher in Drinkers |
| cg04955753 | 13 | 77903678 | Higher in Drinkers |
| cg04955951 | 17 | 48239072 | Higher in Drinkers |
| cg04957730 | 10 | 43278700 | Higher in Drinkers |
| cg04960065 | 4 | 185189300 | Higher in Drinkers |
| cg04960169 | 17 | 2839005 | Higher in Drinkers |
| cg04960880 | 6 | 29577006 | Higher in Drinkers |
| cg04960964 | X | 15267738 | Higher in Drinkers |
| cg04961445 | 16 | 23652859 | Higher in Drinkers |
| cg04962541 | 7 | 44789111 | Higher in Drinkers |

| | | | |
|---|---|---|---|
| cg04966166 | 7 | 92076672 | Higher in Drinkers |
| cg04967538 | X | 119379188 | Higher in Drinkers |
| cg04974751 | 12 | 121282930 | Higher in Drinkers |
| cg04976075 | 10 | 1230850 | Higher in Drinkers |
| cg04981203 | 15 | 75182231 | Higher in Drinkers |
| cg04982748 | 12 | 66696283 | Higher in Drinkers |
| cg04983606 | 1 | 178996021 | Higher in Drinkers |
| cg04984052 | 1 | 46268207 | Higher in Drinkers |
| cg04984200 | 11 | 1784980 | Higher in Drinkers |
| cg04986319 | 11 | 62439072 | Higher in Drinkers |
| cg04987004 | 6 | 30037481 | Higher in Drinkers |
| cg04987614 | 6 | 27805362 | Higher in Drinkers |
| cg04987955 | 14 | 103438392 | Higher in Drinkers |
| cg04992991 | 3 | 155524211 | Higher in Drinkers |
| cg04997235 | 1 | 53790503 | Higher in Drinkers |
| cg04998032 | 5 | 1798359 | Higher in Drinkers |
| cg04999270 | 1 | 14076291 | Higher in Drinkers |
| cg05000987 | 1 | 87379871 | Higher in Drinkers |
| cg05004785 | 1 | 35497437 | Higher in Drinkers |
| cg05005301 | 1 | 110453107 | Higher in Drinkers |
| cg05007035 | 12 | 104234495 | Higher in Drinkers |
| cg05009047 | 16 | 4659466 | Higher in Drinkers |
| cg05009684 | 7 | 116139628 | Higher in Drinkers |
| cg05013129 | 12 | 57482394 | Higher in Drinkers |
| cg05016425 | 1 | 166845755 | Higher in Drinkers |
| cg05019807 | 9 | 139410393 | Higher in Drinkers |
| cg05021686 | 2 | 241067053 | Higher in Drinkers |
| cg05024413 | 4 | 128703335 | Higher in Drinkers |
| cg05030574 | 11 | 65189075 | Higher in Drinkers |
| cg05034432 | 17 | 5372034 | Higher in Drinkers |
| cg05036846 | 1 | 24648984 | Higher in Drinkers |
| cg05037105 | 8 | 142402421 | Higher in Drinkers |
| cg05038121 | 15 | 80444756 | Higher in Drinkers |
| cg05038466 | 2 | 74710528 | Higher in Drinkers |
| cg05044772 | 2 | 231712804 | Higher in Drinkers |

| | | | |
|---|---|---|---|
| cg05045528 | 9 | 132815702 | Higher in Drinkers |
| cg05045969 | 7 | 2154423 | Lower in Drinkers |
| cg05046821 | 22 | 21984468 | Higher in Drinkers |
| cg05047223 | 14 | 24584476 | Higher in Drinkers |
| cg05047367 | 12 | 121019523 | Higher in Drinkers |
| cg05047493 | 1 | 28864580 | Higher in Drinkers |
| cg05049628 | 11 | 72525270 | Higher in Drinkers |
| cg05051117 | 1 | 205719564 | Higher in Drinkers |
| cg05054093 | 2 | 150999911 | Higher in Drinkers |
| cg05054438 | 12 | 112213531 | Higher in Drinkers |
| cg05055230 | 15 | 41099160 | Higher in Drinkers |
| cg05057634 | 17 | 74865178 | Higher in Drinkers |
| cg05059825 | 11 | 62495950 | Higher in Drinkers |
| cg05061073 | 10 | 81061906 | Higher in Drinkers |
| cg05063412 | 12 | 114917737 | Higher in Drinkers |
| cg05063514 | 1 | 172413094 | Higher in Drinkers |
| cg05072774 | 3 | 49840536 | Higher in Drinkers |
| cg05073035 | 3 | 147127193 | Higher in Drinkers |
| cg05074623 | X | 151999750 | Higher in Drinkers |
| cg05077167 | 2 | 43453540 | Higher in Drinkers |
| cg05080787 | 22 | 50277948 | Higher in Drinkers |
| cg05081416 | 6 | 170361242 | Higher in Drinkers |
| cg05081546 | 12 | 7046915 | Higher in Drinkers |
| cg05082963 | 7 | 65669966 | Higher in Drinkers |
| cg05085585 | 16 | 30420623 | Higher in Drinkers |
| cg05086975 | 17 | 48945232 | Higher in Drinkers |
| cg05089296 | 14 | 81636615 | Higher in Drinkers |
| cg05091260 | 3 | 127391221 | Higher in Drinkers |
| cg05091653 | 2 | 231281474 | Higher in Drinkers |
| cg05092310 | 17 | 43226346 | Higher in Drinkers |
| cg05096964 | 11 | 1715292 | Higher in Drinkers |
| cg05097455 | 3 | 47324909 | Higher in Drinkers |
| cg05099145 | 16 | 1796333 | Lower in Drinkers |
| cg05100540 | 6 | 133135557 | Higher in Drinkers |
| cg05102651 | 3 | 28351601 | Higher in Drinkers |

| | | | |
|---|---|---|---|
| cg05105646 | 8 | 142437128 | Higher in Drinkers |
| cg05106463 | X | 15873337 | Higher in Drinkers |
| cg05108179 | 14 | 105767409 | Higher in Drinkers |
| cg05109729 | 16 | 29852922 | Higher in Drinkers |
| cg05109981 | 17 | 40440447 | Higher in Drinkers |
| cg05113000 | 11 | 65343833 | Higher in Drinkers |
| cg05116896 | 16 | 30366237 | Higher in Drinkers |
| cg05118125 | 17 | 7746483 | Higher in Drinkers |
| cg05119432 | 1 | 31274862 | Higher in Drinkers |
| cg05120641 | 15 | 41245706 | Higher in Drinkers |
| cg05122861 | 1 | 206137774 | Higher in Drinkers |
| cg05124756 | 4 | 2263820 | Higher in Drinkers |
| cg05125781 | 6 | 33257638 | Higher in Drinkers |
| cg05128003 | 1 | 6548963 | Lower in Drinkers |
| cg05128246 | 8 | 136470275 | Higher in Drinkers |
| cg05129258 | 4 | 103749208 | Higher in Drinkers |
| cg05129817 | 1 | 210001399 | Higher in Drinkers |
| cg05129930 | 21 | 45719797 | Higher in Drinkers |
| cg05131623 | 3 | 179755285 | Lower in Drinkers |
| cg05133578 | 12 | 46663407 | Higher in Drinkers |
| cg05135523 | 16 | 31085704 | Higher in Drinkers |
| cg05141578 | 10 | 104306658 | Higher in Drinkers |
| cg05142634 | 7 | 36765609 | Higher in Drinkers |
| cg05142833 | 2 | 200604518 | Higher in Drinkers |
| cg05144089 | 1 | 235292386 | Higher in Drinkers |
| cg05145423 | 17 | 62492888 | Higher in Drinkers |
| cg05146307 | 16 | 29227937 | Lower in Drinkers |
| cg05148130 | 6 | 44214880 | Higher in Drinkers |
| cg05148465 | 17 | 7034129 | Higher in Drinkers |
| cg05148722 | 6 | 28199465 | Higher in Drinkers |
| cg05148900 | 5 | 139554558 | Higher in Drinkers |
| cg05151228 | 1 | 110752952 | Higher in Drinkers |
| cg05151241 | 15 | 90808880 | Higher in Drinkers |
| cg05151395 | 17 | 8192371 | Higher in Drinkers |
| cg05151496 | 11 | 65711834 | Lower in Drinkers |

| | | | |
|---|---|---|---|
| cg05151621 | 16 | 89008406 | Higher in Drinkers |
| cg05152867 | 16 | 88568237 | Higher in Drinkers |
| cg05153347 | 5 | 171434267 | Higher in Drinkers |
| cg05155371 | 1 | 11994697 | Higher in Drinkers |
| cg05155578 | 6 | 88032202 | Higher in Drinkers |
| cg05156550 | 15 | 45814198 | Higher in Drinkers |
| cg05156805 | 22 | 21318995 | Higher in Drinkers |
| cg05157340 | 17 | 67577736 | Higher in Drinkers |
| cg05157499 | 12 | 132865380 | Higher in Drinkers |
| cg05157970 | 17 | 80048868 | Higher in Drinkers |
| cg05158197 | 4 | 168155888 | Higher in Drinkers |
| cg05159438 | 11 | 69515681 | Higher in Drinkers |
| cg05164570 | 5 | 140071033 | Higher in Drinkers |
| cg05165689 | 2 | 69534554 | Higher in Drinkers |
| cg05165990 | 12 | 10365908 | Higher in Drinkers |
| cg05166473 | 16 | 88103629 | Lower in Drinkers |
| cg05168491 | 14 | 38080446 | Higher in Drinkers |
| cg05170863 | 8 | 109261119 | Higher in Drinkers |
| cg05173698 | 5 | 102455509 | Higher in Drinkers |
| cg05175466 | 13 | 52586483 | Higher in Drinkers |
| cg05176051 | 8 | 145616945 | Higher in Drinkers |
| cg05176996 | 9 | 98637794 | Higher in Drinkers |
| cg05178316 | 20 | 62661238 | Higher in Drinkers |
| cg05181148 | 12 | 49351152 | Higher in Drinkers |
| cg05184636 | 16 | 25268747 | Higher in Drinkers |
| cg05185146 | 13 | 113390125 | Higher in Drinkers |
| cg05191397 | 7 | 5437001 | Higher in Drinkers |
| cg05191729 | 10 | 74856975 | Higher in Drinkers |
| cg05191792 | 6 | 2765113 | Higher in Drinkers |
| cg05193411 | 4 | 113558554 | Higher in Drinkers |
| cg05193430 | 14 | 68086242 | Higher in Drinkers |
| cg05201956 | 13 | 53024733 | Higher in Drinkers |
| cg05203776 | 11 | 2162582 | Lower in Drinkers |
| cg05204037 | X | 84258754 | Higher in Drinkers |
| cg05204898 | 2 | 99193570 | Higher in Drinkers |

| | | | |
|---|---|---|---|
| cg05204981 | 19 | 3961086 | Higher in Drinkers |
| cg05207227 | 22 | 29703180 | Lower in Drinkers |
| cg05208237 | 18 | 71815698 | Higher in Drinkers |
| cg05209770 | 6 | 89827644 | Higher in Drinkers |
| cg05210501 | 7 | 27219344 | Higher in Drinkers |
| cg05210886 | 1 | 245133216 | Higher in Drinkers |
| cg05214042 | 19 | 41870225 | Higher in Drinkers |
| cg05217755 | 19 | 42758976 | Higher in Drinkers |
| cg05218283 | 7 | 131012399 | Higher in Drinkers |
| cg05221264 | 1 | 15783513 | Higher in Drinkers |
| cg05223847 | 10 | 124913846 | Higher in Drinkers |
| cg05225390 | 11 | 113644407 | Higher in Drinkers |
| cg05230888 | 6 | 15662446 | Higher in Drinkers |
| cg05233094 | 16 | 67976621 | Higher in Drinkers |
| cg05233622 | 11 | 75379501 | Higher in Drinkers |
| cg05233629 | 2 | 24299374 | Higher in Drinkers |
| cg05236418 | 5 | 177581052 | Higher in Drinkers |
| cg05239225 | 15 | 86022419 | Higher in Drinkers |
| cg05239513 | 6 | 34725144 | Higher in Drinkers |
| cg05239811 | 6 | 31734147 | Lower in Drinkers |
| cg05239890 | 3 | 145811273 | Lower in Drinkers |
| cg05242416 | 3 | 48128669 | Lower in Drinkers |
| cg05243144 | 19 | 46273434 | Higher in Drinkers |
| cg05243641 | 2 | 240964548 | Higher in Drinkers |
| cg05249744 | 17 | 78834710 | Lower in Drinkers |
| cg05251814 | 16 | 585386 | Higher in Drinkers |
| cg05253057 | 3 | 101293208 | Higher in Drinkers |
| cg05255351 | 5 | 1503979 | Higher in Drinkers |
| cg05256242 | 12 | 12876945 | Higher in Drinkers |
| cg05256999 | 16 | 88902466 | Lower in Drinkers |
| cg05257947 | X | 11776394 | Higher in Drinkers |
| cg05258027 | 6 | 134273465 | Higher in Drinkers |
| cg05260886 | 14 | 91854239 | Higher in Drinkers |
| cg05261336 | 7 | 1032904 | Higher in Drinkers |
| cg05263682 | 6 | 89673273 | Higher in Drinkers |

| | | | |
|---|---|---|---|
| cg05264101 | 17 | 75880308 | Higher in Drinkers |
| cg05264214 | 18 | 77181423 | Lower in Drinkers |
| cg05266784 | 1 | 160312524 | Higher in Drinkers |
| cg05268564 | 2 | 209131274 | Higher in Drinkers |
| cg05270325 | 17 | 21002712 | Higher in Drinkers |
| cg05271360 | 17 | 38083955 | Higher in Drinkers |
| cg05278186 | 2 | 131303925 | Higher in Drinkers |
| cg05278256 | 22 | 26137980 | Higher in Drinkers |
| cg05278442 | 7 | 92861491 | Higher in Drinkers |
| cg05281544 | 6 | 21597055 | Higher in Drinkers |
| cg05286348 | 19 | 16641544 | Lower in Drinkers |
| cg05289701 | 12 | 27090805 | Higher in Drinkers |
| cg05295685 | 5 | 138677941 | Higher in Drinkers |
| cg05299703 | 18 | 43678513 | Higher in Drinkers |
| cg05300577 | 2 | 241500044 | Higher in Drinkers |
| cg05300937 | 16 | 27561409 | Higher in Drinkers |
| cg05300946 | 14 | 76120656 | Higher in Drinkers |
| cg05301359 | 2 | 27886888 | Higher in Drinkers |
| cg05303524 | 2 | 136876163 | Higher in Drinkers |
| cg05303901 | 7 | 28338625 | Higher in Drinkers |
| cg05304761 | 1 | 43123920 | Higher in Drinkers |
| cg05305986 | 17 | 37185064 | Higher in Drinkers |
| cg05306950 | 19 | 40854151 | Higher in Drinkers |
| cg05307908 | 4 | 37637729 | Higher in Drinkers |
| cg05308484 | 12 | 4429999 | Higher in Drinkers |
| cg05309399 | 4 | 106552544 | Lower in Drinkers |
| cg05309934 | 10 | 5855475 | Higher in Drinkers |
| cg05310309 | 2 | 109257429 | Higher in Drinkers |
| cg05315620 | 7 | 156469001 | Higher in Drinkers |
| cg05316555 | 8 | 126442587 | Higher in Drinkers |
| cg05320382 | 8 | 145017053 | Higher in Drinkers |
| cg05320460 | 15 | 63179548 | Higher in Drinkers |
| cg05322217 | 17 | 36575655 | Higher in Drinkers |
| cg05323058 | 7 | 1969193 | Higher in Drinkers |
| cg05325699 | 17 | 39890756 | Higher in Drinkers |

| | | | |
|---|---|---|---|
| cg05328670 | 16 | 84096367 | Higher in Drinkers |
| cg05329982 | 11 | 62359210 | Higher in Drinkers |
| cg05330691 | 6 | 32862462 | Higher in Drinkers |
| cg05332270 | 2 | 37384401 | Higher in Drinkers |
| cg05333740 | 19 | 44575547 | Higher in Drinkers |
| cg05336268 | 16 | 27788236 | Higher in Drinkers |
| cg05336611 | 11 | 1898787 | Higher in Drinkers |
| cg05336707 | 16 | 3070470 | Higher in Drinkers |
| cg05337222 | 19 | 12751094 | Higher in Drinkers |
| cg05338433 | 1 | 158151363 | Higher in Drinkers |
| cg05338497 | 11 | 93395272 | Higher in Drinkers |
| cg05340255 | 1 | 78470449 | Higher in Drinkers |
| cg05340495 | 14 | 52327368 | Higher in Drinkers |
| cg05340844 | 15 | 90808742 | Higher in Drinkers |
| cg05340865 | 11 | 76432983 | Higher in Drinkers |
| cg05341670 | 1 | 54518153 | Higher in Drinkers |
| cg05343799 | 11 | 35843508 | Higher in Drinkers |
| cg05346166 | 14 | 50779543 | Higher in Drinkers |
| cg05346193 | 11 | 73087168 | Higher in Drinkers |
| cg05346256 | 12 | 25959372 | Higher in Drinkers |
| cg05346832 | 19 | 10680117 | Higher in Drinkers |
| cg05347932 | 12 | 110437047 | Higher in Drinkers |
| cg05348535 | 20 | 18774637 | Higher in Drinkers |
| cg05351302 | 7 | 37563903 | Higher in Drinkers |
| cg05351601 | 7 | 134671244 | Higher in Drinkers |
| cg05352541 | 22 | 28315563 | Higher in Drinkers |
| cg05353317 | 12 | 76742207 | Higher in Drinkers |
| cg05353415 | 7 | 42276004 | Higher in Drinkers |
| cg05353868 | 11 | 65364117 | Lower in Drinkers |
| cg05353983 | 12 | 49075643 | Higher in Drinkers |
| cg05355167 | 4 | 109541739 | Higher in Drinkers |
| cg05355311 | 22 | 50629224 | Higher in Drinkers |
| cg05355679 | 1 | 45241361 | Higher in Drinkers |
| cg05358228 | 10 | 102241434 | Higher in Drinkers |
| cg05360774 | 2 | 151838548 | Higher in Drinkers |

| | | | |
|---|---|---|---|
| cg05362170 | 6 | 3258929 | Higher in Drinkers |
| cg05362835 | 15 | 79055416 | Higher in Drinkers |
| cg05364394 | 1 | 151138315 | Higher in Drinkers |
| cg05365320 | 1 | 200971339 | Higher in Drinkers |
| cg05365954 | 2 | 220374214 | Higher in Drinkers |
| cg05366983 | 19 | 2328991 | Higher in Drinkers |
| cg05368089 | 12 | 53689374 | Higher in Drinkers |
| cg05373792 | 13 | 27648047 | Higher in Drinkers |
| cg05374809 | 14 | 29250912 | Higher in Drinkers |
| cg05375744 | 19 | 54634871 | Higher in Drinkers |
| cg05376469 | 2 | 102649931 | Higher in Drinkers |
| cg05379784 | 14 | 74111382 | Higher in Drinkers |
| cg05380019 | 7 | 19146555 | Higher in Drinkers |
| cg05380296 | 3 | 47620439 | Higher in Drinkers |
| cg05383584 | 20 | 34329791 | Higher in Drinkers |
| cg05385513 | 2 | 56150478 | Lower in Drinkers |
| cg05392644 | 15 | 78454622 | Higher in Drinkers |
| cg05392764 | 1 | 161697052 | Higher in Drinkers |
| cg05392792 | 1 | 154155295 | Higher in Drinkers |
| cg05396178 | 6 | 27833129 | Higher in Drinkers |
| cg05399615 | 1 | 62191127 | Higher in Drinkers |
| cg05400741 | 10 | 70320073 | Higher in Drinkers |
| cg05403484 | 7 | 98973169 | Higher in Drinkers |
| cg05412396 | 15 | 76631569 | Higher in Drinkers |
| cg05412843 | 6 | 52812092 | Higher in Drinkers |
| cg05414338 | 6 | 26250347 | Higher in Drinkers |
| cg05421143 | 13 | 53191491 | Higher in Drinkers |
| cg05425664 | 17 | 57184151 | Higher in Drinkers |
| cg05429895 | 9 | 120466640 | Higher in Drinkers |
| cg05432973 | 10 | 101292651 | Higher in Drinkers |
| cg05434312 | 21 | 39287834 | Higher in Drinkers |
| cg05435065 | 7 | 75544030 | Higher in Drinkers |
| cg05435286 | 3 | 27411063 | Higher in Drinkers |
| cg05438727 | 11 | 2800047 | Higher in Drinkers |
| cg05457941 | 1 | 149858211 | Higher in Drinkers |

| | | | |
|---|---|---|---|
| cg05462359 | 5 | 37837788 | Higher in Drinkers |
| cg05462639 | 3 | 185653812 | Higher in Drinkers |
| cg05463155 | 3 | 58419697 | Higher in Drinkers |
| cg05463819 | 8 | 87520424 | Higher in Drinkers |
| cg05464172 | 8 | 97247954 | Higher in Drinkers |
| cg05467183 | 5 | 150080687 | Higher in Drinkers |
| cg05468251 | 3 | 122920710 | Higher in Drinkers |
| cg05468346 | 11 | 124823826 | Higher in Drinkers |
| cg05469695 | 2 | 37899953 | Higher in Drinkers |
| cg05470497 | 7 | 1521086 | Higher in Drinkers |
| cg05473447 | 8 | 96281195 | Higher in Drinkers |
| cg05474004 | 16 | 28289298 | Higher in Drinkers |
| cg05475156 | 1 | 93811337 | Higher in Drinkers |
| cg05477933 | 12 | 54426537 | Higher in Drinkers |
| cg05479554 | 11 | 73588093 | Higher in Drinkers |
| cg05481041 | 18 | 72922694 | Higher in Drinkers |
| cg05483623 | 22 | 42666165 | Higher in Drinkers |
| cg05485165 | 16 | 29973024 | Higher in Drinkers |
| cg05486650 | 12 | 52448908 | Lower in Drinkers |
| cg05496738 | 2 | 26101556 | Higher in Drinkers |
| cg05497240 | 5 | 154199788 | Higher in Drinkers |
| cg05498476 | 16 | 68877469 | Higher in Drinkers |
| cg05499853 | 10 | 15902324 | Higher in Drinkers |
| cg05505929 | 12 | 72148416 | Higher in Drinkers |
| cg05506498 | 16 | 22236981 | Higher in Drinkers |
| cg05507566 | 2 | 36757828 | Higher in Drinkers |
| cg05508447 | 12 | 133264322 | Higher in Drinkers |
| cg05509327 | 5 | 10441882 | Higher in Drinkers |
| cg05512669 | 6 | 110012488 | Higher in Drinkers |
| cg05514743 | 19 | 14629124 | Higher in Drinkers |
| cg05515516 | 5 | 141392736 | Higher in Drinkers |
| cg05518269 | 16 | 2265528 | Higher in Drinkers |
| cg05519377 | 3 | 48229618 | Higher in Drinkers |
| cg05521982 | 16 | 89159988 | Lower in Drinkers |
| cg05523056 | 16 | 77468458 | Higher in Drinkers |

| | | | |
|---|---|---|---|
| cg05523662 | 6 | 29910101 | Higher in Drinkers |
| cg05525106 | 6 | 74162089 | Higher in Drinkers |
| cg05527530 | 1 | 197882003 | Higher in Drinkers |
| cg05528782 | 4 | 155547985 | Higher in Drinkers |
| cg05530751 | 10 | 45869477 | Higher in Drinkers |
| cg05530858 | 2 | 209130814 | Higher in Drinkers |
| cg05531055 | 22 | 35695625 | Higher in Drinkers |
| cg05532403 | X | 15756920 | Lower in Drinkers |
| cg05534175 | 18 | 32869897 | Higher in Drinkers |
| cg05534403 | 20 | 61583830 | Higher in Drinkers |
| cg05534464 | 16 | 81764129 | Higher in Drinkers |
| cg05535123 | 22 | 24031596 | Higher in Drinkers |
| cg05537360 | 6 | 70506940 | Higher in Drinkers |
| cg05538337 | 10 | 103348072 | Higher in Drinkers |
| cg05541779 | 15 | 45943467 | Higher in Drinkers |
| cg05544396 | 16 | 66959780 | Higher in Drinkers |
| cg05544840 | 13 | 44716513 | Higher in Drinkers |
| cg05545172 | 6 | 32811777 | Higher in Drinkers |
| cg05549685 | 3 | 48538106 | Higher in Drinkers |
| cg05550371 | 3 | 49841167 | Higher in Drinkers |
| cg05554866 | 4 | 83206534 | Higher in Drinkers |
| cg05555681 | 17 | 36886288 | Higher in Drinkers |
| cg05555772 | 3 | 67704970 | Higher in Drinkers |
| cg05556477 | 5 | 131705319 | Higher in Drinkers |
| cg05559557 | 12 | 132429672 | Higher in Drinkers |
| cg05560712 | 16 | 28930947 | Higher in Drinkers |
| cg05561696 | 10 | 3149796 | Higher in Drinkers |
| cg05562327 | 4 | 15005910 | Higher in Drinkers |
| cg05568797 | 12 | 26275050 | Higher in Drinkers |
| cg05569131 | 6 | 36665620 | Higher in Drinkers |
| cg05572410 | 10 | 5882304 | Higher in Drinkers |
| cg05573562 | 2 | 54198159 | Higher in Drinkers |
| cg05575043 | 7 | 99097635 | Higher in Drinkers |
| cg05576949 | 3 | 185540331 | Higher in Drinkers |
| cg05577957 | 4 | 897054 | Higher in Drinkers |

| | | | |
|---|---|---|---|
| cg05579622 | 5 | 10618622 | Higher in Drinkers |
| cg05579703 | 5 | 72112888 | Higher in Drinkers |
| cg05582165 | 3 | 112738652 | Higher in Drinkers |
| cg05584759 | 12 | 57869421 | Higher in Drinkers |
| cg05586209 | 7 | 143079085 | Higher in Drinkers |
| cg05586376 | 7 | 90033375 | Higher in Drinkers |
| cg05590793 | 3 | 136581720 | Higher in Drinkers |
| cg05593009 | 2 | 105654477 | Higher in Drinkers |
| cg05593780 | 22 | 41864983 | Higher in Drinkers |
| cg05597766 | 11 | 3013541 | Higher in Drinkers |
| cg05598064 | 1 | 39339225 | Higher in Drinkers |
| cg05599825 | 5 | 153785055 | Higher in Drinkers |
| cg05600044 | 1 | 222721340 | Higher in Drinkers |
| cg05600126 | 17 | 950540 | Higher in Drinkers |
| cg05600758 | 6 | 32939783 | Higher in Drinkers |
| cg05602648 | 1 | 230778078 | Higher in Drinkers |
| cg05603623 | 19 | 8008081 | Higher in Drinkers |
| cg05604112 | 2 | 38893237 | Higher in Drinkers |
| cg05608188 | 7 | 112430152 | Higher in Drinkers |
| cg05609751 | 17 | 4269695 | Higher in Drinkers |
| cg05610740 | 12 | 96794311 | Higher in Drinkers |
| cg05611007 | 17 | 40172250 | Higher in Drinkers |
| cg05621195 | 12 | 123237031 | Higher in Drinkers |
| cg05622915 | 19 | 571204 | Higher in Drinkers |
| cg05623562 | 18 | 77793509 | Higher in Drinkers |
| cg05635121 | 17 | 7154132 | Higher in Drinkers |
| cg05637265 | 8 | 144884124 | Higher in Drinkers |
| cg05637450 | 1 | 218479177 | Higher in Drinkers |
| cg05638699 | 3 | 124449152 | Higher in Drinkers |
| cg05639842 | 21 | 43639440 | Higher in Drinkers |
| cg05643503 | 1 | 3713094 | Higher in Drinkers |
| cg05647048 | 10 | 75012704 | Higher in Drinkers |
| cg05650764 | 11 | 68227812 | Higher in Drinkers |
| cg05651176 | 12 | 4433983 | Lower in Drinkers |
| cg05654925 | 1 | 10752632 | Higher in Drinkers |

| | | | |
|---|---|---|---|
| cg05655390 | 6 | 30449547 | Higher in Drinkers |
| cg05657462 | 22 | 50781886 | Higher in Drinkers |
| cg05660881 | 13 | 24798240 | Lower in Drinkers |
| cg05661333 | 6 | 29600200 | Higher in Drinkers |
| cg05664197 | 3 | 58292086 | Higher in Drinkers |
| cg05668205 | 19 | 16738998 | Higher in Drinkers |
| cg05671762 | 1 | 39571727 | Higher in Drinkers |
| cg05679836 | 12 | 57472765 | Higher in Drinkers |
| cg05684891 | 9 | 124461171 | Higher in Drinkers |
| cg05687149 | 11 | 112035945 | Higher in Drinkers |
| cg05687194 | 16 | 84178061 | Higher in Drinkers |
| cg05687227 | 13 | 114803626 | Higher in Drinkers |
| cg05692319 | 13 | 103249370 | Higher in Drinkers |
| cg05696811 | 16 | 87725895 | Higher in Drinkers |
| cg05702024 | 17 | 81037982 | Higher in Drinkers |
| cg05704893 | 17 | 7982773 | Higher in Drinkers |
| cg05705094 | 22 | 39930804 | Higher in Drinkers |
| cg05711131 | 19 | 36231948 | Higher in Drinkers |
| cg05712542 | 16 | 22337575 | Higher in Drinkers |
| cg05714334 | 5 | 108746147 | Higher in Drinkers |
| cg05716567 | 8 | 144620690 | Higher in Drinkers |
| cg05720226 | 7 | 116786597 | Higher in Drinkers |
| cg05721427 | 4 | 2948160 | Higher in Drinkers |
| cg05725686 | 16 | 58553352 | Lower in Drinkers |
| cg05726556 | 7 | 157203124 | Higher in Drinkers |
| cg05729995 | 10 | 74386032 | Higher in Drinkers |
| cg05730283 | 2 | 62422808 | Higher in Drinkers |
| cg05731216 | 2 | 216769199 | Higher in Drinkers |
| cg05732749 | 22 | 42467120 | Higher in Drinkers |
| cg05733361 | 15 | 85524456 | Higher in Drinkers |
| cg05735674 | 16 | 2918333 | Higher in Drinkers |
| cg05737417 | 18 | 29522262 | Higher in Drinkers |
| cg05737718 | 16 | 24951793 | Higher in Drinkers |
| cg05740879 | 11 | 2721866 | Higher in Drinkers |
| cg05741161 | 6 | 35699499 | Higher in Drinkers |

| | | | |
|---|---|---|---|
| cg05741132 | 16 | 72127884 | Higher in Drinkers |
| cg05744073 | 17 | 1953268 | Higher in Drinkers |
| cg05746608 | 14 | 50698469 | Higher in Drinkers |
| cg05747448 | 3 | 81810940 | Higher in Drinkers |
| cg05750081 | 19 | 16222926 | Higher in Drinkers |
| cg05750276 | 10 | 122610832 | Higher in Drinkers |
| cg05755441 | 17 | 17001380 | Higher in Drinkers |
| cg05755837 | 7 | 102937659 | Higher in Drinkers |
| cg05756301 | 6 | 128901562 | Higher in Drinkers |
| cg05758489 | 6 | 37467789 | Higher in Drinkers |
| cg05761539 | 21 | 34915395 | Higher in Drinkers |
| cg05765466 | 1 | 45957060 | Higher in Drinkers |
| cg05766601 | 11 | 59328303 | Higher in Drinkers |
| cg05766605 | 1 | 19384827 | Lower in Drinkers |
| cg05767754 | 3 | 112709667 | Higher in Drinkers |
| cg05768041 | 16 | 4847967 | Higher in Drinkers |
| cg05768362 | 1 | 145575570 | Higher in Drinkers |
| cg05769889 | 12 | 89744701 | Higher in Drinkers |
| cg05772692 | 6 | 168681584 | Higher in Drinkers |
| cg05773194 | 1 | 226844154 | Higher in Drinkers |
| cg05774324 | 19 | 58067768 | Higher in Drinkers |
| cg05774464 | 7 | 72738350 | Higher in Drinkers |
| cg05774737 | 11 | 63997720 | Higher in Drinkers |
| cg05777357 | 9 | 126776999 | Higher in Drinkers |
| cg05778154 | 3 | 52260965 | Higher in Drinkers |
| cg05778481 | 11 | 62573255 | Higher in Drinkers |
| cg05780177 | 1 | 197744757 | Higher in Drinkers |
| cg05781826 | 17 | 1165839 | Lower in Drinkers |
| cg05781918 | 4 | 843828 | Higher in Drinkers |
| cg05782454 | 16 | 4702834 | Higher in Drinkers |
| cg05782471 | 1 | 3623389 | Higher in Drinkers |
| cg05782975 | X | 102631408 | Higher in Drinkers |
| cg05783329 | 6 | 34360212 | Higher in Drinkers |
| cg05784201 | 9 | 139407609 | Higher in Drinkers |
| cg05784386 | 16 | 83945881 | Higher in Drinkers |

| | | | |
|---|---|---|---|
| cg05785222 | 7 | 155019550 | Higher in Drinkers |
| cg05785753 | 11 | 71139490 | Higher in Drinkers |
| cg05786548 | 4 | 152330215 | Higher in Drinkers |
| cg05789938 | 3 | 32822789 | Higher in Drinkers |
| cg05792884 | 2 | 220142691 | Higher in Drinkers |
| cg05793299 | 1 | 16481635 | Higher in Drinkers |
| cg05802204 | 16 | 88093422 | Higher in Drinkers |
| cg05805987 | 8 | 109260982 | Higher in Drinkers |
| cg05809174 | 6 | 10723406 | Higher in Drinkers |
| cg05810170 | 4 | 1049609 | Higher in Drinkers |
| cg05812035 | 16 | 87733503 | Higher in Drinkers |
| cg05823218 | 2 | 74725810 | Higher in Drinkers |
| cg05825702 | 19 | 51069461 | Higher in Drinkers |
| cg05831672 | 10 | 103543172 | Higher in Drinkers |
| cg05833251 | 14 | 23938784 | Higher in Drinkers |
| cg05833946 | 8 | 1847999 | Lower in Drinkers |
| cg05834275 | 16 | 10916163 | Higher in Drinkers |
| cg05834354 | 11 | 3116865 | Lower in Drinkers |
| cg05834508 | 14 | 55832634 | Higher in Drinkers |
| cg05834625 | 6 | 170176447 | Higher in Drinkers |
| cg05835456 | 15 | 43785425 | Higher in Drinkers |
| cg05835802 | 12 | 110906488 | Higher in Drinkers |
| cg05837905 | X | 30907698 | Higher in Drinkers |
| cg05839201 | 16 | 30194815 | Higher in Drinkers |
| cg05843387 | 2 | 86850888 | Higher in Drinkers |
| cg05843430 | 2 | 198299934 | Higher in Drinkers |
| cg05846056 | 1 | 59762542 | Higher in Drinkers |
| cg05847772 | 11 | 118122973 | Higher in Drinkers |
| cg05847778 | 2 | 170336167 | Higher in Drinkers |
| cg05848120 | 18 | 4467992 | Higher in Drinkers |
| cg05848279 | 1 | 149764294 | Higher in Drinkers |
| cg05854892 | 15 | 100016352 | Higher in Drinkers |
| cg05855008 | 5 | 139944351 | Higher in Drinkers |
| cg05855689 | 2 | 27435083 | Higher in Drinkers |
| cg05858920 | 18 | 60935959 | Higher in Drinkers |

| | | | |
|---|---|---|---|
| cg05860886 | 17 | 20059029 | Higher in Drinkers |
| cg05866713 | 16 | 84150400 | Higher in Drinkers |
| cg05867215 | 11 | 66112760 | Higher in Drinkers |
| cg05867307 | 4 | 144106066 | Higher in Drinkers |
| cg05869392 | 10 | 75551678 | Lower in Drinkers |
| cg05870058 | 4 | 141445193 | Higher in Drinkers |
| cg05872236 | 18 | 47825225 | Lower in Drinkers |
| cg05874355 | 11 | 71724677 | Higher in Drinkers |
| cg05876864 | 5 | 176831638 | Higher in Drinkers |
| cg05876917 | 17 | 35014676 | Lower in Drinkers |
| cg05879334 | 6 | 160183160 | Higher in Drinkers |
| cg05879919 | 14 | 102976503 | Higher in Drinkers |
| cg05880372 | 2 | 131863352 | Higher in Drinkers |
| cg05884522 | 6 | 13615538 | Higher in Drinkers |
| cg05888406 | 7 | 5280109 | Higher in Drinkers |
| cg05890826 | 6 | 12008908 | Higher in Drinkers |
| cg05894015 | 7 | 1974839 | Higher in Drinkers |
| cg05899183 | 16 | 66968638 | Higher in Drinkers |
| cg05899549 | 16 | 71891347 | Higher in Drinkers |
| cg05903330 | 22 | 39542136 | Higher in Drinkers |
| cg05904213 | 8 | 56757179 | Higher in Drinkers |
| cg05911928 | 2 | 233415245 | Higher in Drinkers |
| cg05915694 | 11 | 82612887 | Higher in Drinkers |
| cg05916588 | 19 | 3700332 | Higher in Drinkers |
| cg05919661 | 12 | 49504308 | Higher in Drinkers |
| cg05923267 | 18 | 77477502 | Higher in Drinkers |
| cg05923595 | 1 | 33547713 | Lower in Drinkers |
| cg05923759 | 15 | 78238416 | Lower in Drinkers |
| cg05924022 | 10 | 30723367 | Higher in Drinkers |
| cg05924068 | 2 | 240046735 | Higher in Drinkers |
| cg05925857 | 5 | 40558574 | Lower in Drinkers |
| cg05926932 | 17 | 72200427 | Higher in Drinkers |
| cg05927645 | 1 | 5943175 | Lower in Drinkers |
| cg05927802 | 8 | 110346865 | Higher in Drinkers |
| cg05929645 | 1 | 52456024 | Higher in Drinkers |

| | | | |
|---|---|---|---|
| cg05931606 | 2 | 74667600 | Higher in Drinkers |
| cg05933762 | 9 | 102586828 | Higher in Drinkers |
| cg05935283 | 3 | 190231667 | Higher in Drinkers |
| cg05937316 | 14 | 45759143 | Higher in Drinkers |
| cg05938207 | 6 | 32489750 | Higher in Drinkers |
| cg05938623 | 1 | 223254899 | Higher in Drinkers |
| cg05941292 | 17 | 8794160 | Higher in Drinkers |
| cg05941540 | 16 | 57570661 | Higher in Drinkers |
| cg05943563 | 16 | 88636557 | Higher in Drinkers |
| cg05944623 | 19 | 54619057 | Higher in Drinkers |
| cg05951044 | 18 | 23597141 | Higher in Drinkers |
| cg05951864 | 11 | 33398245 | Higher in Drinkers |
| cg05952572 | 11 | 72295425 | Lower in Drinkers |
| cg05954702 | 15 | 75931857 | Higher in Drinkers |
| cg05955436 | 20 | 17660833 | Higher in Drinkers |
| cg05956899 | 16 | 75182805 | Higher in Drinkers |
| cg05958166 | 5 | 156569898 | Higher in Drinkers |
| cg05958510 | 12 | 89746351 | Higher in Drinkers |
| cg05959381 | 1 | 55181617 | Higher in Drinkers |
| cg05959392 | 10 | 104613928 | Higher in Drinkers |
| cg05962793 | 16 | 84745615 | Lower in Drinkers |
| cg05969018 | 21 | 47056933 | Higher in Drinkers |
| cg05970398 | 4 | 95129288 | Higher in Drinkers |
| cg05973084 | 6 | 170581039 | Higher in Drinkers |
| cg05978306 | 17 | 1373774 | Higher in Drinkers |
| cg05979232 | 10 | 73496014 | Higher in Drinkers |
| cg05979741 | 2 | 110873485 | Higher in Drinkers |
| cg05981247 | 2 | 8821346 | Higher in Drinkers |
| cg05984533 | 17 | 79479583 | Higher in Drinkers |
| cg05989429 | 19 | 1041026 | Higher in Drinkers |
| cg05989460 | 9 | 82187933 | Higher in Drinkers |
| cg05989656 | 17 | 80011760 | Higher in Drinkers |
| cg05990720 | 9 | 27573650 | Higher in Drinkers |
| cg05992875 | 8 | 144621330 | Lower in Drinkers |
| cg05993488 | 16 | 30597053 | Higher in Drinkers |

| | | | |
|---|---|---|---|
| cg05996169 | 8 | 27132367 | Higher in Drinkers |
| cg05996818 | 15 | 50978243 | Higher in Drinkers |
| cg05998577 | 5 | 176781490 | Higher in Drinkers |
| cg06001836 | 5 | 167913752 | Higher in Drinkers |
| cg06004017 | 22 | 28191222 | Higher in Drinkers |
| cg06007323 | 4 | 6784769 | Higher in Drinkers |
| cg06009475 | 5 | 14142909 | Higher in Drinkers |
| cg06010111 | 2 | 99771192 | Higher in Drinkers |
| cg06012509 | 6 | 43027269 | Higher in Drinkers |
| cg06016176 | 5 | 156692987 | Higher in Drinkers |
| cg06018270 | 19 | 38684260 | Higher in Drinkers |
| cg06020842 | 3 | 47206647 | Higher in Drinkers |
| cg06023646 | 3 | 39093550 | Higher in Drinkers |
| cg06024239 | 12 | 53342595 | Higher in Drinkers |
| cg06024834 | 10 | 104192492 | Higher in Drinkers |
| cg06027057 | 14 | 90849959 | Higher in Drinkers |
| cg06034664 | 6 | 168354502 | Higher in Drinkers |
| cg06034874 | 16 | 75285194 | Higher in Drinkers |
| cg06035754 | 11 | 47198556 | Higher in Drinkers |
| cg06041068 | X | 152990341 | Higher in Drinkers |
| cg06043142 | 7 | 134896415 | Higher in Drinkers |
| cg06044899 | 4 | 91760229 | Higher in Drinkers |
| cg06045799 | 4 | 47465578 | Higher in Drinkers |
| cg06048350 | 3 | 169939876 | Higher in Drinkers |
| cg06051391 | X | 131352293 | Higher in Drinkers |
| cg06052353 | 15 | 71624510 | Higher in Drinkers |
| cg06052984 | 10 | 134671287 | Higher in Drinkers |
| cg06053417 | 16 | 591589 | Higher in Drinkers |
| cg06054026 | 3 | 161089429 | Lower in Drinkers |
| cg06054793 | 7 | 101007442 | Higher in Drinkers |
| cg06055562 | 20 | 3190016 | Higher in Drinkers |
| cg06056644 | 15 | 23111623 | Lower in Drinkers |
| cg06059032 | 2 | 236402544 | Higher in Drinkers |
| cg06061360 | 3 | 134319898 | Higher in Drinkers |
| cg06063729 | 3 | 50374670 | Higher in Drinkers |

| | | | |
|---|---|---|---|
| cg06074143 | 17 | 37774242 | Higher in Drinkers |
| cg06074774 | 11 | 126138802 | Higher in Drinkers |
| cg06074958 | 12 | 57118908 | Higher in Drinkers |
| cg06077079 | 2 | 232527265 | Higher in Drinkers |
| cg06084735 | 8 | 110346664 | Higher in Drinkers |
| cg06085493 | 11 | 47768276 | Higher in Drinkers |
| cg06087623 | 1 | 2203012 | Lower in Drinkers |
| cg06090351 | 1 | 244615600 | Higher in Drinkers |
| cg06090383 | 4 | 174292579 | Higher in Drinkers |
| cg06090864 | 19 | 35842448 | Higher in Drinkers |
| cg06097216 | 3 | 128901401 | Higher in Drinkers |
| cg06100967 | 12 | 38545214 | Lower in Drinkers |
| cg06100991 | 4 | 111119437 | Higher in Drinkers |
| cg06101723 | 8 | 145066662 | Lower in Drinkers |
| cg06103029 | 12 | 58299321 | Higher in Drinkers |
| cg06104877 | 11 | 64660076 | Higher in Drinkers |
| cg06105085 | 10 | 73976264 | Higher in Drinkers |
| cg06107297 | 7 | 93633078 | Higher in Drinkers |
| cg06108461 | 20 | 60628389 | Lower in Drinkers |
| cg06112333 | 21 | 46295113 | Higher in Drinkers |
| cg06112732 | 7 | 5263854 | Higher in Drinkers |
| cg06113665 | 4 | 170913337 | Higher in Drinkers |
| cg06113776 | 6 | 33151943 | Higher in Drinkers |
| cg06115535 | 2 | 131100015 | Higher in Drinkers |
| cg06121450 | 1 | 165798382 | Higher in Drinkers |
| cg06122000 | 6 | 83775663 | Higher in Drinkers |
| cg06124434 | 22 | 26895461 | Higher in Drinkers |
| cg06127885 | 15 | 45421068 | Higher in Drinkers |
| cg06129084 | 16 | 58034153 | Higher in Drinkers |
| cg06130159 | 16 | 14013710 | Higher in Drinkers |
| cg06130277 | 17 | 27182318 | Higher in Drinkers |
| cg06131377 | 17 | 62836426 | Higher in Drinkers |
| cg06135725 | 22 | 20307624 | Higher in Drinkers |
| cg06139438 | 6 | 41303596 | Higher in Drinkers |
| cg06139644 | 12 | 10826950 | Higher in Drinkers |

| | | | |
|---|---|---|---|
| cg06143244 | 16 | 22435202 | Higher in Drinkers |
| cg06147194 | 17 | 72860652 | Higher in Drinkers |
| cg06147733 | 17 | 18128806 | Higher in Drinkers |
| cg06147895 | 10 | 133791401 | Higher in Drinkers |
| cg06153386 | 16 | 89764255 | Higher in Drinkers |
| cg06154903 | 11 | 64642558 | Lower in Drinkers |
| cg06155979 | 2 | 232575824 | Higher in Drinkers |
| cg06156768 | 4 | 128983279 | Higher in Drinkers |
| cg06156849 | 16 | 31519531 | Higher in Drinkers |
| cg06159352 | 7 | 37487613 | Higher in Drinkers |
| cg06160440 | 1 | 155243364 | Higher in Drinkers |
| cg06169648 | 16 | 85646832 | Higher in Drinkers |
| cg06170922 | 6 | 52859660 | Higher in Drinkers |
| cg06171242 | 6 | 24667490 | Higher in Drinkers |
| cg06177446 | 20 | 1093802 | Higher in Drinkers |
| cg06178387 | 17 | 17565774 | Higher in Drinkers |
| cg06179645 | 1 | 151119372 | Higher in Drinkers |
| cg06180363 | 19 | 59056346 | Higher in Drinkers |
| cg06180915 | 7 | 2394179 | Higher in Drinkers |
| cg06181567 | 16 | 50731115 | Higher in Drinkers |
| cg06182040 | 6 | 139456059 | Higher in Drinkers |
| cg06183320 | 6 | 2972097 | Higher in Drinkers |
| cg06186057 | 6 | 28186447 | Higher in Drinkers |
| cg06188024 | 6 | 88182584 | Higher in Drinkers |
| cg06191580 | 17 | 35870477 | Lower in Drinkers |
| cg06191669 | 2 | 27593396 | Higher in Drinkers |
| cg06193775 | 1 | 155145882 | Higher in Drinkers |
| cg06193988 | 2 | 10442521 | Higher in Drinkers |
| cg06195829 | 8 | 66753750 | Higher in Drinkers |
| cg06196122 | 17 | 40021882 | Higher in Drinkers |
| cg06197836 | 1 | 39283522 | Higher in Drinkers |
| cg06200697 | 11 | 57528838 | Higher in Drinkers |
| cg06201207 | 4 | 866302 | Higher in Drinkers |
| cg06203772 | 12 | 1655755 | Higher in Drinkers |
| cg06206793 | 10 | 134969984 | Lower in Drinkers |

| | | | |
|---|---|---|---|
| cg06208339 | 3 | 139258658 | Higher in Drinkers |
| cg06208651 | 1 | 178694334 | Higher in Drinkers |
| cg06210187 | 6 | 26216839 | Higher in Drinkers |
| cg06211255 | 11 | 65153842 | Lower in Drinkers |
| cg06216157 | 17 | 7210363 | Higher in Drinkers |
| cg06216883 | 8 | 2023251 | Higher in Drinkers |
| cg06216926 | 14 | 92572917 | Higher in Drinkers |
| cg06217323 | 3 | 75445502 | Lower in Drinkers |
| cg06218186 | 7 | 99691644 | Higher in Drinkers |
| cg06222517 | 3 | 49577284 | Higher in Drinkers |
| cg06222638 | 17 | 4542859 | Higher in Drinkers |
| cg06225154 | 22 | 37640364 | Higher in Drinkers |
| cg06225979 | 18 | 32957337 | Higher in Drinkers |
| cg06230781 | 20 | 44563141 | Higher in Drinkers |
| cg06233202 | 2 | 64501134 | Higher in Drinkers |
| cg06233552 | 17 | 5322836 | Higher in Drinkers |
| cg06233823 | 10 | 1142583 | Higher in Drinkers |
| cg06236573 | 10 | 100007832 | Higher in Drinkers |
| cg06236976 | 8 | 145066299 | Higher in Drinkers |
| cg06247283 | 18 | 29302528 | Higher in Drinkers |
| cg06247470 | 17 | 79995744 | Higher in Drinkers |
| cg06251832 | 8 | 144952627 | Higher in Drinkers |
| cg06254440 | 9 | 126779285 | Lower in Drinkers |
| cg06257561 | 12 | 50445403 | Higher in Drinkers |
| cg06259052 | 8 | 144100331 | Higher in Drinkers |
| cg06260964 | 7 | 2473003 | Higher in Drinkers |
| cg06267636 | 1 | 156308293 | Higher in Drinkers |
| cg06271956 | 11 | 28132195 | Higher in Drinkers |
| cg06272230 | 16 | 53165410 | Higher in Drinkers |
| cg06272495 | 22 | 17652825 | Higher in Drinkers |
| cg06275130 | 4 | 864840 | Higher in Drinkers |
| cg06275808 | 1 | 32966562 | Higher in Drinkers |
| cg06277638 | 3 | 195424838 | Higher in Drinkers |
| cg06278939 | 4 | 113207141 | Higher in Drinkers |
| cg06279632 | 16 | 85280198 | Higher in Drinkers |

| | | | |
|---|---|---|---|
| cg06280271 | 16 | 32165153 | Lower in Drinkers |
| cg06282462 | 4 | 128886421 | Higher in Drinkers |
| cg06285486 | 11 | 65729635 | Higher in Drinkers |
| cg06287288 | 1 | 21763415 | Higher in Drinkers |
| cg06293294 | 11 | 100557954 | Higher in Drinkers |
| cg06294384 | 16 | 18057597 | Lower in Drinkers |
| cg06298247 | 12 | 6560981 | Higher in Drinkers |
| cg06302803 | 5 | 138609953 | Higher in Drinkers |
| cg06305175 | 2 | 228337254 | Higher in Drinkers |
| cg06305312 | 1 | 19638330 | Higher in Drinkers |
| cg06306260 | 7 | 99330962 | Lower in Drinkers |
| cg06309063 | 20 | 49575081 | Higher in Drinkers |
| cg06310300 | 7 | 100076089 | Higher in Drinkers |
| cg06310690 | 2 | 84682096 | Higher in Drinkers |
| cg06313381 | 10 | 58121080 | Higher in Drinkers |
| cg06320126 | 11 | 66886141 | Higher in Drinkers |
| cg06321808 | 10 | 71389579 | Lower in Drinkers |
| cg06322557 | 3 | 8399147 | Higher in Drinkers |
| cg06323479 | 6 | 167507729 | Higher in Drinkers |
| cg06327150 | 1 | 52195686 | Higher in Drinkers |
| cg06327267 | 7 | 116165142 | Higher in Drinkers |
| cg06329143 | 19 | 48556512 | Higher in Drinkers |
| cg06330722 | 7 | 100201795 | Higher in Drinkers |
| cg06333492 | 15 | 65903461 | Higher in Drinkers |
| cg06335773 | 14 | 58666568 | Higher in Drinkers |
| cg06337870 | 5 | 39074668 | Higher in Drinkers |
| cg06339752 | 16 | 68877402 | Higher in Drinkers |
| cg06340365 | 16 | 87749372 | Higher in Drinkers |
| cg06341939 | 22 | 43045530 | Higher in Drinkers |
| cg06342283 | 1 | 52344726 | Higher in Drinkers |
| cg06348187 | 7 | 899806 | Higher in Drinkers |
| cg06349981 | 2 | 10443745 | Higher in Drinkers |
| cg06352924 | 3 | 150321728 | Higher in Drinkers |
| cg06354692 | 11 | 597466 | Higher in Drinkers |
| cg06360820 | 2 | 242988706 | Higher in Drinkers |

| | | | |
|---|---|---|---|
| cg06364417 | 1 | 156124322 | Higher in Drinkers |
| cg06365412 | 17 | 7580709 | Higher in Drinkers |
| cg06365538 | 11 | 102962656 | Higher in Drinkers |
| cg06368118 | 1 | 107684339 | Higher in Drinkers |
| cg06368369 | 3 | 148709353 | Higher in Drinkers |
| cg06376599 | 10 | 70939989 | Higher in Drinkers |
| cg06377716 | 16 | 4311936 | Lower in Drinkers |
| cg06380039 | 7 | 77684965 | Higher in Drinkers |
| cg06380123 | 12 | 51717978 | Higher in Drinkers |
| cg06381879 | 12 | 125668924 | Higher in Drinkers |
| cg06381933 | 2 | 240288826 | Lower in Drinkers |
| cg06382459 | 1 | 2159373 | Higher in Drinkers |
| cg06383241 | 12 | 116997022 | Higher in Drinkers |
| cg06388099 | 19 | 50400885 | Higher in Drinkers |
| cg06392839 | 3 | 150320923 | Higher in Drinkers |
| cg06395988 | 2 | 242041550 | Higher in Drinkers |
| cg06401027 | 12 | 8234690 | Higher in Drinkers |
| cg06410284 | 16 | 3493133 | Higher in Drinkers |
| cg06412358 | 21 | 34392373 | Higher in Drinkers |
| cg06414605 | 3 | 193853892 | Higher in Drinkers |
| cg06418184 | 9 | 34620572 | Higher in Drinkers |
| cg06419270 | 1 | 23357884 | Higher in Drinkers |
| cg06419568 | 12 | 46776835 | Higher in Drinkers |
| cg06420088 | 1 | 155163590 | Higher in Drinkers |
| cg06422659 | 12 | 57481370 | Higher in Drinkers |
| cg06425443 | 5 | 16466328 | Higher in Drinkers |
| cg06427561 | 5 | 114598649 | Higher in Drinkers |
| cg06432278 | 2 | 101869599 | Higher in Drinkers |
| cg06432538 | 5 | 67512385 | Higher in Drinkers |
| cg06433995 | 6 | 13615570 | Higher in Drinkers |
| cg06439293 | 9 | 93956212 | Higher in Drinkers |
| cg06439777 | 20 | 44509809 | Higher in Drinkers |
| cg06439941 | 7 | 93550756 | Higher in Drinkers |
| cg06441946 | 5 | 145583671 | Higher in Drinkers |
| cg06442736 | X | 48368034 | Higher in Drinkers |

| | | | |
|---|---|---|---|
| cg06444730 | 1 | 84544284 | Higher in Drinkers |
| cg06451739 | 5 | 170108303 | Higher in Drinkers |
| cg06458698 | 2 | 3623210 | Higher in Drinkers |
| cg06459669 | 10 | 111683143 | Higher in Drinkers |
| cg06464111 | 21 | 32931732 | Higher in Drinkers |
| cg06467769 | 19 | 37808668 | Higher in Drinkers |
| cg06469307 | 17 | 42264507 | Higher in Drinkers |
| cg06472554 | 13 | 30002475 | Higher in Drinkers |
| cg06478398 | 19 | 1479426 | Higher in Drinkers |
| cg06478814 | 16 | 58163201 | Higher in Drinkers |
| cg06480843 | 15 | 78442154 | Higher in Drinkers |
| cg06481089 | X | 51075797 | Higher in Drinkers |
| cg06486344 | 9 | 33290885 | Higher in Drinkers |
| cg06488666 | 20 | 3310414C | Higher in Drinkers |
| cg06489418 | X | 48334722 | Higher in Drinkers |
| cg06489433 | 16 | 89491229 | Lower in Drinkers |
| cg06489668 | 3 | 52031194 | Lower in Drinkers |
| cg06489804 | 19 | 12807371 | Higher in Drinkers |
| cg06490385 | 19 | 50169153 | Higher in Drinkers |
| cg06492744 | 11 | 65406254 | Higher in Drinkers |
| cg06493166 | 6 | 144386146 | Higher in Drinkers |
| cg06496198 | 4 | 83294070 | Higher in Drinkers |
| cg06497674 | 19 | 3645760 | Higher in Drinkers |
| cg06505000 | 3 | 122102135 | Higher in Drinkers |
| cg06507072 | 16 | 310683 | Higher in Drinkers |
| cg06507307 | 10 | 134567532 | Higher in Drinkers |
| cg06509993 | 1 | 27692295 | Higher in Drinkers |
| cg06513977 | 6 | 33288998 | Higher in Drinkers |
| cg06514300 | 10 | 7253416 | Higher in Drinkers |
| cg06514371 | 3 | 152880962 | Higher in Drinkers |
| cg06515734 | 16 | 87749852 | Higher in Drinkers |
| cg06516445 | 11 | 102963032 | Higher in Drinkers |
| cg06516720 | 6 | 16266038 | Lower in Drinkers |
| cg06519183 | 17 | 74387073 | Higher in Drinkers |
| cg06520715 | 2 | 28614896 | Higher in Drinkers |

| | | | |
|---|---|---|---|
| cg06520812 | 19 | 46000742 | Higher in Drinkers |
| cg06521299 | 1 | 26325349 | Higher in Drinkers |
| cg06522435 | 8 | 68080400 | Lower in Drinkers |
| cg06522491 | 22 | 42970613 | Higher in Drinkers |
| cg06523128 | 11 | 71159708 | Higher in Drinkers |
| cg06527919 | 1 | 181480848 | Higher in Drinkers |
| cg06531655 | 19 | 11039470 | Higher in Drinkers |
| cg06533728 | 11 | 67236603 | Higher in Drinkers |
| cg06534724 | 12 | 12618591 | Higher in Drinkers |
| cg06534853 | 2 | 662602 | Higher in Drinkers |
| cg06537244 | 5 | 32444803 | Higher in Drinkers |
| cg06538888 | 1 | 16839385 | Higher in Drinkers |
| cg06540105 | 2 | 132235688 | Higher in Drinkers |
| cg06544369 | 2 | 43823281 | Higher in Drinkers |
| cg06545693 | 19 | 507193 | Higher in Drinkers |
| cg06545804 | 4 | 140036278 | Higher in Drinkers |
| cg06546717 | 12 | 113659579 | Higher in Drinkers |
| cg06547557 | 5 | 146606359 | Lower in Drinkers |
| cg06549249 | X | 129040144 | Higher in Drinkers |
| cg06549928 | 1 | 89990868 | Higher in Drinkers |
| cg06550082 | 9 | 34624160 | Higher in Drinkers |
| cg06550309 | 7 | 144533283 | Higher in Drinkers |
| cg06552368 | 11 | 118972898 | Higher in Drinkers |
| cg06552618 | 12 | 54582532 | Higher in Drinkers |
| cg06552734 | 7 | 25902471 | Higher in Drinkers |
| cg06554542 | 12 | 102224375 | Higher in Drinkers |
| cg06556593 | 19 | 4564958 | Higher in Drinkers |
| cg06558952 | X | 43514718 | Higher in Drinkers |
| cg06559318 | 6 | 32526260 | Higher in Drinkers |
| cg06559839 | 10 | 73133003 | Higher in Drinkers |
| cg06560912 | 19 | 56092605 | Higher in Drinkers |
| cg06561723 | 17 | 650113 | Lower in Drinkers |
| cg06562297 | 17 | 77785191 | Higher in Drinkers |
| cg06568454 | 16 | 89940886 | Higher in Drinkers |
| cg06575283 | 12 | 132093736 | Higher in Drinkers |

| | | | |
|---|---|---|---|
| cg06578069 | 5 | 17219128 | Higher in Drinkers |
| cg06579248 | 17 | 1375968 | Higher in Drinkers |
| cg06579829 | 17 | 57970481 | Higher in Drinkers |
| cg06579875 | 19 | 46001962 | Higher in Drinkers |
| cg06585690 | 4 | 71262957 | Lower in Drinkers |
| cg06590268 | 5 | 1386150 | Higher in Drinkers |
| cg06593050 | 4 | 144480206 | Higher in Drinkers |
| cg06595275 | 6 | 35995676 | Higher in Drinkers |
| cg06598196 | 1 | 150185923 | Higher in Drinkers |
| cg06598631 | 6 | 88300029 | Higher in Drinkers |
| cg06599546 | 16 | 1360715 | Higher in Drinkers |
| cg06599914 | 11 | 32915903 | Higher in Drinkers |
| cg06604102 | 12 | 125549789 | Higher in Drinkers |
| cg06609498 | 2 | 240233240 | Higher in Drinkers |
| cg06610559 | 17 | 74554360 | Higher in Drinkers |
| cg06611874 | 16 | 19566878 | Higher in Drinkers |
| cg06612450 | 19 | 35767682 | Higher in Drinkers |
| cg06613203 | 19 | 50143480 | Higher in Drinkers |
| cg06615667 | 9 | 132816229 | Higher in Drinkers |
| cg06616488 | 2 | 87035502 | Higher in Drinkers |
| cg06616806 | 1 | 148556049 | Higher in Drinkers |
| cg06617769 | 17 | 74350629 | Higher in Drinkers |
| cg06618497 | 14 | 102198604 | Higher in Drinkers |
| cg06618740 | 1 | 1100126 | Lower in Drinkers |
| cg06620269 | 17 | 2952258 | Higher in Drinkers |
| cg06620569 | 18 | 56942066 | Higher in Drinkers |
| cg06620731 | 12 | 108909559 | Higher in Drinkers |
| cg06620762 | 15 | 76136437 | Higher in Drinkers |
| cg06623899 | 8 | 142161840 | Lower in Drinkers |
| cg06624711 | 7 | 150076028 | Higher in Drinkers |
| cg06624832 | 17 | 72772340 | Higher in Drinkers |
| cg06626184 | 9 | 126775931 | Lower in Drinkers |
| cg06626224 | 19 | 56111502 | Higher in Drinkers |
| cg06629086 | 12 | 6715037 | Higher in Drinkers |
| cg06634887 | 4 | 967541 | Higher in Drinkers |

| | | | |
|---|---|---|---|
| cg06636077 | 6 | 44224934 | Higher in Drinkers |
| cg06639733 | 16 | 88858204 | Higher in Drinkers |
| cg06640279 | 1 | 207095153 | Higher in Drinkers |
| cg06640840 | 17 | 74353954 | Higher in Drinkers |
| cg06642248 | 10 | 60094109 | Higher in Drinkers |
| cg06642275 | 12 | 54145184 | Higher in Drinkers |
| cg06646708 | 6 | 18123224 | Higher in Drinkers |
| cg06647928 | 5 | 73612203 | Higher in Drinkers |
| cg06648452 | 6 | 33053592 | Higher in Drinkers |
| cg06649520 | 4 | 153700671 | Higher in Drinkers |
| cg06649899 | 16 | 67261154 | Higher in Drinkers |
| cg06652315 | 3 | 69591012 | Higher in Drinkers |
| cg06654076 | 1 | 43202523 | Higher in Drinkers |
| cg06654447 | 9 | 139686019 | Higher in Drinkers |
| cg06658146 | 4 | 58029765 | Higher in Drinkers |
| cg06659310 | 16 | 67907373 | Higher in Drinkers |
| cg06661978 | 19 | 4958260 | Higher in Drinkers |
| cg06662132 | 10 | 104406731 | Higher in Drinkers |
| cg06664023 | 6 | 43395409 | Higher in Drinkers |
| cg06665941 | 21 | 34602869 | Higher in Drinkers |
| cg06666377 | 9 | 7799961 | Higher in Drinkers |
| cg06667222 | 6 | 31648994 | Higher in Drinkers |
| cg06670612 | 19 | 42082485 | Higher in Drinkers |
| cg06672120 | 16 | 85932383 | Higher in Drinkers |
| cg06672226 | 16 | 85611689 | Higher in Drinkers |
| cg06673910 | 10 | 43904777 | Higher in Drinkers |
| cg06675341 | 11 | 20408613 | Higher in Drinkers |
| cg06676621 | 4 | 110736369 | Higher in Drinkers |
| cg06677781 | 11 | 58346199 | Higher in Drinkers |
| cg06678137 | 11 | 495007 | Higher in Drinkers |
| cg06679221 | 3 | 9405070 | Higher in Drinkers |
| cg06679572 | 3 | 16926848 | Higher in Drinkers |
| cg06679752 | 13 | 50367340 | Higher in Drinkers |
| cg06680201 | 11 | 71824165 | Higher in Drinkers |
| cg06684939 | 2 | 85822407 | Higher in Drinkers |

| | | | |
|---|---|---|---|
| cg06685766 | 16 | 50699456 | Higher in Drinkers |
| cg06687102 | 3 | 158441983 | Higher in Drinkers |
| cg06687504 | 6 | 167263454 | Higher in Drinkers |
| cg06687820 | 22 | 50871404 | Higher in Drinkers |
| cg06688323 | 4 | 4858340 | Higher in Drinkers |
| cg06688409 | 7 | 99007151 | Higher in Drinkers |
| cg06692023 | 10 | 12238229 | Higher in Drinkers |
| cg06694641 | 12 | 133533079 | Higher in Drinkers |
| cg06696917 | 16 | 56718412 | Higher in Drinkers |
| cg06699484 | 5 | 132166328 | Higher in Drinkers |
| cg06705772 | 11 | 62439523 | Higher in Drinkers |
| cg06706163 | 13 | 25497100 | Higher in Drinkers |
| cg06707343 | 3 | 62360240 | Higher in Drinkers |
| cg06708720 | 12 | 1099075 | Higher in Drinkers |
| cg06709066 | 9 | 146065047 | Higher in Drinkers |
| cg06709072 | 1 | 111162296 | Higher in Drinkers |
| cg06713261 | 17 | 79478173 | Higher in Drinkers |
| cg06714480 | 2 | 182544307 | Higher in Drinkers |
| cg06717841 | 1 | 40349329 | Higher in Drinkers |
| cg06718276 | 12 | 54134485 | Higher in Drinkers |
| cg06719391 | 11 | 2554330 | Higher in Drinkers |
| cg06723287 | 2 | 112813613 | Higher in Drinkers |
| cg06724305 | 1 | 50887944 | Higher in Drinkers |
| cg06724409 | 10 | 3821491 | Higher in Drinkers |
| cg06725829 | 19 | 12175461 | Higher in Drinkers |
| cg06726262 | 17 | 15602873 | Higher in Drinkers |
| cg06726893 | 16 | 28870846 | Higher in Drinkers |
| cg06727269 | 5 | 160687369 | Higher in Drinkers |
| cg06728551 | 7 | 64531992 | Higher in Drinkers |
| cg06728974 | 19 | 52408322 | Higher in Drinkers |
| cg06730721 | 19 | 1039831 | Higher in Drinkers |
| cg06731059 | 10 | 89622048 | Higher in Drinkers |
| cg06731942 | 15 | 66586493 | Higher in Drinkers |
| cg06732395 | 5 | 180018722 | Higher in Drinkers |
| cg06736554 | 4 | 39378224 | Higher in Drinkers |

| | | | |
|---|---|---|---|
| cg06739403 | 13 | 35516903 | Higher in Drinkers |
| cg06740598 | 2 | 26467551 | Lower in Drinkers |
| cg06741536 | 12 | 69005242 | Higher in Drinkers |
| cg06741909 | 14 | 24767084 | Higher in Drinkers |
| cg06742440 | 1 | 154842717 | Higher in Drinkers |
| cg06747543 | 19 | 18589894 | Higher in Drinkers |
| cg06747831 | 11 | 58825870 | Higher in Drinkers |
| cg06749854 | 11 | 2020030 | Higher in Drinkers |
| cg06752270 | 8 | 42397250 | Higher in Drinkers |
| cg06753092 | 7 | 44795231 | Higher in Drinkers |
| cg06753281 | 1 | 6086652 | Higher in Drinkers |
| cg06754938 | 7 | 1049123 | Higher in Drinkers |
| cg06757784 | 15 | 66994613 | Higher in Drinkers |
| cg06759845 | 1 | 156460474 | Higher in Drinkers |
| cg06762398 | 15 | 78372177 | Higher in Drinkers |
| cg06764565 | 10 | 75910434 | Higher in Drinkers |
| cg06768251 | 10 | 73533035 | Higher in Drinkers |
| cg06768437 | 17 | 28715545 | Higher in Drinkers |
| cg06772157 | 7 | 100728711 | Higher in Drinkers |
| cg06773813 | 1 | 41339683 | Higher in Drinkers |
| cg06774974 | 14 | 105714404 | Higher in Drinkers |
| cg06776953 | 1 | 149859104 | Higher in Drinkers |
| cg06777581 | 6 | 37321919 | Higher in Drinkers |
| cg06784848 | 18 | 49865791 | Higher in Drinkers |
| cg06785624 | 8 | 144990484 | Lower in Drinkers |
| cg06789383 | 6 | 106553538 | Higher in Drinkers |
| cg06790275 | 15 | 68346669 | Higher in Drinkers |
| cg06792847 | 17 | 62773246 | Higher in Drinkers |
| cg06794001 | 5 | 148415048 | Higher in Drinkers |
| cg06794398 | 1 | 156265456 | Higher in Drinkers |
| cg06795078 | 6 | 16332480 | Higher in Drinkers |
| cg06798749 | 11 | 62360527 | Higher in Drinkers |
| cg06799250 | 1 | 110882846 | Higher in Drinkers |
| cg06799790 | 17 | 61951754 | Higher in Drinkers |
| cg06800352 | 13 | 28024821 | Higher in Drinkers |

| | | | |
|---|---|---|---|
| cg06801569 | 6 | 32862729 | Higher in Drinkers |
| cg06805345 | 6 | 41755749 | Higher in Drinkers |
| cg06809635 | 1 | 40533357 | Higher in Drinkers |
| cg06810179 | 16 | 90038862 | Higher in Drinkers |
| cg06812278 | 1 | 200992475 | Higher in Drinkers |
| cg06817572 | 14 | 75643375 | Higher in Drinkers |
| cg06818126 | 11 | 68850279 | Higher in Drinkers |
| cg06818484 | 8 | 145051287 | Higher in Drinkers |
| cg06818514 | 19 | 55850629 | Higher in Drinkers |
| cg06818627 | 12 | 109536430 | Higher in Drinkers |
| cg06820914 | 8 | 99129609 | Higher in Drinkers |
| cg06822120 | 4 | 2060934 | Higher in Drinkers |
| cg06823263 | 1 | 161015119 | Higher in Drinkers |
| cg06827256 | 1 | 226311603 | Higher in Drinkers |
| cg06829157 | 1 | 93450542 | Higher in Drinkers |
| cg06830981 | 1 | 22142491 | Higher in Drinkers |
| cg06834534 | 10 | 15001276 | Higher in Drinkers |
| cg06835581 | 12 | 123433185 | Higher in Drinkers |
| cg06837242 | 1 | 19578761 | Higher in Drinkers |
| cg06838394 | 20 | 47538719 | Higher in Drinkers |
| cg06839896 | 12 | 133342347 | Higher in Drinkers |
| cg06839953 | 1 | 27648457 | Higher in Drinkers |
| cg06844489 | 13 | 113951297 | Higher in Drinkers |
| cg06844939 | 15 | 68569742 | Higher in Drinkers |
| cg06845571 | 6 | 108279703 | Higher in Drinkers |
| cg06850513 | 5 | 175955092 | Lower in Drinkers |
| cg06851224 | 7 | 156742617 | Higher in Drinkers |
| cg06851327 | 1 | 201951874 | Higher in Drinkers |
| cg06854438 | 1 | 220263111 | Higher in Drinkers |
| cg06857316 | 7 | 97846357 | Higher in Drinkers |
| cg06857837 | 2 | 3392499 | Higher in Drinkers |
| cg06860277 | 22 | 19930072 | Higher in Drinkers |
| cg06862474 | 18 | 74206503 | Higher in Drinkers |
| cg06863171 | 15 | 57179893 | Higher in Drinkers |
| cg06864046 | 12 | 89746505 | Higher in Drinkers |

| | | | |
|---|---|---|---|
| cg06867531 | 16 | 66785486 | Higher in Drinkers |
| cg06869971 | 15 | 69706519 | Higher in Drinkers |
| cg06872243 | 16 | 20818527 | Higher in Drinkers |
| cg06872519 | 11 | 6947619 | Higher in Drinkers |
| cg06873121 | 10 | 103880627 | Higher in Drinkers |
| cg06874767 | 2 | 20646825 | Higher in Drinkers |
| cg06878388 | 1 | 24118480 | Higher in Drinkers |
| cg06878866 | 17 | 6915594 | Higher in Drinkers |
| cg06880420 | 1 | 200119987 | Higher in Drinkers |
| cg06881040 | 16 | 30040916 | Higher in Drinkers |
| cg06886022 | 9 | 140095555 | Higher in Drinkers |
| cg06886896 | 2 | 120436636 | Higher in Drinkers |
| cg06889036 | 16 | 1399270 | Higher in Drinkers |
| cg06889350 | 14 | 75530936 | Higher in Drinkers |
| cg06891716 | 3 | 17940941 | Higher in Drinkers |
| cg06893977 | 6 | 30851928 | Higher in Drinkers |
| cg06895137 | 7 | 2321817 | Higher in Drinkers |
| cg06896529 | 16 | 81678968 | Higher in Drinkers |
| cg06896615 | 16 | 8617811 | Higher in Drinkers |
| cg06896909 | 7 | 19813297 | Higher in Drinkers |
| cg06898887 | 7 | 56101644 | Higher in Drinkers |
| cg06899483 | 1 | 208037215 | Higher in Drinkers |
| cg06903569 | 6 | 28304108 | Higher in Drinkers |
| cg06906087 | 17 | 80053205 | Higher in Drinkers |
| cg06907047 | 11 | 126138951 | Higher in Drinkers |
| cg06907160 | 7 | 75988247 | Higher in Drinkers |
| cg06907842 | 18 | 42260451 | Higher in Drinkers |
| cg06908052 | 17 | 78880396 | Higher in Drinkers |
| cg06909646 | 1 | 32681593 | Higher in Drinkers |
| cg06910115 | 14 | 100773048 | Higher in Drinkers |
| cg06911519 | 2 | 28615662 | Higher in Drinkers |
| cg06914197 | 12 | 6586920 | Higher in Drinkers |
| cg06915123 | 22 | 50682930 | Higher in Drinkers |
| cg06916463 | 14 | 60715366 | Higher in Drinkers |
| cg06918925 | 4 | 120987712 | Higher in Drinkers |

| | | | |
|---|---|---|---|
| cg06920740 | 11 | 534896 | Higher in Drinkers |
| cg06922352 | 4 | 57333562 | Higher in Drinkers |
| cg06926426 | 6 | 3259048 | Higher in Drinkers |
| cg06928797 | 11 | 116966699 | Higher in Drinkers |
| cg06932384 | 22 | 39358686 | Lower in Drinkers |
| cg06932756 | 1 | 46153656 | Higher in Drinkers |
| cg06933031 | 6 | 32940391 | Higher in Drinkers |
| cg06933697 | 16 | 15238104 | Higher in Drinkers |
| cg06933899 | 22 | 39917192 | Higher in Drinkers |
| cg06935199 | 16 | 2524534 | Higher in Drinkers |
| cg06936350 | 17 | 66453787 | Higher in Drinkers |
| cg06936731 | 6 | 13814936 | Higher in Drinkers |
| cg06936768 | 12 | 49691316 | Higher in Drinkers |
| cg06938063 | 1 | 207923405 | Higher in Drinkers |
| cg06938467 | 17 | 74261078 | Higher in Drinkers |
| cg06942010 | 12 | 124396683 | Higher in Drinkers |
| cg06942159 | 17 | 7284255 | Higher in Drinkers |
| cg06942904 | 5 | 131926485 | Higher in Drinkers |
| cg06943316 | 17 | 53025387 | Higher in Drinkers |
| cg06945667 | 16 | 19566991 | Higher in Drinkers |
| cg06950567 | 20 | 48807318 | Higher in Drinkers |
| cg06952715 | 1 | 206804680 | Higher in Drinkers |
| cg06954660 | 6 | 32975336 | Lower in Drinkers |
| cg06954720 | 6 | 32525813 | Higher in Drinkers |
| cg06957169 | 1 | 156571551 | Higher in Drinkers |
| cg06960901 | 5 | 36606894 | Higher in Drinkers |
| cg06961313 | 1 | 181002177 | Higher in Drinkers |
| cg06961876 | 22 | 45559239 | Higher in Drinkers |
| cg06962121 | 2 | 71295366 | Higher in Drinkers |
| cg06962428 | 1 | 247370099 | Higher in Drinkers |
| cg06962782 | 7 | 100091575 | Higher in Drinkers |
| cg06964191 | 17 | 38256671 | Higher in Drinkers |
| cg06964756 | 17 | 27046568 | Higher in Drinkers |
| cg06967703 | 18 | 19284831 | Higher in Drinkers |
| cg06971353 | 18 | 77867044 | Higher in Drinkers |

| | | | |
|---|---|---|---|
| cg06972153 | 6 | 21596573 | Higher in Drinkers |
| cg06973463 | 1 | 1002664 | Higher in Drinkers |
| cg06978067 | 2 | 85765644 | Higher in Drinkers |
| cg06981309 | 3 | 146260954 | Higher in Drinkers |
| cg06984945 | 6 | 26660160 | Higher in Drinkers |
| cg06985779 | 1 | 246363697 | Higher in Drinkers |
| cg07000989 | 18 | 33709734 | Higher in Drinkers |
| cg07001963 | 10 | 44879465 | Higher in Drinkers |
| cg07008926 | 4 | 147448047 | Higher in Drinkers |
| cg07010552 | 17 | 7358735 | Higher in Drinkers |
| cg07011163 | 17 | 6947325 | Higher in Drinkers |
| cg07011180 | 11 | 119611809 | Higher in Drinkers |
| cg07015494 | 1 | 149857049 | Higher in Drinkers |
| cg07015725 | 5 | 94982558 | Higher in Drinkers |
| cg07016730 | 22 | 50912306 | Lower in Drinkers |
| cg07018980 | 4 | 895604 | Higher in Drinkers |
| cg07025478 | 12 | 66563505 | Higher in Drinkers |
| cg07031437 | 7 | 66461649 | Higher in Drinkers |
| cg07031532 | 15 | 64995684 | Higher in Drinkers |
| cg07036524 | 18 | 77557781 | Higher in Drinkers |
| cg07038887 | 17 | 28618554 | Higher in Drinkers |
| cg07039975 | 2 | 74592036 | Higher in Drinkers |
| cg07045891 | 15 | 101548676 | Higher in Drinkers |
| cg07046546 | 7 | 128550967 | Higher in Drinkers |
| cg07047815 | 11 | 1909656 | Higher in Drinkers |
| cg07050215 | 12 | 113595504 | Higher in Drinkers |
| cg07055681 | 15 | 23049563 | Higher in Drinkers |
| cg07056645 | 19 | 6230546 | Lower in Drinkers |
| cg07056812 | 1 | 148854228 | Higher in Drinkers |
| cg07064050 | 19 | 19165011 | Higher in Drinkers |
| cg07066356 | 16 | 30905197 | Higher in Drinkers |
| cg07070019 | 3 | 32611876 | Higher in Drinkers |
| cg07070391 | 20 | 21494748 | Higher in Drinkers |
| cg07076850 | 6 | 186671 | Higher in Drinkers |
| cg07079314 | 2 | 234384677 | Higher in Drinkers |

| | | | |
|---|---|---|---|
| cg07080049 | 9 | 96214194 | Higher in Drinkers |
| cg07081759 | 10 | 126330905 | Higher in Drinkers |
| cg07082501 | 17 | 3649552 | Higher in Drinkers |
| cg07086112 | 8 | 22853394 | Higher in Drinkers |
| cg07089242 | X | 149106617 | Higher in Drinkers |
| cg07090138 | 2 | 37035688 | Higher in Drinkers |
| cg07092057 | 12 | 57914300 | Higher in Drinkers |
| cg07093046 | 1 | 236958653 | Higher in Drinkers |
| cg07095459 | 8 | 53626238 | Higher in Drinkers |
| cg07098151 | 1 | 229762071 | Higher in Drinkers |
| cg07103714 | 16 | 2954750 | Higher in Drinkers |
| cg07105046 | 16 | 2261082 | Higher in Drinkers |
| cg07105440 | 3 | 50648946 | Higher in Drinkers |
| cg07106944 | 1 | 27180489 | Higher in Drinkers |
| cg07112531 | 6 | 42016695 | Higher in Drinkers |
| cg07113322 | 16 | 58034658 | Higher in Drinkers |
| cg07117660 | 7 | 138916021 | Higher in Drinkers |
| cg07120134 | 16 | 30886017 | Higher in Drinkers |
| cg07120369 | 3 | 187388281 | Higher in Drinkers |
| cg07125905 | 5 | 140767364 | Lower in Drinkers |
| cg07127456 | 16 | 66583081 | Higher in Drinkers |
| cg07127534 | 5 | 9119105 | Lower in Drinkers |
| cg07129696 | 2 | 209119949 | Higher in Drinkers |
| cg07134804 | 1 | 200969906 | Higher in Drinkers |
| cg07136920 | 1 | 53970693 | Lower in Drinkers |
| cg07137581 | X | 63425776 | Higher in Drinkers |
| cg07138491 | 1 | 43613173 | Higher in Drinkers |
| cg07139811 | 2 | 176033051 | Higher in Drinkers |
| cg07139985 | 11 | 64948822 | Higher in Drinkers |
| cg07140751 | 17 | 3599230 | Higher in Drinkers |
| cg07141002 | 22 | 38201690 | Higher in Drinkers |
| cg07142893 | 6 | 30594605 | Higher in Drinkers |
| cg07144124 | 7 | 151827908 | Higher in Drinkers |
| cg07145783 | 1 | 160855077 | Higher in Drinkers |
| cg07149022 | 11 | 9636089 | Higher in Drinkers |

| | | | |
|---|---|---|---|
| cg07149459 | 10 | 134144864 | Higher in Drinkers |
| cg07149639 | 13 | 113488043 | Higher in Drinkers |
| cg07150680 | X | 53710374 | Higher in Drinkers |
| cg07153921 | 17 | 41440717 | Higher in Drinkers |
| cg07154196 | 1 | 29214064 | Higher in Drinkers |
| cg07155014 | 3 | 195855367 | Higher in Drinkers |
| cg07158747 | 1 | 91196488 | Higher in Drinkers |
| cg07163173 | 2 | 67624373 | Higher in Drinkers |
| cg07165616 | 12 | 498868 | Higher in Drinkers |
| cg07167632 | 11 | 67269440 | Lower in Drinkers |
| cg07170231 | 20 | 5590750 | Higher in Drinkers |
| cg07171867 | 2 | 64681137 | Higher in Drinkers |
| cg07172736 | 12 | 113596827 | Higher in Drinkers |
| cg07173973 | 19 | 45596087 | Higher in Drinkers |
| cg07174453 | 16 | 27476281 | Lower in Drinkers |
| cg07174627 | 1 | 3566769 | Higher in Drinkers |
| cg07175110 | 17 | 27181923 | Higher in Drinkers |
| cg07176563 | 2 | 233924857 | Higher in Drinkers |
| cg07180186 | 1 | 246770778 | Higher in Drinkers |
| cg07180538 | 7 | 4786899 | Lower in Drinkers |
| cg07182616 | 14 | 33409812 | Lower in Drinkers |
| cg07182669 | 6 | 2903535 | Higher in Drinkers |
| cg07187585 | 17 | 10600923 | Higher in Drinkers |
| cg07187971 | 18 | 60481018 | Lower in Drinkers |
| cg07191012 | 1 | 33182372 | Higher in Drinkers |
| cg07195011 | 5 | 11904114 | Higher in Drinkers |
| cg07199827 | 20 | 36156050 | Higher in Drinkers |
| cg07201089 | 19 | 1446280 | Higher in Drinkers |
| cg07202110 | 17 | 38421186 | Higher in Drinkers |
| cg07206725 | 5 | 133702808 | Higher in Drinkers |
| cg07210490 | 12 | 50479634 | Higher in Drinkers |
| cg07211915 | X | 19533544 | Higher in Drinkers |
| cg07215407 | 1 | 41131559 | Higher in Drinkers |
| cg07217851 | 6 | 26553467 | Higher in Drinkers |
| cg07218288 | 6 | 32813211 | Higher in Drinkers |

| | | | |
|---|---|---|---|
| cg07223177 | X | 46434198 | Higher in Drinkers |
| cg07223803 | 12 | 53835152 | Higher in Drinkers |
| cg07229817 | 19 | 1269771 | Higher in Drinkers |
| cg07230792 | 6 | 43457174 | Higher in Drinkers |
| cg07230999 | 7 | 116863357 | Higher in Drinkers |
| cg07231738 | 16 | 67472363 | Higher in Drinkers |
| cg07236342 | 7 | 73133398 | Higher in Drinkers |
| cg07239293 | 8 | 101170671 | Higher in Drinkers |
| cg07239716 | 12 | 89744488 | Higher in Drinkers |
| cg07240043 | 1 | 231379882 | Lower in Drinkers |
| cg07240721 | 6 | 126278255 | Higher in Drinkers |
| cg07241154 | 12 | 12251784 | Higher in Drinkers |
| cg07241568 | 9 | 136150823 | Higher in Drinkers |
| cg07242196 | 7 | 112556814 | Lower in Drinkers |
| cg07242620 | 5 | 114598306 | Higher in Drinkers |
| cg07242901 | 12 | 7047503 | Higher in Drinkers |
| cg07244202 | 10 | 127750970 | Higher in Drinkers |
| cg07249209 | 13 | 19183930 | Higher in Drinkers |
| cg07249369 | 16 | 2034545 | Higher in Drinkers |
| cg07249919 | 5 | 53813391 | Higher in Drinkers |
| cg07250177 | 16 | 57220573 | Higher in Drinkers |
| cg07252171 | 5 | 573376 | Lower in Drinkers |
| cg07257505 | 17 | 8383621 | Higher in Drinkers |
| cg07260128 | 10 | 134894796 | Lower in Drinkers |
| cg07264617 | 12 | 132568670 | Higher in Drinkers |
| cg07265444 | 7 | 76956562 | Higher in Drinkers |
| cg07265541 | 6 | 159071008 | Higher in Drinkers |
| cg07265622 | 17 | 6554855 | Higher in Drinkers |
| cg07266032 | 22 | 43054512 | Higher in Drinkers |
| cg07266910 | 3 | 178745575 | Higher in Drinkers |
| cg07269819 | 20 | 62196641 | Higher in Drinkers |
| cg07270153 | 7 | 19185260 | Higher in Drinkers |
| cg07278158 | 6 | 31122462 | Higher in Drinkers |
| cg07279557 | 21 | 46875417 | Lower in Drinkers |
| cg07280593 | 19 | 55085260 | Higher in Drinkers |

| | | | |
|---|---|---|---|
| cg07281688 | 12 | 57082442 | Higher in Drinkers |
| cg07282944 | 12 | 48499338 | Higher in Drinkers |
| cg07283932 | 11 | 66887736 | Higher in Drinkers |
| cg07285213 | 5 | 1292339 | Lower in Drinkers |
| cg07288445 | 13 | 45009477 | Higher in Drinkers |
| cg07290761 | 10 | 5859460 | Higher in Drinkers |
| cg07295092 | 9 | 130565376 | Higher in Drinkers |
| cg07296147 | 5 | 141392537 | Higher in Drinkers |
| cg07299819 | 1 | 153651009 | Higher in Drinkers |
| cg07300408 | 14 | 21058360 | Higher in Drinkers |
| cg07301952 | 18 | 158011 | Higher in Drinkers |
| cg07304760 | 7 | 127514192 | Higher in Drinkers |
| cg07311250 | 2 | 120984408 | Higher in Drinkers |
| cg07314067 | 10 | 135171574 | Higher in Drinkers |
| cg07318867 | 1 | 33391207 | Higher in Drinkers |
| cg07321171 | 2 | 74692645 | Higher in Drinkers |
| cg07323350 | 11 | 123986080 | Higher in Drinkers |
| cg07326074 | 16 | 2510388 | Higher in Drinkers |
| cg07328209 | 5 | 112630811 | Higher in Drinkers |
| cg07328417 | 8 | 28558817 | Higher in Drinkers |
| cg07328505 | 9 | 113017849 | Higher in Drinkers |
| cg07332734 | 12 | 101802116 | Higher in Drinkers |
| cg07333037 | 17 | 57231856 | Higher in Drinkers |
| cg07333510 | 17 | 4854754 | Higher in Drinkers |
| cg07336016 | 16 | 56417448 | Higher in Drinkers |
| cg07336637 | 5 | 172572037 | Higher in Drinkers |
| cg07338577 | 11 | 288954 | Higher in Drinkers |
| cg07340423 | 15 | 52472383 | Higher in Drinkers |
| cg07343821 | 6 | 27637537 | Higher in Drinkers |
| cg07346836 | 1 | 153931253 | Higher in Drinkers |
| cg07347137 | 1 | 53019316 | Higher in Drinkers |
| cg07349054 | 1 | 3558237 | Lower in Drinkers |
| cg07349094 | 2 | 100759014 | Higher in Drinkers |
| cg07352016 | 18 | 55250568 | Higher in Drinkers |
| cg07356483 | 10 | 99791663 | Higher in Drinkers |

| | | | |
|---|---|---|---|
| cg07357373 | 15 | 48473479 | Lower in Drinkers |
| cg07357445 | 5 | 82429868 | Higher in Drinkers |
| cg07362258 | 13 | 41109707 | Higher in Drinkers |
| cg07365274 | 3 | 114866242 | Higher in Drinkers |
| cg07368396 | 5 | 132945815 | Lower in Drinkers |
| cg07369404 | 3 | 120026159 | Higher in Drinkers |
| cg07370261 | 12 | 49504051 | Higher in Drinkers |
| cg07370464 | 17 | 43394456 | Higher in Drinkers |
| cg07374808 | 18 | 34974004 | Higher in Drinkers |
| cg07376313 | 4 | 15006499 | Higher in Drinkers |
| cg07376527 | 20 | 62461890 | Higher in Drinkers |
| cg07380334 | 19 | 55789002 | Higher in Drinkers |
| cg07381228 | 16 | 70190398 | Higher in Drinkers |
| cg07382129 | 15 | 100249186 | Higher in Drinkers |
| cg07383464 | 10 | 43916495 | Higher in Drinkers |
| cg07383972 | 7 | 135242951 | Higher in Drinkers |
| cg07390141 | 15 | 93427738 | Higher in Drinkers |
| cg07393655 | 5 | 43122148 | Higher in Drinkers |
| cg07394827 | 1 | 1263239 | Higher in Drinkers |
| cg07395378 | 16 | 127952 | Higher in Drinkers |
| cg07395907 | 3 | 39219367 | Higher in Drinkers |
| cg07399094 | 6 | 3163461 | Higher in Drinkers |
| cg07399288 | 7 | 66767504 | Higher in Drinkers |
| cg07399355 | 1 | 155163013 | Higher in Drinkers |
| cg07402800 | 8 | 145582003 | Higher in Drinkers |
| cg07403638 | 18 | 32870369 | Higher in Drinkers |
| cg07406296 | 16 | 30960328 | Higher in Drinkers |
| cg07408211 | 12 | 64798935 | Higher in Drinkers |
| cg07409602 | 6 | 157098562 | Higher in Drinkers |
| cg07414097 | 2 | 232646663 | Higher in Drinkers |
| cg07416187 | 2 | 193373742 | Lower in Drinkers |
| cg07419459 | 12 | 9800748 | Higher in Drinkers |
| cg07419586 | 1 | 1852604 | Higher in Drinkers |
| cg07419704 | 4 | 1398139 | Lower in Drinkers |
| cg07421415 | 12 | 69080898 | Higher in Drinkers |

| | | | |
|---|---|---|---|
| cg07423149 | 1 | 203156246 | Higher in Drinkers |
| cg07423906 | 17 | 79212344 | Higher in Drinkers |
| cg07429591 | 1 | 151139877 | Higher in Drinkers |
| cg07430153 | 12 | 76424847 | Higher in Drinkers |
| cg07432687 | 2 | 97173990 | Higher in Drinkers |
| cg07433769 | 18 | 13620827 | Higher in Drinkers |
| cg07435282 | 11 | 1975236 | Higher in Drinkers |
| cg07436579 | 6 | 29581117 | Higher in Drinkers |
| cg07442657 | 2 | 85198334 | Higher in Drinkers |
| cg07446674 | X | 135333561 | Higher in Drinkers |
| cg07446846 | X | 152952362 | Higher in Drinkers |
| cg07447187 | 16 | 81110516 | Higher in Drinkers |
| cg07447902 | 17 | 38443980 | Higher in Drinkers |
| cg07454192 | 8 | 74888262 | Higher in Drinkers |
| cg07456413 | 13 | 111938804 | Higher in Drinkers |
| cg07457568 | 11 | 11643414 | Higher in Drinkers |
| cg07459652 | 6 | 158957377 | Higher in Drinkers |
| cg07460320 | 13 | 113241827 | Higher in Drinkers |
| cg07462198 | 3 | 129029640 | Higher in Drinkers |
| cg07462677 | 8 | 119124462 | Higher in Drinkers |
| cg07465881 | 4 | 1713556 | Higher in Drinkers |
| cg07467649 | 7 | 72856462 | Higher in Drinkers |
| cg07469555 | 8 | 22423055 | Higher in Drinkers |
| cg07472511 | 20 | 49127687 | Higher in Drinkers |
| cg07474957 | 6 | 30650844 | Higher in Drinkers |
| cg07475247 | 7 | 102938279 | Higher in Drinkers |
| cg07476327 | 2 | 171730024 | Higher in Drinkers |
| cg07476924 | 19 | 47421766 | Higher in Drinkers |
| cg07477282 | 15 | 44956107 | Higher in Drinkers |
| cg07481194 | 14 | 23398747 | Higher in Drinkers |
| cg07481538 | 2 | 223836570 | Higher in Drinkers |
| cg07482826 | 16 | 1502837 | Lower in Drinkers |
| cg07483245 | 15 | 23034598 | Higher in Drinkers |
| cg07487925 | 17 | 25620950 | Higher in Drinkers |
| cg07489624 | 6 | 30294195 | Higher in Drinkers |

| | | | |
|---|---|---|---|
| cg07492320 | 19 | 36545155 | Higher in Drinkers |
| cg07494047 | 19 | 57862713 | Higher in Drinkers |
| cg07495314 | 13 | 27845355 | Higher in Drinkers |
| cg07499607 | 3 | 69789199 | Higher in Drinkers |
| cg07500325 | 21 | 47062264 | Higher in Drinkers |
| cg07501049 | 1 | 981392 | Higher in Drinkers |
| cg07502661 | 2 | 43398339 | Higher in Drinkers |
| cg07503931 | 1 | 43123978 | Higher in Drinkers |
| cg07504864 | 6 | 88412167 | Higher in Drinkers |
| cg07508588 | 14 | 103398439 | Higher in Drinkers |
| cg07509094 | 11 | 60674167 | Higher in Drinkers |
| cg07516225 | 8 | 33371225 | Higher in Drinkers |
| cg07520141 | 5 | 10564205 | Higher in Drinkers |
| cg07526042 | 12 | 94543680 | Higher in Drinkers |
| cg07527906 | 19 | 42746239 | Higher in Drinkers |
| cg07528772 | 5 | 96271255 | Higher in Drinkers |
| cg07529675 | 15 | 22956051 | Higher in Drinkers |
| cg07529738 | 5 | 447797 | Higher in Drinkers |
| cg07530363 | 11 | 46638681 | Higher in Drinkers |
| cg07531158 | 16 | 29818226 | Higher in Drinkers |
| cg07531221 | 6 | 168228374 | Higher in Drinkers |
| cg07533350 | 13 | 53029422 | Higher in Drinkers |
| cg07534331 | 6 | 13574296 | Higher in Drinkers |
| cg07534554 | 11 | 111250338 | Higher in Drinkers |
| cg07535740 | 19 | 5915494 | Higher in Drinkers |
| cg07537133 | 20 | 59965634 | Higher in Drinkers |
| cg07537523 | 12 | 25102311 | Higher in Drinkers |
| cg07544511 | 15 | 75748083 | Higher in Drinkers |
| cg07545140 | 2 | 3468531 | Higher in Drinkers |
| cg07545587 | 14 | 91224592 | Higher in Drinkers |
| cg07546616 | 19 | 42600863 | Higher in Drinkers |
| cg07548367 | 7 | 96654152 | Higher in Drinkers |
| cg07549998 | 6 | 150325970 | Higher in Drinkers |
| cg07550809 | 11 | 65547886 | Higher in Drinkers |
| cg07551199 | 19 | 7894891 | Higher in Drinkers |

| | | | |
|---|---|---|---|
| cg07553475 | 6 | 21665800 | Higher in Drinkers |
| cg07556018 | 11 | 2677341 | Higher in Drinkers |
| cg07556911 | 7 | 2044787 | Higher in Drinkers |
| cg07557337 | 11 | 66035873 | Higher in Drinkers |
| cg07557355 | 1 | 155904306 | Higher in Drinkers |
| cg07560520 | 10 | 23384869 | Higher in Drinkers |
| cg07565422 | 19 | 18452064 | Higher in Drinkers |
| cg07570159 | 2 | 128145896 | Higher in Drinkers |
| cg07571284 | 14 | 23398847 | Higher in Drinkers |
| cg07573061 | 13 | 32420690 | Higher in Drinkers |
| cg07574267 | 1 | 2238720 | Higher in Drinkers |
| cg07574621 | 3 | 14220188 | Higher in Drinkers |
| cg07575174 | 19 | 16308558 | Higher in Drinkers |
| cg07576632 | 6 | 168344079 | Higher in Drinkers |
| cg07576664 | 10 | 34408654 | Higher in Drinkers |
| cg07577565 | 13 | 32527290 | Higher in Drinkers |
| cg07578410 | 5 | 171710114 | Higher in Drinkers |
| cg07582845 | 6 | 125475328 | Higher in Drinkers |
| cg07583667 | 19 | 50528685 | Higher in Drinkers |
| cg07584208 | 15 | 65426194 | Higher in Drinkers |
| cg07585136 | 3 | 196230779 | Higher in Drinkers |
| cg07588308 | 16 | 31724557 | Higher in Drinkers |
| cg07588489 | 19 | 19745340 | Higher in Drinkers |
| cg07589064 | 11 | 65535931 | Lower in Drinkers |
| cg07589143 | 5 | 54603461 | Higher in Drinkers |
| cg07595035 | 13 | 111291582 | Higher in Drinkers |
| cg07595943 | 16 | 84224901 | Lower in Drinkers |
| cg07597763 | 11 | 59382877 | Higher in Drinkers |
| cg07598034 | 7 | 134001087 | Lower in Drinkers |
| cg07599389 | 6 | 4890278 | Higher in Drinkers |
| cg07601985 | 1 | 205091324 | Higher in Drinkers |
| cg07602026 | 14 | 24605350 | Higher in Drinkers |
| cg07602847 | 11 | 65545237 | Higher in Drinkers |
| cg07603941 | 6 | 31379066 | Higher in Drinkers |
| cg07604512 | 1 | 91965349 | Higher in Drinkers |

| | | | |
|---|---|---|---|
| cg07607008 | 7 | 47621905 | Higher in Drinkers |
| cg07608496 | 21 | 47649218 | Higher in Drinkers |
| cg07608813 | 19 | 7587306 | Higher in Drinkers |
| cg07613693 | 19 | 59031343 | Higher in Drinkers |
| cg07613945 | 5 | 140787430 | Higher in Drinkers |
| cg07617764 | 12 | 58218602 | Higher in Drinkers |
| cg07618675 | 16 | 3778217 | Higher in Drinkers |
| cg07620039 | 19 | 22034747 | Higher in Drinkers |
| cg07620844 | 3 | 51430288 | Higher in Drinkers |
| cg07622815 | 8 | 22526588 | Higher in Drinkers |
| cg07623995 | 8 | 37702581 | Higher in Drinkers |
| cg07625546 | 4 | 73077996 | Higher in Drinkers |
| cg07631435 | 11 | 114043903 | Higher in Drinkers |
| cg07632148 | 17 | 78009770 | Higher in Drinkers |
| cg07635744 | 6 | 13365049 | Higher in Drinkers |
| cg07636362 | 8 | 79717261 | Higher in Drinkers |
| cg07638650 | 10 | 43697849 | Higher in Drinkers |
| cg07638935 | 10 | 102821427 | Higher in Drinkers |
| cg07643267 | 19 | 43969769 | Lower in Drinkers |
| cg07645461 | 13 | 42535296 | Higher in Drinkers |
| cg07646377 | 2 | 157189969 | Higher in Drinkers |
| cg07646999 | 19 | 36359211 | Lower in Drinkers |
| cg07648215 | 16 | 46782263 | Higher in Drinkers |
| cg07651857 | 4 | 2471025 | Higher in Drinkers |
| cg07654871 | 11 | 62369460 | Higher in Drinkers |
| cg07656362 | 1 | 32688117 | Higher in Drinkers |
| cg07656648 | 11 | 64085864 | Higher in Drinkers |
| cg07656883 | 10 | 31076781 | Higher in Drinkers |
| cg07658718 | 17 | 30814514 | Higher in Drinkers |
| cg07659872 | 7 | 25019747 | Higher in Drinkers |
| cg07659893 | 17 | 61819838 | Higher in Drinkers |
| cg07660663 | 8 | 117886887 | Higher in Drinkers |
| cg07663404 | 19 | 3979938 | Higher in Drinkers |
| cg07669260 | 2 | 83316847 | Higher in Drinkers |
| cg07671174 | 3 | 58224051 | Higher in Drinkers |

| | | | |
|---|---|---|---|
| cg07671622 | 16 | 70759994 | Higher in Drinkers |
| cg07672449 | 17 | 6916889 | Higher in Drinkers |
| cg07673023 | 2 | 27434729 | Higher in Drinkers |
| cg07676145 | 10 | 73506646 | Higher in Drinkers |
| cg07680505 | 22 | 50223663 | Lower in Drinkers |
| cg07680589 | 4 | 146101723 | Higher in Drinkers |
| cg07682009 | 16 | 29166462 | Higher in Drinkers |
| cg07682037 | 11 | 63974153 | Higher in Drinkers |
| cg07683663 | 4 | 147096828 | Higher in Drinkers |
| cg07689148 | 16 | 24753224 | Higher in Drinkers |
| cg07690692 | 16 | 30347078 | Higher in Drinkers |
| cg07691484 | 11 | 842764 | Higher in Drinkers |
| cg07695590 | 2 | 37459068 | Higher in Drinkers |
| cg07696884 | 20 | 50310579 | Lower in Drinkers |
| cg07698674 | 4 | 55084188 | Higher in Drinkers |
| cg07699613 | 5 | 150603746 | Higher in Drinkers |
| cg07701281 | 5 | 94890855 | Higher in Drinkers |
| cg07702751 | 7 | 133426299 | Lower in Drinkers |
| cg07703017 | 7 | 48128624 | Higher in Drinkers |
| cg07703372 | 3 | 67704629 | Higher in Drinkers |
| cg07705912 | 1 | 154155363 | Higher in Drinkers |
| cg07706362 | 19 | 23578365 | Higher in Drinkers |
| cg07707380 | 11 | 65396146 | Higher in Drinkers |
| cg07713066 | 2 | 220363586 | Higher in Drinkers |
| cg07714708 | 6 | 12290447 | Higher in Drinkers |
| cg07715328 | 19 | 42759035 | Higher in Drinkers |
| cg07721490 | 22 | 29977228 | Higher in Drinkers |
| cg07721866 | 2 | 95742751 | Higher in Drinkers |
| cg07722368 | 17 | 26554907 | Higher in Drinkers |
| cg07722505 | 6 | 26458093 | Higher in Drinkers |
| cg07723558 | 17 | 7184224 | Higher in Drinkers |
| cg07723598 | 2 | 240090667 | Lower in Drinkers |
| cg07725729 | 8 | 11141895 | Higher in Drinkers |
| cg07733728 | 17 | 80210844 | Higher in Drinkers |
| cg07734513 | 7 | 75795931 | Higher in Drinkers |

| | | | |
|---|---|---|---|
| cg07736123 | 19 | 15236457 | Higher in Drinkers |
| cg07737104 | 22 | 50960139 | Higher in Drinkers |
| cg07737135 | 19 | 1356032 | Higher in Drinkers |
| cg07738031 | 20 | 61871027 | Lower in Drinkers |
| cg07738077 | 19 | 53303448 | Higher in Drinkers |
| cg07739113 | 6 | 27255829 | Higher in Drinkers |
| cg07740640 | 7 | 97841941 | Higher in Drinkers |
| cg07741775 | 13 | 77900505 | Higher in Drinkers |
| cg07743144 | 6 | 31855706 | Higher in Drinkers |
| cg07745596 | 10 | 54538682 | Higher in Drinkers |
| cg07746532 | 12 | 132380903 | Higher in Drinkers |
| cg07746918 | 22 | 42229324 | Higher in Drinkers |
| cg07747177 | 4 | 52708877 | Higher in Drinkers |
| cg07747343 | 8 | 27169162 | Higher in Drinkers |
| cg07747635 | 3 | 193853750 | Higher in Drinkers |
| cg07747994 | 16 | 89297799 | Higher in Drinkers |
| cg07748017 | 12 | 7342621 | Higher in Drinkers |
| cg07748036 | 3 | 5230340 | Higher in Drinkers |
| cg07750111 | 6 | 26056168 | Higher in Drinkers |
| cg07750953 | X | 37355187 | Higher in Drinkers |
| cg07756148 | 19 | 14247627 | Higher in Drinkers |
| cg07757497 | 1 | 236305819 | Higher in Drinkers |
| cg07759042 | 18 | 77193502 | Lower in Drinkers |
| cg07759570 | 19 | 35491951 | Higher in Drinkers |
| cg07761367 | 5 | 71146823 | Higher in Drinkers |
| cg07761781 | 19 | 52035161 | Higher in Drinkers |
| cg07764473 | X | 40037510 | Higher in Drinkers |
| cg07764959 | 11 | 57282648 | Higher in Drinkers |
| cg07768107 | 4 | 40201943 | Higher in Drinkers |
| cg07769507 | 4 | 57844949 | Higher in Drinkers |
| cg07773800 | 20 | 43991521 | Higher in Drinkers |
| cg07774299 | 1 | 76253445 | Higher in Drinkers |
| cg07776347 | 4 | 140201065 | Higher in Drinkers |
| cg07780485 | 19 | 3626987 | Higher in Drinkers |
| cg07780979 | 5 | 303287 | Higher in Drinkers |

| | | | |
|---|---|---|---|
| cg07781003 | 17 | 48796772 | Higher in Drinkers |
| cg07781223 | 19 | 10947061 | Higher in Drinkers |
| cg07783855 | 19 | 4402309 | Higher in Drinkers |
| cg07788451 | 12 | 58146524 | Higher in Drinkers |
| cg07791676 | 1 | 106358597 | Lower in Drinkers |
| cg07793203 | 2 | 9771347 | Higher in Drinkers |
| cg07795346 | 16 | 84800637 | Higher in Drinkers |
| cg07798137 | 1 | 17332259 | Lower in Drinkers |
| cg07799491 | X | 149861526 | Higher in Drinkers |
| cg07806164 | 3 | 23244688 | Higher in Drinkers |
| cg07807047 | 3 | 87276377 | Higher in Drinkers |
| cg07809452 | 4 | 1004641 | Higher in Drinkers |
| cg07812957 | 19 | 16466298 | Higher in Drinkers |
| cg07815386 | 2 | 101925384 | Higher in Drinkers |
| cg07815491 | 7 | 878073 | Higher in Drinkers |
| cg07820742 | 1 | 23751517 | Higher in Drinkers |
| cg07820842 | 4 | 152682180 | Higher in Drinkers |
| cg07821197 | 16 | 75631616 | Higher in Drinkers |
| cg07824564 | 1 | 179050911 | Higher in Drinkers |
| cg07824800 | 10 | 69872166 | Lower in Drinkers |
| cg07826058 | X | 21857614 | Higher in Drinkers |
| cg07826859 | 7 | 45020086 | Higher in Drinkers |
| cg07827008 | 12 | 133338719 | Higher in Drinkers |
| cg07827107 | 13 | 113891624 | Higher in Drinkers |
| cg07827943 | 21 | 39289128 | Higher in Drinkers |
| cg07829597 | 10 | 77161705 | Higher in Drinkers |
| cg07832337 | 16 | 84402132 | Lower in Drinkers |
| cg07833779 | 1 | 112050772 | Higher in Drinkers |
| cg07834876 | 17 | 58754980 | Higher in Drinkers |
| cg07836592 | 1 | 8002425 | Higher in Drinkers |
| cg07837434 | 6 | 52149679 | Higher in Drinkers |
| cg07837534 | 1 | 161038506 | Higher in Drinkers |
| cg07840472 | 14 | 36278484 | Higher in Drinkers |
| cg07841195 | 13 | 34116822 | Higher in Drinkers |
| cg07842409 | 1 | 11097872 | Higher in Drinkers |

| | | | |
|---|---|---|---|
| cg07845093 | 16 | 89151447 | Higher in Drinkers |
| cg07848042 | 5 | 137667509 | Higher in Drinkers |
| cg07849581 | 4 | 48272077 | Higher in Drinkers |
| cg07849805 | 19 | 18699423 | Higher in Drinkers |
| cg07850533 | 9 | 4804779 | Higher in Drinkers |
| cg07852557 | 17 | 79422586 | Higher in Drinkers |
| cg07854244 | 3 | 48754518 | Higher in Drinkers |
| cg07855993 | 19 | 19174295 | Higher in Drinkers |
| cg07856616 | 19 | 48866357 | Higher in Drinkers |
| cg07862736 | 8 | 38143885 | Higher in Drinkers |
| cg07867665 | 10 | 32635218 | Higher in Drinkers |
| cg07869135 | 8 | 123794843 | Higher in Drinkers |
| cg07870479 | 16 | 1813987 | Higher in Drinkers |
| cg07870854 | 16 | 791252 | Higher in Drinkers |
| cg07871500 | 13 | 46786175 | Higher in Drinkers |
| cg07876950 | 19 | 40722624 | Higher in Drinkers |
| cg07880135 | 5 | 43557602 | Higher in Drinkers |
| cg07884213 | 16 | 57219487 | Higher in Drinkers |
| cg07884352 | 7 | 143152 | Higher in Drinkers |
| cg07885778 | 11 | 9432355 | Higher in Drinkers |
| cg07886691 | 10 | 64028545 | Higher in Drinkers |
| cg07886696 | 6 | 109762382 | Higher in Drinkers |
| cg07887208 | 22 | 50875606 | Higher in Drinkers |
| cg07889003 | 6 | 32546614 | Higher in Drinkers |
| cg07893471 | 2 | 240118890 | Higher in Drinkers |
| cg07893575 | 8 | 65289751 | Higher in Drinkers |
| cg07894846 | 19 | 1931143 | Higher in Drinkers |
| cg07895132 | 17 | 33325172 | Higher in Drinkers |
| cg07897414 | X | 86772895 | Lower in Drinkers |
| cg07897452 | 16 | 11762209 | Higher in Drinkers |
| cg07898120 | 6 | 31854882 | Higher in Drinkers |
| cg07898651 | 2 | 135810025 | Higher in Drinkers |
| cg07901188 | 1 | 109795659 | Higher in Drinkers |
| cg07904567 | 12 | 133346306 | Higher in Drinkers |
| cg07909497 | 12 | 9600950 | Higher in Drinkers |

| | | | |
|---|---|---|---|
| cg07909749 | 2 | 114647035 | Higher in Drinkers |
| cg07911361 | 22 | 45126040 | Higher in Drinkers |
| cg07914200 | 6 | 22699463 | Higher in Drinkers |
| cg07917614 | 1 | 10833932 | Higher in Drinkers |
| cg07921818 | 17 | 80664485 | Higher in Drinkers |
| cg07922007 | 8 | 67874858 | Higher in Drinkers |
| cg07927484 | 5 | 153826296 | Higher in Drinkers |
| cg07933076 | 12 | 57855338 | Higher in Drinkers |
| cg07933682 | 19 | 3025347 | Higher in Drinkers |
| cg07933757 | X | 150066987 | Higher in Drinkers |
| cg07934031 | 5 | 179105728 | Higher in Drinkers |
| cg07935304 | 11 | 62359415 | Higher in Drinkers |
| cg07942135 | 7 | 27154262 | Lower in Drinkers |
| cg07942687 | 16 | 1476899 | Lower in Drinkers |
| cg07942932 | 19 | 1240652 | Higher in Drinkers |
| cg07949083 | 3 | 133292291 | Higher in Drinkers |
| cg07951135 | 14 | 73393603 | Higher in Drinkers |
| cg07953310 | 19 | 37808882 | Higher in Drinkers |
| cg07955828 | 20 | 37591298 | Higher in Drinkers |
| cg07962672 | 10 | 80827185 | Higher in Drinkers |
| cg07963121 | 6 | 116692748 | Higher in Drinkers |
| cg07963760 | 1 | 120612152 | Higher in Drinkers |
| cg07965041 | 19 | 39369004 | Higher in Drinkers |
| cg07968927 | 13 | 115080364 | Higher in Drinkers |
| cg07970734 | 20 | 61557028 | Higher in Drinkers |
| cg07971474 | 2 | 39005158 | Higher in Drinkers |
| cg07971674 | 14 | 23388846 | Higher in Drinkers |
| cg07971831 | 1 | 32655695 | Higher in Drinkers |
| cg07972322 | 7 | 134832939 | Higher in Drinkers |
| cg07973146 | 20 | 18438185 | Lower in Drinkers |
| cg07974063 | 11 | 59383409 | Higher in Drinkers |
| cg07974615 | 16 | 2060056 | Higher in Drinkers |
| cg07975705 | 5 | 114961891 | Higher in Drinkers |
| cg07976408 | 15 | 41836273 | Higher in Drinkers |
| cg07980404 | 1 | 38490002 | Lower in Drinkers |

| | | | |
|---|---|---|---|
| cg07980854 | 20 | 57586338 | Higher in Drinkers |
| cg07982481 | 10 | 75007255 | Higher in Drinkers |
| cg07984380 | 6 | 32547019 | Higher in Drinkers |
| cg07985354 | 12 | 57646130 | Higher in Drinkers |
| cg07989501 | 12 | 53835350 | Higher in Drinkers |
| cg07989514 | 14 | 77495178 | Higher in Drinkers |
| cg07989796 | 19 | 41082579 | Higher in Drinkers |
| cg07990390 | 16 | 1217211 | Lower in Drinkers |
| cg07990873 | 19 | 58235167 | Higher in Drinkers |
| cg07992143 | 7 | 45146807 | Higher in Drinkers |
| cg07993372 | 16 | 427084 | Lower in Drinkers |
| cg07997689 | 1 | 38156178 | Higher in Drinkers |
| cg07998461 | 10 | 35415601 | Higher in Drinkers |
| cg07999415 | 11 | 71724338 | Lower in Drinkers |
| cg07999887 | 3 | 87526955 | Higher in Drinkers |
| cg08003077 | 20 | 44485762 | Higher in Drinkers |
| cg08003810 | 16 | 3535037 | Higher in Drinkers |
| cg08006956 | 19 | 18418056 | Lower in Drinkers |
| cg08015253 | 18 | 33767315 | Higher in Drinkers |
| cg08016929 | 14 | 24897563 | Higher in Drinkers |
| cg08020051 | 8 | 145137133 | Higher in Drinkers |
| cg08024109 | 3 | 197409951 | Higher in Drinkers |
| cg08027001 | 15 | 45815269 | Higher in Drinkers |
| cg08030851 | 16 | 29606944 | Higher in Drinkers |
| cg08032228 | 1 | 2209957 | Higher in Drinkers |
| cg08032476 | 17 | 27045176 | Higher in Drinkers |
| cg08034663 | 12 | 124893511 | Lower in Drinkers |
| cg08035281 | 12 | 53900003 | Higher in Drinkers |
| cg08036346 | 15 | 68098991 | Lower in Drinkers |
| cg08037541 | 17 | 45973425 | Higher in Drinkers |
| cg08040824 | 3 | 189420438 | Higher in Drinkers |
| cg08041573 | 21 | 33651723 | Higher in Drinkers |
| cg08043042 | 22 | 29601772 | Higher in Drinkers |
| cg08048699 | 11 | 57296305 | Higher in Drinkers |
| cg08048948 | 11 | 68700821 | Higher in Drinkers |

| | | | |
|---|---|---|---|
| cg08051804 | 15 | 74679906 | Lower in Drinkers |
| cg08056903 | 14 | 66974163 | Higher in Drinkers |
| cg08057992 | 1 | 39457593 | Higher in Drinkers |
| cg08060248 | 16 | 84213494 | Higher in Drinkers |
| cg08062233 | 19 | 39600974 | Higher in Drinkers |
| cg08062526 | 6 | 131949551 | Higher in Drinkers |
| cg08065292 | 17 | 62833084 | Higher in Drinkers |
| cg08065501 | X | 48755716 | Higher in Drinkers |
| cg08066123 | 15 | 74287179 | Higher in Drinkers |
| cg08066917 | 6 | 167764146 | Higher in Drinkers |
| cg08067677 | 16 | 67260902 | Higher in Drinkers |
| cg08069480 | 12 | 104532011 | Higher in Drinkers |
| cg08069899 | 12 | 4383770 | Higher in Drinkers |
| cg08071700 | 16 | 81579244 | Higher in Drinkers |
| cg08072480 | 11 | 65292666 | Higher in Drinkers |
| cg08072992 | 19 | 14229581 | Higher in Drinkers |
| cg08075469 | 7 | 93633440 | Higher in Drinkers |
| cg08077726 | 17 | 74734280 | Higher in Drinkers |
| cg08080008 | 16 | 2009616 | Higher in Drinkers |
| cg08080498 | 8 | 22404955 | Higher in Drinkers |
| cg08081708 | 14 | 53162518 | Higher in Drinkers |
| cg08083016 | 6 | 144471643 | Higher in Drinkers |
| cg08083689 | 4 | 8442326 | Higher in Drinkers |
| cg08087404 | 19 | 55629104 | Higher in Drinkers |
| cg08089851 | 3 | 12598413 | Higher in Drinkers |
| cg08096168 | 10 | 61666824 | Higher in Drinkers |
| cg08100233 | 19 | 10946663 | Higher in Drinkers |
| cg08103317 | 6 | 31707527 | Higher in Drinkers |
| cg08104527 | 18 | 13217953 | Higher in Drinkers |
| cg08105529 | 1 | 91852884 | Higher in Drinkers |
| cg08108362 | 16 | 10837690 | Higher in Drinkers |
| cg08113661 | 1 | 39457270 | Higher in Drinkers |
| cg08114293 | 3 | 10028395 | Higher in Drinkers |
| cg08114689 | 12 | 32908941 | Higher in Drinkers |
| cg08115510 | 3 | 134092715 | Higher in Drinkers |

| | | | |
|---|---|---|---|
| cgC8116651 | 16 | 66835939 | Higher in Drinkers |
| cgC8120289 | 20 | 35807421 | Higher in Drinkers |
| cgC8120831 | 12 | 122669186 | Higher in Drinkers |
| cgC8121025 | 14 | 54976315 | Higher in Drinkers |
| cgC8127876 | 14 | 23755478 | Higher in Drinkers |
| cgC8129017 | 17 | 17728660 | Higher in Drinkers |
| cgC8130643 | 3 | 134204850 | Higher in Drinkers |
| cgC8131059 | 2 | 469790 | Lower in Drinkers |
| cgC8133476 | 13 | 114106419 | Higher in Drinkers |
| cgC8135583 | 5 | 179159804 | Higher in Drinkers |
| cgC8135787 | 6 | 26538969 | Higher in Drinkers |
| cgC8135850 | 6 | 26199770 | Higher in Drinkers |
| cgC8138375 | 12 | 56694186 | Higher in Drinkers |
| cgC8139499 | 1 | 100616943 | Higher in Drinkers |
| cgC8139509 | 2 | 54014491 | Higher in Drinkers |
| cgC8141928 | 14 | 62162460 | Higher in Drinkers |
| cgC8143011 | 12 | 27863459 | Higher in Drinkers |
| cgC8148052 | 11 | 63953512 | Higher in Drinkers |
| cgC8149682 | 19 | 1355918 | Higher in Drinkers |
| cgC8150742 | 12 | 49066916 | Higher in Drinkers |
| cgC8151281 | 1 | 167905380 | Higher in Drinkers |
| cgC8152499 | 16 | 85853169 | Higher in Drinkers |
| cgC8157579 | 22 | 42949829 | Higher in Drinkers |
| cgC8158076 | 1 | 90287038 | Higher in Drinkers |
| cgC8158570 | 10 | 77160935 | Higher in Drinkers |
| cgC8160066 | 1 | 46050052 | Higher in Drinkers |
| cgC8161480 | 1 | 226114565 | Higher in Drinkers |
| cgC8165151 | 6 | 88411075 | Higher in Drinkers |
| cgC8166513 | 1 | 233120048 | Lower in Drinkers |
| cgC8166961 | 1 | 234513298 | Higher in Drinkers |
| cgC8167214 | 16 | 81040017 | Higher in Drinkers |
| cgC8168847 | 4 | 68567110 | Higher in Drinkers |
| cgC8170637 | 17 | 79968088 | Higher in Drinkers |
| cgC8173959 | 19 | 426802 | Higher in Drinkers |
| cgC8177746 | 17 | 30264514 | Higher in Drinkers |

| | | | |
|---|---|---|---|
| cg08179907 | 11 | 107799967 | Higher in Drinkers |
| cg08180183 | 4 | 6988306 | Higher in Drinkers |
| cg08184047 | 17 | 79849980 | Higher in Drinkers |
| cg08188400 | 19 | 7969347 | Higher in Drinkers |
| cg08190175 | 22 | 41814253 | Higher in Drinkers |
| cg08192285 | 10 | 60028801 | Higher in Drinkers |
| cg08193333 | 13 | 27998609 | Higher in Drinkers |
| cg08194752 | 16 | 21649186 | Lower in Drinkers |
| cg08195412 | 10 | 134372696 | Higher in Drinkers |
| cg08195505 | 3 | 185326362 | Higher in Drinkers |
| cg08195863 | 19 | 11307969 | Higher in Drinkers |
| cg08197201 | 12 | 1099823 | Higher in Drinkers |
| cg08198488 | 15 | 63333792 | Lower in Drinkers |
| cg08200293 | 11 | 569357 | Higher in Drinkers |
| cg08200546 | 14 | 75441107 | Higher in Drinkers |
| cg08202743 | 11 | 34182570 | Higher in Drinkers |
| cg08203715 | 11 | 126226154 | Higher in Drinkers |
| cg08203850 | 2 | 74881465 | Higher in Drinkers |
| cg08204369 | 17 | 73150733 | Higher in Drinkers |
| cg08204571 | 6 | 3259011 | Higher in Drinkers |
| cg08205700 | 8 | 80696168 | Higher in Drinkers |
| cg08207660 | 14 | 71694874 | Higher in Drinkers |
| cg08209934 | 16 | 69966975 | Higher in Drinkers |
| cg08210001 | 7 | 99699645 | Higher in Drinkers |
| cg08211972 | 14 | 35008877 | Higher in Drinkers |
| cg08212821 | 22 | 31503747 | Higher in Drinkers |
| cg08213351 | 2 | 128283535 | Higher in Drinkers |
| cg08213607 | 16 | 3627243 | Higher in Drinkers |
| cg08216021 | 8 | 110552896 | Higher in Drinkers |
| cg08219099 | 4 | 1325038 | Lower in Drinkers |
| cg08219107 | 4 | 78741208 | Higher in Drinkers |
| cg08219814 | 8 | 1327367 | Lower in Drinkers |
| cg08222399 | 5 | 16936466 | Higher in Drinkers |
| cg08222798 | 9 | 43134033 | Higher in Drinkers |
| cg08223835 | 16 | 71266911 | Lower in Drinkers |

| | | | |
|---|---|---|---|
| cg08224238 | 16 | 87958145 | Lower in Drinkers |
| cg08225020 | 16 | 71894168 | Lower in Drinkers |
| cg08226873 | 14 | 76621106 | Higher in Drinkers |
| cg08228316 | 6 | 32940322 | Higher in Drinkers |
| cg08228995 | 3 | 42264623 | Higher in Drinkers |
| cg08229366 | 7 | 130130747 | Higher in Drinkers |
| cg08233448 | 14 | 21978798 | Higher in Drinkers |
| cg08236123 | 12 | 132219811 | Higher in Drinkers |
| cg08243626 | 10 | 6442501 | Higher in Drinkers |
| cg08248600 | 11 | 65196654 | Higher in Drinkers |
| cg08250273 | 7 | 116593366 | Higher in Drinkers |
| cg08250918 | 7 | 50467921 | Higher in Drinkers |
| cg08252337 | 5 | 87970950 | Higher in Drinkers |
| cg08252871 | 12 | 42534865 | Higher in Drinkers |
| cg08252971 | 4 | 41218767 | Higher in Drinkers |
| cg08253513 | 12 | 53715584 | Higher in Drinkers |
| cg08260236 | 19 | 55987563 | Higher in Drinkers |
| cg08260622 | 9 | 2718952 | Higher in Drinkers |
| cg08260891 | 20 | 44518802 | Higher in Drinkers |
| cg08261837 | 5 | 57878745 | Higher in Drinkers |
| cg08263361 | 15 | 77713262 | Higher in Drinkers |
| cg08263387 | 22 | 46509531 | Higher in Drinkers |
| cg08264376 | 21 | 37833864 | Higher in Drinkers |
| cg08264704 | 1 | 228270414 | Higher in Drinkers |
| cg08266565 | 1 | 24286678 | Higher in Drinkers |
| cg08267245 | 5 | 172410984 | Higher in Drinkers |
| cg08267701 | 19 | 45393621 | Higher in Drinkers |
| cg08268535 | 5 | 34839194 | Higher in Drinkers |
| cg08269949 | 6 | 26538502 | Higher in Drinkers |
| cg08270254 | 8 | 10873964 | Higher in Drinkers |
| cg08270567 | 1 | 2170956 | Higher in Drinkers |
| cg08270573 | 4 | 147443996 | Higher in Drinkers |
| cg08270734 | 12 | 108951574 | Higher in Drinkers |
| cg08273200 | 1 | 39338480 | Higher in Drinkers |
| cg08275242 | X | 69353171 | Higher in Drinkers |

| | | | |
|---|---|---|---|
| cg08278937 | 15 | 44092345 | Higher in Drinkers |
| cg08279577 | 19 | 57751946 | Higher in Drinkers |
| cg08281071 | 14 | 106098539 | Higher in Drinkers |
| cg08281341 | 12 | 2921677 | Higher in Drinkers |
| cg08285934 | 16 | 25026600 | Higher in Drinkers |
| cg08287288 | 16 | 1815103 | Higher in Drinkers |
| cg08287791 | 12 | 100002574 | Higher in Drinkers |
| cg08295258 | 5 | 102455984 | Higher in Drinkers |
| cg08297094 | 19 | 33166201 | Higher in Drinkers |
| cg08299045 | 1 | 228296964 | Higher in Drinkers |
| cg08299976 | 17 | 1552302 | Higher in Drinkers |
| cg08300164 | 4 | 56815263 | Higher in Drinkers |
| cg08301912 | 19 | 34664033 | Higher in Drinkers |
| cg08302003 | 7 | 100435192 | Higher in Drinkers |
| cg08302532 | 21 | 36040789 | Higher in Drinkers |
| cg08303370 | 2 | 99758219 | Higher in Drinkers |
| cg08304608 | 20 | 57594200 | Higher in Drinkers |
| cg08305796 | 19 | 59066652 | Higher in Drinkers |
| cg08308459 | 2 | 38893161 | Higher in Drinkers |
| cg08308556 | 6 | 15734234 | Higher in Drinkers |
| cg08311172 | 2 | 69969004 | Higher in Drinkers |
| cg08312035 | 1 | 228402305 | Higher in Drinkers |
| cg08312149 | 19 | 4475055 | Lower in Drinkers |
| cg08312371 | 2 | 240111396 | Higher in Drinkers |
| cg08314102 | 16 | 46865519 | Higher in Drinkers |
| cg08314206 | 14 | 20929920 | Higher in Drinkers |
| cg08316559 | 5 | 141229648 | Higher in Drinkers |
| cg08320014 | 12 | 133707169 | Higher in Drinkers |
| cg08320225 | 16 | 54689252 | Higher in Drinkers |
| cg08322528 | 2 | 201981135 | Higher in Drinkers |
| cg08325212 | 8 | 11627019 | Higher in Drinkers |
| cg08327423 | 16 | 84150746 | Higher in Drinkers |
| cg08327960 | X | 38663047 | Higher in Drinkers |
| cg08336736 | 6 | 33218730 | Higher in Drinkers |
| cg08337633 | 7 | 55602109 | Higher in Drinkers |

| | | | |
|---|---|---|---|
| cg08346074 | 5 | 75013329 | Higher in Drinkers |
| cg08346269 | 12 | 56110020 | Higher in Drinkers |
| cg08351004 | 2 | 172965650 | Higher in Drinkers |
| cg08351085 | 13 | 113980035 | Higher in Drinkers |
| cg08352292 | 17 | 27503756 | Higher in Drinkers |
| cg08353062 | 4 | 39529052 | Higher in Drinkers |
| cg08354388 | 11 | 121526264 | Higher in Drinkers |
| cg08355340 | 16 | 82203585 | Higher in Drinkers |
| cg08355863 | 6 | 33587496 | Higher in Drinkers |
| cg08356214 | 19 | 7460327 | Higher in Drinkers |
| cg08357601 | 4 | 71554472 | Higher in Drinkers |
| cg08360728 | 1 | 27226980 | Higher in Drinkers |
| cg08361399 | 16 | 53088769 | Higher in Drinkers |
| cg08362804 | 6 | 64282634 | Higher in Drinkers |
| cg08363074 | 22 | 38479288 | Lower in Drinkers |
| cg08366126 | 1 | 24194505 | Higher in Drinkers |
| cg08366132 | 1 | 27191899 | Higher in Drinkers |
| cg08367703 | 9 | 139304491 | Higher in Drinkers |
| cg08368938 | 3 | 167453466 | Higher in Drinkers |
| cg08372326 | 9 | 99212096 | Higher in Drinkers |
| cg08376089 | 11 | 61514925 | Higher in Drinkers |
| cg08377314 | 19 | 56186477 | Higher in Drinkers |
| cg08380539 | 1 | 85039702 | Higher in Drinkers |
| cg08381596 | 16 | 720883 | Higher in Drinkers |
| cg08381620 | 13 | 24062873 | Higher in Drinkers |
| cg08383144 | 6 | 33260015 | Higher in Drinkers |
| cg08385874 | 21 | 46352445 | Higher in Drinkers |
| cg08391894 | 22 | 43559044 | Higher in Drinkers |
| cg08402652 | 11 | 94501461 | Higher in Drinkers |
| cg08402873 | 20 | 10653164 | Higher in Drinkers |
| cg08404509 | 16 | 74700620 | Higher in Drinkers |
| cg08405073 | 19 | 11456957 | Higher in Drinkers |
| cg08406714 | 21 | 45223723 | Higher in Drinkers |
| cg08409375 | 11 | 208403 | Higher in Drinkers |
| cg08409687 | 2 | 201936025 | Higher in Drinkers |

| | | | |
|---|---|---|---|
| cg08413390 | 15 | 84944048 | Higher in Drinkers |
| cg08417595 | 19 | 3811002 | Lower in Drinkers |
| cg08421126 | 2 | 43019854 | Higher in Drinkers |
| cg08424587 | 4 | 41216479 | Higher in Drinkers |
| cg08426896 | 2 | 174916731 | Higher in Drinkers |
| cg08435340 | 19 | 11485234 | Higher in Drinkers |
| cg08437167 | 3 | 9885801 | Higher in Drinkers |
| cg08437835 | X | 14891340 | Higher in Drinkers |
| cg08441138 | 11 | 128555233 | Higher in Drinkers |
| cg08444284 | 6 | 30688882 | Higher in Drinkers |
| cg08445226 | 3 | 99536904 | Higher in Drinkers |
| cg08446255 | 8 | 26434378 | Higher in Drinkers |
| cg08447322 | 19 | 17581125 | Higher in Drinkers |
| cg08452964 | 1 | 28382887 | Higher in Drinkers |
| cg08459627 | 1 | 3773958 | Higher in Drinkers |
| cg08460022 | 6 | 31795392 | Higher in Drinkers |
| cg08460865 | 1 | 161123728 | Higher in Drinkers |
| cg08463543 | 3 | 69788984 | Higher in Drinkers |
| cg08464208 | 6 | 27792307 | Higher in Drinkers |
| cg08466034 | 17 | 16318930 | Higher in Drinkers |
| cg08473138 | 19 | 48248628 | Higher in Drinkers |
| cg08474929 | 11 | 118810923 | Higher in Drinkers |
| cg08475517 | 19 | 2783460 | Higher in Drinkers |
| cg08475931 | 7 | 30634393 | Higher in Drinkers |
| cg08476757 | 3 | 107940931 | Higher in Drinkers |
| cg08476843 | 13 | 33760215 | Higher in Drinkers |
| cg08476956 | 16 | 3645613 | Higher in Drinkers |
| cg08480906 | 19 | 36036175 | Higher in Drinkers |
| cg08483834 | 6 | 33248239 | Higher in Drinkers |
| cg08485071 | 13 | 60738370 | Higher in Drinkers |
| cg08488529 | 16 | 25025983 | Higher in Drinkers |
| cg08489592 | 19 | 21688397 | Higher in Drinkers |
| cg08491025 | 1 | 113498799 | Higher in Drinkers |
| cg08495106 | 7 | 152161143 | Higher in Drinkers |
| cg08497766 | 10 | 6019877 | Higher in Drinkers |

| | | | |
|---|---|---|---|
| cg08498179 | 16 | 334749 | Lower in Drinkers |
| cg08501054 | 8 | 9413133 | Higher in Drinkers |
| cg08502534 | 20 | 3211442 | Higher in Drinkers |
| cg08503002 | 3 | 183903768 | Higher in Drinkers |
| cg08503994 | 16 | 4585287 | Higher in Drinkers |
| cg08506046 | 3 | 23987101 | Higher in Drinkers |
| cg08508576 | 11 | 94781444 | Lower in Drinkers |
| cg08509236 | 12 | 49208409 | Higher in Drinkers |
| cg08510456 | 3 | 49591008 | Lower in Drinkers |
| cg08512940 | 12 | 50016787 | Higher in Drinkers |
| cg08515284 | 8 | 67417589 | Higher in Drinkers |
| cg08518892 | 17 | 62773012 | Higher in Drinkers |
| cg08523505 | 6 | 16762984 | Higher in Drinkers |
| cg08524015 | 11 | 129683974 | Lower in Drinkers |
| cg08526867 | 5 | 85913721 | Higher in Drinkers |
| cg08527328 | 1 | 207925412 | Higher in Drinkers |
| cg08529614 | 1 | 25665474 | Higher in Drinkers |
| cg08530484 | 2 | 220024606 | Higher in Drinkers |
| cg08534679 | 3 | 135913333 | Higher in Drinkers |
| cg08537783 | 1 | 10795394 | Lower in Drinkers |
| cg08538369 | 10 | 133773665 | Higher in Drinkers |
| cg08540840 | 6 | 170123135 | Higher in Drinkers |
| cg08541953 | 1 | 6259338 | Higher in Drinkers |
| cg08542396 | 1 | 145001340 | Lower in Drinkers |
| cg08544721 | 4 | 175205820 | Higher in Drinkers |
| cg08544746 | 1 | 3713043 | Higher in Drinkers |
| cg08545169 | 1 | 161169143 | Higher in Drinkers |
| cg08545574 | 1 | 51443457 | Higher in Drinkers |
| cg08545593 | 20 | 57582856 | Higher in Drinkers |
| cg08547617 | 5 | 1335279 | Higher in Drinkers |
| cg08549241 | 16 | 89440133 | Lower in Drinkers |
| cg08550065 | 3 | 50336684 | Higher in Drinkers |
| cg08550839 | 19 | 35633553 | Higher in Drinkers |
| cg08553156 | 11 | 107730005 | Higher in Drinkers |
| cg08557517 | 7 | 32996981 | Higher in Drinkers |

| | | | |
|---|---|---|---|
| cg08562409 | 6 | 28864258 | Higher in Drinkers |
| cg08562543 | 2 | 27593465 | Higher in Drinkers |
| cg08568075 | 14 | 105220026 | Higher in Drinkers |
| cg08569046 | 7 | 4798827 | Higher in Drinkers |
| cg08573869 | 8 | 144895168 | Lower in Drinkers |
| cg08583059 | 17 | 37887002 | Higher in Drinkers |
| cg08583435 | 6 | 166797128 | Higher in Drinkers |
| cg08586228 | 16 | 1832094 | Higher in Drinkers |
| cg08587397 | 16 | 672930 | Lower in Drinkers |
| cg08591091 | 8 | 30769472 | Higher in Drinkers |
| cg08593157 | 17 | 17684240 | Higher in Drinkers |
| cg08593229 | 19 | 8373488 | Higher in Drinkers |
| cg08593364 | 11 | 107729186 | Higher in Drinkers |
| cg08594146 | 22 | 38712685 | Higher in Drinkers |
| cg08596595 | 11 | 290292 | Higher in Drinkers |
| cg08599266 | 2 | 25142473 | Higher in Drinkers |
| cg08601959 | 6 | 30524577 | Higher in Drinkers |
| cg08602075 | 19 | 41768357 | Higher in Drinkers |
| cg08602305 | 10 | 89623357 | Higher in Drinkers |
| cg08607082 | 19 | 10381924 | Higher in Drinkers |
| cg08610415 | 19 | 38270207 | Higher in Drinkers |
| cg08611833 | 6 | 170862455 | Higher in Drinkers |
| cg08612468 | 5 | 93954175 | Higher in Drinkers |
| cg08613507 | 5 | 123285221 | Lower in Drinkers |
| cg08618981 | 16 | 15744397 | Higher in Drinkers |
| cg08619295 | 10 | 6364079 | Higher in Drinkers |
| cg08619651 | 7 | 127807832 | Higher in Drinkers |
| cg08620585 | 19 | 926717 | Higher in Drinkers |
| cg08620751 | 19 | 1851750 | Higher in Drinkers |
| cg08623223 | 8 | 11141415 | Higher in Drinkers |
| cg08626646 | X | 53123489 | Higher in Drinkers |
| cg08629043 | 2 | 240196078 | Higher in Drinkers |
| cg08633134 | 19 | 50935017 | Higher in Drinkers |
| cg08633154 | 10 | 92980627 | Higher in Drinkers |
| cg08634826 | 11 | 71193572 | Higher in Drinkers |

| | | | |
|---|---|---|---|
| cg08638320 | 1 | 47900265 | Higher in Drinkers |
| cg08639244 | 19 | 41945921 | Higher in Drinkers |
| cg08643131 | 19 | 1356150 | Higher in Drinkers |
| cg08643953 | 3 | 132379052 | Higher in Drinkers |
| cg08650961 | 10 | 104748594 | Lower in Drinkers |
| cg08651034 | 18 | 5895513 | Higher in Drinkers |
| cg08651894 | 1 | 154832235 | Lower in Drinkers |
| cg08652108 | 6 | 44443600 | Higher in Drinkers |
| cg08656267 | 1 | 24742168 | Higher in Drinkers |
| cg08656326 | 9 | 84304414 | Higher in Drinkers |
| cg08657020 | 1 | 115299987 | Higher in Drinkers |
| cg08657161 | 17 | 79670690 | Higher in Drinkers |
| cg08658318 | 21 | 46351329 | Higher in Drinkers |
| cg08660562 | 12 | 66627900 | Lower in Drinkers |
| cg08662532 | 17 | 36412303 | Higher in Drinkers |
| cg08662595 | 17 | 71228602 | Higher in Drinkers |
| cg08663085 | X | 149106624 | Higher in Drinkers |
| cg08668412 | 18 | 44702896 | Higher in Drinkers |
| cg08669018 | 4 | 82392280 | Higher in Drinkers |
| cg08672557 | 10 | 22292767 | Higher in Drinkers |
| cg08677243 | 11 | 1108026 | Higher in Drinkers |
| cg08677755 | 19 | 7604888 | Higher in Drinkers |
| cg08678898 | 19 | 42758009 | Higher in Drinkers |
| cg08680102 | 5 | 148725324 | Higher in Drinkers |
| cg08680384 | 1 | 109103095 | Higher in Drinkers |
| cg08680764 | 19 | 36705713 | Higher in Drinkers |
| cg08681293 | 19 | 1221756 | Higher in Drinkers |
| cg08682341 | 10 | 134351765 | Higher in Drinkers |
| cg08684830 | 9 | 80851119 | Higher in Drinkers |
| cg08691479 | 11 | 9595265 | Higher in Drinkers |
| cg08692374 | 2 | 242684212 | Higher in Drinkers |
| cg08697235 | 13 | 77901013 | Higher in Drinkers |
| cg08698523 | 17 | 33900679 | Higher in Drinkers |
| cg08703337 | 12 | 126346485 | Higher in Drinkers |
| cg08704834 | 19 | 59070524 | Higher in Drinkers |

| | | | |
|---|---|---|---|
| cg08706873 | 11 | 93861954 | Higher in Drinkers |
| cg08708935 | 1 | 156722244 | Higher in Drinkers |
| cg08711063 | 11 | 76571529 | Higher in Drinkers |
| cg08711064 | 5 | 86564577 | Higher in Drinkers |
| cg08712669 | 1 | 151585705 | Higher in Drinkers |
| cg08715469 | 4 | 44728051 | Higher in Drinkers |
| cg08716982 | 5 | 179640174 | Higher in Drinkers |
| cg08719422 | X | 152785722 | Lower in Drinkers |
| cg08719642 | 9 | 139595476 | Higher in Drinkers |
| cg08724371 | 15 | 91442212 | Higher in Drinkers |
| cg08725538 | 1 | 197170353 | Higher in Drinkers |
| cg08726342 | 22 | 50689161 | Higher in Drinkers |
| cg08728520 | 20 | 31331105 | Higher in Drinkers |
| cg08730330 | 17 | 61904790 | Higher in Drinkers |
| cg08730726 | 3 | 37493431 | Higher in Drinkers |
| cg08733315 | 15 | 40401063 | Higher in Drinkers |
| cg08733960 | 6 | 52529248 | Higher in Drinkers |
| cg08734988 | 7 | 132767095 | Higher in Drinkers |
| cg08735211 | 6 | 32920657 | Higher in Drinkers |
| cg08736146 | 17 | 45908635 | Higher in Drinkers |
| cg08737246 | 18 | 74799909 | Higher in Drinkers |
| cg08737743 | 6 | 123318023 | Higher in Drinkers |
| cg08738269 | 16 | 88519222 | Higher in Drinkers |
| cg08738770 | 7 | 6026932 | Higher in Drinkers |
| cg08742095 | 7 | 128383253 | Higher in Drinkers |
| cg08746138 | 1 | 218519552 | Higher in Drinkers |
| cg08746290 | 7 | 104829801 | Higher in Drinkers |
| cg08747368 | 12 | 49961505 | Higher in Drinkers |
| cg08749775 | 6 | 30153760 | Higher in Drinkers |
| cg08751508 | 10 | 134221855 | Higher in Drinkers |
| cg08753297 | 6 | 56716612 | Higher in Drinkers |
| cg08754456 | 14 | 70346059 | Higher in Drinkers |
| cg08757434 | 7 | 57016153 | Higher in Drinkers |
| cg08764805 | 12 | 95867684 | Higher in Drinkers |
| cg08766469 | 17 | 80416005 | Higher in Drinkers |

| | | | |
|---|---|---|---|
| cg08767044 | 16 | 11678785 | Higher in Drinkers |
| cg08767686 | 5 | 51426 | Lower in Drinkers |
| cg08771429 | 7 | 91876374 | Higher in Drinkers |
| cg08771731 | 5 | 17216434 | Higher in Drinkers |
| cg08775963 | 4 | 95129012 | Higher in Drinkers |
| cg08777813 | 13 | 114916698 | Higher in Drinkers |
| cg08780220 | 17 | 62344248 | Higher in Drinkers |
| cg08785922 | 17 | 882831 | Higher in Drinkers |
| cg08786026 | 6 | 126068238 | Higher in Drinkers |
| cg08789697 | 4 | 68801145 | Lower in Drinkers |
| cg08789908 | 16 | 67464707 | Higher in Drinkers |
| cg08792634 | 10 | 105881696 | Higher in Drinkers |
| cg08797106 | 6 | 26021008 | Higher in Drinkers |
| cg08798148 | 7 | 102100221 | Higher in Drinkers |
| cg08799467 | 16 | 30960864 | Higher in Drinkers |
| cg08799865 | 10 | 104953198 | Higher in Drinkers |
| cg08800893 | 22 | 36727569 | Higher in Drinkers |
| cg08806986 | 17 | 40086969 | Higher in Drinkers |
| cg08808042 | 16 | 88053104 | Lower in Drinkers |
| cg08810106 | 16 | 18936940 | Higher in Drinkers |
| cg08814531 | 6 | 33280571 | Higher in Drinkers |
| cg08815583 | 7 | 780240 | Higher in Drinkers |
| cg08816248 | 14 | 70383859 | Higher in Drinkers |
| cg08817867 | 17 | 19656554 | Higher in Drinkers |
| cg08818195 | 12 | 133066505 | Higher in Drinkers |
| cg08820079 | 4 | 3446946 | Higher in Drinkers |
| cg08820821 | 19 | 49588236 | Higher in Drinkers |
| cg08822204 | 5 | 54604158 | Higher in Drinkers |
| cg08822360 | 10 | 94459553 | Higher in Drinkers |
| cg08824692 | 11 | 77790360 | Higher in Drinkers |
| cg08827122 | 7 | 2349748 | Higher in Drinkers |
| cg08829281 | 12 | 133264318 | Higher in Drinkers |
| cg08829765 | 3 | 196229583 | Higher in Drinkers |
| cg08839546 | 17 | 78319353 | Higher in Drinkers |
| cg08840441 | 19 | 19748461 | Lower in Drinkers |

| | | | |
|---|---|---|---|
| cg08841290 | X | 119006122 | Higher in Drinkers |
| cg08844966 | 1 | 18435244 | Lower in Drinkers |
| cg08846327 | 5 | 14359614 | Higher in Drinkers |
| cg08849635 | 10 | 99532386 | Higher in Drinkers |
| cg08850169 | 1 | 161171469 | Higher in Drinkers |
| cg08851943 | 6 | 39062812 | Higher in Drinkers |
| cg08855953 | 9 | 71629130 | Higher in Drinkers |
| cg08857478 | 17 | 74722826 | Higher in Drinkers |
| cg08860136 | 17 | 7111414 | Lower in Drinkers |
| cg08861456 | 1 | 248100276 | Lower in Drinkers |
| cg08862499 | 17 | 44271469 | Higher in Drinkers |
| cg08862778 | 1 | 11322643 | Higher in Drinkers |
| cg08863830 | 1 | 2202028 | Lower in Drinkers |
| cg08871189 | 11 | 36311119 | Higher in Drinkers |
| cg08871467 | 9 | 104161367 | Higher in Drinkers |
| cg08873353 | 11 | 61560534 | Higher in Drinkers |
| cg08876591 | 7 | 87563855 | Higher in Drinkers |
| cg08877142 | 8 | 145661886 | Lower in Drinkers |
| cg08879724 | 3 | 156893035 | Higher in Drinkers |
| cg08881680 | 11 | 94965469 | Higher in Drinkers |
| cg08882882 | 6 | 84937375 | Higher in Drinkers |
| cg08887961 | 10 | 62761027 | Higher in Drinkers |
| cg08894401 | 5 | 1318975 | Higher in Drinkers |
| cg08894534 | 2 | 17934487 | Higher in Drinkers |
| cg08894790 | 4 | 177241590 | Higher in Drinkers |
| cg08896030 | 17 | 73636250 | Higher in Drinkers |
| cg08899592 | 17 | 80369450 | Higher in Drinkers |
| cg08900394 | 1 | 114473102 | Higher in Drinkers |
| cg08901151 | 7 | 2172260 | Higher in Drinkers |
| cg08903604 | 17 | 2305559 | Higher in Drinkers |
| cg08905415 | 17 | 78831518 | Higher in Drinkers |
| cg08906576 | 4 | 8366466 | Higher in Drinkers |
| cg08908148 | 7 | 39606013 | Higher in Drinkers |
| cg08912155 | 1 | 23504146 | Higher in Drinkers |
| cg08913815 | 1 | 193028592 | Higher in Drinkers |

| | | | |
|---|---|---|---|
| cg08914916 | 19 | 39421419 | Higher in Drinkers |
| cg08918811 | 11 | 19262251 | Higher in Drinkers |
| cg08919443 | 21 | 47423639 | Higher in Drinkers |
| cg08922808 | 11 | 47448170 | Higher in Drinkers |
| cg08925398 | 1 | 202937011 | Higher in Drinkers |
| cg08927489 | 1 | 151254500 | Higher in Drinkers |
| cg08934394 | 11 | 118901461 | Higher in Drinkers |
| cg08934600 | 5 | 112043158 | Higher in Drinkers |
| cg08936682 | 1 | 91966074 | Higher in Drinkers |
| cg08936794 | 1 | 43833873 | Higher in Drinkers |
| cg08940490 | 2 | 237514003 | Higher in Drinkers |
| cg08945920 | 1 | 3550149 | Higher in Drinkers |
| cg08946989 | 6 | 13328449 | Higher in Drinkers |
| cg08949650 | 6 | 44120365 | Higher in Drinkers |
| cg08949668 | 6 | 33167969 | Higher in Drinkers |
| cg08952506 | 2 | 201450610 | Higher in Drinkers |
| cg08954353 | 8 | 22925656 | Higher in Drinkers |
| cg08955859 | X | 77360510 | Higher in Drinkers |
| cg08957360 | 14 | 55369030 | Higher in Drinkers |
| cg08960754 | 10 | 89622992 | Higher in Drinkers |
| cg08961388 | 17 | 47865739 | Higher in Drinkers |
| cg08963122 | 2 | 62081768 | Higher in Drinkers |
| cg08963669 | 12 | 66563719 | Higher in Drinkers |
| cg08963712 | 17 | 79604385 | Higher in Drinkers |
| cg08964730 | 6 | 32634009 | Higher in Drinkers |
| cg08968603 | 16 | 1993659 | Higher in Drinkers |
| cg08972261 | 2 | 27594204 | Higher in Drinkers |
| cg08975828 | 12 | 112280180 | Higher in Drinkers |
| cg08979183 | 3 | 13035069 | Higher in Drinkers |
| cg08981421 | 7 | 27199956 | Higher in Drinkers |
| cg08981537 | 2 | 54858444 | Higher in Drinkers |
| cg08981582 | 6 | 37178439 | Higher in Drinkers |
| cg08981702 | 5 | 119799220 | Higher in Drinkers |
| cg08997444 | 20 | 57464970 | Higher in Drinkers |
| cg08999807 | 13 | 92050776 | Higher in Drinkers |

| | | | |
|---|---|---|---|
| cg09000138 | 10 | 119106703 | Higher in Drinkers |
| cg09000830 | 1 | 94883752 | Higher in Drinkers |
| cg09001782 | 14 | 95916138 | Higher in Drinkers |
| cg09003710 | 5 | 49963156 | Higher in Drinkers |
| cg09007236 | 17 | 78228820 | Higher in Drinkers |
| cg09008753 | 6 | 71378252 | Higher in Drinkers |
| cg09009111 | 18 | 2847309 | Higher in Drinkers |
| cg09010346 | 4 | 142557655 | Higher in Drinkers |
| cg09010998 | 10 | 31608207 | Higher in Drinkers |
| cg09011346 | 19 | 37862232 | Higher in Drinkers |
| cg09015484 | 9 | 96929106 | Higher in Drinkers |
| cg09019432 | 17 | 62503014 | Higher in Drinkers |
| cg09022163 | 1 | 41157963 | Higher in Drinkers |
| cg09027985 | 17 | 46973122 | Higher in Drinkers |
| cg09028215 | 2 | 67624308 | Higher in Drinkers |
| cg09028899 | 13 | 114807180 | Lower in Drinkers |
| cg09029293 | 17 | 80625018 | Higher in Drinkers |
| cg09031165 | 17 | 17586474 | Higher in Drinkers |
| cg09033691 | 11 | 10829409 | Higher in Drinkers |
| cg09035838 | 11 | 82400683 | Higher in Drinkers |
| cg09036505 | 1 | 54872792 | Higher in Drinkers |
| cg09039698 | 16 | 30007384 | Higher in Drinkers |
| cg09040174 | 2 | 113337401 | Higher in Drinkers |
| cg09041916 | 10 | 64892889 | Higher in Drinkers |
| cg09045508 | 21 | 19191866 | Higher in Drinkers |
| cg09050461 | 5 | 180072420 | Higher in Drinkers |
| cg09059178 | 1 | 24742199 | Higher in Drinkers |
| cg09060316 | 2 | 26467451 | Higher in Drinkers |
| cg09061216 | 1 | 1553936 | Lower in Drinkers |
| cg09061824 | 6 | 30710648 | Higher in Drinkers |
| cg09061973 | 21 | 44395726 | Higher in Drinkers |
| cg09063372 | 1 | 156721491 | Higher in Drinkers |
| cg09063944 | 1 | 3688921 | Higher in Drinkers |
| cg09064482 | 16 | 3081310 | Lower in Drinkers |
| cg09065658 | 16 | 1802365 | Higher in Drinkers |

| | | | |
|---|---|---|---|
| cg09071112 | 2 | 112813174 | Higher in Drinkers |
| cg09075925 | 2 | 71504843 | Higher in Drinkers |
| cg09079593 | 5 | 180632555 | Higher in Drinkers |
| cg09081913 | 1 | 180199374 | Higher in Drinkers |
| cg09083688 | 10 | 105215053 | Higher in Drinkers |
| cg09084829 | 1 | 211307408 | Higher in Drinkers |
| cg09085823 | 20 | 30795283 | Higher in Drinkers |
| cg09087727 | 8 | 33342521 | Higher in Drinkers |
| cg09092093 | 5 | 58335954 | Higher in Drinkers |
| cg09093418 | 8 | 104409700 | Higher in Drinkers |
| cg09095777 | 12 | 53465912 | Higher in Drinkers |
| cg09097668 | 3 | 49448871 | Higher in Drinkers |
| cg09099830 | 16 | 30485485 | Lower in Drinkers |
| cg09101235 | 7 | 148480326 | Higher in Drinkers |
| cg09105657 | 10 | 135172096 | Higher in Drinkers |
| cg09106556 | 19 | 35168274 | Higher in Drinkers |
| cg09112333 | 13 | 22244713 | Higher in Drinkers |
| cg09113141 | 10 | 23729247 | Higher in Drinkers |
| cg09113665 | 16 | 50059684 | Higher in Drinkers |
| cg09114441 | 19 | 40502678 | Higher in Drinkers |
| cg09116251 | 11 | 797747 | Higher in Drinkers |
| cg09121928 | 16 | 75271179 | Lower in Drinkers |
| cg09123444 | 19 | 51307950 | Higher in Drinkers |
| cg09123961 | 1 | 112267182 | Higher in Drinkers |
| cg09124679 | 17 | 74261130 | Higher in Drinkers |
| cg09125550 | 13 | 103720291 | Lower in Drinkers |
| cg09129132 | 8 | 42136078 | Higher in Drinkers |
| cg09130402 | 18 | 54306120 | Higher in Drinkers |
| cg09131529 | 14 | 50087361 | Higher in Drinkers |
| cg09134012 | 17 | 12921796 | Higher in Drinkers |
| cg09135206 | 1 | 21503313 | Higher in Drinkers |
| cg09142119 | 13 | 113884190 | Higher in Drinkers |
| cg09142408 | 4 | 100484885 | Higher in Drinkers |
| cg09142942 | 7 | 92464481 | Higher in Drinkers |
| cg09143515 | 1 | 151227456 | Higher in Drinkers |

| | | | |
|---|---|---|---|
| cg09144073 | 6 | 147523659 | Higher in Drinkers |
| cg09144196 | 1 | 235324804 | Higher in Drinkers |
| cg09146491 | 3 | 28282853 | Higher in Drinkers |
| cg09150117 | 7 | 96653867 | Higher in Drinkers |
| cg09150815 | 19 | 58919920 | Higher in Drinkers |
| cg09154234 | 17 | 37802070 | Higher in Drinkers |
| cg09154880 | 6 | 32813715 | Lower in Drinkers |
| cg09155852 | 9 | 128469764 | Higher in Drinkers |
| cg09156067 | 15 | 90645907 | Higher in Drinkers |
| cg09158026 | 2 | 106467686 | Higher in Drinkers |
| cg09160037 | 1 | 109584686 | Higher in Drinkers |
| cg09162148 | 11 | 65393389 | Higher in Drinkers |
| cg09164580 | 8 | 97157876 | Higher in Drinkers |
| cg09165274 | 13 | 103249774 | Higher in Drinkers |
| cg09165678 | 2 | 219536837 | Higher in Drinkers |
| cg09168495 | 1 | 154928608 | Higher in Drinkers |
| cg09169615 | 5 | 68665848 | Higher in Drinkers |
| cg09171127 | 8 | 8751325 | Higher in Drinkers |
| cg09171253 | 2 | 10567147 | Higher in Drinkers |
| cg09174205 | 18 | 74155058 | Higher in Drinkers |
| cg09174674 | 1 | 9884042 | Higher in Drinkers |
| cg09182986 | 1 | 40505999 | Higher in Drinkers |
| cg09183468 | 20 | 61291109 | Higher in Drinkers |
| cg09184423 | 6 | 157008889 | Higher in Drinkers |
| cg09189396 | 2 | 85766104 | Higher in Drinkers |
| cg09192294 | X | 64732622 | Higher in Drinkers |
| cg09193981 | 12 | 6644606 | Higher in Drinkers |
| cg09194159 | 17 | 46655588 | Higher in Drinkers |
| cg09195920 | 14 | 67707462 | Higher in Drinkers |
| cg09197074 | 11 | 122933690 | Higher in Drinkers |
| cg09203880 | 16 | 5079026 | Lower in Drinkers |
| cg09205065 | 4 | 69215318 | Higher in Drinkers |
| cg09209002 | 4 | 71554199 | Higher in Drinkers |
| cg09211850 | 12 | 124819453 | Higher in Drinkers |
| cg09214535 | 13 | 30092023 | Higher in Drinkers |

| | | | |
|---|---|---|---|
| cg09215316 | 12 | 7033628 | Higher in Drinkers |
| cg09217565 | 14 | 45605027 | Higher in Drinkers |
| cg09218130 | 12 | 132413611 | Higher in Drinkers |
| cg09220061 | 16 | 69220782 | Higher in Drinkers |
| cg09226173 | 5 | 122111107 | Higher in Drinkers |
| cg09226461 | 13 | 50204663 | Higher in Drinkers |
| cg09226692 | 6 | 43422490 | Higher in Drinkers |
| cg09228051 | 16 | 48265760 | Higher in Drinkers |
| cg09230732 | 5 | 54603874 | Higher in Drinkers |
| cg09231120 | 16 | 74991307 | Higher in Drinkers |
| cg09234859 | 7 | 23145933 | Higher in Drinkers |
| cg09238598 | 5 | 14871908 | Higher in Drinkers |
| cg09241381 | 3 | 122746131 | Higher in Drinkers |
| cg09246043 | 14 | 64109158 | Higher in Drinkers |
| cg09246520 | 2 | 208575839 | Higher in Drinkers |
| cg09246833 | 22 | 39915765 | Higher in Drinkers |
| cg09251771 | 6 | 10695336 | Higher in Drinkers |
| cg09256510 | 21 | 37432782 | Higher in Drinkers |
| cg09261015 | X | 103499647 | Higher in Drinkers |
| cg09262197 | 1 | 3807312 | Higher in Drinkers |
| cg09262729 | 11 | 1567941 | Higher in Drinkers |
| cg09265000 | 12 | 53614270 | Higher in Drinkers |
| cg09267507 | 17 | 26671495 | Higher in Drinkers |
| cg09268125 | 16 | 67695975 | Lower in Drinkers |
| cg09268672 | 19 | 36347441 | Higher in Drinkers |
| cg09269013 | 19 | 12792705 | Higher in Drinkers |
| cg09269866 | 1 | 47900197 | Higher in Drinkers |
| cg09270675 | 6 | 56819612 | Higher in Drinkers |
| cg09271671 | 16 | 70432453 | Lower in Drinkers |
| cg09272642 | 1 | 43312265 | Higher in Drinkers |
| cg09275910 | 15 | 79383861 | Higher in Drinkers |
| cg09276355 | 13 | 50510822 | Higher in Drinkers |
| cg09280429 | 2 | 239111682 | Higher in Drinkers |
| cg09282869 | 16 | 21289947 | Higher in Drinkers |
| cg09284457 | 6 | 28864771 | Higher in Drinkers |

| | | | |
|---|---|---|---|
| cg09286090 | 2 | 39351732 | Higher in Drinkers |
| cg09289463 | 19 | 5787866 | Higher in Drinkers |
| cg09289712 | 7 | 139044435 | Higher in Drinkers |
| cg09291817 | 16 | 29816730 | Higher in Drinkers |
| cg09293560 | 7 | 150068240 | Higher in Drinkers |
| cg09294139 | 7 | 100450368 | Higher in Drinkers |
| cg09295063 | 11 | 118436662 | Higher in Drinkers |
| cg09295382 | 4 | 106068032 | Higher in Drinkers |
| cg09296611 | 2 | 10861704 | Higher in Drinkers |
| cg09297514 | 12 | 121678558 | Higher in Drinkers |
| cg09299082 | 17 | 45286354 | Higher in Drinkers |
| cg09299307 | 5 | 86709023 | Higher in Drinkers |
| cg09299564 | 8 | 145064057 | Higher in Drinkers |
| cg09303043 | 17 | 19552393 | Higher in Drinkers |
| cg09305478 | 16 | 691988 | Higher in Drinkers |
| cg09307034 | 12 | 95466679 | Higher in Drinkers |
| cg09308608 | 16 | 8962727 | Higher in Drinkers |
| cg09308803 | 4 | 100871536 | Higher in Drinkers |
| cg09309913 | 8 | 134583413 | Higher in Drinkers |
| cg09310383 | 3 | 37218128 | Higher in Drinkers |
| cg09310777 | 17 | 79604213 | Higher in Drinkers |
| cg09314803 | 17 | 79180344 | Higher in Drinkers |
| cg09316688 | 21 | 38444692 | Higher in Drinkers |
| cg09317554 | 4 | 151505084 | Higher in Drinkers |
| cg09318248 | 9 | 136891078 | Higher in Drinkers |
| cg09320703 | 7 | 1045249 | Higher in Drinkers |
| cg09322984 | 6 | 25279102 | Higher in Drinkers |
| cg09324018 | 2 | 16839610 | Higher in Drinkers |
| cg09327628 | 1 | 32801665 | Higher in Drinkers |
| cg09327849 | 12 | 121342321 | Higher in Drinkers |
| cg09331956 | 22 | 39101473 | Higher in Drinkers |
| cg09332091 | 19 | 3180708 | Higher in Drinkers |
| cg09337208 | 20 | 43989309 | Higher in Drinkers |
| cg09344348 | 6 | 170581085 | Higher in Drinkers |
| cg09345825 | 14 | 66974634 | Higher in Drinkers |

| | | | |
|---|---|---|---|
| cg09350274 | 5 | 137610396 | Higher in Drinkers |
| cg09351035 | 11 | 748060 | Higher in Drinkers |
| cg09351859 | 5 | 49962613 | Higher in Drinkers |
| cg09352310 | 6 | 32862445 | Higher in Drinkers |
| cg09353354 | 19 | 7460276 | Higher in Drinkers |
| cg09354317 | 3 | 52869307 | Higher in Drinkers |
| cg09358130 | 2 | 230097262 | Lower in Drinkers |
| cg09361958 | 3 | 128947790 | Higher in Drinkers |
| cg09362956 | 22 | 32749962 | Higher in Drinkers |
| cg09364089 | 1 | 92948788 | Higher in Drinkers |
| cg09368485 | 6 | 29974022 | Higher in Drinkers |
| cg09370702 | 14 | 74970002 | Higher in Drinkers |
| cg09371351 | 1 | 119958041 | Higher in Drinkers |
| cg09371829 | 7 | 104654918 | Higher in Drinkers |
| cg09372999 | 17 | 68125093 | Higher in Drinkers |
| cg09373227 | 11 | 69464433 | Higher in Drinkers |
| cg09374774 | 9 | 134151945 | Higher in Drinkers |
| cg09379601 | 19 | 12992224 | Higher in Drinkers |
| cg09380198 | 13 | 41837783 | Higher in Drinkers |
| cg09381737 | 9 | 140173549 | Higher in Drinkers |
| cg09382850 | 7 | 105753147 | Higher in Drinkers |
| cg09389348 | 11 | 74659870 | Higher in Drinkers |
| cg09392045 | 6 | 11094883 | Higher in Drinkers |
| cg09396107 | 8 | 132916815 | Higher in Drinkers |
| cg09397254 | 3 | 160117013 | Higher in Drinkers |
| cg09398544 | 2 | 145147558 | Lower in Drinkers |
| cg09406384 | 19 | 8579163 | Higher in Drinkers |
| cg09407049 | 19 | 50144997 | Higher in Drinkers |
| cg09407916 | 3 | 49977988 | Higher in Drinkers |
| cg09408973 | 6 | 32796660 | Higher in Drinkers |
| cg09409209 | 2 | 241988102 | Higher in Drinkers |
| cg09410841 | 8 | 1729607 | Higher in Drinkers |
| cg09410986 | 14 | 52118390 | Higher in Drinkers |
| cg09413933 | 21 | 30397036 | Higher in Drinkers |
| cg09414863 | 1 | 85049548 | Higher in Drinkers |

| | | | |
|---|---|---|---|
| cg09417774 | 12 | 112037791 | Higher in Drinkers |
| cg09420510 | 17 | 75484303 | Higher in Drinkers |
| cg09424253 | 15 | 80445813 | Higher in Drinkers |
| cg09424923 | 12 | 123635770 | Higher in Drinkers |
| cg09430932 | 7 | 44154322 | Higher in Drinkers |
| cg09432138 | 16 | 67881371 | Higher in Drinkers |
| cg09432613 | 10 | 102497520 | Higher in Drinkers |
| cg09435824 | 16 | 84178604 | Higher in Drinkers |
| cg09436562 | 11 | 18415874 | Higher in Drinkers |
| cg09436871 | 18 | 19321130 | Higher in Drinkers |
| cg09436892 | 7 | 128379016 | Higher in Drinkers |
| cg09438955 | 13 | 74708110 | Higher in Drinkers |
| cg09441963 | 22 | 38198576 | Higher in Drinkers |
| cg09442458 | 8 | 81399093 | Higher in Drinkers |
| cg09442744 | 12 | 122985628 | Higher in Drinkers |
| cg09444070 | 15 | 99658301 | Lower in Drinkers |
| cg09444226 | 12 | 12887740 | Higher in Drinkers |
| cg09445097 | 9 | 130186736 | Higher in Drinkers |
| cg09445448 | 9 | 134151854 | Higher in Drinkers |
| cg09447457 | 6 | 24721528 | Higher in Drinkers |
| cg09451549 | 19 | 3386408 | Higher in Drinkers |
| cg09451574 | 4 | 113069076 | Higher in Drinkers |
| cg09451763 | 11 | 125439061 | Higher in Drinkers |
| cg09459044 | 4 | 106395029 | Higher in Drinkers |
| cg09462269 | 1 | 43751469 | Higher in Drinkers |
| cg09463963 | 10 | 112679647 | Higher in Drinkers |
| cg09464488 | 2 | 175547590 | Higher in Drinkers |
| cg09465142 | 20 | 50109375 | Higher in Drinkers |
| cg09466807 | 11 | 65767062 | Higher in Drinkers |
| cg09469430 | 10 | 103869748 | Higher in Drinkers |
| cg09470010 | 10 | 104094152 | Higher in Drinkers |
| cg09470219 | 16 | 22378015 | Higher in Drinkers |
| cg09473249 | 16 | 16122741 | Higher in Drinkers |
| cg09473847 | 22 | 21213087 | Higher in Drinkers |
| cg09474229 | 19 | 39360330 | Higher in Drinkers |

| | | | |
|---|---|---|---|
| cg09474938 | 6 | 30875843 | Higher in Drinkers |
| cg09477198 | 1 | 24105242 | Higher in Drinkers |
| cg09483247 | 10 | 71906310 | Higher in Drinkers |
| cg09484303 | 5 | 14498661 | Higher in Drinkers |
| cg09486967 | 17 | 1437322 | Higher in Drinkers |
| cg09487167 | 14 | 55518661 | Higher in Drinkers |
| cg09490466 | 5 | 175788536 | Higher in Drinkers |
| cg09491281 | 8 | 56686114 | Higher in Drinkers |
| cg09492086 | 13 | 40177575 | Higher in Drinkers |
| cg09492252 | 21 | 43369331 | Higher in Drinkers |
| cg09499413 | 11 | 9780133 | Higher in Drinkers |
| cg09499703 | 5 | 131133214 | Higher in Drinkers |
| cg09502511 | 6 | 30539237 | Higher in Drinkers |
| cg09507834 | 11 | 67084689 | Higher in Drinkers |
| cg09508022 | 6 | 168971135 | Higher in Drinkers |
| cg09509528 | 17 | 74668195 | Higher in Drinkers |
| cg09509576 | 17 | 73402025 | Higher in Drinkers |
| cg09510976 | 6 | 30689514 | Higher in Drinkers |
| cg09512080 | 7 | 94286219 | Higher in Drinkers |
| cg09514055 | 1 | 43919573 | Higher in Drinkers |
| cg09515568 | 10 | 120101875 | Higher in Drinkers |
| cg09515778 | 7 | 150755072 | Higher in Drinkers |
| cg09516302 | 1 | 84945254 | Higher in Drinkers |
| cg09516959 | 7 | 30721478 | Higher in Drinkers |
| cg09526828 | 3 | 15900542 | Higher in Drinkers |
| cg09531225 | 4 | 82393079 | Higher in Drinkers |
| cg09531492 | 22 | 50632560 | Higher in Drinkers |
| cg09532503 | 4 | 119711185 | Higher in Drinkers |
| cg09532898 | 11 | 721242 | Higher in Drinkers |
| cg09535168 | 19 | 19431582 | Higher in Drinkers |
| cg09536315 | 2 | 179729091 | Higher in Drinkers |
| cg09541740 | 2 | 95831116 | Higher in Drinkers |
| cg09544630 | 7 | 981684 | Lower in Drinkers |
| cg09544705 | 11 | 67007628 | Higher in Drinkers |
| cg09546172 | 21 | 43933663 | Higher in Drinkers |

| | | | |
|---|---|---|---|
| cg09546359 | 5 | 102594340 | Higher in Drinkers |
| cg09548179 | 16 | 2570492 | Higher in Drinkers |
| cg09548897 | 16 | 341277 | Higher in Drinkers |
| cg09554310 | 7 | 5540163 | Higher in Drinkers |
| cg09569536 | 12 | 8849911 | Higher in Drinkers |
| cg09570535 | 17 | 75136971 | Higher in Drinkers |
| cg09575242 | 4 | 41260585 | Higher in Drinkers |
| cg09578113 | 7 | 47420152 | Higher in Drinkers |
| cg09578463 | 16 | 5083743 | Higher in Drinkers |
| cg09579561 | 4 | 2252195 | Lower in Drinkers |
| cg09579933 | 1 | 28198451 | Lower in Drinkers |
| cg09583777 | 1 | 94703079 | Higher in Drinkers |
| cg09591886 | 16 | 22333264 | Higher in Drinkers |
| cg09593402 | 5 | 96270297 | Higher in Drinkers |
| cg09594696 | 7 | 150777854 | Higher in Drinkers |
| cg09600520 | 6 | 4706244 | Higher in Drinkers |
| cg09600532 | 6 | 33231322 | Higher in Drinkers |
| cg09602753 | 10 | 134574192 | Higher in Drinkers |
| cg09603188 | 17 | 41791282 | Higher in Drinkers |
| cg09605111 | 22 | 45560051 | Higher in Drinkers |
| cg09607488 | 8 | 99963657 | Higher in Drinkers |
| cg09608028 | 10 | 43932620 | Higher in Drinkers |
| cg09609418 | 11 | 66079140 | Lower in Drinkers |
| cg09610644 | 3 | 197249274 | Higher in Drinkers |
| cg09610675 | 22 | 29196744 | Higher in Drinkers |
| cg09612534 | 3 | 158435341 | Higher in Drinkers |
| cg09615360 | 2 | 99262816 | Lower in Drinkers |
| cg09619475 | 3 | 93782025 | Higher in Drinkers |
| cg09623771 | 7 | 99717157 | Higher in Drinkers |
| cg09630437 | 19 | 2740301 | Higher in Drinkers |
| cg09631044 | 12 | 50419555 | Higher in Drinkers |
| cg09631309 | 2 | 37458880 | Higher in Drinkers |
| cg09631939 | 20 | 60582478 | Lower in Drinkers |
| cg09635667 | 17 | 2300514 | Higher in Drinkers |
| cg09637172 | 6 | 31545252 | Lower in Drinkers |

| | | | |
|---|---|---|---|
| cg09638556 | 5 | 37370880 | Higher in Drinkers |
| cg09643279 | 12 | 125435221 | Higher in Drinkers |
| cg09644109 | 7 | 97601190 | Higher in Drinkers |
| cg09644830 | 3 | 13692141 | Higher in Drinkers |
| cg09645126 | 3 | 184870685 | Higher in Drinkers |
| cg09645699 | 3 | 12977543 | Higher in Drinkers |
| cg09654562 | 22 | 46467953 | Higher in Drinkers |
| cg09655559 | 20 | 62496256 | Higher in Drinkers |
| cg09656405 | 15 | 69745057 | Higher in Drinkers |
| cg09658429 | 12 | 22094479 | Higher in Drinkers |
| cg09659734 | 16 | 56227065 | Higher in Drinkers |
| cg09659887 | 11 | 9406115 | Higher in Drinkers |
| cg09660878 | 5 | 77142695 | Higher in Drinkers |
| cg09666654 | 2 | 192110658 | Higher in Drinkers |
| cg09667721 | 11 | 126080928 | Lower in Drinkers |
| cg09668344 | 11 | 77122506 | Higher in Drinkers |
| cg09668570 | 15 | 79122644 | Higher in Drinkers |
| cg09678367 | 1 | 25870822 | Higher in Drinkers |
| cg09678829 | 7 | 834456 | Higher in Drinkers |
| cg09679642 | 17 | 79805210 | Higher in Drinkers |
| cg09682727 | 5 | 139953966 | Lower in Drinkers |
| cg09684160 | 1 | 17054957 | Lower in Drinkers |
| cg09685763 | 20 | 30597590 | Lower in Drinkers |
| cg09690449 | 4 | 187998952 | Lower in Drinkers |
| cg09693811 | 5 | 73553751 | Lower in Drinkers |
| cg09694610 | 20 | 36156532 | Higher in Drinkers |
| cg09697880 | 9 | 130370977 | Higher in Drinkers |
| cg09698221 | 16 | 15188353 | Higher in Drinkers |
| cg09699111 | 15 | 28362467 | Higher in Drinkers |
| cg09699128 | 16 | 1359454 | Higher in Drinkers |
| cg09700602 | 3 | 58223062 | Higher in Drinkers |
| cg09701062 | 5 | 133446318 | Higher in Drinkers |
| cg09701144 | 6 | 111180185 | Higher in Drinkers |
| cg09704136 | 7 | 143082002 | Higher in Drinkers |
| cg09704448 | 19 | 10335095 | Higher in Drinkers |

| | | | |
|---|---|---|---|
| cg09705531 | 12 | 133525532 | Higher in Drinkers |
| cg09706573 | 6 | 31936247 | Higher in Drinkers |
| cg09711399 | 5 | 177549014 | Higher in Drinkers |
| cg09720420 | X | 142722174 | Higher in Drinkers |
| cg09720758 | 8 | 8751498 | Higher in Drinkers |
| cg09722643 | 8 | 86375501 | Higher in Drinkers |
| cg09723590 | 11 | 118436713 | Higher in Drinkers |
| cg09726469 | 1 | 150552014 | Higher in Drinkers |
| cg09729624 | 11 | 193112 | Higher in Drinkers |
| cg09730361 | 9 | 20622599 | Higher in Drinkers |
| cg09733045 | 6 | 31855906 | Higher in Drinkers |
| cg09739907 | 7 | 102789396 | Higher in Drinkers |
| cg09740319 | 1 | 231004641 | Higher in Drinkers |
| cg09740815 | 16 | 3777892 | Higher in Drinkers |
| cg09742170 | 7 | 25021208 | Higher in Drinkers |
| cg09745246 | 12 | 123213241 | Higher in Drinkers |
| cg09748770 | 7 | 21467405 | Lower in Drinkers |
| cg09754122 | 13 | 100741804 | Higher in Drinkers |
| cg09756419 | 16 | 67918680 | Higher in Drinkers |
| cg09757353 | 10 | 121062626 | Higher in Drinkers |
| cg09758671 | 8 | 99058522 | Higher in Drinkers |
| cg09761367 | 1 | 25360712 | Higher in Drinkers |
| cg09762778 | 17 | 37783879 | Higher in Drinkers |
| cg09765994 | 1 | 14026605 | Higher in Drinkers |
| cg09767736 | 19 | 50400119 | Higher in Drinkers |
| cg09768944 | 9 | 125590709 | Higher in Drinkers |
| cg09771049 | 17 | 66031798 | Higher in Drinkers |
| cg09771226 | 17 | 45786313 | Lower in Drinkers |
| cg09774179 | 6 | 36652043 | Lower in Drinkers |
| cg09779392 | 19 | 11094753 | Higher in Drinkers |
| cg09787394 | 2 | 99771194 | Higher in Drinkers |
| cg09788666 | 13 | 41345475 | Higher in Drinkers |
| cg09790580 | 1 | 92171309 | Higher in Drinkers |
| cg09791053 | 7 | 97910884 | Higher in Drinkers |
| cg09791812 | 7 | 44121910 | Higher in Drinkers |

| | | | |
|---|---|---|---|
| cg09792598 | 19 | 3505943 | Higher in Drinkers |
| cg09793988 | 16 | 55543053 | Higher in Drinkers |
| cg09795081 | 6 | 34392105 | Lower in Drinkers |
| cg09795614 | 5 | 140041521 | Higher in Drinkers |
| cg09796501 | 1 | 26233435 | Higher in Drinkers |
| cg09797837 | 1 | 17734771 | Higher in Drinkers |
| cg09809672 | 1 | 236557682 | Higher in Drinkers |
| cg09811943 | 7 | 38217818 | Higher in Drinkers |
| cg09812885 | 1 | 1162996 | Higher in Drinkers |
| cg09816912 | 6 | 114178507 | Higher in Drinkers |
| cg09819033 | 12 | 12764631 | Higher in Drinkers |
| cg09821112 | 1 | 205719462 | Higher in Drinkers |
| cg09822001 | 1 | 156561334 | Higher in Drinkers |
| cg09825153 | 5 | 1826997 | Higher in Drinkers |
| cg09826587 | 1 | 14026817 | Higher in Drinkers |
| cg09826784 | 22 | 20307397 | Higher in Drinkers |
| cg09827249 | 10 | 135051256 | Lower in Drinkers |
| cg09828625 | 20 | 23331259 | Higher in Drinkers |
| cg09830678 | 18 | 11908251 | Higher in Drinkers |
| cg09832551 | 6 | 33176267 | Higher in Drinkers |
| cg09834234 | 7 | 72972112 | Higher in Drinkers |
| cg09844185 | 1 | 213031022 | Higher in Drinkers |
| cg09845488 | 1 | 114301553 | Higher in Drinkers |
| cg09845946 | 2 | 204192806 | Higher in Drinkers |
| cg09847476 | 5 | 141293803 | Higher in Drinkers |
| cg09848943 | 6 | 170861929 | Higher in Drinkers |
| cg09852008 | 1 | 10092689 | Higher in Drinkers |
| cg09852697 | 1 | 3616642 | Higher in Drinkers |
| cg09853387 | 7 | 139877374 | Higher in Drinkers |
| cg09855001 | 8 | 99058424 | Higher in Drinkers |
| cg09858107 | 5 | 60240938 | Higher in Drinkers |
| cg09859293 | 2 | 3605851 | Higher in Drinkers |
| cg09859398 | 14 | 59932033 | Higher in Drinkers |
| cg09861476 | 1 | 234617742 | Higher in Drinkers |
| cg09864858 | 1 | 65613311 | Higher in Drinkers |

| | | | |
|---|---|---|---|
| cg09865593 | 7 | 645796 | Higher in Drinkers |
| cg09866102 | 16 | 31214134 | Higher in Drinkers |
| cg09867070 | 16 | 84812668 | Higher in Drinkers |
| cg09867157 | 6 | 31620935 | Higher in Drinkers |
| cg09869042 | 22 | 42343253 | Higher in Drinkers |
| cg09871133 | 16 | 16216108 | Higher in Drinkers |
| cg09871247 | 5 | 98263747 | Higher in Drinkers |
| cg09874127 | 3 | 49851439 | Higher in Drinkers |
| cg09875087 | 1 | 164724775 | Higher in Drinkers |
| cg09875444 | 12 | 52317302 | Higher in Drinkers |
| cg09876519 | 6 | 50675610 | Higher in Drinkers |
| cg09876683 | 5 | 8906741 | Lower in Drinkers |
| cg09879122 | 12 | 132690651 | Lower in Drinkers |
| cg09880012 | 6 | 26123736 | Higher in Drinkers |
| cg09880681 | 16 | 30538664 | Higher in Drinkers |
| cg09881917 | 16 | 70487956 | Higher in Drinkers |
| cg09882550 | 5 | 179920971 | Higher in Drinkers |
| cg09884940 | 7 | 150741161 | Higher in Drinkers |
| cg09887627 | 13 | 30090298 | Higher in Drinkers |
| cg09891393 | 16 | 87738756 | Higher in Drinkers |
| cg09895187 | 8 | 55047972 | Higher in Drinkers |
| cg09896503 | 7 | 99102090 | Higher in Drinkers |
| cg09902061 | 11 | 34126957 | Higher in Drinkers |
| cg09903262 | 2 | 106809735 | Higher in Drinkers |
| cg09904774 | 17 | 3539754 | Higher in Drinkers |
| cg09909750 | X | 19003035 | Higher in Drinkers |
| cg09911083 | 17 | 7754956 | Lower in Drinkers |
| cg09911086 | 16 | 15068421 | Higher in Drinkers |
| cg09911755 | 17 | 45899773 | Higher in Drinkers |
| cg09912768 | 15 | 66585646 | Higher in Drinkers |
| cg09913796 | 17 | 27181988 | Higher in Drinkers |
| cg09915703 | 11 | 62599750 | Higher in Drinkers |
| cg09915940 | 19 | 798935 | Higher in Drinkers |
| cg09917807 | 12 | 31862282 | Higher in Drinkers |
| cg09922871 | 2 | 71559595 | Higher in Drinkers |

| | | | |
|---|---|---|---|
| cg09927483 | 14 | 82000382 | Higher in Drinkers |
| cg09931450 | 22 | 36924810 | Higher in Drinkers |
| cg09932330 | 3 | 52091651 | Higher in Drinkers |
| cg09932345 | 1 | 1710561 | Higher in Drinkers |
| cg09934056 | 19 | 8400203 | Higher in Drinkers |
| cg09936400 | 10 | 82049201 | Higher in Drinkers |
| cg09936581 | 1 | 93544730 | Higher in Drinkers |
| cg09938469 | 16 | 89338688 | Lower in Drinkers |
| cg09941112 | 19 | 38916939 | Higher in Drinkers |
| cg09942303 | 4 | 166248675 | Higher in Drinkers |
| cg09942463 | 4 | 905223 | Higher in Drinkers |
| cg09955298 | 8 | 7213522 | Higher in Drinkers |
| cg09957386 | 7 | 134144062 | Higher in Drinkers |
| cg09959112 | 16 | 10973301 | Higher in Drinkers |
| cg09962984 | 10 | 46167678 | Higher in Drinkers |
| cg09965967 | 6 | 86303767 | Higher in Drinkers |
| cg09966309 | 6 | 166954739 | Lower in Drinkers |
| cg09970483 | 15 | 64455548 | Higher in Drinkers |
| cg09972424 | 14 | 92573067 | Higher in Drinkers |
| cg09973375 | 4 | 159644880 | Higher in Drinkers |
| cg09976724 | 15 | 41186526 | Higher in Drinkers |
| cg09978321 | 19 | 33864421 | Higher in Drinkers |
| cg09990401 | 20 | 633783 | Higher in Drinkers |
| cg09991951 | 16 | 34648842 | Lower in Drinkers |
| cg09993119 | 22 | 41601085 | Higher in Drinkers |
| cg09993606 | 8 | 144545708 | Higher in Drinkers |
| cg09994022 | 13 | 99127189 | Higher in Drinkers |
| cg09998229 | 19 | 3606757 | Higher in Drinkers |
| cg09999907 | 19 | 17530609 | Higher in Drinkers |
| cg10002412 | 19 | 35491296 | Higher in Drinkers |
| cg10005894 | 3 | 186649165 | Higher in Drinkers |
| cg10006762 | 11 | 65342202 | Higher in Drinkers |
| cg10007182 | 7 | 4743146 | Higher in Drinkers |
| cg10008636 | 14 | 103542242 | Higher in Drinkers |
| cg10011083 | 7 | 55639278 | Higher in Drinkers |

| | | | |
|---|---|---|---|
| cg10013169 | 6 | 5997028 | Higher in Drinkers |
| cg10020897 | 1 | 167905730 | Higher in Drinkers |
| cg10021819 | 16 | 81856835 | Higher in Drinkers |
| cg10024281 | 1 | 28969778 | Higher in Drinkers |
| cg10025462 | 17 | 27046956 | Higher in Drinkers |
| cg10027760 | 20 | 60878541 | Higher in Drinkers |
| cg10030436 | X | 48755633 | Higher in Drinkers |
| cg10031769 | 10 | 35483963 | Higher in Drinkers |
| cg10034912 | 10 | 53459408 | Higher in Drinkers |
| cg10040213 | 12 | 93328735 | Higher in Drinkers |
| cg10045354 | 11 | 111169427 | Higher in Drinkers |
| cg10051214 | 1 | 24195031 | Higher in Drinkers |
| cg10052285 | 14 | 77767800 | Higher in Drinkers |
| cg10053162 | 10 | 17685929 | Higher in Drinkers |
| cg10053355 | 16 | 57570671 | Higher in Drinkers |
| cg10054150 | 6 | 31828287 | Lower in Drinkers |
| cg10055222 | 7 | 1125111 | Higher in Drinkers |
| cg10059378 | 16 | 4817345 | Higher in Drinkers |
| cg10060065 | 17 | 32366901 | Higher in Drinkers |
| cg10060574 | 6 | 30712338 | Higher in Drinkers |
| cg10061235 | 7 | 4768697 | Higher in Drinkers |
| cg10064400 | 1 | 90460439 | Higher in Drinkers |
| cg10064814 | X | 149101909 | Higher in Drinkers |
| cg10066151 | 19 | 57874988 | Higher in Drinkers |
| cg10070224 | 2 | 121116501 | Lower in Drinkers |
| cg10072168 | 6 | 163587182 | Lower in Drinkers |
| cg10072309 | 11 | 537558 | Higher in Drinkers |
| cg10074949 | 15 | 52312166 | Higher in Drinkers |
| cg10075405 | 14 | 102685893 | Higher in Drinkers |
| cg10076931 | 6 | 27100556 | Higher in Drinkers |
| cg10077468 | 15 | 91498367 | Higher in Drinkers |
| cg10079318 | 10 | 104154150 | Higher in Drinkers |
| cg10081138 | 17 | 7604803 | Lower in Drinkers |
| cg10081604 | 14 | 89290709 | Higher in Drinkers |
| cg10087060 | 10 | 52419357 | Higher in Drinkers |

| | | | |
|---|---|---|---|
| cg10089647 | 1 | 226298073 | Higher in Drinkers |
| cg10091408 | 17 | 35183637 | Lower in Drinkers |
| cg10091705 | 1 | 202317604 | Higher in Drinkers |
| cg10096579 | 4 | 3572794 | Higher in Drinkers |
| cg10099957 | 16 | 87869757 | Lower in Drinkers |
| cg10101263 | 11 | 130786633 | Higher in Drinkers |
| cg10101783 | 13 | 45493326 | Higher in Drinkers |
| cg10103111 | 19 | 46088331 | Higher in Drinkers |
| cg10103751 | 16 | 14013676 | Higher in Drinkers |
| cg10106264 | 2 | 16847986 | Higher in Drinkers |
| cg10106935 | 7 | 4762236 | Higher in Drinkers |
| cg10107298 | 16 | 729906 | Higher in Drinkers |
| cg10109570 | 16 | 1832978 | Higher in Drinkers |
| cg10110271 | 16 | 87943182 | Higher in Drinkers |
| cg10111146 | 3 | 172471603 | Higher in Drinkers |
| cg10113231 | 3 | 23958877 | Higher in Drinkers |
| cg10113342 | 7 | 5125232 | Higher in Drinkers |
| cg10113467 | 13 | 76056490 | Higher in Drinkers |
| cg10118925 | 6 | 151645532 | Higher in Drinkers |
| cg10119082 | 7 | 98990626 | Higher in Drinkers |
| cg10123352 | 14 | 50234498 | Higher in Drinkers |
| cg10126923 | 19 | 51875451 | Higher in Drinkers |
| cg10127610 | 15 | 85801533 | Higher in Drinkers |
| cg10127660 | 8 | 21996234 | Higher in Drinkers |
| cg10128659 | 10 | 134404064 | Lower in Drinkers |
| cg10131887 | 19 | 6460802 | Higher in Drinkers |
| cg10135178 | 15 | 28834933 | Higher in Drinkers |
| cg10140391 | 3 | 12941126 | Higher in Drinkers |
| cg10141022 | 7 | 140624905 | Higher in Drinkers |
| cg10146112 | 10 | 134566222 | Higher in Drinkers |
| cg10146267 | 1 | 24513865 | Higher in Drinkers |
| cg10149091 | 2 | 61404764 | Higher in Drinkers |
| cg10151085 | 12 | 54654090 | Higher in Drinkers |
| cg10155304 | 12 | 109107559 | Lower in Drinkers |
| cg10163945 | 5 | 115421152 | Higher in Drinkers |

| | | | |
|---|---|---|---|
| cg10165209 | 17 | 46715533 | Lower in Drinkers |
| cg10165518 | 16 | 28510740 | Lower in Drinkers |
| cg10166277 | 7 | 104752828 | Higher in Drinkers |
| cg10170269 | 20 | 62256006 | Higher in Drinkers |
| cg10172107 | 3 | 170075243 | Higher in Drinkers |
| cg10175447 | 3 | 180397342 | Higher in Drinkers |
| cg10178905 | 15 | 63796301 | Higher in Drinkers |
| cg10181180 | 2 | 48648025 | Higher in Drinkers |
| cg10183035 | 7 | 92157937 | Higher in Drinkers |
| cg10183248 | 17 | 42295591 | Higher in Drinkers |
| cg10184864 | 4 | 9693329 | Higher in Drinkers |
| cg10184881 | 1 | 32404326 | Higher in Drinkers |
| cg10191248 | 10 | 134441085 | Higher in Drinkers |
| cg10194844 | 12 | 123258997 | Higher in Drinkers |
| cg10199109 | 5 | 68389620 | Higher in Drinkers |
| cg10200255 | 19 | 20162670 | Higher in Drinkers |
| cg10204320 | 1 | 32709276 | Higher in Drinkers |
| cg10205403 | 12 | 95867231 | Higher in Drinkers |
| cg10205753 | 8 | 54792627 | Higher in Drinkers |
| cg10213821 | 7 | 99005134 | Lower in Drinkers |
| cg10214757 | 16 | 22237075 | Higher in Drinkers |
| cg10215919 | 21 | 37692341 | Higher in Drinkers |
| cg10217503 | 12 | 65153209 | Higher in Drinkers |
| cg10222850 | 1 | 149278818 | Higher in Drinkers |
| cg10223531 | 1 | 35317655 | Higher in Drinkers |
| cg10224107 | 19 | 47813130 | Higher in Drinkers |
| cg10231213 | 10 | 3281984 | Higher in Drinkers |
| cg10231344 | 10 | 104952243 | Higher in Drinkers |
| cg10234952 | 20 | 55926623 | Higher in Drinkers |
| cg10237814 | 17 | 18215543 | Higher in Drinkers |
| cg10245330 | 1 | 243652681 | Lower in Drinkers |
| cg10249132 | 4 | 153458013 | Higher in Drinkers |
| cg10251328 | 17 | 47074713 | Higher in Drinkers |
| cg10252135 | 8 | 66754949 | Higher in Drinkers |
| cg10255675 | 14 | 21737751 | Higher in Drinkers |

| | | | |
|---|---|---|---|
| cg10255761 | 3 | 49210029 | Higher in Drinkers |
| cg10257610 | 10 | 104953200 | Higher in Drinkers |
| cg10258730 | X | 106142861 | Lower in Drinkers |
| cg10258966 | 20 | 61810795 | Higher in Drinkers |
| cg10260935 | 22 | 41844435 | Higher in Drinkers |
| cg10263594 | 11 | 62598680 | Higher in Drinkers |
| cg10264187 | 11 | 47429713 | Higher in Drinkers |
| cg10271192 | 2 | 63279645 | Higher in Drinkers |
| cg10272433 | 7 | 100732423 | Higher in Drinkers |
| cg10272968 | 19 | 2611105 | Higher in Drinkers |
| cg10275272 | 7 | 4784769 | Higher in Drinkers |
| cg10277631 | 14 | 53019580 | Higher in Drinkers |
| cg10280756 | 11 | 57313734 | Higher in Drinkers |
| cg10281105 | 2 | 232379126 | Higher in Drinkers |
| cg10283707 | 15 | 62339161 | Higher in Drinkers |
| cg10288921 | 2 | 3289711 | Lower in Drinkers |
| cg10295800 | 10 | 60145091 | Higher in Drinkers |
| cg10297257 | 3 | 88198751 | Higher in Drinkers |
| cg10298173 | 3 | 14166327 | Higher in Drinkers |
| cg10299941 | 8 | 145009137 | Lower in Drinkers |
| cg10300188 | 11 | 2890577 | Higher in Drinkers |
| cg10301660 | 10 | 43278230 | Higher in Drinkers |
| cg10305851 | 6 | 33386148 | Higher in Drinkers |
| cg10306079 | 6 | 108880961 | Higher in Drinkers |
| cg10307940 | 8 | 6637707 | Higher in Drinkers |
| cg10309340 | 10 | 102747329 | Higher in Drinkers |
| cg10310299 | 10 | 65196311 | Higher in Drinkers |
| cg10310595 | 6 | 32908567 | Higher in Drinkers |
| cg10310824 | X | 23801995 | Higher in Drinkers |
| cg10311173 | 16 | 89682931 | Higher in Drinkers |
| cg10313675 | 1 | 209957739 | Higher in Drinkers |
| cg10314133 | 1 | 2125114 | Higher in Drinkers |
| cg10315321 | 16 | 85589696 | Higher in Drinkers |
| cg10319904 | 7 | 44530440 | Higher in Drinkers |
| cg10323308 | 1 | 55229957 | Higher in Drinkers |

| | | | |
|---|---|---|---|
| cg10323240 | 19 | 54305489 | Higher in Drinkers |
| cg10326447 | 11 | 124609941 | Higher in Drinkers |
| cg10329579 | 1 | 17754830 | Higher in Drinkers |
| cg10330169 | 2 | 232830822 | Lower in Drinkers |
| cg10331073 | 10 | 26856128 | Lower in Drinkers |
| cg10334053 | 1 | 2078117 | Lower in Drinkers |
| cg10336537 | 1 | 38455491 | Higher in Drinkers |
| cg10337772 | 3 | 44803071 | Higher in Drinkers |
| cg10338358 | 12 | 8088931 | Higher in Drinkers |
| cg10338412 | 8 | 74086760 | Higher in Drinkers |
| cg10338518 | 4 | 87895137 | Higher in Drinkers |
| cg10338764 | 2 | 178417690 | Higher in Drinkers |
| cg10339344 | 11 | 60674203 | Higher in Drinkers |
| cg10339542 | 17 | 10600919 | Higher in Drinkers |
| cg10342963 | 15 | 99443213 | Lower in Drinkers |
| cg10348863 | 4 | 184425226 | Higher in Drinkers |
| cg10348922 | 22 | 21319303 | Higher in Drinkers |
| cg10353870 | 2 | 127864778 | Higher in Drinkers |
| cg10354859 | 13 | 53024439 | Higher in Drinkers |
| cg10358194 | 12 | 510688 | Higher in Drinkers |
| cg10361281 | 22 | 24811256 | Lower in Drinkers |
| cg10363443 | 3 | 194790714 | Higher in Drinkers |
| cg10363661 | 16 | 89641360 | Higher in Drinkers |
| cg10366028 | 7 | 1931885 | Higher in Drinkers |
| cg10367296 | 19 | 5066951 | Lower in Drinkers |
| cg10367412 | 14 | 103590195 | Higher in Drinkers |
| cg10368518 | 4 | 71859343 | Higher in Drinkers |
| cg10369796 | 8 | 22550379 | Higher in Drinkers |
| cg10373574 | 19 | 4682574 | Higher in Drinkers |
| cg10373779 | 14 | 90921475 | Higher in Drinkers |
| cg10376058 | 1 | 36690068 | Higher in Drinkers |
| cg10377629 | 17 | 1388950 | Higher in Drinkers |
| cg10380165 | 14 | 50360598 | Higher in Drinkers |
| cg10380362 | 6 | 30646949 | Higher in Drinkers |
| cg10389584 | 19 | 12512226 | Higher in Drinkers |

| | | | |
|---|---|---|---|
| cg10389930 | 19 | 11285331 | Higher in Drinkers |
| cg10391950 | 15 | 68871866 | Higher in Drinkers |
| cg10394610 | 2 | 234215963 | Lower in Drinkers |
| cg10395519 | 6 | 151412304 | Higher in Drinkers |
| cg10397389 | 4 | 100738011 | Higher in Drinkers |
| cg10400937 | 19 | 37329330 | Higher in Drinkers |
| cg10403109 | X | 150585864 | Higher in Drinkers |
| cg10404950 | 11 | 107436442 | Higher in Drinkers |
| cg10405239 | 17 | 26733360 | Higher in Drinkers |
| cg10406753 | 19 | 16582942 | Higher in Drinkers |
| cg10407847 | 16 | 28607531 | Higher in Drinkers |
| cg10410910 | 14 | 63684225 | Higher in Drinkers |
| cg10413291 | 14 | 21979401 | Higher in Drinkers |
| cg10415664 | 7 | 2029293 | Higher in Drinkers |
| cg10418263 | 6 | 35265544 | Higher in Drinkers |
| cg10419343 | 16 | 9102912 | Higher in Drinkers |
| cg10424462 | 11 | 73073652 | Lower in Drinkers |
| cg10429508 | 16 | 85608556 | Higher in Drinkers |
| cg10432360 | 21 | 45579863 | Higher in Drinkers |
| cg10432632 | 6 | 160182818 | Higher in Drinkers |
| cg10436286 | 16 | 32822392 | Higher in Drinkers |
| cg10438879 | 1 | 175130855 | Higher in Drinkers |
| cg10439691 | 13 | 114290256 | Higher in Drinkers |
| cg10444491 | 4 | 7394790 | Lower in Drinkers |
| cg10444928 | 1 | 150902534 | Higher in Drinkers |
| cg10446528 | 11 | 123612020 | Higher in Drinkers |
| cg10449070 | 12 | 112204506 | Higher in Drinkers |
| cg10454258 | 16 | 27443933 | Higher in Drinkers |
| cg10454268 | 11 | 59522542 | Higher in Drinkers |
| cg10456069 | 16 | 3551320 | Higher in Drinkers |
| cg10460813 | 16 | 87749116 | Lower in Drinkers |
| cg10462597 | 3 | 116996975 | Lower in Drinkers |
| cg10464535 | 12 | 70636491 | Higher in Drinkers |
| cg10466107 | 6 | 144607399 | Higher in Drinkers |
| cg10466369 | 16 | 70333434 | Higher in Drinkers |

| | | | |
|---|---|---|---|
| cg10469553 | 12 | 66696092 | Higher in Drinkers |
| cg10469980 | 16 | 85660101 | Higher in Drinkers |
| cg10470408 | 16 | 2285495 | Higher in Drinkers |
| cg10472244 | 3 | 53925831 | Higher in Drinkers |
| cg10473026 | 12 | 34531563 | Higher in Drinkers |
| cg10473508 | 5 | 172068142 | Higher in Drinkers |
| cg10475056 | 5 | 179473016 | Lower in Drinkers |
| cg10475433 | 16 | 71323603 | Higher in Drinkers |
| cg10475477 | 22 | 42196676 | Higher in Drinkers |
| cg10476584 | 17 | 77768722 | Higher in Drinkers |
| cg10477316 | 2 | 241512293 | Higher in Drinkers |
| cg10477603 | 10 | 126849704 | Higher in Drinkers |
| cg10479053 | 17 | 38136919 | Higher in Drinkers |
| cg10480741 | 19 | 46850482 | Higher in Drinkers |
| cg10484485 | 4 | 154387599 | Higher in Drinkers |
| cg10491544 | 10 | 120000926 | Higher in Drinkers |
| cg10494537 | 22 | 17700308 | Higher in Drinkers |
| cg10495754 | 17 | 27039058 | Higher in Drinkers |
| cg10496030 | 11 | 76510466 | Higher in Drinkers |
| cg10496619 | 6 | 151274597 | Higher in Drinkers |
| cg10496690 | 16 | 31724482 | Higher in Drinkers |
| cg10497569 | 6 | 57087038 | Higher in Drinkers |
| cg10498502 | 3 | 185928164 | Higher in Drinkers |
| cg10499166 | 1 | 23345815 | Higher in Drinkers |
| cg10500461 | 5 | 149110563 | Higher in Drinkers |
| cg10500474 | 6 | 32016473 | Higher in Drinkers |
| cg10500581 | 19 | 57998968 | Higher in Drinkers |
| cg10501065 | 11 | 2164976 | Higher in Drinkers |
| cg10501443 | X | 114468791 | Higher in Drinkers |
| cg10504545 | 14 | 74769802 | Higher in Drinkers |
| cg10507028 | 17 | 4981937 | Higher in Drinkers |
| cg10508940 | 22 | 50689915 | Higher in Drinkers |
| cg10511467 | 16 | 81529963 | Higher in Drinkers |
| cg10511618 | 4 | 113436232 | Higher in Drinkers |
| cg10513276 | 9 | 115095793 | Higher in Drinkers |

| | | | |
|---|---|---|---|
| cg10518000 | 14 | 20146493 | Higher in Drinkers |
| cg10518295 | 11 | 11833054 | Higher in Drinkers |
| cg10519406 | 1 | 197115545 | Higher in Drinkers |
| cg10519437 | 14 | 35184556 | Higher in Drinkers |
| cg10519680 | 8 | 37707506 | Higher in Drinkers |
| cg10524983 | 3 | 148708929 | Higher in Drinkers |
| cg10525574 | 12 | 95228036 | Lower in Drinkers |
| cg10525952 | 6 | 49494295 | Higher in Drinkers |
| cg10529930 | 20 | 5986407 | Higher in Drinkers |
| cg10531355 | 5 | 79489249 | Lower in Drinkers |
| cg10533277 | 5 | 176739312 | Higher in Drinkers |
| cg10536916 | 6 | 27841865 | Higher in Drinkers |
| cg10537936 | 17 | 41847146 | Higher in Drinkers |
| cg10539418 | 11 | 69455712 | Higher in Drinkers |
| cg10542336 | 7 | 158235891 | Lower in Drinkers |
| cg10550160 | 7 | 139044797 | Higher in Drinkers |
| cg10553515 | 7 | 5013490 | Higher in Drinkers |
| cg10557253 | 12 | 94543947 | Higher in Drinkers |
| cg10557552 | 14 | 102681613 | Higher in Drinkers |
| cg10569328 | 19 | 1848907 | Higher in Drinkers |
| cg10572951 | 1 | 154744863 | Higher in Drinkers |
| cg10575841 | 5 | 114961393 | Higher in Drinkers |
| cg10575846 | 11 | 476719 | Higher in Drinkers |
| cg10576516 | 17 | 73663407 | Higher in Drinkers |
| cg10577016 | 9 | 114423680 | Higher in Drinkers |
| cg10578681 | 1 | 213223453 | Higher in Drinkers |
| cg10580056 | 15 | 35086928 | Higher in Drinkers |
| cg10581071 | 5 | 10653304 | Higher in Drinkers |
| cg10583311 | 12 | 133082545 | Higher in Drinkers |
| cg10583683 | 15 | 23034700 | Higher in Drinkers |
| cg10585486 | 19 | 41304133 | Higher in Drinkers |
| cg10585584 | 8 | 135843842 | Higher in Drinkers |
| cg10586510 | 7 | 128829365 | Higher in Drinkers |
| cg10586903 | 19 | 41221192 | Higher in Drinkers |
| cg10588770 | 3 | 125314608 | Higher in Drinkers |

| | | | |
|---|---|---|---|
| cg10593493 | 12 | 54411753 | Higher in Drinkers |
| cg10596590 | 6 | 51814836 | Higher in Drinkers |
| cg10598871 | 11 | 119205542 | Higher in Drinkers |
| cg10600568 | 19 | 51611605 | Higher in Drinkers |
| cg10603824 | 17 | 48943588 | Higher in Drinkers |
| cg10604851 | 12 | 103344336 | Higher in Drinkers |
| cg10605724 | 21 | 47966967 | Higher in Drinkers |
| cg10605904 | 1 | 52498915 | Higher in Drinkers |
| cg10606534 | 16 | 66914374 | Higher in Drinkers |
| cg10608256 | 5 | 176046281 | Higher in Drinkers |
| cg10610348 | 19 | 2427956 | Higher in Drinkers |
| cg10619144 | 18 | 43677957 | Higher in Drinkers |
| cg10620501 | 8 | 37620046 | Higher in Drinkers |
| cg10620577 | 8 | 144994835 | Higher in Drinkers |
| cg10622271 | 12 | 50236974 | Higher in Drinkers |
| cg10632811 | 17 | 45918739 | Higher in Drinkers |
| cg10632894 | 6 | 32552453 | Lower in Drinkers |
| cg10633176 | 1 | 151254607 | Higher in Drinkers |
| cg10633619 | 17 | 28706427 | Higher in Drinkers |
| cg10634096 | 1 | 156475258 | Higher in Drinkers |
| cg10634185 | 9 | 73034988 | Higher in Drinkers |
| cg10635645 | 12 | 12938397 | Higher in Drinkers |
| cg10638415 | 19 | 56879369 | Higher in Drinkers |
| cg10639428 | 2 | 25138879 | Higher in Drinkers |
| cg10640371 | 21 | 35446012 | Higher in Drinkers |
| cg10642423 | 2 | 42588460 | Higher in Drinkers |
| cg10648125 | 15 | 28339979 | Higher in Drinkers |
| cg10648197 | 10 | 22634578 | Higher in Drinkers |
| cg10650915 | 6 | 32098218 | Higher in Drinkers |
| cg10651300 | 12 | 53661859 | Higher in Drinkers |
| cg10652641 | 6 | 31744962 | Higher in Drinkers |
| cg10656687 | 6 | 168707831 | Lower in Drinkers |
| cg10657986 | 3 | 53381859 | Higher in Drinkers |
| cg10663055 | 6 | 86159251 | Higher in Drinkers |
| cg10666628 | 5 | 179050666 | Higher in Drinkers |

| | | | |
|---|---|---|---|
| cg10669804 | 6 | 33177561 | Higher in Drinkers |
| cg10670748 | 13 | 31618743 | Higher in Drinkers |
| cg10671830 | 4 | 7652103 | Higher in Drinkers |
| cg10672880 | 8 | 145584004 | Higher in Drinkers |
| cg10673984 | 17 | 58677844 | Higher in Drinkers |
| cg10675453 | 6 | 41754588 | Higher in Drinkers |
| cg10680966 | 13 | 114114325 | Higher in Drinkers |
| cg10685128 | 4 | 141648570 | Lower in Drinkers |
| cg10686375 | 16 | 67464878 | Higher in Drinkers |
| cg10688323 | 15 | 31684499 | Higher in Drinkers |
| cg10693251 | 5 | 178977326 | Higher in Drinkers |
| cg10698549 | 1 | 24969970 | Higher in Drinkers |
| cg10701033 | 17 | 76676243 | Higher in Drinkers |
| cg10701051 | 19 | 38183360 | Higher in Drinkers |
| cg10709704 | X | 47518846 | Higher in Drinkers |
| cg10709785 | 16 | 32359756 | Higher in Drinkers |
| cg10710703 | 22 | 24093130 | Higher in Drinkers |
| cg10712116 | 17 | 74723362 | Higher in Drinkers |
| cg10712201 | 13 | 114797047 | Higher in Drinkers |
| cg10712263 | 17 | 58119753 | Higher in Drinkers |
| cg10712902 | 1 | 1458728 | Higher in Drinkers |
| cg10713951 | 4 | 7044983 | Higher in Drinkers |
| cg10714284 | 6 | 32908901 | Higher in Drinkers |
| cg10714329 | 7 | 100027122 | Higher in Drinkers |
| cg10714492 | 19 | 51321395 | Higher in Drinkers |
| cg10715699 | 6 | 7231665 | Higher in Drinkers |
| cg10717504 | 1 | 94054760 | Higher in Drinkers |
| cg10718618 | 1 | 228328583 | Higher in Drinkers |
| cg10718721 | 11 | 76156626 | Higher in Drinkers |
| cg10723012 | 17 | 79995434 | Lower in Drinkers |
| cg10723444 | 16 | 70100319 | Higher in Drinkers |
| cg10723556 | X | 49125646 | Higher in Drinkers |
| cg10728960 | 3 | 78079111 | Lower in Drinkers |
| cg10738016 | 6 | 160389796 | Higher in Drinkers |
| cg10745802 | 3 | 128445504 | Higher in Drinkers |

| | | | |
|---|---|---|---|
| cg10745988 | 14 | 104192620 | Higher in Drinkers |
| cg10746899 | 19 | 7997653 | Higher in Drinkers |
| cg10747266 | 6 | 31870263 | Higher in Drinkers |
| cg10752545 | 11 | 19734701 | Higher in Drinkers |
| cg10753889 | 11 | 116706520 | Higher in Drinkers |
| cg10755016 | 2 | 23607015 | Higher in Drinkers |
| cg10757684 | 16 | 21289555 | Higher in Drinkers |
| cg10760320 | 17 | 34257659 | Higher in Drinkers |
| cg10761088 | 1 | 21672318 | Higher in Drinkers |
| cg10764068 | 7 | 27289829 | Lower in Drinkers |
| cg10767687 | 5 | 79704443 | Higher in Drinkers |
| cg10769157 | 6 | 111197149 | Higher in Drinkers |
| cg10772210 | 14 | 24605565 | Higher in Drinkers |
| cg10772322 | 19 | 49116839 | Lower in Drinkers |
| cg10772699 | 3 | 42191047 | Higher in Drinkers |
| cg10774480 | 11 | 68191716 | Lower in Drinkers |
| cg10778619 | 12 | 70760907 | Higher in Drinkers |
| cg10781942 | 6 | 87723834 | Lower in Drinkers |
| cg10782218 | 17 | 61518489 | Higher in Drinkers |
| cg10782975 | 19 | 55954276 | Higher in Drinkers |
| cg10786572 | 10 | 54632322 | Higher in Drinkers |
| cg10787548 | 8 | 145064570 | Higher in Drinkers |
| cg10788213 | 22 | 45719176 | Lower in Drinkers |
| cg10788901 | 10 | 123353418 | Higher in Drinkers |
| cg10789151 | 20 | 33735143 | Higher in Drinkers |
| cg10792727 | 6 | 12013467 | Higher in Drinkers |
| cg10794915 | 17 | 33569985 | Higher in Drinkers |
| cg10796022 | 8 | 61227705 | Lower in Drinkers |
| cg10796099 | 5 | 102594140 | Higher in Drinkers |
| cg10797195 | 1 | 45805336 | Higher in Drinkers |
| cg10798292 | 1 | 202976329 | Higher in Drinkers |
| cg10800464 | 12 | 109162641 | Higher in Drinkers |
| cg10800953 | 3 | 184104380 | Lower in Drinkers |
| cg10804363 | 20 | 35580365 | Higher in Drinkers |
| cg10805082 | 1 | 179199199 | Higher in Drinkers |

| | | | |
|---|---|---|---|
| cg10809165 | 12 | 14909556 | Higher in Drinkers |
| cg10809622 | 6 | 167511399 | Lower in Drinkers |
| cg10818272 | 1 | 220263189 | Higher in Drinkers |
| cg10818901 | 4 | 739607 | Lower in Drinkers |
| cg10822352 | 10 | 13876378 | Higher in Drinkers |
| cg10826045 | 19 | 36631318 | Higher in Drinkers |
| cg10827226 | 1 | 20977640 | Higher in Drinkers |
| cg10829227 | 19 | 47200595 | Higher in Drinkers |
| cg10830758 | 10 | 95462430 | Higher in Drinkers |
| cg10830822 | 6 | 30483886 | Higher in Drinkers |
| cg10831504 | 12 | 69005104 | Higher in Drinkers |
| cg10832495 | 1 | 92952103 | Higher in Drinkers |
| cg10832949 | 6 | 45390783 | Higher in Drinkers |
| cg10833014 | 14 | 102605952 | Higher in Drinkers |
| cg10833114 | 12 | 72246108 | Higher in Drinkers |
| cg10833829 | 12 | 10368944 | Lower in Drinkers |
| cg10836034 | 8 | 128747871 | Higher in Drinkers |
| cg10842588 | 6 | 160468343 | Higher in Drinkers |
| cg10844382 | 20 | 828445 | Higher in Drinkers |
| cg10847032 | 5 | 142784522 | Higher in Drinkers |
| cg10848373 | 21 | 39047855 | Lower in Drinkers |
| cg10848882 | 20 | 39765963 | Higher in Drinkers |
| cg10850001 | 14 | 21152358 | Higher in Drinkers |
| cg10851071 | 4 | 148604791 | Higher in Drinkers |
| cg10851835 | 6 | 152623220 | Higher in Drinkers |
| cg10854610 | 19 | 53935034 | Higher in Drinkers |
| cg10854807 | 17 | 79479308 | Higher in Drinkers |
| cg10857387 | X | 148622612 | Higher in Drinkers |
| cg10859151 | 10 | 82297920 | Higher in Drinkers |
| cg10862620 | 17 | 37749866 | Lower in Drinkers |
| cg10865368 | 19 | 36134154 | Higher in Drinkers |
| cg10866461 | 17 | 30505327 | Higher in Drinkers |
| cg10867456 | 4 | 111614644 | Lower in Drinkers |
| cg10877241 | 13 | 52131904 | Higher in Drinkers |
| cg10879418 | 16 | 81479272 | Higher in Drinkers |

| | | | |
|---|---|---|---|
| cg10881306 | 2 | 36583600 | Higher in Drinkers |
| cg10883303 | 7 | 27239024 | Higher in Drinkers |
| cg10884975 | 1 | 213458566 | Higher in Drinkers |
| cg10887945 | 3 | 4805396 | Higher in Drinkers |
| cg10891888 | 12 | 46765615 | Higher in Drinkers |
| cg10892587 | 1 | 32666244 | Higher in Drinkers |
| cg10893370 | 17 | 30228961 | Higher in Drinkers |
| cg10897648 | 18 | 56338258 | Higher in Drinkers |
| cg10898607 | 3 | 101405733 | Higher in Drinkers |
| cg10898923 | 19 | 1940875 | Higher in Drinkers |
| cg10900696 | 8 | 24858119 | Higher in Drinkers |
| cg10900932 | 7 | 29604501 | Higher in Drinkers |
| cg10904699 | 11 | 123301490 | Higher in Drinkers |
| cg10905247 | 1 | 36023225 | Higher in Drinkers |
| cg10908196 | 16 | 4732911 | Higher in Drinkers |
| cg10910617 | 12 | 57039124 | Higher in Drinkers |
| cg10911063 | 3 | 75445095 | Lower in Drinkers |
| cg10911913 | 17 | 33700817 | Higher in Drinkers |
| cg10916494 | 6 | 86388066 | Higher in Drinkers |
| cg10919107 | 20 | 56229586 | Higher in Drinkers |
| cg10921517 | 11 | 1520881 | Higher in Drinkers |
| cg10921922 | 14 | 53174235 | Higher in Drinkers |
| cg10922622 | 9 | 103210153 | Higher in Drinkers |
| cg10924188 | 10 | 116698331 | Higher in Drinkers |
| cg10927068 | 5 | 94982715 | Higher in Drinkers |
| cg10927555 | 2 | 128458845 | Higher in Drinkers |
| cg10929299 | 14 | 50334860 | Higher in Drinkers |
| cg10929442 | 5 | 100236339 | Higher in Drinkers |
| cg10930260 | 14 | 58711355 | Higher in Drinkers |
| cg10932874 | 12 | 58135981 | Higher in Drinkers |
| cg10934032 | 14 | 21249405 | Higher in Drinkers |
| cg10936879 | 10 | 74397277 | Lower in Drinkers |
| cg10937494 | 17 | 80195101 | Higher in Drinkers |
| cg10945667 | 13 | 91999862 | Higher in Drinkers |
| cg10946038 | 5 | 14872384 | Higher in Drinkers |

| | | | |
|---|---|---|---|
| cg10947592 | 16 | 30583168 | Higher in Drinkers |
| cg10951305 | 6 | 31510149 | Higher in Drinkers |
| cg10951873 | 1 | 25254746 | Higher in Drinkers |
| cg10952663 | 22 | 38073334 | Higher in Drinkers |
| cg10952910 | 12 | 57623761 | Higher in Drinkers |
| cg10959786 | 13 | 74708124 | Higher in Drinkers |
| cg10963793 | 12 | 49111321 | Lower in Drinkers |
| cg10965384 | 11 | 64119977 | Higher in Drinkers |
| cg10965575 | 2 | 182321496 | Higher in Drinkers |
| cg10966208 | 4 | 866710 | Higher in Drinkers |
| cg10967178 | 1 | 6454278 | Higher in Drinkers |
| cg10967904 | 12 | 133340907 | Lower in Drinkers |
| cg10968756 | 10 | 102295843 | Higher in Drinkers |
| cg10969229 | 6 | 33385878 | Higher in Drinkers |
| cg10971638 | 6 | 170123105 | Higher in Drinkers |
| cg10977398 | 3 | 124606490 | Higher in Drinkers |
| cg10979742 | 10 | 71906521 | Higher in Drinkers |
| cg10980296 | 7 | 23636795 | Higher in Drinkers |
| cg10981500 | 5 | 865506 | Higher in Drinkers |
| cg10982567 | 10 | 104180479 | Higher in Drinkers |
| cg10982775 | 7 | 30067792 | Higher in Drinkers |
| cg10985576 | 20 | 44441519 | Higher in Drinkers |
| cg10986561 | 6 | 36954133 | Higher in Drinkers |
| cg10987503 | 7 | 922825 | Higher in Drinkers |
| cg10995422 | 6 | 32522872 | Higher in Drinkers |
| cg10995628 | 17 | 33288912 | Higher in Drinkers |
| cg10998744 | 22 | 30685926 | Higher in Drinkers |
| cg11009520 | 8 | 12052164 | Higher in Drinkers |
| cg11010380 | 7 | 101007190 | Higher in Drinkers |
| cg11011602 | 9 | 136215029 | Higher in Drinkers |
| cg11012078 | 13 | 103498143 | Higher in Drinkers |
| cg11015768 | 2 | 86106058 | Higher in Drinkers |
| cg11017226 | 10 | 61666667 | Higher in Drinkers |
| cg11017382 | 5 | 65892090 | Higher in Drinkers |
| cg11018313 | 15 | 85360052 | Higher in Drinkers |

| | | | |
|---|---|---|---|
| cg11027140 | 9 | 127212625 | Higher in Drinkers |
| cg11027637 | 6 | 139488309 | Higher in Drinkers |
| cg11033713 | 5 | 180688274 | Higher in Drinkers |
| cg11036315 | 7 | 636259 | Higher in Drinkers |
| cg11037719 | 6 | 2999695 | Higher in Drinkers |
| cg11039476 | 2 | 127978579 | Higher in Drinkers |
| cg11044575 | 6 | 105401636 | Higher in Drinkers |
| cg11044724 | 2 | 7005733 | Higher in Drinkers |
| cg11045165 | 6 | 31628348 | Higher in Drinkers |
| cg11047973 | 11 | 18034355 | Higher in Drinkers |
| cg11049323 | 11 | 71823943 | Higher in Drinkers |
| cg11050740 | 7 | 128784656 | Higher in Drinkers |
| cg11053574 | 17 | 39992149 | Higher in Drinkers |
| cg11055242 | 12 | 122255755 | Lower in Drinkers |
| cg11057497 | 5 | 43313384 | Higher in Drinkers |
| cg11061343 | 17 | 73993843 | Higher in Drinkers |
| cg11063938 | 19 | 46272660 | Higher in Drinkers |
| cg11064073 | 4 | 164253938 | Higher in Drinkers |
| cg11064537 | 21 | 48024639 | Lower in Drinkers |
| cg11065244 | 16 | 1980032 | Higher in Drinkers |
| cg11070000 | 14 | 64805073 | Higher in Drinkers |
| cg11070260 | 17 | 40713982 | Higher in Drinkers |
| cg11071146 | 22 | 38516736 | Higher in Drinkers |
| cg11072373 | 4 | 100485070 | Higher in Drinkers |
| cg11072887 | 6 | 37322624 | Higher in Drinkers |
| cg11075121 | 12 | 120967065 | Higher in Drinkers |
| cg11077561 | 3 | 197026019 | Higher in Drinkers |
| cg11079517 | X | 25039068 | Higher in Drinkers |
| cg11080085 | X | 117480243 | Higher in Drinkers |
| cg11082232 | 16 | 53089278 | Higher in Drinkers |
| cg11082565 | 17 | 883117 | Higher in Drinkers |
| cg11084266 | 1 | 156187819 | Higher in Drinkers |
| cg11084518 | 1 | 36644849 | Higher in Drinkers |
| cg11088931 | 19 | 6460274 | Higher in Drinkers |
| cg11089071 | 1 | 36397261 | Higher in Drinkers |

| | | | |
|---|---|---|---|
| cg11096441 | 20 | 49548515 | Higher in Drinkers |
| cg11100602 | 5 | 72497917 | Higher in Drinkers |
| cg11103442 | 1 | 1447201 | Higher in Drinkers |
| cg11104443 | 15 | 45021117 | Higher in Drinkers |
| cg11107430 | 10 | 105230660 | Higher in Drinkers |
| cg11110248 | 4 | 103682314 | Higher in Drinkers |
| cg11111740 | 6 | 28584288 | Higher in Drinkers |
| cg11112104 | 11 | 1088711 | Higher in Drinkers |
| cg11113589 | 21 | 46898764 | Higher in Drinkers |
| cg11114063 | 6 | 147524085 | Higher in Drinkers |
| cg11115211 | 3 | 67704890 | Higher in Drinkers |
| cg11116510 | 15 | 75095377 | Higher in Drinkers |
| cg11117896 | 2 | 220094984 | Higher in Drinkers |
| cg11118235 | 3 | 50284010 | Higher in Drinkers |
| cg11119655 | 10 | 46032202 | Higher in Drinkers |
| cg11124130 | 2 | 119067579 | Higher in Drinkers |
| cg11128045 | 9 | 140395219 | Higher in Drinkers |
| cg11129343 | 17 | 27711641 | Higher in Drinkers |
| cg11131811 | 20 | 30467696 | Higher in Drinkers |
| cg11134653 | 20 | 57599184 | Higher in Drinkers |
| cg11137277 | 1 | 234615236 | Higher in Drinkers |
| cg11138679 | 14 | 24740526 | Higher in Drinkers |
| cg11142013 | 13 | 24441476 | Higher in Drinkers |
| cg11150308 | 17 | 74068434 | Higher in Drinkers |
| cg11151021 | 12 | 68051567 | Higher in Drinkers |
| cg11152298 | 5 | 142783383 | Higher in Drinkers |
| cg11154719 | X | 153060450 | Lower in Drinkers |
| cg11158179 | 1 | 61543011 | Higher in Drinkers |
| cg11158239 | 12 | 7037742 | Higher in Drinkers |
| cg11160386 | 12 | 68725932 | Higher in Drinkers |
| cg11161828 | 11 | 128556865 | Higher in Drinkers |
| cg11161853 | 3 | 67705044 | Higher in Drinkers |
| cg11165479 | X | 49056505 | Higher in Drinkers |
| cg11166823 | 21 | 45284425 | Higher in Drinkers |
| cg11168004 | 4 | 13537759 | Higher in Drinkers |

| | | | |
|---|---|---|---|
| cg11171004 | 1 | 202779957 | Higher in Drinkers |
| cg11172332 | 14 | 105676791 | Higher in Drinkers |
| cg11172511 | 1 | 228328483 | Higher in Drinkers |
| cg11177107 | 1 | 228674909 | Higher in Drinkers |
| cg11178443 | 17 | 8192024 | Higher in Drinkers |
| cg11180364 | 10 | 97667244 | Higher in Drinkers |
| cg11193173 | 8 | 99837846 | Higher in Drinkers |
| cg11194725 | 17 | 46178360 | Higher in Drinkers |
| cg11196398 | 1 | 22815751 | Higher in Drinkers |
| cg11198734 | 3 | 53381585 | Higher in Drinkers |
| cg11199428 | 13 | 52027379 | Higher in Drinkers |
| cg11203927 | 22 | 41032991 | Higher in Drinkers |
| cg11204983 | 6 | 82957301 | Higher in Drinkers |
| cg11206576 | 22 | 46431712 | Higher in Drinkers |
| cg11206667 | 2 | 230786584 | Higher in Drinkers |
| cg11206724 | 13 | 114201583 | Higher in Drinkers |
| cg11207385 | 4 | 15781202 | Higher in Drinkers |
| cg11216502 | 21 | 40177847 | Higher in Drinkers |
| cg11216845 | 6 | 30028676 | Higher in Drinkers |
| cg11217367 | 8 | 1449655 | Lower in Drinkers |
| cg11217567 | 6 | 7390340 | Higher in Drinkers |
| cg11219400 | 3 | 36949966 | Higher in Drinkers |
| cg11220908 | 11 | 68541142 | Higher in Drinkers |
| cg11221200 | 2 | 242174625 | Higher in Drinkers |
| cg11224035 | 1 | 53704306 | Higher in Drinkers |
| cg11224232 | 1 | 153940272 | Higher in Drinkers |
| cg11226148 | 2 | 27485298 | Higher in Drinkers |
| cg11227559 | 5 | 10251089 | Higher in Drinkers |
| cg11229390 | 6 | 32122082 | Higher in Drinkers |
| cg11231977 | 16 | 75467423 | Higher in Drinkers |
| cg11235291 | 17 | 38804673 | Higher in Drinkers |
| cg11235543 | 10 | 131557193 | Higher in Drinkers |
| cg11244180 | 1 | 64669412 | Higher in Drinkers |
| cg11244648 | 12 | 149495 | Lower in Drinkers |
| cg11245657 | 1 | 11714873 | Higher in Drinkers |

| | | | |
|---|---|---|---|
| cg11245719 | 17 | 8194731 | Higher in Drinkers |
| cg11250194 | 11 | 61601937 | Higher in Drinkers |
| cg11251499 | 4 | 57774202 | Higher in Drinkers |
| cg11251991 | X | 41193241 | Higher in Drinkers |
| cg11252953 | 17 | 80358829 | Higher in Drinkers |
| cg11253425 | 1 | 244614453 | Higher in Drinkers |
| cg11254439 | 12 | 57335615 | Higher in Drinkers |
| cg11254573 | 8 | 1449634 | Lower in Drinkers |
| cg11255159 | 19 | 18401021 | Higher in Drinkers |
| cg11256364 | 7 | 114562847 | Higher in Drinkers |
| cg11257342 | 6 | 112408828 | Higher in Drinkers |
| cg11257689 | 10 | 116823300 | Higher in Drinkers |
| cg11261908 | 6 | 31697955 | Higher in Drinkers |
| cg11263011 | 17 | 6922223 | Higher in Drinkers |
| cg11263584 | 17 | 73008587 | Higher in Drinkers |
| cg11264711 | X | 67653315 | Higher in Drinkers |
| cg11265952 | 3 | 57231292 | Lower in Drinkers |
| cg11266874 | 3 | 93699352 | Higher in Drinkers |
| cg11267415 | 1 | 154975698 | Higher in Drinkers |
| cg11272200 | 2 | 198317968 | Higher in Drinkers |
| cg11272705 | 5 | 139127701 | Higher in Drinkers |
| cg11275626 | 17 | 47841347 | Higher in Drinkers |
| cg11276230 | 6 | 42713551 | Higher in Drinkers |
| cg11276438 | 1 | 11866529 | Higher in Drinkers |
| cg11277814 | 6 | 157721221 | Lower in Drinkers |
| cg11284231 | 13 | 20967659 | Higher in Drinkers |
| cg11284329 | 4 | 77870605 | Higher in Drinkers |
| cg11285937 | 4 | 39979757 | Higher in Drinkers |
| cg11287521 | 10 | 124134015 | Higher in Drinkers |
| cg11287903 | 10 | 115613834 | Higher in Drinkers |
| cg11292385 | 22 | 29138453 | Higher in Drinkers |
| cg11293610 | 21 | 34755681 | Higher in Drinkers |
| cg11299477 | 5 | 153859854 | Higher in Drinkers |
| cg11301598 | 12 | 121476792 | Higher in Drinkers |
| cg11303425 | 12 | 6798826 | Higher in Drinkers |

| | | | |
|---|---|---|---|
| cg11306428 | 19 | 56136210 | Higher in Drinkers |
| cg11310082 | 15 | 75744460 | Higher in Drinkers |
| cg11311499 | 2 | 47630845 | Higher in Drinkers |
| cg11321090 | 4 | 2415121 | Higher in Drinkers |
| cg11321144 | 4 | 151178020 | Higher in Drinkers |
| cg11325604 | 12 | 2999761 | Higher in Drinkers |
| cg11326134 | 3 | 193966634 | Higher in Drinkers |
| cg11334004 | 1 | 205561137 | Higher in Drinkers |
| cg11335119 | 17 | 80849289 | Higher in Drinkers |
| cg11335436 | 11 | 66360554 | Higher in Drinkers |
| cg11338420 | 8 | 144621219 | Higher in Drinkers |
| cg11339007 | 19 | 1249485 | Higher in Drinkers |
| cg11339587 | 19 | 30298341 | Higher in Drinkers |
| cg11339840 | 1 | 203596058 | Higher in Drinkers |
| cg11343811 | 12 | 132656966 | Higher in Drinkers |
| cg11353329 | 22 | 42764546 | Higher in Drinkers |
| cg11356950 | 4 | 1219707 | Higher in Drinkers |
| cg11359684 | 2 | 153192532 | Higher in Drinkers |
| cg11362192 | 13 | 50069489 | Higher in Drinkers |
| cg11362820 | 15 | 41234614 | Higher in Drinkers |
| cg11363701 | 15 | 64171061 | Higher in Drinkers |
| cg11367841 | 11 | 47270567 | Higher in Drinkers |
| cg11368597 | 3 | 183415483 | Higher in Drinkers |
| cg11369148 | 20 | 25176157 | Higher in Drinkers |
| cg11373563 | 7 | 4798018 | Higher in Drinkers |
| cg11373810 | 20 | 1306281 | Higher in Drinkers |
| cg11374732 | 2 | 234113197 | Higher in Drinkers |
| cg11378575 | 2 | 232265004 | Higher in Drinkers |
| cg11380667 | 1 | 4749165 | Lower in Drinkers |
| cg11382291 | 4 | 160024674 | Higher in Drinkers |
| cg11385165 | 10 | 105388937 | Higher in Drinkers |
| cg11387131 | 11 | 128761211 | Higher in Drinkers |
| cg11387577 | 6 | 146285424 | Higher in Drinkers |
| cg11388507 | 10 | 102027143 | Higher in Drinkers |
| cg11390957 | 10 | 118033312 | Higher in Drinkers |

| | | | |
|---|---|---|---|
| cg11392389 | 12 | 13153689 | Higher in Drinkers |
| cg11392765 | 4 | 13546673 | Higher in Drinkers |
| cg11396485 | 6 | 161413484 | Higher in Drinkers |
| cg11398680 | 8 | 142011853 | Higher in Drinkers |
| cg11399508 | 21 | 38580484 | Higher in Drinkers |
| cg11401682 | 6 | 31830616 | Higher in Drinkers |
| cg11402396 | 10 | 13364856 | Higher in Drinkers |
| cg11404129 | 1 | 150484766 | Lower in Drinkers |
| cg11412036 | 15 | 43941871 | Higher in Drinkers |
| cg11413715 | 19 | 37263704 | Higher in Drinkers |
| cg11416620 | 2 | 129072147 | Higher in Drinkers |
| cg11420782 | 22 | 36598213 | Higher in Drinkers |
| cg11425737 | 22 | 47255697 | Higher in Drinkers |
| cg11429746 | 4 | 120373434 | Higher in Drinkers |
| cg11433608 | 17 | 19246574 | Higher in Drinkers |
| cg11439186 | 3 | 186648857 | Higher in Drinkers |
| cg11439671 | 17 | 73515429 | Higher in Drinkers |
| cg11442185 | 12 | 56693681 | Higher in Drinkers |
| cg11443787 | 10 | 21322403 | Higher in Drinkers |
| cg11455018 | 16 | 30709778 | Higher in Drinkers |
| cg11457044 | 2 | 197664369 | Higher in Drinkers |
| cg11458642 | 3 | 142297295 | Higher in Drinkers |
| cg11461308 | 20 | 5936712 | Higher in Drinkers |
| cg11463271 | 5 | 176936892 | Higher in Drinkers |
| cg11466815 | 5 | 55008477 | Higher in Drinkers |
| cg11468233 | 7 | 102920980 | Higher in Drinkers |
| cg11470399 | 16 | 23690492 | Higher in Drinkers |
| cg11474075 | 14 | 20773935 | Higher in Drinkers |
| cg11474888 | 11 | 73490776 | Higher in Drinkers |
| cg11477847 | 17 | 4693856 | Higher in Drinkers |
| cg11480830 | 2 | 193175037 | Higher in Drinkers |
| cg11481582 | 10 | 74080805 | Higher in Drinkers |
| cg11485154 | 11 | 46265393 | Higher in Drinkers |
| cg11487705 | 5 | 41870746 | Higher in Drinkers |
| cg11489580 | 4 | 76598793 | Higher in Drinkers |

| | | | |
|---|---|---|---|
| cg11491074 | 3 | 52008944 | Higher in Drinkers |
| cg11492896 | 2 | 32581942 | Higher in Drinkers |
| cg11494123 | 11 | 66726233 | Higher in Drinkers |
| cg11496438 | 7 | 25164549 | Higher in Drinkers |
| cg11498870 | 8 | 88886243 | Lower in Drinkers |
| cg11504408 | 2 | 201375037 | Higher in Drinkers |
| cg11505240 | 12 | 6832856 | Higher in Drinkers |
| cg11507178 | 11 | 118781515 | Higher in Drinkers |
| cg11514184 | 1 | 161015941 | Higher in Drinkers |
| cg11514301 | 17 | 42267990 | Higher in Drinkers |
| cg11516606 | 9 | 100175029 | Higher in Drinkers |
| cg11518421 | 5 | 137667529 | Higher in Drinkers |
| cg11518945 | 13 | 44454179 | Higher in Drinkers |
| cg11522265 | 1 | 11333852 | Higher in Drinkers |
| cg11523147 | 16 | 11762212 | Higher in Drinkers |
| cg11526462 | 6 | 30309578 | Lower in Drinkers |
| cg11527656 | 7 | 1544006 | Higher in Drinkers |
| cg11528914 | 5 | 169724768 | Higher in Drinkers |
| cg11529614 | 17 | 59941050 | Higher in Drinkers |
| cg11530914 | 16 | 67281528 | Higher in Drinkers |
| cg11536601 | 5 | 162991542 | Higher in Drinkers |
| cg11540007 | 2 | 145274975 | Higher in Drinkers |
| cg11544721 | 5 | 89705346 | Higher in Drinkers |
| cg11547895 | 7 | 100487657 | Higher in Drinkers |
| cg11551419 | 20 | 30311239 | Higher in Drinkers |
| cg11552077 | 2 | 1607204 | Higher in Drinkers |
| cg11552829 | 5 | 169532721 | Lower in Drinkers |
| cg11553066 | 22 | 44420757 | Higher in Drinkers |
| cg11555067 | 2 | 99081350 | Lower in Drinkers |
| cg11555335 | 2 | 242175421 | Lower in Drinkers |
| cg11558591 | 22 | 21356472 | Higher in Drinkers |
| cg11565585 | 6 | 31926279 | Higher in Drinkers |
| cg11569431 | 19 | 45540995 | Higher in Drinkers |
| cg11570697 | 19 | 649464 | Higher in Drinkers |
| cg11571304 | 6 | 25963022 | Higher in Drinkers |

| | | | |
|---|---|---|---|
| cg11572308 | 4 | 658870 | Higher in Drinkers |
| cg11572381 | 19 | 10827337 | Lower in Drinkers |
| cg11573518 | 7 | 73721031 | Higher in Drinkers |
| cg11574180 | 3 | 37217996 | Higher in Drinkers |
| cg11574612 | 6 | 46620502 | Higher in Drinkers |
| cg11575047 | 12 | 120639236 | Higher in Drinkers |
| cg11585022 | 5 | 110427346 | Lower in Drinkers |
| cg11585280 | 1 | 25292059 | Lower in Drinkers |
| cg11585893 | 12 | 54447430 | Higher in Drinkers |
| cg11585955 | 11 | 18127525 | Higher in Drinkers |
| cg11586519 | 1 | 1509833 | Higher in Drinkers |
| cg11587640 | 1 | 27959253 | Higher in Drinkers |
| cg11588270 | 12 | 112545924 | Higher in Drinkers |
| cg11589573 | 19 | 45681968 | Higher in Drinkers |
| cg11590772 | 19 | 865916 | Higher in Drinkers |
| cg11591535 | 6 | 170755857 | Lower in Drinkers |
| cg11594131 | 2 | 61765360 | Higher in Drinkers |
| cg11594892 | 1 | 150849332 | Higher in Drinkers |
| cg11595794 | 4 | 186317094 | Higher in Drinkers |
| cg11596397 | 11 | 75526167 | Higher in Drinkers |
| cg11599469 | 2 | 241069399 | Higher in Drinkers |
| cg11599981 | 19 | 6475902 | Higher in Drinkers |
| cg11604272 | 11 | 65769511 | Higher in Drinkers |
| cg11607196 | 20 | 44572160 | Higher in Drinkers |
| cg11609472 | 17 | 61895513 | Higher in Drinkers |
| cg11620557 | X | 39963545 | Higher in Drinkers |
| cg11621808 | 7 | 20369301 | Higher in Drinkers |
| cg11624479 | 11 | 9285586 | Higher in Drinkers |
| cg11628076 | 6 | 127583115 | Higher in Drinkers |
| cg11629900 | 6 | 35056069 | Higher in Drinkers |
| cg11631707 | 20 | 6022873 | Higher in Drinkers |
| cg11632238 | 3 | 44040539 | Higher in Drinkers |
| cg11637102 | 6 | 30521159 | Higher in Drinkers |
| cg11637789 | 8 | 145621586 | Higher in Drinkers |
| cg11638071 | 17 | 56405967 | Higher in Drinkers |

| | | | |
|---|---|---|---|
| cg11638842 | 2 | 238343702 | Higher in Drinkers |
| cg11644817 | 17 | 72206742 | Higher in Drinkers |
| cg11646757 | 7 | 128095699 | Higher in Drinkers |
| cg11649654 | 5 | 60240952 | Higher in Drinkers |
| cg11650218 | 12 | 22778020 | Higher in Drinkers |
| cg11652947 | 17 | 80605508 | Higher in Drinkers |
| cg11654737 | 6 | 80816077 | Higher in Drinkers |
| cg11660018 | 11 | 86510915 | Lower in Drinkers |
| cg11663780 | 19 | 1001892 | Higher in Drinkers |
| cg11671913 | 5 | 43017685 | Higher in Drinkers |
| cg11673969 | 7 | 100424945 | Higher in Drinkers |
| cg11674773 | 1 | 54518492 | Higher in Drinkers |
| cg11678610 | 1 | 226313167 | Higher in Drinkers |
| cg11679298 | 20 | 5931834 | Higher in Drinkers |
| cg11682350 | 6 | 33240284 | Higher in Drinkers |
| cg11691189 | 2 | 47743741 | Higher in Drinkers |
| cg11693986 | 7 | 100805303 | Higher in Drinkers |
| cg11694634 | 20 | 18447695 | Higher in Drinkers |
| cg11695601 | 2 | 175870435 | Higher in Drinkers |
| cg11696986 | 7 | 20837778 | Higher in Drinkers |
| cg11698469 | 1 | 15943714 | Higher in Drinkers |
| cg11698762 | 2 | 74648964 | Higher in Drinkers |
| cg11699334 | 12 | 109195889 | Higher in Drinkers |
| cg11699826 | 1 | 26438425 | Higher in Drinkers |
| cg11704012 | 12 | 6561007 | Higher in Drinkers |
| cg11704435 | 12 | 133281175 | Lower in Drinkers |
| cg11706349 | 6 | 36646226 | Higher in Drinkers |
| cg11710924 | 2 | 32503219 | Higher in Drinkers |
| cg11712458 | 15 | 101835094 | Higher in Drinkers |
| cg11713029 | 11 | 118368622 | Higher in Drinkers |
| cg11715575 | 7 | 102036991 | Higher in Drinkers |
| cg11716270 | 1 | 39025311 | Higher in Drinkers |
| cg11716884 | 19 | 4947182 | Higher in Drinkers |
| cg11717557 | 1 | 114448153 | Higher in Drinkers |
| cg11718113 | 1 | 16011424 | Higher in Drinkers |

| | | | |
|---|---|---|---|
| cg11718206 | 1 | 233431520 | Higher in Drinkers |
| cg11721361 | 1 | 145139908 | Higher in Drinkers |
| cg11721913 | 10 | 102825997 | Higher in Drinkers |
| cg11726631 | 1 | 955757 | Higher in Drinkers |
| cg11726658 | 7 | 2585709 | Higher in Drinkers |
| cg11726986 | 11 | 33182894 | Higher in Drinkers |
| cg11731892 | 2 | 98207378 | Higher in Drinkers |
| cg11732257 | 1 | 235492059 | Higher in Drinkers |
| cg11734790 | 6 | 126070235 | Higher in Drinkers |
| cg11737334 | 19 | 17862210 | Higher in Drinkers |
| cg11740690 | 5 | 176943526 | Higher in Drinkers |
| cg11744300 | 17 | 635960 | Higher in Drinkers |
| cg11747081 | 13 | 76444823 | Higher in Drinkers |
| cg11748904 | 20 | 35422334 | Higher in Drinkers |
| cg11748936 | 14 | 75593738 | Higher in Drinkers |
| cg11751545 | 11 | 126434315 | Lower in Drinkers |
| cg11752829 | 6 | 32797232 | Higher in Drinkers |
| cg11754995 | 8 | 90914634 | Higher in Drinkers |
| cg11756136 | 10 | 17243337 | Higher in Drinkers |
| cg11756837 | 12 | 120105372 | Higher in Drinkers |
| cg11760602 | 12 | 9800555 | Higher in Drinkers |
| cg11762018 | 19 | 16394574 | Higher in Drinkers |
| cg11769086 | 1 | 153700382 | Higher in Drinkers |
| cg11769456 | 2 | 241938159 | Higher in Drinkers |
| cg11773933 | 5 | 139737513 | Higher in Drinkers |
| cg11776003 | 15 | 98835651 | Higher in Drinkers |
| cg11780382 | 6 | 24719812 | Higher in Drinkers |
| cg11783264 | 19 | 1905046 | Higher in Drinkers |
| cg11784191 | 19 | 56170509 | Higher in Drinkers |
| cg11785574 | 1 | 241803680 | Higher in Drinkers |
| cg11789281 | 8 | 12573583 | Lower in Drinkers |
| cg11794728 | 13 | 74707860 | Higher in Drinkers |
| cg11794881 | 1 | 112282243 | Higher in Drinkers |
| cg11795674 | 10 | 99392930 | Higher in Drinkers |
| cg11799172 | 10 | 31607441 | Higher in Drinkers |

| | | | |
|---|---|---|---|
| cg11802732 | 17 | 2206917 | Higher in Drinkers |
| cg11802797 | 1 | 10437649 | Higher in Drinkers |
| cg11807942 | 19 | 652937 | Higher in Drinkers |
| cg11810988 | 2 | 6635591 | Higher in Drinkers |
| cg11816918 | 18 | 2656305 | Higher in Drinkers |
| cg11817999 | 17 | 17655531 | Higher in Drinkers |
| cg11819013 | 3 | 49066976 | Higher in Drinkers |
| cg11819707 | 17 | 36507992 | Higher in Drinkers |
| cg11820605 | 11 | 68519066 | Higher in Drinkers |
| cg11823214 | 1 | 163291487 | Higher in Drinkers |
| cg11823654 | 15 | 65117936 | Higher in Drinkers |
| cg11823921 | 7 | 100170929 | Higher in Drinkers |
| cg11824693 | 6 | 33178473 | Higher in Drinkers |
| cg11824945 | 1 | 211519171 | Higher in Drinkers |
| cg11825020 | 15 | 90118707 | Higher in Drinkers |
| cg11826104 | 15 | 25650611 | Higher in Drinkers |
| cg11828430 | 1 | 173446242 | Higher in Drinkers |
| cg11830346 | 14 | 105262276 | Higher in Drinkers |
| cg11839944 | 11 | 17409644 | Lower in Drinkers |
| cg11840540 | 19 | 35644996 | Higher in Drinkers |
| cg11841062 | 1 | 172502778 | Higher in Drinkers |
| cg11843948 | 7 | 5410861 | Lower in Drinkers |
| cg11844110 | 1 | 208042623 | Higher in Drinkers |
| cg11844737 | X | 40037471 | Higher in Drinkers |
| cg11846097 | 21 | 38640053 | Higher in Drinkers |
| cg11850276 | 5 | 126409553 | Higher in Drinkers |
| cg11850311 | 20 | 30192545 | Higher in Drinkers |
| cg11854877 | X | 154114544 | Higher in Drinkers |
| cg11856487 | 1 | 43219796 | Higher in Drinkers |
| cg11857246 | 1 | 11741390 | Higher in Drinkers |
| cg11861730 | 11 | 128392683 | Higher in Drinkers |
| cg11862246 | 15 | 78730200 | Higher in Drinkers |
| cg11862491 | 15 | 78799806 | Higher in Drinkers |
| cg11862779 | 8 | 56757013 | Higher in Drinkers |
| cg11865578 | 3 | 47043996 | Lower in Drinkers |

| | | | |
|---|---|---|---|
| cg11866527 | 2 | 65215494 | Higher in Drinkers |
| cg11872443 | 4 | 178417872 | Higher in Drinkers |
| cg11875085 | 8 | 145747739 | Higher in Drinkers |
| cg11875773 | 22 | 50468633 | Higher in Drinkers |
| cg11878319 | 14 | 104313870 | Higher in Drinkers |
| cg11881599 | 12 | 92814084 | Higher in Drinkers |
| cg11881702 | 14 | 102510689 | Higher in Drinkers |
| cg11885407 | 3 | 193310886 | Higher in Drinkers |
| cg11886511 | 14 | 45722532 | Higher in Drinkers |
| cg11888235 | 19 | 13001884 | Higher in Drinkers |
| cg11890080 | 12 | 123458847 | Higher in Drinkers |
| cg11893139 | 12 | 125598269 | Higher in Drinkers |
| cg11899895 | 7 | 27779695 | Higher in Drinkers |
| cg11907102 | 2 | 201936469 | Higher in Drinkers |
| cg11909137 | 18 | 46461202 | Higher in Drinkers |
| cg11912956 | 7 | 73588697 | Higher in Drinkers |
| cg11914659 | 5 | 180670379 | Higher in Drinkers |
| cg11915218 | 17 | 40335849 | Higher in Drinkers |
| cg11916186 | 1 | 36669760 | Higher in Drinkers |
| cg11918822 | 19 | 50479865 | Higher in Drinkers |
| cg11924806 | 4 | 41875875 | Higher in Drinkers |
| cg11926166 | 1 | 94344604 | Higher in Drinkers |
| cg11926393 | 8 | 71519704 | Higher in Drinkers |
| cg11935027 | 4 | 119200246 | Higher in Drinkers |
| cg11935317 | 2 | 170551099 | Higher in Drinkers |
| cg11937392 | 6 | 28806266 | Higher in Drinkers |
| cg11945235 | 19 | 52552025 | Higher in Drinkers |
| cg11947509 | 2 | 202898349 | Higher in Drinkers |
| cg11947960 | 2 | 112655492 | Higher in Drinkers |
| cg11951844 | 17 | 29378126 | Lower in Drinkers |
| cg11953541 | 1 | 42800229 | Higher in Drinkers |
| cg11956111 | 2 | 74710460 | Higher in Drinkers |
| cg11956146 | 18 | 21718974 | Higher in Drinkers |
| cg11956930 | 8 | 99162490 | Higher in Drinkers |
| cg11957798 | 19 | 2246864 | Lower in Drinkers |

| | | | |
|---|---|---|---|
| cg11958495 | 1 | 167409198 | Higher in Drinkers |
| cg11958594 | 17 | 80055299 | Higher in Drinkers |
| cg11959007 | 13 | 76432094 | Lower in Drinkers |
| cg11961288 | 19 | 45681945 | Higher in Drinkers |
| cg11967103 | 11 | 72004321 | Higher in Drinkers |
| cg11967765 | 7 | 2774195 | Higher in Drinkers |
| cg11967888 | 18 | 59561221 | Higher in Drinkers |
| cg11968366 | 22 | 38200894 | Higher in Drinkers |
| cg11969002 | 6 | 30712282 | Higher in Drinkers |
| cg11970458 | 16 | 31213481 | Higher in Drinkers |
| cg11971248 | 4 | 84203337 | Higher in Drinkers |
| cg11973244 | 11 | 31832367 | Higher in Drinkers |
| cg11973514 | 1 | 244004889 | Higher in Drinkers |
| cg11973877 | 1 | 52195423 | Higher in Drinkers |
| cg11974956 | 6 | 89673528 | Higher in Drinkers |
| cg11979621 | 7 | 155562188 | Higher in Drinkers |
| cg11980481 | 9 | 132605210 | Higher in Drinkers |
| cg11980897 | 1 | 32237457 | Higher in Drinkers |
| cg11982736 | 6 | 43276570 | Higher in Drinkers |
| cg11992241 | 17 | 7036993 | Higher in Drinkers |
| cg11992317 | 20 | 44520160 | Higher in Drinkers |
| cg11995069 | 11 | 47600522 | Higher in Drinkers |
| cg11995741 | 6 | 166797367 | Higher in Drinkers |
| cg12022772 | 2 | 131130468 | Higher in Drinkers |
| cg12024987 | 19 | 6737490 | Higher in Drinkers |
| cg12026956 | 5 | 72112008 | Higher in Drinkers |
| cg12028326 | 19 | 523360 | Lower in Drinkers |
| cg12032396 | 4 | 7057462 | Higher in Drinkers |
| cg12033273 | 1 | 155247785 | Higher in Drinkers |
| cg12034199 | 7 | 75045307 | Higher in Drinkers |
| cg12034297 | 1 | 160137816 | Lower in Drinkers |
| cg12036292 | 4 | 184319704 | Higher in Drinkers |
| cg12039664 | 20 | 61148894 | Higher in Drinkers |
| cg12043106 | 10 | 131909379 | Higher in Drinkers |
| cg12043473 | 7 | 66750978 | Higher in Drinkers |

| | | | |
|---|---|---|---|
| cg12044785 | 1 | 165600491 | Higher in Drinkers |
| cg12046375 | 1 | 150459886 | Higher in Drinkers |
| cg12052812 | 1 | 230778592 | Higher in Drinkers |
| cg12053291 | 12 | 125282342 | Higher in Drinkers |
| cg12054080 | 1 | 220446043 | Higher in Drinkers |
| cg12054421 | 2 | 242090264 | Higher in Drinkers |
| cg12054566 | X | 70752964 | Higher in Drinkers |
| cg12055316 | 2 | 27601353 | Higher in Drinkers |
| cg12055421 | 2 | 74685521 | Higher in Drinkers |
| cg12056618 | 15 | 31619949 | Higher in Drinkers |
| cg12056977 | 12 | 71003625 | Higher in Drinkers |
| cg12062324 | 3 | 178789534 | Higher in Drinkers |
| cg12063580 | 14 | 105783627 | Higher in Drinkers |
| cg12063910 | 9 | 115513525 | Higher in Drinkers |
| cg12064195 | 22 | 47367756 | Higher in Drinkers |
| cg12064202 | 6 | 31038842 | Higher in Drinkers |
| cg12066905 | 13 | 25497207 | Higher in Drinkers |
| cg12068088 | 12 | 34538734 | Lower in Drinkers |
| cg12069925 | 17 | 11900858 | Higher in Drinkers |
| cg12070152 | 1 | 40421272 | Higher in Drinkers |
| cg12074585 | 12 | 7280958 | Lower in Drinkers |
| cg12074707 | 1 | 27019787 | Higher in Drinkers |
| cg12074883 | 6 | 29591155 | Higher in Drinkers |
| cg12074981 | 18 | 43547177 | Higher in Drinkers |
| cg12075144 | 3 | 155588060 | Higher in Drinkers |
| cg12076664 | 1 | 85667454 | Higher in Drinkers |
| cg12077818 | 1 | 44116508 | Higher in Drinkers |
| cg12078092 | 4 | 8378947 | Higher in Drinkers |
| cg12079362 | 1 | 44440160 | Higher in Drinkers |
| cg12079923 | 19 | 53898156 | Higher in Drinkers |
| cg12080715 | 7 | 77325545 | Higher in Drinkers |
| cg12084411 | 6 | 30180789 | Higher in Drinkers |
| cg12092932 | 1 | 198128390 | Higher in Drinkers |
| cg12096988 | 19 | 57702809 | Higher in Drinkers |
| cg12100077 | 7 | 23145212 | Higher in Drinkers |

| | | | |
|---|---|---|---|
| cg12109141 | 4 | 1225729 | Higher in Drinkers |
| cg12113932 | 20 | 388401 | Higher in Drinkers |
| cg12115567 | 11 | 6255973 | Higher in Drinkers |
| cg12115800 | 3 | 73144435 | Higher in Drinkers |
| cg12120457 | 12 | 54120876 | Higher in Drinkers |
| cg12131826 | 15 | 77904385 | Higher in Drinkers |
| cg12133754 | 8 | 134087221 | Higher in Drinkers |
| cg12136126 | 11 | 124823738 | Higher in Drinkers |
| cg12137530 | 19 | 13227698 | Higher in Drinkers |
| cg12139329 | 15 | 63481838 | Higher in Drinkers |
| cg12144689 | 22 | 24820090 | Higher in Drinkers |
| cg12145080 | 2 | 223289560 | Higher in Drinkers |
| cg12148714 | 16 | 69345699 | Higher in Drinkers |
| cg12149905 | 3 | 61547208 | Higher in Drinkers |
| cg12152256 | 14 | 74353709 | Higher in Drinkers |
| cg12152938 | 12 | 76478905 | Higher in Drinkers |
| cg12162751 | 11 | 111944894 | Higher in Drinkers |
| cg12163952 | 2 | 201983233 | Higher in Drinkers |
| cg12164614 | 17 | 40262500 | Higher in Drinkers |
| cg12165772 | 17 | 48070354 | Higher in Drinkers |
| cg12171481 | X | 30907692 | Higher in Drinkers |
| cg12173620 | 19 | 49956415 | Higher in Drinkers |
| cg12175382 | 6 | 170862476 | Higher in Drinkers |
| cg12176933 | X | 70586753 | Higher in Drinkers |
| cg12177454 | X | 100877938 | Higher in Drinkers |
| cg12177942 | 1 | 11120465 | Higher in Drinkers |
| cg12178316 | 15 | 22944125 | Higher in Drinkers |
| cg12183875 | 3 | 169587454 | Higher in Drinkers |
| cg12187213 | 3 | 64673741 | Higher in Drinkers |
| cg12187437 | 12 | 66524584 | Higher in Drinkers |
| cg12188830 | 3 | 57741926 | Higher in Drinkers |
| cg12188928 | 17 | 27309139 | Higher in Drinkers |
| cg12189851 | 19 | 36486603 | Higher in Drinkers |
| cg12190423 | 3 | 9834444 | Higher in Drinkers |
| cg12191422 | 10 | 112631258 | Higher in Drinkers |

| | | | |
|---|---|---|---|
| cg12196901 | 17 | 26630081 | Lower in Drinkers |
| cg12198157 | 3 | 134204547 | Higher in Drinkers |
| cg12204245 | 13 | 114321214 | Higher in Drinkers |
| cg12204897 | 9 | 131486753 | Higher in Drinkers |
| cg12208770 | 1 | 1361666 | Higher in Drinkers |
| cg12210363 | 21 | 35987579 | Higher in Drinkers |
| cg12210770 | 17 | 8022010 | Higher in Drinkers |
| cg12213811 | 12 | 122251152 | Higher in Drinkers |
| cg12214673 | 3 | 196159430 | Higher in Drinkers |
| cg12219531 | 12 | 120966889 | Higher in Drinkers |
| cg12219963 | 12 | 109745037 | Lower in Drinkers |
| cg12220871 | 15 | 43658652 | Higher in Drinkers |
| cg12221212 | 1 | 156474724 | Higher in Drinkers |
| cg12223997 | 11 | 9159596 | Higher in Drinkers |
| cg12224633 | 6 | 34393398 | Higher in Drinkers |
| cg12228611 | 22 | 22020169 | Higher in Drinkers |
| cg12229081 | 16 | 24741196 | Higher in Drinkers |
| cg12232110 | 11 | 121163509 | Higher in Drinkers |
| cg12232373 | 17 | 3563924 | Higher in Drinkers |
| cg12232903 | 4 | 10686413 | Higher in Drinkers |
| cg12233786 | 15 | 51200822 | Higher in Drinkers |
| cg12234392 | 10 | 86998609 | Higher in Drinkers |
| cg12234533 | 3 | 41999075 | Higher in Drinkers |
| cg12234762 | 7 | 1018901 | Lower in Drinkers |
| cg12236003 | 19 | 49588359 | Higher in Drinkers |
| cg12239861 | 3 | 101683592 | Higher in Drinkers |
| cg12239995 | 7 | 635869 | Higher in Drinkers |
| cg12240767 | 19 | 12098572 | Higher in Drinkers |
| cg12241125 | 7 | 73589459 | Higher in Drinkers |
| cg12243255 | 3 | 39194549 | Higher in Drinkers |
| cg12243333 | 2 | 27652320 | Higher in Drinkers |
| cg12245402 | 6 | 30585421 | Higher in Drinkers |
| cg12245530 | 17 | 46178618 | Higher in Drinkers |
| cg12247545 | 10 | 134351165 | Higher in Drinkers |
| cg12249359 | 22 | 42296941 | Higher in Drinkers |

| | | | |
|---|---|---|---|
| cg12251571 | 13 | 113260912 | Higher in Drinkers |
| cg12253543 | 4 | 144434958 | Higher in Drinkers |
| cg12254454 | 22 | 19467326 | Higher in Drinkers |
| cg12255062 | 6 | 32138332 | Higher in Drinkers |
| cg12260435 | 2 | 202484156 | Higher in Drinkers |
| cg12262427 | 7 | 77166345 | Higher in Drinkers |
| cg12265959 | 8 | 11324687 | Higher in Drinkers |
| cg12267497 | 8 | 11053804 | Higher in Drinkers |
| cg12271332 | 8 | 67579608 | Higher in Drinkers |
| cg12271581 | 19 | 45394330 | Higher in Drinkers |
| cg12275370 | 2 | 10425661 | Higher in Drinkers |
| cg12276487 | 1 | 155214425 | Higher in Drinkers |
| cg12282311 | 2 | 95830943 | Higher in Drinkers |
| cg12283674 | 19 | 54693798 | Higher in Drinkers |
| cg12288074 | 5 | 10354432 | Higher in Drinkers |
| cg12291552 | 3 | 16781364 | Higher in Drinkers |
| cg12293275 | 1 | 44115487 | Higher in Drinkers |
| cg12294026 | 5 | 14452155 | Higher in Drinkers |
| cg12294817 | 10 | 126480145 | Higher in Drinkers |
| cg12296644 | 1 | 145516322 | Higher in Drinkers |
| cg12298140 | 22 | 29168611 | Higher in Drinkers |
| cg12300511 | 20 | 2854049 | Higher in Drinkers |
| cg12302830 | 20 | 33297742 | Higher in Drinkers |
| cg12308164 | 11 | 1315468 | Higher in Drinkers |
| cg12309938 | 13 | 98968161 | Lower in Drinkers |
| cg12314510 | 17 | 56161063 | Higher in Drinkers |
| cg12317676 | 19 | 10981810 | Higher in Drinkers |
| cg12323850 | 11 | 94245795 | Higher in Drinkers |
| cg12323884 | 15 | 70392862 | Higher in Drinkers |
| cg12330031 | 22 | 50324138 | Higher in Drinkers |
| cg12335136 | 15 | 82554902 | Higher in Drinkers |
| cg12339809 | 18 | 33709507 | Higher in Drinkers |
| cg12344004 | 15 | 89877906 | Higher in Drinkers |
| cg12347429 | 6 | 21666834 | Higher in Drinkers |
| cg12349030 | 11 | 3818695 | Higher in Drinkers |

| | | | |
|---|---|---|---|
| cg12349884 | 6 | 27106988 | Higher in Drinkers |
| cg12350762 | 18 | 55106285 | Higher in Drinkers |
| cg12351433 | 2 | 48982957 | Higher in Drinkers |
| cg12353788 | 17 | 7792061 | Higher in Drinkers |
| cg12356743 | 3 | 128207586 | Higher in Drinkers |
| cg12358764 | 5 | 139632464 | Higher in Drinkers |
| cg12360330 | 13 | 20469387 | Higher in Drinkers |
| cg12360424 | 4 | 54568961 | Higher in Drinkers |
| cg12361155 | 10 | 64564458 | Higher in Drinkers |
| cg12361165 | 7 | 97823632 | Lower in Drinkers |
| cg12365667 | 6 | 33043976 | Higher in Drinkers |
| cg12366118 | 12 | 62860687 | Higher in Drinkers |
| cg12373566 | 9 | 111695968 | Higher in Drinkers |
| cg12377709 | 3 | 139108535 | Higher in Drinkers |
| cg12377712 | 9 | 117349993 | Higher in Drinkers |
| cg12385021 | 7 | 1606859 | Higher in Drinkers |
| cg12386879 | 12 | 120875837 | Higher in Drinkers |
| cg12390953 | 12 | 125473633 | Higher in Drinkers |
| cg12394067 | 5 | 90679220 | Higher in Drinkers |
| cg12397426 | 3 | 169530434 | Higher in Drinkers |
| cg12399453 | 1 | 27648454 | Higher in Drinkers |
| cg12399484 | 3 | 13032128 | Higher in Drinkers |
| cg12400102 | 15 | 64648507 | Higher in Drinkers |
| cg12401158 | 6 | 28554157 | Higher in Drinkers |
| cg12401731 | 1 | 145713717 | Higher in Drinkers |
| cg12404505 | 12 | 133401877 | Lower in Drinkers |
| cg12406875 | 1 | 1685854 | Higher in Drinkers |
| cg12407784 | 2 | 29469976 | Higher in Drinkers |
| cg12409226 | 7 | 100076985 | Higher in Drinkers |
| cg12411068 | 19 | 11072235 | Higher in Drinkers |
| cg12411309 | 12 | 54582659 | Higher in Drinkers |
| cg12411846 | 5 | 176449687 | Higher in Drinkers |
| cg12421110 | 13 | 42035731 | Higher in Drinkers |
| cg12421819 | 6 | 49431135 | Higher in Drinkers |
| cg12423732 | 7 | 100075506 | Higher in Drinkers |

| | | | |
|---|---|---|---|
| cg12424509 | 17 | 37617673 | Higher in Drinkers |
| cg12424534 | 18 | 13869381 | Higher in Drinkers |
| cg12424548 | 11 | 2591932 | Lower in Drinkers |
| cg12425057 | 3 | 15107106 | Higher in Drinkers |
| cg12427941 | 6 | 43457177 | Higher in Drinkers |
| cg12431087 | 3 | 71355122 | Higher in Drinkers |
| cg12432898 | 17 | 78389106 | Higher in Drinkers |
| cg12432993 | 19 | 77465430 | Lower in Drinkers |
| cg12435611 | 17 | 59941052 | Higher in Drinkers |
| cg12439315 | 1 | 94044755 | Higher in Drinkers |
| cg12441038 | 7 | 155794908 | Higher in Drinkers |
| cg12441669 | 5 | 124311925 | Lower in Drinkers |
| cg12444385 | 6 | 149067627 | Higher in Drinkers |
| cg12444840 | 14 | 94547301 | Higher in Drinkers |
| cg12444845 | 8 | 56685709 | Higher in Drinkers |
| cg12446153 | 15 | 42116798 | Higher in Drinkers |
| cg12446644 | 17 | 37026641 | Higher in Drinkers |
| cg12453778 | 2 | 62132763 | Higher in Drinkers |
| cg12458361 | 7 | 108166803 | Higher in Drinkers |
| cg12459706 | 6 | 32939295 | Higher in Drinkers |
| cg12459932 | 1 | 25292013 | Lower in Drinkers |
| cg12461125 | 1 | 44496257 | Higher in Drinkers |
| cg12464216 | X | 102469889 | Higher in Drinkers |
| cg12466950 | 5 | 1634049 | Higher in Drinkers |
| cg12467096 | 11 | 71936303 | Higher in Drinkers |
| cg12469475 | 7 | 33943666 | Higher in Drinkers |
| cg12471156 | 6 | 155054259 | Higher in Drinkers |
| cg12473036 | 20 | 62611207 | Higher in Drinkers |
| cg12474983 | 10 | 43903196 | Higher in Drinkers |
| cg12476541 | 21 | 43188257 | Higher in Drinkers |
| cg12478290 | 2 | 47403936 | Higher in Drinkers |
| cg12480941 | 8 | 38244226 | Higher in Drinkers |
| cg12491094 | 11 | 62433124 | Higher in Drinkers |
| cg12491738 | X | 117251577 | Higher in Drinkers |
| cg12491839 | 11 | 6494900 | Higher in Drinkers |

| | | | |
|---|---|---|---|
| cg12496363 | 17 | 48918089 | Higher in Drinkers |
| cg12501004 | 12 | 117287232 | Higher in Drinkers |
| cg12502403 | 11 | 6360/025 | Higher in Drinkers |
| cg12502815 | 12 | 57623997 | Higher in Drinkers |
| cg12502823 | 8 | 145754126 | Higher in Drinkers |
| cg12503742 | 8 | 145642421 | Lower in Drinkers |
| cg12505362 | 19 | 6373156 | Higher in Drinkers |
| cg12506121 | 12 | 50239076 | Higher in Drinkers |
| cg12512173 | 13 | 111936059 | Higher in Drinkers |
| cg12514868 | 4 | 2491659 | Higher in Drinkers |
| cg12516305 | 8 | 110552794 | Higher in Drinkers |
| cg12517167 | X | 135962887 | Higher in Drinkers |
| cg12518360 | 11 | 92931304 | Higher in Drinkers |
| cg12522144 | 2 | 97526805 | Higher in Drinkers |
| cg12525224 | 3 | 5229201 | Higher in Drinkers |
| cg12527440 | 19 | 13908134 | Higher in Drinkers |
| cg12529301 | 19 | 1246485 | Higher in Drinkers |
| cg12529801 | 16 | 9184705 | Higher in Drinkers |
| cg12531953 | 8 | 56793075 | Higher in Drinkers |
| cg12531972 | 7 | 133811940 | Higher in Drinkers |
| cg12534328 | 20 | 30449214 | Higher in Drinkers |
| cg12536526 | 7 | 99156782 | Higher in Drinkers |
| cg12542933 | 2 | 85804724 | Higher in Drinkers |
| cg12543132 | X | 23761732 | Higher in Drinkers |
| cg12543649 | 1 | 155176868 | Higher in Drinkers |
| cg12550146 | 8 | 668151 | Higher in Drinkers |
| cg12551567 | 20 | 3777255 | Higher in Drinkers |
| cg12557626 | 13 | 113977332 | Lower in Drinkers |
| cg12562327 | 10 | 134859818 | Higher in Drinkers |
| cg12564285 | 5 | 131593104 | Lower in Drinkers |
| cg12565330 | 1 | 171711323 | Higher in Drinkers |
| cg12567282 | 8 | 124413003 | Higher in Drinkers |
| cg12572011 | 15 | 25684085 | Higher in Drinkers |
| cg12576145 | X | 109560751 | Higher in Drinkers |
| cg12576859 | 19 | 40321086 | Higher in Drinkers |

| | | | |
|---|---|---|---|
| cg12582607 | 14 | 65007035 | Higher in Drinkers |
| cg12583908 | 3 | 186524777 | Higher in Drinkers |
| cg12584458 | 6 | 28447107 | Lower in Drinkers |
| cg12586496 | 19 | 12992070 | Higher in Drinkers |
| cg12588256 | 13 | 77601659 | Higher in Drinkers |
| cg12588890 | 7 | 90226363 | Higher in Drinkers |
| cg12589307 | 1 | 110036571 | Higher in Drinkers |
| cg12591952 | 6 | 30521150 | Higher in Drinkers |
| cg12592463 | 1 | 25574236 | Higher in Drinkers |
| cg12592908 | 6 | 36954170 | Higher in Drinkers |
| cg12594290 | 6 | 11972963 | Lower in Drinkers |
| cg12595461 | 2 | 37012483 | Higher in Drinkers |
| cg12595736 | 1 | 25573955 | Higher in Drinkers |
| cg12596040 | 1 | 18973183 | Higher in Drinkers |
| cg12596182 | 12 | 70082885 | Higher in Drinkers |
| cg12596273 | 18 | 29080595 | Higher in Drinkers |
| cg12598364 | 22 | 38203677 | Higher in Drinkers |
| cg12600766 | X | 132550131 | Higher in Drinkers |
| cg12605796 | 21 | 42792501 | Higher in Drinkers |
| cg12606694 | 6 | 131520996 | Higher in Drinkers |
| cg12610832 | 1 | 27894955 | Higher in Drinkers |
| cg12616683 | 3 | 127323572 | Lower in Drinkers |
| cg12620111 | 22 | 24093496 | Higher in Drinkers |
| cg12622938 | 7 | 74306997 | Higher in Drinkers |
| cg12626085 | 11 | 18610074 | Higher in Drinkers |
| cg12627870 | 15 | 23086580 | Higher in Drinkers |
| cg12628062 | 17 | 40729398 | Higher in Drinkers |
| cg12628956 | 5 | 94982685 | Higher in Drinkers |
| cg12629083 | 12 | 48499284 | Higher in Drinkers |
| cg12632411 | 20 | 17595355 | Lower in Drinkers |
| cg12635606 | 4 | 99849853 | Higher in Drinkers |
| cg12639523 | 1 | 184724208 | Higher in Drinkers |
| cg12641569 | 11 | 70601781 | Higher in Drinkers |
| cg12645742 | 15 | 66994830 | Higher in Drinkers |
| cg12647251 | 1 | 179851094 | Higher in Drinkers |

| | | | |
|---|---|---|---|
| cg12649615 | 1 | 150602426 | Higher in Drinkers |
| cg12650011 | 7 | 120498280 | Higher in Drinkers |
| cg12650685 | 6 | 3284109 | Higher in Drinkers |
| cg12652174 | 7 | 142494773 | Higher in Drinkers |
| cg12653922 | 1 | 235668002 | Higher in Drinkers |
| cg12654743 | 17 | 8023707 | Higher in Drinkers |
| cg12661088 | 5 | 43120934 | Higher in Drinkers |
| cg12661145 | 10 | 104404054 | Higher in Drinkers |
| cg12662497 | 5 | 98264283 | Higher in Drinkers |
| cg12664560 | 15 | 83621517 | Higher in Drinkers |
| cg12664633 | 6 | 33285702 | Higher in Drinkers |
| cg12664806 | 6 | 108862981 | Higher in Drinkers |
| cg12665504 | 5 | 100239050 | Higher in Drinkers |
| cg12675591 | 6 | 31866147 | Higher in Drinkers |
| cg12680071 | 19 | 36139062 | Higher in Drinkers |
| cg12681001 | 6 | 31543540 | Higher in Drinkers |
| cg12684209 | 6 | 393110 | Higher in Drinkers |
| cg12688320 | 20 | 2843565 | Higher in Drinkers |
| cg12691229 | 7 | 149569946 | Higher in Drinkers |
| cg12692199 | 17 | 7138010 | Higher in Drinkers |
| cg12696259 | 2 | 75185645 | Higher in Drinkers |
| cg12698494 | 12 | 57856132 | Higher in Drinkers |
| cg12699768 | 1 | 175115788 | Higher in Drinkers |
| cg12700102 | 1 | 222885791 | Higher in Drinkers |
| cg12710510 | 12 | 3862497 | Higher in Drinkers |
| cg12711814 | 1 | 8939529 | Higher in Drinkers |
| cg12714758 | 4 | 25235467 | Higher in Drinkers |
| cg12720459 | 14 | 56585092 | Higher in Drinkers |
| cg12723350 | 8 | 1725119 | Higher in Drinkers |
| cg12726354 | 15 | 28342256 | Higher in Drinkers |
| cg12727529 | 3 | 42307761 | Higher in Drinkers |
| cg12728623 | 22 | 19938992 | Higher in Drinkers |
| cg12737497 | 18 | 56530420 | Higher in Drinkers |
| cg12737869 | 9 | 111696591 | Higher in Drinkers |
| cg12737971 | 22 | 31892148 | Higher in Drinkers |

| | | | |
|---|---|---|---|
| cg12738264 | 7 | 148725795 | Higher in Drinkers |
| cg12740512 | 20 | 10415952 | Higher in Drinkers |
| cg12740518 | 22 | 32807996 | Higher in Drinkers |
| cg12743894 | 11 | 30344937 | Higher in Drinkers |
| cg12749787 | 12 | 12878379 | Higher in Drinkers |
| cg12759353 | 7 | 151573694 | Higher in Drinkers |
| cg12762683 | 17 | 17943352 | Higher in Drinkers |
| cg12767834 | 20 | 1247058 | Higher in Drinkers |
| cg12769519 | 17 | 76249217 | Higher in Drinkers |
| cg12771715 | 18 | 32621315 | Higher in Drinkers |
| cg12774406 | 11 | 118890027 | Higher in Drinkers |
| cg12777782 | 6 | 41747791 | Higher in Drinkers |
| cg12778430 | 14 | 54863615 | Higher in Drinkers |
| cg12780124 | 19 | 1615798 | Higher in Drinkers |
| cg12781254 | 11 | 2951776 | Higher in Drinkers |
| cg12783573 | 6 | 116989975 | Higher in Drinkers |
| cg12784172 | 15 | 43661957 | Higher in Drinkers |
| cg12785122 | 17 | 10601131 | Higher in Drinkers |
| cg12785675 | 6 | 109169698 | Higher in Drinkers |
| cg12785689 | 20 | 33872408 | Higher in Drinkers |
| cg12786186 | 2 | 129079588 | Higher in Drinkers |
| cg12787072 | 7 | 44887695 | Higher in Drinkers |
| cg12788970 | 3 | 10067899 | Higher in Drinkers |
| cg12789631 | 10 | 75385515 | Higher in Drinkers |
| cg12790134 | 8 | 67578787 | Higher in Drinkers |
| cg12791192 | 17 | 48619753 | Higher in Drinkers |
| cg12793733 | 4 | 47488620 | Higher in Drinkers |
| cg12794131 | 1 | 55024844 | Higher in Drinkers |
| cg12794269 | 18 | 14132481 | Higher in Drinkers |
| cg12800270 | 6 | 32085328 | Higher in Drinkers |
| cg12800600 | 8 | 55016751 | Higher in Drinkers |
| cg12803091 | 20 | 32403338 | Higher in Drinkers |
| cg12805172 | 8 | 29209379 | Higher in Drinkers |
| cg12806282 | 8 | 146052877 | Higher in Drinkers |
| cg12807537 | 10 | 80827367 | Higher in Drinkers |

| | | | |
|---|---|---|---|
| cg12811795 | 2 | 44588955 | Higher in Drinkers |
| cg12813231 | 11 | 75946229 | Higher in Drinkers |
| cg12813922 | 2 | 135809940 | Higher in Drinkers |
| cg12817999 | 3 | 9438877 | Higher in Drinkers |
| cg12818493 | 21 | 44527599 | Higher in Drinkers |
| cg12821421 | 10 | 13390394 | Higher in Drinkers |
| cg12823953 | 3 | 137893743 | Higher in Drinkers |
| cg12827262 | 6 | 35479910 | Higher in Drinkers |
| cg12830299 | 9 | 139334128 | Higher in Drinkers |
| cg12831729 | 3 | 184529767 | Higher in Drinkers |
| cg12833516 | 7 | 5085426 | Higher in Drinkers |
| cg12833720 | 19 | 45251551 | Higher in Drinkers |
| cg12833952 | 11 | 113746456 | Higher in Drinkers |
| cg12834596 | 13 | 113408420 | Higher in Drinkers |
| cg12834820 | 17 | 42852270 | Higher in Drinkers |
| cg12835684 | 12 | 53645647 | Higher in Drinkers |
| cg12836280 | 5 | 50260240 | Higher in Drinkers |
| cg12836424 | 6 | 33168439 | Higher in Drinkers |
| cg12837697 | 3 | 50126711 | Higher in Drinkers |
| cg12840312 | 6 | 3849381 | Lower in Drinkers |
| cg12841566 | 11 | 47296317 | Higher in Drinkers |
| cg12845952 | 3 | 167098119 | Higher in Drinkers |
| cg12847295 | 10 | 102974725 | Higher in Drinkers |
| cg12848467 | 8 | 9911765 | Higher in Drinkers |
| cg12858577 | 17 | 75385278 | Higher in Drinkers |
| cg12858900 | 10 | 24909511 | Lower in Drinkers |
| cg12859382 | 3 | 52445103 | Higher in Drinkers |
| cg12859923 | 19 | 18063313 | Higher in Drinkers |
| cg12860374 | 10 | 105992228 | Higher in Drinkers |
| cg12862611 | 4 | 147443109 | Higher in Drinkers |
| cg12871000 | 20 | 18119033 | Higher in Drinkers |
| cg12876009 | 22 | 37915443 | Higher in Drinkers |
| cg12876855 | 16 | 11681274 | Higher in Drinkers |
| cg12877354 | 10 | 45373196 | Higher in Drinkers |
| cg12882762 | 14 | 53196687 | Higher in Drinkers |

| | | | |
|---|---|---|---|
| cg12885484 | 7 | 6116868 | Higher in Drinkers |
| cg12885832 | 12 | 111843885 | Higher in Drinkers |
| cg12886676 | 2 | 99224936 | Higher in Drinkers |
| cg12891160 | 2 | 119916686 | Higher in Drinkers |
| cg12894524 | 12 | 116997069 | Higher in Drinkers |
| cg12895179 | 22 | 20779482 | Higher in Drinkers |
| cg12897370 | 6 | 155055079 | Higher in Drinkers |
| cg12900467 | 13 | 21635665 | Higher in Drinkers |
| cg12903171 | 7 | 50850564 | Higher in Drinkers |
| cg12904114 | 2 | 96930658 | Higher in Drinkers |
| cg12910561 | 20 | 21081216 | Higher in Drinkers |
| cg12912949 | 22 | 20004611 | Higher in Drinkers |
| cg12918961 | 18 | 24128557 | Higher in Drinkers |
| cg12919977 | 4 | 108852567 | Higher in Drinkers |
| cg12921375 | 6 | 31704104 | Higher in Drinkers |
| cg12925747 | 4 | 185905209 | Higher in Drinkers |
| cg12926341 | 2 | 70330714 | Lower in Drinkers |
| cg12927772 | 9 | 86571585 | Higher in Drinkers |
| cg12934804 | 14 | 68086549 | Higher in Drinkers |
| cg12939547 | 6 | 31744037 | Higher in Drinkers |
| cg12942996 | 6 | 109777307 | Higher in Drinkers |
| cg12947507 | 3 | 183415433 | Higher in Drinkers |
| cg12949296 | 6 | 107077437 | Higher in Drinkers |
| cg12951098 | 5 | 157170574 | Higher in Drinkers |
| cg12952568 | 14 | 21924005 | Higher in Drinkers |
| cg12953256 | 5 | 150603639 | Higher in Drinkers |
| cg12954646 | 18 | 33709853 | Higher in Drinkers |
| cg12954798 | 7 | 4830823 | Higher in Drinkers |
| cg12959048 | 11 | 73096162 | Higher in Drinkers |
| cg12960866 | 19 | 36605860 | Higher in Drinkers |
| cg12961714 | 17 | 49243563 | Higher in Drinkers |
| cg12962778 | 12 | 54778312 | Higher in Drinkers |
| cg12966801 | 19 | 58144833 | Higher in Drinkers |
| cg12968172 | 2 | 239112248 | Higher in Drinkers |
| cg12970542 | 12 | 104851909 | Higher in Drinkers |

| | | | |
|---|---|---|---|
| cg12971526 | 19 | 36001401 | Higher in Drinkers |
| cg12972213 | 2 | 73460425 | Higher in Drinkers |
| cg12974599 | 22 | 46770195 | Higher in Drinkers |
| cg12977448 | 10 | 14920832 | Higher in Drinkers |
| cg12977696 | 17 | 1303516 | Higher in Drinkers |
| cg12979793 | 12 | 96336918 | Higher in Drinkers |
| cg12985418 | 18 | 19320538 | Higher in Drinkers |
| cg12987059 | 3 | 33067108 | Lower in Drinkers |
| cg12989205 | 6 | 146285012 | Higher in Drinkers |
| cg12995121 | 7 | 1892803 | Higher in Drinkers |
| cg12995410 | 6 | 151712734 | Higher in Drinkers |
| cg12996305 | 17 | 2295923 | Higher in Drinkers |
| cg12997958 | 17 | 18161617 | Higher in Drinkers |
| cg12999103 | 1 | 17337842 | Higher in Drinkers |
| cg13000014 | 7 | 135243235 | Higher in Drinkers |
| cg13000080 | 2 | 75043142 | Higher in Drinkers |
| cg13009425 | X | 18693165 | Higher in Drinkers |
| cg13011452 | 6 | 30614382 | Higher in Drinkers |
| cg13012163 | 14 | 23235724 | Higher in Drinkers |
| cg13014219 | 4 | 8262659 | Higher in Drinkers |
| cg13014406 | 1 | 2323870 | Higher in Drinkers |
| cg13014623 | 3 | 18465519 | Higher in Drinkers |
| cg13015042 | 6 | 170102002 | Higher in Drinkers |
| cg13015245 | X | 130207604 | Higher in Drinkers |
| cg13017239 | 2 | 131185379 | Higher in Drinkers |
| cg13022888 | 14 | 82000246 | Higher in Drinkers |
| cg13029731 | 14 | 24037054 | Higher in Drinkers |
| cg13031167 | 6 | 33041406 | Higher in Drinkers |
| cg13032151 | 7 | 105650200 | Higher in Drinkers |
| cg13033283 | X | 153990915 | Lower in Drinkers |
| cg13037550 | 12 | 123477107 | Lower in Drinkers |
| cg13037895 | 7 | 2262292 | Higher in Drinkers |
| cg13038618 | 14 | 77467391 | Higher in Drinkers |
| cg13041160 | 12 | 25539549 | Higher in Drinkers |
| cg13042092 | 7 | 23637017 | Higher in Drinkers |

| | | | |
|---|---|---|---|
| cg13044223 | 1 | 45240849 | Higher in Drinkers |
| cg13046271 | 5 | 133451243 | Higher in Drinkers |
| cg13047843 | 7 | 101386679 | Higher in Drinkers |
| cg13050981 | 17 | 9479965 | Higher in Drinkers |
| cg13054563 | 14 | 23236577 | Higher in Drinkers |
| cg13061403 | 3 | 191178384 | Lower in Drinkers |
| cg13063124 | 6 | 31855702 | Higher in Drinkers |
| cg13065834 | 2 | 85960951 | Higher in Drinkers |
| cg13066630 | 21 | 34863891 | Higher in Drinkers |
| cg13072717 | 3 | 186743989 | Higher in Drinkers |
| cg13080904 | 7 | 143534545 | Higher in Drinkers |
| cg13085065 | 19 | 41769941 | Higher in Drinkers |
| cg13086586 | 4 | 57303149 | Higher in Drinkers |
| cg13093042 | 1 | 207975500 | Higher in Drinkers |
| cg13094267 | 15 | 73076635 | Higher in Drinkers |
| cg13096541 | 6 | 138482936 | Higher in Drinkers |
| cg13098621 | 8 | 28244154 | Higher in Drinkers |
| cg13112249 | 22 | 32870603 | Higher in Drinkers |
| cg13114389 | 10 | 101419241 | Higher in Drinkers |
| cg13117112 | 11 | 1853915 | Higher in Drinkers |
| cg13117164 | 4 | 54960232 | Higher in Drinkers |
| cg13117809 | 9 | 70177846 | Higher in Drinkers |
| cg13119284 | 22 | 32870628 | Higher in Drinkers |
| cg13120771 | 17 | 40333470 | Higher in Drinkers |
| cg13120986 | 12 | 7168012 | Higher in Drinkers |
| cg13124788 | 6 | 33281942 | Higher in Drinkers |
| cg13130201 | 1 | 115124302 | Higher in Drinkers |
| cg13134662 | 9 | 136858680 | Higher in Drinkers |
| cg13134968 | 6 | 31857100 | Higher in Drinkers |
| cg13137465 | 6 | 34857473 | Higher in Drinkers |
| cg13140981 | 2 | 242642316 | Higher in Drinkers |
| cg13141061 | 18 | 74729175 | Higher in Drinkers |
| cg13144004 | 3 | 124449104 | Higher in Drinkers |
| cg13144059 | 2 | 201245077 | Lower in Drinkers |
| cg13145440 | 17 | 47841827 | Higher in Drinkers |

| | | | |
|---|---|---|---|
| cg13146040 | 12 | 125004853 | Higher in Drinkers |
| cg13149127 | 1 | 156390835 | Higher in Drinkers |
| cg13152396 | 11 | 62413763 | Higher in Drinkers |
| cg13156044 | 6 | 31510291 | Higher in Drinkers |
| cg13162609 | 20 | 61288203 | Higher in Drinkers |
| cg13165758 | 11 | 78061467 | Higher in Drinkers |
| cg13168308 | 1 | 149298892 | Higher in Drinkers |
| cg13168746 | 1 | 59165508 | Higher in Drinkers |
| cg13168924 | 19 | 8386583 | Higher in Drinkers |
| cg13169065 | 2 | 166650947 | Higher in Drinkers |
| cg13170468 | 11 | 10531665 | Higher in Drinkers |
| cg13171016 | 1 | 40219054 | Higher in Drinkers |
| cg13174253 | 8 | 146278678 | Higher in Drinkers |
| cg13174850 | 14 | 93673699 | Higher in Drinkers |
| cg13176270 | X | 102318831 | Higher in Drinkers |
| cg13179085 | 12 | 93963345 | Higher in Drinkers |
| cg13179508 | 17 | 7402673 | Higher in Drinkers |
| cg13180064 | 15 | 90895341 | Higher in Drinkers |
| cg13180224 | 21 | 40684269 | Higher in Drinkers |
| cg13188869 | 3 | 50654332 | Higher in Drinkers |
| cg13192688 | 4 | 1742050 | Higher in Drinkers |
| cg13193228 | 1 | 182808939 | Higher in Drinkers |
| cg13193848 | 15 | 66678964 | Higher in Drinkers |
| cg13193962 | 4 | 156875105 | Higher in Drinkers |
| cg13195667 | 18 | 71815255 | Higher in Drinkers |
| cg13198235 | 1 | 193028919 | Higher in Drinkers |
| cg13199822 | 3 | 113466193 | Higher in Drinkers |
| cg13200640 | 7 | 150870270 | Higher in Drinkers |
| cg13200933 | 14 | 66976062 | Higher in Drinkers |
| cg13204093 | 17 | 42277915 | Higher in Drinkers |
| cg13204512 | 17 | 29298184 | Higher in Drinkers |
| cg13208438 | 15 | 78296041 | Higher in Drinkers |
| cg13208590 | 6 | 33541445 | Higher in Drinkers |
| cg13212232 | 17 | 17184151 | Higher in Drinkers |
| cg13217419 | 2 | 3184659 | Higher in Drinkers |

| | | | |
|---|---|---|---|
| cg13219107 | 4 | 151937234 | Higher in Drinkers |
| cg13222768 | 13 | 99105819 | Lower in Drinkers |
| cg13226139 | 14 | 45605129 | Higher in Drinkers |
| cg13226272 | 2 | 173189711 | Lower in Drinkers |
| cg13227551 | 6 | 144011222 | Lower in Drinkers |
| cg13230606 | 17 | 36105337 | Higher in Drinkers |
| cg13232900 | 16 | 75656651 | Higher in Drinkers |
| cg13234997 | 12 | 110011138 | Higher in Drinkers |
| cg13235992 | 1 | 156736799 | Higher in Drinkers |
| cg13236315 | 12 | 53645720 | Higher in Drinkers |
| cg13240385 | 12 | 54982590 | Higher in Drinkers |
| cg13242192 | 10 | 13514168 | Higher in Drinkers |
| cg13244110 | 17 | 40688572 | Higher in Drinkers |
| cg13245375 | 12 | 51785163 | Higher in Drinkers |
| cg13247580 | 14 | 69263103 | Higher in Drinkers |
| cg13249876 | 10 | 32217968 | Higher in Drinkers |
| cg13257331 | 3 | 50368106 | Higher in Drinkers |
| cg13261989 | 11 | 65029383 | Higher in Drinkers |
| cg13264616 | 8 | 22530654 | Higher in Drinkers |
| cg13266096 | 11 | 62366806 | Higher in Drinkers |
| cg13269166 | 7 | 142960561 | Higher in Drinkers |
| cg13271076 | 21 | 48055715 | Higher in Drinkers |
| cg13272546 | 17 | 27313239 | Higher in Drinkers |
| cg13273789 | 14 | 23388442 | Higher in Drinkers |
| cg13277337 | 2 | 240265810 | Higher in Drinkers |
| cg13278334 | 19 | 49954994 | Higher in Drinkers |
| cg13288361 | 15 | 101626347 | Higher in Drinkers |
| cg13289788 | 8 | 583404 | Lower in Drinkers |
| cg13293246 | 2 | 127818101 | Higher in Drinkers |
| cg13293721 | 2 | 88990738 | Higher in Drinkers |
| cg13297881 | 1 | 65614322 | Higher in Drinkers |
| cg13299776 | 3 | 143847007 | Higher in Drinkers |
| cg13302559 | 2 | 113772214 | Higher in Drinkers |
| cg13304274 | 19 | 36909606 | Higher in Drinkers |
| cg13313046 | 5 | 137673134 | Higher in Drinkers |

| | | | |
|---|---|---|---|
| cg13314222 | 6 | 32862734 | Higher in Drinkers |
| cg13314979 | 2 | 216978405 | Higher in Drinkers |
| cg13315471 | 2 | 27258494 | Higher in Drinkers |
| cg13318572 | 8 | 1993007 | Higher in Drinkers |
| cg13319488 | 13 | 44361064 | Higher in Drinkers |
| cg13320626 | 5 | 100238655 | Higher in Drinkers |
| cg13321746 | 19 | 47354149 | Higher in Drinkers |
| cg13333737 | 6 | 132129021 | Higher in Drinkers |
| cg13335388 | 6 | 31550241 | Higher in Drinkers |
| cg13336167 | 19 | 56092141 | Higher in Drinkers |
| cg13336335 | 8 | 42751664 | Lower in Drinkers |
| cg13337697 | 19 | 35168649 | Higher in Drinkers |
| cg13339791 | 2 | 70322659 | Higher in Drinkers |
| cg13339825 | 2 | 69001825 | Higher in Drinkers |
| cg13341907 | 17 | 7402671 | Higher in Drinkers |
| cg13346032 | 22 | 47158756 | Higher in Drinkers |
| cg13348458 | 6 | 27569671 | Lower in Drinkers |
| cg13349606 | 18 | 32720455 | Higher in Drinkers |
| cg13351503 | 19 | 40794895 | Lower in Drinkers |
| cg13351698 | 7 | 26240574 | Higher in Drinkers |
| cg13353244 | 16 | 50099780 | Higher in Drinkers |
| cg13354304 | 17 | 4082105 | Higher in Drinkers |
| cg13355233 | 2 | 118771338 | Higher in Drinkers |
| cg13356884 | 1 | 110881579 | Higher in Drinkers |
| cg13360609 | 17 | 80832970 | Lower in Drinkers |
| cg13361393 | 22 | 24114971 | Higher in Drinkers |
| cg13361703 | 10 | 95653447 | Higher in Drinkers |
| cg13365543 | 11 | 9596475 | Higher in Drinkers |
| cg13365761 | 16 | 23194156 | Higher in Drinkers |
| cg13367936 | 9 | 132598310 | Higher in Drinkers |
| cg13368134 | 1 | 228288514 | Higher in Drinkers |
| cg13370439 | X | 131157113 | Higher in Drinkers |
| cg13376158 | 17 | 73128023 | Higher in Drinkers |
| cg13384501 | 15 | 66534299 | Higher in Drinkers |
| cg13387374 | 1 | 19411106 | Higher in Drinkers |

| | | | |
|---|---|---|---|
| cg13389684 | 2 | 170655297 | Higher in Drinkers |
| cg13392587 | 17 | 40689561 | Higher in Drinkers |
| cg13393964 | 16 | 20753279 | Higher in Drinkers |
| cg13394530 | 9 | 34612526 | Higher in Drinkers |
| cg13395333 | 1 | 202311100 | Higher in Drinkers |
| cg13396037 | 8 | 42996139 | Higher in Drinkers |
| cg13396213 | 19 | 44037225 | Higher in Drinkers |
| cg13404558 | 5 | 168006306 | Higher in Drinkers |
| cg13405423 | 8 | 42011090 | Higher in Drinkers |
| cg13409575 | 2 | 63277708 | Higher in Drinkers |
| cg13409589 | 11 | 3013777 | Higher in Drinkers |
| cg13410877 | 18 | 55712976 | Higher in Drinkers |
| cg13411879 | 7 | 30068273 | Higher in Drinkers |
| cg13419087 | 12 | 124907105 | Higher in Drinkers |
| cg13420112 | 20 | 62600654 | Higher in Drinkers |
| cg13420364 | 1 | 234857659 | Higher in Drinkers |
| cg13422136 | 18 | 42643730 | Lower in Drinkers |
| cg13423394 | 3 | 58223060 | Higher in Drinkers |
| cg13423887 | 6 | 32632694 | Lower in Drinkers |
| cg13425677 | 5 | 56112090 | Higher in Drinkers |
| cg13426098 | 6 | 30654771 | Higher in Drinkers |
| cg13429095 | 1 | 206913187 | Higher in Drinkers |
| cg13430118 | 9 | 5041787 | Higher in Drinkers |
| cg13430678 | 3 | 11596003 | Higher in Drinkers |
| cg13432294 | 1 | 8937640 | Higher in Drinkers |
| cg13433994 | 3 | 23958502 | Higher in Drinkers |
| cg13435464 | 9 | 91927197 | Higher in Drinkers |
| cg13436750 | 1 | 150337476 | Higher in Drinkers |
| cg13438944 | 14 | 76452133 | Higher in Drinkers |
| cg13439582 | 3 | 128879943 | Higher in Drinkers |
| cg13444528 | 4 | 184580379 | Higher in Drinkers |
| cg13445938 | 9 | 93840773 | Lower in Drinkers |
| cg13446199 | 8 | 143762866 | Higher in Drinkers |
| cg13447915 | 4 | 331517 | Higher in Drinkers |
| cg13450057 | 4 | 2231660 | Higher in Drinkers |

| | | | |
|---|---|---|---|
| cg13452658 | 1 | 154680215 | Higher in Drinkers |
| cg13457396 | 1 | 185127093 | Higher in Drinkers |
| cg13460942 | 1 | 52870042 | Higher in Drinkers |
| cg13461390 | 1 | 217312478 | Higher in Drinkers |
| cg13462160 | 22 | 39916704 | Higher in Drinkers |
| cg13462576 | 15 | 74726520 | Higher in Drinkers |
| cg13462890 | 11 | 74394411 | Higher in Drinkers |
| cg13463033 | 9 | 139360276 | Higher in Drinkers |
| cg13468041 | 4 | 74902951 | Higher in Drinkers |
| cg13469633 | 4 | 186125436 | Higher in Drinkers |
| cg13470032 | 9 | 214612 | Higher in Drinkers |
| cg13471184 | 18 | 44702735 | Higher in Drinkers |
| cg13474244 | 11 | 85195100 | Higher in Drinkers |
| cg13474619 | 12 | 131356588 | Higher in Drinkers |
| cg13474680 | 10 | 15036822 | Higher in Drinkers |
| cg13477819 | 6 | 29617973 | Higher in Drinkers |
| cg13482375 | 17 | 57517754 | Higher in Drinkers |
| cg13482925 | 10 | 64028750 | Higher in Drinkers |
| cg13489958 | 1 | 173837191 | Higher in Drinkers |
| cg13494191 | 3 | 57261824 | Higher in Drinkers |
| cg13495167 | 12 | 114395501 | Higher in Drinkers |
| cg13496160 | 9 | 35646755 | Higher in Drinkers |
| cg13497285 | 20 | 8000588 | Higher in Drinkers |
| cg13497939 | 1 | 167905793 | Higher in Drinkers |
| cg13509322 | 5 | 72733052 | Higher in Drinkers |
| cg13512374 | 14 | 103895494 | Lower in Drinkers |
| cg13512977 | 9 | 118918160 | Higher in Drinkers |
| cg13513804 | 10 | 50121894 | Higher in Drinkers |
| cg13514996 | 3 | 113829347 | Lower in Drinkers |
| cg13518195 | 3 | 131100364 | Higher in Drinkers |
| cg13518625 | 8 | 29522838 | Higher in Drinkers |
| cg13519464 | 19 | 9938554 | Higher in Drinkers |
| cg13520782 | 8 | 99057765 | Higher in Drinkers |
| cg13522406 | 6 | 30531820 | Higher in Drinkers |
| cg13523312 | 22 | 39711467 | Higher in Drinkers |

| | | | |
|---|---|---|---|
| cg13524927 | 9 | 107510062 | Higher in Drinkers |
| cg13525333 | 11 | 117049941 | Higher in Drinkers |
| cg13525458 | 20 | 44486289 | Higher in Drinkers |
| cg13527630 | 4 | 76862276 | Higher in Drinkers |
| cg13527974 | 3 | 118945807 | Higher in Drinkers |
| cg13529101 | 7 | 101845425 | Higher in Drinkers |
| cg13531268 | 11 | 95523587 | Higher in Drinkers |
| cg13531562 | 6 | 31747887 | Higher in Drinkers |
| cg13531837 | 6 | 34192005 | Higher in Drinkers |
| cg13531842 | 10 | 38383804 | Higher in Drinkers |
| cg13533616 | 9 | 131889368 | Higher in Drinkers |
| cg13536308 | 9 | 137030252 | Higher in Drinkers |
| cg13540147 | 9 | 140131233 | Higher in Drinkers |
| cg13544027 | 11 | 20465288 | Higher in Drinkers |
| cg13545089 | 19 | 5915037 | Lower in Drinkers |
| cg13545495 | 9 | 118916132 | Lower in Drinkers |
| cg13546173 | 1 | 93645433 | Higher in Drinkers |
| cg13547299 | 11 | 1330611 | Higher in Drinkers |
| cg13548781 | 10 | 104474172 | Higher in Drinkers |
| cg13548810 | 1 | 55349365 | Higher in Drinkers |
| cg13550263 | 9 | 139836978 | Higher in Drinkers |
| cg13551243 | 8 | 146052742 | Higher in Drinkers |
| cg13556806 | 19 | 19612306 | Higher in Drinkers |
| cg13558431 | 9 | 140357706 | Lower in Drinkers |
| cg13562284 | 11 | 32710323 | Higher in Drinkers |
| cg13562917 | 15 | 90776873 | Higher in Drinkers |
| cg13563193 | 19 | 33072644 | Higher in Drinkers |
| cg13564289 | 20 | 62680977 | Higher in Drinkers |
| cg13566430 | 5 | 131992455 | Higher in Drinkers |
| cg13568946 | 8 | 12516530 | Higher in Drinkers |
| cg13569417 | X | 123094304 | Higher in Drinkers |
| cg13571568 | 1 | 204332758 | Higher in Drinkers |
| cg13575885 | 12 | 132406623 | Higher in Drinkers |
| cg13578229 | 9 | 99540409 | Higher in Drinkers |
| cg13579374 | 8 | 62627037 | Higher in Drinkers |

| | | | |
|---|---|---|---|
| cg13579661 | 12 | 124270380 | Lower in Drinkers |
| cg13582542 | 2 | 132795405 | Higher in Drinkers |
| cg13584541 | 2 | 74756882 | Higher in Drinkers |
| cg13585749 | 2 | 875437 | Lower in Drinkers |
| cg13586051 | 3 | 58200471 | Higher in Drinkers |
| cg13588572 | 11 | 65769523 | Higher in Drinkers |
| cg13591091 | 9 | 130254049 | Higher in Drinkers |
| cg13591369 | 1 | 2005564 | Higher in Drinkers |
| cg13592872 | 11 | 2322500 | Higher in Drinkers |
| cg13592947 | 5 | 1111049 | Higher in Drinkers |
| cg13593090 | 19 | 9546723 | Lower in Drinkers |
| cg13595513 | 9 | 124413528 | Higher in Drinkers |
| cg13595904 | 3 | 137834489 | Higher in Drinkers |
| cg13598256 | 5 | 140801286 | Lower in Drinkers |
| cg13598528 | 15 | 34394035 | Higher in Drinkers |
| cg13602232 | 19 | 36505322 | Higher in Drinkers |
| cg13602242 | 6 | 151186614 | Higher in Drinkers |
| cg13603203 | 2 | 220088797 | Higher in Drinkers |
| cg13604592 | 21 | 45393592 | Higher in Drinkers |
| cg13606988 | 17 | 7222582 | Higher in Drinkers |
| cg13609505 | 10 | 100206860 | Higher in Drinkers |
| cg13610392 | 14 | 70078973 | Higher in Drinkers |
| cg13612106 | 2 | 203776860 | Higher in Drinkers |
| cg13612958 | 19 | 18303626 | Higher in Drinkers |
| cg13614946 | 1 | 100315421 | Higher in Drinkers |
| cg13616215 | 7 | 133619041 | Lower in Drinkers |
| cg13620808 | 19 | 55918708 | Higher in Drinkers |
| cg13622267 | 4 | 68411338 | Higher in Drinkers |
| cg13622436 | 4 | 4341397 | Higher in Drinkers |
| cg13622821 | 6 | 31702915 | Higher in Drinkers |
| cg13623351 | 6 | 71276542 | Higher in Drinkers |
| cg13623690 | 16 | 84651800 | Higher in Drinkers |
| cg13625113 | 9 | 125675579 | Higher in Drinkers |
| cg13628514 | 12 | 110271439 | Higher in Drinkers |
| cg13629565 | 19 | 14184743 | Higher in Drinkers |

| | | | |
|---|---|---|---|
| cg13630095 | 9 | 125137594 | Higher in Drinkers |
| cg13630574 | 20 | 2847327 | Higher in Drinkers |
| cg13634242 | 5 | 60921891 | Higher in Drinkers |
| cg13638198 | 11 | 44587403 | Higher in Drinkers |
| cg13643339 | 14 | 76447949 | Higher in Drinkers |
| cg13647052 | 12 | 2800382 | Higher in Drinkers |
| cg13647309 | 5 | 68473620 | Higher in Drinkers |
| cg13647831 | 13 | 111720013 | Higher in Drinkers |
| cg13650689 | 19 | 54618596 | Higher in Drinkers |
| cg13652556 | 16 | 1993336 | Higher in Drinkers |
| cg13654902 | 19 | 38853053 | Higher in Drinkers |
| cg13658921 | 2 | 136499517 | Higher in Drinkers |
| cg13662262 | 21 | 30364895 | Higher in Drinkers |
| cg13666293 | 4 | 468131 | Higher in Drinkers |
| cg13666696 | 7 | 73011675 | Higher in Drinkers |
| cg13669465 | 10 | 99205343 | Higher in Drinkers |
| cg13672649 | 1 | 161102972 | Higher in Drinkers |
| cg13674218 | 20 | 10654703 | Higher in Drinkers |
| cg13674556 | 9 | 77702836 | Higher in Drinkers |
| cg13675389 | 9 | 38069796 | Higher in Drinkers |
| cg13675958 | 13 | 103426305 | Higher in Drinkers |
| cg13678240 | 3 | 69129230 | Higher in Drinkers |
| cg13679837 | 20 | 21283918 | Higher in Drinkers |
| cg13680764 | 4 | 95373949 | Higher in Drinkers |
| cg13689156 | 12 | 50017412 | Higher in Drinkers |
| cg13690943 | 9 | 33952741 | Higher in Drinkers |
| cg13692655 | 9 | 130713088 | Higher in Drinkers |
| cg13694400 | 12 | 13254673 | Higher in Drinkers |
| cg13695906 | 21 | 33942312 | Higher in Drinkers |
| cg13697368 | 17 | 7833663 | Higher in Drinkers |
| cg13698414 | 7 | 1131067 | Higher in Drinkers |
| cg13699558 | 2 | 62132958 | Higher in Drinkers |
| cg13700033 | 7 | 1177901 | Higher in Drinkers |
| cg13700897 | 8 | 109096064 | Higher in Drinkers |
| cg13701249 | 20 | 40247506 | Higher in Drinkers |

| | | | |
|---|---|---|---|
| cg13702678 | 7 | 56174313 | Higher in Drinkers |
| cg13705888 | 6 | 32131722 | Lower in Drinkers |
| cg13707395 | 11 | 130318316 | Higher in Drinkers |
| cg13708635 | 20 | 36149656 | Higher in Drinkers |
| cg13710308 | 7 | 158854763 | Lower in Drinkers |
| cg13712154 | X | 95939171 | Higher in Drinkers |
| cg13714437 | 13 | 114389530 | Lower in Drinkers |
| cg13715319 | 19 | 58129233 | Higher in Drinkers |
| cg13716074 | 7 | 65215894 | Higher in Drinkers |
| cg13717374 | 19 | 40430747 | Higher in Drinkers |
| cg13717541 | 14 | 95727643 | Lower in Drinkers |
| cg13719188 | 1 | 236445668 | Higher in Drinkers |
| cg13719771 | 12 | 4762206 | Higher in Drinkers |
| cg13720744 | 22 | 21271392 | Higher in Drinkers |
| cg13722127 | 7 | 150037890 | Higher in Drinkers |
| cg13722539 | 11 | 64085131 | Higher in Drinkers |
| cg13723693 | 17 | 80656731 | Higher in Drinkers |
| cg13730534 | 1 | 41157553 | Higher in Drinkers |
| cg13739442 | 22 | 29730260 | Higher in Drinkers |
| cg13740985 | 9 | 80930413 | Higher in Drinkers |
| cg13741211 | 7 | 98607297 | Higher in Drinkers |
| cg13743031 | 4 | 178231244 | Higher in Drinkers |
| cg13743731 | 19 | 11204447 | Higher in Drinkers |
| cg13744917 | 1 | 2986538 | Higher in Drinkers |
| cg13745525 | 2 | 152267021 | Higher in Drinkers |
| cg13747195 | X | 102471167 | Lower in Drinkers |
| cg13749424 | 17 | 80416444 | Higher in Drinkers |
| cg13750326 | 7 | 64498824 | Higher in Drinkers |
| cg13752933 | 9 | 90114755 | Higher in Drinkers |
| cg13759418 | 19 | 5895056 | Higher in Drinkers |
| cg13760807 | 13 | 33002128 | Higher in Drinkers |
| cg13766816 | X | 118616721 | Higher in Drinkers |
| cg13768174 | 1 | 211556217 | Higher in Drinkers |
| cg13769046 | 17 | 77389766 | Lower in Drinkers |
| cg13773614 | 7 | 95226193 | Higher in Drinkers |

| | | | |
|---|---|---|---|
| cg13779677 | 6 | 150285071 | Higher in Drinkers |
| cg13779687 | 22 | 46468422 | Higher in Drinkers |
| cg13782176 | 10 | 6264761 | Higher in Drinkers |
| cg13784474 | 4 | 3251105 | Higher in Drinkers |
| cg13784611 | 1 | 87380955 | Higher in Drinkers |
| cg13785189 | 17 | 73150884 | Higher in Drinkers |
| cg13788592 | 19 | 57862612 | Higher in Drinkers |
| cg13789303 | 6 | 108386681 | Higher in Drinkers |
| cg13789523 | 20 | 33104204 | Higher in Drinkers |
| cg13794863 | 1 | 36157016 | Higher in Drinkers |
| cg13795264 | 20 | 47444923 | Higher in Drinkers |
| cg13796158 | 7 | 5385486 | Higher in Drinkers |
| cg13796295 | 14 | 24807658 | Higher in Drinkers |
| cg13799462 | 6 | 33234467 | Higher in Drinkers |
| cg13799898 | 9 | 136358673 | Higher in Drinkers |
| cg13799933 | 15 | 70326383 | Higher in Drinkers |
| cg13801381 | 12 | 4384022 | Higher in Drinkers |
| cg13803003 | 17 | 66453912 | Higher in Drinkers |
| cg13804838 | 17 | 80053022 | Higher in Drinkers |
| cg13806964 | 6 | 31165914 | Higher in Drinkers |
| cg13808508 | 9 | 94187090 | Higher in Drinkers |
| cg13808561 | 11 | 43333782 | Higher in Drinkers |
| cg13808979 | 6 | 31093153 | Higher in Drinkers |
| cg13809469 | 15 | 43802817 | Higher in Drinkers |
| cg13809962 | X | 84498932 | Higher in Drinkers |
| cg13810225 | 22 | 36784323 | Higher in Drinkers |
| cg13810234 | 9 | 139622243 | Higher in Drinkers |
| cg13810628 | 2 | 62932753 | Higher in Drinkers |
| cg13819165 | 14 | 73360990 | Higher in Drinkers |
| cg13819485 | 11 | 118868642 | Higher in Drinkers |
| cg13819869 | 14 | 75745020 | Higher in Drinkers |
| cg13821177 | 3 | 5230131 | Higher in Drinkers |
| cg13822123 | 2 | 54197256 | Higher in Drinkers |
| cg13824271 | 2 | 231917514 | Higher in Drinkers |
| cg13825058 | 4 | 154266213 | Higher in Drinkers |

| | | | |
|---|---|---|---|
| cg13826154 | 19 | 45754942 | Higher in Drinkers |
| cg13827212 | 7 | 99036343 | Higher in Drinkers |
| cg13832045 | 9 | 139923087 | Higher in Drinkers |
| cg13833525 | 11 | 819513 | Higher in Drinkers |
| cg13834453 | 9 | 33167337 | Higher in Drinkers |
| cg13839391 | 12 | 121719066 | Higher in Drinkers |
| cg13844420 | 9 | 86595252 | Higher in Drinkers |
| cg13850355 | 4 | 47034939 | Higher in Drinkers |
| cg13850695 | 9 | 131992409 | Lower in Drinkers |
| cg13852093 | 18 | 74770615 | Higher in Drinkers |
| cg13855345 | 1 | 43312171 | Higher in Drinkers |
| cg13857382 | 1 | 175162153 | Higher in Drinkers |
| cg13857678 | 9 | 75079943 | Higher in Drinkers |
| cg13859478 | 5 | 179126433 | Higher in Drinkers |
| cg13860627 | 7 | 43965935 | Higher in Drinkers |
| cg13865940 | 14 | 104182836 | Higher in Drinkers |
| cg13867669 | 9 | 72130914 | Lower in Drinkers |
| cg13868347 | 6 | 17261498 | Higher in Drinkers |
| cg13868393 | 17 | 75136249 | Higher in Drinkers |
| cg13868565 | 12 | 122250153 | Higher in Drinkers |
| cg13869415 | 8 | 123793492 | Higher in Drinkers |
| cg13869635 | 9 | 33523542 | Higher in Drinkers |
| cg13869971 | 19 | 36036128 | Higher in Drinkers |
| cg13872774 | 9 | 139657079 | Lower in Drinkers |
| cg13873269 | 9 | 114938015 | Higher in Drinkers |
| cg13873762 | 17 | 6544510 | Higher in Drinkers |
| cg13874777 | 3 | 50314344 | Higher in Drinkers |
| cg13874838 | 2 | 27008853 | Higher in Drinkers |
| cg13877574 | 11 | 1756109 | Higher in Drinkers |
| cg13878456 | 17 | 38020344 | Higher in Drinkers |
| cg13878641 | 1 | 110090951 | Higher in Drinkers |
| cg13880225 | 9 | 130889610 | Higher in Drinkers |
| cg13880989 | 1 | 28157155 | Higher in Drinkers |
| cg13882414 | 3 | 39194867 | Higher in Drinkers |
| cg13883202 | 3 | 47422330 | Higher in Drinkers |

| | | | |
|---|---|---|---|
| cg13887370 | 12 | 56224128 | Higher in Drinkers |
| cg13891659 | 6 | 170190454 | Higher in Drinkers |
| cg13894748 | 10 | 102107266 | Higher in Drinkers |
| cg13895966 | 20 | 57467268 | Higher in Drinkers |
| cg13896891 | 9 | 136741139 | Lower in Drinkers |
| cg13897145 | 3 | 113557582 | Higher in Drinkers |
| cg13897925 | 2 | 176866941 | Higher in Drinkers |
| cg13898430 | 1 | 25292274 | Lower in Drinkers |
| cg13901526 | 2 | 127414455 | Higher in Drinkers |
| cg13904704 | 1 | 20693892 | Higher in Drinkers |
| cg13906548 | 16 | 75600564 | Higher in Drinkers |
| cg13906733 | 5 | 176981629 | Higher in Drinkers |
| cg13906749 | 12 | 120933893 | Higher in Drinkers |
| cg13909555 | 15 | 55611321 | Higher in Drinkers |
| cg13913015 | 2 | 47797963 | Higher in Drinkers |
| cg13913149 | 11 | 67033676 | Higher in Drinkers |
| cg13913407 | 5 | 159797918 | Higher in Drinkers |
| cg13915726 | X | 152908309 | Higher in Drinkers |
| cg13916322 | 11 | 63381728 | Higher in Drinkers |
| cg13916740 | 19 | 56904997 | Higher in Drinkers |
| cg13916953 | 6 | 33285755 | Higher in Drinkers |
| cg13917504 | 7 | 130131258 | Higher in Drinkers |
| cg13919496 | 22 | 42915677 | Higher in Drinkers |
| cg13919694 | 12 | 53738960 | Higher in Drinkers |
| cg13921858 | 2 | 86333426 | Higher in Drinkers |
| cg13925924 | 6 | 110501820 | Higher in Drinkers |
| cg13926338 | 1 | 109941043 | Higher in Drinkers |
| cg13927251 | 5 | 180077359 | Higher in Drinkers |
| cg13928802 | 1 | 225965441 | Higher in Drinkers |
| cg13930203 | 1 | 217804429 | Higher in Drinkers |
| cg13930468 | 4 | 18022372 | Higher in Drinkers |
| cg13930682 | 6 | 26393253 | Higher in Drinkers |
| cg13931914 | 12 | 113659048 | Higher in Drinkers |
| cg13937841 | 10 | 28821190 | Higher in Drinkers |
| cg13946902 | 10 | 125352964 | Higher in Drinkers |

| | | | |
|---|---|---|---|
| cg13947892 | 19 | 53466313 | Higher in Drinkers |
| cg13947995 | 15 | 91427821 | Higher in Drinkers |
| cg13949202 | 8 | 142070685 | Lower in Drinkers |
| cg13957126 | 7 | 5597849 | Higher in Drinkers |
| cg13957198 | 7 | 559649 | Higher in Drinkers |
| cg13961709 | 14 | 74486189 | Higher in Drinkers |
| cg13962631 | 1 | 213223461 | Higher in Drinkers |
| cg13963727 | 8 | 90996948 | Higher in Drinkers |
| cg13964084 | 6 | 30594709 | Higher in Drinkers |
| cg13965321 | 5 | 147763705 | Higher in Drinkers |
| cg13970341 | 9 | 139923093 | Higher in Drinkers |
| cg13971574 | 2 | 39102874 | Higher in Drinkers |
| cg13975344 | 2 | 45170979 | Higher in Drinkers |
| cg13976251 | 8 | 64325777 | Lower in Drinkers |
| cg13977073 | 10 | 5979252 | Higher in Drinkers |
| cg13977835 | 1 | 23883338 | Higher in Drinkers |
| cg13979182 | 4 | 2845120 | Higher in Drinkers |
| cg13979884 | 9 | 74061171 | Lower in Drinkers |
| cg13980308 | 7 | 140373235 | Higher in Drinkers |
| cg13982661 | 11 | 121163497 | Higher in Drinkers |
| cg13984808 | 10 | 103326373 | Lower in Drinkers |
| cg13985868 | 9 | 116102304 | Higher in Drinkers |
| cg13986831 | 7 | 73669141 | Higher in Drinkers |
| cg13993274 | 9 | 4742079 | Higher in Drinkers |
| cg13994079 | 5 | 167696229 | Higher in Drinkers |
| cg13999415 | 5 | 81047848 | Higher in Drinkers |
| cg14004527 | 13 | 73356346 | Higher in Drinkers |
| cg14005334 | 15 | 89877925 | Higher in Drinkers |
| cg14006390 | 19 | 48972349 | Higher in Drinkers |
| cg14012249 | 9 | 35748803 | Higher in Drinkers |
| cg14012294 | 5 | 72794041 | Higher in Drinkers |
| cg14015996 | 17 | 28256508 | Higher in Drinkers |
| cg14016518 | 9 | 14692931 | Higher in Drinkers |
| cg14023159 | 1 | 32646132 | Higher in Drinkers |
| cg14024356 | 1 | 154934173 | Higher in Drinkers |

| | | | |
|---|---|---|---|
| cg14030878 | 3 | 195615302 | Higher in Drinkers |
| cg14037218 | 1 | 150522367 | Higher in Drinkers |
| cg14038647 | 3 | 13396729 | Higher in Drinkers |
| cg14039054 | 9 | 33019812 | Higher in Drinkers |
| cg14040633 | 17 | 73996331 | Higher in Drinkers |
| cg14041153 | 9 | 99212478 | Higher in Drinkers |
| cg14041778 | 1 | 33938210 | Higher in Drinkers |
| cg14042132 | 1 | 117112752 | Higher in Drinkers |
| cg14043527 | 11 | 64642516 | Lower in Drinkers |
| cg14043546 | 15 | 50979198 | Higher in Drinkers |
| cg14044057 | 2 | 29033296 | Higher in Drinkers |
| cg14045140 | 9 | 95432176 | Higher in Drinkers |
| cg14047656 | 2 | 201936671 | Higher in Drinkers |
| cg14051366 | X | 49126150 | Higher in Drinkers |
| cg14051592 | 17 | 41798141 | Higher in Drinkers |
| cg14055970 | 9 | 130567715 | Lower in Drinkers |
| cg14058100 | 14 | 104622028 | Lower in Drinkers |
| cg14058584 | 2 | 130939451 | Higher in Drinkers |
| cg14059475 | 2 | 44588633 | Higher in Drinkers |
| cg14063191 | 9 | 131486742 | Higher in Drinkers |
| cg14064229 | 2 | 42588497 | Higher in Drinkers |
| cg14066905 | 11 | 124953090 | Higher in Drinkers |
| cg14069635 | 9 | 88897854 | Higher in Drinkers |
| cg14072120 | 22 | 37640402 | Higher in Drinkers |
| cg14073117 | 9 | 4792649 | Higher in Drinkers |
| cg14074741 | 19 | 39390723 | Higher in Drinkers |
| cg14078309 | 22 | 43539574 | Higher in Drinkers |
| cg14079492 | 11 | 3692562 | Higher in Drinkers |
| cg14079893 | 12 | 108908917 | Higher in Drinkers |
| cg14081474 | 19 | 41870343 | Higher in Drinkers |
| cg14081599 | 19 | 33071884 | Higher in Drinkers |
| cg14081744 | 11 | 12270286 | Higher in Drinkers |
| cg14083372 | 9 | 136324795 | Higher in Drinkers |
| cg14084176 | X | 44401762 | Higher in Drinkers |
| cg14084857 | 1 | 43855620 | Higher in Drinkers |

| | | | |
|---|---|---|---|
| cg14085805 | 19 | 36705804 | Higher in Drinkers |
| cg14086791 | 11 | 69489770 | Higher in Drinkers |
| cg14087341 | 9 | 135232075 | Lower in Drinkers |
| cg14091752 | 3 | 119182317 | Higher in Drinkers |
| cg14093101 | 2 | 27994528 | Higher in Drinkers |
| cg14094999 | 14 | 23299055 | Higher in Drinkers |
| cg14095761 | 9 | 35713238 | Higher in Drinkers |
| cg14097171 | 14 | 21769105 | Higher in Drinkers |
| cg14098468 | 19 | 53140973 | Higher in Drinkers |
| cg14099345 | 9 | 132631088 | Higher in Drinkers |
| cg14102550 | 6 | 146285286 | Higher in Drinkers |
| cg14102811 | 6 | 31649026 | Higher in Drinkers |
| cg14103123 | 9 | 136004821 | Higher in Drinkers |
| cg14103574 | 5 | 162932455 | Higher in Drinkers |
| cg14107561 | 6 | 31789941 | Higher in Drinkers |
| cg14108380 | 9 | 139299357 | Lower in Drinkers |
| cg14112754 | 3 | 194118613 | Higher in Drinkers |
| cg14113010 | 5 | 180671389 | Higher in Drinkers |
| cg14120075 | 13 | 114268127 | Higher in Drinkers |
| cg14120436 | 15 | 52483498 | Higher in Drinkers |
| cg14121020 | 1 | 233431150 | Higher in Drinkers |
| cg14124066 | 9 | 125015960 | Lower in Drinkers |
| cg14128619 | 18 | 43678270 | Higher in Drinkers |
| cg14131039 | 2 | 106360709 | Higher in Drinkers |
| cg14131285 | 17 | 71949210 | Higher in Drinkers |
| cg14134256 | 11 | 94502879 | Higher in Drinkers |
| cg14136506 | 5 | 77656095 | Higher in Drinkers |
| cg14139679 | 9 | 91937674 | Higher in Drinkers |
| cg14139870 | 4 | 141075097 | Higher in Drinkers |
| cg14141517 | 6 | 33538979 | Higher in Drinkers |
| cg14141984 | 16 | 30992128 | Higher in Drinkers |
| cg14147842 | 6 | 33362992 | Higher in Drinkers |
| cg14148981 | 14 | 52708138 | Lower in Drinkers |
| cg14149172 | 1 | 151298905 | Higher in Drinkers |
| cg14149609 | 3 | 53032638 | Higher in Drinkers |

| | | | |
|---|---|---|---|
| cg14151409 | 19 | 55987572 | Higher in Drinkers |
| cg14153897 | 2 | 122513049 | Higher in Drinkers |
| cg14156529 | 15 | 81245866 | Higher in Drinkers |
| cg14157824 | 2 | 223735640 | Higher in Drinkers |
| cg14160607 | 20 | 36156231 | Higher in Drinkers |
| cg14161579 | 18 | 9708890 | Higher in Drinkers |
| cg14162033 | 5 | 151150910 | Higher in Drinkers |
| cg14165766 | 9 | 136211179 | Higher in Drinkers |
| cg14171523 | 1 | 156163644 | Higher in Drinkers |
| cg14175617 | 2 | 242766567 | Lower in Drinkers |
| cg14176797 | 20 | 57426801 | Higher in Drinkers |
| cg14177930 | 5 | 179286124 | Higher in Drinkers |
| cg14178422 | 9 | 117350526 | Higher in Drinkers |
| cg14178748 | 1 | 153652247 | Higher in Drinkers |
| cg14179148 | 13 | 40796151 | Higher in Drinkers |
| cg14179796 | 21 | 33651673 | Higher in Drinkers |
| cg14181947 | 1 | 90228989 | Higher in Drinkers |
| cg14182693 | 1 | 27224189 | Higher in Drinkers |
| cg14184786 | 14 | 94547643 | Higher in Drinkers |
| cg14185323 | 9 | 33448590 | Lower in Drinkers |
| cg14186948 | 9 | 137723167 | Higher in Drinkers |
| cg14193314 | 9 | 131087980 | Higher in Drinkers |
| cg14194956 | 22 | 39378235 | Higher in Drinkers |
| cg14195115 | 9 | 38061778 | Lower in Drinkers |
| cg14196303 | 9 | 6757347 | Higher in Drinkers |
| cg14198291 | 7 | 29724746 | Higher in Drinkers |
| cg14198877 | 8 | 42128569 | Higher in Drinkers |
| cg14200635 | 7 | 27702666 | Higher in Drinkers |
| cg14201528 | 3 | 9791684 | Higher in Drinkers |
| cg14202610 | 12 | 31882280 | Higher in Drinkers |
| cg14202916 | 17 | 78820924 | Higher in Drinkers |
| cg14204791 | 21 | 44394797 | Higher in Drinkers |
| cg14205864 | 13 | 113341719 | Higher in Drinkers |
| cg14207267 | 12 | 113655841 | Higher in Drinkers |
| cg14207553 | 2 | 106071427 | Higher in Drinkers |

| | | | |
|---|---|---|---|
| cg14207589 | 1 | 225865327 | Higher in Drinkers |
| cg14207954 | 2 | 96987397 | Higher in Drinkers |
| cg14209549 | 10 | 3215073 | Higher in Drinkers |
| cg14210634 | 1 | 25870291 | Higher in Drinkers |
| cg14212748 | 12 | 53343703 | Higher in Drinkers |
| cg14214865 | 3 | 197025863 | Higher in Drinkers |
| cg14215728 | 7 | 2076778 | Higher in Drinkers |
| cg14217399 | 8 | 64081098 | Higher in Drinkers |
| cg14219044 | 6 | 32939398 | Higher in Drinkers |
| cg14219124 | 11 | 129992297 | Higher in Drinkers |
| cg14221039 | 1 | 205400120 | Higher in Drinkers |
| cg14221651 | 12 | 129329181 | Higher in Drinkers |
| cg14221939 | 6 | 29981675 | Higher in Drinkers |
| cg14222275 | 1 | 43855771 | Higher in Drinkers |
| cg14225844 | 6 | 43603546 | Higher in Drinkers |
| cg14225868 | 3 | 100119980 | Higher in Drinkers |
| cg14228788 | 20 | 48598378 | Higher in Drinkers |
| cg14230390 | 12 | 122249951 | Higher in Drinkers |
| cg14231270 | 17 | 30960240 | Higher in Drinkers |
| cg14233568 | 2 | 65216118 | Higher in Drinkers |
| cg14233838 | 9 | 139548425 | Higher in Drinkers |
| cg14234898 | 6 | 75953566 | Higher in Drinkers |
| cg14235676 | 17 | 66508939 | Higher in Drinkers |
| cg14236524 | 2 | 60779329 | Higher in Drinkers |
| cg14237189 | 9 | 136679025 | Higher in Drinkers |
| cg14239329 | 2 | 202899299 | Higher in Drinkers |
| cg14239366 | 6 | 14661635 | Higher in Drinkers |
| cg14241507 | 3 | 156535130 | Higher in Drinkers |
| cg14243741 | 11 | 2721817 | Higher in Drinkers |
| cg14256396 | 11 | 46260849 | Higher in Drinkers |
| cg14258675 | 14 | 75348443 | Higher in Drinkers |
| cg14260630 | 1 | 155211040 | Higher in Drinkers |
| cg14261868 | 1 | 149815294 | Higher in Drinkers |
| cg14264489 | 6 | 43018788 | Higher in Drinkers |
| cg14265068 | 17 | 77763497 | Higher in Drinkers |

| | | | |
|---|---|---|---|
| cg14266248 | 8 | 62606211 | Higher in Drinkers |
| cg14268019 | 2 | 114341631 | Higher in Drinkers |
| cg14271231 | 22 | 20759325 | Higher in Drinkers |
| cg14271651 | 17 | 78826369 | Higher in Drinkers |
| cg14272068 | 6 | 32821742 | Higher in Drinkers |
| cg14273822 | 6 | 26271716 | Higher in Drinkers |
| cg14275779 | 17 | 40830236 | Higher in Drinkers |
| cg14276435 | 8 | 22462062 | Higher in Drinkers |
| cg14279151 | 6 | 52369502 | Higher in Drinkers |
| cg14280409 | 1 | 11333535 | Higher in Drinkers |
| cg14280466 | 8 | 101920342 | Higher in Drinkers |
| cg14280947 | 9 | 129595523 | Higher in Drinkers |
| cg14283330 | 10 | 94449250 | Higher in Drinkers |
| cg14284506 | 17 | 25981832 | Higher in Drinkers |
| cg14286845 | 9 | 115513482 | Higher in Drinkers |
| cg14288091 | 8 | 99305661 | Higher in Drinkers |
| cg14290451 | 6 | 35436136 | Higher in Drinkers |
| cg14294076 | 6 | 31697306 | Higher in Drinkers |
| cg14296331 | 4 | 1949947 | Higher in Drinkers |
| cg14297546 | 9 | 139683367 | Lower in Drinkers |
| cg14303330 | 1 | 6259905 | Higher in Drinkers |
| cg14307922 | 19 | 58892495 | Higher in Drinkers |
| cg14311538 | 9 | 139348775 | Lower in Drinkers |
| cg14311559 | 12 | 7060257 | Higher in Drinkers |
| cg14312115 | 15 | 34630047 | Higher in Drinkers |
| cg14312894 | 12 | 57171980 | Higher in Drinkers |
| cg14313398 | 14 | 90008373 | Higher in Drinkers |
| cg14313748 | 9 | 101498661 | Higher in Drinkers |
| cg14314643 | 12 | 76742180 | Higher in Drinkers |
| cg14315058 | 8 | 99182422 | Higher in Drinkers |
| cg14317651 | 15 | 49448126 | Higher in Drinkers |
| cg14320195 | 9 | 117501329 | Higher in Drinkers |
| cg14320796 | 4 | 154265537 | Higher in Drinkers |
| cg14320938 | 9 | 99180324 | Higher in Drinkers |
| cg14322681 | 7 | 26904183 | Higher in Drinkers |

| | | | |
|---|---|---|---|
| cg14326644 | 2 | 29430352 | Lower in Drinkers |
| cg14329989 | 11 | 119192155 | Higher in Drinkers |
| cg14332086 | X | 48755145 | Higher in Drinkers |
| cg14334425 | 2 | 240056134 | Higher in Drinkers |
| cg14335478 | 9 | 137018489 | Higher in Drinkers |
| cg14339664 | 10 | 61122570 | Higher in Drinkers |
| cg14342817 | 6 | 161560695 | Lower in Drinkers |
| cg14344749 | X | 133929361 | Lower in Drinkers |
| cg14345069 | 4 | 186347299 | Higher in Drinkers |
| cg14347670 | 6 | 41908995 | Higher in Drinkers |
| cg14350197 | 18 | 35147162 | Higher in Drinkers |
| cg14356187 | 22 | 22652273 | Higher in Drinkers |
| cg14357226 | 14 | 39902004 | Higher in Drinkers |
| cg14361641 | 2 | 70056642 | Higher in Drinkers |
| cg14363185 | 9 | 35115835 | Higher in Drinkers |
| cg14363636 | 11 | 61129374 | Higher in Drinkers |
| cg14364094 | 11 | 62459317 | Higher in Drinkers |
| cg14365143 | 21 | 48088046 | Higher in Drinkers |
| cg14365457 | 9 | 124029877 | Higher in Drinkers |
| cg14370628 | 3 | 186857397 | Higher in Drinkers |
| cg14370961 | 14 | 105767520 | Higher in Drinkers |
| cg14374504 | 9 | 86322725 | Higher in Drinkers |
| cg14380045 | 9 | 15527817 | Higher in Drinkers |
| cg14381712 | 1 | 12546623 | Higher in Drinkers |
| cg14383815 | 8 | 6282955 | Higher in Drinkers |
| cg14388783 | 9 | 103115158 | Higher in Drinkers |
| cg14390179 | 8 | 145662220 | Higher in Drinkers |
| cg14392746 | 11 | 2721207 | Higher in Drinkers |
| cg14394617 | 12 | 54674541 | Higher in Drinkers |
| cg14395791 | 9 | 140166606 | Higher in Drinkers |
| cg14397500 | 7 | 2214759 | Higher in Drinkers |
| cg14400030 | 12 | 122498111 | Lower in Drinkers |
| cg14404158 | 6 | 21587687 | Higher in Drinkers |
| cg14406138 | 2 | 139259159 | Higher in Drinkers |
| cg14406628 | 15 | 45492442 | Higher in Drinkers |

| | | | |
|---|---|---|---|
| cg14407698 | 9 | 34458886 | Higher in Drinkers |
| cg14407883 | 17 | 29025223 | Higher in Drinkers |
| cg14408969 | 8 | 42396118 | Higher in Drinkers |
| cg14409083 | 12 | 13349724 | Higher in Drinkers |
| cg14410964 | 9 | 139427106 | Higher in Drinkers |
| cg14411503 | 14 | 103589028 | Higher in Drinkers |
| cg14413721 | 9 | 86322043 | Higher in Drinkers |
| cg14414122 | 22 | 50585386 | Higher in Drinkers |
| cg14416047 | 9 | 99329563 | Higher in Drinkers |
| cg14417407 | 1 | 94313600 | Higher in Drinkers |
| cg14418720 | 10 | 75504431 | Higher in Drinkers |
| cg14420589 | 6 | 116601141 | Higher in Drinkers |
| cg14420645 | 22 | 24114857 | Higher in Drinkers |
| cg14421829 | 9 | 117350234 | Higher in Drinkers |
| cg14423735 | 3 | 132757418 | Higher in Drinkers |
| cg14424070 | 14 | 75988820 | Higher in Drinkers |
| cg14424111 | 20 | 36662310 | Higher in Drinkers |
| cg14424295 | 9 | 3527075 | Higher in Drinkers |
| cg14424625 | 17 | 45898841 | Higher in Drinkers |
| cg14425423 | 9 | 130743818 | Higher in Drinkers |
| cg14426312 | 9 | 71395063 | Higher in Drinkers |
| cg14429979 | 11 | 1009801 | Lower in Drinkers |
| cg14430867 | 17 | 37607663 | Higher in Drinkers |
| cg14431006 | 15 | 83952722 | Lower in Drinkers |
| cg14438174 | 17 | 7137923 | Higher in Drinkers |
| cg14442715 | 1 | 1496934 | Higher in Drinkers |
| cg14443090 | 16 | 3184942 | Higher in Drinkers |
| cg14445437 | 17 | 26898124 | Higher in Drinkers |
| cg14450620 | 11 | 50368251 | Higher in Drinkers |
| cg14451701 | 20 | 22567724 | Higher in Drinkers |
| cg14452121 | 9 | 111776163 | Higher in Drinkers |
| cg14452392 | 5 | 86708659 | Higher in Drinkers |
| cg14458834 | 17 | 46655394 | Higher in Drinkers |
| cg14461547 | 9 | 134731659 | Lower in Drinkers |
| cg14465355 | 14 | 102483309 | Higher in Drinkers |

| | | | |
|---|---|---|---|
| cg14467955 | 12 | 109490248 | Higher in Drinkers |
| cg14468090 | 3 | 129032864 | Higher in Drinkers |
| cg14469684 | 9 | 138997380 | Higher in Drinkers |
| cg14470409 | X | 146993125 | Higher in Drinkers |
| cg14472716 | 9 | 137236548 | Higher in Drinkers |
| cg14473123 | 8 | 48921407 | Higher in Drinkers |
| cg14473516 | 2 | 309026 | Higher in Drinkers |
| cg14478610 | 2 | 127864964 | Higher in Drinkers |
| cg14479037 | X | 106242642 | Higher in Drinkers |
| cg14482068 | 15 | 49447245 | Higher in Drinkers |
| cg14482093 | 8 | 22461488 | Higher in Drinkers |
| cg14487878 | 9 | 111775927 | Higher in Drinkers |
| cg14492347 | 15 | 85292323 | Higher in Drinkers |
| cg14495243 | 12 | 82752005 | Higher in Drinkers |
| cg14495953 | 18 | 24284634 | Lower in Drinkers |
| cg14498572 | 7 | 1997713 | Higher in Drinkers |
| cg14499387 | 22 | 31668786 | Higher in Drinkers |
| cg14500050 | 13 | 114852691 | Higher in Drinkers |
| cg14501061 | 17 | 26904058 | Higher in Drinkers |
| cg14501697 | 9 | 135545019 | Higher in Drinkers |
| cg14505161 | 7 | 30544458 | Higher in Drinkers |
| cg14507038 | 9 | 130690399 | Higher in Drinkers |
| cg14507193 | 5 | 57755944 | Higher in Drinkers |
| cg14508777 | 3 | 42847116 | Lower in Drinkers |
| cg14509623 | 3 | 72898069 | Higher in Drinkers |
| cg14509895 | 9 | 113017921 | Higher in Drinkers |
| cg14510638 | 12 | 132423726 | Higher in Drinkers |
| cg14511768 | 1 | 26362707 | Higher in Drinkers |
| cg14512425 | 2 | 16080622 | Higher in Drinkers |
| cg14513222 | 9 | 140079404 | Lower in Drinkers |
| cg14513731 | 2 | 101618883 | Higher in Drinkers |
| cg14518302 | 21 | 40721356 | Higher in Drinkers |
| cg14519125 | 3 | 49893811 | Higher in Drinkers |
| cg14519793 | 12 | 66696305 | Higher in Drinkers |
| cg14520448 | X | 48755206 | Higher in Drinkers |

| | | | |
|---|---|---|---|
| cg14522373 | 6 | 43597660 | Higher in Drinkers |
| cg14522873 | 20 | 21283801 | Higher in Drinkers |
| cg14523284 | 5 | 131993614 | Higher in Drinkers |
| cg14525059 | 3 | 128485954 | Higher in Drinkers |
| cg14526204 | 19 | 44174404 | Higher in Drinkers |
| cg14529173 | 6 | 28048874 | Higher in Drinkers |
| cg14530006 | 17 | 75472168 | Higher in Drinkers |
| cg14533068 | 6 | 158507953 | Lower in Drinkers |
| cg14533133 | X | 144902897 | Higher in Drinkers |
| cg14538055 | 11 | 66035834 | Higher in Drinkers |
| cg14538319 | 15 | 93464153 | Higher in Drinkers |
| cg14538502 | 12 | 77269813 | Lower in Drinkers |
| cg14538537 | 12 | 6939048 | Higher in Drinkers |
| cg14542238 | 2 | 85555574 | Higher in Drinkers |
| cg14542802 | 6 | 15663170 | Higher in Drinkers |
| cg14543412 | 6 | 26224100 | Higher in Drinkers |
| cg14547996 | 9 | 136891620 | Higher in Drinkers |
| cg14549057 | 9 | 99638182 | Higher in Drinkers |
| cg14549249 | 7 | 3083541 | Higher in Drinkers |
| cg14550422 | 18 | 46066011 | Higher in Drinkers |
| cg14550519 | 17 | 58180026 | Higher in Drinkers |
| cg14550570 | 1 | 3712988 | Higher in Drinkers |
| cg14551279 | 8 | 42294139 | Higher in Drinkers |
| cg14555127 | 7 | 35841578 | Higher in Drinkers |
| cg14556618 | 6 | 160390829 | Higher in Drinkers |
| cg14557825 | 1 | 9551398 | Higher in Drinkers |
| cg14558191 | 3 | 45943637 | Lower in Drinkers |
| cg14560001 | 3 | 44038250 | Higher in Drinkers |
| cg14564237 | 8 | 23314907 | Higher in Drinkers |
| cg14564692 | 17 | 34257764 | Higher in Drinkers |
| cg14567593 | 19 | 13265338 | Higher in Drinkers |
| cg14571620 | 12 | 123717888 | Higher in Drinkers |
| cg14572111 | 11 | 61348901 | Higher in Drinkers |
| cg14572728 | 9 | 98279112 | Higher in Drinkers |
| cg14574404 | 11 | 122931178 | Higher in Drinkers |

| | | | |
|---|---|---|---|
| cg14585050 | 6 | 351609 | Lower in Drinkers |
| cg14585611 | 2 | 175260420 | Higher in Drinkers |
| cg14588027 | 1 | 212872986 | Higher in Drinkers |
| cg14595083 | 9 | 140652711 | Lower in Drinkers |
| cg14596702 | 9 | 123898189 | Higher in Drinkers |
| cg14599023 | 11 | 27384909 | Higher in Drinkers |
| cg14599362 | 9 | 139133513 | Higher in Drinkers |
| cg14601312 | X | 135333917 | Higher in Drinkers |
| cg14601550 | 17 | 40346443 | Higher in Drinkers |
| cg14601938 | 1 | 150122016 | Higher in Drinkers |
| cg14604475 | 9 | 139781630 | Higher in Drinkers |
| cg14605134 | 1 | 155036362 | Higher in Drinkers |
| cg14606116 | 20 | 53092818 | Higher in Drinkers |
| cg14606328 | 21 | 45177639 | Higher in Drinkers |
| cg14607813 | 1 | 225965727 | Higher in Drinkers |
| cg14610973 | 17 | 13600687 | Higher in Drinkers |
| cg14611727 | 6 | 76022250 | Higher in Drinkers |
| cg14611892 | 4 | 113067071 | Higher in Drinkers |
| cg14612335 | 3 | 170074131 | Higher in Drinkers |
| cg14615537 | 9 | 137091808 | Lower in Drinkers |
| cg14616251 | 1 | 24648696 | Higher in Drinkers |
| cg14616584 | 1 | 57388124 | Higher in Drinkers |
| cg14616651 | X | 119004996 | Higher in Drinkers |
| cg14617448 | 9 | 138852499 | Higher in Drinkers |
| cg14617594 | 6 | 3118749 | Higher in Drinkers |
| cg14630947 | 20 | 47894888 | Higher in Drinkers |
| cg14634247 | 11 | 107728952 | Higher in Drinkers |
| cg14637317 | 22 | 39077763 | Higher in Drinkers |
| cg14639753 | 1 | 1913799 | Higher in Drinkers |
| cg14640367 | 5 | 1660156 | Lower in Drinkers |
| cg14642832 | X | 135963137 | Higher in Drinkers |
| cg14642833 | 10 | 58121299 | Higher in Drinkers |
| cg14643686 | 12 | 12264390 | Higher in Drinkers |
| cg14644204 | 12 | 123518833 | Higher in Drinkers |
| cg14648167 | 7 | 39605777 | Higher in Drinkers |

| | | | |
|---|---|---|---|
| cg14649272 | 22 | 46402476 | Higher in Drinkers |
| cg14652629 | 21 | 40177852 | Higher in Drinkers |
| cg14652657 | 9 | 134735624 | Higher in Drinkers |
| cg14655905 | 11 | 10512693 | Higher in Drinkers |
| cg14657159 | 12 | 56211136 | Higher in Drinkers |
| cg14658630 | 6 | 107390422 | Higher in Drinkers |
| cg14659956 | 5 | 17189703 | Higher in Drinkers |
| cg14661813 | 4 | 77870773 | Higher in Drinkers |
| cg14664458 | 13 | 21750341 | Higher in Drinkers |
| cg14668821 | 17 | 77704760 | Higher in Drinkers |
| cg14670310 | 11 | 65746023 | Higher in Drinkers |
| cg14673722 | 17 | 71065768 | Higher in Drinkers |
| cg14675513 | 6 | 5004368 | Higher in Drinkers |
| cg14680939 | 3 | 42055928 | Higher in Drinkers |
| cg14681854 | 1 | 93250590 | Higher in Drinkers |
| cg14685245 | 19 | 3456463 | Higher in Drinkers |
| cg14685339 | 14 | 77787351 | Higher in Drinkers |
| cg14686845 | 8 | 6565560 | Higher in Drinkers |
| cg14688751 | 7 | 30066350 | Higher in Drinkers |
| cg14688905 | 12 | 51403056 | Higher in Drinkers |
| cg14689122 | 3 | 122809537 | Higher in Drinkers |
| cg14689655 | 19 | 58087972 | Higher in Drinkers |
| cg14689715 | 6 | 3140660 | Higher in Drinkers |
| cg14690315 | 11 | 65268175 | Higher in Drinkers |
| cg14693487 | 11 | 117198998 | Higher in Drinkers |
| cg14697475 | 3 | 142720940 | Higher in Drinkers |
| cg14697835 | 11 | 79151202 | Higher in Drinkers |
| cg14701856 | 20 | 2505462 | Higher in Drinkers |
| cg14702264 | 7 | 66385829 | Higher in Drinkers |
| cg14710165 | 8 | 126104387 | Higher in Drinkers |
| cg14710524 | 16 | 30662724 | Higher in Drinkers |
| cg14710934 | 5 | 138725705 | Higher in Drinkers |
| cg14711016 | 16 | 790766 | Higher in Drinkers |
| cg14717725 | 11 | 129620945 | Higher in Drinkers |
| cg14720838 | 17 | 7835468 | Higher in Drinkers |

| | | | |
|---|---|---|---|
| cg14723014 | 13 | 20436987 | Higher in Drinkers |
| cg14728276 | 1 | 26798723 | Higher in Drinkers |
| cg14732699 | 8 | 128750039 | Higher in Drinkers |
| cg14733867 | 8 | 144884056 | Lower in Drinkers |
| cg14734630 | 12 | 29553564 | Higher in Drinkers |
| cg14741141 | 20 | 24973699 | Higher in Drinkers |
| cg14747813 | 8 | 23848786 | Lower in Drinkers |
| cg14750277 | 8 | 73164024 | Higher in Drinkers |
| cg14751481 | 12 | 133009355 | Lower in Drinkers |
| cg14759342 | 5 | 115911760 | Higher in Drinkers |
| cg14759931 | 18 | 77631636 | Higher in Drinkers |
| cg14762316 | 6 | 28831507 | Higher in Drinkers |
| cg14770102 | 11 | 58984446 | Higher in Drinkers |
| cg14773282 | 19 | 19754574 | Higher in Drinkers |
| cg14779106 | 5 | 133747446 | Higher in Drinkers |
| cg14780066 | 19 | 6373131 | Higher in Drinkers |
| cg14780845 | 17 | 41323115 | Higher in Drinkers |
| cg14780914 | 20 | 18447767 | Higher in Drinkers |
| cg14782237 | 7 | 155433645 | Higher in Drinkers |
| cg14784788 | 5 | 137667435 | Higher in Drinkers |
| cg14785511 | 20 | 62680998 | Higher in Drinkers |
| cg14787483 | 22 | 39052528 | Higher in Drinkers |
| cg14791413 | 12 | 129338870 | Higher in Drinkers |
| cg14792904 | 6 | 88299623 | Higher in Drinkers |
| cg14793430 | 5 | 1289007 | Lower in Drinkers |
| cg14793891 | 2 | 220109985 | Higher in Drinkers |
| cg14794065 | 19 | 16296078 | Higher in Drinkers |
| cg14797438 | 18 | 9615155 | Higher in Drinkers |
| cg14799304 | 11 | 46867314 | Higher in Drinkers |
| cg14800299 | 19 | 17691465 | Higher in Drinkers |
| cg14801238 | 6 | 31275664 | Higher in Drinkers |
| cg14806146 | 17 | 41476317 | Higher in Drinkers |
| cg14808739 | 17 | 17741098 | Higher in Drinkers |
| cg14809544 | 19 | 46366591 | Higher in Drinkers |
| cg14809912 | 11 | 1306817 | Higher in Drinkers |

| | | | |
|---|---|---|---|
| cg14815724 | 4 | 48271893 | Higher in Drinkers |
| cg14819132 | 17 | 17495032 | Higher in Drinkers |
| cg14821008 | 6 | 64283529 | Higher in Drinkers |
| cg14823076 | 6 | 32158439 | Higher in Drinkers |
| cg14825408 | 17 | 11924870 | Higher in Drinkers |
| cg14827149 | 1 | 22441051 | Higher in Drinkers |
| cg14831380 | 8 | 144510421 | Higher in Drinkers |
| cg14833160 | 19 | 49457855 | Higher in Drinkers |
| cg14836868 | 8 | 42196054 | Higher in Drinkers |
| cg14837635 | 1 | 116943618 | Lower in Drinkers |
| cg14838017 | 1 | 160232450 | Higher in Drinkers |
| cg14838256 | 4 | 56212685 | Higher in Drinkers |
| cg14838970 | 11 | 7533817 | Higher in Drinkers |
| cg14839440 | 15 | 43213257 | Higher in Drinkers |
| cg14839932 | 6 | 43139162 | Higher in Drinkers |
| cg14840081 | 7 | 152551660 | Higher in Drinkers |
| cg14840163 | 8 | 22921537 | Higher in Drinkers |
| cg14841796 | 6 | 29596285 | Higher in Drinkers |
| cg14843842 | 6 | 41888877 | Higher in Drinkers |
| cg14844679 | 8 | 146278000 | Higher in Drinkers |
| cg14847243 | 3 | 184104362 | Lower in Drinkers |
| cg14848767 | 17 | 17991639 | Higher in Drinkers |
| cg14848832 | 1 | 155058696 | Higher in Drinkers |
| cg14850181 | 22 | 37416188 | Higher in Drinkers |
| cg14851346 | 12 | 38532713 | Higher in Drinkers |
| cg14853734 | 11 | 59577941 | Higher in Drinkers |
| cg14854487 | X | 119603098 | Higher in Drinkers |
| cg14859317 | 7 | 100853623 | Lower in Drinkers |
| cg14860917 | 8 | 19871440 | Higher in Drinkers |
| cg14865535 | 21 | 45363474 | Higher in Drinkers |
| cg14868530 | 15 | 73976679 | Higher in Drinkers |
| cg14869845 | 5 | 111093017 | Higher in Drinkers |
| cg14870383 | 12 | 7126003 | Higher in Drinkers |
| cg14871113 | 19 | 39936655 | Higher in Drinkers |
| cg14871704 | 11 | 124670745 | Higher in Drinkers |

| | | | |
|---|---|---|---|
| cg14872530 | 5 | 162386528 | Higher in Drinkers |
| cg14872736 | 9 | 139685801 | Higher in Drinkers |
| cg14880079 | 3 | 194120150 | Higher in Drinkers |
| cg14890631 | 8 | 42772400 | Higher in Drinkers |
| cg14890726 | 3 | 113233993 | Higher in Drinkers |
| cg14892058 | 12 | 14956310 | Higher in Drinkers |
| cg14892570 | 19 | 15559628 | Higher in Drinkers |
| cg14893576 | 2 | 23604202 | Higher in Drinkers |
| cg14893857 | 14 | 102554969 | Higher in Drinkers |
| cg14896306 | 19 | 51611929 | Higher in Drinkers |
| cg14897791 | 18 | 74533923 | Higher in Drinkers |
| cg14898263 | 13 | 113462013 | Higher in Drinkers |
| cg14898822 | 15 | 83478541 | Higher in Drinkers |
| cg14899547 | 2 | 113521923 | Higher in Drinkers |
| cg14903202 | 12 | 133393115 | Higher in Drinkers |
| cg14908653 | 18 | 911900 | Lower in Drinkers |
| cg14911242 | 14 | 105892412 | Higher in Drinkers |
| cg14912896 | 2 | 73461180 | Higher in Drinkers |
| cg14914982 | 12 | 4382995 | Higher in Drinkers |
| cg14916108 | 12 | 2027993 | Higher in Drinkers |
| cg14922732 | 1 | 3731959 | Higher in Drinkers |
| cg14924091 | 15 | 40763073 | Higher in Drinkers |
| cg14925722 | 6 | 139695464 | Higher in Drinkers |
| cg14927083 | 9 | 132175840 | Higher in Drinkers |
| cg14928293 | 20 | 37591018 | Higher in Drinkers |
| cg14928532 | 9 | 133454630 | Higher in Drinkers |
| cg14930471 | 10 | 71883768 | Higher in Drinkers |
| cg14931686 | 11 | 47870114 | Higher in Drinkers |
| cg14932016 | 1 | 236849653 | Higher in Drinkers |
| cg14933899 | 2 | 242041835 | Higher in Drinkers |
| cg14935378 | 7 | 86849013 | Higher in Drinkers |
| cg14938730 | 6 | 10723588 | Higher in Drinkers |
| cg14939691 | 3 | 53289981 | Higher in Drinkers |
| cg14944738 | 10 | 72621786 | Higher in Drinkers |
| cg14954836 | 19 | 2349979 | Higher in Drinkers |

| | | | |
|---|---|---|---|
| cg14955617 | 17 | 78800264 | Higher in Drinkers |
| cg14958505 | 3 | 197025873 | Higher in Drinkers |
| cg14958889 | 1 | 6320471 | Higher in Drinkers |
| cg14962363 | 11 | 133939265 | Higher in Drinkers |
| cg14962548 | 2 | 99952717 | Higher in Drinkers |
| cg14964115 | 10 | 116634877 | Lower in Drinkers |
| cg14964494 | 19 | 57901031 | Higher in Drinkers |
| cg14964658 | 1 | 160255030 | Higher in Drinkers |
| cg14966519 | 19 | 35739200 | Higher in Drinkers |
| cg14971781 | 1 | 226374753 | Higher in Drinkers |
| cg14971998 | 5 | 139488181 | Higher in Drinkers |
| cg14973366 | X | 153599377 | Higher in Drinkers |
| cg14973369 | 3 | 195163860 | Higher in Drinkers |
| cg14974722 | 17 | 35306061 | Higher in Drinkers |
| cg14975206 | 11 | 1860654 | Higher in Drinkers |
| cg14976978 | 11 | 67159397 | Higher in Drinkers |
| cg14977037 | 12 | 57480798 | Higher in Drinkers |
| cg14981573 | 1 | 70671146 | Higher in Drinkers |
| cg14985231 | 22 | 21271315 | Higher in Drinkers |
| cg14988503 | 4 | 76555547 | Higher in Drinkers |
| cg14989202 | 1 | 9714843 | Higher in Drinkers |
| cg14995433 | 17 | 41174471 | Higher in Drinkers |
| cg14996807 | 19 | 17759239 | Lower in Drinkers |
| cg15005908 | 6 | 114292723 | Higher in Drinkers |
| cg15006843 | 1 | 205720633 | Higher in Drinkers |
| cg15006881 | 8 | 97158052 | Higher in Drinkers |
| cg15011209 | 3 | 12705694 | Higher in Drinkers |
| cg15011249 | 3 | 37218150 | Higher in Drinkers |
| cg15012054 | 12 | 13253742 | Higher in Drinkers |
| cg15014361 | 6 | 32609212 | Higher in Drinkers |
| cg15020801 | 17 | 46022809 | Higher in Drinkers |
| cg15022984 | 6 | 26056706 | Higher in Drinkers |
| cg15023858 | 3 | 69812434 | Lower in Drinkers |
| cg15025054 | 1 | 212964885 | Higher in Drinkers |
| cg15026998 | 2 | 160761622 | Higher in Drinkers |

| | | | |
|---|---|---|---|
| cg15027249 | 19 | 15490215 | Higher in Drinkers |
| cg15029192 | 15 | 49447345 | Higher in Drinkers |
| cg15030415 | 17 | 2908068 | Higher in Drinkers |
| cg15031826 | 1 | 208136952 | Higher in Drinkers |
| cg15031983 | 6 | 28510376 | Higher in Drinkers |
| cg15032001 | 20 | 48807623 | Higher in Drinkers |
| cg15033036 | 9 | 133556841 | Higher in Drinkers |
| cg15037663 | 7 | 24797835 | Higher in Drinkers |
| cg15041487 | X | 48958242 | Higher in Drinkers |
| cg15044248 | 17 | 75369224 | Higher in Drinkers |
| cg15044954 | 7 | 39874365 | Higher in Drinkers |
| cg15046965 | 17 | 19648718 | Higher in Drinkers |
| cg15047833 | 16 | 57496411 | Higher in Drinkers |
| cg15048430 | X | 54384161 | Higher in Drinkers |
| cg15049274 | 1 | 118472180 | Higher in Drinkers |
| cg15051332 | 6 | 41514432 | Higher in Drinkers |
| cg15052747 | 9 | 138942591 | Lower in Drinkers |
| cg15054972 | 2 | 111435817 | Higher in Drinkers |
| cg15055674 | 19 | 44529452 | Higher in Drinkers |
| cg15056751 | 3 | 3169441 | Lower in Drinkers |
| cg15058605 | 2 | 208031878 | Higher in Drinkers |
| cg15059932 | 18 | 74535233 | Higher in Drinkers |
| cg15060929 | 18 | 23670778 | Higher in Drinkers |
| cg15061008 | 22 | 24407907 | Higher in Drinkers |
| cg15064019 | 1 | 225965678 | Higher in Drinkers |
| cg15066577 | 1 | 212459293 | Higher in Drinkers |
| cg15067401 | 12 | 88536400 | Higher in Drinkers |
| cg15076023 | 2 | 175260335 | Higher in Drinkers |
| cg15076217 | 1 | 207975699 | Higher in Drinkers |
| cg15082635 | 5 | 180670110 | Higher in Drinkers |
| cg15083255 | 17 | 72772540 | Higher in Drinkers |
| cg15084921 | 5 | 14143207 | Higher in Drinkers |
| cg15086653 | 1 | 38026153 | Higher in Drinkers |
| cg15087448 | 3 | 128720250 | Higher in Drinkers |
| cg15090714 | 17 | 60142985 | Higher in Drinkers |

| | | | |
|---|---|---|---|
| cg15090909 | 5 | 179306345 | Higher in Drinkers |
| cg15093402 | 1 | 147071403 | Higher in Drinkers |
| cg15094912 | 21 | 46707781 | Higher in Drinkers |
| cg15097876 | 10 | 71993604 | Higher in Drinkers |
| cg15099410 | 1 | 28585832 | Higher in Drinkers |
| cg15100209 | 1 | 19670446 | Higher in Drinkers |
| cg15101633 | 14 | 101293726 | Higher in Drinkers |
| cg15101634 | 5 | 39665570 | Higher in Drinkers |
| cg15102179 | 11 | 2965028 | Higher in Drinkers |
| cg15105081 | 11 | 77532226 | Higher in Drinkers |
| cg15106925 | 6 | 108169535 | Higher in Drinkers |
| cg15107117 | 7 | 105817781 | Lower in Drinkers |
| cg15109221 | 6 | 15245772 | Higher in Drinkers |
| cg15110127 | 8 | 132916222 | Higher in Drinkers |
| cg15110353 | 10 | 102985377 | Higher in Drinkers |
| cg15115797 | 11 | 66205994 | Higher in Drinkers |
| cg15116488 | 11 | 64794988 | Higher in Drinkers |
| cg15117252 | 11 | 77850838 | Higher in Drinkers |
| cg15117253 | 12 | 53835834 | Higher in Drinkers |
| cg15117548 | 12 | 26279160 | Higher in Drinkers |
| cg15118204 | 17 | 79876231 | Higher in Drinkers |
| cg15120635 | 1 | 155990282 | Higher in Drinkers |
| cg15121053 | 7 | 138818439 | Higher in Drinkers |
| cg15122716 | 9 | 140050568 | Higher in Drinkers |
| cg15123365 | 8 | 144328928 | Higher in Drinkers |
| cg15124968 | 5 | 140855469 | Higher in Drinkers |
| cg15125438 | 12 | 113684389 | Higher in Drinkers |
| cg15125634 | 15 | 66161842 | Higher in Drinkers |
| cg15127791 | 11 | 128729883 | Higher in Drinkers |
| cg15128849 | 1 | 70820718 | Higher in Drinkers |
| cg15128917 | 7 | 149172002 | Higher in Drinkers |
| cg15131282 | 2 | 233925030 | Higher in Drinkers |
| cg15133133 | 1 | 230202495 | Higher in Drinkers |
| cg15133448 | 10 | 95327325 | Lower in Drinkers |
| cg15142246 | 8 | 37553287 | Higher in Drinkers |

| | | | |
|---|---|---|---|
| cg15144540 | 8 | 144621379 | Higher in Drinkers |
| cg15145873 | 2 | 74685517 | Higher in Drinkers |
| cg15153791 | 1 | 955083 | Higher in Drinkers |
| cg15155209 | 3 | 14502277 | Higher in Drinkers |
| cg15158977 | 17 | 62962238 | Higher in Drinkers |
| cg15159420 | 3 | 195545327 | Lower in Drinkers |
| cg15159588 | 17 | 26672798 | Higher in Drinkers |
| cg15160780 | 2 | 159825180 | Higher in Drinkers |
| cg15167646 | 17 | 47653306 | Higher in Drinkers |
| cg15168294 | 8 | 143419464 | Higher in Drinkers |
| cg15170442 | 8 | 144521607 | Higher in Drinkers |
| cg15170456 | 2 | 61769768 | Higher in Drinkers |
| cg15172061 | 8 | 144638852 | Higher in Drinkers |
| cg15174310 | 6 | 161413442 | Higher in Drinkers |
| cg15175091 | 3 | 51016232 | Higher in Drinkers |
| cg15175577 | 22 | 32808177 | Higher in Drinkers |
| cg15176664 | 19 | 45681828 | Higher in Drinkers |
| cg15183126 | 3 | 33138421 | Higher in Drinkers |
| cg15185001 | 19 | 35739448 | Higher in Drinkers |
| cg15185774 | 8 | 101363275 | Higher in Drinkers |
| cg15185936 | 6 | 32764951 | Higher in Drinkers |
| cg15194935 | 19 | 10405955 | Higher in Drinkers |
| cg15198739 | 22 | 26908541 | Higher in Drinkers |
| cg15199408 | 4 | 76649756 | Higher in Drinkers |
| cg15199800 | 15 | 44069791 | Higher in Drinkers |
| cg15202447 | 6 | 29720635 | Higher in Drinkers |
| cg15208756 | 4 | 144480363 | Higher in Drinkers |
| cg15210596 | 1 | 246887325 | Higher in Drinkers |
| cg15213565 | 6 | 30294117 | Higher in Drinkers |
| cg15214069 | 9 | 139333582 | Higher in Drinkers |
| cg15222651 | 19 | 9609152 | Higher in Drinkers |
| cg15222709 | 11 | 118889154 | Higher in Drinkers |
| cg15227231 | 6 | 170467425 | Lower in Drinkers |
| cg15227574 | 17 | 76183323 | Higher in Drinkers |
| cg15227982 | 10 | 104535854 | Higher in Drinkers |

| | | | |
|---|---|---|---|
| cg15228247 | 6 | 34122832 | Higher in Drinkers |
| cg15233114 | 10 | 60145133 | Higher in Drinkers |
| cg15238128 | 19 | 50355350 | Higher in Drinkers |
| cg15239703 | 4 | 169931051 | Higher in Drinkers |
| cg15239874 | 12 | 121148841 | Higher in Drinkers |
| cg15239888 | 19 | 7996745 | Higher in Drinkers |
| cg15242490 | 3 | 138313011 | Higher in Drinkers |
| cg15244290 | 6 | 42134430 | Higher in Drinkers |
| cg15246619 | 8 | 21905462 | Higher in Drinkers |
| cg15247434 | 13 | 95201296 | Higher in Drinkers |
| cg15248135 | 19 | 56154954 | Higher in Drinkers |
| cg15254237 | 17 | 76986702 | Higher in Drinkers |
| cg15260250 | 5 | 115177504 | Higher in Drinkers |
| cg15260839 | 17 | 57642861 | Higher in Drinkers |
| cg15261837 | 17 | 17064703 | Higher in Drinkers |
| cg15262336 | 2 | 44223417 | Higher in Drinkers |
| cg15264052 | 11 | 27528011 | Higher in Drinkers |
| cg15268622 | 1 | 167189846 | Higher in Drinkers |
| cg15269027 | 6 | 31865759 | Higher in Drinkers |
| cg15270235 | 3 | 195682595 | Higher in Drinkers |
| cg15271056 | 8 | 87520737 | Higher in Drinkers |
| cg15273230 | 20 | 25038391 | Higher in Drinkers |
| cg15279236 | 10 | 74127457 | Higher in Drinkers |
| cg15279766 | 6 | 26402511 | Higher in Drinkers |
| cg15287024 | 15 | 34393715 | Higher in Drinkers |
| cg15287052 | 9 | 132648283 | Higher in Drinkers |
| cg15291410 | 22 | 20105008 | Higher in Drinkers |
| cg15298594 | 2 | 15701366 | Higher in Drinkers |
| cg15303052 | 7 | 158526867 | Lower in Drinkers |
| cg15309264 | 2 | 58274034 | Higher in Drinkers |
| cg15309361 | 7 | 2152625 | Higher in Drinkers |
| cg15311460 | 11 | 406997 | Higher in Drinkers |
| cg15313325 | 11 | 58869663 | Higher in Drinkers |
| cg15315493 | 6 | 32941389 | Higher in Drinkers |
| cg15315630 | 1 | 35497506 | Higher in Drinkers |

| | | | |
|---|---|---|---|
| cg15318532 | 13 | 37393521 | Higher in Drinkers |
| cg15318861 | 22 | 36044328 | Higher in Drinkers |
| cg15322207 | 1 | 211689087 | Higher in Drinkers |
| cg15326795 | 6 | 26217500 | Higher in Drinkers |
| cg15328005 | 3 | 43389621 | Higher in Drinkers |
| cg15328328 | 2 | 122124207 | Higher in Drinkers |
| cg15337006 | 16 | 31271009 | Higher in Drinkers |
| cg15344914 | 12 | 54567476 | Higher in Drinkers |
| cg15350455 | 2 | 24270357 | Higher in Drinkers |
| cg15350925 | 8 | 86132775 | Higher in Drinkers |
| cg15353389 | 12 | 120525027 | Higher in Drinkers |
| cg15355859 | 11 | 79149352 | Higher in Drinkers |
| cg15356226 | 22 | 41843734 | Higher in Drinkers |
| cg15356780 | 14 | 90422831 | Higher in Drinkers |
| cg15356885 | 2 | 99953699 | Higher in Drinkers |
| cg15358657 | 14 | 78082484 | Higher in Drinkers |
| cg15360774 | 4 | 48782043 | Higher in Drinkers |
| cg15363996 | 14 | 90452965 | Higher in Drinkers |
| cg15364335 | 3 | 53925231 | Higher in Drinkers |
| cg15366555 | 2 | 74601926 | Higher in Drinkers |
| cg15369821 | 6 | 164281903 | Higher in Drinkers |
| cg15373403 | 6 | 111576740 | Higher in Drinkers |
| cg15378492 | 1 | 183387305 | Higher in Drinkers |
| cg15380715 | 5 | 104265747 | Higher in Drinkers |
| cg15383141 | 2 | 75878327 | Higher in Drinkers |
| cg15383732 | 15 | 45879275 | Higher in Drinkers |
| cg15383811 | 10 | 127585442 | Higher in Drinkers |
| cg15388309 | 20 | 42142559 | Higher in Drinkers |
| cg15388895 | 19 | 49955167 | Higher in Drinkers |
| cg15390365 | 14 | 91976690 | Higher in Drinkers |
| cg15391499 | 5 | 112630623 | Higher in Drinkers |
| cg15392845 | 14 | 73360933 | Higher in Drinkers |
| cg15393197 | 17 | 37213172 | Higher in Drinkers |
| cg15395193 | 1 | 145516314 | Higher in Drinkers |
| cg15401405 | 6 | 33360035 | Higher in Drinkers |

| | | | |
|---|---|---|---|
| cg15405028 | 17 | 20945555 | Higher in Drinkers |
| cg15406666 | 10 | 91011667 | Higher in Drinkers |
| cg15410276 | 6 | 27778076 | Higher in Drinkers |
| cg15410835 | 8 | 143125637 | Higher in Drinkers |
| cg15410903 | 10 | 106028780 | Higher in Drinkers |
| cg15412291 | 17 | 66244249 | Higher in Drinkers |
| cg15412736 | 10 | 89622073 | Higher in Drinkers |
| cg15412971 | 4 | 956119 | Higher in Drinkers |
| cg15415160 | 2 | 26569060 | Higher in Drinkers |
| cg15415462 | 14 | 90092049 | Higher in Drinkers |
| cg15416577 | 3 | 113234093 | Higher in Drinkers |
| cg15418926 | 12 | 39836712 | Higher in Drinkers |
| cg15428296 | 19 | 9518095 | Higher in Drinkers |
| cg15428949 | 8 | 1308280 | Higher in Drinkers |
| cg15430883 | 1 | 11073233 | Higher in Drinkers |
| cg15432938 | 10 | 99078812 | Higher in Drinkers |
| cg15434056 | 7 | 43909259 | Higher in Drinkers |
| cg15434403 | 3 | 113775581 | Higher in Drinkers |
| cg15436096 | 14 | 59931922 | Higher in Drinkers |
| cg15437053 | 19 | 34311123 | Higher in Drinkers |
| cg15440973 | 14 | 24610792 | Higher in Drinkers |
| cg15442105 | 7 | 99227437 | Higher in Drinkers |
| cg15442370 | 6 | 33284125 | Higher in Drinkers |
| cg15442728 | 14 | 91580280 | Higher in Drinkers |
| cg15442811 | 2 | 219824401 | Higher in Drinkers |
| cg15443174 | 6 | 146284796 | Higher in Drinkers |
| cg15444566 | 15 | 63796413 | Higher in Drinkers |
| cg15446210 | 7 | 11014165 | Higher in Drinkers |
| cg15449350 | 15 | 49265390 | Higher in Drinkers |
| cg15453599 | 14 | 50155052 | Higher in Drinkers |
| cg15454383 | 4 | 39978232 | Higher in Drinkers |
| cg15456099 | 17 | 34957969 | Higher in Drinkers |
| cg15457276 | 19 | 4832024 | Higher in Drinkers |
| cg15457598 | 17 | 74723419 | Higher in Drinkers |
| cg15458155 | 1 | 86861956 | Higher in Drinkers |

| | | | |
|---|---|---|---|
| cg15469104 | 12 | 123012300 | Higher in Drinkers |
| cg15469321 | 1 | 221049931 | Higher in Drinkers |
| cg15475145 | 19 | 10943197 | Higher in Drinkers |
| cg15478817 | 2 | 118572196 | Higher in Drinkers |
| cg15479752 | 19 | 35940862 | Higher in Drinkers |
| cg15480012 | 6 | 30647083 | Higher in Drinkers |
| cg15480137 | 13 | 53226436 | Higher in Drinkers |
| cg15486645 | 11 | 27528489 | Higher in Drinkers |
| cg15488402 | 20 | 48429173 | Higher in Drinkers |
| cg15488822 | 13 | 37393523 | Higher in Drinkers |
| cg15492104 | 14 | 74417249 | Higher in Drinkers |
| cg15496871 | 19 | 36208495 | Higher in Drinkers |
| cg15502903 | 22 | 17566297 | Higher in Drinkers |
| cg15507391 | 11 | 66139221 | Higher in Drinkers |
| cg15510593 | 13 | 67955960 | Higher in Drinkers |
| cg15512961 | 5 | 150537567 | Higher in Drinkers |
| cg15514896 | 1 | 229074115 | Higher in Drinkers |
| cg15517836 | 2 | 114647352 | Higher in Drinkers |
| cg15518345 | 16 | 58426864 | Higher in Drinkers |
| cg15520477 | 19 | 34012957 | Higher in Drinkers |
| cg15522118 | 14 | 50155002 | Higher in Drinkers |
| cg15529532 | 10 | 1507747C | Higher in Drinkers |
| cg15529680 | 5 | 5422880 | Higher in Drinkers |
| cg15535092 | 19 | 7985071 | Higher in Drinkers |
| cg15536575 | 5 | 147763508 | Higher in Drinkers |
| cg15539395 | 19 | 59086703 | Higher in Drinkers |
| cg15541609 | 14 | 100705844 | Higher in Drinkers |
| cg15549761 | 5 | 98106108 | Higher in Drinkers |
| cg15549931 | 6 | 30710788 | Higher in Drinkers |
| cg15554087 | 1 | 8404216 | Higher in Drinkers |
| cg15554466 | 19 | 39936040 | Higher in Drinkers |
| cg15560061 | 19 | 8576679 | Lower in Drinkers |
| cg15561201 | 1 | 24742516 | Higher in Drinkers |
| cg15561613 | 1 | 245851610 | Higher in Drinkers |
| cg15562758 | 2 | 15209081 | Higher in Drinkers |

| | | | |
|---|---|---|---|
| cg15566619 | 20 | 44486216 | Higher in Drinkers |
| cg15568439 | 6 | 33168776 | Higher in Drinkers |
| cg15570803 | X | 70288412 | Higher in Drinkers |
| cg15572535 | 21 | 30671155 | Higher in Drinkers |
| cg15573846 | 11 | 126152723 | Higher in Drinkers |
| cg15573861 | 17 | 79247945 | Higher in Drinkers |
| cg15576859 | 1 | 118149570 | Higher in Drinkers |
| cg15578615 | 3 | 170074599 | Higher in Drinkers |
| cg15583285 | 6 | 99287924 | Higher in Drinkers |
| cg15584531 | 13 | 99739316 | Higher in Drinkers |
| cg15585372 | 7 | 97910571 | Higher in Drinkers |
| cg15589126 | 2 | 232263534 | Higher in Drinkers |
| cg15592143 | 7 | 76021307 | Higher in Drinkers |
| cg15595044 | 3 | 128336857 | Higher in Drinkers |
| cg15602423 | 6 | 32552095 | Lower in Drinkers |
| cg15602969 | 17 | 37356328 | Higher in Drinkers |
| cg15605853 | 6 | 47755961 | Higher in Drinkers |
| cg15605897 | 2 | 132250229 | Higher in Drinkers |
| cg15607642 | 6 | 107391589 | Higher in Drinkers |
| cg15610667 | 17 | 7287271 | Lower in Drinkers |
| cg15613100 | 5 | 72804620 | Higher in Drinkers |
| cg15613465 | 2 | 85830203 | Higher in Drinkers |
| cg15613917 | 2 | 68873233 | Higher in Drinkers |
| cg15616111 | 1 | 154955537 | Higher in Drinkers |
| cg15619745 | 10 | 112327325 | Higher in Drinkers |
| cg15620384 | 6 | 34164405 | Higher in Drinkers |
| cg15621458 | 12 | 97300429 | Higher in Drinkers |
| cg15622860 | 6 | 151055105 | Lower in Drinkers |
| cg15623249 | 19 | 48896947 | Higher in Drinkers |
| cg15624072 | 1 | 93811136 | Higher in Drinkers |
| cg15625117 | 11 | 4407026 | Higher in Drinkers |
| cg15627457 | 8 | 141535348 | Lower in Drinkers |
| cg15629447 | 6 | 47594195 | Higher in Drinkers |
| cg15631323 | 14 | 34420468 | Higher in Drinkers |
| cg15632808 | 17 | 55333474 | Higher in Drinkers |

| | | | |
|---|---|---|---|
| cg15633981 | 6 | 33281768 | Higher in Drinkers |
| cg15637484 | 5 | 14145264 | Higher in Drinkers |
| cg15639464 | 19 | 10421076 | Higher in Drinkers |
| cg15639581 | 19 | 13318873 | Higher in Drinkers |
| cg15639592 | 12 | 110156459 | Lower in Drinkers |
| cg15644389 | 22 | 32341492 | Higher in Drinkers |
| cg15644675 | 1 | 54666143 | Higher in Drinkers |
| cg15645079 | 20 | 3140569 | Higher in Drinkers |
| cg15650240 | 1 | 15736530 | Higher in Drinkers |
| cg15651941 | 11 | 2722084 | Higher in Drinkers |
| cg15657206 | 11 | 10772781 | Higher in Drinkers |
| cg15658376 | 5 | 177631524 | Higher in Drinkers |
| cg15662184 | 19 | 10464842 | Lower in Drinkers |
| cg15663173 | 17 | 7132748 | Lower in Drinkers |
| cg15663348 | 18 | 67617289 | Higher in Drinkers |
| cg15664067 | 5 | 86564490 | Higher in Drinkers |
| cg15664152 | 7 | 129008407 | Higher in Drinkers |
| cg15665385 | 2 | 150443752 | Higher in Drinkers |
| cg15666516 | 19 | 49999555 | Higher in Drinkers |
| cg15668500 | 10 | 99052215 | Higher in Drinkers |
| cg15668538 | 17 | 15931082 | Lower in Drinkers |
| cg15674680 | 20 | 60982522 | Higher in Drinkers |
| cg15676405 | 17 | 61525677 | Higher in Drinkers |
| cg15677364 | 6 | 30687221 | Higher in Drinkers |
| cg15679331 | 19 | 50179634 | Higher in Drinkers |
| cg15679532 | 19 | 6588838 | Higher in Drinkers |
| cg15680020 | 20 | 61560627 | Higher in Drinkers |
| cg15680707 | 3 | 185303904 | Higher in Drinkers |
| cg15682511 | 20 | 388534 | Higher in Drinkers |
| cg15682608 | 3 | 50337172 | Higher in Drinkers |
| cg15682993 | Y | 21729251 | Higher in Drinkers |
| cg15687659 | 3 | 128445120 | Higher in Drinkers |
| cg15695962 | 6 | 37620478 | Higher in Drinkers |
| cg15697646 | 3 | 49057813 | Higher in Drinkers |
| cg15698340 | 3 | 51854175 | Higher in Drinkers |

| | | | |
|---|---|---|---|
| cg15698953 | X | 52923437 | Higher in Drinkers |
| cg15699766 | 11 | 58975573 | Higher in Drinkers |
| cg15699971 | 2 | 157189241 | Higher in Drinkers |
| cg15700020 | 1 | 15944322 | Higher in Drinkers |
| cg15704055 | 6 | 57181701 | Higher in Drinkers |
| cg15705175 | 10 | 135073499 | Higher in Drinkers |
| cg15707544 | 1 | 10093239 | Higher in Drinkers |
| cg15710695 | 11 | 77850908 | Higher in Drinkers |
| cg15711240 | 10 | 32856510 | Higher in Drinkers |
| cg15713729 | 1 | 32757367 | Higher in Drinkers |
| cg15715542 | 19 | 44100966 | Higher in Drinkers |
| cg15717446 | 5 | 171234429 | Higher in Drinkers |
| cg15720127 | 3 | 23958673 | Higher in Drinkers |
| cg15723641 | 1 | 78245331 | Higher in Drinkers |
| cg15724965 | 22 | 35777001 | Higher in Drinkers |
| cg15725808 | 11 | 62538738 | Higher in Drinkers |
| cg15727925 | 19 | 9546735 | Lower in Drinkers |
| cg15732812 | 1 | 206808946 | Higher in Drinkers |
| cg15733507 | 9 | 139965275 | Higher in Drinkers |
| cg15734422 | 10 | 121356865 | Higher in Drinkers |
| cg15735287 | 7 | 155090783 | Higher in Drinkers |
| cg15748192 | 2 | 170440819 | Higher in Drinkers |
| cg15750461 | 4 | 991553 | Higher in Drinkers |
| cg15754405 | 9 | 107510767 | Higher in Drinkers |
| cg15757745 | 22 | 47558489 | Higher in Drinkers |
| cg15758138 | 19 | 40324226 | Higher in Drinkers |
| cg15762244 | 4 | 47916193 | Higher in Drinkers |
| cg15765896 | 12 | 53472985 | Higher in Drinkers |
| cg15767901 | 22 | 42473469 | Higher in Drinkers |
| cg15768282 | 12 | 56122242 | Higher in Drinkers |
| cg15769256 | 15 | 75746558 | Higher in Drinkers |
| cg15771370 | 17 | 1619730 | Higher in Drinkers |
| cg15774137 | 4 | 185377667 | Higher in Drinkers |
| cg15775674 | 15 | 42694733 | Higher in Drinkers |
| cg15776653 | 6 | 26538476 | Higher in Drinkers |

| | | | |
|---|---|---|---|
| cg15777910 | 17 | 3488907 | Lower in Drinkers |
| cg15783696 | 16 | 68564277 | Higher in Drinkers |
| cg15787116 | 14 | 105282974 | Higher in Drinkers |
| cg15787604 | 19 | 17501969 | Higher in Drinkers |
| cg15792766 | 7 | 43769288 | Higher in Drinkers |
| cg15793244 | 4 | 71705590 | Higher in Drinkers |
| cg15795630 | 4 | 126237513 | Higher in Drinkers |
| cg15798279 | 7 | 6523691 | Higher in Drinkers |
| cg15801573 | 8 | 128750924 | Higher in Drinkers |
| cg15806518 | 9 | 127177817 | Higher in Drinkers |
| cg15807035 | 4 | 140374443 | Higher in Drinkers |
| cg15815631 | 12 | 2922933 | Higher in Drinkers |
| cg15816267 | 6 | 30458048 | Higher in Drinkers |
| cg15816511 | 8 | 95731770 | Higher in Drinkers |
| cg15817542 | 16 | 31343056 | Higher in Drinkers |
| cg15817967 | 19 | 49588362 | Higher in Drinkers |
| cg15818800 | 10 | 22292583 | Higher in Drinkers |
| cg15822015 | X | 114960155 | Higher in Drinkers |
| cg15822656 | 7 | 30321030 | Higher in Drinkers |
| cg15825304 | 2 | 241505201 | Higher in Drinkers |
| cg15827677 | 15 | 41522925 | Higher in Drinkers |
| cg15828645 | 22 | 20748269 | Higher in Drinkers |
| cg15832314 | 15 | 40401289 | Higher in Drinkers |
| cg15832822 | 15 | 45018591 | Higher in Drinkers |
| cg15836710 | 6 | 31923035 | Higher in Drinkers |
| cg15839448 | 8 | 41166530 | Higher in Drinkers |
| cg15840419 | 6 | 147828010 | Higher in Drinkers |
| cg15840985 | 3 | 32023475 | Higher in Drinkers |
| cg15843845 | 9 | 123837236 | Higher in Drinkers |
| cg15844785 | 12 | 54582946 | Higher in Drinkers |
| cg15845333 | 8 | 144417025 | Higher in Drinkers |
| cg15847249 | 5 | 180238795 | Higher in Drinkers |
| cg15853329 | 3 | 48481696 | Higher in Drinkers |
| cg15853715 | 14 | 60955348 | Lower in Drinkers |
| cg15854547 | 12 | 114939057 | Higher in Drinkers |

| | | | |
|---|---|---|---|
| cg15855184 | 11 | 45792964 | Higher in Drinkers |
| cg15857731 | 12 | 58146359 | Higher in Drinkers |
| cg15858483 | 20 | 56073589 | Higher in Drinkers |
| cg15858897 | 11 | 67889051 | Higher in Drinkers |
| cg15863178 | 6 | 147829913 | Higher in Drinkers |
| cg15867717 | 15 | 35838514 | Higher in Drinkers |
| cg15871157 | 13 | 21901649 | Higher in Drinkers |
| cg15871991 | 2 | 10829907 | Higher in Drinkers |
| cg15872043 | 3 | 183960177 | Higher in Drinkers |
| cg15874031 | 5 | 177580860 | Higher in Drinkers |
| cg15876000 | 3 | 49067026 | Higher in Drinkers |
| cg15879692 | X | 153603126 | Higher in Drinkers |
| cg15880211 | 22 | 50250494 | Lower in Drinkers |
| cg15883154 | 14 | 77495248 | Higher in Drinkers |
| cg15883451 | 12 | 49075826 | Higher in Drinkers |
| cg15884202 | 7 | 158649092 | Higher in Drinkers |
| cg15884223 | 17 | 49242847 | Higher in Drinkers |
| cg15884411 | 2 | 96932403 | Higher in Drinkers |
| cg15888087 | 5 | 134735104 | Higher in Drinkers |
| cg15888569 | 4 | 15033042 | Higher in Drinkers |
| cg15890292 | 6 | 3722621 | Higher in Drinkers |
| cg15890332 | 12 | 107067104 | Higher in Drinkers |
| cg15896306 | 7 | 1200143 | Higher in Drinkers |
| cg15903784 | 12 | 104350504 | Higher in Drinkers |
| cg15906151 | 13 | 50018157 | Higher in Drinkers |
| cg15908791 | 7 | 127775817 | Higher in Drinkers |
| cg15909016 | 12 | 96000818 | Lower in Drinkers |
| cg15910994 | 2 | 97001734 | Higher in Drinkers |
| cg15914316 | 7 | 2083197 | Lower in Drinkers |
| cg15918921 | 2 | 74212782 | Higher in Drinkers |
| cg15923127 | X | 44731813 | Higher in Drinkers |
| cg15924259 | 1 | 9687259 | Higher in Drinkers |
| cg15924583 | 3 | 47045470 | Lower in Drinkers |
| cg15924868 | 11 | 2322674 | Higher in Drinkers |
| cg15930596 | 12 | 5018229 | Higher in Drinkers |

| | | | |
|---|---|---|---|
| cg15935070 | 6 | 29944146 | Higher in Drinkers |
| cg15939915 | 11 | 118436769 | Higher in Drinkers |
| cg15942362 | 10 | 98273924 | Higher in Drinkers |
| cg15943437 | 11 | 68670865 | Higher in Drinkers |
| cg15944026 | 14 | 91883673 | Higher in Drinkers |
| cg15946904 | 17 | 957249 | Lower in Drinkers |
| cg15963326 | 19 | 50037085 | Higher in Drinkers |
| cg15963563 | 5 | 158528040 | Higher in Drinkers |
| cg15964468 | 6 | 28351351 | Higher in Drinkers |
| cg15967188 | 4 | 2470700 | Higher in Drinkers |
| cg15969681 | 6 | 31659444 | Higher in Drinkers |
| cg15969776 | 4 | 166248399 | Higher in Drinkers |
| cg15972516 | 7 | 98545950 | Higher in Drinkers |
| cg15975865 | 2 | 127413831 | Higher in Drinkers |
| cg15977278 | 12 | 104234975 | Higher in Drinkers |
| cg15977719 | 7 | 25021503 | Higher in Drinkers |
| cg15982261 | 7 | 30492035 | Higher in Drinkers |
| cg15987124 | 12 | 6603172 | Higher in Drinkers |
| cg15988394 | 3 | 183736102 | Higher in Drinkers |
| cg15990015 | 1 | 44679006 | Higher in Drinkers |
| cg15993402 | 16 | 89723979 | Higher in Drinkers |
| cg15994999 | 5 | 154317917 | Higher in Drinkers |
| cg15995714 | 10 | 134222445 | Higher in Drinkers |
| cg16000739 | 1 | 116697147 | Higher in Drinkers |
| cg16001793 | 1 | 161369711 | Higher in Drinkers |
| cg16004377 | 11 | 63272909 | Higher in Drinkers |
| cg16006934 | 12 | 120907680 | Higher in Drinkers |
| cg16007680 | 8 | 144349898 | Higher in Drinkers |
| cg16007772 | 14 | 59950363 | Higher in Drinkers |
| cg16012919 | 14 | 73925622 | Higher in Drinkers |
| cg16013618 | 1 | 28833588 | Higher in Drinkers |
| cg16014168 | 12 | 109729677 | Higher in Drinkers |
| cg16019782 | 10 | 25305105 | Higher in Drinkers |
| cg16020069 | 1 | 156897638 | Higher in Drinkers |
| cg16020551 | 9 | 130890638 | Higher in Drinkers |

| | | | |
|---|---|---|---|
| cg16022344 | 2 | 98262540 | Higher in Drinkers |
| cg16023943 | 10 | 27541331 | Lower in Drinkers |
| cg16028599 | 7 | 5400758 | Higher in Drinkers |
| cg16028986 | 2 | 74881292 | Higher in Drinkers |
| cg16031283 | 22 | 20861701 | Higher in Drinkers |
| cg16034458 | 7 | 44646072 | Higher in Drinkers |
| cg16037142 | 9 | 131419157 | Higher in Drinkers |
| cg16037711 | 1 | 59280841 | Lower in Drinkers |
| cg16039960 | 1 | 161369277 | Higher in Drinkers |
| cg16046954 | 17 | 74733379 | Higher in Drinkers |
| cg16047223 | 3 | 195610084 | Lower in Drinkers |
| cg16049707 | 14 | 77965284 | Higher in Drinkers |
| cg16050333 | 14 | 70234252 | Higher in Drinkers |
| cg16050468 | 14 | 105011965 | Lower in Drinkers |
| cg16050957 | 16 | 24550743 | Higher in Drinkers |
| cg16054546 | 17 | 7738110 | Higher in Drinkers |
| cg16056105 | 14 | 36003201 | Higher in Drinkers |
| cg16056311 | 15 | 101606267 | Higher in Drinkers |
| cg16057598 | 2 | 172967819 | Higher in Drinkers |
| cg16063587 | 6 | 31691227 | Higher in Drinkers |
| cg16064237 | 12 | 132654984 | Higher in Drinkers |
| cg16065270 | 6 | 31370796 | Higher in Drinkers |
| cg16066195 | 7 | 73703691 | Higher in Drinkers |
| cg16066797 | 15 | 65341736 | Higher in Drinkers |
| cg16067781 | 12 | 57039048 | Higher in Drinkers |
| cg16068063 | 21 | 43640131 | Higher in Drinkers |
| cg16068923 | 17 | 40896484 | Higher in Drinkers |
| cg16075384 | 7 | 66386859 | Higher in Drinkers |
| cg16080450 | 7 | 100034191 | Higher in Drinkers |
| cg16085178 | 6 | 135818824 | Higher in Drinkers |
| cg16086269 | 7 | 1991495 | Higher in Drinkers |
| cg16087630 | 11 | 67890322 | Higher in Drinkers |
| cg16090392 | 4 | 87928170 | Higher in Drinkers |
| cg16091995 | 2 | 202484320 | Higher in Drinkers |
| cg16092645 | 19 | 3971417 | Higher in Drinkers |

| | | | |
|---|---|---|---|
| cg16093537 | 10 | 81924880 | Higher in Drinkers |
| cg16099404 | 2 | 202336282 | Lower in Drinkers |
| cg16107640 | 17 | 79803698 | Higher in Drinkers |
| cg16109953 | 14 | 24701739 | Higher in Drinkers |
| cg16110788 | 7 | 22602133 | Lower in Drinkers |
| cg16116407 | 2 | 231852154 | Higher in Drinkers |
| cg16117248 | 1 | 29451235 | Higher in Drinkers |
| cg16119372 | 1 | 202321656 | Higher in Drinkers |
| cg16120828 | 1 | 108507340 | Higher in Drinkers |
| cg16120927 | 11 | 63536330 | Higher in Drinkers |
| cg16121444 | 1 | 169337314 | Higher in Drinkers |
| cg16124337 | 6 | 90062879 | Higher in Drinkers |
| cg16125564 | 17 | 648074 | Higher in Drinkers |
| cg16126137 | 14 | 101367300 | Higher in Drinkers |
| cg16128638 | 19 | 48113110 | Higher in Drinkers |
| cg16131534 | 22 | 47158239 | Higher in Drinkers |
| cg16133945 | 7 | 156686123 | Higher in Drinkers |
| cg16135451 | 1 | 3772534 | Lower in Drinkers |
| cg16136098 | 1 | 107683532 | Higher in Drinkers |
| cg16136939 | 10 | 13344341 | Higher in Drinkers |
| cg16139011 | 11 | 9596224 | Higher in Drinkers |
| cg16139199 | 18 | 19180362 | Higher in Drinkers |
| cg16139749 | 1 | 113044432 | Higher in Drinkers |
| cg16140321 | 6 | 161575256 | Higher in Drinkers |
| cg16144193 | 1 | 200271455 | Higher in Drinkers |
| cg16144293 | 14 | 75469539 | Higher in Drinkers |
| cg16145821 | 11 | 66056771 | Higher in Drinkers |
| cg16145825 | 1 | 228363521 | Higher in Drinkers |
| cg16147957 | 9 | 34665504 | Higher in Drinkers |
| cg16148773 | 11 | 111749571 | Higher in Drinkers |
| cg16151494 | 5 | 56595163 | Higher in Drinkers |
| cg16157821 | 3 | 58419758 | Higher in Drinkers |
| cg16158407 | X | 106449030 | Higher in Drinkers |
| cg16161425 | 5 | 79950956 | Higher in Drinkers |
| cg16162970 | 14 | 105779952 | Higher in Drinkers |

| | | | |
|---|---|---|---|
| cg16164732 | 22 | 36851465 | Higher in Drinkers |
| cg16166762 | 16 | 1706873 | Higher in Drinkers |
| cg16167485 | 12 | 56367262 | Higher in Drinkers |
| cg16173562 | 4 | 52771925 | Higher in Drinkers |
| cg16175497 | X | 48328591 | Higher in Drinkers |
| cg16176301 | 11 | 8933372 | Higher in Drinkers |
| cg16179748 | 1 | 223254706 | Higher in Drinkers |
| cg16180367 | 3 | 42544082 | Higher in Drinkers |
| cg16182447 | 11 | 69264617 | Higher in Drinkers |
| cg16185365 | 3 | 196230308 | Higher in Drinkers |
| cg16189954 | 22 | 29138267 | Higher in Drinkers |
| cg16191024 | 12 | 12870069 | Higher in Drinkers |
| cg16192203 | 3 | 119217218 | Higher in Drinkers |
| cg16192821 | 3 | 13028642 | Higher in Drinkers |
| cg16193196 | 17 | 75398290 | Lower in Drinkers |
| cg16193765 | 21 | 45527559 | Higher in Drinkers |
| cg16199879 | 14 | 58667190 | Higher in Drinkers |
| cg16201674 | 13 | 95364586 | Higher in Drinkers |
| cg16203607 | 17 | 62500946 | Higher in Drinkers |
| cg16206743 | 13 | 37633760 | Higher in Drinkers |
| cg16206836 | 20 | 36157266 | Higher in Drinkers |
| cg16208491 | 6 | 4021748 | Higher in Drinkers |
| cg16219182 | 2 | 112816903 | Higher in Drinkers |
| cg16219968 | 12 | 40500016 | Higher in Drinkers |
| cg16221201 | 5 | 71781569 | Higher in Drinkers |
| cg16223967 | 7 | 634037 | Lower in Drinkers |
| cg16224902 | 12 | 48513167 | Higher in Drinkers |
| cg16226300 | 6 | 133136135 | Higher in Drinkers |
| cg16229376 | 6 | 46459256 | Higher in Drinkers |
| cg16230352 | 8 | 42123158 | Higher in Drinkers |
| cg16235008 | 14 | 75530741 | Higher in Drinkers |
| cg16235707 | 5 | 75698461 | Higher in Drinkers |
| cg16235861 | 10 | 95653642 | Higher in Drinkers |
| cg16236108 | 4 | 84457579 | Higher in Drinkers |
| cg16236770 | 11 | 62573142 | Higher in Drinkers |

| | | | |
|---|---|---|---|
| cg16236875 | 12 | 7245112 | Higher in Drinkers |
| cg16237409 | 6 | 31797421 | Higher in Drinkers |
| cg16237545 | 7 | 150929216 | Higher in Drinkers |
| cg16238921 | 8 | 71581516 | Higher in Drinkers |
| cg16243644 | X | 123095766 | Higher in Drinkers |
| cg16245510 | 1 | 25559209 | Higher in Drinkers |
| cg16250330 | 1 | 184943561 | Higher in Drinkers |
| cg16252717 | 19 | 39390344 | Higher in Drinkers |
| cg16253551 | 6 | 30685136 | Higher in Drinkers |
| cg16257086 | 1 | 207925400 | Higher in Drinkers |
| cg16259317 | 10 | 80733297 | Higher in Drinkers |
| cg16261619 | 7 | 50132977 | Higher in Drinkers |
| cg16265640 | 15 | 34502435 | Higher in Drinkers |
| cg16266669 | 1 | 1144558 | Higher in Drinkers |
| cg16266698 | 3 | 42244474 | Higher in Drinkers |
| cg16266895 | 12 | 101674004 | Higher in Drinkers |
| cg16268863 | 14 | 78227565 | Higher in Drinkers |
| cg16269196 | 4 | 141264721 | Higher in Drinkers |
| cg16270231 | 4 | 8468878 | Higher in Drinkers |
| cg16270819 | 7 | 129588864 | Higher in Drinkers |
| cg16274098 | 8 | 92053265 | Higher in Drinkers |
| cg16286249 | 1 | 33625400 | Higher in Drinkers |
| cg16286735 | 17 | 45371778 | Higher in Drinkers |
| cg16286925 | 5 | 108339964 | Lower in Drinkers |
| cg16288246 | 7 | 87230087 | Higher in Drinkers |
| cg16291112 | 11 | 64949173 | Higher in Drinkers |
| cg16292382 | 11 | 85339571 | Higher in Drinkers |
| cg16299341 | 1 | 52082824 | Higher in Drinkers |
| cg16304527 | 18 | 29264431 | Higher in Drinkers |
| cg16306498 | 19 | 12146696 | Higher in Drinkers |
| cg16309944 | 5 | 122847756 | Higher in Drinkers |
| cg16310374 | 11 | 61891497 | Higher in Drinkers |
| cg16311410 | 22 | 31892793 | Higher in Drinkers |
| cg16311462 | 5 | 171591509 | Higher in Drinkers |
| cg16312414 | 1 | 109633444 | Higher in Drinkers |

| | | | |
|---|---|---|---|
| cg16312647 | 15 | 64455677 | Higher in Drinkers |
| cg16314369 | 4 | 185655609 | Higher in Drinkers |
| cg16314432 | 6 | 158595050 | Higher in Drinkers |
| cg16314672 | 4 | 6674847 | Higher in Drinkers |
| cg16314733 | 10 | 98909007 | Lower in Drinkers |
| cg16315417 | 1 | 2187457 | Higher in Drinkers |
| cg16317441 | 11 | 93861839 | Higher in Drinkers |
| cg16317459 | 5 | 158527463 | Higher in Drinkers |
| cg16319136 | 8 | 54852030 | Higher in Drinkers |
| cg16320339 | 21 | 38740894 | Higher in Drinkers |
| cg16323843 | 3 | 49711263 | Higher in Drinkers |
| cg16325191 | 19 | 58966932 | Higher in Drinkers |
| cg16328273 | 8 | 95908119 | Higher in Drinkers |
| cg16332365 | 12 | 120125215 | Higher in Drinkers |
| cg16336056 | 1 | 26126514 | Higher in Drinkers |
| cg16336494 | 6 | 151188259 | Higher in Drinkers |
| cg16337273 | 11 | 126160920 | Higher in Drinkers |
| cg16337339 | 6 | 163349952 | Higher in Drinkers |
| cg16337430 | 12 | 124876433 | Higher in Drinkers |
| cg16341495 | 8 | 142228727 | Lower in Drinkers |
| cg16344227 | 20 | 56064964 | Higher in Drinkers |
| cg16348491 | 18 | 3262664 | Higher in Drinkers |
| cg16349424 | 19 | 56170507 | Higher in Drinkers |
| cg16357763 | 17 | 62658854 | Higher in Drinkers |
| cg16357866 | 4 | 25162481 | Higher in Drinkers |
| cg16359547 | 16 | 86589005 | Higher in Drinkers |
| cg16362949 | 17 | 1390671 | Higher in Drinkers |
| cg16369911 | 14 | 96358354 | Higher in Drinkers |
| cg16370061 | 5 | 179226009 | Higher in Drinkers |
| cg16370869 | 10 | 105881826 | Higher in Drinkers |
| cg16372047 | 12 | 95397610 | Higher in Drinkers |
| cg16373023 | 15 | 62682852 | Higher in Drinkers |
| cg16373765 | 1 | 16363293 | Higher in Drinkers |
| cg16375728 | 17 | 79980611 | Higher in Drinkers |
| cg16377923 | 3 | 197279261 | Higher in Drinkers |

| | | | |
|---|---|---|---|
| cg16385225 | 10 | 60094629 | Higher in Drinkers |
| cg16385941 | 7 | 1579643 | Lower in Drinkers |
| cg16390570 | 7 | 100860924 | Higher in Drinkers |
| cg16394646 | 7 | 139416078 | Higher in Drinkers |
| cg16402879 | 10 | 97321208 | Higher in Drinkers |
| cg16403659 | 14 | 105908693 | Lower in Drinkers |
| cg16403932 | 12 | 57881247 | Higher in Drinkers |
| cg16406226 | 20 | 42086458 | Higher in Drinkers |
| cg16406611 | 11 | 300404 | Higher in Drinkers |
| cg16408081 | 11 | 67205869 | Lower in Drinkers |
| cg16409339 | 1 | 146556239 | Higher in Drinkers |
| cg16410115 | 1 | 24240000 | Higher in Drinkers |
| cg16411204 | 10 | 101379813 | Higher in Drinkers |
| cg16412986 | 2 | 204400341 | Higher in Drinkers |
| cg16416261 | 2 | 37424104 | Higher in Drinkers |
| cg16417374 | 1 | 26098310 | Higher in Drinkers |
| cg16417416 | 4 | 6284031 | Higher in Drinkers |
| cg16418630 | 9 | 131133870 | Higher in Drinkers |
| cg16418735 | 3 | 97483530 | Higher in Drinkers |
| cg16419136 | 16 | 88752807 | Higher in Drinkers |
| cg16420247 | 2 | 10442859 | Higher in Drinkers |
| cg16421157 | 6 | 5036597 | Higher in Drinkers |
| cg16424519 | 16 | 21531031 | Higher in Drinkers |
| cg16424683 | 5 | 177541051 | Higher in Drinkers |
| cg16430072 | 5 | 113696863 | Higher in Drinkers |
| cg16430404 | 14 | 94547586 | Higher in Drinkers |
| cg16430880 | 7 | 21985708 | Higher in Drinkers |
| cg16433833 | 15 | 41056141 | Higher in Drinkers |
| cg16433860 | 16 | 50402640 | Higher in Drinkers |
| cg16436232 | 3 | 75485448 | Higher in Drinkers |
| cg16438210 | 14 | 91885492 | Higher in Drinkers |
| cg16438397 | 5 | 77591635 | Higher in Drinkers |
| cg16440299 | 16 | 56779141 | Higher in Drinkers |
| cg16442044 | 10 | 129705218 | Higher in Drinkers |
| cg16442050 | 2 | 27294098 | Higher in Drinkers |

| | | | |
|---|---|---|---|
| cg16442715 | 22 | 39796206 | Higher in Drinkers |
| cg16446408 | 2 | 169313621 | Higher in Drinkers |
| cg16447058 | 15 | 64231444 | Higher in Drinkers |
| cg16447486 | 17 | 5095239 | Higher in Drinkers |
| cg16447589 | 7 | 45961865 | Higher in Drinkers |
| cg16449186 | 3 | 186545470 | Higher in Drinkers |
| cg16451134 | 11 | 134104882 | Higher in Drinkers |
| cg16453615 | 3 | 111393328 | Higher in Drinkers |
| cg16453630 | 8 | 12573543 | Lower in Drinkers |
| cg16456728 | 7 | 65580328 | Higher in Drinkers |
| cg16458153 | 6 | 33160192 | Higher in Drinkers |
| cg16458170 | 11 | 36311174 | Higher in Drinkers |
| cg16459391 | 7 | 99217644 | Higher in Drinkers |
| cg16460860 | 17 | 17744282 | Higher in Drinkers |
| cg16462073 | 16 | 28995843 | Higher in Drinkers |
| cg16463378 | 12 | 6619248 | Higher in Drinkers |
| cg16465430 | 14 | 23289114 | Higher in Drinkers |
| cg16466278 | 15 | 43429893 | Higher in Drinkers |
| cg16466635 | 7 | 66093826 | Higher in Drinkers |
| cg16467465 | 7 | 44240564 | Higher in Drinkers |
| cg16470309 | 15 | 60883803 | Higher in Drinkers |
| cg16477417 | 17 | 73342168 | Higher in Drinkers |
| cg16480634 | 2 | 65496336 | Higher in Drinkers |
| cg16487101 | 5 | 41904311 | Higher in Drinkers |
| cg16489895 | 1 | 156890244 | Higher in Drinkers |
| cg16490062 | 16 | 12211322 | Higher in Drinkers |
| cg16493090 | 10 | 121410910 | Higher in Drinkers |
| cg16500018 | 19 | 7702178 | Higher in Drinkers |
| cg16512239 | 15 | 51058050 | Higher in Drinkers |
| cg16512868 | 14 | 75760996 | Higher in Drinkers |
| cg16513905 | 5 | 137879008 | Higher in Drinkers |
| cg16514059 | 12 | 9600888 | Higher in Drinkers |
| cg16514513 | 17 | 48263159 | Lower in Drinkers |
| cg16516219 | 6 | 28805302 | Higher in Drinkers |
| cg16517198 | 6 | 41040614 | Higher in Drinkers |

| | | | |
|---|---|---|---|
| cg16518742 | 17 | 40811438 | Higher in Drinkers |
| cg16520539 | 6 | 29890872 | Higher in Drinkers |
| cg16521594 | 17 | 56084977 | Higher in Drinkers |
| cg16522462 | 20 | 1875565 | Higher in Drinkers |
| cg16523621 | 5 | 172721053 | Higher in Drinkers |
| cg16524193 | 3 | 99979582 | Higher in Drinkers |
| cg16527441 | 11 | 65545949 | Higher in Drinkers |
| cg16528895 | 2 | 108994311 | Higher in Drinkers |
| cg16533561 | X | 47699239 | Higher in Drinkers |
| cg16534499 | 19 | 44555960 | Higher in Drinkers |
| cg16535999 | 7 | 102988366 | Higher in Drinkers |
| cg16537350 | 14 | 50329699 | Higher in Drinkers |
| cg16541385 | 20 | 52825030 | Higher in Drinkers |
| cg16542322 | 11 | 5617288 | Higher in Drinkers |
| cg16543294 | 9 | 132404763 | Higher in Drinkers |
| cg16546503 | 18 | 12307329 | Higher in Drinkers |
| cg16551665 | 17 | 30814028 | Higher in Drinkers |
| cg16553052 | 7 | 2349605 | Higher in Drinkers |
| cg16553574 | 7 | 64839175 | Higher in Drinkers |
| cg16555341 | 16 | 89160798 | Higher in Drinkers |
| cg16558348 | 9 | 86322296 | Higher in Drinkers |
| cg16563151 | 8 | 144640403 | Higher in Drinkers |
| cg16563180 | 7 | 1570208 | Higher in Drinkers |
| cg16565696 | 20 | 44834899 | Higher in Drinkers |
| cg16568472 | 20 | 3190600 | Higher in Drinkers |
| cg16569430 | 8 | 91658185 | Higher in Drinkers |
| cg16570980 | 16 | 438561 | Lower in Drinkers |
| cg16573542 | 16 | 48399834 | Higher in Drinkers |
| cg16573987 | 6 | 33284127 | Higher in Drinkers |
| cg16575564 | 11 | 67236756 | Higher in Drinkers |
| cg16577707 | 5 | 154181866 | Higher in Drinkers |
| cg16578355 | 14 | 76127164 | Higher in Drinkers |
| cg16578537 | 3 | 194408556 | Higher in Drinkers |
| cg16578737 | 14 | 73494024 | Higher in Drinkers |
| cg16579136 | 3 | 137677134 | Higher in Drinkers |

| | | | |
|---|---|---|---|
| cg16579225 | 1 | 2322553 | Higher in Drinkers |
| cg16579351 | 14 | 105708255 | Higher in Drinkers |
| cg16579431 | 16 | 433439 | Higher in Drinkers |
| cg16580616 | 1 | 235256519 | Lower in Drinkers |
| cg16580759 | 8 | 6693379 | Lower in Drinkers |
| cg16582214 | 1 | 153914492 | Lower in Drinkers |
| cg16584945 | 4 | 128982446 | Higher in Drinkers |
| cg16589807 | 16 | 75328793 | Higher in Drinkers |
| cg16590635 | 16 | 87641681 | Lower in Drinkers |
| cg16592950 | 10 | 102820042 | Higher in Drinkers |
| cg16597169 | 10 | 60095403 | Higher in Drinkers |
| cg16599266 | 1 | 2518110 | Higher in Drinkers |
| cg16599568 | 1 | 165567358 | Higher in Drinkers |
| cg16604136 | 1 | 163291493 | Higher in Drinkers |
| cg16608617 | 2 | 202898681 | Higher in Drinkers |
| cg16611736 | 16 | 25123254 | Higher in Drinkers |
| cg16611852 | 1 | 228675670 | Higher in Drinkers |
| cg16613990 | 16 | 89982618 | Higher in Drinkers |
| cg16614613 | 3 | 50605258 | Higher in Drinkers |
| cg16615451 | 19 | 58326288 | Higher in Drinkers |
| cg16618104 | 12 | 104853100 | Higher in Drinkers |
| cg16623710 | 22 | 45073049 | Higher in Drinkers |
| cg16624013 | 6 | 35437101 | Higher in Drinkers |
| cg16624076 | 6 | 33359652 | Higher in Drinkers |
| cg16626387 | 9 | 98266788 | Higher in Drinkers |
| cg16627358 | 16 | 88540175 | Higher in Drinkers |
| cg16632994 | 5 | 158690246 | Higher in Drinkers |
| cg16633750 | 7 | 2559692 | Higher in Drinkers |
| cg16633848 | 11 | 85780144 | Higher in Drinkers |
| cg16635108 | 11 | 134281328 | Higher in Drinkers |
| cg16635274 | 18 | 44497831 | Higher in Drinkers |
| cg16636944 | 1 | 16970920 | Higher in Drinkers |
| cg16637188 | 13 | 114278193 | Higher in Drinkers |
| cg16637941 | 16 | 58035216 | Higher in Drinkers |
| cg16639138 | 7 | 100861083 | Higher in Drinkers |

| | | | |
|---|---|---|---|
| cg16639766 | 2 | 234763386 | Higher in Drinkers |
| cg16644177 | 19 | 58125438 | Higher in Drinkers |
| cg16648324 | 12 | 510772 | Higher in Drinkers |
| cg16653057 | X | 74144727 | Higher in Drinkers |
| cg16653395 | 1 | 169863438 | Higher in Drinkers |
| cg16654851 | 7 | 148725968 | Higher in Drinkers |
| cg16655404 | 1 | 16161388 | Higher in Drinkers |
| cg16658579 | 7 | 208005 | Higher in Drinkers |
| cg16660717 | 12 | 56211781 | Higher in Drinkers |
| cg16663344 | 5 | 92920256 | Higher in Drinkers |
| cg16664532 | 3 | 173113519 | Higher in Drinkers |
| cg16664537 | 13 | 50366648 | Higher in Drinkers |
| cg16666698 | 16 | 71842293 | Higher in Drinkers |
| cg16667251 | 2 | 54697181 | Higher in Drinkers |
| cg16668180 | 16 | 46963261 | Higher in Drinkers |
| cg16670155 | 19 | 18557220 | Lower in Drinkers |
| cg16672925 | 10 | 90967113 | Higher in Drinkers |
| cg16677162 | 22 | 22465502 | Higher in Drinkers |
| cg16679034 | 10 | 104263792 | Higher in Drinkers |
| cg16681830 | 20 | 62586920 | Higher in Drinkers |
| cg16685607 | 13 | 21715006 | Higher in Drinkers |
| cg16690876 | 17 | 19845638 | Higher in Drinkers |
| cg16695354 | 15 | 52030164 | Higher in Drinkers |
| cg16696923 | 8 | 95229872 | Higher in Drinkers |
| cg16697620 | 1 | 32092196 | Higher in Drinkers |
| cg16698731 | 21 | 46221955 | Higher in Drinkers |
| cg16701467 | 17 | 7475727 | Higher in Drinkers |
| cg16703762 | 5 | 76932047 | Higher in Drinkers |
| cg16706240 | 12 | 124872365 | Higher in Drinkers |
| cg16710791 | 1 | 193028559 | Higher in Drinkers |
| cg16715162 | 6 | 150463990 | Higher in Drinkers |
| cg16716608 | 7 | 102715129 | Higher in Drinkers |
| cg16717690 | 1 | 1208709 | Higher in Drinkers |
| cg16718891 | 12 | 54813155 | Higher in Drinkers |
| cg16720495 | 4 | 140478487 | Higher in Drinkers |

| | | | |
|---|---|---|---|
| cg16720946 | 2 | 43454210 | Higher in Drinkers |
| cg16721265 | 7 | 99686390 | Higher in Drinkers |
| cg16723803 | 9 | 35096453 | Higher in Drinkers |
| cg16730737 | 6 | 31702632 | Higher in Drinkers |
| cg16732643 | 8 | 37619930 | Higher in Drinkers |
| cg16734526 | 18 | 6733414 | Higher in Drinkers |
| cg16736300 | 19 | 8579199 | Higher in Drinkers |
| cg16737213 | 11 | 105948489 | Higher in Drinkers |
| cg16738984 | 19 | 14519121 | Higher in Drinkers |
| cg16739096 | 17 | 62131731 | Lower in Drinkers |
| cg16742675 | X | 153602721 | Higher in Drinkers |
| cg16746631 | 8 | 82598140 | Higher in Drinkers |
| cg16747427 | 6 | 30458078 | Higher in Drinkers |
| cg16750914 | 2 | 55646622 | Higher in Drinkers |
| cg16751623 | 3 | 12837930 | Higher in Drinkers |
| cg16752778 | 1 | 77685229 | Higher in Drinkers |
| cg16757724 | 20 | 43935528 | Higher in Drinkers |
| cg16758041 | 9 | 32573371 | Higher in Drinkers |
| cg16759443 | 16 | 89200506 | Higher in Drinkers |
| cg16759888 | 6 | 46620647 | Higher in Drinkers |
| cg16767968 | 17 | 75085390 | Higher in Drinkers |
| cg16770309 | 15 | 102292955 | Lower in Drinkers |
| cg16773043 | 7 | 1963149 | Lower in Drinkers |
| cg16774946 | 13 | 24798195 | Lower in Drinkers |
| cg16776035 | 17 | 74542680 | Higher in Drinkers |
| cg16776372 | 18 | 5294815 | Higher in Drinkers |
| cg16779626 | 15 | 41709933 | Higher in Drinkers |
| cg16780860 | 11 | 67119362 | Higher in Drinkers |
| cg16784555 | 15 | 41708739 | Higher in Drinkers |
| cg16792875 | 8 | 70602469 | Higher in Drinkers |
| cg16793129 | 12 | 101673815 | Higher in Drinkers |
| cg16793249 | 6 | 32135070 | Lower in Drinkers |
| cg16794633 | 3 | 143690145 | Higher in Drinkers |
| cg16795352 | 15 | 60368845 | Higher in Drinkers |
| cg16798247 | 7 | 37026686 | Higher in Drinkers |

| | | | |
|---|---|---|---|
| cg16803232 | 16 | 29196538 | Higher in Drinkers |
| cg16803817 | 21 | 34851621 | Higher in Drinkers |
| cg16809914 | 18 | 77465673 | Higher in Drinkers |
| cg16817134 | 4 | 175204699 | Higher in Drinkers |
| cg16818931 | 4 | 89299948 | Higher in Drinkers |
| cg16825643 | 16 | 88802743 | Higher in Drinkers |
| cg16829453 | 17 | 48636646 | Higher in Drinkers |
| cg16830078 | 17 | 2303343 | Higher in Drinkers |
| cg16830870 | 12 | 95397608 | Higher in Drinkers |
| cg16831185 | 17 | 29158530 | Lower in Drinkers |
| cg16833264 | 17 | 75052603 | Higher in Drinkers |
| cg16835502 | 17 | 4710020 | Higher in Drinkers |
| cg16850077 | 20 | 47662639 | Higher in Drinkers |
| cg16856342 | 1 | 67895909 | Higher in Drinkers |
| cg16857192 | 11 | 124628143 | Higher in Drinkers |
| cg16858615 | 6 | 11872778 | Higher in Drinkers |
| cg16859420 | 8 | 41219116 | Higher in Drinkers |
| cg16859906 | 16 | 68298978 | Higher in Drinkers |
| cg16860267 | 18 | 11908803 | Higher in Drinkers |
| cg16861047 | 1 | 116518978 | Higher in Drinkers |
| cg16862821 | 6 | 32938469 | Higher in Drinkers |
| cg16875280 | 19 | 46087775 | Higher in Drinkers |
| cg16883533 | 12 | 7079667 | Higher in Drinkers |
| cg16891965 | 8 | 110657877 | Higher in Drinkers |
| cg16892681 | 21 | 34961251 | Higher in Drinkers |
| cg16893707 | 18 | 74830377 | Higher in Drinkers |
| cg16893868 | 19 | 55084269 | Higher in Drinkers |
| cg16896647 | 9 | 93563776 | Higher in Drinkers |
| cg16897103 | 15 | 96894342 | Lower in Drinkers |
| cg16898493 | 22 | 50046451 | Higher in Drinkers |
| cg16903885 | 10 | 134795548 | Lower in Drinkers |
| cg16905100 | 3 | 72149974 | Higher in Drinkers |
| cg16912088 | 10 | 31797750 | Higher in Drinkers |
| cg16914552 | 11 | 1714584 | Higher in Drinkers |
| cg16917537 | 7 | 73098262 | Higher in Drinkers |

| | | | |
|---|---|---|---|
| cg16918585 | 1 | 39492570 | Higher in Drinkers |
| cg16919615 | 2 | 55459782 | Higher in Drinkers |
| cg16922167 | 1 | 27961746 | Higher in Drinkers |
| cg16922861 | 12 | 46384569 | Higher in Drinkers |
| cg16925970 | 13 | 25496605 | Higher in Drinkers |
| cg16926930 | 15 | 56657658 | Higher in Drinkers |
| cg16929299 | 17 | 47308140 | Lower in Drinkers |
| cg16933706 | 6 | 30181934 | Higher in Drinkers |
| cg16935370 | 5 | 154393281 | Higher in Drinkers |
| cg16940801 | 15 | 72523516 | Higher in Drinkers |
| cg16943697 | 2 | 120280763 | Lower in Drinkers |
| cg16944070 | 10 | 11783848 | Higher in Drinkers |
| cg16945098 | 5 | 139127710 | Higher in Drinkers |
| cg16951385 | 10 | 65029115 | Higher in Drinkers |
| cg16951550 | 11 | 62600022 | Higher in Drinkers |
| cg16954928 | 19 | 56135916 | Higher in Drinkers |
| cg16959606 | 1 | 169074934 | Higher in Drinkers |
| cg16960990 | 12 | 117595754 | Higher in Drinkers |
| cg16968514 | 6 | 33232604 | Higher in Drinkers |
| cg16969458 | 6 | 30687942 | Higher in Drinkers |
| cg16969586 | 18 | 10726666 | Higher in Drinkers |
| cg16969852 | 9 | 111775933 | Higher in Drinkers |
| cg16970702 | 2 | 38978664 | Higher in Drinkers |
| cg16970804 | 5 | 43042108 | Higher in Drinkers |
| cg16970828 | 3 | 49851353 | Higher in Drinkers |
| cg16975367 | 4 | 8390148 | Higher in Drinkers |
| cg16975973 | 12 | 77459865 | Higher in Drinkers |
| cg16977570 | 13 | 24152974 | Higher in Drinkers |
| cg16978367 | 8 | 37593814 | Higher in Drinkers |
| cg16980736 | 17 | 73789706 | Higher in Drinkers |
| cg16981259 | 6 | 31509434 | Higher in Drinkers |
| cg16982435 | 7 | 93602908 | Higher in Drinkers |
| cg16983159 | 5 | 138862441 | Higher in Drinkers |
| cg16983422 | 8 | 101322179 | Higher in Drinkers |
| cg16984335 | 12 | 53159051 | Higher in Drinkers |

| | | | |
|---|---|---|---|
| cg16986494 | 3 | 61237206 | Higher in Drinkers |
| cg16990513 | 5 | 77656921 | Higher in Drinkers |
| cg16991768 | 1 | 3664047 | Higher in Drinkers |
| cg16995606 | 13 | 108920803 | Higher in Drinkers |
| cg16998718 | 8 | 19674847 | Higher in Drinkers |
| cg17001703 | X | 64754863 | Higher in Drinkers |
| cg17003199 | 17 | 19186646 | Higher in Drinkers |
| cg17008454 | 5 | 118724372 | Higher in Drinkers |
| cg17010100 | 5 | 59188112 | Higher in Drinkers |
| cg17012202 | 6 | 31830656 | Higher in Drinkers |
| cg17012575 | 11 | 125757631 | Higher in Drinkers |
| cg17014849 | 21 | 43299412 | Higher in Drinkers |
| cg17015575 | 5 | 139947773 | Higher in Drinkers |
| cg17016011 | 10 | 134422782 | Higher in Drinkers |
| cg17017278 | 10 | 116697894 | Higher in Drinkers |
| cg17019143 | 1 | 85666673 | Higher in Drinkers |
| cg17019350 | 7 | 2649920 | Higher in Drinkers |
| cg17019518 | 6 | 28806931 | Higher in Drinkers |
| cg17020337 | 7 | 150076495 | Higher in Drinkers |
| cg17020582 | 15 | 70392177 | Higher in Drinkers |
| cg17022635 | 16 | 31190875 | Higher in Drinkers |
| cg17027776 | 1 | 39339172 | Higher in Drinkers |
| cg17028218 | 11 | 67261122 | Higher in Drinkers |
| cg17034082 | 5 | 153418793 | Higher in Drinkers |
| cg17035698 | 5 | 180258852 | Higher in Drinkers |
| cg17036624 | 3 | 8611601 | Higher in Drinkers |
| cg17036641 | 3 | 52723544 | Lower in Drinkers |
| cg17039369 | 21 | 46341006 | Higher in Drinkers |
| cg17039842 | 1 | 178511459 | Higher in Drinkers |
| cg17043193 | 5 | 142861369 | Higher in Drinkers |
| cg17044768 | 5 | 138739971 | Higher in Drinkers |
| cg17047311 | 8 | 28610801 | Higher in Drinkers |
| cg17047982 | 6 | 24403115 | Higher in Drinkers |
| cg17059624 | 11 | 85358760 | Higher in Drinkers |
| cg17061853 | 12 | 27091905 | Higher in Drinkers |

| | | | |
|---|---|---|---|
| cg17063452 | 10 | 103450447 | Higher in Drinkers |
| cg17068760 | 6 | 164009896 | Higher in Drinkers |
| cg17069650 | 7 | 73663536 | Higher in Drinkers |
| cg17070113 | 13 | 46542006 | Lower in Drinkers |
| cg17073432 | 10 | 104221224 | Higher in Drinkers |
| cg17076921 | 10 | 75634595 | Higher in Drinkers |
| cg17077776 | 5 | 110074606 | Higher in Drinkers |
| cg17078656 | 1 | 12535113 | Higher in Drinkers |
| cg17079325 | 7 | 130131480 | Higher in Drinkers |
| cg17079328 | 6 | 33374387 | Higher in Drinkers |
| cg17079688 | 4 | 83821767 | Higher in Drinkers |
| cg17079987 | 10 | 557562 | Higher in Drinkers |
| cg17081436 | 3 | 51456307 | Higher in Drinkers |
| cg17086370 | 15 | 41849953 | Higher in Drinkers |
| cg17088462 | 10 | 106014545 | Higher in Drinkers |
| cg17089214 | 22 | 22089827 | Higher in Drinkers |
| cg17097571 | 1 | 149858312 | Higher in Drinkers |
| cg17098850 | 15 | 22968689 | Higher in Drinkers |
| cg17099889 | 12 | 49412140 | Higher in Drinkers |
| cg17101748 | 1 | 224517614 | Higher in Drinkers |
| cg17106415 | 1 | 6105003 | Higher in Drinkers |
| cg17106419 | 10 | 103880236 | Higher in Drinkers |
| cg17112155 | 20 | 30639990 | Higher in Drinkers |
| cg17114084 | 1 | 203595871 | Higher in Drinkers |
| cg17114246 | 19 | 37708884 | Higher in Drinkers |
| cg17115258 | 15 | 102192853 | Higher in Drinkers |
| cg17119612 | 8 | 81786193 | Higher in Drinkers |
| cg17127132 | 2 | 85786382 | Higher in Drinkers |
| cg17128256 | 7 | 5342540 | Higher in Drinkers |
| cg17129809 | 2 | 23840282 | Lower in Drinkers |
| cg17130580 | 2 | 32264983 | Higher in Drinkers |
| cg17135503 | 4 | 154266588 | Higher in Drinkers |
| cg17139983 | 19 | 58987604 | Higher in Drinkers |
| cg17140647 | 11 | 66384868 | Higher in Drinkers |
| cg17143376 | 10 | 135202839 | Higher in Drinkers |

| | | | |
|---|---|---|---|
| cg17143565 | 17 | 33569990 | Higher in Drinkers |
| cg17144508 | 2 | 128283727 | Higher in Drinkers |
| cg17148556 | 1 | 229643984 | Higher in Drinkers |
| cg17149920 | 10 | 101190611 | Higher in Drinkers |
| cg17153568 | 2 | 175199315 | Higher in Drinkers |
| cg17157498 | 19 | 1383493 | Higher in Drinkers |
| cg17159201 | 1 | 159750490 | Higher in Drinkers |
| cg17159537 | 19 | 7554074 | Higher in Drinkers |
| cg17161026 | 1 | 212588397 | Higher in Drinkers |
| cg17161883 | 8 | 25317027 | Higher in Drinkers |
| cg17165311 | 17 | 1466280 | Higher in Drinkers |
| cg17166103 | 19 | 49298422 | Higher in Drinkers |
| cg17167972 | 17 | 29158999 | Higher in Drinkers |
| cg17168093 | 2 | 85531486 | Lower in Drinkers |
| cg17169333 | 8 | 96281960 | Higher in Drinkers |
| cg17170088 | 8 | 145159375 | Higher in Drinkers |
| cg17176195 | 11 | 71639533 | Higher in Drinkers |
| cg17177931 | 6 | 31870344 | Higher in Drinkers |
| cg17179571 | 1 | 6138086 | Higher in Drinkers |
| cg17183009 | 3 | 120277827 | Higher in Drinkers |
| cg17185401 | 1 | 110052093 | Higher in Drinkers |
| cg17185817 | 1 | 27719012 | Higher in Drinkers |
| cg17194243 | 13 | 37633605 | Higher in Drinkers |
| cg17195852 | 6 | 153324001 | Higher in Drinkers |
| cg17198200 | 4 | 164074320 | Lower in Drinkers |
| cg17203313 | 17 | 42907937 | Higher in Drinkers |
| cg17211223 | 3 | 52156741 | Higher in Drinkers |
| cg17213616 | 1 | 5933044 | Higher in Drinkers |
| cg17214737 | 10 | 75757811 | Higher in Drinkers |
| cg17216737 | 20 | 60580224 | Higher in Drinkers |
| cg17217295 | 17 | 42462958 | Higher in Drinkers |
| cg17221463 | 6 | 31371322 | Higher in Drinkers |
| cg17227014 | 4 | 6642450 | Higher in Drinkers |
| cg17228960 | 3 | 126707271 | Higher in Drinkers |
| cg17232393 | 4 | 926418 | Higher in Drinkers |

| | | | |
|---|---|---|---|
| cg17232883 | 11 | 69318136 | Higher in Drinkers |
| cg17237063 | 3 | 29323182 | Higher in Drinkers |
| cg17237603 | 7 | 148876528 | Higher in Drinkers |
| cg17238522 | X | 147583279 | Higher in Drinkers |
| cg17242144 | 19 | 10531498 | Higher in Drinkers |
| cg17248540 | 16 | 69143500 | Higher in Drinkers |
| cg17253884 | 3 | 51976254 | Higher in Drinkers |
| cg17255062 | 10 | 104614001 | Higher in Drinkers |
| cg17259952 | 20 | 58838244 | Higher in Drinkers |
| cg17263823 | 21 | 33942142 | Higher in Drinkers |
| cg17267064 | 15 | 28389917 | Higher in Drinkers |
| cg17269137 | 1 | 85666874 | Higher in Drinkers |
| cg17272491 | 12 | 133405852 | Higher in Drinkers |
| cg17275624 | 7 | 148876639 | Higher in Drinkers |
| cg17278771 | 1 | 151319974 | Higher in Drinkers |
| cg17280350 | 2 | 20853360 | Higher in Drinkers |
| cg17283899 | 5 | 10564369 | Higher in Drinkers |
| cg17284609 | 11 | 16424673 | Higher in Drinkers |
| cg17285834 | 6 | 112364920 | Higher in Drinkers |
| cg17285947 | 10 | 97416722 | Higher in Drinkers |
| cg17286435 | 3 | 75834648 | Higher in Drinkers |
| cg17287725 | 19 | 12267592 | Higher in Drinkers |
| cg17288102 | 10 | 111683471 | Lower in Drinkers |
| cg17290868 | 5 | 1801904 | Higher in Drinkers |
| cg17293600 | 11 | 65620771 | Higher in Drinkers |
| cg17294081 | 20 | 3452173 | Higher in Drinkers |
| cg17294308 | 17 | 883294 | Higher in Drinkers |
| cg17295489 | 12 | 57998192 | Higher in Drinkers |
| cg17297305 | 1 | 185287148 | Higher in Drinkers |
| cg17297653 | 12 | 121837761 | Higher in Drinkers |
| cg17298181 | 3 | 187456175 | Higher in Drinkers |
| cg17298429 | 3 | 120026692 | Higher in Drinkers |
| cg17299732 | 8 | 128747564 | Higher in Drinkers |
| cg17299902 | 1 | 151032301 | Higher in Drinkers |
| cg17300307 | 2 | 191744975 | Higher in Drinkers |

| | | | |
|---|---|---|---|
| cg17303845 | 19 | 49965045 | Higher in Drinkers |
| cg17304553 | 7 | 76623419 | Higher in Drinkers |
| cg17305800 | 12 | 89919388 | Higher in Drinkers |
| cg17313420 | 22 | 21921879 | Higher in Drinkers |
| cg17313494 | 19 | 8645769 | Higher in Drinkers |
| cg17318645 | 14 | 77787612 | Higher in Drinkers |
| cg17318990 | 12 | 90101606 | Higher in Drinkers |
| cg17321639 | 7 | 2759063 | Lower in Drinkers |
| cg17322163 | 12 | 51632344 | Higher in Drinkers |
| cg17322444 | 19 | 33572249 | Higher in Drinkers |
| cg17323045 | 14 | 58764804 | Higher in Drinkers |
| cg17323833 | 19 | 14117336 | Higher in Drinkers |
| cg17325674 | 10 | 47655962 | Higher in Drinkers |
| cg17330496 | 22 | 46732299 | Higher in Drinkers |
| cg17330983 | 14 | 23770641 | Higher in Drinkers |
| cg17333886 | 10 | 711676 | Lower in Drinkers |
| cg17335237 | 19 | 59086638 | Higher in Drinkers |
| cg17338352 | 4 | 123653805 | Higher in Drinkers |
| cg17341361 | 7 | 5414170 | Lower in Drinkers |
| cg17341703 | 6 | 88182369 | Higher in Drinkers |
| cg17341965 | 11 | 128761202 | Higher in Drinkers |
| cg17345036 | X | 100306958 | Higher in Drinkers |
| cg17345373 | X | 64754885 | Higher in Drinkers |
| cg17346237 | 14 | 56047471 | Higher in Drinkers |
| cg17349515 | 5 | 140134 | Lower in Drinkers |
| cg17350006 | 7 | 37488858 | Higher in Drinkers |
| cg17351882 | 17 | 4692162 | Higher in Drinkers |
| cg17357132 | 11 | 111750174 | Higher in Drinkers |
| cg17363084 | X | 118603274 | Higher in Drinkers |
| cg17364044 | 2 | 64371202 | Higher in Drinkers |
| cg17365504 | 7 | 75932840 | Higher in Drinkers |
| cg17367194 | 17 | 40716859 | Higher in Drinkers |
| cg17369059 | 17 | 38804281 | Higher in Drinkers |
| cg17369830 | 8 | 141545599 | Higher in Drinkers |
| cg17370412 | 17 | 20180146 | Higher in Drinkers |

| | | | |
|---|---|---|---|
| cg17370697 | 19 | 492365 | Higher in Drinkers |
| cg17371249 | 1 | 241682474 | Higher in Drinkers |
| cg17371908 | 6 | 30624016 | Higher in Drinkers |
| cg17374051 | 18 | 72265663 | Higher in Drinkers |
| cg17374227 | 4 | 140374776 | Higher in Drinkers |
| cg17375083 | 21 | 45735791 | Higher in Drinkers |
| cg17377491 | 11 | 112096999 | Higher in Drinkers |
| cg17377690 | 8 | 59572467 | Higher in Drinkers |
| cg17383793 | 5 | 52405638 | Higher in Drinkers |
| cg17383940 | 21 | 38936403 | Higher in Drinkers |
| cg17385318 | 4 | 852022 | Higher in Drinkers |
| cg17385737 | 12 | 96589144 | Higher in Drinkers |
| cg17389738 | 6 | 30711642 | Higher in Drinkers |
| cg17391107 | X | 48379816 | Lower in Drinkers |
| cg17395619 | 19 | 4607540 | Lower in Drinkers |
| cg17401719 | 7 | 36429848 | Higher in Drinkers |
| cg17403702 | 11 | 6499575 | Higher in Drinkers |
| cg17411949 | 17 | 40540650 | Higher in Drinkers |
| cg17414733 | 19 | 21688647 | Higher in Drinkers |
| cg17416722 | 6 | 32554385 | Higher in Drinkers |
| cg17418085 | 1 | 31229122 | Higher in Drinkers |
| cg17420019 | 2 | 136742849 | Higher in Drinkers |
| cg17421072 | 12 | 93963555 | Higher in Drinkers |
| cg17422836 | 5 | 72861187 | Higher in Drinkers |
| cg17428324 | 19 | 52531703 | Higher in Drinkers |
| cg17428496 | 19 | 2151817 | Higher in Drinkers |
| cg17428913 | 1 | 36563557 | Higher in Drinkers |
| cg17429424 | 5 | 172197911 | Higher in Drinkers |
| cg17434366 | 4 | 2746469 | Lower in Drinkers |
| cg17434483 | 19 | 19257032 | Higher in Drinkers |
| cg17437033 | 5 | 132072786 | Higher in Drinkers |
| cg17444293 | 5 | 211954 | Higher in Drinkers |
| cg17445101 | 4 | 854688 | Higher in Drinkers |
| cg17449851 | 5 | 66300406 | Higher in Drinkers |
| cg17450930 | 7 | 150065170 | Higher in Drinkers |

| | | | |
|---|---|---|---|
| cg17453767 | 4 | 144277796 | Higher in Drinkers |
| cg17455688 | 11 | 3819097 | Higher in Drinkers |
| cg17457701 | 15 | 86313860 | Higher in Drinkers |
| cg17460200 | 19 | 47777129 | Higher in Drinkers |
| cg17461735 | 9 | 82185498 | Higher in Drinkers |
| cg17462109 | 8 | 134584347 | Higher in Drinkers |
| cg17463161 | 19 | 58298117 | Higher in Drinkers |
| cg17470103 | 1 | 151252719 | Higher in Drinkers |
| cg17473318 | 19 | 19033250 | Higher in Drinkers |
| cg17473896 | 11 | 67272980 | Higher in Drinkers |
| cg17474260 | 1 | 76252117 | Higher in Drinkers |
| cg17479303 | 3 | 37218212 | Higher in Drinkers |
| cg17479943 | 1 | 119546928 | Higher in Drinkers |
| cg17481703 | 13 | 76444831 | Higher in Drinkers |
| cg17482706 | 9 | 77643371 | Higher in Drinkers |
| cg17483510 | 3 | 179168677 | Higher in Drinkers |
| cg17491846 | 19 | 19431584 | Higher in Drinkers |
| cg17493164 | 11 | 65382825 | Higher in Drinkers |
| cg17495250 | 5 | 2727907 | Higher in Drinkers |
| cg17500103 | 4 | 164254082 | Higher in Drinkers |
| cg17507749 | 15 | 85114479 | Higher in Drinkers |
| cg17508549 | X | 153707810 | Higher in Drinkers |
| cg17511829 | 1 | 149510892 | Higher in Drinkers |
| cg17512868 | 1 | 9970773 | Higher in Drinkers |
| cg17514608 | 6 | 28193279 | Higher in Drinkers |
| cg17514654 | 1 | 40368198 | Higher in Drinkers |
| cg17515155 | 1 | 11714790 | Higher in Drinkers |
| cg17515773 | 5 | 57755861 | Higher in Drinkers |
| cg17516556 | 3 | 17784454 | Higher in Drinkers |
| cg17518884 | 12 | 133517772 | Higher in Drinkers |
| cg17518899 | 12 | 50017006 | Higher in Drinkers |
| cg17519570 | 10 | 101190924 | Higher in Drinkers |
| cg17520176 | 1 | 35734836 | Higher in Drinkers |
| cg17523027 | 22 | 37447622 | Higher in Drinkers |
| cg17524624 | 7 | 142960387 | Higher in Drinkers |

| | | | |
|---|---|---|---|
| cg17524821 | 19 | 15535460 | Higher in Drinkers |
| cg17528700 | 6 | 99968879 | Higher in Drinkers |
| cg17533245 | 2 | 153574016 | Higher in Drinkers |
| cg17539479 | 7 | 129007618 | Higher in Drinkers |
| cg17541142 | 7 | 1546826 | Higher in Drinkers |
| cg17545334 | 7 | 26241071 | Higher in Drinkers |
| cg17552650 | X | 48957963 | Higher in Drinkers |
| cg17554553 | 10 | 31321002 | Higher in Drinkers |
| cg17557874 | 3 | 106959585 | Higher in Drinkers |
| cg17560338 | 17 | 42441417 | Higher in Drinkers |
| cg17560527 | 6 | 564069 | Higher in Drinkers |
| cg17561030 | 5 | 72794050 | Higher in Drinkers |
| cg17565360 | 11 | 4115872 | Higher in Drinkers |
| cg17566592 | 6 | 144417471 | Higher in Drinkers |
| cg17573270 | 22 | 42950376 | Higher in Drinkers |
| cg17573594 | 12 | 110338513 | Higher in Drinkers |
| cg17574857 | 5 | 147763476 | Higher in Drinkers |
| cg17575299 | 10 | 102672737 | Higher in Drinkers |
| cg17576613 | 4 | 47487235 | Higher in Drinkers |
| cg17583369 | 2 | 170441340 | Higher in Drinkers |
| cg17586321 | 4 | 87928361 | Higher in Drinkers |
| cg17586984 | 13 | 96329587 | Higher in Drinkers |
| cg17588094 | 8 | 128755270 | Higher in Drinkers |
| cg17596554 | 17 | 54671073 | Higher in Drinkers |
| cg17603857 | 19 | 56111499 | Higher in Drinkers |
| cg17604239 | X | 100307203 | Higher in Drinkers |
| cg17605084 | 12 | 54891491 | Higher in Drinkers |
| cg17605107 | 5 | 125936881 | Higher in Drinkers |
| cg17606287 | 9 | 99776144 | Higher in Drinkers |
| cg17606675 | 1 | 144615272 | Higher in Drinkers |
| cg17609050 | 7 | 92861606 | Higher in Drinkers |
| cg17612148 | 17 | 26898533 | Higher in Drinkers |
| cg17618194 | 7 | 100861352 | Higher in Drinkers |
| cg17621054 | 12 | 80034980 | Higher in Drinkers |
| cg17623341 | 20 | 32273902 | Higher in Drinkers |

| | | | |
|---|---|---|---|
| cg17623882 | 6 | 41773611 | Lower in Drinkers |
| cg17626301 | 6 | 32820201 | Lower in Drinkers |
| cg17632831 | 3 | 52312190 | Higher in Drinkers |
| cg17633523 | 17 | 37841458 | Higher in Drinkers |
| cg17636193 | 11 | 101785595 | Higher in Drinkers |
| cg17638137 | 5 | 145826831 | Higher in Drinkers |
| cg17638213 | 13 | 114164151 | Higher in Drinkers |
| cg17639265 | 6 | 35887853 | Higher in Drinkers |
| cg17641104 | 12 | 96794247 | Higher in Drinkers |
| cg17642426 | 10 | 124739963 | Higher in Drinkers |
| cg17647004 | 7 | 132937623 | Higher in Drinkers |
| cg17648451 | 2 | 159386608 | Lower in Drinkers |
| cg17651855 | 11 | 109920791 | Higher in Drinkers |
| cg17652206 | 4 | 120133663 | Higher in Drinkers |
| cg17653341 | 17 | 60556736 | Higher in Drinkers |
| cg17660245 | 19 | 41190252 | Higher in Drinkers |
| cg17660384 | 11 | 101918145 | Higher in Drinkers |
| cg17660945 | 3 | 149511095 | Lower in Drinkers |
| cg17661300 | 8 | 144329544 | Higher in Drinkers |
| cg17664265 | 3 | 186285263 | Higher in Drinkers |
| cg17668135 | 15 | 83478367 | Higher in Drinkers |
| cg17668562 | 5 | 68466250 | Higher in Drinkers |
| cg17669009 | 19 | 51920885 | Higher in Drinkers |
| cg17670641 | X | 49023115 | Higher in Drinkers |
| cg17675199 | 6 | 35436792 | Higher in Drinkers |
| cg17677112 | 7 | 77428730 | Higher in Drinkers |
| cg17678946 | 2 | 32235925 | Higher in Drinkers |
| cg17680211 | 10 | 31907941 | Higher in Drinkers |
| cg17681255 | 17 | 21030613 | Higher in Drinkers |
| cg17685622 | 2 | 242737344 | Higher in Drinkers |
| cg17690263 | 7 | 150690969 | Higher in Drinkers |
| cg17693669 | 2 | 8711075 | Lower in Drinkers |
| cg17694409 | 7 | 39605996 | Higher in Drinkers |
| cg17696234 | 3 | 38164516 | Higher in Drinkers |
| cg17696379 | 11 | 61103807 | Higher in Drinkers |

| | | | |
|---|---|---|---|
| cg17705658 | 1 | 32707140 | Higher in Drinkers |
| cg17706456 | 11 | 5617367 | Higher in Drinkers |
| cg17707660 | 15 | 65134046 | Higher in Drinkers |
| cg17709464 | 6 | 158927809 | Higher in Drinkers |
| cg17714794 | 5 | 172571566 | Higher in Drinkers |
| cg17717549 | 12 | 7261691 | Higher in Drinkers |
| cg17718036 | 6 | 27219983 | Higher in Drinkers |
| cg17723508 | 6 | 31474240 | Higher in Drinkers |
| cg17727989 | 9 | 27529519 | Higher in Drinkers |
| cg17729873 | X | 134186456 | Higher in Drinkers |
| cg17732597 | 6 | 30689710 | Higher in Drinkers |
| cg17735043 | 5 | 21459472 | Higher in Drinkers |
| cg17737141 | 1 | 173793901 | Higher in Drinkers |
| cg17738375 | 19 | 12900572 | Higher in Drinkers |
| cg17739038 | 17 | 1957496 | Higher in Drinkers |
| cg17740327 | 19 | 45250638 | Higher in Drinkers |
| cg17740950 | 20 | 2489557 | Higher in Drinkers |
| cg17745251 | 10 | 21806139 | Higher in Drinkers |
| cg17746833 | 17 | 39805051 | Higher in Drinkers |
| cg17747332 | 19 | 11071239 | Higher in Drinkers |
| cg17749356 | 2 | 118692673 | Higher in Drinkers |
| cg17753356 | 2 | 60711641 | Higher in Drinkers |
| cg17755964 | 1 | 2461834 | Higher in Drinkers |
| cg17756238 | 1 | 146697187 | Higher in Drinkers |
| cg17757079 | 22 | 21321368 | Lower in Drinkers |
| cg17761990 | 3 | 53042940 | Lower in Drinkers |
| cg17765461 | 19 | 1408416 | Higher in Drinkers |
| cg17779707 | 20 | 48807327 | Higher in Drinkers |
| cg17783031 | 3 | 48673137 | Higher in Drinkers |
| cg17783982 | 5 | 88180093 | Higher in Drinkers |
| cg17784596 | 6 | 32122010 | Higher in Drinkers |
| cg17787005 | 2 | 231851943 | Higher in Drinkers |
| cg17790400 | 4 | 25314231 | Higher in Drinkers |
| cg17791766 | 19 | 55791675 | Higher in Drinkers |
| cg17792564 | 3 | 187461975 | Higher in Drinkers |

| | | | |
|---|---|---|---|
| cg17796897 | 19 | 18403201 | Higher in Drinkers |
| cg17803467 | 17 | 42297979 | Higher in Drinkers |
| cg17804886 | 13 | 114871422 | Higher in Drinkers |
| cg17808823 | 4 | 153600942 | Higher in Drinkers |
| cg17813364 | 7 | 149321879 | Higher in Drinkers |
| cg17814596 | 5 | 180632375 | Higher in Drinkers |
| cg17815891 | 5 | 111496370 | Higher in Drinkers |
| cg17817350 | 17 | 80195737 | Higher in Drinkers |
| cg17817474 | 15 | 90809403 | Higher in Drinkers |
| cg17818847 | 12 | 133402661 | Higher in Drinkers |
| cg17820022 | 1 | 2425860 | Lower in Drinkers |
| cg17821079 | 1 | 244614869 | Higher in Drinkers |
| cg17825156 | 1 | 67391082 | Higher in Drinkers |
| cg17825277 | 15 | 59949336 | Higher in Drinkers |
| cg17826786 | 2 | 3322489 | Higher in Drinkers |
| cg17830040 | 1 | 44457185 | Higher in Drinkers |
| cg17831662 | 8 | 109261184 | Higher in Drinkers |
| cg17833980 | 5 | 70883096 | Higher in Drinkers |
| cg17837967 | 21 | 35014635 | Higher in Drinkers |
| cg17840164 | 10 | 104262570 | Higher in Drinkers |
| cg17840355 | 4 | 8472895 | Higher in Drinkers |
| cg17843101 | 12 | 56478329 | Lower in Drinkers |
| cg17844313 | 19 | 16738790 | Higher in Drinkers |
| cg17853057 | X | 54070497 | Higher in Drinkers |
| cg17853833 | 22 | 31885141 | Higher in Drinkers |
| cg17854265 | 7 | 54826915 | Higher in Drinkers |
| cg17855016 | 13 | 113272518 | Higher in Drinkers |
| cg17857070 | 19 | 14320475 | Higher in Drinkers |
| cg17858005 | 2 | 20851058 | Higher in Drinkers |
| cg17867194 | 2 | 32390673 | Higher in Drinkers |
| cg17867243 | 15 | 42371653 | Higher in Drinkers |
| cg17867605 | 6 | 31634162 | Higher in Drinkers |
| cg17873919 | 5 | 134094447 | Higher in Drinkers |
| cg17875845 | 4 | 87932378 | Higher in Drinkers |
| cg17876641 | 1 | 200960141 | Higher in Drinkers |

| | | | |
|---|---|---|---|
| cg17877656 | 10 | 105110211 | Higher in Drinkers |
| cg17878425 | 12 | 7342771 | Higher in Drinkers |
| cg17878951 | X | 7066487 | Higher in Drinkers |
| cg17879912 | 5 | 118628530 | Higher in Drinkers |
| cg17882322 | 19 | 50413014 | Higher in Drinkers |
| cg17883371 | 1 | 91359225 | Higher in Drinkers |
| cg17885031 | 12 | 95867808 | Higher in Drinkers |
| cg17888086 | 1 | 37945057 | Higher in Drinkers |
| cg17888096 | 17 | 48624434 | Higher in Drinkers |
| cg17889402 | 18 | 55862872 | Higher in Drinkers |
| cg17890983 | 13 | 37394336 | Lower in Drinkers |
| cg17894293 | 20 | 32436418 | Higher in Drinkers |
| cg17897879 | 1 | 12123437 | Higher in Drinkers |
| cg17898189 | 19 | 36606599 | Higher in Drinkers |
| cg17899492 | 19 | 12771866 | Higher in Drinkers |
| cg17905198 | 18 | 9103090 | Higher in Drinkers |
| cg17906179 | 3 | 194991500 | Higher in Drinkers |
| cg17907525 | 7 | 2594000 | Higher in Drinkers |
| cg17910375 | 12 | 57023577 | Higher in Drinkers |
| cg17914881 | 12 | 121838395 | Higher in Drinkers |
| cg17915922 | 7 | 6911211 | Lower in Drinkers |
| cg17916407 | 14 | 50234392 | Higher in Drinkers |
| cg17918875 | 8 | 17780190 | Higher in Drinkers |
| cg17919331 | 5 | 112312406 | Higher in Drinkers |
| cg17919570 | 2 | 234763381 | Higher in Drinkers |
| cg17921248 | 17 | 64298993 | Higher in Drinkers |
| cg17927889 | 8 | 1733497 | Lower in Drinkers |
| cg17927926 | 2 | 39103310 | Higher in Drinkers |
| cg17930583 | 6 | 29591082 | Higher in Drinkers |
| cg17932394 | 19 | 48866706 | Higher in Drinkers |
| cg17942925 | 5 | 130611441 | Higher in Drinkers |
| cg17945282 | 3 | 142297905 | Higher in Drinkers |
| cg17946284 | 3 | 72937052 | Higher in Drinkers |
| cg17948386 | 12 | 50451212 | Higher in Drinkers |
| cg17948846 | 16 | 68119548 | Higher in Drinkers |

| | | | |
|---|---|---|---|
| cg17958132 | 17 | 915739 | Higher in Drinkers |
| cg17959549 | 6 | 36410508 | Higher in Drinkers |
| cg17960442 | 5 | 110559531 | Higher in Drinkers |
| cg17960769 | 1 | 36772837 | Higher in Drinkers |
| cg17960926 | 19 | 42901374 | Higher in Drinkers |
| cg17963039 | 9 | 139743185 | Higher in Drinkers |
| cg17964980 | 11 | 7534989 | Higher in Drinkers |
| cg17965019 | 6 | 27858545 | Higher in Drinkers |
| cg17965926 | 8 | 140716970 | Higher in Drinkers |
| cg17966167 | 7 | 37488564 | Higher in Drinkers |
| cg17967728 | 15 | 52263786 | Higher in Drinkers |
| cg17967973 | 11 | 126139042 | Higher in Drinkers |
| cg17969298 | 1 | 213189164 | Higher in Drinkers |
| cg17970282 | X | 70712810 | Higher in Drinkers |
| cg17971171 | 1 | 156737145 | Higher in Drinkers |
| cg17971531 | 1 | 24882680 | Higher in Drinkers |
| cg17972708 | 19 | 57874796 | Higher in Drinkers |
| cg17975245 | 1 | 20959890 | Higher in Drinkers |
| cg17976065 | 17 | 15902694 | Higher in Drinkers |
| cg17977580 | 17 | 20920818 | Higher in Drinkers |
| cg17979479 | 12 | 112035680 | Higher in Drinkers |
| cg17980625 | 11 | 94965587 | Higher in Drinkers |
| cg17981742 | 5 | 131746161 | Higher in Drinkers |
| cg17986264 | 10 | 64576256 | Higher in Drinkers |
| cg17988310 | 22 | 40355732 | Higher in Drinkers |
| cg17988524 | 2 | 74681873 | Higher in Drinkers |
| cg17994050 | 6 | 30029062 | Higher in Drinkers |
| cg17995403 | 2 | 95831296 | Higher in Drinkers |
| cg17998333 | 10 | 121356721 | Higher in Drinkers |
| cg18000924 | 2 | 203130365 | Higher in Drinkers |
| cg18001714 | 5 | 14871894 | Higher in Drinkers |
| cg18007524 | 2 | 27994656 | Higher in Drinkers |
| cg18008269 | 17 | 38277761 | Higher in Drinkers |
| cg18011274 | 17 | 43213270 | Higher in Drinkers |
| cg18011946 | 5 | 65440816 | Higher in Drinkers |

| | | | |
|---|---|---|---|
| cg18014844 | 1 | 55230402 | Higher in Drinkers |
| cg18014983 | 6 | 29618382 | Higher in Drinkers |
| cg18015985 | 5 | 176779051 | Higher in Drinkers |
| cg18016254 | 3 | 122296505 | Higher in Drinkers |
| cg18016304 | 15 | 31287286 | Higher in Drinkers |
| cg18020679 | 6 | 33168031 | Higher in Drinkers |
| cg18023401 | 8 | 125985512 | Higher in Drinkers |
| cg18031747 | 19 | 9929709 | Higher in Drinkers |
| cg18031978 | 3 | 9851572 | Higher in Drinkers |
| cg18034041 | 6 | 32811884 | Higher in Drinkers |
| cg18036573 | 7 | 92219856 | Higher in Drinkers |
| cg18037578 | 6 | 30313418 | Higher in Drinkers |
| cg18038666 | 10 | 101380417 | Higher in Drinkers |
| cg18042079 | 17 | 30229074 | Higher in Drinkers |
| cg18042229 | 2 | 219922729 | Higher in Drinkers |
| cg18042632 | 21 | 42520902 | Lower in Drinkers |
| cg18043455 | 3 | 127771761 | Higher in Drinkers |
| cg18046311 | 12 | 49222623 | Higher in Drinkers |
| cg18047032 | 5 | 90576987 | Higher in Drinkers |
| cg18047794 | 19 | 55770732 | Higher in Drinkers |
| cg18048562 | 11 | 57232463 | Higher in Drinkers |
| cg18052778 | 17 | 46030312 | Higher in Drinkers |
| cg18052823 | 5 | 108744905 | Higher in Drinkers |
| cg18053345 | 5 | 37370947 | Higher in Drinkers |
| cg18058813 | 6 | 105307561 | Higher in Drinkers |
| cg18062360 | 19 | 59084588 | Higher in Drinkers |
| cg18063222 | 8 | 146052715 | Higher in Drinkers |
| cg18063495 | 5 | 50262796 | Higher in Drinkers |
| cg18064171 | 12 | 47219956 | Higher in Drinkers |
| cg18068664 | 4 | 177713244 | Higher in Drinkers |
| cg18070033 | 2 | 220025364 | Higher in Drinkers |
| cg18073380 | 3 | 101396084 | Higher in Drinkers |
| cg18074184 | 4 | 48485090 | Higher in Drinkers |
| cg18078821 | 10 | 103578534 | Higher in Drinkers |
| cg18082680 | 1 | 33798023 | Lower in Drinkers |

| | | | |
|---|---|---|---|
| cg18084554 | 19 | 929046 | Lower in Drinkers |
| cg18088775 | 18 | 48724276 | Higher in Drinkers |
| cg18091435 | 5 | 100237279 | Higher in Drinkers |
| cg18098714 | 6 | 32935404 | Higher in Drinkers |
| cg18100425 | 19 | 1833162 | Higher in Drinkers |
| cg18100887 | 17 | 34611341 | Higher in Drinkers |
| cg18101140 | 11 | 67142001 | Higher in Drinkers |
| cg18101474 | X | 134478119 | Higher in Drinkers |
| cg18103606 | 22 | 32146197 | Higher in Drinkers |
| cg18104645 | 17 | 75447504 | Higher in Drinkers |
| cg18106844 | 15 | 64386011 | Higher in Drinkers |
| cg18106923 | 2 | 123289581 | Lower in Drinkers |
| cg18107727 | 1 | 225615856 | Higher in Drinkers |
| cg18108262 | 15 | 40857029 | Higher in Drinkers |
| cg18108507 | 3 | 51975897 | Higher in Drinkers |
| cg18114053 | 6 | 373609 | Lower in Drinkers |
| cg18114173 | 7 | 99149806 | Higher in Drinkers |
| cg18114463 | 1 | 1476551 | Higher in Drinkers |
| cg18120111 | 21 | 43917047 | Lower in Drinkers |
| cg18123790 | 12 | 6772186 | Higher in Drinkers |
| cg18125241 | 1 | 36026419 | Higher in Drinkers |
| cg18125957 | 7 | 139044318 | Higher in Drinkers |
| cg18127410 | 11 | 9113184 | Higher in Drinkers |
| cg18128546 | 1 | 113162116 | Higher in Drinkers |
| cg18131141 | 1 | 36043002 | Higher in Drinkers |
| cg18136311 | 1 | 160232565 | Higher in Drinkers |
| cg18136930 | 7 | 4831038 | Higher in Drinkers |
| cg18141902 | 1 | 2781275 | Higher in Drinkers |
| cg18144073 | X | 54835328 | Higher in Drinkers |
| cg18145026 | 8 | 99180585 | Higher in Drinkers |
| cg18145105 | 2 | 97166422 | Higher in Drinkers |
| cg18145189 | 11 | 66137134 | Higher in Drinkers |
| cg18150584 | 1 | 23887816 | Higher in Drinkers |
| cg18150721 | 3 | 134514881 | Higher in Drinkers |
| cg18151030 | 21 | 43222961 | Higher in Drinkers |

| | | | |
|---|---|---|---|
| cg18151993 | 10 | 43904861 | Higher in Drinkers |
| cg18153061 | 17 | 291152 | Higher in Drinkers |
| cg18156686 | 10 | 134893401 | Higher in Drinkers |
| cg18158177 | 1 | 39492193 | Higher in Drinkers |
| cg18161803 | 14 | 62217806 | Higher in Drinkers |
| cg18161950 | 5 | 42995203 | Higher in Drinkers |
| cg18163727 | 19 | 18391883 | Higher in Drinkers |
| cg18164599 | 4 | 175443867 | Higher in Drinkers |
| cg18165259 | 1 | 17240955 | Higher in Drinkers |
| cg18168387 | 12 | 120933482 | Higher in Drinkers |
| cg18175410 | 18 | 21083641 | Higher in Drinkers |
| cg18175672 | 5 | 179680193 | Higher in Drinkers |
| cg18176336 | 1 | 9648587 | Higher in Drinkers |
| cg18181070 | 2 | 74756634 | Higher in Drinkers |
| cg18181161 | 7 | 128415663 | Higher in Drinkers |
| cg18185393 | 1 | 118472782 | Higher in Drinkers |
| cg18190164 | 22 | 30234456 | Higher in Drinkers |
| cg18191540 | 14 | 107281437 | Higher in Drinkers |
| cg18197398 | 17 | 5095012 | Higher in Drinkers |
| cg18200261 | 15 | 83781859 | Higher in Drinkers |
| cg18200270 | 5 | 79950815 | Higher in Drinkers |
| cg18206768 | 7 | 2582681 | Higher in Drinkers |
| cg18212591 | 13 | 103425442 | Higher in Drinkers |
| cg18213440 | 3 | 100428172 | Higher in Drinkers |
| cg18219490 | 4 | 89206110 | Higher in Drinkers |
| cg18221028 | 6 | 30523418 | Higher in Drinkers |
| cg18226668 | 15 | 50646438 | Higher in Drinkers |
| cg18226957 | 2 | 128604857 | Higher in Drinkers |
| cg18227995 | 7 | 1882029 | Higher in Drinkers |
| cg18228531 | 14 | 105147702 | Higher in Drinkers |
| cg18228590 | 5 | 77142469 | Higher in Drinkers |
| cg18229647 | 19 | 44123486 | Higher in Drinkers |
| cg18230417 | 1 | 6845419 | Higher in Drinkers |
| cg18231848 | 1 | 26499103 | Higher in Drinkers |
| cg18237277 | 1 | 3774198 | Higher in Drinkers |

| | | | |
|---|---|---|---|
| cg18239763 | 12 | 49525542 | Higher in Drinkers |
| cg18243598 | 7 | 2172011 | Higher in Drinkers |
| cg18245652 | 19 | 39897242 | Higher in Drinkers |
| cg18248022 | 17 | 71162159 | Higher in Drinkers |
| cg18249991 | 19 | 46366442 | Higher in Drinkers |
| cg18250212 | 7 | 90032604 | Higher in Drinkers |
| cg18251360 | 22 | 20067313 | Higher in Drinkers |
| cg18251767 | 6 | 31627090 | Higher in Drinkers |
| cg18254819 | 19 | 50922194 | Higher in Drinkers |
| cg18261823 | 18 | 74533371 | Higher in Drinkers |
| cg18263642 | 9 | 129485131 | Higher in Drinkers |
| cg18263696 | 1 | 217904728 | Higher in Drinkers |
| cg18270280 | 1 | 100504403 | Higher in Drinkers |
| cg18276016 | 1 | 156076340 | Higher in Drinkers |
| cg18276145 | 4 | 72052432 | Higher in Drinkers |
| cg18276437 | 6 | 152554982 | Higher in Drinkers |
| cg18277507 | 5 | 883880 | Higher in Drinkers |
| cg18289682 | 6 | 33264318 | Higher in Drinkers |
| cg18295838 | 4 | 15005434 | Higher in Drinkers |
| cg18296189 | 14 | 70564650 | Lower in Drinkers |
| cg18296227 | 10 | 99205774 | Higher in Drinkers |
| cg18298494 | 14 | 76447327 | Higher in Drinkers |
| cg18304280 | 14 | 103010894 | Higher in Drinkers |
| cg18304813 | 14 | 24615913 | Higher in Drinkers |
| cg18307333 | 19 | 507490 | Higher in Drinkers |
| cg18307604 | X | 119603221 | Higher in Drinkers |
| cg18310774 | 2 | 240026709 | Higher in Drinkers |
| cg18311384 | 17 | 34842312 | Higher in Drinkers |
| cg18313182 | 11 | 818903 | Higher in Drinkers |
| cg18314814 | 2 | 98611695 | Higher in Drinkers |
| cg18315103 | 16 | 67571472 | Higher in Drinkers |
| cg18315695 | 6 | 31782898 | Higher in Drinkers |
| cg18315896 | 5 | 112043131 | Higher in Drinkers |
| cg18318704 | 5 | 133968668 | Higher in Drinkers |
| cg18319687 | 5 | 179225515 | Higher in Drinkers |

| | | | |
|---|---|---|---|
| cg18320370 | 14 | 73183046 | Higher in Drinkers |
| cg18323835 | 5 | 130500266 | Higher in Drinkers |
| cg18323993 | 9 | 73034238 | Higher in Drinkers |
| cg18324123 | 1 | 65614514 | Higher in Drinkers |
| cg18331004 | 20 | 1784313 | Higher in Drinkers |
| cg18331022 | 22 | 47458079 | Higher in Drinkers |
| cg18334392 | 5 | 9547825 | Higher in Drinkers |
| cg18336453 | 6 | 43082296 | Higher in Drinkers |
| cg18341116 | 6 | 82957506 | Higher in Drinkers |
| cg18342494 | 5 | 170845157 | Lower in Drinkers |
| cg18342714 | 6 | 120867717 | Higher in Drinkers |
| cg18352882 | 10 | 22725345 | Lower in Drinkers |
| cg18353345 | 21 | 46961669 | Higher in Drinkers |
| cg18357563 | 4 | 153456325 | Higher in Drinkers |
| cg18360690 | 15 | 80351522 | Higher in Drinkers |
| cg18367110 | 1 | 111992173 | Higher in Drinkers |
| cg18367631 | 7 | 653309 | Lower in Drinkers |
| cg18367735 | 17 | 79674897 | Higher in Drinkers |
| cg18368807 | 14 | 51026939 | Higher in Drinkers |
| cg18374625 | 19 | 50004152 | Higher in Drinkers |
| cg18374830 | 11 | 75525835 | Higher in Drinkers |
| cg18375494 | 11 | 134146324 | Higher in Drinkers |
| cg18379455 | 17 | 41446167 | Higher in Drinkers |
| cg18381283 | 1 | 156561353 | Higher in Drinkers |
| cg18382389 | 13 | 43148017 | Higher in Drinkers |
| cg18383391 | 16 | 77224198 | Higher in Drinkers |
| cg18388639 | 10 | 12084756 | Higher in Drinkers |
| cg18394848 | 12 | 25403102 | Higher in Drinkers |
| cg18395993 | 1 | 249152672 | Higher in Drinkers |
| cg18397308 | 19 | 18672850 | Higher in Drinkers |
| cg18398512 | 6 | 88411013 | Higher in Drinkers |
| cg18399551 | X | 154299773 | Higher in Drinkers |
| cg18403673 | 11 | 63828569 | Higher in Drinkers |
| cg18405297 | 19 | 45681503 | Higher in Drinkers |
| cg18405330 | 6 | 164171960 | Higher in Drinkers |

| | | | |
|---|---|---|---|
| cg18406718 | 4 | 102269374 | Higher in Drinkers |
| cg18407309 | 17 | 34417530 | Higher in Drinkers |
| cg18412613 | 7 | 44240514 | Higher in Drinkers |
| cg18413240 | 3 | 112280241 | Higher in Drinkers |
| cg18413449 | 7 | 155605350 | Lower in Drinkers |
| cg18422603 | 3 | 156878604 | Higher in Drinkers |
| cg18426224 | 15 | 34874862 | Higher in Drinkers |
| cg18428201 | 8 | 54821956 | Higher in Drinkers |
| cg18429235 | 19 | 46216541 | Higher in Drinkers |
| cg18430624 | 11 | 10326585 | Higher in Drinkers |
| cg18436324 | 6 | 32820583 | Higher in Drinkers |
| cg18440470 | 1 | 180601735 | Higher in Drinkers |
| cg18440893 | 6 | 16760537 | Higher in Drinkers |
| cg18446520 | 12 | 106981513 | Higher in Drinkers |
| cg18450500 | 14 | 104690201 | Higher in Drinkers |
| cg18450553 | 15 | 42867888 | Higher in Drinkers |
| cg18451982 | 1 | 119715385 | Higher in Drinkers |
| cg18452880 | 6 | 170151829 | Higher in Drinkers |
| cg18453904 | 3 | 105088217 | Higher in Drinkers |
| cg18455978 | 19 | 39421261 | Higher in Drinkers |
| cg18456691 | 20 | 54934110 | Higher in Drinkers |
| cg18461649 | 14 | 56585102 | Higher in Drinkers |
| cg18461989 | 6 | 16760179 | Higher in Drinkers |
| cg18463595 | 7 | 105222699 | Lower in Drinkers |
| cg18465199 | 6 | 37506304 | Lower in Drinkers |
| cg18467110 | 3 | 140661601 | Higher in Drinkers |
| cg18469103 | 3 | 120068673 | Higher in Drinkers |
| cg18469326 | 17 | 29158893 | Higher in Drinkers |
| cg18469811 | 11 | 76432985 | Higher in Drinkers |
| cg18470455 | X | 102001134 | Higher in Drinkers |
| cg18470594 | 3 | 119012749 | Higher in Drinkers |
| cg18473162 | 19 | 56631888 | Higher in Drinkers |
| cg18474135 | 9 | 116038303 | Higher in Drinkers |
| cg18474185 | 14 | 105817353 | Lower in Drinkers |
| cg18474865 | 21 | 46292084 | Higher in Drinkers |

| | | | |
|---|---|---|---|
| cg18476948 | 19 | 41082749 | Higher in Drinkers |
| cg18477117 | 2 | 127830703 | Higher in Drinkers |
| cg18478394 | 8 | 109455254 | Higher in Drinkers |
| cg18481587 | 14 | 105707308 | Higher in Drinkers |
| cg18482813 | 22 | 26908758 | Higher in Drinkers |
| cg18483976 | 19 | 33571768 | Higher in Drinkers |
| cg18484294 | 2 | 202645530 | Higher in Drinkers |
| cg18486630 | 20 | 21283939 | Higher in Drinkers |
| cg18489606 | 19 | 2927396 | Higher in Drinkers |
| cg18491230 | 7 | 36429601 | Higher in Drinkers |
| cg18496271 | 19 | 1388932 | Higher in Drinkers |
| cg18496382 | 5 | 176450179 | Higher in Drinkers |
| cg18500714 | 14 | 100706288 | Higher in Drinkers |
| cg18503381 | 19 | 58144462 | Higher in Drinkers |
| cg18504532 | 1 | 174129335 | Higher in Drinkers |
| cg18505103 | 19 | 3115035 | Lower in Drinkers |
| cg18505879 | 18 | 60382658 | Higher in Drinkers |
| cg18506744 | 19 | 1102627 | Higher in Drinkers |
| cg18507125 | X | 100646106 | Higher in Drinkers |
| cg18509826 | 3 | 52017385 | Higher in Drinkers |
| cg18511989 | 8 | 145634287 | Higher in Drinkers |
| cg18512092 | 2 | 27274554 | Higher in Drinkers |
| cg18512515 | 15 | 96897414 | Higher in Drinkers |
| cg18515046 | 5 | 1223167 | Higher in Drinkers |
| cg18516317 | 2 | 54950679 | Higher in Drinkers |
| cg18516833 | 19 | 57350313 | Lower in Drinkers |
| cg18520634 | 10 | 135192152 | Higher in Drinkers |
| cg18520994 | 2 | 234262964 | Higher in Drinkers |
| cg18521536 | 2 | 203241570 | Higher in Drinkers |
| cg18522266 | 19 | 11072136 | Higher in Drinkers |
| cg18525965 | 19 | 46145630 | Higher in Drinkers |
| cg18530189 | 12 | 76742306 | Higher in Drinkers |
| cg18536827 | 7 | 37264586 | Higher in Drinkers |
| cg18537617 | 5 | 156729852 | Higher in Drinkers |
| cg18541047 | 15 | 75917977 | Higher in Drinkers |

| | | | |
|---|---|---|---|
| cg18543035 | 10 | 8374526 | Higher in Drinkers |
| cg18544085 | 7 | 45026350 | Higher in Drinkers |
| cg18547611 | 5 | 14581699 | Higher in Drinkers |
| cg18555199 | 3 | 180630509 | Higher in Drinkers |
| cg18557684 | 14 | 22362441 | Higher in Drinkers |
| cg18558859 | 3 | 69063189 | Higher in Drinkers |
| cg18559901 | 9 | 140356475 | Higher in Drinkers |
| cg18560915 | 4 | 54430218 | Lower in Drinkers |
| cg18561930 | 10 | 101769283 | Higher in Drinkers |
| cg18563153 | 8 | 128886343 | Higher in Drinkers |
| cg18565103 | 1 | 26633265 | Higher in Drinkers |
| cg18571156 | 20 | 3766344 | Higher in Drinkers |
| cg18573204 | 11 | 798458 | Higher in Drinkers |
| cg18574463 | 11 | 85955766 | Higher in Drinkers |
| cg18575406 | 10 | 5932529 | Higher in Drinkers |
| cg18575809 | 14 | 21540329 | Higher in Drinkers |
| cg18579195 | 6 | 38607379 | Higher in Drinkers |
| cg18580327 | 3 | 53925981 | Higher in Drinkers |
| cg18581221 | 2 | 152118200 | Higher in Drinkers |
| cg18581762 | 5 | 150827158 | Higher in Drinkers |
| cg18585273 | 17 | 66197086 | Higher in Drinkers |
| cg18585396 | 10 | 44123853 | Lower in Drinkers |
| cg18589481 | 6 | 30647034 | Higher in Drinkers |
| cg18591945 | 14 | 105962171 | Higher in Drinkers |
| cg18594963 | 17 | 1375253 | Higher in Drinkers |
| cg18599124 | 14 | 24564067 | Higher in Drinkers |
| cg18602806 | 12 | 69633273 | Higher in Drinkers |
| cg18604888 | 8 | 124408541 | Higher in Drinkers |
| cg18606310 | 20 | 25228899 | Higher in Drinkers |
| cg18606700 | 22 | 25756156 | Lower in Drinkers |
| cg18607418 | 19 | 15667338 | Higher in Drinkers |
| cg18613834 | 7 | 65215902 | Higher in Drinkers |
| cg18615133 | 12 | 116997095 | Higher in Drinkers |
| cg18616862 | 14 | 77606068 | Higher in Drinkers |
| cg18619398 | 20 | 57416506 | Higher in Drinkers |

| | | | |
|---|---|---|---|
| cg18619804 | 19 | 51611763 | Higher in Drinkers |
| cg18620396 | 18 | 12703241 | Higher in Drinkers |
| cg18622413 | 4 | 13429541 | Lower in Drinkers |
| cg18623708 | 5 | 137369098 | Higher in Drinkers |
| cg18625627 | 14 | 81426015 | Higher in Drinkers |
| cg18627852 | 12 | 96252602 | Higher in Drinkers |
| cg18630811 | 19 | 10791805 | Higher in Drinkers |
| cg18631201 | 12 | 110151328 | Higher in Drinkers |
| cg18634443 | 6 | 134308414 | Higher in Drinkers |
| cg18634981 | 12 | 34478161 | Higher in Drinkers |
| cg18635645 | 1 | 85667791 | Higher in Drinkers |
| cg18638253 | 2 | 158485309 | Higher in Drinkers |
| cg18638581 | 2 | 75059602 | Higher in Drinkers |
| cg18639499 | 5 | 126366538 | Higher in Drinkers |
| cg18641050 | 10 | 102045846 | Higher in Drinkers |
| cg18649459 | 18 | 12253749 | Higher in Drinkers |
| cg18649939 | 1 | 28199256 | Higher in Drinkers |
| cg18649979 | 19 | 21688263 | Higher in Drinkers |
| cg18651821 | 6 | 170894141 | Higher in Drinkers |
| cg18652446 | 4 | 25162289 | Higher in Drinkers |
| cg18654049 | 15 | 102192769 | Higher in Drinkers |
| cg18663498 | 6 | 27487068 | Higher in Drinkers |
| cg18664508 | 3 | 169487465 | Higher in Drinkers |
| cg18664856 | 14 | 105240263 | Higher in Drinkers |
| cg18665023 | 21 | 35287873 | Higher in Drinkers |
| cg18666238 | 1 | 78444712 | Higher in Drinkers |
| cg18668836 | 2 | 113103184 | Higher in Drinkers |
| cg18670092 | 15 | 42841167 | Higher in Drinkers |
| cg18671784 | 3 | 119121029 | Lower in Drinkers |
| cg18672602 | 3 | 197355158 | Higher in Drinkers |
| cg18674234 | 14 | 78107677 | Higher in Drinkers |
| cg18678067 | 19 | 52674854 | Higher in Drinkers |
| cg18679920 | 14 | 105957522 | Higher in Drinkers |
| cg18680107 | 4 | 120971108 | Higher in Drinkers |
| cg18680230 | 12 | 89747628 | Higher in Drinkers |

| | | | |
|---|---|---|---|
| cg18689925 | 6 | 31371254 | Higher in Drinkers |
| cg18692596 | 11 | 10879861 | Higher in Drinkers |
| cg18695429 | X | 100074974 | Higher in Drinkers |
| cg18701343 | 14 | 37053601 | Higher in Drinkers |
| cg18701461 | 5 | 150632526 | Higher in Drinkers |
| cg18703238 | 13 | 108922361 | Higher in Drinkers |
| cg18704691 | 1 | 221052468 | Higher in Drinkers |
| cg18705039 | 11 | 118307669 | Higher in Drinkers |
| cg18705916 | 5 | 1800069 | Higher in Drinkers |
| cg18710738 | 6 | 28324650 | Higher in Drinkers |
| cg18710985 | 20 | 16554249 | Higher in Drinkers |
| cg18712494 | 14 | 51559758 | Lower in Drinkers |
| cg18718234 | 5 | 175874660 | Higher in Drinkers |
| cg18719814 | 4 | 47916640 | Higher in Drinkers |
| cg18720726 | 4 | 3392318 | Higher in Drinkers |
| cg18721673 | 6 | 27636496 | Higher in Drinkers |
| cg18723409 | 11 | 1911547 | Higher in Drinkers |
| cg18728760 | 7 | 99717576 | Higher in Drinkers |
| cg18733820 | 17 | 65362741 | Higher in Drinkers |
| cg18734433 | 7 | 150086169 | Higher in Drinkers |
| cg18735473 | 18 | 35015946 | Higher in Drinkers |
| cg18739887 | 10 | 109675284 | Higher in Drinkers |
| cg18740711 | 5 | 115421035 | Higher in Drinkers |
| cg18745507 | 19 | 10415557 | Higher in Drinkers |
| cg18749990 | 3 | 35678023 | Higher in Drinkers |
| cg18750407 | 12 | 49463988 | Higher in Drinkers |
| cg18751674 | 19 | 58196591 | Higher in Drinkers |
| cg18757962 | 18 | 55254164 | Higher in Drinkers |
| cg18758622 | 17 | 79010831 | Higher in Drinkers |
| cg18760324 | 15 | 49103180 | Higher in Drinkers |
| cg18762695 | 5 | 14337031 | Higher in Drinkers |
| cg18763046 | 16 | 1664086 | Higher in Drinkers |
| cg18765464 | 6 | 27661785 | Higher in Drinkers |
| cg18766809 | 19 | 12512039 | Higher in Drinkers |
| cg18769074 | 3 | 133464867 | Higher in Drinkers |

| | | | |
|---|---|---|---|
| cg18769303 | X | 151806352 | Higher in Drinkers |
| cg18770186 | 8 | 141521259 | Higher in Drinkers |
| cg18772361 | 1 | 184723253 | Higher in Drinkers |
| cg18772858 | 7 | 2296703 | Lower in Drinkers |
| cg18775736 | 18 | 74153999 | Higher in Drinkers |
| cg18776764 | 3 | 187463562 | Higher in Drinkers |
| cg18776793 | 22 | 23605565 | Higher in Drinkers |
| cg18779283 | 3 | 45636154 | Higher in Drinkers |
| cg18786126 | 14 | 77494107 | Higher in Drinkers |
| cg18786969 | 5 | 612372 | Higher in Drinkers |
| cg18787012 | 11 | 15230314 | Higher in Drinkers |
| cg18788872 | 11 | 32605728 | Higher in Drinkers |
| cg18789261 | 12 | 82752393 | Higher in Drinkers |
| cg18791205 | 7 | 19146324 | Higher in Drinkers |
| cg18792170 | 7 | 92219872 | Higher in Drinkers |
| cg18794664 | 1 | 42922694 | Higher in Drinkers |
| cg18795599 | 2 | 132251253 | Higher in Drinkers |
| cg18797232 | 3 | 50387146 | Higher in Drinkers |
| cg18798036 | 6 | 31595656 | Lower in Drinkers |
| cg18798934 | 6 | 28972654 | Higher in Drinkers |
| cg18799866 | X | 46618164 | Higher in Drinkers |
| cg18801599 | 17 | 42092187 | Higher in Drinkers |
| cg18802611 | 5 | 881228 | Higher in Drinkers |
| cg18803246 | 11 | 58939818 | Higher in Drinkers |
| cg18804734 | 19 | 4402429 | Higher in Drinkers |
| cg18808261 | 3 | 18464935 | Higher in Drinkers |
| cg18809074 | 12 | 29394828 | Lower in Drinkers |
| cg18809151 | 15 | 41694502 | Higher in Drinkers |
| cg18811255 | 12 | 66524493 | Higher in Drinkers |
| cg18811789 | 8 | 22462110 | Higher in Drinkers |
| cg18815006 | 10 | 71906516 | Higher in Drinkers |
| cg18819978 | 15 | 57998711 | Higher in Drinkers |
| cg18827179 | X | 153640466 | Higher in Drinkers |
| cg18827470 | 15 | 75471200 | Higher in Drinkers |
| cg18828631 | 14 | 74083455 | Higher in Drinkers |

| | | | |
|---|---|---|---|
| cg18829560 | 17 | 7298064 | Higher in Drinkers |
| cg18834729 | 12 | 117798135 | Higher in Drinkers |
| cg18834990 | 19 | 42724480 | Higher in Drinkers |
| cg18835048 | 5 | 10249761 | Higher in Drinkers |
| cg18836267 | 12 | 27676995 | Higher in Drinkers |
| cg18840151 | 7 | 6098981 | Higher in Drinkers |
| cg18841894 | 21 | 33031735 | Higher in Drinkers |
| cg18844850 | 12 | 6833560 | Higher in Drinkers |
| cg18845289 | 12 | 121124611 | Higher in Drinkers |
| cg18845960 | 2 | 37387350 | Lower in Drinkers |
| cg18852096 | 1 | 1564425 | Lower in Drinkers |
| cg18853071 | 3 | 23847494 | Higher in Drinkers |
| cg18855426 | 11 | 20631935 | Higher in Drinkers |
| cg18858378 | 1 | 93426981 | Higher in Drinkers |
| cg18862610 | 10 | 6019621 | Higher in Drinkers |
| cg18864164 | 10 | 115934049 | Higher in Drinkers |
| cg18867283 | 1 | 94374612 | Higher in Drinkers |
| cg18867653 | 5 | 10760375 | Higher in Drinkers |
| cg18874060 | 11 | 47198996 | Higher in Drinkers |
| cg18877200 | 6 | 29720927 | Higher in Drinkers |
| cg18878034 | 6 | 43197151 | Higher in Drinkers |
| cg18884037 | 6 | 62996214 | Higher in Drinkers |
| cg18884060 | 10 | 126370288 | Lower in Drinkers |
| cg18884137 | 17 | 7348490 | Higher in Drinkers |
| cg18884237 | 8 | 41347795 | Higher in Drinkers |
| cg18886147 | 12 | 1609741 | Higher in Drinkers |
| cg18888657 | 5 | 149381473 | Higher in Drinkers |
| cg18890825 | 5 | 95294366 | Lower in Drinkers |
| cg18891081 | 2 | 47382427 | Higher in Drinkers |
| cg18893138 | 11 | 44748327 | Higher in Drinkers |
| cg18894028 | 11 | 68156978 | Higher in Drinkers |
| cg18894938 | 9 | 140063488 | Higher in Drinkers |
| cg18898185 | 7 | 30066428 | Higher in Drinkers |
| cg18904832 | 17 | 79871405 | Higher in Drinkers |
| cg18905676 | 2 | 70370129 | Higher in Drinkers |

| | | | |
|---|---|---|---|
| cg18905952 | 2 | 27651203 | Higher in Drinkers |
| cg18907495 | 17 | 53828548 | Higher in Drinkers |
| cg18908524 | 11 | 64002295 | Higher in Drinkers |
| cg18913332 | 2 | 113914682 | Higher in Drinkers |
| cg18914215 | 12 | 113659206 | Higher in Drinkers |
| cg18917667 | 8 | 21999543 | Higher in Drinkers |
| cg18918423 | 11 | 86667042 | Higher in Drinkers |
| cg18925923 | 4 | 144480237 | Higher in Drinkers |
| cg18928362 | 14 | 68283524 | Higher in Drinkers |
| cg18931895 | 2 | 239112214 | Higher in Drinkers |
| cg18935479 | 7 | 151217026 | Higher in Drinkers |
| cg18937330 | 4 | 80994550 | Higher in Drinkers |
| cg18945035 | 1 | 150122690 | Higher in Drinkers |
| cg18952599 | 14 | 102226785 | Higher in Drinkers |
| cg18952878 | 1 | 44457743 | Higher in Drinkers |
| cg18954388 | 11 | 20621495 | Higher in Drinkers |
| cg18955691 | 11 | 107434614 | Higher in Drinkers |
| cg18956095 | 8 | 124287111 | Higher in Drinkers |
| cg18957462 | 15 | 42066506 | Higher in Drinkers |
| cg18958263 | 17 | 73105928 | Higher in Drinkers |
| cg18959411 | 6 | 160182805 | Higher in Drinkers |
| cg18961281 | 7 | 3083773 | Higher in Drinkers |
| cg18969171 | 14 | 35591572 | Higher in Drinkers |
| cg18973817 | 1 | 114471878 | Higher in Drinkers |
| cg18976869 | 4 | 146102046 | Higher in Drinkers |
| cg18977283 | 6 | 29579492 | Higher in Drinkers |
| cg18991240 | 2 | 71298920 | Higher in Drinkers |
| cg19001871 | 6 | 16238672 | Higher in Drinkers |
| cg19003708 | 17 | 73780620 | Higher in Drinkers |
| cg19005335 | 12 | 124942016 | Higher in Drinkers |
| cg19006060 | 12 | 15374609 | Higher in Drinkers |
| cg19006127 | 4 | 3794737 | Higher in Drinkers |
| cg19009405 | 11 | 62493477 | Higher in Drinkers |
| cg19009714 | 6 | 4776669 | Higher in Drinkers |
| cg19010858 | 15 | 30396121 | Higher in Drinkers |

| | | | |
|---|---|---|---|
| cg19014302 | 19 | 18303893 | Higher in Drinkers |
| cg19015511 | 17 | 3698179 | Higher in Drinkers |
| cg19016253 | 10 | 101945959 | Higher in Drinkers |
| cg19017312 | 11 | 75111280 | Higher in Drinkers |
| cg19026029 | 1 | 205785957 | Higher in Drinkers |
| cg19027827 | 5 | 140474578 | Higher in Drinkers |
| cg19028369 | 3 | 14693598 | Higher in Drinkers |
| cg19029131 | 11 | 487083 | Higher in Drinkers |
| cg19029220 | 2 | 64067822 | Higher in Drinkers |
| cg19038968 | 11 | 61559962 | Higher in Drinkers |
| cg19040032 | 8 | 146277255 | Higher in Drinkers |
| cg19041132 | 17 | 74380824 | Higher in Drinkers |
| cg19042540 | 19 | 17448497 | Higher in Drinkers |
| cg19042643 | 10 | 135083932 | Higher in Drinkers |
| cg19044279 | 18 | 658447 | Higher in Drinkers |
| cg19045733 | 2 | 227656248 | Higher in Drinkers |
| cg19049809 | 17 | 56085409 | Higher in Drinkers |
| cg19051225 | 12 | 121837829 | Higher in Drinkers |
| cg19051578 | 5 | 59996328 | Higher in Drinkers |
| cg19053686 | 7 | 43479485 | Higher in Drinkers |
| cg19054815 | 17 | 2496733 | Higher in Drinkers |
| cg19058585 | 2 | 112944963 | Higher in Drinkers |
| cg19060120 | 17 | 78915878 | Higher in Drinkers |
| cg19060387 | X | 129299908 | Higher in Drinkers |
| cg19062189 | X | 101771625 | Higher in Drinkers |
| cg19063972 | 13 | 95364908 | Higher in Drinkers |
| cg19065314 | 4 | 146019368 | Higher in Drinkers |
| cg19067791 | 2 | 166809971 | Higher in Drinkers |
| cg19074496 | 2 | 220117368 | Higher in Drinkers |
| cg19074970 | 2 | 228189846 | Higher in Drinkers |
| cg19078236 | 11 | 67250309 | Higher in Drinkers |
| cg19078769 | 12 | 124457941 | Higher in Drinkers |
| cg19081759 | 2 | 9771089 | Higher in Drinkers |
| cg19082920 | 1 | 202830751 | Higher in Drinkers |
| cg19082970 | 1 | 91852891 | Higher in Drinkers |

| | | | |
|---|---|---|---|
| cg19083497 | 5 | 121465173 | Lower in Drinkers |
| cg19084508 | 5 | 150530152 | Higher in Drinkers |
| cg19084629 | 12 | 117407879 | Higher in Drinkers |
| cg19086455 | 22 | 51066757 | Higher in Drinkers |
| cg19088572 | 1 | 24525983 | Higher in Drinkers |
| cg19089073 | 7 | 74020924 | Higher in Drinkers |
| cg19089314 | 22 | 50919938 | Higher in Drinkers |
| cg19091830 | 5 | 180286094 | Higher in Drinkers |
| cg19092293 | X | 118110194 | Higher in Drinkers |
| cg19092489 | 4 | 185375724 | Higher in Drinkers |
| cg19092999 | 3 | 113415735 | Higher in Drinkers |
| cg19095187 | 6 | 108437051 | Lower in Drinkers |
| cg19098091 | 2 | 131100595 | Higher in Drinkers |
| cg19100061 | 8 | 28347842 | Higher in Drinkers |
| cg19102404 | 1 | 116941269 | Higher in Drinkers |
| cg19106168 | 3 | 133182835 | Higher in Drinkers |
| cg19110523 | 5 | 148206224 | Higher in Drinkers |
| cg19111030 | 2 | 71204600 | Higher in Drinkers |
| cg19111459 | 10 | 122708739 | Higher in Drinkers |
| cg19115941 | 12 | 187284 | Higher in Drinkers |
| cg19117777 | 5 | 109024969 | Higher in Drinkers |
| cg19118533 | 6 | 111927323 | Higher in Drinkers |
| cg19122720 | 17 | 75884349 | Higher in Drinkers |
| cg19126471 | 15 | 65425420 | Higher in Drinkers |
| cg19128271 | 22 | 19842843 | Higher in Drinkers |
| cg19131103 | 20 | 62205648 | Higher in Drinkers |
| cg19133023 | 11 | 891017 | Higher in Drinkers |
| cg19133875 | 7 | 128096196 | Higher in Drinkers |
| cg19134705 | 2 | 173293182 | Higher in Drinkers |
| cg19143629 | 17 | 61920732 | Higher in Drinkers |
| cg19144392 | 22 | 42666664 | Higher in Drinkers |
| cg19144531 | 2 | 200771915 | Higher in Drinkers |
| cg19151292 | 6 | 33653502 | Higher in Drinkers |
| cg19151665 | 7 | 22122819 | Higher in Drinkers |
| cg19151849 | 3 | 12883145 | Higher in Drinkers |

| | | | |
|---|---|---|---|
| cg19153120 | 13 | 21894260 | Higher in Drinkers |
| cg19154173 | 12 | 112451600 | Higher in Drinkers |
| cg19158325 | 17 | 8339163 | Higher in Drinkers |
| cg19160209 | 11 | 86013123 | Higher in Drinkers |
| cg19160958 | 17 | 35807884 | Higher in Drinkers |
| cg19162158 | 8 | 32405427 | Higher in Drinkers |
| cg19163348 | 1 | 155247357 | Higher in Drinkers |
| cg19163814 | 4 | 122722220 | Higher in Drinkers |
| cg19168192 | 6 | 28493664 | Higher in Drinkers |
| cg19168507 | 11 | 107436485 | Higher in Drinkers |
| cg19169838 | X | 153631347 | Higher in Drinkers |
| cg19175123 | 10 | 103411746 | Higher in Drinkers |
| cg19176072 | 10 | 135083742 | Higher in Drinkers |
| cg19177307 | 11 | 2021658 | Higher in Drinkers |
| cg19177744 | 2 | 8711042 | Lower in Drinkers |
| cg19178320 | 3 | 56224201 | Higher in Drinkers |
| cg19180156 | 2 | 59400971 | Lower in Drinkers |
| cg19184160 | 6 | 144611885 | Lower in Drinkers |
| cg19190699 | 15 | 101514156 | Higher in Drinkers |
| cg19191231 | 8 | 103209781 | Higher in Drinkers |
| cg19191883 | 19 | 12780323 | Higher in Drinkers |
| cg19192223 | 10 | 35105210 | Higher in Drinkers |
| cg19197328 | 15 | 91454823 | Higher in Drinkers |
| cg19198913 | 2 | 129495073 | Higher in Drinkers |
| cg19199204 | 6 | 29944130 | Higher in Drinkers |
| cg19202020 | 12 | 56320952 | Higher in Drinkers |
| cg19204328 | 18 | 66379577 | Higher in Drinkers |
| cg19204693 | 11 | 68206027 | Higher in Drinkers |
| cg19208477 | X | 140271604 | Higher in Drinkers |
| cg19219435 | 19 | 15354051 | Higher in Drinkers |
| cg19219672 | 17 | 79804113 | Higher in Drinkers |
| cg19220825 | 12 | 50353951 | Higher in Drinkers |
| cg19231290 | 10 | 3827321 | Higher in Drinkers |
| cg19232815 | 6 | 31439148 | Higher in Drinkers |
| cg19235307 | 3 | 129160154 | Higher in Drinkers |

| | | | |
|---|---|---|---|
| cg19236768 | 1 | 161509970 | Higher in Drinkers |
| cg19239018 | 1 | 27227109 | Higher in Drinkers |
| cg19241973 | 4 | 8262688 | Higher in Drinkers |
| cg19242448 | 6 | 80816807 | Higher in Drinkers |
| cg19243373 | 1 | 154909541 | Higher in Drinkers |
| cg19243721 | 6 | 166851830 | Higher in Drinkers |
| cg19245498 | 1 | 59884012 | Higher in Drinkers |
| cg19247001 | 10 | 127512041 | Higher in Drinkers |
| cg19251352 | 3 | 186524300 | Higher in Drinkers |
| cg19254558 | 3 | 183602222 | Higher in Drinkers |
| cg19255118 | 12 | 8234656 | Higher in Drinkers |
| cg19259030 | 15 | 76553926 | Higher in Drinkers |
| cg19260474 | 13 | 113500172 | Higher in Drinkers |
| cg19267259 | 1 | 6453427 | Higher in Drinkers |
| cg19269661 | 17 | 61850865 | Higher in Drinkers |
| cg19270858 | 12 | 53342770 | Higher in Drinkers |
| cg19271753 | 7 | 5396704 | Higher in Drinkers |
| cg19272382 | 1 | 211848938 | Higher in Drinkers |
| cg19272744 | 1 | 161049677 | Higher in Drinkers |
| cg19272891 | 17 | 76250642 | Higher in Drinkers |
| cg19274676 | 6 | 17988463 | Higher in Drinkers |
| cg19275536 | 6 | 52926650 | Higher in Drinkers |
| cg19276952 | 6 | 30525036 | Higher in Drinkers |
| cg19281693 | 22 | 42666674 | Higher in Drinkers |
| cg19282389 | 15 | 86338423 | Higher in Drinkers |
| cg19285119 | 11 | 105948212 | Higher in Drinkers |
| cg19285383 | 18 | 5295803 | Higher in Drinkers |
| cg19287823 | 6 | 155316843 | Higher in Drinkers |
| cg19288027 | 6 | 131384431 | Higher in Drinkers |
| cg19292625 | 11 | 105951315 | Higher in Drinkers |
| cg19293995 | 22 | 30685271 | Higher in Drinkers |
| cg19294311 | 15 | 62358920 | Higher in Drinkers |
| cg19297234 | 19 | 49149692 | Higher in Drinkers |
| cg19299739 | 19 | 49865342 | Higher in Drinkers |
| cg19300632 | 2 | 55746645 | Higher in Drinkers |

| | | | |
|---|---|---|---|
| cg19302555 | 20 | 21283637 | Higher in Drinkers |
| cg19306496 | 19 | 37569299 | Higher in Drinkers |
| cg19309549 | 1 | 100435460 | Higher in Drinkers |
| cg19309676 | 19 | 50191439 | Higher in Drinkers |
| cg19314352 | 17 | 38501397 | Higher in Drinkers |
| cg19315638 | 7 | 108091611 | Lower in Drinkers |
| cg19318326 | 6 | 111580704 | Higher in Drinkers |
| cg19322509 | 1 | 43851891 | Higher in Drinkers |
| cg19323338 | 1 | 1242997 | Higher in Drinkers |
| cg19324172 | 4 | 159644759 | Higher in Drinkers |
| cg19333507 | 10 | 116852186 | Higher in Drinkers |
| cg19338212 | 19 | 20012149 | Higher in Drinkers |
| cg19338277 | 6 | 26285358 | Higher in Drinkers |
| cg19339841 | 4 | 104119196 | Higher in Drinkers |
| cg19341309 | 12 | 124948140 | Higher in Drinkers |
| cg19343871 | 19 | 46103651 | Higher in Drinkers |
| cg19345678 | 6 | 6952995 | Higher in Drinkers |
| cg19346193 | 10 | 127513190 | Higher in Drinkers |
| cg19346621 | 4 | 120975643 | Higher in Drinkers |
| cg19349920 | 13 | 114237599 | Higher in Drinkers |
| cg19350469 | 4 | 15704453 | Lower in Drinkers |
| cg19350479 | 12 | 104199610 | Higher in Drinkers |
| cg19355919 | 13 | 48346593 | Higher in Drinkers |
| cg19358590 | 6 | 158654166 | Higher in Drinkers |
| cg19365615 | 6 | 2999313 | Higher in Drinkers |
| cg19365706 | 7 | 100414918 | Lower in Drinkers |
| cg19367522 | 17 | 16492836 | Higher in Drinkers |
| cg19369616 | 19 | 53447272 | Higher in Drinkers |
| cg19371286 | 1 | 28520866 | Higher in Drinkers |
| cg19372063 | 2 | 11118387 | Lower in Drinkers |
| cg19372226 | 11 | 111945000 | Higher in Drinkers |
| cg19374476 | 12 | 133225617 | Higher in Drinkers |
| cg19375627 | 6 | 44116510 | Higher in Drinkers |
| cg19376090 | 7 | 150942732 | Higher in Drinkers |
| cg19376806 | 1 | 181999336 | Higher in Drinkers |

| | | | |
|---|---|---|---|
| cg19383211 | 6 | 32527588 | Higher in Drinkers |
| cg19387936 | 7 | 128045543 | Higher in Drinkers |
| cg19391239 | 15 | 42566272 | Higher in Drinkers |
| cg19397765 | 6 | 30181764 | Higher in Drinkers |
| cg19398196 | 7 | 155504138 | Higher in Drinkers |
| cg19398748 | 17 | 43567928 | Higher in Drinkers |
| cg19402939 | 3 | 184104481 | Lower in Drinkers |
| cg19403014 | 2 | 48982950 | Higher in Drinkers |
| cg19404484 | 8 | 67579207 | Higher in Drinkers |
| cg19408145 | 1 | 160661530 | Higher in Drinkers |
| cg19410732 | 3 | 194305082 | Higher in Drinkers |
| cg19417549 | 19 | 59067502 | Higher in Drinkers |
| cg19422652 | 12 | 53574585 | Higher in Drinkers |
| cg19424060 | 19 | 56102908 | Higher in Drinkers |
| cg19426572 | 20 | 61919450 | Lower in Drinkers |
| cg19431244 | 3 | 140617283 | Higher in Drinkers |
| cg19431963 | 5 | 90679134 | Higher in Drinkers |
| cg19440670 | 3 | 197464091 | Higher in Drinkers |
| cg19442264 | 17 | 4168034 | Higher in Drinkers |
| cg19449219 | 2 | 61244635 | Higher in Drinkers |
| cg19453618 | 10 | 94833548 | Higher in Drinkers |
| cg19455335 | 8 | 22457658 | Higher in Drinkers |
| cg19458410 | 21 | 35985263 | Higher in Drinkers |
| cg19460016 | 5 | 179306266 | Higher in Drinkers |
| cg19464106 | 6 | 31632821 | Higher in Drinkers |
| cg19471553 | 17 | 41393123 | Higher in Drinkers |
| cg19473068 | 5 | 179597454 | Higher in Drinkers |
| cg19473994 | 7 | 1163084 | Higher in Drinkers |
| cg19476368 | 11 | 121763552 | Lower in Drinkers |
| cg19479609 | 2 | 208390216 | Higher in Drinkers |
| cg19483330 | 2 | 153191749 | Higher in Drinkers |
| cg19484886 | 12 | 62997435 | Higher in Drinkers |
| cg19490266 | 1 | 153949898 | Higher in Drinkers |
| cg19496125 | 19 | 1259661 | Higher in Drinkers |
| cg19496328 | 14 | 74416831 | Higher in Drinkers |

| | | | |
|---|---|---|---|
| cg19496639 | 8 | 22492772 | Lower in Drinkers |
| cg19500851 | 17 | 37840957 | Higher in Drinkers |
| cg19500949 | 17 | 37009491 | Higher in Drinkers |
| cg19502700 | 4 | 113558183 | Higher in Drinkers |
| cg19503640 | 5 | 1503763 | Higher in Drinkers |
| cg19503860 | 4 | 25162275 | Higher in Drinkers |
| cg19506755 | 20 | 54967495 | Higher in Drinkers |
| cg19507498 | 14 | 103374781 | Higher in Drinkers |
| cg19510999 | 16 | 66586309 | Higher in Drinkers |
| cg19512961 | 12 | 133363341 | Higher in Drinkers |
| cg19513868 | 19 | 55895400 | Higher in Drinkers |
| cg19514725 | X | 83757504 | Higher in Drinkers |
| cg19514765 | 6 | 27805693 | Higher in Drinkers |
| cg19515530 | 4 | 68566579 | Higher in Drinkers |
| cg19518963 | 4 | 90032521 | Higher in Drinkers |
| cg19520879 | 12 | 131528311 | Lower in Drinkers |
| cg19528373 | 10 | 60027100 | Higher in Drinkers |
| cg19529645 | 17 | 79196743 | Higher in Drinkers |
| cg19530728 | 1 | 45279132 | Higher in Drinkers |
| cg19535394 | 4 | 6577205 | Higher in Drinkers |
| cg19538890 | 4 | 142054810 | Higher in Drinkers |
| cg19540943 | 12 | 10264389 | Lower in Drinkers |
| cg19541147 | 11 | 111957761 | Higher in Drinkers |
| cg19545116 | 5 | 131132943 | Lower in Drinkers |
| cg19545348 | 1 | 211434133 | Higher in Drinkers |
| cg19545851 | 5 | 162887230 | Higher in Drinkers |
| cg19546875 | 21 | 45432889 | Higher in Drinkers |
| cg19552044 | 7 | 124570047 | Higher in Drinkers |
| cg19559213 | 17 | 18162372 | Higher in Drinkers |
| cg19562400 | 15 | 91260453 | Higher in Drinkers |
| cg19567052 | 8 | 61592727 | Higher in Drinkers |
| cg19569081 | 10 | 103892506 | Higher in Drinkers |
| cg19572362 | 1 | 110091012 | Higher in Drinkers |
| cg19573456 | 19 | 16607087 | Higher in Drinkers |
| cg19573564 | 2 | 74607697 | Higher in Drinkers |

| | | | |
|---|---|---|---|
| cg19579446 | 11 | 57335474 | Higher in Drinkers |
| cg19580263 | 14 | 74462914 | Higher in Drinkers |
| cg19584871 | 2 | 11810508 | Higher in Drinkers |
| cg19587377 | 19 | 50432935 | Higher in Drinkers |
| cg19592742 | 10 | 1034166 | Higher in Drinkers |
| cg19594024 | 19 | 58919948 | Higher in Drinkers |
| cg19598875 | 13 | 101326192 | Higher in Drinkers |
| cg19599856 | 3 | 38295981 | Higher in Drinkers |
| cg19599951 | 11 | 118754280 | Higher in Drinkers |
| cg19602187 | 10 | 134439616 | Higher in Drinkers |
| cg19602614 | 14 | 64932086 | Higher in Drinkers |
| cg19602931 | 12 | 51632444 | Higher in Drinkers |
| cg19603847 | 7 | 42276981 | Higher in Drinkers |
| cg19612890 | 12 | 131356591 | Higher in Drinkers |
| cg19616083 | 15 | 74908514 | Higher in Drinkers |
| cg19619320 | 1 | 1477931 | Higher in Drinkers |
| cg19619653 | 11 | 118938469 | Higher in Drinkers |
| cg19621460 | 19 | 14225945 | Higher in Drinkers |
| cg19621814 | 8 | 146033842 | Higher in Drinkers |
| cg19622358 | 15 | 80444736 | Higher in Drinkers |
| cg19623624 | 10 | 135279901 | Lower in Drinkers |
| cg19623981 | 1 | 197115958 | Higher in Drinkers |
| cg19624765 | 1 | 46153765 | Higher in Drinkers |
| cg19625216 | 1 | 249132106 | Higher in Drinkers |
| cg19625377 | 1 | 11322792 | Higher in Drinkers |
| cg19630506 | 22 | 31477530 | Higher in Drinkers |
| cg19632953 | 13 | 113635898 | Higher in Drinkers |
| cg19633205 | 1 | 35544470 | Higher in Drinkers |
| cg19635158 | 1 | 27561056 | Higher in Drinkers |
| cg19635533 | 19 | 13249050 | Higher in Drinkers |
| cg19637814 | 7 | 102914896 | Higher in Drinkers |
| cg19638572 | 1 | 206733139 | Higher in Drinkers |
| cg19642100 | 12 | 9102345 | Higher in Drinkers |
| cg19642231 | 4 | 8399409 | Higher in Drinkers |
| cg19642394 | 15 | 74753978 | Higher in Drinkers |

| | | | |
|---|---|---|---|
| cg19642920 | 12 | 6810328 | Lower in Drinkers |
| cg19643441 | 19 | 19417142 | Higher in Drinkers |
| cg19644351 | 5 | 149340142 | Higher in Drinkers |
| cg19648605 | 5 | 179297440 | Higher in Drinkers |
| cg19649173 | 19 | 58987877 | Higher in Drinkers |
| cg19653440 | 1 | 31381728 | Higher in Drinkers |
| cg19655069 | 15 | 63340444 | Higher in Drinkers |
| cg19655704 | 2 | 178295152 | Higher in Drinkers |
| cg19657603 | 15 | 26095616 | Higher in Drinkers |
| cg19669439 | 10 | 103113668 | Higher in Drinkers |
| cg19671395 | 2 | 240259915 | Lower in Drinkers |
| cg19673664 | 6 | 28606468 | Higher in Drinkers |
| cg19676312 | 1 | 201951586 | Higher in Drinkers |
| cg19676835 | 3 | 115377773 | Higher in Drinkers |
| cg19678561 | 7 | 129252859 | Higher in Drinkers |
| cg19683960 | 5 | 171484376 | Higher in Drinkers |
| cg19685632 | 6 | 112318507 | Higher in Drinkers |
| cg19692996 | 6 | 170862576 | Higher in Drinkers |
| cg19697981 | 6 | 106487820 | Higher in Drinkers |
| cg19699170 | 2 | 110402734 | Higher in Drinkers |
| cg19705764 | 20 | 30458626 | Higher in Drinkers |
| cg19708901 | 1 | 180882655 | Higher in Drinkers |
| cg19709095 | 1 | 1198047 | Higher in Drinkers |
| cg19709354 | 2 | 190526349 | Higher in Drinkers |
| cg19709822 | 1 | 226186804 | Higher in Drinkers |
| cg19710444 | 14 | 73360162 | Higher in Drinkers |
| cg19710672 | 22 | 21982391 | Higher in Drinkers |
| cg19719120 | 19 | 12780479 | Higher in Drinkers |
| cg19719311 | 1 | 51443992 | Higher in Drinkers |
| cg19719475 | 3 | 23849714 | Higher in Drinkers |
| cg19720917 | 19 | 36606221 | Higher in Drinkers |
| cg19721215 | 19 | 13001564 | Higher in Drinkers |
| cg19723459 | 12 | 113658936 | Higher in Drinkers |
| cg19724680 | 14 | 50329901 | Higher in Drinkers |
| cg19724698 | 12 | 133380384 | Higher in Drinkers |

| | | | |
|---|---|---|---|
| cg19726128 | 14 | 69564942 | Higher in Drinkers |
| cg19728601 | 7 | 99526949 | Higher in Drinkers |
| cg19730147 | 8 | 124253706 | Higher in Drinkers |
| cg19735335 | 7 | 144532933 | Higher in Drinkers |
| cg19736660 | 2 | 129050050 | Higher in Drinkers |
| cg19736900 | 1 | 150132950 | Higher in Drinkers |
| cg19738283 | 2 | 176976802 | Higher in Drinkers |
| cg19740491 | 6 | 31510208 | Higher in Drinkers |
| cg19744173 | 2 | 112913178 | Higher in Drinkers |
| cg19744723 | 2 | 96971423 | Higher in Drinkers |
| cg19744773 | 1 | 22110159 | Higher in Drinkers |
| cg19744952 | 19 | 42788966 | Higher in Drinkers |
| cg19746591 | 12 | 118589087 | Higher in Drinkers |
| cg19747640 | 17 | 1812145 | Higher in Drinkers |
| cg19749688 | 1 | 246862638 | Higher in Drinkers |
| cg19752627 | 7 | 98467380 | Higher in Drinkers |
| cg19753609 | 14 | 80324276 | Lower in Drinkers |
| cg19754746 | 6 | 31795171 | Higher in Drinkers |
| cg19757539 | 19 | 11098499 | Higher in Drinkers |
| cg19758758 | 1 | 153963408 | Higher in Drinkers |
| cg19760441 | 6 | 32825139 | Higher in Drinkers |
| cg19763279 | 4 | 84256190 | Higher in Drinkers |
| cg19763809 | 2 | 98703475 | Higher in Drinkers |
| cg19768036 | 1 | 1464063 | Higher in Drinkers |
| cg19768727 | 2 | 242609496 | Higher in Drinkers |
| cg19769920 | 15 | 41166443 | Higher in Drinkers |
| cg19772723 | 7 | 77326842 | Higher in Drinkers |
| cg19774553 | 14 | 50087255 | Higher in Drinkers |
| cg19776272 | 11 | 33758214 | Higher in Drinkers |
| cg19788429 | 3 | 142838003 | Higher in Drinkers |
| cg19789762 | 19 | 11640043 | Higher in Drinkers |
| cg19795082 | 4 | 38312560 | Higher in Drinkers |
| cg19795793 | 2 | 206551844 | Higher in Drinkers |
| cg19802138 | 13 | 112722719 | Higher in Drinkers |
| cg19806933 | 11 | 63742453 | Higher in Drinkers |

| | | | |
|---|---|---|---|
| cg19807612 | 21 | 35014421 | Higher in Drinkers |
| cg19809165 | 19 | 7599590 | Higher in Drinkers |
| cg19809659 | 6 | 33163443 | Higher in Drinkers |
| cg19809735 | 11 | 43380484 | Higher in Drinkers |
| cg19813135 | 6 | 138200071 | Lower in Drinkers |
| cg19813284 | 1 | 16271762 | Higher in Drinkers |
| cg19816445 | 22 | 50682500 | Higher in Drinkers |
| cg19818642 | 15 | 91260404 | Higher in Drinkers |
| cg19828791 | 7 | 100823400 | Higher in Drinkers |
| cg19829455 | 11 | 34200124 | Higher in Drinkers |
| cg19837214 | 12 | 133402551 | Higher in Drinkers |
| cg19837587 | 15 | 51201261 | Higher in Drinkers |
| cg19844203 | 22 | 17592017 | Higher in Drinkers |
| cg19845926 | 3 | 49058251 | Higher in Drinkers |
| cg19848126 | 5 | 175788878 | Higher in Drinkers |
| cg19848529 | 6 | 170483067 | Lower in Drinkers |
| cg19850565 | 19 | 35168394 | Higher in Drinkers |
| cg19851179 | 11 | 73309269 | Higher in Drinkers |
| cg19851560 | 2 | 68390167 | Higher in Drinkers |
| cg19852264 | 19 | 10662619 | Higher in Drinkers |
| cg19854017 | 16 | 15068424 | Higher in Drinkers |
| cg19857457 | 18 | 47018947 | Higher in Drinkers |
| cg19862912 | 8 | 142436487 | Higher in Drinkers |
| cg19863003 | 5 | 112257612 | Higher in Drinkers |
| cg19864271 | 18 | 61093491 | Higher in Drinkers |
| cg19864468 | 2 | 113346566 | Higher in Drinkers |
| cg19865159 | 6 | 31134165 | Lower in Drinkers |
| cg19870365 | 6 | 41041678 | Higher in Drinkers |
| cg19876689 | 17 | 44799518 | Higher in Drinkers |
| cg19876775 | 11 | 76381937 | Higher in Drinkers |
| cg19881481 | 20 | 18118358 | Higher in Drinkers |
| cg19885331 | 19 | 12512166 | Higher in Drinkers |
| cg19888535 | 8 | 124553488 | Higher in Drinkers |
| cg19891001 | 14 | 100438221 | Higher in Drinkers |
| cg19893834 | 18 | 13722236 | Higher in Drinkers |

| | | | |
|---|---|---|---|
| cg19895503 | 2 | 113239201 | Higher in Drinkers |
| cg19899385 | 1 | 200422671 | Higher in Drinkers |
| cg19901523 | 14 | 107253273 | Higher in Drinkers |
| cg19906694 | 5 | 60629770 | Higher in Drinkers |
| cg19907055 | 16 | 69345210 | Higher in Drinkers |
| cg19907326 | 13 | 33002597 | Higher in Drinkers |
| cg19910128 | 1 | 1496936 | Higher in Drinkers |
| cg19913563 | 6 | 30720261 | Higher in Drinkers |
| cg19916794 | 1 | 16061406 | Higher in Drinkers |
| cg19920899 | 9 | 88969839 | Higher in Drinkers |
| cg19921561 | 1 | 46859680 | Lower in Drinkers |
| cg19923683 | 2 | 106510087 | Higher in Drinkers |
| cg19923798 | 17 | 26698570 | Higher in Drinkers |
| cg19924025 | 1 | 65720054 | Higher in Drinkers |
| cg19924248 | 3 | 42003785 | Higher in Drinkers |
| cg19925653 | 13 | 51796887 | Higher in Drinkers |
| cg19925755 | 10 | 104915551 | Higher in Drinkers |
| cg19927780 | 1 | 90286561 | Higher in Drinkers |
| cg19929355 | 4 | 48272059 | Higher in Drinkers |
| cg19933135 | 15 | 86338399 | Higher in Drinkers |
| cg19933772 | 5 | 133862682 | Higher in Drinkers |
| cg19933908 | 11 | 114310002 | Higher in Drinkers |
| cg19934686 | 7 | 99588657 | Higher in Drinkers |
| cg19935397 | 16 | 3332644 | Higher in Drinkers |
| cg19935505 | 3 | 33482718 | Higher in Drinkers |
| cg19935671 | 3 | 121468093 | Higher in Drinkers |
| cg19937480 | 1 | 45987798 | Higher in Drinkers |
| cg19939555 | 1 | 153931149 | Higher in Drinkers |
| cg19939969 | 1 | 209801351 | Higher in Drinkers |
| cg19940644 | 1 | 12112386 | Higher in Drinkers |
| cg19941439 | 4 | 119606584 | Higher in Drinkers |
| cg19942454 | 10 | 1559193 | Higher in Drinkers |
| cg19944876 | 17 | 8905866 | Higher in Drinkers |
| cg19947061 | 3 | 111697672 | Higher in Drinkers |
| cg19949959 | 22 | 50928444 | Higher in Drinkers |

| | | | |
|---|---|---|---|
| cg19950090 | 7 | 139931278 | Higher in Drinkers |
| cg19953620 | 5 | 43603353 | Higher in Drinkers |
| cg19954613 | 22 | 22020219 | Higher in Drinkers |
| cg19954954 | 17 | 80747795 | Higher in Drinkers |
| cg19956224 | 16 | 1369381 | Higher in Drinkers |
| cg19959647 | 3 | 193853226 | Higher in Drinkers |
| cg19971804 | 2 | 39102883 | Higher in Drinkers |
| cg19972223 | 7 | 128095759 | Higher in Drinkers |
| cg19982570 | 3 | 42728041 | Higher in Drinkers |
| cg19982668 | 17 | 61753497 | Higher in Drinkers |
| cg19987142 | 5 | 139145322 | Higher in Drinkers |
| cg19988558 | 8 | 144794916 | Higher in Drinkers |
| cg19990379 | 1 | 145611441 | Higher in Drinkers |
| cg19991639 | 14 | 59104318 | Higher in Drinkers |
| cg19996838 | 1 | 244211323 | Higher in Drinkers |
| cg19998289 | 12 | 121861616 | Higher in Drinkers |
| cg20002283 | 18 | 24128625 | Higher in Drinkers |
| cg20006140 | 20 | 57463455 | Higher in Drinkers |
| cg20009594 | 12 | 8549511 | Higher in Drinkers |
| cg20011794 | 22 | 37447915 | Higher in Drinkers |
| cg20016845 | 18 | 47814312 | Higher in Drinkers |
| cg20018057 | 20 | 57465139 | Higher in Drinkers |
| cg20023524 | 22 | 25761020 | Higher in Drinkers |
| cg20025403 | X | 135850058 | Higher in Drinkers |
| cg20027050 | 11 | 71791715 | Higher in Drinkers |
| cg20028233 | 4 | 114681544 | Higher in Drinkers |
| cg20031900 | 4 | 2733908 | Higher in Drinkers |
| cg20033256 | 12 | 123756791 | Higher in Drinkers |
| cg20036889 | 19 | 49927309 | Higher in Drinkers |
| cg20037999 | 6 | 33256950 | Higher in Drinkers |
| cg20040765 | 8 | 67358546 | Higher in Drinkers |
| cg20043969 | 13 | 45491859 | Higher in Drinkers |
| cg20049294 | 12 | 120875556 | Higher in Drinkers |
| cg20052355 | 15 | 73075404 | Higher in Drinkers |
| cg20053829 | 3 | 155524234 | Higher in Drinkers |

| | | | |
|---|---|---|---|
| cg20053981 | 10 | 70091610 | Higher in Drinkers |
| cg20054248 | 12 | 56414508 | Higher in Drinkers |
| cg20059511 | 11 | 2422256 | Higher in Drinkers |
| cg20060178 | 11 | 119039643 | Higher in Drinkers |
| cg20063141 | 18 | 55101965 | Higher in Drinkers |
| cg20064231 | 18 | 74608296 | Higher in Drinkers |
| cg20064569 | 19 | 3572546 | Higher in Drinkers |
| cg20065718 | 12 | 133430224 | Lower in Drinkers |
| cg20067272 | 6 | 29571693 | Higher in Drinkers |
| cg20067477 | 6 | 30181183 | Higher in Drinkers |
| cg20069090 | 13 | 28240007 | Higher in Drinkers |
| cg20069972 | 12 | 49981340 | Higher in Drinkers |
| cg20071506 | 7 | 97834891 | Higher in Drinkers |
| cg20073050 | 4 | 106395643 | Higher in Drinkers |
| cg20073910 | 13 | 32889539 | Higher in Drinkers |
| cg20078879 | 4 | 4580814 | Higher in Drinkers |
| cg20080039 | 20 | 2853902 | Higher in Drinkers |
| cg20081767 | 19 | 53193466 | Higher in Drinkers |
| cg20095825 | 10 | 95242170 | Higher in Drinkers |
| cg20096365 | 14 | 99828104 | Higher in Drinkers |
| cg20099147 | 19 | 56652066 | Higher in Drinkers |
| cg20099458 | 7 | 5272275 | Higher in Drinkers |
| cg20100641 | 17 | 60781261 | Higher in Drinkers |
| cg20102080 | 17 | 1359383 | Higher in Drinkers |
| cg20103201 | 1 | 2458021 | Higher in Drinkers |
| cg20103938 | 4 | 140005223 | Higher in Drinkers |
| cg20109361 | 12 | 670712 | Higher in Drinkers |
| cg20110801 | 19 | 56014812 | Higher in Drinkers |
| cg20111321 | 8 | 900076 | Lower in Drinkers |
| cg20113693 | 19 | 55740757 | Lower in Drinkers |
| cg20115910 | 12 | 49934906 | Higher in Drinkers |
| cg20116569 | 3 | 11313900 | Higher in Drinkers |
| cg20116574 | 20 | 44718168 | Higher in Drinkers |
| cg20118134 | 15 | 42565691 | Higher in Drinkers |
| cg20118409 | 3 | 99879106 | Higher in Drinkers |

| | | | |
|---|---|---|---|
| cg20118557 | 19 | 41168801 | Higher in Drinkers |
| cg20118857 | 17 | 48228624 | Higher in Drinkers |
| cg20119749 | 6 | 33239997 | Higher in Drinkers |
| cg20121427 | X | 43514483 | Higher in Drinkers |
| cg20122491 | 7 | 99102313 | Higher in Drinkers |
| cg20122548 | 15 | 45694411 | Higher in Drinkers |
| cg20123452 | 1 | 204464079 | Higher in Drinkers |
| cg20125159 | 1 | 52520593 | Higher in Drinkers |
| cg20126878 | 20 | 57464571 | Higher in Drinkers |
| cg20127188 | 22 | 21996426 | Higher in Drinkers |
| cg20133000 | 6 | 28219773 | Higher in Drinkers |
| cg20136444 | 3 | 183903974 | Higher in Drinkers |
| cg20136584 | 1 | 204121503 | Higher in Drinkers |
| cg20140363 | 2 | 26624458 | Higher in Drinkers |
| cg20147335 | 22 | 22020155 | Higher in Drinkers |
| cg20147595 | 8 | 110349212 | Higher in Drinkers |
| cg20148727 | 7 | 1534881 | Higher in Drinkers |
| cg20149431 | 10 | 3168685 | Higher in Drinkers |
| cg20149741 | 19 | 10216727 | Higher in Drinkers |
| cg20149766 | 5 | 6714666 | Higher in Drinkers |
| cg20150667 | 10 | 102747550 | Higher in Drinkers |
| cg20150743 | 7 | 99679295 | Higher in Drinkers |
| cg20156774 | 6 | 32803500 | Higher in Drinkers |
| cg20157484 | 12 | 46385525 | Higher in Drinkers |
| cg20176875 | 6 | 166797125 | Higher in Drinkers |
| cg20177485 | 4 | 908414 | Higher in Drinkers |
| cg20184271 | 12 | 14413090 | Higher in Drinkers |
| cg20187418 | 7 | 2186513 | Lower in Drinkers |
| cg20191066 | 17 | 56413977 | Higher in Drinkers |
| cg20193453 | 10 | 119805875 | Higher in Drinkers |
| cg20193771 | 20 | 20033025 | Higher in Drinkers |
| cg20194973 | 22 | 50524676 | Higher in Drinkers |
| cg20199655 | 12 | 25404314 | Higher in Drinkers |
| cg20200388 | 22 | 50869841 | Higher in Drinkers |
| cg20204634 | 1 | 87380163 | Higher in Drinkers |

| | | | |
|---|---|---|---|
| cg20206204 | 12 | 13067269 | Higher in Drinkers |
| cg20206377 | 11 | 2323272 | Higher in Drinkers |
| cg20216998 | 3 | 121468260 | Higher in Drinkers |
| cg20218460 | 2 | 238583504 | Higher in Drinkers |
| cg20220639 | 6 | 30295328 | Higher in Drinkers |
| cg20222376 | 19 | 15530606 | Higher in Drinkers |
| cg20224517 | 2 | 40006561 | Higher in Drinkers |
| cg20224751 | 19 | 58258452 | Higher in Drinkers |
| cg20225275 | 5 | 172410975 | Higher in Drinkers |
| cg20227976 | 9 | 35757314 | Higher in Drinkers |
| cg20229014 | 8 | 134529378 | Higher in Drinkers |
| cg20235051 | 17 | 59489852 | Higher in Drinkers |
| cg20240601 | 1 | 11322805 | Higher in Drinkers |
| cg20243073 | 19 | 57998481 | Higher in Drinkers |
| cg20243898 | 17 | 2602006 | Higher in Drinkers |
| cg20245503 | 12 | 58026705 | Higher in Drinkers |
| cg20247600 | 2 | 178129336 | Higher in Drinkers |
| cg20248691 | 11 | 532330 | Higher in Drinkers |
| cg20249550 | 19 | 13001990 | Higher in Drinkers |
| cg20250874 | 13 | 47127354 | Higher in Drinkers |
| cg20254231 | 2 | 128569115 | Higher in Drinkers |
| cg20254353 | 19 | 36347626 | Higher in Drinkers |
| cg20254725 | 19 | 44529414 | Higher in Drinkers |
| cg20255094 | 1 | 160771763 | Higher in Drinkers |
| cg20255723 | 22 | 45073031 | Higher in Drinkers |
| cg20256120 | 1 | 91853089 | Higher in Drinkers |
| cg20256820 | 3 | 137893779 | Higher in Drinkers |
| cg20256881 | 10 | 134428463 | Higher in Drinkers |
| cg20258580 | 15 | 99434759 | Higher in Drinkers |
| cg20263826 | 1 | 100176425 | Higher in Drinkers |
| cg20263839 | 18 | 42259560 | Higher in Drinkers |
| cg20266104 | 17 | 21116851 | Higher in Drinkers |
| cg20268018 | 2 | 210867683 | Higher in Drinkers |
| cg20268039 | 7 | 25900167 | Higher in Drinkers |
| cg20275462 | 17 | 60501228 | Higher in Drinkers |

| | | | |
|---|---|---|---|
| cg20276061 | 1 | 55680804 | Higher in Drinkers |
| cg20276947 | 17 | 80056775 | Higher in Drinkers |
| cg20280925 | 18 | 77588682 | Higher in Drinkers |
| cg20283221 | 3 | 197475520 | Higher in Drinkers |
| cg20289746 | 10 | 106075738 | Higher in Drinkers |
| cg20299810 | 22 | 42463911 | Higher in Drinkers |
| cg20301340 | 19 | 41815941 | Higher in Drinkers |
| cg20303245 | 11 | 8751512 | Higher in Drinkers |
| cg20303592 | 10 | 116697907 | Higher in Drinkers |
| cg20306234 | 17 | 18162366 | Higher in Drinkers |
| cg20310749 | 15 | 49256375 | Higher in Drinkers |
| cg20311251 | 10 | 105218160 | Lower in Drinkers |
| cg20311619 | 2 | 43453962 | Higher in Drinkers |
| cg20311673 | 2 | 1746207 | Lower in Drinkers |
| cg20315257 | 2 | 85665172 | Higher in Drinkers |
| cg20316380 | 10 | 104261862 | Higher in Drinkers |
| cg20316397 | 17 | 18581010 | Higher in Drinkers |
| cg20316440 | 1 | 8457758 | Higher in Drinkers |
| cg20316549 | 7 | 156810507 | Higher in Drinkers |
| cg20316713 | 11 | 66053304 | Higher in Drinkers |
| cg20317180 | 19 | 56111252 | Higher in Drinkers |
| cg20320936 | 1 | 26231584 | Higher in Drinkers |
| cg20321756 | 11 | 111848400 | Higher in Drinkers |
| cg20323571 | 1 | 176999034 | Lower in Drinkers |
| cg20324491 | 7 | 149128397 | Higher in Drinkers |
| cg20324969 | 8 | 144922104 | Higher in Drinkers |
| cg20325032 | 7 | 149129312 | Higher in Drinkers |
| cg20326572 | 17 | 79655163 | Higher in Drinkers |
| cg20326853 | 8 | 145635294 | Higher in Drinkers |
| cg20327784 | 17 | 73703307 | Higher in Drinkers |
| cg20327820 | 4 | 78979807 | Higher in Drinkers |
| cg20329966 | 1 | 185126242 | Higher in Drinkers |
| cg20338399 | X | 3994377 | Higher in Drinkers |
| cg20345973 | 1 | 26798271 | Higher in Drinkers |
| cg20346122 | 3 | 129158634 | Higher in Drinkers |

| | | | |
|---|---|---|---|
| cg20346826 | 7 | 2977037 | Higher in Drinkers |
| cg20347101 | 7 | 66147509 | Higher in Drinkers |
| cg20347268 | 2 | 24307657 | Higher in Drinkers |
| cg20349567 | 10 | 91405298 | Higher in Drinkers |
| cg20349695 | 8 | 33330484 | Higher in Drinkers |
| cg20350269 | 16 | 23160019 | Higher in Drinkers |
| cg20352410 | 11 | 8710644 | Higher in Drinkers |
| cg20352932 | 11 | 114271235 | Higher in Drinkers |
| cg20355486 | 2 | 27305360 | Lower in Drinkers |
| cg20358124 | 22 | 35796625 | Higher in Drinkers |
| cg20360212 | 22 | 30642820 | Higher in Drinkers |
| cg20362559 | 2 | 96931853 | Higher in Drinkers |
| cg20367072 | 19 | 51869687 | Higher in Drinkers |
| cg20367266 | X | 102585123 | Higher in Drinkers |
| cg20368979 | 4 | 73935086 | Higher in Drinkers |
| cg20374041 | 13 | 103497941 | Higher in Drinkers |
| cg20376313 | 8 | 25041651 | Higher in Drinkers |
| cg20377447 | 6 | 41010217 | Higher in Drinkers |
| cg20381182 | 6 | 16238434 | Higher in Drinkers |
| cg20386575 | 5 | 64331634 | Higher in Drinkers |
| cg20387272 | 8 | 144640401 | Higher in Drinkers |
| cg20388168 | 6 | 43153885 | Higher in Drinkers |
| cg20393975 | 9 | 140499623 | Higher in Drinkers |
| cg20403409 | 10 | 126752037 | Higher in Drinkers |
| cg20408175 | 12 | 53693169 | Lower in Drinkers |
| cg20408402 | 10 | 72362452 | Higher in Drinkers |
| cg20409358 | 4 | 174255887 | Higher in Drinkers |
| cg20411049 | 11 | 77530668 | Higher in Drinkers |
| cg20413993 | 7 | 158770296 | Lower in Drinkers |
| cg20417500 | 5 | 73109241 | Higher in Drinkers |
| cg20418725 | 2 | 202122474 | Higher in Drinkers |
| cg20419127 | 17 | 26662475 | Higher in Drinkers |
| cg20422052 | 8 | 143474721 | Lower in Drinkers |
| cg20423745 | 12 | 63038420 | Higher in Drinkers |
| cg20426571 | 12 | 114843919 | Higher in Drinkers |

| | | | |
|---|---|---|---|
| cg20430631 | 11 | 76340765 | Higher in Drinkers |
| cg20433952 | 17 | 55607898 | Higher in Drinkers |
| cg20438427 | 17 | 60555597 | Higher in Drinkers |
| cg20441130 | 7 | 834565 | Higher in Drinkers |
| cg20441175 | 10 | 75007251 | Higher in Drinkers |
| cg20442586 | 15 | 45444606 | Higher in Drinkers |
| cg20444381 | 8 | 109456000 | Higher in Drinkers |
| cg20450123 | 8 | 19540210 | Higher in Drinkers |
| cg20451718 | 21 | 46360372 | Higher in Drinkers |
| cg20452563 | 16 | 8891910 | Higher in Drinkers |
| cg20463945 | 6 | 30615578 | Higher in Drinkers |
| cg20466761 | 6 | 2766613 | Higher in Drinkers |
| cg20466767 | 20 | 13619655 | Higher in Drinkers |
| cg20470275 | 5 | 122180934 | Higher in Drinkers |
| cg20475221 | 14 | 75179930 | Higher in Drinkers |
| cg20476223 | 20 | 62681003 | Higher in Drinkers |
| cg20477070 | 14 | 68086717 | Higher in Drinkers |
| cg20478089 | 14 | 35099711 | Higher in Drinkers |
| cg20479805 | 18 | 43684716 | Higher in Drinkers |
| cg20480045 | 1 | 168194946 | Higher in Drinkers |
| cg20480233 | 14 | 23451154 | Higher in Drinkers |
| cg20483016 | 14 | 20774219 | Higher in Drinkers |
| cg20483112 | 1 | 11954174 | Higher in Drinkers |
| cg20488757 | 11 | 16760046 | Higher in Drinkers |
| cg20488820 | 3 | 42922860 | Higher in Drinkers |
| cg20496270 | 6 | 158653940 | Higher in Drinkers |
| cg20501355 | 17 | 48785009 | Higher in Drinkers |
| cg20504202 | X | 54467052 | Higher in Drinkers |
| cg20518994 | 2 | 25141532 | Higher in Drinkers |
| cg20522029 | 22 | 43343992 | Higher in Drinkers |
| cg20524216 | 3 | 47555100 | Higher in Drinkers |
| cg20534997 | 10 | 61122716 | Higher in Drinkers |
| cg20535715 | 11 | 34127020 | Higher in Drinkers |
| cg20536921 | 15 | 99994825 | Higher in Drinkers |
| cg20539690 | 10 | 101190675 | Higher in Drinkers |

| | | | |
|---|---|---|---|
| cg20541249 | 6 | 52151806 | Higher in Drinkers |
| cg20545976 | 2 | 152118471 | Higher in Drinkers |
| cg20547724 | 5 | 131607888 | Higher in Drinkers |
| cg20548175 | 14 | 74552097 | Higher in Drinkers |
| cg20548765 | 14 | 73360764 | Higher in Drinkers |
| cg20551965 | 2 | 70520865 | Higher in Drinkers |
| cg20558299 | 2 | 240322833 | Higher in Drinkers |
| cg20559608 | 3 | 131754012 | Higher in Drinkers |
| cg20560141 | 12 | 90104064 | Higher in Drinkers |
| cg20562678 | 13 | 28369080 | Higher in Drinkers |
| cg20563447 | 15 | 67359289 | Higher in Drinkers |
| cg20565740 | 16 | 85061215 | Higher in Drinkers |
| cg20565980 | 5 | 43019873 | Higher in Drinkers |
| cg20566897 | 11 | 313527 | Higher in Drinkers |
| cg20567847 | 7 | 155167038 | Higher in Drinkers |
| cg20573631 | 16 | 89882393 | Higher in Drinkers |
| cg20586091 | 17 | 45570133 | Higher in Drinkers |
| cg20590175 | 12 | 132530165 | Lower in Drinkers |
| cg20591408 | 2 | 241516333 | Higher in Drinkers |
| cg20592378 | 7 | 92861504 | Higher in Drinkers |
| cg20592656 | 7 | 5417060 | Lower in Drinkers |
| cg20593887 | 7 | 2106784 | Higher in Drinkers |
| cg20598457 | 14 | 103576399 | Higher in Drinkers |
| cg20602642 | 4 | 120375409 | Higher in Drinkers |
| cg20603609 | 14 | 69728089 | Higher in Drinkers |
| cg20605103 | 12 | 124930650 | Higher in Drinkers |
| cg20607293 | 1 | 147112703 | Higher in Drinkers |
| cg20612299 | 8 | 131308633 | Higher in Drinkers |
| cg20614671 | 7 | 2321431 | Higher in Drinkers |
| cg20615951 | 1 | 246730188 | Higher in Drinkers |
| cg20616186 | 17 | 7468154 | Higher in Drinkers |
| cg20617093 | 19 | 6532849 | Higher in Drinkers |
| cg20617957 | 13 | 100085203 | Higher in Drinkers |
| cg20622056 | X | 70151134 | Higher in Drinkers |
| cg20622964 | 15 | 90895335 | Higher in Drinkers |

| | | | |
|---|---|---|---|
| cg20623763 | 12 | 112123893 | Higher in Drinkers |
| cg20628205 | 19 | 12833490 | Higher in Drinkers |
| cg20628335 | 19 | 57352185 | Higher in Drinkers |
| cg20630889 | 1 | 203764635 | Higher in Drinkers |
| cg20630943 | 20 | 44563219 | Higher in Drinkers |
| cg20635409 | 12 | 103359273 | Lower in Drinkers |
| cg20638426 | 19 | 19843991 | Higher in Drinkers |
| cg20638626 | 8 | 12523153 | Higher in Drinkers |
| cg20639218 | 15 | 75660322 | Higher in Drinkers |
| cg20639890 | 15 | 25683349 | Higher in Drinkers |
| cg20640246 | 12 | 89749718 | Higher in Drinkers |
| cg20641280 | X | 153707793 | Higher in Drinkers |
| cg20643274 | 12 | 13717392 | Lower in Drinkers |
| cg20644426 | 2 | 74375147 | Higher in Drinkers |
| cg20646217 | 22 | 21356059 | Higher in Drinkers |
| cg20649848 | 18 | 14132538 | Higher in Drinkers |
| cg20659418 | 6 | 114176105 | Higher in Drinkers |
| cg20661893 | 13 | 46961813 | Higher in Drinkers |
| cg20662616 | 2 | 30454643 | Higher in Drinkers |
| cg20662859 | X | 150151609 | Higher in Drinkers |
| cg20663376 | 15 | 31372997 | Higher in Drinkers |
| cg20664468 | 13 | 29233282 | Higher in Drinkers |
| cg20665341 | 4 | 152732024 | Higher in Drinkers |
| cg20668450 | 11 | 64812208 | Higher in Drinkers |
| cg20677142 | 3 | 119012899 | Higher in Drinkers |
| cg20680674 | 10 | 129809770 | Higher in Drinkers |
| cg20682991 | 2 | 74981952 | Higher in Drinkers |
| cg20685713 | 1 | 156066986 | Higher in Drinkers |
| cg20686963 | 1 | 19923342 | Higher in Drinkers |
| cg20688987 | 12 | 56110162 | Higher in Drinkers |
| cg20689054 | 4 | 153457152 | Higher in Drinkers |
| cg20691408 | 11 | 61659465 | Higher in Drinkers |
| cg20691595 | 15 | 38184354 | Higher in Drinkers |
| cg20692059 | 14 | 23563979 | Higher in Drinkers |
| cg20694619 | 1 | 209929496 | Higher in Drinkers |

| | | | |
|---|---|---|---|
| cg20695562 | 1 | 78225636 | Higher in Drinkers |
| cg20695760 | 1 | 212591689 | Higher in Drinkers |
| cg20699899 | 15 | 101143162 | Higher in Drinkers |
| cg20701977 | 5 | 180644504 | Higher in Drinkers |
| cg20704266 | 5 | 41904694 | Higher in Drinkers |
| cg20707008 | 6 | 160210612 | Higher in Drinkers |
| cg20710842 | 4 | 140201262 | Higher in Drinkers |
| cg20711912 | 5 | 1326034 | Lower in Drinkers |
| cg20715824 | 14 | 100752144 | Higher in Drinkers |
| cg20716688 | 11 | 1411018 | Higher in Drinkers |
| cg20717059 | 8 | 11324617 | Higher in Drinkers |
| cg20717612 | 12 | 21810983 | Higher in Drinkers |
| cg20721750 | 2 | 183943506 | Higher in Drinkers |
| cg20722088 | 12 | 89742886 | Higher in Drinkers |
| cg20727728 | 11 | 129234245 | Higher in Drinkers |
| cg20728639 | 11 | 34379053 | Higher in Drinkers |
| cg20729316 | 21 | 33104864 | Higher in Drinkers |
| cg20731693 | 13 | 114107876 | Higher in Drinkers |
| cg20732690 | 21 | 47648911 | Higher in Drinkers |
| cg20734268 | 6 | 2764974 | Higher in Drinkers |
| cg20735282 | 11 | 69481734 | Higher in Drinkers |
| cg20735442 | 6 | 36390970 | Higher in Drinkers |
| cg20736028 | 19 | 3931982 | Lower in Drinkers |
| cg20737712 | 11 | 124492803 | Higher in Drinkers |
| cg20741078 | 6 | 28891917 | Higher in Drinkers |
| cg20742234 | 3 | 71113603 | Higher in Drinkers |
| cg20743065 | 4 | 53588673 | Higher in Drinkers |
| cg20744304 | 19 | 12146615 | Higher in Drinkers |
| cg20746807 | 20 | 60747786 | Higher in Drinkers |
| cg20749584 | 11 | 66102055 | Lower in Drinkers |
| cg20753523 | 18 | 33552393 | Higher in Drinkers |
| cg20753620 | 11 | 9406013 | Higher in Drinkers |
| cg20754844 | 5 | 149462180 | Higher in Drinkers |
| cg20755408 | 12 | 498145 | Higher in Drinkers |
| cg20756101 | 22 | 32058040 | Higher in Drinkers |

| | | | |
|---|---|---|---|
| cg20757519 | 18 | 5238310 | Higher in Drinkers |
| cg20757526 | 17 | 79995330 | Higher in Drinkers |
| cg20758219 | 3 | 138738597 | Higher in Drinkers |
| cg20760063 | 17 | 41277580 | Higher in Drinkers |
| cg20762290 | 17 | 46125559 | Higher in Drinkers |
| cg20763943 | X | 124336388 | Higher in Drinkers |
| cg20773023 | 20 | 17949862 | Higher in Drinkers |
| cg20775109 | 6 | 168358086 | Higher in Drinkers |
| cg20776317 | 9 | 139292793 | Higher in Drinkers |
| cg20776540 | 13 | 103870665 | Higher in Drinkers |
| cg20777176 | 1 | 231376761 | Higher in Drinkers |
| cg20777508 | 20 | 31887074 | Higher in Drinkers |
| cg20777796 | 7 | 1980117 | Higher in Drinkers |
| cg20778582 | 11 | 63753376 | Higher in Drinkers |
| cg20785333 | 3 | 119013442 | Higher in Drinkers |
| cg20787122 | 1 | 111889042 | Higher in Drinkers |
| cg20787903 | 22 | 30278994 | Higher in Drinkers |
| cg20788479 | 3 | 179169536 | Higher in Drinkers |
| cg20793087 | 3 | 48956177 | Higher in Drinkers |
| cg20793193 | X | 49056861 | Higher in Drinkers |
| cg20793532 | 4 | 6344361 | Higher in Drinkers |
| cg20794334 | 2 | 131797972 | Higher in Drinkers |
| cg20797697 | 1 | 45805522 | Higher in Drinkers |
| cg20797699 | 17 | 61776851 | Higher in Drinkers |
| cg20799963 | 20 | 42839934 | Higher in Drinkers |
| cg20803370 | 1 | 161136162 | Higher in Drinkers |
| cg20806502 | 4 | 148605412 | Higher in Drinkers |
| cg20817150 | 21 | 34776492 | Higher in Drinkers |
| cg20823940 | 1 | 95007489 | Higher in Drinkers |
| cg20824109 | 16 | 30386837 | Higher in Drinkers |
| cg20825506 | 6 | 21589356 | Higher in Drinkers |
| cg20826379 | 1 | 16011358 | Higher in Drinkers |
| cg20827193 | 1 | 109969084 | Higher in Drinkers |
| cg20836412 | 8 | 82543285 | Higher in Drinkers |
| cg20839149 | 1 | 156786601 | Higher in Drinkers |

| | | | |
|---|---|---|---|
| cg20839768 | 12 | 56511953 | Higher in Drinkers |
| cg20844545 | 12 | 132312875 | Higher in Drinkers |
| cg20845126 | 12 | 27091856 | Higher in Drinkers |
| cg20846236 | 1 | 32645337 | Higher in Drinkers |
| cg20848987 | 17 | 41116355 | Higher in Drinkers |
| cg20852846 | 19 | 3968872 | Higher in Drinkers |
| cg20857228 | 8 | 101170192 | Higher in Drinkers |
| cg20861510 | 13 | 114161522 | Higher in Drinkers |
| cg20863409 | 2 | 24272539 | Higher in Drinkers |
| cg20863668 | 17 | 73518382 | Higher in Drinkers |
| cg20863715 | 8 | 86132552 | Higher in Drinkers |
| cg20871277 | 6 | 33656548 | Higher in Drinkers |
| cg20884098 | 2 | 74710615 | Higher in Drinkers |
| cg20884502 | 12 | 112546705 | Higher in Drinkers |
| cg20894084 | 9 | 42367869 | Higher in Drinkers |
| cg20894246 | 22 | 41682263 | Higher in Drinkers |
| cg20898522 | 6 | 32806156 | Higher in Drinkers |
| cg20899382 | 14 | 90421174 | Higher in Drinkers |
| cg20899713 | 3 | 75668924 | Higher in Drinkers |
| cg20912439 | 3 | 3221099 | Higher in Drinkers |
| cg20913372 | 9 | 140190455 | Higher in Drinkers |
| cg20916646 | 4 | 852691 | Higher in Drinkers |
| cg20919615 | 5 | 137667621 | Higher in Drinkers |
| cg20919922 | 2 | 75185588 | Higher in Drinkers |
| cg20921688 | 2 | 71357800 | Higher in Drinkers |
| cg20921874 | 19 | 12034925 | Higher in Drinkers |
| cg20922377 | 15 | 48623205 | Higher in Drinkers |
| cg20925434 | 21 | 35014276 | Higher in Drinkers |
| cg20927307 | 2 | 242518158 | Higher in Drinkers |
| cg20928950 | 13 | 113976443 | Higher in Drinkers |
| cg20929143 | 13 | 32527171 | Higher in Drinkers |
| cg20933005 | 20 | 20033039 | Higher in Drinkers |
| cg20933631 | 3 | 113666370 | Higher in Drinkers |
| cg20934652 | 4 | 100871993 | Higher in Drinkers |
| cg20935106 | 12 | 6561229 | Higher in Drinkers |

| | | | |
|---|---|---|---|
| cg20935553 | 7 | 2272059 | Higher in Drinkers |
| cg20941699 | 15 | 64386307 | Higher in Drinkers |
| cg20950033 | 14 | 20898781 | Lower in Drinkers |
| cg20951334 | 2 | 86669446 | Higher in Drinkers |
| cg20951825 | 5 | 122461157 | Lower in Drinkers |
| cg20953990 | 3 | 197354190 | Higher in Drinkers |
| cg20955576 | 19 | 18043542 | Higher in Drinkers |
| cg20955831 | 6 | 25279788 | Higher in Drinkers |
| cg20961642 | 6 | 30690567 | Higher in Drinkers |
| cg20962543 | 1 | 85666741 | Higher in Drinkers |
| cg20969529 | 11 | 65387182 | Higher in Drinkers |
| cg20971536 | X | 48535266 | Higher in Drinkers |
| cg20973129 | 6 | 33548009 | Higher in Drinkers |
| cg20975414 | 1 | 145715571 | Lower in Drinkers |
| cg20977198 | 6 | 164061673 | Lower in Drinkers |
| cg20979296 | 4 | 169401717 | Higher in Drinkers |
| cg20984251 | 10 | 69523844 | Higher in Drinkers |
| cg20984663 | 19 | 14543883 | Higher in Drinkers |
| cg20987610 | 8 | 95222020 | Lower in Drinkers |
| cg20988728 | 22 | 31688502 | Higher in Drinkers |
| cg20989409 | 12 | 15091896 | Higher in Drinkers |
| cg20991102 | 2 | 242182726 | Higher in Drinkers |
| cg20993868 | 7 | 22813445 | Higher in Drinkers |
| cg20999901 | 10 | 105615046 | Higher in Drinkers |
| cg21004490 | 1 | 26872337 | Higher in Drinkers |
| cg21008684 | 2 | 157719870 | Higher in Drinkers |
| cg21008709 | 3 | 42622950 | Higher in Drinkers |
| cg21008894 | 15 | 67489038 | Higher in Drinkers |
| cg21011691 | 4 | 71553895 | Higher in Drinkers |
| cg21012057 | 1 | 15538911 | Lower in Drinkers |
| cg21012737 | 14 | 105393171 | Higher in Drinkers |
| cg21026078 | 7 | 124569713 | Higher in Drinkers |
| cg21028211 | 17 | 74497614 | Higher in Drinkers |
| cg21028460 | 15 | 22467578 | Higher in Drinkers |
| cg21029201 | 6 | 26022192 | Higher in Drinkers |

| | | | |
|---|---|---|---|
| cg21033632 | 5 | 64486421 | Lower in Drinkers |
| cg21036854 | 14 | 77506705 | Higher in Drinkers |
| cg21036914 | 5 | 177100448 | Higher in Drinkers |
| cg21038502 | 19 | 2799962 | Higher in Drinkers |
| cg21041181 | 2 | 42721947 | Higher in Drinkers |
| cg21041911 | 6 | 37673439 | Higher in Drinkers |
| cg21042970 | 21 | 27011436 | Higher in Drinkers |
| cg21044797 | 8 | 142138325 | Higher in Drinkers |
| cg21044833 | 19 | 13010694 | Lower in Drinkers |
| cg21046413 | X | 129299367 | Higher in Drinkers |
| cg21047583 | 2 | 231917885 | Higher in Drinkers |
| cg21048422 | 15 | 31617764 | Higher in Drinkers |
| cg21048501 | 7 | 43909515 | Higher in Drinkers |
| cg21050392 | 11 | 125758146 | Higher in Drinkers |
| cg21062891 | 6 | 31122520 | Higher in Drinkers |
| cg21064641 | 6 | 153324063 | Higher in Drinkers |
| cg21075870 | 1 | 155715476 | Higher in Drinkers |
| cg21076271 | 14 | 32546633 | Higher in Drinkers |
| cg21079394 | 12 | 32908049 | Higher in Drinkers |
| cg21082427 | 16 | 2918679 | Higher in Drinkers |
| cg21085001 | 1 | 167691333 | Higher in Drinkers |
| cg21085160 | 9 | 88696742 | Higher in Drinkers |
| cg21085625 | 2 | 120124643 | Higher in Drinkers |
| cg21091247 | 14 | 69258861 | Higher in Drinkers |
| cg21092177 | 17 | 73128031 | Higher in Drinkers |
| cg21092413 | 5 | 175964616 | Higher in Drinkers |
| cg21092674 | 5 | 111093286 | Higher in Drinkers |
| cg21093236 | 3 | 44379930 | Higher in Drinkers |
| cg21096898 | 4 | 3318625 | Lower in Drinkers |
| cg21097105 | 17 | 19265900 | Higher in Drinkers |
| cg21098005 | 20 | 44538605 | Higher in Drinkers |
| cg21099488 | 14 | 56585486 | Higher in Drinkers |
| cg21101386 | 20 | 35125857 | Higher in Drinkers |
| cg21103913 | 9 | 99180898 | Higher in Drinkers |
| cg21107044 | 13 | 114800796 | Higher in Drinkers |

| | | | |
|---|---|---|---|
| cg21109136 | 4 | 103748470 | Higher in Drinkers |
| cg21115433 | 1 | 27961868 | Higher in Drinkers |
| cg21116410 | 17 | 33905650 | Higher in Drinkers |
| cg21117678 | 7 | 101459024 | Higher in Drinkers |
| cg21118367 | 1 | 184460875 | Higher in Drinkers |
| cg21119962 | 1 | 246670217 | Higher in Drinkers |
| cg21120664 | 21 | 44299807 | Higher in Drinkers |
| cg21122529 | 19 | 16652680 | Higher in Drinkers |
| cg21128539 | 18 | 74116273 | Lower in Drinkers |
| cg21132649 | 13 | 46626913 | Higher in Drinkers |
| cg21133251 | 2 | 242566890 | Higher in Drinkers |
| cg21133266 | 8 | 11973029 | Higher in Drinkers |
| cg21135273 | 4 | 25916067 | Higher in Drinkers |
| cg21139845 | 12 | 7053993 | Higher in Drinkers |
| cg21142977 | 1 | 179924316 | Higher in Drinkers |
| cg21143446 | 13 | 108922340 | Higher in Drinkers |
| cg21143899 | 1 | 165866296 | Higher in Drinkers |
| cg21144161 | 5 | 423903 | Lower in Drinkers |
| cg21145245 | 5 | 150593684 | Higher in Drinkers |
| cg21146221 | 22 | 30279857 | Higher in Drinkers |
| cg21146503 | 11 | 20178677 | Higher in Drinkers |
| cg21155521 | 6 | 31632833 | Higher in Drinkers |
| cg21157115 | 9 | 33001303 | Higher in Drinkers |
| cg21158528 | 1 | 211501629 | Lower in Drinkers |
| cg21159993 | 5 | 139554405 | Higher in Drinkers |
| cg21160192 | 5 | 180229544 | Higher in Drinkers |
| cg21163552 | 12 | 32908175 | Higher in Drinkers |
| cg21164303 | 15 | 79603277 | Higher in Drinkers |
| cg21165137 | 11 | 67810310 | Higher in Drinkers |
| cg21166347 | 6 | 33240215 | Higher in Drinkers |
| cg21166775 | 12 | 48152204 | Higher in Drinkers |
| cg21170636 | 9 | 136215141 | Higher in Drinkers |
| cg21170920 | 1 | 18957373 | Lower in Drinkers |
| cg21171978 | 22 | 32029943 | Higher in Drinkers |
| cg21172011 | 21 | 36577638 | Higher in Drinkers |

| | | | |
|---|---|---|---|
| cg21172319 | 8 | 18067770 | Higher in Drinkers |
| cg21172540 | 1 | 32827840 | Higher in Drinkers |
| cg21174644 | 6 | 32939507 | Higher in Drinkers |
| cg21176475 | 12 | 122667627 | Higher in Drinkers |
| cg21178434 | 22 | 50683719 | Higher in Drinkers |
| cg21182322 | 1 | 167189623 | Higher in Drinkers |
| cg21182700 | 9 | 129374141 | Higher in Drinkers |
| cg21183455 | 22 | 50052396 | Higher in Drinkers |
| cg21184111 | 9 | 4792285 | Higher in Drinkers |
| cg21184132 | 5 | 149109531 | Higher in Drinkers |
| cg21187194 | 3 | 127311169 | Higher in Drinkers |
| cg21191622 | 6 | 33423774 | Higher in Drinkers |
| cg21192621 | 3 | 128880118 | Higher in Drinkers |
| cg21195185 | 4 | 76555782 | Higher in Drinkers |
| cg21197066 | 13 | 45563869 | Higher in Drinkers |
| cg21197361 | 17 | 30454658 | Higher in Drinkers |
| cg21197905 | 11 | 111602136 | Higher in Drinkers |
| cg21199093 | 1 | 35836009 | Higher in Drinkers |
| cg21200667 | 2 | 30628085 | Higher in Drinkers |
| cg21200923 | 18 | 9481257 | Higher in Drinkers |
| cg21201285 | 19 | 1847690 | Higher in Drinkers |
| cg21202716 | 11 | 70508022 | Higher in Drinkers |
| cg21206133 | 1 | 151511319 | Higher in Drinkers |
| cg21206353 | 1 | 16053913 | Higher in Drinkers |
| cg21209113 | 6 | 26272576 | Higher in Drinkers |
| cg21210124 | 9 | 92219187 | Higher in Drinkers |
| cg21212389 | 20 | 61569206 | Higher in Drinkers |
| cg21215436 | 9 | 137300911 | Lower in Drinkers |
| cg21215818 | 9 | 126169333 | Higher in Drinkers |
| cg21217225 | 10 | 121632640 | Higher in Drinkers |
| cg21217733 | 3 | 142315326 | Higher in Drinkers |
| cg21218476 | 17 | 7117863 | Higher in Drinkers |
| cg21219398 | 14 | 36278495 | Higher in Drinkers |
| cg21219529 | 9 | 104296226 | Higher in Drinkers |
| cg21220247 | 14 | 106321936 | Lower in Drinkers |

| | | | |
|---|---|---|---|
| cg21220927 | 14 | 77787328 | Higher in Drinkers |
| cg21224347 | 9 | 127534610 | Higher in Drinkers |
| cg21224609 | 12 | 132221123 | Lower in Drinkers |
| cg21226225 | 12 | 104680742 | Higher in Drinkers |
| cg21226353 | 9 | 99419714 | Higher in Drinkers |
| cg21227347 | 9 | 117374170 | Higher in Drinkers |
| cg21229536 | 5 | 82373428 | Higher in Drinkers |
| cg21234779 | 8 | 145057141 | Higher in Drinkers |
| cg21244191 | 8 | 145554489 | Higher in Drinkers |
| cg21245287 | 2 | 231276538 | Higher in Drinkers |
| cg21245453 | 13 | 20357060 | Higher in Drinkers |
| cg21245981 | 5 | 36607390 | Higher in Drinkers |
| cg21257892 | 6 | 99963170 | Higher in Drinkers |
| cg21262649 | 1 | 223566643 | Lower in Drinkers |
| cg21273013 | 1 | 23670943 | Higher in Drinkers |
| cg21273437 | 11 | 67236952 | Higher in Drinkers |
| cg21275702 | 20 | 18269109 | Higher in Drinkers |
| cg21279015 | 15 | 67546624 | Higher in Drinkers |
| cg21280171 | 6 | 139349736 | Higher in Drinkers |
| cg21283739 | 17 | 26594300 | Higher in Drinkers |
| cg21284034 | X | 102883667 | Higher in Drinkers |
| cg21287330 | 17 | 7154245 | Higher in Drinkers |
| cg21289738 | 17 | 8383742 | Higher in Drinkers |
| cg21290280 | 1 | 44422050 | Higher in Drinkers |
| cg21290393 | 22 | 19467302 | Higher in Drinkers |
| cg21291356 | 19 | 52692821 | Higher in Drinkers |
| cg21291383 | 1 | 42800883 | Higher in Drinkers |
| cg21291896 | 3 | 14444133 | Higher in Drinkers |
| cg21293902 | 19 | 49994097 | Higher in Drinkers |
| cg21295104 | 22 | 29168639 | Higher in Drinkers |
| cg21296675 | 2 | 89064965 | Lower in Drinkers |
| cg21297562 | 6 | 45389862 | Higher in Drinkers |
| cg21308020 | 4 | 99182242 | Higher in Drinkers |
| cg21308197 | 19 | 59084138 | Higher in Drinkers |
| cg21310173 | 14 | 102973313 | Higher in Drinkers |

| | | | |
|---|---|---|---|
| cg21312066 | 19 | 45942777 | Higher in Drinkers |
| cg21312144 | 2 | 32235240 | Higher in Drinkers |
| cg21316470 | 15 | 63340581 | Higher in Drinkers |
| cg21316772 | 9 | 33167933 | Higher in Drinkers |
| cg21321735 | 2 | 241760164 | Higher in Drinkers |
| cg21322149 | 3 | 101232006 | Higher in Drinkers |
| cg21325732 | 17 | 16256937 | Higher in Drinkers |
| cg21327609 | 12 | 7013997 | Higher in Drinkers |
| cg21328779 | 3 | 111629875 | Higher in Drinkers |
| cg21329628 | 19 | 8373296 | Higher in Drinkers |
| cg21331324 | 20 | 57583000 | Higher in Drinkers |
| cg21332729 | 5 | 95170798 | Higher in Drinkers |
| cg21334449 | 12 | 25403230 | Higher in Drinkers |
| cg21335714 | 6 | 30166479 | Higher in Drinkers |
| cg21336456 | 2 | 101014002 | Higher in Drinkers |
| cg21337984 | 17 | 6544054 | Higher in Drinkers |
| cg21339533 | 7 | 23221367 | Higher in Drinkers |
| cg21340070 | 2 | 60783960 | Higher in Drinkers |
| cg21349637 | 18 | 13218607 | Higher in Drinkers |
| cg21351140 | 17 | 57234919 | Higher in Drinkers |
| cg21351151 | 5 | 139937192 | Higher in Drinkers |
| cg21355619 | 7 | 1008260 | Higher in Drinkers |
| cg21359335 | 12 | 49284769 | Higher in Drinkers |
| cg21363128 | 4 | 108852555 | Higher in Drinkers |
| cg21365899 | 1 | 231558446 | Higher in Drinkers |
| cg21367972 | 7 | 116166824 | Higher in Drinkers |
| cg21372200 | 3 | 50375735 | Higher in Drinkers |
| cg21380024 | 17 | 61042803 | Lower in Drinkers |
| cg21382768 | 15 | 41047027 | Higher in Drinkers |
| cg21386373 | 3 | 52279602 | Higher in Drinkers |
| cg21388793 | 19 | 2427982 | Higher in Drinkers |
| cg21390575 | 4 | 185747721 | Higher in Drinkers |
| cg21394787 | 1 | 36235644 | Higher in Drinkers |
| cg21399795 | 17 | 16120693 | Higher in Drinkers |
| cg21401737 | 1 | 38455939 | Higher in Drinkers |

| | | | |
|---|---|---|---|
| cg21409449 | 7 | 2128263 | Higher in Drinkers |
| cg21409722 | 17 | 55162050 | Higher in Drinkers |
| cg21410080 | 21 | 43639862 | Higher in Drinkers |
| cg21413258 | 5 | 68665223 | Higher in Drinkers |
| cg21415530 | 8 | 140715802 | Higher in Drinkers |
| cg21416739 | 12 | 132429311 | Higher in Drinkers |
| cg21417259 | 7 | 5401609 | Higher in Drinkers |
| cg21418076 | 14 | 24777878 | Higher in Drinkers |
| cg21419428 | 11 | 111473938 | Higher in Drinkers |
| cg21430685 | 8 | 29387008 | Higher in Drinkers |
| cg21435684 | 17 | 80255457 | Higher in Drinkers |
| cg21437481 | 1 | 161067985 | Higher in Drinkers |
| cg21437548 | 17 | 75277645 | Higher in Drinkers |
| cg21443261 | 8 | 27169256 | Higher in Drinkers |
| cg21446955 | 4 | 86851425 | Higher in Drinkers |
| cg21452538 | 4 | 870773 | Higher in Drinkers |
| cg21457676 | 12 | 95611957 | Higher in Drinkers |
| cg21464091 | 20 | 5100652 | Higher in Drinkers |
| cg21465754 | 15 | 40986972 | Higher in Drinkers |
| cg21472099 | X | 16737680 | Higher in Drinkers |
| cg21473439 | 12 | 49717011 | Higher in Drinkers |
| cg21477317 | 3 | 48488082 | Higher in Drinkers |
| cg21478177 | 3 | 183146663 | Higher in Drinkers |
| cg21479519 | 19 | 1419464 | Higher in Drinkers |
| cg21480165 | 13 | 25670170 | Higher in Drinkers |
| cg21480743 | 10 | 89621419 | Higher in Drinkers |
| cg21482403 | 19 | 12889342 | Higher in Drinkers |
| cg21483842 | 13 | 49821938 | Higher in Drinkers |
| cg21484680 | 2 | 27593328 | Higher in Drinkers |
| cg21490793 | 19 | 38827205 | Higher in Drinkers |
| cg21491240 | X | 135578826 | Higher in Drinkers |
| cg21504385 | 1 | 113616118 | Higher in Drinkers |
| cg21506441 | 12 | 122150246 | Higher in Drinkers |
| cg21509721 | 12 | 79955369 | Lower in Drinkers |
| cg21510789 | 11 | 108339364 | Higher in Drinkers |

| | | | |
|---|---|---|---|
| cg21511925 | 5 | 175788234 | Higher in Drinkers |
| cg21515283 | 3 | 53916412 | Higher in Drinkers |
| cg21515898 | 4 | 109088237 | Higher in Drinkers |
| cg21517261 | 7 | 38217791 | Higher in Drinkers |
| cg21518937 | 12 | 49741245 | Higher in Drinkers |
| cg21519787 | 19 | 49133421 | Higher in Drinkers |
| cg21521454 | 19 | 48972670 | Higher in Drinkers |
| cg21521683 | 12 | 22487682 | Higher in Drinkers |
| cg21527360 | 6 | 4135862 | Higher in Drinkers |
| cg21531069 | 19 | 21203493 | Higher in Drinkers |
| cg21531702 | 11 | 66035773 | Higher in Drinkers |
| cg21533667 | 11 | 126152933 | Higher in Drinkers |
| cg21537245 | 1 | 20960434 | Higher in Drinkers |
| cg21541120 | 5 | 112630413 | Higher in Drinkers |
| cg21545988 | 6 | 31502516 | Higher in Drinkers |
| cg21546874 | 1 | 9294571 | Higher in Drinkers |
| cg21548788 | 4 | 77997565 | Higher in Drinkers |
| cg21549011 | 2 | 87087878 | Higher in Drinkers |
| cg21550006 | 2 | 97760606 | Higher in Drinkers |
| cg21550024 | 4 | 123747533 | Higher in Drinkers |
| cg21550360 | 15 | 73075372 | Higher in Drinkers |
| cg21551340 | 2 | 1609508 | Lower in Drinkers |
| cg21553893 | 11 | 126081455 | Higher in Drinkers |
| cg21556389 | 17 | 1957370 | Higher in Drinkers |
| cg21560413 | 2 | 27346765 | Higher in Drinkers |
| cg21561470 | 13 | 114773108 | Higher in Drinkers |
| cg21564527 | 19 | 12807645 | Higher in Drinkers |
| cg21569394 | 12 | 96253460 | Higher in Drinkers |
| cg21569844 | 2 | 86564582 | Higher in Drinkers |
| cg21571658 | 15 | 70785399 | Higher in Drinkers |
| cg21573601 | 10 | 89622589 | Higher in Drinkers |
| cg21573745 | 19 | 48640719 | Higher in Drinkers |
| cg21575198 | 12 | 104324793 | Higher in Drinkers |
| cg21576151 | 16 | 561444 | Higher in Drinkers |
| cg21580173 | 6 | 32940045 | Higher in Drinkers |

| | | | |
|---|---|---|---|
| cg21580220 | 12 | 49435106 | Lower in Drinkers |
| cg21580746 | 19 | 45001471 | Higher in Drinkers |
| cg21584983 | 19 | 11640070 | Higher in Drinkers |
| cg21587477 | 7 | 128696983 | Higher in Drinkers |
| cg21590967 | 2 | 120517099 | Higher in Drinkers |
| cg21593899 | 22 | 39826973 | Higher in Drinkers |
| cg21595092 | 2 | 42950061 | Lower in Drinkers |
| cg21595175 | 5 | 180670701 | Higher in Drinkers |
| cg21596317 | 5 | 102201545 | Higher in Drinkers |
| cg21599798 | 6 | 26521005 | Higher in Drinkers |
| cg21602614 | 12 | 1949586 | Higher in Drinkers |
| cg21603615 | 2 | 74211440 | Higher in Drinkers |
| cg21606887 | X | 118603301 | Higher in Drinkers |
| cg21606915 | 11 | 5743470 | Higher in Drinkers |
| cg21606923 | 7 | 26331446 | Higher in Drinkers |
| cg21608605 | 6 | 152128258 | Higher in Drinkers |
| cg21610516 | 6 | 151186758 | Higher in Drinkers |
| cg21614408 | 6 | 52228023 | Higher in Drinkers |
| cg21614638 | 4 | 100737821 | Higher in Drinkers |
| cg21615765 | 19 | 10362629 | Higher in Drinkers |
| cg21618501 | 7 | 2314863 | Higher in Drinkers |
| cg21618929 | 19 | 44259493 | Higher in Drinkers |
| cg21619639 | 4 | 155471134 | Higher in Drinkers |
| cg21622152 | 16 | 2961642 | Higher in Drinkers |
| cg21626986 | 4 | 9534041 | Higher in Drinkers |
| cg21631583 | 3 | 15247517 | Higher in Drinkers |
| cg21644703 | 19 | 10735482 | Lower in Drinkers |
| cg21646520 | 7 | 139614808 | Higher in Drinkers |
| cg21646557 | 1 | 110036808 | Higher in Drinkers |
| cg21647220 | 1 | 156675879 | Higher in Drinkers |
| cg21648245 | 4 | 109541405 | Higher in Drinkers |
| cg21648457 | 1 | 156167267 | Higher in Drinkers |
| cg21649013 | 12 | 132381683 | Higher in Drinkers |
| cg21649118 | 2 | 75277363 | Higher in Drinkers |
| cg21651436 | 11 | 65381610 | Higher in Drinkers |

| | | | |
|---|---|---|---|
| cg21651776 | 12 | 105351945 | Higher in Drinkers |
| cg21652107 | 4 | 48782392 | Higher in Drinkers |
| cg21655710 | 1 | 54856511 | Higher in Drinkers |
| cg21679970 | 2 | 10581770 | Higher in Drinkers |
| cg21682057 | 6 | 2245849 | Higher in Drinkers |
| cg21684681 | 11 | 64002635 | Higher in Drinkers |
| cg21685750 | 2 | 37193358 | Higher in Drinkers |
| cg21685776 | 18 | 19929517 | Higher in Drinkers |
| cg21686900 | 12 | 51632663 | Higher in Drinkers |
| cg21690091 | 1 | 202830756 | Higher in Drinkers |
| cg21693780 | 2 | 15731793 | Higher in Drinkers |
| cg21695171 | 1 | 223307306 | Higher in Drinkers |
| cg21697512 | 1 | 208081541 | Higher in Drinkers |
| cg21698840 | 4 | 76598899 | Higher in Drinkers |
| cg21700863 | 16 | 15069460 | Higher in Drinkers |
| cg21701774 | 12 | 7126016 | Higher in Drinkers |
| cg21702497 | 16 | 22309096 | Higher in Drinkers |
| cg21705394 | 11 | 30344510 | Higher in Drinkers |
| cg21705844 | 17 | 3539499 | Higher in Drinkers |
| cg21708867 | 13 | 114138225 | Higher in Drinkers |
| cg21710060 | 13 | 114321749 | Higher in Drinkers |
| cg21710451 | 11 | 11643326 | Higher in Drinkers |
| cg21721825 | 12 | 97300410 | Higher in Drinkers |
| cg21722362 | 18 | 56807043 | Higher in Drinkers |
| cg21725158 | 19 | 2191154 | Higher in Drinkers |
| cg21725976 | 19 | 2479184 | Higher in Drinkers |
| cg21727117 | 19 | 2269525 | Higher in Drinkers |
| cg21727214 | 17 | 75085328 | Higher in Drinkers |
| cg21728101 | 7 | 1979360 | Higher in Drinkers |
| cg21734090 | 17 | 7620948 | Higher in Drinkers |
| cg21734487 | 8 | 27695307 | Higher in Drinkers |
| cg21735516 | 15 | 41150573 | Higher in Drinkers |
| cg21735648 | 20 | 46130382 | Higher in Drinkers |
| cg21736186 | 2 | 232826186 | Higher in Drinkers |
| cg21739049 | 19 | 38688199 | Higher in Drinkers |

| | | | |
|---|---|---|---|
| cg21739289 | 11 | 64645963 | Higher in Drinkers |
| cg21740055 | 8 | 668667 | Higher in Drinkers |
| cg21742383 | 6 | 31870100 | Higher in Drinkers |
| cg21745248 | 20 | 55926117 | Higher in Drinkers |
| cg21746724 | 3 | 47624064 | Higher in Drinkers |
| cg21749538 | 20 | 43588937 | Higher in Drinkers |
| cg21754746 | 6 | 33256912 | Higher in Drinkers |
| cg21755153 | 8 | 145624994 | Higher in Drinkers |
| cg21756353 | 19 | 12792451 | Higher in Drinkers |
| cg21756476 | 15 | 61182765 | Higher in Drinkers |
| cg21757043 | 3 | 128444882 | Higher in Drinkers |
| cg21763814 | 6 | 46816905 | Higher in Drinkers |
| cg21764708 | 7 | 151493629 | Higher in Drinkers |
| cg21765441 | 6 | 31924492 | Higher in Drinkers |
| cg21767402 | 20 | 50808824 | Higher in Drinkers |
| cg21771714 | 6 | 119031342 | Higher in Drinkers |
| cg21788755 | 3 | 48508391 | Lower in Drinkers |
| cg21789674 | 6 | 100056686 | Higher in Drinkers |
| cg21789898 | 13 | 29293245 | Higher in Drinkers |
| cg21792144 | 11 | 73498894 | Higher in Drinkers |
| cg21792150 | 3 | 101567884 | Higher in Drinkers |
| cg21793517 | 6 | 157323292 | Higher in Drinkers |
| cg21805118 | 12 | 122712153 | Higher in Drinkers |
| cg21806917 | 11 | 66384012 | Higher in Drinkers |
| cg21811592 | X | 70712619 | Higher in Drinkers |
| cg21814178 | 12 | 51720755 | Higher in Drinkers |
| cg21816001 | 8 | 86019311 | Higher in Drinkers |
| cg21818383 | 15 | 57179837 | Higher in Drinkers |
| cg21818602 | 3 | 32535895 | Higher in Drinkers |
| cg21824114 | 17 | 41322603 | Higher in Drinkers |
| cg21826900 | 1 | 244013668 | Higher in Drinkers |
| cg21827969 | 4 | 56212299 | Higher in Drinkers |
| cg21830313 | 1 | 3528077 | Higher in Drinkers |
| cg21831501 | 1 | 173446253 | Higher in Drinkers |
| cg21832096 | 17 | 3837544 | Higher in Drinkers |

| | | | |
|---|---|---|---|
| cg21832150 | 1 | 902025 | Higher in Drinkers |
| cg21832951 | 4 | 67927955 | Higher in Drinkers |
| cg21833476 | 4 | 95129167 | Higher in Drinkers |
| cg21835622 | 5 | 146833431 | Higher in Drinkers |
| cg21839620 | 13 | 45776247 | Higher in Drinkers |
| cg21840121 | 14 | 70721531 | Higher in Drinkers |
| cg21849289 | 1 | 53686523 | Higher in Drinkers |
| cg21852842 | 7 | 1896827 | Higher in Drinkers |
| cg21854332 | 1 | 144989624 | Higher in Drinkers |
| cg21855205 | 11 | 67166421 | Higher in Drinkers |
| cg21856744 | 8 | 663745 | Higher in Drinkers |
| cg21857885 | 14 | 60337864 | Higher in Drinkers |
| cg21859337 | 1 | 117210332 | Higher in Drinkers |
| cg21861174 | 1 | 3831314 | Lower in Drinkers |
| cg21863878 | 20 | 3748616 | Higher in Drinkers |
| cg21865941 | 15 | 93363764 | Higher in Drinkers |
| cg21868050 | 1 | 155231980 | Higher in Drinkers |
| cg21870469 | 6 | 16238691 | Higher in Drinkers |
| cg21873885 | 6 | 33267214 | Higher in Drinkers |
| cg21877498 | 5 | 139944509 | Higher in Drinkers |
| cg21877855 | 1 | 63989125 | Higher in Drinkers |
| cg21881434 | 17 | 6915833 | Higher in Drinkers |
| cg21881798 | 11 | 8931708 | Higher in Drinkers |
| cg21885897 | 19 | 44008145 | Higher in Drinkers |
| cg21890394 | 19 | 2785838 | Higher in Drinkers |
| cg21893764 | 6 | 33145523 | Higher in Drinkers |
| cg21899942 | 14 | 72943540 | Higher in Drinkers |
| cg21899992 | 5 | 179306587 | Higher in Drinkers |
| cg21901227 | 12 | 125434661 | Lower in Drinkers |
| cg21903324 | 18 | 21718824 | Higher in Drinkers |
| cg21903646 | 6 | 28447115 | Lower in Drinkers |
| cg21903826 | 3 | 53195039 | Higher in Drinkers |
| cg21906602 | 3 | 196158975 | Higher in Drinkers |
| cg21906728 | 3 | 138634677 | Higher in Drinkers |
| cg21908488 | 17 | 17991580 | Higher in Drinkers |

| | | | |
|---|---|---|---|
| cg21909475 | 1 | 169764459 | Higher in Drinkers |
| cg21909782 | 11 | 17249882 | Higher in Drinkers |
| cg21909859 | 8 | 97345750 | Higher in Drinkers |
| cg21915666 | 6 | 31370916 | Higher in Drinkers |
| cg21915672 | 11 | 102188280 | Higher in Drinkers |
| cg21915799 | 8 | 10282809 | Higher in Drinkers |
| cg21915863 | 6 | 4874032 | Higher in Drinkers |
| cg21916655 | 1 | 244624521 | Higher in Drinkers |
| cg21918786 | 6 | 109611834 | Lower in Drinkers |
| cg21919599 | 1 | 247579312 | Higher in Drinkers |
| cg21925414 | 10 | 101300305 | Higher in Drinkers |
| cg21927975 | 1 | 6320757 | Higher in Drinkers |
| cg21929860 | 1 | 11024261 | Higher in Drinkers |
| cg21930839 | 11 | 3444479 | Higher in Drinkers |
| cg21931656 | 11 | 72462963 | Higher in Drinkers |
| cg21931792 | 8 | 77912326 | Higher in Drinkers |
| cg21931972 | 14 | 104000955 | Higher in Drinkers |
| cg21933664 | 13 | 113530259 | Higher in Drinkers |
| cg21934910 | 1 | 40506769 | Higher in Drinkers |
| cg21937593 | 3 | 167098088 | Higher in Drinkers |
| cg21940081 | 2 | 131103235 | Lower in Drinkers |
| cg21943652 | 1 | 114472049 | Higher in Drinkers |
| cg21946667 | 17 | 40839643 | Higher in Drinkers |
| cg21947488 | 16 | 2185289 | Higher in Drinkers |
| cg21949305 | 22 | 24828655 | Higher in Drinkers |
| cg21950493 | 12 | 110907285 | Higher in Drinkers |
| cg21950534 | 6 | 152128483 | Higher in Drinkers |
| cg21951975 | 1 | 209979733 | Lower in Drinkers |
| cg21961583 | 2 | 170684455 | Higher in Drinkers |
| cg21964391 | 1 | 218253368 | Lower in Drinkers |
| cg21968598 | 18 | 48724274 | Higher in Drinkers |
| cg21971919 | 11 | 66035643 | Higher in Drinkers |
| cg21972837 | 11 | 17207724 | Higher in Drinkers |
| cg21978618 | 19 | 49293898 | Higher in Drinkers |
| cg21985356 | 5 | 76383200 | Higher in Drinkers |

| | | | |
|---|---|---|---|
| cg21988119 | 19 | 17958937 | Higher in Drinkers |
| cg21989023 | 1 | 178063067 | Higher in Drinkers |
| cg21991830 | 8 | 53626936 | Higher in Drinkers |
| cg21995484 | 6 | 171026390 | Higher in Drinkers |
| cg21998512 | 7 | 92077031 | Higher in Drinkers |
| cg21999726 | 7 | 4000258 | Higher in Drinkers |
| cg22002668 | 9 | 131936651 | Higher in Drinkers |
| cg22003469 | 19 | 44669119 | Higher in Drinkers |
| cg22004151 | 6 | 42952586 | Higher in Drinkers |
| cg22004443 | 2 | 10953237 | Higher in Drinkers |
| cg22005393 | 7 | 102985332 | Higher in Drinkers |
| cg22010582 | 8 | 109455852 | Higher in Drinkers |
| cg22015030 | 1 | 54411349 | Higher in Drinkers |
| cg22017015 | 1 | 156100165 | Higher in Drinkers |
| cg22017146 | 15 | 75500859 | Higher in Drinkers |
| cg22019158 | 1 | 27926683 | Higher in Drinkers |
| cg22019649 | 5 | 139027535 | Higher in Drinkers |
| cg22020752 | 12 | 22697546 | Higher in Drinkers |
| cg22021322 | 1 | 33359576 | Higher in Drinkers |
| cg22023604 | 17 | 4072974 | Higher in Drinkers |
| cg22023770 | 6 | 13486545 | Higher in Drinkers |
| cg22023797 | 6 | 32163552 | Higher in Drinkers |
| cg22024508 | 19 | 16771032 | Higher in Drinkers |
| cg22032283 | 13 | 111936044 | Higher in Drinkers |
| cg22032989 | 1 | 156695942 | Higher in Drinkers |
| cg22033754 | 1 | 211828290 | Lower in Drinkers |
| cg22035501 | 5 | 112073398 | Higher in Drinkers |
| cg22037077 | 21 | 19191843 | Higher in Drinkers |
| cg22037687 | 20 | 50140611 | Higher in Drinkers |
| cg22043361 | 14 | 64970199 | Higher in Drinkers |
| cg22048228 | 1 | 3585225 | Higher in Drinkers |
| cg22051204 | 5 | 76373803 | Higher in Drinkers |
| cg22053796 | 13 | 21304026 | Lower in Drinkers |
| cg22055705 | 7 | 129465668 | Higher in Drinkers |
| cg22056044 | 10 | 98347055 | Higher in Drinkers |

| | | | |
|---|---|---|---|
| cg22058112 | 15 | 42566300 | Higher in Drinkers |
| cg22063247 | 11 | 133994642 | Higher in Drinkers |
| cg22063685 | 19 | 7999345 | Higher in Drinkers |
| cg22063966 | 19 | 56160065 | Higher in Drinkers |
| cg22068093 | 5 | 171284818 | Higher in Drinkers |
| cg22077262 | 1 | 172413232 | Higher in Drinkers |
| cg22077313 | 4 | 6691093 | Higher in Drinkers |
| cg22077361 | 1 | 24195347 | Lower in Drinkers |
| cg22078638 | 1 | 207495363 | Higher in Drinkers |
| cg22078859 | 9 | 127952320 | Higher in Drinkers |
| cg22080628 | 1 | 45473666 | Higher in Drinkers |
| cg22083790 | 12 | 133532978 | Higher in Drinkers |
| cg22086973 | 5 | 77590574 | Higher in Drinkers |
| cg22088219 | 7 | 74064567 | Higher in Drinkers |
| cg22092745 | 9 | 37485802 | Higher in Drinkers |
| cg22095490 | 18 | 77560089 | Lower in Drinkers |
| cg22100228 | 8 | 94929017 | Higher in Drinkers |
| cg22104153 | 5 | 70883106 | Higher in Drinkers |
| cg22106577 | 5 | 137514936 | Higher in Drinkers |
| cg22109623 | 22 | 50250816 | Higher in Drinkers |
| cg22111043 | 7 | 45019005 | Higher in Drinkers |
| cg22111442 | 1 | 31441196 | Higher in Drinkers |
| cg22112144 | 5 | 72112333 | Higher in Drinkers |
| cg22112360 | 17 | 75366750 | Higher in Drinkers |
| cg22118131 | 15 | 78369834 | Higher in Drinkers |
| cg22122361 | 4 | 79697742 | Higher in Drinkers |
| cg22124648 | 1 | 27941866 | Higher in Drinkers |
| cg22124673 | 4 | 71705677 | Higher in Drinkers |
| cg22125370 | 12 | 93966485 | Higher in Drinkers |
| cg22127027 | 11 | 18417840 | Higher in Drinkers |
| cg22127703 | 7 | 91570873 | Higher in Drinkers |
| cg22129807 | 5 | 876338 | Higher in Drinkers |
| cg22136013 | 6 | 33091591 | Higher in Drinkers |
| cg22136118 | 6 | 150390404 | Higher in Drinkers |
| cg22136326 | 16 | 57278759 | Higher in Drinkers |

| | | | |
|---|---|---|---|
| cg22138278 | 8 | 145158307 | Higher in Drinkers |
| cg22138302 | 11 | 119019412 | Lower in Drinkers |
| cg22145651 | 15 | 91419540 | Higher in Drinkers |
| cg22149555 | 12 | 133410880 | Higher in Drinkers |
| cg22152688 | 7 | 97840113 | Higher in Drinkers |
| cg22153239 | 22 | 42095773 | Higher in Drinkers |
| cg22153481 | 12 | 49412872 | Higher in Drinkers |
| cg22158415 | 6 | 33256657 | Higher in Drinkers |
| cg22159557 | 15 | 65067668 | Higher in Drinkers |
| cg22162323 | 8 | 144990644 | Higher in Drinkers |
| cg22166325 | 15 | 74988540 | Higher in Drinkers |
| cg22168205 | 13 | 24477659 | Higher in Drinkers |
| cg22168222 | 7 | 2584609 | Higher in Drinkers |
| cg22168489 | 12 | 122356033 | Higher in Drinkers |
| cg22169206 | 19 | 56136215 | Higher in Drinkers |
| cg22174191 | 6 | 111136363 | Higher in Drinkers |
| cg22176097 | 17 | 27229885 | Higher in Drinkers |
| cg22176353 | 13 | 114897925 | Higher in Drinkers |
| cg22176895 | 1 | 214162039 | Higher in Drinkers |
| cg22182610 | 17 | 7233150 | Higher in Drinkers |
| cg22182975 | 6 | 167571172 | Higher in Drinkers |
| cg22184145 | 4 | 57845401 | Higher in Drinkers |
| cg22185065 | 6 | 6318785 | Lower in Drinkers |
| cg22186853 | 19 | 57946589 | Higher in Drinkers |
| cg22191873 | 6 | 28219744 | Higher in Drinkers |
| cg22192692 | 20 | 2451760 | Higher in Drinkers |
| cg22192879 | 9 | 131872920 | Higher in Drinkers |
| cg22193736 | 11 | 18127676 | Higher in Drinkers |
| cg22194305 | 4 | 2264032 | Higher in Drinkers |
| cg22195011 | 5 | 125759262 | Higher in Drinkers |
| cg22196952 | 12 | 52400663 | Higher in Drinkers |
| cg22199628 | 12 | 80327755 | Higher in Drinkers |
| cg22200067 | 11 | 107436549 | Higher in Drinkers |
| cg22202154 | 17 | 79895100 | Higher in Drinkers |
| cg22202182 | 2 | 75874453 | Higher in Drinkers |

| | | | |
|---|---|---|---|
| cg22207171 | 2 | 219524576 | Higher in Drinkers |
| cg22215392 | 3 | 12973168 | Higher in Drinkers |
| cg22216355 | 6 | 83777339 | Higher in Drinkers |
| cg22221131 | 13 | 51484590 | Higher in Drinkers |
| cg22221320 | 1 | 89664340 | Higher in Drinkers |
| cg22225258 | 1 | 1447235 | Higher in Drinkers |
| cg22225546 | 12 | 56212269 | Higher in Drinkers |
| cg22228754 | 7 | 73534658 | Higher in Drinkers |
| cg22230640 | 6 | 32805807 | Higher in Drinkers |
| cg22232207 | 20 | 44746825 | Higher in Drinkers |
| cg22232327 | 18 | 53447594 | Higher in Drinkers |
| cg22235727 | 16 | 89043281 | Higher in Drinkers |
| cg22237401 | 19 | 13228070 | Higher in Drinkers |
| cg22238923 | 2 | 74781587 | Higher in Drinkers |
| cg22239483 | 19 | 20150159 | Higher in Drinkers |
| cg22243662 | 2 | 10862305 | Higher in Drinkers |
| cg22244113 | 6 | 80714048 | Higher in Drinkers |
| cg22248011 | 6 | 52442391 | Higher in Drinkers |
| cg22249281 | 19 | 41082756 | Higher in Drinkers |
| cg22249390 | 6 | 27145293 | Higher in Drinkers |
| cg22255355 | 19 | 58838374 | Higher in Drinkers |
| cg22256853 | 3 | 111840865 | Higher in Drinkers |
| cg22257056 | 3 | 32462766 | Higher in Drinkers |
| cg22260503 | 12 | 7070317 | Higher in Drinkers |
| cg22262895 | 4 | 129315055 | Lower in Drinkers |
| cg22265142 | X | 47479101 | Higher in Drinkers |
| cg22269622 | 17 | 60501544 | Higher in Drinkers |
| cg22272282 | 6 | 27107670 | Higher in Drinkers |
| cg22275306 | 2 | 198380764 | Higher in Drinkers |
| cg22276896 | 19 | 42946985 | Higher in Drinkers |
| cg22282265 | 11 | 44582836 | Higher in Drinkers |
| cg22284222 | 9 | 132566032 | Higher in Drinkers |
| cg22289360 | 9 | 79073906 | Higher in Drinkers |
| cg22294849 | 4 | 4292494 | Higher in Drinkers |
| cg22303873 | 19 | 12807618 | Higher in Drinkers |

| | | | |
|---|---|---|---|
| cg22307009 | 19 | 48018781 | Higher in Drinkers |
| cg22307230 | 13 | 40229780 | Higher in Drinkers |
| cg22309566 | 19 | 30155122 | Lower in Drinkers |
| cg22309826 | 17 | 17184440 | Higher in Drinkers |
| cg22313322 | 6 | 160212070 | Higher in Drinkers |
| cg22317004 | 11 | 1360335 | Higher in Drinkers |
| cg22317537 | 8 | 144099822 | Higher in Drinkers |
| cg22319470 | 3 | 13521370 | Higher in Drinkers |
| cg22321089 | 13 | 21649722 | Higher in Drinkers |
| cg22325480 | 8 | 131029139 | Higher in Drinkers |
| cg22325580 | 8 | 1899943 | Higher in Drinkers |
| cg22325715 | 17 | 40951156 | Higher in Drinkers |
| cg22336633 | 11 | 17099688 | Higher in Drinkers |
| cg22339338 | 1 | 159891638 | Higher in Drinkers |
| cg22339486 | 1 | 151762630 | Higher in Drinkers |
| cg22340644 | 7 | 75368344 | Higher in Drinkers |
| cg22343640 | 19 | 49866923 | Higher in Drinkers |
| cg22343980 | 1 | 168148117 | Higher in Drinkers |
| cg22344912 | 15 | 81282399 | Higher in Drinkers |
| cg22345246 | 19 | 12722009 | Higher in Drinkers |
| cg22345576 | 19 | 36000517 | Higher in Drinkers |
| cg22351880 | 19 | 6212534 | Higher in Drinkers |
| cg22352818 | 2 | 97193289 | Higher in Drinkers |
| cg22356009 | 2 | 25143672 | Higher in Drinkers |
| cg22356198 | 2 | 192015914 | Higher in Drinkers |
| cg22358708 | 1 | 185126161 | Higher in Drinkers |
| cg22366350 | 12 | 57082604 | Higher in Drinkers |
| cg22367144 | 15 | 48010299 | Higher in Drinkers |
| cg22367350 | 20 | 3801622 | Higher in Drinkers |
| cg22368426 | 2 | 26523591 | Higher in Drinkers |
| cg22370252 | 12 | 54446289 | Higher in Drinkers |
| cg22372182 | 1 | 223566669 | Lower in Drinkers |
| cg22373112 | 17 | 40307717 | Higher in Drinkers |
| cg22373415 | 15 | 66996361 | Higher in Drinkers |
| cg22376415 | 6 | 150326323 | Higher in Drinkers |

| | | | |
|---|---|---|---|
| cg22379708 | 1 | 962918 | Lower in Drinkers |
| cg22393765 | 4 | 40319286 | Higher in Drinkers |
| cg22394119 | 7 | 99869529 | Higher in Drinkers |
| cg22395250 | 11 | 62495981 | Higher in Drinkers |
| cg22403971 | 6 | 119671423 | Higher in Drinkers |
| cg22406543 | 6 | 18155584 | Higher in Drinkers |
| cg22410544 | 20 | 47242218 | Higher in Drinkers |
| cg22412612 | 16 | 25123200 | Higher in Drinkers |
| cg22413379 | 15 | 86338234 | Higher in Drinkers |
| cg22425355 | 12 | 100660827 | Higher in Drinkers |
| cg22429121 | 1 | 27901805 | Higher in Drinkers |
| cg22431262 | 1 | 149144849 | Higher in Drinkers |
| cg22432367 | 6 | 157098650 | Higher in Drinkers |
| cg22434226 | 5 | 139554488 | Higher in Drinkers |
| cg22436081 | 4 | 122791769 | Higher in Drinkers |
| cg22439857 | 7 | 77166225 | Higher in Drinkers |
| cg22447839 | 9 | 101569843 | Higher in Drinkers |
| cg22450733 | 6 | 30164801 | Higher in Drinkers |
| cg22451189 | 3 | 139062925 | Higher in Drinkers |
| cg22451358 | 17 | 55938871 | Higher in Drinkers |
| cg22456785 | 19 | 36822770 | Higher in Drinkers |
| cg22457660 | 12 | 27091278 | Higher in Drinkers |
| cg22458065 | 6 | 31108108 | Higher in Drinkers |
| cg22463444 | 3 | 170146757 | Higher in Drinkers |
| cg22464447 | 15 | 91054211 | Lower in Drinkers |
| cg22464548 | 3 | 185000648 | Higher in Drinkers |
| cg22465238 | 3 | 163966982 | Higher in Drinkers |
| cg22471695 | X | 54522366 | Higher in Drinkers |
| cg22478328 | 22 | 32340140 | Higher in Drinkers |
| cg22484503 | X | 150565302 | Higher in Drinkers |
| cg22485363 | 1 | 872385 | Lower in Drinkers |
| cg22486699 | 6 | 166825896 | Higher in Drinkers |
| cg22488975 | 1 | 184724009 | Higher in Drinkers |
| cg22491171 | 6 | 42989183 | Higher in Drinkers |
| cg22492068 | 1 | 226070656 | Higher in Drinkers |

| | | | |
|---|---|---|---|
| cg22494001 | 6 | 119400041 | Higher in Drinkers |
| cg22500183 | 17 | 33914271 | Higher in Drinkers |
| cg22500585 | 3 | 52739706 | Higher in Drinkers |
| cg22501143 | 1 | 21110436 | Lower in Drinkers |
| cg22502459 | 8 | 141108998 | Higher in Drinkers |
| cg22502856 | 1 | 209825678 | Higher in Drinkers |
| cg22503499 | 6 | 30294449 | Higher in Drinkers |
| cg22508530 | 1 | 44454816 | Lower in Drinkers |
| cg22509399 | 6 | 31707513 | Higher in Drinkers |
| cg22511455 | 1 | 207096773 | Higher in Drinkers |
| cg22512536 | 5 | 154134507 | Higher in Drinkers |
| cg22514253 | 22 | 18507014 | Higher in Drinkers |
| cg22515201 | 22 | 38577827 | Higher in Drinkers |
| cg22515636 | 2 | 109150313 | Higher in Drinkers |
| cg22515937 | 1 | 157790499 | Higher in Drinkers |
| cg22516975 | 17 | 1617465 | Higher in Drinkers |
| cg22518127 | 22 | 30820257 | Higher in Drinkers |
| cg22518733 | 17 | 34417575 | Higher in Drinkers |
| cg22537081 | 7 | 45151378 | Higher in Drinkers |
| cg22539914 | 12 | 56435921 | Higher in Drinkers |
| cg22544007 | 2 | 133037006 | Higher in Drinkers |
| cg22546055 | 2 | 37311445 | Higher in Drinkers |
| cg22553081 | 3 | 53289290 | Higher in Drinkers |
| cg22553641 | 7 | 100136710 | Higher in Drinkers |
| cg22556020 | 1 | 246952914 | Lower in Drinkers |
| cg22560214 | 4 | 13531213 | Higher in Drinkers |
| cg22563040 | 5 | 53606129 | Higher in Drinkers |
| cg22565033 | 10 | 111968112 | Higher in Drinkers |
| cg22569627 | X | 119385611 | Higher in Drinkers |
| cg22575261 | 15 | 75471218 | Higher in Drinkers |
| cg22575599 | 12 | 56211698 | Higher in Drinkers |
| cg22580905 | 12 | 56843287 | Higher in Drinkers |
| cg22582569 | 11 | 111636425 | Higher in Drinkers |
| cg22585224 | 4 | 122617723 | Higher in Drinkers |
| cg22587509 | 13 | 50356916 | Lower in Drinkers |

| | | | |
|---|---|---|---|
| cg22593889 | 19 | 53951781 | Higher in Drinkers |
| cg22594055 | 5 | 131832675 | Higher in Drinkers |
| cg22595315 | 3 | 31494702 | Higher in Drinkers |
| cg22595391 | 17 | 80407031 | Higher in Drinkers |
| cg22595719 | 3 | 126328018 | Higher in Drinkers |
| cg22599148 | 4 | 1334055 | Lower in Drinkers |
| cg22600945 | 13 | 27825611 | Higher in Drinkers |
| cg22601421 | 4 | 40632299 | Higher in Drinkers |
| cg22608147 | 4 | 77069698 | Higher in Drinkers |
| cg22609068 | 16 | 31711784 | Higher in Drinkers |
| cg22610423 | 21 | 26930131 | Higher in Drinkers |
| cg22614355 | 1 | 19991237 | Higher in Drinkers |
| cg22617819 | 1 | 44378782 | Higher in Drinkers |
| cg22618240 | 19 | 35645556 | Higher in Drinkers |
| cg22619386 | 3 | 179280643 | Higher in Drinkers |
| cg22624926 | 14 | 35761401 | Higher in Drinkers |
| cg22631818 | 13 | 114875001 | Higher in Drinkers |
| cg22633769 | 20 | 60982531 | Higher in Drinkers |
| cg22635717 | 5 | 137367832 | Higher in Drinkers |
| cg22637872 | 16 | 67875820 | Higher in Drinkers |
| cg22638268 | 16 | 87416934 | Higher in Drinkers |
| cg22638491 | 14 | 73706676 | Higher in Drinkers |
| cg22640209 | 2 | 225905741 | Higher in Drinkers |
| cg22640213 | 5 | 149340154 | Higher in Drinkers |
| cg22645062 | 19 | 49494771 | Lower in Drinkers |
| cg22647970 | 19 | 38993309 | Higher in Drinkers |
| cg22651493 | 17 | 35242447 | Higher in Drinkers |
| cg22655767 | 20 | 39312602 | Higher in Drinkers |
| cg22658884 | 19 | 14192470 | Higher in Drinkers |
| cg22659049 | 4 | 41646672 | Lower in Drinkers |
| cg22659922 | 5 | 34532576 | Higher in Drinkers |
| cg22660341 | 10 | 11343613 | Lower in Drinkers |
| cg22660933 | 17 | 46608355 | Lower in Drinkers |
| cg22661950 | 4 | 76861805 | Higher in Drinkers |
| cg22663489 | 11 | 64107720 | Higher in Drinkers |

| | | | |
|---|---|---|---|
| cg22666115 | 6 | 30182186 | Higher in Drinkers |
| cg22668249 | 12 | 117188015 | Higher in Drinkers |
| cg22671726 | 19 | 41305423 | Higher in Drinkers |
| cg22671939 | 10 | 1000300 | Higher in Drinkers |
| cg22676424 | 19 | 17337071 | Higher in Drinkers |
| cg22678739 | 6 | 1555080 | Lower in Drinkers |
| cg22681246 | 12 | 6304747 | Higher in Drinkers |
| cg22682215 | 1 | 228589691 | Higher in Drinkers |
| cg22684008 | 4 | 122871528 | Higher in Drinkers |
| cg22684041 | 19 | 1904554 | Higher in Drinkers |
| cg22685463 | 17 | 7387363 | Higher in Drinkers |
| cg22687416 | 1 | 47184410 | Higher in Drinkers |
| cg22690576 | 15 | 91260127 | Higher in Drinkers |
| cg22691746 | 11 | 76381450 | Higher in Drinkers |
| cg22692281 | 6 | 30104900 | Higher in Drinkers |
| cg22693042 | 3 | 120068225 | Higher in Drinkers |
| cg22694526 | 17 | 17875567 | Higher in Drinkers |
| cg22696214 | 5 | 55033753 | Lower in Drinkers |
| cg22698023 | 5 | 400494 | Higher in Drinkers |
| cg22703115 | 17 | 46621297 | Higher in Drinkers |
| cg22706980 | 19 | 8495776 | Higher in Drinkers |
| cg22708752 | 2 | 54853191 | Lower in Drinkers |
| cg22713892 | X | 47342160 | Higher in Drinkers |
| cg22718540 | 1 | 39874874 | Higher in Drinkers |
| cg22718774 | 11 | 236527 | Higher in Drinkers |
| cg22721186 | 8 | 124408918 | Higher in Drinkers |
| cg22721993 | 13 | 110522149 | Lower in Drinkers |
| cg22722933 | 12 | 53473604 | Higher in Drinkers |
| cg22723056 | 11 | 7273378 | Higher in Drinkers |
| cg22726373 | 15 | 79048467 | Lower in Drinkers |
| cg22729543 | 7 | 98991418 | Higher in Drinkers |
| cg22745781 | 7 | 16461244 | Higher in Drinkers |
| cg22748573 | 1 | 41327924 | Higher in Drinkers |
| cg22748850 | 5 | 137667638 | Higher in Drinkers |
| cg22750483 | 8 | 119964248 | Higher in Drinkers |

| | | | |
|---|---|---|---|
| cg22752895 | 6 | 3118674 | Higher in Drinkers |
| cg22756555 | 2 | 162017219 | Higher in Drinkers |
| cg22761619 | 7 | 135242648 | Higher in Drinkers |
| cg22762076 | 19 | 7069572 | Higher in Drinkers |
| cg22764338 | 5 | 141257604 | Higher in Drinkers |
| cg22764374 | 12 | 12163421 | Higher in Drinkers |
| cg22767735 | 17 | 19551663 | Higher in Drinkers |
| cg22770592 | 15 | 63797403 | Higher in Drinkers |
| cg22770727 | 20 | 4573424 | Higher in Drinkers |
| cg22772355 | 19 | 55865356 | Higher in Drinkers |
| cg22776235 | 6 | 362023 | Lower in Drinkers |
| cg22777890 | 14 | 64761409 | Higher in Drinkers |
| cg22782492 | 3 | 10134007 | Higher in Drinkers |
| cg22784589 | 14 | 73359812 | Higher in Drinkers |
| cg22784898 | 19 | 4237215 | Higher in Drinkers |
| cg22785468 | 12 | 49741527 | Higher in Drinkers |
| cg22786826 | 16 | 2564780 | Higher in Drinkers |
| cg22788646 | 12 | 132512003 | Higher in Drinkers |
| cg22790934 | 14 | 55368442 | Higher in Drinkers |
| cg22792272 | 6 | 43597128 | Higher in Drinkers |
| cg22793129 | 19 | 2085297 | Higher in Drinkers |
| cg22794795 | 12 | 113623087 | Higher in Drinkers |
| cg22795185 | 1 | 174129340 | Higher in Drinkers |
| cg22797570 | 3 | 24563278 | Higher in Drinkers |
| cg22799656 | 7 | 142494564 | Higher in Drinkers |
| cg22800332 | 5 | 138775207 | Higher in Drinkers |
| cg22801296 | 19 | 44031497 | Higher in Drinkers |
| cg22801561 | 17 | 55562964 | Higher in Drinkers |
| cg22802068 | 17 | 900285 | Higher in Drinkers |
| cg22802759 | 1 | 185015193 | Higher in Drinkers |
| cg22803868 | 17 | 27045164 | Higher in Drinkers |
| cg22807592 | X | 101967307 | Higher in Drinkers |
| cg22807608 | 17 | 17594719 | Higher in Drinkers |
| cg22808351 | 1 | 156783633 | Higher in Drinkers |
| cg22812516 | 3 | 93698768 | Higher in Drinkers |

| | | | |
|---|---|---|---|
| cg22814929 | 6 | 26458213 | Higher in Drinkers |
| cg22816213 | 6 | 3091462 | Higher in Drinkers |
| cg22822446 | 10 | 26883013 | Lower in Drinkers |
| cg22824767 | 3 | 141497263 | Higher in Drinkers |
| cg22827524 | 1 | 222910746 | Higher in Drinkers |
| cg22831315 | 13 | 36921003 | Higher in Drinkers |
| cg22833292 | 11 | 64126806 | Higher in Drinkers |
| cg22836370 | 18 | 51751085 | Higher in Drinkers |
| cg22837499 | 11 | 18417924 | Higher in Drinkers |
| cg22844499 | X | 19002190 | Higher in Drinkers |
| cg22849526 | 7 | 6199437 | Higher in Drinkers |
| cg22852353 | 1 | 165171672 | Lower in Drinkers |
| cg22852489 | 19 | 12904394 | Higher in Drinkers |
| cg22853526 | 1 | 113216965 | Higher in Drinkers |
| cg22855052 | 12 | 6982535 | Higher in Drinkers |
| cg22857872 | 1 | 39492366 | Higher in Drinkers |
| cg22858872 | 22 | 21984431 | Higher in Drinkers |
| cg22859370 | 7 | 2805124 | Higher in Drinkers |
| cg22859423 | 1 | 154842362 | Higher in Drinkers |
| cg22859847 | 21 | 30396798 | Higher in Drinkers |
| cg22863042 | 6 | 136571719 | Higher in Drinkers |
| cg22863629 | 6 | 31593323 | Higher in Drinkers |
| cg22865050 | 19 | 11457020 | Higher in Drinkers |
| cg22866085 | 1 | 31538712 | Higher in Drinkers |
| cg22870994 | 11 | 71340352 | Higher in Drinkers |
| cg22871604 | 1 | 26146196 | Higher in Drinkers |
| cg22873130 | 8 | 6264171 | Higher in Drinkers |
| cg22873562 | 3 | 133969914 | Higher in Drinkers |
| cg22874695 | 8 | 42397328 | Higher in Drinkers |
| cg22874829 | X | 115004495 | Higher in Drinkers |
| cg22874893 | 6 | 17281624 | Higher in Drinkers |
| cg22874960 | 16 | 15737314 | Higher in Drinkers |
| cg22876425 | X | 150152212 | Higher in Drinkers |
| cg22877281 | 22 | 20077456 | Higher in Drinkers |
| cg22877380 | 2 | 131804299 | Higher in Drinkers |

| | | | |
|---|---|---|---|
| cg22873469 | 5 | 235427 | Higher in Drinkers |
| cg22880714 | 6 | 43136798 | Higher in Drinkers |
| cg22885526 | 10 | 63326774 | Higher in Drinkers |
| cg22885821 | 20 | 57465921 | Higher in Drinkers |
| cg22891408 | 3 | 131221887 | Higher in Drinkers |
| cg22891988 | 11 | 30607959 | Higher in Drinkers |
| cg22894353 | 11 | 9112989 | Higher in Drinkers |
| cg22898334 | 5 | 169013399 | Higher in Drinkers |
| cg22900705 | 1 | 155023903 | Higher in Drinkers |
| cg22903286 | 14 | 77564084 | Higher in Drinkers |
| cg22903848 | 3 | 194924418 | Higher in Drinkers |
| cg22911074 | 5 | 6632973 | Higher in Drinkers |
| cg22911113 | 14 | 106089857 | Lower in Drinkers |
| cg22911799 | 1 | 156475319 | Higher in Drinkers |
| cg22912011 | X | 47696222 | Higher in Drinkers |
| cg22914389 | 3 | 44379917 | Higher in Drinkers |
| cg22914762 | 4 | 117220908 | Higher in Drinkers |
| cg22916254 | 12 | 96256561 | Lower in Drinkers |
| cg22918432 | 16 | 31471293 | Higher in Drinkers |
| cg22919370 | 6 | 27840212 | Higher in Drinkers |
| cg22924269 | 13 | 50069722 | Higher in Drinkers |
| cg22929104 | 3 | 101396044 | Higher in Drinkers |
| cg22929787 | 5 | 141737266 | Higher in Drinkers |
| cg22931309 | 12 | 123718298 | Higher in Drinkers |
| cg22931362 | 14 | 73493944 | Higher in Drinkers |
| cg22932313 | 11 | 34535189 | Lower in Drinkers |
| cg22934035 | 6 | 31549480 | Higher in Drinkers |
| cg22935207 | 14 | 90701850 | Higher in Drinkers |
| cg22938488 | 5 | 1501670 | Higher in Drinkers |
| cg22944122 | 2 | 148779335 | Higher in Drinkers |
| cg22945302 | 1 | 26606601 | Higher in Drinkers |
| cg22948319 | 19 | 39620117 | Higher in Drinkers |
| cg22949881 | 12 | 9601149 | Higher in Drinkers |
| cg22952566 | 6 | 30457271 | Higher in Drinkers |
| cg22955449 | 10 | 106028519 | Higher in Drinkers |

| | | | |
|---|---|---|---|
| cg22959667 | 2 | 109745614 | Higher in Drinkers |
| cg22964183 | 5 | 68533366 | Higher in Drinkers |
| cg22968175 | 19 | 42721878 | Higher in Drinkers |
| cg22968727 | 1 | 24018140 | Higher in Drinkers |
| cg22974452 | 2 | 36825379 | Higher in Drinkers |
| cg22974837 | 8 | 25315063 | Higher in Drinkers |
| cg22975147 | 17 | 8021903 | Higher in Drinkers |
| cg22976832 | 10 | 112295835 | Higher in Drinkers |
| cg22981738 | 19 | 56136128 | Higher in Drinkers |
| cg22983529 | 7 | 93551132 | Higher in Drinkers |
| cg22984099 | 6 | 33216195 | Higher in Drinkers |
| cg22985785 | 1 | 22352096 | Higher in Drinkers |
| cg22989161 | 8 | 145531953 | Higher in Drinkers |
| cg22990967 | 6 | 167567203 | Higher in Drinkers |
| cg22992472 | 10 | 96305176 | Higher in Drinkers |
| cg22992815 | 6 | 28641704 | Higher in Drinkers |
| cg22996215 | 19 | 44037154 | Higher in Drinkers |
| cg22997601 | 19 | 5115624 | Higher in Drinkers |
| cg23000464 | 19 | 633785 | Higher in Drinkers |
| cg23005387 | 12 | 4382878 | Higher in Drinkers |
| cg23009044 | 17 | 8736293 | Lower in Drinkers |
| cg23010452 | 19 | 34013117 | Higher in Drinkers |
| cg23017542 | 4 | 103266043 | Higher in Drinkers |
| cg23021584 | 12 | 124876101 | Higher in Drinkers |
| cg23023263 | 3 | 42003964 | Higher in Drinkers |
| cg23024262 | 10 | 54715153 | Higher in Drinkers |
| cg23027345 | 5 | 114598653 | Higher in Drinkers |
| cg23029185 | 19 | 42588594 | Lower in Drinkers |
| cg23033866 | 17 | 79670804 | Higher in Drinkers |
| cg23035555 | 19 | 3500370 | Higher in Drinkers |
| cg23037918 | 19 | 7600138 | Higher in Drinkers |
| cg23044136 | 5 | 141223416 | Higher in Drinkers |
| cg23044391 | 19 | 7685239 | Higher in Drinkers |
| cg23047134 | 19 | 643164 | Higher in Drinkers |
| cg23047920 | 14 | 90864981 | Higher in Drinkers |

| | | | |
|---|---|---|---|
| cg23048334 | 4 | 99850664 | Higher in Drinkers |
| cg23051664 | 8 | 23020966 | Higher in Drinkers |
| cg23053658 | 13 | 113508799 | Lower in Drinkers |
| cg23054676 | 5 | 7869265 | Higher in Drinkers |
| cg23058673 | 7 | 5422234 | Higher in Drinkers |
| cg23062115 | 5 | 143550050 | Higher in Drinkers |
| cg23065576 | 20 | 25207247 | Higher in Drinkers |
| cg23068124 | 14 | 58711505 | Higher in Drinkers |
| cg23076591 | 22 | 28197571 | Higher in Drinkers |
| cg23077461 | 19 | 57946619 | Higher in Drinkers |
| cg23082845 | 1 | 1159282 | Lower in Drinkers |
| cg23091406 | 4 | 185395982 | Higher in Drinkers |
| cg23094339 | 2 | 43036991 | Higher in Drinkers |
| cg23097277 | 12 | 27676539 | Higher in Drinkers |
| cg23097935 | 8 | 22552961 | Higher in Drinkers |
| cg23098371 | 1 | 92012061 | Higher in Drinkers |
| cg23101259 | 11 | 76156096 | Higher in Drinkers |
| cg23102026 | 19 | 35493343 | Higher in Drinkers |
| cg23104592 | 17 | 47443155 | Higher in Drinkers |
| cg23115390 | 6 | 45784526 | Lower in Drinkers |
| cg23116670 | 14 | 102493911 | Higher in Drinkers |
| cg23117565 | 22 | 21817930 | Lower in Drinkers |
| cg23118401 | 20 | 36032645 | Higher in Drinkers |
| cg23119628 | 8 | 141629666 | Higher in Drinkers |
| cg23120042 | 17 | 71088875 | Higher in Drinkers |
| cg23121301 | 14 | 96001268 | Higher in Drinkers |
| cg23121587 | 20 | 8000706 | Higher in Drinkers |
| cg23123362 | 5 | 157158174 | Higher in Drinkers |
| cg23123679 | 12 | 49351256 | Higher in Drinkers |
| cg23129292 | 6 | 42847165 | Higher in Drinkers |
| cg23130766 | 6 | 149969500 | Higher in Drinkers |
| cg23142935 | 16 | 22385308 | Higher in Drinkers |
| cg23145622 | 1 | 206859650 | Higher in Drinkers |
| cg23146565 | 17 | 46100661 | Higher in Drinkers |
| cg23146632 | 3 | 52393309 | Higher in Drinkers |

| | | | |
|---|---|---|---|
| cg23154620 | 8 | 100025155 | Higher in Drinkers |
| cg23155606 | 13 | 19172793 | Higher in Drinkers |
| cg23157637 | 14 | 20881440 | Higher in Drinkers |
| cg23163999 | 3 | 125803012 | Higher in Drinkers |
| cg23165208 | 16 | 30007561 | Higher in Drinkers |
| cg23166740 | 15 | 45440540 | Higher in Drinkers |
| cg23167178 | 3 | 126701687 | Higher in Drinkers |
| cg23167246 | 13 | 114150035 | Lower in Drinkers |
| cg23170237 | 6 | 31595725 | Higher in Drinkers |
| cg23172606 | 16 | 4784147 | Higher in Drinkers |
| cg23172877 | 12 | 12878810 | Higher in Drinkers |
| cg23172898 | 14 | 34931803 | Higher in Drinkers |
| cg23173495 | 5 | 65018638 | Higher in Drinkers |
| cg23173517 | 15 | 81567548 | Higher in Drinkers |
| cg23178308 | 21 | 45148879 | Higher in Drinkers |
| cg23180925 | 17 | 80753497 | Higher in Drinkers |
| cg23182539 | 10 | 121355708 | Higher in Drinkers |
| cg23187205 | 6 | 109416245 | Higher in Drinkers |
| cg23193153 | 6 | 34192178 | Higher in Drinkers |
| cg23194024 | 17 | 38278610 | Higher in Drinkers |
| cg23194281 | 11 | 85565930 | Higher in Drinkers |
| cg23196732 | 7 | 140397039 | Higher in Drinkers |
| cg23196783 | 10 | 71139842 | Higher in Drinkers |
| cg23199335 | 3 | 177315882 | Higher in Drinkers |
| cg23202349 | 5 | 178053533 | Higher in Drinkers |
| cg23204556 | 15 | 42066489 | Higher in Drinkers |
| cg23211158 | 6 | 28872382 | Higher in Drinkers |
| cg23213442 | 4 | 47916056 | Higher in Drinkers |
| cg23213696 | 7 | 43622379 | Higher in Drinkers |
| cg23217233 | 6 | 5039003 | Lower in Drinkers |
| cg23225637 | 17 | 76989965 | Higher in Drinkers |
| cg23229228 | 3 | 98312354 | Higher in Drinkers |
| cg23233589 | 6 | 152958624 | Higher in Drinkers |
| cg23233605 | 9 | 130548199 | Higher in Drinkers |
| cg23234154 | 4 | 103682690 | Higher in Drinkers |

| | | | |
|---|---|---|---|
| cg23235291 | 2 | 220094601 | Higher in Drinkers |
| cg23237976 | 1 | 236318493 | Lower in Drinkers |
| cg23239754 | 6 | 27760147 | Higher in Drinkers |
| cg23243400 | 7 | 20818844 | Higher in Drinkers |
| cg23243994 | 7 | 139045033 | Higher in Drinkers |
| cg23244997 | 1 | 169763992 | Higher in Drinkers |
| cg23246509 | 11 | 60689766 | Higher in Drinkers |
| cg23249336 | 13 | 47127304 | Higher in Drinkers |
| cg23249717 | 6 | 167507105 | Lower in Drinkers |
| cg23252902 | 6 | 711405 | Higher in Drinkers |
| cg23253272 | 20 | 31989417 | Higher in Drinkers |
| cg23253448 | 8 | 22548828 | Higher in Drinkers |
| cg23254184 | 14 | 53620237 | Higher in Drinkers |
| cg23256899 | 11 | 68177462 | Higher in Drinkers |
| cg23257110 | 1 | 153935815 | Higher in Drinkers |
| cg23266151 | 14 | 102263636 | Higher in Drinkers |
| cg23267944 | 2 | 232329239 | Higher in Drinkers |
| cg23270617 | 7 | 90032717 | Higher in Drinkers |
| cg23271318 | 20 | 44509620 | Higher in Drinkers |
| cg23271606 | 7 | 92464891 | Higher in Drinkers |
| cg23271998 | 2 | 3260576 | Higher in Drinkers |
| cg23276829 | 6 | 166720114 | Higher in Drinkers |
| cg23277389 | 8 | 49834543 | Higher in Drinkers |
| cg23278235 | 12 | 133101168 | Higher in Drinkers |
| cg23279559 | 21 | 17101917 | Higher in Drinkers |
| cg23280339 | X | 48754501 | Higher in Drinkers |
| cg23280681 | 16 | 12070416 | Higher in Drinkers |
| cg23285320 | 19 | 36546349 | Higher in Drinkers |
| cg23285573 | 7 | 95064174 | Higher in Drinkers |
| cg23288755 | 1 | 1957320 | Higher in Drinkers |
| cg23300897 | 9 | 132598185 | Higher in Drinkers |
| cg23302845 | 6 | 33386057 | Higher in Drinkers |
| cg23307385 | 19 | 50316618 | Higher in Drinkers |
| cg23310538 | 12 | 45610452 | Higher in Drinkers |
| cg23313005 | 5 | 176965046 | Higher in Drinkers |

| | | | |
|---|---|---|---|
| cg23314506 | 13 | 46626917 | Higher in Drinkers |
| cg23316671 | 5 | 60241324 | Higher in Drinkers |
| cg23320056 | 1 | 155948742 | Higher in Drinkers |
| cg23322432 | 20 | 48770456 | Higher in Drinkers |
| cg23324824 | 7 | 5634408 | Higher in Drinkers |
| cg23326824 | 6 | 30585730 | Higher in Drinkers |
| cg23329902 | 22 | 24951519 | Higher in Drinkers |
| cg23330842 | 15 | 65810167 | Higher in Drinkers |
| cg23338737 | 6 | 31636396 | Higher in Drinkers |
| cg23338922 | 7 | 98608683 | Higher in Drinkers |
| cg23340525 | 11 | 94227081 | Higher in Drinkers |
| cg23340875 | 17 | 48711990 | Higher in Drinkers |
| cg23342323 | 5 | 71398999 | Higher in Drinkers |
| cg23343264 | 12 | 118454133 | Higher in Drinkers |
| cg23345642 | 6 | 33378010 | Higher in Drinkers |
| cg23345951 | 5 | 132080727 | Higher in Drinkers |
| cg23352145 | 13 | 21751331 | Higher in Drinkers |
| cg23354778 | 10 | 68281544 | Higher in Drinkers |
| cg23355992 | 20 | 48998616 | Higher in Drinkers |
| cg23358625 | 19 | 23945641 | Higher in Drinkers |
| cg23358871 | 17 | 78121069 | Higher in Drinkers |
| cg23359706 | 19 | 11491839 | Higher in Drinkers |
| cg23361608 | 21 | 38446389 | Higher in Drinkers |
| cg23363526 | 22 | 25003552 | Higher in Drinkers |
| cg23363818 | 19 | 12142606 | Higher in Drinkers |
| cg23363911 | 17 | 8055756 | Higher in Drinkers |
| cg23365345 | 19 | 35455225 | Higher in Drinkers |
| cg23366752 | 15 | 78556502 | Higher in Drinkers |
| cg23370170 | 4 | 12634832 | Higher in Drinkers |
| cg23371106 | 7 | 147960123 | Higher in Drinkers |
| cg23371683 | 20 | 61443040 | Higher in Drinkers |
| cg23378840 | 6 | 47443521 | Higher in Drinkers |
| cg23381028 | 6 | 164088958 | Higher in Drinkers |
| cg23388020 | 14 | 70512877 | Lower in Drinkers |
| cg23390865 | X | 47518016 | Higher in Drinkers |

| | | | |
|---|---|---|---|
| cg23391171 | 13 | 41634374 | Higher in Drinkers |
| cg23391641 | 14 | 92970263 | Higher in Drinkers |
| cg23394653 | 13 | 77601699 | Higher in Drinkers |
| cg23396403 | 5 | 94890852 | Higher in Drinkers |
| cg23398886 | 19 | 16308494 | Higher in Drinkers |
| cg23405870 | 13 | 96329610 | Higher in Drinkers |
| cg23409608 | 8 | 128878013 | Higher in Drinkers |
| cg23410627 | 10 | 90966807 | Higher in Drinkers |
| cg23411652 | 3 | 19989218 | Higher in Drinkers |
| cg23411735 | 2 | 62423075 | Higher in Drinkers |
| cg23414228 | 1 | 155043413 | Higher in Drinkers |
| cg23417523 | 13 | 114108012 | Higher in Drinkers |
| cg23424268 | 15 | 41056053 | Higher in Drinkers |
| cg23424988 | 6 | 111929206 | Lower in Drinkers |
| cg23425324 | 12 | 26986193 | Higher in Drinkers |
| cg23428387 | 22 | 49814324 | Lower in Drinkers |
| cg23433113 | 8 | 9008373 | Higher in Drinkers |
| cg23435080 | 3 | 193852995 | Higher in Drinkers |
| cg23435821 | 12 | 109592934 | Higher in Drinkers |
| cg23437836 | 1 | 1335601 | Higher in Drinkers |
| cg23443106 | 17 | 26898719 | Higher in Drinkers |
| cg23444101 | 5 | 122758823 | Higher in Drinkers |
| cg23449541 | 21 | 47855893 | Higher in Drinkers |
| cg23450974 | 17 | 47022343 | Higher in Drinkers |
| cg23451324 | 19 | 11708147 | Higher in Drinkers |
| cg23454289 | 7 | 101843143 | Higher in Drinkers |
| cg23455785 | 1 | 200117203 | Higher in Drinkers |
| cg23456595 | 11 | 67203434 | Lower in Drinkers |
| cg23459997 | 3 | 9932426 | Higher in Drinkers |
| cg23460369 | 17 | 79260991 | Higher in Drinkers |
| cg23463917 | 5 | 112258131 | Higher in Drinkers |
| cg23466054 | 19 | 22018892 | Higher in Drinkers |
| cg23466183 | 2 | 3622655 | Higher in Drinkers |
| cg23467443 | 4 | 174255725 | Higher in Drinkers |
| cg23468927 | 11 | 67206263 | Lower in Drinkers |

| | | | |
|---|---|---|---|
| cg23472166 | 5 | 130600109 | Higher in Drinkers |
| cg23472930 | 16 | 15150079 | Higher in Drinkers |
| cg23475053 | 19 | 36705660 | Higher in Drinkers |
| cg23478105 | 15 | 65579253 | Higher in Drinkers |
| cg23479988 | 7 | 87225898 | Higher in Drinkers |
| cg23480985 | 3 | 5018700 | Higher in Drinkers |
| cg23481986 | 3 | 49507266 | Higher in Drinkers |
| cg23494853 | 2 | 150443987 | Higher in Drinkers |
| cg23500601 | 19 | 17502346 | Higher in Drinkers |
| cg23512558 | 12 | 116997079 | Higher in Drinkers |
| cg23513504 | 21 | 45432403 | Higher in Drinkers |
| cg23515921 | 17 | 80747189 | Higher in Drinkers |
| cg23516949 | 15 | 44092937 | Higher in Drinkers |
| cg23517548 | 16 | 28962521 | Higher in Drinkers |
| cg23520726 | 13 | 45563622 | Higher in Drinkers |
| cg23524524 | X | 49020116 | Higher in Drinkers |
| cg23525200 | 11 | 49581783 | Higher in Drinkers |
| cg23526071 | 3 | 126749321 | Higher in Drinkers |
| cg23526353 | 4 | 100484905 | Higher in Drinkers |
| cg23527366 | 3 | 52010415 | Higher in Drinkers |
| cg23529390 | 18 | 74843361 | Higher in Drinkers |
| cg23530288 | 11 | 236658 | Higher in Drinkers |
| cg23533073 | 14 | 89884062 | Higher in Drinkers |
| cg23536277 | 3 | 149470345 | Higher in Drinkers |
| cg23536530 | 3 | 107647202 | Lower in Drinkers |
| cg23538468 | 9 | 140588019 | Higher in Drinkers |
| cg23542308 | 14 | 105940762 | Higher in Drinkers |
| cg23545322 | 17 | 43025282 | Higher in Drinkers |
| cg23547892 | 14 | 93170710 | Higher in Drinkers |
| cg23548928 | 12 | 14720249 | Lower in Drinkers |
| cg23550757 | 12 | 120755296 | Higher in Drinkers |
| cg23553659 | 13 | 46627004 | Higher in Drinkers |
| cg23554129 | 6 | 53413076 | Higher in Drinkers |
| cg23554546 | X | 118987202 | Higher in Drinkers |
| cg23555471 | 12 | 113534591 | Lower in Drinkers |

| | | | |
|---|---|---|---|
| cg23556238 | 12 | 125298876 | Higher in Drinkers |
| cg23556447 | 6 | 90529595 | Higher in Drinkers |
| cg23561979 | 2 | 42329535 | Higher in Drinkers |
| cg23566411 | 11 | 65264681 | Higher in Drinkers |
| cg23577550 | 6 | 100677145 | Higher in Drinkers |
| cg23582405 | 14 | 74551333 | Higher in Drinkers |
| cg23583291 | 18 | 56807054 | Higher in Drinkers |
| cg23585978 | 2 | 72377758 | Higher in Drinkers |
| cg23588553 | 12 | 57623699 | Higher in Drinkers |
| cg23590699 | X | 11776935 | Higher in Drinkers |
| cg23592730 | 17 | 33570795 | Higher in Drinkers |
| cg23594345 | 14 | 106329607 | Higher in Drinkers |
| cg23594461 | 1 | 201088537 | Higher in Drinkers |
| cg23599843 | 8 | 75234269 | Higher in Drinkers |
| cg23604012 | 2 | 223289173 | Higher in Drinkers |
| cg23607253 | 4 | 128801899 | Higher in Drinkers |
| cg23609821 | 14 | 20937494 | Higher in Drinkers |
| cg23610420 | 1 | 206859216 | Higher in Drinkers |
| cg23611233 | 1 | 249133059 | Higher in Drinkers |
| cg23614852 | 5 | 140769482 | Higher in Drinkers |
| cg23615741 | 10 | 101297642 | Higher in Drinkers |
| cg23616126 | 1 | 247463678 | Higher in Drinkers |
| cg23616139 | 1 | 221051907 | Higher in Drinkers |
| cg23620904 | 19 | 30165018 | Higher in Drinkers |
| cg23623436 | 14 | 32030546 | Higher in Drinkers |
| cg23623478 | 14 | 100784731 | Higher in Drinkers |
| cg23631842 | 1 | 38259884 | Higher in Drinkers |
| cg23632706 | 2 | 171830093 | Higher in Drinkers |
| cg23633526 | 3 | 39448019 | Higher in Drinkers |
| cg23633679 | 1 | 173793655 | Higher in Drinkers |
| cg23633937 | 19 | 45575142 | Higher in Drinkers |
| cg23634079 | 6 | 31712195 | Higher in Drinkers |
| cg23636072 | 11 | 1216443 | Lower in Drinkers |
| cg23636324 | 1 | 92351686 | Higher in Drinkers |
| cg23639257 | 17 | 73663270 | Higher in Drinkers |

| | | | |
|---|---|---|---|
| cg23644213 | 9 | 35096058 | Higher in Drinkers |
| cg23646212 | 1 | 40997434 | Higher in Drinkers |
| cg23647086 | 4 | 47916581 | Higher in Drinkers |
| cg23651798 | 6 | 31630885 | Higher in Drinkers |
| cg23652484 | 1 | 211872653 | Lower in Drinkers |
| cg23652866 | 11 | 63438791 | Higher in Drinkers |
| cg23656755 | 1 | 230203043 | Higher in Drinkers |
| cg23661183 | 10 | 116286593 | Higher in Drinkers |
| cg23661306 | 3 | 57541993 | Higher in Drinkers |
| cg23662097 | 3 | 4873008 | Higher in Drinkers |
| cg23665065 | 14 | 102781012 | Higher in Drinkers |
| cg23668257 | 7 | 99102081 | Higher in Drinkers |
| cg23669517 | 19 | 4247058 | Higher in Drinkers |
| cg23670101 | 10 | 46168396 | Higher in Drinkers |
| cg23671824 | 19 | 10450323 | Higher in Drinkers |
| cg23674107 | 1 | 154580093 | Higher in Drinkers |
| cg23675485 | 12 | 351262 | Lower in Drinkers |
| cg23676475 | 2 | 64455515 | Higher in Drinkers |
| cg23676798 | 7 | 91763850 | Higher in Drinkers |
| cg23677173 | 2 | 197664308 | Higher in Drinkers |
| cg23678114 | 17 | 43212777 | Higher in Drinkers |
| cg23680936 | 10 | 64564801 | Higher in Drinkers |
| cg23684603 | 4 | 185747386 | Higher in Drinkers |
| cg23685155 | 12 | 54396440 | Higher in Drinkers |
| cg23688420 | 17 | 26879359 | Higher in Drinkers |
| cg23688510 | 6 | 166581929 | Higher in Drinkers |
| cg23689080 | 12 | 56159704 | Higher in Drinkers |
| cg23691246 | 10 | 105207034 | Lower in Drinkers |
| cg23691251 | 10 | 123688108 | Higher in Drinkers |
| cg23699670 | 19 | 33664258 | Higher in Drinkers |
| cg23701776 | 19 | 5680879 | Higher in Drinkers |
| cg23702610 | 15 | 100017287 | Higher in Drinkers |
| cg23704066 | 7 | 96339024 | Higher in Drinkers |
| cg23705847 | 14 | 74253388 | Higher in Drinkers |
| cg23706422 | 10 | 89420014 | Higher in Drinkers |

| | | | |
|---|---|---|---|
| cg23715700 | 19 | 16188274 | Higher in Drinkers |
| cg23717686 | 20 | 44044727 | Higher in Drinkers |
| cg23718924 | 2 | 60778617 | Higher in Drinkers |
| cg23723262 | 22 | 31066629 | Higher in Drinkers |
| cg23727043 | 15 | 79104124 | Higher in Drinkers |
| cg23729277 | 12 | 6658945 | Higher in Drinkers |
| cg23729763 | 11 | 129991544 | Higher in Drinkers |
| cg23731846 | 1 | 153921619 | Higher in Drinkers |
| cg23732003 | 5 | 179049816 | Higher in Drinkers |
| cg23732560 | 3 | 45267976 | Higher in Drinkers |
| cg23733753 | 14 | 100151063 | Higher in Drinkers |
| cg23736297 | 17 | 78915881 | Higher in Drinkers |
| cg23743449 | 4 | 141294535 | Higher in Drinkers |
| cg23749163 | 14 | 77563968 | Higher in Drinkers |
| cg23752198 | 20 | 30311963 | Higher in Drinkers |
| cg23761196 | 16 | 58664510 | Higher in Drinkers |
| cg23763424 | 2 | 172967795 | Higher in Drinkers |
| cg23773252 | 7 | 99527224 | Higher in Drinkers |
| cg23779331 | 17 | 4614312 | Higher in Drinkers |
| cg23781003 | 4 | 120988207 | Higher in Drinkers |
| cg23784912 | 18 | 14132582 | Higher in Drinkers |
| cg23789846 | 21 | 30375227 | Higher in Drinkers |
| cg23790220 | 6 | 75994771 | Higher in Drinkers |
| cg23794671 | 6 | 32977580 | Higher in Drinkers |
| cg23796818 | 12 | 56325715 | Higher in Drinkers |
| cg23798332 | 12 | 74932007 | Higher in Drinkers |
| cg23808521 | 12 | 120639051 | Higher in Drinkers |
| cg23813556 | 5 | 68855873 | Higher in Drinkers |
| cg23815915 | 6 | 27440984 | Higher in Drinkers |
| cg23817529 | 2 | 26569797 | Higher in Drinkers |
| cg23818046 | 5 | 64859282 | Higher in Drinkers |
| cg23821145 | 4 | 170696031 | Higher in Drinkers |
| cg23821541 | 2 | 20251993 | Higher in Drinkers |
| cg23821914 | 11 | 66411447 | Higher in Drinkers |
| cg23825069 | 22 | 39795886 | Higher in Drinkers |

| | | | |
|---|---|---|---|
| cg23825482 | 18 | 46503012 | Higher in Drinkers |
| cg23828765 | 12 | 78340971 | Lower in Drinkers |
| cg23830037 | 17 | 17991318 | Higher in Drinkers |
| cg23830326 | 16 | 88637332 | Higher in Drinkers |
| cg23832438 | 7 | 148937111 | Higher in Drinkers |
| cg23834064 | 7 | 73098156 | Higher in Drinkers |
| cg23837867 | 2 | 219849133 | Higher in Drinkers |
| cg23837897 | 17 | 53046270 | Higher in Drinkers |
| cg23840493 | 1 | 154965483 | Higher in Drinkers |
| cg23841361 | 6 | 30524010 | Higher in Drinkers |
| cg23843953 | 1 | 230262390 | Higher in Drinkers |
| cg23848568 | 5 | 55008353 | Higher in Drinkers |
| cg23851027 | 19 | 51857538 | Higher in Drinkers |
| cg23858605 | 6 | 30153868 | Higher in Drinkers |
| cg23863055 | 10 | 15902080 | Higher in Drinkers |
| cg23863900 | 8 | 92082779 | Higher in Drinkers |
| cg23864210 | 21 | 30365465 | Higher in Drinkers |
| cg23865067 | 15 | 52860622 | Higher in Drinkers |
| cg23870903 | 6 | 2790694 | Higher in Drinkers |
| cg23875319 | 10 | 126296314 | Higher in Drinkers |
| cg23877323 | 15 | 90895989 | Higher in Drinkers |
| cg23878603 | 4 | 177241851 | Higher in Drinkers |
| cg23880794 | 22 | 39715126 | Higher in Drinkers |
| cg23881697 | 11 | 64622239 | Higher in Drinkers |
| cg23883215 | 8 | 26240324 | Higher in Drinkers |
| cg23884421 | 19 | 5623195 | Higher in Drinkers |
| cg23884502 | 22 | 21537792 | Higher in Drinkers |
| cg23886314 | 7 | 116272127 | Higher in Drinkers |
| cg23887043 | 12 | 64173542 | Higher in Drinkers |
| cg23888423 | 2 | 242254170 | Higher in Drinkers |
| cg23892439 | 7 | 39332384 | Lower in Drinkers |
| cg23894553 | 22 | 29280180 | Higher in Drinkers |
| cg23895273 | 1 | 18427152 | Higher in Drinkers |
| cg23896816 | 22 | 39473253 | Higher in Drinkers |
| cg23896876 | 7 | 1367727 | Higher in Drinkers |

| | | | |
|---|---|---|---|
| cg23903076 | 11 | 1311527 | Higher in Drinkers |
| cg23903597 | 17 | 61704154 | Higher in Drinkers |
| cg23903723 | 6 | 30655567 | Higher in Drinkers |
| cg23905789 | 6 | 32549935 | Higher in Drinkers |
| cg23907837 | 7 | 129691259 | Higher in Drinkers |
| cg23910787 | 5 | 179234439 | Higher in Drinkers |
| cg23913963 | 1 | 17766917 | Higher in Drinkers |
| cg23918047 | 17 | 79828356 | Higher in Drinkers |
| cg23918388 | 1 | 207991593 | Higher in Drinkers |
| cg23919549 | 19 | 576047 | Higher in Drinkers |
| cg23919568 | 19 | 16296265 | Higher in Drinkers |
| cg23919794 | 10 | 135172031 | Higher in Drinkers |
| cg23919916 | 10 | 103825097 | Higher in Drinkers |
| cg23920472 | 11 | 47448172 | Higher in Drinkers |
| cg23921459 | 1 | 207224567 | Higher in Drinkers |
| cg23923462 | 10 | 99186006 | Higher in Drinkers |
| cg23924647 | 12 | 122227872 | Higher in Drinkers |
| cg23926649 | 3 | 9745850 | Higher in Drinkers |
| cg23933032 | 4 | 69215920 | Higher in Drinkers |
| cg23933345 | 1 | 114447334 | Higher in Drinkers |
| cg23941942 | 2 | 183988968 | Higher in Drinkers |
| cg23942065 | 10 | 21815183 | Higher in Drinkers |
| cg23942974 | 5 | 42995123 | Higher in Drinkers |
| cg23944925 | 3 | 196366897 | Higher in Drinkers |
| cg23947872 | X | 149862363 | Higher in Drinkers |
| cg23951861 | 7 | 72426239 | Higher in Drinkers |
| cg23952644 | 13 | 27131780 | Higher in Drinkers |
| cg23955723 | 19 | 45458052 | Higher in Drinkers |
| cg23955979 | 17 | 45126661 | Higher in Drinkers |
| cg23956071 | 17 | 4710044 | Higher in Drinkers |
| cg23962478 | 22 | 50354086 | Higher in Drinkers |
| cg23965019 | 6 | 31795144 | Higher in Drinkers |
| cg23966361 | 17 | 80006606 | Higher in Drinkers |
| cg23967249 | 4 | 141445247 | Higher in Drinkers |
| cg23969976 | 20 | 36156592 | Higher in Drinkers |

| | | | |
|---|---|---|---|
| cg23970785 | 16 | 11036526 | Higher in Drinkers |
| cg23971069 | 1 | 214158686 | Higher in Drinkers |
| cg23971110 | 6 | 99275960 | Lower in Drinkers |
| cg23974202 | 2 | 135676486 | Higher in Drinkers |
| cg23982527 | 11 | 864807 | Higher in Drinkers |
| cg23986133 | 13 | 45694582 | Higher in Drinkers |
| cg23986772 | 8 | 24858570 | Higher in Drinkers |
| cg23987222 | 19 | 12996266 | Higher in Drinkers |
| cg23989156 | 17 | 27572583 | Higher in Drinkers |
| cg23989297 | 20 | 271347 | Higher in Drinkers |
| cg23991418 | 11 | 362007 | Higher in Drinkers |
| cg23992808 | 1 | 93544692 | Higher in Drinkers |
| cg24005340 | 5 | 168006702 | Higher in Drinkers |
| cg24005743 | 11 | 32112810 | Higher in Drinkers |
| cg24008219 | 15 | 89973121 | Higher in Drinkers |
| cg24008544 | 17 | 41363899 | Higher in Drinkers |
| cg24008668 | 6 | 26158556 | Higher in Drinkers |
| cg24012157 | 10 | 70661472 | Higher in Drinkers |
| cg24014780 | 5 | 141348532 | Higher in Drinkers |
| cg24019620 | 10 | 104210098 | Higher in Drinkers |
| cg24020157 | 10 | 43697521 | Higher in Drinkers |
| cg24022067 | 11 | 67156961 | Lower in Drinkers |
| cg24023097 | 4 | 152330337 | Higher in Drinkers |
| cg24023553 | 20 | 42285728 | Higher in Drinkers |
| cg24029050 | 5 | 141691561 | Lower in Drinkers |
| cg24030086 | 12 | 123868728 | Higher in Drinkers |
| cg24031355 | 10 | 22634439 | Higher in Drinkers |
| cg24031505 | 6 | 4779396 | Higher in Drinkers |
| cg24036510 | 1 | 100817875 | Higher in Drinkers |
| cg24036523 | 14 | 73712256 | Higher in Drinkers |
| cg24037358 | 14 | 100776386 | Higher in Drinkers |
| cg24037361 | 11 | 75110743 | Higher in Drinkers |
| cg24040502 | 19 | 55477810 | Higher in Drinkers |
| cg24040725 | 14 | 45356233 | Lower in Drinkers |
| cg24041239 | 11 | 2922635 | Higher in Drinkers |

| | | | |
|---|---|---|---|
| cg24041799 | 1 | 11322809 | Higher in Drinkers |
| cg24042744 | 8 | 145509547 | Higher in Drinkers |
| cg24043236 | 3 | 98312515 | Higher in Drinkers |
| cg24044651 | 1 | 24105262 | Higher in Drinkers |
| cg24044763 | 1 | 160370683 | Higher in Drinkers |
| cg24047137 | 22 | 20119849 | Higher in Drinkers |
| cg24054653 | X | 119763829 | Higher in Drinkers |
| cg24059115 | 7 | 134143489 | Higher in Drinkers |
| cg24059197 | 6 | 90348542 | Higher in Drinkers |
| cg24059871 | 19 | 30101451 | Higher in Drinkers |
| cg24062157 | 16 | 3724848 | Higher in Drinkers |
| cg24064173 | 13 | 114761210 | Higher in Drinkers |
| cg24064264 | 11 | 615945 | Higher in Drinkers |
| cg24066601 | 6 | 26271455 | Higher in Drinkers |
| cg24069340 | 7 | 75623858 | Higher in Drinkers |
| cg24072013 | 1 | 25559262 | Higher in Drinkers |
| cg24072093 | 6 | 168378603 | Higher in Drinkers |
| cg24075680 | 22 | 39541462 | Higher in Drinkers |
| cg24076778 | 1 | 151512662 | Higher in Drinkers |
| cg24082795 | 2 | 85555413 | Higher in Drinkers |
| cg24082826 | 12 | 26985738 | Higher in Drinkers |
| cg24083702 | 19 | 41281104 | Higher in Drinkers |
| cg24083923 | 12 | 56123522 | Higher in Drinkers |
| cg24085570 | 1 | 1397412 | Higher in Drinkers |
| cg24088751 | 15 | 59949482 | Higher in Drinkers |
| cg24098203 | 6 | 35227659 | Higher in Drinkers |
| cg24117473 | 19 | 911655 | Lower in Drinkers |
| cg24117723 | 11 | 77185398 | Higher in Drinkers |
| cg24119077 | 1 | 40349270 | Higher in Drinkers |
| cg24119612 | 7 | 140098460 | Higher in Drinkers |
| cg24120411 | 12 | 56223501 | Higher in Drinkers |
| cg24123824 | 5 | 142410650 | Higher in Drinkers |
| cg24125937 | 5 | 140233357 | Higher in Drinkers |
| cg24127866 | 17 | 67322737 | Higher in Drinkers |
| cg24134304 | 15 | 45003680 | Higher in Drinkers |

| | | | |
|---|---|---|---|
| cg24135606 | 17 | 4851674 | Higher in Drinkers |
| cg24137136 | X | 151081284 | Lower in Drinkers |
| cg24140832 | 11 | 236743 | Higher in Drinkers |
| cg24143701 | 7 | 150783199 | Higher in Drinkers |
| cg24143766 | 7 | 97846988 | Higher in Drinkers |
| cg24145210 | 5 | 170814287 | Higher in Drinkers |
| cg24148882 | 17 | 80772927 | Higher in Drinkers |
| cg24150012 | 1 | 180165936 | Higher in Drinkers |
| cg24151087 | 17 | 19450271 | Higher in Drinkers |
| cg24156006 | 1 | 147599126 | Higher in Drinkers |
| cg24156746 | X | 153775711 | Higher in Drinkers |
| cg24161647 | 7 | 44249290 | Higher in Drinkers |
| cg24163658 | 3 | 58182370 | Higher in Drinkers |
| cg24165667 | 5 | 71616247 | Higher in Drinkers |
| cg24170511 | 14 | 23341280 | Higher in Drinkers |
| cg24172324 | 2 | 232258363 | Higher in Drinkers |
| cg24182300 | 7 | 97736853 | Higher in Drinkers |
| cg24187797 | 5 | 177571022 | Higher in Drinkers |
| cg24196046 | 1 | 36396054 | Higher in Drinkers |
| cg24197116 | X | 68110972 | Higher in Drinkers |
| cg24198977 | 3 | 120461209 | Higher in Drinkers |
| cg24199112 | 11 | 69590328 | Higher in Drinkers |
| cg24204740 | 6 | 83903813 | Higher in Drinkers |
| cg24206111 | 15 | 65186032 | Higher in Drinkers |
| cg24210523 | 17 | 35062671 | Higher in Drinkers |
| cg24210742 | 15 | 88380383 | Lower in Drinkers |
| cg24211478 | 6 | 106773719 | Higher in Drinkers |
| cg24212855 | 11 | 22850888 | Higher in Drinkers |
| cg24214386 | 11 | 82782984 | Higher in Drinkers |
| cg24222390 | 17 | 19410596 | Higher in Drinkers |
| cg24224803 | 6 | 160183104 | Higher in Drinkers |
| cg24226087 | 19 | 10490782 | Higher in Drinkers |
| cg24228012 | 4 | 156875082 | Higher in Drinkers |
| cg24229579 | 11 | 71189582 | Higher in Drinkers |
| cg24232236 | 22 | 38142998 | Higher in Drinkers |

| | | | |
|---|---|---|---|
| cg24238341 | 17 | 76221980 | Higher in Drinkers |
| cg24242082 | 20 | 61448325 | Higher in Drinkers |
| cg24242334 | 6 | 32551954 | Lower in Drinkers |
| cg24245305 | 7 | 43351320 | Lower in Drinkers |
| cg24247865 | 11 | 89956517 | Higher in Drinkers |
| cg24249583 | 10 | 111963599 | Higher in Drinkers |
| cg24260135 | 11 | 17479394 | Higher in Drinkers |
| cg24261808 | 11 | 93474459 | Higher in Drinkers |
| cg24262486 | 8 | 141556397 | Higher in Drinkers |
| cg24265610 | 10 | 102989311 | Higher in Drinkers |
| cg24266261 | 10 | 124134980 | Higher in Drinkers |
| cg24266542 | 12 | 106752006 | Higher in Drinkers |
| cg24268236 | 3 | 134204538 | Higher in Drinkers |
| cg24274165 | 4 | 106395314 | Higher in Drinkers |
| cg24274600 | 5 | 95066816 | Higher in Drinkers |
| cg24276395 | 3 | 193419891 | Higher in Drinkers |
| cg24283842 | 15 | 69745592 | Higher in Drinkers |
| cg24285721 | 7 | 44046988 | Higher in Drinkers |
| cg24286770 | 20 | 35918162 | Higher in Drinkers |
| cg24289501 | 12 | 110562188 | Higher in Drinkers |
| cg24290010 | 20 | 18118420 | Higher in Drinkers |
| cg24291718 | 7 | 128172288 | Higher in Drinkers |
| cg24293567 | 9 | 135754124 | Higher in Drinkers |
| cg24294399 | 6 | 31508923 | Higher in Drinkers |
| cg24298409 | 3 | 50379246 | Higher in Drinkers |
| cg24299389 | 19 | 51670552 | Higher in Drinkers |
| cg24302127 | 1 | 197778303 | Lower in Drinkers |
| cg24304518 | 2 | 113299015 | Higher in Drinkers |
| cg24304789 | 2 | 43451423 | Higher in Drinkers |
| cg24305770 | 2 | 97217869 | Lower in Drinkers |
| cg24309730 | 5 | 167913298 | Higher in Drinkers |
| cg24311251 | 13 | 44453387 | Higher in Drinkers |
| cg24312896 | 19 | 58331005 | Higher in Drinkers |
| cg24313640 | 11 | 57425161 | Higher in Drinkers |
| cg24314877 | 8 | 128656055 | Higher in Drinkers |

| | | | |
|---|---|---|---|
| cg24315186 | 7 | 77428849 | Higher in Drinkers |
| cg24315913 | 1 | 153631633 | Higher in Drinkers |
| cg24317935 | 1 | 31769543 | Higher in Drinkers |
| cg24320091 | 8 | 82754313 | Higher in Drinkers |
| cg24323958 | 1 | 108741884 | Higher in Drinkers |
| cg24325996 | 15 | 78632194 | Higher in Drinkers |
| cg24330485 | 2 | 207023983 | Higher in Drinkers |
| cg24331079 | 2 | 192016205 | Higher in Drinkers |
| cg24336398 | 9 | 139236777 | Higher in Drinkers |
| cg24337193 | 1 | 44720997 | Higher in Drinkers |
| cg24337600 | 19 | 1438247 | Higher in Drinkers |
| cg24341299 | 19 | 50879573 | Higher in Drinkers |
| cg24341722 | 1 | 46598727 | Higher in Drinkers |
| cg24345136 | 15 | 86337433 | Higher in Drinkers |
| cg24346733 | 8 | 146125713 | Higher in Drinkers |
| cg24347950 | 1 | 200378667 | Higher in Drinkers |
| cg24349555 | 6 | 139456526 | Higher in Drinkers |
| cg24350884 | 17 | 33570047 | Higher in Drinkers |
| cg24351198 | X | 48455856 | Higher in Drinkers |
| cg24352369 | 2 | 114163184 | Higher in Drinkers |
| cg24352938 | 1 | 200008808 | Higher in Drinkers |
| cg24353236 | 11 | 47270908 | Higher in Drinkers |
| cg24353489 | 1 | 70820534 | Higher in Drinkers |
| cg24354368 | 17 | 66201707 | Higher in Drinkers |
| cg24354954 | 17 | 43138489 | Higher in Drinkers |
| cg24356797 | 19 | 18682387 | Higher in Drinkers |
| cg24357276 | 1 | 114472822 | Higher in Drinkers |
| cg24364723 | 1 | 22838414 | Higher in Drinkers |
| cg24364760 | 4 | 89513922 | Higher in Drinkers |
| cg24366702 | 19 | 58951778 | Higher in Drinkers |
| cg24368101 | 12 | 56435669 | Higher in Drinkers |
| cg24372565 | 18 | 71815078 | Higher in Drinkers |
| cg24375895 | 1 | 247374146 | Higher in Drinkers |
| cg24376022 | 2 | 3215598 | Higher in Drinkers |
| cg24378009 | 4 | 153788518 | Lower in Drinkers |

| | | | |
|---|---|---|---|
| cg24378470 | 17 | 9478950 | Higher in Drinkers |
| cg24378945 | 11 | 105947912 | Higher in Drinkers |
| cg24380053 | 3 | 13028632 | Higher in Drinkers |
| cg24381155 | 10 | 103289745 | Higher in Drinkers |
| cg24383329 | 3 | 53228322 | Higher in Drinkers |
| cg24384331 | 8 | 142183860 | Higher in Drinkers |
| cg24389386 | 6 | 29854740 | Higher in Drinkers |
| cg24391122 | 19 | 7986137 | Higher in Drinkers |
| cg24391240 | 18 | 47792928 | Higher in Drinkers |
| cg24395307 | 7 | 39990042 | Higher in Drinkers |
| cg24399720 | 7 | 121036541 | Higher in Drinkers |
| cg24402070 | 1 | 17046932 | Higher in Drinkers |
| cg24403649 | 4 | 39172243 | Higher in Drinkers |
| cg24405664 | 12 | 95611285 | Higher in Drinkers |
| cg24407092 | 2 | 242031617 | Higher in Drinkers |
| cg24411488 | 10 | 1167737 | Higher in Drinkers |
| cg24417391 | 10 | 90751139 | Higher in Drinkers |
| cg24419198 | 11 | 18727321 | Higher in Drinkers |
| cg24423251 | 20 | 18774681 | Higher in Drinkers |
| cg24428389 | 1 | 22438310 | Higher in Drinkers |
| cg24429081 | 19 | 55741476 | Lower in Drinkers |
| cg24433586 | 17 | 79210494 | Higher in Drinkers |
| cg24435024 | 20 | 49411312 | Higher in Drinkers |
| cg24438423 | 17 | 40171937 | Higher in Drinkers |
| cg24440827 | 11 | 18478135 | Higher in Drinkers |
| cg24441022 | 1 | 154946677 | Higher in Drinkers |
| cg24441810 | 2 | 120436039 | Lower in Drinkers |
| cg24441872 | 4 | 53525715 | Higher in Drinkers |
| cg24445996 | 18 | 32923878 | Higher in Drinkers |
| cg24446269 | 17 | 54911857 | Higher in Drinkers |
| cg24448326 | 1 | 85930306 | Higher in Drinkers |
| cg24449014 | 19 | 42829665 | Higher in Drinkers |
| cg24450312 | 1 | 206681158 | Higher in Drinkers |
| cg24451990 | 1 | 70671119 | Higher in Drinkers |
| cg24457897 | 15 | 101835872 | Higher in Drinkers |

| | | | |
|---|---|---|---|
| cg24458428 | 1 | 25757288 | Higher in Drinkers |
| cg24459529 | 2 | 183989107 | Higher in Drinkers |
| cg24460917 | 20 | 18269097 | Higher in Drinkers |
| cg24464927 | 8 | 42996206 | Higher in Drinkers |
| cg24471254 | 7 | 100253792 | Higher in Drinkers |
| cg24477309 | 12 | 109730121 | Higher in Drinkers |
| cg24478096 | 2 | 160761085 | Higher in Drinkers |
| cg24478630 | 2 | 74692696 | Higher in Drinkers |
| cg24479382 | 21 | 46675571 | Lower in Drinkers |
| cg24480859 | 1 | 9129791 | Higher in Drinkers |
| cg24481594 | 1 | 2190850 | Lower in Drinkers |
| cg24481891 | 1 | 93426922 | Higher in Drinkers |
| cg24483552 | 8 | 67687060 | Higher in Drinkers |
| cg24488861 | 17 | 49198150 | Higher in Drinkers |
| cg24489972 | 7 | 105817320 | Higher in Drinkers |
| cg24490859 | 3 | 184429760 | Higher in Drinkers |
| cg24494967 | 13 | 60738294 | Higher in Drinkers |
| cg24496645 | 1 | 147400967 | Higher in Drinkers |
| cg24497897 | 11 | 65658826 | Higher in Drinkers |
| cg24505713 | 11 | 10770035 | Higher in Drinkers |
| cg24507239 | 11 | 65292939 | Higher in Drinkers |
| cg24511898 | 2 | 242576823 | Higher in Drinkers |
| cg24515283 | 11 | 17229012 | Higher in Drinkers |
| cg24517377 | 11 | 118869147 | Higher in Drinkers |
| cg24517800 | 6 | 42989357 | Higher in Drinkers |
| cg24518943 | 6 | 71123805 | Higher in Drinkers |
| cg24520871 | 10 | 73074265 | Higher in Drinkers |
| cg24525400 | 2 | 20340544 | Higher in Drinkers |
| cg24525872 | 4 | 149363678 | Higher in Drinkers |
| cg24526103 | 13 | 110433784 | Lower in Drinkers |
| cg24527001 | 14 | 92588234 | Higher in Drinkers |
| cg24528297 | 14 | 103995361 | Higher in Drinkers |
| cg24528923 | 15 | 90119427 | Higher in Drinkers |
| cg24530460 | 14 | 37053689 | Higher in Drinkers |
| cg24533690 | 10 | 103880622 | Higher in Drinkers |

| | | | |
|---|---|---|---|
| cg24536965 | 1 | 8492032 | Higher in Drinkers |
| cg24537275 | 17 | 9151174 | Higher in Drinkers |
| cg24538372 | 2 | 105953882 | Higher in Drinkers |
| cg24539339 | 1 | 45226304 | Higher in Drinkers |
| cg24543400 | 2 | 12857652 | Higher in Drinkers |
| cg24545461 | 8 | 61193313 | Higher in Drinkers |
| cg24546984 | 7 | 25219914 | Higher in Drinkers |
| cg24553170 | 1 | 49243472 | Higher in Drinkers |
| cg24553773 | 1 | 53746271 | Higher in Drinkers |
| cg24554054 | 7 | 99216405 | Higher in Drinkers |
| cg24554059 | 6 | 166797120 | Higher in Drinkers |
| cg24558977 | 5 | 70883341 | Higher in Drinkers |
| cg24562565 | 11 | 27494352 | Higher in Drinkers |
| cg24563015 | 22 | 38597914 | Higher in Drinkers |
| cg24567694 | 7 | 154719693 | Higher in Drinkers |
| cg24569270 | 16 | 98730409 | Higher in Drinkers |
| cg24572577 | 3 | 125803249 | Higher in Drinkers |
| cg24577137 | 1 | 186344558 | Higher in Drinkers |
| cg24577220 | 21 | 46387052 | Higher in Drinkers |
| cg24581262 | 17 | 16395449 | Higher in Drinkers |
| cg24584002 | 2 | 3606104 | Higher in Drinkers |
| cg24584951 | 6 | 41888893 | Higher in Drinkers |
| cg24592364 | 5 | 14871736 | Higher in Drinkers |
| cg24594292 | 6 | 111179867 | Lower in Drinkers |
| cg24594678 | 15 | 63796908 | Higher in Drinkers |
| cg24595791 | 13 | 21348132 | Higher in Drinkers |
| cg24602245 | 1 | 3706705 | Higher in Drinkers |
| cg24604109 | 3 | 44803341 | Higher in Drinkers |
| cg24607575 | 2 | 215675637 | Higher in Drinkers |
| cg24608218 | 3 | 17219239 | Higher in Drinkers |
| cg24609890 | 7 | 23339235 | Higher in Drinkers |
| cg24611631 | 9 | 4490288 | Higher in Drinkers |
| cg24613514 | 3 | 194868507 | Higher in Drinkers |
| cg24618716 | 2 | 232573223 | Higher in Drinkers |
| cg24621034 | 2 | 62639260 | Higher in Drinkers |

| | | | |
|---|---|---|---|
| cg24622544 | 12 | 121021673 | Lower in Drinkers |
| cg24623608 | 7 | 116503366 | Higher in Drinkers |
| cg24628013 | 6 | 29580367 | Higher in Drinkers |
| cg24631950 | 10 | 60094625 | Higher in Drinkers |
| cg24634519 | 20 | 13765725 | Higher in Drinkers |
| cg24635178 | 1 | 6685087 | Higher in Drinkers |
| cg24635903 | 11 | 124823917 | Higher in Drinkers |
| cg24640588 | 4 | 1283718 | Higher in Drinkers |
| cg24641027 | 7 | 128050275 | Higher in Drinkers |
| cg24641254 | 1 | 245848637 | Higher in Drinkers |
| cg24643012 | 15 | 93353380 | Higher in Drinkers |
| cg24649346 | 22 | 39268751 | Higher in Drinkers |
| cg24649554 | 5 | 169291240 | Higher in Drinkers |
| cg24650296 | 5 | 639205 | Higher in Drinkers |
| cg24654963 | 7 | 106808956 | Higher in Drinkers |
| cg24657347 | 2 | 20261756 | Higher in Drinkers |
| cg24663255 | 8 | 146228920 | Higher in Drinkers |
| cg24663663 | 5 | 37986714 | Higher in Drinkers |
| cg24665839 | 6 | 135375929 | Higher in Drinkers |
| cg24669932 | 1 | 8877431 | Higher in Drinkers |
| cg24670566 | 4 | 120433619 | Higher in Drinkers |
| cg24674703 | 11 | 60869960 | Higher in Drinkers |
| cg24675730 | 1 | 28994850 | Lower in Drinkers |
| cg24680163 | 3 | 127842675 | Higher in Drinkers |
| cg24680979 | 2 | 85788672 | Higher in Drinkers |
| cg24686009 | 12 | 69004486 | Higher in Drinkers |
| cg24686901 | 15 | 59225454 | Higher in Drinkers |
| cg24687253 | 7 | 100865887 | Higher in Drinkers |
| cg24688856 | 8 | 145064186 | Higher in Drinkers |
| cg24693803 | 4 | 171013537 | Higher in Drinkers |
| cg24694913 | 19 | 58978210 | Higher in Drinkers |
| cg24698537 | 1 | 19229364 | Higher in Drinkers |
| cg24699976 | 11 | 66384069 | Higher in Drinkers |
| cg24700388 | 1 | 206300911 | Lower in Drinkers |
| cg24700760 | 7 | 42951217 | Higher in Drinkers |

| | | | |
|---|---|---|---|
| cg24701097 | 6 | 30159594 | Higher in Drinkers |
| cg24703717 | 6 | 29691168 | Higher in Drinkers |
| cg24703757 | 4 | 183838736 | Higher in Drinkers |
| cg24705286 | 16 | 27215306 | Higher in Drinkers |
| cg24707023 | 6 | 27860984 | Higher in Drinkers |
| cg24707505 | 2 | 178977215 | Higher in Drinkers |
| cg24707688 | X | 101397542 | Higher in Drinkers |
| cg24709033 | 7 | 27224568 | Higher in Drinkers |
| cg24710179 | 11 | 642975 | Higher in Drinkers |
| cg24711367 | 17 | 41755339 | Higher in Drinkers |
| cg24712417 | 20 | 33543845 | Higher in Drinkers |
| cg24717029 | 18 | 60384542 | Higher in Drinkers |
| cg24720006 | 19 | 17448183 | Higher in Drinkers |
| cg24732856 | 19 | 1095186 | Higher in Drinkers |
| cg24734301 | 7 | 1937945 | Higher in Drinkers |
| cg24734643 | 22 | 39898247 | Higher in Drinkers |
| cg24738006 | 20 | 60717729 | Higher in Drinkers |
| cg24738217 | 1 | 153919230 | Higher in Drinkers |
| cg24740195 | 10 | 6186637 | Higher in Drinkers |
| cg24741598 | 1 | 242011743 | Higher in Drinkers |
| cg24750920 | 6 | 33267354 | Higher in Drinkers |
| cg24751129 | 6 | 42928920 | Higher in Drinkers |
| cg24755177 | 19 | 54850645 | Lower in Drinkers |
| cg24755189 | 11 | 62475373 | Higher in Drinkers |
| cg24759070 | 12 | 62752479 | Higher in Drinkers |
| cg24760647 | 2 | 220408209 | Higher in Drinkers |
| cg24763126 | 4 | 119606544 | Higher in Drinkers |
| cg24765188 | 8 | 81399235 | Higher in Drinkers |
| cg24768093 | 17 | 48228034 | Higher in Drinkers |
| cg24768163 | 4 | 103655432 | Lower in Drinkers |
| cg24768999 | 3 | 127394912 | Lower in Drinkers |
| cg24770596 | 10 | 104170513 | Higher in Drinkers |
| cg24770927 | 14 | 24911599 | Higher in Drinkers |
| cg24771570 | 17 | 73401965 | Higher in Drinkers |
| cg24774154 | 11 | 34127519 | Higher in Drinkers |

| | | | |
|---|---|---|---|
| cg24774891 | 17 | 3867847 | Higher in Drinkers |
| cg24775313 | 12 | 56210898 | Higher in Drinkers |
| cg24775832 | 6 | 75953667 | Higher in Drinkers |
| cg24788090 | 8 | 74332815 | Higher in Drinkers |
| cg24788636 | 1 | 40562667 | Higher in Drinkers |
| cg24790419 | 19 | 18385930 | Higher in Drinkers |
| cg24791380 | 7 | 23052972 | Higher in Drinkers |
| cg24792209 | 17 | 61503104 | Higher in Drinkers |
| cg24792813 | 11 | 118978076 | Higher in Drinkers |
| cg24793625 | 19 | 56165307 | Higher in Drinkers |
| cg24797363 | 12 | 50899425 | Higher in Drinkers |
| cg24797471 | 19 | 13262683 | Higher in Drinkers |
| cg24799795 | 11 | 5959658 | Higher in Drinkers |
| cg24803138 | 11 | 66636369 | Higher in Drinkers |
| cg24804707 | 8 | 134094173 | Higher in Drinkers |
| cg24805384 | 8 | 61564519 | Higher in Drinkers |
| cg24805411 | 19 | 56158851 | Higher in Drinkers |
| cg24807354 | 19 | 10629035 | Higher in Drinkers |
| cg24809011 | 1 | 26219196 | Higher in Drinkers |
| cg24815853 | 19 | 51538416 | Lower in Drinkers |
| cg24817053 | 3 | 183898897 | Higher in Drinkers |
| cg24822503 | 13 | 31248597 | Higher in Drinkers |
| cg24823832 | 8 | 67974235 | Higher in Drinkers |
| cg24824178 | 5 | 141263222 | Higher in Drinkers |
| cg24825937 | 2 | 128639118 | Higher in Drinkers |
| cg24826645 | 13 | 113952209 | Higher in Drinkers |
| cg24827992 | 6 | 33260021 | Higher in Drinkers |
| cg24830872 | 19 | 41945512 | Higher in Drinkers |
| cg24830876 | 3 | 56836259 | Higher in Drinkers |
| cg24833335 | 19 | 41870097 | Higher in Drinkers |
| cg24834740 | 20 | 37434552 | Higher in Drinkers |
| cg24839789 | 1 | 236135296 | Higher in Drinkers |
| cg24844441 | 3 | 183898841 | Higher in Drinkers |
| cg24846030 | 6 | 30884683 | Higher in Drinkers |
| cg24848535 | 16 | 87417581 | Higher in Drinkers |

| | | | |
|---|---|---|---|
| cg24849267 | 2 | 172374169 | Higher in Drinkers |
| cg24849563 | 18 | 56807424 | Higher in Drinkers |
| cg24852548 | 4 | 57522632 | Higher in Drinkers |
| cg24854292 | 7 | 7221711 | Higher in Drinkers |
| cg24855943 | 6 | 26235224 | Higher in Drinkers |
| cg24858591 | 3 | 44803638 | Higher in Drinkers |
| cg24861394 | 8 | 11141871 | Higher in Drinkers |
| cg24863262 | 19 | 55738529 | Higher in Drinkers |
| cg24868790 | 12 | 56326222 | Higher in Drinkers |
| cg24870662 | 19 | 16179321 | Higher in Drinkers |
| cg24871046 | 11 | 33758223 | Higher in Drinkers |
| cg24872076 | 19 | 16683269 | Higher in Drinkers |
| cg24876012 | 15 | 42067090 | Higher in Drinkers |
| cg24876035 | 19 | 7682769 | Lower in Drinkers |
| cg24876683 | 5 | 172386517 | Higher in Drinkers |
| cg24878594 | 1 | 11708564 | Lower in Drinkers |
| cg24879257 | 22 | 19167120 | Higher in Drinkers |
| cg24882203 | 19 | 6105592 | Higher in Drinkers |
| cg24882290 | 19 | 17577254 | Higher in Drinkers |
| cg24883333 | 1 | 25071513 | Higher in Drinkers |
| cg24885794 | 7 | 94286086 | Higher in Drinkers |
| cg24886563 | 17 | 3820150 | Higher in Drinkers |
| cg24886770 | 19 | 22018538 | Higher in Drinkers |
| cg24889207 | 12 | 120124618 | Higher in Drinkers |
| cg24890104 | 6 | 27648895 | Higher in Drinkers |
| cg24892120 | 4 | 513008 | Higher in Drinkers |
| cg24893562 | 17 | 19014466 | Higher in Drinkers |
| cg24893891 | 19 | 10629027 | Higher in Drinkers |
| cg24895623 | 11 | 86013348 | Higher in Drinkers |
| cg24899292 | 19 | 41798372 | Lower in Drinkers |
| cg24900654 | 19 | 44285594 | Lower in Drinkers |
| cg24902139 | 6 | 30181222 | Higher in Drinkers |
| cg24909975 | 6 | 160147912 | Higher in Drinkers |
| cg24911123 | 19 | 38085748 | Higher in Drinkers |
| cg24923975 | 12 | 101801647 | Higher in Drinkers |

| | | | |
|---|---|---|---|
| cg24924051 | 3 | 32408427 | Higher in Drinkers |
| cg24926364 | 13 | 114748575 | Higher in Drinkers |
| cg24926760 | 5 | 68530394 | Higher in Drinkers |
| cg24931592 | 11 | 105948506 | Higher in Drinkers |
| cg24931632 | 1 | 47899667 | Higher in Drinkers |
| cg24933173 | 15 | 45492494 | Higher in Drinkers |
| cg24937706 | 13 | 48877719 | Higher in Drinkers |
| cg24941703 | 7 | 2262479 | Higher in Drinkers |
| cg24946408 | 19 | 49375720 | Higher in Drinkers |
| cg24955592 | 6 | 26271227 | Higher in Drinkers |
| cg24955743 | 1 | 2454705 | Lower in Drinkers |
| cg24961958 | 3 | 47450718 | Higher in Drinkers |
| cg24962545 | 3 | 50606606 | Higher in Drinkers |
| cg24966682 | 6 | 24666810 | Higher in Drinkers |
| cg24968964 | 11 | 134026755 | Higher in Drinkers |
| cg24969036 | 21 | 11099885 | Higher in Drinkers |
| cg24974477 | 4 | 110650657 | Higher in Drinkers |
| cg24975666 | 17 | 80416629 | Higher in Drinkers |
| cg24976104 | 22 | 45097940 | Higher in Drinkers |
| cg24984818 | 19 | 7600102 | Higher in Drinkers |
| cg24988884 | 13 | 30424332 | Higher in Drinkers |
| cg24989061 | 4 | 185747383 | Higher in Drinkers |
| cg24989534 | 2 | 216878510 | Higher in Drinkers |
| cg24993194 | 6 | 25963187 | Higher in Drinkers |
| cg24993443 | 15 | 25123549 | Higher in Drinkers |
| cg24994755 | 21 | 44878479 | Higher in Drinkers |
| cg24995352 | 10 | 13203403 | Higher in Drinkers |
| cg24997202 | 1 | 228353591 | Higher in Drinkers |
| cg24997916 | 7 | 100291848 | Higher in Drinkers |
| cg24998020 | 3 | 98311910 | Higher in Drinkers |
| cg25001794 | 4 | 130014687 | Higher in Drinkers |
| cg25002781 | 2 | 42166456 | Lower in Drinkers |
| cg25006254 | 5 | 138775137 | Higher in Drinkers |
| cg25008156 | 6 | 170393875 | Higher in Drinkers |
| cg25011252 | 8 | 61777859 | Higher in Drinkers |

| | | | |
|---|---|---|---|
| cg25011475 | 10 | 88517608 | Higher in Drinkers |
| cg25012898 | 1 | 156252137 | Higher in Drinkers |
| cg25012987 | Y | 19691491 | Higher in Drinkers |
| cg25017777 | 1 | 9298817 | Higher in Drinkers |
| cg25020728 | 12 | 123011538 | Higher in Drinkers |
| cg25022925 | 5 | 126112600 | Higher in Drinkers |
| cg25025879 | 12 | 53359317 | Higher in Drinkers |
| cg25026287 | 6 | 33175644 | Higher in Drinkers |
| cg25026500 | 6 | 34855987 | Higher in Drinkers |
| cg25026767 | 11 | 85195094 | Higher in Drinkers |
| cg25027501 | 1 | 110283223 | Higher in Drinkers |
| cg25028996 | 14 | 23398580 | Higher in Drinkers |
| cg25044635 | 2 | 25565267 | Higher in Drinkers |
| cg25045098 | 20 | 5100907 | Higher in Drinkers |
| cg25046720 | 4 | 183801938 | Higher in Drinkers |
| cg25047243 | 2 | 32502969 | Higher in Drinkers |
| cg25053232 | 7 | 2394393 | Higher in Drinkers |
| cg25054052 | 13 | 22245066 | Higher in Drinkers |
| cg25054196 | 6 | 160426171 | Higher in Drinkers |
| cg25057892 | 13 | 45695040 | Higher in Drinkers |
| cg25059436 | 11 | 47574990 | Higher in Drinkers |
| cg25060632 | 22 | 46683277 | Lower in Drinkers |
| cg25062184 | 1 | 167089558 | Higher in Drinkers |
| cg25065658 | 10 | 96305388 | Higher in Drinkers |
| cg25066583 | 13 | 60971266 | Higher in Drinkers |
| cg25067153 | 11 | 58912240 | Higher in Drinkers |
| cg25067702 | 17 | 70723227 | Higher in Drinkers |
| cg25067849 | 18 | 48346660 | Higher in Drinkers |
| cg25067940 | 19 | 7693593 | Lower in Drinkers |
| cg25069596 | 17 | 916509 | Higher in Drinkers |
| cg25072262 | 17 | 78336438 | Higher in Drinkers |
| cg25073031 | 12 | 42878192 | Higher in Drinkers |
| cg25079743 | 16 | 30441674 | Higher in Drinkers |
| cg25080524 | 4 | 24586249 | Higher in Drinkers |
| cg25082671 | 13 | 21951379 | Lower in Drinkers |

| | | | |
|---|---|---|---|
| cg25084477 | 14 | 57856838 | Higher in Drinkers |
| cg25089332 | 3 | 14220171 | Higher in Drinkers |
| cg25094636 | 3 | 104221851 | Higher in Drinkers |
| cg25100404 | X | 15870481 | Higher in Drinkers |
| cg25101273 | 2 | 196522935 | Higher in Drinkers |
| cg25102735 | 1 | 11751079 | Higher in Drinkers |
| cg25104118 | 12 | 125621344 | Lower in Drinkers |
| cg25104124 | 10 | 74021022 | Higher in Drinkers |
| cg25104671 | 1 | 89149378 | Higher in Drinkers |
| cg25106220 | 2 | 113522384 | Higher in Drinkers |
| cg25106844 | 5 | 74532880 | Higher in Drinkers |
| cg25107268 | 6 | 89673349 | Higher in Drinkers |
| cg25107978 | 12 | 57916571 | Higher in Drinkers |
| cg25110043 | 12 | 56511951 | Higher in Drinkers |
| cg25110511 | 6 | 32821376 | Higher in Drinkers |
| cg25110932 | 20 | 60503451 | Higher in Drinkers |
| cg25113767 | 12 | 124907367 | Higher in Drinkers |
| cg25114075 | 3 | 134205717 | Higher in Drinkers |
| cg25114580 | 2 | 198364757 | Higher in Drinkers |
| cg25118574 | 9 | 127177646 | Higher in Drinkers |
| cg25119002 | 20 | 60783405 | Higher in Drinkers |
| cg25119690 | 3 | 55524048 | Higher in Drinkers |
| cg25121810 | 14 | 103800166 | Higher in Drinkers |
| cg25122841 | 14 | 24911839 | Higher in Drinkers |
| cg25123308 | 2 | 113300087 | Higher in Drinkers |
| cg25127896 | 14 | 74111686 | Higher in Drinkers |
| cg25129765 | 6 | 99872940 | Higher in Drinkers |
| cg25131818 | 5 | 173000177 | Higher in Drinkers |
| cg25133475 | 4 | 120133741 | Higher in Drinkers |
| cg25134071 | 19 | 51506362 | Higher in Drinkers |
| cg25134890 | 7 | 157200205 | Lower in Drinkers |
| cg25135706 | 15 | 86301987 | Higher in Drinkers |
| cg25136310 | 19 | 5690528 | Higher in Drinkers |
| cg25140945 | 1 | 3816479 | Higher in Drinkers |
| cg25142283 | 18 | 51684211 | Higher in Drinkers |

| | | | |
|---|---|---|---|
| cg25143824 | 20 | 9819820 | Higher in Drinkers |
| cg25146268 | 2 | 96068665 | Higher in Drinkers |
| cg25147139 | 12 | 49740718 | Higher in Drinkers |
| cg25149510 | 4 | 119606506 | Higher in Drinkers |
| cg25149677 | 21 | 15755452 | Higher in Drinkers |
| cg25156915 | 4 | 174427388 | Higher in Drinkers |
| cg25160593 | 3 | 44666684 | Higher in Drinkers |
| cg25160915 | 3 | 113252350 | Higher in Drinkers |
| cg25166322 | 8 | 146228165 | Higher in Drinkers |
| cg25175370 | 7 | 2595131 | Higher in Drinkers |
| cg25187463 | 12 | 31226441 | Higher in Drinkers |
| cg25191716 | 20 | 32077802 | Higher in Drinkers |
| cg25194415 | 4 | 6784170 | Higher in Drinkers |
| cg25198716 | 1 | 46153712 | Higher in Drinkers |
| cg25198894 | 1 | 77685135 | Higher in Drinkers |
| cg25198967 | 3 | 52325846 | Higher in Drinkers |
| cg25201280 | 15 | 35838552 | Higher in Drinkers |
| cg25201418 | 6 | 33217615 | Higher in Drinkers |
| cg25201980 | 8 | 146127417 | Higher in Drinkers |
| cg25207528 | 11 | 47447843 | Higher in Drinkers |
| cg25210936 | 11 | 60683046 | Higher in Drinkers |
| cg25215594 | 13 | 30981649 | Lower in Drinkers |
| cg25217257 | 12 | 133219288 | Higher in Drinkers |
| cg25217625 | 15 | 42783080 | Higher in Drinkers |
| cg25218905 | 12 | 92538613 | Higher in Drinkers |
| cg25220300 | 3 | 141206348 | Higher in Drinkers |
| cg25221719 | 3 | 141319318 | Higher in Drinkers |
| cg25224760 | 8 | 144790772 | Lower in Drinkers |
| cg25225517 | 22 | 49812267 | Lower in Drinkers |
| cg25225632 | 5 | 1324090 | Higher in Drinkers |
| cg25227335 | 11 | 27528703 | Higher in Drinkers |
| cg25229802 | 1 | 16011501 | Higher in Drinkers |
| cg25230117 | 4 | 146104495 | Higher in Drinkers |
| cg25230708 | 3 | 48477621 | Higher in Drinkers |
| cg25231096 | 3 | 9774301 | Higher in Drinkers |

| | | | |
|---|---|---|---|
| cg25233816 | 3 | 106959817 | Higher in Drinkers |
| cg25235849 | 4 | 2935996 | Higher in Drinkers |
| cg25236446 | 17 | 74137418 | Higher in Drinkers |
| cg25237542 | X | 142722494 | Higher in Drinkers |
| cg25239586 | 11 | 3078610 | Higher in Drinkers |
| cg25239767 | 7 | 130791807 | Higher in Drinkers |
| cg25240254 | 19 | 56000944 | Lower in Drinkers |
| cg25240463 | 2 | 242660065 | Higher in Drinkers |
| cg25243721 | 5 | 82373346 | Higher in Drinkers |
| cg25245418 | 1 | 24286282 | Higher in Drinkers |
| cg25245969 | 10 | 125754632 | Higher in Drinkers |
| cg25253419 | 19 | 49403890 | Higher in Drinkers |
| cg25256924 | 11 | 67205739 | Lower in Drinkers |
| cg25259815 | X | 134182119 | Lower in Drinkers |
| cg25261377 | 6 | 30313517 | Higher in Drinkers |
| cg25263140 | 6 | 106959651 | Higher in Drinkers |
| cg25264265 | 3 | 185080997 | Higher in Drinkers |
| cg25267930 | 19 | 48707029 | Higher in Drinkers |
| cg25268422 | 9 | 136659313 | Higher in Drinkers |
| cg25271404 | 15 | 34875138 | Higher in Drinkers |
| cg25272712 | 1 | 40349284 | Higher in Drinkers |
| cg25277174 | 19 | 58874439 | Higher in Drinkers |
| cg25278187 | 17 | 46102509 | Higher in Drinkers |
| cg25278576 | 11 | 118559966 | Lower in Drinkers |
| cg25279613 | 7 | 24956523 | Higher in Drinkers |
| cg25282037 | 6 | 31937072 | Higher in Drinkers |
| cg25284031 | 12 | 111099321 | Higher in Drinkers |
| cg25284492 | 1 | 9295432 | Higher in Drinkers |
| cg25286333 | 1 | 6269448 | Higher in Drinkers |
| cg25294759 | 17 | 65714530 | Higher in Drinkers |
| cg25295218 | 4 | 89080179 | Higher in Drinkers |
| cg25296939 | 12 | 120884387 | Higher in Drinkers |
| cg25298161 | 15 | 41806135 | Higher in Drinkers |
| cg25303336 | 6 | 33756862 | Higher in Drinkers |
| cg25303396 | 1 | 59282018 | Higher in Drinkers |

| | | | |
|---|---|---|---|
| cg25306939 | 11 | 2722086 | Higher in Drinkers |
| cg25312474 | 6 | 142468512 | Higher in Drinkers |
| cg25316898 | 18 | 33552869 | Higher in Drinkers |
| cg25317911 | 12 | 9800438 | Higher in Drinkers |
| cg25321549 | 5 | 60629121 | Higher in Drinkers |
| cg25321935 | 11 | 47440348 | Higher in Drinkers |
| cg25322095 | 16 | 215002 | Higher in Drinkers |
| cg25325588 | 2 | 145281622 | Higher in Drinkers |
| cg25325612 | 16 | 46723166 | Higher in Drinkers |
| cg25329939 | 13 | 98085947 | Higher in Drinkers |
| cg25330514 | 12 | 110152300 | Higher in Drinkers |
| cg25333056 | 10 | 135107159 | Higher in Drinkers |
| cg25335775 | 1 | 174992314 | Higher in Drinkers |
| cg25336000 | 8 | 63951076 | Higher in Drinkers |
| cg25340515 | 17 | 7210196 | Higher in Drinkers |
| cg25344017 | 8 | 145509651 | Higher in Drinkers |
| cg25344639 | 17 | 75137144 | Higher in Drinkers |
| cg25346583 | 19 | 1629609 | Higher in Drinkers |
| cg25346972 | 14 | 70826282 | Higher in Drinkers |
| cg25350411 | 6 | 144328917 | Higher in Drinkers |
| cg25351036 | 4 | 48018582 | Higher in Drinkers |
| cg25352908 | 12 | 88429178 | Higher in Drinkers |
| cg25353171 | 8 | 9755804 | Lower in Drinkers |
| cg25354334 | 3 | 172859049 | Lower in Drinkers |
| cg25354657 | 11 | 129991445 | Higher in Drinkers |
| cg25355501 | 6 | 31239910 | Higher in Drinkers |
| cg25355635 | 12 | 53576509 | Higher in Drinkers |
| cg25358653 | 3 | 46448631 | Higher in Drinkers |
| cg25365794 | 17 | 8022404 | Higher in Drinkers |
| cg25366140 | 7 | 157561161 | Lower in Drinkers |
| cg25371803 | 1 | 156308296 | Higher in Drinkers |
| cg25372881 | 1 | 9276474 | Higher in Drinkers |
| cg25373595 | 17 | 2699713 | Higher in Drinkers |
| cg25375329 | X | 119006108 | Higher in Drinkers |
| cg25381775 | 1 | 6259495 | Higher in Drinkers |

| | | | |
|---|---|---|---|
| cg25382265 | 19 | 50169375 | Higher in Drinkers |
| cg25385272 | 1 | 222763149 | Higher in Drinkers |
| cg25385940 | 15 | 99789637 | Higher in Drinkers |
| cg25388061 | 5 | 178215887 | Lower in Drinkers |
| cg25397922 | 4 | 113431869 | Lower in Drinkers |
| cg25410310 | 19 | 48902803 | Higher in Drinkers |
| cg25410641 | 2 | 240322702 | Higher in Drinkers |
| cg25410739 | 1 | 223743086 | Lower in Drinkers |
| cg25411699 | 7 | 37393045 | Higher in Drinkers |
| cg25413298 | 11 | 517070 | Lower in Drinkers |
| cg25414924 | 1 | 114472856 | Higher in Drinkers |
| cg25416363 | 1 | 110881820 | Higher in Drinkers |
| cg25418748 | 5 | 178977236 | Higher in Drinkers |
| cg25420298 | 19 | 11456894 | Higher in Drinkers |
| cg25424556 | X | 55515463 | Higher in Drinkers |
| cg25431597 | 22 | 41842845 | Higher in Drinkers |
| cg25436849 | 19 | 37569540 | Higher in Drinkers |
| cg25436946 | 3 | 69101463 | Higher in Drinkers |
| cg25444339 | 7 | 75194698 | Higher in Drinkers |
| cg25446676 | 20 | 19997871 | Higher in Drinkers |
| cg25449655 | 7 | 26331472 | Higher in Drinkers |
| cg25449924 | 12 | 125020192 | Higher in Drinkers |
| cg25453681 | 19 | 44100691 | Higher in Drinkers |
| cg25454890 | 11 | 14913620 | Higher in Drinkers |
| cg25456477 | 12 | 86230367 | Lower in Drinkers |
| cg25456747 | 15 | 75074012 | Higher in Drinkers |
| cg25456772 | 12 | 70133054 | Higher in Drinkers |
| cg25456968 | 19 | 44115850 | Higher in Drinkers |
| cg25457331 | 6 | 16238547 | Higher in Drinkers |
| cg25461267 | 7 | 91875786 | Higher in Drinkers |
| cg25462795 | 19 | 39340760 | Higher in Drinkers |
| cg25462903 | 11 | 47206835 | Higher in Drinkers |
| cg25468683 | 19 | 40327585 | Lower in Drinkers |
| cg25471916 | 5 | 79552177 | Higher in Drinkers |
| cg25475516 | 2 | 192109755 | Higher in Drinkers |

| | | | |
|---|---|---|---|
| cg25476713 | 3 | 8102121 | Higher in Drinkers |
| cg25478109 | 3 | 179322476 | Higher in Drinkers |
| cg25478600 | 11 | 2890605 | Higher in Drinkers |
| cg25479565 | 19 | 18502206 | Lower in Drinkers |
| cg25486386 | 2 | 133014663 | Higher in Drinkers |
| cg25490145 | 17 | 80358850 | Higher in Drinkers |
| cg25491704 | 6 | 33048879 | Higher in Drinkers |
| cg25493687 | 8 | 27288214 | Higher in Drinkers |
| cg25497877 | 13 | 32890352 | Higher in Drinkers |
| cg25503044 | 2 | 74730557 | Higher in Drinkers |
| cg25503565 | 17 | 38264529 | Higher in Drinkers |
| cg25504229 | 15 | 28567528 | Higher in Drinkers |
| cg25506256 | 6 | 42714906 | Higher in Drinkers |
| cg25507518 | 7 | 2405875 | Higher in Drinkers |
| cg25509428 | 10 | 75118432 | Higher in Drinkers |
| cg25511286 | 10 | 27793050 | Higher in Drinkers |
| cg25512587 | 9 | 136344026 | Higher in Drinkers |
| cg25519056 | 19 | 48952640 | Higher in Drinkers |
| cg25520679 | 17 | 1959121 | Higher in Drinkers |
| cg25520939 | 4 | 44728034 | Higher in Drinkers |
| cg25523559 | 5 | 893076 | Higher in Drinkers |
| cg25531249 | 21 | 30671681 | Higher in Drinkers |
| cg25533220 | 19 | 2328480 | Higher in Drinkers |
| cg25539392 | 20 | 34043435 | Higher in Drinkers |
| cg25544073 | 3 | 98656304 | Higher in Drinkers |
| cg25547361 | 5 | 76926079 | Higher in Drinkers |
| cg25547663 | X | 48456173 | Higher in Drinkers |
| cg25547957 | 6 | 73972768 | Higher in Drinkers |
| cg25550823 | 2 | 190192866 | Higher in Drinkers |
| cg25553015 | 19 | 39109861 | Higher in Drinkers |
| cg25554744 | 7 | 150102660 | Higher in Drinkers |
| cg25555505 | 7 | 4791054 | Higher in Drinkers |
| cg25555657 | X | 48334381 | Higher in Drinkers |
| cg25555753 | 19 | 3133435 | Higher in Drinkers |
| cg25558099 | 17 | 18219121 | Higher in Drinkers |

| | | | |
|---|---|---|---|
| cg25559949 | 2 | 12003848 | Higher in Drinkers |
| cg25563189 | 12 | 89746328 | Higher in Drinkers |
| cg25564901 | 17 | 17140463 | Higher in Drinkers |
| cg25565608 | X | 47930609 | Higher in Drinkers |
| cg25568114 | 2 | 128158438 | Lower in Drinkers |
| cg25568716 | 11 | 16760490 | Higher in Drinkers |
| cg25575065 | 22 | 51066394 | Lower in Drinkers |
| cg25575732 | 10 | 52177880 | Higher in Drinkers |
| cg25576352 | 19 | 11640011 | Higher in Drinkers |
| cg25578064 | 20 | 42086787 | Higher in Drinkers |
| cg25582403 | 17 | 37844421 | Higher in Drinkers |
| cg25584355 | 10 | 101946020 | Higher in Drinkers |
| cg25584626 | 5 | 119800234 | Higher in Drinkers |
| cg25591670 | X | 75392807 | Higher in Drinkers |
| cg25593075 | 1 | 154966318 | Higher in Drinkers |
| cg25594661 | 7 | 138818594 | Higher in Drinkers |
| cg25599475 | 7 | 853038 | Higher in Drinkers |
| cg25600027 | 14 | 23388339 | Higher in Drinkers |
| cg25602759 | 10 | 43916511 | Higher in Drinkers |
| cg25604183 | 5 | 180542318 | Lower in Drinkers |
| cg25605550 | 8 | 101256880 | Higher in Drinkers |
| cg25608370 | 4 | 83719250 | Higher in Drinkers |
| cg25608973 | 2 | 21022431 | Higher in Drinkers |
| cg25611476 | 5 | 88179989 | Higher in Drinkers |
| cg25614222 | 11 | 130184756 | Higher in Drinkers |
| cg25619707 | 15 | 23377763 | Higher in Drinkers |
| cg25622802 | 8 | 61606295 | Higher in Drinkers |
| cg25623459 | 11 | 1861344 | Higher in Drinkers |
| cg25625670 | 11 | 57232742 | Higher in Drinkers |
| cg25625860 | 17 | 58677502 | Higher in Drinkers |
| cg25627913 | 2 | 162165232 | Higher in Drinkers |
| cg25629326 | 8 | 95274342 | Higher in Drinkers |
| cg25629694 | 17 | 62657497 | Higher in Drinkers |
| cg25630066 | 13 | 114827301 | Higher in Drinkers |
| cg25631650 | 19 | 633157 | Higher in Drinkers |

| | | | |
|---|---|---|---|
| cg25631723 | 17 | 10533122 | Lower in Drinkers |
| cg25631940 | 20 | 43589250 | Higher in Drinkers |
| cg25634545 | 10 | 104154207 | Higher in Drinkers |
| cg25637226 | 13 | 111355112 | Higher in Drinkers |
| cg25642069 | 8 | 144408230 | Higher in Drinkers |
| cg25645462 | 16 | 57653702 | Higher in Drinkers |
| cg25647583 | 15 | 91427184 | Higher in Drinkers |
| cg25648203 | 5 | 395444 | Higher in Drinkers |
| cg25648250 | 5 | 86564633 | Higher in Drinkers |
| cg25650661 | 6 | 29856278 | Higher in Drinkers |
| cg25651476 | 19 | 55476717 | Higher in Drinkers |
| cg25653917 | 10 | 45470493 | Higher in Drinkers |
| cg25654697 | 7 | 7680075 | Higher in Drinkers |
| cg25660405 | 4 | 57253385 | Higher in Drinkers |
| cg25660646 | 19 | 571323 | Higher in Drinkers |
| cg25662041 | 5 | 176759170 | Higher in Drinkers |
| cg25662680 | 16 | 67880587 | Higher in Drinkers |
| cg25662963 | 7 | 69062887 | Higher in Drinkers |
| cg25665573 | 5 | 137369222 | Higher in Drinkers |
| cg25667202 | 1 | 153963072 | Higher in Drinkers |
| cg25667712 | 13 | 32605332 | Higher in Drinkers |
| cg25670376 | 17 | 49295249 | Lower in Drinkers |
| cg25673720 | 17 | 74188601 | Higher in Drinkers |
| cg25678088 | 7 | 96632460 | Higher in Drinkers |
| cg25678150 | 13 | 113488452 | Higher in Drinkers |
| cg25680645 | 17 | 435759 | Lower in Drinkers |
| cg25682097 | 14 | 105954118 | Higher in Drinkers |
| cg25683444 | 15 | 42841115 | Higher in Drinkers |
| cg25690202 | 19 | 38684328 | Lower in Drinkers |
| cg25691777 | 6 | 167250541 | Lower in Drinkers |
| cg25692732 | X | 153715426 | Higher in Drinkers |
| cg25694542 | 14 | 73493846 | Higher in Drinkers |
| cg25695041 | 4 | 68567439 | Higher in Drinkers |
| cg25701781 | 10 | 74033558 | Higher in Drinkers |
| cg25704638 | 17 | 62658371 | Higher in Drinkers |

| | | | |
|---|---|---|---|
| cg25706342 | 1 | 147736359 | Higher in Drinkers |
| cg25706474 | 2 | 239161157 | Higher in Drinkers |
| cg25706861 | 2 | 220404357 | Higher in Drinkers |
| cg25712246 | 22 | 24407975 | Higher in Drinkers |
| cg25714826 | 16 | 85784062 | Higher in Drinkers |
| cg25714850 | 17 | 57184489 | Higher in Drinkers |
| cg25730237 | 4 | 8279150 | Higher in Drinkers |
| cg25730309 | 12 | 121177142 | Higher in Drinkers |
| cg25730440 | 19 | 4688549 | Higher in Drinkers |
| cg25730573 | 18 | 60987425 | Higher in Drinkers |
| cg25730577 | 1 | 110453002 | Higher in Drinkers |
| cg25736986 | 2 | 99797489 | Higher in Drinkers |
| cg25738529 | 12 | 49938018 | Higher in Drinkers |
| cg25738958 | 15 | 74220255 | Higher in Drinkers |
| cg25739316 | 19 | 39897275 | Higher in Drinkers |
| cg25746844 | 3 | 107941491 | Higher in Drinkers |
| cg25748647 | 1 | 206858094 | Higher in Drinkers |
| cg25749376 | 12 | 133191659 | Higher in Drinkers |
| cg25750609 | 3 | 101280791 | Higher in Drinkers |
| cg25756166 | 22 | 42372528 | Higher in Drinkers |
| cg25757829 | 2 | 232573226 | Higher in Drinkers |
| cg25759517 | 17 | 79895006 | Higher in Drinkers |
| cg25762396 | 11 | 57117479 | Higher in Drinkers |
| cg25768756 | 18 | 21083253 | Higher in Drinkers |
| cg25772738 | 11 | 76092056 | Higher in Drinkers |
| cg25776555 | 19 | 52531777 | Higher in Drinkers |
| cg25785630 | 8 | 9413989 | Higher in Drinkers |
| cg25787940 | 6 | 33217303 | Higher in Drinkers |
| cg25791620 | 17 | 1472984 | Lower in Drinkers |
| cg25791888 | 21 | 45080032 | Higher in Drinkers |
| cg25794153 | 16 | 31805151 | Higher in Drinkers |
| cg25796062 | 10 | 127511723 | Higher in Drinkers |
| cg25798013 | 19 | 19754582 | Higher in Drinkers |
| cg25798647 | 6 | 41303391 | Higher in Drinkers |
| cg25799361 | 2 | 3111397 | Higher in Drinkers |

| | | | |
|---|---|---|---|
| cg25806558 | 4 | 40058716 | Higher in Drinkers |
| cg25809215 | 3 | 16306823 | Higher in Drinkers |
| cg25809635 | 19 | 37341103 | Higher in Drinkers |
| cg25810379 | 11 | 64578055 | Higher in Drinkers |
| cg25811766 | 13 | 21894605 | Higher in Drinkers |
| cg25815027 | 12 | 113552571 | Lower in Drinkers |
| cg25820475 | 12 | 56510568 | Higher in Drinkers |
| cg25821974 | 3 | 126486192 | Lower in Drinkers |
| cg25822552 | 1 | 17222405 | Higher in Drinkers |
| cg25824226 | 8 | 110551708 | Higher in Drinkers |
| cg25826404 | 17 | 78061566 | Higher in Drinkers |
| cg25827351 | 3 | 38066270 | Higher in Drinkers |
| cg25827710 | 13 | 46742802 | Higher in Drinkers |
| cg25829945 | 3 | 159706383 | Higher in Drinkers |
| cg25830708 | 11 | 9406625 | Higher in Drinkers |
| cg25833597 | 17 | 30823145 | Higher in Drinkers |
| cg25834632 | 8 | 144590015 | Lower in Drinkers |
| cg25835307 | 11 | 87908134 | Higher in Drinkers |
| cg25839807 | 1 | 246958421 | Higher in Drinkers |
| cg25845890 | 3 | 48593844 | Higher in Drinkers |
| cg25846765 | 18 | 9615093 | Higher in Drinkers |
| cg25848060 | 4 | 1713374 | Higher in Drinkers |
| cg25848875 | 2 | 3261530 | Higher in Drinkers |
| cg25853833 | 2 | 101869024 | Higher in Drinkers |
| cg25858682 | 3 | 48481793 | Higher in Drinkers |
| cg25859998 | 6 | 1042432C | Higher in Drinkers |
| cg25862644 | 10 | 77168553 | Higher in Drinkers |
| cg25868465 | 2 | 47630172 | Higher in Drinkers |
| cg25869317 | 15 | 101792241 | Higher in Drinkers |
| cg25871420 | X | 23348969 | Higher in Drinkers |
| cg25873214 | 11 | 47587499 | Higher in Drinkers |
| cg25880537 | 1 | 2365337 | Lower in Drinkers |
| cg25880958 | 11 | 74394337 | Higher in Drinkers |
| cg25881723 | 1 | 181998471 | Higher in Drinkers |
| cg25883141 | 2 | 3689356 | Higher in Drinkers |

| | | | |
|---|---|---|---|
| cg25886875 | 19 | 40477185 | Higher in Drinkers |
| cg25894123 | 15 | 23313138 | Lower in Drinkers |
| cg25894201 | 20 | 21106495 | Higher in Drinkers |
| cg25894806 | 17 | 7387291 | Higher in Drinkers |
| cg25896754 | 17 | 7590877 | Higher in Drinkers |
| cg25903375 | 4 | 140476877 | Higher in Drinkers |
| cg25903851 | 21 | 45367182 | Higher in Drinkers |
| cg25906435 | 7 | 2123600 | Higher in Drinkers |
| cg25911245 | 6 | 143832390 | Higher in Drinkers |
| cg25913233 | 5 | 151066683 | Higher in Drinkers |
| cg25913612 | 10 | 30818641 | Higher in Drinkers |
| cg25917220 | 7 | 143078782 | Higher in Drinkers |
| cg25918726 | 19 | 36869377 | Higher in Drinkers |
| cg25919221 | 1 | 9006680 | Higher in Drinkers |
| cg25923345 | 7 | 100304669 | Lower in Drinkers |
| cg25927687 | 7 | 158734704 | Higher in Drinkers |
| cg25930340 | 5 | 179160251 | Higher in Drinkers |
| cg25930451 | 8 | 680776 | Higher in Drinkers |
| cg25930842 | 5 | 148929549 | Higher in Drinkers |
| cg25932787 | 19 | 19887486 | Higher in Drinkers |
| cg25942691 | 19 | 36705733 | Higher in Drinkers |
| cg25943131 | 12 | 30848710 | Higher in Drinkers |
| cg25945158 | 6 | 31671246 | Higher in Drinkers |
| cg25946869 | 12 | 113796432 | Higher in Drinkers |
| cg25947970 | 3 | 186220484 | Higher in Drinkers |
| cg25947998 | 8 | 42948467 | Higher in Drinkers |
| cg25949649 | X | 44733352 | Higher in Drinkers |
| cg25951430 | 11 | 57192432 | Higher in Drinkers |
| cg25958361 | 2 | 99797532 | Higher in Drinkers |
| cg25959300 | 13 | 52159104 | Higher in Drinkers |
| cg25960191 | 8 | 30601454 | Higher in Drinkers |
| cg25961579 | 3 | 135915963 | Higher in Drinkers |
| cg25964534 | 6 | 31731300 | Higher in Drinkers |
| cg25966128 | 20 | 18447905 | Higher in Drinkers |
| cg25967165 | 7 | 1939814 | Higher in Drinkers |

| | | | |
|---|---|---|---|
| cg25967957 | 7 | 44646819 | Higher in Drinkers |
| cg25970032 | 1 | 119683285 | Higher in Drinkers |
| cg25971086 | 6 | 138189304 | Higher in Drinkers |
| cg25971314 | 5 | 82373254 | Higher in Drinkers |
| cg25972405 | 9 | 114245045 | Higher in Drinkers |
| cg25972578 | 10 | 92548822 | Higher in Drinkers |
| cg25974485 | 7 | 66461693 | Higher in Drinkers |
| cg25975805 | 17 | 34838641 | Higher in Drinkers |
| cg25975818 | 17 | 77704298 | Higher in Drinkers |
| cg25976786 | 12 | 53662079 | Higher in Drinkers |
| cg25977744 | 12 | 58146274 | Higher in Drinkers |
| cg25980344 | 5 | 170815414 | Higher in Drinkers |
| cg25984791 | 11 | 108535797 | Higher in Drinkers |
| cg25985583 | 7 | 26404716 | Lower in Drinkers |
| cg25992382 | 14 | 93066811 | Higher in Drinkers |
| cg25993158 | 1 | 2450205 | Higher in Drinkers |
| cg25994603 | 10 | 75936573 | Higher in Drinkers |
| cg26000393 | 22 | 39378224 | Higher in Drinkers |
| cg26003336 | 19 | 14116507 | Higher in Drinkers |
| cg26005212 | 6 | 37759419 | Higher in Drinkers |
| cg26005844 | 11 | 57298432 | Higher in Drinkers |
| cg26006245 | 6 | 30166858 | Higher in Drinkers |
| cg26009773 | 6 | 101329304 | Higher in Drinkers |
| cg26011138 | 1 | 35734376 | Higher in Drinkers |
| cg26011222 | 10 | 77155697 | Higher in Drinkers |
| cg26012103 | 16 | 11349372 | Higher in Drinkers |
| cg26017457 | 17 | 4634601 | Higher in Drinkers |
| cg26017880 | 18 | 76829239 | Higher in Drinkers |
| cg26023204 | 7 | 99699378 | Higher in Drinkers |
| cg26023751 | 1 | 169763990 | Higher in Drinkers |
| cg26028810 | 6 | 31371164 | Higher in Drinkers |
| cg26030450 | 14 | 50154989 | Higher in Drinkers |
| cg26035615 | 6 | 30038254 | Higher in Drinkers |
| cg26035837 | 20 | 56885003 | Higher in Drinkers |
| cg26035915 | 1 | 193028107 | Higher in Drinkers |

| | | | |
|---|---|---|---|
| cg26038461 | 2 | 25108362 | Higher in Drinkers |
| cg26038700 | 14 | 74225349 | Higher in Drinkers |
| cg26042725 | 20 | 3827226 | Higher in Drinkers |
| cg26044026 | 3 | 115503319 | Higher in Drinkers |
| cg26045220 | 1 | 109656325 | Higher in Drinkers |
| cg26046435 | 5 | 158636842 | Higher in Drinkers |
| cg26046658 | 20 | 1447728 | Higher in Drinkers |
| cg26046968 | 14 | 57857884 | Higher in Drinkers |
| cg26055420 | 1 | 118148456 | Higher in Drinkers |
| cg26055522 | 1 | 148853922 | Higher in Drinkers |
| cg26059822 | 3 | 51976165 | Higher in Drinkers |
| cg26061772 | 17 | 38296295 | Higher in Drinkers |
| cg26063087 | 22 | 35695661 | Higher in Drinkers |
| cg26064895 | 4 | 46271121 | Higher in Drinkers |
| cg26065580 | 1 | 41707906 | Higher in Drinkers |
| cg26075747 | 6 | 30457407 | Higher in Drinkers |
| cg26079618 | 13 | 113973896 | Higher in Drinkers |
| cg26094004 | 17 | 42075116 | Higher in Drinkers |
| cg26094714 | 3 | 48481771 | Higher in Drinkers |
| cg26095194 | 5 | 172197489 | Higher in Drinkers |
| cg26097573 | 20 | 4721490 | Higher in Drinkers |
| cg26104816 | 1 | 42922390 | Higher in Drinkers |
| cg26104986 | 11 | 75275303 | Higher in Drinkers |
| cg26106524 | 19 | 19517029 | Higher in Drinkers |
| cg26106626 | 22 | 50946971 | Higher in Drinkers |
| cg26111157 | 22 | 29076113 | Higher in Drinkers |
| cg26112353 | 4 | 79696708 | Higher in Drinkers |
| cg26114642 | 2 | 32852760 | Higher in Drinkers |
| cg26114884 | 11 | 64136975 | Higher in Drinkers |
| cg26116525 | 11 | 62371596 | Higher in Drinkers |
| cg26118637 | 7 | 155353417 | Higher in Drinkers |
| cg26119746 | X | 108976838 | Higher in Drinkers |
| cg26121561 | 14 | 50053030 | Higher in Drinkers |
| cg26124466 | 3 | 197347235 | Higher in Drinkers |
| cg26125131 | 7 | 102715617 | Higher in Drinkers |

| | | | |
|---|---|---|---|
| cg26130488 | 17 | 9530104 | Lower in Drinkers |
| cg26131893 | 17 | 47492353 | Higher in Drinkers |
| cg26131911 | 1 | 33118503 | Higher in Drinkers |
| cg26132647 | 3 | 50298315 | Higher in Drinkers |
| cg26134665 | 16 | 31021544 | Higher in Drinkers |
| cg26135134 | 15 | 99500715 | Higher in Drinkers |
| cg26135345 | 6 | 28806907 | Higher in Drinkers |
| cg26135528 | 6 | 30524499 | Higher in Drinkers |
| cg26135722 | 3 | 42642776 | Higher in Drinkers |
| cg26135967 | 3 | 33839866 | Higher in Drinkers |
| cg26138776 | 20 | 32273636 | Higher in Drinkers |
| cg26140007 | 5 | 64395544 | Lower in Drinkers |
| cg26144265 | 7 | 16685680 | Higher in Drinkers |
| cg26145228 | 1 | 107682504 | Higher in Drinkers |
| cg26151310 | 3 | 148803905 | Higher in Drinkers |
| cg26151510 | 13 | 101327190 | Higher in Drinkers |
| cg26151597 | 3 | 44802853 | Higher in Drinkers |
| cg26151740 | 19 | 54641525 | Higher in Drinkers |
| cg26152388 | 7 | 77166136 | Higher in Drinkers |
| cg26155719 | 21 | 47918693 | Lower in Drinkers |
| cg26155828 | X | 38664606 | Higher in Drinkers |
| cg26157802 | 2 | 220042863 | Higher in Drinkers |
| cg26158235 | 22 | 43089920 | Lower in Drinkers |
| cg26159934 | 7 | 105029497 | Higher in Drinkers |
| cg26160153 | 2 | 27373014 | Higher in Drinkers |
| cg26160196 | 6 | 18264854 | Higher in Drinkers |
| cg26161747 | 7 | 101562348 | Higher in Drinkers |
| cg26166004 | 2 | 201983237 | Higher in Drinkers |
| cg26166170 | 15 | 39996716 | Higher in Drinkers |
| cg26173203 | 5 | 114598574 | Higher in Drinkers |
| cg26178446 | 2 | 192542437 | Higher in Drinkers |
| cg26179022 | 14 | 65569348 | Higher in Drinkers |
| cg26182712 | 1 | 1387256 | Lower in Drinkers |
| cg26187219 | 5 | 52095812 | Higher in Drinkers |
| cg26188072 | 6 | 30034424 | Higher in Drinkers |

| | | | |
|---|---|---|---|
| cg26188825 | 6 | 15578074 | Higher in Drinkers |
| cg26195667 | 18 | 32873288 | Higher in Drinkers |
| cg26201589 | 12 | 56710225 | Higher in Drinkers |
| cg26205981 | 8 | 24856821 | Lower in Drinkers |
| cg26207017 | X | 23761589 | Higher in Drinkers |
| cg26209516 | 19 | 56015332 | Higher in Drinkers |
| cg26212303 | 15 | 41220719 | Higher in Drinkers |
| cg26213780 | 12 | 12764752 | Higher in Drinkers |
| cg26213873 | 1 | 112939056 | Higher in Drinkers |
| cg26215113 | 2 | 234369962 | Higher in Drinkers |
| cg26216891 | 17 | 30669342 | Higher in Drinkers |
| cg26222132 | 19 | 11998485 | Higher in Drinkers |
| cg26222723 | 18 | 77679167 | Higher in Drinkers |
| cg26223987 | 6 | 157802912 | Higher in Drinkers |
| cg26223996 | 15 | 74906395 | Higher in Drinkers |
| cg26224305 | 1 | 934197 | Higher in Drinkers |
| cg26225646 | 19 | 50381231 | Higher in Drinkers |
| cg26226110 | 1 | 1395945 | Higher in Drinkers |
| cg26226951 | 20 | 61558004 | Higher in Drinkers |
| cg26227101 | 1 | 14075870 | Higher in Drinkers |
| cg26228014 | 1 | 47073138 | Higher in Drinkers |
| cg26228591 | 1 | 16054846 | Higher in Drinkers |
| cg26229591 | 5 | 174905345 | Higher in Drinkers |
| cg26234900 | 6 | 32820214 | Lower in Drinkers |
| cg26236235 | 2 | 10534541 | Higher in Drinkers |
| cg26242866 | 19 | 5711310 | Higher in Drinkers |
| cg26243263 | 19 | 38826367 | Higher in Drinkers |
| cg26244738 | 4 | 40859344 | Higher in Drinkers |
| cg26246933 | 20 | 629120 | Higher in Drinkers |
| cg26248082 | 8 | 42356127 | Higher in Drinkers |
| cg26248486 | 12 | 76742361 | Higher in Drinkers |
| cg26249857 | 12 | 6643607 | Higher in Drinkers |
| cg26251909 | 1 | 39874809 | Higher in Drinkers |
| cg26252253 | 1 | 150980797 | Higher in Drinkers |
| cg26254393 | 20 | 36322169 | Higher in Drinkers |

| | | | |
|---|---|---|---|
| cg26256539 | 22 | 19895585 | Higher in Drinkers |
| cg26257177 | 19 | 10828928 | Higher in Drinkers |
| cg26257265 | 3 | 82035330 | Lower in Drinkers |
| cg26258399 | 8 | 103877083 | Higher in Drinkers |
| cg26260201 | 19 | 1490631 | Higher in Drinkers |
| cg26260819 | 11 | 45869049 | Higher in Drinkers |
| cg26265657 | 4 | 122619170 | Higher in Drinkers |
| cg26273886 | 20 | 17950694 | Higher in Drinkers |
| cg26278703 | 11 | 58910052 | Higher in Drinkers |
| cg26286408 | 3 | 12851742 | Higher in Drinkers |
| cg26288249 | 9 | 112810954 | Higher in Drinkers |
| cg26288748 | 6 | 33257542 | Higher in Drinkers |
| cg26291698 | 6 | 43445274 | Higher in Drinkers |
| cg26293830 | 11 | 66512047 | Higher in Drinkers |
| cg26296653 | 11 | 3899234 | Higher in Drinkers |
| cg26298054 | 10 | 131935323 | Higher in Drinkers |
| cg26299281 | 4 | 75719320 | Higher in Drinkers |
| cg26299322 | 16 | 1660612 | Higher in Drinkers |
| cg26299767 | 20 | 30062987 | Higher in Drinkers |
| cg26301639 | 3 | 93781795 | Higher in Drinkers |
| cg26302230 | 2 | 219733839 | Higher in Drinkers |
| cg26307862 | 20 | 34043103 | Higher in Drinkers |
| cg26309244 | 6 | 31514636 | Higher in Drinkers |
| cg26310240 | 20 | 30192190 | Higher in Drinkers |
| cg26314512 | 10 | 629625 | Lower in Drinkers |
| cg26315802 | 6 | 33281972 | Higher in Drinkers |
| cg26321476 | 10 | 99206194 | Higher in Drinkers |
| cg26322721 | 12 | 94071071 | Higher in Drinkers |
| cg26333594 | 19 | 58330952 | Higher in Drinkers |
| cg26334856 | 1 | 45672409 | Higher in Drinkers |
| cg26336731 | 22 | 42016984 | Higher in Drinkers |
| cg26336814 | 1 | 112297799 | Higher in Drinkers |
| cg26339797 | 1 | 100715363 | Higher in Drinkers |
| cg26339924 | 3 | 47029475 | Higher in Drinkers |
| cg26341661 | 15 | 52069389 | Higher in Drinkers |

| | | | |
|---|---|---|---|
| cg26346032 | 2 | 220143912 | Higher in Drinkers |
| cg26348939 | 11 | 65641335 | Higher in Drinkers |
| cg26349454 | 17 | 73150870 | Higher in Drinkers |
| cg26357017 | 14 | 23790225 | Higher in Drinkers |
| cg26357820 | 6 | 33161849 | Higher in Drinkers |
| cg26361052 | 2 | 70417980 | Higher in Drinkers |
| cg26361540 | 1 | 46597981 | Higher in Drinkers |
| cg26362079 | 8 | 22865026 | Lower in Drinkers |
| cg26366459 | 1 | 46049026 | Higher in Drinkers |
| cg26366480 | 10 | 102820327 | Higher in Drinkers |
| cg26366663 | 2 | 97523357 | Higher in Drinkers |
| cg26368024 | 22 | 19132208 | Higher in Drinkers |
| cg26370464 | 3 | 104007460 | Higher in Drinkers |
| cg26373411 | 3 | 124085620 | Higher in Drinkers |
| cg26373663 | 2 | 165698219 | Higher in Drinkers |
| cg26373949 | 5 | 159545806 | Higher in Drinkers |
| cg26375461 | 6 | 29716541 | Higher in Drinkers |
| cg26376749 | 17 | 30677620 | Higher in Drinkers |
| cg26380350 | 13 | 113362275 | Higher in Drinkers |
| cg26380756 | 22 | 39097154 | Higher in Drinkers |
| cg26382075 | 19 | 18077834 | Higher in Drinkers |
| cg26386886 | 12 | 12871924 | Higher in Drinkers |
| cg26388152 | 17 | 27944453 | Higher in Drinkers |
| cg26392005 | 14 | 81421297 | Higher in Drinkers |
| cg26396278 | 1 | 248814155 | Higher in Drinkers |
| cg26397172 | 17 | 27047272 | Higher in Drinkers |
| cg26401236 | 17 | 19881329 | Higher in Drinkers |
| cg26402417 | 11 | 94841384 | Higher in Drinkers |
| cg26403975 | 4 | 109571414 | Higher in Drinkers |
| cg26405759 | 21 | 45140424 | Higher in Drinkers |
| cg26406256 | 4 | 89619393 | Higher in Drinkers |
| cg26407034 | 1 | 14730610 | Higher in Drinkers |
| cg26409978 | 12 | 56511862 | Higher in Drinkers |
| cg26421181 | 17 | 73937284 | Higher in Drinkers |
| cg26429449 | 20 | 10415898 | Higher in Drinkers |

| | | | |
|---|---|---|---|
| cg26429508 | 6 | 31615385 | Higher in Drinkers |
| cg26429530 | 14 | 58765206 | Higher in Drinkers |
| cg26430059 | 14 | 89770384 | Higher in Drinkers |
| cg26430074 | 14 | 20811419 | Higher in Drinkers |
| cg26434225 | 8 | 80942688 | Higher in Drinkers |
| cg26434988 | 14 | 50999636 | Higher in Drinkers |
| cg26437564 | 7 | 45308727 | Higher in Drinkers |
| cg26442458 | 11 | 65728985 | Higher in Drinkers |
| cg26444623 | 18 | 47792921 | Higher in Drinkers |
| cg26451835 | 6 | 117996421 | Higher in Drinkers |
| cg26455413 | 6 | 144164357 | Higher in Drinkers |
| cg26455579 | 13 | 100153786 | Higher in Drinkers |
| cg26457013 | 19 | 55740188 | Higher in Drinkers |
| cg26460931 | 1 | 6762130 | Higher in Drinkers |
| cg26461907 | 4 | 47465727 | Higher in Drinkers |
| cg26462136 | 17 | 42276323 | Higher in Drinkers |
| cg26462239 | 17 | 45608823 | Higher in Drinkers |
| cg26462504 | 11 | 59435997 | Higher in Drinkers |
| cg26463088 | 22 | 31743738 | Higher in Drinkers |
| cg26464439 | 7 | 100173533 | Higher in Drinkers |
| cg26467918 | 11 | 63932088 | Higher in Drinkers |
| cg26469586 | 11 | 2019626 | Higher in Drinkers |
| cg26469597 | 16 | 30366960 | Higher in Drinkers |
| cg26471469 | 12 | 31226801 | Higher in Drinkers |
| cg26474057 | 5 | 180688755 | Higher in Drinkers |
| cg26477746 | 16 | 3727482 | Higher in Drinkers |
| cg26483578 | 6 | 130686708 | Higher in Drinkers |
| cg26485011 | 12 | 125473597 | Higher in Drinkers |
| cg26485563 | 12 | 56652449 | Higher in Drinkers |
| cg26489176 | 4 | 1901132 | Higher in Drinkers |
| cg26493629 | 11 | 68065258 | Higher in Drinkers |
| cg26496204 | 20 | 57427210 | Higher in Drinkers |
| cg26499487 | 19 | 46195349 | Higher in Drinkers |
| cg26499663 | 8 | 61835175 | Higher in Drinkers |
| cg26501502 | 11 | 66206439 | Higher in Drinkers |

| | | | |
|---|---|---|---|
| cg26503018 | 7 | 94286243 | Higher in Drinkers |
| cg26505371 | 19 | 5210732 | Lower in Drinkers |
| cg26507427 | 6 | 100054548 | Higher in Drinkers |
| cg26508844 | 17 | 49244169 | Higher in Drinkers |
| cg26509254 | 6 | 30685303 | Higher in Drinkers |
| cg26509722 | 12 | 6833059 | Higher in Drinkers |
| cg26514337 | 18 | 57026503 | Lower in Drinkers |
| cg26515676 | 12 | 7341666 | Higher in Drinkers |
| cg26517376 | 10 | 126428813 | Higher in Drinkers |
| cg26519500 | 15 | 67547208 | Higher in Drinkers |
| cg26525568 | 6 | 31929592 | Lower in Drinkers |
| cg26526397 | 6 | 33232433 | Higher in Drinkers |
| cg26530061 | 7 | 27265522 | Higher in Drinkers |
| cg26530063 | 5 | 180670944 | Higher in Drinkers |
| cg26530502 | 22 | 39415703 | Lower in Drinkers |
| cg26531737 | 1 | 25572862 | Higher in Drinkers |
| cg26536358 | 1 | 203830875 | Higher in Drinkers |
| cg26536460 | 1 | 1456875 | Lower in Drinkers |
| cg26540127 | 2 | 114647103 | Higher in Drinkers |
| cg26544685 | 11 | 93276720 | Higher in Drinkers |
| cg26546882 | 16 | 89165605 | Higher in Drinkers |
| cg26548134 | 22 | 41185283 | Higher in Drinkers |
| cg26553682 | 7 | 99214201 | Higher in Drinkers |
| cg26557854 | 8 | 128746395 | Higher in Drinkers |
| cg26559015 | 17 | 40687919 | Higher in Drinkers |
| cg26561148 | 3 | 33318851 | Higher in Drinkers |
| cg26561943 | 19 | 719632 | Higher in Drinkers |
| cg26569634 | 2 | 10760591 | Higher in Drinkers |
| cg26571009 | 7 | 1544333 | Higher in Drinkers |
| cg26571870 | 16 | 85723150 | Higher in Drinkers |
| cg26572163 | 1 | 110527156 | Higher in Drinkers |
| cg26574895 | 1 | 119682877 | Higher in Drinkers |
| cg26576136 | 12 | 95612105 | Higher in Drinkers |
| cg26579491 | 7 | 65878976 | Higher in Drinkers |
| cg26592411 | 6 | 125622976 | Higher in Drinkers |

| | | | |
|---|---|---|---|
| cg26604901 | 18 | 43684385 | Higher in Drinkers |
| cg26606327 | 7 | 98972104 | Higher in Drinkers |
| cg26606904 | 1 | 247242975 | Higher in Drinkers |
| cg26612129 | 20 | 25755634 | Higher in Drinkers |
| cg26612165 | 1 | 181059499 | Higher in Drinkers |
| cg26612175 | 1 | 100503886 | Higher in Drinkers |
| cg26613586 | 1 | 16847289 | Lower in Drinkers |
| cg26616932 | 1 | 115333490 | Lower in Drinkers |
| cg26618210 | 15 | 41576042 | Higher in Drinkers |
| cg26620472 | 13 | 95248662 | Higher in Drinkers |
| cg26621098 | 5 | 74965039 | Higher in Drinkers |
| cg26621911 | 19 | 59063026 | Higher in Drinkers |
| cg26624796 | 16 | 30406176 | Higher in Drinkers |
| cg26626089 | 19 | 54385865 | Lower in Drinkers |
| cg26627346 | 17 | 8090553 | Higher in Drinkers |
| cg26634885 | 17 | 43209687 | Higher in Drinkers |
| cg26636835 | 12 | 133391157 | Higher in Drinkers |
| cg26637795 | 10 | 27793165 | Higher in Drinkers |
| cg26640205 | 17 | 19281613 | Higher in Drinkers |
| cg26641022 | 12 | 125000767 | Higher in Drinkers |
| cg26649394 | 18 | 32870462 | Higher in Drinkers |
| cg26653714 | 8 | 22932056 | Higher in Drinkers |
| cg26654851 | 18 | 21269104 | Higher in Drinkers |
| cg26656113 | 4 | 72897613 | Lower in Drinkers |
| cg26656208 | 6 | 157008139 | Higher in Drinkers |
| cg26660541 | 7 | 5013536 | Higher in Drinkers |
| cg26660801 | 13 | 20532108 | Higher in Drinkers |
| cg26661257 | 14 | 62163091 | Higher in Drinkers |
| cg26662347 | 1 | 23345754 | Higher in Drinkers |
| cg26662512 | 7 | 2113177 | Higher in Drinkers |
| cg26664539 | 9 | 134270251 | Higher in Drinkers |
| cg26666029 | 8 | 145027741 | Higher in Drinkers |
| cg26669876 | 1 | 90099257 | Higher in Drinkers |
| cg26671183 | 1 | 207226604 | Higher in Drinkers |
| cg26672104 | 14 | 52327433 | Higher in Drinkers |

| | | | |
|---|---|---|---|
| cg26674800 | 17 | 7108653 | Higher in Drinkers |
| cg26674929 | 15 | 78730741 | Higher in Drinkers |
| cg26675753 | 16 | 21675326 | Higher in Drinkers |
| cg26676845 | 2 | 153280733 | Lower in Drinkers |
| cg26680127 | 16 | 46783018 | Higher in Drinkers |
| cg26680428 | 1 | 226322870 | Higher in Drinkers |
| cg26680885 | 6 | 167370215 | Higher in Drinkers |
| cg26682717 | 7 | 128503126 | Higher in Drinkers |
| cg26685197 | 1 | 10003173 | Higher in Drinkers |
| cg26686927 | 3 | 195599256 | Higher in Drinkers |
| cg26687567 | 3 | 186501284 | Higher in Drinkers |
| cg26688472 | 2 | 203638928 | Higher in Drinkers |
| cg26688923 | X | 72782837 | Higher in Drinkers |
| cg26690744 | 4 | 757456 | Higher in Drinkers |
| cg26691175 | 1 | 229761129 | Higher in Drinkers |
| cg26691567 | 1 | 178511749 | Higher in Drinkers |
| cg26691953 | 12 | 49110790 | Higher in Drinkers |
| cg26694386 | 1 | 244868765 | Higher in Drinkers |
| cg26697477 | 16 | 1836234 | Higher in Drinkers |
| cg26698580 | 16 | 67695984 | Higher in Drinkers |
| cg26698638 | 7 | 134001922 | Higher in Drinkers |
| cg26703664 | 12 | 89746258 | Higher in Drinkers |
| cg26705583 | 5 | 65017946 | Higher in Drinkers |
| cg26705720 | 20 | 10652787 | Higher in Drinkers |
| cg26707202 | 4 | 146403866 | Higher in Drinkers |
| cg26707263 | 2 | 241526101 | Higher in Drinkers |
| cg26708759 | 6 | 33385437 | Higher in Drinkers |
| cg26714129 | 8 | 142310710 | Lower in Drinkers |
| cg26715884 | 5 | 137549131 | Higher in Drinkers |
| cg26716323 | 7 | 22862328 | Higher in Drinkers |
| cg26718357 | 8 | 22554232 | Higher in Drinkers |
| cg26719735 | 3 | 69062888 | Higher in Drinkers |
| cg26719831 | 16 | 67279967 | Higher in Drinkers |
| cg26721993 | 5 | 1344908 | Higher in Drinkers |
| cg26727372 | 18 | 48404491 | Lower in Drinkers |

| | | | |
|---|---|---|---|
| cg26731473 | 15 | 34394138 | Higher in Drinkers |
| cg26733142 | 17 | 1733691 | Higher in Drinkers |
| cg26735793 | 10 | 127511350 | Higher in Drinkers |
| cg26736273 | 19 | 18303998 | Higher in Drinkers |
| cg26736450 | 2 | 63278211 | Higher in Drinkers |
| cg26738024 | 6 | 33228461 | Lower in Drinkers |
| cg26740644 | 7 | 43946455 | Higher in Drinkers |
| cg26741954 | 19 | 48954979 | Higher in Drinkers |
| cg26745757 | 11 | 1715454 | Higher in Drinkers |
| cg26745770 | 19 | 1513065 | Higher in Drinkers |
| cg26752655 | 20 | 23331282 | Higher in Drinkers |
| cg26755083 | 2 | 153032670 | Higher in Drinkers |
| cg26756340 | 16 | 58717807 | Higher in Drinkers |
| cg26759191 | 4 | 76439966 | Higher in Drinkers |
| cg26766900 | 4 | 129730719 | Higher in Drinkers |
| cg26774205 | 6 | 151412063 | Higher in Drinkers |
| cg26778908 | 10 | 13629255 | Higher in Drinkers |
| cg26779945 | 6 | 134273199 | Higher in Drinkers |
| cg26781886 | 5 | 49737336 | Higher in Drinkers |
| cg26783523 | 19 | 18043562 | Higher in Drinkers |
| cg26784546 | 10 | 135103553 | Higher in Drinkers |
| cg26789634 | 9 | 70152283 | Higher in Drinkers |
| cg26790897 | 7 | 56147772 | Higher in Drinkers |
| cg26795789 | 11 | 827488 | Higher in Drinkers |
| cg26803184 | 10 | 94333922 | Higher in Drinkers |
| cg26804336 | 5 | 67521733 | Higher in Drinkers |
| cg26805405 | 11 | 64491434 | Higher in Drinkers |
| cg26805585 | X | 47035685 | Higher in Drinkers |
| cg26809911 | 16 | 23464207 | Higher in Drinkers |
| cg26810157 | 15 | 57579076 | Higher in Drinkers |
| cg26810281 | 6 | 31465714 | Higher in Drinkers |
| cg26811705 | 11 | 118781408 | Higher in Drinkers |
| cg26813693 | 19 | 32836297 | Higher in Drinkers |
| cg26814847 | 12 | 123237152 | Higher in Drinkers |
| cg26815021 | 17 | 74733172 | Higher in Drinkers |

| | | | |
|---|---|---|---|
| cg26816128 | 11 | 57434555 | Higher in Drinkers |
| cg26818390 | 2 | 153032445 | Higher in Drinkers |
| cg26819427 | 16 | 2028435 | Higher in Drinkers |
| cg26820118 | 7 | 148036601 | Higher in Drinkers |
| cg26820233 | 16 | 833206 | Higher in Drinkers |
| cg26820641 | 20 | 30326728 | Higher in Drinkers |
| cg26822438 | X | 119134368 | Higher in Drinkers |
| cg26825650 | 1 | 204182957 | Lower in Drinkers |
| cg26826223 | 20 | 44486424 | Higher in Drinkers |
| cg26829395 | 15 | 40217855 | Lower in Drinkers |
| cg26830834 | 2 | 74007273 | Higher in Drinkers |
| cg26831148 | 20 | 57607406 | Higher in Drinkers |
| cg26833602 | 9 | 95821549 | Higher in Drinkers |
| cg26839284 | 1 | 110162246 | Higher in Drinkers |
| cg26843008 | 20 | 35724227 | Higher in Drinkers |
| cg26844459 | 20 | 61147623 | Higher in Drinkers |
| cg26846590 | 6 | 30181248 | Higher in Drinkers |
| cg26849909 | 17 | 79177197 | Higher in Drinkers |
| cg26849931 | 5 | 141014062 | Higher in Drinkers |
| cg26850559 | 10 | 3214952 | Higher in Drinkers |
| cg26851727 | 3 | 118959928 | Higher in Drinkers |
| cg26852170 | 6 | 29720448 | Higher in Drinkers |
| cg26857370 | 16 | 34442283 | Higher in Drinkers |
| cg26858605 | 17 | 45771108 | Higher in Drinkers |
| cg26858704 | 12 | 4918848 | Higher in Drinkers |
| cg26861525 | 15 | 74287168 | Higher in Drinkers |
| cg26864061 | 3 | 45730815 | Higher in Drinkers |
| cg26865446 | 3 | 181438328 | Higher in Drinkers |
| cg26869604 | 10 | 72142638 | Higher in Drinkers |
| cg26870941 | 6 | 31671069 | Higher in Drinkers |
| cg26872149 | 2 | 157191396 | Higher in Drinkers |
| cg26872475 | 11 | 119039430 | Higher in Drinkers |
| cg26874323 | 11 | 2909709 | Higher in Drinkers |
| cg26884180 | 1 | 15369795 | Higher in Drinkers |
| cg26885268 | 7 | 149389941 | Lower in Drinkers |

| | | | |
|---|---|---|---|
| cg26886307 | 16 | 57333810 | Higher in Drinkers |
| cg26888225 | 16 | 75032603 | Higher in Drinkers |
| cg26892251 | 6 | 28872373 | Higher in Drinkers |
| cg26896729 | 19 | 17416810 | Higher in Drinkers |
| cg26904406 | 6 | 111927312 | Higher in Drinkers |
| cg26904702 | 1 | 153746899 | Higher in Drinkers |
| cg26905268 | 19 | 11308417 | Higher in Drinkers |
| cg26906021 | 1 | 155146940 | Higher in Drinkers |
| cg26906639 | 16 | 2963569 | Higher in Drinkers |
| cg26908611 | 1 | 40421002 | Higher in Drinkers |
| cg26910230 | 17 | 8124658 | Higher in Drinkers |
| cg26910594 | 6 | 30710687 | Higher in Drinkers |
| cg26912312 | 20 | 61274254 | Higher in Drinkers |
| cg26918442 | 15 | 43622840 | Higher in Drinkers |
| cg26919527 | 22 | 21133973 | Higher in Drinkers |
| cg26920632 | 19 | 50094770 | Higher in Drinkers |
| cg26921533 | 11 | 67810300 | Higher in Drinkers |
| cg26921987 | 11 | 119548369 | Higher in Drinkers |
| cg26922028 | 6 | 138171829 | Higher in Drinkers |
| cg26923779 | 14 | 31677445 | Higher in Drinkers |
| cg26926632 | 1 | 150848739 | Higher in Drinkers |
| cg26928531 | 6 | 32407714 | Higher in Drinkers |
| cg26929012 | 19 | 57988860 | Higher in Drinkers |
| cg26930135 | 19 | 4371810 | Higher in Drinkers |
| cg26931208 | 19 | 49244592 | Higher in Drinkers |
| cg26931437 | 1 | 154452498 | Higher in Drinkers |
| cg26932976 | 17 | 2615186 | Higher in Drinkers |
| cg26933314 | 5 | 53944899 | Lower in Drinkers |
| cg26934034 | 12 | 113861110 | Higher in Drinkers |
| cg26935020 | 7 | 151217007 | Higher in Drinkers |
| cg26938153 | 7 | 137686926 | Higher in Drinkers |
| cg26940109 | 1 | 32095849 | Higher in Drinkers |
| cg26940725 | 13 | 27825886 | Higher in Drinkers |
| cg26943137 | 6 | 28574953 | Higher in Drinkers |
| cg26944552 | 8 | 145150752 | Higher in Drinkers |

| | | | |
|---|---|---|---|
| cg26946276 | 13 | 31736202 | Higher in Drinkers |
| cg26948626 | 11 | 125462551 | Higher in Drinkers |
| cg26949393 | 7 | 150827298 | Higher in Drinkers |
| cg26949796 | 14 | 35183363 | Higher in Drinkers |
| cg26957370 | 1 | 161087723 | Higher in Drinkers |
| cg26957405 | 16 | 83949156 | Higher in Drinkers |
| cg26960647 | 6 | 138188928 | Higher in Drinkers |
| cg26963844 | 17 | 47929214 | Higher in Drinkers |
| cg26974158 | 5 | 118788130 | Higher in Drinkers |
| cg26974738 | 6 | 33386261 | Higher in Drinkers |
| cg26975459 | 5 | 132209564 | Higher in Drinkers |
| cg26976181 | 19 | 18434160 | Higher in Drinkers |
| cg26977769 | 2 | 113240454 | Higher in Drinkers |
| cg26984869 | 15 | 45927218 | Higher in Drinkers |
| cg26985658 | 16 | 20818513 | Higher in Drinkers |
| cg26986558 | 5 | 81574325 | Higher in Drinkers |
| cg26993251 | 11 | 63934014 | Higher in Drinkers |
| cg26997085 | 7 | 94286110 | Higher in Drinkers |
| cg26997905 | 14 | 31554343 | Higher in Drinkers |
| cg26998044 | 17 | 8869155 | Higher in Drinkers |
| cg26998900 | 18 | 5238137 | Higher in Drinkers |
| cg27003776 | 7 | 2093976 | Lower in Drinkers |
| cg27003827 | 12 | 120906953 | Higher in Drinkers |
| cg27008316 | 12 | 34753697 | Higher in Drinkers |
| cg27012396 | 2 | 240233043 | Higher in Drinkers |
| cg27014625 | 22 | 46663777 | Higher in Drinkers |
| cg27024417 | 1 | 32645813 | Higher in Drinkers |
| cg27025758 | 6 | 112408447 | Higher in Drinkers |
| cg27026786 | 13 | 24798133 | Lower in Drinkers |
| cg27032957 | 6 | 31165819 | Higher in Drinkers |
| cg27034902 | 3 | 182971430 | Higher in Drinkers |
| cg27037103 | 6 | 37666346 | Higher in Drinkers |
| cg27037943 | 1 | 84972490 | Higher in Drinkers |
| cg27041794 | 10 | 11059708 | Higher in Drinkers |
| cg27042767 | X | 41192872 | Higher in Drinkers |

| | | | |
|---|---|---|---|
| cg27044202 | 11 | 8681335 | Higher in Drinkers |
| cg27044593 | 1 | 6639904 | Higher in Drinkers |
| cg27048140 | 7 | 99058641 | Higher in Drinkers |
| cg27049566 | 8 | 61430303 | Higher in Drinkers |
| cg27051767 | 10 | 102133548 | Higher in Drinkers |
| cg27053785 | 7 | 1024142 | Lower in Drinkers |
| cg27055842 | 21 | 33765028 | Higher in Drinkers |
| cg27058497 | 1 | 25291546 | Higher in Drinkers |
| cg27060104 | 21 | 45744833 | Higher in Drinkers |
| cg27061947 | 5 | 74307308 | Higher in Drinkers |
| cg27062573 | 22 | 39549099 | Higher in Drinkers |
| cg27063170 | 10 | 124740175 | Higher in Drinkers |
| cg27064708 | 14 | 69030612 | Higher in Drinkers |
| cg27065415 | 6 | 31763547 | Higher in Drinkers |
| cg27072603 | 15 | 40660990 | Higher in Drinkers |
| cg27072683 | 10 | 102289885 | Higher in Drinkers |
| cg27073113 | 16 | 56228744 | Higher in Drinkers |
| cg27073561 | 17 | 8045617 | Higher in Drinkers |
| cg27073809 | 11 | 108536195 | Higher in Drinkers |
| cg27076777 | 19 | 12344868 | Higher in Drinkers |
| cg27078464 | 2 | 113918666 | Higher in Drinkers |
| cg27078522 | 7 | 4815167 | Higher in Drinkers |
| cg27078591 | X | 149737335 | Higher in Drinkers |
| cg27080259 | 16 | 3037875 | Higher in Drinkers |
| cg27081603 | 5 | 175788876 | Higher in Drinkers |
| cg27082292 | 8 | 145001361 | Higher in Drinkers |
| cg27083344 | 16 | 89782458 | Higher in Drinkers |
| cg27084965 | 7 | 103871917 | Higher in Drinkers |
| cg27091100 | 19 | 36128359 | Higher in Drinkers |
| cg27093273 | 13 | 5892213 | Higher in Drinkers |
| cg27093645 | 12 | 57482538 | Higher in Drinkers |
| cg27093989 | 2 | 102314611 | Higher in Drinkers |
| cg27097846 | 12 | 53443485 | Higher in Drinkers |
| cg27101004 | 13 | 113174225 | Lower in Drinkers |
| cg27105465 | 17 | 40337623 | Higher in Drinkers |

| | | | |
|---|---|---|---|
| cg27105827 | 18 | 55862577 | Higher in Drinkers |
| cg27108047 | 17 | 73257296 | Higher in Drinkers |
| cg27108419 | 6 | 30095762 | Higher in Drinkers |
| cg27108452 | 3 | 32822410 | Higher in Drinkers |
| cg27109971 | 18 | 267637 | Higher in Drinkers |
| cg27114086 | 1 | 155658701 | Higher in Drinkers |
| cg27117179 | 3 | 75410789 | Higher in Drinkers |
| cg27119415 | 17 | 38137936 | Higher in Drinkers |
| cg27122042 | 11 | 75110449 | Higher in Drinkers |
| cg27124109 | 12 | 46121515 | Higher in Drinkers |
| cg27132050 | 15 | 45021149 | Higher in Drinkers |
| cg27137576 | 6 | 31922361 | Lower in Drinkers |
| cg27138059 | 19 | 6272597 | Higher in Drinkers |
| cg27138727 | 3 | 107150777 | Higher in Drinkers |
| cg27139933 | 6 | 170600026 | Higher in Drinkers |
| cg27141427 | 14 | 70079160 | Higher in Drinkers |
| cg27148193 | 7 | 148927030 | Higher in Drinkers |
| cg27150370 | 21 | 34863940 | Higher in Drinkers |
| cg27150476 | 4 | 1844878 | Higher in Drinkers |
| cg27151980 | 16 | 30772821 | Higher in Drinkers |
| cg27157038 | 10 | 98063999 | Higher in Drinkers |
| cg27159032 | 19 | 9272145 | Higher in Drinkers |
| cg27161852 | 7 | 64408298 | Higher in Drinkers |
| cg27166713 | 6 | 118880109 | Higher in Drinkers |
| cg27167221 | 1 | 7103111 | Lower in Drinkers |
| cg27168976 | 1 | 52521353 | Higher in Drinkers |
| cg27170260 | 1 | 38156575 | Higher in Drinkers |
| cg27180443 | 12 | 125348871 | Higher in Drinkers |
| cg27182555 | 4 | 83821584 | Higher in Drinkers |
| cg27182764 | 1 | 168148096 | Higher in Drinkers |
| cg27184438 | 7 | 4690819 | Higher in Drinkers |
| cg27184623 | 4 | 17616433 | Higher in Drinkers |
| cg27186133 | 4 | 36245571 | Higher in Drinkers |
| cg27187671 | X | 70752936 | Higher in Drinkers |
| cg27191184 | 16 | 580239 | Higher in Drinkers |

| | | | |
|---|---|---|---|
| cg27191312 | 19 | 12750958 | Higher in Drinkers |
| cg27191651 | 6 | 31122406 | Higher in Drinkers |
| cg27193005 | 6 | 26382695 | Higher in Drinkers |
| cg27194081 | 22 | 50640274 | Higher in Drinkers |
| cg27197744 | 11 | 66206230 | Higher in Drinkers |
| cg27198824 | X | 147582727 | Higher in Drinkers |
| cg27201802 | 6 | 30138225 | Higher in Drinkers |
| cg27203437 | 16 | 81129991 | Higher in Drinkers |
| cg27205791 | 12 | 54719080 | Higher in Drinkers |
| cg27206295 | 15 | 60618474 | Lower in Drinkers |
| cg27206903 | 17 | 80006003 | Higher in Drinkers |
| cg27210536 | 22 | 51012546 | Higher in Drinkers |
| cg27212520 | 7 | 1912334 | Higher in Drinkers |
| cg27213352 | 17 | 32907731 | Higher in Drinkers |
| cg27218469 | 2 | 7005960 | Higher in Drinkers |
| cg27218685 | 3 | 194238917 | Higher in Drinkers |
| cg27221266 | 10 | 96122679 | Higher in Drinkers |
| cg27225443 | 2 | 70056465 | Higher in Drinkers |
| cg27228276 | 1 | 151119210 | Higher in Drinkers |
| cg27230044 | 7 | 94285993 | Higher in Drinkers |
| cg27231712 | 6 | 33257806 | Higher in Drinkers |
| cg27234648 | 15 | 91077406 | Higher in Drinkers |
| cg27235218 | 4 | 1208675 | Higher in Drinkers |
| cg27235726 | 7 | 750819 | Higher in Drinkers |
| cg27237039 | 6 | 7592994 | Higher in Drinkers |
| cg27237189 | 10 | 21815683 | Higher in Drinkers |
| cg27239243 | 2 | 101945867 | Higher in Drinkers |
| cg27239828 | 3 | 185136561 | Lower in Drinkers |
| cg27239920 | 6 | 32862697 | Higher in Drinkers |
| cg27244120 | 16 | 70610434 | Higher in Drinkers |
| cg27245950 | 16 | 88493613 | Higher in Drinkers |
| cg27247569 | 16 | 88097866 | Lower in Drinkers |
| cg27250362 | 16 | 67597316 | Higher in Drinkers |
| cg27250759 | 6 | 20401608 | Higher in Drinkers |
| cg27253580 | 4 | 175205025 | Higher in Drinkers |

| | | | |
|---|---|---|---|
| cg27256934 | 11 | 61197489 | Higher in Drinkers |
| cg27258283 | 16 | 89337103 | Higher in Drinkers |
| cg27263448 | 7 | 127637871 | Higher in Drinkers |
| cg27263632 | 17 | 79496290 | Higher in Drinkers |
| cg27263778 | 11 | 71201682 | Higher in Drinkers |
| cg27264993 | 6 | 33084608 | Higher in Drinkers |
| cg27266479 | 1 | 9294882 | Higher in Drinkers |
| cg27268513 | 11 | 9596214 | Higher in Drinkers |
| cg27269442 | 3 | 99979679 | Higher in Drinkers |
| cg27269962 | 7 | 127540997 | Higher in Drinkers |
| cg27272605 | 3 | 138634607 | Higher in Drinkers |
| cg27281285 | 12 | 120315368 | Higher in Drinkers |
| cg27284088 | 4 | 84031130 | Higher in Drinkers |
| cg27286957 | 6 | 33740409 | Higher in Drinkers |
| cg27287181 | 12 | 98901037 | Higher in Drinkers |
| cg27291138 | 3 | 122283635 | Higher in Drinkers |
| cg27291501 | 17 | 17494835 | Higher in Drinkers |
| cg27292230 | 1 | 156571424 | Higher in Drinkers |
| cg27292953 | 4 | 2964910 | Higher in Drinkers |
| cg27297192 | 10 | 134578999 | Higher in Drinkers |
| cg27298159 | 6 | 116937488 | Higher in Drinkers |
| cg27298324 | 1 | 182587340 | Higher in Drinkers |
| cg27300967 | 1 | 6685162 | Higher in Drinkers |
| cg27304047 | 2 | 97001659 | Higher in Drinkers |
| cg27304813 | 3 | 120068385 | Higher in Drinkers |
| cg27305525 | 1 | 154955752 | Higher in Drinkers |
| cg27309139 | 16 | 1464772 | Higher in Drinkers |
| cg27309905 | 3 | 115556374 | Lower in Drinkers |
| cg27309920 | 12 | 6798957 | Higher in Drinkers |
| cg27310024 | 15 | 90950101 | Higher in Drinkers |
| cg27310963 | 16 | 30596419 | Higher in Drinkers |
| cg27311476 | 18 | 77794419 | Higher in Drinkers |
| cg27312203 | 7 | 631951 | Higher in Drinkers |
| cg27313501 | 16 | 2034198 | Higher in Drinkers |
| cg27313662 | 4 | 106395321 | Higher in Drinkers |

| | | | |
|---|---|---|---|
| cg27316808 | 1 | 6453995 | Higher in Drinkers |
| cg27317150 | 6 | 110012180 | Higher in Drinkers |
| cg27320816 | 10 | 7830127 | Higher in Drinkers |
| cg27321538 | 2 | 220252231 | Higher in Drinkers |
| cg27322071 | 16 | 87384763 | Higher in Drinkers |
| cg27323049 | 6 | 30295227 | Higher in Drinkers |
| cg27325460 | 13 | 45945296 | Higher in Drinkers |
| cg27326481 | 15 | 91204347 | Higher in Drinkers |
| cg27330824 | 6 | 106440663 | Higher in Drinkers |
| cg27333567 | 16 | 88106229 | Higher in Drinkers |
| cg27334938 | 18 | 77167042 | Higher in Drinkers |
| cg27336300 | 19 | 42778755 | Higher in Drinkers |
| cg27337199 | 8 | 9046478 | Higher in Drinkers |
| cg27338607 | 20 | 20351833 | Higher in Drinkers |
| cg27342087 | 1 | 186344651 | Higher in Drinkers |
| cg27344462 | 9 | 34401074 | Higher in Drinkers |
| cg27345282 | 3 | 196295526 | Higher in Drinkers |
| cg27346882 | 19 | 48111271 | Higher in Drinkers |
| cg27347496 | 11 | 107496475 | Higher in Drinkers |
| cg27364583 | 17 | 8090248 | Higher in Drinkers |
| cg27368538 | 5 | 78906004 | Higher in Drinkers |
| cg27369423 | 16 | 56228901 | Higher in Drinkers |
| cg27370344 | 10 | 35379631 | Higher in Drinkers |
| cg27373063 | 15 | 40987107 | Higher in Drinkers |
| cg27376617 | 7 | 30518048 | Higher in Drinkers |
| cg27377749 | 7 | 39605536 | Higher in Drinkers |
| cg27382691 | 15 | 76552771 | Higher in Drinkers |
| cg27384587 | 6 | 32095761 | Higher in Drinkers |
| cg27385443 | 19 | 11145789 | Higher in Drinkers |
| cg27388618 | 18 | 60986547 | Higher in Drinkers |
| cg27391191 | 2 | 220248720 | Higher in Drinkers |
| cg27392956 | 20 | 62887462 | Higher in Drinkers |
| cg27394563 | 12 | 108954529 | Higher in Drinkers |
| cg27395450 | 3 | 52322044 | Higher in Drinkers |
| cg27397625 | 6 | 42952298 | Higher in Drinkers |

| | | | |
|---|---|---|---|
| cg27399387 | 17 | 71062041 | Higher in Drinkers |
| cg27400746 | 16 | 89904261 | Higher in Drinkers |
| cg27410136 | 17 | 6913946 | Higher in Drinkers |
| cg27412680 | 6 | 73332963 | Higher in Drinkers |
| cg27413820 | 17 | 17701697 | Lower in Drinkers |
| cg27419474 | 18 | 47814612 | Higher in Drinkers |
| cg27420674 | 19 | 49974121 | Lower in Drinkers |
| cg27423510 | 19 | 10589815 | Higher in Drinkers |
| cg27425136 | 15 | 28357718 | Higher in Drinkers |
| cg27431396 | 20 | 32250213 | Higher in Drinkers |
| cg27436286 | 15 | 65670863 | Higher in Drinkers |
| cg27438456 | 10 | 134458916 | Higher in Drinkers |
| cg27439427 | 15 | 64648470 | Higher in Drinkers |
| cg27442054 | 1 | 2449541 | Lower in Drinkers |
| cg27443310 | 7 | 90225778 | Higher in Drinkers |
| cg27444899 | 16 | 565493 | Lower in Drinkers |
| cg27449114 | 2 | 241501342 | Higher in Drinkers |
| cg27451531 | 1 | 222648256 | Higher in Drinkers |
| cg27455049 | 17 | 29253411 | Higher in Drinkers |
| cg27461883 | 16 | 27561453 | Higher in Drinkers |
| cg27467734 | 12 | 53646162 | Higher in Drinkers |
| cg27467996 | 5 | 179921670 | Higher in Drinkers |
| cg27468976 | 16 | 89410322 | Lower in Drinkers |
| cg27470303 | 10 | 21823447 | Higher in Drinkers |
| cg27470373 | 2 | 64836764 | Higher in Drinkers |
| cg27470406 | 12 | 1704156 | Higher in Drinkers |
| cg27471124 | 11 | 109292789 | Lower in Drinkers |
| cg27477419 | 17 | 75567407 | Higher in Drinkers |
| cg27478035 | 2 | 175260614 | Higher in Drinkers |
| cg27479455 | 19 | 7529920 | Higher in Drinkers |
| cg27480700 | 19 | 52800524 | Higher in Drinkers |
| cg27481141 | 11 | 68816453 | Higher in Drinkers |
| cg27482619 | 10 | 30818479 | Higher in Drinkers |
| cg27482956 | 7 | 99214447 | Higher in Drinkers |
| cg27484805 | 10 | 22726730 | Higher in Drinkers |

| | | | |
|---|---|---|---|
| cg27486151 | 17 | 7367439 | Higher in Drinkers |
| cg27487704 | 16 | 50840647 | Higher in Drinkers |
| cg27490352 | 17 | 63053354 | Higher in Drinkers |
| cg27493117 | 2 | 106468123 | Higher in Drinkers |
| cg27493484 | 17 | 37793215 | Higher in Drinkers |
| cg27493965 | 19 | 12767784 | Higher in Drinkers |
| cg27495336 | 19 | 11708223 | Higher in Drinkers |
| cg27495964 | 7 | 148876387 | Higher in Drinkers |
| cg27496267 | 7 | 90895466 | Higher in Drinkers |
| cg27499747 | 11 | 57092930 | Higher in Drinkers |
| cg27500838 | 9 | 139839439 | Higher in Drinkers |
| cg27500856 | 3 | 48957559 | Higher in Drinkers |
| cg27501265 | 6 | 33281775 | Higher in Drinkers |
| cg27503970 | 2 | 99953877 | Higher in Drinkers |
| cg27504195 | 3 | 113342400 | Lower in Drinkers |
| cg27509867 | 8 | 129165585 | Higher in Drinkers |
| cg27511957 | 1 | 16754499 | Higher in Drinkers |
| cg27512082 | 17 | 57232889 | Higher in Drinkers |
| cg27513517 | 1 | 183439365 | Higher in Drinkers |
| cg27513935 | 13 | 28552610 | Higher in Drinkers |
| cg27515966 | 1 | 246862720 | Higher in Drinkers |
| cg27517652 | 1 | 179050673 | Higher in Drinkers |
| cg27517861 | 19 | 49845798 | Higher in Drinkers |
| cg27518993 | 3 | 52088253 | Lower in Drinkers |
| cg27525614 | 6 | 26252141 | Higher in Drinkers |
| cg27526774 | 1 | 233099089 | Higher in Drinkers |
| cg27527922 | 1 | 6260181 | Higher in Drinkers |
| cg27529930 | 15 | 40697959 | Higher in Drinkers |
| cg27530239 | 17 | 46909074 | Higher in Drinkers |
| cg27530316 | 19 | 49497072 | Higher in Drinkers |
| cg27531366 | 1 | 27627058 | Higher in Drinkers |
| cg27534796 | 6 | 143382067 | Higher in Drinkers |
| cg27536187 | 1 | 2159365 | Higher in Drinkers |
| cg27537053 | 1 | 4406790 | Higher in Drinkers |
| cg27537937 | 1 | 155948318 | Higher in Drinkers |

| | | | |
|---|---|---|---|
| cg27540823 | 10 | 50746389 | Higher in Drinkers |
| cg27543431 | 16 | 27499592 | Higher in Drinkers |
| cg27543493 | 17 | 38137097 | Higher in Drinkers |
| cg27545367 | 6 | 30711644 | Higher in Drinkers |
| cg27546682 | 1 | 36851860 | Higher in Drinkers |
| cg27546949 | 19 | 57999003 | Higher in Drinkers |
| cg27547043 | 2 | 202316262 | Higher in Drinkers |
| cg27547283 | 1 | 156698502 | Higher in Drinkers |
| cg27547873 | 2 | 37424360 | Higher in Drinkers |
| cg27550270 | 6 | 117086996 | Higher in Drinkers |
| cg27550498 | X | 70340920 | Higher in Drinkers |
| cg27550721 | 15 | 79381747 | Higher in Drinkers |
| cg27552483 | 16 | 11268210 | Higher in Drinkers |
| cg27553501 | 19 | 37340694 | Higher in Drinkers |
| cg27559747 | 1 | 27916108 | Higher in Drinkers |
| cg27561786 | 1 | 8525010 | Higher in Drinkers |
| cg27562005 | 6 | 525032 | Lower in Drinkers |
| cg27562311 | 12 | 8766941 | Higher in Drinkers |
| cg27563668 | 14 | 103995759 | Higher in Drinkers |
| cg27568306 | 17 | 46136797 | Higher in Drinkers |
| cg27568321 | 4 | 113152709 | Higher in Drinkers |
| cg27568631 | 11 | 63438816 | Higher in Drinkers |
| cg27574071 | 4 | 1219498 | Lower in Drinkers |
| cg27574244 | 17 | 80709357 | Higher in Drinkers |
| cg27577760 | 4 | 190567323 | Lower in Drinkers |
| cg27582173 | 6 | 38120063 | Lower in Drinkers |
| cg27583088 | 1 | 182758324 | Higher in Drinkers |
| cg27589368 | 17 | 43923255 | Lower in Drinkers |
| cg27589796 | 5 | 1338514 | Higher in Drinkers |
| cg27590748 | 5 | 142149936 | Higher in Drinkers |
| cg27592523 | 17 | 8024253 | Higher in Drinkers |
| cg27593688 | 19 | 8386083 | Higher in Drinkers |
| cg27597504 | 10 | 72142304 | Higher in Drinkers |
| cg27599329 | 16 | 47175842 | Higher in Drinkers |
| cg27601855 | 11 | 47197938 | Higher in Drinkers |

| | | | |
|---|---|---|---|
| cg27601906 | 8 | 95271635 | Higher in Drinkers |
| cg27606002 | 17 | 76142461 | Higher in Drinkers |
| cg27607340 | 12 | 49110506 | Higher in Drinkers |
| cg27610178 | 5 | 43313951 | Higher in Drinkers |
| cg27610961 | 12 | 67663042 | Higher in Drinkers |
| cg27613852 | 5 | 39075062 | Higher in Drinkers |
| cg27615590 | X | 70752883 | Higher in Drinkers |
| cg27618379 | 4 | 855988 | Higher in Drinkers |
| cg27619149 | 12 | 93963520 | Higher in Drinkers |
| cg27619353 | 22 | 38071651 | Lower in Drinkers |
| cg27620174 | 7 | 102034278 | Higher in Drinkers |
| cg27624178 | 15 | 34393959 | Higher in Drinkers |
| cg27625481 | 15 | 63967230 | Higher in Drinkers |
| cg27626141 | 8 | 103876469 | Higher in Drinkers |
| cg27627006 | 11 | 96072706 | Higher in Drinkers |
| cg27628536 | 5 | 43017351 | Higher in Drinkers |
| cg27629931 | 1 | 26633232 | Higher in Drinkers |
| cg27631114 | 8 | 86019854 | Higher in Drinkers |
| cg27632493 | 6 | 29853169 | Lower in Drinkers |
| cg27633342 | 15 | 52588279 | Higher in Drinkers |
| cg27633903 | 12 | 57917206 | Higher in Drinkers |
| cg27636047 | 4 | 1581088 | Higher in Drinkers |
| cg27636813 | 6 | 28872287 | Higher in Drinkers |
| cg27640833 | 3 | 128713016 | Higher in Drinkers |
| cg27643099 | 2 | 203679262 | Higher in Drinkers |
| cg27645858 | 2 | 238005812 | Higher in Drinkers |
| cg27648095 | 21 | 33762341 | Higher in Drinkers |
| cg27650434 | 1 | 40368189 | Higher in Drinkers |
| cg27651220 | 16 | 87641133 | Lower in Drinkers |
| cg27659903 | 2 | 236514471 | Lower in Drinkers |
| cg27662877 | 18 | 71959595 | Higher in Drinkers |
| cg27665449 | 2 | 71204401 | Higher in Drinkers |
| ch.1.107099706F | 1 | 107298183 | Higher in Drinkers |
| ch.1.113470988R | 1 | 113669465 | Higher in Drinkers |
| ch.1.1187063R | 1 | 37453448 | Higher in Drinkers |

| | | | |
|---|---|---|---|
| ch.1.156669547F | 1 | 158402923 | Higher in Drinkers |
| ch.1.162207702R | 1 | 163941078 | Higher in Drinkers |
| ch.1.169608016R | 1 | 171341392 | Higher in Drinkers |
| ch.1.173201084F | 1 | 174934461 | Higher in Drinkers |
| ch.1.1854513R | 1 | 66883628 | Higher in Drinkers |
| ch.1.190144434F | 1 | 191877811 | Higher in Drinkers |
| ch.1.198578402R | 1 | 200311779 | Higher in Drinkers |
| ch.1.207058233R | 1 | 208991610 | Higher in Drinkers |
| ch.1.220071960R | 1 | 222005337 | Higher in Drinkers |
| ch.1.226360333F | 1 | 228293710 | Higher in Drinkers |
| ch.1.227099949R | 1 | 229033326 | Higher in Drinkers |
| ch.1.230766435F | 1 | 232699812 | Higher in Drinkers |
| ch.1.234902740R | 1 | 236836117 | Higher in Drinkers |
| ch.1.24684R | 1 | 1190026 | Higher in Drinkers |
| ch.1.2799899R | 1 | 120906506 | Higher in Drinkers |
| ch.1.2968748F | 1 | 154230586 | Higher in Drinkers |
| ch.1.3307476R | 1 | 169082848 | Higher in Drinkers |
| ch.1.47C7864F | 1 | 237351020 | Higher in Drinkers |
| ch.1.55746252R | 1 | 55973664 | Higher in Drinkers |
| ch.1.56581040R | 1 | 56808452 | Higher in Drinkers |
| ch.1.587982R | 1 | 17293256 | Higher in Drinkers |
| ch.1.87505147F | 1 | 87732559 | Higher in Drinkers |
| ch.1.893623F | 1 | 27102602 | Higher in Drinkers |
| ch.1.95642235F | 1 | 95869647 | Higher in Drinkers |
| ch.1.976694F | 1 | 29531247 | Higher in Drinkers |
| ch.10.1028651F | 10 | 44969997 | Higher in Drinkers |
| ch.10.116792202R | 10 | 116802212 | Higher in Drinkers |
| ch.10.120590236F | 10 | 120600246 | Higher in Drinkers |
| ch.10.133109453R | 10 | 133219463 | Higher in Drinkers |
| ch.10.1418365R | 10 | 69703635 | Higher in Drinkers |
| ch.10.1515233F | 10 | 73039321 | Higher in Drinkers |
| ch.10.17390829F | 10 | 17350823 | Higher in Drinkers |
| ch.10.1853020F | 10 | 88491461 | Higher in Drinkers |
| ch.10.20627146F | 10 | 20587140 | Higher in Drinkers |
| ch.10.2420334F | 10 | 115122200 | Higher in Drinkers |

| | | | |
|---|---|---|---|
| ch.10.2774258R | 10 | 129113226 | Higher in Drinkers |
| ch.10.344997F | 10 | 12216551 | Higher in Drinkers |
| ch.10.6019805R | 10 | 5979799 | Higher in Drinkers |
| ch.10.65169555F | 10 | 65499549 | Higher in Drinkers |
| ch.10.72059822F | 10 | 72389816 | Higher in Drinkers |
| ch.10.96879639F | 10 | 96889649 | Higher in Drinkers |
| ch.10.983355R | 10 | 43130566 | Higher in Drinkers |
| ch.11.101068432R | 11 | 101563272 | Higher in Drinkers |
| ch.11.110329410F | 11 | 110824200 | Higher in Drinkers |
| ch.11.130657691R | 11 | 131152481 | Higher in Drinkers |
| ch.11.24196551F | 11 | 24239977 | Higher in Drinkers |
| ch.11.25488742R | 11 | 25532168 | Higher in Drinkers |
| ch.11.2619180F | 11 | 125545646 | Higher in Drinkers |
| ch.11.28744729R | 11 | 28788153 | Higher in Drinkers |
| ch.11.310923R | 11 | 11458355 | Higher in Drinkers |
| ch.11.61132480F | 11 | 61375904 | Higher in Drinkers |
| ch.11.69043358R | 11 | 69334177 | Higher in Drinkers |
| ch.11.91717525F | 11 | 92077877 | Higher in Drinkers |
| ch.11.91906385F | 11 | 92266737 | Higher in Drinkers |
| ch.11.930275R | 11 | 45476506 | Higher in Drinkers |
| ch.11.96774805R | 11 | 97269595 | Higher in Drinkers |
| ch.11.97728705F | 11 | 98223495 | Higher in Drinkers |
| ch.12.105153690R | 12 | 106629560 | Higher in Drinkers |
| ch.12.12432R | 12 | 539860 | Higher in Drinkers |
| ch.12.129703717R | 12 | 131137764 | Higher in Drinkers |
| ch.12.19126263F | 12 | 19234996 | Higher in Drinkers |
| ch.12.19627204F | 12 | 19735937 | Higher in Drinkers |
| ch.12.2586863F | 12 | 123245624 | Higher in Drinkers |
| ch.12.28612808R | 12 | 28721541 | Higher in Drinkers |
| ch.12.29939875F | 12 | 30048608 | Higher in Drinkers |
| ch.12.31424680R | 12 | 31533413 | Higher in Drinkers |
| ch.12.41606343F | 12 | 43320076 | Higher in Drinkers |
| ch.12.88942289F | 12 | 90418158 | Higher in Drinkers |
| ch.12.96843545R | 12 | 98319414 | Higher in Drinkers |
| ch.13.112874825F | 13 | 113326824 | Higher in Drinkers |

| | | | |
|---|---|---|---|
| ch.13.1834088F | 13 | 112692382 | Higher in Drinkers |
| ch.13.531804F | 13 | 42379589 | Higher in Drinkers |
| ch.13.75704157F | 13 | 76806156 | Higher in Drinkers |
| ch.13.78325399R | 13 | 79427398 | Higher in Drinkers |
| ch.13.88042588R | 13 | 89244587 | Higher in Drinkers |
| ch.13.97330936R | 13 | 98532935 | Higher in Drinkers |
| ch.14.1421228R | 14 | 90730328 | Higher in Drinkers |
| ch.14.25380199R | 14 | 26310359 | Higher in Drinkers |
| ch.14.25380211R | 14 | 26310371 | Higher in Drinkers |
| ch.14.28343813R | 14 | 29274062 | Higher in Drinkers |
| ch.14.37665462F | 14 | 38595711 | Higher in Drinkers |
| ch.14.471449F | 14 | 45480793 | Higher in Drinkers |
| ch.14.52809496F | 14 | 53739746 | Higher in Drinkers |
| ch.14.68214257F | 14 | 69144504 | Higher in Drinkers |
| ch.14.71061373R | 14 | 71991620 | Higher in Drinkers |
| ch.14.92683308R | 14 | 93613555 | Higher in Drinkers |
| ch.14.955325R | 14 | 6935C231 | Higher in Drinkers |
| ch.15.1454355R | 15 | 86300571 | Higher in Drinkers |
| ch.15.1530357F | 15 | 89865772 | Higher in Drinkers |
| ch.15.1614682R | 15 | 92356301 | Higher in Drinkers |
| ch.15.23721785F | 15 | 26170692 | Higher in Drinkers |
| ch.15.23774000R | 15 | 26222907 | Higher in Drinkers |
| ch.15.31224719R | 15 | 33437427 | Higher in Drinkers |
| ch.15.62563063R | 15 | 64776010 | Higher in Drinkers |
| ch.15.77890571R | 15 | 80103516 | Higher in Drinkers |
| ch.16.1230298R | 16 | 56326795 | Higher in Drinkers |
| ch.16.1297555R | 16 | 58606277 | Higher in Drinkers |
| ch.16.1357260F | 16 | 61383344 | Higher in Drinkers |
| ch.16.271253R | 16 | 5918149 | Higher in Drinkers |
| ch.16.46462247F | 16 | 47904746 | Higher in Drinkers |
| ch.16.47020004F | 16 | 48462503 | Higher in Drinkers |
| ch.16.48036688F | 16 | 49479387 | Higher in Drinkers |
| ch.16.64814095R | 16 | 66256594 | Higher in Drinkers |
| ch.16.72302375R | 16 | 73744674 | Higher in Drinkers |
| ch.16.82416228R | 16 | 83858727 | Higher in Drinkers |

| | | | |
|---|---|---|---|
| ch.16.84131625R | 16 | 85574124 | Higher in Drinkers |
| ch.16.85547084R | 16 | 86989583 | Higher in Drinkers |
| ch.16.8889012F | 16 | 8981511 | Higher in Drinkers |
| ch.17.1102270R | 17 | 40721716 | Higher in Drinkers |
| ch.17.1247542F | 17 | 45755671 | Higher in Drinkers |
| ch.17.1874959R | 17 | 71154188 | Higher in Drinkers |
| ch.17.2138644F | 17 | 77985282 | Higher in Drinkers |
| ch.17.21699132R | 17 | 21775005 | Higher in Drinkers |
| ch.17.33847170F | 17 | 36593644 | Higher in Drinkers |
| ch.17.52597345F | 17 | 55242346 | Higher in Drinkers |
| ch.17.702520F | 17 | 25952472 | Higher in Drinkers |
| ch.17.74596917R | 17 | 77085322 | Higher in Drinkers |
| ch.17.75301806F | 17 | 77687213 | Higher in Drinkers |
| ch.17.75722220R | 17 | 78107625 | Higher in Drinkers |
| ch.18.400468R | 18 | 20395250 | Higher in Drinkers |
| ch.19.1004238R | 19 | 30753371 | Higher in Drinkers |
| ch.19.1364541R | 19 | 42374382 | Higher in Drinkers |
| ch.19.1922431F | 19 | 58795738 | Higher in Drinkers |
| ch.19.24052292F | 19 | 24260452 | Higher in Drinkers |
| ch.19.45344413F | 19 | 40652573 | Higher in Drinkers |
| ch.19.57789982R | 19 | 53098170 | Higher in Drinkers |
| ch.19.714487R | 19 | 16978952 | Higher in Drinkers |
| ch.2.1030760R | 2 | 43232845 | Higher in Drinkers |
| ch.2.107376196R | 2 | 108009764 | Higher in Drinkers |
| ch.2.117200887F | 2 | 117484417 | Higher in Drinkers |
| ch.2.121457425R | 2 | 121740955 | Higher in Drinkers |
| ch.2.12395676F | 2 | 12478225 | Higher in Drinkers |
| ch.2.126989343R | 2 | 127272873 | Higher in Drinkers |
| ch.2.128981206F | 2 | 129264738 | Higher in Drinkers |
| ch.2.1365132F | 2 | 59899176 | Higher in Drinkers |
| ch.2.148072779R | 2 | 148356309 | Higher in Drinkers |
| ch.2.154349706F | 2 | 154641460 | Higher in Drinkers |
| ch.2.1564633R | 2 | 69351951 | Higher in Drinkers |
| ch.2.161489025R | 2 | 161780779 | Higher in Drinkers |
| ch.2.1615265F | 2 | 71303421 | Higher in Drinkers |

| | | | |
|---|---|---|---|
| ch.2.164393752R | 2 | 164685506 | Higher in Drinkers |
| ch.2.165639268R | 2 | 165931022 | Higher in Drinkers |
| ch.2.184672693R | 2 | 184964448 | Higher in Drinkers |
| ch.2.1892000F | 2 | 85858578 | Higher in Drinkers |
| ch.2.1904847R | 2 | 86300405 | Higher in Drinkers |
| ch.2.217484879F | 2 | 217776634 | Higher in Drinkers |
| ch.2.233259725R | 2 | 233551481 | Higher in Drinkers |
| ch.2.235177505R | 2 | 235512766 | Higher in Drinkers |
| ch.2.242496996F | 2 | 242848323 | Higher in Drinkers |
| ch.2.2562807F | 2 | 2583800 | Higher in Drinkers |
| ch.2.2578847R | 2 | 123587590 | Higher in Drinkers |
| ch.2.2685596F | 2 | 128768557 | Higher in Drinkers |
| ch.2.26857817R | 2 | 27004313 | Higher in Drinkers |
| ch.2.30415474F | 2 | 30561970 | Higher in Drinkers |
| ch.2.30727973R | 2 | 30874469 | Higher in Drinkers |
| ch.2.39602547R | 2 | 39749043 | Higher in Drinkers |
| ch.2.47848289F | 2 | 47994785 | Higher in Drinkers |
| ch.2.62306258F | 2 | 62452754 | Higher in Drinkers |
| ch.2.66207210F | 2 | 66353706 | Higher in Drinkers |
| ch.2.6726424R | 2 | 6808973 | Higher in Drinkers |
| ch.2.71774667F | 2 | 71921159 | Higher in Drinkers |
| ch.2.7317635R | 2 | 7400184 | Higher in Drinkers |
| ch.2.74841720R | 2 | 74988212 | Higher in Drinkers |
| ch.2.79384614F | 2 | 79531106 | Higher in Drinkers |
| ch.20.101975CF | 20 | 46409797 | Higher in Drinkers |
| ch.20.1437006F | 20 | 60748300 | Higher in Drinkers |
| ch.20.18164830R | 20 | 18216830 | Higher in Drinkers |
| ch.20.24070907R | 20 | 24122907 | Higher in Drinkers |
| ch.20.325487R | 20 | 15546513 | Higher in Drinkers |
| ch.20.327316F | 20 | 15628644 | Higher in Drinkers |
| ch.20.38346083F | 20 | 38912669 | Higher in Drinkers |
| ch.20.437154R | 20 | 20495441 | Higher in Drinkers |
| ch.20.44558307R | 20 | 45124900 | Higher in Drinkers |
| ch.20.46655034F | 20 | 47221627 | Higher in Drinkers |
| ch.20.54687769F | 20 | 55254362 | Higher in Drinkers |

| | | |
|---|---|---|
| ch.20.90543lR 20 | 42339567 | Higher in Drinkers |
| ch.21.17404405R | 21 18482534 | Higher in Drinkers |
| ch.21.36723363F | 21 37801493 | Higher in Drinkers |
| ch.21.377520F 21 | 34119431 | Higher in Drinkers |
| ch.21.40139802R | 21 41217932 | Higher in Drinkers |
| ch.22.137888R 22 | 21290185 | Higher in Drinkers |
| ch.22.16454022F | 22 18074022 | Higher in Drinkers |
| ch.22.26442001R | 22 28112001 | Higher in Drinkers |
| ch.22.33863861F | 22 35533861 | Higher in Drinkers |
| ch.22.38010425R | 22 39680479 | Higher in Drinkers |
| ch.22.569473R 22 | 36895405 | Higher in Drinkers |
| ch.3.1012570R 3 | 48208271 | Higher in Drinkers |
| ch.3.1112198BR 3 | 51728593 | Higher in Drinkers |
| ch.3.19571190R 3 | 19598186 | Higher in Drinkers |
| ch.3.22673962R 3 | 22698953 | Higher in Drinkers |
| ch.3.2567129F 3 | 129201672 | Higher in Drinkers |
| ch.3.32825606F 3 | 32850802 | Higher in Drinkers |
| ch.3.35408643R 3 | 35433639 | Higher in Drinkers |
| ch.3.5198520F 3 | 5223520 | Higher in Drinkers |
| ch.3.6830780F 3 | 6855780 | Higher in Drinkers |
| ch.3.70573422F 3 | 70490732 | Higher in Drinkers |
| ch.3.78427614R 3 | 78344924 | Higher in Drinkers |
| ch.3.82259654F 3 | 82176964 | Higher in Drinkers |
| ch.3.90857F 3 | 4990079 | Higher in Drinkers |
| ch.4.10535887R 4 | 10976789 | Higher in Drinkers |
| ch.4.125673769F | 4 125454319 | Higher in Drinkers |
| ch.4.134210136F | 4 133990686 | Higher in Drinkers |
| ch.4.142726813F | 4 142507363 | Higher in Drinkers |
| ch.4.165600943F | 4 165381493 | Higher in Drinkers |
| ch.4.171062660F | 4 170826085 | Higher in Drinkers |
| ch.4.178543248R | 4 178306254 | Higher in Drinkers |
| ch.4.185006926F | 4 184769932 | Higher in Drinkers |
| ch.4.190900747R | 4 190663753 | Higher in Drinkers |
| ch.4.22775409R 4 | 23166311 | Higher in Drinkers |
| ch.4.2701555R 4 | 148210593 | Higher in Drinkers |

| | | | |
|---|---|---|---|
| ch.4.27623090R | 4 | 28013992 | Higher in Drinkers |
| ch.4.28965407R | 4 | 29356309 | Higher in Drinkers |
| ch.4.43738163F | 4 | 44043406 | Higher in Drinkers |
| ch.4.46116426R | 4 | 46421669 | Higher in Drinkers |
| ch.4.72691992R | 4 | 72473128 | Higher in Drinkers |
| ch.4.73355803R | 4 | 73136939 | Higher in Drinkers |
| ch.4.83718914R | 4 | 83499890 | Higher in Drinkers |
| ch.4.89078329R | 4 | 88859305 | Higher in Drinkers |
| ch.5.1906008F | 5 | 103300577 | Higher in Drinkers |
| ch.5.1992431R | 5 | 108685192 | Higher in Drinkers |
| ch.5.2259325F | 5 | 123967034 | Higher in Drinkers |
| ch.5.23338039R | 5 | 23302282 | Higher in Drinkers |
| ch.5.240336F | 5 | 7757969 | Higher in Drinkers |
| ch.5.3291566R | 5 | 3238566 | Higher in Drinkers |
| ch.5.3315058R | 5 | 173165015 | Higher in Drinkers |
| ch.5.45171762F | 5 | 45136005 | Higher in Drinkers |
| ch.5.52554191R | 5 | 52518434 | Higher in Drinkers |
| ch.5.52674027R | 5 | 52638270 | Higher in Drinkers |
| ch.5.5427157F | 5 | 5374157 | Higher in Drinkers |
| ch.5.55361480F | 5 | 55325723 | Higher in Drinkers |
| ch.5.6026528F | 5 | 5973528 | Higher in Drinkers |
| ch.5.71339689R | 5 | 71303933 | Higher in Drinkers |
| ch.6.105025291R | 6 | 104918598 | Higher in Drinkers |
| ch.6.107578927F | 6 | 107472234 | Higher in Drinkers |
| ch.6.108097463R | 6 | 107990770 | Higher in Drinkers |
| ch.6.122367561R | 6 | 122325862 | Higher in Drinkers |
| ch.6.1255267F | 6 | 53131782 | Higher in Drinkers |
| ch.6.139914509F | 6 | 139872816 | Higher in Drinkers |
| ch.6.144195587R | 6 | 144153894 | Higher in Drinkers |
| ch.6.14670643R | 6 | 14562664 | Higher in Drinkers |
| ch.6.164862012R | 6 | 164942022 | Higher in Drinkers |
| ch.6.21652857R | 6 | 21544873 | Higher in Drinkers |
| ch.6.2510917R | 6 | 131096695 | Higher in Drinkers |
| ch.6.27712C2R | 6 | 144123518 | Higher in Drinkers |
| ch.6.347904R | 6 | 13786377 | Higher in Drinkers |

| | | | |
|---|---|---|---|
| ch.6.40116829F | 6 | 40008851 | Higher in Drinkers |
| ch.6.44693872F | 6 | 44585894 | Higher in Drinkers |
| ch.6.57755616R | 6 | 57647657 | Higher in Drinkers |
| ch.6.614588F | 6 | 24874614 | Higher in Drinkers |
| ch.6.738234R | 6 | 30679284 | Higher in Drinkers |
| ch.6.77755434R | 6 | 77698715 | Higher in Drinkers |
| ch.6.949970F | 6 | 38261208 | Higher in Drinkers |
| ch.7.109948253R | 7 | 110161017 | Higher in Drinkers |
| ch.7.114165642F | 7 | 114378406 | Higher in Drinkers |
| ch.7.130936447R | 7 | 131285907 | Higher in Drinkers |
| ch.7.134603089F | 7 | 134952549 | Higher in Drinkers |
| ch.7.137529584R | 7 | 137879044 | Higher in Drinkers |
| ch.7.1628533R | 7 | 73938938 | Higher in Drinkers |
| ch.7.1667959R | 7 | 75693231 | Higher in Drinkers |
| ch.7.1701599F | 7 | 77282985 | Higher in Drinkers |
| ch.7.2371643F | 7 | 111377460 | Higher in Drinkers |
| ch.7.24057216F | 7 | 24090691 | Higher in Drinkers |
| ch.7.2660938R | 7 | 128612087 | Higher in Drinkers |
| ch.7.2897584R | 7 | 138762727 | Higher in Drinkers |
| ch.7.3114411F | 7 | 148859697 | Higher in Drinkers |
| ch.7.32670294R | 7 | 32703769 | Higher in Drinkers |
| ch.7.3273335R | 7 | 154752264 | Higher in Drinkers |
| ch.7.3333777R | 7 | 156646977 | Higher in Drinkers |
| ch.7.33727552F | 7 | 33761027 | Higher in Drinkers |
| ch.7.42519133R | 7 | 42552608 | Higher in Drinkers |
| ch.7.44221780F | 7 | 44255235 | Higher in Drinkers |
| ch.7.50621990F | 7 | 50654496 | Higher in Drinkers |
| ch.7.51771937F | 7 | 51804443 | Higher in Drinkers |
| ch.7.8314F | 7 | 211714 | Higher in Drinkers |
| ch.7.84099448F | 7 | 84261512 | Higher in Drinkers |
| ch.7.84780R | 7 | 1851537 | Higher in Drinkers |
| ch.8.10440381R | 8 | 10402971 | Higher in Drinkers |
| ch.8.117193312F | 8 | 117124134 | Higher in Drinkers |
| ch.8.123133581F | 8 | 123064400 | Higher in Drinkers |
| ch.8.128185533F | 8 | 128116351 | Higher in Drinkers |

| | | | |
|---|---|---|---|
| ch.8.131497396R | 8 | 131428214 | Higher in Drinkers |
| ch.8.132836635R | 8 | 132767453 | Higher in Drinkers |
| ch.8.1382856F | 8 | 64280766 | Higher in Drinkers |
| ch.8.1681415R | 8 | 80999431 | Higher in Drinkers |
| ch.8.2598327F | 8 | 131124146 | Higher in Drinkers |
| ch.8.33052751R | 8 | 32933209 | Higher in Drinkers |
| ch.8.34134444F | 8 | 34014902 | Higher in Drinkers |
| ch.8.49587141F | 8 | 49424588 | Higher in Drinkers |
| ch.8.53573583F | 8 | 53411030 | Higher in Drinkers |
| ch.8.56925254R | 8 | 56762700 | Higher in Drinkers |
| ch.8.72742858R | 8 | 72580304 | Higher in Drinkers |
| ch.8.74124882F | 8 | 73962328 | Higher in Drinkers |
| ch.8.745965F | 8 | 30420648 | Higher in Drinkers |
| ch.8.89640933F | 8 | 89571817 | Higher in Drinkers |
| ch.8.90327161R | 8 | 90258045 | Higher in Drinkers |
| ch.8.93711588R | 8 | 93642412 | Higher in Drinkers |
| ch.8.975024F | 8 | 41396493 | Higher in Drinkers |
| ch.9.109254566R | 9 | 110214745 | Higher in Drinkers |
| ch.9.126316596R | 9 | 127276775 | Higher in Drinkers |
| ch.9.13245070R | 9 | 13255070 | Higher in Drinkers |
| ch.9.1355968F | 9 | 96414449 | Higher in Drinkers |
| ch.9.22677811R | 9 | 22687811 | Higher in Drinkers |
| ch.9.2793549R | 9 | 2803549 | Higher in Drinkers |
| ch.9.377428R | 9 | 19439561 | Higher in Drinkers |
| ch.9.77250961R | 9 | 78061141 | Higher in Drinkers |
| ch.9.79515146F | 9 | 80325326 | Higher in Drinkers |
| ch.9.80193246F | 9 | 81003426 | Higher in Drinkers |
| ch.9.88862796F | 9 | 89672976 | Higher in Drinkers |
| ch.9.97139671F | 9 | 98099850 | Higher in Drinkers |
| ch.X.1023208F | X | 67291364 | Higher in Drinkers |
| ch.X.107997386R | X | 108110730 | Higher in Drinkers |
| ch.X.108232304R | X | 108345648 | Higher in Drinkers |
| ch.X.112119442F | X | 112231786 | Higher in Drinkers |
| ch.X.16035608F | X | 16125687 | Higher in Drinkers |
| ch.X.68408155R | X | 68491430 | Higher in Drinkers |

| 2225 | | 2226 |
|---|---|---|
| ch.X.89171221R X | 89284565 | Higher in Drinkers |
| ch.X.92148261F X | 92261605 | Higher in Drinkers |
| ch.X.92543860F X | 92657204 | Higher in Drinkers |
| ch.X.93511680F X | 93625024 | Higher in Drinkers |
| ch.X.97737721F X | 97851065 | Higher in Drinkers |

Appendix E

| | | | |
|---|---|---|---|
| A2LD1 | ABCC8 | ACACB | ACSL4 |
| A4GALT | ABCD3 | ACAD10 | ACSS1 |
| AAAS | ABCD4 | ACADS | ACTC1 |
| AACS | ABCE1 | ACADSB | ACTG1 |
| AAK1 | ABCF1 | ACAP2 | ACTL6A |
| AARS | ABCF3 | ACAT2 | ACTL6B |
| AARS2 | ABCG1 | ACBD3 | ACTN1 |
| AARSD1 | ABCG2 | ACBD4 | ACTN2 |
| AASDH | ABCG4 | ACCN1 | ACTR10 |
| AASDHPPT | ABHD1 | ACCN2 | ACTR1A |
| AATF | ABHD10 | ACER2 | ACTR1B |
| AATK | ABHD14A | ACER3 | ACTR2 |
| ABCA2 | ABHD2 | ACO2 | ACTR3 |
| ABCA5 | ABHD3 | ACOT11 | ACTR3B |
| ABCA7 | ABHD6 | ACOT13 | ACTR8 |
| ABCB1 | ABI2 | ACOT6 | ACVR1C |
| ABCB8 | ABL2 | ACOT7 | ACY1 |
| ABCB9 | ABLIM1 | ACOT9 | ACYP1 |
| ABCC1 | ABO | ACOX3 | ADAD2 |
| ABCC11 | ABR | ACRV1 | ADAL |
| ABCC2 | ABTB1 | ACSF3 | ADAM10 |
| ABCC3 | ABTB2 | ACSL1 | ADAM11 |
| ABCC5 | ACAA1 | ACSL3 | ADAM12 |

| | | | |
|---|---|---|---|
| ADAM15 | ADCYAP1 | AGAP1 | AHSA2 |
| ADAM22 | ADD1 | AGAP2 | AICDA |
| ADAM8 | ADHFE1 | AGAP3 | AIDA |
| ADAM9 | ADIPOR2 | AGBL2 | AIFM1 |
| ADAMTS10 | ADK | AGBL3 | AIFM2 |
| ADAMTS15 | ADM | AGBL4 | AIFM3 |
| ADAMTS18 | ADM2 | AGBL5 | AIG1 |
| ADAMTS6 | ADNP | AGFG1 | AIM1 |
| ADAMTS7 | ADNP2 | AGFG2 | AIP |
| ADAMTS9 | ADO | AGK | AJAP1 |
| ADAMTSL4 | ADORA3 | AGL | AK3 |
| ADAMTSL5 | ADPGK | AGPAT1 | AK3L1 |
| ADAP1 | ADPRHL1 | AGPAT3 | AK5 |
| ADAP2 | ADRB2 | AGPAT4 | AK7 |
| ADAR | ADRBK1 | AGPAT5 | AKAP1 |
| ADARB2 | ADRM1 | AGPAT9 | AKAP10 |
| ADAT1 | ADSL | AGPHD1 | AKAP11 |
| ADC | ADSS | AGPS | AKAP12 |
| ADCK2 | AEBP2 | AGRN | AKAP13 |
| ADCK4 | AFAP1L1 | AGXT2L2 | AKAP2 |
| ADCK5 | AFF1 | AHCYL1 | AKAP5 |
| ADCY2 | AFF2 | AHCYL2 | AKAP7 |
| ADCY3 | AFF3 | AHDC1 | AKAP8 |
| ADCY8 | AFMID | AHI1 | AKAP8L |
| ADCY9 | AGA | AHRR | AKAP9 |

| | | | |
|---|---|---|---|
| AKD1 | ALK | AMOTL2 | ANKRD31 |
| AKIRIN1 | ALKBH3 | AMPD2 | ANKRD32 |
| AKR1B1 | ALKBH4 | AMPD3 | ANKRD33B |
| AKR7A2 | ALKBH6 | AMZ2 | ANKRD36B |
| AKT1 | ALKBH7 | ANAPC11 | ANKRD37 |
| AKT1S1 | ALKBH8 | ANAPC2 | ANKRD39 |
| AKT3 | ALOX12 | ANAPC5 | ANKRD40 |
| ALAD | ALOX12B | ANGEL2 | ANKRD52 |
| ALCAM | ALOX15 | ANGPTL4 | ANKRD53 |
| ALDH16A1 | ALOX5 | ANK1 | ANKRD9 |
| ALDH18A1 | ALOXE3 | ANKFY1 | ANKS1A |
| ALDH2 | ALPK2 | ANKH | ANKS1B |
| ALDH3A1 | ALPK3 | ANKHD1 | ANKS3 |
| ALDH3A2 | ALS2 | ANKLE1 | ANKS6 |
| ALDH4A1 | ALS2CR11 | ANKLE2 | ANKZF1 |
| ALDH5A1 | ALS2CR8 | ANKMY1 | ANLN |
| ALDH6A1 | AMD1 | ANKRD10 | ANO10 |
| ALDH9A1 | AMDHD1 | ANKRD11 | ANO6 |
| ALDOA | AMDHD2 | ANKRD12 | ANP32A |
| ALDOC | AMFR | ANKRD13A | ANP32E |
| ALG11 | AMIGO1 | ANKRD13D | ANTXR1 |
| ALG14 | AMMECR1 | ANKRD16 | ANTXR2 |
| ALG3 | AMMECR1L | ANKRD20A2 | ANUBL1 |
| ALG5 | AMN1 | ANKRD27 | ANXA11 |
| ALG8 | AMOTL1 | ANKRD28 | ANXA4 |

| | | | |
|---|---|---|---|
| ANXA5 | APC | ARF3 | ARHGEF10 |
| ANXA6 | APEH | ARF6 | ARHGEF12 |
| AOAH | APH1A | ARFGAP1 | ARHGEF17 |
| AOX1 | API5 | ARFGAP2 | ARHGEF18 |
| AP1AR | APIP | ARFGEF2 | ARHGEF2 |
| AP1B1 | APLF | ARFIP1 | ARHGEF3 |
| AP1G1 | APLP1 | ARFIP2 | ARHGEF4 |
| AP1G2 | APLP2 | ARG2 | ARHGEF6 |
| AP1M1 | APOA1 | ARHGAP11B | ARHGEF7 |
| AP1S2 | APOA1BP | ARHGAP12 | ARID1A |
| AP2A2 | APOB48R | ARHGAP17 | ARID1B |
| AP2B1 | APOBEC3A | ARHGAP19 | ARID3A |
| AP2M1 | APOBEC3B | ARHGAP20 | ARID3C |
| AP2S1 | APOBEC3D | ARHGAP21 | ARID5A |
| AP3B1 | APOBEC3G | ARHGAP23 | ARID5B |
| AP3D1 | APOL4 | ARHGAP24 | ARL1 |
| AP3M2 | APOL6 | ARHGAP25 | ARL11 |
| AP3S1 | APOLD1 | ARHGAP26 | ARL13B |
| AP4E1 | APOOL | ARHGAP29 | ARL15 |
| AP4S1 | APPL1 | ARHGAP30 | ARL2BP |
| APAF1 | APTX | ARHGAP5 | ARL4D |
| APBA1 | AQP5 | ARHGAP6 | ARL6 |
| APBB1IP | ARAP1 | ARHGAP9 | ARL6IP6 |
| APBB2 | ARAP2 | ARHGDIA | ARL8A |
| APBB3 | ARF1 | ARHGEF1 | ARMC10 |

| | | | |
|---|---|---|---|
| ARMC2 | ASFMR1 | ATN1 | ATP5SL |
| ARMC5 | ASNSD1 | ATOH1 | ATP6V0A2 |
| ARMC6 | ASPH | ATOH8 | ATP6V0B |
| ARMC7 | ASPM | ATP10A | ATP6V0C |
| ARMCX3 | ASXL2 | ATP10D | ATP6V0D1 |
| ARNT | ATAD2 | ATP11A | ATP6V0E1 |
| ARPC1B | ATAD3A | ATP11B | ATP6V0E2 |
| ARPC4 | ATAD3C | ATP13A1 | ATP6V1A |
| ARPM1 | ATAD5 | ATP13A2 | ATP6V1C2 |
| ARPP19 | ATE1 | ATP1A4 | ATP6V1F |
| ARRB2 | ATF2 | ATP1B1 | ATP6V1G1 |
| ARRDC1 | ATF4 | ATP1B3 | ATP6V1G2 |
| ARRDC3 | ATF6B | ATP2A2 | ATP9A |
| ARSA | ATG16L2 | ATP2A3 | ATP9B |
| ARSK | ATG2A | ATP2B4 | ATPAF2 |
| ARVCF | ATG4B | ATP2C2 | ATPBD4 |
| ARX | ATG4D | ATP5A1 | ATR |
| ASAH1 | ATG5 | ATP5B | ATRIP |
| ASAP1 | ATG7 | ATP5C1 | ATRN |
| ASAP1IT1 | ATG9A | ATP5D | ATRNL1 |
| ASB6 | ATHL1 | ATP5E | ATRX |
| ASCC1 | ATIC | ATP5G1 | ATXN1 |
| ASCC2 | ATL1 | ATP5J2 | ATXN1L |
| ASCC3 | ATL3 | ATP5O | ATXN2 |
| ASF1B | ATM | ATP5S | ATXN3 |

| | | | |
|---|---|---|---|
| ATXN7L3 | BAD | BBX | BCL9 |
| AURKA | BAG3 | BCAP31 | BCL9L |
| AURKB | BAGE4 | BCAR1 | BCOR |
| AUTS2 | BAHCC1 | BCAR3 | BCORL1 |
| AVEN | BAIAP2 | BCAS2 | BCR |
| AVPI1 | BAIAP3 | BCAS3 | BCYRN1 |
| AXIN1 | BAK1 | BCAS4 | BDH1 |
| AZI1 | BANP | BCAT1 | BDNFOS |
| AZIN1 | BARD1 | BCAT2 | BEND3 |
| B2M | BASP1 | BCCIP | BEND7 |
| B3GALNT2 | BAT1 | BCDIN3D | BEST3 |
| B3GAT1 | BAT2 | BCKDHA | BET1 |
| B3GNT2 | BAT2L2 | BCKDHB | BET1L |
| B3GNT7 | BAT3 | BCL11A | BEX1 |
| B3GNTL1 | BAT4 | BCL2 | BEX4 |
| B4GALNT1 | BAT5 | BCL2L1 | BFSP2 |
| B4GALNT3 | BATF | BCL2L11 | BHLHA15 |
| B4GALT1 | BATF3 | BCL2L12 | BHLHB9 |
| B4GALT2 | BAX | BCL2L13 | BHLHE41 |
| B4GALT4 | BAZ1B | BCL2L2 | BICD1 |
| B4GALT6 | BAZ2A | BCL3 | BIK |
| B4GALT7 | BAZ2B | BCL6 | BIN1 |
| B9D1 | BBS10 | BCL7A | BIN2 |
| B9D2 | BBS5 | BCL7B | BIN3 |
| BACH1 | BBS7 | BCL7C | BIRC3 |

| | | | |
|---|---|---|---|
| BIRC6 | BPTF | BST1 | C10orf140 |
| BIRC7 | BRAF | BTBD12 | C10orf2 |
| BLCAP | BRCA2 | BTBD19 | C10orf26 |
| BLM | BRCC3 | BTBD3 | C10orf32 |
| BLMH | BRD1 | BTBD9 | C10orf35 |
| BLOC1S1 | BRD2 | BTC | C10orf4 |
| BLOC1S2 | BRD3 | BTF3 | C10orf41 |
| BLOC1S3 | BRD4 | BTG1 | C10orf46 |
| BLZF1 | BRD7 | BTG3 | C10orf50 |
| BMF | BRD8 | BTN2A1 | C10orf75 |
| BMI1 | BRD9 | BTN2A2 | C10orf78 |
| BMP2K | BRF1 | BTN3A1 | C10orf79 |
| BMP8B | BRF2 | BTRC | C10orf84 |
| BMPER | BRI3 | BUB1 | C10orf95 |
| BMPR1A | BRIP1 | BUB3 | C11orf1 |
| BMPR2 | BRMS1 | BUD13 | C11orf10 |
| BMS1 | BRP44 | BUD31 | C11orf17 |
| BNC1 | BRP44L | BZRAP1 | C11orf21 |
| BNIP1 | BRPF1 | BZW2 | C11orf30 |
| BNIP3 | BRSK2 | C10orf10 | C11orf35 |
| BNIP3L | BRUNOL4 | C10orf105 | C11orf46 |
| BOLA3 | BRWD1 | C10orf107 | C11orf48 |
| BOP1 | BSCL2 | C10orf119 | C11orf51 |
| BPHL | BSG | C10orf125 | C11orf54 |
| BPNT1 | BSN | C10orf131 | C11orf57 |

| | | | |
|---|---|---|---|
| C11orf58 | C12orf47 | C14orf166 | C16orf5 |
| C11orf60 | C12orf48 | C14orf179 | C16orf53 |
| C11orf61 | C12orf5 | C14orf181 | C16orf57 |
| C11orf63 | C12orf51 | C14orf23 | C16orf58 |
| C11orf65 | C12orf52 | C14orf33 | C16orf59 |
| C11orf67 | C12orf53 | C14orf4 | C16orf62 |
| C11orf68 | C12orf57 | C14orf43 | C16orf65 |
| C11orf70 | C12orf61 | C14orf45 | C16orf67 |
| C11orf71 | C12orf65 | C14orf49 | C16orf7 |
| C11orf73 | C12orf73 | C14orf72 | C16orf70 |
| C11orf75 | C13orf1 | C14orf73 | C16orf72 |
| C11orf80 | C13orf15 | C14orf80 | C16orf74 |
| C11orf83 | C13orf18 | C14orf93 | C16orf79 |
| C11orf84 | C13orf27 | C15orf24 | C16orf80 |
| C11orf87 | C13orf31 | C15orf29 | C16orf86 |
| C11orf9 | C14orf1 | C15orf37 | C16orf87 |
| C11orf93 | C14orf101 | C15orf39 | C16orf91 |
| C11orf95 | C14orf104 | C15orf40 | C17orf100 |
| C12orf11 | C14orf106 | C15orf41 | C17orf101 |
| C12orf23 | C14orf118 | C15orf42 | C17orf106 |
| C12orf26 | C14orf119 | C15orf44 | C17orf28 |
| C12orf29 | C14orf142 | C15orf57 | C17orf37 |
| C12orf34 | C14orf147 | C16orf35 | C17orf42 |
| C12orf41 | C14orf149 | C16orf45 | C17orf44 |
| C12orf42 | C14orf159 | C16orf46 | C17orf48 |

| | | | |
|---|---|---|---|
| C17orf56 | C19orf29 | C1orf151 | C1orf63 |
| C17orf62 | C19orf35 | C1orf156 | C1orf65 |
| C17orf63 | C19orf39 | C1orf159 | C1orf66 |
| C17orf70 | C19orf43 | C1orf163 | C1orf69 |
| C17orf73 | C19orf44 | C1orf174 | C1orf70 |
| C17orf75 | C19orf48 | C1orf177 | C1orf74 |
| C17orf76 | C19orf50 | C1orf183 | C1orf83 |
| C17orf80 | C19orf52 | C1orf194 | C1orf84 |
| C17orf81 | C19orf56 | C1orf198 | C1orf85 |
| C17orf82 | C19orf57 | C1orf200 | C1orf86 |
| C17orf89 | C19orf60 | C1orf203 | C1orf88 |
| C17orf91 | C19orf61 | C1orf21 | C1orf9 |
| C17orf95 | C19orf76 | C1orf210 | C1orf91 |
| C17orf99 | C1GALT1 | C1orf212 | C1orf92 |
| C18orf1 | C1GALT1C1 | C1orf213 | C1orf93 |
| C18orf18 | C1orf101 | C1orf220 | C1orf97 |
| C18orf19 | C1orf103 | C1orf25 | C1QL2 |
| C18orf21 | C1orf105 | C1orf27 | C1QTNF2 |
| C18orf22 | C1orf107 | C1orf31 | C1QTNF5 |
| C18orf25 | C1orf109 | C1orf35 | C1R |
| C18orf55 | C1orf113 | C1orf38 | C1RL |
| C18orf8 | C1orf123 | C1orf55 | C1S |
| C19orf20 | C1orf127 | C1orf56 | C20orf108 |
| C19orf22 | C1orf128 | C1orf57 | C20orf111 |
| C19orf25 | C1orf130 | C1orf61 | C20orf112 |

| | | | |
|---|---|---|---|
| C20orf114 | C22orf28 | C3orf17 | C5AR1 |
| C20orf117 | C22orf30 | C3orf18 | C5orf13 |
| C20orf12 | C22orf34 | C3orf19 | C5orf30 |
| C20orf144 | C22orf45 | C3orf21 | C5orf32 |
| C20orf160 | C22orf9 | C3orf23 | C5orf35 |
| C20orf166 | C2CD2 | C3orf26 | C5orf36 |
| C20orf199 | C2CD2L | C3orf31 | C5orf37 |
| C20orf27 | C2CD4A | C3orf33 | C5orf4 |
| C20orf29 | C2orf15 | C3orf38 | C5orf45 |
| C20orf3 | C2orf28 | C3orf54 | C5orf51 |
| C20orf4 | C2orf29 | C3orf57 | C5orf56 |
| C20orf7 | C2orf39 | C3orf58 | C6orf108 |
| C20orf94 | C2orf42 | C3orf64 | C6orf114 |
| C20orf96 | C2orf43 | C3orf70 | C6orf115 |
| C21orf119 | C2orf44 | C3orf71 | C6orf120 |
| C21orf130 | C2orf49 | C3orf75 | C6orf122 |
| C21orf45 | C2orf52 | C4orf10 | C6orf124 |
| C21orf59 | C2orf60 | C4orf23 | C6orf129 |
| C21orf66 | C2orf61 | C4orf32 | C6orf134 |
| C21orf67 | C2orf64 | C4orf33 | C6orf136 |
| C21orf70 | C2orf65 | C4orf34 | C6orf150 |
| C21orf91 | C2orf76 | C4orf41 | C6orf153 |
| C22orf13 | C3orf1 | C4orf44 | C6orf25 |
| C22orf24 | C3orf10 | C4orf49 | C6orf26 |
| C22orf25 | C3orf16 | C4orf52 | C6orf27 |

| | | | |
|---|---|---|---|
| C6orf35 | C7orf51 | C9orf64 | CACNA1H |
| C6orf47 | C7orf52 | C9orf66 | CACNA2D2 |
| C6orf48 | C7orf54 | C9orf7 | CACNA2D4 |
| C6orf52 | C7orf60 | C9orf72 | CACNB3 |
| C6orf57 | C7orf63 | C9orf75 | CACNG2 |
| C6orf62 | C7orf68 | C9orf78 | CAD |
| C6orf64 | C8G | C9orf85 | CAGE1 |
| C6orf70 | C8orf33 | C9orf91 | CALCA |
| C6orf89 | C8orf37 | C9orf95 | CALCOCO1 |
| C7orf10 | C8orf40 | C9orf96 | CALCOCO2 |
| C7orf20 | C8orf41 | C9orf98 | CALHM1 |
| C7orf23 | C8orf46 | CA2 | CALHM2 |
| C7orf25 | C8orf58 | CA5A | CALM1 |
| C7orf26 | C8orf59 | CA5B | CALM2 |
| C7orf27 | C8orf76 | CA6 | CALR |
| C7orf30 | C9orf123 | CA8 | CALU |
| C7orf31 | C9orf130 | CABC1 | CALY |
| C7orf36 | C9orf140 | CABIN1 | CAMK2D |
| C7orf38 | C9orf163 | CABLES1 | CAMK2G |
| C7orf40 | C9orf167 | CABLES2 | CAMK4 |
| C7orf42 | C9orf23 | CABYR | CAMKK1 |
| C7orf44 | C9orf25 | CACNA1A | CAMKK2 |
| C7orf47 | C9orf3 | CACNA1C | CAMTA1 |
| C7orf49 | C9orf41 | CACNA1E | CAMTA2 |
| C7orf50 | C9orf6 | CACNA1G | CAND1 |

| | | | |
|---|---|---|---|
| CAND2 | CATSPER2 | CCDC112 | CCDC59 |
| CANT1 | CATSPERG | CCDC117 | CCDC6 |
| CANX | CAV1 | CCDC122 | CCDC62 |
| CAP1 | CAV2 | CCDC124 | CCDC64 |
| CAPN1 | CBARA1 | CCDC126 | CCDC64B |
| CAPN10 | CBFA2T2 | CCDC127 | CCDC69 |
| CAPN3 | CBFA2T3 | CCDC132 | CCDC7 |
| CAPN8 | CBLL1 | CCDC134 | CCDC72 |
| CAPNS1 | CBLN1 | CCDC138 | CCDC74A |
| CAPS | CBLN3 | CCDC14 | CCDC77 |
| CAPZA2 | CBR1 | CCDC141 | CCDC79 |
| CAPZB | CBR4 | CCDC15 | CCDC83 |
| CARD10 | CBX1 | CCDC159 | CCDC84 |
| CARD11 | CBX2 | CCDC24 | CCDC85B |
| CARHSP1 | CBX3 | CCDC28A | CCDC85C |
| CARKD | CBX4 | CCDC28B | CCDC88A |
| CARM1 | CBX5 | CCDC34 | CCDC88B |
| CARS | CBX6 | CCDC39 | CCDC88C |
| CARS2 | CBX7 | CCDC40 | CCDC90A |
| CASC2 | CBY3 | CCDC42 | CCDC90B |
| CASC3 | CC2D1B | CCDC42B | CCDC93 |
| CASP2 | CCDC102A | CCDC45 | CCDC94 |
| CASP8 | CCDC104 | CCDC48 | CCDC96 |
| CASP8AP2 | CCDC106 | CCDC51 | CCDC97 |
| CASZ1 | CCDC11 | CCDC52 | CCDC99 |

| | | | |
|---|---|---|---|
| CCHCR1 | CCT7 | CD79A | CDH23 |
| CCK | CD160 | CD80 | CDH4 |
| CCL3 | CD164 | CD82 | CDH8 |
| CCM2 | CD1D | CD8A | CDK10 |
| CCNB1 | CD226 | CD8B | CDK11B |
| CCND1 | CD247 | CD97 | CDK12 |
| CCND2 | CD248 | CD99L2 | CDK13 |
| CCND3 | CD276 | CDADC1 | CDK17 |
| CCNE2 | CD2AP | CDC123 | CDK18 |
| CCNF | CD2BP2 | CDC14A | CDK19 |
| CCNG2 | CD320 | CDC14B | CDK2AP1 |
| CCNH | CD34 | CDC23 | CDK3 |
| CCNI | CD38 | CDC25A | CDK4 |
| CCNL1 | CD40 | CDC25B | CDK5 |
| CCNL2 | CD44 | CDC25C | CDK5R1 |
| CCNT1 | CD46 | CDC42BPB | CDK5R2 |
| CCNT2 | CD48 | CDC42EP3 | CDK5RAP1 |
| CCNYL1 | CD5 | CDC42SE2 | CDK6 |
| CCR7 | CD55 | CDC6 | CDK7 |
| CCR9 | CD58 | CDC7 | CDK9 |
| CCRL2 | CD59 | CDCA4 | CDKAL1 |
| CCS | CD63 | CDCA7L | CDKL2 |
| CCT3 | CD70 | CDGAP | CDKL3 |
| CCT6A | CD72 | CDH17 | CDKL5 |
| CCT6P1 | CD74 | CDH22 | CDKN1A |

| | | | |
|---|---|---|---|
| CDKN1B | CENPM | CHAC1 | CHMP4A |
| CDKN2AIPNL | CENPN | CHAF1A | CHMP4B |
| CDKN2BAS | CENPQ | CHAF1B | CHN1 |
| CDKN2C | CENPT | CHCHD2 | CHORDC1 |
| CDKN2D | CENPV | CHCHD3 | CHP |
| CDKN3 | CEP110 | CHCHD4 | CHPF |
| CDR2 | CEP120 | CHCHD5 | CHPF2 |
| CDV3 | CEP135 | CHCHD8 | CHRAC1 |
| CDYL | CEP152 | CHD2 | CHRD |
| CEACAM21 | CEP164 | CHD3 | CHRNA10 |
| CEBPB | CEP250 | CHD4 | CHRNB1 |
| CEBPG | CEP350 | CHD6 | CHST10 |
| CEBPZ | CEP63 | CHD7 | CHST11 |
| CELA2A | CEP70 | CHD9 | CHST12 |
| CELSR1 | CEP72 | CHEK2 | CHST14 |
| CELSR2 | CEP76 | CHERP | CHST2 |
| CEMP1 | CEP78 | CHFR | CHST7 |
| CENPA | CETN3 | CHI3L1 | CHSY1 |
| CENPB | CETP | CHID1 | CHURC1 |
| CENPBD1 | CFDP1 | CHKA | CIAO1 |
| CENPC1 | CFL2 | CHKB | CIB1 |
| CENPE | CFLAR | CHL1 | CIC |
| CENPJ | CGB8 | CHMP1A | CIDEA |
| CENPK | CGRRF1 | CHMP2A | CIDECP |
| CENPL | CH25H | CHMP2B | CIITA |

| | | | |
|---|---|---|---|
| CIR1 | CLIP2 | CMIP | COG3 |
| CIRBP | CLIP4 | CMPK2 | COG6 |
| CISD1 | CLK2 | CMTM7 | COG7 |
| CISD3 | CLK3 | CMTM8 | COG8 |
| CISH | CLK4 | CNBP | COL11A2 |
| CIT | CLLU1OS | CNIH | COL18A1 |
| CITED2 | CLMN | CNKSR2 | COL19A1 |
| CITED4 | CLN3 | CNN2 | COL1A1 |
| CKAP2 | CLN5 | CNNM2 | COL4A2 |
| CKAP2L | CLN8 | CNNM4 | COL4A3BP |
| CKAP5 | CLNK | CNOT1 | COL5A1 |
| CKLF | CLP1 | CNOT10 | COL6A1 |
| CKS2 | CLPB | CNOT2 | COL8A2 |
| CLASP1 | CLPTM1 | CNOT3 | COL9A3 |
| CLCN6 | CLPTM1L | CNOT6 | COLEC11 |
| CLCN7 | CLSPN | CNOT6L | COMMD1 |
| CLDN11 | CLSTN1 | CNR2 | COMMD10 |
| CLDN12 | CLTB | CNST | COMMD2 |
| CLDN14 | CLTC | CNTD1 | COMMD7 |
| CLDN19 | CLU | CNTNAP1 | COMMD8 |
| CLDN2 | CLUAP1 | CNTNAP2 | COMMD9 |
| CLEC16A | CLVS2 | COASY | COMT |
| CLIC1 | CLYBL | COBLL1 | COPA |
| CLIC4 | CMAH | COBRA1 | COPB1 |
| CLIC6 | CMC1 | COG2 | COPB2 |

| | | | |
|---|---|---|---|
| COPG | COX5A | CRABP1 | CRY2 |
| COPG2 | COX5B | CRABP2 | CRYBA1 |
| COPS3 | COX6A1 | CRADD | CRYM |
| COPS4 | COX6B1 | CRAMP1L | CS |
| COPS5 | COX6B2 | CRAT | CSDE1 |
| COPS6 | COX6C | CRBN | CSE1L |
| COPS7A | COX7A2 | CRCP | CSF1 |
| COPS8 | COX7A2L | CREB3L2 | CSF1R |
| COPZ1 | COX7B | CREB5 | CSGALNACT1 |
| COQ10B | COX7C | CREBBP | CSH2 |
| COQ2 | COX8A | CREBL2 | CSK |
| COQ4 | CP110 | CREM | CSNK1A1 |
| COQ5 | CPD | CRHR2 | CSNK1D |
| COQ6 | CPEB2 | CRIM1 | CSNK1E |
| CORO1A | CPNE3 | CRIP1 | CSNK1G1 |
| CORO1B | CPNE4 | CRIP2 | CSNK1G2 |
| CORO1C | CPNE7 | CRIP3 | CSNK1G3 |
| CORO2B | CPNE9 | CRK | CSNK2A1 |
| CORO6 | CPOX | CRKL | CSNK2B |
| COTL1 | CPSF1 | CRLS1 | CSPG5 |
| COX11 | CPSF4 | CRNKL1 | CSPP1 |
| COX16 | CPSF6 | CROCC | CSRNP1 |
| COX18 | CPSF7 | CRTAC1 | CSRP2 |
| COX19 | CPT1A | CRTC2 | CSTF2 |
| COX4NB | CPT1B | CRTC3 | CSTF3 |

| | | | |
|---|---|---|---|
| CTAGE5 | CUGBP1 | CYB5R1 | DACT1 |
| CTBP1 | CUGBP2 | CYB5R3 | DACT2 |
| CTBP2 | CUL1 | CYB5RL | DAG1 |
| CTBS | CUL2 | CYBASC3 | DAK |
| CTCF | CUL4A | CYC1 | DALRD3 |
| CTCFL | CUL7 | CYCS | DAP |
| CTDP1 | CUL9 | CYFIP1 | DAPK1 |
| CTDSP1 | CUTA | CYFIP2 | DAPK2 |
| CTDSP2 | CUX1 | CYorf15A | DAPK3 |
| CTNNAL1 | CUX2 | CYP26A1 | DAPP1 |
| CTNNBIP1 | CWF19L1 | CYP27B1 | DARS |
| CTNNBL1 | CXCL12 | CYP2R1 | DAXX |
| CTNND1 | CXCL17 | CYP2U1 | DAZAP1 |
| CTNND2 | CXCL3 | CYP2W1 | DAZAP2 |
| CTNS | CXCR4 | CYP39A1 | DBF4 |
| CTR9 | CXCR5 | CYP3A7 | DBN1 |
| CTRL | CXorf26 | CYP46A1 | DBNDD1 |
| CTSA | CXorf40B | CYP51A1 | DBNL |
| CTSH | CXorf42 | CYTH1 | DBR1 |
| CTSO | CXorf58 | CYTH2 | DBT |
| CTSZ | CXXC1 | CYTSA | DBX1 |
| CTTN | CXXC5 | CYTSB | DCAF11 |
| CTTNBP2NL | CYB561 | D2HGDH | DCAF4 |
| CTU1 | CYB561D1 | DAAM1 | DCAF4L2 |
| CUEDC2 | CYB5A | DAB2IP | DCAF5 |

| | | | |
|---|---|---|---|
| DCAF6 | DDAH2 | DDX54 | DGCR8 |
| DCAF8 | DDB1 | DDX55 | DGKA |
| DCAKD | DDHD1 | DDX60L | DGKD |
| DCC | DDI2 | DEAF1 | DGKE |
| DCDC2B | DDIT3 | DECR1 | DGKG |
| DCK | DDIT4 | DEDD | DGKQ |
| DCLK2 | DDR1 | DEDD2 | DGKZ |
| DCLRE1A | DDX1 | DEF6 | DHCR24 |
| DCLRE1B | DDX10 | DEF8 | DHCR7 |
| DCP1A | DDX11 | DEFB124 | DHPS |
| DCP1B | DDX12 | DEK | DHRS1 |
| DCP2 | DDX18 | DENND1A | DHRS11 |
| DCTD | DDX19A | DENND1B | DHRS13 |
| DCTN1 | DDX19B | DENND1C | DHRS7B |
| DCTN3 | DDX21 | DENND3 | DHTKD1 |
| DCTN4 | DDX24 | DENND4B | DHX15 |
| DCTN5 | DDX31 | DENND5A | DHX16 |
| DCTN6 | DDX3X | DENR | DHX29 |
| DCTPP1 | DDX4 | DEPDC1B | DHX30 |
| DCUN1D2 | DDX41 | DET1 | DHX33 |
| DCUN1D4 | DDX42 | DEXI | DHX35 |
| DCUN1D5 | DDX46 | DFFB | DHX37 |
| DCXR | DDX49 | DFNA5 | DHX38 |
| DDA1 | DDX5 | DGCR14 | DHX40 |
| DDAH1 | DDX50 | DGCR6L | DHX58 |

| | | | |
|---|---|---|---|
| DHX9 | DLGAP2 | DNAJC16 | DOC2A |
| DIABLO | DLGAP3 | DNAJC18 | DOCK1 |
| DIAPH2 | DLGAP4 | DNAJC2 | DOCK10 |
| DIAPH3 | DLK2 | DNAJC22 | DOCK3 |
| DIDO1 | DLL1 | DNAJC25 | DOCK4 |
| DIP2A | DLL4 | DNAJC28 | DOCK5 |
| DIP2B | DLST | DNAJC3 | DOCK9 |
| DIP2C | DLX2 | DNAJC30 | DOHH |
| DIS3 | DLX3 | DNAJC4 | DOK3 |
| DIS3L | DLX5 | DNAJC9 | DOK5 |
| DIS3L2 | DLX6AS | DNAL1 | DOM3Z |
| DISP2 | DMAP1 | DNALI1 | DONSON |
| DIXDC1 | DMKN | DNASE1L1 | DOPEY1 |
| DKC1 | DMPK | DNASE1L2 | DOT1L |
| DKFZP434H168 | DMRTA2 | DNASE1L3 | DPAGT1 |
| DKFZp761E198 | DNAH1 | DNASE2 | DPEP1 |
| DKFZp779M0652 | DNAH10 | DNER | DPF3 |
| DKKL1 | DNAJA4 | DNHD1 | DPH5 |
| DLEU2 | DNAJB1 | DNM1P35 | DPP6 |
| DLG1 | DNAJB2 | DNM2 | DPP8 |
| DLG2 | DNAJB4 | DNMBP | DPP9 |
| DLG3 | DNAJB6 | DNMT3A | DPY19L2P2 |
| DLG4 | DNAJC1 | DNPEP | DPY19L4 |
| DLG5 | DNAJC11 | DNTT | DPY30 |
| DLGAP1 | DNAJC14 | DNTTIP2 | DPYD |

| | | | |
|---|---|---|---|
| DPYSL2 | DUSP23 | E2F2 | EED |
| DPYSL3 | DUSP27 | E2F3 | EEF1A1 |
| DR1 | DUSP28 | E2F5 | EEF1B2 |
| DRAP1 | DUSP3 | E2F7 | EEF1DP3 |
| DRG2 | DUSP4 | E2F8 | EEF2 |
| DSCC1 | DUSP6 | EAPP | EEF2K |
| DSCR3 | DUSP7 | EBAG9 | EFCAB10 |
| DSCR9 | DUSP9 | EBF1 | EFCAB2 |
| DSE | DUT | EBF3 | EFCAB4A |
| DSG2 | DVL1 | EBI3 | EFCAB4B |
| DSG3 | DVL2 | EBP | EFCAB5 |
| DST | DVWA | ECE1 | EFEMP1 |
| DTD1 | DYNC1H1 | ECHDC1 | EFEMP2 |
| DTNBP1 | DYNC1LI1 | ECHDC3 | EFHD2 |
| DTX1 | DYNC1LI2 | ECHS1 | EFNA3 |
| DTX3 | DYNLL1 | ECM1 | EFNA4 |
| DTX4 | DYNLL2 | ECSIT | EFNB1 |
| DUOX1 | DYNLRB1 | ECT2 | EFR3A |
| DUS3L | DYNLT3 | EDARADD | EFTUD1 |
| DUSP1 | DYRK1A | EDC3 | EGFL8 |
| DUSP11 | DYRK1B | EDC4 | EGLN1 |
| DUSP14 | DYRK2 | EDEM1 | EGLN2 |
| DUSP15 | DYRK3 | EDEM2 | EGLN3 |
| DUSP19 | DZIP1L | EDEM3 | EGR2 |
| DUSP2 | E2F1 | EDN1 | EGR3 |

| | | | |
|---|---|---|---|
| EHBP1 | EIF4E | ELOF1 | ENTPD5 |
| EHBP1L1 | EIF4E2 | ELOVL1 | ENTPD6 |
| EHD1 | EIF4EBP1 | ELOVL2 | ENTPD7 |
| EHD4 | EIF4ENIF1 | ELOVL3 | ENY2 |
| EHMT1 | EIF4G1 | ELOVL4 | EP400 |
| EHMT2 | EIF4G2 | ELOVL6 | EP400NL |
| EI24 | EIF4G3 | ELP2 | EPAS1 |
| EIF1AD | EIF4H | EMB | EPB41 |
| EIF2AK1 | EIF5 | EME2 | EPB41L2 |
| EIF2AK2 | EIF5A | EMID1 | EPC1 |
| EIF2AK3 | EIF5A2 | EMID2 | EPHA1 |
| EIF2B1 | EIF5B | EMILIN1 | EPHA2 |
| EIF2B2 | EIF6 | EMILIN2 | EPHA3 |
| EIF2B4 | ELAC2 | EML3 | EPHB1 |
| EIF2B5 | ELF2 | EML6 | EPHB4 |
| EIF2C2 | ELF4 | EMP1 | EPM2AIP1 |
| EIF2C3 | ELF5 | ENDOD1 | EPN1 |
| EIF2S2 | ELK3 | ENG | EPN2 |
| EIF3B | ELL | ENO1 | EPN3 |
| EIF3D | ELL2 | ENO3 | EPOR |
| EIF3E | ELL3 | ENOX1 | EPR1 |
| EIF3M | ELMO1 | ENPP1 | EPS15L1 |
| EIF4A1 | ELMOD1 | ENPP7 | EPS8L2 |
| EIF4A2 | ELMOD2 | ENSA | EPSTI1 |
| EIF4A3 | ELN | ENTPD4 | ERAL1 |

| | | | |
|---|---|---|---|
| ERBB2 | ESR2 | EXOC3 | FAM100B |
| ERBB3 | ESRRA | EXOC4 | FAM101B |
| ERC1 | ESRRG | EXOC8 | FAM102A |
| ERCC2 | ESX1 | EXOSC9 | FAM102B |
| ERCC4 | ESYT2 | EXT1 | FAM105A |
| ERCC5 | ETAA1 | EXTL1 | FAM108A1 |
| ERCC6 | ETF1 | EXTL3 | FAM109B |
| ERF | ETFA | EYA3 | FAM111A |
| ERG | ETFB | EZH1 | FAM114A1 |
| ERGIC2 | ETHE1 | EZR | FAM117A |
| ERGIC3 | ETNK1 | F12 | FAM117B |
| ERI3 | ETNK2 | F13A1 | FAM118A |
| ERICH1 | ETS1 | F3 | FAM118B |
| ERLEC1 | ETS2 | F8 | FAM119A |
| ERLIN1 | ETV1 | FAAH | FAM120A |
| ERLIN2 | ETV2 | FADD | FAM120C |
| ERN1 | ETV3 | FADS2 | FAM122A |
| ERO1L | ETV4 | FADS3 | FAM122B |
| ERO1LB | ETV5 | FAF1 | FAM123B |
| ERP27 | EVI5 | FAF2 | FAM124A |
| ESAM | EVI5L | FAH | FAM125A |
| ESCO1 | EVL | FAHD2A | FAM126A |
| ESPL1 | EWSR1 | FAHD2B | FAM126B |
| ESPNP | EXO1 | FAIM3 | FAM127B |
| ESR1 | EXOC2 | FAM100A | FAM128A |

| | | | |
|---|---|---|---|
| FAM129A | FAM178A | FAM49A | FAM86B1 |
| FAM133B | FAM179B | FAM50B | FAM86C |
| FAM134A | FAM182B | FAM53B | FAM86D |
| FAM135A | FAM183A | FAM53C | FAM91A1 |
| FAM138D | FAM184A | FAM54A | FAM96A |
| FAM13B | FAM186B | FAM54B | FAM96B |
| FAM13C | FAM188A | FAM57A | FANCA |
| FAM158A | FAM190B | FAM57B | FANCC |
| FAM160A1 | FAM192A | FAM60A | FANCF |
| FAM160A2 | FAM193A | FAM63A | FANCG |
| FAM160B1 | FAM193B | FAM65A | FANK1 |
| FAM161A | FAM195A | FAM65B | FAR2 |
| FAM161B | FAM196B | FAM66B | FARP1 |
| FAM162A | FAM20B | FAM66D | FARSA |
| FAM162B | FAM20C | FAM69A | FAS |
| FAM164A | FAM21C | FAM72A | FASN |
| FAM164C | FAM32A | FAM72B | FASTK |
| FAM165B | FAM36A | FAM73A | FASTKD5 |
| FAM167A | FAM38A | FAM76B | FAT3 |
| FAM167B | FAM38B | FAM78A | FAT4 |
| FAM168A | FAM3C | FAM7A3 | FAU |
| FAM171A2 | FAM40B | FAM82A2 | FBF1 |
| FAM173B | FAM43A | FAM82B | FBL |
| FAM175A | FAM46C | FAM83D | FBLN7 |
| FAM177B | FAM48A | FAM83E | FBN1 |

| | | | |
|---|---|---|---|
| FBRSL1 | FBXW4 | FGD6 | FKBP4 |
| FBXL12 | FBXW5 | FGF17 | FKBP9 |
| FBXL14 | FBXW7 | FGF18 | FKBPL |
| FBXL15 | FBXW8 | FGF19 | FLAD1 |
| FBXL18 | FBXW9 | FGF2 | FLCN |
| FBXL19 | FCGRT | FGF22 | FLII |
| FBXL2 | FCHO1 | FGF4 | FLJ10357 |
| FBXL22 | FCRL1 | FGF9 | FLJ10661 |
| FBXL3 | FCRLB | FGFR1OP | FLJ20184 |
| FBXL6 | FDXACB1 | FGFR1OP2 | FLJ22536 |
| FBXO15 | FDXR | FGFR2 | FLJ23834 |
| FBXO16 | FECH | FGFRL1 | FLJ30058 |
| FBXO18 | FEM1B | FGGY | FLJ31306 |
| FBXO2 | FEM1C | FGR | FLJ32810 |
| FBXO21 | FEN1 | FH | FLJ35220 |
| FBXO31 | FER | FHIT | FLJ37453 |
| FBXO32 | FERD3L | FHOD1 | FLJ39582 |
| FBXO33 | FERMT3 | FHOD3 | FLJ40125 |
| FBXO36 | FES | FICD | FLJ40330 |
| FBXO38 | FEV | FILIP1 | FLJ40504 |
| FBXO46 | FEZ2 | FIZ1 | FLJ41350 |
| FBXO6 | FEZF2 | FKBP10 | FLJ41856 |
| FBXO7 | FFAR1 | FKBP14 | FLJ43663 |
| FBXO8 | FFAR2 | FKBP1B | FLJ44606 |
| FBXW11 | FGD1 | FKBP3 | FLJ45079 |

| | | | |
|---|---|---|---|
| FLNA | FOXO3 | FUCA1 | GABARAPL1 |
| FLOT1 | FOXP1 | FUCA2 | GABARAPL2 |
| FLT4 | FOXP4 | FUK | GABBR1 |
| FLYWCH1 | FOXRED1 | FUNDC1 | GABPB1 |
| FLYWCH2 | FOXRED2 | FURIN | GABRB1 |
| FMNL1 | FPGS | FUS | GABRD |
| FMNL2 | FRAS1 | FUT10 | GABRQ |
| FMO5 | FRAT1 | FUT8 | GADD45G |
| FN3KRP | FREQ | FUZ | GAK |
| FNBP1 | FRMD1 | FXN | GAL3ST2 |
| FNBP4 | FRMD4A | FXR1 | GALC |
| FNIP1 | FRMD6 | FXYD1 | GALK2 |
| FOS | FRMD8 | FXYD5 | GALM |
| FOSL2 | FRS3 | FYN | GALNS |
| FOXA3 | FRY | FYTTD1 | GALNT10 |
| FOXD2 | FRYL | FZD1 | GALNT12 |
| FOXD4L5 | FSCN1 | FZD3 | GALNT2 |
| FOXF1 | FSCN2 | FZD4 | GALNT3 |
| FOXI1 | FSD1L | FZD7 | GALNT6 |
| FOXJ1 | FSIP1 | FZR1 | GALNT7 |
| FOXJ3 | FSTL4 | G3BP1 | GALNT9 |
| FOXK1 | FTL | G3BP2 | GALNTL1 |
| FOXK2 | FTSJ1 | GAA | GALNTL4 |
| FOXN3 | FTSJD1 | GAB1 | GANAB |
| FOXN4 | FUBP1 | GAB2 | GANC |

| | | | |
|---|---|---|---|
| GAP43 | GDE1 | GHDC | GLT8D1 |
| GAPDH | GDF11 | GHITM | GLTPD1 |
| GAR1 | GDF6 | GIN1 | GLTPD2 |
| GARS | GDI2 | GINS2 | GLTSCR1 |
| GAS2L1 | GDNF | GINS3 | GLTSCR2 |
| GATA2 | GDPD5 | GINS4 | GLYATL3 |
| GATAD1 | GEM | GIPC3 | GLYCTK |
| GATAD2A | GEMIN4 | GJB7 | GM2A |
| GATAD2B | GEMIN5 | GJC1 | GMCL1 |
| GATC | GEMIN6 | GJC2 | GMDS |
| GATS | GEN1 | GJC3 | GMEB1 |
| GATSL3 | GFER | GLB1 | GMEB2 |
| GBA | GFI1 | GLB1L | GMFG |
| GBAS | GFOD1 | GLB1L2 | GMIP |
| GBE1 | GFOD2 | GLB1L3 | GMPPA |
| GBF1 | GFRA1 | GLG1 | GMPR |
| GBP4 | GFRA3 | GLI1 | GMPR2 |
| GCAT | GGA1 | GLI2 | GMPS |
| GCDH | GGA2 | GLI3 | GNA11 |
| GCET2 | GGA3 | GLI4 | GNA12 |
| GCH1 | GGCT | GLRX3 | GNA13 |
| GCHFR | GGCX | GLRX5 | GNAI2 |
| GCLM | GGH | GLS | GNAI3 |
| GCNT1 | GGPS1 | GLT1D1 | GNAO1 |
| GDAP2 | GGT1 | GLT25D1 | GNAS |

| | | | |
|---|---|---|---|
| GNASAS | GOT1 | GPR153 | GRB2 |
| GNB1L | GOT2 | GPR172A | GRHL3 |
| GNB2L1 | GP5 | GPR21 | GRIK3 |
| GNB4 | GPAA1 | GPR3 | GRIN1 |
| GNB5 | GPATCH1 | GPR31 | GRIN2B |
| GNG10 | GPATCH2 | GPR44 | GRIN2D |
| GNG11 | GPATCH3 | GPR56 | GRIN3B |
| GNG2 | GPATCH4 | GPR81 | GRINA |
| GNG7 | GPATCH8 | GPR89A | GRINL1A |
| GNL1 | GPBP1L1 | GPR89B | GRK1 |
| GNL3 | GPC4 | GPR97 | GRK4 |
| GNMT | GPC5 | GPRASP2 | GRK5 |
| GNPAT | GPD2 | GPRIN1 | GRK7 |
| GNPDA1 | GPER | GPS1 | GRLF1 |
| GNPDA2 | GPHN | GPSM1 | GRPEL2 |
| GNPTAB | GPN3 | GPSM3 | GRSF1 |
| GNRHR2 | GPR107 | GPT2 | GRTP1 |
| GNS | GPR108 | GPX4 | GRWD1 |
| GOLGA3 | GPR113 | GPX5 | GSDMD |
| GOLGA7 | GPR114 | GRAMD1A | GSG1 |
| GOLGA8B | GPR120 | GRAMD1C | GSK3A |
| GOLGB1 | GPR133 | GRAMD3 | GSN |
| GOLIM4 | GPR135 | GRAP2 | GSS |
| GOLSYN | GPR137B | GRASP | GSTA4 |
| GOLT1A | GPR144 | GRB10 | GSTK1 |

| | | | |
|---|---|---|---|
| GSTM3 | GYS1 | HBP1 | HDLBP |
| GSTO1 | H19 | HBS1L | HDX |
| GSTO2 | H1F0 | HCCA2 | HEATR2 |
| GSTZ1 | H2AFV | HCG11 | HEATR3 |
| GTF2A2 | H2AFX | HCG18 | HEATR5B |
| GTF2F2 | H2AFY | HCG26 | HECA |
| GTF2H2C | H2AFZ | HCG27 | HECTD1 |
| GTF2H4 | H6PD | HCG9 | HECTD2 |
| GTF2H5 | HAAO | HCK | HECTD3 |
| GTF2IRD1 | HABP4 | HCLS1 | HECW1 |
| GTF3A | HACE1 | HCN3 | HELB |
| GTF3C1 | HACL1 | HCRT | HELLS |
| GTF3C3 | HADH | HCRTR1 | HEMK1 |
| GTPBP1 | HADHA | HDAC1 | HERC1 |
| GTPBP3 | HADHB | HDAC10 | HERC2 |
| GTPBP4 | HAGH | HDAC11 | HERC2P2 |
| GTPBP5 | HAP1 | HDAC2 | HERC2P4 |
| GTPBP8 | HAPLN3 | HDAC3 | HERC3 |
| GUCA1A | HARS | HDAC4 | HERC4 |
| GUCY2E | HAS3 | HDAC7 | HERC5 |
| GUK1 | HAUS1 | HDDC2 | HERC6 |
| GXYLT1 | HAUS2 | HDGF | HES1 |
| GXYLT2 | HAUS3 | HDGF2 | HES2 |
| GYG1 | HAX1 | HDHD1A | HES5 |
| GYPC | HBM | HDHD2 | HES7 |

| | | | |
|---|---|---|---|
| HEXIM1 | HIPK2 | HIST1H4A | HLA-DRA |
| HEXIM2 | HIPK3 | HIST1H4C | HLA-DRB1 |
| HEY1 | HIRA | HIST1H4H | HLA-DRB5 |
| HEY2 | HIRIP3 | HIST1H4L | HLA-DRB6 |
| HFM1 | HIST1H1C | HIST2H2AA3 | HLA-E |
| HGC6.3 | HIST1H1D | HIST2H2AB | HLA-F |
| HGFAC | HIST1H2AE | HIST2H2AC | HLA-H |
| HGS | HIST1H2AG | HIST2H2BA | HLA-J |
| HGSNAT | HIST1H2AL | HIST2H2BE | HLA-L |
| HHAT | HIST1H2AM | HIST2H2BF | HLTF |
| HHEX | HIST1H2BC | HIVEP1 | HLX |
| HHIPL2 | HIST1H2BD | HIVEP2 | HMBOX1 |
| HHLA3 | HIST1H2BF | HJURP | HMG20A |
| HIAT1 | HIST1H2BG | HK1 | HMG20B |
| HIATL2 | HIST1H2BH | HK2 | HMGA1 |
| HIBADH | HIST1H2BI | HLA-A | HMGB1L1 |
| HIC1 | HIST1H2BK | HLA-C | HMGB2 |
| HIF1A | HIST1H2BN | HLA-DMA | HMGB3 |
| HIF1AN | HIST1H3A | HLA-DMB | HMGCR |
| HIGD1A | HIST1H3D | HLA-DOA | HMGCS1 |
| HINT1 | HIST1H3E | HLA-DPA1 | HMGN1 |
| HINT3 | HIST1H3G | HLA-DPB1 | HMGN2 |
| HIP1 | HIST1H3H | HLA-DPB2 | HMGN4 |
| HIP1R | HIST1H3I | HLA-DQA1 | HMGXB3 |
| HIPK1 | HIST1H3J | HLA-DQB1 | HMHB1 |

| | | | |
|---|---|---|---|
| HMMR | HOXA11AS | HSD11B1L | HTATIP2 |
| HMOX1 | HOXA13 | HSD11B2 | HTATSF1 |
| HN1 | HOXA3 | HSD17B11 | HTR1E |
| HNF1B | HOXB1 | HSD17B4 | HTR2C |
| HNRNPA1 | HOXB2 | HSD17B6 | HTR6 |
| HNRNPA1L2 | HOXB4 | HSD17B8 | HTR7 |
| HNRNPAB | HOXC4 | HSD3B2 | HTR7P |
| HNRNPC | HOXC9 | HSDL1 | HTRA2 |
| HNRNPD | HOXD12 | HSF1 | HTRA3 |
| HNRNPF | HP1BP3 | HSF2BP | HUNK |
| HNRNPH1 | HPCA | HSP90AA1 | HUWE1 |
| HNRNPH3 | HPCAL1 | HSP90AB1 | HVCN1 |
| HNRNPK | HPGD | HSPA13 | HYAL2 |
| HNRNPL | HPS1 | HSPA1A | HYAL3 |
| HNRNPR | HPS3 | HSPA1B | HYDIN |
| HNRNPU | HPS6 | HSPA2 | HYI |
| HNRNPUL1 | HPSE | HSPA4L | HYLS1 |
| HNRNPUL2 | HRAS | HSPA8 | HYMAI |
| HOMER2 | HRASLS2 | HSPB1 | IBTK |
| HOMEZ | HRNBP3 | HSPBP1 | ICA1L |
| HOOK2 | HS1BP3 | HSPC072 | ICAM1 |
| HOOK3 | HS2ST1 | HSPC157 | ICAM3 |
| HOPX | HS6ST1 | HSPC159 | ICAM5 |
| HOXA1 | HS6ST2 | HSPE1 | ICK |
| HOXA10 | HSCB | HSPH1 | ICT1 |

| | | | |
|---|---|---|---|
| ID1 | IGBP1 | IL16 | INO80 |
| ID2 | IGDCC3 | IL17RA | INO80B |
| ID3 | IGF1R | IL18 | INO80E |
| IDE | IGF2AS | IL1RAP | INPP4A |
| IDH1 | IGF2BP1 | IL20RB | INPP5A |
| IDH2 | IGF2BP2 | IL21R | INPP5D |
| IDH3A | IGF2R | IL27 | INPP5E |
| IDH3G | IGFBP3 | IL28RA | INPPL1 |
| IDUA | IGHMBP2 | IL4I1 | INSC |
| IER2 | IGSF21 | IL7 | INSIG1 |
| IER3 | IGSF22 | ILF3 | INSL6 |
| IER3IP1 | IGSF3 | ILKAP | INSM2 |
| IER5 | IGSF8 | ILVBL | INTS1 |
| IFFO1 | IHH | IMMP2L | INTS10 |
| IFI27L1 | IK | IMP3 | INTS3 |
| IFITM1 | IKBKAP | IMP4 | INTS6 |
| IFITM5 | IKBKB | IMPA1 | IP6K2 |
| IFNAR2 | IKBKG | IMPDH1 | IPMK |
| IFNGR2 | IKZF1 | IMPDH2 | IPO13 |
| IFRD2 | IKZF3 | INCENP | IPO7 |
| IFT122 | IKZF4 | ING1 | IPO8 |
| IFT140 | IL12A | ING2 | IPPK |
| IFT57 | IL13 | ING3 | IQCC |
| IFT80 | IL15 | ING4 | IQCD |
| IFT81 | IL15RA | ING5 | IQCE |

| | | | |
|---|---|---|---|
| IQCH | ISY1 | ITPR2 | JUN |
| IQGAP1 | ISYNA1 | ITPR3 | JUND |
| IQGAP2 | ITFG2 | ITPRIP | KANK2 |
| IQSEC1 | ITFG3 | ITSN1 | KANK3 |
| IQSEC3 | ITGA1 | IVD | KARS |
| IRAK1 | ITGA2 | IVNS1ABP | KATNAL1 |
| IRAK1BP1 | ITGA2B | IWS1 | KATNB1 |
| IRAK3 | ITGA4 | IZUMO1 | KAZALD1 |
| IREB2 | ITGA5 | JAG1 | KBTBD3 |
| IRF1 | ITGA6 | JAG2 | KBTBD4 |
| IRF2 | ITGA9 | JAGN1 | KBTBD5 |
| IRF2BP1 | ITGAE | JAK2 | KBTBD7 |
| IRF3 | ITGAL | JAK3 | KCMF1 |
| IRF4 | ITGAM | JAM2 | KCNA1 |
| IRF6 | ITGB1BP3 | JAM3 | KCNA6 |
| IRF7 | ITGB2 | JARID2 | KCNAB2 |
| IRF8 | ITGB3 | JMJD1C | KCNC4 |
| IRS1 | ITGB3BP | JMJD5 | KCNG2 |
| IRS2 | ITGB5 | JMJD6 | KCNG3 |
| IRX6 | ITGB8 | JMY | KCNH1 |
| ISCA1 | ITLN1 | JOSD1 | KCNH3 |
| ISG20L2 | ITPA | JPH1 | KCNH4 |
| ISL2 | ITPKA | JPH3 | KCNIP1 |
| ISM2 | ITPKB | JTB | KCNJ1 |
| ISPD | ITPR1 | JUB | KCNJ11 |

| | | | |
|---|---|---|---|
| KCNJ16 | KCTD9 | KIAA0406 | KIAA1210 |
| KCNJ5 | KDELR2 | KIAA0415 | KIAA1244 |
| KCNJ6 | KDM1A | KIAA0427 | KIAA1257 |
| KCNK12 | KDM1B | KIAA0467 | KIAA1370 |
| KCNK7 | KDM2A | KIAA0494 | KIAA1377 |
| KCNK9 | KDM3A | KIAA0495 | KIAA1407 |
| KCNMB4 | KDM4A | KIAA0513 | KIAA1430 |
| KCNN1 | KDM4B | KIAA0528 | KIAA1539 |
| KCNN2 | KDM4C | KIAA0556 | KIAA1543 |
| KCNN3 | KDM5A | KIAA0562 | KIAA1549 |
| KCNN4 | KDM5C | KIAA0564 | KIAA1614 |
| KCNQ1 | KDM6A | KIAA0652 | KIAA1632 |
| KCNQ1DN | KDM6B | KIAA0664 | KIAA1683 |
| KCNQ1OT1 | KEAP1 | KIAA0753 | KIAA1688 |
| KCNQ2 | KHDC1 | KIAA0754 | KIAA1712 |
| KCNQ5 | KHDRBS2 | KIAA0892 | KIAA1715 |
| KCNV2 | KHDRBS3 | KIAA0895L | KIAA1731 |
| KCP | KIAA0040 | KIAA0907 | KIAA1737 |
| KCTD1 | KIAA0182 | KIAA0913 | KIAA1751 |
| KCTD15 | KIAA0196 | KIAA0922 | KIAA1919 |
| KCTD17 | KIAA0226 | KIAA0947 | KIAA1949 |
| KCTD18 | KIAA0232 | KIAA1009 | KIAA1967 |
| KCTD2 | KIAA0247 | KIAA1012 | KIAA2018 |
| KCTD4 | KIAA0317 | KIAA1143 | KIAA2022 |
| KCTD7 | KIAA0368 | KIAA1191 | KIAA2026 |

| | | | |
|---|---|---|---|
| KIF13A | KLF10 | KPNA2 | LARP7 |
| KIF15 | KLF12 | KPNA3 | LAS1L |
| KIF16B | KLF13 | KPNB1 | LASP1 |
| KIF18A | KLF6 | KRAS | LASS6 |
| KIF18B | KLF7 | KRBA1 | LATS2 |
| KIF1A | KLHDC10 | KREMEN1 | LBH |
| KIF1B | KLHDC2 | KREMEN2 | LBR |
| KIF1C | KLHDC4 | KRIT1 | LBX2 |
| KIF21A | KLHDC8B | KRR1 | LCAT |
| KIF21B | KLHDC9 | KRT18 | LCMT1 |
| KIF22 | KLHL11 | KRTCAP2 | LCN15 |
| KIF23 | KLHL13 | KY | LCORL |
| KIF26A | KLHL18 | L3MBTL | LCP1 |
| KIF26B | KLHL22 | L3MBTL2 | LCP2 |
| KIF2A | KLHL23 | L3MBTL4 | LDB1 |
| KIF2C | KLHL24 | LAGE3 | LDB3 |
| KIF3A | KLHL25 | LAMA3 | LDHA |
| KIF4B | KLHL29 | LAMB3 | LDHAL6A |
| KIFC1 | KLHL33 | LAMC1 | LDHB |
| KILLIN | KLHL4 | LAMP1 | LDLR |
| KIRREL2 | KLHL7 | LAMP2 | LDLRAD2 |
| KIRREL3 | KLK12 | LAPTM4A | LDLRAP1 |
| KLC1 | KLK9 | LAPTM5 | LDOC1 |
| KLC4 | KLRAQ1 | LARP1 | LEAP2 |
| KLF1 | KNTC1 | LARP1B | LEF1 |

| | | | |
|---|---|---|---|
| LEMD2 | LILRA2 | LMNA | LOC100134368 |
| LENEP | LILRA4 | LMNB1 | LOC100134713 |
| LEO1 | LIMCH1 | LMO4 | LOC100190939 |
| LEPRE1 | LIMD1 | LMO7 | LOC100268168 |
| LEPREL2 | LIMD2 | LMTK2 | LOC100272217 |
| LETM1 | LIMK1 | LMX1A | LOC100272228 |
| LETM2 | LIMK2 | LNPEP | LOC100286844 |
| LFNG | LIMS1 | LNX1 | LOC100289511 |
| LGALS1 | LIN52 | LOC100128071 | LOC100292680 |
| LGALS12 | LIN7C | LOC100128731 | LOC100302401 |
| LGMN | LIN9 | LOC100128822 | LOC100303728 |
| LGR4 | LINS1 | LOC100128977 | LOC100329108 |
| LGR5 | LIPA | LOC100129637 | LOC113230 |
| LHCGR | LIPT1 | LOC100129716 | LOC139201 |
| LHFP | LITAF | LOC100129726 | LOC145783 |
| LHFPL2 | LLGL1 | LOC100130274 | LOC145845 |
| LHPP | LLPH | LOC100130987 | LOC146880 |
| LHX2 | LMAN1 | LOC100131434 | LOC148696 |
| LHX4 | LMAN2 | LOC100132111 | LOC148709 |
| LHX6 | LMAN2L | LOC100132215 | LOC149134 |
| LHX8 | LMBR1 | LOC100132707 | LOC150527 |
| LHX9 | LMBR1L | LOC100133315 | LOC151534 |
| LIF | LMBRD1 | LOC100133612 | LOC152225 |
| LIG1 | LMF1 | LOC100133957 | LOC153684 |
| LIG4 | LMF2 | LOC100134229 | LOC154761 |

| | | | |
|---|---|---|---|
| LOC202181 | LOC388692 | LOC729338 | LRGUK |
| LOC220729 | LOC389791 | LOC729678 | LRIG1 |
| LOC221710 | LOC400027 | LOC729991-MEF2B | LRIG2 |
| LOC222699 | LOC400657 | LOC730101 | LRP10 |
| LOC253724 | LOC400931 | LOC730668 | LRP5 |
| LOC256880 | LOC401588 | LOC81691 | LRP5L |
| LOC25845 | LOC401629 | LOC91316 | LRP8 |
| LOC282997 | LOC440040 | LOC93622 | LRPPRC |
| LOC283050 | LOC440839 | LOC96610 | LRRC1 |
| LOC283922 | LOC440944 | LOH12CR1 | LRRC14 |
| LOC284440 | LOC441046 | LONP1 | LRRC16A |
| LOC284632 | LOC552889 | LONP2 | LRRC16B |
| LOC285205 | LOC595101 | LONRF3 | LRRC18 |
| LOC285375 | LOC619207 | LOXL1 | LRRC20 |
| LOC285456 | LOC645323 | LOXL3 | LRRC23 |
| LOC285696 | LOC646762 | LOXL4 | LRRC25 |
| LOC285830 | LOC646813 | LPCAT1 | LRRC26 |
| LOC285847 | LOC646851 | LPCAT2 | LRRC27 |
| LOC286016 | LOC653653 | LPCAT3 | LRRC29 |
| LOC338758 | LOC728411 | LPCAT4 | LRRC31 |
| LOC339290 | LOC728606 | LQK1 | LRRC32 |
| LOC344595 | LOC728613 | LRBA | LRRC33 |
| LOC374443 | LOC728723 | LRCH1 | LRRC34 |
| LOC387646 | LOC728743 | LRCH2 | LRRC42 |
| LOC388588 | LOC729082 | LRCH4 | LRRC43 |

| | | | |
|---|---|---|---|
| LRRC45 | LSM6 | M6PR | MAML2 |
| LRRC46 | LSP1 | MACF1 | MAML3 |
| LRRC47 | LSR | MACROD1 | MAN1A1 |
| LRRC4B | LTB | MACROD2 | MAN1C1 |
| LRRC50 | LTB4R2 | MAD1L1 | MAN2A1 |
| LRRC56 | LTBP2 | MAD2L1 | MAN2A2 |
| LRRC57 | LTK | MAD2L1BP | MAN2B1 |
| LRRC58 | LTV1 | MAD2L2 | MAN2B2 |
| LRRC66 | LUC7L | MADD | MAN2C1 |
| LRRC8B | LUC7L2 | MAEA | MANBA |
| LRRC8C | LUC7L3 | MAF | MANBAL |
| LRRC8D | LY6E | MAF1 | MANEAL |
| LRRCC1 | LY6G5C | MAFF | MAOA |
| LRRFIP1 | LY75 | MAFG | MAP1LC3B2 |
| LRRFIP2 | LY9 | MAFK | MAP2K1 |
| LRRK1 | LYN | MAGEA4 | MAP2K4 |
| LRRN4 | LYPD3 | MAGED2 | MAP2K5 |
| LRSAM1 | LYPLA1 | MAGEF1 | MAP2K6 |
| LRTOMT | LYPLA2 | MAGIX | MAP2K7 |
| LSAMP | LYRM1 | MAGOH | MAP3K1 |
| LSG1 | LYRM2 | MAK16 | MAP3K11 |
| LSM10 | LYRM4 | MALAT1 | MAP3K13 |
| LSM11 | LYSMD1 | MALL | MAP3K14 |
| LSM14A | LYSMD2 | MALT1 | MAP3K15 |
| LSM4 | LZTS2 | MAML1 | MAP3K3 |

| 2301 | | | 2302 |
|---|---|---|---|
| MAP3K4 | MAPKAPK3 | MBOAT7 | MDGA1 |
| MAP3K6 | MAPKBP1 | MBP | MDH2 |
| MAP3K7 | MAPKSP1 | MBTD1 | MDK |
| MAP3K7IP1 | MAPRE2 | MBTPS1 | MDM1 |
| MAP3K7IP3 | MARCKS | MBTPS2 | MDN1 |
| MAP3K8 | MARCKSL1 | MCART1 | ME2 |
| MAP3K9 | MARK2 | MCAT | MECR |
| MAP4 | MARK3 | MCC | MED1 |
| MAP4K1 | MARK4 | MCCC2 | MED11 |
| MAP4K4 | MARS | MCEE | MED12 |
| MAP4K5 | MASP2 | MCF2L | MED13 |
| MAP6 | MAST2 | MCF2L2 | MED15 |
| MAP7D1 | MAST3 | MCL1 | MED20 |
| MAP7D3 | MAST4 | MCM10 | MED22 |
| MAP9 | MAT1A | MCM2 | MED23 |
| MAPK1 | MAT2A | MCM3 | MED26 |
| MAPK14 | MAT2B | MCM3APAS | MED27 |
| MAPK1IP1L | MATN1 | MCM5 | MED28 |
| MAPK6 | MAVS | MCM7 | MED7 |
| MAPK7 | MAX | MCM8 | MED8 |
| MAPK8IP2 | MAZ | MCOLN1 | MEF2A |
| MAPK8IP3 | MBD2 | MCPH1 | MEF2C |
| MAPK9 | MBD6 | MCRS1 | MEF2D |
| MAPKAP1 | MBLAC1 | MDC1 | MEG3 |
| MAPKAPK2 | MBNL2 | MDFIC | MEG8 |

| | | | |
|---|---|---|---|
| MEGF11 | MEX3B | MGC72080 | MIR1229 |
| MEGF6 | MEX3C | MGEA5 | MIR1237 |
| MEGF8 | MFAP3 | MGLL | MIR1276 |
| MEI1 | MFAP3L | MGMT | MIR129-2 |
| MEIG1 | MFHAS1 | MGRN1 | MIR132 |
| MEMO1 | MFSD2A | MGST2 | MIR140 |
| MEN1 | MFSD4 | MGST3 | MIR1470 |
| MEPCE | MFSD5 | MIA | MIR150 |
| MERTK | MFSD6 | MIB1 | MIR17HG |
| MESDC1 | MFSD6L | MIB2 | MIR1909 |
| MESDC2 | MFSD8 | MICA | MIR191 |
| MESP2 | MGAT1 | MICAL1 | MIR193B |
| MEST | MGAT2 | MICAL2 | MIR194-2 |
| MESTIT1 | MGAT3 | MICAL3 | MIR195 |
| METAP1 | MGAT4A | MICB | MIR1973 |
| METAP2 | MGAT4B | MID1IP1 | MIR210 |
| METRNL | MGAT5 | MID2 | MIR2110 |
| METT5D1 | MGAT5B | MIDN | MIR25 |
| METTL1 | MGC12982 | MIER1 | MIR27A |
| METTL10 | MGC16275 | MIER2 | MIR29C |
| METTL14 | MGC23284 | MIIP | MIR328 |
| METTL2A | MGC2752 | MIOS | MIR33A |
| METTL3 | MGC29506 | MIOX | MIR34A |
| METTL6 | MGC45800 | MIPEP | MIR484 |
| METTL9 | MGC70857 | MIR107 | MIR488 |

| | | | |
|---|---|---|---|
| MIR492 | MLLT3 | MORG1 | MREG |
| MIR548D1 | MLLT4 | MORN1 | MRFAP1 |
| MIR548N | MLX | MORN2 | MRM1 |
| MIR570 | MLXIP | MORN4 | MRO |
| MIR614 | MLXIPL | MOSPD2 | MRP63 |
| MIR636 | MLYCD | MOSPD3 | MRPL11 |
| MITF | MMADHC | MOV10 | MRPL12 |
| MKI67IP | MMP11 | MOV10L1 | MRPL15 |
| MKL1 | MMP14 | MPG | MRPL16 |
| MKLN1 | MMP17 | MPHOSPH6 | MRPL18 |
| MKNK1 | MMP24 | MPI | MRPL19 |
| MKRN2 | MN1 | MPND | MRPL20 |
| MKX | MND1 | MPP1 | MRPL21 |
| MLC1 | MNT | MPP5 | MRPL23 |
| MLEC | MOBKL2A | MPPE1 | MRPL28 |
| MLF1 | MOBKL2B | MPPED2 | MRPL3 |
| MLF1IP | MOBKL3 | MPRIP | MRPL30 |
| MLF2 | MOCOS | MPST | MRPL33 |
| MLL | MOCS2 | MPV17 | MRPL34 |
| MLL2 | MOCS3 | MPV17L2 | MRPL36 |
| MLL4 | MOGS | MPZL1 | MRPL39 |
| MLL5 | MON1B | MPZL3 | MRPL4 |
| MLLT1 | MON2 | MR1 | MRPL44 |
| MLLT10 | MORC3 | MRC2 | MRPL46 |
| MLLT11 | MORC4 | MRE11A | MRPL47 |

| | | | |
|---|---|---|---|
| MRPL48 | MSL1 | MTL5 | MXD4 |
| MRPL50 | MSL2 | MTM1 | MXI1 |
| MRPL52 | MSL3 | MTMR1 | MYBL1 |
| MRPL55 | MSRA | MTMR10 | MYBL2 |
| MRPS12 | MSRB2 | MTMR3 | MYBPC2 |
| MRPS14 | MST1 | MTMR9 | MYC |
| MRPS16 | MST1P2 | MTMR9L | MYCBP |
| MRPS18B | MST1R | MTOR | MYCBP2 |
| MRPS22 | MST4 | MTP18 | MYCL1 |
| MRPS24 | MSTO2P | MTR | MYCN |
| MRPS25 | MTA1 | MTRF1 | MYEOV2 |
| MRPS28 | MTA2 | MTRF1L | MYH10 |
| MRPS31 | MTAP | MTRR | MYH3 |
| MRPS33 | MTCH1 | MTUS2 | MYH9 |
| MRPS35 | MTCH2 | MUC1 | MYL12B |
| MRPS5 | MTDH | MUC2 | MYL2 |
| MRPS9 | MTERFD1 | MUM1 | MYL4 |
| MRS2 | MTERFD2 | MUS81 | MYL6B |
| MRS2P2 | MTF2 | MUSTN1 | MYLK3 |
| MRTO4 | MTFR1 | MUTYH | MYO10 |
| MSH2 | MTG1 | MVD | MYO15A |
| MSH3 | MTHFD1L | MVK | MYO18A |
| MSH4 | MTHFD2L | MVP | MYO18B |
| MSH5 | MTHFSD | MX1 | MYO1B |
| MSI2 | MTIF3 | MXD3 | MYO1C |

| | | | |
|---|---|---|---|
| MYO1D | NAF1 | NBN | NCRNA00120 |
| MYO1G | NAGA | NBPF11 | NCRNA00164 |
| MYO5C | NAGK | NBPF9 | NCRNA00167 |
| MYO7B | NAGLU | NBR1 | NCRNA00171 |
| MYO9A | NAGPA | NBR2 | NCRNA00219 |
| MYOF | NAMPT | NCAN | NDE1 |
| MYOM2 | NAP1L1 | NCAPD2 | NDEL1 |
| MYPN | NAP1L4 | NCAPD3 | NDRG4 |
| MYSM1 | NAP1L5 | NCAPG | NDST1 |
| MYST2 | NAPA | NCAPH | NDST2 |
| MZF1 | NAPEPLD | NCAPH2 | NDUFA1 |
| N4BP2 | NARF | NCDN | NDUFA10 |
| N4BP2L1 | NARFL | NCEH1 | NDUFA11 |
| N4BP3 | NASP | NCK1 | NDUFA12 |
| N6AMT2 | NAT1 | NCK2 | NDUFA4 |
| NAA20 | NAT10 | NCKAP1L | NDUFA6 |
| NAA25 | NAT15 | NCL | NDUFA7 |
| NAA30 | NAT6 | NCLN | NDUFA8 |
| NAAA | NAT8L | NCOA3 | NDUFA9 |
| NAB2 | NAV2 | NCOA5 | NDUFAB1 |
| NACA | NAV3 | NCOR2 | NDUFAF1 |
| NACC1 | NBAS | NCR2 | NDUFAF2 |
| NACC2 | NBEA | NCRNA00081 | NDUFAF3 |
| NADK | NBEAL1 | NCRNA00094 | NDUFB1 |
| NADSYN1 | NBEAL2 | NCRNA00119 | NDUFB10 |

| | | | |
|---|---|---|---|
| NDUFB3 | NEK7 | NFXL1 | NKX2-2 |
| NDUFB4 | NEK9 | NFYA | NKX2-3 |
| NDUFB5 | NELF | NFYB | NKX3-2 |
| NDUFB6 | NELL2 | NFYC | NLRC3 |
| NDUFB8 | NETO2 | NGDN | NLRC5 |
| NDUFC2 | NEU1 | NGFRAP1 | NLRP2 |
| NDUFS2 | NEURL1B | NGRN | NLRP3 |
| NDUFS3 | NEURL3 | NHEJ1 | NLRX1 |
| NDUFS5 | NEURL4 | NHLRC1 | NME2 |
| NDUFS6 | NEUROD1 | NHP2 | NMNAT1 |
| NDUFS7 | NEUROD2 | NHSL2 | NMNAT2 |
| NDUFV1 | NEUROG2 | NIP7 | NNAT |
| NDUFV2 | NFATC1 | NIPA1 | NNT |
| NEAT1 | NFATC2 | NIPA2 | NOC2L |
| NECAB1 | NFATC2IP | NIPAL1 | NOC3L |
| NECAB3 | NFATC3 | NIPAL2 | NOD1 |
| NECAP1 | NFATC4 | NIPAL3 | NOD2 |
| NEDD1 | NFE2L1 | NIPSNAP1 | NOG |
| NEDD4L | NFE2L2 | NIPSNAP3A | NOL10 |
| NEDD9 | NFIA | NKD1 | NOL11 |
| NEIL1 | NFIC | NKG7 | NOL7 |
| NEIL2 | NFIL3 | NKIRAS1 | NOM1 |
| NEIL3 | NFKB2 | NKIRAS2 | NOP10 |
| NEK10 | NFKBIL2 | NKPD1 | NOP56 |
| NEK2 | NFKBIZ | NKTR | NOP58 |

| | | | |
|---|---|---|---|
| NOS1 | NR4A2 | NSUN5 | NUDT5 |
| NOS3 | NR4A3 | NSUN5B | NUF2 |
| NOTCH1 | NR5A1 | NSUN5C | NUFIP1 |
| NOTCH2 | NR5A2 | NT5C | NUMA1 |
| NPAS3 | NR6A1 | NT5C2 | NUMB |
| NPEPPS | NRBF2 | NT5C3L | NUMBL |
| NPFFR2 | NRBP1 | NT5DC1 | NUP107 |
| NPHP4 | NRBP2 | NT5DC3 | NUP133 |
| NPLOC4 | NRCAM | NT5E | NUP153 |
| NPM1 | NRD1 | NTAN1 | NUP155 |
| NPM3 | NRF1 | NTN1 | NUP160 |
| NPR1 | NRG1 | NTNG1 | NUP205 |
| NPY1R | NRGN | NTSR2 | NUP210 |
| NQO2 | NRIP1 | NUB1 | NUP35 |
| NR1D1 | NRN1L | NUBP1 | NUP50 |
| NR1D2 | NRP2 | NUBP2 | NUP54 |
| NR1H2 | NRXN2 | NUBPL | NUP62 |
| NR1H3 | NRXN3 | NUCB1 | NUP62CL |
| NR2C1 | NSDHL | NUCKS1 | NUP93 |
| NR2C2 | NSF | NUDCD2 | NUP98 |
| NR2E1 | NSFL1C | NUDCD3 | NUPL2 |
| NR2F1 | NSMAF | NUDT10 | NUS1 |
| NR3C1 | NSUN2 | NUDT16 | NVL |
| NR3C2 | NSUN3 | NUDT16L1 | NXF1 |
| NR4A1 | NSUN4 | NUDT3 | NXN |

| | | | |
|---|---|---|---|
| NXPH3 | OPN5 | OSTC | PACSIN2 |
| NXT1 | OPRL1 | OTOP2 | PACSIN3 |
| OASL | OR2L13 | OTP | PAFAH1B1 |
| OAZ1 | OR2T27 | OTUB1 | PAFAH2 |
| OAZ2 | ORAI3 | OTUD1 | PAICS |
| OBFC2A | ORAOV1 | OTUD4 | PAIP1 |
| OBSCN | ORC1L | OTUD5 | PAIP2 |
| OCA2 | ORC3L | OTUD6B | PAK1 |
| OCEL1 | ORC4L | OTX1 | PAK4 |
| ODC1 | ORC6L | OXA1L | PAK7 |
| ODF2L | ORMDL2 | OXCT1 | PALM |
| ODZ4 | ORMDL3 | OXNAD1 | PAM |
| OGDH | OSBP | OXSR1 | PAN2 |
| OGFOD2 | OSBPL10 | OXTR | PANK1 |
| OGFR | OSBPL11 | P2RX1 | PANK3 |
| OGFRL1 | OSBPL2 | P2RX2 | PANK4 |
| OGG1 | OSBPL3 | P2RX3 | PANX1 |
| OGT | OSBPL5 | P2RX5 | PAOX |
| OLFM2 | OSBPL7 | P4HA1 | PAPL |
| ONECUT2 | OSBPL9 | P4HB | PAPLN |
| OPA1 | OSGEP | PABPC3 | PAPPA |
| OPA3 | OSGIN2 | PABPN1 | PAPSS2 |
| OPHN1 | OSR1 | PACRG | PAQR8 |
| OPN1SW | OSR2 | PACS2 | PAQR9 |
| OPN3 | OSTBETA | PACSIN1 | PARD3 |

| | | | |
|---|---|---|---|
| PARD6A | PCCA | PDCD6 | PDLIM5 |
| PARL | PCDH1 | PDCD6IP | PDP1 |
| PARP10 | PCDHB2 | PDCD7 | PDP2 |
| PARP15 | PCDHGA4 | PDCL | PDPR |
| PARP16 | PCDHGB4 | PDE12 | PDS5A |
| PARP2 | PCGF3 | PDE2A | PDSS2 |
| PARP4 | PCGF5 | PDE4A | PDXDC1 |
| PARP8 | PCGF6 | PDE4C | PDXDC2 |
| PARP9 | PCID2 | PDE4D | PDXK |
| PARS2 | PCIF1 | PDE4DIP | PDZD8 |
| PARVB | PCK2 | PDE5A | PECI |
| PARVG | PCM1 | PDE6B | PEF1 |
| PASK | PCMTD1 | PDE6D | PEG3 |
| PATL1 | PCMTD2 | PDE7A | PELI1 |
| PATZ1 | PCNA | PDE8A | PELI2 |
| PAWR | PCNP | PDGFA | PELI3 |
| PAX3 | PCNT | PDGFRL | PEMT |
| PAX5 | PCNXL2 | PDHB | PEPD |
| PAX6 | PCNXL3 | PDIA2 | PER1 |
| PAX7 | PCOLCE | PDIA4 | PER2 |
| PAXIP1 | PCP2 | PDIA5 | PET112L |
| PBK | PCTP | PDIA6 | PET117 |
| PBX2 | PDCD10 | PDIK1L | PEX1 |
| PBXIP1 | PDCD2 | PDK4 | PEX11G |
| PC | PDCD5 | PDLIM4 | PEX12 |

| | | | |
|---|---|---|---|
| PEX13 | PGM2 | PHLDA1 | PIGK |
| PEX19 | PGM3 | PHLDA2 | PIGL |
| PEX5 | PGM5P2 | PHLDB1 | PIGM |
| PEX5L | PGP | PHLDB2 | PIGO |
| PFDN1 | PGPEP1 | PHLDB3 | PIGP |
| PFDN2 | PHACTR2 | PHLPP1 | PIGS |
| PFDN4 | PHACTR4 | PHOSPHO1 | PIGT |
| PFDN5 | PHAX | PHPT1 | PIGV |
| PFDN6 | PHB | PHRF1 | PIH1D1 |
| PFKFB2 | PHB2 | PHTF1 | PIH1D2 |
| PFKFB3 | PHC2 | PHTF2 | PIK3IP1 |
| PFKFB4 | PHF1 | PI4K2B | PIK3R1 |
| PFKL | PHF10 | PI4KA | PIK3R3 |
| PFKM | PHF11 | PI4KAP2 | PIK3R4 |
| PFKP | PHF13 | PI4KB | PIK3R5 |
| PFN1 | PHF14 | PIAS1 | PIK3R6 |
| PFN2 | PHF15 | PIAS2 | PIKFYVE |
| PFN4 | PHF17 | PIAS3 | PILRA |
| PGAM1 | PHF2 | PIBF1 | PIM3 |
| PGAP2 | PHF23 | PICALM | PINK1 |
| PGAP3 | PHF7 | PID1 | PINX1 |
| PGBD2 | PHF8 | PIF1 | PION |
| PGBD4 | PHGDH | PIGB | PIP4K2A |
| PGGT1B | PHKA2 | PIGC | PIP5K1C |
| PGK1 | PHKG1 | PIGG | PIP5KL1 |

| | | | |
|---|---|---|---|
| PITPNA | PLCG2 | PLK1 | PMVK |
| PITPNB | PLCH2 | PLK1S1 | PNP |
| PITPNM1 | PLCL2 | PLK2 | PNPLA2 |
| PITPNM2 | PLCXD2 | PLK4 | PNPLA6 |
| PITRM1 | PLD2 | PLN | PNPLA7 |
| PJA2 | PLD3 | PLOD1 | PNPLA8 |
| PKD1 | PLD4 | PLOD3 | PNPO |
| PKHD1 | PLDN | PLRG1 | PNRC2 |
| PKM2 | PLEC1 | PLS1 | PODNL1 |
| PKN1 | PLEKHA1 | PLSCR1 | POFUT1 |
| PKN2 | PLEKHA2 | PLSCR3 | POFUT2 |
| PKNOX1 | PLEKHA8 | PLTP | POLA2 |
| PKP4 | PLEKHB2 | PLXNA1 | POLB |
| PLA2G12A | PLEKHF1 | PLXNB2 | POLD2 |
| PLA2G16 | PLEKHG1 | PLXNC1 | POLD4 |
| PLA2G4D | PLEKHG4B | PM20D2 | POLE |
| PLA2G6 | PLEKHG5 | PMEPA1 | POLE2 |
| PLAC8 | PLEKHH3 | PMF1 | POLE3 |
| PLAGL1 | PLEKHM1 | PML | POLE4 |
| PLAUR | PLEKHM1P | PMM2 | POLG |
| PLBD1 | PLEKHM2 | PMPCB | POLG2 |
| PLBD2 | PLEKHN1 | PMS2 | POLI |
| PLCD1 | PLEKHO1 | PMS2L11 | POLK |
| PLCD3 | PLEKHO2 | PMS2L3 | POLL |
| PLCG1 | PLIN3 | PMS2L4 | POLM |

| | | | |
|---|---|---|---|
| POLR1A | POT1 | PPIL5 | PPP1R8 |
| POLR1B | POU2AF1 | PPM1A | PPP1R9B |
| POLR1D | POU2F1 | PPM1D | PPP2CA |
| POLR1E | POU2F2 | PPM1F | PPP2R1A |
| POLR2A | POU3F1 | PPM1H | PPP2R1B |
| POLR2B | POU5F1 | PPM1K | PPP2R2C |
| POLR2C | POU6F1 | PPM1L | PPP2R3C |
| POLR2D | POU6F2 | PPM1M | PPP2R4 |
| POLR2E | PPA1 | PPOX | PPP2R5A |
| POLR2I | PPA2 | PPP1CA | PPP2R5C |
| POLR2J4 | PPAN | PPP1R10 | PPP2R5D |
| POLR3B | PPARA | PPP1R11 | PPP2R5E |
| POLR3C | PPARGC1B | PPP1R12A | PPP3CA |
| POLR3E | PPCDC | PPP1R12B | PPP3CB |
| POLRMT | PPFIA1 | PPP1R12C | PPP4C |
| POLS | PPFIBP1 | PPP1R13B | PPP4R1 |
| POMP | PPFIBP2 | PPP1R14C | PPP5C |
| POMT2 | PPIA | PPP1R15A | PPP6C |
| PON2 | PPIB | PPP1R16B | PPPDE1 |
| POP1 | PPID | PPP1R1A | PPRC1 |
| POP4 | PPIE | PPP1R1B | PPT1 |
| POP5 | PPIG | PPP1R3B | PPT2 |
| POP7 | PPIH | PPP1R3E | PPTC7 |
| POR | PPIL2 | PPP1R3F | PQBP1 |
| PORCN | PPIL4 | PPP1R7 | PQLC1 |

| | | | |
|---|---|---|---|
| PRCC | PRKAG1 | PROSC | PRR5-ARHGAP8 |
| PRCP | PRKAG2 | PROX1 | PRR5L |
| PRDM1 | PRKAR1A | PRPF18 | PRRC1 |
| PRDM12 | PRKAR1B | PRPF19 | PRRT2 |
| PRDM13 | PRKCA | PRPF31 | PRSS16 |
| PRDM15 | PRKCD | PRPF4 | PRSS23 |
| PRDM16 | PRKCE | PRPF40B | PRTFDC1 |
| PRDM2 | PRKCG | PRPF4B | PSAT1 |
| PRDM6 | PRKCI | PRPF6 | PSCA |
| PRDX1 | PRKCSH | PRPF8 | PSD |
| PRDX5 | PRKCZ | PRPH | PSD3 |
| PRDX6 | PRKD2 | PRPS1 | PSD4 |
| PREB | PRKG1 | PRPSAP1 | PSENEN |
| PREPL | PRKRA | PRR11 | PSMA3 |
| PREX1 | PRKRIP1 | PRR12 | PSMA5 |
| PRF1 | PRKRIR | PRR13 | PSMA6 |
| PRHOXNB | PRMT1 | PRR14 | PSMA7 |
| PRIC285 | PRMT10 | PRR15 | PSMB1 |
| PRICKLE1 | PRMT2 | PRR15L | PSMB2 |
| PRICKLE4 | PRMT3 | PRR16 | PSMB3 |
| PRIM2 | PRMT5 | PRR18 | PSMB6 |
| PRKAB1 | PRNT | PRR23B | PSMB7 |
| PRKACA | PROCA1 | PRR24 | PSMB8 |
| PRKACB | PROKR1 | PRR3 | PSMB9 |
| PRKACG | PROL1 | PRR5 | PSMC1 |

| | | | |
|---|---|---|---|
| PSMC2 | PTBP1 | PTPN12 | PVT1 |
| PSMC3 | PTCD2 | PTPN18 | PWP2 |
| PSMC3IP | PTCD3 | PTPN22 | PWWP2A |
| PSMC4 | PTCH1 | PTPN23 | PWWP2B |
| PSMC5 | PTCRA | PTPN4 | PXDN |
| PSMC6 | PTDSS1 | PTPN6 | PXMP2 |
| PSMD11 | PTDSS2 | PTPN9 | PXMP3 |
| PSMD12 | PTEN | PTPRA | PXT1 |
| PSMD13 | PTER | PTPRB | PYCARD |
| PSMD14 | PTGER4 | PTPRCAP | PYCR1 |
| PSMD3 | PTGES3 | PTPRE | PYCR2 |
| PSMD4 | PTGS1 | PTPRF | PYDC2 |
| PSMD6 | PTH2 | PTPRG | PYGB |
| PSME1 | PTK2 | PTPRN2 | PYGO2 |
| PSME4 | PTK2B | PTPRS | PYY |
| PSMF1 | PTK7 | PTRF | PYY2 |
| PSMG2 | PTMA | PTS | QARS |
| PSMG4 | PTOV1 | PTTG1IP | QSER1 |
| PSORS1C1 | PTP4A1 | PUM1 | QSOX1 |
| PSORS1C2 | PTP4A2 | PURA | QSOX2 |
| PSPC1 | PTP4A3 | PURB | R3HDM1 |
| PSPH | PTPLAD1 | PUS1 | RAB11A |
| PSTK | PTPLB | PUSL1 | RAB11FIP3 |
| PSTPIP1 | PTPMT1 | PVRL1 | RAB13 |
| PTAFR | PTPN1 | PVRL4 | RAB18 |

| | | | |
|---|---|---|---|
| RAB1B | RAB7A | RALBP1 | RASA3 |
| RAB21 | RAB8A | RALGAPA1 | RASAL1 |
| RAB22A | RAB8B | RALGAPA2 | RASD1 |
| RAB23 | RABAC1 | RALGDS | RASGEF1A |
| RAB24 | RABEP2 | RALGPS2 | RASGEF1B |
| RAB28 | RABGAP1L | RAN | RASGEF1C |
| RAB2A | RABGGTA | RANBP1 | RASGRF1 |
| RAB30 | RABGGTB | RANGAP1 | RASGRP4 |
| RAB31 | RABL3 | RANGRF | RASL11A |
| RAB33B | RABL4 | RAP1B | RASL12 |
| RAB34 | RABL5 | RAP1GAP2 | RASSF1 |
| RAB37 | RAC2 | RAP1GDS1 | RASSF2 |
| RAB38 | RAC3 | RAP2A | RASSF4 |
| RAB39 | RACGAP1 | RAP2B | RASSF5 |
| RAB3A | RAD17 | RAP2C | RASSF8 |
| RAB3B | RAD21 | RAPGEF3 | RASSF9 |
| RAB3C | RAD51 | RAPH1 | RAX |
| RAB3GAP1 | RAD51AP1 | RARA | RB1 |
| RAB3GAP2 | RAD51L1 | RARG | RB1CC1 |
| RAB3IP | RAD9A | RARRES1 | RBAK |
| RAB40B | RAE1 | RARRES2 | RBBP4 |
| RAB40C | RAET1K | RARS | RBBP5 |
| RAB5A | RAF1 | RARS2 | RBBP6 |
| RAB5B | RAI1 | RASA1 | RBCK1 |
| RAB5C | RALB | RASA2 | RBL1 |

| | | | |
|---|---|---|---|
| RBL2 | RBM6 | RECQL5 | RFX1 |
| RBM10 | RBMS3 | REEP1 | RFX2 |
| RBM14 | RBMX | REEP4 | RFX3 |
| RBM15 | RBP1 | REEP5 | RFX4 |
| RBM15B | RBP5 | REEP6 | RFX5 |
| RBM16 | RBPJL | RELL1 | RFXAP |
| RBM18 | RBPMS | RELT | RG9MTD1 |
| RBM19 | RBPMS2 | REM1 | RG9MTD2 |
| RBM22 | RBX1 | REPIN1 | RGL2 |
| RBM23 | RCAN1 | REPS1 | RGMB |
| RBM24 | RCAN3 | RER1 | RGNEF |
| RBM25 | RCBTB2 | RERE | RGP1 |
| RBM26 | RCC2 | RERG | RGS12 |
| RBM27 | RCCD1 | REST | RGS16 |
| RBM28 | RCE1 | REXO1 | RGS20 |
| RBM33 | RCHY1 | REXO2 | RGS6 |
| RBM34 | RCL1 | RFC2 | RHBDF2 |
| RBM39 | RCN1 | RFC4 | RHEB |
| RBM4 | RCN2 | RFC5 | RHEBL1 |
| RBM41 | RCN3 | RFESD | RHOA |
| RBM42 | RCOR2 | RFFL | RHOB |
| RBM43 | RCOR3 | RFNG | RHOBTB1 |
| RBM45 | RDBP | RFPL3 | RHOBTB2 |
| RBM47 | RDM1 | RFTN1 | RHOBTB3 |
| RBM5 | RECQL4 | RFWD3 | RHOF |

| | | | |
|---|---|---|---|
| RHOH | RNASET2 | RNF213 | RORA |
| RHOT1 | RNF103 | RNF216L | RP2 |
| RHOT2 | RNF113A | RNF25 | RP5-1022P6.2 |
| RHOV | RNF126 | RNF26 | RPA1 |
| RIC8A | RNF130 | RNF31 | RPA3 |
| RICTOR | RNF135 | RNF32 | RPAIN |
| RIF1 | RNF14 | RNF34 | RPAP1 |
| RILP | RNF145 | RNF39 | RPAP2 |
| RIMKLB | RNF146 | RNF4 | RPE |
| RIMS2 | RNF149 | RNF40 | RPF1 |
| RIMS3 | RNF150 | RNF44 | RPGR |
| RIN1 | RNF152 | RNF8 | RPGRIP1 |
| RIN3 | RNF157 | RNFT1 | RPIA |
| RING1 | RNF160 | RNFT2 | RPL10A |
| RINL | RNF168 | RNGTT | RPL11 |
| RIPK1 | RNF169 | RNH1 | RPL17 |
| RIPK3 | RNF17 | RNPEP | RPL19 |
| RIPK4 | RNF170 | RNPEPL1 | RPL21 |
| RMND5B | RNF181 | RNU5E | RPL22 |
| RNASE12 | RNF187 | RNU6ATAC | RPL23A |
| RNASE4 | RNF19A | ROCK1 | RPL24 |
| RNASE6 | RNF19B | ROD1 | RPL26 |
| RNASEH1 | RNF2 | ROGDI | RPL26L1 |
| RNASEH2B | RNF20 | ROMO1 | RPL27A |
| RNASEK | RNF207 | ROPN1L | RPL29 |

| | | | |
|---|---|---|---|
| RPL30 | RPS15 | RRAS | RTKN2 |
| RPL31 | RPS15A | RRBP1 | RTN1 |
| RPL34 | RPS19 | RREB1 | RTN2 |
| RPL35A | RPS20 | RRM1 | RTN4 |
| RPL36 | RPS23 | RRM2 | RTN4IP1 |
| RPL36A | RPS26 | RRM2B | RTN4RL2 |
| RPL36AL | RPS27 | RRN3 | RTP3 |
| RPL38 | RPS27A | RRN3P3 | RUFY1 |
| RPL39L | RPS28 | RRP1 | RUFY2 |
| RPL41 | RPS29 | RRP15 | RUNDC2A |
| RPL5 | RPS3 | RRP7A | RUNX1 |
| RPL6 | RPS6KA1 | RRP7B | RUNX2 |
| RPL7 | RPS6KA2 | RRP9 | RUNX3 |
| RPL7L1 | RPS6KA4 | RRS1 | RUVBL1 |
| RPLP0 | RPS6KB1 | RSBN1L | RUVBL2 |
| RPLP1 | RPS6KC1 | RSF1 | RWDD1 |
| RPN2 | RPS7 | RSL24D1 | RWDD2B |
| RPP14 | RPSA | RSPH1 | RXRA |
| RPP21 | RPSAP58 | RSPH4A | RXRB |
| RPP40 | RPTOR | RSPO2 | RYBP |
| RPRD2 | RPUSD1 | RSPRY1 | RYK |
| RPS10 | RPUSD3 | RSRC2 | RYR1 |
| RPS11 | RPUSD4 | RTCD1 | RYR2 |
| RPS12 | RQCD1 | RTF1 | S100B |
| RPS13 | RRAD | RTKN | S1PR2 |

| | | | |
|---|---|---|---|
| S1PR5 | SARNP | SCD5 | SDK1 |
| SAA2 | SARS | SCGB1C1 | SDR39U1 |
| SAAL1 | SART1 | SCGB3A1 | SDSL |
| SAC3D1 | SART3 | SCMH1 | SEC1 |
| SACM1L | SAT1 | SCN3B | SEC11C |
| SACS | SATB1 | SCNM1 | SEC14L1 |
| SAFB | SATB2 | SCNN1G | SEC14L5 |
| SAFB2 | SBDS | SCO1 | SEC16A |
| SAG | SBF1 | SCOC | SEC22A |
| SAMD10 | SBK1 | SCRIB | SEC22B |
| SAMD11 | SBNO2 | SCRN2 | SEC22C |
| SAMD14 | SC4MOL | SCRT1 | SEC23B |
| SAMD5 | SC5DL | SCTR | SEC24B |
| SAMHD1 | SCAF1 | SCUBE2 | SEC24C |
| SAP130 | SCAMP1 | SCYL1 | SEC24D |
| SAP18 | SCAMP3 | SCYL2 | SEC61A1 |
| SAP25 | SCAMP4 | SCYL3 | SEC61G |
| SAP30 | SCAND3 | SDC3 | SEC63 |
| SAP30BP | SCARB1 | SDCBP2 | SECISBP2 |
| SAP30L | SCARF2 | SDCCAG3 | SEL1L |
| SAPS1 | SCARNA10 | SDCCAG8 | SELI |
| SAPS2 | SCARNA16 | SDF2L1 | SELK |
| SAPS3 | SCARNA2 | SDF4 | SELM |
| SAR1B | SCCPDH | SDHA | SELO |
| SARM1 | SCD | SDHAF1 | SELT |

| | | | |
|---|---|---|---|
| SEMA3B | SERINC5 | SF3B3 | SFXN4 |
| SEMA4A | SERP1 | SF3B5 | SFXN5 |
| SEMA4B | SERPINB6 | SF4 | SGCB |
| SEMA4C | SERPINB9 | SFI1 | SGCE |
| SEMA4F | SERPINH1 | SFMBT1 | SGK196 |
| SEMA5A | SESN1 | SFMBT2 | SGK3 |
| SEMA5B | SESN2 | SFPQ | SGMS1 |
| SEMA6A | SESN3 | SFRP1 | SGOL1 |
| SEMA6C | SETBP1 | SFRP5 | SGPL1 |
| SEMA6D | SETD1A | SFRS1 | SGPP2 |
| SEMA7A | SETD1B | SFRS11 | SGSM3 |
| SENP1 | SETD2 | SFRS12 | SGTA |
| SENP2 | SETD3 | SFRS13B | SGTB |
| SENP3 | SETD4 | SFRS15 | SH2B2 |
| SENP7 | SETD6 | SFRS16 | SH2B3 |
| SEPHS1 | SETD7 | SFRS18 | SH2D2A |
| SEPN1 | SETD8 | SFRS2 | SH2D3C |
| SEPSECS | SETDB1 | SFRS2IP | SH2D4A |
| SEPX1 | SETDB2 | SFRS6 | SH2D4B |
| SERAC1 | SEZ6 | SFRS7 | SH3BGRL3 |
| SERBP1 | SEZ6L2 | SFRS8 | SH3BP2 |
| SERGEF | SF3A2 | SFT2D2 | SH3BP5L |
| SERHL2 | SF3A3 | SFT2D3 | SH3GL1 |
| SERINC3 | SF3B1 | SFXN1 | SH3PXD2A |
| SERINC4 | SF3B14 | SFXN2 | SH3RF3 |

| | | | |
|---|---|---|---|
| SH3TC1 | SIGIRR | SKIV2L | SLC1A4 |
| SH3TC2 | SIGLEC10 | SKIV2L2 | SLC20A2 |
| SHANK2 | SIGLEC6 | SKP1 | SLC22A15 |
| SHARPIN | SIGLECP3 | SLA2 | SLC22A18AS |
| SHB | SIGMAR1 | SLBP | SLC22A23 |
| SHC1 | SIK1 | SLC10A2 | SLC22A5 |
| SHC3 | SIK2 | SLC10A4 | SLC25A1 |
| SHC4 | SIK3 | SLC10A7 | SLC25A10 |
| SHE | SIN3A | SLC11A2 | SLC25A15 |
| SHF | SIN3B | SLC12A2 | SLC25A16 |
| SHFM1 | SIPA1 | SLC12A4 | SLC25A17 |
| SHH | SIPA1L3 | SLC12A6 | SLC25A19 |
| SHISA5 | SIRPA | SLC12A7 | SLC25A23 |
| SHISA7 | SIRT2 | SLC12A9 | SLC25A24 |
| SHKBP1 | SIRT3 | SLC16A1 | SLC25A26 |
| SHMT1 | SIRT5 | SLC16A11 | SLC25A27 |
| SHMT2 | SIRT7 | SLC16A13 | SLC25A28 |
| SHOC2 | SIVA1 | SLC16A14 | SLC25A29 |
| SHPK | SIX3 | SLC16A3 | SLC25A34 |
| SHPRH | SIX5 | SLC16A8 | SLC25A35 |
| SHQ1 | SKA2 | SLC17A9 | SLC25A36 |
| SIAH1 | SKA3 | SLC19A1 | SLC25A42 |
| SIAH2 | SKAP2 | SLC19A2 | SLC25A44 |
| SIDT1 | SKI | SLC1A1 | SLC25A46 |
| SIDT2 | SKIL | SLC1A3 | SLC25A5 |

| | | | |
|---|---|---|---|
| SLC26A10 | SLC35B4 | SLC41A3 | SLC7A5P2 |
| SLC26A2 | SLC35E1 | SLC43A1 | SLC7A6 |
| SLC26A6 | SLC35F2 | SLC43A2 | SLC7A7 |
| SLC27A1 | SLC36A1 | SLC43A3 | SLC8A3 |
| SLC27A3 | SLC36A4 | SLC44A2 | SLC9A7 |
| SLC29A1 | SLC37A1 | SLC45A1 | SLC9A8 |
| SLC29A2 | SLC37A2 | SLC45A4 | SLCO4A1 |
| SLC29A4 | SLC37A3 | SLC46A1 | SLCO4C1 |
| SLC2A1 | SLC37A4 | SLC46A3 | SLCO5A1 |
| SLC2A13 | SLC38A1 | SLC47A1 | SLFN11 |
| SLC2A3 | SLC38A10 | SLC4A11 | SLFN12L |
| SLC2A4 | SLC38A2 | SLC4A2 | SLFN5 |
| SLC2A5 | SLC38A4 | SLC4A4 | SLFNL1 |
| SLC2A6 | SLC38A5 | SLC5A11 | SLIT1 |
| SLC2A8 | SLC38A7 | SLC5A3 | SLITRK2 |
| SLC2A9 | SLC38A9 | SLC6A13 | SLITRK4 |
| SLC30A3 | SLC39A1 | SLC6A19 | SLK |
| SLC30A4 | SLC39A10 | SLC6A20 | SLMAP |
| SLC30A5 | SLC39A11 | SLC6A5 | SLTM |
| SLC30A6 | SLC39A13 | SLC6A6 | SMAD1 |
| SLC35A1 | SLC39A3 | SLC6A8 | SMAD3 |
| SLC35A3 | SLC39A4 | SLC6A9 | SMAD4 |
| SLC35A4 | SLC39A6 | SLC7A1 | SMAD6 |
| SLC35A5 | SLC39A7 | SLC7A3 | SMAD7 |
| SLC35B2 | SLC39A8 | SLC7A5 | SMAP1 |

| | | | |
|---|---|---|---|
| SMARCA4 | SMURF2 | SNORD116-13 | SNRPA1 |
| SMARCA5 | SMYD1 | SNORD123 | SNRPB |
| SMARCAD1 | SMYD3 | SNORD15A | SNRPC |
| SMARCD1 | SNAI1 | SNORD1C | SNRPD2 |
| SMARCD2 | SNAI2 | SNORD24 | SNRPE |
| SMARCD3 | SNAPC1 | SNORD27 | SNRPF |
| SMARCE1 | SNAPC2 | SNORD34 | SNRPG |
| SMC3 | SNAPC4 | SNORD42B | SNRPN |
| SMCHD1 | SNAPIN | SNORD43 | SNTB2 |
| SMCR5 | SND1 | SNORD45C | SNUPN |
| SMCR7L | SNED1 | SNORD55 | SNW1 |
| SMCR8 | SNF8 | SNORD7 | SNX10 |
| SMEK1 | SNHG3-RCC1 | SNORD76 | SNX12 |
| SMEK2 | SNHG4 | SNORD83A | SNX14 |
| SMG1 | SNHG5 | SNORD84 | SNX15 |
| SMG6 | SNHG7 | SNORD85 | SNX16 |
| SMO | SNHG8 | SNORD88A | SNX17 |
| SMOC1 | SNHG9 | SNORD94 | SNX18 |
| SMOC2 | SNN | SNORD95 | SNX19 |
| SMPD2 | SNORA14B | SNPH | SNX2 |
| SMPD4 | SNORA21 | SNRK | SNX22 |
| SMTN | SNORA26 | SNRNP200 | SNX24 |
| SMTNL1 | SNORA54 | SNRNP35 | SNX25 |
| SMUG1 | SNORA7A | SNRNP48 | SNX27 |
| SMURF1 | SNORA9 | SNRNP70 | SNX29 |

| | | | |
|---|---|---|---|
| SNX30 | SOX4 | SPC25 | SPTAN1 |
| SNX32 | SOX6 | SPCS3 | SPTB |
| SNX5 | SOX9 | SPDYA | SPTBN1 |
| SNX6 | SP1 | SPDYE1 | SPTLC2 |
| SNX8 | SP100 | SPEF1 | SQRDL |
| SNX9 | SP140L | SPG11 | SQSTM1 |
| SOAT1 | SP2 | SPG20 | SR140 |
| SOCS1 | SP4 | SPHK1 | SRA1 |
| SOCS2 | SP9 | SPHK2 | SRC |
| SOCS6 | SPAG1 | SPI1 | SRCAP |
| SOCS7 | SPAG6 | SPIB | SRCIN1 |
| SOD1 | SPAG9 | SPIN1 | SRCRB4D |
| SOLH | SPARC | SPIRE2 | SRD5A3 |
| SON | SPATA1 | SPNS1 | SREBF1 |
| SORBS1 | SPATA13 | SPOCK2 | SREBF2 |
| SORBS2 | SPATA16 | SPOCK3 | SRF |
| SORBS3 | SPATA17 | SPOPL | SRGAP3 |
| SORCS2 | SPATA18 | SPPL2A | SRM |
| SORL1 | SPATA2 | SPPL2B | SRP68 |
| SORT1 | SPATA20 | SPPL3 | SRP72 |
| SOS2 | SPATA21 | SPRED2 | SRP9 |
| SOX1 | SPATA24 | SPRY4 | SRPK1 |
| SOX18 | SPATA2L | SPRYD3 | SRPK2 |
| SOX21 | SPATA5L1 | SPSB2 | SRPR |
| SOX2OT | SPATS2L | SPSB3 | SRR |

| | | | |
|---|---|---|---|
| SRRM1 | ST7L | STK38 | SUB1 |
| SRRM2 | ST8SIA1 | STK39 | SUCLG1 |
| SRRM5 | ST8SIA4 | STK40 | SUCLG2 |
| SRXN1 | STAC3 | STMN1 | SUFU |
| SS18 | STAG2 | STMN2 | SUGT1 |
| SS18L1 | STAG3L2 | STMN3 | SUGT1P1 |
| SSB | STAM | STOML2 | SULF2 |
| SSBP2 | STAM2 | STRADA | SULT1A2 |
| SSBP3 | STARD13 | STRADB | SULT1C4 |
| SSC5D | STARD3 | STRBP | SUMF2 |
| SSH1 | STARD3NL | STRN | SUPT5H |
| SSR2 | STARD9 | STT3A | SUPT7L |
| SST | STAT3 | STUB1 | SUPV3L1 |
| SSTR2 | STAT4 | STX11 | SUSD1 |
| SSU72 | STAT5A | STX12 | SUSD3 |
| SSX2IP | STAT6 | STX1A | SUV39H2 |
| ST3GAL1 | STAU2 | STX1B | SUV420H2 |
| ST3GAL2 | STIM1 | STX2 | SUZ12 |
| ST3GAL3 | STIP1 | STX3 | SVIP |
| ST3GAL4 | STK10 | STX5 | SYAP1 |
| ST3GAL5 | STK11 | STX8 | SYCE2 |
| ST5 | STK17A | STXBP2 | SYDE2 |
| ST6GAL1 | STK24 | STXBP5 | SYF2 |
| ST6GALNAC5 | STK3 | STYK1 | SYK |
| ST7 | STK36 | STYX | SYN1 |

| 2351 | | 2352 | |
|---|---|---|---|
| SYNE1 | TAF1C | TAX1BP1 | TBR1 |
| SYNE2 | TAF2 | TAZ | TBRG1 |
| SYNGAP1 | TAF4 | TBC1D1 | TBRG4 |
| SYNJ2 | TAF5 | TBC1D10B | TBX5 |
| SYNJ2BP | TAF6 | TBC1D12 | TBXA2R |
| SYNM | TAF6L | TBC1D14 | TBXAS1 |
| SYP | TAF8 | TBC1D16 | TCEA3 |
| SYPL1 | TAF9 | TBC1D22A | TCEAL1 |
| SYS1 | TAGLN2 | TBC1D23 | TCEAL6 |
| SYT17 | TALDO1 | TBC1D24 | TCEAL7 |
| SYT7 | TANC1 | TBC1D2B | TCEB1 |
| SYT8 | TANC2 | TBC1D4 | TCERG1 |
| SYT9 | TANK | TBC1D5 | TCF12 |
| SYTL1 | TAOK1 | TBC1D7 | TCF23 |
| SYTL3 | TAOK3 | TBC1D9 | TCF25 |
| T | TAP1 | TBC1D9B | TCF3 |
| TACC3 | TAP2 | TBCB | TCF7 |
| TACR1 | TAPBP | TBCC | TCF7L1 |
| TADA1 | TAPBPL | TBCCD1 | TCHP |
| TADA2A | TARBP1 | TBCD | TCIRG1 |
| TADA2B | TARBP2 | TBCEL | TCP1 |
| TAF1 | TARDBP | TBKBP1 | TCP11L2 |
| TAF11 | TARS2 | TBL1X | TDP1 |
| TAF12 | TASP1 | TBL3 | TDRD3 |
| TAF1A | TATDN3 | TBPL1 | TDRD7 |

| | | | |
|---|---|---|---|
| TDRKH | TFIP11 | THUMPD2 | TLK2 |
| TEAD2 | TG | THUMPD3 | TLL2 |
| TEC | TGDS | TIAL1 | TLN1 |
| TECPR1 | TGFB2 | TIAM1 | TLN2 |
| TELO2 | TGFB3 | TICAM1 | TLR4 |
| TENC1 | TGFBR3 | TIFA | TLR5 |
| TEP1 | TGM1 | TIGD2 | TLR9 |
| TERT | TGOLN2 | TIMELESS | TLX2 |
| TES | TGS1 | TIMM10 | TM2D1 |
| TESC | THADA | TIMM13 | TM2D3 |
| TESK2 | THAP11 | TIMM17B | TM6SF1 |
| TET1 | THAP3 | TIMM22 | TM7SF2 |
| TET2 | THAP4 | TIMM23 | TM9SF2 |
| TET3 | THAP8 | TIMM44 | TM9SF3 |
| TEX10 | THAP9 | TIMM50 | TM9SF4 |
| TEX264 | THBS2 | TIMM8B | TMBIM4 |
| TEX9 | THBS3 | TIPRL | TMCC2 |
| TF | THG1L | TIRAP | TMCO1 |
| TFAM | THNSL1 | TJAP1 | TMCO3 |
| TFAMP1 | THOC1 | TK2 | TMCO4 |
| TFAP2A | THOP1 | TKT | TMCO7 |
| TFAP2E | THRA | TLE1 | TMED1 |
| TFAP4 | THRAP3 | TLE2 | TMED10 |
| TFDP1 | THSD4 | TLE3 | TMED3 |
| TFG | THUMPD1 | TLE4 | TMED5 |

| | | | |
|---|---|---|---|
| TMED7 | TMEM149 | TMEM206 | TMEM70 |
| TMED7-TICAM2 | TMEM14C | TMEM208 | TMEM79 |
| TMEM101 | TMEM150A | TMEM214 | TMEM86B |
| TMEM104 | TMEM151B | TMEM217 | TMEM87A |
| TMEM106A | TMEM154 | TMEM219 | TMEM87B |
| TMEM108 | TMEM158 | TMEM222 | TMEM88B |
| TMEM109 | TMEM167B | TMEM30A | TMEM8A |
| TMEM11 | TMEM168 | TMEM38A | TMEM91 |
| TMEM111 | TMEM173 | TMEM39A | TMF1 |
| TMEM115 | TMEM177 | TMEM41A | TMOD2 |
| TMEM116 | TMEM179B | TMEM42 | TMPPE |
| TMEM117 | TMEM180 | TMEM5 | TMPRSS11A |
| TMEM120A | TMEM181 | TMEM50A | TMPRSS3 |
| TMEM120B | TMEM183B | TMEM50B | TMSB15A |
| TMEM126A | TMEM184A | TMEM51 | TMSL3 |
| TMEM126B | TMEM188 | TMEM53 | TMTC1 |
| TMEM127 | TMEM189 | TMEM55A | TMTC3 |
| TMEM130 | TMEM194A | TMEM55B | TMTC4 |
| TMEM131 | TMEM196 | TMEM57 | TMUB1 |
| TMEM132E | TMEM198 | TMEM59 | TMUB2 |
| TMEM134 | TMEM20 | TMEM62 | TMX3 |
| TMEM140 | TMEM200B | TMEM63A | TMX4 |
| TMEM141 | TMEM200C | TMEM63B | TNF |
| TMEM143 | TMEM201 | TMEM64 | TNFAIP1 |
| TMEM147 | TMEM205 | TMEM68 | TNFAIP3 |

| | | | |
|---|---|---|---|
| TNFAIP8 | TNS3 | TP53I3 | TRAF7 |
| TNFRSF10B | TNXB | TP53INP2 | TRAIP |
| TNFRSF10D | TOB2 | TP63 | TRAK1 |
| TNFRSF11B | TOLLIP | TP73 | TRAK2 |
| TNFRSF12A | TOM1 | TPCN1 | TRAM1 |
| TNFRSF19 | TOM1L1 | TPCN2 | TRAM2 |
| TNFRSF25 | TOM1L2 | TPD52 | TRANK1 |
| TNFRSF8 | TOMM22 | TPD52L1 | TRAP1 |
| TNFSF11 | TOMM34 | TPD52L2 | TRAPPC1 |
| TNFSF13B | TOMM40 | TPH2 | TRAPPC10 |
| TNFSF9 | TOMM40L | TPK1 | TRAPPC4 |
| TNIP1 | TOMM5 | TPM1 | TRAPPC6B |
| TNIP2 | TOMM6 | TPM3 | TRAPPC9 |
| TNK1 | TOMM7 | TPM4 | TRDMT1 |
| TNK2 | TOMM70A | TPP2 | TREX1 |
| TNKS | TOP1MT | TPPP | TRIB1 |
| TNKS1BP1 | TOP2A | TPST1 | TRIB2 |
| TNN | TOP3A | TPX2 | TRIM11 |
| TNNI2 | TOR1AIP1 | TRA2B | TRIM15 |
| TNNT2 | TOR1B | TRABD | TRIM2 |
| TNPO1 | TOR3A | TRAF2 | TRIM21 |
| TNPO2 | TOX2 | TRAF3IP2 | TRIM26 |
| TNPO3 | TOX4 | TRAF3IP3 | TRIM27 |
| TNRC18 | TP53 | TRAF5 | TRIM28 |
| TNRC6A | TP53BP1 | TRAF6 | TRIM3 |

| | | | |
|---|---|---|---|
| TRIM35 | TRMT2B | TSN | TTC17 |
| TRIM36 | TRMT61A | TSNARE1 | TTC18 |
| TRIM37 | TRMU | TSPAN1 | TTC19 |
| TRIM38 | TRNT1 | TSPAN11 | TTC21B |
| TRIM39 | TROAP | TSPAN12 | TTC23 |
| TRIM40 | TROVE2 | TSPAN17 | TTC23L |
| TRIM41 | TRPC1 | TSPAN2 | TTC25 |
| TRIM44 | TRPC3 | TSPAN3 | TTC26 |
| TRIM46 | TRPC4AP | TSPAN31 | TTC27 |
| TRIM50 | TRPM1 | TSPAN32 | TTC28 |
| TRIM52 | TRPM6 | TSPAN33 | TTC3 |
| TRIM56 | TRPM7 | TSPAN4 | TTC30B |
| TRIM6 | TRPS1 | TSPO | TTC31 |
| TRIM62 | TRPV1 | TSPO2 | TTC32 |
| TRIM65 | TRPV2 | TSPYL4 | TTC35 |
| TRIM66 | TRPV4 | TSR2 | TTC38 |
| TRIM6-TRIM34 | TRRAP | TSSC1 | TTC4 |
| TRIM7 | TRUB1 | TSSC4 | TTC5 |
| TRIM8 | TSC2 | TSSK4 | TTC7A |
| TRIM9 | TSC22D1 | TSTD2 | TTC7B |
| TRIO | TSC22D4 | TTBK2 | TTC8 |
| TRIOBP | TSEN54 | TTC1 | TTC9 |
| TRIP13 | TSGA10IP | TTC13 | TTC9B |
| TRIT1 | TSGA13 | TTC14 | TTC9C |
| TRMT1 | TSHR | TTC15 | TTK |

| 2361 | | 2362 | |
|---|---|---|---|
| TTL | TUSC2 | UBA52 | UBE2Q2 |
| TTLL10 | TUSC4 | UBA6 | UBE2QP1 |
| TTLL12 | TUT1 | UBA7 | UBE2S |
| TTLL3 | TWF2 | UBAC1 | UBE2T |
| TTLL8 | TXLNA | UBAC2 | UBE2U |
| TTLL9 | TXN | UBAP2 | UBE2V2 |
| TTPAL | TXNDC12 | UBAP2L | UBE3A |
| TTTY18 | TXNDC16 | UBE2C | UBE4B |
| TUBA1B | TXNDC17 | UBE2CBP | UBIAD1 |
| TUBA4A | TXNDC9 | UBE2D1 | UBL3 |
| TUBA4B | TXNL1 | UBE2D2 | UBL4A |
| TUBB | TXNL4B | UBE2D3 | UBL5 |
| TUBB1 | TXNRD1 | UBE2E1 | UBL7 |
| TUBB2C | TXNRD2 | UBE2E2 | UBLCP1 |
| TUBB6 | TXNRD3IT1 | UBE2G1 | UBN2 |
| TUBE1 | TYK2 | UBE2G2 | UBP1 |
| TUBG2 | TYMS | UBE2H | UBQLN1 |
| TUBGCP2 | TYRO3 | UBE2I | UBR2 |
| TUBGCP3 | TYSND1 | UBE2J1 | UBR3 |
| TUBGCP4 | U2AF1 | UBE2J2 | UBR4 |
| TUBGCP6 | U2AF2 | UBE2K | UBR5 |
| TUFT1 | UACA | UBE2L3 | UBTD2 |
| TULP1 | UBA1 | UBE2L6 | UBTF |
| TULP3 | UBA3 | UBE2M | UBXN11 |
| TULP4 | UBA5 | UBE2O | UBXN4 |

| | | | |
|---|---|---|---|
| UBXN7 | UNG | USP25 | UTP3 |
| UBXN8 | UNK | USP28 | UTP6 |
| UCHL1 | UNKL | USP3 | UTRN |
| UCK2 | UPF2 | USP30 | UVRAG |
| UCKL1AS | UPF3B | USP31 | UXS1 |
| UEVLD | UPP1 | USP33 | VAC14 |
| UFC1 | UQCR | USP35 | VAMP4 |
| UFD1L | UQCRB | USP38 | VAMP8 |
| UFSP1 | UQCRC2 | USP39 | VANGL2 |
| UFSP2 | URB1 | USP40 | VARS |
| UGDH | URB2 | USP42 | VARS2 |
| UGP2 | URGCP | USP45 | VAT1 |
| UGT1A5 | URM1 | USP46 | VAT1L |
| UHRF1 | USF1 | USP48 | VAV2 |
| UHRF1BP1L | USF2 | USP49 | VAV3 |
| ULBP1 | USO1 | USP51 | VCAN |
| ULBP3 | USP10 | USP53 | VCL |
| ULK1 | USP12 | USP6NL | VCPIP1 |
| ULK4 | USP14 | USP7 | VEGFB |
| UMPS | USP15 | UST | VEGFC |
| UNC119 | USP16 | UTP11L | VENTX |
| UNC119B | USP2 | UTP14A | VEZT |
| UNC13A | USP20 | UTP15 | VGLL4 |
| UNC5B | USP22 | UTP20 | VHL |
| UNC84A | USP24 | UTP23 | VIPR1 |

| | | | |
|---|---|---|---|
| VIPR2 | WAC | WDR44 | WDR90 |
| VIT | WAPAL | WDR45 | WDR91 |
| VKORC1L1 | WARS2 | WDR45L | WDTC1 |
| VMA21 | WASF1 | WDR46 | WDYHV1 |
| VMAC | WASF3 | WDR47 | WEE1 |
| VOPP1 | WASH2P | WDR48 | WFDC3 |
| VPRBP | WBP1 | WDR5 | WFIKKN2 |
| VPS11 | WBP11 | WDR51A | WFS1 |
| VPS13B | WBP4 | WDR51B | WHAMM |
| VPS13D | WBSCR16 | WDR53 | WHSC1 |
| VPS16 | WBSCR27 | WDR54 | WHSC1L1 |
| VPS18 | WDFY2 | WDR59 | WIBG |
| VPS24 | WDFY4 | WDR5B | WIPF1 |
| VPS26B | WDR1 | WDR60 | WIPF2 |
| VPS36 | WDR11 | WDR62 | WIPI1 |
| VPS4A | WDR13 | WDR65 | WIPI2 |
| VPS52 | WDR16 | WDR66 | WIZ |
| VPS53 | WDR20 | WDR67 | WNK3 |
| VPS54 | WDR27 | WDR77 | WNT2B |
| VPS8 | WDR31 | WDR8 | WNT5B |
| VRK2 | WDR33 | WDR81 | WNT6 |
| VRK3 | WDR34 | WDR82 | WNT8B |
| VTA1 | WDR36 | WDR86 | WRAP53 |
| VWA3B | WDR37 | WDR88 | WRB |
| VWA5A | WDR4 | WDR89 | WRN |

| | | | |
|---|---|---|---|
| WRNIP1 | YDJC | ZBTB16 | ZC3H15 |
| WSB1 | YEATS2 | ZBTB17 | ZC3H18 |
| WTAP | YIF1A | ZBTB2 | ZC3H3 |
| XAB2 | YIPF4 | ZBTB20 | ZC3H7B |
| XBP1 | YIPF5 | ZBTB22 | ZC3HAV1 |
| XKR4 | YKT6 | ZBTB25 | ZC3HC1 |
| XKR5 | YME1L1 | ZBTB3 | ZCCHC11 |
| XKR6 | YOD1 | ZBTB33 | ZCCHC12 |
| XKR9 | YPEL1 | ZBTB4 | ZCCHC17 |
| XPC | YTHDC1 | ZBTB40 | ZCCHC2 |
| XPNPEP1 | YTHDF3 | ZBTB41 | ZCCHC4 |
| XPNPEP3 | YWHAE | ZBTB43 | ZCCHC6 |
| XPO1 | YWHAG | ZBTB44 | ZCCHC8 |
| XPOT | YWHAQ | ZBTB45 | ZDHHC12 |
| XPR1 | YY1 | ZBTB47 | ZDHHC13 |
| XRCC3 | YY1AP1 | ZBTB48 | ZDHHC14 |
| XRCC4 | ZADH2 | ZBTB6 | ZDHHC16 |
| XRCC6 | ZBBX | ZBTB7B | ZDHHC18 |
| XRN1 | ZBED3 | ZBTB9 | ZDHHC20 |
| XRN2 | ZBED4 | ZC3H10 | ZDHHC21 |
| XRRA1 | ZBED5 | ZC3H11A | ZDHHC22 |
| XYLB | ZBTB1 | ZC3H12A | ZDHHC23 |
| XYLT2 | ZBTB10 | ZC3H12C | ZDHHC3 |
| YARS2 | ZBTB11 | ZC3H12D | ZDHHC5 |
| YBX2 | ZBTB12 | ZC3H13 | ZDHHC8 |

| | | | |
|---|---|---|---|
| ZEB1 | ZFYVE20 | ZMYND12 | ZNF200 |
| ZEB2 | ZFYVE21 | ZMYND8 | ZNF202 |
| ZFAND2A | ZFYVE26 | ZNF10 | ZNF207 |
| ZFAND3 | ZFYVE28 | ZNF100 | ZNF211 |
| ZFAND6 | ZGLP1 | ZNF131 | ZNF212 |
| ZFAT | ZGPAT | ZNF132 | ZNF213 |
| ZFP1 | ZHX1 | ZNF133 | ZNF215 |
| ZFP161 | ZHX2 | ZNF134 | ZNF222 |
| ZFP3 | ZIC1 | ZNF14 | ZNF223 |
| ZFP36 | ZIM2 | ZNF141 | ZNF224 |
| ZFP36L1 | ZKSCAN1 | ZNF142 | ZNF226 |
| ZFP36L2 | ZKSCAN2 | ZNF143 | ZNF227 |
| ZFP41 | ZKSCAN3 | ZNF146 | ZNF230 |
| ZFP62 | ZKSCAN4 | ZNF165 | ZNF236 |
| ZFP64 | ZKSCAN5 | ZNF167 | ZNF24 |
| ZFP82 | ZMAT2 | ZNF17 | ZNF25 |
| ZFP91 | ZMAT3 | ZNF174 | ZNF250 |
| ZFP92 | ZMIZ1 | ZNF18 | ZNF251 |
| ZFPM1 | ZMIZ2 | ZNF180 | ZNF252 |
| ZFR | ZMYM1 | ZNF181 | ZNF254 |
| ZFR2 | ZMYM2 | ZNF184 | ZNF263 |
| ZFY | ZMYM4 | ZNF192 | ZNF264 |
| ZFYVE1 | ZMYM5 | ZNF193 | ZNF266 |
| ZFYVE16 | ZMYM6 | ZNF197 | ZNF271 |
| ZFYVE19 | ZMYND11 | ZNF2 | ZNF28 |

| | | | |
|---|---|---|---|
| ZNF281 | ZNF385A | ZNF474 | ZNF548 |
| ZNF284 | ZNF394 | ZNF48 | ZNF550 |
| ZNF286A | ZNF395 | ZNF480 | ZNF551 |
| ZNF286B | ZNF396 | ZNF487 | ZNF552 |
| ZNF296 | ZNF398 | ZNF496 | ZNF557 |
| ZNF3 | ZNF41 | ZNF497 | ZNF560 |
| ZNF302 | ZNF410 | ZNF498 | ZNF565 |
| ZNF304 | ZNF414 | ZNF500 | ZNF569 |
| ZNF311 | ZNF416 | ZNF503 | ZNF572 |
| ZNF317 | ZNF419 | ZNF507 | ZNF573 |
| ZNF321 | ZNF420 | ZNF509 | ZNF575 |
| ZNF322A | ZNF428 | ZNF510 | ZNF576 |
| ZNF323 | ZNF429 | ZNF512B | ZNF579 |
| ZNF324 | ZNF43 | ZNF513 | ZNF581 |
| ZNF324B | ZNF430 | ZNF516 | ZNF582 |
| ZNF326 | ZNF432 | ZNF517 | ZNF584 |
| ZNF335 | ZNF433 | ZNF518B | ZNF585A |
| ZNF33B | ZNF438 | ZNF519 | ZNF592 |
| ZNF343 | ZNF442 | ZNF526 | ZNF594 |
| ZNF345 | ZNF444 | ZNF527 | ZNF597 |
| ZNF346 | ZNF445 | ZNF532 | ZNF598 |
| ZNF366 | ZNF446 | ZNF540 | ZNF605 |
| ZNF367 | ZNF449 | ZNF542 | ZNF614 |
| ZNF37A | ZNF467 | ZNF546 | ZNF616 |
| ZNF384 | ZNF469 | ZNF547 | ZNF622 |

| | | | |
|---|---|---|---|
| ZNF625 | ZNF703 | ZNF778 | ZNF880 |
| ZNF627 | ZNF704 | ZNF781 | ZNF91 |
| ZNF628 | ZNF707 | ZNF784 | ZNF92 |
| ZNF630 | ZNF709 | ZNF785 | ZNF93 |
| ZNF638 | ZNF711 | ZNF787 | ZNHIT1 |
| ZNF644 | ZNF717 | ZNF79 | ZNHIT3 |
| ZNF646 | ZNF720 | ZNF790 | ZNRD1 |
| ZNF649 | ZNF721 | ZNF791 | ZNRF1 |
| ZNF655 | ZNF74 | ZNF792 | ZNRF2 |
| ZNF664 | ZNF740 | ZNF799 | ZNRF3 |
| ZNF668 | ZNF746 | ZNF8 | ZPBP |
| ZNF670 | ZNF749 | ZNF804A | ZSCAN12 |
| ZNF671 | ZNF76 | ZNF805 | ZSCAN20 |
| ZNF672 | ZNF761 | ZNF81 | ZSCAN22 |
| ZNF682 | ZNF764 | ZNF816A | ZSCAN29 |
| ZNF684 | ZNF765 | ZNF821 | ZSWIM1 |
| ZNF687 | ZNF767 | ZNF828 | ZSWIM3 |
| ZNF688 | ZNF768 | ZNF83 | ZSWIM4 |
| ZNF689 | ZNF770 | ZNF830 | ZSWIM5 |
| ZNF69 | ZNF771 | ZNF836 | ZSWIM6 |
| ZNF691 | ZNF772 | ZNF837 | ZSWIM7 |
| ZNF692 | ZNF774 | ZNF843 | ZUFSP |
| ZNF7 | ZNF775 | ZNF844 | ZW10 |
| ZNF70 | ZNF776 | ZNF853 | ZWINT |
| ZNF700 | ZNF777 | ZNF860 | ZXDA |

2375                                    2376

ZYX

ZZZ3

What is claimed is:

1. A kit for determining the methylation status of at least one CpG dinucleotide, the kit comprising:
at least one first nucleic acid primer at least 8 nucleotides in length that is complementary to a bisulfite-converted nucleic acid sequence comprising a CpG dinucleotide at position 373378 of chromosome 5 within the aryl hydrocarbon receptor repressor (AHRR) gene, wherein the at least one first nucleic acid primer detects the unmethylated CpG dinucleotide.

2. The kit of claim 1, further comprising at least one second nucleic acid primer at least 8 nucleotides in length that is complementary to a bisulfite-converted nucleic acid sequence comprising a CpG dinucleotide at position 373378 of chromosome 5 within the AHRR gene, wherein the at least one second nucleic acid primer detects the methylated CpG dinucleotide.

3. The kit of claim 2, further comprising at least a third nucleic acid primer at least 8 nucleotides in length that is complementary to a nucleic acid sequence upstream of the CpG dinucleotide at position 373378 of chromosome 5 within the AHRR gene.

4. The kit of claim 3, further comprising at least a fourth nucleic acid primer at least 8 nucleotides in length that is complementary to a nucleic acid sequence downstream of the CpG dinucleotide at position 373378 of chromosome 5 within the AHRR gene.

5. The kit of claim 3, wherein the at least third nucleic acid primer is complementary to a bisulfite-converted nucleic acid sequence.

6. The kit of claim 4, wherein the at least fourth nucleic acid primer is complementary to a bisulfite-converted nucleic acid sequence.

7. The kit of claim 1, wherein the at least one first nucleic acid primer comprises one or more nucleotide analogs.

8. The kit of claim 1, wherein the at least one first nucleic acid primer comprises one or more synthetic or non-natural nucleotides.

9. The kit of claim 1, further comprising a solid substrate to which the at least one first nucleic acid primer is bound.

10. The kit of claim 9, wherein the substrate is a polymer, glass, semiconductor, paper, metal, gel or hydrogel.

11. The kit of claim 9, wherein the solid substrate is a microarray or microfluidics card.

12. The kit of claim 1, further comprising a detectable label.

13. A kit for determining the methylation status of at least one CpG dinucleotide, the kit comprising:
at least one first nucleic acid primer at least 8 nucleotides in length that is complementary to a bisulfite-converted nucleic acid sequence comprising a CpG dinucleotide at position 373378 of chromosome 5 within the aryl hydrocarbon receptor repressor (AH RR) gene, wherein the at least one first nucleic acid primer comprises one or more nucleotide analogs or one or more synthetic or non-natural nucleotides, and wherein the at least one nucleic acid primer detects either the unmethylated CpG dinucleotide or the methylated CpG dinucleotide.

14. The kit of claim 13, further comprising at least one second nucleic acid primer at least 8 nucleotides in length that is complementary to a bisulfite-converted nucleic acid sequence comprising a CpG dinucleotide at position 373378 of chromosome 5 within the AHRR gene, wherein the at least one second nucleic acid primer detects the unmethylated CpG dinucleotide or the methylated CpG dinucleotide, the opposite that is detected by the at least one first nucleic acid primer.

15. The kit of claim 13, wherein the at least one first nucleic acid primer detects the unmethylated CpG dinucleotide.

16. The kit of claim 13, wherein the at least one first nucleic acid primer detects the methylated CpG dinucleotide.

17. The kit of claim 14, wherein the at least one first nucleic acid primer detects the unmethylated CpG dinucleotide and wherein the at least one second nucleic acid primer detects the methylated CpG dinucleotide.

18. The kit of claim 14, wherein the at least one first nucleic acid primer detects the methylated CpG dinucleotide and wherein the at least one second nucleic acid primer detects the unmethylated CpG dinucleotide.

19. The kit of claim 14, further comprising at least a third nucleic acid primer at least 8 nucleotides in length that is complementary to a nucleic acid sequence upstream of the CpG dinucleotide at position 373378 of chromosome 5 within the AHRR gene.

20. The kit of claim 19, further comprising at least a fourth nucleic acid primer at least 8 nucleotides in length that is complementary to a nucleic acid sequence downstream of the CpG dinucleotide at position 373378 of chromosome 5 within the AHRR gene.

21. The kit of claim 19, wherein the at least third nucleic acid primer is complementary to a bisulfite-converted nucleic acid sequence.

22. The kit of claim 20, wherein the at least fourth nucleic acid primer is complementary to a bisulfite-converted nucleic acid sequence.

23. The kit of claim 14, wherein the at least one second nucleic acid primer comprises one or more nucleotide analogs.

24. The kit of claim 14, wherein the at least one second nucleic acid primer comprises one or more synthetic or non-natural nucleotides.

25. The kit of claim 13, further comprising a solid substrate to which the at least one first nucleic acid primer is bound.

26. The kit of claim 25, wherein the substrate is a polymer, glass, semiconductor, paper, metal, gel or hydrogel.

27. The kit of claim 25, wherein the solid substrate is a microarray or microfluidics card.

28. The kit of claim 13, further comprising a detectable label.

29. A kit for determining the methylation status of at least one CpG dinucleotide, the kit comprising:
at least one first nucleic acid primer at least 8 nucleotides in length that is complementary to a bisulfite-converted nucleic acid sequence comprising a CpG dinucleotide at position 373378 of chromosome 5 within the aryl hydrocarbon receptor repressor (AH RR) gene, and wherein the at least one nucleic acid primer detects either the unmethylated CpG dinucleotide or the methylated CpG dinucleotide; and
a detectable label selected from the group consisting of an enzyme label, a fluorescent label, and a colorimetric label.

30. The kit of claim 29, further comprising at least one second nucleic acid primer at least 8 nucleotides in length that is complementary to a bisulfite-converted nucleic acid sequence comprising a CpG dinucleotide at position 373378 of chromosome 5 within the AHRR gene, wherein the at least one second nucleic acid primer detects the unmethylated CpG dinucleotide or the methylated CpG dinucleotide, the opposite that is detected by the at least one first nucleic acid primer.

31. The kit of claim 29, wherein the at least one first nucleic acid primer detects the unmethylated CpG dinucleotide.

32. The kit of claim 29, wherein the at least one first nucleic acid primer detects the methylated CpG dinucleotide.

33. The kit of claim 30, wherein the at least one first nucleic acid primer detects the unmethylated CpG dinucleotide and wherein the at least one second nucleic acid primer detects the methylated CpG dinucleotide.

34. The kit of claim 30, wherein the at least one first nucleic acid primer detects the methylated CpG dinucleotide and wherein the at least one second nucleic acid primer detects the unmethylated CpG dinucleotide.

35. The kit of claim 30, further comprising at least a third nucleic acid primer at least 8 nucleotides in length that is complementary to a nucleic acid sequence upstream of the CpG dinucleotide at position 373378 of chromosome 5 within the AHRR gene.

36. The kit of claim 30, further comprising at least a fourth nucleic acid primer at least 8 nucleotides in length that is complementary to a nucleic acid sequence downstream of the CpG dinucleotide at position 373378 of chromosome 5 within the AHRR gene.

37. The kit of claim 35, wherein the at least third nucleic acid primer is complementary to a bisulfite-converted nucleic acid sequence.

38. The kit of claim 37, wherein the at least fourth nucleic acid primer is complementary to a bisulfite-converted nucleic acid sequence.

39. The kit of claim 29, wherein the at least one first nucleic acid primer comprises one or more nucleotide analogs.

40. The kit of claim 29, wherein the at least one first nucleic acid primer comprises one or more synthetic or non-natural nucleotides.

41. The kit of claim 29, further comprising a solid substrate to which the at least one first nucleic acid primer is bound.

42. The kit of claim 41, wherein the substrate is a polymer, glass, semiconductor, paper, metal, gel or hydrogel.

43. The kit of claim 41, wherein the solid substrate is a microarray or microfluidics card.

44. A kit for determining the methylation status of at least one CpG dinucleotide, the kit comprising:
at least one first nucleic acid primer at least 8 nucleotides in length that is complementary to a bisulfite-converted nucleic acid sequence comprising a CpG dinucleotide at position 373378 of chromosome 5 within the aryl hydrocarbon receptor repressor (AH RR) gene, and wherein the at least one nucleic acid primer detects either the unmethylated CpG dinucleotide or the methylated CpG dinucleotide; and
a solid substrate to which the at least one first nucleic acid primer is bound.

45. The kit of claim 44, further comprising at least one second nucleic acid primer at least 8 nucleotides in length that is complementary to a bisulfite-converted nucleic acid sequence comprising a CpG dinucleotide at position 373378 of chromosome 5 within the AHRR gene, wherein the at least one second nucleic acid primer detects the unmethylated CpG dinucleotide or the methylated CpG dinucleotide, the opposite that is detected by the at least one first nucleic acid primer.

46. The kit of claim 44, wherein the at least one first nucleic acid primer detects the unmethylated CpG dinucleotide.

47. The kit of claim 44, wherein the at least one first nucleic acid primer detects the methylated CpG dinucleotide.

48. The kit of claim 45, wherein the at least one first nucleic acid primer detects the unmethylated CpG dinucleotide and wherein the at least one second nucleic acid primer detects the methylated CpG dinucleotide.

49. The kit of claim 45, wherein the at least one first nucleic acid primer detects the methylated CpG dinucleotide and wherein the at least one second nucleic acid primer detects the unmethylated CpG dinucleotide.

50. The kit of claim 45, further comprising at least a third nucleic acid primer at least 8 nucleotides in length that is complementary to a nucleic acid sequence upstream of the CpG dinucleotide at position 373378 of chromosome 5 within the AHRR gene.

51. The kit of claim 50, further comprising at least a fourth nucleic acid primer at least 8 nucleotides in length that is complementary to a nucleic acid sequence downstream of the CpG dinucleotide at position 373378 of chromosome 5 within the AHRR gene.

52. The kit of claim 50, wherein the at least third nucleic acid primer is complementary to a bisulfite-converted nucleic acid sequence.

53. The kit of claim 51, wherein the at least fourth nucleic acid primer is complementary to a bisulfite-converted nucleic acid sequence.

54. The kit of claim 44, wherein the at least one first nucleic acid primer comprises one or more nucleotide analogs.

55. The kit of claim 44, wherein the at least one first nucleic acid primer comprises one or more synthetic or non-natural nucleotides.

56. The kit of claim 44, wherein the substrate is a polymer, glass, semiconductor, paper, metal, gel or hydrogel.

57. The kit of claim 44, wherein the solid substrate is a microarray or microfluidics card.

58. The kit of claim 44, further comprising a detectable label.

* * * * *

UNITED STATES PATENT AND TRADEMARK OFFICE
CERTIFICATE OF CORRECTION

PATENT NO. : 9,273,358 B2  
APPLICATION NO. : 14/039023  
DATED : March 1, 2016  
INVENTOR(S) : Robert Philibert and Anup Madan Page 1 of 1

It is certified that error appears in the above-identified patent and that said Letters Patent is hereby corrected as shown below:

In the Claims

In Claim 13 (Column 2386, line 60), delete "(AH RR)" and insert -- (AHRR) -- therefor.

In Claim 29 (Column 2387, line 55), delete "(AH RR)" and insert -- (AHRR) -- therefor.

In Claim 36 (Column 2388, line 20), delete "claim 30," and insert -- claim 35 -- therefor.

In Claim 38 (Column 2388, line 28), delete "claim 37," and insert -- claim 36, -- therefor.

In Claim 44 (Column 2388, line 48), delete "(AH RR)" and insert -- (AHRR) -- therefor.

Signed and Sealed this  
Tenth Day of May, 2016

Michelle K. Lee  
*Director of the United States Patent and Trademark Office*